United States Patent
Chenchik et al.

(10) Patent No.: US 11,655,510 B2
(45) Date of Patent: May 23, 2023

(54) EXPERIMENTALLY VALIDATED SETS OF GENE SPECIFIC PRIMERS FOR USE IN MULTIPLEX APPLICATIONS

(71) Applicant: Cellecta, Inc., Mountain View, CA (US)

(72) Inventors: Alex Chenchik, Redwood City, CA (US); Costa Frangou, Sunnyvale, CA (US); Mikhail Makhanov, San Francisco, CA (US)

(73) Assignee: Cellecta, Inc., Mountain View, CA (US)

( * ) Notice: Subject to any disclaimer, the term of this patent is extended or adjusted under 35 U.S.C. 154(b) by 516 days.

(21) Appl. No.: 15/914,895

(22) Filed: Mar. 7, 2018

(65) Prior Publication Data

US 2018/0245164 A1 Aug. 30, 2018

Related U.S. Application Data

(63) Continuation-in-part of application No. 15/133,184, filed on Apr. 19, 2016, now Pat. No. 10,975,440.

(60) Provisional application No. 62/150,166, filed on Apr. 20, 2015.

(51) Int. Cl.
*C12Q 1/6886* (2018.01)

(52) U.S. Cl.
CPC ..... *C12Q 1/6886* (2013.01); *C12Q 2600/156* (2013.01); *C12Q 2600/158* (2013.01); *C12Q 2600/16* (2013.01)

(58) Field of Classification Search
CPC .......... C12Q 2537/143; C12Q 2600/16; C12Q 2525/155; C12Q 1/686; C12Q 1/6806; C12Q 2525/161
See application file for complete search history.

(56) References Cited

U.S. PATENT DOCUMENTS

| | | | |
|---|---|---|---|
| 5,565,340 A | 10/1996 | Chenchik et al. | |
| 5,994,076 A | 11/1999 | Chenchik et al. | |
| 6,207,372 B1 * | 3/2001 | Shuber | C12Q 1/686 435/6.12 |
| 8,323,897 B2 * | 12/2012 | Andersen | C12Q 1/6827 435/6.12 |
| 2003/0082758 A1 | 5/2003 | Rosen et al. | |
| 2003/0121452 A1 | 7/2003 | Lyons et al. | |
| 2003/0186246 A1 | 10/2003 | Willey et al. | |
| 2008/0050393 A1 | 2/2008 | Tang et al. | |
| 2013/0123120 A1 | 5/2013 | Zimmermann et al. | |
| 2013/0244897 A1 | 9/2013 | Lueking et al. | |
| 2015/0038343 A1 | 2/2015 | Leamon et al. | |
| 2015/0259734 A1 | 9/2015 | Asbury et al. | |

FOREIGN PATENT DOCUMENTS

| | | |
|---|---|---|
| WO | WO2004051218 A2 | 6/2004 |
| WO | WO2008069906 A2 | 6/2008 |
| WO | WO2011014811 A1 | 2/2011 |
| WO | WO2013081864 A1 | 6/2013 |
| WO | WO2013128281 A1 | 9/2013 |

OTHER PUBLICATIONS

Broude et al., "Multiplex allele-specific target amplification based on PCR suppression," PNAS, Jan. 2, vol. 98, No. 1, pp. 206-211. (Year: 2001).*
Jareborg et al., "Comparative Analysis of Noncoding Regions of 77 Orthologous Mouse and Human Gene Pairs," Genome Research, vol. 9, pp. 815-824. (Year: 1999).*
Kaiser, Jocelyn, "There are about 20,000 human genes. So why do scientists only study a small fraction of them?", Sep. 18, pp. 1-3. (Year: 2018).*
Sint et al., "Advances in multiplex PCR: balancing primer efficiencies and improving detection success," Methods in Ecology and Evolution, vol. 3, pp. 898-905. (Year: 2012).*
Henegariu et al., "Multiplex PCR: Critical Parameters and Step-by-Step Protocol," BioTechniques, vol. 23, No. 3, pp. 504-511. (Year: 1997).*
Giardina et al., Whole genome amplification and real-time PCR in forensic casework, BMC Genomics, Biomed Central, vol. 10, No. 1, Apr. 14, 2009, p. 159.
Mertes et al., Targeted Enrichment of Genomic DNA Regions for Next-Generation Sequencing, Brief Funct Genomics. Nov. 2011;10(6):374-86.
Assay ID No. Hs00176369_m1, retrieved on-line from www.thermofisher.com; retrieved on May 20, 2020 (Year: 2020).
Assay ID No. Hs00173565_m1, retrieved on-line from www.thermofisher.com; retrieved on May 20, 2020 (Year: 2020).
Myllykangas et al., Chapter 2 Overview of Sequencing Technology Platforms, Bioinformatics for High Throughput Sequencing (2012), 11-25.
Clarke et al., Modular tagging of amplicons using a single PCR for high-throughput sequencing, Molecular Ecology Resources (2014), 14:117-121.
Parkinson et al., Preparation of high-quality next-generation sequencing libraries from pictogram quantities of target DNA, Genome Research (2012), 22:125-133.
Head et al., Library construction for next-generation sequencing: Overviews and challenges, BioTechniques (2014) 56(2):61-77.

(Continued)

*Primary Examiner* — Young J Kim
(74) *Attorney, Agent, or Firm* — Mandar A. Joshi; Bret E. Field; Bozicevic, Field & Francis LLP

(57) ABSTRACT

Sets of experimentally validated gene specific primer pairs are provided. Embodiments of the sets include 10 or more gene specific primer pairs of forward and reverse primers. The forward and reverse primers of each primer pair include gene specific primers that are experimentally validated as suitable for use in a multiplex amplification assay. In some instances, each of the forward and reverse primers includes an anchor domain that includes a universal primer binding site. The sets find use in a variety of different applications, including high-throughput sequencing applications.

4 Claims, 258 Drawing Sheets

Specification includes a Sequence Listing.

(56) References Cited

OTHER PUBLICATIONS

Blomquist et al., Targeted RNA-Sequencing with Competitive Multiplex-PCR Amplicon Libraries, PLOS One (2013), 8(11):e79120, 14 pages.
Markoulatos et al., Multiplex polymerase chain reaction: a practical approach. Journal of Clinical Laboratory Analysis (2002), 16:47-51.
Shen et al., MPprimer: a program for reliable multiplex PCR primer design, BMC Bioinformatics (2010) 11:143.
Zhao et al., Comparison of RNA-Seq and Microarray in Transcriptome Profiling of Activated T Cells, PLOS One (2014), 9(1):e78644, 13 pages.
CoPrimers by Co-Disgnoticsm Inc., downloaded in Apr. 2015, 1 page.
Karn, High-Throughput Gene Expression and Mutation Profiling: Current Methods and Future Perspectives, Breast Care (2013), 8:401-406.
Langmann et al., Real-time reverse transcription-PCR expression profiling of the complete human ATP-binding cassette transporter superfamily in various tissues, Clin Chem. Feb. 2003;49(2):230-8.
Lin et al., Multiplex genotype determination at a large number of gene loci, Proc Natl Acad Sci U S A. Mar. 19, 1996; 93(6): 2582-2587.

\* cited by examiner

| GeneName | Forward Primer | Reverse Primer | SEQ ID NOs | | GeneName | Forward Primer | Reverse Primer | SEQ ID NOs | |
|---|---|---|---|---|---|---|---|---|---|
| ACSM1 | GCCCAAGGATCAGGAGGA | TCCCAGTAGGTGGGCACA | 249 | & 250 | ADAMTS6 | GCCTCCATCAATGCAGCA | CTTCAGCACCAGTGGGCA | 355 | & 356 |
| ACSM3 | CACTCTCCAAGTACCCA | GGTTCCCCAGCACTCACA | 251 | & 252 | ADAMTS7 | CCTGAACCCAGGACCTCAA | CGGCGTTCCTGACAACCA | 357 | & 358 |
| ACSS1 | GGCATCTGCATGCACCA | AGGCCTGGGAGATGCACA | 253 | & 254 | ADAMTS8 | TGAGTGCAAGGACCCCGA | CCCCAGCATACTTGGGGA | 359 | & 360 |
| ACSS2 | CCACACCTTCAGCCCCAA | GGTGTGGCAATGGGGCCA | 255 | & 256 | ADAMTS9 | GCTACCCTGCCTAGACCA | CCCAAGGTCACGAGGCA | 361 | & 362 |
| ACTA1 | CTGGGATCGCTGACCGA | AGGTGACAGCGAGGGCCA | 257 | & 258 | ADAMTSL1 | GCTGACTGAGAGACACCA | TCCCAGGATCCAGGACCA | 363 | & 364 |
| ACTA2 | GAGACCCTGTTCAGCCA | GTGCCCCCTGATAGGACA | 259 | & 260 | ADAMTSL2 | CTCAAGGGCCAGGACCA | GCGCAGAACCTCGTCGACA | 365 | & 366 |
| ACTC1 | GAGAATGAGATGGCCACA | GTGTCTCAGGACAGCGGA | 261 | & 262 | ADAMTSL3 | GCCCTGTAACATCCGGGA | GGAGACACCACCTGCACA | 367 | & 368 |
| ACTG2 | GACCAAGACTGAAGGACA | GAAGAGGGTCTCAGGGCA | 263 | & 264 | ADAMTSL4 | GGGAACCTCACTGACCGA | GACCCAGGGGATCCACA | 369 | & 370 |
| ACTL7B | CGGGCTTCAAGGAGGAGA | TCTCAGGAGCGGCAGCCA | 265 | & 266 | ADAMTSL5 | GTCTACACCCGAGACACA | TGTAGGCTCCCGAGGGA | 371 | & 372 |
| ACTN1 | TGATCAGTCGAGAGGGCGA | TGGCATCCCGGGTCAGGA | 267 | & 268 | ADAR | CCCTCAAGGTCCCAGA | AGCACCGGTGGCTCAGCA | 373 | & 374 |
| ACTN2 | GCCATACATCCTGGCGGA | CTCCCGTAGAGTGCGGA | 269 | & 270 | ADARB2 | CCGTGTACCTGCAGAGCA | CACTCAGCCGCTCGAGGA | 375 | & 376 |
| ACTN3 | TGGGCTACGGCAGCAGGA | GCTCCAGCCACGCAGGA | 271 | & 272 | ADCK1 | CCTCCCCAGATCAGCCA | CGGCCTCAATGCCACGA | 377 | & 378 |
| ACTN4 | TCATGTCGCGGGAGACCA | GGCCCTGCTATGGCGCCA | 273 | & 274 | ADCK3 | GGTCATGGAAGAGCGCCA | CGAGACGGTGCCTCAGCA | 379 | & 380 |
| ACTR2 | CTCTATGAACCCAACCA | CCCTCCAGCAATATCCA | 275 | & 276 | ADCY1 | GCAGGCCCCAGTACGACA | AGGGGCACCTTCTCAGCA | 381 | & 382 |
| ACTR3 | AACGGACGTTGACGGTA | ACATACCCTTCAGCGACA | 277 | & 278 | ADCY2 | AGAACGACGGAGCCCTCA | AGTACGGGTCATGGGGA | 383 | & 384 |
| ACVR1 | AGCCATTGCCCATCGAGA | TTGGTGCCCACACGGGGA | 279 | & 280 | ADCY3 | CGAGGCCTTGGTCACCAA | AAGTTGGGCAGGGAGGGCA | 385 | & 386 |
| ACVR1B | GGTTCAGGGAAGCAGAGA | GCCAGCCCACTAGCAGCA | 281 | & 282 | ADCY6 | TGCGGCTGCTCAACGAGA | GCATGGCGTAGTCAGCCA | 387 | & 388 |
| ACVR1C | GACGGTCATGCTGCGACA | TGAASGTGTGCCAGACCA | 283 | & 284 | ADCY7 | GCAACCTCACCAAGCCCA | TAGGCAGTCCAAGCGGCA | 389 | & 390 |
| ACVR2A | TACACCTAAGCCACCCTA | GTACAGGAGGGTAGGCCA | 285 | & 286 | ADCY8 | CTCAGGAGCTGGTCAGGA | GGGCTCAGGAGGTCAGGA | 391 | & 392 |
| ACVR2B | GGACAGGCTAGGCACGAGA | TGCAGCCTTGCAGCGAGA | 287 | & 288 | ADCY9 | CGAGCAGTTCTGCCAGGA | ACCTCCTCATGCCCAGGA | 393 | & 394 |
| ACVRL1 | ACAACCCGAGAGTGGGCA | GGGTCATTGGGCACCACA | 289 | & 290 | ADCYAP1 | GAGATGTGCCCACGGGA | GGGGCACGAGGGACTGCA | 395 | & 396 |
| ACYP1 | GGGGTGTTTTCCGTAAGCA | CGCACCTTGGAGATGGGA | 291 | & 292 | ADCYAP1R1 | GAGGCAATGAGTCACGCA | AGCCCTGGAAGGAGCCCA | 397 | & 398 |
| ACYP2 | CGTGACAGGCCAAGTGCA | CGAGAACTAGGGCTTCA | 293 | & 294 | ADD1 | CGACGAAGCTTCCGAGGA | TGGCACGCAGACACCGGA | 399 | & 400 |
| ADA | CCAGATGACCAAACGGGA | CAGAGGCTGAAGGTGGCA | 295 | & 296 | ADD2 | CCGAAGCCCGTCTACAGA | GGCTGAAGGGGTTGGGCA | 401 | & 402 |
| ADAD1 | GCCTAAAGGATCAGCCCA | CTCCCTGTACACCAAGCA | 297 | & 298 | ADD3 | GAGAGAAGCCTAGGCACA | TGAGAGGAGAGTGGCA | 403 | & 404 |
| ADAM10 | GCAAACTGAAACCTGGGA | CTGGGCAGAGAGCTGTGA | 299 | & 300 | ADGRB1 | TCATGGGACGACCCAGA | AGAGGAAGCCGCTTGCGGA | 405 | & 406 |
| ADAM11 | CTACCACAGGGCAAGGA | AGCGATGGTCCAGGGCACA | 301 | & 302 | ADGRG1 | TGGCCATGCTAGCCACCA | CCCAGCAGTGTCAGCACA | 407 | & 408 |
| ADAM12 | CCGCCAGATTCTACCCA | GGTGSGAGGGAGGAGGAAGCA | 303 | & 304 | ADH1A | CCCATCCAGGAGGTGCTA | GGTACCCTACGATGACA | 409 | & 410 |
| ADAM15 | ACCAGTTCCCTGACCCA | CGGTTCAGAGGGACCAGA | 305 | & 306 | ADH1B | CATGTGGCACAAGGTCA | GTCCAGTCAGTAGCAGCA | 411 | & 412 |
| ADAM17 | CTGCGAGAGGGAACAGCA | CAGCATCGACATAGGGCA | 307 | & 308 | ADH4 | AGCCCTGGGAGCCACTGA | CCTGCACAGTCAAGGGCA | 413 | & 414 |
| ADAM18 | ACCTTGTGAAGGAAGGA | GGACCACACATGGTGCCA | 309 | & 310 | ADH5 | ACAAGGGCTGGGGGTCA | ACCAGCTGGAATGGATGA | 415 | & 416 |
| ADAM19 | CCGCCTTCTGCAACCA | GCCTCAGCTTGGAAGGGA | 311 | & 312 | ADH7 | GGGCAAACCAGTCCACA | CAGCTGACTTACAGCCCA | 417 | & 418 |
| ADAM2 | AAATGCCAGTGCTCAGGA | GGATCTAAGCGAGGCTGA | 313 | & 314 | ADIPOQ | CCAGGCCGTGATGGGAGA | CCCGAAAAGCCTCGGGGA | 419 | & 420 |
| ADAM22 | TCGTGGAGCGGCAGAGCA | TCGAGCGCGTCGTGCCGA | 315 | & 316 | ADIPOR1 | TACTGCTCCCCACAGCCA | ACGACGCCTGCCAAGCCA | 421 | & 422 |
| ADAM23 | CTGCGGGAAGGATGGCCA | CACATATAGACGGGCCA | 317 | & 318 | ADIPOR2 | GCCTAGGCCTGAGTGGAA | AGAGGCTGGCCATCAGCA | 423 | & 424 |
| ADAM28 | TGCCCTACCTGCCACCA | CCATACCAACTAAGGCCA | 319 | & 320 | ADM | CATCCGAGTCAAGCGCTA | GCACGTCCCGAAGCGGGA | 425 | & 426 |
| ADAM29 | GAACCTGTCATGACCGCAA | GTCATTGAAGGGAGCCCA | 321 | & 322 | ADM2 | AGGCACCCGACCACCCGA | GCACAGCCCACTCGCA | 427 | & 428 |
| ADAM32 | GAGACCAGTCTGTCGGCAA | CAACAGTCTGCAGGTCCA | 323 | & 324 | ADORA1 | CCAAGTCGCTGGCCCTCA | CTTGTGGAGGACGGGCA | 429 | & 430 |
| ADAM7 | GCAGGGTCATATGCAGA | CTTAGGACAGCGAGGCGA | 325 | & 326 | ADORA2A | GCGACGACAGCTGAAGGA | GATGTGTAGGGGCATGCA | 431 | & 432 |
| ADAM9 | ACCCTTGCTGCGAAGGAA | CCTCCTGGAAGGAACCGA | 327 | & 328 | ADORA2B | CTGGAGTGGAACCACGAA | GAAGCTGCCTGCAGGCCA | 433 | & 434 |
| ADAMDEC1 | GTCACATGAGCTGGGCCA | AGGCCTTCACAGCAGAGA | 329 | & 330 | ADRA1A | GCACATGATGAGGAGGACA | AGGAACACCGTTCAGCCA | 435 | & 436 |
| ADAMTS1 | AAGCCAGGCCAGACCAGA | CCCTCCATCATGGGACA | 331 | & 332 | ADRA1B | TCGGTGACCAGGGAGGAA | CATGCAGCGTAGGAAGCA | 437 | & 438 |
| ADAMTS10 | CCTGAAGGGAGACCAGA | TGGTCCCAGCTAGAGGCA | 333 | & 334 | ADRA1D | CGCCAAGACCAAGGGCCACA | AAGGCAGCCAGCAGAGGA | 439 | & 440 |
| ADAMTS12 | GCAACAACCCGAGCCAA | AGGGGTGGACGTTGCACA | 335 | & 336 | ADRA2A | CCAAGGCCAAGGGCCACA | AGCCAAGCGGTAGAGCGA | 441 | & 442 |
| ADAMTS13 | GGAGACGATGGTGAGGA | CTAGCAGTCCAAGGCCA | 337 | & 338 | ADRA2B | CGTTCCGGACGCCGCTA | GTGTGGCCGAGATGAGCCA | 443 | & 444 |
| ADAMTS14 | GCAGACGAGACCACCCA | ACTCCTCCGTCACCCACA | 339 | & 340 | ADRA2C | GGTGCTCGTGCCAGGA | TCTGAAGGCGCGGGCCA | 445 | & 446 |
| ADAMTS15 | GCACCACCACCAACCA | GCCTTGACACAGACGGA | 341 | & 342 | ADRB1 | GCACTGCAAGGTGCCCCA | AGGATCCTCGGAAGGGA | 447 | & 448 |
| ADAMTS16 | GCACCACCACCAACCA | CTGAGGGATTGCGCACA | 343 | & 344 | ADRB2 | CATCAGCCTGGACCGCTA | GACGCCGAGATGAGCCA | 449 | & 450 |
| ADAMTS17 | GCGTGTACCAGTGTGACA | GGCAGAGCATGCTGACCA | 345 | & 346 | ADRB3 | GAAGGCCTTCACCCGGA | GATGGGGTTGAAGGCCGA | 451 | & 452 |
| ADAMTS18 | CAGACCTGAGCTGTGAGGA | CGCTCCACGAAGAAGCGA | 347 | & 348 | ADRBK1 | CCACCCACCAGGAAGCCA | AGACCTTGGAGTAGACGA | 453 | & 454 |
| ADAMTS19 | CCTGCAGCATACAGGCCA | CCACGGCATGTCCTGACA | 349 | & 350 | ADRBK2 | CCGGCAGCAACCAGCCAA | CATCGCCAGTCCAGGA | 455 | & 456 |
| ADAMTS2 | CCTCAGCAGAGGTGACA | TGCGACCGGATGGCACA | 351 | & 352 | ADRM1 | TACCCTGACCTCCCCCA | AGGCAGCCGAACTGGCA | 457 | & 458 |
| ADAMTS5 | CGCTCATGTGTGGAGGA | GGGCATGAGACTGCAGGA | 353 | & 354 | ADSL | CCACTGGCACTCAGGGCA | GTGCACTGATGCCCCAA | 459 | & 460 |

FIG. 1 (cont.)

| GeneName | Forward Primer | Reverse Primer | SEQ ID NOs | | GeneName | Forward Primer | Reverse Primer | SEQ ID NOs | |
|---|---|---|---|---|---|---|---|---|---|
| AEBP1 | TCCCAATTGCCAAGCGCA | TCCAGTTGGAGCGAGCCA | 461 & 462 | | AK3 | GCACCTCTCCAGCGGGGA | TCATGAAGGGCCAGCGGA | 567 & 568 |
| AEN | GATCCAGGTGGGCCAGCA | CCTCGGGGCAGGTTCAGA | 463 & 464 | | AKAP1 | GAGCGAGATGACAGGGGAA | CAAGGCCTTGCTCCACCA | 569 & 570 |
| AFAP1L2 | AGCCACCCCGTTGCAGA | GCAGGACAACGTCGGGGA | 465 & 466 | | AKAP10 | TGCAGGGAAGGTGGGCCA | GACTCATCAGGAGGGGCA | 571 & 572 |
| AFF1 | TCAGCACCCAGTCACCA | TGAGGGCCAAGGTGCACA | 467 & 468 | | AKAP11 | CGGTGCCCTTGGCAGGAA | ACTTGGGCAGAATCACCA | 573 & 575 |
| AFF2 | CCCATCAGCGTGTCCAGA | CCCATCAGCGTGTCCAGA | 469 & 470 | | AKAP12 | GCAGAGACGAGAGGCAGA | GGGTGGTCTGCCCACCA | 575 & 576 |
| AFF3 | GGGCCAGTGGAAAGAGCA | GACGATGGTCACGGGGA | 471 & 472 | | AKAP13 | TTGGACACCAGAGCCCGA | GGGTGCTGCACTCAGGCA | 577 & 578 |
| AFF4 | GACGAGTGGCAGCAGCAA | TGGAGGACAGTTAGAGGA | 473 & 474 | | AKAP2 | CTGAAGAGGCTGCCGGAA | CGTGTGGCCTCGAGGACA | 579 & 580 |
| AFG3L2 | CGCTGCTAGCTAAGGCCA | GGACTCTAGCAGGGCCTA | 475 & 476 | | AKAP4 | GAACAAGCAGCCTCGGCA | CTGGGAGGCTGCAATCCA | 581 & 582 |
| AFM | GGGGCTGCCACAAAAGCA | CCGGATCCAGGGTAGGGA | 477 & 478 | | AKAP6 | GAAGGAGCTGCAGAGGGCA | CCTCATCCTCCACAGACA | 583 & 584 |
| AFP | TATGCCAACAGGAGGCCA | CACCCTGAGCTTGGCACA | 479 & 480 | | AKAP7 | TGAAAAGAACCGAGGGGA | GCACCGCGTTCTCCACA | 585 & 586 |
| AGA | GGAAGTCAGCCACCACA | GGCTGGCAATTCCGAGCA | 481 & 482 | | AKAP8 | CGAGGAGCCAGACACCAA | GCCTCCAGAGTGCGAGA | 587 & 588 |
| AGAP2 | GCTAGATTGAGGCCCCGA | TCGGAGTCACTACCCCGA | 483 & 484 | | AKAP9 | GCATCAGAAGGCTGAAGGA | GGGAGACTGCAGTGAAGA | 589 & 590 |
| AGER | GGCCACCCATTCCAGCCA | AGCCCTGATCTCTCCCACA | 485 & 486 | | AKR1A1 | CAGGTGGAATGCCACCCA | GGTTCCTCCAGCAGGACA | 591 & 592 |
| AGFG1 | CCAGTAGCACCAAGCAGCA | ACGACCTACAAACTGGGGA | 487 & 488 | | AKR1B1 | TCAACAACGGGCGCCAAGA | CTGGTACACATGGGCACA | 593 & 594 |
| AGGF1 | AGGGCAGGTTAGGAGCCA | TGAACAGATTGCAGGAGCA | 489 & 490 | | AKR1B10 | CTGTGACACCAGCAGCA | CAGTTACAGGCCCTTCCA | 595 & 596 |
| AGK | CTGGGCACAACCACAGGA | CAATGGTGACAGCTGCA | 491 & 492 | | AKR1C1 | AAGCACAAGCGCAACCCA | AGCTCTTGGCCAGGACCA | 597 & 598 |
| AGL | GGAATGCTGGTCCCCAGA | AGGCCCACAATTCCACA | 493 & 494 | | AKR1C2 | GTCTGCAACCAGGTGGAA | CTGGGTCCTCCAAGAGCA | 599 & 600 |
| AGMAT | GCGCCAGGGACACAGGGACA | ACAGCAGGTTAGCCGCCA | 495 & 496 | | AKR1C3 | ACCGCAGGCAGCTGGAGA | CTCCAAGGACCAGGGGA | 601 & 602 |
| AGPAT3 | GCGGAAGTGGGAGGAGGA | TCCCCTCGCAGTACAGGA | 497 & 498 | | AKR1D1 | CCCTGGAGAGGACACTCA | ATCGCCTCCCAAGTGGCA | 603 & 604 |
| AGPAT4 | CGGGCACCTTCCCAGAGA | CCATCGAACTCCCACGGA | 499 & 500 | | AKT1 | GCTGCACAAACGAGGGGA | TAGCAATGAAGGTGCCA | 605 & 606 |
| AGPAT6 | GCTCCCATGACTACAGAA | TCCCACAAGGCAGGTCACA | 501 & 502 | | AKT1S1 | CAACGAGGAGGTCGACGA | CGGGGTCTGACTCACAGA | 607 & 608 |
| AGPS | GAGTGGGCAAGTTACGGCA | ACAGACTTCAGCATCCA | 503 & 504 | | AKT2 | ACGTCCGAGGTGCAGGA | TGCTGGCCAGTAGGAGA | 609 & 610 |
| AGR2 | CTGGCCAGAGCTGCTGGGCA | TGGAGAGGGTCTGGGGCA | 505 & 506 | | AKT3 | GCAGCCACCATGAAGACA | GACAACCCTAGGCCCCA | 611 & 612 |
| AGR3 | CAACAAGAGCACTGGCCAA | GCAATGGCAAGGTTGGA | 507 & 508 | | AKTIP | GTCAACACAAGGTCACGCA | TCGAACACCAAGCGTGGA | 613 & 614 |
| AGRN | GGGTCTCACTGGCGAAGCA | ATGGCACCGTCGAAGCCA | 509 & 510 | | ALAD | CGGGATGTATACGGGAAGGA | AGACTGTGTACAGGAGGA | 615 & 616 |
| AGRP | AGACCTGCAGGACCGCGA | CGGCAGTAGCAGAAGGCA | 511 & 512 | | ALAS1 | GTGAACCGCGGAGCACA | CCACTTGCCCAGCACCA | 617 & 618 |
| AGT | GCCCAGAGTCTACCCA | CCCAGGAAGTGCAGGGCA | 513 & 514 | | ALAS2 | AAGGGAGAGGAGGGCCAA | AGGGTGCCAAGCGCAGGA | 619 & 620 |
| AGTPBP1 | CCAACACTCCATGACCCA | GGAGGCGGAATGTGACCA | 515 & 516 | | ALB | TTGGTGAACAGCGACCA | ACGAGTCAACAAGTGCA | 621 & 622 |
| AGTR1 | CCCGCTTCGAGCAGGGA | GGCCCAGCCTATCGGGA | 517 & 518 | | ALCAM | ACGATGAGGCAGACGAGA | ACACCAGCAACAAGGGCA | 623 & 624 |
| AGTRAP | ACATGCTGCACATCAGCA | AACCAGTGTGGAACAGGA | 519 & 520 | | ALDH16A1 | TGGCCTCGAGGCTGGAGA | AGCAGGGACACGAAGGCA | 625 & 626 |
| AGXT | GGCTTCCTCACGAGTCACA | TCCGTCACGCGGTCCACA | 521 & 522 | | ALDH18A1 | CTGCACACAGCAACCGGA | ACCAGTTGGGAAGAGCCA | 627 & 628 |
| AGXT2L2 | GCCACAAGGACACCAGCA | TGTCCAGGTGAAGCACA | 523 & 524 | | ALDH1A1 | GGGCATTGCCAAGAGGGA | GGAGTGATCAGAGGGCCA | 629 & 630 |
| AHCTF1 | AGGGAAGTGGAATCCCGA | GCATGCAGATAGCAGGA | 525 & 526 | | ALDH1A2 | CTGAGCAGGGTCCCCAGA | CCAGCTGTTCCCACAGCA | 631 & 632 |
| AHCY | GGCAGTGGCTGAAGCCA | GAAGGGCCATCACAGGA | 527 & 528 | | ALDH1A3 | CGGACGCTGACTTGGA | GACCTGCTCTCCACGAA | 633 & 634 |
| AHCYL2 | GAACTGACCTGGGAGCA | TAGCGACCCTCAGGAGCA | 529 & 530 | | ALDH1L1 | GTGAAGGAGCGGAGGACA | ACACCAGCAACCGGAGGCTCA | 635 & 636 |
| AHNAK | CCCAAATCACTGGGGCA | ACTTCCACACTGGGGCCA | 531 & 532 | | ALDH9A1 | GAGGAGATCTTCGGGGCA | TGAAGACAGCTGCGGCCA | 637 & 638 |
| AHNAK2 | GTCCCTAGCCGACAAGGA | CCACCTTCAGCGCAGACA | 533 & 534 | | ALDOA | GACGGCTGCTGCCAAGCA | GGATGTAGTCAGGGGCCA | 639 & 640 |
| AHR | AACCATCCCCATACCCA | GGCACTGATACATGCACA | 535 & 536 | | ALDH3A1 | CAAGGCCCTGAATGACCA | ACAGGACGGCTGATGAGA | 641 & 642 |
| AHSG | AGCTGGCTCACCCCACA | CTCTCGAGGGTGACCCCA | 537 & 538 | | ALDH3A2 | TGGGAGGTCACAGGCAA | GGAGTGATCAGAGGGCCA | 643 & 644 |
| AHSP | GCTGAACACTCTGGCCAA | GCGGTTGGGTGACTCCGGA | 539 & 540 | | ALDH6A1 | GCCAGAGCTGGTGGAGCA | CCAGCTGTTCCCACAGCA | 645 & 646 |
| AICDA | CAATAAGAACGGCTGCCA | TCGGGCACAGTCGTAGCA | 541 & 542 | | ALDH7A1 | GCCTGATGGTGCAGGAGA | GAGCACCTATGCTCACA | 647 & 648 |
| AIF1 | GCAGAGAGAGAGGCTGGA | CCCGGAGCCACTGGACA | 543 & 544 | | ALDH8A1 | GGGGAAGAAATCCTTGCCA | CACCATCCACACACA | 649 & 650 |
| AIFM1 | TCCCGAATACCTCAGCA | CATTGGGCTCCAGGCCA | 545 & 546 | | ALDH9A1 | GGACATCCAACGGGCTCA | TGACGGTCGCCATGGCAA | 651 & 652 |
| AIFM2 | GGTGAGGGCCACAGCAA | AGAGGCCTGCTTCACA | 547 & 548 | | ALDH2 | GGCTCTGAGTGACCACA | CCAGAACAGTGTGCAGGA | 653 & 654 |
| AIFM13 | CACAGGCTTCCTACACAGA | AGGGGGAAGGTGACAGCA | 549 & 550 | | ALDH3A1 | CAAGGCCCTGAATGACCA | AGGGCCTTGTACACAGCA | 655 & 656 |
| AIG1 | GCACGGGGACTTACCGCA | GGGTACACCACATGCCA | 551 & 552 | | ALDOC | CCATTCTGGAGAACGCCA | CCACACCTTCATGGGCA | 657 & 658 |
| AIM1 | CTGGCCAAGGAGGACAGAA | CGGGCATCCATTGCAGA | 553 & 554 | | ALG1 | CCAGAAGCACTTCCAGCA | CCATCCAACTGACACCA | 659 & 660 |
| AIM2 | AAGAAGGCAAGCCAGGAGA | AACACAGGTGAGGCGCTA | 555 & 556 | | ALG10B | GCGCTACTGTGAGGGCCA | ATGAGCTCGAGATCCACA | 661 & 662 |
| AIMP2 | GACATCGTGATCACCGGA | AGGCACGCGTCTGACCGA | 557 & 558 | | ALG5 | GTGGAAAAGGTGGAGGCGA | CCTCTGAACAGTGTCACA | 663 & 664 |
| AIRE | TCAGAGACGTGTCACCCA | GTGCTCGTCGTCAGAAGGGA | 559 & 560 | | ALG9 | ACGATATGCCTGGAACGA | AGGGCAGAAGGTCACCACA | 665 & 666 |
| AIU6A | CTGAGGGGCTGTGAGGACA | GGCAACCATGGCAGAGCA | 561 & 562 | | ALK | ATGGAAGGCCACGGGGAA | GCTGGCACAAGTGCAGGA | 667 & 668 |
| AK1 | CGGATTGGACAGCCCTA | CTGTCCACGGAGCCCTA | 563 & 564 | | ALKBH1 | CGCTCTTGAACCACGCA | GACAGCGCATCTGAAGCA | 669 & 670 |
| AK2 | ACCCTCCAAAAGAGCCCA | GGTAGGCTTGCAGGCGGA | 565 & 566 | | ALKBH5 | ATCAAGGAGCGCCGAGCA | GGCAGATGGAGCTGGGGA | 671 & 672 |
| | | | | | ALLC | CTCACGCCAGGCTCACCA | | | |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| ALMS1 | TCAACTGGCCCTGGACCA | GGTCAGCTGGTCCAGGGA | 673 & 674 | ANKRD2 | AGCGGACACGTGCGACCA | GCTGTGCAGTCCAGCCGA | 779 & 780 |
| ALOX12 | ACAATGCGGATGCCCCA | AGACAGGCCTGCCCGGACA | 675 & 676 | ANKRD20A4 | CTGGACAAGCAGCACAGA | GCGCCATGTTCCAGCAGA | 781 & 782 |
| ALOX12B | CACCTGCTCTGCCAAGCA | ACGCTGGGAAGTTGGGCA | 677 & 678 | ANKRD26 | GCCTACCTCAGATGACGA | GGAAGGCTTTCAACCACA | 783 & 784 |
| ALOX15 | GGGCCAGCATGAGGAGGA | GCAGGTACTCGTAGGGCA | 679 & 680 | ANKRD54 | GCAACATGAGCAGTGAGA | AAGCTGGCCAGGAGGTCA | 785 & 786 |
| ALOX15B | GCATCGCCACCTTCTCAGA | GGTAGGTGTAGGGCAGCA | 681 & 682 | ANKRD55 | CAGCCTCCCATAGGGCA | CAGGCGCCGGACACTGAGCA | 787 & 788 |
| ALOX5 | CGGCCGAGGTGGTTAGACA | CGCATTGGGGATCCAGGA | 683 & 684 | ANKRD57 | ACGACGCCGTGTTGGACA | CGTCAGGGCTCCCACCA | 789 & 790 |
| ALOX5AP | GCTTCCAGAGGAGCGGGAA | CGGACATGAGGAACAGGA | 685 & 686 | ANKZF1 | GGAGGAGCGTGAACGAGA | AGTCAGGGCCTTGGAGGGA | 791 & 792 |
| ALPI | CCCGATTACCAGCAGCA | GACAGGCCAGGAACACA | 687 & 688 | ANLN | AGCCAATGCAGGGACACA | TCAGGTTGCCACGAGGGA | 793 & 794 |
| ALPK3 | AGCCCAAAGGAGAGGCCA | CCGGAAGTGCTAACCCA | 689 & 690 | ANO1 | GGGTCACAGTCACAGCCA | CATCGGCTATGCAGCCA | 795 & 796 |
| ALPL | TGCATGAGGCGGTGGAGA | CTCGTTCACCGCCACCA | 691 & 692 | ANO4 | CAGAGTTCTGAGTGGGAGA | GCATCCACTAGGGTGCA | 797 & 798 |
| ALPP | ACAGCCAAGGTGGGACCA | CACAGACGGGTTCAGGGA | 693 & 694 | ANO7 | GCAGGTACTTCGGGGAGA | ACACAGAAGCAGCCCA | 799 & 800 |
| ALPPL2 | ACGCGTGCAGGAGCA | CTGCCAGCAGGAGGAGCA | 695 & 696 | ANP32E | GAACAGATCCCCGAGA | GGGAAGCCGGCCAGCGA | 801 & 802 |
| ALS2 | CCCAGTGACAAAGCCGCA | ATCCTGGGAAGGGAGGCA | 697 & 698 | AMPEP | CTACACCCTGAACCCGGA | GAGAACGAGCCACCACCA | 803 & 804 |
| ALS2CL | CTTAGAGCGCAAGGGCCA | CCTCCCGGCTCATGAAGCA | 699 & 700 | ANTXR1 | GGAGAAAAGGGCTCCACA | AGTAGGACCCACAAGGCA | 805 & 806 |
| AMACR | CTGGCAAGGGTCAGGTCA | CGAGGTGCTTCCCACAGA | 701 & 702 | ANTXR2 | AAGGATCTCCACCA | CCTCCACCCCTCGACCA | 807 & 808 |
| AMBN | GCGGGAGGAAGAACCCAA | GGTGGCAGGCACTGGGGA | 703 & 704 | ANXA1 | CACCAGAAGCTATCCACA | CACGATAGCTGTGAGGCA | 809 & 810 |
| AMBP | CTGCCAGGGCAACGGAA | CATCACCATCACCAGGGA | 705 & 706 | ANXA10 | GGGACCAGAGAGGAAGGA | GACAGGCTTCCCATAGGA | 811 & 812 |
| AMD1 | AGTGAGCTTGACCAGCA | CCACTCTCACGAGTGACA | 707 & 708 | ANXA13 | CATCAGGCGACTTGCAGA | CCCCGCACCCTTCATCGA | 813 & 814 |
| AMER1 | GCCCAGAAACAGGGAGA | TAGGTCACCAGGCAGGAA | 709 & 710 | ANXA2 | CCCGCAGTGAAGTTGGACA | ATCTCCACACACAGGTA | 815 & 816 |
| AMFR | CCTCCAGCAAGCTCGCAA | CAGCATCCTTCGACGCA | 711 & 712 | ANXA3 | GTCAAATGCACAGCGCGA | GAGTCACTAGGGCACCA | 817 & 818 |
| AMH | CCGAGACTACCAGGCCA | GGCGGTTGGGCACGCAGGCA | 713 & 714 | ANXA4 | CAAACTTACCAGCAGCA | ATCCTCCCACCAAGCTGA | 819 & 820 |
| AMHR2 | CCAGGTATTGCCACCGA | TGAGTAGGGGTTCCAGGCA | 715 & 716 | ANXA5 | LCGCGAGACTTCTGGCAA | CTGCAAGGTAGGCAGGTA | 821 & 822 |
| AMICA1 | GCCCGGAAGAGCCTCGAA | TCAGAACAGGGAGGCAGCA | 717 & 718 | ANXA9 | TCCAGGAAACTGAGCCCA | CAGCCCTGCACAAGGCCA | 823 & 824 |
| AMIGO1 | GCAGGTGCAGGTCGAGGA | CAAGGACCACACTAAGGA | 719 & 720 | AOAH | CAGTCCCAGCCATGACCA | CCTGGAGGCAGTTCAGGA | 825 & 826 |
| AMIGO2 | GACTCCATGCCCCTGCAA | CGTTCATCAGCGGAGGCA | 721 & 722 | AOC2 | GGGAACGGTGCACACACA | TTCCAGGGGCAGCCACA | 827 & 828 |
| AMMECR1 | CGCCACCTACCTGCGA | GATGCTGCGATGAGCAA | 723 & 724 | AOC3 | GGAAGGAGAGGAGGCCCA | CTGTCACCCAGGCCACA | 829 & 830 |
| AMOT | CAAGACAGGCGACATGACCA | GCTGGAGCAGCAGCAGA | 725 & 726 | AOX1 | GGAGAAGGCCGAAGGGCCA | GGACCAAGTGTGCAGA | 831 & 832 |
| AMOTL2 | TGGAGGCGACATGGACA | TGGCCACCAGTGAGACCA | 727 & 728 | AP1G1 | GCGCCTACAAGCAAACCA | GGGAGTGAGGGGGGCA | 833 & 834 |
| AMPD1 | AGTTGGAGCCTCCAGA | GGTGACATGGCGGATGGGA | 729 & 730 | AP1M1 | CCAACAACGTTGGAGATCA | AAGGACTTGATGACCACA | 835 & 836 |
| AMPD3 | GGAAGCTGGAGGAGGCAA | CCAGCGCATGTTGGGAGA | 731 & 732 | AP1M2 | CAGTGTGGGCAGCGCCA | TGTAGCGAACCCAGGGGA | 837 & 838 |
| AMPH | CAAGAGGAAACCCAGCA | AGAGGCCTTCCTTGCAGA | 733 & 734 | AP2B1 | GCACTACCACTGCAAGGA | CAAGGTCACTGCCAAGCA | 839 & 840 |
| AMTN | ACCCAGGGAACCCAGCA | GCAGGGTTGGTCACTGCA | 735 & 736 | AP2M1 | TCAAGCGCATGGCAGGGA | TAGCGACCTTGAGGCCA | 841 & 842 |
| AMY2A | GTATGATATAATGGGAGCAACCA | GTCCAGCAGGAAGACCA | 737 & 738 | AP2S1 | ACACGCTGCTGGACGAGA | GGGACTGTAGCATCAGCA | 843 & 844 |
| ANAPC10 | CCAAGCAGTTGGAAAGGA | GCAAGATGAGAGTGACCA | 739 & 740 | AP3B1 | GCCTTGATCCAGAGCAGA | GCCATCACAACACTGCCA | 845 & 846 |
| ANAPC5 | ACATGGCCATGCAGCCGA | TCGATGGCAGCTCCAGA | 741 & 742 | AP3S1 | GGCTTAGCAGGAGCTCCA | AAGAGGGCACACTGGACCA | 847 & 848 |
| ANG | TGCCAGTACCGAGGCCA | GACTGAATCCAAGTGGACA | 743 & 744 | AP4B1 | GCAAAGCCCACTGGGCAA | GGGCTCCAGAATCAGGGA | 849 & 850 |
| ANGEL1 | GTGGCGAGAATGGCAGGA | GCATCAGTCTGCTGAGCA | 745 & 746 | APAF1 | GGAGCTGCTACCCATGGA | AGTGACAACGTTCCACCA | 851 & 852 |
| ANGPT1 | CTGAGCCGATGGACACA | CAACCTCCCCCATTGACA | 747 & 748 | APBB1 | AGTGGAGCCACAGAGCCA | CATGCAGGCTGGTGGGCGA | 853 & 854 |
| ANGPT2 | GGAAGAGCCATGGACACA | GGACACGGTTAGGGGCTGGA | 749 & 750 | APBB2 | CATGGACACGGGGAACCA | CGGCCTGGCTACCAAGCA | 855 & 856 |
| ANGPT4 | ACTACCACGCTCCCGACA | TCATGCGAGAGGCAGCA | 751 & 752 | APC | AGGTCAAGGAGTGGGAGA | AGCTGGATGAGGAGGAGGA | 857 & 858 |
| ANGPTL1 | AGCAAAGAAAGCTGGGCA | ATAACAGTCCAACCCCA | 753 & 754 | APC2 | GGCAGAGCACCTGAGCAA | AAGGAGAGCTGCATGCGGGA | 859 & 860 |
| ANGPTL2 | CACCACCTTGGAACTGAGCCA | TCCTGGAACTCAGCCCA | 755 & 756 | APCDD1 | TCAACGGTCAGAGGCCCA | AGGAGGCACACTGGACCA | 861 & 862 |
| ANGPTL4 | GGGACAAGAAGCTGCCCA | CCCGCCAGGTCTTCCAGA | 757 & 758 | APC5 | CCTGGGGCAGGAACAGGA | TTGGCAGGGAGAGGGGTA | 863 & 864 |
| ANGPTL6 | CAACGGTGTGTTGCGCACGA | GAATATTGCCCCACCAAGGA | 759 & 760 | APEX1 | TGACCTTCGCAACCCCAA | CCAGTGGCACAGCCTGCA | 865 & 866 |
| ANGPTL7 | CTACCGGGACTGGAAGCA | GTCTGGAGAGGCCGGTGGA | 761 & 762 | APH1A | CTGACATCGGGACTGACA | AGTGTGTGATGAAGGCCCA | 867 & 868 |
| ANK1 | GGACAAGACCCTGAGAGCA | AGGCACCAGGTTCCCAGA | 763 & 764 | APLNR | GTTACGCACCACCGGGGA | CCACGGTGGTGGACAGGA | 869 & 870 |
| ANK2 | TCAGCAGGGTCACACGGA | CACGGAGATGTAGCCCA | 765 & 766 | APLP1 | CCGAGAAGGCACAGAGCAGA | TCTGGTCAAGCAGGCCCA | 871 & 872 |
| ANK3 | TGACCAGGGGACACAGACA | CCGAACTGAAGGAGCCGGA | 767 & 768 | APLP2 | CTCGAGGGACGAGAGGCGGAA | TCACAGGCTGATGAGGA | 873 & 874 |
| ANKD01A | CTATCAGGAGCGCACGA | TCCTGCCAATGGCCACGA | 769 & 770 | APOA1 | GCTCAGCGAGAAGGCTGA | GAGCGCTCAGGAAGCTGA | 875 & 876 |
| ANKH | AGCCCTGCTCATCCCGA | GCTCACCAGAAGCTCACGA | 771 & 772 | APOA1BP | GGGAACCGTTCCACAGCA | ACGTCCCATCCTGAGGGA | 877 & 878 |
| ANKRB1 | CCAGATCTGATGAGCCA | TCATGAGGGCCAGCCCA | 773 & 774 | APOA2 | GCTTCAGGCGCGAGGCA | ACACTTCACTGGGTGGCA | 879 & 880 |
| ANKLE2 | CTCGAGGGTCACCAGGGAA | GTCGAGGGGTGAGTAGCA | 775 & 776 | APOA5 | CGACCAGGAGACTGAGGA | CATCCACGGGCCTGCA | 881 & 882 |
| ANKRA2 | AAAGTGGGGGCTACAGCTA | AGCCTAGGGCTACAGCTA | 777 & 778 | APOB | CTGACCTGCGCAACGAGA | GAATCTGGGGCAGGCCCA | 883 & 884 |

FIG. 1 (cont.)

| GeneName | Forward Primer | Reverse Primer | SEQ ID NOs | | GeneName | Forward Primer | Reverse Primer | SEQ ID NOs | |
|---|---|---|---|---|---|---|---|---|---|
| APOBEC2 | GGTTGAAGCACAGGGCAA | ACCGCAGGGCTGGGTCGA | 885 | & 886 | ARHGAP4 | CCCTCTGGACACAGACGA | AAGGCCTGGCGACAGA | 991 | & 992 |
| APOBEC3A | AGCGCCTGGACAATGGCA | CCCGGCACAGCCCCAGGA | 887 | & 888 | ARHGAP5 | GAGCCCAATTCCTGCCAA | AGCTTGAGCAGCACTGCA | 993 | & 994 |
| APOBEC3F | CCTGGCCAGGCACAGCAA | GCCATGATCTCCACGGA | 889 | & 890 | ARHGAP6 | CAGACCCCTTCTCACCA | GCCTGGCCACGATGGAGA | 995 | & 996 |
| APOBEC3G | GCTGGACCTGGAGCAGGA | GCGGGCAGTGAAGATGCA | 891 | & 892 | ARHGD1A | GAAGAGATAGTGTCCGGCA | CCTCTCCAGGGGGGTCA | 997 | & 998 |
| APOC1 | AAGGTCCTGCAGGGCAGGA | CAAGACGATGGACAGAACCA | 893 | & 894 | ARHGD1B | AGATCCGAAAGCCCCAA | CGAGGTCCATAGCTCGCA | 999 | & 1000 |
| APOC2 | CTCACCCAGGTGAAGGAA | ATCTACAGCGGGCAGGTA | 895 | & 896 | ARHGDIG | CGGTGGAGGAAGCGCCGA | CCAGTCCTGGCAGATGCA | 1001 | & 1002 |
| APOC3 | GCAGGGTTACATGAAGCA | CTGCTGGGCACCTGGGA | 897 | & 898 | ARHGEF10 | GCACTTCCGAGTGGAGGA | AGTGGAGCCGTGAGACA | 1003 | & 1004 |
| APOC4 | TGACGACCACCTGGGGGA | ACAGAACAAGCCTGGGGCA | 899 | & 900 | ARHGEF11 | GGGCTTCCTCAGACAGAA | CCAGCTTGGAGCTGCAA | 1005 | & 1006 |
| APOD | ACCCCAGTTAACCTCACA | GATCCAGTACGGTGCCGA | 901 | & 902 | ARHGEF12 | CACTTACCCTGCAGCCCA | CAGCGCTGCTGGACCAGA | 1007 | & 1008 |
| APOE | AGGAGCAGGCCCAGCAGA | CTTCCACAGGGGGCTCGA | 903 | & 904 | ARHGEF2 | AGGCTTACCTGCGGCGAA | GACCCTCCAGTTCACGGA | 1009 | & 1010 |
| APOF | GGCAACGGTGCCCAGGAA | CACTGATCCGTAGACCCA | 905 | & 906 | ARHGEF3 | CACCACCGGGAGCACAGA | GCTACAGCTTCAGGCTGA | 1011 | & 1012 |
| APOH | GAGCCGTACGTCTATACGA | GGAGGGCAGATGATGGGA | 907 | & 908 | ARHGEF6 | CCAAAAGCCGTCAAAGGA | ACCTTCCACAAGTACTCAGA | 1013 | & 1014 |
| APOL1 | CCCGGGTCACTGAGCCAA | AGAAGCTTACAGGGGCCA | 909 | & 910 | ARHGEF7 | GCAGGAATGGGTGCAGCA | GGAGGGGAGGGTATGAGA | 1015 | & 1016 |
| APOL2 | TGCAGAGGAGGTTGAGCA | GCTCCAGACCCATGCCA | 911 | & 912 | ARHGEF9 | ACCCCACCTCAGCGAGA | ATCTGCTGCAAGAGGGCGA | 1017 | & 1018 |
| APOL3 | GAACGATTGCAGGACACA | CCACATCCAGTCAAGGA | 913 | & 914 | ARID1A | GCAGCCAAGGAGAGCAGA | CCTGAGCAGAGACTGCCA | 1019 | & 1020 |
| APOL6 | TGGGACCTTGCGAAGCCGA | CACACAGACACAGACA | 915 | & 916 | ARID1B | TGAGCAGCATGACCCCA | AGGGAGAGCTGGAAGCCA | 1021 | & 1022 |
| APOM | AGTCCCACCAAGGAGGA | ATGCGGATGGTAGCACGA | 917 | & 918 | ARID2 | GCTCACGGAAATGGGAGA | GCTAGTGCATCAGGGCCA | 1023 | & 1024 |
| APOOL | TACTGCCACCACCCTCA | AACCAGTTCCAGTGCGGA | 919 | & 920 | ARID4A | ACGAACAGAGGAGGAGGA | TCCGTTGCAGACACCCA | 1025 | & 1026 |
| APP | GGCCGAGGAGGATTCAGGA | CGGGCATCAACAGGGCTCA | 921 | & 922 | ARID4B | AGAAGGCAGCCCGGCAGGA | CCCAGCAACACTATCCA | 1027 | & 1028 |
| APPBP2 | CGGTTGCGAGATCGGCAA | TCAGGAAGGACTGCACCA | 923 | & 924 | ARID5B | CGCACAAACTACCCGCA | AGAGCTGGAACTGGGAGA | 1029 | & 1030 |
| APRT | CCCTTGAGCCAGGACAGA | TCAGCTCCACCAGGCTCA | 925 | & 926 | ARL16 | GCCCAGCGGTGGGCACCA | GAGAGCTGGGTGGGGTCA | 1031 | & 1032 |
| AQP3 | CCAATGGCACTAGCCGGA | GTTGACGGCATAGCCGGA | 927 | & 928 | ARL3 | CCGAGTCTGGCAGGTCTA | CAGACCCAGTTCATGCA | 1033 | & 1034 |
| AQP7 | CGTATGGAAGCACCACGGA | GTTGGCAGGGCTCACAGA | 929 | & 930 | ARL6IP1 | GAAGAACAGCTGCAAGGA | AACGCGGACAGAACAGA | 1035 | & 1036 |
| AQP9 | ACCCAGCTCGAGACCTGA | AAGGGCCCACTACAGGAA | 931 | & 932 | ARL8A | CTGGGACAATTGGGGGACA | CCTGGTCAGCAGCATCCA | 1037 | & 1038 |
| AQPEP | GGCACTGGGAAGCCACA | CCTTCACCAGGCCGGAGA | 933 | & 934 | ARL8B | GGGCTTCAACATGAGGAA | TGCAATACCGCTCCACA | 1039 | & 1040 |
| AQR | CCCACCTGGTACAGGGAA | CTTCCATGACCAAGACGCA | 935 | & 936 | ARMC5 | TAGCCCAACCTCCCAGCA | TCCTCACCAGCCTCACCA | 1041 | & 1042 |
| AR | ACAGCCCAGGCCAAGAGCA | GAGACAGGGTAGGACCGCA | 937 | & 938 | ARNT | ACAGTTGGGCAGGGCCAGCA | GATCTCCAGCATGGACA | 1043 | & 1044 |
| ARAF | GCAACGGTCACTCCCCA | GCGCGAGTAGGCAGGCCA | 939 | & 940 | ARNT2 | CAGCAGGGAACCCAGCAGA | GCCCGTTGGAAGAAGAGGA | 1045 | & 1046 |
| ARAP2 | GCCCACCGCAGTTGGAGA | CCGCGTTTAGCGAGGAGACA | 941 | & 942 | ARNTL | CAGGCTCAGGAGAACCCA | AGTCAACAGGGCCACCA | 1047 | & 1048 |
| ARAP3 | CAGCTGTGCAAGACCCA | CGGGACTGCAGTACAGGA | 943 | & 944 | ARPC1A | GCCATGACTGCTGCCCAA | CGGAAGCGTTCCATGGCA | 1049 | & 1050 |
| ARCN1 | CGAGATGACAGTGGCAGA | CATTGGGCTGCCCAGGAA | 945 | & 946 | ARPC3 | CCAAAAGCCAAGGTGAGA | AACCAGGCTCTCCAGGAA | 1051 | & 1052 |
| AREG | GGTGTGCAGGAAAGTCCA | AACAGTTGTGAGGATCACA | 947 | & 948 | ARPC5L | TGTGGACGAGCAGGCTGCA | GAGTTCCGCAAGCCTGCA | 1053 | & 1054 |
| ARF1 | CAGAGAGCCGTGTGAACGA | GGAGGACAGCATCCCGGA | 949 | & 950 | ARPP21 | AAGGGTCACTCCCAGCCA | GCTGACATCACTGGGACA | 1055 | & 1056 |
| ARF4 | TAGGGGAGATAGTCACCA | TTGACCACCAACATCCCA | 951 | & 952 | ARRB1 | GACCCCTTCTACCCAGGA | ACAGGGTGCTCAGAGGCCA | 1057 | & 1058 |
| ARF6 | GGGAAGTGAAGGGGACGCA | GCACAGGAGCATCCCACA | 953 | & 954 | ARRB2 | CGTGAAGGAGGCAGCACCA | CGCCTCGAGACACCACCA | 1059 | & 1060 |
| ARFGAP1 | GCTTCACCACTGGGAGCA | GCCAACTGAGAGACCCCA | 955 | & 956 | ARSA | CCCGTCTACCCAGACGA | CACCAGGGTCCTTGGACA | 1061 | & 1062 |
| ARFGAP3 | GCATGCAAGTCGACGGAA | TGCTTGAGAGGGCGAGCGA | 957 | & 958 | ARSB | ACCGGGAGCTCATCCACA | TTCCACAGCTCGAAGCCA | 1063 | & 1064 |
| ARFGEF1 | GGGAAGGAGGTTCAGCAGA | ACAGCAGAAGTTCAGGA | 959 | & 960 | ARSD | GAGTCCTGTGCCCAGCA | CCTCGTGCATGAACAGA | 1065 | & 1066 |
| ARFGEF2 | GTGAGACAGCTCAGGGA | GGACAACAGCACAGAGGA | 961 | & 962 | ARSE | TGATTGGCGAGCCCACGA | TCCCCAGGAGCAAGGGCA | 1067 | & 1068 |
| ARFIP1 | GGTCTCTCAGAAACCCAA | GCCAGTCGACTAGCTGCA | 963 | & 964 | ARSG | GGGAAGTCCAGCCAAGGA | TGGGCCAGGGCTACCACA | 1069 | & 1070 |
| ARFIP2 | TGAGAAGCTGCTGGGGAGA | AAGTAGGCGGACACAGCA | 965 | & 966 | ARSI | GGTGGTACCACCTCAGGA | GCAGCGGGGGTGTTCCAGA | 1071 | & 1072 |
| ARG1 | GGCTGGCAAGGGTGGCAGA | AGTGTGAGCATCCACCCA | 967 | & 968 | ARSK | GCATGGCTTCCACAGA | GTCCAGCCTTCCACGA | 1073 | & 1074 |
| ARG2 | GGGGGACTTAACCTATCGA | GAGGTGGCCAACTGAGGA | 969 | & 970 | ART3 | GAGGGCTAAACCAAGGCA | GCCAGCCCCTCCTGTGA | 1075 | & 1076 |
| ARHGAP10 | ATCCAGGCCAGACCCGA | CACGGATACACGGCTCGA | 971 | & 972 | ART4 | CCTACACAGGGCCACCA | GTGCACCCAGGCAGGTGA | 1077 | & 1078 |
| ARHGAP15 | CGCCAAATGTGACCCA | CGCAGAAGGGTAGGTCCAA | 973 | & 974 | ART5 | AAGGCAGTGGCCACAGA | CCCACCCAGATAGGCGCA | 1079 | & 1080 |
| ARHGAP22 | AGGAGGTTCACCAGGGACA | GATGGGCACCTCCAGGGA | 975 | & 976 | ARTN | CTCAGCCTGGCCAGCCTA | TGACGTCCATGAAGGAGA | 1081 | & 1082 |
| ARHGAP25 | TAAGGCAGGGGAGGAAGGCA | ACCTGCAGGGAAGGGA | 977 | & 978 | ARVCF | GCTGCAGTCTGAGACCGA | TGTTGAGCACCGCCACCA | 1083 | & 1084 |
| ARHGAP26 | TCAGGAGGCAGAGACGCCA | TGCAGGAGGCAGACAGA | 979 | & 980 | ASAH1 | CTCAAGAAGTGACCGTA | TATACAAGGGTCAGGGCA | 1085 | & 1086 |
| ARHGAP27 | GTGGAAACCTGCCACCA | CCGCAATGAACTGCCGA | 981 | & 982 | ASAH2 | CCTGAGCAGAGGTCCAGA | ACACTATCTCCACGA | 1087 | & 1088 |
| ARHGAP28 | TCGAGCGGGAGACTGCAA | GTGAGCATGGACCCGTA | 983 | & 984 | ASB13 | ACTACACGTGGAGCAGCA | TCCAGCCCTCCGGACGCCA | 1089 | & 1090 |
| ARHGAP29 | CCCAGTGCACTCCAGGAA | GACAGGAGCGAGAGGGGTA | 985 | & 986 | ASB15 | TGCTGAAACATGGAGGCA | AACAGCACCGACGCCCA | 1091 | & 1092 |
| ARHGAP35 | GTGCAGGACTCACCA | TCACAATGCGACTCACCA | 987 | & 988 | ASB7 | CACTACGGCAGGGACTCA | GATCACGGCGTATGCAA | 1093 | & 1094 |
| ARHGAP36 | GACGCAGGAACTTGAGGA | TCGTCATGGGAACGGGCA | 989 | & 990 | ASB9 | CAGTGGGCCAGGAGACAGCCA | CTGAGGGCACCAGCTTCCA | 1095 | & 1096 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| ASCL1 | CAACGAGCGGAGCGCAA | GATGTACTCGACGCGCGA | 1097 & 1098 | ATP2C1 | ACCTCCTCGCAACTGGAA | CTCGTAGCTCACGCCAGA | 1203 & 1204 |
| ASCL2 | CGCTACTCGTCGGACGA | ACCAGCTGGAGAAGTCGA | 1099 & 1100 | ATP2C2 | CCCTCAACGCCATGCAGA | AGGATGGTGTCCCGCACA | 1205 & 1206 |
| ASF1B | GGCCATAGAGACCCAGGA | TGCAGCCAGGGAGCCCCA | 1101 & 1102 | ATF4A | CCAAGGCCATTGCAGCCA | ACCTGGTCTACGGGCACA | 1207 & 1208 |
| ASGR1 | ACGGGACGGACTACAGGA | GGTAGGGCTCTTGGCAGA | 1103 & 1104 | ATF4B | CCAGCCCACTACAGCAA | CCGCCATGACCTTGCACA | 1209 & 1210 |
| ASGR2 | GGCTGTCACTCAGCAGA | CTCACACCCAGCGGTA | 1105 & 1106 | ATP5A1 | AACCAGGGCTATGAAGCA | TCAGTTAGACGCAGGCCA | 1211 & 1212 |
| ASH1L | CAAAGGCAGGGCCAGGACA | ACGACAGCCTGAAGGGGA | 1107 & 1108 | ATP5B | GAGGACCCGTGAAGGCAA | GCAGACACCTCTGAACCA | 1213 & 1214 |
| ASL | ACCTGGTCCGCAAAGGGA | ACAGCTGGTTGAGGGCGA | 1109 & 1110 | ATP5D | CAACGTCCGGCAGGTGGA | ATGGAACCGCTGCTCACA | 1215 & 1216 |
| ASNS | TGCTAGAAGGTGGCAGA | GGAGAAGGAGCCTTGTGA | 1111 & 1112 | ATP5E | GCCGGCTGAGCCTGACA | CAGATCTGGAGAGTATGCGA | 1217 & 1218 |
| ASPM | TGGCCCAGAGTGCAGCAA | AGCAAGACTTGCACAGCA | 1113 & 1114 | ATP5F1 | TCATACAGGGCAGCCACA | AGATAAGCCAGTTCCGA | 1219 & 1220 |
| ASPSCR1 | CAGTCCTGGACGACCACA | GCAGATGGGAGAATGGCA | 1115 & 1116 | ATP5G1 | GACGGGAGTTCCAGACCA | AGAGACCGGGTTCCTGGCA | 1221 & 1222 |
| ASS1 | CCGCACTGGCCTTGAGGA | ACACCTGGCCCTTGAGGA | 1117 & 1118 | ATP5G2 | GCCGCAGCTTCCAAACCA | CCAGAACCAGACCACCA | 1223 & 1224 |
| AST1 | GGTCCCATGCCCACAGCA | CCTCCCGCACTGGAACCA | 1119 & 1120 | ATP5G3 | GGAGAGGGCTCTACGGTA | CAGAACCAGCCACTCCTA | 1225 & 1226 |
| ASTN1 | GCCTGGAACCTGCACCA | ATCATCCACCACGGGGCA | 1121 & 1122 | ATP5H | CAAGGCCAATGTGCCAA | TCGGCATCCACCTGGGCA | 1227 & 1228 |
| ASXL1 | CCCTGGGTGATCAGAGCA | GGAGTCTGTACCCCACCA | 1123 & 1124 | ATP5I | CGGTGCGGAGGTCAGGGA | GTGGCTCCGTAGGCACA | 1229 & 1230 |
| ATAD1 | AGTTGCCCAGGAAACTGA | GCTGTTGAACAGGCCGAA | 1125 & 1126 | ATP5J | GGCCGGAAGTAGAGCGGA | ACTGAGGGTCTGACCGA | 1231 & 1232 |
| ATAD2 | GTACGGTCAAGCAGGCAA | TCGTAGCACCAATGACCA | 1127 & 1128 | ATP5J2 | CCCAGTACCAGTGAAGGA | TAGGACTGAAGTCCCGCA | 1233 & 1234 |
| ATAD2B | GGAGGCCGGTTATCCCAGA | GTGCATGCCCTGAAGACA | 1129 & 1130 | ATP5L | CTCCACCCCTGCTGAGA | TCAACACTCAGTGGCCA | 1235 & 1236 |
| ATAD5 | GAAAGCTGCTGCCTGGA | GTCCTCATGAACACAGCA | 1131 & 1132 | ATP5O | GGAGAGGTACCTTGCACA | GCACAATCATTCCACCCA | 1237 & 1238 |
| ATAT1 | CCCAAGAGAGCAGAGGGA | GGGGCAGAGGGCCGAAGGA | 1133 & 1134 | ATP5S | GGCGTAAAGAAAACTCCCA | CCTGGCCATGGTAGCGCA | 1239 & 1240 |
| ATF1 | CCCTCGATGGACAGCAGA | TGAGAGGTGAGAGTCACA | 1135 & 1136 | ATP6AP1 | AGGTCACAGGGCCCAGCA | TGAGCAGCCCATCCAGA | 1241 & 1242 |
| ATF2 | AGGCGAAAGCTGTAGGCA | AGGAAGGAGCTATAACGA | 1137 & 1138 | ATP6AP2 | AAGCGAAAGAACCCAGCAA | TAATCACGCCAAGGCCA | 1243 & 1244 |
| ATF3 | CAAGAACGAGAAGCAGCA | CCATTCTGAGCCCGGACA | 1139 & 1140 | ATP6V0A1 | GTGAAGAGCTTGGCTGGGA | CAACCCAGTTGTAAGCGCA | 1245 & 1246 |
| ATF4 | CCCAGACGGTGAACCCAA | GGACAGGACCCCTGGGGA | 1141 & 1142 | ATP6V0A4 | GACCAGCCATACCAGGA | GGCTGAGGATGACACCGA | 1247 & 1248 |
| ATF5 | GAGGTACCGCCAGCGGAA | GATCTGGCCGCTCACGGA | 1143 & 1144 | ATP6V0B | CCGATGCTCAGAACCCCA | ATTGCGACGATGACCCCA | 1249 & 1250 |
| ATF6 | GCCATTGGCAAAGCAGCA | GTGTGACTCCCCAGCAA | 1145 & 1146 | ATP6V0C | GGCAGTCCTCATCGCCAA | CCCAGATGCCGATGGGA | 1251 & 1252 |
| ATF7IP | GTGCCAACAAGTGGACCA | ACCTGCCGAACACAGAGA | 1147 & 1148 | ATP6V0D1 | GGTCAAGAACGTGCGCGA | ACTGGTTCAGGAAGGCCA | 1253 & 1254 |
| ATF7IP2 | CCAGAACCAGCAGCACCA | CAAGTCAGGGAATGCCCA | 1149 & 1150 | ATP6V0D2 | GGAAGGACGTGCAGGCCA | GCAGCAGCTTCCAGCCCA | 1255 & 1256 |
| ATG10 | CGCAACAGGAACATTCCA | AGAGGTAGATTCAGCCCA | 1151 & 1152 | ATP6V1C1 | GGAGAAAACCTGTCAGCA | CATCTGACAAGCCAACCA | 1257 & 1258 |
| ATG12 | GAACCATTCAAGGACTCA | GGTCTGGGGAAGGAGCAA | 1153 & 1154 | ATP6V1F | ACCAGTACATGCCAGAGA | TCTCCAGGACAGGGGGA | 1259 & 1260 |
| ATG16L1 | CTGGAGGCATGGACCGCA | CCTGAGACAATCCGCGCA | 1155 & 1156 | ATP6V1G1 | ACCGCCTGCAGAGGGAGA | GCTGCAACTGCCACGGGA | 1261 & 1262 |
| ATG4B | CCGAGCAGGAATGCGTCGGA | CTAGGGACAGGTTCAGGA | 1157 & 1158 | ATP6V1H | GAACACTGCGTGGCCTA | CCGGCACCGCACTGCACA | 1263 & 1264 |
| ATG5 | GTTGCACACACTGACAGA | TCACTAGCCACTGCAGA | 1159 & 1160 | ATP7A | GGATGGGATCTGCAGCAA | TCTGGCTCCGCAGCGGGA | 1265 & 1266 |
| ATG7 | TGCCAGCAGCAGTGACGA | AATGCCAGGCTGACGGGA | 1161 & 1162 | ATP8B1 | GTTGAAGGCGGAGGAGCA | GATGGCATCAAGCCGCGA | 1267 & 1268 |
| ATHL1 | CCGCATGACCTGGAGCA | CCGTGCACCCGAAGACCA | 1163 & 1164 | ATP8B4 | CCAGGATGTGAGTGACCA | CACTGACCACCAATGACCA | 1269 & 1270 |
| ATIC | GTACACTGCAGCCGCCA | GGAATTCCAACAGCACCA | 1165 & 1166 | ATP9A | TGGCGCTGACCATCCAA | AGAACACCAGGGAGGCGA | 1271 & 1272 |
| ATL2 | GGACCAGCTTGAAGCTGA | GGCCAATGAAGCCAGTCA | 1167 & 1168 | ATPAF1 | GCATTCCAGGCAAGGTGA | GGACTGAGCCCGGTTCCA | 1273 & 1274 |
| ATM | CCGATGGCAAGGGAGGAGGA | CTTCGCTGAGAGAGGGGA | 1169 & 1170 | ATR | GAATGGGAGGATGGGGCA | ACACGATTGGGAGCGGCCA | 1275 & 1276 |
| ATMIN | CCCAGAGCCCCTGAGAGA | GGCGTAGGGACAGCCGCA | 1171 & 1172 | ATRN | GAGATTGCCACCGGGCA | AAGGAGCCACGTAGGCA | 1277 & 1278 |
| ATN1 | CCCTTGCACGAGAACGA | TGCTGACATCGGGGACAA | 1173 & 1174 | ATRN1 | GGAAGATGATGGCACCA | CCAGTCTGTTGGAGCAGA | 1279 & 1280 |
| ATOH8 | AACTGGCCATCCTTGAGGA | TGCGGGTGCAGCGCTGCA | 1175 & 1176 | ATRX | CAGAAGGGCTCCAGCAGCA | GCATCATGAGGTGACCCA | 1281 & 1282 |
| ATOX1 | CTGAAGCACAGTCGCAT | TGGAAGCCAGGCGGGGAGGA | 1177 & 1178 | ATXN1 | CCCTTCCAAGGAGCGAGA | AGGCCACGGACTGCACCA | 1283 & 1284 |
| ATP10A | GAGGATTACCGCCACGA | CAATGCCCAAGCTGGAGCA | 1179 & 1180 | ATXN2 | CCCACTGGACAGCAGCAA | GAGGGTGGAGTTGGCGCA | 1285 & 1286 |
| ATP11A | CAGCCTCATCGGAGCAGCA | TGAACACGCGGCCAGCGA | 1181 & 1182 | ATXN3L | CAGAAGGAGGAGTCACCA | CCCAGAACTTCAAGGCA | 1287 & 1288 |
| ATP13A1 | GATGCCAGCATCGCAGCA | TAGGCCAGGATGAGGGCA | 1183 & 1184 | AUH | GATGAAGACGGAGGACGA | TTAAGGTCCAAGAGTCCAGA | 1289 & 1290 |
| ATP13A5 | ATCCCTCCAGGAGGTCACAGA | CAGCTGCCAGGTCACAGA | 1185 & 1186 | AURKA | CATCTTCCAGGAGGACCA | GAACTCCCAAGGTCCAGA | 1291 & 1292 |
| ATP1A1 | AGAGAGTACGGGTCGGCCA | GATGACCAAGCTGGCCCA | 1187 & 1188 | AURKB | AGCAGCGAACAGCCACGA | GCACTCCAATGCACCACA | 1293 & 1294 |
| ATP1A3 | CGTCTGAAGAAGGCCGA | CCTGTGACGATGGAAGCA | 1189 & 1190 | AURKC | AACAGCTGCACAGCCACGA | GTGTGCAGACCAGGCCA | 1295 & 1296 |
| ATP1B1 | GTGCACTGGCAAGGCGAGA | CGGCCAGCAGGGGCTGCA | 1191 & 1192 | AUTS2 | GGAGCCGGAAGGAAGACCA | GAATGCCCGTCACCCCA | 1297 & 1298 |
| ATP1B3 | GAGCCTGGCCGAGTGCAA | ATGAGAGAGTGCAGCCA | 1193 & 1194 | AVL9 | TGGGAGGGAGGTGACGAA | GCAGTGTGGCAGCCAGCA | 1299 & 1300 |
| ATP2A1 | GGGCTTCAACCACCAGCA | ACGGTGGCTGCACCCCA | 1195 & 1196 | AVP | CGACCTGGGAGCTGAGACA | GCCGGACTGGCAGGGCGA | 1301 & 1302 |
| ATP2A2 | CCCCGGAACCCAAAGGAA | CTTGGACCCTGCAGGA | 1197 & 1198 | AVPI1 | CTTTAGGCAAGCAGCCCA | GGAAGGACTGTGGCAGGA | 1303 & 1304 |
| ATP2B1 | TGTCTCAGAACCAACGCA | CAGTTCCAGCAATACCCA | 1199 & 1200 | AVPR1A | AGCAAGGGTGCAGCGAA | CGGACATGGGATCCAGA | 1305 & 1306 |
| ATP2B4 | GGCTCATCCGCAACGAGA | TGGGAGAAGATCGCGCCA | 1201 & 1202 | AVPR1B | CCACCTTAGCTGCCACCA | GAAGAAGGGAGCCCAGCA | 1307 & 1308 |

| GeneName | Forward Primer | Reverse Primer | SEQ ID NOs | GeneName | Forward Primer | Reverse Primer | SEQ ID NOs |
|---|---|---|---|---|---|---|---|
| CCDC28A | AAACGAGCTGCGAGGA | CCCCTTCGCAACCGCA | 2157 & 2158 | CCNL1 | AGGGACAGGCGTGAACGA | CCTGAGCGACTGCCACCA | 2263 & 2264 |
| CCDC3 | CTGTTCGCAAGGGCAGCA | GAGGAGCACATGAGGCCTA | 2159 & 2160 | CCNL2 | CCGTGAACGGCTTGCCAA | CGCTGATCGGGGATGGGGA | 2265 & 2266 |
| CCDC41 | GAGGCTGAAGTAGTCGGAA | AGCCTGCATCTCAGCCAA | 2161 & 2162 | CCNO | GAAGCTCTGGAAGCGCAA | CTCCAGTCGCAAGTCA | 2267 & 2268 |
| CCDC6 | GTCGACAAGCTCTCCGAGA | GTAAGGGATCGGGCTGGA | 2163 & 2164 | CCNT1 | GGGCATAGCTCAGACACA | GGCTGAACACCTCGGGCA | 2269 & 2270 |
| CCDC63 | GAGGCTGAGATCCGACCA | TGAAGGGGTCAGCCCCA | 2165 & 2166 | CCR1 | GGTGATCGCCTACAGGCA | CCACGGAGAGGGAAGGGGA | 2271 & 2272 |
| CCDC69 | TGAGGCCTGAGAGAAGGA | CAGAGGGAAGGCAGGCGA | 2167 & 2168 | CCR10 | CAGGGGAAGGCCAACGA | CGGCAGTATCCAGCAGCA | 2273 & 2274 |
| CCDC80 | GGACCCAAGGAGAAGCACA | TGAGGGAGGTTGGGCGCAA | 2169 & 2170 | CCR2 | CCAAGGAGAGCGGTGAA | GATGAGGAGCGACCAGCA | 2275 & 2276 |
| CCDC85A | CTGAACGCAGCAGCA | CCCTGGCTCTGGGGAGA | 2171 & 2172 | CCR3 | GCTGCATGAACCGGTTGA | GCCCAGGTGCATGAGCAA | 2277 & 2278 |
| CCDC88A | GGCCACAAAGCCACAGCA | TCACTTCCGGGGAACCA | 2173 & 2174 | CCR4 | GACTATGCCATCCAGGCCA | CCACAGTATTGGCAGAGCA | 2279 & 2280 |
| CCDC88B | TCAGGGTCCAGGGACCA | ACCAACTCGGCTTGGGGA | 2175 & 2176 | CCR5 | AGAGGCACAGGGCTGTGA | AGGTGTTCAGGAGAAGGA | 2281 & 2282 |
| CCDC99 | GAAGATGCAAGGGCAAGCA | GCTCCAACATGGCAAGCA | 2177 & 2178 | CCR6 | AACACTACCGCGACAAGCA | AGAGTAGCTCAAGCCCCA | 2283 & 2284 |
| CCK | GCTGCAGCGGGCAGAGGA | GCCCAGGTGCGCTCGGGA | 2179 & 2180 | CCR7 | GGCCACAGCGGTGGCCAA | TGCGGAACTTGACGCCGA | 2285 & 2286 |
| CCKAR | CAGCAGCAGCAGGGCCAA | AGGAGGAGGTGTAGGACA | 2181 & 2182 | CCR8 | GCATAAGCCAACAGCTGA | CACAGCTCTCCCTAGGCA | 2287 & 2288 |
| CCKBR | AGAAGCGCGTGGTGCGAA | GGGACAGCGTGCATGAAGGA | 2183 & 2184 | CCR9 | CACCCTCGATACAACGCAA | GAGAACAGGGTTCAGGCA | 2289 & 2290 |
| CCL1 | GATGTGGACAGCAAGAGCA | GCCTCTGAACCCATCCA | 2185 & 2186 | CCRL2 | GTTCAGGGAGCAGGTTGATGCA | CAGGAGAGGGTTGATGCA | 2291 & 2292 |
| CCL11 | AGGAGAATCACCAGTGGCA | CATGGAATCCTGCACCCA | 2187 & 2188 | CCRN4L | GACCCTGCAGTGCAAGGA | CATTGAAGTCCCCACACA | 2293 & 2294 |
| CCL13 | AGATGCACTCAAGCTCCA | GACAGCTTCTGGGGACA | 2189 & 2190 | CCT2 | GCAGGTGTGGAACGCCTA | GTTGAGTGGCACCACGCA | 2295 & 2296 |
| CCL14 | CTATGAGACCAAGACGGA | GGGGTTGGTACAGACGGA | 2191 & 2192 | CCT3 | GGCCCATGCGTTGACAGA | GTGCTTGGCCGCAAGTCA | 2297 & 2298 |
| CCL15 | CCTTGGATCCCAGGCCA | TCATGAGTGAACACGGGA | 2193 & 2194 | CCT4 | GTGCTGTGGAAGAGAGAGA | CTAACTCAGCAGAACCCA | 2299 & 2300 |
| CCL16 | CACAACCCCAATGACGA | AGGAGCTGGGGTTGACCA | 2195 & 2196 | CCT5 | CACTGGAGGTCATCCCA | CAGTCGATGCCAAGAAGCA | 2301 & 2302 |
| CCL17 | GAGTACTTCAAGGGAGCCA | GTTGGGGTCAAGACA | 2197 & 2198 | CCT6A | TGAACACAGGTGAGCCAA | GGTGGCAATCACAGTGCA | 2303 & 2304 |
| CCL18 | GTGAGTTTCCAAGGCCA | CACAGGAGCAGAGGGCA | 2199 & 2200 | CCT7 | CAAGCTGCGGGCTCGGGA | ATCAGGCACGCAAGCCTCA | 2305 & 2306 |
| CCL19 | CAACTCTGAGTGGCACCAA | GTGAACACTACAGCAGGCA | 2201 & 2202 | CCT8 | GTGACAAACGATGCAGCA | AATTCCAGGGAGAGCTCCA | 2307 & 2308 |
| CCL2 | AGGGCTCGCTCAGCAGA | GCTGGGGTCAGCACAGA | 2203 & 2204 | CD109 | CTCCAAGCCTTCCAACCA | CCCATCCTCACTCGGGAA | 2309 & 2310 |
| CCL20 | GAATCAGAAGCAGCAAGCA | GGATTTGCACACAGACA | 2205 & 2206 | CD14 | CTAAAGGACTGCCAGGCAA | CAGTTCCAGGAGGCACAGGAA | 2311 & 2312 |
| CCL21 | AAAGGAAGATTCCGGCA | CTGGAATGGAGCAGCCTA | 2207 & 2208 | CD151 | GGCGAGACAGTGAGTGGA | CACCACCGTCTTGCAGCA | 2313 & 2314 |
| CCL22 | GCGCCAACATGGAAGACA | GTTAGCAACACCACGCA | 2209 & 2210 | CD160 | GGAACTACACAGTGACGGGA | CAAGGCTGGTGACCAAGCA | 2315 & 2316 |
| CCL23 | TCTCTACACCCAAGCAA | GATGACACCCGCTTGGA | 2211 & 2212 | CD163 | GGGAAGGAACAGGGCCCA | GCCTGCACACACCCCA | 2317 & 2318 |
| CCL24 | GGCAGGGCTGATGACCA | GAAACATGCAGCAGGGAGA | 2213 & 2214 | CD164 | AGCACCCGAAACGTGACGA | GGTGACCAGCGGGAGGGA | 2319 & 2320 |
| CCL25 | CCCGTGTCCACACCAA | CGCAGCAGGCAGATTGCA | 2215 & 2216 | CD164L2 | CAGTCCCTGAGGCCCAA | CCTGAGGAAGTGCAGCA | 2321 & 2322 |
| CCL26 | CACTGTGGAACTGCCACA | GCCTTGGCACCCAGGTCA | 2217 & 2218 | CD180 | AGCCAACAAGCCTGACA | AGGGAGGAGACGGGGTGA | 2323 & 2324 |
| CCL27 | CCTACTGCCACCACGA | GCCAGGTGAAGCACGA | 2219 & 2220 | CD19 | ACCGTGGCAACCTGACA | CACAAGGGAACAACAGGCA | 2325 & 2326 |
| CCL28 | CCAGCTGTTGCACGGA | GAAGGATGAACAGCAGCCAA | 2221 & 2222 | CD1A | CTGGAAATATGCCAAGCA | CCTGCATCAAGAAGACCCA | 2327 & 2328 |
| CCL3 | CTCCCGCAGATTCCACA | GACACCGGCTTGGAGCA | 2223 & 2224 | CD1B | TGAGATCCAGGGCATAGCA | GGAAGGCACACATGAAGCA | 2329 & 2330 |
| CCL3L3 | GCCAGTGCTCAGACACA | CTCACTGGGTCAGCACA | 2225 & 2226 | CD1C | AACAGGAGCAACTGGGCA | ACTCGACAAGACAGGCCA | 2331 & 2332 |
| CCL4 | AGCCGTCTCAGCACCA | GCTGGCTGGAGCAGA | 2227 & 2228 | CD1D | TGCCCAATGCTGACGGGA | AAGCCACAATGAGGGAGGA | 2333 & 2334 |
| CCL5 | CGTGCCCACATCAAGGA | GATGTACTCCCGAACCCA | 2229 & 2230 | CD1E | CAGGGGAGTTCAGAACTGAA | CGTCAGCATTAGGCAGGA | 2335 & 2336 |
| CCL7 | GCAGAGGGTGCCAGCCA | ATCCCAACTGGCTGAGCA | 2231 & 2232 | CD2 | GCAGGGAACAAAAGTCAGCA | AACGAGCCCACAA | 2337 & 2338 |
| CCL8 | GGGACTTGCTCAGCCAGA | CCTTCAGCGAGACAGA | 2233 & 2234 | CD200 | CACCTTCAGCGAGAACCA | GCGGGCAGTGGCAGAGCA | 2339 & 2340 |
| CCM2 | AGACAATTGGCGTGAAGGA | CGAGATCATGCCGTCCA | 2235 & 2236 | CD200R1L | ACACCGAAGTGAACCTA | CCTCTGGGATCCAGGAGA | 2341 & 2342 |
| CCNA1 | GCACAGACCCAAAGCACA | CTTCCCAACCTCCACCA | 2237 & 2238 | CD207 | AGTGACGGCATGGAGCCA | TCAGGAACTGAGAACGCA | 2343 & 2344 |
| CCNA2 | AAGACAGGCAGCGGTTGCA | ACATGAATGTGAACGCA | 2239 & 2240 | CD209 | CCAGCGGAACTGGCACGA | ACAGAGGTGAGCGTCCA | 2345 & 2346 |
| CCNB1 | CTGCCTCTCCAAGCCCA | CAGTGACTTCCCGACCCA | 2241 & 2242 | CD22 | GCCGGTGAAGGTTCAGCA | CGCTGGAGCCTTGAGCCCA | 2347 & 2348 |
| CCNB1IP1 | CGCACAGACTCAGTTCA | GAAGGCCAGCAGTCCGGA | 2243 & 2244 | CD226 | GATGCGAGATGGGCAGCAGGA | GAGCAGGAATAGTAGCCAAACA | 2349 & 2350 |
| CCNB2 | GCAGTCCATAAACCCACA | CCATAATGCCAACCCAACA | 2245 & 2246 | CD24 | GGGACATGGGGACAGGTA | GGCAACCCAGTAGAGTTGGA | 2351 & 2352 |
| CCNC | ACATGGGCCAAGAAGACA | GCTGTACAACAAGGCTA | 2247 & 2248 | CD244 | ATCACGAGCAGGAGCAGA | GGGAGCAGAAGACTGGGA | 2353 & 2354 |
| CCND1 | TCCGCAAACACGCGCAGA | TGAGGCGTAGTAGGACA | 2249 & 2250 | CD247 | CCATCCTCAGAGGCACA | CAGGAACAAGGCAGTGAGA | 2355 & 2356 |
| CCND2 | CACGGTCGATGATGGCAA | TTGAGGAGCACCGCCTCA | 2251 & 2252 | CD248 | TTGCCAGCCACGAGCCAGA | CCCAGCATGGATGACCCA | 2357 & 2358 |
| CCND3 | ACGCCCTTGGACTCAGA | AGAGAGAGCCGTGCAGA | 2253 & 2254 | CD27 | ACCCACTGGCCACAGGA | TCTGCAGCCTCCACAGGA | 2359 & 2360 |
| CCNDBP1 | GGGTTGCGTGCCAGCAGA | AGGCCAGATGAAGGGTCA | 2255 & 2256 | CD274 | CGGCTGTTGAAGACCA | TGTAGTCGGCACCACA | 2361 & 2362 |
| CCNE1 | GGACAGTGTGGGAGCCA | AGGTGTGGGATCAGGGA | 2257 & 2258 | CD276 | GCAGATGGCCAAGCAGGA | GACAGACAGCCCA | 2363 & 2364 |
| CCNF | GGAGCTGAGACAGCAGA | ATCCGGTGAGGTCCACA | 2259 & 2260 | CD28 | GGTGAAGCAGTCGCCCA | CAACAGACAGACTTCCACAGCA | 2365 & 2366 |
| CCNG1 | CACGATAATGGCCTCAGA | GCAGCTCAGTCAACACA | 2261 & 2262 | CD2AIP | GGTGGAGTGAAGTAGGCCCA | ATAGGTGAAGTAGGCCCA | 2367 & 2368 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| CD300A | GCCAGCACCACCAAGGGA | TCCCGAGGCCTCTGAGCA | 2369 & 2370 | CDC14A | AGGCAGGCTTCAAGGCCA | CGGTGTAGGAGGGTCGGA | 2475 & 2476 |
| CD300LF | AGCAGAAAGCAGCCGGGA | CCTTCGGCAAGGAAGCCA | 2371 & 2372 | CDC14B | GCACCCTACTGATGCCA | CAGATCCTGACCCACGCA | 2477 & 2478 |
| CD300LG | CCAGTCCAGCTCTCAGCA | AGGCCTGCCGGCTGACAGA | 2373 & 2374 | CDC20 | GGAGCTCATCTCAGGCCA | GATGCCACTGTGGCCCCA | 2479 & 2480 |
| CD302 | GCACATCAAGACACAGTGA | CCGTGCTAGCAATCACCA | 2375 & 2376 | CDC23 | GAGAGTGGAGCTCAGCAA | ACCAGGCTCCCAATGCA | 2481 & 2482 |
| CD320 | ACCAGTCTGAAGCCCAA | TGGCCACCAGTAACCCA | 2377 & 2378 | CDC25A | AATACGAGGGAGGCCACA | CTCTCACATACCGGCACA | 2483 & 2484 |
| CD33 | AGAGCCAGGAGGAGGGGA | GCTCACAGGCCAGGGACA | 2379 & 2380 | CDC25B | GGACAGTGACCACCGAGA | TGCCGTCAATAGGGCCA | 2485 & 2486 |
| CD34 | GTTCACCACCCCAGCCAA | CACACAGCACTCGGGCCA | 2381 & 2382 | CDC25C | GTCTGCGTGAAGAGGACA | GGCTTCGACACCTCAGCA | 2487 & 2488 |
| CD36 | AACCCAGGACGCTGAGGA | GCAGTGCCACAGCCAGA | 2383 & 2384 | CDC27 | GAGTTGAAGGCATGAGGA | ACACCAGGGCTTCTGGCA | 2489 & 2490 |
| CD37 | GCGCGCAGGGGCTCCAGA | AGAGCGTCATGAACCCGA | 2385 & 2386 | CDC34 | GCGTGAAGGTGCCCACCA | CTCATCGTCCCGAAGCA | 2491 & 2492 |
| CD38 | CACAGGTTCAGCGGGGACA | GAGCATCATGGACCACA | 2387 & 2388 | CDC37 | GCAGGACGCCATCAGCAA | TAGAGTTGGGACCCAGA | 2493 & 2494 |
| CD3D | TGGAGCTGGGAAACGCA | TGGATCCAGCTCCACACA | 2389 & 2390 | CDC42 | AGCTATCACTCCACACA | AGTGCAGAACACTCAGGA | 2495 & 2496 |
| CD3E | CCCAGAGGAAGCAAACCA | GTAAACCAGCAGCAGCAA | 2391 & 2392 | CDC42BPA | TCAGCAAGGTCATCGCA | AGAGCCCTCGACGGGGA | 2497 & 2498 |
| CD3EAP | CAGCCTGAAGCCAGGGCA | GGAGCCTCTCCCCAGA | 2393 & 2394 | CDC42BPB | TAGTTGCAGCCCCACCA | GAGGCTCGCAGTTGAGGA | 2499 & 2500 |
| CD3G | CCAAGGACCCTCGAGGGA | GAAGCTCTCGACTGGCGA | 2395 & 2396 | CDC42BPG | TGCCATCCTCGACCAGGA | CACACAGCACGACCAGGA | 2501 & 2502 |
| CD4 | GCTGAGTGACTCGGGACA | GCCAGGCACCTGACACGA | 2397 & 2398 | CDC42EP1 | CCGCTCGGAAAAGCCCA | CTGAGGAGTGAGGGGCCA | 2503 & 2504 |
| CD40 | GGACAAGCTGTGAGACCA | AGCACCAAGAGGATGGCA | 2399 & 2400 | CDC42EP2 | AGGGAGGGAGTGTGAGACA | TGGAAGGCCCAGGTCCA | 2505 & 2506 |
| CD40LG | GAGTCAAATACCCACA | GCCAAAGGACGTGAAGCCA | 2401 & 2402 | CDC42EP4 | CCCCTCCTGATGAGCA | CAGGTCGATGTGGAAGGA | 2507 & 2508 |
| CD44 | AGTCACAGACCTGCCCA | TGGACATGCCGGGTGCCA | 2403 & 2404 | CDC42SE2 | GTGGATACGAAGGGGGA | CAGCTGAAGGAAATGCAGGA | 2509 & 2510 |
| CD46 | GGAGCGGTAAGCACGCCAA | TGGAGCAGCACGACTCCA | 2405 & 2406 | CDC45 | AGAAGCAGCTGCGAGCCA | CCGGCCTAGAGAACAGCA | 2511 & 2512 |
| CD47 | CCAGAGAAGGTGAAACGA | CTCATCCATACCACCGA | 2407 & 2408 | CDC5L | CGAGGATGGAATGGCAGA | TAGGGCAGGAGGAGGCCCA | 2513 & 2514 |
| CD48 | GAGGCAACAAGACCACTACA | AGACTCGCCAGGTATCACA | 2409 & 2410 | CDC6 | CAGGATGACCTTGACGCA | ACTGCCTGATCAAGAGCA | 2515 & 2516 |
| CD5 | GCAGCATCTGTGAAGGCA | CGTCCAGCACTCGATAGGA | 2411 & 2412 | CDC7 | AGGGCAGGTACACCAGGA | CCTGCAGACCACATGTCA | 2517 & 2518 |
| CD52 | GACAAAACGACACAGCCA | CTGAAGCAGAAGAGGTGGA | 2413 & 2414 | CDCA3 | GAAGACCAGGAGTGGAGA | ACTGGTACCAGAGGGCA | 2519 & 2520 |
| CD53 | AGCGTGGGACTCCATCCA | TCGCATAGCAACCCTCCA | 2415 & 2416 | CDCA8 | CTCAGGCCTGACACCA | CTGCAAGTCACTGGCCAA | 2521 & 2522 |
| CD55 | ATGCCTAATCCGGAGGAGA | GGGTCACTCCACTGGACA | 2417 & 2418 | CDCP1 | CTAACTGCAGCCCACGA | ATGATGAAGCCGAGGGCA | 2523 & 2524 |
| CD58 | GCTGGGCACTGCCGCAGA | CATTCCCATACACAACACCA | 2419 & 2420 | CDCP2 | CCGTGACCTCAAGGCACA | TCGCCCTCAGTGGACCCA | 2525 & 2526 |
| CD59 | ACAACCCGCTTGAGGGAA | AATGGAGTCACCAGCAGA | 2421 & 2422 | CDH1 | GATGCCCCAATACCCA | CCAGCACATCCACGGTGA | 2527 & 2528 |
| CD5L | CCTCTTCAGAGACGTGCCA | CTGGCACTGCTCCAGCCA | 2423 & 2424 | CDH10 | GCACAGGCACACTGACCA | TGCAGAGGAGGATGGCGA | 2529 & 2530 |
| CD6 | CCACCTTTGGAGTGAAGGA | GGTGATACTGAGGGCCCA | 2425 & 2426 | CDH11 | GCACAAACCCTCACCA | TGCAGGCGAGGAATGGCGA | 2531 & 2532 |
| CD63 | CAACGAGAAGGCGATCCA | CTGCTGCAGCTACCACCA | 2427 & 2428 | CDH12 | GCGGGATTGAAACCCGA | ATCAACGCCCAGTGCTA | 2533 & 2534 |
| CD68 | CTTCCCCAGCAGCACA | ACCAGGGCGAGGAGGGCA | 2429 & 2430 | CDH15 | CGCCTCAGGACATGAGCA | GTGTGCAGGCGGCACA | 2535 & 2536 |
| CD69 | AATGCATCAGCAGCACCA | ACAGCAAGAGTAGCACCA | 2431 & 2432 | CDH16 | CCTGGATTGGGAGCCAGA | CCCACCAGCTTCGCACCA | 2537 & 2538 |
| CD7 | CTCAGGGTCACCAGGACAA | CCTCTGTCACCAGGACCA | 2433 & 2434 | CDH17 | GTCTACCAGGCCACAGA | CCCAACAGTGGGTATCCCA | 2539 & 2540 |
| CD70 | ATGGACCAGAGCTGGACA | AGCAGATTCCCACGCCA | 2435 & 2436 | CDH18 | CATCCACCCTGGAAAGCA | AGCGAGCTGATAGACCCA | 2541 & 2542 |
| CD72 | CATGCGGCTTCAGCAGACA | AGAGCTGAGGCAGTCCA | 2437 & 2438 | CDH19 | CAAGCGCTGAGATCAGGA | AGCGTAGGTCTGAGGGGA | 2543 & 2544 |
| CD74 | CCCCGAGAGGACCAAGTGCA | CCTGGCCAGCGAGGAGCA | 2439 & 2440 | CDH2 | CTTGAGCCAGCTGCAGGA | GCTGCAGATCGGACCGGA | 2545 & 2546 |
| CD79A | GCAACGAGTCATACCAGCA | GCGCAGAACAGGAGGA | 2441 & 2442 | CDH20 | CATGGTCCGCTACGACGA | AGCACGTAGCTGCTGGACA | 2547 & 2548 |
| CD79B | GGAGCAGAATCCCCAGCA | ATGGTGAGGGTGGCGAGA | 2443 & 2444 | CDH23 | CCCATCTTCAGCAGCCA | CCTGCAGTGAAGCGGGGA | 2549 & 2550 |
| CD80 | AGTTGGCACAAACTGCA | GCAGAGCCAGGATGACA | 2445 & 2446 | CDH24 | CTGAGCAGCACTGCCACA | GGGCACGAAGCAGGATGA | 2551 & 2552 |
| CD81 | CCGGGAAGCTGTACCTCA | GTTCCGGATGCCAACAGA | 2447 & 2448 | CDH3 | TGACGGTGATCAGGGCCA | GCAGCAACGACAGGAGGA | 2553 & 2554 |
| CD82 | TGCAGGAGAACCTTGGGCA | GGAATGGACAGTCCATGGCA | 2449 & 2450 | CDH4 | GCTCATTGACCCGAGGA | GCTCATCCACCGCACGCA | 2555 & 2556 |
| CD83 | CCGGATGGGCAGAGAA | CAATCACTGGCCAATGGA | 2451 & 2452 | CDH5 | CTCCGAGTCCATAGTCGA | AGCCGTCAGCTCAGCCA | 2557 & 2558 |
| CD84 | ACACGTGTACAGCCCAGA | ATAACCAGGAGCCAGAGGCA | 2453 & 2454 | CDH6 | CCTCCACCAACCAACCA | GGTCACTGACCTCCAGCGA | 2559 & 2560 |
| CD86 | ACGGTTACCCAGAACCTA | ACATAGCCAGCACGCTCA | 2455 & 2456 | CDH8 | ATCTTCCACTGAGCAGCA | CCAGATGACTAACAGCA | 2561 & 2562 |
| CD8A | CCGAGGAACAGCCGGGCTA | GCTCGTAACATCAGGGAA | 2457 & 2458 | CDH9 | GACGCAGACCCAAGTGCA | CCCCAGTCACGAGGTA | 2563 & 2564 |
| CD8B | GAGGTGGAACAGGAGAAGA | CTGGCAGGAAGACCGGCA | 2459 & 2460 | CDHR1 | GAGGATGCAGAGGAACCCA | GGGCATCCAGGGAGCGGA | 2565 & 2566 |
| CD9 | AACGCTGAAAGCCATCCA | TCCCGACGATCATGCAGAA | 2461 & 2462 | CDHR2 | TCAGGACTTGCTGACGGA | GCAACACAGAAGGCCA | 2567 & 2568 |
| CD93 | CCAGCATCCATCACGCCA | GATGGCATCCAGGACAGGA | 2463 & 2464 | CDHR3 | GAGTCAGGCCACCAGGGA | ACCAGCATCCTCAGCCA | 2569 & 2570 |
| CD96 | CCCACAACTGCCAATGGA | GGAGTAGGATGGCCACCA | 2465 & 2466 | CDHR4 | GATTCCTCAGGAGCCACA | GGTCACTGTGCACCAGGA | 2571 & 2572 |
| CD97 | GGCAGCACCACCTGCCAA | CAATCACTGGCCAATGGA | 2467 & 2468 | CDHR5 | CCTCCACCAACCAACCA | ACAAGGACCGGCGAGGCCA | 2573 & 2574 |
| CD99 | AGAAGGGGAAGAGGCCGA | GGAGCCCACCGAAGAGGCA | 2469 & 2470 | CDK1 | CAGGTCAAGTGGTAGCCA | TGTACTGACCAGGAGGGA | 2575 & 2576 |
| CDA | ATCGCAGTGACATGCAA | CTCCAGCCACCGGCACCA | 2471 & 2472 | CDK12 | CAAGCAGTTACCAGGGCA | GGAATGGCTTGCCGACCA | 2577 & 2578 |
| CDADC1 | GCAGCATGACCGGTCAGA | GGTCATGTACACGGCCA | 2473 & 2474 | CDK13 | CCTGAGCGTACCAGGAGGA | TCACCATAGCGAGGCCCA | 2579 & 2580 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| CDK2 | GGGCATCAAGTCAGCAGA | CCTGGCCACCACCACCTCA | 2581 & 2582 | CENPJ | GGGCATCAGCAGCAGAGA | GAGGATCTCGAGGGCTCA | 2687 & 2688 |
| CDK4 | AGCCGACCAGGTTGGGCAA | CATCTCAGGTACCACCTGA | 2583 & 2584 | CENPN | GTGAGGAAAAGCGTGCAA | CCAGGCAATTCGAATCCA | 2689 & 2690 |
| CDK5 | GGGGAAGGCACCTACGGA | AGGGCGGAACTCGGCACA | 2585 & 2586 | CEP152 | GGCCGAGTCTCTAAGGA | GCATGGTGTCCAGCAGCA | 2691 & 2692 |
| CDK5R1 | GTGCTACCGCTCGAAGCA | GGTACAGGCATGTCAGCA | 2587 & 2588 | CEP170 | AGCAGCAGAGCCTCCCGA | AGACGGATGACAGCAGCA | 2693 & 2694 |
| CDK5RAP2 | TACCAGGACAGCCAGGA | AAGGTCATCAGGTGGGCA | 2589 & 2590 | CEP192 | CGCATGCCACTGTGTCCA | CTGCTAGCGCAGTGACCA | 2695 & 2696 |
| CDK6 | GGTGACCAGCAGCGGACA | TATGCAGCCAACACTCCA | 2591 & 2592 | CEP250 | TGGAGCGAGAACGAGAGA | GCTGAGCTTGCAGCAGGA | 2697 & 2698 |
| CDK7 | CAGTGCAGCAGGAGAGCAGA | GGCCGTAATTCGAGCACA | 2593 & 2594 | CEP57 | CCATGCCGTGGTAGCCAA | ATACCGTTGGAGGAGGGA | 2699 & 2700 |
| CDK8 | GGCTATGCAGGACCCTA | GGGATTTGACAACGGCA | 2595 & 2596 | CEP72 | CTGCACGCAACGACGGCA | AAGGCGGCTTTGCAGGGA | 2701 & 2702 |
| CDK9 | CAAGGGCCAGAAGCGGAA | GCATGGGGTCGGACCAGA | 2597 & 2598 | CER1 | CTGCCAAGTTCACCACGA | ACTGGCACTCCTCCACCA | 2703 & 2704 |
| CDKN1A | GCTGAGCCGCGACTGTGA | AAGACAGTGACAGGTCCA | 2599 & 2600 | CERCAM | CCAGCACCCAACGAGCA | GCATAGTTGGGTAGGGGCA | 2705 & 2706 |
| CDKN1B | GCGACTGCATCAACCGGA | AGAACCGGCATTTGGGGA | 2601 & 2602 | CES1 | ACCCAGGCTCTGTGTCACCA | GAAGTGAGGGCCATCGCCA | 2707 & 2708 |
| CDKN1C | TGAGAAGTCGTCGGGCGA | CGGGGTCTGCTCCACCGA | 2603 & 2604 | CES3 | CTCGGACGCACAGACCAA | TCAGCCTTCACCCAGGGA | 2709 & 2710 |
| CDKN2A | GTTACGGTCGGAGGCCGA | AATCGAAGCGCTACCTGA | 2605 & 2606 | CES4A | TGGCTGGATGCAACCACA | TCACACCACCATCCACCA | 2711 & 2712 |
| CDKN2AIP | CCAGCCAAAGGACAGCA | CCAACAGGGCACCTTCGA | 2607 & 2608 | CES5A | CCCTTACCTGGAGGCCA | TCTTCAGGCACCTCAGGA | 2713 & 2714 |
| CDKN2B | CCTGCCACTCTCACCCGA | GCCAAGTCACGGGCAGA | 2609 & 2610 | CETP | GGGCTTCAACACCAACCA | GGCAGGAGATCTTGGGCA | 2715 & 2716 |
| CDKN2C | CATGATGCGGCCAGAGCA | GCTTCACCAGGAACTCCA | 2611 & 2612 | CFB | GCAACCATGGCAGGCCAA | CAGACACCACAGCCCCCA | 2717 & 2718 |
| CDKN2D | CGGGCACTTCCAATCCA | CTGCAGTGCCAGCTCCAA | 2613 & 2614 | CFC1 | CACTCAGAAGCACCGACA | GAAGCTGCCCAGCACGCA | 2719 & 2720 |
| CDKN3 | CAATGCCATGCACCGGA | CCCAAGTTCCCATAGCA | 2615 & 2616 | CFC1B | GACGCCTGACCGCTGTGA | GCAGAGTGCGCGAGGGGA | 2721 & 2722 |
| CDNF | GCAGCCACAAAGATCCTA | CAACTGATGCCAAGTCCA | 2617 & 2618 | CFD | GGACAGCTGCAAGGGTGA | CTGTCGATCCAGGCCGCA | 2723 & 2724 |
| CDO1 | GAACATCAGCCATACGGA | GTTCTCCAGCGAGCCCGA | 2619 & 2620 | CFH | AGGCGGGTGAGCAAGTGA | GGGCGGATTCACACAGGA | 2725 & 2726 |
| CDON | CGGTTCGAGTCCCAGGAA | GATGCCACGGCGTGAGAA | 2621 & 2622 | CFHR1 | GATGGTCACAAACACCAA | GGGCGGATTCACAGCA | 2727 & 2728 |
| CDR2 | CTGCATCAGGAGGGCA | AGTTCCCAGCGCGTGGCA | 2623 & 2624 | CFHR3 | TGGTCACCAGCAGTACCA | GCATCTGGGAGTTAGGAGA | 2729 & 2730 |
| CD51 | ACGAAACGCAGAGCACCA | TCAGCATGAAAGGATCCA | 2625 & 2626 | CFHR4 | GAAACACCACCAGGTTCCA | ATAGGTGGAGGAGGCCCA | 2731 & 2732 |
| CD5N | ATCCCAGCCAGTCGGCA | CCAACAGAGCTGGACCCA | 2627 & 2628 | CFHR5 | AGGGTCAACAGTGACGTA | CACACATGGATCTAGGGA | 2733 & 2734 |
| CDX2 | GCAGAGCAGGAGGAGGGA | TGCAGGGAAGACACCGGA | 2629 & 2630 | CFI | AGACTGGATACACCCGA | ATGGAACGAGGCAGTCTCA | 2735 & 2736 |
| CDY1 | AGGGAAAACTTCCTTCCGGA | GAAGCAGTAACTGAGCCA | 2631 & 2632 | CFL1 | GGGCCAAGACTGTCGACGA | ATAGAGGGCATAGCGGCA | 2737 & 2738 |
| CDYL | GCAGGAGGCGTGTGGCAA | GCGCACGAGGGCTTTGGA | 2633 & 2634 | CFLAR | AAGCGAGGGCGTGTGCACA | GCATCGCAGGTACAGGGA | 2739 & 2740 |
| CDYL2 | TCCAGACGCCTCACCGCA | GCTGAACGTGGTGGCCA | 2635 & 2636 | CFP | GCTGCCACGGTGTGAGGA | AGCAGGCGTGTAGGACA | 2741 & 2742 |
| CEACAM1 | GCAACACCACCCTCAGCA | ACCAGGGCCTCACTACTCCA | 2637 & 2638 | CFTR | GCCTTCTGGGAGGAGGGA | GCTCCAGTGATCCAGCA | 2743 & 2744 |
| CEACAM18 | GCTGAGATCGGCTCCCA | TGCATCGGTAACGGCCA | 2639 & 2640 | CGA | AGGTCACCTCAGAGTCA | ACAAGTACTGCAGTTGGCA | 2745 & 2746 |
| CEACAM19 | GCACATGGGATGGCGCACA | GACACCAGGAGGACTGGA | 2641 & 2642 | CGB | GGTGTGCAACTACCGGCA | GGAGGGCCCTTTGAGGAA | 2747 & 2748 |
| CEACAM21 | CCCATCAGGAGGAGGA | GCCACCAGGAGAGACTCCA | 2643 & 2644 | CGB2 | GCCGCTACTCCGCCACCA | CCACGGCGTCAGGTGAGGA | 2749 & 2750 |
| CEACAM3 | TGAACCTCAAGGAGCAGCA | GGCAGTGGAGAGAGGGGGGA | 2645 & 2646 | CGB5 | GCTGACCAGTGAGAGGA | GCAGCAGCAACAGCAGCA | 2751 & 2752 |
| CEACAM5 | GCAAACCGCAGTGACCCA | AGAGGCGAGTGGCCAGCA | 2647 & 2648 | CGB7 | GTGCGGGCTACTGCCCCA | AGGAAGAGGAGGCCTGGA | 2753 & 2754 |
| CEACAM6 | GGCCTCAATAGGACACA | GAGCCACCCTGGCCAGCA | 2649 & 2650 | CGRF1 | AGTGCTCTGCAGACCCAGGA | TGAGGCTACTCCGGGA | 2755 & 2756 |
| CEACAM7 | AGCCACCCAAGCCCTCA | GAGAGCAGCAGCCTGGGA | 2651 & 2652 | CGRRF1 | TGAAGCTCTGCAGAAGCA | GCTACCAATGGATAGGGCA | 2757 & 2758 |
| CEACAM8 | GCCCAGATGCCCCCACCA | GGTGGATTAGGAGGCCGCA | 2653 & 2654 | CH25H | GCCCTCCTGCCCCACGAA | TGCTGGTACAGCCAGGGCA | 2759 & 2760 |
| CEBPB | AGAAGGAGGAGGCGGCAGA | CGAGCAGGCGCTCGGCGA | 2655 & 2656 | CHAC1 | GATGCTCCTGACCAACCA | TGAAGTCTCCGAACCGCA | 2761 & 2762 |
| CEBPD | ACCAGGAGATGCAGCAGA | CCAGTCAGGTGAAGGCGGA | 2657 & 2658 | CHAD | CCTTGGACAGCCTGGCTGA | AACTTGGCAGGTGAGGCA | 2763 & 2764 |
| CECR1 | AACACCCGCAGTCAGGA | GACAAGCCTTTGGCACCA | 2659 & 2660 | CHADL | GCTGCACCTGGACAGGAA | GAAGAGGTGCTGCAGCGA | 2765 & 2766 |
| CECR5 | GCGTCTACAATCCAGGA | ACCAGCTGCACAGCCTCA | 2661 & 2662 | CHAF1A | CTTCCAGGCAGACACCGA | TCGGAAGCGGCTCCACA | 2767 & 2768 |
| CEL | ACAGCGGCTACCTAGCGA | TGAGGGTCCAGTAGCGCA | 2663 & 2664 | CHAMP1 | TCCCAAACCCAGAAGCA | TGGAGATGCAGTCTGGGA | 2769 & 2770 |
| CELA2A | CGGCACCATTCTACCCAA | ACGCCATCACCCCCAGCA | 2665 & 2666 | CHAT | CTACAACCCCCAGCGCAA | TCTCAGTAGGGCGCAGGA | 2771 & 2772 |
| CELA2B | ACCGCCGTGAAGACGAA | GTGAGGCTGCCGATGGCA | 2667 & 2668 | CHCHD10 | CGCTTACGGAGATCAGGCA | GGAACTCAGACCATGGTA | 2773 & 2774 |
| CELA3A | AGGTCACGTGTGTGACCA | CCAGTGATGAAGGCCGGA | 2669 & 2670 | CHD1 | GAACAAGAGCCCCAACCAA | GGCAACCTTGAACTGGGA | 2775 & 2776 |
| CELA3B | CCCAGACAAGCTGCAGGA | GGTTCCTCCAGAGTCACCA | 2671 & 2672 | CHD1L | AGCCAGATCCGCTGAGCGA | GACAGGACATTGGAACGA | 2777 & 2778 |
| CELF2 | GCGTCTACAATCCAGGA | GGCTGTACAGAGTGGGCA | 2673 & 2674 | CHD2 | TCCACCATGGGAAGCGA | CTTCCGGAAGCGGCTCACA | 2779 & 2780 |
| CELF4 | ACCCCTACCCAGCACGA | ATTGGAGGCGGCTGAGGA | 2675 & 2676 | CHD3 | GGGAGAAGGAAGAAGGGGA | GGAATGCAGGCAGGGGA | 2781 & 2782 |
| CELSR1 | GTCCAGGAACCAGGACACA | TCAGGAGGACGAAAGGCCA | 2677 & 2678 | CHD4 | GGCCTCCAGAAACCCAA | CAGGAGAAGCCCAACCA | 2783 & 2784 |
| CELSR2 | TGAGCGGCTACAGCGGAA | TGTGTGGCAGACAGCCCA | 2679 & 2680 | CHD5 | GGGCTTCAATGCCCGACA | CTCGAAGGTCCCGCACCA | 2785 & 2786 |
| CENPA | GGCTAAAGGAGAGATCCGAA | CCAGGCGCTGCAAGGGCA | 2681 & 2682 | CHD6 | CACGTGGGAGCTAGAGGA | CCAGTGGTACTTCCCGGA | 2787 & 2788 |
| CENPE | GGGAGAAAAGGCAGCAGGCA | TTGAGCGCACACTGCA | 2683 & 2684 | CHD7 | GGAGCGGAGCAGAAGGAGA | AGTGAGCGACTGGAGA | 2789 & 2790 |
| CENPF | GCTGACATCCGCACAGGA | GCCGAGACTCAGTGGGGA | 2685 & 2686 | CHD8 | CTCTGAGTGGCCCAAGGA | GGGACTGGAGAGTCACCA | 2791 & 2792 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| CHD9 | GGGTCGCGTCACTGAGCA | AATACGAGGCTGCCAGCA | 2793 & 2794 | CHTF8 | TCGAGGCTTGCTACAGCA | CAGTCCTGATCCCAGGA | 2899 & 2900 |
| CHEK1 | GGGACCAACCCAGTGACA | CTCTGACACACCACCTGA | 2795 & 2796 | CHUK | GGACCGTGTGCTCAAGGA | CCTACAAGGGACCGGGCA | 2901 & 2902 |
| CHEK2 | GCAAGAGGAGGCAGAGCCA | GAAGGTACTGCACAGCCA | 2797 & 2798 | CIC | GGGCAGAACGGCTACACA | GAGTACGATGCAGGGCCA | 2903 & 2904 |
| CHFR | CCCTTCTGCAAGGAAGCCA | CCCAGTACAGGTGGCAGA | 2799 & 2800 | CIDEA | CGCCGAAGAGGTCGGGAA | GCACCGGATGTCGTAGGA | 2905 & 2906 |
| CHGA | GATGGACCAGTGGCTCCA | CCGGGAGGATGGCCTTCA | 2801 & 2802 | CIDEB | GCAGCACGTGGTACAGGA | CACAGCTGAGTCCCACGA | 2907 & 2908 |
| CHGB | AGGGAAGTGGCAGCAGCA | CCACTGCGAGAGGCGTCGTA | 2803 & 2804 | CIITA | TGGTGGGCAACCTGGAGA | AGGCCCTAGGGTTGGACA | 2909 & 2910 |
| CHI3L1 | AGGATACGACGACAGGA | TGGTGAGAGGGAAGCGCUA | 2805 & 2806 | CILP | GTCACTGACCAGAGCCCA | GGAGAAGCCGTCAGAGGA | 2911 & 2912 |
| CHI3L2 | GTCATGGGCATCCCACA | ATAGGCAGGAAGCCTGA | 2807 & 2808 | CILP2 | TATGAAGCCCCACCAGGA | GCCATCAGTGGGAACCGA | 2913 & 2914 |
| CHIA | TGGGCCTATGCCAAGGA | CCAGATCAATGGCCCAGA | 2809 & 2810 | CIR1 | GTCATCCGGAGGGCGCACA | GGTGGTGGGAGTGAGCA | 2915 & 2916 |
| CHIC2 | GGAAGAGGAGGACGAGGA | TACGGTGACGTGACCGGA | 2811 & 2812 | CIRH1A | GCCCACCAATGTACGGCA | GGTATCAGCAGTGCAGGA | 2917 & 2918 |
| CHID1 | GCCAGTACATCCAGAGA | TAGAGACCCCAACGCCA | 2813 & 2814 | CISH | GGATGAAGGTGCCCAGGA | GCGAGTTCCGAAGCACCA | 2919 & 2920 |
| CHIT1 | GCCCTTCTGAACCTGAGCG | GGATTGGGAATAGAGCCCA | 2815 & 2816 | CIT | CCGGGGACTGTGAACGGA | GGGACCCATGAACTGGGA | 2921 & 2922 |
| CHKA | TTCAAGGGGCTGAGGCCA | CCAGTCGGCCTTGGGGAA | 2817 & 2818 | CITED2 | CAGTCAGGACCAAGCCCA | CCAGCAGCTCCTGAGCA | 2923 & 2924 |
| CHKB | AAGCCACAGGGAGCCCCA | GACTGAGGGTCAGGGCCA | 2819 & 2820 | CKAP4 | AGGGACCCAGCTGAGGACA | GGAATTCTCGGCGGACCA | 2925 & 2926 |
| CHML | CGCAGGACAGGTGGTGACA | CGGCCAACCTCCGTGACA | 2821 & 2822 | CKAP5 | GCACAGGCGGTGTGGACA | TCACTCCGTCACACCA | 2927 & 2928 |
| CHMP1A | GCCAAACTGACGGGGACA | GCAGCAAGCTCCATGGTA | 2823 & 2824 | CKB | GTGTGAAAGGCCACGTGA | TGGTAAGGACCGCTGGGA | 2929 & 2930 |
| CHMP4A | CCTCCGAACTCCACAGCA | CTCCCGAAGTGGACCA | 2825 & 2826 | CKLF | ACAGGTGGCGTTGGACACA | GCTTCACACCATCCACCA | 2931 & 2932 |
| CHMP4C | GGGAGTGAAATGTGCAGA | ACGAGCGTGTAAGGTCA | 2827 & 2828 | CKM | AAGCGTGGTACTGCGAGA | CGATGACCAGTTGCACCA | 2933 & 2934 |
| CHN1 | AGTGTGCAGAGACGCGCA | GGAAGTCAGGCGTGAGCA | 2829 & 2830 | CKMT1A | ACTCGAGCAGAGCGACGA | TGCAGTCAGCAACGGGGA | 2935 & 2936 |
| CHPF | GGCCAGGGAAGAGGAGGAA | TGCAGTCTCGCAGGGAGA | 2831 & 2832 | CKMT1B | GGATCCCAAAGCTCAGCA | GCGGCAGTGTCCACCA | 2937 & 2938 |
| CHPF2 | GGCACTGCAAAGGCA | GGGAACAGGGCACACACA | 2833 & 2834 | CKMT2 | GCTGGTCCCTAAAACCA | CGGAACGCAAGATGTGA | 2939 & 2940 |
| CHRD | CCGGGTATGCAGAGGGAG | AAGCGGGACAGACCTTCA | 2835 & 2836 | CKS1B | AGCCGAGACCTTGAGGAA | TCATACTCAGCAGCACCA | 2941 & 2942 |
| CHRDL1 | CTCGCACTTCAGACCCA | CTTCCCGCATGCACACA | 2837 & 2838 | CLASP1 | GAGCAGGAGGTGATGCTA | TCGAGAGGCTGGAGAGGA | 2943 & 2944 |
| CHRDL2 | CTGCAGGACGAAAGCGA | CCGACATCAGGATGCCGA | 2839 & 2840 | CLASP2 | GTGACAATCAAAGGGCGA | ATGACCACAGACGACCA | 2945 & 2946 |
| CHRFAM7A | GCAGCTGGCCAAGTAGCCA | AGCACAGCCAGTAGCCCA | 2841 & 2842 | CLC | GCACCGTGGGAAAGGACA | AGCATTGGACACGGGGA | 2947 & 2948 |
| CHRM1 | CCAGTCAAGGAGGGACACA | GCTGCAATAGCCGTACCA | 2843 & 2844 | CLCA1 | CATAAGCACCCCAAGCCA | GGCCAGCTGGAACTCCCA | 2949 & 2950 |
| CHRM2 | CTCGAGCAGATGGACCA | GACCCGGAAGCTTGAGCA | 2845 & 2846 | CLCA2 | GGATTGACCCCACAGACA | GCACATGACAAGTCAGGA | 2951 & 2952 |
| CHRM3 | CAGCATCGCTCGCAACCA | ACCACACCGTGTCAGGGA | 2847 & 2848 | CLCC1 | TCAACCGTCAGGTGCCA | CCTTGGCCGAGCGCCACA | 2953 & 2954 |
| CHRM4 | CAAGCGCCAATTGGGCCA | GAGCAGCTGCTGGAGACA | 2849 & 2850 | CLCF1 | GGCACTGCACAGGGACCAA | CCCCAACAATGCCACCA | 2955 & 2956 |
| CHRM5 | AAAGTGCCATGGAGGGGA | ACACGGCTAGGGTTCCGA | 2851 & 2852 | CLCN3 | CTGATCGTCAGCAGGGCA | GCAAGCTGCTCCACCGCA | 2957 & 2958 |
| CHRNA1 | TGCACCACGTAGCCACCA | TGAACAGGCATGGAAGA | 2853 & 2854 | CLCN4 | GAACGCCAGAACAGAGGCA | ACGGGCTGCTGTCAGGA | 2959 & 2960 |
| CHRNA10 | GAGGAGGACAGATGGGCA | CAGCATCCTCAGACCGCA | 2855 & 2856 | CLCN5 | GAAGCGAAAGACACCCCA | CAGCCGGCTGTCAGGA | 2961 & 2962 |
| CHRNA2 | CGTCCGTGGTCAAGGACA | TCCAGGGGGCTGCTGAGGA | 2857 & 2858 | CLCNKA | CCACACTGGCCAAGGACA | GCAGATGCCTACCAGGA | 2963 & 2964 |
| CHRNA4 | CTGCAGGAGACAAAGCCGA | TGGAACAGGGCTTCCALGA | 2859 & 2860 | CLDN1 | CCTGCCTGTGCGAGACA | ATGCCAACGGTGGCCACA | 2965 & 2966 |
| CHRNA7 | CGGTGCACACTGGGGCA | GTGGTGCGGCGTCAGCGA | 2861 & 2862 | CLDN11 | CCACCGTGAGACACCCA | GGATGACACAGCCACCA | 2967 & 2968 |
| CHRNA9 | CGATGCGCTGAAGAGGA | GGTACGTGGCGTCCAGGA | 2863 & 2864 | CLDN14 | GCATCTACCAGTGCCAGA | AGACGGCCACCATGCACA | 2969 & 2970 |
| CHRNB1 | ACTGGAAGTACGTCGCCA | GGAAGAGAGGCTGCAGGA | 2865 & 2866 | CLDN15 | CCCGGAACCAAGTACGA | GTCCTGTCGAGCCGCA | 2971 & 2972 |
| CHRNB2 | CCCAGCAACCTCTGAGCA | CCATGACAGGCCGTCACA | 2867 & 2868 | CLDN16 | GCCATCTAAGGGCCA | TGACCATTCCCACCAGA | 2973 & 2974 |
| CHRND | TGCCCCAGCTGTCGAGGA | GATCGACCATCCCGAGGA | 2869 & 2870 | CLDN18 | CCCTGAAATGCATCGCA | CCCACGAACAGAGCCGCA | 2975 & 2976 |
| CHRNG | TGGGCATCCCGCTGGACA | TGTCGTAGGAGAGGCGGA | 2871 & 2872 | CLDN19 | CACCTGGTGACCCAGGA | CTCCGGGCATGTGCAGCA | 2977 & 2978 |
| CHST1 | CGACTATCCCTCGGGCA | GGGCATACAGGLGTLGGA | 2873 & 2874 | CLDN3 | CCAAGGCCAAGATCACCA | TCTGCCCTCCGGCACCA | 2979 & 2980 |
| CHST10 | TCCGGAGCCCTTCGAGA | ACCGCTTGTGGAAGGAGA | 2875 & 2876 | CLDN4 | TGGAGGATGAAAGCCCA | TGTGGGCCTCCAGGACA | 2981 & 2982 |
| CHST11 | TGCCCCAGCTGTCGAGGA | CCAGGGGGATCTTGGGCA | 2877 & 2878 | CLDN5 | CGTGTGGCCCTCACGGGA | TGTACAGCCTGCCCCA | 2983 & 2984 |
| CHST12 | ACTCCAGGTCGCTGGGCA | AGGGGCTGATGCTCCCGGA | 2879 & 2880 | CLDN6 | CAGGACCTGCAGGCTGCA | TCCAGGAGGTGAGCACCA | 2985 & 2986 |
| CHST13 | CTACGACGTCGTGGGCAA | TAGAAGAACCTTCCAAGGA | 2881 & 2882 | CLDN7 | TAGCCATGGGGTAGACGGA | AGAGCGGGCTTACACCCA | 2987 & 2988 |
| CHST15 | GGCCAGCTCTGCAAGGA | TAGGAGGGAGGAGCCCGA | 2883 & 2884 | CLDN8 | AGGGACAGCCAGAGGACTGA | GCACCACCATGCCCGTGA | 2989 & 2990 |
| CHST2 | CCGTCAAGACACTACGGA | CTTGGAGGAGGGGTACAGA | 2885 & 2886 | CLDN9 | GCACGCCATCATCCAGGA | ATGGAGTAGCCCAGCCGA | 2991 & 2992 |
| CHST3 | CCGCGACGTGCTCAAGCA | TGACGAAGGGCGTACAGCA | 2887 & 2888 | CLDND1 | GCAAGGCACACCTAGGCCA | TGAAGAGGCAGAAGCCA | 2993 & 2994 |
| CHST4 | GCCAAGGCAGCTGGAGA | CCAAGCTTCATAGCGCA | 2889 & 2890 | CLEC10A | GAAGGCACACCTAGGCCA | CAGCCTGGGCAGAGGACA | 2995 & 2996 |
| CHST5 | CGGGAGATCGGCAGTACACA | TGGTCCCGAGTACACA | 2891 & 2892 | CLEC11A | CGTGGTCGAGCTGACCCA | AGCTTCGAAGTCGCGCGA | 2997 & 2998 |
| CHST6 | CGTCAGGAATGCGTCTCA | TCAGGCCTCGTGGAGCA | 2893 & 2894 | CLEC16A | CTCCACCTTCACTCAGLA | CGAGCTGGTGCCTCCACA | 2999 & 3000 |
| CHST7 | ACACGGCTGCGAGCGCA | GCAACAGGGGCACCAGCA | 2895 & 2896 | CLEC18A | CTGAGGATGCAGCGGAGA | CCAGATAGAAGGCGAGGA | 3001 & 3002 |
| CHST8 | CATGAGGAGACAGTAGCAA | CGAAGTACTGTGTGGCGCA | 2897 & 2898 | CLEC18B | CCCCGGAGGCAACTGGGA | GCCAGGGGGACAGTGGCA | 3003 & 3004 |
| CHSY3 | CAGGAGGATGGTGCCACA | ACACACTGAGTCCCACCA | | | | | |

| GeneName | Forward Primer | Reverse Primer | SEQ ID NOs | | GeneName | Forward Primer | Reverse Primer | SEQ ID NOs | |
|---|---|---|---|---|---|---|---|---|---|
| COL6A2 | GGTGCAGTACAGCCACGA | GCCCGTCCGTGATGACCA | 3217 | & 3218 | CPE | AGGAGACCTTGTGGCCAA | AGAGTATGCCGGGCCAA | 3323 | & 3324 |
| COL6A3 | ACAGCGCTGAGACACCA | CAACTGCCACTCTGGCGA | 3219 | & 3220 | CPEB1 | GGCTTGACCCCAGCAGGA | CAATCCGGCATACACCA | 3325 | & 3326 |
| COL6A6 | GAATGCCCAGTGCACCA | AGGCGTCTGAGAAGCGCA | 3221 | & 3222 | CPEB2 | GATGAATGCCAGGGCGCA | TGGAACTCACGTCAGCA | 3327 | & 3328 |
| COL7A1 | TCGAGGCGAGAAGGAGA | TGAGAGACGCGGAAGCACA | 3223 | & 3224 | CPEB3 | CACACGCTGTGTGTGGAA | CGGAACGTGGACGTGACA | 3329 | & 3330 |
| COL8A1 | GGACCAATAGGTGCCCA | GGAGGCCCTACTTCACCA | 3225 | & 3226 | CPM | AGCCGTTCAAAAAGCCTGA | GGAGGTTTGGACAGAGGA | 3331 | & 3332 |
| COL8A2 | CACAGCGGCTACAACCA | CTTGTACAGGGCCACCA | 3227 | & 3228 | CPN1 | CGAGCCCTTGGAACCAGA | TCCGGAACTCCTCGCACA | 3333 | & 3334 |
| COL9A1 | GGTCTCCCAGGTGACCCA | AGGAGGCTGGCTCACAGA | 3229 | & 3230 | CPN2 | CCGGACGAAAGCAAGGCA | GAGCTGGACGTTCAGCCA | 3335 | & 3336 |
| COL9A2 | CGTGGGTCAGATCTGGCAA | GGCCGAAGCTCCAAGGCA | 3231 | & 3232 | CPNE1 | AGGCTGCACATCAAGCCA | AAGTCAGCACCACCACA | 3337 | & 3338 |
| COL9A3 | GGTCGGACCCAAAGGAGA | TGCCAGGAACACCCCGGGA | 1233 | & 3234 | CPNE2 | CACAACACGCGACGGCCA | GGAACTCCATGGCAGCGA | 3339 | & 3340 |
| COLEC10 | GATGAAGCTGCCAACACA | ACACAGTTCCATGACCA | 3235 | & 3236 | CPO | AAGCTCAGATCACGCCA | CCCAGCAGCATAGTGGCA | 3341 | & 3342 |
| COLEC11 | ACTCTGACCACTCCCCA | GGCCACCATCTCACGCA | 3237 | & 3238 | CPOX | TGACAGCATGGTCAGGA | GGAACTACAGCCCTCGGCA | 3343 | & 3344 |
| COLEC12 | GGTAGGGAGAGAGAGAGACCAGA | CCCATGGCCATGACCCCA | 3239 | & 3240 | CPS1 | CTGAAGGTGGCTCAGGCA | GGAAGGCCTCAACAAGCA | 3345 | & 3346 |
| COLQ | CCTTCCGAGAGAGACCAGA | CCATCTCCACAGTAGGCA | 3241 | & 3242 | CPT1A | CCCAGACGGTGGAACAGA | AGGCAGAAGAGGTGACGA | 3347 | & 3348 |
| COMP | TGATGCTCCGACGACGA | CAGCGTTCTCCGGACACA | 3243 | & 3244 | CPT2 | CCATGGCCAGCTGACCAA | CCAGGTAGAGCTCAGGCA | 3349 | & 3350 |
| COMT | ACCGGTACCTGCGCGCA | GCTAGGAAGTTCTGGCGCA | 3245 | & 3246 | CPVL | GGCATGGACTGGAAAGGA | GCCGATGTAACCAGCCA | 3351 | & 3352 |
| COPA | CCCAGCAGCTCATCACCA | TGAGGGCTGTAGGACAGCA | 3247 | & 3248 | CPXM1 | CAGGAGTGGTGAGGGACA | CGGCACTGGCAGTCACCA | 3353 | & 3354 |
| COPB1 | GCAGCAGATCCCCTAGCA | GCCAAGTGATGAAGGAGCA | 3249 | & 3250 | CPXM2 | GCTGCGAGACCAGGAGCA | ATAGGAGTAGGGCCAGCA | 3355 | & 3356 |
| COPB2 | GAGGACAGAGGTTGCACA | CACTCCTGGCTAGGCGCA | 3251 | & 3252 | CPZ | ACAGCTTCACGGGAAGGA | GGTGCACCCGGTGTCACGA | 3357 | & 3358 |
| COPE | CTGACAAGTGCTCGCCCA | GGACGATGAAGGTTGACCA | 3253 | & 3254 | CR1 | ATGTGACCCCCACCCAGA | AGTTCACAGCGCAGGGGCA | 3359 | & 3360 |
| COPS2 | ACAGGAGGCCAAGCGTA | ACCAGCAAGCTCTCCACA | 3255 | & 3256 | CR1L | CCCACCCAGACAGAGGGA | AGTTCACAGCAGGAGGGCA | 3361 | & 3362 |
| COPS5 | TCGGAGGCAACTTGGAA | TATGCAGCCTGAGCA | 3257 | & 3258 | CR2 | CACTGTCACCCTCCACA | GGGCAGGGCAGTCAAGGA | 3363 | & 3364 |
| COPS6 | GGCCTCTGAAGCGGGGCA | GGTAGGCCATGAAGCCCCA | 3259 | & 3260 | CRABP1 | ACGGACGCAAGTGCAGGA | GGCCAGCTCACGGGTCCA | 3365 | & 3366 |
| COPS7B | GCAGCAGGTAGAAGCAGA | TGCTCAGCTGAGGGGGGA | 3261 | & 3262 | CRABP2 | CAAGACTCGTGGACCA | CGTAGACCCTGGTGCACA | 3367 | & 3368 |
| COQ3 | GGCTCACAAATGTGGGA | CCACAGCAACGTCA | 3263 | & 3264 | CRAT | CCAGTTGCTCCCAGCAA | GTTGTAGGCCGACAGGGA | 3369 | & 3370 |
| COQ5 | GGCACTGCGAAGAGCTCA | GGACAGGGATGACCTGGA | 3265 | & 3266 | CRB1 | GGGCTGTACCATCAGCA | AGGGACCCGGTGTAGCCA | 3371 | & 3372 |
| COQ6 | GTGGATGCCAAAAGCCGA | CCCTGTCCTGCAAGCGGA | 3267 | & 3268 | CRB2 | TGCCTCGATGGCAGCCCA | GGTGCCCCATTCAAGCA | 3373 | & 3374 |
| COQ9 | GCCGAGAAGAGGAAGACA | GTCCCCAGCGTAATGACA | 3269 | & 3270 | CRB3 | CAGAAGCCATCACTGCTA | CCCGAAGCTTCCGCACCA | 3375 | & 3376 |
| CORIN | CCCCGCTACAGTGGGAGCA | CTCCGGGTTGGGCCAAGCA | 3271 | & 3272 | CREB1 | CCAGCAGAGTGGGAGCAGCA | GAGTTACGGTGGGAGCAGGA | 3377 | & 3378 |
| CORO1A | TGAGAAGGACACCGTCCCA | AAGGGGCCTCGGAAGTGA | 3273 | & 3274 | CREB3L2 | ACCCACAGCCCTTCCAGA | GGGATGGATAGTCCTCA | 3379 | & 3380 |
| CORT | GGTGGGAGAGAAGCTCA | GGCCACCCTCCAGGGGCA | 3275 | & 3276 | CREB5 | CCAGTTGCTCCAGCAA | TACCACCTCGCTGACCGA | 3381 | & 3382 |
| COX10 | CCACATGGACCTTCCCCA | GGTGGCCACAGGGCTGCAGA | 3277 | & 3278 | CREBBP | CAGATCAGCAGCCCCCAA | CCGGTGCCTAGAAGGAGGA | 3383 | & 3384 |
| COX11 | CCCGTGTCGCCGTGGGCA | CTGAGGCATGACCTGCAA | 3279 | & 3280 | CREG1 | CACCATCTCACGCTGGA | GCAGGTTGCACGGCAGGCA | 3385 | & 3386 |
| COX15 | AGCCGTTGGCATGAAAGGA | GCAACTTGTGCGGAGGGA | 3281 | & 3282 | CREG2 | GCCAGAATCACAAGGGGA | GAGGCGTTAACTGGACACA | 3387 | & 3388 |
| COX17 | GACCAAGAAGGGCGCGA | TCACACAGCAGACACCA | 3283 | & 3284 | CRELD1 | GCTGGCTGCTAAGGGCGA | ATGAAGCCCTCCAGCACA | 3389 | & 3390 |
| COX4I1 | TAGTTGGCAAGCGAGCAA | GCAGAAGGGTCTTGACA | 3285 | & 3286 | CRELD2 | CTGCACAGCCTGTGACA | GCCGCACACGTCTCACA | 3391 | & 3392 |
| COX5A | GGCCTGTGCCGCAACCA | TGIACCCATGGGAATAGCA | 3287 | & 3288 | CREM | AGCAACACGCAAACGAGA | TCAAGCACAGCCACAGA | 3393 | & 3394 |
| COX5B | TTGGCTGCACAAAGGCGA | CCAGCTGCTGGGGCCACCA | 3289 | & 3290 | CRH | CTCGGCGCTGCTCGACA | CTTCCGGAGGAGGTGGA | 3395 | & 3396 |
| COX6A1 | CCGGGGTGCAGCTAGCA | GGAGATGGGTAGGCGA | 3291 | & 3292 | CRHBP | GGTAGTTCCACACCAGCA | CTCGCAACCTCTGAGGA | 3397 | & 3398 |
| COX6A2 | GCCAGCCTGCCAAAGGA | TGAAGGTGCAGAGGGCCA | 3293 | & 3294 | CRHR2 | AAGGCTGCTACCTGCACA | AGGGCACGATGATGGGGA | 3399 | & 3400 |
| COX6B1 | CTGGCAGAACTACCTGGA | GTACACACGCTGGTACCA | 3295 | & 3296 | CRIP2 | GAGGCGCTGCGGGAAGACA | CCTTGGGTCCGAAGAGGA | 3401 | & 3402 |
| COX6C | GTTTTGCCAAAACCTGGA | CTTTGATCAGCCACAGA | 3297 | & 3298 | CRISP1 | CAACAAGGATCACCTGA | GGCAGGCTTCACATGGA | 3403 | & 3404 |
| COX7A1 | AGAACCGAGTGCGGGAGA | CCTGGGGAAGAGGCCA | 3299 | & 3300 | CRISP2 | GGTGGGCAAACAAGTGCA | AGGCAATTCCACAGCCTA | 3405 | & 3406 |
| COX7A2 | GTCAGATTGGGAGAGAGA | AGGGCATCAGCTACCCA | 3301 | & 3302 | CRISP3 | CCAAAGACTTCCAAACCA | GCCAATTACCAAGCAGGA | 3407 | & 3408 |
| COX7B | AGAGCCACCAATAGAACGTA | CTCTCCAACAGGGGGACA | 3303 | & 3304 | CRISPLD2 | CGTGCAGTCCCTCAGCAA | AACGGCACCAGCTGAGCA | 3409 | & 3410 |
| CP | CGCGGAAATGATGGAGCGTA | GGCCACATGTGGAGCGTA | 3305 | & 3306 | CRK | GCGAAGGCAAGAAGCATGGAA | GGTTGGGCATAGGCCCA | 3411 | & 3412 |
| CPA1 | GGACCTACAGCCAGGGCA | TGATGGTCAGAAGGCGTA | 3307 | & 3308 | CRKL | CCACACGAGTGGAGGACA | CCCCAGGAGAACCGGAA | 3413 | & 3414 |
| CPA2 | AAGGCAGTGGAGGAAGCA | CCTCGGCTGTGGGCAGGA | 3309 | & 3310 | CRLF1 | GCTACCGAGTGGAGGACA | TGCAGGCACTTGCACGA | 3415 | & 3416 |
| CPA3 | GCCACCTAACCATGAGGA | CAGCAGTGTCATAAGCCA | 3311 | & 3312 | CRMP1 | CCAGCACCAATGCAGCCA | CGGGGTCCAGATGACCA | 3417 | & 3418 |
| CPA4 | CAGCTAGCGGACAGCCA | GCTGGCGAGGAAGAAGCCA | 3313 | & 3314 | CRNKL1 | TGAGGAGCACCCGGGAGCA | CATCAGGGTGCAGGAGGA | 3419 | & 3420 |
| CPAMD8 | TGAGGGTTCCGAGGAGA | AGAACCTGATGCAGCCA | 3315 | & 3316 | CROCC | TCAACAGCACCCGGGACA | GCAGTTCAGGTCAGCCA | 3421 | & 3422 |
| CPB1 | CTCACTGCAGGGCACCA | CCTGCAGGTAGCCGGA | 3317 | & 3318 | CROT | ATCTCACGGGGAAGGAA | TGAGCTGCAGGACCGCA | 3423 | & 3424 |
| CPB2 | GAGGTGGGACGATTGGA | TGTAACGCTCGGCAGCA | 3319 | & 3320 | CRP | CATCTTGGGACGGAGCA | GGACTGAAGGGCCGCCA | 3425 | & 3426 |
| CPD | CCTGGGCAGCATGAAGGA | CTGCCCACAAGGAAGGGA | 3321 | & 3322 | CRTAC1 | CTGGAGTGTGGCCAAGGA | TGTCTCGAGGGCACAGGA | 3427 | & 3428 |

| GeneName | Forward Primer | Reverse Primer | SEQ ID NOs | | GeneName | Forward Primer | Reverse Primer | SEQ ID NOs | |
|---|---|---|---|---|---|---|---|---|---|
| CXCL12 | CGTTCAGCCTGAGCTACAGA | GGCTACAAATCTGAAGGGCA | 3641 | & 3642 | CYP2J2 | GGTGCAGAGAATGGGCAA | GCAGGTGGTACCCAGCA | 3747 | & 3748 |
| CXCL13 | ATCATAGTCTGGAAGAAGAACA | GAGCAGGGAATAAGGGAAGA | 3643 | & 3644 | CYP2R1 | GCCAGCTGCTGAAGCAGA | GACATGGGGAAGCTCGGA | 3749 | & 3750 |
| CXCL14 | GAAGCCAAAGTACCCGCA | GACCTTCGGTACCTGGACA | 3645 | & 3646 | CYP2S1 | CCATGGGAATACCCCGCA | TGGAGCCAAGGAGGGGGA | 3751 | & 3752 |
| CXCL16 | GGACCCATGGGCTTCAGGAA | GAGTGGACTGCAAGGTGGA | 3647 | & 3648 | CYP2W1 | ACACAGTGGCAGACCCA | CAGGCGCTCCCAACACA | 3753 | & 3754 |
| CXCL17 | GACACAAAGGCACCACA | GAAGAGTGGGCGCTCAGA | 3649 | & 3650 | CYP39A1 | AGGCCATTATGGAAGGCA | CCAGTCATCCTCAGACA | 3755 | & 3756 |
| CXCL2 | CCACTGCGCCAACCGA | CGATGCGGGGTTGAGACA | 3651 | & 3652 | CYP3A5 | GAGAAACTTGAGGCGGGA | CCATGCTGTAGGCCCCAA | 3757 | & 3758 |
| CXCL3 | GCTGAGCCCCATGGCCCA | GCAAGCACTGGCAGGCA | 3653 | & 3654 | CYP46A1 | AGGAGGTTCCTGCCGACA | GCAGAGGTTCGTGACCA | 3759 | & 3760 |
| CXCL5 | TGACCAGCGAAGGCCA | ATGGCGAAACATTGCAGA | 3655 | & 3656 | CYP4A11 | AGTGTGGCCCAACCAGA | TGGTGGGGATCAGGCAGA | 3761 | & 3762 |
| CXCL6 | GCTGAGAGTAAACCCAA | GGCTTCCGGTCCAGACA | 3657 | & 3658 | CYP4A22 | GGAACCACCTGGACCAGA | TCAGGGAAGGTGACGGGA | 3763 | & 3764 |
| CXCL8 | ACACTGCGCCAACACAGA | CACAACCCTCTGCACCCA | 3659 | & 3660 | CYP4B1 | GAGAGGAGGTTCCGCGAGA | GCAGGTAGAGACCGGCCA | 3765 | & 3766 |
| CXCL9 | TCAGCACCACACAGGCA | AGGAAGGGCTTGGGGCAA | 3661 | & 3662 | CYP4F11 | GCCATGACACTAACAGGA | ATGACCGGGACTGACGGA | 3767 | & 3768 |
| CXCR1 | ACACAGCAAAATGCGCGGA | TTGTAGGGCAGCCAGCAA | 3663 | & 3664 | CYP4F2 | GGGTTCATCCCAAAGGCA | TCAGGGTCCGGCCACACA | 3769 | & 3770 |
| CXCR2 | ATACAGCAAACTGCGCGGA | GGACCAGGTTGTAGGGCA | 3665 | & 3666 | CYP4F22 | CCCGACAACCCACAGCA | GTGCCACAACCACGCGCA | 3771 | & 3772 |
| CXCR3 | GCCGAGAAAGCAGGGGTAGA | GCAAGAGCAGCATCCA | 3667 | & 3668 | CYP4F3 | CGTTCGCGATGGCGGAGA | CGGTGTGGTCAGGCAGGA | 3773 | & 3774 |
| CXCR4 | CAACGTCAGTGAGGCAGA | GGATGACAATACCAGGCA | 3669 | & 3670 | CYPAX1 | GGGGAGGAGGTCAGGGCA | ATGGAGGGACTGACAGGA | 3775 | & 3776 |
| CXCR5 | GAACCAAGCAGAAACGCA | GTGGTAGGGTGACCAGCA | 3671 | & 3672 | CYP7A1 | CCTGGGTGACAGAAGGGA | CCTGCTACCAGGGCTGGA | 3777 | & 3778 |
| CXCR6 | GCAGCACACACTGGGAA | GAGCACAGGGTTAAGGCA | 3673 | & 3674 | CYP7B1 | GATGCAAGGATGGTCAGA | GTTTGCACAGAGGCCA | 3779 | & 3780 |
| CXCR7 | AGGAGTGGCTGATGGGA | TGTCCAGACGACACGGCA | 3675 | & 3676 | CYP8B1 | ACATCCACCCTGAGACA | AGAACTCCCCAGGGGCA | 3781 | & 3782 |
| CXorf57 | CGGGAGGGGTGATCCGAA | TACAGGCACCACCTCCGA | 3677 | & 3678 | CYR61 | CGGCCTTGTGGACAGGCA | GCATCGGCCGTCCACGCA | 3783 | & 3784 |
| CXXC1 | CGCTTGCCAAGCGCA | GCAGTATCAGGGCCAGCA | 3679 | & 3680 | CYSLTR1 | CTGCCACATGCCATGACA | AGACCACACGGAGAGGCA | 3785 | & 3786 |
| CYB5A | AGCTTCATCCAGATGACA | ACATCAAGGCGACGGCCA | 3681 | & 3682 | CYTH2 | CCCCAAACAACAAGGGCA | AAGGGGTCCACACTCACA | 3787 | & 3788 |
| CYB5B | GGAGGTTGGCAAAGCCCA | GAAGCGGGTGACATCGTA | 3683 | & 3684 | CYTH4 | ACCGCATCTCAGCCACA | AGAAGGGGACACCAGGTGA | 3789 | & 3790 |
| CYB5D2 | CGGAGTGGAGCTCAGCCA | AGCTTCCTGGGGACGGCA | 3685 | & 3686 | CYTIP | GTCGGCAGATGCAGTACAGA | CCCAAAGGGAGACATGGA | 3791 | & 3792 |
| CYB5R1 | GGACAGGAATCACCCAA | CATCCCCTGGAGCGGGCA | 3687 | & 3688 | CYTL1 | GAAGGACAAAGCACGGAA | GGACCGTAGTCACTGGGA | 3793 | & 3794 |
| CYB5R3 | CGACTCGAGCTGATGGAA | GTGGAAGGTGGTCCGGA | 3689 | & 3690 | D2HGDH | TCAGCACCCTGCAGACA | ATCGGTCACCAGCCGGA | 3795 | & 3796 |
| CYB5R4 | GAGAGCAGCAGGATCAGA | CATTCTGCCAACCAGGCA | 3691 | & 3692 | DAB2 | CTCCCTCAGGCAGGACCA | CAAGCATTGGTGCCACA | 3797 | & 3798 |
| CYB8 | GGAGGCCAACTTGGGA | CACTCCCGAGGGCCAGA | 3693 | & 3694 | DACH1 | TACTCAAACCGTCCCCA | TGCACACCGGCGTGA | 3799 | & 3800 |
| CYC1 | CCAGACACGACCATCGA | TGGTGTAGACAGGGCCA | 3695 | & 3696 | DACH2 | AGGAGGCGGATCCCAGGA | GAGAGGGAGATCCCAGA | 3801 | & 3802 |
| CYFIP2 | CCTGCGGAAGATGGCAGA | TGACAATGCTTCCAGGGA | 3697 | & 3698 | DAD1 | CCCAAGAACAAAGCCGGA | GCAGGATGGTGCTGGCAA | 3803 | & 3804 |
| CYGB | CCTTGTGGGAAAGCCCA | GGTGGGAAGTCACTGGCA | 3699 | & 3700 | DAG1 | GCAAGAAGCGGAAGGGGCA | GGAGTGGTCTCGGCACA | 3805 | & 3806 |
| CYHR1 | CTCGAGACCTTGGGGA | CACAACGCCCTTGGGGA | 3701 | & 3702 | DAGLB | CCGACACATGCCAGACA | TCATCAGCGAGCGGGTGA | 3807 | & 3808 |
| CYLD | CTGCACCCGTCCAAGGA | CCCGTGATGTCCCTGCAGA | 3703 | & 3704 | DAK | GGCCAGACAATCCAAGGA | GCAGCAGGAACTCAGGA | 3809 | & 3810 |
| CYP11B1 | CACCTCCAGGTGAGACA | TGAAGGTGAGGAGGGGGA | 3705 | & 3706 | DAND5 | ACATCCCTGGCCTGGA | GACACCCTCGATCAGCA | 3811 | & 3812 |
| CYP11B2 | CGGCAGGAGAACTTCCACA | TCAGCAGTGGTGCAGA | 3707 | & 3708 | DAO | CGAACTGGCTTCCGGCCA | GGCTGCCTCCAGGGACA | 3813 | & 3814 |
| CYP17A1 | GAATCAGCGGGCAAGCCCA | GGGGATGCCTTCCAGGGA | 3709 | & 3710 | DAP | GACAAGGATGACACCAGGA | GGGGAGTGACCCAGAGA | 3815 | & 3816 |
| CYP19A1 | CCTGCTGCCACATGCCA | AGTTGCAGGCACTGCCGA | 3711 | & 3712 | DAPK1 | GGCTGATGAGGAGGACGA | CATTCACCCACAGGCGGA | 3817 | & 3818 |
| CYP1A1 | CCTGAGACCTTCCGACA | CACAACGCCCTTGGGGA | 3713 | & 3714 | DAPK2 | CCGGTGACAACCAGCAA | TCATCAGCGAGCGGGTGA | 3819 | & 3820 |
| CYP1A2 | CTAACCTGCCTGCCTGCAGA | CCCGTGATGTCCCTGACA | 3715 | & 3716 | DAPP1 | CTCTGTGCAAAGACGGA | TGAACACCGAGATCGGA | 3821 | & 3822 |
| CYP1B1 | GACTCGAGTGGCAGCAGA | AGGCAGGACATAGGGCA | 3717 | & 3718 | DARC | TGGCAGAAGGCCTGGCA | ATCCTTCAGGGAGGGGCA | 3823 | & 3824 |
| CYP21A2 | GGAGGAGCTAGAACCAGA | GGGCAAGGCTAAGGGCA | 3719 | & 3720 | DARS | AGTTCTACGTTCAGCAGCA | CATCCAGCTGCAGGGGCA | 3825 | & 3826 |
| CYP26A1 | AGTGGAGGTGGCCAGGCA | GCAGGGAGATTGTCACA | 3721 | & 3722 | DAXX | GAGCTCGGCTCCAAGGCA | TCTGGAGGCAGAAGGGCA | 3827 | & 3828 |
| CYP26B1 | CGGGACACCTGGCAGACA | AGCGCGTGTGTAGCCA | 3723 | & 3724 | DAZAP2 | CACCCAGGGGCTGCACA | ACCAGACTGTGAGCCA | 3829 | & 3830 |
| CYP27A1 | AGCCTGCTGTACCCAGGA | GGATCAGCCTTGCGAGGA | 3725 | & 3726 | DBH | CGTGCACTACTACCCCA | CCTGAGGGCCAGGTGCAGA | 3831 | & 3832 |
| CYP27B1 | CCCGAAGTTCCAGACAGCA | TGACCACCGCTTCAGA | 3727 | & 3728 | DBI | TGAGAAGCTGCGAGGA | GGCATAGATGGTCAAGACA | 3833 | & 3834 |
| CYP2A6 | GGAGGCTGCAAGTGATCACA | GGGGTCTCTCAGCACAGA | 3729 | & 3730 | DBN1 | CTGCCACTGCTGACACA | GTTGAAGAGGGTTGGCACA | 3835 | & 3836 |
| CYP2A7 | CAAGAACCGGCCAGCCCAA | CTCTCAGCACGGAGCCCA | 3731 | & 3732 | DBNL | CAGCCGACGACACAGAGA | CCACAGTAGTTGGCAGGGA | 3837 | & 3838 |
| CYP2B6 | CCCATATGCCCTCAGA | GGGTGACAATGTGGGGCA | 3733 | & 3734 | DBP | GAACAAGGAGGCAGCCAA | GCTCCTGGCGACAGGCCA | 3839 | & 3840 |
| CYP2C18 | CCTGTATGGGCAGCAGGA | GGGCAGGTTGGTGGGGGA | 3735 | & 3736 | DBR1 | AGGGGATCTACGGCTGCA | GGTGCCACCCAGACGACCA | 3841 | & 3842 |
| CYP2C19 | CCACATGCCCTCACACAGA | AGTCACAGGTCACTGCA | 3737 | & 3738 | DBT | GCCTATGTGGGAGACAGGA | TCCATTGTGCCAGACGCA | 3843 | & 3844 |
| CYP2C8 | GACACAGGAGCCCCTGCA | CCGGTGGGGACAAGGTCA | 3739 | & 3740 | DCAF10 | GCTTGCCCAAAGAAGCCA | AACCCGTCCACTAAGGCA | 3845 | & 3846 |
| CYP2C9 | TGATTGGCAGAAACCGGA | TGGACCTGTGCACCACA | 3741 | & 3742 | DCAF11 | CAGTTCGTGGGAGCGGGAA | GATTGGGGCACTGGGCA | 3847 | & 3848 |
| CYP2E1 | TGATTGGGCAGGGCACGA | GCAGGTTGGAGGGCACGA | 3743 | & 3744 | DCAF4L2 | CCCGTGCATGTGAACGGA | GCAGGTGGCCATGACGGA | 3849 | & 3850 |
| CYP2F1 | CCACTACGACCCCAGCCA | GCCCAGCTGCTGAGAAGGGGCA | 3745 | & 3746 | DCBLD2 | ATGTCAGGGCACCCACA | GGCCTGCGCCTGAGGAGCA | 3851 | & 3852 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| DCC | CCTCACACAGTCAGCCA | GGGATGGCGCTCACGACA | 3853 & 3854 | DEFB110 | GGACTTGAGGAGGAGAGTGCA | GCAAGCAGCAATGAGTTCCA | 3959 & 3960 |
| DCHS1 | GTCCATGCAGGAGGCACA | AGGGTCAGGGTCAGCACA | 3855 & 3856 | DEFB116 | CAATGGCAAGAGCCGAGA | CACAGAAAGTTTCAGGCAGGA | 3961 & 3962 |
| DCLRE1B | GGAATCACTGCTGGAGGA | ACTGCATCGATGCCGGCCA | 3857 & 3858 | DEFB118 | CTGGAACAGATGAGGGCA | GTGGGAGATGTCGCAGGA | 3963 & 3964 |
| DCN | TCTGGCCAACACGCCTCA | CCAGGTGGGCAGAAGTCA | 3859 & 3860 | DEFB119 | AAACGCCACATTCCTTCGA | GGACTGGAGGCAGCAGGA | 3965 & 3966 |
| DCP1A | CAGGTTGACCCCACAGCA | AACACCTTAGGCTGCACA | 3861 & 3862 | DEFB125 | TATACTCGAGGACCAGCA | GGGAGTAGTGGCCTCAGA | 3967 & 3968 |
| DCP5 | CCGGATGAAGGGAGACCA | GCCTAGGGTCACACTTCCA | 3863 & 3864 | DEFB130 | GAAAGGGGTGTGCAGAGA | GGGCTCAAGTATCCACCA | 3969 & 3970 |
| DCSTAMP | GATGGCAACAAACCACAGA | TCCAACCACAAGGGCCTCA | 3865 & 3866 | DEFB132 | GTGAGTAACACCCCAGGA | GCAGGAAGGAGTAGCTGA | 3971 & 3972 |
| DCT | GCCACATTCAGCGTCCAA | TGTGACCAATAGGGGCCA | 3867 & 3868 | DEFB134 | GGGATCCAGTGCTGTGGCA | CCTTTGACACAGCACTCCA | 3973 & 3974 |
| DCTN1 | GCGAATGCCAGGGACAGA | GCCAGTTCCTCCAGAGCA | 3869 & 3870 | DEFB135 | AGGTAGAAGTGGACCCAA | GCCGGCAAGTACCTTGCA | 3975 & 3976 |
| DCTN4 | ACCCAGCCAAGACCACCA | GGTTCCTGCCAACCGCCA | 3871 & 3872 | DEFB4A | GCCTTAAGAGTGGAGCCA | TGTTCCAGGGAGACCACA | 3977 & 3978 |
| DCTPP1 | TCCCCCAGCACTGCTGCAGGGGCA | AGAGCACTGCTGCAGGGGCA | 3873 & 3874 | DEGS1 | CCTGGCAAAGTATCCAGA | AAGGCAGCCATTGTGGGCA | 3979 & 3980 |
| DCX | CCAGCTCTCTACCCCAA | CATCCAAGGACAGAGGCA | 3875 & 3876 | DEK | CACAAGGAAAGGGGCAGA | AGCCACTGAACTGACCCA | 3981 & 3982 |
| DCXR | CCAAGGGTGCCCTGGACA | CCTGGCCCATGGACGTCA | 3877 & 3878 | DENND2D | CATGGACAGCCCTATGGAA | TGATCCCTGACCAAGAGA | 3983 & 3984 |
| DDAH1 | ACCGCTACGGACAAACTCA | CCGGGGTTCGGTGCAGCA | 3879 & 3880 | DENND4A | GGGCCCTTGGATAAGGAA | GGGACTTGGAAGGTGCCA | 3985 & 3986 |
| DDAH2 | CAAAAGGCTGTCCGGGCA | GGCACACCAGGCAACCCA | 3881 & 3882 | DENND5A | CCGGAACATCGGCAAGGA | TGATGGGGCAGTCAGCCA | 3987 & 3988 |
| DDB1 | AGGATAAGGCTGTGCACCA | GGGTGGAAGTCTCACCCA | 3883 & 3884 | DENND5B | GCAGTCGAGAGTACCAGCA | CACCAGAGAAGCAGAGA | 3989 & 3990 |
| DDB2 | TGTGGGCGCAGATACCCGA | AACCCATTGCAGAGGCCA | 3885 & 3886 | DENR | TCAAGGAACAGCAGGGGA | CAAAGTTGCAAGGCCACA | 3991 & 3992 |
| DDC | TTGCCACCTCAGGGACCA | GTGCCGGAACTCAGGGCA | 3887 & 3888 | DEPDC1 | GCAATGGGTACGAGGTCA | CTTCCAGCAAGAAGGTCA | 3993 & 3994 |
| DDIT3 | GGAGCCAGAACCAGCAGA | TGAGCCAGGGAGCTCTGA | 3889 & 3890 | DEPDC1B | TGAGGATGATGGCAAGGA | ACACAAGATGCAACGGGA | 3995 & 3996 |
| DDIT4 | AGCTGGCACTGCACCCA | GAAGGGAGAGTTGGCGGA | 3891 & 3892 | DEPDC5 | GACGAGGACGAGTGGCAA | ATCATGCGATCCGAGCGA | 3997 & 3998 |
| DDOST | CCGGCTAGGGCTCACACA | GTAGTAGGGGTAGGCGCA | 3893 & 3894 | DES | TCAGACTTGACCCAGGCA | CGCAGGTGTAGGGACTGGA | 3999 & 4000 |
| DDR1 | TGGGCAGCTCACCGACGA | TCCTCTGCCAGGAACCGA | 3895 & 3896 | DFFA | CAGCGGCTGCAGCACACA | ATGTGGCTGCCAGACGCA | 4001 & 4002 |
| DDR2 | CGAGATCTGGCCACACGA | CCCAAGACATCCAGCGGA | 3897 & 3898 | DFFB | ACAGCTGTGAGAGCCCGA | AGCGAGGAGACCAGGA | 4003 & 4004 |
| DDT | AGGACAACCGCCAGCCACA | GCCAAGGACTCCAAGGGGA | 3899 & 3900 | DFNA5 | CCTGAGCACCAGACAGACA | CCCACCTGTAAGCTGCA | 4005 & 4006 |
| DDX10 | CCTGAGGATGCCACCA | GAAGAAGCTGCTGCACCA | 3901 & 3902 | DFNB31 | CCAGACCAGACAGCCACA | GCCTCGCCAGCATCACA | 4007 & 4008 |
| DDX11 | GGAAGGCTCTGTGTGGAGA | ATCGCTGGTCCAGGAGCA | 3903 & 3904 | DGAT1 | AGTGGATGGTCCCCACCA | AGCCACGGCATTCAGGCA | 4009 & 4010 |
| DDX17 | GGAGCACAAGCAGGCCAA | GCTCCTAAGTGCCAGCA | 3905 & 3906 | DGCR2 | CACCTGCCATGGAGGGGA | GCCATCTGGGTCCAGACA | 4011 & 4012 |
| DDX18 | AAGTCAGGCCAAGGGAGGCA | GATCAACGAAGGGGAGGCA | 3907 & 3908 | DGCR8 | GTCACCTGGTCCAGGCA | GGCTTGACGGGGACACA | 4013 & 4014 |
| DDX20 | CTGGGCTGTGACAGGCAA | ATCTGGGGAGTGACACA | 3909 & 3910 | DGKA | ACCGCTGGATCTGAGCAA | ATTGCACCCTCCAGCCA | 4015 & 4016 |
| DDX21 | TGCCACGTGCGTAGACCA | GGCACAGAGAGCTGCCA | 3911 & 3912 | DGKG | CGGTGGGGAACTCAGAGA | TTGGGCACGCAGCAGCCA | 4017 & 4018 |
| DDX25 | CTGACCGTGGAGCAGCGA | ACATCAATCCCTCGGGCA | 3913 & 3914 | DGKH | CTCCCAGGCTGCAGGAGA | ATTCAGGGCATGGAGGCA | 4019 & 4020 |
| DDX28 | GGACTGGTCCCTCAGGAA | ACAACAGCTCCACACCA | 3915 & 3916 | DGUOK | GCTCTCCATGGAAGGCGA | GGGTGCCAGGCCTGGA | 4021 & 4022 |
| DDX3X | CAGCAAGAGGACTGGACA | AATGAGGTTGCCAGGCCA | 3917 & 3918 | DHCR24 | TCTGGGAGCTCCAGGACA | GGTCAGCTTCAGGAGGGA | 4023 & 4024 |
| DDX4 | CAGAGAGCGGGAGCCACA | CAACACCACCGTAGCGCCA | 3919 & 3920 | DHCR7 | AGCAGGCGGGAGCTCCACA | CCAGACAGTCGCCCCA | 4025 & 4026 |
| DDX41 | GCTCGGAGAAACACGGCA | AATGCAGACAGTCTCAGCA | 3921 & 3922 | DHDDS | GAGGTGACAGTCTACGCA | GCAATCAGGGAGGCGTCA | 4027 & 4028 |
| DDX5 | GCAGTACCAAAACAGGCA | ACCCCTGGAACGACCTGA | 3923 & 3924 | DHFR | ACCTCCACAAGGAGCTCA | ACTGCCACCAACTATCCA | 4029 & 4030 |
| DDX58 | GGAGAGTCTTCAGGCCCA | CACTGACGCATCAAGAGA | 3925 & 3926 | DHFRL1 | CGGAAAGGGCTGCCGGAA | GGCCACTTGGTCTCCACA | 4031 & 4032 |
| DDX6 | CTCAGCCAAGCACACAGA | GTGAGAGGTCACATCCGAA | 3927 & 3928 | DHH | GCACTCACCCAAGGCCGA | CCGTGTACAGCTGCACCA | 4033 & 4034 |
| DDX60 | GGACACATGGGAAGAGA | TGGGGTGCAACGTACACGA | 3929 & 3930 | DHODH | CATCAACACAGCCCAGGA | AAGACTCAGGGAGGCGTCA | 4035 & 4036 |
| DEAF1 | ACTCCCACCAAAGCGGCA | TGAGCAAGGAGTTGACCA | 3931 & 3932 | DHPS | CCCACAAGATGACAACCA | GGTTATCCACCAAGGCCA | 4037 & 4038 |
| DECR1 | GGCACAGCCTTCGTGACA | CCTGAACCAGTCTCAGCA | 3933 & 3934 | DHRS1 | GACAGAACTGCTGAAGGA | AGGCTGAAGAAGAAGCCCA | 4039 & 4040 |
| DEF6 | GCGCAGGCCAGGAAGGAA | GAGCTGCTGCTGACCGGA | 3935 & 3936 | DHRS11 | ATGTGGACGATGGGCACA | GTCAGCGCAGTGACGGCA | 4041 & 4042 |
| DEF8 | GCTCTGCAGAGAGGGGCGA | CCGGGCACACTTGGGACA | 3937 & 3938 | DHRS2 | AGCCCTGCTGCTGACCGA | TGTAGACACCACCGCCA | 4043 & 4044 |
| DEFA1 | GAAGACCTCGGAGCAGAGGA | GCAGGGCCACCAGGAGA | 3939 & 3940 | DHRS3 | CATCAACACCCTGGGCA | GACAGTCAGCAGCCCCA | 4045 & 4046 |
| DEFA3 | GACCCCAGCCATGAAGGA | CATGCAAGGGAAACAACCA | 3941 & 3942 | DHRS4 | GCTCTGGATGGCACAAGGA | AGACACGACACGATCACCA | 4047 & 4048 |
| DEFA4 | GGCCAGAAGACCAGGACA | AGGCAGTTCCAACAACGA | 3943 & 3944 | DHRS4L2 | TGAAGGCCCCAGCCTGA | TGGAAGACACGATCACCA | 4049 & 4050 |
| DEFA5 | GGCAAGAGCCAACTGCTA | GATTTCACACACCCGGA | 3945 & 3946 | DHRS7 | CCCACAAGATGACAACCA | GGTTATCCACCAAGGCCA | 4051 & 4052 |
| DEFB103A | GCCTAGGACGTCATGAGGA | GCAGTTCAGGGACCAGCA | 3947 & 3948 | DHRS7B | GGACACCACCACAGCCTA | AGGCTGAAGAAGAAGCCCA | 4053 & 4054 |
| DEFB104A | GGAAGAAATGTCGCCAGGAA | CGACTTCAGGGACCACA | 3949 & 3950 | DHRS9 | GCCTAGGACGTCATGAGGA | GGAGTATAGCCCCTCCA | 4055 & 4056 |
| DEFB105A | TCAGGGTGCCAGGAGGA | TCCCGACCAAGCTTGCA | 3951 & 3952 | DHRSX | AAGCCACGTGACCGCCA | CCAGACGGTGGCCCAGA | 4057 & 4058 |
| DEFB106A | ACCCCAGCCAAGAATGCA | CCGACAGCATTCAGAGA | 3953 & 3954 | DHX15 | GGCCAAGAAAAGCCGTCAGA | GTCTGCCGGACATCAGGGA | 4059 & 4060 |
| DEFB107A | TCCAAGCCAGAAGCA | CCCACTGATATCCGACGCA | 3955 & 3956 | DHX16 | TCCGTGTACCGGCAAGGCA | AGCCACCTCCAGAAGCCA | 4061 & 4062 |
| DEFB108B | GGGGCAAATTCAAGGGAGA | GTTGATGCCCAGAGGGCA | 3957 & 3958 | DHX29 | TCTACCAGCTGGGAAGGA | GGCCGTCTCCACAATGCA | 4063 & 4064 |
| | | | | DHX30 | TGACACGCGCAGTGACCA | GTCCGTGGGATGAAGCGCA | | |

| GeneName | Forward Primer | Reverse Primer | SEQ ID NOs | GeneName | Forward Primer | Reverse Primer | SEQ ID NOs |
| --- | --- | --- | --- | --- | --- | --- | --- |
| DRD1 | GGCACAAGGCAAAACCCA | TCATGATGGCCACAGGGA | 4277 & 4278 | EBAG9 | GATCTGGCAGAGGACGGA | CTTCATCCCAGGAAGTCCA | 4383 & 4384 |
| DRD2 | GGAACCTCCTCAAGGACCA | TGTACAGGACAGGCGGGA | 4279 & 4280 | EBF1 | CACTCCCAGCAGACCAA | CAGCTGAGCCGTTGAGGA | 4385 & 4386 |
| DRD3 | GCCGGTTCACTACCAGCA | AGAGGGCAGGACACAGCA | 4281 & 4282 | EBI3 | CTGCTCCAAACTCCACCA | GACATTGAGCACGTAGGGA | 4387 & 4388 |
| DRD4 | CCCAGAGACTTCACCGACA | GCGTGATGTGCACCAGGA | 4283 & 4284 | EBP | AGTATGCCAAGGGAGACA | AGGGGATCACCACCCACA | 4389 & 4390 |
| DRD5 | CCTGCGTCAGTGAGACCA | AGAAGTGGCTGCACCCCA | 4285 & 4286 | ECD | GGACCAGGAACTAGCACA | TGGAAGCAGGTCCTGCCA | 4391 & 4392 |
| DROSHA | GTGGAATTCGGCAGCCCA | CAACAGCATCACCAGGA | 4287 & 4288 | ECE1 | CACACGCTTCCTCACGGA | CTTGAAGGCCTCCACGGA | 4393 & 4394 |
| DSC1 | CAACTTCGGCTTGGCGAA | GCTGCAGCAACCTACTGA | 4289 & 4290 | ECE2 | GCTGGCTGGGAACGGAGA | AACCGGCCTTCAGGGACA | 4395 & 4396 |
| DSC2 | GGAGAACATGTACGGGGA | TCATCAGGATCAACCGGA | 4291 & 4292 | ECH1 | ACCATTGGTTGGCCGGGA | AGTCGTGGCCTTGAACCGA | 4397 & 4398 |
| DSC3 | GACCGCATGCTCATCCCAA | TCACTGCAGCAGCCCACA | 4293 & 4294 | ECHS1 | TGCCGGTTGAGAAGGCCCA | GCTGAGATCCGTCACCA | 4399 & 4400 |
| DSCAML1 | TGTGAAAGGGCCACCCA | TGGTGCAAGGAGACGCCA | 4295 & 4296 | ECM1 | ATGGAAGGCCTGTGGAGGA | TTGGGGTTAAGGAGCCCGA | 4401 & 4402 |
| DSCC1 | TGGATGCGACGGTCCAGA | GGCACAGCGTGGGCTCCA | 4297 & 4298 | ECM2 | GCACACTGCGCCTTGCCAA | CATCTGGGATGGAGCGGA | 4403 & 4404 |
| DSE | GACAGACTGAGGAGGCCA | TCAGGGACAGCATCCACA | 4299 & 4300 | ECSIT | GGAAGAGACGCCGGAGGA | GGTCATGAGCACCCGCCA | 4405 & 4406 |
| DSG2 | CTGCAGGGAAGCACAGCA | CGCAATGCACATCAGCA | 4301 & 4302 | ECT2 | CAGTCAGCAAGGTCGGCAA | GGTGCAAGGATAGGTCCA | 4407 & 4408 |
| DSG3 | GAGGATGGCCAGGAAGCA | AACAACCCACGGAGCCCA | 4303 & 4304 | EDAR | GGGCATGACAGAGCGGCA | CACAAGGACTCCAAGCA | 4409 & 4410 |
| DSG4 | GACCTGTGATGAGCCGGA | ATGGGGGATGTGAGCCCA | 4305 & 4306 | EDC4 | GCCACATGAAGAGCCGGA | TGCTGCACCTCAGCACGA | 4411 & 4412 |
| DSP | ACCAAGACATGGCCACCA | CCAGGAAGCCGCTGGCCA | 4307 & 4308 | EDEM1 | CGATAAGGGTCCTGGGAA | AAGCAGGGAGGAGCCGCA | 4413 & 4414 |
| DSPP | TGGAATGGGGACACAGGA | TCTTGGACAACGCGACA | 4309 & 4310 | EDEM2 | CCATGACCAGGCAAGGGA | GAAGGGCTGACTGGGGCA | 4415 & 4416 |
| DST | GCAGGGCCAAAGGAAGGA | GCGCAGCCTGCACTGGACA | 4311 & 4312 | EDEM3 | CAGAGGCAGTCAGTGAGAA | CCACAAGTGCTCCAGCA | 4417 & 4418 |
| DTD1 | GCTCGAAAAACAGCAGCA | GAGGACACAGTCGCCCTA | 4313 & 4314 | EDF1 | GCGGACTATGAGAGCGGA | CCCGAGCTTGAGGCCA | 4419 & 4420 |
| DTNA | CTCCAGACCTGTAACCA | CTGAGGCAGCCCTAGCCA | 4315 & 4316 | EDIL3 | TACAAATGCTCAGGCCCA | AGTCCGTGAGTAGAGGA | 4421 & 4422 |
| DTNB | AGGCACAGCAGAACCCA | TCTCTTGCAGGCGGACGA | 4317 & 4318 | EDN1 | TTGCCAAGGAGCTCCAGA | ATCCATCAGGACGAGCA | 4423 & 4424 |
| DTX1 | TACGCAGCACGTCTGGGA | CCCAGGCCGTGATGAGCA | 4319 & 4320 | EDN2 | CTCCTGGCTGGCAGAAGGA | GTCCCTGGCACTGGAGCA | 4425 & 4426 |
| DTX2 | AGTGCCCCACAGATGAGGA | GTACATGGCCAGGAGGCA | 4321 & 4322 | EDN3 | AAACTTCTGGACGTCAGCA | GGAGCGAGGGCGAGTCCA | 4427 & 4428 |
| DTX4 | CCACAGGCCAGTCAGACA | GGGCAGGGCATCCAGCCA | 4323 & 4324 | EDNRA | AGCGTCGAGAAGTGGCAA | ACAGCAGCAGGAGGCA | 4429 & 4430 |
| DUOX1 | TCCGAGAGGTGGAGGAGA | AGTGGGTGATGGAGTGCA | 4325 & 4326 | EDNRB | GCCAAGGACCCATCGAGA | TGCAGCAGGTCTCCCAGA | 4431 & 4432 |
| DUSP1 | CCTGGTTCAACGGAGGCCA | TCTGCCGAACAGTGCGGA | 4327 & 4328 | EED | CGTAGAAGGGCACAGAGA | AATGCCTAACCATCGCA | 4433 & 4434 |
| DUSP13 | GCAAGTTCCAGGTGGACA | CAGAGCGGCTTACCCCA | 4329 & 4330 | EEF1A2 | CGGTCATGCACTGCCACA | CCGGCACATCTCCAGA | 4435 & 4436 |
| DUSP14 | GTCATCAGGCTGCCAACGTA | ACGTCGGGAACTATGCCA | 4331 & 4332 | EEF1B2 | ACGATTACCTTGGCGGACA | AACGTAGGGCATGCAGGA | 4437 & 4438 |
| DUSP2 | CAAAACCAGCCTGATGCCA | AGGACGGCTGTGATGCCA | 4333 & 4334 | EEF2 | CCCAACATCCTTCACCGA | CGTGGACGTTCAAGGGCA | 4439 & 4440 |
| DUSP22 | GTGCATCCAGCAGCGGA | GTGCAGGGCATCCTCCA | 4335 & 4336 | EFEMP1 | TCAGAAGCAGGGGAGCA | CCCAGGACTGCACTGGCA | 4441 & 4442 |
| DUSP3 | CTCGTCCACTGCCGGGAA | CTCACGATGCTCAGGGCA | 4337 & 4338 | EFEMP2 | CCGCTGGTGGACACCAA | GCGAGTTCCAGCACGGA | 4443 & 4444 |
| DUSP4 | ACGGTGAGGGTCAGGA | AGTGCAGCCCACGGAGA | 4339 & 4340 | EFHC1 | GCAAGTACCTTGGCAGGA | AGGATGATGAACCGTGA | 4445 & 4446 |
| DUSP5 | CAGCTCCTGCAGTACGAA | TGCAGTAGGCACCCTGCA | 4341 & 4342 | EFHD1 | CAAGTCAGCTTCCGGGA | AGGGCCACATCGATCTCA | 4447 & 4448 |
| DUSP6 | GCAGCAGGACTGGAACGAGA | TTGGACAGCGGACTACCA | 4343 & 4344 | EFNA1 | TCACAGTCCTTCAGGCCA | CAGTCAAGGCAAGTGGGA | 4449 & 4450 |
| DUSP7 | CCTGGACGTGCTCAGGGA | AGCTGATGGCCTTCAGGGA | 4345 & 4346 | EFNA2 | CAACGAGACACCCTGTACGA | GGGTCCAGGACACGGGGA | 4451 & 4452 |
| DUSP8 | CAGCAACTCCTGCCCCA | GATGGCGATGGTGGCAGA | 4347 & 4348 | EFNA3 | GCCCACTCACAACCTGCA | CCATGGTGAACTTGGGGGA | 4453 & 4454 |
| DUSP9 | CCTCAATGTCACCCCAA | CCCGCAGTTCTGGGACA | 4349 & 4350 | EFNA4 | GAAGTCTGAGTGCAGCCA | AGACAGAGGGGCTGGGA | 4455 & 4456 |
| DUT | CGCTGCGTCGAAGGGCGA | GAAGGAAGTCCTATCTGA | 4351 & 4352 | EFNA5 | CATGAGTCAGCCGAGCCA | CCAAGAGCAAGACAGTAGGA | 4457 & 4458 |
| DUX4L2 | AGGGGCAGATTGCAAGGCA | CCAGGAGCTCATCCAAGA | 4353 & 4354 | EFNB1 | CCAGGAGTTCAGCCCCA | GGCCGTCACAGCATTGGGA | 4459 & 4460 |
| DVL2 | CAGGGTCGATCCGACACA | GAAGCCCCACTGCAGCCA | 4355 & 4356 | EFNB2 | CGCTAAGGACTGCGGACA | CCGGGCTCTGCGGGGGCA | 4461 & 4462 |
| DYNC1H1 | TCAGGACGTTCAGCAGGA | CACCGTGAGTGGGACCA | 4357 & 4358 | EFNB3 | GGGAAGGAGAACCTGCCA | CTCCGCCAACACATGGCA | 4463 & 4464 |
| DYNC2H1 | GCGCTAAGACACCGGA | GAAGGATCACCACCGGA | 4359 & 4360 | EFR3A | CCGGGTTCGACAGGTA | ATTCAACGCTGAGACGGA | 4465 & 4466 |
| DYRK1A | GCTCATCGGGGGACAAGCA | TCCATGGCCTGCACGGCA | 4361 & 4362 | EFS | TGGGCAATGCCAGAGCCA | CCAGGCGTGAGCAGCCA | 4467 & 4468 |
| DYRK2 | CAGCGAGGAGAGATCCGAA | TGCAGAATCGAGTGGGGCA | 4363 & 4364 | EFTUD2 | AACCGAACCCCGGAGGCAA | TGCCAGGCCATCAAGCA | 4469 & 4470 |
| DYRK3 | CCAGACCTTCCTCACCA | TTCCAACAACTGGAGGGA | 4365 & 4366 | EGF | GCTGCTGACACTTGGGA | GCCTGGCCATCCTCACCA | 4471 & 4472 |
| D21P1 | GGAAGGCGAAATGCAGGACA | ATCCTCCACATCCGACA | 4367 & 4368 | EGFL6 | TGGCATGGGAGAAGAACCA | AGAGCGCCATCCACTGCCA | 4473 & 4474 |
| E2F1 | CCCTCATCCTCACCCACA | CGGAGAAGTCCTTCCCGA | 4369 & 4370 | EGFL7 | ACCCGACAGGGAGTGGACA | TGTGCAGTGGGGCCAGCA | 4475 & 4476 |
| E2F2 | CCCATCCTTGGAGCAGGA | GTCCCAAGGTCGTAGGA | 4371 & 4372 | EGFL8 | CATGGAGGGGTCCCCAGA | GCAGCTCTTCAGGCGGCA | 4477 & 4478 |
| E2F3 | CAACGTTCTTGGAAGGCA | GGCCTTGAGCACTGGGCA | 4373 & 4374 | EGFLAM | CAGGCAAATCCCAGGCA | CCACGGCATCTTCCAGGA | 4479 & 4480 |
| E2F4 | CCATCAAGGCAGACCCCA | AGACGAAGCAGAGGGGCA | 4375 & 4376 | EGFR | GATGGATGTGAACCCCGA | CGGACGCCAGCGAGCGTGA | 4481 & 4482 |
| E2F5 | GCGCTAAGACACCACCGGA | TGGAGTCAAGGACTGGGA | 4377 & 4378 | EGLN2 | TAGTGAGCCAGGAGGGCCA | ACATGGGCCATGAGGGCA | 4483 & 4484 |
| E2F8 | GCAAGAAGGGCCACCAA | GTGCCCTGTCACAGCAA | 4379 & 4380 | EGLN3 | AGGAGAAGGTCTAAGGCAA | ATGCAGGTGATGCAGCGA | 4485 & 4486 |
| EAF2 | CAGGCTCAGGTGCCAGA | CACAGTGTGGAAGGCGCA | 4381 & 4382 | EGR2 | GAGGAAGCGCCACACCAA | GAGAGGAGCAAGGGGGGA | 4487 & 4488 |

| GeneName | Forward Primer | Reverse Primer | SEQ ID NOs | GeneName | Forward Primer | Reverse Primer | SEQ ID NOs |
|---|---|---|---|---|---|---|---|
| EPHA5 | CGAGCACGTACAGCAGCA | GCTGTAGCCACACCGCCA | 4701 & 4702 | ESAM | CCCAAGAGCTCAGACACA | AGGGCCTGGCTGGAGAGA | 4807 & 4808 |
| EPHA6 | CCCAGCTTCCTGAGGGCA | CTCGGAGCATTCCGACCA | 4703 & 4704 | ESM1 | CACAGTTCTCAGGCATGGA | CATCCCGAAGGTGCCGTA | 4809 & 4810 |
| EPHA7 | AGTTGGGAGCACAGGGCGAA | GAGGGAGCTGCTTGACCA | 4705 & 4706 | ESPL1 | GAAGCTGGCTGGACGAGGA | TCAAGGAAGCGGGCACCA | 4811 & 4812 |
| EPHA8 | CTTCCTGAGGAACCACGA | CTCGGTGGACATAGCCCA | 4707 & 4708 | ESR1 | CAACCTGGCAGACAGGGA | GAGCGGCCAGCAGGACCA | 4813 & 4814 |
| EPHB1 | GGAACTTGGCTGCTAGGGA | ATCCTGGAGGTAGGCGGGA | 4709 & 4710 | ESR2 | CCTGACCAAGTTGGCCGA | GGTCAATTGAGCGCCACA | 4815 & 4816 |
| EPHB2 | CATGGGCCAGTTCGACCA | AAGGAGTCCAGGGAGGCA | 4711 & 4712 | ESRP1 | GCACTGCAGCCCTCACA | TGTGGAGGGACACCGCTA | 4817 & 4818 |
| EPHB3 | GAAGGTGGGCTACACCGA | CCCGCAACATGCCCACCA | 4713 & 4714 | ESRP2 | CGCTCATTCCCACGGAGA | AGGCTCCTGACTGGGACA | 4819 & 4820 |
| EPHB4 | GCGGCTAAACGAGGAGACA | GGATGTTGGAGCAGCGA | 4715 & 4716 | ESRRA | GCGAGAAGCTTGCACGA | CCCTCAGCTTCACCCA | 4821 & 4822 |
| EPHB6 | GTGGTCACCAAGAGCTCGA | ACAGCGAGCGATGGACGA | 4717 & 4718 | ESYT1 | ATCACCTCCTCAGCCCCA | CGAAGGGACCGGCAACCA | 4823 & 4824 |
| EPHX1 | CCCAGAAGCATGAGCGGA | GCTCCAGCACCGACAGGA | 4719 & 4720 | ETFA | AGTGATCGACCAGAGCTA | CGGGAAGCACCAACTGCA | 4825 & 4826 |
| EPHX2 | CCCACCTGAAAAGGGGA | GGCATCAGAATTCCAGGCA | 4721 & 4722 | ETFB | TGCTGGGCAAACAGGCCA | CTGTCACCACTGTTGGCA | 4827 & 4828 |
| EPHX3 | AGCTCCGGGAGTTCCAGA | TGGGGGCACCACTGACCA | 4723 & 4724 | ETFDH | AGACCGTCCTGCCACGGA | TCAGAGTCCACGGTCCA | 4829 & 4830 |
| EPN2 | TGAACCAGCTTCGGGGA | TACCACACTGCCCACCA | 4725 & 4726 | ETHE1 | CCGTGGAGGAGGAGGAGGA | TCTGCACCCCACAGCGCA | 4831 & 4832 |
| EPO | GCCTTCGCAGCGTCACCA | TCGGAGTGGAGCAGCTGA | 4727 & 4728 | ETS1 | CAGCTTCGACTCAGAGGGA | GGTCAGCACGGTCCGCA | 4833 & 4834 |
| EPOR | CCCTTCACGAGGAGCCA | TGCCCACTGGCTTCCAGA | 4729 & 4730 | ETS2 | CGAAGATGACTGCAGGTA | CCAGCACGTCAGGTTA | 4835 & 4836 |
| EPR5 | CCGAGCTGGCAGAACCAA | TGAATTCCCAACGACCA | 4731 & 4732 | ETV3 | AGGCTCCCGGCAGATCCA | AGGCGATGACATGGCGGA | 4837 & 4838 |
| EPS15 | GCAGCAGTGAAACAGCCA | CAGTCAACCAGAAGGCA | 4733 & 4734 | ETV4 | AGCCTGAGGAGGTGCCA | GATTGTCCGGGAAGGCCA | 4839 & 4840 |
| EPS8L1 | CCGAGACTTGGACCAGAA | CGCTGCTTGACCGACA | 4735 & 4736 | ETV5 | CCCCCTTACCAGAGGCGA | CCTCGACCTGTCCAGGCA | 4841 & 4842 |
| EPS8L2 | GCAGTTGAACCAGCGGGAA | TCAGGTCCAGAGGCCCGA | 4737 & 4738 | ETV6 | AGCTGATGCCCAGCCCCA | ATGCAGCCCGTCCTCCGGA | 4843 & 4844 |
| EPSTI1 | ACGGCAGCAGCAAGAGCA | CCAGATTGCTCGAGGCCA | 4739 & 4740 | EVA1A | CAGAGAGCAGCAGCAGCGA | TCCGCAGAGGTGAACACA | 4845 & 4846 |
| EPX | CATGGCCACCCCTGCCA | GCTGGGAGAACCCTGTGA | 4741 & 4742 | EVI2B | AACTTGCCCCTGCCACCA | AGGTGGAGGTGGCAACGA | 4847 & 4848 |
| EPYC | GGAAGAGGAAGGGAGGGA | GCCCCAGAACCCTGTGA | 4743 & 4744 | EVI5 | AGGGGCTTCTCAGGCCAA | CTGCCACTGCGGGTCCA | 4849 & 4850 |
| ERAP1 | CACAGTTGAGGGGAGGAA | ACATGCCAGGTACCCA | 4745 & 4746 | EVL | CAGACAAGGCCAGCCGAGA | CACAGGCTTCTCACCGA | 4851 & 4852 |
| ERAP2 | GGCCTGTGAACCTGAACCA | TGTCTGAGGCACCCACAGA | 4747 & 4748 | EVPL | TCCGCGAGAAGGGACCAGA | AGGCCTCGTATGGGGACA | 4853 & 4854 |
| ERBB2 | GGCACAGTCTTACAAGGGCA | GGAGCCCACCACAGCA | 4749 & 4750 | EVX1 | ACCTGCCTGCAGAAACCACA | CCGGCGAGTAGTAGGGCA | 4855 & 4856 |
| ERBB2IP | GGCCATCTCACCAAACGA | GTAGAGCCTGGATCACCA | 4751 & 4752 | EWSR1 | GGAAACGTCCAGCACCGA | CCAGATCCATGAGGGCCA | 4857 & 4858 |
| ERBB3 | GAACCGGAGGAGAAGGCA | TACAGGGTGGAGTGGGGCA | 4753 & 4754 | EXO1 | CTAAGCTACGCTCGGGCAA | GAATGGGCAGGCATAGCA | 4859 & 4860 |
| ERBB4 | CCCAGACTACCTGCAGGA | TGTAAGGTGGAGGCGGGCA | 4755 & 4756 | EXOC1 | GGCATAAGGGAGGAGGAA | GAGTGCCACCACCTGCA | 4861 & 4862 |
| ERC1 | GGGGACAACAAGCTGGAGA | GGTGTCAGCCTGCAAGGA | 4757 & 4758 | EXOC2 | TCGCTCACGCATCCAGA | CAACGTGGCCATTACGCA | 4863 & 4864 |
| ERC2 | CAACAGTTCCTCGGCCGAA | TGGAGGCAGACAATTCCA | 4759 & 4760 | EXOC4 | TGCCAGCACTGGACGAGA | CTCGCAGATAGGCGCTCA | 4865 & 4866 |
| ERCC1 | CCAGGGCCCTCAAGGA | GTCTCCAGGTACCGCCA | 4761 & 4762 | EXOC8 | CCGAAGGCTACTCGCAGA | TCGATGCGAAGCTGACGA | 4867 & 4868 |
| ERCC3 | GTGCCTCAAGACCCAGGA | GGGCACCAGACCTCCAGA | 4763 & 4764 | EXOSC1 | AGGAAGATGTCCGAGCAA | GGGCTACCACCTCCCA | 4869 & 4870 |
| ERCC4 | AGGCCAGCATCTGCAGA | ATGTCAATGCCCCGACGA | 4765 & 4766 | EXOSC10 | GCGGCAAGAGATCAACGA | TAGCCATCCGAGGGGGCA | 4871 & 4872 |
| ERCC5 | CCAAAGGCTCTCGGACTCA | AGGAGGCTCTCGGACTCA | 4767 & 4768 | EXOSC2 | AGTGCTGAGGTCCAGGCA | CCGAGAATCACTGAGGGA | 4873 & 4874 |
| ERCC6 | GACGTGCTGGAACCAGGA | GAGGTCATCCAGGACCGA | 4769 & 4770 | EXOSC3 | CTCTCAGCAGACCAGGA | AGATCTCCAACCTGCACA | 4875 & 4876 |
| ERCC6L | GCAAGGATGAACGGACCA | CCTGTGAGGAGGAGGCGA | 4771 & 4772 | EXOSC4 | TGGATGGCCGGGATACCCA | TCCATCTCAAGCAGCGCA | 4877 & 4878 |
| ERCC8 | TGGTACTAGAGGGACCCAA | GTCATAACGTGGAGAACCA | 4773 & 4774 | EXOSC5 | TGCAGAGAAGAGCCGGGA | ATCAGAGTCCAGGAGCGCA | 4879 & 4880 |
| EHEG | CGGGAGGAGGATGGAGA | ACTTGAGCCACACGTGGA | 4775 & 4776 | EXOSC7 | ATGACATTGGCACCAGGA | CACCACATTCCAGAAGCA | 4881 & 4882 |
| EHG | ATCCAGGCAGTGGGCACGA | CGGGCCACCTGCTCGCAGA | 4777 & 4778 | EXOSC8 | GGCCCAAGTTGGCTAGCCA | CCATGCTAGTCAGCGCGGA | 4883 & 4884 |
| ERGIC1 | CCAGCCAGAACCCAGA | CCAGGGGGTTGGAGGTGA | 4779 & 4780 | EXOSC9 | ACCTGGCAGGCAGTCAGA | CATAAGGCCACGATTGCA | 4885 & 4886 |
| ERGIC3 | CCCCGGACCACACCAA | TCACCATATCATGGGCGAGA | 4781 & 4782 | EXPH5 | GCTTATCGCAGCGGGACA | GGCACCTGACTACTGGGA | 4887 & 4888 |
| ERH | CGAGCTGATACCCACGAA | GTTGGGCCTGCCGACGAA | 4783 & 4784 | EXT1 | GGTGGACCAATTGGCCA | GAGAGTGGATCAGCGCGA | 4889 & 4890 |
| ERLIN1 | GCCCACACACTTCAGGAA | TAGTGAGACCTTGGGGCCA | 4785 & 4786 | EXT2 | CCCAAGGTGCTACAGGA | ACAACCGGGACACAGGCA | 4891 & 4892 |
| ERLIN2 | TCCAGACAGATGAGGTGA | ACACTGCGTTCGGGACCA | 4787 & 4788 | EXTL1 | GTGCCAGAGCTTCCCAGA | CGGCTGTGTGGAGAACCA | 4893 & 4894 |
| ERMAP | GCCAGAAGGGAAAGGGCCA | TCCTGAAGGGCTGGGCCA | 4789 & 4790 | EXTL2 | ACTCATCAGCTACCCCAGA | ATGAGGCTCCAATCAGCA | 4895 & 4896 |
| ERN1 | GCCCAATGCAGCACCGGA | TCTGTGCCAGGCACCCA | 4791 & 4792 | EYA4 | GGGTCAAAGTCAGAGGA | GTGCATAAGACCCGGTGA | 4897 & 4898 |
| ERN2 | GGGGACATCAGTGCGAGA | GGACGAAGGCATCAGGGA | 4793 & 4794 | EYS | CCCTGCCAAAATCAGGA | AGGAGGCTGTTGAGACA | 4899 & 4900 |
| ERO1L | CTGGCCTACATGCAAGCA | GGCGCTCGAAGAATGGTA | 4795 & 4796 | EZH1 | CTGCCAGTGCAACCAGA | CAGTGCTCGAGGCCCA | 4901 & 4902 |
| ERO1LB | GGAGAGTGTGGAGCAGCA | CGCCTGACCATTGGCCA | 4797 & 4798 | EZH2 | CGGTTGACCATTGGAGA | CAGCCTGCCACGTCAGA | 4903 & 4904 |
| ERP27 | GTGCTGCCCAGGAACCCA | CCTATGACAGCCACCTCA | 4799 & 4800 | EZR | GGAGAAGCTGGAAGAGACA | GCCTCTTCCAGGAGGGCA | 4905 & 4906 |
| ERP29 | GCAGCGGCTGCACACCA | CCAACTTAACTGCCCCA | 4801 & 4802 | F10 | CCACGCTGATGACGCAGA | TGCCGTCCACGTAGGGCA | 4907 & 4908 |
| ERP44 | GGCAGATTACATCATGCA | AGGCACAGTCATCATGCA | 4803 & 4804 | F11 | CCCAGGATCGTTGGAGGA | CCAATGATGGAGCCTCCA | 4909 & 4910 |
| ERRFI1 | CTACCTGAACGACCACCA | GGCTGAAGATATACCGCA | 4805 & 4806 | F12 | GTGCCAGACCCCAACCCA | CGCGGGTCATCGAAGACA | 4911 & 4912 |

| GeneName | Forward Primer | Reverse Primer | SEQ ID NOs | GeneName | Forward Primer | Reverse Primer | SEQ ID NOs |
|---|---|---|---|---|---|---|---|
| GNA15 | CCGACGCCTCTTCAGCCA | CGAGCACCGAGTCCCGCA | 5973 & 5974 | GPD2 | CACAGCATCTTGCGCCA | CAGGCGAGTACGACGTGA | 6079 & 6080 |
| GNAI1 | CTGAGGCGGAAGAAGTGGA | AGCTAGAACCAGGTCGTA | 5975 & 5976 | GPER | ACGAGCGGTACTACGACA | CAGCGTGGCTGCACTGAGGA | 6081 & 6082 |
| GNAI2 | GCGTAAAGACCACGGGGGA | CGCTCAGACCGCTGACCA | 5977 & 5978 | GPHA2 | GGGCTCCACGTGGCACA | TGGTGCAGCACTGAGAGA | 6083 & 6084 |
| GNAI3 | GGAAGCTGCCAGGGCAGA | AAGCAAGCTTGTACCCCA | 5979 & 5980 | GPHN | TGCTGATGGCCCAGGAGA | CTTGGCCGAGCTTGCACCA | 6085 & 6086 |
| GNAO1 | CGCCTACATCCAAGGCACA | CGTCGAACACCACCTGGA | 5981 & 5982 | GPI | GGTGTGAGACACACGCCA | CTTGACCGGGATGAGGAA | 6087 & 6088 |
| GNAQ | TGATGGACCCAGAGAGA | GGCGCACGTGAAGTGGGA | 5983 & 5984 | GPIHBP1 | CCAAGACGGTGGAGGGGA | CCAGGGTGGGACATTGCA | 6089 & 6090 |
| GNAS | GACTATGTGCCGAGCGA | GGCCACCCACGTCAA | 5985 & 5986 | GPKOW | CGGACAGATGAAGGCCGA | CCCAGCACCACCATCACA | 6091 & 6092 |
| GNAT1 | AGAAGGCGCACCTCAGCA | TGAGCTCGAGGAACTGCA | 5987 & 5988 | GPLD1 | GCCACTCGCATGTACGCA | CTCAAGCTGGAAGCGCA | 6093 & 6094 |
| GNB2 | CACCACCGGCTCTGACGA | AGTCGTCGTAGCCAGCGA | 5989 & 5990 | GPNMB | AGGGAGCATTCCCACGGA | CCCAGGGTGAGGTTCACA | 6095 & 6096 |
| GNB2L1 | CAAGGCAGAACCACCCCA | CAATGGTCACCTGCCACA | 5991 & 5992 | GPR1 | AGTCACCATTCACCACA | CAGCAACTGCAGGACCGGA | 6097 & 6098 |
| GNB4 | GCCCAGCACCACCACCA | GTGGCATCATCAGAGCCA | 5993 & 5994 | GPR107 | CCACCGAGGGAGGGCACGA | GAACACGGCAGTTGAAGGA | 6099 & 6100 |
| GNB5 | GGACGTGGAAGCGTGGGCA | GCACTGGCCGGAGCGCA | 5995 & 5996 | GPR108 | CATCAACAGCCAGGGGCA | CCTGCATGGGGATCACGA | 6101 & 6102 |
| GNE | GTGGAAGCCATGGGTGCA | TGAATGGAGCGCACCCA | 5997 & 5998 | GPR11D | GACATCGTGACGTGCCAA | AGCCTCGATGATCAGGGA | 6103 & 6104 |
| GNG12 | ATAGCCCAGGCAAGGAGA | GGACATGAGGTCCGGTGA | 5999 & 6000 | GPR112 | CCTGAGGCATCCTCCAGA | GGCAGAGGCATGGCACCA | 6105 & 6106 |
| GNG2 | GTCCAAGGCAGCTGCAGA | AAGCCGAACAGGGGGTCA | 6001 & 6002 | GPR123 | AGGGCACTTCTTGGACA | GCAGCATGCCCACCAGA | 6107 & 6108 |
| GNG7 | AAGCCGGGATTGAGCGCA | AGGCAGGGACTCCGACCA | 6003 & 6004 | GPR124 | CTCTGGGCACAGAACCCCA | GGAAGTGCGTGCCACCA | 6109 & 6110 |
| GNGT1 | GGACCTGACAGAAAAGGA | CAGTGGATCCTCGGCAGA | 6005 & 6006 | GPR125 | CGTGGAACAGCTCGACA | CGCTGAAGACACTGCACA | 6111 & 6112 |
| GNGT2 | CAAAGGCATCCCTGAGGAGA | CCCTGGGGCATCCTAGGAGA | 6007 & 6008 | GPR126 | GGATGGGGTAGAAGCAA | ACACCACTAAGGCAGCCA | 6113 & 6114 |
| GNL3 | CCAGGCTGATGCTCGACA | GTCAAGATGTAGGGGGA | 6009 & 6010 | GPR132 | CCGGTACTACTACGCCA | GGGCAGCGCTTAAGCCCA | 6115 & 6116 |
| GNLY | CGGAGAAACTGCCAGCA | AGCGAGGAGCCGGCAGA | 6011 & 6012 | GPR133 | GCTGCACTTCACTTCACCA | CCAGCACGGCGAAGGACA | 6117 & 6118 |
| GNMT | GCGAGCATGGTGCGGGCA | GGTAGTAGGAGAGCCGGA | 6013 & 6014 | GPR158 | ACCTGAACCCAGGCACCA | TCTGAAGGCACGGACA | 6119 & 6120 |
| GNPAT | CTGCTTCAGAAGCCCGGCA | GCATAAGCCCATGCACCA | 6015 & 6016 | GPR162 | TCCGGAGGGAGATCACCA | CTCAAGGGGACCCAAGGGA | 6121 & 6122 |
| GNPDA1 | AGGAGGGAGTGAACCACA | TGTACAAGGGGTCCACCA | 6017 & 6018 | GPR171 | GCTGCAAGATCTACCGAA | GAAGGACCATTAGCCACA | 6123 & 6124 |
| GNPTG | CGAGTGGGAGATGCCCAA | GCTCGGACACATGGGCCA | 6019 & 6020 | GPR174 | ACTCCTCAGAACCAGTGA | TAACAACGGACTGGGCCA | 6125 & 6126 |
| GNRH1 | GGAAAGAGAGATGCCGAA | CAGGTCTCAGCAGGAGGA | 6021 & 6022 | GPR18 | TGACCCTGACCACGACA | ATGACCAAGTAGCACCCA | 6127 & 6128 |
| GNRH2 | AGACATCACAGCATGGCACA | CAGGTTCTCAGGAGAGA | 6023 & 6024 | GPR182 | TGGAGGGCCCTGAGCCCA | CGGCAGGCTGTCTCAGCACA | 6129 & 6130 |
| GNRHR | CCTCAGCTTCAGCCAGGA | GCATCACTTGGGAGGCCA | 6025 & 6026 | GPR183 | CACCGCTTTGCCTACACGA | AGAGGGTGCACCACAGCA | 6131 & 6132 |
| GNS | GCAACCTCCACCTGA | ACATCCCATCCAGTGGCA | 6027 & 6028 | GPR19 | CGAAGGGTGAGGAGGACA | AAGGCAGCCAGGAGACCAGA | 6133 & 6134 |
| GOLGA4 | CTGCAGCCGAACCAGGCA | AACCCCTGAAGGTGCGACA | 6029 & 6030 | GPR25 | GCTGCGGCCAACCAGCTCA | CCGGAACGGAACACGGA | 6135 & 6136 |
| GOLGA5 | CAGCGAGGAGAGCAGCAGA | CCACGGAGGGCACCCGGA | 6031 & 6032 | GPR3 | CAGCAAGGGCATTGCCACA | TGTAGGTGCAGGAGGCA | 6137 & 6138 |
| GOLGA6L6 | AGCGCCTCGAACAGCAGA | GGAACATTTCGCAGACGA | 6033 & 6034 | GPR32 | CATAGGCACCTGCGCCCA | GTCGGCCACAGATGGACCA | 6139 & 6140 |
| GOLGA7 | GGAAGCCTAAGGAGGGGA | CTGGTAGCGACAGGAGA | 6035 & 6036 | GPR56 | GGTGTGAGACCGTCAGGA | TGGTGACAAGGGTCAGGA | 6141 & 6142 |
| GOLGA7B | AGACTACAGCAGGTGGCACA | AGGGTCTGCAGGAGGA | 6037 & 6038 | GPR65A | GCAACCGGAAAGTCTACCA | ATGCAGGGAATCAGCAGCA | 6143 & 6144 |
| GOLGA8B | CCTCTGCATGGAGACCCA | GTAAGTAGGAGGCCTCGA | 6039 & 6040 | GPR5C | CGATGTGACCACAGAGCA | CCTTGCTGGACAGGAGGA | 6145 & 6146 |
| GOLM1 | AAGGAGCCGTGACCAGCAGA | ACATCCCCAAGCCTCTTCA | 6041 & 6042 | GPRIN2 | CCAGACCCTGCAGGGGGA | GGGATGTAGCTCAGGGGGA | 6147 & 6148 |
| GOPC | CAGGAAGGGTCCAACAGA | CTGCAGGGCTCGGATCACA | 6043 & 6044 | GPS1 | CTGAAGGTGGTCAAGCCA | GAATCACCAAGCACCGGCCA | 6149 & 6150 |
| GORAB | CGACAACAACTTCAGCGA | CACCAACCAGGGGGAGGTGA | 6045 & 6046 | GPS2 | GTGATAGGGAGGAAGCCGCA | GAAGATGGCCAACCACCA | 6151 & 6152 |
| GOSR2 | ACGACTCTGACACCACCA | AAGCCCAGCATGTTGGCA | 6047 & 6048 | GPSM2 | GTAGAGGGAGGAAGCCGAA | CGAAGCCAAGCCACCA | 6153 & 6154 |
| GOT1 | TGACCCAACTCCGAGCA | TAGGCAATGGCCCAGGCA | 6049 & 6050 | GPT | GGTATCCCCAACAGCCA | CCCAGCCATTGGCACCA | 6155 & 6156 |
| GOT2 | CCGGAACAGTGGAAGGAA | GCTCCTACACGCTCACCA | 6051 & 6052 | GPX1 | GGACGAGGTTGTACCAGGA | GGTCATCCAGGCCACCCA | 6157 & 6158 |
| GP2 | CACTCGGAGAGGTGCACA | AGCCAAGCAGGAGGAGGACA | 6053 & 6054 | GPX2 | TGCTCCTCACCACAGCA | GAAGGACCAGAAGGCCCA | 6159 & 6160 |
| GP6 | CATGACCGCTGAACCCA | CAGACAGACATGGCCGA | 6055 & 6056 | GPX3 | GGACCATGACCTCAGCA | CACATCCGCACAGGCCA | 6161 & 6162 |
| GP9 | CAGGCTTACCAGCTGGGCA | GTGGCACAGAGCAGGGCA | 6057 & 6058 | GPX4 | GAGAGCGTGACGAGCCAGA | GGAGCTGCTGGAGATGACA | 6163 & 6164 |
| GPAM | ATCCAAGGAGGACCACCGA | GGTTCTGGAACAGAGGACCA | 6059 & 6060 | GPX5 | CAGATGCAGCCAACAGGA | TGGATGAAGGGGAGCCGA | 6165 & 6166 |
| GPC1 | CTTCAGGCGCTCAGCGA | GGCCATCCCTTCCAGCA | 6061 & 6062 | GPX6 | GGTATCCCCAACAGCCA | TTAGACGAAGCCCTGGCA | 6167 & 6168 |
| GPC2 | TGACCAACTCCGCAGCA | TAGGCAATGGCCCAGGCA | 6063 & 6064 | GPX7 | GGACGAGGTGTACCAGGA | GGAGGTGAGTGGAAGGA | 6169 & 6170 |
| GPC3 | CCGGAACAGTGGAAGGAA | GCTCCTACACGCTCACCA | 6065 & 6066 | GCCAGCTCCAGCGACGA | TCGTTGCGACACACCGGA | 6171 & 6172 |
| GPC4 | CAACCACAGGAGCTCGGGCA | AGCCAAGCAGGAGGAGGACA | 6067 & 6068 | GAAGGACAGAGCTTCCCTA | CGGGACCGCAGGGTCCAA | 6173 & 6174 |
| GPC5 | AGGCACTCAATCTGGGCA | CAGACAGACATGGCCGA | 6069 & 6070 | CAGGAAGAGCTTGCACCA | GGCGGTCAGATGTACCCA | 6175 & 6176 |
| GPC6 | CACGTCCAACGAGGAGGA | GGCCGAGTGATGGTCCACA | 6071 & 6072 | CAGTGAGGCAAGACCGAA | CGAACTGGTTACACGCGGA | 6177 & 6178 |
| GPCPD1 | GGATGCCTGAACAACCAA | AAGCGGCTAACAGTGGAA | 6073 & 6074 | GGACCCTGTAAAGGTCCA | GCTTCAACTACGCCAGGA | 6179 & 6180 |
| GPD1 | GTGCAAGAGGTGGCACA | CTCCAAGAAGGTTGGCAGA | 6075 & 6076 | GGCGAGGAGTACATCCAA | AGCCACTACCTGGACACA | 6181 & 6182 |
| GPD1L | GCTGTGGAGACAACACCA | CCCCGCAGCTCTCTAGGA | 6077 & 6078 | CTACCGAGCCCTGCAGCA | GGGCACCCAGTACCGGTGA | 6183 & 6184 |

| GeneName | Forward Primer | Reverse Primer | SEQ ID NOs | GeneName | Forward Primer | Reverse Primer | SEQ ID NOs |
|---|---|---|---|---|---|---|---|
| HAL | CGCAGCCACGGAGGACCA | CTTACAACAGAGCGCACCA | 6397 & 6398 | HEPH | GGAGATGGTTGGCCAGCAA | GGATCTGCATGCCAGCA | 6503 & 6504 |
| HAMP | GAGACACCCACTTCCCCA | CTTGCAGCACATCCCACA | 6399 & 6400 | HERC2 | TCGTGACACCCAACGGAA | GCCAGCTGCTTCCAGACA | 6505 & 6506 |
| HAND1 | GGAGACGGCACTGAGAGCA | CCTTGGCCAGCACGTCCA | 6401 & 6402 | HERC3 | CCCAAGCCAGCCCACAGA | CAGCTCCTGAGAGAGACA | 6507 & 6508 |
| HAO1 | TGGGGCTCGACAACTCGA | AACACAGCCTTGGCGCCA | 6403 & 6404 | HERC6 | GTGGGAGAAAGAACAGCCA | TACGCCCACTGAGGGCCA | 6509 & 6510 |
| HAO2 | CGGGGTCCGAACTGGCAA | GGCAGCCTGTAAGGGCCA | 6405 & 6406 | HES1 | CTGCAAGCTGGGCAGCCA | GTGTAGACGGGGATGACA | 6511 & 6512 |
| HAPLN1 | GGAGTCAGGAACTACGGA | GGGTAGCGGACGCTGCCA | 6407 & 6408 | HES6 | CGGGATCCCCAATACCCA | CCTCAGCAGGAGCCTGA | 6513 & 6514 |
| HAPLN2 | GGGATCCGCAGCTACGGA | GCACTGGTCTAGCCCGGA | 6409 & 6410 | HESX1 | CTGCAGCTCATCAGGGAA | GGGTGATCCACCACGCTA | 6515 & 6516 |
| HAPLN3 | GATCGCCAAGGTGGGACA | TAGGATGCGGGTGAACCA | 6411 & 6412 | HEXA | CGAAAGGCTGTGGAGCAA | AGGGGTTGGGCCTGGACA | 6517 & 6518 |
| HAPLN4 | CAACTACGGGTATGCGCA | AGCGGCTCAGCAGCTGCA | 6413 & 6414 | HEXB | GCCGTACTCAGAAACAGA | AGTCTCTCACCAACAGCA | 6519 & 6520 |
| HARS | CGACCCCAAAGGGCGCAA | GTGCAGATGCCACAAGCA | 6415 & 6416 | HEXIM1 | AGAAGGGGGTGAGGAGGA | CCGAGAAGTCCGCTGCA | 6521 & 6522 |
| HARS2 | AACTCAGGCTGGGAGGGA | AACATGCCACCAGCCCA | 6417 & 6418 | HEY1 | ACGGCCTCACCCAGGGAA | AGGCCGACAGGGAGGTCA | 6523 & 6524 |
| HAS1 | CCAACCGCATGCTCAGCA | GGAACAGGCCGGAGACCA | 6419 & 6420 | HEY2 | AGCCTGCTTCCAGCCCAA | AGGTGGAGAGAGGTGGCA | 6525 & 6526 |
| HAS2 | GGATGACTACGAAGGGA | CCTCTAAGCAGCTGGCA | 6421 & 6422 | HEYL | GGGCATCTTCCACCGGA | AGCCACGTAAGCAGCCGA | 6527 & 6528 |
| HAT1 | GGAGAAGAAACTGGCAGA | GTTGACAGGCTACCAGCA | 6423 & 6424 | HFE | GGATTGGAGAGCAGCAGAA | GGTCACTGGAAGAGGTCACA | 6529 & 6530 |
| HAUS3 | GAGCAAAGCACAGCAGCA | CGAGCTGCAGTCTAGCCA | 6425 & 6426 | HFE2 | CTGGGAACCACATGTGGAGA | GTTCAGCTGAGAAGGACCA | 6531 & 6532 |
| HAVCR1 | CCCACGTCACCTATCGGA | ATACGCCACTGTCAGACA | 6427 & 6428 | HGF | GAGAAGGCTACAGGGGCA | AGCAGTAGCCAACTCGGA | 6533 & 6534 |
| HAVCR2 | CAACGTGGTGCTCAGGA | CGGCAGCAGTAGATCCCA | 6429 & 6430 | HGFAC | CTTCAACCGCACGACGGA | CTGCGAGCCTGTGGCACA | 6535 & 6536 |
| HAX1 | ATGGCTATGACCCTCTGGA | GCCAAGACCCTCCTGGA | 6431 & 6432 | HGSNAT | AGGGGCTGTGTGACAGCAA | AGAGGGACAGTGGACAGA | 6537 & 6538 |
| HBB | GGCAAAGAATTCACCCCA | GGGCCAGGGCATTAGCCA | 6433 & 6434 | HHEX | GGAGAACCCTCAAAGCAA | GGAGGCAGGGGAGGGCGA | 6539 & 6540 |
| HBD | CATGGCAAGAAGGTGCTA | CACAGTGCAGCTCACTCA | 6435 & 6436 | HHIP | CAAGTCAGGAGGACCAGCA | AAGAGACGTTGCGAGCCA | 6541 & 6542 |
| HBEGF | GGCCACCCAAACAAGGA | ACTGGGAGGCTCAGCCCA | 6437 & 6438 | HHIPL1 | CGAGTGTGGACCGTAAGGA | GCCACGGTCGAAGAGACA | 6543 & 6544 |
| HBQ1 | CCACTTGCACGCGTGCA | GGGGAGGGTTACCAGCA | 6439 & 6440 | HHIPL2 | GGCAGGCTCACATGGCAA | GTCCAGCACAACGCCA | 6545 & 6546 |
| HBXIP | GCTGTGTGGTGGAAAGGA | GCTCCAAGGTCGCCTCCA | 6441 & 6442 | HHLA1 | CCGAGTCCAACCAAGGCA | GAAGAGTGGCTGGAGGACA | 6547 & 6548 |
| HBZ | CCCGCACTTCGACCTGCA | TGACCGGGTCCACGCGCA | 6443 & 6444 | HHLA2 | AGCCAGGAGGAGCAGACA | GCACTGGGAACAGCGCGTCA | 6549 & 6550 |
| HCAR2 | GCCAAGATCAAGAGAGCA | GAAACGCAAATGGACCGGCA | 6445 & 6446 | HBADH | CACGATCTGGGAACTTCA | CCAGTCCAACAGTCTCA | 6551 & 6552 |
| HCAR3 | GAGACAAATGGACCGGCA | ACACACAGGGGTCCAGCA | 6447 & 6448 | HIC1 | GTAGCAGGAGGAGGACCCCA | TGCCGCACGGAATGCACA | 6553 & 6554 |
| HCCS | AGGACTACCAGTTCACCA | TCCAAGCCACCAAGCGA | 6449 & 6450 | HIF1A | TGCACTGCACAGCCCACA | TCAGCCAAGCCAGGTCA | 6555 & 6556 |
| HCFC1 | TCACTACCACGGCTGCCA | GGGTGATGATGGCCGACA | 6451 & 6452 | HINFP | CCCTCCAGGACAACCCCA | CCCCTGGGGCTTCAGACA | 6557 & 6558 |
| HCK | GAGTACACGGCTGCGGAA | CACGCTCCAGAGCTCGGA | 6453 & 6454 | HINT1 | GAAGATCATCCGCAAGGA | TTCAGSCCCAGATCAGCA | 6559 & 6560 |
| HCLS1 | CAGGCATGAGGAGCAGGA | GCCACAGCCCAGCCCA | 6455 & 6456 | HINT2 | CTGGACAAGAGCCTCCA | GCTTGGCTAATCCGAGGA | 6561 & 6562 |
| HCN1 | ACCAACCTGACCCGGGAA | CCGTCACGGTTGAGGGA | 6457 & 6458 | HIP1 | CTGGCCAGCACAAGAGGAA | ATCCAGACCCAGCGCA | 6563 & 6564 |
| HCN4 | TGCACATGCACCGGGAGA | GGAAGATGGCAGCAGGCA | 6459 & 6460 | HIRA | GAGACTCCTGCAGGAGGA | GCAGCTGAGACTGGACA | 6565 & 6566 |
| HDAC1 | TGGCCCTGGATACGGAGA | GGGATGGCGTCCTCAGGA | 6461 & 6462 | HIST1H1B | CTCTGCCGGACGCAGCA | GCTCCTTAGAAGCAGCCA | 6567 & 6568 |
| HDAC10 | GGAGAACTCCACACCCA | TCCTCTGGGGAGGCACA | 6463 & 6464 | HIST1H2AE | AAGCTCGGGCCAAAAGCTA | ATTCCAGCACCGCTGCA | 6569 & 6570 |
| HDAC11 | GGGCATCGTGAGACGGGA | CCAATGAGCCCAAGCGA | 6465 & 6466 | HIST1H2AL | CATCCGCAACGACGAGGA | ATGTTGGGACCAGACACCA | 6571 & 6572 |
| HDAC2 | CCATAAAGCCACTGCCGA | CCAGCAACTGAACCGCCA | 6467 & 6468 | HIST1H2BB | CACCGGCATCTCATCCAA | GTAGTGAGCCAGGCGAGA | 6573 & 6574 |
| HDAC3 | CCTCAGCATCCAGGGCCA | CGGGCAACATTTCGGACA | 6469 & 6470 | HIST1H2BC | ACAACAAGCGCTCGACCA | TGGCAGCTCTCCGGGAA | 6575 & 6576 |
| HDAC4 | GGATCACCAGCTGAGGA | GGGGTCTTCGCACAGACA | 6471 & 6472 | HIST1H2BG | CATCCAAGGCGCAGAGGCTA | GTAGTGGGCCAGAGGGGA | 6577 & 6578 |
| HDAC5 | GATGCCATTGCCATGGA | GCGGTGACAGAGTAGCCA | 6473 & 6474 | HIST1H2BK | CAGCCGCAAGGAGAGCTA | CACCCGGATGCGTTCGA | 6579 & 6580 |
| HDAC6 | GGACCTTGGAGCTAGGCA | AATGGGGACACCAGGGCA | 6475 & 6476 | HIST1H2BO | TCCACCCGCACACCGGCA | TCGCCAGCGATGGCGTCA | 6581 & 6582 |
| HDAC7 | ACGATGCCATTGCCAA | ACCTCATCCAACAGCCCA | 6477 & 6478 | HIST1H3B | CCAGCGCGTCCTGGTGCGAGA | TGCAGGCGCATCACCGCA | 6583 & 6584 |
| HDAC8 | ACGATCAGCTGCGCCAA | TGTGCAGGGACACGGTCA | 6479 & 6480 | HIST1H4B | GGAGAACGTGATCCGGGA | CCCATCATGCAGTTGA | 6585 & 6586 |
| HDAC9 | CTGGAACCCAGGCACACA | AACAGAGGGCAGCAGGGGA | 6481 & 6482 | HIST1H4C | GCCGTTGCCGTCAAGCGCA | AGGTGACGGCGTCTCGAA | 6587 & 6588 |
| HDC | TCCAGTTGCAGGCCAGGAA | TGCAACTGAGGGGAGCGCA | 6483 & 6484 | HIST1H4H | GCCATAACATCCAGGGCA | TAAGTGACGTAGACCACTCA | 6589 & 6590 |
| HDGFL1 | GCACATGACCAGCCAGCCA | GGCTAATGGGCAGTCGGA | 6485 & 6486 | HIST1H4I | GTATCACCAAGCCAGCTA | GCGCGTAGAACCACGTCA | 6591 & 6592 |
| HDLBP | GCCAAGGCACCTTCAGA | GGAGGGCTTGGGAGCCA | 6487 & 6488 | HIST3H2A | GCACCGGTTGCTCCGCAA | CGGCAGTCAAGTACTTCGA | 6593 & 6594 |
| HEATR2 | CGGCATGACGGATCAGA | ACTGCAGCCAGGTGACCA | 6489 & 6490 | HK1 | GCACCAGACGGTTGAAGGA | TGCGTAACCGCACGGCCA | 6595 & 6596 |
| HEATR4 | AAGTTCTCCGAGCTGACGGA | GGTTCTCCGAGGAGCAGA | 6491 & 6492 | HK2 | GCACGTGTGACGAACAGA | GGGTCCCATCCACACCCA | 6597 & 6598 |
| HEATR5A | GATGTGCAGACCTGGCCA | CAGCATGAGTAGGCAGGCA | 6493 & 6494 | HK3 | GGTGGAGAAGATCCGGGA | AGGCAACAGCGGTGACCA | 6599 & 6600 |
| HEBP1 | CAATGCCCAAGGTCGCAA | TCATTGGGGAACACAGCA | 6495 & 6496 | HKDC1 | GCACGTGTGAGGAGGAGCA | GTGCCGTCCACACCACA | 6601 & 6602 |
| HECA | GGATGGCAGCTGGCACCA | GATCACCGGCTTCCCACA | 6497 & 6498 | HLA-A | GCCTTCTGGAGGAGGAGCA | TACAAGCTGTGAGGGACA | 6603 & 6604 |
| HELB | AGTGGAGGACCCACACA | CGAAGAGGCCTCCTCCA | 6499 & 6500 | HLA-B | GACCACCAGCAGGAGA | CAGCGACCACGCTCGA | 6605 & 6606 |
| HELLS | GCCATGCTAGAAGAGGAA | CTATCCCAAGACATGCGA | 6501 & 6502 | HLA-C | ATCAACACTGACCTGGCA | CTTGTCCAGAAGGCACCA | 6607 & 6608 |

| GeneName | Forward Primer | Reverse Primer | SEQ ID NOs | GeneName | Forward Primer | Reverse Primer | SEQ ID NOs |
|---|---|---|---|---|---|---|---|
| HSPA4 | GCTAGAGTGGAGCCACCA | GCAGGCGATAAGATGGCA | 6821 & 6822 | IDE | GAGGTGCTCAGCAGGCAA | ACTATGGCAACCCGGACA | 6927 & 6928 |
| HSPA4L | AAGAACCATCCTGCGCCCA | ACTGATGCGCTAGCCACA | 6823 & 6824 | IDH1 | GGTTAGCCCAGAGAGCAA | GTCATGAAGCCAGCCTCA | 6929 & 6930 |
| HSPA5 | ATCAACGAGCCTACGGCA | CGAAGGTTCCGCCACCA | 6825 & 6826 | IDH2 | GGGGAAGCTGGATGGGAA | GCTGAGGCCGTGAATGCA | 6931 & 6932 |
| HSPA6 | AGGAGGAGGTGGAGGAGGA | GCTCCAGCCAGGCAAGGA | 6827 & 6828 | IDH3A | ATGGGACGGCTCCAAGACA | CGCAGCATCATCACGGCA | 6933 & 6934 |
| HSPA8 | AGAGAAAGCCCTTGAGGA | GAGTGACATCCAAGAGCA | 6829 & 6830 | IDH3B | AGAGCAGAAGAGAAGGGGA | CCTCACAGACTGCAGGA | 6935 & 6936 |
| HSPA9 | GGACTGCCATTCAGGGA | CATCAGCGGCAGTAGAGA | 6831 & 6832 | IDH3G | CCGGCAAGAGTATCGCCA | GGCCGTTGATGACGCGGA | 6937 & 6938 |
| HSPB1 | CCACGCAGTTCAACGAGA | GGCGCAGTCTCATCGGA | 6833 & 6834 | IDI1 | GCCCTTGGAGTGAGGGGA | GGAACCTCTTCCAAGGGA | 6939 & 6940 |
| HSPB2 | CCAGCGCCTGGACCGCCA | GGGAAGAAGCAGCCTCGGA | 6835 & 6836 | IDO1 | AAAGGCAACCCCCAGCTA | TGGAGGAACTGAGACGCA | 6941 & 6942 |
| HSPB8 | CAGCTTCAAGCCAAGAGGA | CCTCTGCAGGAAGCTGGA | 6837 & 6838 | IDS | ATGGAGCGCCAGGCAA | CACGGGGATTACCAGGGA | 6943 & 6944 |
| HSPB8AP1 | TCCTTGGGAGCCCACACA | GGGCTCAGTGTAACCGCA | 6839 & 6840 | IDUA | GAGCAGCTCTGGGCGAA | CGCTCGCGTAGATCAGCA | 6945 & 6946 |
| HSPD1 | GTGGCAGTCAAGGCTCCA | CTGCACCACACAGTAGCAA | 6841 & 6842 | IER2 | GAAGAGGAGGGAGGCGTCA | GCAGTTCAGGAGGCGGGA | 6947 & 6948 |
| HSPE1 | CTGTAACCCAAAGGAGGCA | AACCTGATCCAACACAGCGA | 6843 & 6844 | IER3 | GACGCCCCTAACGCCGCA | GCTGAGGTCCAGAGGCGTA | 6949 & 6950 |
| HSPH1 | AGGACAGGGCTGCAGCA | TGAGCACGTACAACTGGA | 6845 & 6846 | IER3IP1 | TGGGGAACAGACCAGGGA | CAAGTGCAAGGTCAGCCA | 6951 & 6952 |
| HTATIP2 | AGGCAAGAATCTCGCCCA | CTCTAACCACGGTCACCA | 6847 & 6848 | IER5 | GGAGATGGAGACCCGGGAA | TCCGTAGGAGTCCGAGGA | 6953 & 6954 |
| HTR1A | CAGTGAAGACGCTCGGGCA | GTTGGAGTCCAGCCCGGCA | 6849 & 6850 | IFI16 | CCTTCGAGGCCAACCGCA | GATGGAGGCATCTGAGGA | 6955 & 6956 |
| HTR1B | TGGTGAACACCGACCACA | TGCGGCCATAGAGGGGCGA | 6851 & 6852 | IFI27 | TGCAGTCACTGGGAGCAA | CTCGAATGAACAGCCGCA | 6957 & 6958 |
| HTR1D | CAGTGCCCTGGAACGCAA | AGAAGGAGTCCCGGCAGA | 6853 & 6854 | IFI27L2 | GCAGCTGGACTCTTCCACA | GGGTTCAGCTGGGAGAGA | 6959 & 6960 |
| HTR1E | TGGACAAGGTGCCATGGAGA | ACAGAGGGGCATGGAGGA | 6855 & 6856 | IFI30 | CATGCAGCCCAACCGCCA | GGCAGACAAGGGTAAGGA | 6961 & 6962 |
| HTR1F | GCAGCCACTACCCTGGGA | GATACCCAAGCCATGCCA | 6857 & 6858 | IFI35 | GGGAGCTACTGCCAGGGA | ACCAGTACCGAGCGGGGA | 6963 & 6964 |
| HTR2A | AGGCAGGAGGAGACTATGCA | AGCAGGCCCCAATGACA | 6859 & 6860 | IFI44 | GCCTGTGCAGGGATGACA | GCCACATGTACCACACCA | 6965 & 6966 |
| HTR2B | CACCGAAAAGGTGGCAA | AGGGACACACATAAGCA | 6861 & 6862 | IFI44L | TAACCCAGCGTGTATAGGA | CTGCCCCATCTAGCCCA | 6967 & 6968 |
| HTR2C | ACCAGAACCCACGCCGAA | GGGCACCACATGATGAGA | 6863 & 6864 | IFIH1 | AGGAGTCAAAGCCCACCA | TGACGAGCCATTAACGGA | 6969 & 6970 |
| HTR3A | GCGGGATGAGATCCAGA | GCCAGATGGACCAGAGCA | 6865 & 6866 | IFIT1 | ACCTGGACAAGGTGGAGA | ACAGCCTGCCTTAGGGGA | 6971 & 6972 |
| HTR4 | TCAACAAGCCCTACGGCA | AGGCCTGCTCTCGGAGGA | 6867 & 6868 | IFIT2 | GCCTTGGAGAAAGCCCA | GCCTATAGCAGCACCCA | 6973 & 6974 |
| HTR5A | CTGCAACAGCCAGCAGGA | AGGGAGCTCAGCAGACCA | 6869 & 6870 | IFITM1 | CCGTGATCAACATCCAA | GCCAGAAGCCAGGCACA | 6975 & 6976 |
| HTR6 | ACAGCACCATGAACCCA | GGTGCGCAGTGATGGCGA | 6871 & 6872 | IFITM2 | CAGCGGCCAGCCTCCCAA | TGCTATGAAGCCCAGGCA | 6977 & 6978 |
| HTR7 | CTGTGGGTGGAGGAGGACA | GGTACTGGCACTGGAGCA | 6873 & 6874 | IFITM3 | TCCAATCCGCAGCGAGA | GGCCAGATGTTCAGGCA | 6979 & 6980 |
| HTRA1 | GCACCGGGACTTCCCAGA | CATCATTGGCGGAGACCA | 6875 & 6876 | IFLTD1 | CAGCAGCATCTGAAGCA | ATAGGGGTGACCACGCA | 6981 & 6982 |
| HTRA2 | TGACCCTGAGTCCAGCA | TCACATCACCAGGCCGCA | 6877 & 6878 | IFNA1 | GAGGAGAGGGGTGGAGAGA | CAACCTCCCAGGCACA | 6983 & 6984 |
| HTRA3 | GCAAGAGGTTGCGCCGAA | GCAGCTCACTGGAGTCCA | 6879 & 6880 | IFNA10 | GGTTGGGGTTGGAAGAGA | CAACCTCCCAGGCACA | 6985 & 6986 |
| HTRA4 | GTGGAGAAGTGGGCGCCA | CCCCATTCTGGAGCACCA | 6881 & 6882 | IFNA13 | GCTGGATAACAGGGAGGA | AGGACAGGATGGCTGGA | 6987 & 6988 |
| HUS1 | AAGCTGGCTAATGGAGGA | CTGCAGAGACACCCTCA | 6883 & 6884 | IFNA14 | TCCAGAAAGCTCAAGCA | ACACAGGCTTCCAGGTCA | 6989 & 6990 |
| HUWE1 | TCCTACGGCAGTCCACGA | GACGGACATGCACAGCCA | 6885 & 6886 | IFNA16 | CCTGGCACAAATGGGAAGA | TCTCATCCCAAGCAGCAGA | 6991 & 6992 |
| HYAL1 | CCTGGATGAGTGTGAGACA | CCCAGCTCACCCAGAGCA | 6887 & 6888 | IFNA2 | GGTGGGGGTGACAGAGA | CAACCTCCCAGGCACA | 6993 & 6994 |
| HYAL2 | CGGGGTACACACAAGCA | CTGCAGCTGGGGTTCACCA | 6889 & 6890 | IFNA21 | GGGAACAGAGCCTCTTAGA | CAGCAGGATGGAGGTTCCA | 6995 & 6996 |
| HYDIN | GGTGCAGGAGAGACAGCAA | TTCGGAGGGGCAGACGGA | 6891 & 6892 | IFNA4 | CTGAATGACCTGGAAGCA | CCTCACAGCCAGGATGGA | 6997 & 6998 |
| HYOU1 | GGACAAGCTGAGGCCCA | CCTCTGGCAAGTCAGGCA | 6893 & 6894 | IFNA5 | GAGGTTGGAGTGGAAGACA | CAACCTCCATGCACA | 6999 & 7000 |
| IAPP | TGGCACATGTCGACGCA | GATGAGAAGAATGGCACCA | 6895 & 6896 | IFNA6 | GCAGCTGAATGACCTGGA | TCTCACAGCCAGGATGGA | 7001 & 7002 |
| IARS | CCCACTGTTGGGGTCAGGA | GAACCTGAGCATAGGGCA | 6897 & 6898 | IFNA8 | GGAAGTTGGGGTGATAGA | CAACCTCCCAGGCACA | 7003 & 7004 |
| IBSP | TACGAGGGGAGTACGA | GCCGGATGCAAAGCCAGA | 6899 & 6900 | IFNAR1 | CCGCAGCCGCAAGGTGGAA | AGTCACATTCCCGACAGA | 7005 & 7006 |
| ICA1 | GACCCCAAGGGCCCAGACA | GCAGTCAGGTCTGAGGCA | 6901 & 6902 | IFNAR2 | CCCAGGAGCTCGAGGAGGA | TCTCACAGGGCCCACTCA | 7007 & 7008 |
| ICAM1 | CAAGAACCAGACCCGGGA | GACACTTGAGCTCGGGCA | 6903 & 6904 | IFNB1 | AGCAGTTCCAGAAGGAGGA | AGCCAGGAGGTTCTCAACA | 7009 & 7010 |
| ICAM2 | CAAACACTCAGCCCCGAA | GCAGGACAGATGTCACGA | 6905 & 6906 | IFNG | GAATGTCCAAGGCAAAGCA | TTGCAGGCAGGACAACCA | 7011 & 7012 |
| ICAM3 | GTCCAGCTCACGAGGGCA | CGATAGTCACGCACGCCA | 6907 & 6908 | IFNGR1 | ACTCACGCAGGAAGGAAGA | AGTTGTAACACCCCACACA | 7013 & 7014 |
| ICAM4 | CGGCAGCCATTACACTGA | ATAGGTACGCAGCGCCCA | 6909 & 6910 | IFNGR2 | GAGCTGGGAGCACTCA | CCGTGAGGTATCAGCGA | 7015 & 7016 |
| ICAM5 | CCTGTCCCAAGTCACCAGA | CGCATTGGTGGCCACACA | 6911 & 6912 | IFNK | ATGAAACCCTCAGAAGCCA | GGACAATCTCCCAGGCACA | 7017 & 7018 |
| ICK | CTCCAGGAGGACAAGGCA | GTCATCCAAGTCAGCCCA | 6913 & 6914 | IFNL1 | GCTGCACCGGCTCCAGGA | CTCGCCTGGAGGCGGA | 7019 & 7020 |
| ICOS | GGGGCCAAATACTCGCGA | CCAGAACTTCAGCTGGCA | 6915 & 6916 | IFNL2 | TGGACCAGCCCCTTCACA | TGGAGCCGGTACAGCCAA | 7021 & 7022 |
| ICOSLG | AGCCCTACCGGAACCGA | TGACTTGAACAAGGCGA | 6917 & 6918 | IFNW1 | TAAAAGGGAGAGCCAGTTGCA | CATGTTCCAGGCAGCAGA | 7023 & 7024 |
| ID1 | AGGTGAGCAAGGTGGAGA | GCGGAGCCCGGACCGGCA | 6919 & 6920 | IFRD1 | GCCTTGGCAACAGATGGA | CCTCACTGCCCTCAGGA | 7025 & 7026 |
| ID2 | AGGAGCTTGGTGCCCAGCA | GATGGAGTCCAGGGCGA | 6921 & 6922 | IFT88 | CGCATAAAGTCAGGCAGA | CCACTATCACCGCTAGCA | 7027 & 7028 |
| ID3 | CAGCTGAGGAGCGGCTGA | TCGGAGCTCCGGGTACCA | 6923 & 6924 | IGF1 | CACAGGGGTATGCGCCA | TGGCGTGGGCACGGACA | 7029 & 7030 |
| ID4 | GGAGGCTGGTGCCCCACCA | GCGCCAGCTCCAGGTCCA | 6925 & 6926 | IGF1R | CCAGGAACAACGGGGAGA | CCAGCTGTTGGAGGCCGCA | 7031 & 7032 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| IGF2 | CCGGACAACCTCCCCAGA | CACGCAGGAGGGGCAGGCA | 7033 & 7034 | IL17RB | GTGGCAAGAGCAGGAGA | GGGGACAACTGAGAGCA | 7139 & 7140 |
| IGF2BP1 | AGGCTCCCGAGCAGGAGA | TGATGGAGGCGGCTGGCAA | 7035 & 7036 | IL17RC | CAAAACCCCGGTGGCACA | GTCAGGTTCCAGAGGCCA | 7141 & 7142 |
| IGF2R | ATCAGGCGTCCACAGCCA | GGGCCAGAGACTTGCAGA | 7037 & 7038 | IL17RE | GGATACCCAAGCCCAGCA | CTGGACATCTGACCGCCA | 7143 & 7144 |
| IGFALS | CTTCCAGGGGCTGGGCAA | CCAAGAGGGTGTTGGGCA | 7039 & 7040 | IL18 | CGGGGCAGATCACCAGA | CCAGGCTAGAGCGCAA | 7145 & 7146 |
| IGFBP1 | GGCCCCTTCTGAAGAGGA | TGGAGAGCCTTCACACCA | 7041 & 7042 | IL18BP | GCTAAGGCAGTGTCCAGCA | GGGGCAAGGTTGCCCTCA | 7147 & 7148 |
| IGFBP2 | CTCCCTGCACATCCCAA | GGGGTTCACACACCAGCA | 7043 & 7044 | IL18R1 | GGCTGATATCCCAGGCCA | CTAGGCACATACTGCCA | 7149 & 7150 |
| IGFBP3 | CAAGTTCCACCCCTCA | CCGGCTTGGACTCGGAGGA | 7045 & 7046 | IL18RAP | CCAGTTCCGTCCAACTGA | GGTAGGTTCCGGTACAGCA | 7151 & 7152 |
| IGFBP4 | GGATGGGCAGCGTGGCAA | CCAGCTGGTGGCAGTCCA | 7047 & 7048 | IL19 | TGCCACCAGAGTCATCA | GTCGAGCTTCCCCAGGGA | 7153 & 7154 |
| IGFBP5 | GCCCAATTGTGACCGCAA | CTTGTCCACGCACCAAGCA | 7049 & 7050 | IL1A | TCTGGGAAACTCACGGCA | CCCTGCCAAGCACACCCA | 7155 & 7156 |
| IGFBP6 | GCAGAGACAACAGAGGA | GCTGCAGCCACTGAGTCCA | 7051 & 7052 | IL1B | GAACTGCACGCTCCGGGA | AGGACATGGAGAACACCA | 7157 & 7158 |
| IGFBP7 | GCGAGCAAGGTCCTTCCA | TGTCCGGTGCATCAGGGA | 7053 & 7054 | IL1R1 | GTTGCAGGAGACGGAGGA | CAGCCACATTCATCACGA | 7159 & 7160 |
| IGFBPL1 | ACGGTCGCTCGTACCCCA | AGCCCTCACTTCACAGGA | 7055 & 7056 | IL1R2 | TAAGTGTGAGGGCAGGCA | ACACAGGTGGTAATAGCCA | 7161 & 7162 |
| IGFL1 | TGCCAGCCACACAAGAGA | GGGTCCTGGCCAAGGGCA | 7057 & 7058 | IL1RAP | GGGACCTTGAGGAGCCAA | GGCCGGAACCACAGCACA | 7163 & 7164 |
| IGFL2 | CCCGCTGGCTCAGAACCA | GCAAGGCCAGAAGGTGCA | 7059 & 7060 | IL1RAPL2 | ATGAGATACCAGCCACGA | TGAG1AGCGTCAGAGGCA | 7165 & 7166 |
| IGFL3 | TGTGCCAGCCGAACCCTCA | TCATACCCAGAAACCCTCA | 7061 & 7062 | IL1RL1 | AGTGGGAGGAGGACCACA | TTCTGGCAGCCAAGGGA | 7167 & 7168 |
| IGJ | CTACAGAAGTGGAGCTGGGA | CCACCATATACGAGTGGGA | 7063 & 7064 | IL1RL2 | CCCTGATCCAGGACGGA | TGCAGCAGCTGGACCGGA | 7169 & 7170 |
| IGLL1 | TGAGGAGCTCCAAGCCAA | ACCGTCAAGATTCCCGGA | 7065 & 7066 | IL1RN | GACCTGAGCGAGAACAGA | GGGCAAGGCGGCAGACTCA | 7171 & 7172 |
| IGLON5 | GACTGCTGCAGCCGGCGA | CCAGGAATCCTTCGGCGCA | 7067 & 7068 | IL2 | GCCAAGAAGCCCACCAGA | TCAGATCCCTTTAGTTCCAGA | 7173 & 7174 |
| IGSF1 | GGCTCAGAGACAGACGGA | GGAACGGGCAGTTCCACA | 7069 & 7070 | IL20 | GTGCAAGCCAAAGATGGA | ATGGCGCAGGAGGAGCA | 7175 & 7176 |
| IGSF11 | CACAGAGTCAGTCAGCCA | TGTTGACCCGGGACCAGA | 7071 & 7072 | IL20RA | GCACACAGACTCGGAGGA | CCCTCCTCCGAGCCCA | 7177 & 7178 |
| IGSF21 | GCTCCACGACACACA | GTGGGGCCAATGGAACCA | 7073 & 7074 | IL20RB | GGCCTACTGGAGGAGGGA | CGACCACAAGGATCAGCA | 7179 & 7180 |
| IGSF2Z | GAATGCCCCTACCCAGGA | ACTGAGCTGGGATGGCACA | 7075 & 7076 | IL21 | GCTGAAGTGAAAACGAGACCA | GTCCCAAGAAGATGACCA | 7181 & 7182 |
| IGSF3 | TCAGCCTCACCGTCAGA | GGGCTCCAGAACCGACA | 7077 & 7078 | IL21R | CCGGCCTGGATATGGACA | GTGGCGGAGGAATGACCA | 7183 & 7184 |
| IGSF6 | ACAGGAGGAGGAGACCACA | AGAGGAGTATGAAGGCCA | 7079 & 7080 | IL22 | CCCTATATCACCAACCGCA | TCAGATTGAGGGAACAGCA | 7185 & 7186 |
| IGSF8 | GGTGGAGCGACCAGAGGA | GTCGGCATGCTGCACCCA | 7081 & 7082 | IL22RA1 | GGGGAGGGAGGGACACCA | CACACAAGGGACTCCAGGA | 7187 & 7188 |
| IHH | GGCTGACAATCACACGGA | AGAAGGCCAACTTGAGCCA | 7083 & 7084 | IL22RA2 | AAGTGGATGCTGGCAGCA | TGAATAGCTCCCAGCCGA | 7189 & 7190 |
| IK8KAP | ACTGGACGACTTCAGCCA | GTGCACATGGGAGGCGGA | 7085 & 7086 | IL23A | CCCAAGGACCTCAGGGACA | GCTGAGGGCCCAGTAGGGA | 7191 & 7192 |
| IK8K8 | CTCAGCAGCTCAGGGAA | CGCCCACAGAGCTCCACA | 7087 & 7088 | IL23R | AACGCACTTAGGCATGGA | TGACGGCTGCAGAAGGTA | 7193 & 7194 |
| IK8KE | TCAGCAGCAGCCTGGGAA | GGGAGCATCTGGAGAGGA | 7089 & 7090 | IL24 | CCATCAGAGACAGTGCACA | GGGAACAAAACAGTGCCA | 7195 & 7196 |
| IK8KG | TTCCAGGCTGAGAGGCA | GCCTGGGAGACCTCGA | 7091 & 7092 | IL25 | CCCCAGGACCTCTACCA | GTGTAGGACGAGCTCCGA | 7197 & 7198 |
| IK2F2 | GCGATTCAGCTACCCAGA | CTGGGCCACTTCAGCGA | 7093 & 7094 | IL26 | CATTGCCAAGACAAGCA | AGCGTCAACAGCTTGGGA | 7199 & 7200 |
| IK2F4 | CGCCAAAGAGGAGCCCA | TGAAGCCATGGCAGCCCA | 7095 & 7096 | IL27 | CCCGGAGGAGGAGGAGGA | GCCAGGCTTGGACCCA | 7201 & 7202 |
| IL10 | CCCCAAGCTGAGAACCA | AGGGAAGAAAATCGATGACA | 7097 & 7098 | IL27RA | AGAGGTTCCCAAGGGACCA | CAGCTCCAGGGGACCCCA | 7203 & 7204 |
| IL10RA | GCTGCAGTGACCTGGGAA | GGCTAGAGATGAGGGGCA | 7099 & 7100 | IL2RA | CACGGGAAGACAAGGGTGGA | GTTGTGACGAGGGCAGGAA | 7205 & 7206 |
| IL10RB | AGCTGGGGAATGCAGTGA | GCAAGGCAGCCAGGCCGA | 7101 & 7102 | IL2RB | CCTGAAGTGTAACACCCGA | GCGAGATCTCAGGTGCCA | 7207 & 7208 |
| IL11 | AGGCCTGCGAGACGGACCTA | GCAGGGCCAGGCGGGACCTA | 7103 & 7104 | IL2RG | GGACTGACTGGGACCACA | ACCACGGCTTCCAATGCA | 7209 & 7210 |
| IL11RA | GCTACACACGCAGCCAGA | ACTGAGGCCAAGAACCCA | 7105 & 7106 | IL3 | AGGCCAAACCTGGAGGCA | CGGCCGTTGCCAGGGGCA | 7211 & 7212 |
| IL12A | AGGTGGAGTTCAAGACCA | AGGGCCTGCATCAGCTCA | 7107 & 7108 | IL31 | CTCACTCAGGCCCCTCGA | CAGGGCTGAACACGGCA | 7213 & 7214 |
| IL12B | GAACTTGCAGCTGAAGCCA | CCTGGACCTGAACGCAGAA | 7109 & 7110 | IL32 | TGAGGAGCAGCACCCAGA | CTGCATGGACCAGGGCCA | 7215 & 7216 |
| IL12RB1 | AGGCCAAGGCGCCACCAGGA | TGGTTCAGGCCAGGACCA | 7111 & 7112 | IL34 | CCCCAGGGCCAAACCTGA | GGGCTGCAAGACTGAGGA | 7217 & 7218 |
| IL12RB2 | CTGCTCCAACTGGCCACA | GGGAGCACCGTCCAGGGA | 7113 & 7114 | IL37 | CTGGCTGCCCAAAAGGAA | GTCACCCACCAAGGCTCA | 7219 & 7220 |
| IL13 | GCATGTCCGAGACACA | GAAGACGGCAGACACA | 7115 & 7116 | IL3RA | CAGGCGTCAACAGTACGA | GAACCGCTGGAGAGTCGA | 7221 & 7222 |
| IL13RA1 | CCCGAGGGAGCCAGCTCA | TGCTACACTGGGACCCCA | 7117 & 7118 | IL4 | CCACGGACACAAGTGCGA | CGGTCAACTCGGTGCACA | 7223 & 7224 |
| IL13RA2 | CAAGGGCATTGAAGCGAA | GCATGATCCAAGCCCTCA | 7119 & 7120 | IL4I1 | GACTCCAGTACAGCCGGA | TCCCGTCAGGCATGTGACGA | 7225 & 7226 |
| IL15 | GGCTTCCTAAAACAAGAAGCCA | TTGCAACTGGGGTGAACA | 7121 & 7122 | IL4R | GGAGGAGGAGGTTAGAGGA | TTCCAGGGCATGTGAGCA | 7227 & 7228 |
| IL15RA | GGCACCCCCTCTCAGACA | TGAGGTAGCATGCCAGGA | 7123 & 7124 | IL5 | GTATGCCATCCCACAGAA | ACAGTACCCCTTGCACA | 7229 & 7230 |
| IL16 | TCTCAAGGGGACCACGCA | CCAGTGTCACGTGCAGA | 7125 & 7126 | IL5RA | CTGCAGAACGACCACTCA | GCCAACAAGCCAGGTGCA | 7231 & 7232 |
| IL17A | CGCATGGGAACGTGGA | CCCTGGCAGGACCAGGA | 7127 & 7128 | IL6 | GAAAGCAGCAAAGAGGCA | CCAGATTGGAAGCATTCCA | 7233 & 7234 |
| IL17B | CGCATGGAGGAGTATGAGA | GGACATCCACAGCTGCAA | 7129 & 7130 | IL6R | TCCACCCCATGCAGCAA | GGAGCGTTCCAAGGCCA | 7235 & 7236 |
| IL17C | AGGACCGCTCATCCACAGA | TGAACGGGGCAGCACGCA | 7131 & 7132 | IL6ST | GCGCTGTGGAGACGCGGA | ACAAGGCTTGCACTAGCCA | 7237 & 7238 |
| IL17D | GCTGTTCGGCAGGAGGA | AGGCAGGTGCAGCCA | 7133 & 7134 | IL7 | GCTCGGCAAGTTGAGGCAA | TGGGCTTCACCCAGGGGA | 7239 & 7240 |
| IL17F | GGAAGTTGTACAGCCCA | AGGTGCAGCCAACAGTCA | 7135 & 7136 | IL7R | TAGCTCAGGGGATGATGGA | ATCGGGGACTTGGGCCA | 7241 & 7242 |
| IL17RA | GGTACCCGCTCATGGACA | ACCAGTCGGGACAAGGCGGA | 7137 & 7138 | IL8 | AGCCACCGGAGCACTCCA | AGGCTGCCAAGAGAGCCA | 7243 & 7244 |

FIG. 1 (cont.)

| GeneName | Forward Primer | Reverse Primer | SEQ ID NOs | | GeneName | Forward Primer | Reverse Primer | SEQ ID NOs | |
|---|---|---|---|---|---|---|---|---|---|
| IL9R | CTGGAGACCCAGCAAGGA | ACCGAGCCTTGCTGAGGA | 7245 & 7246 | IRAK3 | GGCCTGAGGGATAGACAGA | CACAAGAAGAACTGGGCA | 7351 & 7352 |
| ILDR1 | CCCTCATCCAGTGCAGGCA | GGAGGGCAAGGAGGAGGAGA | 7247 & 7248 | IRAK4 | AGGGTGCAGCTAATGGCA | TCCACAGCTGGAAGTCCA | 7353 & 7354 |
| ILDR2 | CTGCCCATGCTGCCCAGA | ACACCGGAAGACAGAGGGA | 7249 & 7250 | IREB2 | GGCTGCCAAAGGACCGTA | CTTACCGGAGAGGCCCA | 7355 & 7356 |
| ILF2 | ACAGGGCGCTGCTTGCAGA | GTGAGAGGATTCGGACGA | 7251 & 7252 | IRF1 | AGCTGTAAGGAGGAGGCCA | GGATGGAGGGCAACCGGA | 7357 & 7358 |
| ILF3 | GGCGGCTCCTCATACCAA | TAGGAGCTGGGAGGGCCA | 7253 & 7254 | IRF2 | CGGCCTTCTAAGAAAGGA | GTTGAAGTCAGGACCGCA | 7359 & 7360 |
| ILK | GCTGGCAGGGCAATGACA | GGTGGAGACTGGCAGGCA | 7255 & 7256 | IRF3 | CTTCACGGCGAAGGAAGGCGGA | ACAACCTTGACCATCACGA | 7361 & 7362 |
| ILVBL | CCTCAGCCACAGCAGCAA | CCCACATCTCCCTGCACA | 7257 & 7258 | IRF4 | GCCAGCTGGACATCTCAGA | AGGGGTGGCTCATGGA | 7363 & 7364 |
| IMMT | AGAGCTCTGCCCTGAGGA | GCTAGCTCCAGATCACCA | 7259 & 7260 | IRF5 | CAGACCAACACCCCACCA | GTCGAGCTGCTACAGGCA | 7365 & 7366 |
| IMP3 | GTGGACCAAGGGCACGTA | CTTGGACGAGTCCACCA | 7261 & 7262 | IRF6 | CCCACCAGAAAGGACAGA | GAGATCTGCAGGCGGACA | 7367 & 7368 |
| IMP4 | GAAGACAGAACACCGCAA | GTAAGGGTGCCAGGCGCA | 7263 & 7264 | IRF7 | GGAACTGTGACACCCCA | TGGACAGGGAGAGGGTGA | 7369 & 7370 |
| IMPA2 | GCTGCATGCCAAGGCGCA | GTCGAGGGGTCCACCCGA | 7265 & 7266 | IRF8 | CTTCCGAGAGTGCAGCA | ATCACGAGGCGGCTCCA | 7371 & 7372 |
| IMPDH1 | TGACAGCAGCCCAGGCCA | TGGAGGCTCCAAGGGCCA | 7267 & 7268 | IRF9 | CATCCTAGTGGCCAGCAA | TCTGAAGAGCTCCACGCA | 7373 & 7374 |
| IMPDH2 | TGCCAAGAGCTTGACCCA | TGGAGGCTATGGACGCCA | 7269 & 7270 | IRG1 | GGAGCATGAAGCCCGTCA | GAGGGTACTCCAGCTCCA | 7375 & 7376 |
| IMPG1 | GGTACCAGAGCGACGCGA | GGTCGTTGGAGAAGGCCA | 7271 & 7272 | IRGM | AGCCTCAGCAGATGGGAA | GGAACATCCATTGCCAGA | 7377 & 7378 |
| IMPG2 | CTCCACCTGCTAGAGGA | GCCAAGCCACACTAACCA | 7273 & 7274 | IRS1 | TACGTGGACACCTCGGCA | AAGGCGCTCATGCCCCA | 7379 & 7380 |
| INCENP | GCACTTGGAGGATGAGGA | AGGTCGGGGTCATGAGCA | 7275 & 7276 | IRS2 | CGACTTCAGCTCCCCAA | CGGCTGCAGAGACGACGA | 7381 & 7382 |
| ING1 | TCGACCCAACGAAACCCA | GCACTTGGGACAGTACCA | 7277 & 7278 | IRS4 | GGGCTCAGGAGGAAAACCA | TGGCCACCACCTGAGCCA | 7383 & 7384 |
| ING2 | TCCTGACCGGGACGCGA | CATGTCGTGGAGCTGGGA | 7279 & 7280 | IRX6 | CGACTCTCAGTCCCCAGA | TCCAGACGGGTACTGGCA | 7385 & 7386 |
| ING3 | AACTCCGGCGACAGCGA | GTGAAGCGGTCCCGCAGA | 7281 & 7282 | ISCA1 | GCAGCCCTCACCTGACA | CCCTGGTTCGGACACCA | 7387 & 7388 |
| ING4 | TGGATCCCAACGAACCCA | TTGGGAGCACGCGTGGGCA | 7283 & 7284 | ISCU | GGAAAAGACCGTGGAGGAA | CAGCATGGAGCAGTGCA | 7389 & 7390 |
| ING5 | CAGGAGACATCAGAGGA | CGTGGTAAGGTCACGCA | 7285 & 7286 | ISG15 | GCAAGTGAGCGGGCTGGA | CAGGGGCTTGAGGCCGTA | 7391 & 7392 |
| INHA | CCCAGTGGAGGGGAGAGA | TCCACCGTTCCCAGCCCA | 7287 & 7288 | ISG20 | GGGTCACCCCTCAGCACA | TCAGGTCATGACCCCA | 7393 & 7394 |
| INHBA | CCACCAAGCTGAGACCCA | ACCCACACTTCCACGA | 7289 & 7290 | ISG20L2 | CCCAGAAGTTGCCACGGA | CAATGCTACATGGAGCCA | 7395 & 7396 |
| INHBB | TGGTGAACCAGTACCGCA | GCACGTCCCGCTTGACGA | 7291 & 7292 | ISLR | GACAACGACGGCTTGACCA | GCCTCAGGGTTCCACGCA | 7397 & 7398 |
| INHBC | GGCAGTTGCCCACTACACA | GGCCCTTGGGTACAGCA | 7293 & 7294 | ISLR2 | CGTACCTCGAGTCCGAGA | TGGACTGGGACTCTACCA | 7399 & 7400 |
| INHBE | CACTCCTCGGTCCCACCA | TGGTGCTCAGCCAGGAGA | 7295 & 7296 | ISM1 | CCGCATCCAAGCGCAAGGA | GGGACAGGCATGGAGCGGA | 7401 & 7402 |
| INHMT | CGATGTCCACCTGGGCAA | CCACAATGTAGGAGCGGGA | 7297 & 7298 | ISM2 | GCAGTTGGGAACTGCAGCA | TGCCAGGACAGGAGGAGGCA | 7403 & 7404 |
| INPP4A | GAACGTGCATGCCCGACA | GCTCCAGTGTCCACCGACA | 7299 & 7300 | ISOC1 | AGTTGCCGAGCAGGTCGA | ATCCCGGTTCGAGCGACA | 7405 & 7406 |
| INPP4B | CCCAAGACCAACCCCCA | TCCCCACATTGGCCCACA | 7301 & 7302 | ITCH | CAATGGGAAGACCCCAGA | GCTGACACCAGAACCGGA | 7407 & 7408 |
| INPP5A | TCCGAGACAACAACGGCA | AGCACCAGCTCCTTGGCA | 7303 & 7304 | ITGA1 | ACTGCCATATGGAGGGAA | GGGTGACACGTACTGCA | 7409 & 7410 |
| INPP5D | CACAGGAGTCAGGGACCCCA | GAAGGAACTCAGGAGGACCCA | 7305 & 7306 | ITGA10 | CCTCAAGAGAGAGGCCA | GACTCGGCCTCAGGAGA | 7411 & 7412 |
| INPP5F | TTCTGAACAGGCCCACA | AAGCATGCTGGAAGGGGA | 7307 & 7308 | ITGA2 | AGAGTTGCCCGCGAGGA | GCTTCAAGGGCAGGGCTA | 7413 & 7414 |
| INPPL1 | TGGAGCGGGAGAAGCACA | GGTCAACACCATGAGGGCA | 7309 & 7310 | ITGA2B | GATGGAACGCAGCCAACGA | CCAGCTCACACAGCACCA | 7415 & 7416 |
| INS | CTAGTGTGCGGGAACGA | CCAGGCAAGGCTGCA | 7311 & 7312 | ITGA3 | CAGGGCCATCATCCCACA | GATGGGGCACTCTAGCCA | 7417 & 7418 |
| INSR | CCCTGCTGCGGGACAGA | GTCAAGGACAGCTGGACA | 7313 & 7314 | ITGA4 | AGCCAGCATACTACCGA | GCATTGAGGCGTTGCACGA | 7419 & 7420 |
| INSIG1 | GTCTGGACCTGCCAGCCA | AAGAGGACCGGGAGGAGTCA | 7315 & 7316 | ITGA5 | GCCTCAGAAGGAGGAGGGA | TTCCAGAGCCTGGGGACA | 7421 & 7422 |
| INS-IGF2 | GACCGGAGGCGACCGTGA | GGCAGGGGCTGCAGGCCA | 7317 & 7318 | ITGA6 | GGCTGCCAAATGCCAGGCA | GCATCAAGATCCCAGCGA | 7423 & 7424 |
| INSL3 | GAGGAAAATCAGGGGCCCA | GGGCATCTGTCACCCCA | 7319 & 7320 | ITGA7 | CATGCAGTCTGAGCGCGGA | TGAGGAAGGCAACGTCCA | 7425 & 7426 |
| INSL5 | ACTCTGCGGCCATGCAA | GTGCAATCAACCGTGAGA | 7321 & 7322 | ITGA9 | GATGGCTGACGTGGCCAA | CGTTCACATGGGCCACA | 7427 & 7428 |
| INSL6 | CAGCAAGGGCGCTCAGGCA | GCAGGCACCTTGCAGGA | 7323 & 7324 | ITGAE | CATGCCCACAGAGGGGAGA | CAGTGTAGTCGGTCCAGGA | 7429 & 7430 |
| INSM1 | CGGTCAACGAGTCAGGCA | TGGACACCACTCCCAGGA | 7325 & 7326 | ITGAL | TGGCAGAGGGTGTCCCGAA | GATGGGGCACTCTAGCCA | 7431 & 7432 |
| INSM2 | CTACCTGGAGGGTGGCACA | AGGGCGTGAGGTGGCACA | 7327 & 7328 | ITGAM | CGAGTACGTGCCACACA | CAGCAGGGCGTGAACAGGA | 7433 & 7434 |
| INTS3 | CCAGCTGGAACACAGGGGA | GCCTGCCGCTCCAGCACA | 7329 & 7330 | ITGAV | GCAAGGTGAGCGGGACCA | GCACTGAGCAAACTCCACA | 7435 & 7436 |
| IP6K1 | CTGACTGAGTCAAGGCA | AAGTCGATCATGCGCACA | 7331 & 7332 | ITGAX | GGGTCAAGACTTCACCCA | ACCCCACCCAGAGCACA | 7437 & 7438 |
| IP6K2 | GAGGAAATCAGGCAGGAA | GTCATCAGGGGCAGGGGA | 7333 & 7334 | ITGB1 | AGGTAGAAAGTCGGGACA | ATTCCAGCACACCACCA | 7439 & 7440 |
| IPCEF1 | CAGTGGGAGAACCAGAGCCCA | TGATGAGCCCTGCACGCA | 7335 & 7336 | ITGB1BP1 | CAGTTCCCAAAGTAGGGA | GTGTCGAGGCTGGCCACA | 7441 & 7442 |
| IPO11 | CAGGAAACCAGAGCCCA | AGAAGCTCGGGAGCCACA | 7337 & 7338 | ITGB1BP2 | TGGCATCCAGACCCTGA | GGCCATATACAGTTCACCA | 7443 & 7444 |
| IPO4 | CCCAACAGGTCAGGGAA | AAGGGGTAGTAGCTGCCA | 7339 & 7340 | ITGB1BP3 | GAGTGCAAGTGGAGGAGA | CCACACCGTTGGCCTTCA | 7445 & 7446 |
| IPO7 | GTGGACAAGCCGACAGCA | ACTTAGCAGGGTGCGGGA | 7341 & 7342 | ITGB2 | TGAGCGCTACAACGGCCA | GCATACCGTTGCACACGCA | 7447 & 7448 |
| IPO9 | GCCTGGAGATGAGAATGCA | TGGCATCACGGATAGCA | 7343 & 7344 | ITGB3 | GGGAGGCCTACATGACGA | CGGCAAGGCCAATGAGGCA | 7449 & 7450 |
| IQGAP1 | CCACAATTCGGAACCAGGA | TGCCATTCGGAACCAGGA | 7345 & 7346 | ITGB4 | GGAGGACCAAGAGGGCAA | CCGTTGAAGCTGCAGGGA | 7451 & 7452 |
| IQGAP2 | TCAACCTGCCCGACAGA | GGAGGGAGCTGGACGACA | 7347 & 7348 | ITGB5 | GCAGTGCCAATGCACGGA | TCCAGAGTGGAGCAGACA | 7453 & 7454 |
| IRAK1 | CACAGGCACGGGAAGCCA | TGCAGGTACTCGACGGGCA | 7349 & 7350 | ITGB6 | ATCCCTCCTGCAGCGGAA | TCCAGCCGCTCCTGCACA | 7455 & 7456 |

| GeneName | Forward Primer | Reverse Primer | SEQ ID NOs | GeneName | Forward Primer | Reverse Primer | SEQ ID NOs |
|---|---|---|---|---|---|---|---|
| LGALS3BP | ACCTCCCCACCATCCAGA | CGAAGAGCCCTTCGCAGA | 8093 & 8094 | LLGL2 | GCCCTGACATGCAGGAA | CGCCCAGGTTGGTAAGGA | 8199 & 8200 |
| LGALS4 | CGGTACCGTGGTCCGGAA | CACCCTCTGGAAGGCCGA | 8095 & 8096 | LMAN1 | CAAGCAGCTGAACCGGCA | GCCATGCTGCCCAGGGA | 8201 & 8202 |
| LGALS7 | GCTGTCGCGGGAGGAGCA | CTGACGCGATGATGAGCA | 8097 & 8098 | LMAN2 | ACACGCCGCACGAGGAGA | GATGCCCAGGAGGAGGCA | 8203 & 8204 |
| LGALS8 | ACAGGATCGGCCCAGAGA | AGCTGGGCGCTGCCAGA | 8099 & 8100 | LMAN2L | CACAGCCAATTGTCCGCAA | TGATGGAGGAGGTGCCGA | 8205 & 8206 |
| LGALS9 | GGGGGTCTGAGGAGCGAA | GCTGACCATCCACGCCGA | 8101 & 8102 | LMNA | GACCTGGTGTGGAAGGCA | CCACAGTCACTGAGGCGA | 8207 & 8208 |
| LGALS9B | CCCAGCTCCCATTACCCA | GGATGGCGGAGTAGAGA | 8103 & 8104 | LMNB1 | GTGACAGTATCCCGACCA | TCCAGTGGCTGAGGCGGA | 8209 & 8210 |
| LGALS9C | AGGTGATGGTGAACGGGA | CACCTGGGAGGAACGGCA | 8105 & 8106 | LMNB2 | TCTTGGAGGGGGAGGAGA | CGCCATCCGCGTTAACCA | 8211 & 8212 |
| LGI1 | GGAAAAGACCTTCCGGAA | TAGATGTGAGAGCCACCA | 8107 & 8108 | LMO1 | CCTCTACCACCAAGGCAA | CCCGCATCACCATCTCGA | 8213 & 8214 |
| LGI2 | CATCCCAACATGGAGGA | CCACCTCATGACCCGGGA | 8109 & 8110 | LMO2 | GGACTGCCTGAGCTGCGA | TGTCAGGGATGCGCAGA | 8215 & 8216 |
| LGI3 | GAGTCGCACCCAAGAAGCA | TGTAGTCGGCTGAGGCACA | 8111 & 8112 | LMO7 | CAGTCAGTGGGAAGCGCA | GAAGAGCCTCCGAGGTCA | 8217 & 8218 |
| LGI4 | GCTCATCCCAAGAGGACCA | TGTCAGCCCAAGGGCGA | 8113 & 8114 | LMOD1 | GCAAAGGCAGGCACAGGA | AGGGGTGGAGCCAAGGGA | 8219 & 8220 |
| LGMN | AGCAGCTCCTGTCCGAGA | GGAGTGCCAGTTGAAGCA | 8115 & 8116 | LMX1A | CCAGATGCCTGGAGACCA | CCCACTCTGGACTGCAGA | 8221 & 8222 |
| LGR4 | CCTCAGTCCCGAGGACA | GCGCCTGTAGGGTGGGCA | 8117 & 8118 | LNPEP | ACTCAGCTCACACCCGAA | GTGACTGAAGAGCCTGA | 8223 & 8224 |
| LGR6 | CCAGGTCGAGATGAGGAGGA | CAGCGAACACGGTCAGCA | 8119 & 8120 | LNX1 | AGTGTTGAGCCCGGAGGA | AGTTCGACCCCATCCACA | 8225 & 8226 |
| LHB | GGCATGGCATCCACCAGGA | TAGGTGCACACCACCTGA | 8121 & 8122 | LNX2 | GTGTCGCAACCTGCACA | CCATTCGCGTCCAGGCCA | 8227 & 8228 |
| LHCGR | TTACCAAGACACCCCGA | CTGAGGCTATGAGCAGCA | 8123 & 8124 | LONP2 | GATGAAGAGGTCCGCCCA | CTCCAGCTGGGAAGTGCA | 8229 & 8230 |
| LHFP | GGCTGGGACAGTGAGGAA | CGTGCAGTAGTAGGCCCA | 8125 & 8126 | LONRF1 | GCACTGCCGACATTGAA | CGTGGGTCTACAGGGAGAA | 8231 & 8232 |
| LHPP | GCCCAGGTGACGAGGTCA | GCTCAGCAGCAGCAGGTCCA | 8127 & 8128 | LOX | CGGCATGGTGCGGCAGA | GCCACGAGCTGCCGAGA | 8233 & 8234 |
| LHX1 | GACATCCTCGGCGCACCA | CGCCCACCGTTGACCGA | 8129 & 8130 | LOXL1 | TCTGCTGGAGGACAGA | CGATCCACTGGCAGTCGA | 8235 & 8236 |
| LHX2 | GCGCAACTTCTACGGCA | TGAGCGAGGCGTTGGAGA | 8131 & 8132 | LOXL2 | GACCACCTACCTGGAGGA | TCTGGGAGGAGAAGCGCA | 8237 & 8238 |
| LHX9 | TCTGACCACGGGCGACCA | TGAAGTAAGGCAGGGCCA | 8133 & 8134 | LOXL3 | CCCATCATGGCACCACA | AGGCGGTCTCCTGCACCA | 8239 & 8240 |
| LIF | ACATACCGGGACTCAGA | ACACACGTTGCTAAGGA | 8135 & 8136 | LOXL4 | ATGGACTGCCCCTACGGA | TCAGCCACCTTGGAGCCA | 8241 & 8242 |
| LIFR | AGTGAGGGACTGCACA | GCCCTCTCACAGGGTCA | 8137 & 8138 | LPA | GCCTCAAGTGAGGCCGAA | AGAAGCAGTCAGCACCCA | 8243 & 8244 |
| LIG1 | TGTGGAGACAGAGGGCGA | CATCAGCCCCTCGCAGGA | 8139 & 8140 | LPAL2 | CGACGGATCCCAATGTCA | TAACAGTCAGAGGCACGA | 8245 & 8246 |
| LIG3 | CAAGTGTGCACACGGGCA | GTGATTCTCCACAGGGA | 8141 & 8142 | LPAR1 | GGCGGAATCGGGAGATACCA | ATAGGCCAGCACGTCGGA | 8247 & 8248 |
| LIG4 | AAGCTCACCAAGGCAGA | AAACGCAAGGTGCAGCCA | 8143 & 8144 | LPAR6 | GTGATCGGAGGGAAGTGCA | AAGCAGGCTTCTGAGGCA | 8249 & 8250 |
| LILRA1 | CACCCTCAGCCCATCACA | GCAGAATCCGAGGACCA | 8145 & 8146 | LPCAT3 | GGGCAAGGCAAAGTGGGA | CGTGCCAGAGGGCCAGGA | 8251 & 8252 |
| LILRA2 | CCAAGCGCAGCACCTGGGAGA | AGGGGGTCACTCGGGAGA | 8147 & 8148 | LPHN1 | GGAACCACCTGCTGACCA | CAGGGTGTCCATGCACCA | 8253 & 8254 |
| LILRA3 | CCGTGAGCCAAGTCGCA | GTCGTAGCCGGCATCAGA | 8149 & 8150 | LPHN2 | CTTACGGGGCAGCAGCAA | GGGTTGGTACAGAAGGGA | 8255 & 8256 |
| LILRA4 | GATGCTACGGGCCACACA | CGGTTCCATGACTGACA | 8151 & 8152 | LPIN1 | AGTGATGAGGAGGCGCGA | GCTCGGAAGTCAGCCGGA | 8257 & 8258 |
| LILRA5 | CTGTGAACCCCAGCCACA | AGGTGTGAGGCAGTCCCA | 8153 & 8154 | LPIN2 | GGGCAAAGACTGGACCCA | GAACAAGCTGCTGGGGGA | 8259 & 8260 |
| LILRA6 | CAAAGAAGGGGCAGGCCA | TCAGAGGACTCATGGGGA | 8155 & 8156 | LPL | ATGGCACCGTGGCCAGA | GCCGGAACGTGGCCAGA | 8261 & 8262 |
| LILRB1 | CTCCAGACCTAGGAGAGA | GGGGCTTCAGATGCAGCA | 8157 & 8158 | LPO | CTCTCAGCCGGCAGACA | CCCGACCCCTTTCCACCA | 8263 & 8264 |
| LILRB2 | CCTGAACTCCAGCCCA | CGGCTGCACTGAGAGTGA | 8159 & 8160 | LPPR1 | CAACAAGCTCCGAGGGGCA | CTCGGAGAATCCGCTCCA | 8265 & 8266 |
| LILRB3 | GATGAAGACCCCAGCGA | GAGGCTTCAGATGCAGCA | 8161 & 8162 | LPPR2 | AACAGGCTGTCTGCAGA | ACCAGCAATCACGTCCGA | 8267 & 8268 |
| LILRB4 | TACAGGGTCAGTCCCCCA | GACGCCAGTGTTGGAGGA | 8163 & 8164 | LPPR3 | CGGTCACCTACACAGCGA | GCACAACGCAGGTGACCA | 8269 & 8270 |
| LIMA1 | CGTTCCACCCTGCCGAA | CGGAAGCAGCTGATGTGA | 8165 & 8166 | LPPR4 | CACGCAGTACCGCAGCCA | AGGCCAGGTAGGCAGCGA | 8271 & 8272 |
| LIMCH1 | CTCCCAGTGAAAGGCGGA | GCCCACAAGAAGCACA | 8167 & 8168 | LPXN | CCTGCGGAGAAAAGGCAA | ATAAGCCCTGTGTGGGGGA | 8273 & 8274 |
| LIME1 | AGAGCACAGCAGGGGGAA | AGGCTTGCAGACCTTGGA | 8169 & 8170 | LRAT | CACAGTGCCCAAGGGCCA | GGGGATTAGGCCAAGCCA | 8275 & 8276 |
| LIMK1 | TCAAGAAGCCAGACCGCA | CGCACAGGACGATCCCA | 8171 & 8172 | LRBA | GGCACTGCTCAACGAGGA | GGACTGATCGGGGGTGCCA | 8277 & 8278 |
| LIN28A | AGCATCGAGAACGCAGA | GGGACAATGAGGCTACCA | 8173 & 8174 | LRCH3 | CGTGACCACGTGACAGA | CAGTAGTCAAGGCGCCA | 8279 & 8280 |
| LIN28B | GAGTCAATACGGGTAACAGGA | GATGATCAAGGCCACACCA | 8175 & 8176 | LRDD | AGAGGCGCACTCGGAGGA | GGGTAGCACGCAGCCGA | 8281 & 8282 |
| LINGO1 | AGGGAGAGGCCAACAGCA | AGAAGAGGACGACGGCCA | 8177 & 8178 | LRFN4 | CCTCCTGGGAGAACACAGA | GAGGCCTGTGATGCCAGA | 8283 & 8284 |
| LIPA | GAAGTGCTGGGTACCCA | TGCACAGAAGTTCCAGCA | 8179 & 8180 | LRFN5 | CTGACCTCAGGCCACCA | CCCGAACACGAAGGCCA | 8285 & 8286 |
| LIPC | GGGAAGTGCCCCAGGGA | CGATCGCTCGTGGGAGCA | 8181 & 8182 | LRG1 | GGCAACACAAGGTCACCA | TGGACACGCAGGGCCAGA | 8287 & 8288 |
| LIPE | CTGCTGGGGCATCAAGCA | GGTCCATGAGGCCAGGA | 8183 & 8184 | LRIG1 | TGACCAGAACCTGAGGGA | ACTTGGCCACTGCCAGGA | 8289 & 8290 |
| LIPF | GTGGAACGTGGCCAAGGA | GGGCATCCATTGCCCAGA | 8185 & 8186 | LRIG3 | CTCAGGCCAATGGGCACA | ACGAGACCCAGCACAGA | 8291 & 8292 |
| LIPG | GGTCTACACGAAGGCAGGA | GCGGGTTGAGACAGGTA | 8187 & 8188 | LRMP | GGCCACTGTTGGACCGAA | GATCAGTAGGCCAGGCGCA | 8293 & 8294 |
| LIPH | CAAGGTACAAGCTCAGGA | TCATACGGACACAGCTGA | 8189 & 8190 | LRP1 | GAAAAGGACAAGGAAGCCA | GTGGAGCCGATCCAAGA | 8295 & 8296 |
| LIPI | TGCAACCACCAGAGAGCA | ACAGTCACAGTCCACACA | 8191 & 8192 | LRP10 | CGCTGGAAGTGTGACCGGA | ATCAGAGCCGGTCCCACA | 8297 & 8298 |
| LIPM | AGCAGGAGGAGGTCAGGA | CTCACACCGTCCTGGGA | 8193 & 8194 | LRP11 | TCACTGCCCCTAGAGCA | CATCTTCCCAGGGCCAGGA | 8299 & 8300 |
| LITAF | ATACCAGCAGCCCCA | AGCCGCTATGCACCCCA | 8195 & 8196 | LRP1B | GCTACTCCACAGGAGGA | TTGCGCTCCAGGCCAGA | 8301 & 8302 |
| LLGL1 | GGTGAGCGCGGAAGACCAA | ACCCAGGTTGGTGAGGCA | 8197 & 8198 | LRP1B | CGCTGCATCCCCAAGAGA | CTGGGAATGCAACGCCCA | 8303 & 8304 |

| GeneName | Forward Primer | Reverse Primer | SEQ ID NOs | GeneName | Forward Primer | Reverse Primer | SEQ ID NOs |
|---|---|---|---|---|---|---|---|
| MALL | GCCTGTACCACGGGACCA | GAAGAACGAGGCTGCCGA | 8517 & 8518 | MAPKBP1 | TGAGCAGCCGAGAGGCAA | GTCAGGGTTGAGACGGCA | 8623 & 8624 |
| MALT1 | TTACCGGGAGCAGCCCAA | CATCCACAGCATTACGCA | 8519 & 8520 | MAPRE1 | ACTCAACGTCAGTGACCA | TTCAAGGCAATGGAGCCA | 8625 & 8626 |
| MAMDC2 | CCCACTTCCTACACAGGA | CCAGAGACTCCTCGGCAGA | 8521 & 8522 | MAPT | GCGAGAAGCGCCAAAGCCA | GCTGGGCGAGTCTACCA | 8627 & 8628 |
| MAMDC4 | GACCACCACACAGGCCAA | CTCATGGCTAGGCGCAGA | 8523 & 8524 | MARCO | CAGAAGGGAGACCACGGGA | GTAACCACGCATGCGGCA | 8629 & 8630 |
| MAML1 | CCTGGCAGCATCAGGGAGA | CTGAGCTCATGGGAGGCA | 8525 & 8526 | MARK2 | GAACAGCTGCCAGAGCGA | TCGAACCCGTTGAGAGA | 8631 & 8632 |
| MAML2 | CCACTTACCTTAGGGCCA | GAAGCGGACTCTGCAGA | 8527 & 8528 | MARK3 | TAGTGCAGCCACCCAGA | GGAGAGGCAGGAGGGCCA | 8633 & 8634 |
| MAN1A1 | CGCAAGTCTAGCAGCGGA | CATCAGCCCGAGTGCGA | 8529 & 8530 | MARK4 | CAGCCACAGCAAAGGGCA | TGCAGGGGATGGGCACA | 8635 & 8636 |
| MAN2B1 | AAGGACGATGGACGCGGA | GGGCTGTGTCCAGCAGCA | 8531 & 8532 | MAS1L | CATGGCAGTGGGACAGCA | TAAGAACCCACTGCTCGA | 8637 & 8638 |
| MAN2B2 | GAAAGGCCATCGCAAGGGGA | TGCAGCACAGCCTCCAGA | 8533 & 8534 | MASP1 | GAGCTGTTGGAGAGCCCA | AGCCGCTGACGATGACCA | 8639 & 8640 |
| MANBA | GCCGTAGTGCCAGGCGAGA | CTCAAGAGAAGCCCAGGA | 8535 & 8536 | MASP2 | TGCAGAGGTGACAGCGGA | TCATGGAACCCCAGGACA | 8641 & 8642 |
| MANEA | CGTCATGGGAACACGCAA | TGAAGTGCGGCACTCAGA | 8537 & 8538 | MAST1 | CCCCACTAGAGTCGGAA | GCGAGAAGCAGGAAGAGA | 8643 & 8644 |
| MANEAL | CTATGAGACGGCCCTGCA | GGTGAGGCAGGTAGTCCA | 8539 & 8540 | MAST2 | TCAAAGGCCGAGACCGGA | ATCCAGAGAGGCCTGAGGA | 8645 & 8646 |
| MANSC1 | GCAGTTCCTCCCAGGGCA | CCGAGAGGATTCTACCCA | 8541 & 8542 | MAST3 | CTCCACCGGTTCAGCAA | CTCAGCCGGATGTCAGCA | 8647 & 8648 |
| MAOA | TCGGGAAGGTGACGGAGA | GATCTTCAGCAGGGCAGA | 8543 & 8544 | MAST4 | AGCCCTGACTGGGAGGTA | CATGGCACGAGGTTGGA | 8649 & 8650 |
| MAOB | CACAGCCCATCACCACA | TTGTGGGCCAGGAAGCCA | 8545 & 8546 | MAT2A | TCTACCACCTACAGCAA | TTTGCCACCCAACGAGCA | 8651 & 8652 |
| MAP1B | GGTCGACAAGGCTGCAGA | AGGTTCTCGGCCAGGAGA | 8547 & 8548 | MATN1 | GGGTCCGTTCCACACCAA | GCCTAGCCCCACTGGACA | 8653 & 8654 |
| MAP1S | CCTCACCCACAGTGACCA | ACCAGGCACAGGTCCACA | 8549 & 8550 | MATN2 | GGCTGGCCCTGAAACACA | CGTCCGTCGGTGAACACA | 8655 & 8656 |
| MAP2 | ACCCCGACGACTGCACAA | CAGTGACATCTCAGCCA | 8551 & 8552 | MATN3 | CCCATGGGTGTCAGCACA | GGCCCATCACTCACACA | 8657 & 8658 |
| MAP2K1 | CCCCGCAGAGAGCAGA | GAGCAGAGCCAACCTGCA | 8553 & 8554 | MATN4 | GAGCTGTCAGGTCCGGA | CGCACGCTCTTGGAGCCA | 8659 & 8660 |
| MAP2K2 | CCTCCGAGAGAAGCACCA | CGACGGCAGCTCCACCA | 8555 & 8556 | MATR3 | CGGGAGCCACCATACAGA | GGGTTGAGACTAGGACCA | 8661 & 8662 |
| MAP2K3 | GGAGCCTGGGCATCACCA | GGGACGGCTCCTCCACCA | 8557 & 8558 | MAV5 | CGACGGAAGTTCCAGGA | GCCGGTACAGCACCACCA | 8663 & 8664 |
| MAP2K4 | CTTCGGCATCAGTGGACA | CAGACATCAGCGGACA | 8559 & 8560 | MAX | GGCTGACAAACGGGTCA | ATGGGACTGAGTCCGCA | 8665 & 8666 |
| MAP2K6 | AGGGGCCGATCATGGCA | GGTGACAGTGAATGGGACA | 8561 & 8562 | MAZ | CAGCCAGGGTCCTCACCA | GCTGAGAGCTCACAGGGA | 8667 & 8668 |
| MAP2K7 | CGCTTCTGCCGGACACA | CCTTGAACCAGGACGCCA | 8563 & 8564 | MB | CCCCGTGAAGTACCTTGGA | GCCCCTCAGACATCTGGGA | 8669 & 8670 |
| MAP3K1 | GCAGTGGGAAGCACCGGA | GTAGACAGGGTGCAGCCA | 8565 & 8566 | MBD1 | CCCATCACAGTCCCACAA | CTGACCAGACTCTGGGCA | 8671 & 8672 |
| MAP3K11 | GCAAGGTGTACAGGGGCA | GCACAGCCCAGTTGACCA | 8567 & 8568 | MBD2 | GAAGAGCGAGTACAGCAA | TATCAGCAGCTCGCGACA | 8673 & 8674 |
| MAP3K13 | TGGCAGAGAAGCTAGACGA | CACAGCTTGCCCAGAGACA | 8569 & 8570 | MBD3 | CCGACGAGGACATCAGGA | CCTCCCGTCACGGGCCA | 8675 & 8676 |
| MAP3K3 | GCAAACGCCTGCAGCCCA | CCACCACAGTGCAGCCCA | 8571 & 8572 | MBD4 | CCATCCCACGAACACAGA | AGCCATGAAGAAGCTTCCA | 8677 & 8678 |
| MAP3K4 | TCAGCCGGGTCATGCCAA | TCCACGGGGTCAATGGCA | 8573 & 8574 | MBD5 | CCAGCCTTCAGCAGGAGA | CCTTGGAAACGCCTGAGA | 8679 & 8680 |
| MAP3K5 | AGGCCGGTACAGACAGCCA | TCACGCTGAGGTAGGCA | 8575 & 8576 | MBD6 | CAAGTGTCACCACGGCAA | CCCAACTGGCCAGAGAGA | 8681 & 8682 |
| MAP3K6 | GCCACAGGGAGCAGAAGCA | GGTCTGTGCAGAAGCGCA | 8577 & 8578 | MBL2 | GAACAGGAGGTGAACCCAA | GGAACTGGCCAGACGGCCA | 8683 & 8684 |
| MAP3K7 | AGTGATAACGCCTGGGAA | CATTGAAGGGCGCTGGGA | 8579 & 8580 | MBNL1 | ACCAACGGTTGCCACGCA | GGGAACACTTGTGGCAGA | 8685 & 8686 |
| MAP3K8 | GCTGCTGAGTAGGAAGGA | GATTGAAGTAGGCCAGGCA | 8581 & 8582 | MBOAT2 | GGGATCTTGGCAGGGCCA | TAACAAGGACAGCCCACA | 8687 & 8688 |
| MAP3K9 | GCAATGGGTTGAGATCCCA | TGCCGGTTGCAGAAGGA | 8583 & 8584 | MBP | CCTGCCCCAGAAGTTCACA | GGTGTGCGAGGCGTCACA | 8689 & 8690 |
| MAP4K1 | GCACACCTGAGATCCCA | CACTACAGCCTGTCAGGGA | 8585 & 8586 | MBTD1 | TGCCATATGCACAGCCCA | GGAATCCGTCAGCTAGCA | 8691 & 8692 |
| MAP4K2 | CATGAAGCAGGAGGGAGGA | CACGCAGTAGAGCCAGGA | 8587 & 8588 | MBTPS1 | TGGCCGCTACAACCAGGA | AGAAGGCCAGGACCACCA | 8693 & 8694 |
| MAP4K3 | CCAGATTACCCCCACACA | GGTGTTGGAGGAAGACCA | 8589 & 8590 | MC2R | GGGCCATCACACTTGACCA | TCTGGGCTCCGGAAGGGCA | 8695 & 8696 |
| MAP6 | AGTGCCATGGCACCACCA | TCAGCACGTTGAGCCA | 8591 & 8592 | MC3R | GCATCATGCACGTCGAGGA | AGAGGGTTGCCCATGAGGA | 8697 & 8698 |
| MAP7 | TTCTGCAGCACCACCCA | CAGCACACGTTGAGCCA | 8593 & 8594 | MCAM | ACGTCAACGGCACGGACA | CCAGCTCAAGGAAGAGGA | 8699 & 8700 |
| MAP9 | GGATCTGAGGGGAAACGCA | CAAGGTCATCAGCAGTCA | 8595 & 8596 | MCCC1 | GTACGGCAAGGAGACGAA | GTCAATGCCGCCTGGCGA | 8701 & 8702 |
| MAPK1 | GGAACAGGCTGTTCCCAA | CCAGATATGGGGTGGGCCA | 8597 & 8598 | MCCC2 | GGCCACGATAACAAGGA | AACTGAGACCCAGAACCA | 8703 & 8704 |
| MAPK10 | TGACCCAGCGCACCTGAAGGA | ACTGCTGCCACCTGAAGGA | 8599 & 8600 | MCCD1 | AGATGACGTTCCCTCCA | GGGCCTGGTTACAGCTCA | 8705 & 8706 |
| MAPK11 | TTGAGGGCAAGGAGTGCA | GGGGCTTGAAGCTGAAGGA | 8601 & 8602 | MCEE | CCAGACTTCAAGCTCCCA | TCCACACAGAACTGTCA | 8707 & 8708 |
| MAPK12 | ATGAAGGGCTCCCCGAA | CCAAGTAGGGAGTCAGGCCA | 8603 & 8604 | MCF2L | CGGAGATCGTGAAGGAGGA | CCACAGGTTGTGAGGCCA | 8709 & 8710 |
| MAPK13 | GCTGGCCGACATGGCAGA | AGTGCATCCAGTCGAGGA | 8605 & 8606 | MCFD2 | GGGGAGTGAACAGGCACCA | ATAACCAGGAGATGGCCAA | 8711 & 8712 |
| MAPK14 | ACTGGCTCGGCAGCACAGA | CAGTCAACAGCTCCGCCA | 8607 & 8608 | MCHR1 | CAGCCGCATACGTGAGGA | AGTAGGGTGCCCAGGACA | 8713 & 8714 |
| MAPK3 | CGGATCACAGTGGGAGGAA | GCTCCATGGCGAAGGTGA | 8609 & 8610 | MCHR2 | GGATGCCAGATGCTGCAA | ACATGATAAGGGGCAGCA | 8715 & 8716 |
| MAPK7 | AGCGACCTGCACCAGA | CAGGCACGAGCCA | 8611 & 8612 | MCL1 | ACCTTCGGGAGCCAGGCCA | CATCCCAACCGTCCGTA | 8717 & 8718 |
| MAPK8 | CAGAAGCTCACCACCAA | GACGACGATGATGATGGA | 8613 & 8614 | MCM10 | GCGGATCTGCAGTCA | TGAAGCTGCATACGAGGCA | 8719 & 8720 |
| MAPK8IP3 | GCACGTCATCCAGCCCAA | AGTCCAGGCGGATGATGACA | 8615 & 8616 | MCM2 | CCATTACGGTGCGGCACA | TCTCCAGCATCACGCGGA | 8721 & 8722 |
| MAPKAP1 | GAAGCAGAGCGAGCCCAA | GTTCTCGCCGACCAGGCA | 8617 & 8618 | MCM3 | TCGCCAGCCAGATGCCAA | ACACATCCAAGAGGGCCA | 8723 & 8724 |
| MAPKAPK2 | CCAAAGGCCACCACACAA | GGGGATACCACACAGGCA | 8619 & 8620 | MCM3AP | GGACGCCGTTGAGAAGGA | GTCAGGGAATGGGGGCA | 8725 & 8726 |
| MAPKAPK3 | CACAGAGACCCCACTCCACA | CGCATAGTGCGCAAGGCA | 8621 & 8622 | MCM4 | CCGCTTAGCAGAGAAGCCCA | ACGATGCCAGTCCCGGGA | 8727 & 8728 |

| GeneName | Forward Primer | Reverse Primer | SEQ ID NOs | GeneName | Forward Primer | Reverse Primer | SEQ ID NOs |
|---|---|---|---|---|---|---|---|
| MYL4 | CAAGGAGGAGGGCACCTA | CTCCCAGGGTGGCAAGGA | 9365 & 9366 | NAPA | CGAACAGGTGGGGACCAA | GCATTCCGGGAATCAGA | 9471 & 9472 |
| MYL7 | GAGTGTCCCAGAGGAGGA | ACATGCGGAAGGCACTCA | 9367 & 9368 | NAPEPLD | TACATGGGTCCAAAGCGA | CTCCTCCCACCAGTCAA | 9473 & 9474 |
| MYL9 | GAAGCTGAACGGCACGGA | TGGTGAGCAGCTCCCGGA | 9369 & 9370 | NAPG | AAAGATGTGTCCGGGAGA | CTCAGGCCCAGCTTAGCA | 9475 & 9476 |
| MYLK | GCCCATGGGCAATGCCAA | ACACCTGGCACTGGAGCA | 9371 & 9372 | NAPSA | CCCTCATCACAGGACCCA | CGGACAAGCACAGAGGCGGA | 9477 & 9478 |
| MYLK4 | CTCGGAGGAGGGCAAGGA | TCCTGGGCATCAGAGCCA | 9373 & 9374 | NARF | CAGACATGCGGCCAAGGA | ATCCTCCAGCACAGGCGA | 9479 & 9480 |
| MYLPF | GAGGATGTGATCACCGGA | CACACTGCGTGCTCAGCA | 9375 & 9376 | NASP | GTGAAGGAGGCTGAAGGA | GGCAATCATGGAGACTGA | 9481 & 9482 |
| MYO15A | GGTCAGCACTGCACGAGA | TGATGCCCACGTGGGACA | 9377 & 9378 | NAT1 | GACCATTGATGGCAGGAA | AACGGAAGACACAAGGCA | 9483 & 9484 |
| MYO19 | CACACAGCCAGGAAGCCA | GCCTCAGCCGAGTCACCA | 9379 & 9380 | NAT10 | CATGGGGAAGCCAGCCCA | CCCCAAGAGAAGAGGCCA | 9485 & 9486 |
| MYO1B | GAAGCAACGCTGGAGAGA | CTCCTGTACCAGGCGGGA | 9381 & 9382 | NAT8 | GCACAGACATGTCTGACA | CAGGCAGAGCTCTACCA | 9487 & 9488 |
| MYO1C | GCTAAACCTGAGGCGCCA | AGGGCTGATACTTCCGGCA | 9383 & 9384 | NAV2 | GCAGTTACGGCCTGAGGA | AGCGGGTTCACCTTCAGCA | 9489 & 9490 |
| MYO1E | CGCTCAGGACACAGACGA | TAGTCGACCAGTCCACCA | 9385 & 9386 | NAV3 | CTCTGCAGGCAGCAAGGA | CATGATGGCTGAGGGGGA | 9491 & 9492 |
| MYO1F | GAGGAGATGCGGGGAGGAA | CACACTTGGGCGTCAGGA | 9387 & 9388 | MBEAL1 | GCATCAACCATTAGCCA | CCTGAACGCATCTCAGCA | 9493 & 9494 |
| MYO1G | GCAAGGGCTTCGTCAGGA | AGCACAGCCCGAAGCCA | 9389 & 9390 | NBL1 | CCCAACACCTTCCCACA | GGGCACTCCAGCGTCACA | 9495 & 9496 |
| MYO3A | TACCCGGCACCGTCGGAA | AGGTCAGCTAGTGGAGGA | 9391 & 9392 | NBN | CAAGAAGCAGCCTCCACA | AGACAACTGCGGAACTCA | 9497 & 9498 |
| MYO5B | TGAGGAGGAGGTGGAGCA | GCAGTAGCTGTGTGCAGA | 9393 & 9394 | NCAM1 | GCAGTGAGTCAGAGGCCA | TCACACAATCACGGCA | 9499 & 9500 |
| MYO5C | GTCCTCAGGAGCCAAGGA | GAGAGTCTGCGTAGCGCA | 9395 & 9396 | NCAM2 | GCTCTCAGAACCCGCCA | GCCCTGCAGACATAAGGA | 9501 & 9502 |
| MYO9A | CCTGACACCACTGACCCA | GACACAGAAGGCAACCGA | 9397 & 9398 | NCAN | GGGGTCTTCGACACAGCA | GCTGTACACTGAGGGCCA | 9503 & 9504 |
| MYO9B | GTTCCCAGAAGACGCCGA | CCAGGTTGCACAGGACGA | 9399 & 9400 | MCAPD2 | GACCACCATGGAGGAGCA | TCTCGCAGACATGCCACGA | 9505 & 9506 |
| MYOC | CAGCACCGATGAGGGCCAA | GGTGTACAAGGTGCCACA | 9401 & 9402 | MCAPH | TGAACACTCCAGAAGCCA | CGGAGAGCGCTGTCAGCA | 9507 & 9508 |
| MYOF | GAGCTTCCTCCTGAAGAGA | AGAAGGTCACCCACCGGA | 9403 & 9404 | NCAPH2 | GGAGACAGAGCTGAGCCA | GAGGCCAGCATGGAACGA | 9509 & 9510 |
| MYOG | GAGTTCAGGCGCCAACCA | CACGATGGAGGTGAGGGA | 9405 & 9406 | NCBP1 | TAGAGAGGCTGCACTGACA | ACTGCTGGAACACGCCA | 9511 & 9512 |
| MYOM1 | GGTTCGAGGCTTCAAGGA | GGAGGGTCTCTTGCCGA | 9407 & 9408 | NCEH1 | GCCCGTCTAAACTGGACA | CGGAGCGGGCATCCAGGA | 9513 & 9514 |
| MYOM2 | GGAAACCTGACCCGGAA | GCTCCACTTCACCGAGA | 9409 & 9410 | NCF2 | ACAGCCAGGTGCGGGACA | ACACACAGAGTCAGGCA | 9515 & 9516 |
| MYOM3 | GCCATCAGGGCTCAAGCA | GGTCCAGGAAGTAGCCCA | 9411 & 9412 | NCF4 | GGAGCTCACAAGGCGGGA | TCATCCGACAGCAGCCGA | 9517 & 9518 |
| MYO1 | ATAACCAGTCCCACGCCA | AGGTTGGCCACGCTGAGGA | 9413 & 9414 | MCK2 | GCAGCTACAACGGCCAGGA | CACATGCACCACGAGGCGGA | 9519 & 9520 |
| MYO21 | AGAAGGCTCCAAACGCA | GTCTACAGGGCTCCCAGA | 9415 & 9416 | MCKAP1 | CCCTGCTATAGAAGGGCA | TGGAGGATGCAAGGCCA | 9521 & 9522 |
| MYST1 | GTACTGGAAGGGCCAGCA | TGAGGCAGACGGAGTCCA | 9417 & 9418 | MCKAP1L | TGCAGCTGGGCACGAGGA | TAGGTGGAAGGCCCGAGA | 9523 & 9524 |
| MYST2 | TAGACATCTCCAGGAGA | ACAGCCTGGTGTAGGACA | 9419 & 9420 | MCKIPSD | GCGAGGGACATGTCAGAGA | GTGTCCAAGGGCGTCCGCCA | 9525 & 9526 |
| MYST3 | GCTGCAGCAGTTGACCAA | GGAGTCCCAGTTAAGGGA | 9421 & 9422 | NCL | AAGCTGCTCAAGGAGGCCA | CGGCCTCCTCTACCACA | 9527 & 9528 |
| MYST4 | GCAACTCACCCAGCCAGA | TCGGAGGCTCTCCACCA | 9423 & 9424 | NCOA1 | CCCGACTGAGACACACA | GTACATGGACGTCAGCA | 9529 & 9530 |
| MZB1 | CACAGCCCACAACTGGA | TGCAGGCATCACAGCGCA | 9425 & 9426 | NCOA2 | GCAGCTGCTGACCACCAA | GGCCAAGTTCCACAGGGGA | 9531 & 9532 |
| NABP2L2 | GCTTGGGAAATGAAGCCA | CGATCCAACATCTGAGCA | 9427 & 9428 | NCOA3 | CCACAAGCTCCTCCGCAA | GATTCTGGGAGGGAGCCA | 9533 & 9534 |
| N6AMT2 | GAATTGGCAAACTGAGCCA | GGGCACTCACACATGCGA | 9429 & 9430 | MCOA4 | GATGCTCGTGGAACCCAA | CCTGATAAGCCACTCCGA | 9535 & 9536 |
| NAA11 | GGCCAAAATGGAGGAGGA | GCTTCTGGGGCCAGGCCGA | 9431 & 9432 | NCOA6 | GCCAAGGGCTAGACACCA | AGCCTACACTGGTGCGGGA | 9537 & 9538 |
| NAA38 | GGACGGAGAGCGCGAGGA | GCAGAGGAAGCAGCGGA | 9433 & 9434 | NCOA7 | CAAAGCGCCAGGAAGCACA | CAGGAAGGCTGTCGGGCCA | 9539 & 9540 |
| NAAA | AAGACTCAGAGGCCACA | ATCAGCCAGCTGACGGGA | 9435 & 9436 | NCOR1 | TGTCAGAGGGCTCCACCA | ACGACAGGGTCCACCCCA | 9541 & 9542 |
| NAALADL1 | CAGCCAGGATCTCACCCA | CAGTCACCAGAGCGCCCA | 9437 & 9438 | NCOR2 | ACAACCAGCCCTCCGACA | GGTCATAGGCGTGGCAGA | 9543 & 9544 |
| NAB2 | GAAGCAGCCTCTCGAGA | TCCTCGAAGCCACCACCA | 9439 & 9440 | NCR1 | GGGATCACACTGCCGACA | GCCAGTCTTCAACCAGGA | 9545 & 9546 |
| NACA | CAAGCCCAGCTGCGGCA | CCGAAGACCCAGTTGGA | 9441 & 9442 | NCR3 | TCGGGACAGGGAATGGGA | CCCACGCCACAGAGAGA | 9547 & 9548 |
| NADSYN1 | GGAGGAAGCAGCAGGGAA | GATGTCCGCACTGGAGCA | 9443 & 9444 | MCR3LG1 | GCCTTGCGAGACAACCCA | CTGGAGGAGGTTCCAGA | 9549 & 9550 |
| NAGA | GCATCCTAGGGAGCAGGA | AGGGAGGAGCAGTGTAGCGA | 9445 & 9446 | MCS1 | GAAAACAAGGACGGGGCGA | GTAGAGCTTGAAGGCCCA | 9551 & 9552 |
| NAGK | AGGTGCTTCAGCAGAGAGA | TCTTCCACACAGAGCCCA | 9447 & 9448 | NCSTN | CCGAGAGCAGTGCCAGGCA | CGTGCAGTAGAACGCACA | 9553 & 9554 |
| NAGLU | GACCTCACTCGGGCAGGA | GCAGCAGCTCATAGGCCA | 9449 & 9450 | NDCB0 | CCAGAGGGCAAAGAAGCGA | ACAAGGCAGTTGGCACCA | 9555 & 9556 |
| NAGPA | CCCCTGTAACTGCAGCCA | ATGCCAGCCAAGGGGACA | 9451 & 9452 | NDP | AGCACTGTCTCTCAAGCAA | ACCGGTAGGTGGCAGTGA | 9557 & 9558 |
| NAGS | CCTGGTGTGCAAGCCGA | GGTGATGACCGCGAGGA | 9453 & 9454 | NDRG1 | CTGGAGATTGAGCGACCA | GAAGTGACGCTGGAACCA | 9559 & 9560 |
| NALCN | CTCAACAGCCACCACCA | CGGTCACCATGCTCAGGA | 9455 & 9456 | NDRG2 | AACTGGACCCACCCAGA | CAGAGAGGCTGTACGAGA | 9561 & 9562 |
| NAMPT | AGAAGTACACAGGGCACA | AACTTCCACCAGAACCGA | 9457 & 9458 | NDST1 | GCGGCTCTTCACACACA | AGGAGTGCAGGAAGTGCA | 9563 & 9564 |
| NANOG | CCACCAGTTCCCAAAGGCA | ACACACAGCTGGGTGGAAGA | 9459 & 9460 | NDST2 | CTGCGTACCAACCCAGCA | CTCCGGCCTAGACAGGA | 9565 & 9566 |
| NANOS1 | CCGGCTGTGAAGCCCA | TAGCGCGCAGCACGGGA | 9461 & 9462 | NDST3 | GACCCTTCAGACCCCGA | CAAGGCTTCTGAGCTCCGA | 9567 & 9568 |
| NANOS2 | CCAAGAGATTGAGGAGCCA | CACACGTAGTGCCCTCAGGA | 9463 & 9464 | NDUFA1 | TGGAAAAGAGATAGGCGCA | AGCAGGGGTAGAATGGCCA | 9569 & 9570 |
| NANP | GGAGGCCCCTCAATGCAGGA | GGAGTAACTCTAGCACA | 9465 & 9466 | NDUFA10 | GAAGCCCCTCGGCACCGA | GGTCAGCAAGGCTCTCAA | 9571 & 9572 |
| NAP1L1 | GTGCACAGATAGAAGCCA | GCCTGATAGAGAACGCA | 9467 & 9468 | NDUFA2 | CAGCCAGGGCTCAGGGA | CATCGCAAGCATTCGCGGA | 9573 & 9574 |
| NAP1L2 | AGGAGGAGGAGGACGACA | CTGAGGGGCTCGCCAGGA | 9469 & 9470 | NDUFA3 | GCCCCATTGAGCCCCTA | GGCTGGGCACGTCGGGCA | 9575 & 9576 |

FIG. 1 (cont.)

| GeneName | Forward Primer | Reverse Primer | SEQ ID NOs | GeneName | Forward Primer | Reverse Primer | SEQ ID NOs |
| --- | --- | --- | --- | --- | --- | --- | --- |
| NDUFA7 | CAGGCAAGCCAGCAGAGA | GTCCGCAGGACAGCTCCCA | 9577 & 9578 | NFE2L3 | GCTACTACCCAGAACCCA | GACTTCCCAGGCCACGGA | 9683 & 9684 |
| NDUFA9 | CTGTCCAAGGAAGCTGGA | TTCCAGCCCAAGGAACCA | 9579 & 9580 | NFIB | GAGTATCCAGAACGCCCA | CTGAAGATTGACCCCGA | 9685 & 9686 |
| NDUFA4 | GCCTCCTGCGAGAGCAGA | ACCTGCAAGGAAGACACA | 9581 & 9582 | NFIL3 | ACGAGCACGAACCCTGA | GCAGCTTCCCTGCACAGA | 9687 & 9688 |
| NDUFB1 | CCGAGGTCGCAGCTTCCA | GAACCCAGTGGTCCCGCA | 9583 & 9584 | NFKB1 | ATAGACGAGTCCGAGACA | GAGAGTTAGCACGTGAGGCA | 9689 & 9690 |
| NDUFB2 | CGCAGGCGACTGCTGGGA | ACCACATGAGTCCGCTGA | 9585 & 9586 | NFKB2 | GGCATGGAGACTCAGCCA | GCCTCCACTTCAGCCCA | 9691 & 9692 |
| NDUFB3 | GCCGCAATGAAGCTTGGA | GCTCCTACAGCTACCACA | 9587 & 9588 | NFKB1A | GCTGCCAGAGAGTGAGGA | CACAGTTCATCATAGGGCA | 9693 & 9694 |
| NDUFB4 | AGCCCAAGCTGAAACGAGA | CTTGCATAGGCCCAAGGA | 9589 & 9590 | NFKB1B | TGGAGGCTGAAAACTACGA | CCCTCAGGAGAAGCTCCA | 9695 & 9696 |
| NDUFB6 | GAAACTGCGGCTGCAGCA | CCGGCTCCGAGGGCTCA | 9591 & 9592 | NFKB1D | AGGTTGACCTGGAAGCCA | CAACGTTAAGGCGCCAGGA | 9697 & 9698 |
| NDUFB7 | CTTCCCGAACGCAAGGA | GGGCGCAGTAGTCCCGCA | 9593 & 9594 | NFKB1E | CCCAGGTAGATGCCCGCA | CGCAGCAGGGAGTCAGCA | 9699 & 9700 |
| NDUFB8 | TGCACTGGCACCTAGACA | AGGCTGGTAGACAGGGTA | 9595 & 9596 | NFKB12 | GCCCAAGGAGAAGGGCA | GCCCGATGTTCACCAGA | 9701 & 9702 |
| NDUFB9 | CTGCAGGAGGAAACGCCA | ACCACACAGTGGGGGCA | 9597 & 9598 | NFS1 | CAGAGCGGCTGATACAGA | GGGCTCCAGGGATGCAGA | 9703 & 9704 |
| NDUFC1 | GTTGACGCCCCACGGA | GGGAAAGGGACGACGCAGCA | 9599 & 9600 | NFX1 | AGTGCCAGCCTTGCAGA | AGTTTGGCCACAGGGGCA | 9705 & 9706 |
| NDUFS1 | GGCAAAGATGTGGCAGCA | GCCTCTTCCACACCAGCA | 9601 & 9602 | NFYA | CCAGCAGTGGGCAAGGGA | GGCACAGAGCCAGCCCA | 9707 & 9708 |
| NDUFS2 | GGAACTTGCCGAAGACCCA | CATCTCCTCCACCCGGCA | 9603 & 9604 | NFYC | AAGCCCAACAGGGCCCAGA | CATTCAGCTGCACGGGGA | 9709 & 9710 |
| NDUFS3 | CCTCAGGGATCACACAA | CGTGAGTTGAAGCGCAGA | 9605 & 9606 | NGB | CAGCTGGGCATGAGGCAGA | TCCAGCTGTAGAGCAGA | 9711 & 9712 |
| NDUFS4 | CAGTGGTACTGAGCGCAGA | CCTGGTCGGAACCCTGGA | 9607 & 9608 | NGEF | CCGGCAGATTCCAGGAGA | CGTTCTCCAGCAGCCGCA | 9713 & 9714 |
| NDUFS6 | GGGAGAAGGTCACGACA | TCGCACGGTATCACCGGA | 9609 & 9610 | NGF | AGACACCGCCACAGACA | CACCCGCTGTCAACGGGA | 9715 & 9716 |
| NDUFS7 | AGCTGCCCAACGGAGGA | CTCGGCCGTAGGTGGGGA | 9611 & 9612 | NGFR | GCTACCAGCCCGAGCACA | TGCACAGAATCTCCACGA | 9717 & 9718 |
| NDUFS8 | GGACCACCCGCTATGACA | ACGATGGCATCCACGGGA | 9613 & 9614 | NGLY1 | GTGTGGCGAGTGGGCCAA | TGCATCACAGTGCAGCCA | 9719 & 9720 |
| NDUFV1 | CCCTGTGGGAGATCAGCA | CGGATCAGACCCTGCACA | 9615 & 9616 | NGRN | TACCCACATTGGAGCAGA | TGCTGCAGCGAGTGGGCA | 9721 & 9722 |
| NDUFV3 | ACACAGGAGCCAGGGCCA | CGGCCTGAGGAGGGCTGA | 9617 & 9618 | NHLH2 | CTACCCGCACCCGACGA | TGAAGCTTCCAGCCTGGA | 9723 & 9724 |
| NEB | GTCCCTGACACGCCA | CTTGCCAACTCGAGGGCA | 9619 & 9620 | NHP2 | CGGTGAAGCAGAAGCAGA | AGCCTGCGGCTGCACCA | 9725 & 9726 |
| NECAB1 | CTACCAAGAAGCTCCAA | CAGGCCATTGAATGCACA | 9621 & 9622 | NHP2L1 | CGCGAGCCACTGCGAGA | GACAAGAACAGGCGATGACA | 9727 & 9728 |
| NECAB3 | CTGCAGGGACTTCCACCGA | TACAGGGTGAAGGAGGCA | 9623 & 9624 | NID1 | CCTACATGGACGGCACGA | CTGATCCAACCCAGCAGA | 9729 & 9730 |
| NEDD4 | AGTGCCCATTCGCCAGGA | ACAGTCGACTGGCCTGA | 9625 & 9626 | NID2 | GAGCAGAGCCTTGACGA | TGGCACGGGATTCACCA | 9731 & 9732 |
| NEDD4L | GTCACAGGGACATCGCGA | GGAGGTAAGTCAAGGCGA | 9627 & 9628 | NIN | CGGTGACTGCAGTGAGCA | CCAGTCTTGGGGAGGGGA | 9733 & 9734 |
| NEDD9 | AGGCATTGTCCAGGCAA | TGCATCAGTCAGAGGGA | 9629 & 9630 | NRJ1 | GATGGCCAACGCGTCCA | CAAGGAAGATGAGCAGCA | 9735 & 9736 |
| NEFH | TATGCGTCAGCGCAGGA | GAGCAATGTCGGCCTGA | 9631 & 9632 | NP7 | AAAGGCCTGGTGCAGAGA | CTGCACGTGAGTACACCA | 9737 & 9738 |
| NEGR1 | CAACGTGACACAGGAGA | TTAAGAGGCAGGCTGCA | 9633 & 9634 | NPA2 | CACAAGCTAGGTGATCCA | GCAGCAGAATCAAGCCA | 9739 & 9740 |
| NEK2 | GCTTGCTAAGGAACGGA | ACAGGGCTTGAGCCCGCA | 9635 & 9636 | NPBL | CGGAGTTGGGAAGCACAGA | TGTCTACCCAAGGACCA | 9741 & 9742 |
| NEK7 | GCAGTGCATTGGAACACA | TAGAACGCCAAGAGAACCA | 9637 & 9638 | NIPSNAP3B | GTGGAATGAGAGTGCAGA | TTTCCGAACAGCCGGCA | 9743 & 9744 |
| NEK8 | TCCAAGGCCTTGAGCGCA | TCCAACTGCACTGGCCGA | 9639 & 9640 | NISCH | TGCTGGAGCACATCCGA | GCCGTACTTGAGCACCA | 9745 & 9746 |
| NEK9 | TCAGTCCCACAGAGGCCA | GAGATGGGCTGTCAGGCA | 9641 & 9642 | NIT2 | AATCTGACCACTGGACCA | GTGGCCACATACACCTGA | 9747 & 9748 |
| NELL1 | GCCACTCATTGCCCCAA | TGCAGGGAGATCCAGCCA | 9643 & 9644 | NKD1 | GACCAAGCCCACTGCAGGA | GAGCGAGATCGAGTGGGA | 9749 & 9750 |
| NELL2 | GCCTGAATGTGACCCAA | CCACATCTGGCAAGGCA | 9645 & 9646 | NKG7 | GTGGGACCAGCCTCCACA | AGGACGGGACCTCCACA | 9751 & 9752 |
| NET1 | GTAACAGCTGGCAGCCA | CTAGGCGACTTCGAGGGA | 9647 & 9648 | NKX2-1 | ACAAGGCCACGCGCCAGGA | GGTCCGACCGTATAGCAA | 9753 & 9754 |
| NETO1 | TGCACTCTCAGAGGGACA | GGACAGCCTGCTCAGGCA | 9649 & 9650 | NKX2-2 | CATGCAGTACAACGCCCA | ACTGCTGGGCCTGGACCA | 9755 & 9756 |
| NETO2 | GCGTCAAACAAAGCAGGA | CAGGGCCTCGCTCAGGGCA | 9651 & 9652 | NKX2-3 | GGAGGACGAGGAAGACGA | GCACGAGTCTCGCAGGA | 9757 & 9758 |
| NEUROD1 | ACACGAACCCTCCGCGA | ATGCGGGATCTCGCAGCGA | 9653 & 9654 | NKX2-5 | GAAACTCACGTTCACGA | ATTGAGGCCCACGCCGTA | 9759 & 9760 |
| NEUROG2 | GTTCCCCGAGGAGCGCAA | GGTGCAACTCACGTGGA | 9655 & 9656 | NKX2-8 | GCGGTGGCGAGGTGGGAA | GAAGAGGCCAAGCGCCGA | 9761 & 9762 |
| NEUROG3 | CGACGCAAGGAGCTCACCA | GCCAGGACTCAGGCTGCCA | 9657 & 9658 | NKX3-1 | GGGAGACTTGGAGAAGCA | GCCACGCAGTACAGGTA | 9763 & 9764 |
| NF1 | GGGTCAGGAGCGCAGCA | AGCCAGTTTCCCAGGACA | 9659 & 9660 | NKX6-1 | TGCACAGCATGGCCAGGA | GGAGGGGCGACGAGGAGGA | 9765 & 9766 |
| NF2 | GGAGCGAAGAGCCAAGCA | CGAAAGACAGGCTGTCACCA | 9661 & 9662 | NLGN1 | TACCAAGACGACCCCAGA | TGACGCTCAGCCCAGTCA | 9767 & 9768 |
| NFAM1 | TGGGCACACAGAGAACCAGA | CACTCAGGACACTCAGGA | 9663 & 9664 | NLGN2 | CACCAATTGGGTGGCACCA | TGACCAGGCACTCGAGCA | 9769 & 9770 |
| NFASC | GGGACACCCAGTGTGGGGA | ACCATGCAGTGTGGGGA | 9665 & 9666 | NLGN3 | TGGAGCACCAAGGCGGCCA | CACGAGGGTTCTCCACCA | 9771 & 9772 |
| NFAT5 | GCAGCAGATTCAGCCGA | GGCAGCTGACTAGAAGCA | 9667 & 9668 | NLGN4Y | CCACCAAACGCCCAGCAA | GTTGAGGAAGAGGAGCGA | 9773 & 9774 |
| NFATC1 | CGTGAGGAAAGCCCGAGA | ATGGCGGGATCTCAACCA | 9669 & 9670 | NLN | GGAAGCCGGATGATGGCA | TGTCTCAGGAGAGAGGGGA | 9775 & 9776 |
| NFATC2 | CCATCAAGAAGCGGAGCCCA | ATGAAGCCCCGTGCGGA | 9671 & 9672 | NLRC5 | GACTTGGAGCCCACCA | AGCAGCAGGGAACTGGCA | 9777 & 9778 |
| NFATC3 | ACAACAAGCTTCCCGCAA | GGAGACGGTGATGAGGCA | 9673 & 9674 | NLRP1 | GCCTGGATACGGGAGAGA | CAGGAGAAGGCACGCCACA | 9779 & 9780 |
| NFATC4 | CTGTCCCCGAGTACACCA | CTCGCCCATTGGAGACA | 9675 & 9676 | NLRP3 | TGGACTGCAGAAGGCCGGA | AGGTAGTACATGCGCGGCA | 9781 & 9782 |
| NFE2 | TGAGCTGGAGGGGACAGA | TTCATGGCCAAGGCCCGA | 9677 & 9678 | NLRP5 | GTGCAGGGGACTGAAGCA | CAGATGCCGGTTGCAGGA | 9783 & 9784 |
| NFE2L1 | CCGCATGAGCCTCCACCA | TCGGCTGAGTCACGGGCA | 9679 & 9680 | NLRP8 | CACGAGGAGGAGGAACCA | CTCGCGCCAAGTGACACA | 9785 & 9786 |
| NFE2L2 | TGCCACAGTCAACACAGA | AAGTAGCAGGTGAGGGCA | 9681 & 9682 | MMB | TGGGACAGCTCCCCACA | GCAGGAGGATTCCGAGCA | 9787 & 9788 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| NMBR | GGACCTGTGTGAAGGCCA | AGCTACTGATGCGAAGCCA | 9789 & 9790 | NPM1 | ACGAGATACTCCAGGCAA | TCAGTCATCCGGAAGCAA | 9895 & 9896 |
| NME1 | ACTCCAAGCCTGGGACCA | TCCACAGAATCACTGCCA | 9791 & 9792 | NPMT | TCGGCAGCCAGGGAAGTA | GGAGTGTGCCAGAGTGCA | 9897 & 9898 |
| NME1-NME2 | GTGGTGAAGACAGGCCGA | CCTGCCAACCTGAATGCA | 9793 & 9794 | NPPA | CCTGACCGGGGAAGTCA | CGCAGGCTCCGAGGGGCA | 9899 & 9900 |
| NME2 | GACCTGAAAGACCACCA | CACGTTCAGCCCTCCCA | 9795 & 9796 | NPPB | AGGTAGCCACCGAGGGCA | AGCAGCTCAGACCCTTGCA | 9901 & 9902 |
| NME3 | GCTCATCGAGCCACGAA | GCGGGCACTCTCCACCGA | 9797 & 9798 | NPPC | CCTGCCGTGGACACCAA | GCCGAAGCAGCCCTTGGA | 9903 & 9904 |
| NME4 | CCAGGACTGCGGAGGAA | TGGGGCAGCCTCAGCCGA | 9799 & 9800 | NPR1 | GGACCCAGAGCAAGGACA | TCCACGTGGAAGACCCGA | 9905 & 9906 |
| NME8 | ACCTGAGGTTCGAAGCCA | CGGGAAGAAAAGCATCCA | 9801 & 9802 | NPR2 | GGTCAACGCCATGCACCA | AGGCCAACAACCCCAGCA | 9907 & 9908 |
| NMI | GAGGTTACGCGCGGTCCA | CATAGTCCACGCGGTCCA | 9803 & 9804 | NPR3 | TGGCATGACCAGTGGAGA | GACTGTCTGCAGGGACGA | 9909 & 9910 |
| NMS | AATGCACCTGGCTGCCA | GTGAAGTCCACTGCAGCA | 9805 & 9806 | NPS | CCAGATTGGACAGGAGCA | CCCCGAGTCCTTTGCACA | 9911 & 9912 |
| NMT1 | CCAGGAGGAGGTGGAGCA | ATGGTGGAGGGCAGTCGTA | 9807 & 9808 | NPS R1 | ATGGGAAACTGTGCAGCA | GGAGCTGCTGAAGACACA | 9913 & 9914 |
| NMU | CAGAAGTTGGGGAACGA | CATGCAGGTGAGGAACGA | 9809 & 9810 | NPTN | GTCAGCGCCTCCTAAAGCA | GTGGGGGTTAGCCAACTGA | 9915 & 9916 |
| NMUR1 | GCACCTGGCCTTCCAGCA | TCTGAGGCGATGGCAGCA | 9811 & 9812 | NPTX1 | CTACCAGGATGGCACGGA | AGTGGCCAGCTCACCCA | 9917 & 9918 |
| NMNT | CGCTCAGGAACCTCGGCA | CCAGGGGGAGGCTTGGAGA | 9813 & 9814 | NPTX2 | AGTGGGGCAACAACCCCA | CCTGGAATGCTCCCACA | 9919 & 9920 |
| NNT | GCTACGGATGCAGAGCA | CAGTAGGAGGAGGGGCAGA | 9815 & 9816 | NPTXR | CGCCTGGACCACAAGGGA | AGCCAGGTTCTCACCGGA | 9921 & 9922 |
| NOB1 | CAGCTGCGACTCTCCCA | TAGCTGAGGGCCTGGAGA | 9817 & 9818 | NPVF | GCCACACTTCTTCTCCAA | TCACAGGGCTCACCTCCA | 9923 & 9924 |
| NOC4L | ACACCCGCTACCACACCA | GCAGGCTCACGGCAGACA | 9819 & 9820 | NPW | GGAGCTCCCAGGCAGGGA | CAGCTCCCGCTCGAAGTCCA | 9925 & 9926 |
| NOD2 | GCTGCAGTGCATGGCCAA | GGTCAGGGTGGTCAAGGA | 9821 & 9822 | NPY | CCAGCCCAGAGACACTGA | GCAGGGTCTTCAAGCCGA | 9927 & 9928 |
| NODAL | GGAGTGGGGCAACAAGGA | AACTCCTCCCCAACAGGA | 9823 & 9824 | NPY1R | CAGGTCCAGTGAAACCAA | CTGTGAGGTGGCAACTGA | 9929 & 9930 |
| MOG | GCACCTGGCCTTCCAGCA | TCTGGGCACGGAGCACGA | 9825 & 9826 | NPY2R | GACCACTACCATCAGCGA | AAGTGGAGCACATGGCGA | 9931 & 9932 |
| NOL3 | CAAGAAGCTGCGGAGGAA | GGGTGCTCCGGCGTCA | 9827 & 9828 | NPY5R | CTGGCAGCATAAATGGA | AAGTGGGACCCCTGGTA | 9933 & 9934 |
| NOL8 | GGGCCAGAGTACGAGGCA | GGCAGTTTCCAAGCCAGA | 9829 & 9830 | NQO1 | GAAGCTGAAGCCTACAAGGA | TACATGGAGCACTGCCA | 9935 & 9936 |
| NOLC1 | TGAGTACAAGGCCAGAGA | CCGCAACTCGTGAATCA | 9831 & 9832 | NQO2 | CCACGAAGCTTACAAGCA | CCATCCAGCCTTCAGGA | 9937 & 9938 |
| NOMO2 | CTGCCAAGGAGGCAGAGA | CAGGGACTGGCCAAGGGA | 9833 & 9834 | NR0B2 | TGGGCACTGCGCCAGGA | TGGAGGCCGTGAGGAGGA | 9939 & 9940 |
| NOMO3 | CAGAAGGCAACGACCACA | GGGCCAACACTGTAGGCA | 9835 & 9836 | NR1D2 | CTCAATGGGAGCAGGGGA | TCTGCAGATACCAGGACA | 9941 & 9942 |
| NONO | GAGATCCACGGGAAGGCA | GCCATCTGACCCATCCA | 9837 & 9838 | NR1H3 | GCCAACGTGCAGAACCA | GGGGATGGTGGATGGAGA | 9943 & 9944 |
| NOP14 | GATGGAAGCTGAGAGGA | GCAGCAGTCAGCTCAGCA | 9839 & 9840 | NR1H4 | TGGACCATGAAGACCAGA | TAGGTCAGAATGCCCAGA | 9945 & 9946 |
| NOP16 | GCTCTGGAAACAGCAGGA | GGTCCACAGCAACCCGA | 9841 & 9842 | NR112 | GACCAGCTGCAGGAGGCA | TGCGGAGCTCGGTGAGCA | 9947 & 9948 |
| NOP2 | ATGCTCCACATCCGACA | GGTCCACAGCAACCCCA | 9843 & 9844 | NR2F1 | AGTACCCCAACCAGCCA | GAGCTGCTCGATGACCGA | 9949 & 9950 |
| NOP56 | GCAGCAGTTGTGCCAGGA | GCTGGAACGAGCAGCAGA | 9845 & 9846 | NR2F2 | CCTGCAGATCACGGACCA | TCAGAGAGACACAGGGCA | 9951 & 9952 |
| NOS1 | GCTGGAGAAGCTGAGGGA | GTCCATGCCCATGAGGA | 9847 & 9848 | NR3C1 | CAGCAGGCCACTACAGGA | CCTCAACAGTGACACCA | 9953 & 9954 |
| NOS1AP | TGTGGGGCGTCACCA | TCGCAGGGTGACTCCA | 9849 & 9850 | NR3C2 | CCCTGGTCAACACAGGCA | AGCGGTTGAGCGTGGAGA | 9955 & 9956 |
| NOS2 | GACCCCTAAGCCAGAGGA | ACTGCTACTTCCGAGGCGA | 9851 & 9852 | NR4A1 | GTCACCGGCTGACCAGGA | GGGACCTTGAAGGGCCA | 9957 & 9958 |
| NOS3 | GACATCCACCACAGCCCCA | GCAGGAAGCCAGCAGACA | 9853 & 9854 | NR4A2 | CTGCCCAAAGCCGACCAA | GTGACCATAGCCAGGGGA | 9959 & 9960 |
| NOTCH1 | GTGCTGCGGGATCAGCAA | CTGACGCTCCTGCAAGGA | 9855 & 9856 | NR4A3 | GCCTGTCAGCACTGAGCA | GTTCTACCAGGGCACCCA | 9961 & 9962 |
| NOTCH2 | CAGGAGCCCAACTGCGAGA | CAGGCACACTCGTAGGCA | 9857 & 9858 | NR6A1 | TGCCAGCCTGCAGGACCA | CCTGCCACGTAGAGCTCA | 9963 & 9964 |
| NOTCH3 | CCCATTGATCGACGGCA | CTCCTGGCAGAGAAGGCCA | 9859 & 9860 | NRAP | GAGATGGTCTCCAGGCCGA | TCAGCTTGGCCAGCAGGA | 9965 & 9966 |
| NOTCH4 | GCAACCCGGTGTACGAGA | CTGGCACAATCCAGCCCA | 9861 & 9862 | NRAS | CTCAGCCAAGACCAGACA | ATACAACCTGCAGTCGA | 9967 & 9968 |
| NOTUM | GCTAACTCTCCCCAGGA | TTCCAGGGCTCAGGACA | 9863 & 9864 | NRG1 | GGCTCAAGGAGGAGGCCACA | AGGGCACCCGTTGCACA | 9969 & 9970 |
| NOV | CAGACTGCCTCGAACGA | CACCAGAACACAGGGCA | 9865 & 9866 | NRG2 | CCGAGGAGCTGTACCAGA | TTGCAGTAGCCAGCACCA | 9971 & 9972 |
| NOVA1 | GCCAGAGCAGCAACAGA | CCATCACTGCAGACCCA | 9867 & 9868 | NRG3 | TGTGGAACCGGCAGCAGA | CCATAGGTCGGTGGGCA | 9973 & 9974 |
| NOX3 | TCAGCAGTGGCCAGCACA | CCTAGAATGGCACTGGA | 9869 & 9870 | NRIP1 | TCTCACAGGTCACAGCA | CTGTGTGGGCGGAGAAGCA | 9975 & 9976 |
| NOX4 | TGGAACTGCCCTGACAGA | AGAAGAGCAGCGAAGGGA | 9871 & 9872 | NRIP2 | CTGCAAGTTGCCAGGACCA | GCAAGTTGTGCAGGGCCA | 9977 & 9978 |
| NPB | CCTCAGTCAAACAGAATGGGA | GGTCCAACAACAGAAACACCA | 9873 & 9874 | NRNL1 | ACAGCAAGAAAGTCGCA | CAGGCGCTGTAGCCCGCA | 9979 & 9980 |
| NPC1 | CGCTCCCAGCCTACAGA | GGGGACGTCCTGGACGCA | 9875 & 9876 | NRP1 | GTGAGGAAGCACCGGAGAGA | CGCGTGGAGAGAGCTGGA | 9981 & 9982 |
| NPC1L1 | CTCTGACTTCCGGAAGGCA | TGGTGCCATGGCCAAGGA | 9877 & 9878 | NRP2 | ACCGAAGGAGGCCACA | CACAGGGCCTCCTGCACA | 9983 & 9984 |
| NPC2 | CCATCAGCCAGCCACAGA | TCAGGAGGTTGAGGGGGA | 9879 & 9880 | NRTN | GCTGCCGACGACTGCGCCA | GGCTGTGCCGCTCCAGGA | 9985 & 9986 |
| NPEPPS | AGCCCATGCCAAACCCAA | AGGGAACTTGGGACGCCA | 9881 & 9882 | NRXN1 | CAGGGAAAGAGCAGGGGCCA | GAAGAAGGCACTTCACCA | 9987 & 9988 |
| NPFF | GGAACTGCCCAAACCTGGAGA | CCTCAGATCAGCGGAGAGA | 9883 & 9884 | NRXN2 | TAACGTGGGCACGGACGA | CGCTTCGAGTGAAGCGCA | 9989 & 9990 |
| NPFFR2 | AGACCTGCCCGGAGCAA | CAGGCTCCAGAACTGGGA | 9885 & 9886 | NRXN3 | CAGCCAATGACAGGCCA | AGCTGGAGGAAGTCACCA | 9991 & 9992 |
| NPHP1 | GGTGTCAGGAAGAAGCA | GTTGCCGAATACGCAGCA | 9887 & 9888 | NSD1 | CAGGAGGCTCCACACACA | GCCAGGTAGGGAAGCAGA | 9993 & 9994 |
| NPHP4 | GCTTCTGGAGGAAGGGAA | AGGGCCAGTTGTGAAGGCA | 9889 & 9890 | NSDHL | CATCCTGGCGGCAGGACA | GGCTCAGCTGGATGACA | 9995 & 9996 |
| NPHS1 | CTGGGAGAGACTTGGGAGA | CATCTGCGCATTGTCCACA | 9891 & 9892 | NT5C | TGTGCGGGAGATGAACCGA | CTCTCCACCGACCGGTA | 9997 & 9998 |
| NPL | CCTCAGGCCATGGACCAA | GCCCTTGGAAGGTGGGGA | 9893 & 9894 | NT5DC2 | ATGCGCAGTTCGGCAGCA | AGAGCTGGTCCATCCAGA | 9999 & 10000 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| NT5DC3 | GCACGACCAGAACCCAA | GCAGGAGAGGGGTTCCGA | 10001 & 10002 | OAS2 | GATCTTGGACCCAGCCGA | GCAGGGAGGAGGATAACCA | 10107 & 19108 |
| NT5E | CGTGCACCGCTAAGCGCA | GAGGGTCATAACTGGGCA | 10003 & 10004 | OAS3 | GGGCACAGACCTAAGGGA | CCCACAGCATCGAAGGCA | 10109 & 10110 |
| NTF3 | CGCGATGTAAGGAAGCCA | GTATCCACCGCCAGCCCA | 10005 & 10006 | OASL | AGACCATCCCTCCGAGA | CCAACCAGTCTGCAGGA | 10111 & 10112 |
| NTF4 | GCGAAACTGCACACGCGA | CGCCCACGCAAGTCCACA | 10007 & 10008 | OAT | GTTCCAAGACCCAACCA | AGAGCTCTGCACTCCA | 10113 & 10114 |
| NTRL1 | CCAAGTCCCCAGAGGAGA | TCTGCTGGCCGAAGCCCA | 10009 & 10010 | OBFC2A | GACGGCCATGAAGTGAGA | GATCTCATCCACACGGA | 10115 & 10116 |
| NTN | GCCTCACCTGCATAGCAA | GCCACGTCATTGGAGGCA | 10011 & 10012 | OBP2B | CCTGGTACGTGAAGGCCA | CCAACTTCCACCGCCA | 10117 & 10118 |
| NTN1 | CCACCTCCTGAAGGCGGA | CCTCCGCGTTGCCCAGGA | 10013 & 10014 | OC90 | GCCTCAAGTCCCCAAGCA | CCTCAGAGCTGGAGCCCA | 10119 & 10120 |
| NTN3 | CGACCCGCACCGGCAGCA | GCAGGCTCACGAAGACCA | 10015 & 10016 | OCEL1 | CGCAGTGTTCCAGGACCA | AGCTCAGCAGGGCCTCA | 10121 & 10122 |
| NTN4 | GGAGGCAGCTGATGGCAA | CTGAGTTGGCAGGAAGGA | 10017 & 10018 | OCLN | GACACTGGCCTACAGGGA | ATTCATCAGCAGCAGCCA | 10123 & 10124 |
| NTN5 | GAACCTGCAACCAGACCA | TGCTGGTAGCCAGGGGCA | 10019 & 10020 | OCRL | GACCCCTGGAATGCAGGA | TGTCGGCAGATCCGGGGA | 10125 & 10126 |
| RTNG1 | ACTGCCAGAACGGCAGGGA | GCCAGAGCTCGGAGGCCA | 10021 & 10022 | ODAM | ACAACCAGGCCCCAGTCA | GTTCCAGGGTAGGACCA | 10127 & 10128 |
| RTNG2 | ACGACCGGTTGCAACGAGA | GCACACGTTGGGGTAGCA | 10023 & 10024 | ODC1 | CCACGCTCAGAACCAGCA | CACAGCGGGCATCAGAGA | 10129 & 10130 |
| NTRK1 | CCCACGTCAACAACGGCA | AAGACGGCCAGGCCACA | 10025 & 10026 | ODF1 | GAGCTTGCCAAACTGAGA | TCTCCCGCTCAGCCGACA | 10131 & 10132 |
| NTRK2 | GAGAGCCCCACATGAGGA | GTCCAGGTAGACCGGAGA | 10027 & 10028 | ODF2 | AGCCGGAAGAGAGCGAGGA | GTAGCGCTCCTCAGGA | 10133 & 10134 |
| NTRK3 | AGACTTGGCCACCAGGAA | TCAGGAGGCATCCAGCGA | 10029 & 10030 | OFD1 | CTGCAGGGAACATCCAA | GCTGATATGAGAGGGGCA | 10135 & 10136 |
| NU4K1 | CCAGGTAACCTCCCACA | GGCTGTAGCTCCGGGAGA | 10031 & 10032 | OGDH | CCCAGATGTCCTGCCAGA | GCTTCCGGATGGCAGCA | 10137 & 10138 |
| NUB1 | GATGCACTCGTTGGCCGAA | CTCTCGGCCGACAGCGGCA | 10033 & 10034 | OGFR | GGTGAGGAAGCGGAGGAA | AGGGCCAAGGTCTGGGCA | 10139 & 10140 |
| NUBPL | TCTCACGCCCACAGGACA | CAAGGCCAAGGACGGGCA | 10035 & 10036 | OGG1 | CAAGGATCACCTCGAGGA | GAGGAGGAGCGTCGAGGA | 10141 & 10142 |
| NUCB1 | GAGATGGAAGGAGGAGCGA | CGGTGTAGGCAGGGTGCA | 10037 & 10038 | OIT3 | GCAGTACACATCCCGGGA | CTCGTCCAACATCCACA | 10143 & 10144 |
| NUDT11 | AAGCCGTGCACGCCGAA | CTGGCGAGGATGGGGCCA | 10039 & 10040 | OLFM1 | CCATCTCAAGAGCCCGCA | TGGCGTACACGGCCCACA | 10145 & 10146 |
| NUDT12 | CCAACTGTGGAAATGCA | ACGCCATTGAGACTAGGA | 10041 & 10042 | OLFM2 | CCGGGGTCAGTAACCCA | AGTCTCCCAGGGTACGGA | 10147 & 10148 |
| NUDT14 | TGGAGGAGGGTGAGCTCA | CGCCAGGGTCTTGGGGA | 10043 & 10044 | OLFM3 | TCCACCAAAACCTCACA | GGGTGACATTGAACAGCA | 10149 & 10150 |
| NUDT15 | CCAGGAGTCGGAGTCGGA | GACCTCCAGGGAGTTGGA | 10045 & 10046 | OLFM4 | CTCCTCCCACTCCAGGGA | ATTCAATGGGCCACCCA | 10151 & 10152 |
| NUDT19 | CCCCACAGTTCTACGAA | TGGACCATCCATCAGGA | 10047 & 10048 | OLFML1 | CCCATGCAGAAGCCACGGA | GAAGAACAAGTTGGGCA | 10153 & 10154 |
| NUDT21 | TGAGCACCGGCTACCCA | CTCCATCTGACGACCCA | 10049 & 10050 | OLFML2A | CAACAGGCAGAGGAAGGCA | GCTCGTTGAGGAAGCGCA | 10155 & 10156 |
| NUDT4 | GGTACCCAGACCAGTGGA | ACTTCCCTCACGGCAGCA | 10051 & 10052 | OLFML2B | CGGACCTGAGCACACAGA | CGAACAGCAGCCTGGGGA | 10157 & 10158 |
| NUFIP1 | CCCCTTCGACGCCCAGA | TACCACGATGTGGAAGCA | 10053 & 10054 | OLFML3 | CCTGGCAGCTGATGAGGA | GACATAGAGGGTCCCACA | 10159 & 10160 |
| NUMA1 | GGCCAGCTATGCAGATCA | CGGGTCTCAGCATCAGCA | 10055 & 10056 | OLIG2 | CTGGAGGAGGATGAAGCGA | TGGAGCCGACCGAGGGCA | 10161 & 10162 |
| NUMB | GTCCCAGCCCTGCAACCA | GCCACCATCTGGGAGGGA | 10057 & 10058 | OLR1 | AGGAACCCCAGCTACCCA | GGGAGACAGCGCCTCGGA | 10163 & 10164 |
| NUP107 | GGAATGACAGAAGAGGCA | CACCCGGAAGTAGGCCCA | 10059 & 10060 | OMD | GATGGGCTAGTAAACTTGACCA | GAAGGCAAACCAAGGAGGCA | 10165 & 10166 |
| NUP133 | CTGGAGCCGAAGGAGGCAA | GATAGCAGCCTGCAGCA | 10061 & 10062 | ONECUT1 | AGGCCATCTTCGCGCAGA | CCTGCAGCCACTTCCACA | 10167 & 10168 |
| NUP153 | CCCAGCCAACAGACCCA | CACTGCCATGATGACCCA | 10063 & 10064 | OPA1 | CTGAGCCAGGTTACACCA | CTGGCCAGCTGGAAGGTA | 10169 & 10170 |
| NUP155 | GTCACAGCCGATCCAAGGA | CTGACAGTACACGAGCA | 10065 & 10066 | OPCML | GGAACACCAATGCCAGCA | GAGGGTCCCTGATAGGCCA | 10171 & 10172 |
| NUP205 | AAACGGACCCGCAGAGCA | ACCTGGCACAGCTGGAGA | 10067 & 10068 | OPRD1 | CCAAGGAGAAGGACCGCA | ATGACAGGTGCAGCGCA | 10173 & 10174 |
| NUP210 | TCCTCCACATCGACCCA | TCTGAGGACAGCTGACCA | 10069 & 10070 | OPRK1 | ACCTGCGTAGGATACCA | AGCCTAAGGCGCATGA | 10175 & 10176 |
| NUP214 | TTGGGCAAGTGGGCAGCA | GGCACGGAACTGAACCCA | 10071 & 10072 | OPRM1 | GCCTCAAGAGTGTCCGCA | TGGAGTCCAGCAGAACGA | 10177 & 10178 |
| NUP50 | TAATGGGGAACAGTCAGCA | TATCCAATCCGCACGGA | 10073 & 10074 | OPTC | CTGCAGCCTTCAGGGCAA | GGTTGCCATCCAGGCGGA | 10179 & 10180 |
| NUP85 | TGTGGCCACCTGACAGA | TGTGCAGCTCAGAGAACGA | 10075 & 10076 | OPTN | CGAAGACCGAGGGAGGCA | GGGCAGGAATGAATCGGA | 10181 & 10182 |
| NUP93 | GCGCAGTTTGAAGCAGCA | AAGCAAGGAGGGTCACCA | 10077 & 10078 | OR10AG1 | CCCAAGAATGCTCATGGA | ATAGCCACGTAGCGGTCA | 10183 & 10184 |
| NUP98 | ACACAGACCCTCAGCGA | ACTGGGTAAGGCTGCGCA | 10079 & 10080 | OR10G7 | CCCTCCTGGCCACCGGCA | AGGACAGCACTATCAGGA | 10185 & 10186 |
| NUPL1 | ACCACAGGGGCCTCCACA | CAGAGGTAGGAGATTGGACA | 10081 & 10082 | OR10G9 | GCCCTACTGTGGACCCAA | CACAGGCAGTTTCAGGA | 10187 & 10188 |
| NUPR1 | CCTTCCACATCGACACCA | CGAGTAGGAATGGGCCA | 10083 & 10084 | OR10R2 | CTTCACCATGGTTCAGGA | CCAGGTGATGACACTGA | 10189 & 10190 |
| NUSAP1 | AGCCAACGACGCTCGCAA | TGCCCCAGACACGGTCA | 10085 & 10086 | OPRM1 | CCTTCCCGCCACTCATGCA | ACAGCCAGGTGGGAGCCA | 10191 & 10192 |
| NUTM1 | CCCAAGGAGATCCCACA | TATCTCAGGAGACCTGGA | 10087 & 10088 | OR1L2 | TGCGAACACCATCCCCA | GGGAGCCACATGTGGACA | 10193 & 10194 |
| NXF1 | CTGAGCGGAATTGGACA | GAGGGGAAGACAAGGCTA | 10089 & 10090 | OR1L8 | CACCATGAGCCACCACA | AGCACAGGCCTGAAGGTCA | 10195 & 10196 |
| NXPH1 | GCGACTTCCTGTCACGA | TCCTCAGCCAGTCCCAGA | 10091 & 10092 | OR1M1 | CAGGGATGGTGATAGCCA | GGACACAGAATAGAGCCA | 10197 & 10198 |
| NXPH2 | ACAGTCTCCGCTGCCCAA | GTTGGCCAGCCAATCCCA | 10093 & 10094 | OR2A2 | GCTGAGAGTGTGCACGA | AGAGGCCCGACTAAGACA | 10199 & 10200 |
| NXPH3 | ACGCTCGAGAGCTCAGCA | GGCACACCTTCTGGACCA | 10095 & 10096 | OR2L13 | AACTCCTTGGCACCCAA | TAGGACTCCACCAGGA | 10201 & 10202 |
| NXPH4 | CGAGCACACGAGCAGACCA | GGCACACGAGCAGACCA | 10097 & 10098 | OR2M4 | ATCACAGTCCCACCCCA | GTTCCACAACCTGCCAGA | 10203 & 10204 |
| NXT1 | CTGCAGAGCTGCTGAGGA | GGCAGTCTACCACCTGA | 10099 & 10100 | OR2T11 | AACTGGCCTGTGCAGACA | TGTGGAAGGACTGGGGCA | 10205 & 10206 |
| NYX | CAGAACCAGCGGCCACCA | AGGAGAGGCTGTCGGACA | 10101 & 10102 | OR2T33 | CAGTCTTCGAAAACGCCA | GTAGAGCGCATGTGCAGA | 10207 & 10208 |
| OAF | TGGAGCAGCGTGCGACA | GCAGCTCCGGATGCGACA | 10103 & 10104 | OR2T34 | CCAGCTCATACACCCTCA | AGGAAGACCGAAGAGCA | 10209 & 10210 |
| OAS1 | AGCACACTCCAGGCAGCA | CCCAAGATGCACTGGCA | 10105 & 10106 | OR4C13 | CATCACTGAGATCCCCA | AGTGCAAGGGCTTGCAGA | 10211 & 10212 |

| GeneName | Forward Primer | Reverse Primer | SEQ ID NOs | GeneName | Forward Primer | Reverse Primer | SEQ ID NOs |
| --- | --- | --- | --- | --- | --- | --- | --- |
| PHF1 | CAATCAGCCGGAGCCCA | GCTGGGGGATGGTGGAGA | 10849 & 10850 | PIK3CD | CAAGCCCAGACCAAGGA | CCACGCAGACTTCAGCA | 10955 & 10956 |
| PHF10 | GGACAGTCCTCCTGGCAA | CCCAGGAAGTGACTTGGA | 10851 & 10852 | PIK3CG | ACAGTGGGCAACACGGGA | GCCACACAGTAGCCTGCA | 10957 & 10958 |
| PHF11 | AGAGGAGCCACCGTGGGA | GATGATCGGGGAATTGAGCA | 10853 & 10854 | PIK3P1 | GCCGATGAACTTCAAGGA | TGAAGGCAGACAAGGGCA | 10959 & 10960 |
| PHF12 | AGAACCACACCGTCGCA | GGCAGGCTTGGGACAGGA | 10855 & 10856 | PIK3R1 | CGACAGCCTGCACCAGCA | CCCCAGTACCATTCAGCA | 10961 & 10962 |
| PHF13 | TCCGAGATGGAGGACAGCA | GCAAGTCACGAAGGTCCCA | 10857 & 10858 | PIK3R2 | ATCAACCGCACGCAGGCA | CGTGCCGGTAGATGACGCA | 10963 & 10964 |
| PHF14 | CGGGAGTGATGAAGACGA | CAACCCCCTCACTGGCA | 10859 & 10860 | PIK3R3 | CTCCATTACCAGCAGACA | GCATGAACAGGGATGGGCA | 10965 & 10966 |
| PHF17 | GCCCTGGAAGTGAAGGCA | AGCTCTCTGGGACACCA | 10861 & 10862 | PIK3R5 | ACCCCTGGTATGAGCCGA | TGTCAGCCAGGATGGGCA | 10967 & 10968 |
| PHF19 | CCAGATGGACAGCTGGGCA | CTTGAGGTGGGACAGGGA | 10863 & 10864 | PIKFYVE | GATTGAGGGACGAGGGGCA | GAGGCAACAGCCTGCGCA | 10969 & 10970 |
| PHF2 | CCCTACAGCCCAACACGA | CGGTCTCGATGGAAGGCA | 10865 & 10866 | PILRB | CCAGCAGCACAACCACCA | TGAGCACAGCGACAGGCCA | 10971 & 10972 |
| PHF20 | GCTGGGACAGAGGTGGAGA | CCCAGTGTAGTCCAGGCA | 10867 & 10868 | PIM1 | CCGCTACCCATGCTACCA | TGGTCTCAGGGCCAAGCA | 10973 & 10974 |
| PHF21B | CCTGGAGCACCGGAAGGAA | ACCTGGGCACACACCACA | 10869 & 10870 | PIM2 | CGACCCTCACTGGAAGAGA | TAGCAAGGCACCAAGGCCAA | 10975 & 10976 |
| PHF23 | GCTCCAGTGAAGGCGAGA | AGGTGGATCCACGTCCCA | 10871 & 10872 | PIM3 | CTCTCCAGAGTGCCAGCA | CAGGGTCGAGGGTGCACA | 10977 & 10978 |
| PHF3 | GGCAAGCAGCAGGACAGGA | TGTGTGACAGGCCAGGCA | 10873 & 10874 | PIN1 | TAACGCCAGCCAGTGTGGA | GCAGGTGCGAGCAGCGGA | 10979 & 10980 |
| PHF5A | GCAACATCCAGGAGGAAGGA | GAAGGGCCACCCACCAA | 10875 & 10876 | PINX1 | GGGCATCGCGGACAGAGA | TGGACACCTCTGGGGCCA | 10981 & 10982 |
| PHF6 | GGCACAGTCCAGTCGCA | ATAGTAGCACCAGGCTGA | 10877 & 10878 | PINX1 | CCAAGTTTGGCCAGCAA | GGTAGCTCGAGTCCA | 10983 & 10984 |
| PHF7 | CCACGAACCCACAGGGA | AAGGAAGGTTCTGGCCAA | 10879 & 10880 | PIP | TCAGGGCCAGCCTGCCA | TGAACTGCAAGCACTGCA | 10985 & 10986 |
| PHF8 | GGCTAGGCTGATGGCAGA | AAGGCTTGCACAGGGGCA | 10881 & 10882 | PIP5K1A | AGCAGGCTCCAGTGGCAA | GGAATAGGCCGAGCCCTCA | 10987 & 10988 |
| PHGDH | GAGCAAGGCTTCGGGGAA | GGTAGGACAGCACGCGCA | 10883 & 10884 | PIROX | CAGCAGGTCTTCTGGACA | GGTCGGGACACAAGGCCA | 10989 & 10990 |
| PHIP | GGCGAGGGGAAGCACAGA | GTCCCATCACGACTGCCA | 10885 & 10886 | PITPNB | CCAGTCAGTCAAGACCAA | TAGGCACACATCTGGGGA | 10991 & 10992 |
| PHKA2 | ATCCTCGACGACCCGAGA | CCGAGAGCAGCGTCAGCA | 10887 & 10888 | PITX2 | TGCAGCCTCACGACGACA | TCACTGCTGAGGGCACCA | 10993 & 10994 |
| PHKG1 | TCTGGCACCGGAAGCAGA | GGGGTTGCACTACCAGGA | 10889 & 10890 | PITX3 | CGGCTACTCGTACGGCAA | GATGGAGCTGGGTGGCGA | 10995 & 10996 |
| PHKG2 | ACCCATGTGTACGGCCA | CCGTAGAGCCGGAAGGCA | 10891 & 10892 | PIWIL4 | TGCCCAGTCCACAGCGCA | GTTAACACTGGCCACGCA | 10997 & 10998 |
| PHLDA1 | GCCGGTCAAGCTCAAGGA | GCACCATCTGCAGCGTGA | 10893 & 10894 | PKD1 | GGTCACCGTGCTGAACGA | TGTGGACCCTCAGGGACA | 10999 & 11000 |
| PHLDA2 | CGGGGTGCTCACCTCCGA | TGCGCTCCACGCAGTCCA | 10895 & 10896 | PKD2 | GGGCAAGGAGGAGGAGGCAA | CATCCAGGCTTCGAGGGA | 11001 & 11002 |
| PHLDA3 | CCGCTCAAGGCCGTGGA | TGGGCGTTCCAGCCGGGA | 10897 & 10898 | PKD2L2 | GCTGGATCACAAGAGGGA | GCCAGGAATTCTGCCACCA | 11003 & 11004 |
| PHLDB2 | TGCCCTTCGGGAACGGAA | CAGCACAGAGACTGAGGA | 10899 & 10900 | PKDCC | CATCCTACCACCACCGGGA | AAGGCCCGACACTGGGCA | 11005 & 11006 |
| PHOX2A | CAGCCGCTCAAGGGCGCA | GGAGGACAGAACCCCGGA | 10901 & 10902 | PKDREJ | AGTGGGACCCCAACAGCGA | GCACAGGAAGGTGGCGA | 11007 & 11008 |
| PHOX2B | GACCTCAGAGAAGGTCAGA | GTCCCTGGAAGAGTCAGA | 10903 & 10904 | PKHD1 | GGAGTCTCACGAGGACCA | TCCCGAAGCAACGCACA | 11009 & 11010 |
| PHTF2 | GGAACAACTCACAGCACA | CACACAAGAGACACGCGA | 10905 & 10906 | PKHD1L1 | CAACCGAGTTCCGAGGGAA | CCTGGGCAAGGTTCACCA | 11011 & 11012 |
| PI15 | CCCGGCAGCAAATATGGAA | GTGTGCACATGGGACCAA | 10907 & 10908 | PKIA | GGGGAAGCCCAGGGAGA | GCAATGCAGCACAGCCA | 11013 & 11014 |
| PI3 | GAGGCAGTCGTCCAGGGA | GGGATTCAACATGGCGCA | 10909 & 10910 | PKLR | CCAACGAGGGCAAGAGACA | AAGGCAGCCTCCACAGCA | 11015 & 11016 |
| PI4KA | TCGGCAACAAGCCAGCA | CGATCTCAGTGGCCAGCA | 10911 & 10912 | PKM2 | GCGACCCCACAGAAGCCA | GGATTCCGGGTCACAGCA | 11017 & 11018 |
| PIAS1 | CAGTATCCCGCCACCCAA | ACCGAGACGAGTGTAGGA | 10913 & 10914 | PKN1 | CCCAGGGGATGATGAAGGA | CGATGCTTCCGGCCGACA | 11019 & 11020 |
| PIAS2 | CCCTCCTGCCAAAAGGAA | AGCAGCAGGATCAACCGA | 10915 & 10916 | PKNOX1 | AGGGCAGAGCTGAGGAGGACGA | CCAAGACAGCCCCCTGA | 11021 & 11022 |
| PIAS3 | ACATCTGGCCACCAGCA | GCTCCCAGTTGGGAAGGCA | 10917 & 10918 | PKNOX2 | GCCCAAGCATGCCACCAA | CAAGCATGCGGTCTGCAGGA | 11023 & 11024 |
| PICALM | GCATCGGAAATGGAACCA | TAGTAGCAGGGATAGGCCA | 10919 & 10920 | PKF1 | GCAACGCCTCACCCGAGA | GGCTCATGCCACTGGACA | 11025 & 11026 |
| PICK1 | CTCCAGATGCGCCAAGGA | AGACGTCGGCATCCGCA | 10921 & 10922 | PKF2 | GGCCATTAGTGCAGGCGA | CGTGTGTGCCACAGAGA | 11027 & 11028 |
| PID1 | CTCCTGAAAATCCGGCCA | CGGGCCACCTGGAAGGTA | 10923 & 10924 | PKF3 | CACGAAGGTGGTGAGCCA | TACAGCAGGTCTCGGCCA | 11029 & 11030 |
| PIF1 | GGGCCGATGTCATCCACA | GGTCACAGCGAACCGGCA | 10925 & 10926 | PKF4 | GACTGTCCGAAGTCCCCA | GCTCCACAAGGATGGGGA | 11031 & 11032 |
| PIGK | CAGCGTGGCCGCTAGTCA | ATCGGGATGTACACACA | 10927 & 10928 | PLA1A | TTCGTCAACGGAGGCCAA | TCCAGACAGCGTCCAGCA | 11033 & 11034 |
| PIGL | GAGTAAGTGCGCCACAGA | TTGAGCACGAAGAGGACA | 10929 & 10930 | PLA2G10 | GTGCTGCCATGGCCACGA | ATGAGCGCACTGCCAGGA | 11035 & 11036 |
| PIGO | GTGCTCTGAACACGACA | ACCATGGTGAACACGGCA | 10931 & 10932 | PLA2G12A | CCTCCTGGAGGCGAGGA | GTCAGGGAAGGGATACCA | 11037 & 11038 |
| PIGR | CCACACTGAGAGCACCA | CGGTGCTGGACTGGAGCA | 10933 & 10934 | PLA2G12B | GGGTCTCAAGGTACCAGA | CCGCTTAAGGTCAGAGCA | 11039 & 11040 |
| PIGT | CTGGTGAACCTGCCGACA | GGAAGGTTCGGGTGAGGA | 10935 & 10936 | PLA2G15 | GGCTGGTGGAAGCCACGA | GTACCATCGCCGTCACCA | 11041 & 11042 |
| PIGX | AAGATGGAGAAGCCTCGA | AAGCAGGGGCGTCCA | 10937 & 10938 | PLA2G1B | AGGCCAAGAAGGGCTGACA | CAGGTGATTGCTCAGCCA | 11043 & 11044 |
| PIG2 | GGCGAGACATGGCAGCGA | AGGCAGATAGCAGGGCCA | 10939 & 10940 | PLA2G2A | GGCAGAGGATCCCCAA | GCAAAACAGGTGGCAGCA | 11045 & 11046 |
| PIK3AP1 | TCAGTGTGAGCAGCGGGA | GGGGTTCTCGAGGGGACA | 10941 & 10942 | PLA2G2C | CCGTGGATGACACTGACA | GTTCAACACAGGCTGGCA | 11047 & 11048 |
| PIK3C2A | ACCCCAAACTACAGACGCA | CCAGAAAAACGAAGCTGAGCA | 10943 & 10944 | PLA2G2D | ACTGCCTCTGACAAGGGAA | GCTTCAGGCAGGAAGGCCA | 11049 & 11050 |
| PIK3C2B | GGGAAGAAGACCAGAGCA | GCACAACGTAGCCAAGCA | 10945 & 10946 | PLA2G2E | CGAGAAGATGCAGGGCAA | AGTCTGGTCCACGGGCCA | 11051 & 11052 |
| PIK3C2G | TGACAAAGTCGGGCCACA | GCAGTCCTGCATACAGCA | 10947 & 10948 | PLA2G3 | GCCTCGACAGAAGCAGCA | CAAGCCTGGGAGAGACCA | 11053 & 11054 |
| PIK3C3 | GGATCTACCTCAAGAGGCCA | CGCATCCGGGCAACACA | 10949 & 10950 | PLA2G4A | CACACGAACCCAAAGGCA | TGAGATTCAAGCCTCACCA | 11055 & 11056 |
| PIK3CA | GGAGCCCAAGAATGCACA | GCATTCCAGAGCCAAGCA | 10951 & 10952 | PLA2G4B | GGTCAGGAAGCCAGTGACA | TTGGGAGCCCATCCAGA | 11057 & 11058 |
| PIK3CB | CAGTTCACCCCCTGAACCCA | TCAATGAGGCCAGAGCGA | 10953 & 10954 | PLA2G4F | ACTGCCTGGACCGAGGAA | GTGCAGCACAATGGGGGA | 11059 & 11060 |

FIG. 1 (cont.)

| GeneName | Forward Primer | Reverse Primer | SEQ ID NOs | GeneName | Forward Primer | Reverse Primer | SEQ ID NOs |
| --- | --- | --- | --- | --- | --- | --- | --- |
| PLA2G5 | CCCCAAGGATGGCACCGA | GCAGGTGACCACGCCCCA | 11061 & 11062 | PLXNB1 | CCAAACTGCCATGCCCCA | AGTCAGTGGCTCCACTCGA | 11167 & 11168 |
| PLA2G6 | GGCCAAGGAACTGGGCAA | CCCAGAGGGCGGTTGACCA | 11063 & 11064 | PLXNB2 | CCCACGATGCCAACGAGA | CAGGGCCTCATACACGGA | 11169 & 11170 |
| PLA2G7 | AGGTACGGCAAAGAGCAA | ATCATGCATCCAGGGGA | 11065 & 11066 | PLXNC1 | GCGAGCTCCGGAAAGAGA | AGCACCTGGACTCAGGGA | 11171 & 11172 |
| PLA2R1 | GCCGGTGCAGTACACACA | GCTGCTTGACAAGGACA | 11067 & 11068 | PM20D1 | ATCAGGACCACCACGGCA | CAGAAGGGCGTGACGGGGA | 11173 & 11174 |
| PLAC1 | AGCAAGAGCAGGCCCACA | ACAAGGTGGACAATCGGA | 11069 & 11070 | PMAIP1 | GGACACCCGATCCCAGCA | GAGTAGGCACACTCGACTTCCA | 11175 & 11176 |
| PLAC8 | GCAAGACAGGCATGTGTGA | ATAGATCCAGGGATGGCA | 11071 & 11072 | PMCH | TTCCAGCTGGAGAATGGA | GCCAACAAGGTCGGTAGA | 11177 & 11178 |
| PLAC9 | TGGAGGAGATGGGTAGAGA | GCTCCTCCAGCAGGCCCA | 11073 & 11074 | PMEL | GGGTACCACACTGGCAGA | GACCTTCAGGCTCAGGGA | 11179 & 11180 |
| PLAG1 | TTCCAGGAAGAAGGCAGA | GCTGACAGTGAGTGCAGA | 11075 & 11076 | PMEPA1 | GCTGGAACTGAACCGGGA | CCAGCTGGCACTATCCA | 11181 & 11182 |
| PLAGL1 | TATGCAGCCGCTGCCAGA | GAGGCTCTTGCAGAGGCA | 11077 & 11078 | PML | GGGAATTCCAGGAGGCCA | GGTAGACATGCTGGGCCA | 11183 & 11184 |
| PLAT | CCATCCAGCCGCTGCACA | GCGGCCATGCTTCAGACA | 11079 & 11080 | PMM1 | CCTGGAGGAGAGGATCGA | TGTCCAGCCTCGGGGA | 11185 & 11186 |
| PLAU | GGTGATCAGCGCACACA | CGGATCTTCACGCAAGGCA | 11081 & 11082 | PMM2 | ACGTGGATGGGACCCTCA | AGTCCGATCCGCTACCA | 11187 & 11188 |
| PLAUR | CGCCTTCAGCATGAACCA | GTGAGGCTGAGATGGGGCA | 11083 & 11084 | PMP22 | ACCAAACGAATGGCTGCA | ACGTGGTAGATGGCCGCA | 11189 & 11190 |
| PLB1 | TCCAACAGGGCCTGGACA | AGCTGCCAGCATGGCACA | 11085 & 11086 | PMPCA | GGAGCTGGAACGAGCCAA | TGGAGCGAGTGGCCAGCA | 11191 & 11192 |
| PLBD2 | CAAAGCCTGCAACCCCA | CATGGGAGCCCTGAGCA | 11087 & 11088 | PMS1 | CCTGCGGCAACAGTTCGA | ACGCTTGTGGCACCAGCA | 11193 & 11194 |
| PLCB1 | GAAGGAGCAGACTGCAGA | TCCAGGGCTTCCATGAGA | 11089 & 11090 | PMS2 | GACCTTCGGACCCCAGGA | CATCACCGACTTCCGGCA | 11195 & 11196 |
| PLCB2 | GCCTGCACAGTGAGAGCA | GGAAGGGCTTCTCAGGCA | 11091 & 11092 | PMVK | GGGAGAGGAGAAAACGCCA | ACCACTGCATGTCAGACA | 11197 & 11198 |
| PLCB4 | GAAAGGCCAACACGCCA | ACCACAGAGGCCAGGGCA | 11093 & 11094 | PNKD | TACAACCTGGCCACACGA | ACTCATGACCAGGCCACA | 11199 & 11200 |
| PLCG1 | TGAAGCAGGAGCCCAAGA | CTCTCGCACGAAGGAAGGA | 11095 & 11096 | PNLIP | CTGGGAAGGGACTCGAGA | GCAGCCTCCACTTGGACA | 11201 & 11202 |
| PLCG2 | CCCTTCACGACGTCAGCA | GATGAGGGCACCACGGCA | 11097 & 11098 | PNLIPRP1 | TCCCAATGGAGGAGAGA | GTGCAGGGATATGCAGCA | 11203 & 11204 |
| PLCH2 | GCACAGGACATGACGCA | TCCACGCAGCGGCAGCCA | 11099 & 11100 | PNLIPRP3 | ATCAACGGTTCACGGGAA | ACCCAGCTTCCCAGCCA | 11205 & 11206 |
| PLCL1 | GAGGAGGAAAGGCACAGA | GACTGGCAATTGGAGGGA | 11101 & 11102 | PNMA1 | GGTCCTAGAGGAGTGGCA | GAGCTCGAAGCCCCCA | 11207 & 11208 |
| PLD1 | GATGACCCAAGTGAGGACA | CATTGGGAAGGCACCGGA | 11103 & 11104 | PNMT | GGAGGCTGTGAGCCCAGA | CCTCAGACACTTGGCACA | 11209 & 11210 |
| PLD2 | GGCTGAGAGCAACGCCAA | TGAGGGGGAAGTGGACCA | 11105 & 11106 | PNP | AGGCCCATCCAAGCCAGA | CTGAGAATCCACGCCTCA | 11211 & 11212 |
| PLEC | TCACCGAGTTCGCCGACA | TGTCCAGGATGCCAGGCA | 11107 & 11108 | PNO1 | GAGAATGTGACACGGACA | CTGCTAGCACAGCTTCGA | 11213 & 11214 |
| PLEK | AGACCTGCCTACCTGCA | TCCACTGAAGTACACACA | 11109 & 11110 | PNOC | CGAGCCTGGCATGGAGGA | CCCCGGTGAAGCCCCCA | 11215 & 11216 |
| PLEK2 | CCAACAGCTTCACGGCCA | AGGAACTGCTCCGGCCAGA | 11111 & 11112 | PNP | GTGAGCTACAGGAAGGCA | CCCAGCTTCTGCAGACA | 11217 & 11218 |
| PLEKHA1 | CTTGCCAAGGTCAAGCA | CTGACCGGAAGCTCGCA | 11113 & 11114 | PNPLA4 | CAACGCCAAAACAGAGA | GAGGCTTCCGTCCACCCA | 11219 & 11220 |
| PLEKHA8 | GGAAAGGTTGCAAAGGGA | TGGCTGATCCCAGGGCCA | 11115 & 11116 | PNPLA7 | GGACCAGCAGAATCGAGGA | GGGGACATGTAACCGCAA | 11221 & 11222 |
| PLEKHG2 | CCCTCCAACTTCACCCA | GCAGTTGGAACATGGGCA | 11117 & 11118 | PNPLA8 | ACAGCAAGAAAACCCCA | AAGTAGCCTCAGGCAGCA | 11223 & 11224 |
| PLEKHG3 | GGCACAGGAGGGACACAA | GAGCTGACGAGCTGGGGA | 11119 & 11120 | PNPT1 | GATGATCAGGAGCAGCAA | GAAGCAGTACCGCAGTCA | 11225 & 11226 |
| PLEKHG4B | GCTCAGGAGGCCATGGCA | AGCGGTACTTGGCCACA | 11121 & 11122 | PNRC1 | CCCTCCGATGGTGACCA | GAGGAGTGCCTCCGCCA | 11227 & 11228 |
| PLEKHG5 | GCAGGAGGAAGGAAGAGGA | TCCCCAGGCTTACCACA | 11123 & 11124 | POCS | TCGGAGGAGGCCAGCGGA | GCTGCAGATCCTGCACCA | 11229 & 11230 |
| PLG | CATCCTGGGTGCACACCA | TCAGTGATGACGGCAGGA | 11125 & 11126 | PODNL1 | GGTGCTGCCCCACAACCA | CCAGCGGTTATAGGCCCA | 11231 & 11232 |
| PLIN1 | CAGAGACACCGGAGGGGA | GTGCCACACACCCAGGA | 11127 & 11128 | PODXL | GCCGAGCAGTCAAAGCCA | ACACATCCTGGCAGGGGA | 11233 & 11234 |
| PLIN2 | CTCAGCACCTGCAGACCA | CGCCTGCCATCACCCCA | 11129 & 11130 | POF1B | GCCAGCAAATCCAAGCCA | TACGCCCAGAATCAGCAA | 11235 & 11236 |
| PLIN3 | CCGCCGCCAGGTGGAGGA | CCCACGAGCCACGTGACA | 11131 & 11132 | POFUT1 | CCATGCTGAAGGACGGGA | CTTCAGGTCAGGCAGGCA | 11237 & 11238 |
| PLK1 | GCAAGAGAGGGCTGAGGA | CATTGAAGAGCACCCCA | 11133 & 11134 | POFUT2 | TGAACCCACGTGGGGAGGA | ACCTGGCGTGTGCGCAGA | 11239 & 11240 |
| PLK2 | CCAAGAGAGCCCAGGGCA | AGGAGGCTCATGTGAGCA | 11135 & 11136 | POGLUT1 | CCAAAAACCACACAGGA | CAAGTGAGCCACACAGGA | 11241 & 11242 |
| PLK3 | GCAGTGGGTGCAAGAACGA | CTGCCGAGGTCTGGAGA | 11137 & 11138 | POLA1 | AGAGCCAACCTGTCGCAA | CAGCTGGGTGTACAGGGA | 11243 & 11244 |
| PLK4 | CTCCAACACAGGCACCAA | AAGACACTCCTGCTGCA | 11139 & 11140 | POLA2 | CAACATGACCGGCCAGA | ACAGCTCATGGTGCACA | 11245 & 11246 |
| PLP | TGCCGACACCCGTACCA | CAGGTCAACTGCCGCAGA | 11141 & 11142 | POLB | CAGAATCAACCAAACAGCCA | GAAGCTGGCAAAACACCCA | 11247 & 11248 |
| PLN | GCCTCAACAGCCGCGTCAA | AGCAGAACTTCAGAGAAGCA | 11143 & 11144 | POLD1 | GCTGGCAAGGAGACAGA | AGATCTCCAGGCACGGCA | 11249 & 11250 |
| PLOD1 | CTACTACACCAGGGCCCA | GTAGGCAGGAACCGACA | 11145 & 11146 | POLD2 | CTTCCCAGAGTGCCCGCA | GCACTGAAGCTCAGGGACA | 11251 & 11252 |
| PLOD2 | AGTCAAGCCGGAAGCCAGA | GACTCAATGCTCCCCAGA | 11147 & 11148 | POLD3 | GCTGAGTCACCATCCCA | GAAGGAGGTTCAGGCTCA | 11253 & 11254 |
| PLOD3 | ATGTGCCCACCGTTGGACA | GTGTGTGGCCGCAGAGA | 11149 & 11150 | POLD4 | CGGGATCACACGGCTGCA | TGCCACCCTCGTGGGGGA | 11255 & 11256 |
| PLP1 | CACCTGGACACCTGCCA | GACAGAAGGTTGGAGCCA | 11151 & 11152 | POLE | GCTACCTGGAACCAGGGA | TGCCACAGTGTCAGCA | 11257 & 11258 |
| PLS3 | AGGAAGGTGAACCACGGA | CCACTGACAACATCAGCA | 11153 & 11154 | POLE3 | ATGCCGTGATCACCAGGA | GAGAGCACATCACTTGGCA | 11259 & 11260 |
| PSCR1 | AGCTCCACCCCACCA | GGTACCCTGCAGCTCCA | 11155 & 11156 | POLE4 | AGGGAGTCCTGCAGCCCA | AGGCTTCCCTGCGCCCA | 11261 & 11262 |
| PSCR4 | TGCCAGACAAGAGCTGA | GAATCTGAACCACACGA | 11157 & 11158 | POLG2 | GCAGCAGCTTAGCCGGGA | CCTGCTCCCTGAACACA | 11263 & 11264 |
| PLTP | AGGTCCAGCTGTCCAGCA | TGGGATCAGAGCCAGCGA | 11159 & 11160 | POLH | CCCAACAGCCAAAGCA | CACACTTCTCACAGGGCA | 11265 & 11266 |
| PLXDC1 | CCAGCAAGGTCACCAGCA | GCCTCTGTGCACAGCCA | 11161 & 11162 | POLK | ATGAGCGTTGAGAGGACA | AGATCTCGAGCAAGCTCA | 11267 & 11268 |
| PLXNA1 | TGACGGTCACGACGGCA | CACAGGGTTGGCCACAGA | 11163 & 11164 | POLL | GAGCCCTGCGAAAACCA | CAGTGGGAGTGGGCAGCA | 11269 & 11270 |
| PLXNA4 | GAGGGACCCAAGTGACCA | TGTCCACCTGCACCGACA | 11165 & 11166 | POLQ | TCTGGGCGATACGAGAGCA | AGCAGTACTGAGAGGGGCA | 11271 & 11272 |

| GeneName | Forward Primer | Reverse Primer | SEQ ID NOs | GeneName | Forward Primer | Reverse Primer | SEQ ID NOs |
|---|---|---|---|---|---|---|---|
| PRDM13 | TAAGCCCAAGACCGGCCA | CTTGCCGCAGAACTCGCA | 11485 & 11486 | PRLH | TCGGTCGGAGGAGGGCAA | CACCGCCTTCCAGGGGGA | 11591 & 11592 |
| PRDM14 | GCGAGTCCACTCTGGAGA | GAAGGGCTTCTCCCTCGGA | 11487 & 11488 | PRLR | GGCAACCCAGCAGAGGGA | AAGGGTTTAGCCGGAGCCA | 11593 & 11594 |
| PRDM15 | GGAAGCCTCGAACCCACA | AGACGTCAGTCTGGGGCA | 11489 & 11490 | PRM2 | GGCTGCACCGGATCCACA | CCTCCGGTGCCTGCAGGA | 11595 & 11596 |
| PRDM16 | TTCGAACCTCCAGCGGCA | CGACTCTGAGGTGGGAGA | 11491 & 11492 | PRMT1 | GCCTGCAAGTGAAGCCGA | CCAGTGCGTGTACGGGGA | 11597 & 11598 |
| PRDM2 | GAGGCCAAGAGAGCGGAGA | AAGAGCAAGAGGGGACCA | 11493 & 11494 | PRMT2 | CTTCCACCCACCACGA | CAGCCCAGTCAGGACGA | 11599 & 11600 |
| PRDM4 | CGGTGTTGCAGGCGAGCA | ATGGAGTCACTGCAGGGCA | 11495 & 11496 | PRMT3 | CATCCATGTGCACGGCCA | GGCCGTAGAGAACACGA | 11601 & 11602 |
| PRDM5 | CACCATCTCAGGAGCAGA | TCCAGGTAGCCAATCAGA | 11497 & 11498 | PRMT5 | GGCTCCAGAGAAAGCAGA | AGGAAGAGATGGGAGCCA | 11603 & 11604 |
| PRDM7 | GGACAAGGGGCATCCAA | AGTGCAGACCCAGTGGCA | 11499 & 11500 | PRMT6 | CTACGGACTCCTGCACA | CCGACAAATCCTGCACA | 11605 & 11606 |
| PRDM8 | GCAGAACTGGTGCGCCAA | GTGGCGCTCCCTGAAGGA | 11501 & 11502 | PRMT7 | ATGGTGATGCCCAGGCGA | TCCCTGAAGTCCAGGGCA | 11607 & 11608 |
| PRDM9 | GGCTGCATCACCAAGGGGA | CATCCCATACCAGACCA | 11503 & 11504 | PRMT8 | CATGACCTGCATCCGGGA | CTGCAGGCAGAATGCAGA | 11609 & 11610 |
| PRDX1 | GCGCACCATTGCTCAGGA | TCCAGCCAGCTGGGCACA | 11505 & 11506 | PRNP | GTCAGTGGAACAAGCCGA | CCCAGCATGTAGCGCCCA | 11611 & 11612 |
| PRDX2 | CGGCGTGCTGAAAACAGA | GGCTTCCAGCCAGCGGGA | 11507 & 11508 | PROCR | CGGTATGAACTGCGGGAA | ATGCCTACAGCCAACCA | 11613 & 11614 |
| PRDX3 | GGCCACATGAACATCGCA | ACGCCTTCACCAAGCGGA | 11509 & 11510 | PRODH | ACTGCGCAGGATGGAGGA | CCTCAAGAGCTCCAGCCA | 11615 & 11616 |
| PRDX4 | CCGGACTCGCTGAAGAGGA | GGCGACCGAATACCCGGGA | 11511 & 11512 | PROK1 | GGAAACGCAAGCACCACA | GTCAGTGGAGCAGTCGGTA | 11617 & 11618 |
| PRDX5 | CCACAAGGCGGAAGGCAA | GTGCCAGGCTGCAGGTGA | 11513 & 11514 | PROK2 | TGGGCAAACTGGAGACA | GCCTGGCAGCATGGGCA | 11619 & 11620 |
| PRDX6 | AGTACCACTGCCAGGGA | GTTGGAAGGACCATCACA | 11515 & 11516 | PROKR2 | TCGCATGAGCAACAGCA | AGGGACGCCAGTGAGCA | 11621 & 11622 |
| PREB | CTACGTTGAGGGGAGGCCA | CGACACAGCAGGAGCA | 11517 & 11518 | PROLL | CCCCGCAGCATCTACTGA | GGACAGTGGCATTGAGCA | 11623 & 11624 |
| PRELP | CCTGAGAACGTGCACA | TCATGAGGCCAGTGGGGA | 11519 & 11520 | PROM1 | CAAAGAGGCGTTGAAGGA | GGATGCACCAAGCACAGA | 11625 & 11626 |
| PREP | ATCAGAGGAGGTGGCGAA | GCCACTAAGAGGGCTCCA | 11521 & 11522 | PROM2 | AGGAGGTGACTCAGCGCA | TGCACCATGCCAGGCAGA | 11627 & 11628 |
| PREX1 | GCGAGTACGAAGGAGAGCA | CTCTGACAGCGTCACCA | 11523 & 11524 | PROP1 | GAACCGCAGAGCTAAGCA | GGCTGGGGAAGGAGGAGGCA | 11629 & 11630 |
| PRF1 | AGGAGCTTCGGCAAAGTGA | GGGGACATAGTCCAGGCA | 11525 & 11526 | PROS1 | CTGGAGTTGTGCAACACA | CATCTGGAAGGCACCCA | 11631 & 11632 |
| PRG2 | GAGGTGCTACAGGGGCACA | AGCGACCCGAGCCTGTGA | 11527 & 11528 | PROZ | GGAAGTGTGGTCACCAGA | CCTTGGTGACAAGGACCA | 11633 & 11634 |
| PRG3 | CTGGACTGATGGGAGCCA | GGTGCATAGGGCCACACA | 11529 & 11530 | PRPF3 | GTACAGCCAAAGACCGGA | ACAGATTCACTCAGCGCA | 11635 & 11636 |
| PRG4 | GACACCAACTCCCCGCAA | CGGGAGTAACTTCAGGCA | 11531 & 11532 | PRPF31 | GGACCCTGCAGAAGCAGA | GGAGTGGGGTGAAGGCCA | 11637 & 11638 |
| PRH2 | GGACCACCCCAACAGGGA | CCTCGAGGAGGACGGGGA | 11533 & 11534 | PRPF4B | CCTCGAGAAGGGACAGA | TCTACGACCCACCGCGTGA | 11639 & 11640 |
| PRIC285 | TCCTGGACCTGAGGCAGA | CCTGTGGGAACTGCACCA | 11535 & 11536 | PRPF8 | GGAGACGAGTGAAGGCGA | GCAGCAGCCTGTTGAGCA | 11641 & 11642 |
| PRIM1 | CCTGGCTGGAGTGGGAGA | GGCATCCAATTCACGGCA | 11537 & 11538 | PRPS1 | CCAATGAAGTGCACCGA | TGCCAAGTGTCAGCCA | 11643 & 11644 |
| PRKAA1 | GCACCTTCGGCAAAGTGA | ACCACATCAAGGCTTCGA | 11539 & 11540 | PRPS2 | GGTGGGCGACGTGAAGGA | TGGCTCCAGTGACAGGA | 11645 & 11646 |
| PRKAA2 | CACAACTGCAGAGAGCCA | GTGTGACTGCCCAGGCGA | 11541 & 11542 | PRRS1 | TCCAGTTCGGTGCAGGGA | GGACAATGGACGAGGGCA | 11647 & 11648 |
| PRKAB1 | TGAACAAGGAGACAGGGGA | GGGTTGCGCTGAGCACCA | 11543 & 11544 | PRRT3 | GCAACGTTGGTGCAGGCA | CCACCGTTGCGGGACA | 11649 & 11650 |
| PRKAB2 | GTCTGGAAGGAGGCAAGGA | CAAGCTGACTGGTAACCA | 11545 & 11546 | PRRT4 | GGCAGGGCCAGTGAGAGA | GACTGAGGACGCAGACCA | 11651 & 11652 |
| PRKACA | AGTACCTGCCCCTGAGA | AGTGAAGTGGGAAGGGA | 11547 & 11548 | PRX1 | GCAGGAATGAGAGAGGTA | TCGGAGCCAAGGCAGGTA | 11653 & 11654 |
| PRKAG1 | GAAGCAGAGGTTCACCGA | CTCCACCTGTGAGACCA | 11549 & 11550 | PRSS1 | CTACCCAGACGAGCTGCA | CTCCCTCAAGGAAGCCCA | 11655 & 11656 |
| PRKARJA | GGGGCATGCACCGAGACA | GACCGACGTTGTAGCACA | 11551 & 11552 | PRSS12 | TGCCAGGAGACAGCAGCGGA | TCCACACGCATCCCCA | 11657 & 11658 |
| PRKAR2A | GGAACAGGAGGTGAGA | ACTGCATAAGCTGAGGCA | 11553 & 11554 | PRSS16 | GCACAGCTGAGCAGGCCA | GACAAGGTGAAGAGCCA | 11659 & 11660 |
| PRKAR2B | GGTCAAAGATGGGGAGCA | TAAGGCCAGTTCGCCGAA | 11555 & 11556 | PRSS21 | TGCCCAAGGCGGGAAGGA | CCGATTGGGCCGACCACA | 11661 & 11662 |
| PRKCA | ATGACGTGGAGTGCACA | ATGACGAAGTACAAGCCGA | 11557 & 11558 | PRSS22 | AAGGTGCCTGTCAGACA | CCAGCCTGAGATCCAGA | 11663 & 11664 |
| PRKCB | GGGGTGACAACCAAGACA | AGGGTGCCTGCCAGCCA | 11559 & 11560 | PRSS23 | CAGCCATGCCCGTCACCA | GCAGGAGGCGTCACCCA | 11665 & 11666 |
| PRKCD | AAGCGGAGGTTGACGGAA | GAAGCCAGCGAATTGCAGA | 11561 & 11562 | PRSS27 | CGAGAGGGCCAAGAAGGA | GGCACAGCCCTCACCCA | 11667 & 11668 |
| PRKCDBP | AGGCCGAAGTTGAGAGA | GCGCTCCGGCACAGGCCA | 11563 & 11564 | PRSS3 | TGCTGACTACCAGACGA | CTCCCTCAAGGAAGCCCA | 11669 & 11670 |
| PRKCE | GGCCGACAATGAGGACGA | GGCATGCCACAAGCCCA | 11565 & 11566 | PRSS33 | CGTTGGTGAGCCTGGGCAA | GACGCGAGCCTGAATCCA | 11671 & 11672 |
| PRKCG | GTCCAGACAGTCCACA | ACCAGGTGCAGTGCACA | 11567 & 11568 | PRSS35 | CCACGGGGTTCAAGAAGGA | CCGTGAATCCAGAAGGA | 11673 & 11674 |
| PRKCH | GGTGTCACCAGGGTCACA | GCCAGGTAGGGTAGACCA | 11569 & 11570 | PRSS36 | CCTGTCCAGATGACGGA | CAGGCCTCTTCAGGACCA | 11675 & 11676 |
| PRKCI | AGGATTACGGCCAGGAGA | GAGCACTTCCAAGAGCCCA | 11571 & 11572 | PRSS37 | AGAAAACAGTGGCCGACA | TGAAGTAGCAACGGCCA | 11677 & 11678 |
| PRKCQ | AGGAGATGCCAATCAGCA | GCGACTCGACCAATCAGCA | 11573 & 11574 | PRSS38 | ACCTGCTCTACGGACACA | CGGACTGCCCCTACACA | 11679 & 11680 |
| PRKCSH | CTACGACGAGCAGACGA | GACAAGCTTGAAGGGGCA | 11575 & 11576 | PRSS42 | GGTGCTGACGGCAGGCCA | TGGAGAAGGGCAAGGTCA | 11681 & 11682 |
| PRKCZ | TCACCGACAACCCGGACA | GGGAGCGGCTTTGACGGACA | 11577 & 11578 | PRSS50 | CAGAAGACGGAGGCCCCA | GCAGTGGGAGTGCCAGGA | 11683 & 11684 |
| PRKD1 | CCTTCCAGCCATCACCA | CCTTGGGAATGACGGGCA | 11579 & 11580 | PRSS53 | AGCCCTGGTGTCAGGGA | GAGCTGCTTCAGGCCCA | 11685 & 11686 |
| PRKD2 | GAGCCACATCTCAGCTGGA | CAGCTCTCGGAGGTCCA | 11581 & 11582 | PRSS54 | GCTTGGGGGACCCAGGGA | CAGGCACGTCTCACCA | 11687 & 11688 |
| PRKG1 | CAGGGACCTCAAGCACA | GTGGGCTTGCCAGTCAGGA | 11583 & 11584 | PRSS55 | TGACCCAGCTAGAGGGCA | GACTCCCGAGACTGGGGA | 11689 & 11690 |
| PRKG2 | GCTGAACAAGCTGCACA | TGGAGAGAGACCAATCCA | 11585 & 11586 | PRSS8 | CAACCTCTGTGGCAGCCA | ATGGGAGAGGAGGCCCA | 11691 & 11692 |
| PRKX | CTGGACCTGCATGGACA | CAGGTACCGTGAGGGACA | 11587 & 11588 | PRTG | TTACACCGTGAAGGGCCA | AGTACTGCGCTCCACA | 11693 & 11694 |
| PRL | CCATCAACAGCTGCCACA | CAGAGAGGTCATTCCAGGA | 11589 & 11590 | PRTN3 | GCTGAGCAGCCCAGCCAA | GCCGGCAGAAGAAGGTGA | 11695 & 11696 |

| GeneName | Forward Primer | Reverse Primer | SEQ ID NOs | GeneName | Forward Primer | Reverse Primer | SEQ ID NOs |
| --- | --- | --- | --- | --- | --- | --- | --- |
| RGMB | GGCCCATGTCTTACGAGGGA | CAGTGTGTAGCCAAGGCCA | 12333 & 12334 | RNASEL | CCACGTGCACAGCCGGGAA | CTCACAGAGGGTGACACA | 12439 & 12440 |
| RGN | ACCTGCAGACAGGACAGA | ACCCAGAGCTTCCCCTCA | 12335 & 12336 | RNASET2 | CAGCACTGGCCTGAGACA | CAGGCCAGTATGCCCTCA | 12441 & 12442 |
| RGS1 | GACTTCCGCACTCGAGAA | CCCTTCAGCCAGGGACCA | 12337 & 12338 | RND3 | AGGACTGCTTCCCCGAGA | ATCAGCACAGCATCCGAA | 12443 & 12444 |
| RGS11 | ATGACGCCCAGCTGCACA | TCCCAGCCTCTGCCAGGA | 12339 & 12340 | RNF103 | CATGTGAAAGGAAGGGGA | ATAAGAAGGCCACCGGCA | 12445 & 12446 |
| RGS12 | CCGAGAAGGACAAGGGCA | GCTCACAGAGTCCGGACA | 12341 & 12342 | RNF11 | GACTCGGCTAGCAACTCA | GGCACGTGAAGGATCTCA | 12447 & 12448 |
| RGS16 | CGAGGATGAACCTGCAGA | GCGGCTGAGGCTTGGGCA | 12343 & 12344 | RNF123 | GGGCACTGACATCCGAGA | CCAGGAGGTTCCTCACCA | 12449 & 12450 |
| RGS3 | ACCCCCTCTACCTCCAGA | GTTCCTCCGACAGGCACCA | 12345 & 12346 | RNF128 | AGCAGGAAGCAGAGGCAA | CAGCCATGGGTCAACACA | 12451 & 12452 |
| RGS4 | GGGAAGAGACAAGGCGA | AGCTGGACGGGTTGACCA | 12347 & 12348 | RNF130 | AAGATCAGCCCTGGCGA | AGGGCACTGAGGAGGCCA | 12453 & 12454 |
| RHAG | GCCACCCTTGCTGGAGGA | TGCCTGCAAGGCTCCCA | 12349 & 12350 | RNF144B | ACTTGGCCACTCAAGAGCA | CCGACAGGACTTGCAGACA | 12455 & 12456 |
| RHBDD3 | CCAGTTCTCCCCAGGGA | TGGCCCGTCAAGAAGCGA | 12351 & 12352 | RNF146 | GAAGAACTCAAGGCAGCA | TCGTACTGCCACCACCA | 12457 & 12458 |
| RHBDF2 | TCACAGGCAACCTGCACA | AGTCGAAGATGTGGGCGA | 12353 & 12354 | RNF148 | GGGGAGAATGCACATGCA | AGGCAATTGTGGAGGCCA | 12459 & 12460 |
| RHCE | AAGTCGGCCAAGATCTGA | ACCTTCCCAAGACAGCA | 12355 & 12356 | RNF150 | CACCATCGGAACCCCGAA | GACGAGCCATGCGAGGGA | 12461 & 12462 |
| RHCG | ACATCCTGAGGACCCCA | AGGGTACCGAGGAAGCCA | 12357 & 12358 | RNF167 | ACCCTGCCTCAGAAAGGA | GGGAGCTGGGGCTAAGGA | 12463 & 12464 |
| RHD | TCAGCGTGTGACAGCCA | CCGACGAGGATCAGCCCA | 12359 & 12360 | RNF19A | TGGAGTCTCAGCAGGCAA | CTGCCAGTCAGCCCACCA | 12465 & 12466 |
| RHEBL1 | CATCTGTGTGGACAGCCA | AGCTATGCAGAGAGGTGA | 12361 & 12362 | RNF19B | TGGAAGCAGCACGAAGGA | TCACTGCCTCCGCCACCA | 12467 & 12468 |
| RHO | GCCACCACAGAAGGCCA | GGCAAAGAACGCTGGGA | 12363 & 12364 | RNF2 | ATCAGGAAGCAGGGCCTA | AACAGTGGCGTTACCAGA | 12469 & 12470 |
| RHOA | GACACAGCTGGGCAGGAA | GATGGGCACCGTTGGGACA | 12365 & 12366 | RNF207 | CAGGCTGGCAGAGAGGAA | GGCCAAGCTGAGGAAGGA | 12471 & 12472 |
| RHOB | GCCCGCATGAAGTGCGAA | GCCAGACGTGCTGCAGGTA | 12367 & 12368 | RNF213 | GCCATCTGCAGACGACCA | GTCCTGCAAGACATCACCA | 12473 & 12474 |
| RHOBTB3 | CGACAGTGCCAGCCCACA | GGAGAACACATGGCCTGGA | 12369 & 12370 | RNF219 | AGCAGCCTGGCTCATCCA | CAGAACTGGTGTCACACA | 12475 & 12476 |
| RHOC | GGCCAAGATGAAGCAGGA | TGCGGACCTGAGGGCCA | 12371 & 12372 | RNF220 | GAAGGCTCGGGCTCAGAGA | AGCACTCCTCGCAGTGCA | 12477 & 12478 |
| RHOD | ACCACAGGGCCAGCAGGA | CCTGGAAGACGGGCGTGGA | 12373 & 12374 | RNF31 | CAGTCTACGCACTCCCA | CACACTCCTTGGGCAAGCA | 12479 & 12480 |
| RHOF | GCTCGGAACAGATCGGA | TCAGAGGCTGAGAGCCA | 12375 & 12376 | RNF34 | GCAGGATGAGGAAGACGA | CACCACTACTTCGGCACA | 12481 & 12482 |
| RHOG | ACTGGCCAAGACAGATCCA | GGTTGAGCACGCCCGGA | 12377 & 12378 | RNF4 | CCCAGGACCCATGCTGACA | AGGCCTGTAGCCGCCCTA | 12483 & 12484 |
| RHOH | AGCCCACAGTGTACGAGA | GCACAGGGGTACAGGGCA | 12379 & 12380 | RNF43 | AGAAACCCGGAGTCCCCA | GAGGCGTCAACTGGGCCA | 12485 & 12486 |
| RHOQ | GCAAGACTGCCTACTCA | GGTCGAAGACGGTGGGCA | 12381 & 12382 | RNF71 | ACTCCACAGTGAAGCAA | GCCGAATTCTGAAGAGGA | 12487 & 12488 |
| RHOT1 | GCCCAGGAGGAGAAGGAGA | CGTCGAAGCACAGTCCAA | 12383 & 12384 | RNH1 | TCCTCAGGGCCAAGGAGA | GCTGAAGTGGGAGCAGCA | 12489 & 12490 |
| RHOT2 | TCACCAGCTGCGCCACA | AGCTGAAGGACTGCGGCCA | 12385 & 12386 | RNLS | CCAAAGGCAGCAACTCGA | GGAGACGAAGCGTATGCA | 12491 & 12492 |
| RHPN2 | CTGCACCCTTGGCCACA | CCTGTGCGGCACAGCACA | 12387 & 12388 | RNMT | GGAAAAGACACTCCATCCA | GCCTTCAGCATCACCACA | 12493 & 12494 |
| RIBC2 | TCAACAAGAGCCAGCCCA | GCGGGTTCTCGGAGAAGCA | 12389 & 12390 | RNMTL1 | CGACTCGGACTGGACAGA | GGCTGTCCACACCAGGGA | 12495 & 12496 |
| RICTOR | AGCCCAAGCAGTGTACGAGA | GGCTTGATCTGGCACGA | 12391 & 12392 | RNPEP | AGACCCTCGCCAAGGAGA | GCCAGATCTGCTGGACA | 12497 & 12498 |
| RIMBP2 | CAGGAGATTACGGGCGAGA | GGGAGCCTTCCGGCACCA | 12393 & 12394 | RNPS1 | GCTCAGGAAGCTCCAGCA | TGTCTGCGCGGAAGAGGA | 12499 & 12500 |
| RIMS1 | TCACGCCTCAGCAGCACA | GCTCCAATGTACCCACA | 12395 & 12396 | ROBO1 | GGATACGGATGCGCCAGA | CATGGACCCGTGCACAGA | 12501 & 12502 |
| RIMS2 | TCGACAGGCAAGCCGAGA | CGTCCACTAGCTCGAGCA | 12397 & 12398 | ROBO2 | CCAGTGTGTACTGCGAGGA | GACCGGTGAGTGTAGCAGA | 12503 & 12504 |
| RIN2 | CTGACAGCAAACCCCGA | TGACCAGGGAGGCAGGA | 12399 & 12400 | ROBO4 | GGAGCTGCAAGTGATGCAA | GCTGGAGGAGATGACGA | 12505 & 12506 |
| RIOK3 | GGCCTGGGAACGCAGAGA | CAGCATAAGGTCACTGGA | 12401 & 12402 | ROCK1 | GAAGTGCAGGTTAGGGCGA | GAGCGTTTCCAAGCCA | 12507 & 12508 |
| RIPK1 | CCCAGTGCTGAGACCAA | GATGAACTCGTCCCACCA | 12403 & 12404 | ROPN1 | GGTGAGAGAGGCGGTCTGA | TCCGTGAAGCGACCCACA | 12509 & 12510 |
| RIPK2 | AGAAGCCTGCCTTAACCA | GGTAAGCTCGAAGACCCA | 12405 & 12406 | ROR1 | GAAGACTGCCACCCAGA | TGGGCTGGCACTGCAGGGA | 12511 & 12512 |
| RIPPLY1 | GACTAGCCAGGGCCTTCA | AGAAGCCAGGGCCTTCA | 12407 & 12408 | RORA | CGGGAGGTGATGTGCAA | AGGCAGGCACATTCTGA | 12513 & 12514 |
| RIT1 | AGTCCGACGTACTGAGGA | GTAGCGGTATGCAGACGA | 12409 & 12410 | RORB | GATACCAACCATCACGGA | CCGGTGGCACAGTCCAGGA | 12515 & 12516 |
| RIT2 | CGGGAGCAGTACATGCGA | TGTTACCCACCAGCACCA | 12411 & 12412 | RORC | GAGGCTGTGTAGCCAGA | AAGCGGCTTGGACCACGA | 12517 & 12518 |
| RLN3 | CCTGACCAAGTCACCCCA | ACATCTCGGCTGCCCCGA | 12413 & 12414 | ROS1 | CCTCTAGGCTCCCAGGAA | AGGCCTTGCCAGAAGGGCA | 12519 & 12520 |
| RNASE1 | GCCCAAGGAGGAGAACA | GAGTCTCCACAGAAGACA | 12415 & 12416 | RP1 | ACCCAGAGCTTCGGCAGA | CGCCACACAGCTCCAGA | 12521 & 12522 |
| RNASE10 | TAGGCTTGACCAGAGAGCA | CCCTTGAGCTTCACAGGCA | 12417 & 12418 | RPA1 | AAGAGCTATGAAGACGCCA | CACAGTGTAGCAGTCACCA | 12523 & 12524 |
| RNASE11 | CAATTCCCCAGGTTGCCA | GAGAATGACCTGTCAGCA | 12419 & 12420 | RPA2 | GAGCCCGAGCCCAGCCA | CCCATTGGCGAACGTCA | 12525 & 12526 |
| RNASE12 | TCAGGGAACCTGACCCA | GTACCTGCAGGCAGGGTA | 12421 & 12422 | RPA3 | TAACCGCCAAGGCCACCA | ACTGAGGGAAGTTCATGGA | 12527 & 12528 |
| RNASE2 | ATGGGCAGACACCAGCA | CCAGGTGAACTGGAACCA | 12423 & 12424 | RPE | CACCATGGGCTAATCAGA | ATAGCACTGCCAGACACA | 12529 & 12530 |
| RNASE3 | CCATTGCAATGCGGGCAA | ACCGGAATCTACTCCGA | 12425 & 12426 | RPGR | CAGCCATCAGCAAGGCAA | CGGAATTGTCACCCCACA | 12531 & 12532 |
| RNASE4 | AGGGCACCCAACTGCACA | GGGTTACCCTCACAGGCA | 12427 & 12428 | RPGRIP1 | GACCACAGGAGGAGCAGCAA | ACTCCAGGATCTGCCACA | 12533 & 12534 |
| RNASE6 | AACTGCCACCAGCTCA | CTATAGCGGCACTGGGGA | 12429 & 12430 | RPL10 | GGCCCTGCCAGGACCCA | GAACTTGGTGAAGCCCA | 12535 & 12536 |
| RNASE7 | GCTCACCTTCAGGGAAGCA | GGGGAGGCTTACAGGCCA | 12431 & 12432 | RPL10l | AGAACGAGGAGCATGTGA | AAGGGGCCATGACTGGGA | 12537 & 12538 |
| RNASE8 | CCAGACCTCAAGGCATGA | GGTGATGGCCACACTGGA | 12433 & 12434 | RPL14 | AAGTGAGGAGGAACAGGCCA | GGTGGGCACTGTGCGGAA | 12539 & 12540 |
| RNASEH1 | GACAAACCAAAGAGCCGA | AGCCTCCAGTGCCACA | 12435 & 12436 | RPL18 | CCGAGAGGGTGTACGGCA | GCCCTTGGAGGACGTA | 12541 & 12542 |
| RNASEH2A | TGGCTCAGGCTACCCCAA | TGCGCCAGTGAACCGGA | 12437 & 12438 | RPL19 | GCCCGAATGCCAGAGA | GCTTGGTCAGCCAGGA | 12543 & 12544 |

| GeneName | Forward Primer | Reverse Primer | SEQ ID NOs | GeneName | Forward Primer | Reverse Primer | SEQ ID NOs |
|---|---|---|---|---|---|---|---|
| SBDS | AGAGACCATACACCGTGA | GGATGAACCGAAGCCTCA | 12757 & 12758 | SDCCAG8 | GAAGGAGCTGGAGAGGCA | GGGCCTCCAGTTGGGCAA | 12863 & 12864 |
| SBNO2 | CCTGGACGTGGGAGGAAGGA | TCCTCGATACCGGGAGCA | 12759 & 12760 | SDF2 | CAGTGTGTGGGAGCGTGA | CTCACCCAGTAGGGTCCA | 12865 & 12866 |
| SCSDL | ATCAAGTCCGTCGAGAGA | TCCAGCAAGAACAGTGCA | 12761 & 12762 | SDF2L1 | ACAGCACTGGGAGCCGTGA | CCTATGCTGCCCATGGA | 12867 & 12868 |
| SCAF1 | GAAGGGGTCTCGTCGGAA | CCGGGAAGAACAGGAGGA | 12763 & 12764 | SDF4 | CGCCATCAGGCTCAACGA | CCTCCTCCGTCAGCAGCA | 12869 & 12870 |
| SCAI | CGCAGAGGGCTCATGGGAA | CTTGTGAGGAGCAAGGCA | 12765 & 12766 | SDHA | GGGAAGCGTGTTGCAAGAA | GATGGTCTGCAGCGCA | 12871 & 12872 |
| SCAMP3 | CCGAAGGGCAACACAGCA | GCACCGCAGGGTTGGAGA | 12767 & 12768 | SDHAF2 | CTGTCAAGGCACAGCTA | CTCCTGCCATGGAGGCAA | 12873 & 12874 |
| SCARB1 | CGGTCACGGGAATCCCA | GGCAGATGACAGGGACCA | 12769 & 12770 | SDHB | ACTGGACGGGCTTCACGA | TCCAGTCGATAGGCCTGCA | 12875 & 12876 |
| SCARB2 | GACTCACACAGTTGACGA | GAGAGATATCGGGCTGA | 12771 & 12772 | SDHC | GGCCAAAGAAGACATGGA | AACAGGCCGACATGCCA | 12877 & 12878 |
| SCARF1 | CTGAGCACCTTGGAAGCCA | CGGAAGACAGAGCGGACA | 12773 & 12774 | SDHD | CTTGTCACCGAGCCACCA | GAGTGAGGGCTGCAGGCCA | 12879 & 12880 |
| SCD | CTTGTGCGCAAACACCCA | GGGCAGCACTGTTCACCA | 12775 & 12776 | SDPR | CCGAGAGGGAGAAAGGCA | CCACCAGAGCGCTGGCGA | 12881 & 12882 |
| SCEL | CACACGGAAGCAGCACCCTA | CGGTTGAGCACCACCCTA | 12777 & 12778 | SEC14L1 | GCGGATGAACAAGCGCGA | TGCTGCCATCAAGGCTA | 12883 & 12884 |
| SCFD1 | GGCCAGATATCACAGACA | AGGGCCTCTGGAAGCTGA | 12779 & 12780 | SEC14L2 | CTGCAGAGGAGCTGGAGA | ACTGACGAGGCATCACA | 12885 & 12886 |
| SCG2 | GACTGAGGGCCTACCAGA | ACATGTGGAATCCAGGCA | 12781 & 12782 | SEC14L3 | CCAAGATGGGAGAGAGGCA | CCGCAGGAGCATAGATGCCA | 12887 & 12888 |
| SCG3 | CAGTGAAGAACAACTTGAGGA | GGAAAACACCTTCTTCTGGAGA | 12783 & 12784 | SEC16B | CATGTACGTGCGGGACCA | AAGCCGATGGTCCGCACCA | 12889 & 12890 |
| SCG5 | CACCCTGACACTGCTGA | CACTTGCCAAGCCTGGA | 12785 & 12786 | SEC22B | TGAGCCAGGGAGCAAGGCA | CCGAAGTTGCGCTAGTCA | 12891 & 12892 |
| SCGB1C1 | AAGATGCCAAGGCAGCAA | GCACCAGCAGCTTGAACCA | 12787 & 12788 | SEC22C | GAACACGTCCCTACCAGA | GTCGGGACACAGTGGGCA | 12893 & 12894 |
| SCGB1D1 | TGCTACCGGGCAAATGCA | GGCCATGTATCCACGGA | 12789 & 12790 | SEC24D | CACTCTGGAGACACAGA | GAGCAGGCTCCAAGTGCA | 12895 & 12896 |
| SCGB1D2 | CTGCTGCTACCAGGGCA | ACAGCTTCCGAGGGGCA | 12791 & 12792 | SEC31A | CCAGATGCCAGGGAGGGA | TAGTGACCAGGGGAGGGA | 12897 & 12898 |
| SCGB1D4 | AGCTGAGCTCACAGCCGA | AGAAGCAACAGTGGGCA | 12793 & 12794 | SEC31B | GTACGCAGCAGCAGCACCA | GGCAGCTCACTGGCAGCA | 12899 & 12900 |
| SCGB2A2 | CCCGACTGAACACTGA | CAATAAGGGCAGCCAGA | 12795 & 12796 | SEC61A1 | AGGGTCCAAGACACAGA | AGGAGTCTCAGGCAGGGA | 12901 & 12902 |
| SCGB3A1 | TGCTGAGCAGCTGGGGA | GCCTGGGACCCAGTCA | 12797 & 12798 | SEC61B | AGCTGAAGGAGCAGCAGA | CGCCTAGGAAGTCAGCCA | 12903 & 12904 |
| SCGN | ACTGGACACAGCGTGGA | CTCGGAGGAAGTTGCGGA | 12799 & 12800 | SEC61G | CTGTGGGACAAGGAGTGCA | GGCCAACTTTGAGCCCA | 12905 & 12906 |
| SCHIP1 | CCACGACCTGAGAGACA | ATGTCCACCAGCATGGCA | 12801 & 12802 | SEC1SBP2 | GATTGCCATGGCAAGCAA | CCCTCACACTTGTTCACCA | 12907 & 12908 |
| SCLT1 | TGGGCACAGAGGTAGGAA | CAGAGTTCCACAGCCTGA | 12803 & 12804 | SECTM1 | GGAGATCCCCAAGGCAA | AACTGGTCATCACCACCA | 12909 & 12910 |
| SCMH1 | CAGCACCTCTGGGAACGA | TCCGACCCTGGGAACGA | 12805 & 12806 | SEL1L | CAGCTCCAGGTTCAGGGA | ACAGCGGCACCTGTACCA | 12911 & 12912 |
| SCML2 | CCCCAAGAGAGCAGTCCCA | GCCTGAAGAGGTCGGCGA | 12807 & 12808 | SEL1L | AGCTGAAGCCAGCCCAGA | GTTCCCAACAGCAGCGCA | 12913 & 12914 |
| SCN10A | CAGGAGCAGCTGCAGCAA | TCAGCAGGGACCTGAGGA | 12809 & 12810 | SEL1L2 | CGAGTCCAGATGCCCACA | CCAGGAACAATGGAGGCCA | 12915 & 12916 |
| SCN11A | TGCGTGTGGCAAAGCCA | GGCCATCAGGGCCACCGA | 12811 & 12812 | SELE | GCCTGGCAGTTCCGGAGA | TTCCGAAGCCAGGAGGGA | 12917 & 12918 |
| SCN1A | GACACGGAGAGAGAGCA | AGGTCCACCAACCAAGGA | 12813 & 12814 | SELENBP1 | CAGTGCCTGGGACAAGGA | TAGCGGAGTCATGGGCA | 12919 & 12920 |
| SCN1B | GGACAAAGCCAACAGAGA | GCCAGGTATTCCGAGGCA | 12815 & 12816 | SELI | ATGCAGTGGCCATGGAGA | TCAGAGCAGCTGAAGGCA | 12921 & 12922 |
| SCN2A | GAGCAGAGCGGGATCCGA | TCCATCCCAGCCAGCAGA | 12817 & 12818 | SELO | GCTGCAGAGGAGGAACCA | TGGCGTGCATCACGCGCA | 12923 & 12924 |
| SCN3A | CCATACCTCGCCAGCAA | GGGAGACGAGCTTCAGCA | 12819 & 12820 | SELP | CTGCACAAACAAGCATGCCA | GTAGAGCCCACCCTCCA | 12925 & 12926 |
| SCN3B | CGAGGAGGCTGGAGAGGA | GGGATGGCAAGGTAGTCA | 12821 & 12822 | SELPLG | TCCATGGCAGCCAGCAA | CCTCACCCCATCAGGCA | 12927 & 12928 |
| SCN4A | TGGACCTGGGCATCCA | GGTTGCCCACAGTGAGCA | 12823 & 12824 | SELT | GCCAGCGGTACCCAGACA | CCCCACTGCCAGATGCTA | 12929 & 12930 |
| SCN4B | GCTCCAAGAAGCCCAGA | TAGTAGTGGCCGAAGGGA | 12825 & 12826 | SEMA3A | GGCAATTCCAGAGGCGAA | AACCCATGTTCCACGCA | 12931 & 12932 |
| SCN5A | GGAGAAGTTCGAGCTGA | ACCCGCTTGGTGAAAGCA | 12827 & 12828 | SEMA3C | ACGGACAAATGGTCCCCA | AGTGGCTGAATGCCCCA | 12933 & 12934 |
| SCN8A | AGCGAAGGGAGATCCGCA | AGCAATCCATCCCAGCCA | 12829 & 12830 | SEMA3D | GCAAAGCCCAGGAGCACA | TCAACGTGACTCAGCCA | 12935 & 12936 |
| SCN9A | AGCCATGGAAGCAGGACCA | ACAACACCCAGTAGGCCGA | 12831 & 12832 | SEMA3E | GCAGCCTTCAAGGACCA | CGGATGCCATCATCAGGA | 12937 & 12938 |
| SCN1A | CAACCGGGACTTCCAGA | CAGAAGGCCAGTCAGCCA | 12833 & 12834 | SEMA3F | CGGAAAACCCATCAGCCA | GTGCAGGAGTAGAGGCCA | 12939 & 12940 |
| SCNN1B | GGAACCGCCTCACAACGA | CGTCACAGGGTGACCA | 12835 & 12836 | SEMA3G | GCGAGTTCTTGCACACGGA | GGACCACAGTCTGGGAGA | 12941 & 12942 |
| SCNN1D | CATGGAGAGCCCAGTCAA | GGCGCGCAATGATAGAGA | 12837 & 12838 | SEMA4A | TGGACAGCCACGACCAGA | CTTCAATGGGGAGGCCA | 12943 & 12944 |
| SCNN1G | GCAAGTGAGGACCACCA | AGGGTCCAGTTGGCTCGGA | 12839 & 12840 | SEMA4B | AGCCAGCTACTGCCAGA | AGCAGCACGGCAGCAGCA | 12945 & 12946 |
| SCRN1 | ATGCCGACGTGCGCGCA | CTTGCCCGAGTGCGCGCA | 12841 & 12842 | SEMA4C | GCCCTGTCCTGAACCAGA | GCCGAGTTGGAGAAGGCA | 12947 & 12948 |
| SCRN2 | GGATGCCCCTGGACGGGA | CCTTCTGCAGCAGCCCA | 12843 & 12844 | SEMA4D | GCGTGTTGAAGGCCGAGA | AGGCACTGTGACCCCA | 12949 & 12950 |
| SCT | TTCCAACGAGAAGCGGCA | TGGACAGGGCCACGAAGGA | 12845 & 12846 | SEMA4F | GGACACCTCCACCGAGCA | GCTCTGGAGACGCCCACCA | 12951 & 12952 |
| SCTR | GCTACATCGAGTCCCCA | CATCCTCGATGGGCAGGA | 12847 & 12848 | SEMA4G | GCCTGAGGACAGTGGCAA | AGGATGAGGCAGAGGCCA | 12953 & 12954 |
| SCUBE1 | AGGAGGCCTTGCCACTGA | GTTCCCACTGGGCAACGA | 12849 & 12850 | SEMA5A | GCAACAACCCGAACCCA | GGGACCAGCAAGACCACA | 12955 & 12956 |
| SCUBE2 | CCAAGCATGAAGGGGCCA | TCCCCACCACTGACAGA | 12851 & 12852 | SEMA5B | GGAGAAGTCGGAAGCCA | CTTGAACTCCACGCCGCA | 12957 & 12958 |
| SCUBE3 | GGGCCTCTGGACAAGGAA | CCCACCAGGACACAGA | 12853 & 12854 | SEMA6A | AGCAGAAGCGGAAGCCA | CGTAGGATTACAGGGGA | 12959 & 12960 |
| SDC1 | ACCTTGACAACAGCTCCA | TCATCAGCTCCCGAGCCA | 12855 & 12856 | SEMA6D | AGAAGACCCTGCAGGCCA | GGGGAATGAGGTGGCGGA | 12961 & 12962 |
| SDC2 | ATGCCATCACTTGCGGCA | AGATGAGCAGTGTGACCA | 12857 & 12858 | SEMG1 | AAGGCCGGATCCCAAAGCA | GTGCCAGGAACAGAGTGA | 12963 & 12964 |
| SDC3 | CACTGTGCAGGGAGCAA | AGGATCAGGAAGACGGCA | 12859 & 12860 | SEPHS1 | TGGCCTACCAGGAGGGGA | TCTTGGCCAGCCAGGGA | 12965 & 12966 |
| SDC4 | ACCCTGCCAATCCAGGAA | TACCAGTTACAGGAGGCCA | 12861 & 12862 | SEPHS2 | GCTGTCATGCCCACCAA | CCTGATAGGCCAGCTCCA | 12967 & 12968 |
| SDCBP | | | | | | | |

| GeneName | Forward Primer | Reverse Primer | SEQ ID NOs | GeneName | Forward Primer | Reverse Primer | SEQ ID NOs |
| --- | --- | --- | --- | --- | --- | --- | --- |
| URB2 | CACGCTCTTGGAAGCCGA | ACACCCTGGTAGAGGGCA | 15513 & 15514 | VGF | CCCTTCCCGAAACCCACA | CCTTGGACAGGGGTGCA | 15619 & 15620 |
| UROD | CCGTGATGTGGCCAAGCA | CCAACCACCTCATAGCCA | 15515 & 15516 | VHL | CCACAGCTACCGAGGTCA | GGCTCCGGACAACCTGGA | 15621 & 15622 |
| USH1C | GGAGCCAGGGAGGAGGAGGA | CCACCATGCCGCTCAGGA | 15517 & 15518 | VIL1 | TGGACACCTGGGCAGGAGA | CCTGCTTGACCAGCACGA | 15623 & 15624 |
| USH2A | GTGTGACACCTTCAGTGACA | TGCAAGGCAGAACAGAGGA | 15519 & 15520 | VIM | CAATGAGCCCTTGCGCCA | CACGAAGGTGACGAGCCA | 15625 & 15626 |
| USP1 | CAAGGAATCCAGTGACCA | AGCAACCACTTCCCCTCA | 15521 & 15522 | VIP | GGGAGCAAATGAACCTGA | CCATCAGCATGCCTGGCA | 15627 & 15628 |
| USP11 | CAACAAGGACACAGCGGCA | CTCAGAGCTGGGTGGGGA | 15523 & 15524 | VIPH1 | GAACCCCAAATACCGGCA | GGCTTGGAAGCTGAGAGGA | 15629 & 15630 |
| USP12 | AGGAAGGACACACAAACGGA | GGACCACTTCCACAGTGA | 15525 & 15526 | VIPR2 | GTACAAGAGGCTGGCCAA | AGTAGAGGACGGCACCA | 15631 & 15632 |
| USP14 | AATGATGGGTCAGTGCAGA | GCTCTCAAGGCACCTGCA | 15527 & 15528 | VIT | CAACTTCGCCTGGAGCA | CCTTCAGATGGGCAGCCA | 15633 & 15634 |
| USP15 | GGGGACACCTGGTACCTA | AGTGACTGGGCATCACCA | 15529 & 15530 | VKORC1 | CGCTTGCGACGTGGGCA | AGCGAGAGACACCAGGGA | 15635 & 15636 |
| USP16 | CCAAGGCAGGAACCGCAA | GTAGGCACAGCTTGCACA | 15531 & 15532 | VKORC1L1 | GCGGAGAGAGGAGGCGGGA | GTAGGCCAGGTACAGGGA | 15637 & 15638 |
| USP18 | GCACGTGGGAGATGGCAGA | GTCTTCCCAGGAGTACACAA | 15533 & 15534 | VLDLR | GCCTGGCCAGCACCACAGA | AGAATGGGCCTCATGCCGCA | 15639 & 15640 |
| USP21 | GCCAGTTGACAAAGCCGGA | ACCAGTCTGCACCACGGCA | 15535 & 15536 | VMO1 | CGTCCTAGGCAATACGCA | GTGGGTGCCTCCACGCGA | 15641 & 15642 |
| USP25 | GGCATTGGGAACGACCAGA | CGTTTGGGACCGGAACCA | 15537 & 15538 | VN1R4 | GCACAGACACTGCGTGCA | GGGAGGGTCTGGGGGAGA | 15643 & 15644 |
| USP26 | TGGCAATGCACAGAACGA | AACCCACTGGTGTCAGGA | 15539 & 15540 | VNN1 | GTACCCAAGGAGCCTGAGA | CCTCATGCCCATAGCCCA | 15645 & 15646 |
| USP28 | GAAGGTGGCTCAAGCGAA | CCCTTCATCAGCAGGGCA | 15541 & 15542 | VNN2 | ACAACTTGTGGACGGCA | ATAGGCCCAGATGATCCA | 15647 & 15648 |
| USP29 | TGCAAGGCAAGAGCAGGA | CCATCAGTGAGTCAGGCA | 15543 & 15544 | VNN3 | GCACACAGTAGAAGGCCA | GGGGCAAGCTGACTCCCA | 15649 & 15650 |
| USP3 | GTCCACACCTGAGCTTCA | GGACCGGCACACGCTGCA | 15545 & 15546 | VOPP1 | CGGCCAGGAGCCCAGCA | GCCATGGAATTCCCGACA | 15651 & 15652 |
| USP40 | CCCTCCATGAGCAGAGACA | TCCCCAGGTCGATGGAGA | 15547 & 15548 | VPREB1 | TGAGGAACGAACCATGGCA | CTCAGGCTGCACCACCGA | 15653 & 15654 |
| USP6 | GCACTGTGCATACCCGGA | CTGTGGGCACCAAGCACA | 15549 & 15550 | VPREB3 | ACCAGCAGCGGGCAGGCA | CCGAGAATCGATCGGGGA | 15655 & 15656 |
| USP6Y | CCAGAGGGAACAAGGGCAA | GCAAAACAGGGAACCACCCA | 15551 & 15552 | VPS28 | CATGCACCGCATGAGCCA | ACGCCGACATGCCGCTCA | 15657 & 15658 |
| UTP20 | AGTAGCCCAAGCAGCAGA | CTCAGATGCAGCAGCCGA | 15553 & 15554 | VPS37B | CTTCCCACTCAGCAAGGA | CCGGCTGGTGTGGAGGGA | 15659 & 15660 |
| UTY | CCCAGTATCACCAGGCAA | GAGAGGTGACTGTGTCAGCA | 15555 & 15556 | VPS37D | GCATGCTGGGAGTCCCCA | AAGGCTCCGACGCCGCA | 15661 & 15662 |
| UVRAG | AAACGGAGGCGCACGCGAA | ACTCGCTTGGAAGCTGGA | 15557 & 15558 | VPS45 | CTCTCATCAGGAGGCAGCA | AGCAATGGGGTGATGGCA | 15663 & 15664 |
| UXS1 | GAAGTGCGAGTGGCTCAGA | CCTGGACGCCTGCAGGGA | 15559 & 15560 | VPS4B | CAGTCTCACGGAACGACAGA | TCAATGGCACCAGGGTCA | 15665 & 15666 |
| UXT | GGAAGCTAAGCACTTCGGA | AGGAGAGAGCTCTTACGA | 15561 & 15562 | VRK1 | GCTGCAAAACCAGAGCAA | ATGTAGACCAGACCCCCA | 15667 & 15668 |
| VAMP1 | AGCAGTGCTGCCAAGCTA | ACTACCACGATGATGGCA | 15563 & 15564 | VRTN | GGCTGAGGAGGAAGCAGGA | TGGCTCAGCAAGGGCCCA | 15669 & 15670 |
| VAMP2 | AGCCAAGCTCAAGCGCAA | GATGAGGATGATGGCGCA | 15565 & 15566 | VSIG1 | TCAGGAGCCTGCCCACGA | GCTCCAGCTCCAGCTCGA | 15671 & 15672 |
| VAMP3 | GGTTCTGGAAAGAGACCA | GAGAAGCCGTCGCCTGCA | 15567 & 15568 | VSIG10 | CCAGCTGTCGGATGGGCA | AGCGTCACATTGCCCCCA | 15673 & 15674 |
| VAMP4 | ATTGAGAGAGGGAGAGA | TGCATCCACGCCACCACA | 15569 & 15570 | VSIG4 | TGCCCCAGGAGAATGAGGA | GGCCCTTGGCAGTGCAGA | 15675 & 15676 |
| VAMP5 | CAGCAGCGTTCAGACCAA | TCAGGATGATGAGCAGGA | 15571 & 15572 | VSTM1 | GAGCTCGGCAGAAAACGA | TGCAGCTGAAGATGGCGA | 15677 & 15678 |
| VAMP7 | GGTTCAAGAGCACAGACA | AGTGTGCAGCTAAGACA | 15573 & 15574 | VSTM2A | AGGGGCAGAATGTGGAGA | TGTGCGGCAAGAGCTTCCA | 15679 & 15680 |
| VAMP8 | GGCGAACCTGCAACATGA | GGGCCAGGATCCGCTTCA | 15575 & 15576 | VSTM2B | CCGTAGCTACACCAAGA | CCAAGAGCAGCCTCAAGGA | 15681 & 15682 |
| VANGL1 | CAACGGCATGACCCCCAA | GAGGCTGAAGTCCAAGCA | 15577 & 15578 | VSTM2L | CGACTTCAGCGACGGCAA | CGGGAGGGGCTTCGGGGA | 15683 & 15684 |
| VAPA | CTGTGTGGAAAGAGGCAA | GAAGTGACAGTCGGAGCA | 15579 & 15580 | VTCN1 | TGCCAAAGCAACAGGGGA | GCATCAGGTAAGGGCTGA | 15685 & 15686 |
| VASH1 | AGAAGGTGGCGCAACGGA | ACAGCTTCAGGCGCTCA | 15581 & 15582 | VT1A | LGTGAAAAGACTTCGGGAA | TCCCTAGGATGGCGAGCA | 15687 & 15688 |
| VASP | GACCACTTCCGAGACCCA | CCTCAGCTCCTTGGACGAA | 15583 & 15584 | VTN | CTGCCACCTGTGAACCCA | CCAGCCAGTACTGAGGGA | 15689 & 15690 |
| VAV1 | ATCGCAGGGCTCAGGACA | TGAGGAGGGCACCATGGACA | 15585 & 15586 | VWA1 | CCAGCAGCTGCCAGGGAA | GCACGTTCACCTCCACACA | 15691 & 15692 |
| VAV2 | GGCACCTTCTACCAGGGA | ACCCTCCCACCAGGAGA | 15587 & 15588 | VWA2 | CTGCCCAAGACTGCAGGA | CCCATCTCACCTCCACACA | 15693 & 15694 |
| VAV3 | GTCCAAAAGCCTGCGCCA | AACCAGCCCACCCTGCCA | 15589 & 15590 | VWA3B | GAGAGAAGCCCAGGAGGA | GCTGATGCCGTGGGAGGA | 15695 & 15696 |
| VBP1 | GCTGGATGAAACAGTACCA | TACATTAGCCCCAACCA | 15591 & 15592 | VWA5A | ATGCCAGCTGACCGGGA | AGCAAGGACTTGGCAGCA | 15697 & 15698 |
| VCAM1 | CAGGGTGGAAGAAGCAGA | CGGATGGTATAGGCGCCA | 15593 & 15594 | VWA5B1 | TCCAGGCTACTGACGCGA | CCGAGGTCGACTCCACA | 15699 & 15700 |
| VCAN | GGCACAGACCACTGCAGA | GGCAGGCTTCTCCAGA | 15595 & 15596 | VWC2 | CCACGTGCAACAGGCCA | ACACACTCCGCTTCGGGGA | 15701 & 15702 |
| VCL | CCACAGTGAAGGCCACCA | GGGCATTGTGAACCAGCA | 15597 & 15598 | VWCE | GGGAAGGAAGGTGGCGAA | AGCAGTCCCCAAGGAAGCA | 15703 & 15704 |
| VCPIP1 | GGTACACCAGGCAGGAA | GCTGCAGCAGACTGACCA | 15599 & 15600 | VWDE | GAAAACAACCAGGCCCCA | TGCCCCTTCAGGACCAGA | 15705 & 15706 |
| VDAC1 | GGTACACAGCGCCTTCGTA | GGCCAGCCAGCCCCCTGT | 15601 & 15602 | VWF | ACTGCAGCTCGCTCCAGGA | GACACTGCCTCCCAAGGA | 15707 & 15708 |
| VDAC2 | CATCAGGTACCAACTGCA | AACTTCCAGGGCCGAGCCCA | 15603 & 15604 | WARS | CGAGGACAAGCTGCGAGGA | CTGCCGGATCAAGGGCTGCA | 15709 & 15710 |
| VDAC3 | CCTTCACCCAGAAATGGA | CTGATAGCCAGCAAGGCA | 15605 & 15606 | WAS | CAGGGCAGGAATCAGCGA | ACAGGGGGCAGTGGACCA | 15711 & 15712 |
| VDR | CGTGAAAAGCCGGACA | TCCTGCACCCACACGGA | 15607 & 15608 | WASF1 | GAGCAGGCGTGAACAGGAA | AACACCAATACGGCGAGA | 15713 & 15714 |
| VEGFA | TCAGCGCAGCTACTGCCA | CAGTGGGCACACACTTCA | 15609 & 15610 | WASF2 | CAGCCAAACAAGGAGGAGCA | AGCAGGTCCTACGGGCA | 15715 & 15716 |
| VEGFC | CCTGGAAGAACAACAGCCA | ACAGAACCGGGCTTGGGGA | 15611 & 15612 | WASF3 | AGCCTGCACAGCCACCAA | CGCTGTACTCCACGGCAA | 15717 & 15718 |
| VEGFG | ACAGACTGCCCTCCACCA | CCAGCTGCCAGGCCCGA | 15613 & 15614 | WASL | ACAGCTGCACCTCCACA | CCACTGGCCCCTCCCCCA | 15719 & 15720 |
| VEPH1 | GACATACCTGGTGAGGCA | AGGGCCCAAGATTGAGGA | 15615 & 15616 | WBP11 | CCTGCATGATGCGCCCA | CCAGGGTTTGGCAAGGGA | 15721 & 15722 |
| VEZF1 | CCATCGCTGGGGACAGCA | CAGACTGGGTCACTGGGA | 15617 & 15618 | WDR24 | GCACGTCAACTGCAGCCA | TGCAGCCCTGGCACCACA | 15723 & 15724 |

| GeneName | Forward Primer | Reverse Primer | SEQ ID NOs | GeneName | Forward Primer | Reverse Primer | SEQ ID NOs |
|---|---|---|---|---|---|---|---|
| AGGF1 | CACATGCAGGCTTGGGGA | GGCATAGTTCCTGGGTCA | 16997 & 16998 | AIP | CCTGCCTCAAGAACTGCAGA | AGGATGGAAGAGCAGTGGTCCA | 17103 & 17104 |
| AGK | CTGGGCACAACCACAAGGA | TCAATGGTGGACAGCTGCA | 16999 & 17000 | AIPL1 | GGAGACCTGGAAACCTGAGCAA | TCAGCCACTGCACCTCCCA | 17105 & 17106 |
| AGL | TTGCCGGTACCCTGAGGCA | AATCCTGGATACACTGCAGCCA | 17001 & 17002 | AIRE | TGGGTCCTGAGGGTCAGGACA | GCACGCCAGTGGAAGGCA | 17107 & 17108 |
| AGMAT | GCGCCAGGGACAAGGGACA | ACAGCAGGTTAGCCGCCA | 17003 & 17004 | A1AP1 | GCCTTCCAACCAGTCCCAGCAA | ACCATGATGAGGGAGGAGGTGA | 17109 & 17110 |
| AGMO | TGGGGCTGGACACCAAACACA | AAGGGGGTATGAAGAGGGCCA | 17005 & 17006 | A1UBA | CTCTGAGGGCTGTGAGGACA | GGCAACCATGGCAGAGCA | 17111 & 17112 |
| AGO1 | GACACCAACATCACCACCCA | TGTGGCACAGTCTGGTACGTCA | 17007 & 17008 | AK1 | CGGATTGGACAGCCCACA | CTGTCCACGGAGCCTCA | 17113 & 17114 |
| AGO2 | GGCACGACTGTGGACACGAA | CCAGAGGACGGTGATAGTGCGA | 17009 & 17010 | AK2 | CAACCCTCCAAAAGAGCCCA | GGTAGGCTTGCAGGCGGA | 17115 & 17116 |
| AGO3 | CTCCAGTATGGAGGACGGAA | CTGTGTGGCAAAACAAGCGA | 17011 & 17012 | AK3 | GCACCTTCTCAGCGGGGA | TCATGAAGGGCAGCCGA | 17117 & 17118 |
| AGO4 | CAGACTTCCCGGCAGGAGA | AATCAGCAGCTCTCGAACCA | 17013 & 17014 | AK4 | AGGACAAGCCGAAGCCCTGGA | CCGCTAGGAGGGTGAATCA | 17119 & 17120 |
| AGPAT1 | TCTTCATCGACCGGAAGCGCA | CATTGTCCCGAGGTGAAGCGA | 17015 & 17016 | AK5 | CTCGGCAGACACCATGACCAA | CGGGGATGGACGCTGGGTA | 17121 & 17122 |
| AGPAT2 | TCCCCACCAGCGGCCTCA | TGCACGCCAGACCCGCA | 17017 & 17018 | AK6 | CAGGTACACCAGGGGTTGGAA | ATGAAACACGGCTTCAGGGA | 17123 & 17124 |
| AGPAT3 | GCGAAGTGGAGGAAGGA | GTCCCCTGCAGTACAGGA | 17019 & 17020 | AK7 | GAGCTCAAGCAAATGGAGGA | GCCAAGTCATCACCGTCGA | 17125 & 17126 |
| AGPAT4 | CGGGCACCTTCCCAGAGA | CCATCGAACTCCACGGA | 17021 & 17022 | AK8 | TAATGCCCCGTTCACCCCGA | TTCATGAGGAGGCTGTCAGGA | 17127 & 17128 |
| AGPAT5 | AGAATTACACCGGGGTCCAGA | AACACCCATACAATGGCAGCCA | 17023 & 17024 | AK9 | CAAACTTCAGGGTGCAGAGGAA | CACAGGACATGTACGTCCCCA | 17129 & 17130 |
| AGPS | TGGAGTGCCAAGTTACGGA | TTGACAGACTTCAGCATCCCA | 17025 & 17026 | AKAP1 | GAGCGAGATGACGGGAA | CAAGGCCTCGCTCCCA | 17131 & 17132 |
| AGR2 | ACTCTGGCCAGAGATACCACA | TGGAGAGGGTCTGGGGCA | 17027 & 17028 | AKAP10 | TGCAGGGAAGGTGGGCCA | GAGACTCATCAGGAGGGCCA | 17133 & 17134 |
| AGR3 | TCCAACAAGAGACTGGCCAA | GAGACCCAAAGCTGAGTGTAGCA | 17029 & 17030 | AKAP11 | CGGTGCCCTTGGCAGGAA | GCACTTGGGCAGAATCACCA | 17135 & 17136 |
| AGRN | CAGGGTCTCACTGGAGCGAA | ATGCAGCCTGCAAGCCA | 17031 & 17032 | AKAP12 | GTGCAGAGACAGAGCAGA | GGGTGCTTGCCCACCA | 17137 & 17138 |
| AGRP | AGAACCTGCAGACCGCGA | GCGGCAGTAGCAGAAGGCA | 17033 & 17034 | AKAP13 | TTGGACACCAGAGCCCGA | GGGTGCTGCACTCAGCCA | 17139 & 17140 |
| AGT | GAGCCACAGAGTCTACCCA | CCCAGGAAGTGCAGGGCA | 17035 & 17036 | AKAP14 | AAAATGCTGGACACATGGCGTA | GTGCTACGGGTAGGTCAGCA | 17141 & 17142 |
| AGTPBP1 | GACCAACACTCCATGACCCA | GGAGCGCGAATGTGTGACCA | 17037 & 17038 | AKAP17A | CTGCAGCCCGTCCTGGACA | GGAGAGCCATCCTGGGGA | 17143 & 17144 |
| AGTR1 | CCCGCCTTCGACGACA | GGGCCAGCCTATCGGGA | 17039 & 17040 | AKAP2 | CTGAAGAGGGCTGCCGAA | CGTGTGGCCTGCGAGCA | 17145 & 17146 |
| AGTR2 | ATAACCCGTGACCAAGTCCTGA | GGAACCCTAAACACACTGCGGA | 17041 & 17042 | AKAP4 | GAACAAGCAGCCTCGGCA | CTGGGAGGCTGCAATCCA | 17147 & 17148 |
| AGTRAP | GACATCGTGCACATCAGCA | GAAACCAGTGTGGACCAGGA | 17043 & 17044 | AKAP5 | TGGGGCTGAAAGGCAGAAGGCA | ACATCAGCATCTTCAGAGCCA | 17149 & 17150 |
| AGXT | CGGCTTCCCACAGTCACA | TCCGTCACGCGGTCCACA | 17045 & 17046 | AKAP6 | GGAAGGAGGCTGCAGAGGCA | CTTCCTCCATCTCCAGAGGA | 17151 & 17152 |
| AGXT2 | GATGGCCAGGGCCACTCA | GTTGGCAACCTGTCCCACCA | 17047 & 17048 | AKAP7 | AAGAACCGAGGGAGCCCGA | CTGCTGGACAGCCTTGAGCA | 17153 & 17154 |
| AHCTF1 | GAGGGAAGTGGAATCCCGA | CTGCATGCAGACTAGGACGGA | 17049 & 17050 | AKAP8 | TACGAGGAGCCAGAGACACCAA | GCCTCCCAGAGTCGCAGA | 17155 & 17156 |
| AHCY | GGCAGTGGCTGAAGCCCA | GAAGGGGCATCACAGGA | 17051 & 17052 | AKAP8L | AAGAAGGGTGGAGGAGCCCA | GTTGAGAATACTGCGTCCCCA | 17157 & 17158 |
| AHCYL1 | GGAGCTGACGTGGGAGGCGA | CAAAGGTTGGGAACTGTGGAGCA | 17053 & 17054 | AKAP9 | CCCAGAAAGCCTCTGAGAGA | CAAGAAGTACTTGGGACACCA | 17159 & 17160 |
| AHCYL2 | CAGAACTGACCTCGCGAGCGA | TATAGCGACCCTCAGGAGCA | 17055 & 17056 | AKIP1 | AGAGGCGAGTCGAAGCTGCA | TTGAGCCACAGTGACAGA | 17161 & 17162 |
| AHDC1 | CATTTCCCACCGCTGGGCCA | CTTGAGGACCTCGCAGGCA | 17057 & 17058 | AKIRIN2 | CCTCCCGCCTCACCACAGA | TAATGGTGAGGATGCTGCAGA | 17163 & 17164 |
| AHI1 | TGGAAACGACTCCTGGGCA | GGATATCCATCCGGCTGGCA | 17059 & 17060 | AKNA | TTCAACTCCCCAAGCA | AGCGCAGGGTGGATAAGGCA | 17165 & 17166 |
| AHNAK | CCCAAATCACTAGTGGGCCA | ACTTCCACACTGGGGCCA | 17061 & 17062 | AKNAD1 | AGCTGCCCAGAACAAGCCAGA | CTCGGACTGGGTGCCGTCA | 17167 & 17168 |
| AHNAK2 | CTGTCCCTAGCCGACAAGGA | CCACCTTCACTGATACATCGACA | 17063 & 17064 | AKRJA1 | CAGGTGGAATGCCACCCA | CTGGTTCCTCCAGCAGGACA | 17169 & 17170 |
| AHR | GAACCATCCCCATACCCA | GCTGCACTTGATACATGGACA | 17065 & 17066 | AKR1B1 | TCAACAACGGCCAGGGA | TCTGGTACACATGGCGA | 17171 & 17172 |
| AHRR | AGCCACCTTCCCTACCAGGA | GTGCACAGAGCTGGTTGGGGA | 17067 & 17068 | AKR1B10 | CGTGACACCAGCACGCGA | AACAGTTACAGGCCCTCCA | 17173 & 17174 |
| AHSA1 | TAGAAGCCAGAGAGAGGTGA | CAGGAGCAGGGATGCCTCGA | 17069 & 17070 | AKR1B15 | CTCACGCAGGAGAGAAACTGATCCA | AGGTCTATCCGGAGAGCCCA | 17175 & 17176 |
| AHSA2 | GAGATGTGGGGGTCAGCCAGA | CATTTAGGGAGGTGCAGCTGCA | 17071 & 17072 | AKR1C1 | AAGCACAAGCGAACCCA | AGCTCTTGGCCAGGACCA | 17177 & 17178 |
| AHSG | AGTGGCTCACCCCAGA | CTCCTGAGGGTGACCCA | 17073 & 17074 | AKR1C2 | CTGTCTGAACCAGGTTGGAA | GACTGGGTCCTCCAAGAGACA | 17179 & 17180 |
| AHSP | GAGCTGAACACTTCTGCCAA | GCGGTGGGTGACTCGGGA | 17075 & 17076 | AKR1C3 | GTGGATGGTGACGCAGAGGA | CTGAAGTGCTAAACAGGACGGA | 17181 & 17182 |
| AICDA | AGAATGCTGCCAGTCGGGAA | CAGTCGTAGCAGGGGCTCA | 17077 & 17078 | AKR1C4 | CAGGTGAGACGACCACTACCAA | CACCCGATGGACTTGCCA | 17183 & 17184 |
| AIDA | TGCTGGAGATGCACTGGCTGA | TAGGGATTGCAGCCACTGCCA | 17079 & 17080 | AKR1D1 | ACCCTAAGGGAGCCTGTGCA | CTCCTGATGGCCCCCA | 17185 & 17186 |
| AIF1 | CAGCAGGAAGAGAGGCTGA | CCCCGGAGCCACTGGACA | 17081 & 17082 | AKR1E2 | ATCCCGGGATCTATCACCCAA | TGGGAACATGGCCAGTCGGA | 17187 & 17188 |
| AIF1L | CTGCCGAGATCAACCGGGA | AGGTGGGTCTTGGGGACACCA | 17083 & 17084 | AKR7A2 | TAGCTGGGAAGTGGCCGAGA | CCAGTCAGCAGGCCCCA | 17189 & 17190 |
| AIFM1 | CTCCCGAATACTCAGCA | CATTGGGCCTCCAGGCCA | 17085 & 17086 | AKR7A3 | ATCGCTACTGGAAGGAGCACCA | AGTGGTGGTACATCCACCGGA | 17191 & 17192 |
| AIFM2 | GGTGGAGGCGCACAGCAA | AGAGGCCGCTGCTTCACA | 17087 & 17088 | AKR7L | TGGGACTCAGTGGGGAGAGA | CGCATACGCGCCTGCA | 17193 & 17194 |
| AIFM3 | CCACAGGCTTCCTGAGGCA | AGGGGGAAGGTGACAGCA | 17089 & 17090 | AKT1 | GCTGCACAAACGAGGAGGGA | GTAGCCAATGAAGGTGCCA | 17195 & 17196 |
| AIG1 | GCAGGGACTTACCGCCA | GGGTACACCACCATGGCA | 17091 & 17092 | AKT1S1 | GACAGCAGGGAGGACGAGGA | CTCGGGGTCGACTTCACAGA | 17197 & 17198 |
| AIM1 | CTGCCAAGGAGACAGA | CGGGCATCCCATTGCAGA | 17093 & 17094 | AKT2 | ACGTCCGAGGTGCACA | GATGCTGGCCGAGTAGGAGA | 17199 & 17200 |
| AIM1L | CGGGCCACATCGCAGCCA | CTCATCCGGCTCCATAGCA | 17095 & 17096 | AKT3 | ATGCAGCCACCATGAAGACA | GACAACCCTAGGCCCA | 17201 & 17202 |
| AIM2 | CCCAAGAAGGCAAGCAGGAGA | CTAACACGTTGAGGCGCTA | 17097 & 17098 | AKTIP | CAGTCAACAAATGGCACGA | TCCAACACCAAGCGTGGA | 17203 & 17204 |
| AMP1 | GATGTCGGAGAAATAGCCCA | CAGACCCATTTGGAGGAGCCA | 17099 & 17100 | ALAD | CGGGATGTTACGCGGAGGA | AGACGTGGTACACGCGGA | 17205 & 17206 |
| AMP2 | AAAGACATCGTGATCAACGCA | AGGCACGCTCTTGACCGA | 17101 & 17102 | ALAS2 | AAGGGAGAGAGGAGGGCCAA | AGGGTGCCAAGCGCAGGA | 17207 & 17208 |

| GeneName | Forward Primer | Reverse Primer | SEQ ID NOs | GeneName | Forward Primer | Reverse Primer | SEQ ID NOs |
| --- | --- | --- | --- | --- | --- | --- | --- |
| ANO9 | ATCCAGTACGGCTTCCACCACA | GCACACCGATGGTCTCCAGCA | 17633 & 17634 | AP5M1 | ACTCAGCCACAGAAACAGCCA | GGTGGGGAGACTTCAAGCTGA | 17739 & 17740 |
| ANOS1 | TCCGGCTTCCTGAGAAAGCCA | GACAGGTGTGTCCACACCCA | 17635 & 17636 | AP5S1 | CACGCTCCGGCTGCTGACA | AAAAGCAGCTGACCATGTGGCA | 17741 & 17742 |
| ANP32A | AAGCTCCTCCGCAACTCACA | CTCATCATCCAGGCCTTCCA | 17637 & 17638 | AP5Z1 | GTGGTGGAGCTGGCAAGAGA | CGTCAGCGTGGTCATCAGCA | 17743 & 17744 |
| ANP32B | GACTCAGATGCCGAGGTGGA | CTGACTTCATCGTCGTCCTCA | 17639 & 17640 | APAF1 | AAGGAGCTGCTACCCATGGA | CCCAGTGACAACGTTCCACCA | 17745 & 17746 |
| ANP32E | GTTAAGGAACAGATCCCGGA | TGGGAAGCCGGGCCAGCGAA | 17641 & 17642 | APBA1 | TCTGTCCACCTGCCAGAGCA | TCTCGTGGGGGGTGGCA | 17747 & 17748 |
| ANPEP | GCTACACCCTGAACCCGGA | GGAGAACGAGCCACCACCA | 17643 & 17644 | APBA2 | CCCACGGTGATCCTGGCCAA | CATTCTGCACGCTGAAGCGCA | 17749 & 17750 |
| ANTXR1 | GGGAGAAAAGGGCTCCACA | TCAGTAGGACCCACAAGGCA | 17645 & 17646 | APBA3 | CGTCACCACGGCCATCATCCA | GGCCACCACACTTCTGCCA | 17751 & 17752 |
| ANTXR2 | TAAGGATCCTCCACCACTA | CCTCAACCCTCGACCA | 17647 & 17648 | APBB1 | CTAGTGGAGCACCAGCAGCA | CATGCAGGCTGGTGCGGA | 17753 & 17754 |
| ANTXRL | GCCTGAGACACAGCCCGGA | GCACCTGGAGGAGCAGGTGA | 17649 & 17650 | APBB1IP | GGCAGAGAAAGAGTCCTTGCA | CTGATACCAGCTGGCAGCAACA | 17755 & 17756 |
| ANXA1 | ACCACCAGAAGCTATCCAGA | TCACGATGCTGTGAGGCA | 17651 & 17652 | APBB2 | CATGGACACGGGGAACCA | CGGCCTGGCTACCAAGCA | 17757 & 17758 |
| ANXA10 | ATGGGAAGCCAGCTCCTGA | GCAACAGCAGCTCCTGA | 17653 & 17654 | APBB3 | GCCAGTACAGAGGAGGAGCCA | CCTCGAGCTGCAGAGGCCA | 17759 & 17760 |
| ANXA11 | CTGTATGCGGCCGGGGAGA | GCCAGCATGCCCTCCTCA | 17655 & 17656 | APC | CACCTGTGGCAAGGAAACCAA | CAACACAATACACCCGTGGCA | 17761 & 17762 |
| ANXA13 | AACATCAGGGACTTGCAGA | CCCGCACCCTCATCGA | 17657 & 17658 | APC2 | CGGCAGACCACCTGAGCAA | AAGGAGCCTGCATCGGGA | 17763 & 17764 |
| ANXA2 | CCCGCAGTGAAGTGCACA | GTCATCTCCACCACACAGGTA | 17659 & 17660 | APCDD1 | TCAACGGTCAGAGGCCCA | GAGAGGCACACTGGACCA | 17765 & 17766 |
| ANXA2R | AGGAACCGAGGTCTGTGACA | TAGTCCACAGATCCGTGA | 17661 & 17662 | APCDD1L | CGTCCACCTCCTACCAAGCA | GCAGAAGTGGGAAGGGGGCTA | 17767 & 17768 |
| ANXA3 | GTCAAATGCACCGCGCA | TGGAGTCACTAGGGCCACCA | 17663 & 17664 | APC5 | GTCCTGGGGCAGGAAACAGGA | TTTCTGGGGGCAGCACAGA | 17769 & 17770 |
| ANXA4 | GCCAAACTACCAGCAGCA | ATCCCTCCACAGTGA | 17665 & 17666 | APEH | AGCCACCCCAGAGCAAGAGA | GGGCATGACCACCATGGGCA | 17771 & 17772 |
| ANXA5 | CCGCGAGACTTCTGGCA | TCTCTGCAGCATAGGCAGGTA | 17667 & 17668 | APELA | CTTATCAGCGCAGCAAGACCA | GTACTCGTGAATGGAGGCA | 17773 & 17774 |
| ANXA6 | CAGGCACGGGAAGATGCCA | ACTCCTGGAAGACTCTCCGGA | 17669 & 17670 | APEX1 | TGACCTTCGCAACCCAA | CCAGTGGCACAGCCTGCA | 17775 & 17776 |
| ANXA7 | TTGTGTCCATGTGCCAGGGAA | TATCCGGAAACTCACGGCTCA | 17671 & 17672 | APEX2 | AAGCCCAAGTGCGCTCAACCA | ATGTCAGGAGAGGCTTGGGGA | 17777 & 17778 |
| ANXA8 | CAGGCGAAAGATTCGTGGGA | GGCCTCCTCCAGTGAGCCA | 17673 & 17674 | APH1A | CTACTGACATCGGAGCTGACA | CAGCTGTGATGAAGGCCCA | 17779 & 17780 |
| ANXA8L1 | GATACGAAGCCAAGGAGCTGCA | TTCTCGCTGCCGCATACAGA | 17675 & 17676 | APH1B | ATAAACCAGGTGAGACAGGA | TCCGCAGCTAAGAATGCCA | 17781 & 17782 |
| ANXA9 | CTCAGGAAACTGAGCGCA | CAGCCCTGCACAAGGCCA | 17677 & 17678 | APIS | TGGGCCGAAAACTTCCAGA | TACCCTGAGAGCTAAGCGA | 17783 & 17784 |
| AOAH | CAGTCCCAGCCATGACCA | GACCTGGAGGCAGTTCAGGA | 17679 & 17680 | APIP | TCACTGGGACTGCGAGGAGGAA | AGAAGTGTGCCATCACAGCA | 17785 & 17786 |
| AOC1 | CACAGCCACACTCGGGA | CGTTGTCCCGAGGCCACA | 17681 & 17682 | APTD1-CORT | CCAACAGAGGCTAAAGGCAGCA | CTGTGGAAAGTCAGCTCCGA | 17787 & 17788 |
| AOC2 | CCCATGCCAGGACATCCAA | CAAAGTAGACACTGCCAGGGGA | 17683 & 17684 | APLF | CCAGGGCGACTCACTTCAGGA | TTGCCCCATACATGCAGGA | 17789 & 17790 |
| AOC3 | GGAACCAAGTGTCAGAGCACA | CAAAGACCATATCCTCGGCCCA | 17685 & 17686 | APLN | ATGCCGCTTCACCGGGAA | CCTCGACCTCCTGCA | 17791 & 17792 |
| AOX1 | GGAGAAAGGCGACCAAGGCA | CTGAGCCAGAGTGTGCAGA | 17687 & 17688 | APLNR | GTTACGCACACCGGGCGA | CCACGGTGCTGGACGAGA | 17793 & 17794 |
| AP1AR | GAAGACATTCTACGGGCCAGA | TCCCACTCCAGCCATTGGA | 17689 & 17690 | APLP1 | CCGAGAAGGGCACAGCAGA | TCTGGTCAAGCAGGCCA | 17795 & 17796 |
| AP1B1 | CATGGACCTGCAGCTGACCAA | TCCATCTTCATGACCGAGCCCA | 17691 & 17692 | APLP2 | CTCGAGGAAGAGGCGGGAA | CATCACCAGGCTGATGATGA | 17797 & 17798 |
| AP1G1 | CTGCGCCTACAAGCAAACCA | GGGACTGAGGCAGGGGCA | 17693 & 17694 | APMAP | AGACAACATCCGGCCCAGCA | GAAGGCACCCGTCTGCTGA | 17799 & 17800 |
| AP1G2 | CCTGTGTACCTCCACCA | AGTCTGAGACTCTTGGGCACA | 17695 & 17696 | APOA1 | GCTCAGCGGAAGGCCAA | GAGAGCCCTCAGGAAGCTGA | 17801 & 17802 |
| AP1M1 | GCCAACAACGTGGAGATCCA | GGAAGGACTTGATGGACCACA | 17697 & 17698 | APOA2 | GCTTCAGGGCGAGGCCA | GACACTTCACTGGGTGGCA | 17803 & 17804 |
| AP1M2 | CAGTGTGGGCAGCGCCAA | TGTAGGGAACCCAGGGCA | 17699 & 17700 | APOA4 | AAGCCCTGGTGCAGCAGA | CTGTTGCTCCAGCTCAGGGA | 17805 & 17806 |
| AP1S1 | CAGTGTGTGCAGTCTGGACA | CAAACCACTCTCCAGCA | 17701 & 17702 | APOA5 | CATGACCAGGAGACTGAGGA | CATCAGACGGGGCTGCA | 17807 & 17808 |
| AP1S2 | AGTCGTCAGGGAAAGCTTCGA | CAGATCTCGCCACTCAAGGA | 17703 & 17704 | APOB | CTGACCTGCGCAACAGA | GAATCTGGGGCAGGCCCA | 17809 & 17810 |
| AP1S3 | CCCGTGGTCAGGAGGACAAGCA | TGTCCAGCAGCTCCACGTA | 17705 & 17706 | APOBEC1 | CAAAATGCGGCAAGGTCTCAGGGA | GCAGCTCCAGTGCGTACAACA | 17811 & 17812 |
| AP2A1 | AGTTCTTCCAGGAGACAAGCA | TTTCAGGGTTGGGGTCCACA | 17707 & 17708 | APOBEC2 | GTGGTTGAAGCACAGGGCAA | ACGGCAGGGGCTGGGTCGA | 17813 & 17814 |
| AP2A2 | GCCCAGCACGGTGCAGA | CGGAAGGCGGCAGCCACAGA | 17709 & 17710 | APOBEC3A | AGCGCCTGGACAATGGCA | CCCGGCACAGCCCAGGA | 17815 & 17816 |
| AP2B1 | TGGACTACCACTGCAACGA | CCAAGGTCACTGCCAAGCA | 17711 & 17712 | APOBEC3B | GCTGGGGCCCAAGTTCTCA | GATTCTGGAGAATGGCCCGCA | 17817 & 17818 |
| AP2M1 | GAATCGCAGAATCAGCGCAGAGA | TGAAGGCAGAGGGGCGA | 17713 & 17714 | APOBEC3C | TGCAGGGGAGGTTGGCCGA | TCCACAGGCACCCTTCCTGA | 17819 & 17820 |
| AP2S1 | ACACAGCTGTGTGACAGCA | TCCAGGAGTGTAGCATCAGCA | 17715 & 17716 | APOBEC3D | ACGAGGTCACCTGTACACA | CCTGGCCAGGAACTCGGCA | 17821 & 17822 |
| AP3B1 | CAGCCTTGATCCAGAGCAGA | AAGCCATCACACACTGCCA | 17717 & 17718 | APOBEC3F | CCTGGCCAGGCACAGCAA | GCCATGATCCTCCACGGA | 17823 & 17824 |
| AP3B2 | GAGTCCTGGACCACCTGAGGA | CACTCATGAACACAGGGGCCA | 17719 & 17720 | APOBEC3G | GCTGGACCTGGACCAAGGA | GCGGGCAGTGAAGATGCA | 17825 & 17826 |
| AP3D1 | GGAGGAGCGGACCAAAGGCAA | GTAGCTGGACTCCAGGCGGGA | 17721 & 17722 | APOBEC3H | CGACCATCTGAACCTGGGCA | GCCCATGACCTCACCGGGA | 17827 & 17828 |
| AP3M1 | ACATACCATGGCGTCGGGCA | GCAAGCATCAATGACCCCTGA | 17723 & 17724 | APOBEC4 | CTCTCCGGAGCCTGGCA | TGTCAGCCAGTGCTCTCCA | 17829 & 17830 |
| AP3M2 | TCCATCACAGGGGACACACACA | GTTTGGAAGCTCCAGCTGA | 17725 & 17726 | APOBR | AACTGAGGATGGAGGAGGCGGA | CGAGTCCAGCCTTGCCA | 17831 & 17832 |
| AP3S1 | GCAGAAATGGTGATGGGGGGGA | GCTGATACAGGCTCAGGGA | 17727 & 17728 | APOC1 | AAGGTCTGCCGGGCAGGA | CCAAGACGCTGCAGAACCA | 17833 & 17834 |
| AP3S2 | TAGTCCTCAAGCGGGATGACA | ACCCATCACCACTCCTGGA | 17729 & 17730 | APOC2 | TCCTCACCCAGGTTACATGAAGCA | TCATCTACAGCGGGGCAGGTA | 17835 & 17836 |
| AP4B1 | ACCTGCTGAGTGCCAGGACA | AATGCCAACTAAGAGGAGGCGA | 17731 & 17732 | APOC3 | CATGCAGGGTTACATGAAGCA | CTGCTGGGCCACTGGGA | 17837 & 17838 |
| AP4E1 | AGGGCCTTACAAACTCCCCA | GACTGTCGTCCAGTGAAGCCA | 17733 & 17734 | APOC4 | CCACAGACAAGCCTGGGGCA | CCAAGAGATCGAGAACCA | 17839 & 17840 |
| AP4M1 | TGAGAGGTTATGGCCACTGACA | GCCTGCCACTGCACA | 17735 & 17736 | APOD | GCCACCAGTTAACCTCACA | GGATCCAGTGCCAGGTA | 17841 & 17842 |
| AP5B1 | GCCAGCCTCCTACCAGCTA | GCCCAGTCATCGGTCCCGCA | 17737 & 17738 | APOE | AGGAGCAAGGCCCAGCAGA | CTTCCACCAGGGCCTCGA | 17843 & 17844 |

| GeneName | Forward Primer | Reverse Primer | SEQ ID NOs | GeneName | Forward Primer | Reverse Primer | SEQ ID NOs |
| --- | --- | --- | --- | --- | --- | --- | --- |
| ARHGEF33 | CCAACAGAGGTTCCCAAAGCGAA | AGCTTGCGGAAGGAGCTGGGA | 18057 & 18058 | ARMC12 | TACAACGAACAGTCCCTGCA | CTGGGGATACTGCAGGGTGA | 18163 & 18164 |
| ARHGEF35 | AGAGAGTTGGGATGGGGGCA | GAGACAGAGCTGCGGGGGGA | 18059 & 18060 | ARMC2 | AGAGGCAGAGGACGTGCTCA | TGATCACCAGCTCCTCACA | 18165 & 18166 |
| ARHGEF37 | AGCAGGTATGGCCCTGGGAA | TGTAGTTTCCAGCCGCGCACA | 18061 & 18062 | ARMC3 | CTCAGCCAAAAGGCCACCAA | GAAATCAGGGTCAGAGGGAGGA | 18167 & 18168 |
| ARHGEF38 | GAGGAGTGATGGCCAAAGCGGGA | ACAATGACAGCAGCTTGGCTGA | 18063 & 18064 | ARMC4 | ATGAGGCCAGAGACGTGGAA | ATGAGAAGTCTTCAGCAGCCGA | 18169 & 18170 |
| ARHGEF39 | TGCTCAGTGACGCCAGGCAA | AGTGGCCAAAGCACCCTGCTGA | 18065 & 18066 | ARMC5 | TAGCCAACCTCCCAGCA | TCCTCACCAGCCTCACA | 18171 & 18172 |
| ARHGEF4 | GGAGGACGGGAAGGAGCAGAGA | CCTGGCAAAGGCCTTGAGCCA | 18067 & 18068 | ARMC6 | TAAGCCCGACAACAGCCGCA | TCTCACAGTCACGGTGGGCA | 18173 & 18174 |
| ARHGEF40 | ACAGGCAGCCACACAACAAGGA | GGGCCGGCATGCTCAAAGGA | 18069 & 18070 | ARMC7 | GTCCTCGCCAACCTCGCCAA | AGCAAACTCCACCAGGGTCTCA | 18175 & 18176 |
| ARHGEF5 | AACATCCGGGACCTCGGACGA | TGCAGGTACGACTCGGAGGA | 18071 & 18072 | ARMC8 | GACTACTGTCCCAGACTGA | ATAGGGGGACTGCTAAGCA | 18177 & 18178 |
| ARHGEF6 | GAAGCAACGGCCAGACCA | GCTTCAAAAGCCTCCGCA | 18073 & 18074 | ARMC9 | TGCTGCACTCCACGAGCGA | CTTCAGCCTTCCCTCCAGCA | 18179 & 18180 |
| ARHGEF7 | GCAGGAATGGGTGGAGCA | TGGGAGGGGAGGGTATGAGA | 18075 & 18076 | ARMCX1 | GCAAAGGGCCTAGGGTGGGTA | CCCCGGCCCTAGATCCA | 18181 & 18182 |
| ARHGEF9 | ACCCCGACCTGAAGCAGCGA | CATCTGCTGCAAGAGGCGA | 18077 & 18078 | ARMCX2 | TCAGACTCTGAGCCGAGA | ACCTTCTGAGATCCGAGACA | 18183 & 18184 |
| ARID1A | CAGCAGCCAAGGAGGAGACAGA | GTCCTGAGGCAGAGCTGAGCA | 18079 & 18080 | ARMCX3 | GCTGAGGGTGGATCTGGGA | TTCAGTCCAATCCGAGCCAGA | 18185 & 18186 |
| ARID1B | TGAGCAGCATGACCCCA | GTAGGGAGAGCTGGAAGCCA | 18081 & 18082 | ARMCX4 | TGCCTGGGAGTCAGACGAA | GGCTATCCAGGACCCAGCA | 18187 & 18188 |
| ARID2 | AIGCTCACGGAAATGGGAGA | CAGCTAGTGCATCAGGGCCA | 18083 & 18084 | ARMCX5 | ACAGAAGGGAAGAAGACCAAGCA | TTCTTCAGGCCAGAACCAGGA | 18189 & 18190 |
| ARID3A | GCCCAAGCTGCCCATGAGCA | TTGATCTCCACGACATGCTGA | 18085 & 18086 | ARMCX6 | GCACTGAGGACAGGGCCTCA | GAGGTCCAGAACAACTGCCA | 18191 & 18192 |
| ARID3B | CGGCAGGGAAGACAGAGCAGA | AGACCCCTGATGAGGTGGA | 18087 & 18088 | ARMS2 | CTGAGGCCGGAGGGAAAGGA | TAGCAGCTGGGATCATGGA | 18193 & 18194 |
| ARID3C | ACTGGGACCTACACGGGAGA | GGCAGGAAACTGGGGGGCA | 18089 & 18090 | ARMT1 | AAGTGTGGGGGCTGACTGGGAA | ATGGTACAGAGTGGTGCAGGA | 18195 & 18196 |
| ARID4A | ACCCTGCCTAACACGGAACCA | ATCCGTCAGCCTTCACCCA | 18091 & 18092 | ARNT | ACAGTGCCAGGGCAGCA | CTGATCTCCCACAGCA | 18197 & 18198 |
| ARID4B | AGAAGGCAGCCGGCAGCA | CTCCCAGCAACACTATCCA | 18093 & 18094 | ARNT2 | GCAGCAGGAACCCAGCAGA | GGCCCGTGGGAAGAAGAGGA | 18199 & 18200 |
| ARID5A | ATGCCAAGAAGTTGTGGGGCCAA | AGGACGTTGGGGGGAAGTGCA | 18095 & 18096 | ARNTL | CCAGCCATTGAACATCACGA | GCCTGGCCTGATAGTAGGCCA | 18201 & 18202 |
| ARID5B | CGCACAAACCTACCGGCA | CCTAAGACTTGGAACTGGGAGA | 18097 & 18098 | ARNTL2 | AATCTTCCACGCTGGAAGAGACA | ATCTTCCAATGCCACCAAGGCA | 18203 & 18204 |
| ARIH1 | GCCAACACAAAGGAATGTCCCA | TGGTTCCATGGGCCAAGACA | 18099 & 18100 | ARPC1A | GCCATGACTGCTGCCAA | CGGAAGCGTTCATGGCA | 18205 & 18206 |
| ARIH2 | ACATACCAGCGGATTCACGAGA | CTTCCTGGGTCCAGACTCCA | 18101 & 18102 | ARPC1B | GGGCCTAGACTCGCTGCACA | ATCCAGATACTCATGCGCCA | 18207 & 18208 |
| ARIH2OS | TCCTGGCGTCAGTGGAGCAGA | TCTGGGGCCACCCTGCGA | 18103 & 18104 | ARPC2 | AAGGAAGAGAGAACAGGGCA | TCCGTGCGTAAAGAGGA | 18209 & 18210 |
| ARL1 | GTGACCTGAACCGAATTGGCA | TCAAGGCAGGTAACCAAGTGA | 18105 & 18106 | ARPC3 | GACCTGCCCCCAGAAGACA | AGTGGAAAACCAGGCTCTCA | 18211 & 18212 |
| ARL10 | GCTGGAAGGCACATCCCA | CTTGTTGGCCACCACGACGA | 18107 & 18108 | ARPC4 | AAGGAAGCCTGTGTGGAGGGGTA | TCTTCAGCCACAATGCGGGCA | 18213 & 18214 |
| ARL11 | AGATGAAGCCGCTTACCCGA | CTCCCAGCAGTGGTCCTGGA | 18109 & 18110 | ARPC5 | AGGTAGAGGCAGCGCCAAGA | CGGAAGCGGGCCGACGACA | 18215 & 18216 |
| ARL13A | GGAGACCTGCAAGGGCCGGA | TCCAGAGCAAAACAAGCCCA | 18111 & 18112 | ARPCSL | TGTGGACCAGCAGCAGGAGGA | GAGTTCCCAAGGCTGCA | 18217 & 18218 |
| ARL13B | GAAGATGAGAGACAACCGGCCA | CGTTGGACTCTCAGGAGCACA | 18113 & 18114 | C15orf38-AP3S2 | CCTCACCCCCGACCACACA | CAATGAATCCAGGAAGGGACCA | 18219 & 18220 |
| ARL14 | TGACTGCTGAGGACATCACCA | TTCCTGAACCCTGGGCA | 18115 & 18116 | ARPP19 | TCATCTGGGACAAAAGCTTGGA | TATCGGAGCTGCAGTAGGA | 18221 & 18222 |
| ARL14EP | AACCGCTGGTTCAGACAGACA | TCATACAGGCCACTTGCGGTCA | 18117 & 18118 | ARPP21 | AAGGGTCACTCCCAGCCA | CTAGTGACATCACTGGGACA | 18223 & 18224 |
| ARL14EPL | TGCCCGAAGTGTAACTCCAACA | GTGACGATGGCATCGTAAACCCA | 18119 & 18120 | ARR3 | TGTGGACACGGCTGGAACCCA | CAAGTCACCAGCGGCATAGCGA | 18225 & 18226 |
| ARL15 | TGGAGCCGCTACTACCAAGGA | TGAGCAGGGCTGTAGAATCCA | 18121 & 18122 | ARRB1 | CTGACCCCTTCCTAGCCAA | CAACAGGGTGCTAGAGGCCA | 18227 & 18228 |
| ARL16 | GCCCAGGTGGGCACCAA | GAGAGTGGGTGGGGGTCA | 18123 & 18124 | ARRB2 | TGACAGGAGGGAAAAGGGGGA | TCTTGAAGGAATGGGGGCGAGA | 18229 & 18230 |
| ARL17A | GGATACAGCTGGAAAACCACCA | CCAACATCCCAGACAGGGA | 18125 & 18126 | ARRDC1 | CGCACCACCAGCAGCGA | GTGCAGCGGTGTGAGCGA | 18231 & 18232 |
| ARL17B | TTCCTCCCCCATGACAGCA | CTGAGGTCCTTGCAGCAGCGA | 18127 & 18128 | ARRDC2 | GCACTGGCGGATCCCCA | GCTACCACCTCCGAGTACTCA | 18233 & 18234 |
| ARL2 | CTGCCAGGGCGGAGGCTTCAGA | GCGGATGCGTTAGAGGACA | 18129 & 18130 | ARRDC3 | GTAACAGAGGAACAAAAGGCCGGA | AAGAGGTGGAGGCAAGAATCGA | 18235 & 18236 |
| ARL2BP | AACATGCCAAGGGTGAGGGACA | ATTGTTCTGGGAAGCTGGGCAGA | 18131 & 18132 | ARRDC4 | AGCAGCTCCAGCCAGACGACGA | AGGTGGGGGTTGAAACCGGA | 18237 & 18238 |
| ARL3 | GACCGAGTCTGGCAGATCA | GCAGACCCAGTTCATGCA | 18133 & 18134 | ARRDC5 | GACCCGCTTCAACACCACCAA | GGCAGGTGCACGGTGGTGA | 18239 & 18240 |
| ARL4A | TACCAGATGCACAGATGGCA | ATTGCACAGGTAGGCTGCAA | 18135 & 18136 | ARSA | CCCGTCTTACCCAGACGA | CTCACCAGGGTCTTGGACA | 18241 & 18242 |
| ARL4C | GGAGCTGCACAGGTGACCAA | TGGCCGGGAATTAAGCTCGTGCA | 18137 & 18138 | ARSB | ACCGGGAGCTCATCCACA | TTCCACACGTCGAAGCCA | 18243 & 18244 |
| ARL4D | CTGCCAACAGCAGCCA | GACCGTCCACAGCGTCGA | 18139 & 18140 | ARSD | GAGTCTGTGCCCACGA | ATCCTGTGGCATGAACAGA | 18245 & 18246 |
| ARL5A | TGGACATACAGAACAGAGAGAGGA | CGCCAGTTAGAGCACAGCA | 18141 & 18142 | ARSE | TGATTGGCGAGCCCACGA | TCCCCAGGAGCAAGGGGCA | 18247 & 18248 |
| ARL5B | GATAGCATTGACAGGGAAGGA | CCTGTGAGAGCACAGCAGGA | 18143 & 18144 | ARSF | GTCGCATCAGTGTCAGGAGGA | TGAGCCTTCCAAACTGACCCA | 18249 & 18250 |
| ARL5C | GCAGGACGTGAAGGACTCCA | CCTTCCCTGGTGAGGGCACA | 18145 & 18146 | ARSG | GAAGTCCAGCCAGCGTTAACAAGGCA | GTCCACGCGTTAACAAGGCA | 18251 & 18252 |
| ARL6 | TGAGGGACCCTCTGCAGATCA | GGGCGCAGGAGCTGGCAACA | 18147 & 18148 | ARSI | CAGGTGGTACCACCTCAGA | GCACGGCGGGTGTTCCAGA | 18253 & 18254 |
| ARL6IP1 | TGGAAGAACAGCTGCAAGGA | GAAACGCCAGCAGAACAGA | 18149 & 18150 | ARSJ | AAAACAGACAATGTCTGCCTGGA | TAAGCAGGAAAGCATGGCAGCA | 18255 & 18256 |
| ARL6IP4 | ATCAGCTGGCACAGCATCCAAGGA | GGGTCACCACCCTTGCGGA | 18151 & 18152 | ARSK | TGTGTCGTGAGACAGATGCCA | TGTTCATGGCCAGCTCTCA | 18257 & 18258 |
| ARL6IP5 | TGAAGAAGTCGCTACCCACGA | TGTTCTAGGCGCATCCAGGACA | 18153 & 18154 | ART1 | TGATGCATGAGACACGGGACA | GGTTCTGCGAGCTACCAGAGA | 18259 & 18260 |
| ARL6IP6 | AGGAGGAGGGGATGCGACCAA | CGGCCGCGGGAAAGATACCA | 18155 & 18156 | ART3 | GGAGGGCTAAACCAAGCCA | GCCAGCCCCTTCCTGTGA | 18261 & 18262 |
| ARL8A | TTCAACGAGGACATGATCCCA | CGCTCCACATGCTGCGGA | 18157 & 18158 | ART4 | CCTACACAGGGGCCACCA | GTGCACCCAGGCAGGTGA | 18263 & 18264 |
| ARL8B | GTGGGCTTCAACATGGGAA | TGCAATACCGCTCCCACA | 18159 & 18160 | ART5 | TTCCCTTCAAGGCCTGCA | GGCTGCCCACACCTCGA | 18265 & 18266 |
| ARL9 | AGAGTGCGGCCCACGTGGAA | TGCTTCATCCAGGCCCAGCA | 18161 & 18162 | ARV1 | TCGAATGCAACCAGGAGGCCAA | TGAAGCTGCCACCACCTCA | 18267 & 18268 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| ARVCF | CTGCTGCAGTCTGTGAGACCGA | TGTTGAGCACCGCCACCA | 18269 & 18270 | ASPG | CTGGAGGAAGCAGGGACGGA | GTAGAAAGGCCACCACTGCCA | 18375 & 18376 |
| ARX | GGACTTGACCGAGGCCCGA | GCGTCCAGGTAGGGCTGA | 18271 & 18272 | ASPH | GAGACCAAGACCTGGGAGGAA | CGGATGCCACACATCCACGA | 18377 & 18378 |
| AS3MT | CACATCCGGGAAGCCTTGCAA | TTCACCAACCAGCTGGCTA | 18273 & 18274 | ASPHD1 | GGCACTGAGGGGCCTTCGAA | AAGAGTCGTCCACCAGTAGACA | 18379 & 18380 |
| ASAH1 | GTCCTCAACAAGCTGACCGTA | AACCTATACAAGGGTCAGGGCA | 18275 & 18276 | ASPHD2 | ATGTGGAAGTGCTGGAACGGAA | ACACGAATGCACGCGTTCCCA | 18381 & 18382 |
| ASAH2 | GATGTCCTGCAGCAGCA | CGAGTCTCCAGGAGGCA | 18277 & 18278 | ASPM | TCCTGGGAGCCTCAGGGA | CACGAAACAGCGGCTGGA | 18383 & 18384 |
| ASAH2B | AGGGATATGAGGGAGCATGA | GGCTGCAGGACACTCCCGAA | 18279 & 18280 | ASPN | GGTGCAGCCACACCAGGA | GCAGAGCACAAAGCCAGGA | 18385 & 18386 |
| ASAP1 | TGTTCACCCAAGGCTCAGGA | GTACGGGCGTCTCTTGGCAGA | 18281 & 18282 | ASPRV1 | GGGGATCTGGACACCCTGCA | AGCTTCAGCTTGCCTAGGGACA | 18387 & 18388 |
| ASAP2 | GGCTGACAAGTCCACCCA | CATCGGGGTTGTCAGCCA | 18283 & 18284 | ASPSCR1 | AACAGTCCTGGACGACACA | GCAGATGGGGAGATGCA | 18389 & 18390 |
| ASAP3 | CCAGCCAAGCCCCACCCAA | CGGAGCTGAATCTGACGGGGA | 18285 & 18286 | ASRGL1 | TTGCCTTGGACTGCAAAGGGA | TGGAACAGGGTGAGTCTAGCCA | 18391 & 18392 |
| ASB1 | CCTCATCAGGTACGGGGCTGA | ACAGCATCCATGACGCACCCA | 18287 & 18288 | ASS1 | CCGCCACTGCATGCCAA | ACACCTGGCCCTTGAGGA | 18393 & 18394 |
| ASB11 | AGCCAGTGTCGACCATGGCA | CAGGCGCAGAGCTGGGA | 18289 & 18290 | ASTE1 | ACGGCTGGGCACAAGACTGGA | CTACAGGCGTCGATGCTAGCA | 18395 & 18396 |
| ASB12 | GCAGTCTACGGGCACCTGGA | TTGTGAGGTCAGGTCAAGGGA | 18291 & 18292 | ASTL | GGGCGCAGTGGAGGAGGATGCA | GTGCTGTGCAGAAGCCCA | 18397 & 18398 |
| ASB13 | TGAACTACACGTCGAGCAGGA | TCCAGCCCTCGGACGCGA | 18293 & 18294 | ASTN1 | TAGTGACCAACCACAGACCCA | AAGCAGTGGAGTCACATGCACA | 18399 & 18400 |
| ASB14 | AGCTCTCACGAAGCAGCCA | CAGCAAGAGCAAGGAGGAGTGAA | 18295 & 18296 | ASTN2 | CTCAGGGAAAGGGGATGTGA | TAGCTGGCTGAACATCCACCCA | 18401 & 18402 |
| ASB15 | AAGCAGCCAAGCAAGGCGAA | GTGACCATACTCGGCAGCGA | 18297 & 18298 | ASXL1 | GCCCTGGGTGTCAGAGCA | TGGAGTCTGTACCCACCA | 18403 & 18404 |
| ASB16 | AGATGCTGAAACACTGCGCCAA | CGCACAGCTAGTCGGGCTA | 18299 & 18300 | ASXL2 | TACTGCCGCTTGAAAGCCA | AACGACAAGGCAGGAAGGACGACGA | 18405 & 18406 |
| ASB17 | CCAAGCCCATTAAGTGCA | CAGCCAATTCACGATCAACCA | 18301 & 18302 | ASXL3 | GTAAGGGCTACTTGGCAGGGA | TGATGCCGGAACTGATGACACA | 18407 & 18408 |
| ASB18 | CTCACCCACCGCTGCCTGCA | CAGGGCGACCAGTGTCAAAGCA | 18303 & 18304 | AS21 | CTCGACCGCACGTCTCAGAA | GAATCTAGGAGCCTCTGGACCA | 18409 & 18410 |
| ASB2 | ACTGGGCCGTCATCAAGGAGA | GGAGCGGCAAGGTGTCTAGGA | 18305 & 18306 | ATAD1 | GAAGTTGCCCAGGAAACTGA | CTGCTGTTGAACAGGCCGAA | 18411 & 18412 |
| ASB3 | TACTAACCGGGCCTGTGACA | GGAAAGCCATGCACACAGGAGA | 18307 & 18308 | ATAD2 | CAGTACGGTCAAGCAGGCAA | GTTCGTAGCACCAATGACCA | 18413 & 18414 |
| ASB4 | TAAATCTCCCTGCACAAGGCA | TAGCAGATTCCAAGGCTGGGCA | 18309 & 18310 | ATAD2B | CGGAGGCGTTATCCCAGA | TAGTGCATGCCCTGAAGACA | 18415 & 18416 |
| ASB5 | GCACAAGCCTGCCTTGGGAGA | GCTTGGACTGCCTTGGGAGCA | 18311 & 18312 | ATAD3A | GGCCAACCAACCAGAAGA | CCCGACATGGCCCTCGCTA | 18417 & 18418 |
| ASB6 | CGACGGGGTGACAGATCACGA | GTCCCCTCCCACGGTCTCA | 18313 & 18314 | ATAD3B | ACTGTGCCATCAACAGCGCGA | GACCCGTCTTGGAGGCA | 18419 & 18420 |
| ASB7 | CCACTACGGCCAGGGACTCA | GATCACGGCTATCGCAA | 18315 & 18316 | ATAD3C | GATCCATCCCTGCCGCGAA | GTCAGCAAAGGGTGGTGGGA | 18421 & 18422 |
| ASB8 | CTCCACAGAGCTGTTGGAGA | GAGTTCCTGGAGCTGAGCACA | 18317 & 18318 | ATAD5 | AGGGCCAACAGGAGTGGAGAA | GTCTACCACTGCCTGGGAA | 18423 & 18424 |
| ASB9 | CAGTGGCCAGGGACAAGCCA | CTGGAGGCCACCAGTTCA | 18319 & 18320 | ATAT1 | CGAGATGAGATGGGGACCA | GGAGATCCGGCTTCCCAAGGA | 18425 & 18426 |
| ASCC1 | ATCATGGGGTTGCAGCAAGCA | AAGAACATCCACCATGCCAGGA | 18321 & 18322 | ATCAY | GAGCACCGTATAGACCTGCACA | GGAAGGAAGCAGGGCTGCGAA | 18427 & 18428 |
| ASCC2 | CGCATGTCCACTCAGCAAGGA | GAGACAGGAGGAGTCCAAGGA | 18323 & 18324 | ATE1 | CAGTTCACCCTTGAGGACAGA | GGAGGATGTCAATCACCCCA | 18429 & 18430 |
| ASCC3 | GAATGCTTGGCAGGGACAGAA | AATAACAGCATGGGCGGGAAGA | 18325 & 18326 | ATF1 | AGACCTCTGATGGACACAGA | GTCTGAGAGGTGAGAGTCACA | 18431 & 18432 |
| ASCL1 | ACGAGCATGACGGCGGTGA | CGTAAGAGCCCTCGTCCGA | 18327 & 18328 | ATF2 | CAAGGCAGAAGCTGTAGCCA | GGGAGGAAGGAGCATAACGA | 18433 & 18434 |
| ASCL2 | CGCCTACTCGTCGGACGA | CTAACCAGCTGGAGAAGTCGA | 18329 & 18330 | ATF3 | GAAGACGAGAGTGCCTGCAGAA | GGGCGATGAAGGTTGAGCA | 18435 & 18436 |
| ASCL3 | CACTTTCCACTGCTCGCCCCA | GGGTGAAGGCTGGCCCGTA | 18331 & 18332 | ATF4 | CCCAGACGGTGAACCAA | GGACAGGGACCTGGGCA | 18437 & 18438 |
| ASCL5 | CTCCCCGCATCCCCCCA | TGAGGGAGAAAAAATCACAGTTCCCA | 18333 & 18334 | ATF5 | GAGGTACCGCCAGCGGAA | GATCTCGCGTCCACGGA | 18439 & 18440 |
| ASF1A | CCTTCGAGTGCCATGGAGGA | CTTCCTGCGGGAACAGGA | 18335 & 18336 | ATF6 | GCCATTGGCAAAGGAGA | CTGTGTCGACTCCCCAGCAA | 18441 & 18442 |
| ASF1B | CCATGGACAGGAGTTCATCCGA | GTTCCGCTGAGCTTGGGAGA | 18337 & 18338 | ATF6B | CTCGAGGCTTGCTGACGA | AGTTGCAGGCTGGCCACA | 18443 & 18444 |
| ASGR1 | CCCAGCTGGAGAACAGCA | CCCGGAGCGGAGAACCA | 18339 & 18340 | ATF7 | ACAAACGAGGACCACCTGGCA | ATTGAGAGTCCCACCTCCTCA | 18445 & 18446 |
| ASGR2 | GGGCTGTCACTCAGCCAGA | TCTCACACACCAGCGGTA | 18341 & 18342 | ATF7IP | GGTGCAACAAGTGGACCA | ACCTGCCGAACAGCAGGA | 18447 & 18448 |
| ASH1L | CAAAGGCCAGTCAGCAGA | ACGACAGGCCAAGGGGA | 18343 & 18344 | ATF7IP2 | CCAGAACCAAGCCACCA | CAAGTCAGGGCAATGCCA | 18449 & 18450 |
| ASH2L | TGGGTCCAGCCCTCTAGGAA | GTCTTCCCTGTCCATAGCCAGA | 18345 & 18346 | ATG10 | TGCTACAGGGACCATGGGACA | TGGCCTACAATGCTCAGCCA | 18451 & 18452 |
| ASIC1 | CATGGTCAAGATCCCCAGCAA | GCCCGATGAACAGCCCA | 18347 & 18348 | ATG101 | CAAGATGCCCACACAGTGGGA | TGGTGGGTACTGAGGTGCCCA | 18453 & 18454 |
| ASIC2 | GTGAGTGCCGATCCTCAGAGA | TCAGGGGTACAAAAGGGGCA | 18349 & 18350 | ATG12 | CACGAACCATCCAAGGACTCA | TGGTCTGGGGAAGGAGCAA | 18455 & 18456 |
| ASIC3 | GCCTGCTCACCATCTGGGA | TGGGAGGTGTCTGGGGCCCA | 18351 & 18352 | ATG13 | CACCCTTCTGACAGAACCCA | ATCCAAACTCTGCAGGGTCA | 18457 & 18458 |
| ASIC4 | CTGAAGCCATGGAGAGCGA | AGGATCTTCCAGCAACGTGAGGA | 18353 & 18354 | ATG14 | AACCACTGCTATCCCTCAGGA | CACAAACCGGGGACTAGGCA | 18459 & 18460 |
| ASIC5 | AAGAAGCCACTGCCATCTCCA | TCACAAGTGAGACTGAGCCCA | 18355 & 18356 | ATG16L1 | CTGGAGGCATGGACCGCA | CCTGAGACAATCCGCGCA | 18461 & 18462 |
| ASIP | AAGTGGTGCGCCGCCGCA | GAGGCTGAGCACCGCGCA | 18357 & 18358 | ATG16L2 | TGCTCAGCTGTTCCCAGACA | CCCGGTGTCCACATCCCAGA | 18463 & 18464 |
| ASL | GCTGCTCCGAGCAGAACTCAA | GAGATGGGTCATGCACACGCGA | 18359 & 18360 | ATG2A | GCTTCACCGTCTGAGGTCCCA | TAGCCCAGCACCTTGTCACA | 18465 & 18466 |
| ASMT | CTTGTCAGACGAGGAAGGGGCA | CTGAAGCCAGCAGCAGAAGAGGA | 18361 & 18362 | ATG2B | CCTGAGGGAAGGTGTGGCCAA | GGTTTCACCACTGCCGGAGGA | 18467 & 18468 |
| ASMTL | CTCAGCAGGGTGCCGAGA | AGCAAGCAGTGATACTCGCCCA | 18363 & 18364 | ATG3 | GTGCAGTGCAGAGATCACCTA | GCACCGCTTATAGCACGGGA | 18469 & 18470 |
| ASNA1 | GGCTGCTCAACTTCCCA | GTTCGCTGACTGCCTGGA | 18365 & 18366 | ATG4A | TGCAGTCCCCACAGCGAA | CACTTCTGCCTTGCGTGGA | 18471 & 18472 |
| ASNS | GGCTGCTAGAAAGTGTCGGCAGA | CAGGAGAAGGAGCCCTTGTGA | 18367 & 18368 | ATG4B | CCGCATGAGCATGCGCGA | GAATCTAGGGACAGGTTCAGGA | 18473 & 18474 |
| ASNSD1 | AGGAAGGGCGGGACTAAAGGAA | TCCTTCTGGGCCACTAACCA | 18369 & 18370 | ATG4C | AAGTTACTGCAGAGTCGGGA | GGCCAGGTCCAAGCTCTACCA | 18475 & 18476 |
| ASPA | ACCCCGGGATGAAAATGA | ACAAACACGGGGTACACGGTA | 18371 & 18372 | ATG4D | TCCTGCAGCCACGCGGTA | CTGTGCAGGGAGCCGGA | 18477 & 18478 |
| ASPDH | GTGGATGTAGAGCTGAGCGGA | CCTGGAGGGAGGCTGGCA | 18373 & 18374 | ATG5 | GGACAGTTGCACACTAGGAGA | GTTCACTCAGCCACTGCAGA | 18479 & 18480 |

| GeneName | Forward Primer | Reverse Primer | SEQ ID NOs | GeneName | Forward Primer | Reverse Primer | SEQ ID NOs |
|---|---|---|---|---|---|---|---|
| C11orf82 | CGGCCGGAAAGAGTCCAGGA | AGTGAGATTCGCTAGGGGGA | 19541 & 19542 | C16orf54 | CCGCCACAGGCCTGGGTGA | GGCTGGAGGCCCCACTCA | 19647 & 19648 |
| C11orf91 | TACCAGAGCTTGGGCAGCCA | GCACATAGAGGAGGAGAGACCA | 19543 & 19544 | C16orf58 | ATCCTAAGGGCCGCCACACA | CTCGGTCTTCCAGCCGGCA | 19649 & 19650 |
| C11orf94 | CCCTGGCAACTCTCGCAGCCA | GCGCTGCTGCGGCCCTAGACA | 19545 & 19546 | C16orf59 | TGTGCTTCGGGGACCCAGAGA | GGAGTCCAGGAGCCTTAGGAA | 19651 & 19652 |
| C11orf95 | CGACCACTGGCGGCTGGCA | TGCTGAGCTTGAGGGTGGCCA | 19547 & 19548 | C16orf62 | GCCAACCAAGTGCTCTCCCAA | AAACAGGCACCCCATGTTCAGGA | 19653 & 19654 |
| C11orf96 | CTGTCGCTGCAGCGGGAGGCA | GCCGAGTCGGAGTCGCTGGA | 19549 & 19550 | C16orf70 | TGCAGGGATACCAAGGGTCCA | ATCTGCTAATAGGCCAGGTCA | 19655 & 19656 |
| C11orf98 | GGCCCCGAACGGAGCTGA | CTTGAGGTGGTGCCGCGTGA | 19551 & 19552 | C16orf71 | TGAAGACACAGCTGGATCACGA | TGGCTCAGGAACATCCCCA | 19657 & 19658 |
| C12orf10 | TACACTGACCAGGCTGGACA | TGGACGAAGATGCAGCCA | 19553 & 19554 | C16orf72 | GAGAGGGAGGGGAGGATGGA | GGATTGGAGGGACAGGGAGA | 19659 & 19660 |
| C12orf29 | AGGAGCCTTCTCTCAAAAGGGA | TCGAGCCCAAAGGTATGGCTGA | 19555 & 19556 | C16orf74 | CTGGACGACAAGCACTTGGA | CTGGGCACGACCCTGTCTA | 19661 & 19662 |
| C12orf4 | TAGGAGCCCAGTTGAAGACCA | GTAAAACCAGGCCACAGAGAGA | 19557 & 19558 | C16orf78 | GGACGCCGCCTCCTACCGAA | GATGTAGCTGCCAGGGACCA | 19663 & 19664 |
| C12orf40 | ACACAGGGACCTTCAGTGTCA | ATCAGAACCCTGGACCGGGA | 19559 & 19560 | C16orf86 | AGTCGGAGCTCCAGGAGGAA | GGGCCTCACAATGGAGACCA | 19665 & 19666 |
| C12orf42 | CCCGAGCATCCAAAGCAGA | GTCCCGGGGTATGAGGA | 19561 & 19562 | C16orf87 | AAGAGGAGGCGAACAAGAGAGA | ATTCTGCCAAGGCGACTGA | 19667 & 19668 |
| C12orf43 | TACAGGAGTCAGCCATCCA | TGGGGGTGGTGGCAGCGA | 19563 & 19564 | C15orf89 | GAACCGGGACGGACGAGCA | CCCTCATTCTGGCCCAGA | 19669 & 19670 |
| C12orf45 | GCCAGCGGAGGTATATGGGGCA | TTGAAACGACCAGGTGGTGCA | 19565 & 19566 | C16orf90 | CCGAGGGAGGGGGCAGAAGCA | AGCCCGGCTCCCAGGTACA | 19671 & 19672 |
| C12orf49 | AACGTCCTAGCACGAAGCA | CGGCTGCCCGGTTGAGGA | 19567 & 19568 | C16orf91 | CTCCAGCAAAGCCAACCTCA | TCCCACACCTGTCTCAACCA | 19673 & 19674 |
| C12orf50 | TCCAGCCAGTGAAGAAGGCCTCA | GGAAGGTGCATTCAACGCGACA | 19569 & 19570 | C16orf92 | ATCCGGACTTCAGACCAAGCCA | TATGTGGGTGCAGAACTTGGA | 19675 & 19676 |
| C12orf54 | ACCTTCCAAGCAGCAGAGAAGCA | CTCATCCCTCGAATCCCAGCA | 19571 & 19572 | C16orf95 | CGCGCAGGATGGGCAGGCAA | CAACAGGCACTCATCACCGCA | 19677 & 19678 |
| C12orf56 | GCCGCCGAGGTCTACGA | TGGCCAGGACGTCCGGCA | 19573 & 19574 | C16orf96 | AAAGGGCCGCGTGAACAGCCA | GCAGCAGAGGTGGCAGGGA | 19679 & 19680 |
| C12orf57 | CAAGTCCTACGAAGCCAGCA | GCCACGCTGCCAGCAGGA | 19575 & 19576 | C17orf100 | AGACCTCCCAGCGCCGCA | GGCTCTGACGTGGCGGCA | 19681 & 19682 |
| C12orf60 | GAGACTGATTCAAGCTGCCAA | CCCAGAGCACATGGCCA | 19577 & 19578 | C17orf105 | AACCTCCAGTGGGCGCACACA | TCCAGCAATCCACCTTGGCA | 19683 & 19684 |
| C12orf65 | TCCAGATGGCAGGCAAGGAAGGA | TACAACGATGCCTGAGGGGA | 19579 & 19580 | C17orf50 | CGCCCCACGCAGCGACA | CAGAGCGGATCTGAAATACCCAA | 19685 & 19686 |
| C12orf66 | CATGACGGGACCGCACATCTGA | TAAGGGCAAGTGAGAACTTCA | 19581 & 19582 | C17orf51 | CCTCGCCATGCATGCACGGGAA | GGACAAGGAGGCGTGACCCA | 19687 & 19688 |
| C12orf71 | GGGCATGGGGGACTCAGAAGGA | GGAGCCAATGTCAGCCGGGAA | 19583 & 19584 | C17orf53 | GCTAGGCTGGATGGAGAGAGA | CATTGTGCTCCGAGTCAGGGA | 19689 & 19690 |
| C12orf73 | CACAGGTACTACCGACCGGA | CGGCTAAACATCCACTGAGCA | 19585 & 19586 | C17orf58 | CGCTGTACCTCACCCCGA | ATTGCAGCTGGAGGAGTCA | 19691 & 19692 |
| C12orf74 | CACCTGGGGAAGCTGGGGA | AGTGGAGTTCAAGGGTGACA | 19587 & 19588 | C17orf62 | ATGTGAGCGTGGAGGGAGGAGA | CACATCACTGCGGTGGCCCA | 19693 & 19694 |
| C12orf75 | CCCTGCAGGAGCAGGCCA | ACAACGTCCCACGGAGGCCA | 19589 & 19590 | C17orf64 | ACAAGTACACCAAGAGCAGCCA | ATGCATGGCAGAGCTTGGGCA | 19695 & 19696 |
| C12orf76 | GGCCAGTGGAGAAGGTTGGAACCA | ACAGTTCAGAAACACTGAGAAGCGGA | 19591 & 19592 | C17orf67 | GGCGACCAGGATAGACCAAGCA | TGCAGTGAGGGTTCAGCCA | 19697 & 19698 |
| C14orf1 | TGCAGAGCTTCCGAGACCA | AACTCAGAGGAGAAATGCCCCA | 19593 & 19594 | C17orf74 | AGAGCGGGCCTGCCTCCTCAA | ACGCTTGGGCATGCAGCGCA | 19699 & 19700 |
| C14orf105 | ATCTTGAACAGAGAGTGCCACATCTGA | GTCAGAGGTTGAACTGTCCCA | 19595 & 19596 | C17orf75 | AAGGGCCTGCAGGAGTCACA | AGTCCTTGAAGATGGCCACA | 19701 & 19702 |
| C14orf119 | GGTCAGGTCCCAGCGTGA | GCGCTCCTGCTCAGCCCA | 19597 & 19598 | C17orf80 | CCGAGGGAGAACGACTTACCA | TTGGTGAAGGGCTCTGAGGA | 19703 & 19704 |
| C14orf159 | GAGGCTGTGAGGAGGCACA | TGTAGAGTGCGCAGGCCA | 19599 & 19600 | C17orf97 | AAACCAGAGCACAGACAGAGCA | TCGGGAGGCCTGACGGTGGA | 19705 & 19706 |
| C14orf166 | CACAGCAGGCGACTGGCCCAA | TAGCCAAAGCGACTGGCCCAA | 19601 & 19602 | C17orf98 | GTACAGGGAAGGGATGGCTGGA | ATGCCCAGTTCACTGCTGGA | 19707 & 19708 |
| C14orf177 | CATAACGAGGGACAAAAGCCGA | CCTTGGTGAGCGTCAGGGCA | 19603 & 19604 | C17orf99 | GAAGGTGTTGAAGACCCAGA | TGGGCACCTCAGGTGAGAGGA | 19709 & 19710 |
| C14orf180 | CAGAGAGGGAGGGACAACAGGAA | CGGAACCACACGCGCCTCGA | 19605 & 19606 | C18orf21 | CGCGGGGACTGCACGACA | ATCCAGAACCAACAGCTGGA | 19711 & 19712 |
| C14orf2 | TATGGATCCCCATGAAGCCCTA | GACCAGGAGCAGGCGCTGA | 19607 & 19608 | C18orf25 | TCCGAAGCCCCACCAAAAGCA | AGCCAGGTGACCACTAGAGGA | 19713 & 19714 |
| C14orf28 | AGGAGGATCAGCAGCGACA | ACAACAAAGAGGGTGCCCCA | 19609 & 19610 | C18orf43 | TGAAGCTGCAAGAATGCCACGAA | GGTTAACTCCCAACGCCCA | 19715 & 19716 |
| C14orf37 | ATGGACACAGTCAGGGCCAA | CAAAGCAGGAAGTGCAGGGGGA | 19611 & 19612 | C18orf54 | TGCTGGCAAGCTGCACCCTGA | TCCAGTGCTTGCACCAGGA | 19717 & 19718 |
| C14orf79 | CTCGGAATAGATGCTGCGCA | GCATGGAGGGGGTCTTCAGGAA | 19613 & 19614 | C18orf63 | AGACTGCCAGCACCTGAGCTA | ATAGCCATACAGGGCATCCCA | 19719 & 19720 |
| C14orf80 | CGAGAGGATGGGGCAGCA | TAGCACGTCCTCAGCGCA | 19615 & 19616 | C18orf8 | ATCGCTGCCGTGATAGCCA | CGCACCGCCTCTTGAGGA | 19721 & 19722 |
| C14orf94 | ACCCCAGAGAGCAGGACCAGA | AAGGCACTGTTCAGCGCA | 19617 & 19618 | C19orf12 | GTGGACGGACGCGTGCA | ATACTGGGATCTCGGCCCGA | 19723 & 19724 |
| C15orf39 | CAGAAGTCACCGGCCCCAA | CTGGTAGCAGGGGTAGGGGA | 19619 & 19620 | C19orf18 | ATGGACTCCATCCCACTGGAA | GTAGGGGATGCAGGCGTGGA | 19725 & 19726 |
| C15orf40 | ATGCTCACCATAGCCATCCA | AAGATACCGACAGAGCCTCAGCA | 19621 & 19622 | C19orf24 | CGCCACAACAAGCACGACA | CGCTGTCCAGCGAGGCCA | 19727 & 19728 |
| C15orf41 | TCCCAGTCAATGCCAGGCA | ATTGGCCAGGTCAGGGGCA | 19623 & 19624 | C19orf25 | CAGGATGATGAGGATGCGGA | GGCTCGCTGCTCAGGAGCTA | 19729 & 19730 |
| C15orf48 | TGACTGTGGCGGCGGGTGGA | GAGGTACAGTAGGGTCCACA | 19625 & 19626 | C19orf33 | TCCCAAGCTCAGTCTCCA | GCAGCGTGGGACTTCACA | 19731 & 19732 |
| C15orf52 | GGGAGGAGCTTGGTAGGAGA | AAATGGGCTTGTGGACGGAGA | 19627 & 19628 | C19orf38 | TGCCAGAAGGAAGACCCGGCCA | AATTCGGGGGTCTCAGGGGA | 19733 & 19734 |
| C15orf53 | TGACTCCAAGAAGTCAGCACA | TCCCAAGTAGCAGCCCCA | 19629 & 19630 | C19orf43 | TGTCGGGCGCGGGTTCGA | TGGTCGGGTCGCTGCGGA | 19735 & 19736 |
| C15orf57 | AGCCCTGACTCTACAGCCACA | ACAGCTGGCTGGACAGCA | 19631 & 19632 | C19orf44 | AGACCTTCCACAAACAGCCGA | CGTCAGGAGGCGCAGGA | 19737 & 19738 |
| C15orf59 | TGTGACGATGAGGGAGGGGA | GTGGCGGCTGGTCAGTGGA | 19633 & 19634 | C19orf45 | GCCAACCTCCACTTGCAGCA | TGAAGAAGGCAGTCCA | 19739 & 19740 |
| C15orf61 | CCTGAGGGAGGGCCACGA | ACCGGCAGTTGAAGTGCGA | 19635 & 19636 | C19orf47 | CAAGGCCAGTCCCCAGCA | TCAACCCAGGCCGTGAGGA | 19741 & 19742 |
| C15orf62 | CCCTTCACCACAGCTCAGAGA | AGAAGTGAAATCCCCAGGTTCA | 19637 & 19638 | C19orf48 | ACCCAACCCAGTGCACAGGA | TCTCACGGTGGGTATGGACA | 19743 & 19744 |
| C15orf65 | ATGAACAGACCGCAACCGGGA | ATTGCCAGGGTTCACACAAGGA | 19639 & 19640 | C19orf53 | TCTGAAAAGAATGGGGCCCA | GGGGCCTTCAGCAGTGCCA | 19745 & 19746 |
| C16orf45 | ACAACCATGATGCGCAGGAGGA | TTTCTGGGATGGCGACCAA | 19641 & 19642 | C19orf54 | TCAGCTGTGGGACTACGACCA | AGGCCAGCCCGTACCCCA | 19747 & 19748 |
| C16orf46 | GTAGAACCCCTGGGAATAAGCA | GACTGACGGGGAGGAGGAA | 19643 & 19644 | C19orf57 | CCTCAGACTGGCAGGCA | TCGAAGTCAGGAGGCGTCCA | 19749 & 19750 |
| C16orf52 | GGACTGGATCAACACCGGGA | GTGACCCACTTCCGGGGGA | 19645 & 19646 | C19orf60 | GAGATGTGGGAAACGGGGCGA | GCAGGAAGGTCAGCAGCCA | 19751 & 19752 |

| GeneName | Forward Primer | Reverse Primer | SEQ ID NOs | GeneName | Forward Primer | Reverse Primer | SEQ ID NOs |
|---|---|---|---|---|---|---|---|
| CCL17 | GGACCAATGTGGGCCGGGA | CAAAAACGATGGCATCCCTGGA | 21025 & 21026 | CCR3 | GCTGCATGAACCGGGTGA | GCCCAGATGCATGAGCAA | 21131 & 21132 |
| CCL18 | TGTGAGTTTCCAAGCCCA | CACAGGAGCAGAGGGCCA | 21027 & 21028 | CCR4 | TGATCATCAGGACCTTGCAGGAA | GCTCCACCAGGGTCTCTAGGA | 21133 & 21134 |
| CCL19 | CCAACTCTGAGTGCTGCCAA | GTGGTGAACACTACAGCCAGGCA | 21029 & 21030 | CCR5 | GTTTGCGTCTCTCCAGGAA | CCATGACAAGCAGCCGGCA | 21135 & 21136 |
| CCL2 | AGGGCTCTGCAGCCGAGA | CTGCTTGGGGTCAGCACAGA | 21031 & 21032 | CCR6 | GCATGGACCGGTACATCGCA | GATGATGACTGACAGCCCCA | 21137 & 21138 |
| CCL20 | GCGAATCAGAAGCAGCAGCA | GGATTTGCGLACACAGACA | 21033 & 21034 | CCR7 | GGCCCAGACGGTGGCCAA | TGCGGAACTTGACGCGA | 21139 & 21140 |
| CCL21 | CAAAGGAAGATTCCGCCA | GCTGGGATGGAGCAGCCTA | 21035 & 21036 | CCR8 | AGAAGCTGAGGAGCATCACAGA | TCCAAACCCACTCGGTCCA | 21141 & 21142 |
| CCL22 | GCGCAACATGGAAGACA | GGTTAGCAACACCACGCCA | 21037 & 21038 | CCR9 | TTCACCTCTGATACAAGCCAA | ATAGAGAACAGGGTTCAGGCA | 21143 & 21144 |
| CCL23 | CATCTCTACACCCACGAA | GATGACACCCGGCTTGGA | 21039 & 21040 | CCRL2 | TAAGGTTCAGGGAGCAGAGGTA | TACAGGAGAGGGTTGATGTCA | 21145 & 21146 |
| CCL24 | GGCAGGCCTCATGACCA | AAGAACATGCAGCAGGGAGA | 21041 & 21042 | CCS | GATGACCTGGGCCGGGGA | GGCCTGCTCCTCCCAGA | 21147 & 21148 |
| CCL25 | CCCGTCTGCACACCCAA | CGCAGCAGGCAGATTGCA | 21043 & 21044 | CCSAP | CTGAGCCTGACAGACCAACAA | CTCCCAGCCATAAAGAGCA | 21149 & 21150 |
| CCL26 | CCACTTGGAACTGTGCACA | GCTTCGCACCCAGGTCCA | 21045 & 21046 | CCSER1 | GATGTAACAGAACGGGCAGGA | AAGTTGTCACACTGGGATGCCA | 21151 & 21152 |
| CCL27 | TCTACCGAAAGCCACTCTCAGA | TGCCTTGAGCCAGGTGAAGCA | 21047 & 21048 | CCSER2 | GAGCATTACCACTCCAGCCA | CCTGAACCATGTGCCGAA | 21153 & 21154 |
| CCL28 | CTCCAGCTGTTGCACGGA | ATGAAGGATGACAGCAGCCAA | 21049 & 21050 | CCT2 | TGCAGGTGTGGAACGCCTA | GTTGAGTGGCCACCACGCA | 21155 & 21156 |
| CCL3 | CTCCCGGCAGATCCACA | GACACCGGGCTTGGAGCA | 21051 & 21052 | CCT3 | GGCCCATGCCTTGACAGA | GTGCTTGGCCCGAAGGGA | 21157 & 21158 |
| CCL3L3 | ACCTCAGCTCCACAGATTCCACAGA | CACTCAGCTCCAGGTCACTGA | 21053 & 21054 | CCT4 | GAAAATGCCGGCCTGAATCCCA | GCTGGACAACCTTGTTCTCGA | 21159 & 21160 |
| CCL4 | TCCAGCGCTCTCAGCACCA | TGGACCCAGGATTCACTGGGA | 21055 & 21056 | CCT5 | GCACTGGAGGTCATCCCA | AACAGTCGATGCCAAGAGCA | 21161 & 21162 |
| CCL5 | CCGTGCCCACATCAAGGA | TGATGTACTCCGAACCCA | 21057 & 21058 | CCT6A | CCTGAACACAGGTGAGCCAA | TGGTGGCAATCACAGTGCA | 21163 & 21164 |
| CCL8 | CAGAGGCTGGAGAGTACACA | GATGCTTCATGGAATCCCTGA | 21059 & 21060 | CCT6B | GTCAATATATGCGCCGGCCGA | TCATCGAGCAGCATTGCCA | 21165 & 21166 |
| CCM2 | AGAACATTGGCGTGAAGGA | CGAGATCATGCGGTCCA | 21061 & 21062 | CCT7 | CAAGTCGCGGGCTCGGCA | ATCAGGCACGCAGCCTCA | 21167 & 21168 |
| CCM2L | AACCGCTCGACCCGCAGGA | GACCTGACGATGAGTGCGCA | 21063 & 21064 | CCT8 | TGTGACAAACGATGCAGCA | AGCTAATTCCAGGAGAGCTCCA | 21169 & 21170 |
| CCNA1 | GGGACAAGACCCAAAGCACA | CTTCCCAACTCCACCA | 21065 & 21066 | CCT8L2 | GACCCTCACACTGGGACA | CTGAGAACCACAGTGAGGGCA | 21171 & 21172 |
| CCNA2 | GAAGACGAGACGGGTTGCA | CCACATGAATGGTGAAGCA | 21067 & 21068 | CCZ1 | CGACGCCTCTGTCCACCAA | GGGTGCACGGAAGTGAGCGA | 21173 & 21174 |
| CCNB1 | CTGCCTCTCAAGCCCAA | CCAGTGACTTCCGACCCA | 21069 & 21070 | CCZ18 | TACCGGACCCTTGAACCTCA | TCACAGATGTCAGAGGCCA | 21175 & 21176 |
| CCNB1IP1 | TCCGCACAGAACTCAGTCA | GAAGGCCAGGCTCCGGA | 21071 & 21072 | CD101 | TGATGAGCCGTCAGCCGCAA | GCTGGAACTGCCACGTCACA | 21177 & 21178 |
| CCNB2 | TGCAGTCCATAAACCACA | ATCCATAATGCCAACGCACA | 21073 & 21074 | CD109 | GCTCCAAGCCTTCACA | CCCCATCTCACTGGGA | 21179 & 21180 |
| CCNB3 | AGATGACCCTGCAGGAATACCA | ATGCTCCAGGAAGGGAACCCA | 21075 & 21076 | CD14 | CGCTGCGCAACACAGGAA | GTTCAGGGCGCTGGACCA | 21181 & 21182 |
| CCNC | GGACATGGGCCAAGAAGACA | CTGCTGTACAACAGGCTA | 21077 & 21078 | CD151 | CTGGCGAGACAGTGAGTGGA | CACCACCGTCTTGCAGCA | 21183 & 21184 |
| CCND1 | TCCGCAAACACGGCAGA | GTGTGAGCGCGGTAGTAGGACA | 21079 & 21080 | CD160 | GGGAACTACACAGTCACGGGA | GGGCACCAAGGCTGGTGA | 21185 & 21186 |
| CCND2 | CACCGTGATGATCGCAA | TTGAGAGCACCGCTCTA | 21081 & 21082 | CD163 | ATGGGAGAAGAGGACTGGCA | GGTCAGTCCCTGACCA | 21187 & 21188 |
| CCND3 | ACGCCCTGACCATGCAA | CAGAGAGCCGGTGCAGA | 21083 & 21084 | CD163L1 | CTATGGGACTGTCACGGCAA | AGAACCAGGAGAAGGAGGCCA | 21189 & 21190 |
| CCNE1 | TCCTGATCCCCACCTGA | TGCCAGCTCAGTACAGGCA | 21085 & 21086 | CD164 | AGCACCCGAACGTTGACGA | GGTGACCAGGCGGAGGGA | 21191 & 21192 |
| CCNE2 | AATCAGGCAGAAGAAGGAA | ATGCAAGGACTGATCCCCCA | 21087 & 21088 | CD164L2 | CCAGTCCCTGAAGGCCACA | GCCTTGAGGAAGTGCAGACA | 21193 & 21194 |
| CCNF | GTGGAGCTGAGAACCCAGGA | ATCCGGTGAGGTCCACA | 21089 & 21090 | CD177 | CCCCGAATGACCTGCCCCA | TGAGAGACTTCAGGCCCTCA | 21195 & 21196 |
| CCNG1 | TGCACACGATAATGGCCTCAGA | AAAGCAGCTCAGTCCAACACA | 21091 & 21092 | CD180 | TAAGCCACAACAGCCTGACA | AGGGAGGAGACGGCGGGTGA | 21197 & 21198 |
| CCNG2 | GCACAGCCACCATCTACGTCTGA | ACTGGGAGGAGAGCTGCTGA | 21093 & 21094 | CD19 | ACCGTGCAACCTGACA | CCACAAGGGAACACGCA | 21199 & 21200 |
| CCNJ | TCGGCCAGCCAGGACCA | GGATGAGCCTGTACTCCCCGA | 21095 & 21096 | CD1A | GCGGCAAGTGAAGCCCGA | TCCCATCAGCACTGGGCA | 21201 & 21202 |
| CCNJL | CCGGATGTCCACCACCA | TGGTAGGGCAGGTGTGCA | 21097 & 21098 | CD1B | TTGAGATCCAGGGCATAGCA | GGGAAGGCACACATGAAGCA | 21203 & 21204 |
| CCNK | ATCCATGGCCTGCCGTGA | TGCCATCGCACTGGGCA | 21099 & 21100 | CD1C | GAACAGGAGCAACTGGGCA | TCACTCGACAAGACAGCCCA | 21205 & 21206 |
| CCNL1 | CCGTGAAGGCTTGCCAA | CGCTGATCCGGTTGGGA | 21101 & 21102 | CD1D | GCACTCAGCCAGGCAGCA | GGAACAGCCAACACGCCA | 21207 & 21208 |
| CCNL2 | CGAAGCTCTGGAAGCGCAA | GTCTTCCAGTCGCAAGTCCA | 21103 & 21104 | CD1E | GGGAAGTTCAGCAGAGGGGAGA | GAGGAGGAACAGGAGCAGCA | 21209 & 21210 |
| CCNO | CCTGGGACATAGCTCAGAGAA | GGCTGAACACCCTGGGCA | 21105 & 21106 | CD2 | CTGTGAGAGGGAGCGACGA | GAAAGTGAGCCAGTGCCACAA | 21211 & 21212 |
| CCNT1 | AGTATCGCATCCTAGCTCAGA | TTGAAGAGCTGGAAGCTGAGAGGA | 21107 & 21108 | CD200 | TGTCTCACCCAAATGGGACCA | TAAAGTCGGTCACAGTCCCA | 21213 & 21214 |
| CCNT2 | ACTCGATATGGGCAGCAGCAGA | GCCAGCAGGATCGCCCTA | 21109 & 21110 | CD200R1 | GAGGCCAGCCTTCCTGCACA | TCATGAGTGATGGCCACGGTA | 21215 & 21216 |
| CCNY | ACAACCCAGAGCAGAAGCAGA | TGGTAGGGCAGGTGTGCA | 21111 & 21112 | CD200R1L | GGAAGCCAGCTGCCCAGA | ATGGGAGCATGGCATTCCA | 21217 & 21218 |
| CCNYL1 | CTGCCAGATCCTCAAGGACA | ATCTGCTAAGGAGCGGAAGGTCA | 21113 & 21114 | CD207 | GACCTCAGAGAGTGAGCAGGA | GAATGGCGTGTCATCACCCA | 21219 & 21220 |
| CCP110 | AGAAGAGGCAATGAAGACGGA | GTGAGTCCGCTTGAGACAGCA | 21115 & 21116 | CD209 | CCAGCGGAACTGGCACGA | CAACAGAGGTGAGCGTCA | 21221 & 21222 |
| CCPG1 | TAGAGCAAGGAGGAGAAAGAAGCCA | GGCTGCTCAGGAAGGAAGAGCCCA | 21117 & 21118 | CD22 | CTGTGAGAGGGACGGCAA | GAGGGTGCTGAGAGGCGA | 21223 & 21224 |
| CCR1 | GGTGATCGCGCTACACGG | CCACGGAGGAGGAAGGGGA | 21119 & 21120 | CD226 | GATCGGGCAGCAGGA | GAGAGCAGGAAATAGTAGCCACA | 21225 & 21226 |
| CCR10 | TCTATGCCGCCGCGA | GCCAGGAAGGCGTAGAGA | 21121 & 21122 | CD24 | GGGACATGGGCACAGA | GGCCAACCCAGAGTTGA | 21227 & 21228 |
| CCR2 | TACCAACGAGAGCGGTGAA | TAAGGATGAGGAGGACCAGCA | 21123 & 21124 | CD244 | CCAGGAAGTCTGATCCAGGA | TCTTTGCGGCTCAATGCAGCA | 21229 & 21230 |
| | | | 21125 & 21126 | CD247 | GAAGTTCAGCAGGAGGGCAGA | CCATCCAGGGTTCCCGCCA | 21231 & 21232 |
| | | | 21127 & 21128 | CD248 | TTGCCGACCAGCCAGA | CCCAGCATGGATGACCCA | 21233 & 21234 |
| | | | 21129 & 21130 | CD27 | ACCCACTGGCCACCCCAA | GGCTCTGCAGGGTCCACA | 21235 & 21236 |

| GeneName | Forward Primer | Reverse Primer | SEQ ID NOs | GeneName | Forward Primer | Reverse Primer | SEQ ID NOs |
|---|---|---|---|---|---|---|---|
| CFAP44 | AGCTAGCACGAGAGATGGGAGA | GGGAGAGGGGGTTGACGGA | 21873 & 21874 | CHCHD5 | AGTGCACATTCCTCCCACCCAA | TGCTCTGACAGTTGCCCACA | 21979 & 21980 |
| CFAP45 | AGAGAGTGGGCAGAAAGGAA | GAGCCCGAAGAATCCTCTCGA | 21875 & 21876 | CHCHD6 | CAGAGCTAAGACGCCGTGACA | AGTGGAGAATCTGGGCCTGCA | 21981 & 21982 |
| CFAP46 | TGTATGGGCTGCCGCACCAA | AGGTGGGGATGGGTTGGCAGA | 21877 & 21878 | CHCHD7 | CGGTAACACAGAGGCTGAGAGA | CCAGACATCTGGTGGAAGCA | 21983 & 21984 |
| CFAP47 | CCACACGAAGGTTCCCTGCCA | GAACTTCACCTCAGCCGGGA | 21879 & 21880 | CHD1 | GTAGCCCTGAAGAAGCAGCCA | GAGTTGGAGAGCGGTACTACCA | 21985 & 21986 |
| CFAP52 | AGGGAGGCCCTGAAGGAACACA | CTGAGACGCCACAAGGTCCCA | 21881 & 21882 | CHD1L | AGCGATCCGCTGAGCCA | CCAGACAGGAGACATGGAAGGA | 21987 & 21988 |
| CFAP53 | TGAAGCAGGTGTAGCAGCA | CGGTGGAAGCTTACTGGGGCA | 21883 & 21884 | CHD2 | TCCACCATGGGGAAGCGA | CTTCCGGAACGGTGGGGCA | 21989 & 21990 |
| CFAP54 | CAGATCAATCCGACACAGCAGA | CCAAGTGGAATGCAAGCCTGAA | 21885 & 21886 | CHD3 | GGGAGGAAGGGACGAAGGA | ACACAGGAGGTAACTGAGCCA | 21991 & 21992 |
| CFAP57 | ACACCACCAGCCTAGAGA | TTTGGCATCTGGGGAGACA | 21887 & 21888 | CHD4 | GGCCTTCCAGAAACGCCAA | CCAGGAGAAGCGCAACCA | 21993 & 21994 |
| CFAP58 | AGACAACAAGCCTCGAGACA | ATCATTGCCGCCAACAAGCTGA | 21889 & 21890 | CHD5 | GGGCTTCCAATGCCCGACA | CTCGAAGGTCCCGCACCA | 21995 & 21996 |
| CFAP61 | CCGTCCACTTCCCGCCCA | CGGGGGTGAGATGGGGCA | 21891 & 21892 | CHD6 | AGCACGTGGGAGCTAGAGGA | CCAGCTGGTACTTCCCGGA | 21997 & 21998 |
| CFAP65 | CAGCCGCAAGCTCCATGGA | TCAACGACCTCAATGCCCCA | 21893 & 21894 | CHD7 | GGGAGCGAGCAGAAGAAGGA | CAGCTGGAGCAGATGGAGA | 21999 & 22000 |
| CFAP69 | GACTGGTCTGCAGCACAGGA | GCCTCGCCACCTGTACCA | 21895 & 21896 | CHD8 | CCCTGAGTGGCCCAAGGA | TGGGACTGGAGAGTCACCA | 22001 & 22002 |
| CFAP70 | GAGCTCACAGAGGCTGAGGA | TCAGGCAGACAGAGCCA | 21897 & 21898 | CHD9 | GGGTCGGCTCACTGAGCA | CAATACGAGGTGCCAGCA | 22003 & 22004 |
| CCDC42B | ATTCAGAACACAGCAGCGGGAGA | TCCTCGATGTCCAGGGTGGGA | 21899 & 21900 | CHDH | GTGCACCTGTAAGATGGGCCA | CGTTCAGGTTGCCGCTGACCA | 22005 & 22006 |
| C9orf171 | CCCGTCAATCAACAGGAGA | CCGAGTGGAGAAGTGTCCAGGA | 21901 & 21902 | CHEK1 | ATGGGACCAACCCAGTGACA | AGACTCTGACACACCAGTGA | 22007 & 22008 |
| CFAP97 | GCCTTCAGTGCACCCGGGAA | TTGGGGATGATCAGCCGA | 21903 & 21904 | CHEK2 | CAGCAAGAGAGGCAGACCCA | CATGAAGGTACTGCACAGCCA | 22009 & 22010 |
| CFAP99 | ATCAGCGGGCAAGGAGGAA | CCCACCTCAAGGCTGCGGA | 21905 & 21906 | CHERP | CCACGACAGGGCCAGGAA | ACGAGCCTGAAGACTTGGAGGA | 22011 & 22012 |
| CFB | GAGTCCCTATGCTGACCCAA | GCAGACATCCACTACTCCCA | 21907 & 21908 | CHFR | CCCTCTGCAAGGAGCGA | CCCCAGTACAGGTGGCACA | 22013 & 22014 |
| CFC1 | CCCACGCTCACGGCGCA | AAGTCCCGGCCTTCCGCA | 21909 & 21910 | CHGA | AGGAGGAGGACAACCGGGACA | CAAGGCTGTCCTCCCGGGA | 22015 & 22016 |
| CFD | GGGACAGCTGCAAGGGTGA | CTGTCGATCCAGGGCCGCA | 21911 & 21912 | CHGB | AGGGAAGTGGCAGCAGCA | TCCACTGAGAGGAGGGTCGTA | 22017 & 22018 |
| CFDP1 | CAGAGCATTCCAGGCCAAGAA | ATTGAGGAAGCTTGGCCCA | 21913 & 21914 | CHI3L2 | GTCATGGGCATCCCACA | ATAATAGGCCAGGAAGCCTGA | 22019 & 22020 |
| CFH | AGGCGGGTGAGCAAGTGA | GGGCGGATTCACACAGGA | 21915 & 21916 | CHIA | TCCCAGTGGCCAGCGGGAA | TACGTGACTTCATTCACGCA | 22021 & 22022 |
| CFHR1 | AAGGATGGTTCACCAACACCAA | GGGCGGATTCACACAGGA | 21917 & 21918 | CHIC1 | CAGGGAAGGTGGCCCCAGA | GCAACCCAGTGTGCAACAGCA | 22023 & 22024 |
| CFHR2 | CATAACGTCGCACAGCAAGAAGGA | TGCATTTGGGAGGAGTGGACCA | 21919 & 21920 | CHIC2 | GCTGCTCAAGTACTCGCCGGA | AAAGGCAGCCACAAAGTAGCCA | 22025 & 22026 |
| CFHR3 | GGTGGTCACCAGGTATCCA | GGATGCATTCTGGGAGTGAGGA | 21921 & 21922 | CHID1 | GGGGCCAGGTACATCCAGACA | TAGAGACCCCAACGCCA | 22027 & 22028 |
| CFHR4 | TTCCAGCAGCTGCAGGACA | GCATGGGACCGTTGGTGACCA | 21923 & 21924 | CHIT1 | CAGCCCTCTGAACCTGAGCA | GAGGATTGGGATAGAGCCCA | 22029 & 22030 |
| CFHR5 | AAGGATGGTCACCAACACCGA | AGCTGCATATGGGAGGAGTGGA | 21925 & 21926 | CHKA | TTCAAGGGCTTGGGGAA | CCAGTCGGCCTTCGGGAA | 22031 & 22032 |
| CFI | GTAGACTGGATAACCGGGCCGA | GATGGAACGAGGCAGCTCA | 21927 & 21928 | CHKB | CTAGAGTCTACCCATCGCCA | TGTACTCGAAGTCCACAGCA | 22033 & 22034 |
| CFL1 | GGGCCAGAGTGTCGACGA | CATAGAGGGCATAGCGGCA | 21929 & 21930 | CHML | AAGCCACAGGAGGCCCA | GACTGAAGGGTCAGGCCCA | 22035 & 22036 |
| CFL2 | ACTGTAGAGGACCCCTACACA | GGTGCACTTCAGGAGCCCA | 21931 & 21932 | CHML | AGATTCTTCGGGAATCAGCAGA | GATTTGGAGGTGGAGGGCAGA | 22037 & 22038 |
| CFLAR | AAGCGAGGGCTGTGACA | GGCACTGCAGGTACAGGGA | 21933 & 21934 | CHMP1A | CGCAGGAGCCAGGTGGACA | CGGCCAACCTCCGTGACA | 22039 & 22040 |
| CFP | GATCACGAAGGCTGCAGCGA | GCAAGGTCGACAGAGCCCA | 21935 & 21936 | CHMP1B | CACTCCCCAGACCAAGTGTGA | AGTTCATCCTGCCCACTGCA | 22041 & 22042 |
| CFTR | GCCTTCTGGGAGGAGGGA | CTGCTCCAGTGGATCCAGCA | 21937 & 21938 | CHMP2A | TGAAGTTGCCCCAGATCCAGA | TTTTCCACCAGCAGGCCA | 22043 & 22044 |
| CGA | GATGTGCAGGATTGCCCA | TTGGACCTTAGTGGAGTTGGGA | 21939 & 21940 | CHMP2B | TGACGAAGAAAGAAAGCCAGGA | GCAGATGGTAAGCTTCGAGCA | 22045 & 22046 |
| CGB5 | CTCAAAGGGCCCTCCCCCA | GGGAGAGAGGCTGCGGGGTGTCGA | 21941 & 21942 | RNF103-CHMP3 | ATTCAGAGATTCAGGGCACCA | GGCAGCCATCGCTCCTGGA | 22047 & 22048 |
| CGGBP1 | TTCAGTGCAACAGTACTGCGCA | AAGCACGGACTGTCTCCAGA | 21943 & 21944 | CHMP4A | GGCACAAACTGACGGGACA | GGCAGCAAGCTCCATGGTA | 22049 & 22050 |
| CGN | GATCGGGGAGGACTTAAGCA | AAGTCGGCTCACTTGCATCACCA | 21945 & 21946 | CHMP4B | CGCAAGAAGCACGGCACCAA | CAGGGCCTCCGCTGGAA | 22051 & 22052 |
| CGN11 | GGATGCTGAAGGCTGGAGGA | TCATCATCCAGCAGCCCATCCA | 21947 & 21948 | CHMP4C | GCAACAGGATATCGCCAAGA | CGGGATGCAGCTGACAGTTGGA | 22053 & 22054 |
| CGREF1 | GGATCTGAGCCGGAGGA | CCCGGTTGGGTAGGAGA | 21949 & 21950 | CHMP5 | CAGCGGGACAATCTTGCCCA | CTGGGGTGCCATAACTGCCA | 22055 & 22056 |
| CGRRF1 | ATGGAAGAGAACAGGAAGAAGGA | CTGAACAAACTGCCTGCACA | 21951 & 21952 | CHMP6 | TAGACGAGCTCCTGGCAGGA | TCTCAGGAAGGGGCTCGGA | 22057 & 22058 |
| CH25H | GCCCTCCTGCCCAAGGAA | TGCGGTACAGCCAGGGCA | 21953 & 21954 | CHMP7 | AGAGCTCTGTGACACCCAGGA | ATTGCCGGGGTTGTCAGGCA | 22059 & 22060 |
| CHAC1 | CAAGATGCTCTGACCAACAA | CATGAAGTCGCCAGGGCA | 21955 & 21956 | CHN1 | TCAGGAGGTGAAATGTGCAGA | TCACGAGGCGTGTAAGGTCA | 22061 & 22062 |
| CHAC2 | AAAAAGGAGGCTACAGAACCACA | TCCACTTGGACCAGCTGCA | 21957 & 21958 | CHN2 | CTGCCCTCACACACAACGACA | ATCCACAGTCTGAGCACCGGA | 22063 & 22064 |
| CHAD | CCCTTGCGACAGCCTGGAGA | GAACTTGGCAGGTGAGGCA | 21959 & 21960 | CHODL | TGAGGGAGGAGTCCTTCCTCA | TGGTAGAGATCTGGGCAGGGA | 22065 & 22066 |
| CHADL | AAGCTGCACCTGGACTGGAGAA | GAAGAGTGCTGCCAGCGA | 21961 & 21962 | CHORDC1 | CTGGCATCAGACTTGGAGGTGA | TCAAGGCTTGCCACTGCA | 22067 & 22068 |
| CHAF1A | GCTTCCAGGCAGCACACGGA | TCCGGAAGCGGCCTCCACA | 21963 & 21964 | CHP1 | GCCTTCACGCCGGTTCACCA | CATTGATGATCCGGTCCCCA | 22069 & 22070 |
| CHAF1B | AGCAAGACAACACCCCGGAGA | CTCTCGGGGGACTTGCCCTGA | 21965 & 21966 | CHP2 | GATGGAGCCAGGGAGTTGGA | CTGTCACTGTACCCCAACCA | 22071 & 22072 |
| CHAMP1 | TCCCAAACCCCAGAAGCA | TGGGAGATGCAGTCTGGGGA | 21967 & 21968 | CHPF | AGTGTTGCAGAAGAGCCGA | GGAAGTCTCGAGAGCA | 22073 & 22074 |
| CHAT | GCTACAACCCCACGCAGA | TCTCAGTAGGCGGCAGCA | 21969 & 21970 | CHPF2 | CAGGCAGGAGGAAGAGGAGA | TGCAGTCTCCAGGGAGA | 22075 & 22076 |
| CHCHD1 | CTAGCTAACCGCTCGGGGA | CACAATCGAGGAAGCCCTGGA | 21971 & 21972 | CHPT1 | GATCACTATAGCAGGCACCA | AAGACCTGGCCCCAAAAAGACA | 22077 & 22078 |
| CHCHD10 | GCGCTACGAGATCAGGCA | CAGGGAGCTCAGACCATGGTA | 21973 & 21974 | CHRAC1 | AAAGACAAGGGGCGGGGAGCA | GTGACCTTGGCCGTGAGCA | 22079 & 22080 |
| CHCHD3 | AGCTGCTGAAGAGTGGAAGCA | CTGGGTGGCCAGAGCGGA | 21975 & 21976 | CHRD | GGCACCTGGCAAAAGGCA | GGGAGACCAGGCACCA | 22081 & 22082 |
| CHCHD4 | AGCCGGTCCCTGTGGAGAACA | GCATTCCTGCATGCCCGGAA | 21977 & 21978 | CHRDL1 | GCCGGGTATGCAGAGGAGA | AAGCGGGACAAGAGACTTCCA | 22083 & 22084 |

| GeneName | Forward Primer | Reverse Primer | SEQ ID NOs | | GeneName | Forward Primer | Reverse Primer | SEQ ID NOs |
|---|---|---|---|---|---|---|---|---|
| CMC4 | GGATCCGTGCCAGAAGCA | ACTGAGCACAACACTTACGCA | 22509 & 22510 | | CNOT9 | TTGCCAATTGCATCCTCCAGA | TGCTTCAGCAGACGGGCA | 22615 & 22616 |
| CMIP | GTAACCAGTGCCTGCGCCGA | TCTTCATGGAGCTCAGGGCCA | 22511 & 22512 | | CNP | AGGCCTTCACGCTGACCA | CGTCAGCTGCACAGCCGA | 22617 & 22618 |
| CMKLR1 | ACAGCTTGCATGAACCCCA | TAGAGCATTGACCAGGCGA | 22513 & 22514 | | CNPPD1 | GCCTCACTGACTCCTCCACCA | CAGGCATGGCAGGTTGGGGA | 22619 & 22620 |
| CMPK1 | CAGAGGAAATGGATCAGACAA | CGAAAGATACATCTGCCTTCCCA | 22515 & 22516 | | CNPY1 | ACTTATCGCCCAGGAGACACA | CAGCAGAACGGCAGCTCCTAGA | 22621 & 22622 |
| CMPK2 | GAAGACCAGGGAAGAAGCAGA | AGGGGCTGGCATCAACCA | 22517 & 22518 | | CNPY2 | GATATGTGACCGGATGAAGGA | CCGGCCACTACACGTACGTA | 22623 & 22624 |
| CMSS1 | CAGCATTCAGAGGAGGACGGCA | TCCCGGAGTTCTACACCCA | 22519 & 22520 | | CNPY3 | TAGCCTGCACAAGGAGAGGA | TCAAACTCTTCCACAGCACA | 22625 & 22626 |
| CMTM2 | GCTCTTGGGGCACCGCTGAGA | TAAAGCAAAAACTCCAGCCGCA | 22521 & 22522 | | CNPY4 | GGATGTTGAAGGAGGAGGACGA | GCACCTGCCCCAGCTCCA | 22627 & 22628 |
| CMTM3 | CTCACAGCGCTCTGCTGGA | AACACCCAGGGCTTTGGA | 22523 & 22524 | | CNR1 | CTCTGGAAGGTCTACAGCCA | TGCAAGCAGGGCCCCA | 22629 & 22630 |
| CMTM4 | GCGACTGCGGCATATGCA | CGCTGGATCTCAGGGCGA | 22525 & 22526 | | CNR2 | TACGCTCAGTGACCAGGTCA | CAGGCAGTGATGGCAGA | 22631 & 22632 |
| CMTM5 | CAGGGCTTCGCGGTGGACAA | GAGATGAGGCCGTGAAGCA | 22527 & 22528 | | CNRIP1 | AACGGCAACCATCCAGA | GGGGCTTCCCACTGGCA | 22633 & 22634 |
| CMTM6 | GGAGCGGTGCAACAGCCGCA | AGCAGAGACAGCAACCAGCTGCA | 22529 & 22530 | | CNST | TGGAGCCCTGGGGTGTGGA | CTCGGAGGACTTGGGTGTTGGA | 22635 & 22636 |
| CMTM7 | GCCCTGCTGAAAGTGGGGCAA | AACCAAAGATCGACAGGGGCCA | 22531 & 22532 | | CNTD1 | CCCAGTCAGCTGCAAGGGGAA | TCCCACTCCGTGAGTCAGGA | 22637 & 22638 |
| CMTM8 | CGCCAGCTCCTTCGCAGAGA | ATGAGGAAGAAGACGGTGGAGGA | 22533 & 22534 | | CNTF | AGGCAGAGCGACTCCAAGAGA | AAAGGCAGGCAGCTTGGAGAAGA | 22639 & 22640 |
| CMTR1 | GCAGATCATTGCCCA | TGGGAGTCATGCACACGA | 22535 & 22536 | | CNTFR | AGACACCAGACCAGCAGA | TGATAGGGGACGGCTGACA | 22641 & 22642 |
| CMTR2 | CCCCTGAGGACCTGCA | AAGCAGGCCCCCTTAAGGA | 22537 & 22538 | | CNTN1 | TGGGTGGGTGAAGAAGGGTCA | GCAGCTGCGTCCGGCTCA | 22643 & 22644 |
| CMYA5 | GACGTCAGAGTGGCTACCCA | TCTTCCTCCGGGAAGGACA | 22539 & 22540 | | CNTN2 | CCGCGTGTGAGCAACCAA | CTACATCTGAAGGAGCCACA | 22645 & 22646 |
| CMBD2 | CTGCTCACTGGAAGCACCCTA | AGTTCTGAGCTTAGGCCAGGA | 22541 & 22542 | | CNTN3 | CTCAGGACTCAGCGGAGGA | GAAGGACAGGTAGCGCGA | 22647 & 22648 |
| CNBP | CCCAAGAGAGAGCGAGGACAA | GCATGGTGCAGTCAGGA | 22543 & 22544 | | CNTN4 | GGAGAACAGCAGGTAGCACCA | CACCATCAGAACGTAGCACCA | 22649 & 22650 |
| CNDP1 | CACCCAGTATCTCGCACAA | CCCAGCGGAATTAGCACCA | 22545 & 22546 | | CNTN5 | GAGGAGATGGCAGCAGA | TTCGAAGTGGAAGCCCA | 22651 & 22652 |
| CNDP2 | GAGCCAGACTTGACCAGGGA | CTGACCCCACAGGCAGCA | 22547 & 22548 | | CNTN6 | CAGTTCCGAAGACAGCACCCA | GCAGCTGCGTCCGGTCA | 22653 & 22654 |
| CNEP1R1 | TGGAGCAGGCGGAAGATCTCA | TAACCAGTTCCAGGCACCA | 22549 & 22550 | | CNTNAP1 | ATGAACCTCAACTGCCCCAA | GTATAAGACCTCATAGCCCAGCA | 22655 & 22656 |
| CNFN | CCTGCCCGCTATCTCCGACGA | CAGAGGGCGCAGGGCAGA | 22551 & 22552 | | CNTNAP2 | TGAGCCGGCCAGTGCA | CGGGACAGGCCGACCA | 22657 & 22658 |
| CNGA1 | CTGCAAACCAGGTTTGCCCGA | TTCCGCTCCAGGTCCCTCA | 22553 & 22554 | | CNTNAP3 | CGCTGGAGCTCTACAGCCA | GCTGGTGCAATGGCCCGA | 22659 & 22660 |
| CNGA2 | CAACTACATCCACCCTGA | CAGCAGGCGGTTGAAGCCCA | 22555 & 22556 | | CNTNAP4 | GGTGCACACAAGCAGGTGCA | GGAGAAAGGGACCTCCCAGA | 22661 & 22662 |
| CNGA3 | GCTGAAGGCTGGAATCGCCA | GGGTCGCAGCTTCAGCACCA | 22557 & 22558 | | CNTNAP5 | CACCCACCCACTTCAACGAGA | TCCACCCACGAAGAGCTGA | 22663 & 22664 |
| CNGA4 | CTGAGCTGGAGTCCAGCGCA | TCCTCAGGTCACCCTCGTCA | 22559 & 22560 | | CNTRL | GATGAGCGGGAACCACTTCACACA | GGAACCGGGTCATGATGACCGA | 22665 & 22666 |
| CNGB1 | GGCGCATGCTGAGAAGCA | TCCTGTCATAGCGGAGGGA | 22561 & 22562 | | CNTRO8 | AAAGTGGGCAGAGACAGGGGCA | GGAAGACTCCAGCTGAGACAGA | 22667 & 22668 |
| CNGB3 | GAAGCACTGGACACAGCTGA | CTCCGCCTCAGCAGAAGCA | 22563 & 22564 | | COA1 | GTATTCCACCGCCTCGTCCACA | CCGAGCCTGGTAGCCTCTGA | 22669 & 22670 |
| CMH1 | CTCCCAGAGTACCTCATCCA | CATGATGACTTGCAGGCCGA | 22565 & 22566 | | COA3 | AGCCATCCCGAGGGCACAGGAA | TCGTCAAGGTGCCACCTCTGA | 22671 & 22672 |
| CNH2 | AGGAAGCTGGTCCCCAGA | CGTCATGCCCGCTGCGA | 22567 & 22568 | | COA4 | GAGAGGCCCGGTTCGCTCA | CCGATGCCTAGGCCGGTCA | 22673 & 22674 |
| CNH3 | ATGCGAGGGAACGGTTGAGGAA | CGCCTTGGTAGCCCA | 22569 & 22570 | | COA5 | AGAAAGACGATGAGGAGGAGGA | GTGGTGGCCATTGCCGCCA | 22675 & 22676 |
| CNH4 | GGAAGACCAAATGCAAGGA | ACTTGCCCGCCAAGCCCA | 22571 & 22572 | | COA6 | AGCTGATGCTAGGCCCCCAGA | GTAGAGCGGGCAGACTGAA | 22677 & 22678 |
| CNKSR1 | AGTGGCACAGGCTGAAGGGCA | AAGGGCCTTCATGTCAGGGGA | 22573 & 22574 | | COA7 | CTTGAGCCAAGGGCGGGCGA | GAAGCTCTCTGCCCGCCA | 22679 & 22680 |
| CNKSR2 | CAGACTTCGCCCCTGAAGGA | TTCGCTCGGGTGATCATGAAGCA | 22575 & 22576 | | COASY | TACCACGAGAAGGACCCGGA | TCCAGGCTTCTCACAGCCA | 22681 & 22682 |
| CNKSR3 | CTTCCACAGCACGCCACGA | TGAGCGCGTAAACCAGCTGA | 22577 & 22578 | | COASY | AGCTGGCCGCAGGAGAGA | GCCAGCCGCCTTCAAGCA | 22683 & 22684 |
| LECT1 | CGACCCTAGACTGGGATCACGA | CATGATGACTTGCAGGCCGA | 22579 & 22580 | | COBL | GCCATTGCCAAGGCGCATAGGA | AGTGACAGGTGGTGCAGCCA | 22685 & 22686 |
| CNN1 | CACCAACAAGGAGCCAGGCA | CGTCATGCCCGCTGCGA | 22581 & 22582 | | COBL1 | GTGCCCACGACCACTATCTA | TGTTGGCTGGAGGTTGGACCA | 22687 & 22688 |
| CNN2 | CTCGACCATCAGCTGCCA | CGCCCTGGTGTAGCCCA | 22583 & 22584 | | COCH | GATGTCCAAGGCCTCGA | CCAGAGGTGCCCAAGCCA | 22689 & 22690 |
| CNN3 | AGGCAGGGATGTTAGCACCA | ACTTGCCCGCCAAGCCCA | 22585 & 22586 | | COG1 | CTGACAAGCTTCAGGAGCA | GTTCGCTGCACCAGGCTGA | 22691 & 22692 |
| CNNM1 | CTCAGTTCCATCCTGAGCGA | AAGGCCTTCATGTCAGGGGA | 22587 & 22588 | | COG2 | CTGGACAAGGTTCAGGAGCA | GGAGGGCACACAGGCTGA | 22693 & 22694 |
| CNNM2 | GGTCACGGACCGATCCCTACAACGA | TTCGCTCGGGTGATCATGAAGCA | 22589 & 22590 | | COG3 | CAATCCTAGACACCAGACCACA | CTCTGACGCTCCAAGTAAGGA | 22695 & 22696 |
| CNNM3 | CCTGAGACAGCGGCTGCA | AGGGCTGCCCTAAACCAGCTGA | 22591 & 22592 | | COG4 | CAGCACAGCCATCAACGACGGA | ACTTTCTCCAACTCGACCGGA | 22697 & 22698 |
| CNNM4 | CACTCGGCAGCAGTACCAGA | TCTCGTCACCACAGGGA | 22593 & 22594 | | COG6 | TCACTGACAGATGTCTTGGA | TCTGGGGCTGACAGATAACGA | 22699 & 22700 |
| CNOT1 | GCCAGCCATGAAGCAA | CGCAGCAGAAGGTTCAGCA | 22595 & 22596 | | COG7 | TAACCAGCAGGCCCACCA | GTGAGACTTAAAGGCGGGCA | 22701 & 22702 |
| CNOT10 | CCCCTCAGTGCTACCCA | TTGAAGCCGCCTGGTGGA | 22597 & 22598 | | COG8 | GAAGTGCCGCAGTCATGCA | GAAGACGTCCAGTCGCCGCA | 22703 & 22704 |
| CNOT11 | CACCCCAGCCAAACTTCCTGA | GACGCACCAACCGATTCTGCA | 22599 & 22600 | | COIL | GTGCAGAGTCAGAGACCAA | TGAGCCAGAAGCGCTCCA | 22705 & 22706 |
| CNOT2 | CAGCAGAGACAGACCCAGGAA | AAGGTGAAGATGCCCAGGGTGA | 22601 & 22602 | | COL10A1 | ATGGAGAGGCTGGCCGA | GCTATGCCAGCTGGGCCA | 22707 & 22708 |
| CNOT3 | AACGCTCCACCTGACCGA | GAGTCAGGGCCGGTGAGGCA | 22603 & 22604 | | COL11A1 | GCAGCCCAAGGTGGACCA | GAAGGTGGACCTAAGGGGA | 22709 & 22710 |
| CNOT4 | GAACCACACAGCCAAACCCA | TGTGAGGGCCTGAAGGGA | 22605 & 22606 | | COL11A2 | GGCTGCCAGCACAGCCAA | TGAAGCAGACAGGCCCCA | 22711 & 22712 |
| CNOT6 | CTCAGCTGAACACCTTAGGCA | AGGAAAGGCAGTAAGAGCTCCA | 22607 & 22608 | | COL12A1 | CAGAAGCCCCTACAGAGCCA | GTCCCAATGCTCCAGGA | 22713 & 22714 |
| CNOT6L | ATCTCGCAGTTCATCCAGAGCA | CATATAGCTGCCGGGTAGCGTA | 22609 & 22610 | | COL13A1 | GGCTCCTCCAGGAGATCCGGA | TGGAGGGCCTGGCAGTCCAA | 22715 & 22716 |
| CNOT7 | GCAAGGAGAATACCTCCAGGA | CCTTCACGAGGACCACTCCA | 22611 & 22612 | | COL14A1 | CCAGGCGTTGGAACCCAA | CCAGGCTGGCCAGAAGGA | 22717 & 22718 |
| CNOT8 | ACCAGGCAGGCTCAGACTCA | TGGGCAGAGTCCACATCCTCA | 22613 & 22614 | | COL15A1 | CGGCAGGGAGCAGAAGCAGA | TCCTGAGGGACCTCTCAGCA | 22719 & 22720 |

| GeneName | Forward Primer | Reverse Primer | SEQ ID NOs | GeneName | Forward Primer | Reverse Primer | SEQ ID NOs |
| --- | --- | --- | --- | --- | --- | --- | --- |
| COX6A1 | CCGGGGTGGCAGTCAGCA | GGAGATGGGGGTAGGCGA | 22933 & 22934 | CPT1C | GGGCAGCACATTGAGGACGCA | CCCAGTCTGGCGGGAGAGA | 23039 & 23040 |
| COX6A2 | GCCAGGGCTGCCAAAGGA | TGAAGGTGCAGAGGGCCA | 22935 & 22936 | CPT2 | CCATGGCCAGCTGACCAA | GTCCAGGTAGAGCTCAGGCA | 23041 & 23042 |
| COX6B1 | CTGCTGGCCAGAACTACCTGGA | CTGGTACACACGCTGGTACCA | 22937 & 22938 | CPTP | GTGCCCACGGAGCTGAGCAA | CCTCGGGGCTGGTACGCA | 23043 & 23044 |
| COX6B2 | CCAGCCAGAACCAGATCCGTA | CCAGCTCTCCACCCAGCTGA | 22939 & 22940 | CPVL | GGGCATGGACTGGAAAGGA | GCCGGATGTAACCAGCCA | 23045 & 23046 |
| COX6C | AAGTTTGCCAAAACCTGGA | TCTTTGATCAGCCACACGA | 22941 & 22942 | CPXM1 | GCAGGAGTGTGTGAGGGACA | CGGGACTGGCAGTCACCA | 23047 & 23048 |
| COX7A1 | AGAACCGAGTGCGCGAGA | CCTGGGAAGGAGGCCCA | 22943 & 22944 | CPXM2 | GCTGCCGAGACCAGAGCA | GGCATAGGAGTAGGCCAGCCA | 23049 & 23050 |
| COX7A2 | TCGTCAGATTGGGCGAGAGGA | AGGGCATCAGCTACCCA | 22945 & 22946 | CPZ | ACAGCTTCAGGGAGGCA | GGTGCACCGTCTCAGGA | 23051 & 23052 |
| COX7A2L | ACGCAGAGAGTTGGCAGGAGCA | CCATAGTGTTCGGTAAAGGA | 22947 & 22948 | CR1 | ATGTGACCCCACCCAGA | AGTTCACAGCGAGGGGCA | 23053 & 23054 |
| COX7B | TGGCAAGGCAGAGCCACCAGA | GCCAACAGGGGACAGGTTCCA | 22949 & 22950 | CR1L | CCCACCCAGACAGAGGGA | AGTTCACAGGCACTGACAGCA | 23055 & 23056 |
| COX8A | GCCGCGCGCCAAGATCCA | TAGGTCTCCAGGTGTGACAGGA | 22951 & 22952 | CR2 | CCCTGGGCCAGAAAGAGGA | CATGTGAGCACTGACAGCA | 23057 & 23058 |
| COX8C | GTGCTAGGGCACTCAACCTGAAGCA | GTTGCATCAACTCAACTAGGCA | 22953 & 22954 | CRABP1 | ACGGACCGACCAAGTGCAGGA | GGCACGCTCAGCGGGTCCA | 23059 & 23060 |
| CP | CGCGGAAATGAGGGCCGA | GGCCACATGTGGAGCGTA | 22955 & 22956 | CRABP2 | CCCAAGACCTCGTGGACCA | GACGTAGACCCTGGTGCACA | 23061 & 23062 |
| CPA1 | GGACCTACAGCCAGGGCA | TGATGGTCAGAAGCGCCA | 22957 & 22958 | CRACR2A | AGCAGCTCACCCAGAAGACAGA | CTCCAGGAAGTCCGTCCA | 23063 & 23064 |
| CPA2 | CAAGCCAGTGGAGGAAGCA | CCTCGGCTGTGGCAGGA | 22959 & 22960 | CRACR2B | CATCACCAAGCACGACCTGCA | GAACTCCTGGGCGGTGAGGA | 23065 & 23066 |
| CPA3 | CTGCCACCTAACCATGAAGGA | GCCCAGGTCATAAGCCA | 22961 & 22962 | CRADD | GGATCCCTGCACATCCTCA | GGCCTCCACCACTGGA | 23067 & 23068 |
| CPA5 | ACTGGGCCTATGACAGTGGCA | CCATGATGTCCGAAGCGCCA | 22963 & 22964 | CRAMP1L | TCCCAGAGAAGAGCCGGAA | GGGCCAGGTCATTGAACCGA | 23069 & 23070 |
| CPA6 | CTGGGCAGACGATCACGA | CATGCACGTTAAACACAGGCA | 22965 & 22966 | CRAT | TGGACACCTTCCACGCA | CTGTTGTAGGCCGACAGGGA | 23071 & 23072 |
| CPAMD8 | AGTCGAGGGTTCCCGAGAGA | ATGCAGCCACCTTGGTGCACA | 22967 & 22968 | CRB2 | CATGGGACTGGGAAGTCAGCA | CCCACCTCCTACAGGATAAGGA | 23073 & 23074 |
| CPB1 | CTCACTGCACGGCACCAA | CCTCGCAGGTAGCCCGGA | 22969 & 22970 | CRB3 | GTCCAGAAGCCATCACTGCTA | CCCGAAGCTTCCGCACCA | 23075 & 23076 |
| CPB2 | GAGGTGGGGACGATTGGA | TGTAACGCTCCGGCAGCA | 22971 & 22972 | CRBN | CACCAGTCTGCCGACATCACA | AATGTCTGTCCGGGAATCAGGA | 23077 & 23078 |
| CPD | CCTGGGCACAAGGAAGGGA | CTGCCACAAGGAAGGGA | 22973 & 22974 | CRCP | TGCTGAACCACCGCCTGTGA | CCTCTGGCTTCAGCTCCAGCA | 23079 & 23080 |
| CPE | GAGGAGACCTTGTGGCAA | AGAGTATGCCCGGGCAA | 22975 & 22976 | CRCT1 | GCTGCTGCTTCCCAAGGAGA | CAGCCGGAGCAGCATCCTGA | 23081 & 23082 |
| CPEB1 | GGCTTGACCCCAGCAGGA | CAATCCGGCATACACCA | 22977 & 22978 | CREB1 | CCAGCAGAGTGGGAGATGCA | TAGAGTTACGGTGGGAGCAGA | 23083 & 23084 |
| CPEB2 | GATGAATGCCAGGGCGCA | TATGGAACTCACGTCCAGCA | 22979 & 22980 | CREB3 | CTCCTTGACACAAGGGGGGA | GTACAGTGTCAGCCGTCCA | 23085 & 23086 |
| CPEB3 | CACACGCTGTGTGTGGAA | CGGAACGGACGTGACGA | 22981 & 22982 | CREB3L1 | GTTCTCCTCCGGCTCCAGA | CCCATAAGCGTGCCCGTCA | 23087 & 23088 |
| CPEB4 | GAATGGGGAAAGAGTGGAACGA | CCAATCCACAATCAGAGGGGCCA | 22983 & 22984 | CREB3L2 | ACCCACAGCCCCTCCAGA | GGGGATGGGATAGCCCTCA | 23089 & 23090 |
| CPLX1 | GCATCCGAGACAAGTACGGCA | CTCCACCTGCCTCCCGCA | 22985 & 22986 | CREB3L3 | GTACAGGAGAGCCGAGTGCTGAA | ACATGCGAGTCTCCAGGCCA | 23091 & 23092 |
| CPLX2 | GGACAAAGCACGTCTTGGAGCA | TTGAGCACCGTGTCCAGGA | 22987 & 22988 | CREB3L4 | TGGTAGCTCAGCTCCGCCA | AAGCTGGGCAGGATGATGAAGA | 23093 & 23094 |
| CPLX3 | ATGGCAGGTGGAGACGTGGA | AGTGAGGGTTGCAAGCCCA | 22989 & 22990 | CREB5 | CCAGCTTGCTCCAGCAA | TACCACCTGCTGACCGA | 23095 & 23096 |
| CPM | GAAGCCGTCAAAAGCCTGA | CATGGAGGTTTGCAGAGAGGA | 22991 & 22992 | CREBBP | CAGATCAGCAGCCCCAA | CACCGGTTGCTAGAAGGAGGA | 23097 & 23098 |
| CPN1 | GACCACCTGGAATCCACGA | TCCGGAACTCCTCGCACAGA | 22993 & 22994 | CREBL2 | CAGGAGGAGGAAGAGCA | CCAGCACAATAGCCGAGGCA | 23099 & 23100 |
| CPN2 | CCGGACGAAAGCAAGGCA | GAGCTGAGATCCACCAGGCA | 22995 & 22996 | CREBRF | GTGGTGCAGTGGGCAAAGAGACA | TCTCCTGCGTCAAGTGACCCA | 23101 & 23102 |
| CPNE1 | AGGCTGCACATCAGGGGA | CAAAGTCAGCACCACCACCA | 22997 & 22998 | CREB2F | TGATGGGGCTGAGAGTTCGA | GCAGTCCCALGCGCGCTCA | 23103 & 23104 |
| CPNE2 | CACAACAGGCAGCGGCCA | GGAACTCAGCCAGCGCA | 22999 & 23000 | CREG1 | CACCATCTCCACGCTGGA | GCAGTTGCTCACGGAGA | 23105 & 23106 |
| CPNE3 | ATAATGGGAGGATGTCAGCTGA | TGAGGAGGTATCTGAGCCGCA | 23001 & 23002 | CRELD1 | GCTGCTCCTAAGGGCGA | GATGAAGCCCTCCAGCACA | 23107 & 23108 |
| CPNE4 | TATCACAGACATGGCCGACA | AGAATCCCATCATCACCGTCCA | 23003 & 23004 | CRELD2 | ATCTGCACAGCTGTGACGA | GCCGCACACTCGTCCACA | 23109 & 23110 |
| CPNE5 | CGCAGCCTGCGCACTGTGA | AGCAGCACCGAGTACTGGGA | 23005 & 23006 | CREM | GAAGCAAACAGGAAACTCATGGAGA | TCAAGCACAGCCACACGA | 23111 & 23112 |
| CPNE6 | TCGTTGCCCCAGATCCA | AGTCAGCACCCTGCCTGA | 23007 & 23008 | CRH | CACAGCAACAGGAAACTCATGGAGA | AGAGCGCTATGGTACAGA | 23113 & 23114 |
| CPNE7 | GCAACGCCGACTTCACCGACA | CTCCACCACCTGCTTCGGGA | 23009 & 23010 | CRHBP | CCTGGTAGTTCCACACGTGCA | CTCGCAACCTGCTGCAGGA | 23115 & 23116 |
| CPNE8 | TGCTCAGCCCACTTCCCTCA | AAGCCTCCATGAACCCCTGA | 23011 & 23012 | CRHR1 | GTCCGCATCTCATGACCAA | GTAGATGAAGACGACCGGGA | 23117 & 23118 |
| CPNE9 | GGACTTCACTGGGAGGGCCA | TCTCAGGCAAGGAGGCCGA | 23013 & 23014 | CRHR2 | CCAAAGGCCAAGGCTCTGA | TGCAGGGACACAGGGACGGA | 23119 & 23120 |
| CPO | GAAGCTCAGATCAGTGGCA | CCCAGACGATAGTGGCA | 23015 & 23016 | CRIM1 | CAGAACCCTCACGCACCCA | CAGAAGGGCAGGACTTCAGAGA | 23121 & 23122 |
| CPOX | GTGACCAGCATAGGTCCAGA | AAGGAACTACAGCCCTGGCA | 23017 & 23018 | CRIP1 | GCCCTTGCCTGCAAGTGCGAGA | CGCCAAAGCCTTTAGGCCCA | 23123 & 23124 |
| CPQ | CAGGGCCATCATGAGGGA | CTGGCTTCCAGGCACTCA | 23019 & 23020 | CRIP2 | GAGCGCTGCGGGAAGACA | CCCTTGGGTCCAAGAGGA | 23125 & 23126 |
| CPS1 | GCTGAAGGTGCCTCAACAAGCA | TAGGAAGGCCTCAACAAGCA | 23021 & 23022 | CRIP3 | TGGCACCGACCGTGTCTGA | CAGGTAGCCGTAGCAGGGGA | 23127 & 23128 |
| CPSF1 | ACCACCATGCTGCCACACCA | GCGGTTGAGCAGCTCCCCA | 23023 & 23024 | CRIPAK | GCACACAGCCACAAAGCCA | GCCACACTCCTGGAGGCA | 23129 & 23130 |
| CPSF2 | TGAAGGACGCTTCGATGGGGA | TCTTTCCACCAAAGGCGGA | 23025 & 23026 | CRISP1 | GGCCAACAAGGATCACCTGA | GGCAGGCTTCACATGGA | 23131 & 23132 |
| CPSF3 | AGGGTCACAGTTGGACGGGAA | TCTCGTGCAGCCAGCTCCA | 23027 & 23028 | CRISP2 | GGTGGGCAACAAGTGCA | CAGTAGGCAATTCACCAGCCTA | 23133 & 23134 |
| CPSF4 | GAGATAGGCCATGGCAGCCA | TTGCATAGGCCACCAGCCA | 23029 & 23030 | CRISP3 | GCCAAAGACTCCCAACGA | TAGCCAATTACCACCAGGA | 23135 & 23136 |
| CPSF6 | CCAGCTCCGCATGTGAACCCA | TCATATTGGTGGAGGTCCGCCA | 23031 & 23032 | CRISPLD1 | CATGACACACCCATGTCCGGACA | TGCAGGGACACAGCGACCGGGA | 23137 & 23138 |
| CPSF7 | GGCCAGGTCAGATTGGCA | TCATCATTGGCAACCCAGGA | 23033 & 23034 | CRISPLD2 | CGTGCAGTCCTCCAGCAA | AAGGGCGATAGGGCCA | 23139 & 23140 |
| CPT1A | GCCCAGAGCAGAAGGTGACGA | TAAAGGCAGAAGAGGTGACGA | 23035 & 23036 | CRK | GCGAGCAGGAAGAGGGA | GGTTGGGCATAGGGCCA | 23141 & 23142 |
| CPT1B | CCTGTACCAGCGAGTCCACA | GAGACGCCAGGGTTCCGAGA | 23037 & 23038 | CRKL | CCACACGGGAAAGCATGGAA | CCCCAGGAGAACCGGAA | 23143 & 23144 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| CRLF1 | CCGCTACCGACTTGCAGGACA | TGCAGCGGCACTTGCACGA | 23145 & 23146 | CSMD1 | CGGCACGCGGATGTGAGA | GTGCTCAGATCCCCTGTGA | 23251 & 23252 |
| CRLF2 | CACCAACGACTCCCAAACCAA | GTATCTCAAAGAGCCCGGGGA | 23147 & 23148 | CSMD2 | AAGTTCTCCCAGCCACACA | GCCCTCCAGGAAGAAGCCA | 23253 & 23254 |
| CRLF3 | GATATGACTCTCTGCACGCGGA | TCAAACGTGCACAGTGGACCCA | 23149 & 23150 | CSMD3 | CGCAAAGGGGAAAGCCGA | GCGGCCACATTTAGCGCA | 23255 & 23256 |
| CRLS1 | CCAACACCAGAACACTTGCCA | ACCTGAACAGTCTTCCGGCCA | 23151 & 23152 | CSNK1S1 | CTTTCCAGCAGTCAACCAA | CATGAGCAGTGGGATTGGAGA | 23257 & 23258 |
| CRMP1 | CACCTGTACCAGCGCGTCAA | CTGAAGGAGCGGGAGTTGCA | 23153 & 23154 | CSN2 | CAGCAGGTCCCTCAGCCTA | CTCTGAGGGTAGGGCACCA | 23259 & 23260 |
| CRNKL1 | TGAGGAGCAAGCCTGGCA | CATCAGGGTGCACGAGGA | 23155 & 23156 | CSN3 | GTAGTTAGGGCCACATGCCCAA | GGTTTGGGCGACGTACCACA | 23261 & 23262 |
| CRNN | GGAGGGGCTAGGAGAACAGGGA | TCACAGTCGCCTTGGGGTGA | 23157 & 23158 | CSNK1A1 | TCTGGGACCTAGCCTCGAA | ACAGTGACGCCCAATACCCA | 23263 & 23264 |
| CROCC | TCAACAGCACCCGGGACA | CTGCAGTTCCAGGTCAGCCA | 23159 & 23160 | CSNK1A1L | GGACGTAGCAGTGAAGCTGGA | GCTGGGTCCCAGAAGGTCA | 23265 & 23266 |
| CROCC2 | GAGACAGCTCGCTCTCGGCA | TTCGGAGGCCCCACATGCA | 23161 & 23162 | CSNK1D | GTCTCCGGCATGGAGAGAGA | GTGAGGTGGACATGCGAGA | 23267 & 23268 |
| CRP | CATCTTGGGGCAGGAGCA | GGACTGAAGGGCCCGCA | 23163 & 23164 | CSNK1E | GCGGTTGAGCACAAGCCCGA | ACCCCGTAGTGCCCCA | 23269 & 23270 |
| CRTAC1 | CACTTCAGGACCAGCCGA | TCGAGGCACACGAATGGGA | 23165 & 23166 | CSNK1G1 | GCAAGACCTCAAGGCTGACACA | TCAAAGAAGTCCAGCCGCCTGA | 23271 & 23272 |
| CRTAM | GTGCCTAACGTAACCTGCAA | TCATGGTGGAGCACATGAGTACA | 23167 & 23168 | CSNK1G2 | CCAGCCGCACAGCAAAAACCA | GGCCACCTCCACCTCTGCA | 23273 & 23274 |
| CRTAP | GCGAGGGTTCCAGGGAGA | GAGCAGATAGCTGACTGCACA | 23169 & 23170 | CSNK1G3 | ATACAAAACGGGCTACACCAA | CTGAACTGCACCCACTGGA | 23275 & 23276 |
| CRTC1 | GCTTCGACTCCGACAGCCA | CTGGGTCGGCCAGAACCA | 23171 & 23172 | CSNK2A1 | GTGAAGGACCAGGCTCGAA | ATCCAAGGGGGTTGGCA | 23277 & 23278 |
| CRTC2 | TCAACCACAGAACTTGACCCA | GGCACAGAGCTCTCGTGGA | 23173 & 23174 | CSNK2A2 | GGACCAGAGCTCTCGTGGA | CCAGAACCTTGGCAATGCGAA | 23279 & 23280 |
| CRTC3 | ATCCAGCTGCTATGACCCA | GTGAGAGGGCTGACGGGA | 23175 & 23176 | CSNK2A3 | TGCACAGAGATGTCAAGCCCA | AAGTATCGGGAAGCAACTCGGA | 23281 & 23282 |
| CRX | TCAGCGGCCTAGACCCTA | CCTGATAGGGAGGTGGGGGA | 23177 & 23178 | CSNK2B | CAGACATCCCAGGTGAAGCA | CAGTGCCGAAGTAGGCGCCA | 23283 & 23284 |
| CRY1 | AAATATCCCAGGTTGTAGACGCA | ACGTTTCCCACACTGAGACCA | 23179 & 23180 | CSPG4 | AGTACGCAGGGTCCAGCCCTGAA | CGAAGGCCAGCCGCCTGAA | 23285 & 23286 |
| CRY2 | TCAGGTGAACGCAGGGA | GGCCGTGGGTAGTCCACA | 23181 & 23182 | CSPG5 | CTGCGAGTCCATCATCACCGA | GAGCTCAGATGGGGTCCGGA | 23287 & 23288 |
| CRYAA | GCTACCGCCTGCCGTCCA | CGGCGTGGGTGGCATCCA | 23183 & 23184 | CSPP1 | GCTCCGTGCAGAGAGGAGA | GACAGGAGCTTGCAACCGA | 23289 & 23290 |
| CRYAB | CCATCCACCACCCTGGA | CCAGGCGGATCTCTGAGA | 23185 & 23186 | CSRNP1 | GCCTGGACAACATCGAGGCA | TCGGCAGCTCTGCTCGGAGAA | 23291 & 23292 |
| CRYBA1 | GGTGGAAAGTTGGCGCTGGA | GCATTACTCCCACTCCAGGCA | 23187 & 23188 | CSRNP2 | CACTTGCAGAGTGCAGAGGA | GGCACAGCTCTTTGGGGA | 23293 & 23294 |
| CRYBA4 | CAGTTGAACAGGGGGTGCGGCA | CAGGGGGAGGCAGAAGGAGGA | 23189 & 23190 | CSRNP3 | ATACTTGAAAGGCCCCTCCAA | GACTGTCTCAACCACGGGTGA | 23295 & 23296 |
| CRYBB1 | ATCAGGGGACGACGCA | TGGCATTTGGAGCCCCCA | 23191 & 23192 | CSRP1 | GAGGTTCAGTGCGAAGGCAA | TGCCGTTAGCAGGACTTGCA | 23297 & 23298 |
| CRYBB2 | TGAGGCCCATCAAAGTGGACA | TACAAATCCACCACTCTCCGCA | 23193 & 23194 | CSRP2 | CCACGCAGAAGAGGTGCA | GCCCTGCCATAACCGTA | 23299 & 23300 |
| CRYBB3 | ATAGTGGATGATGACGTGCCCA | CAGGCCAGAAGCCCA | 23195 & 23196 | CSRP3 | CAGTCCCAAAGCGCGGCA | CACAGATGGCACAGCCGA | 23301 & 23302 |
| CRYGA | CTTCCTGCGGTTGCCCAGCA | TCCCTCACAATGCTCAGA | 23197 & 23198 | CST1 | GATAGGATAAATCCCGGGTGGCA | GCTCTTAGTACCGCCAGCGGA | 23303 & 23304 |
| CRYGB | GAGGCCTTGGAAGCCTACAGAA | GCATTACTCCCACTCCAAGGA | 23199 & 23200 | CST11 | CCTCCCCTACCAAGCAAGGAA | TAAGGACTCGGAAGATCCTGA | 23305 & 23306 |
| CRYGC | CCCTCAATGTGTCGGAGGGCA | GACCCGTCTCAAAGAGCCGA | 23201 & 23202 | CST2 | TGGGCCGAACCATATGTACCA | TGAACCTGGAATTCACCA | 23307 & 23308 |
| CRYGN | GGTCCTCTACGAGCTGCCCAA | TACAAATCCACCACTCTCCGCA | 23203 & 23204 | CST3 | ACGTGGAGCTGGGCCGAA | CTGGTCATGGAAGGGGCA | 23309 & 23310 |
| CRYGS | TCAACAGGCAGAAGCTGGA | CAGGCGAGAGGCCCA | 23205 & 23206 | CST4 | CGAGTACAACAAGGCCACCGA | GGTACATATGGTGCGGCCCA | 23311 & 23312 |
| CRYL1 | GGCCTCAACGACACCCTCAGCA | AAAATGCAGACACCCTCCAGCA | 23207 & 23208 | CST5 | GCATCCATGCCACCGACCTCA | GTAGGCAGCCATCACCGGA | 23313 & 23314 |
| CRYM | TCATGTCAGAAGGCTTGGGCA | TCATCAGGGACCTTCATGCACA | 23209 & 23210 | CST6 | GCACATCATCCAAGGCGCA | GGGCAAGTGGTGAGGTCGA | 23315 & 23316 |
| CRYZ | AGAGGATGCACTGACCACCA | ACATTTCCATCCATGACCGCCA | 23211 & 23212 | CST7 | ACCAACCACACCTTGAAGCAGA | CGGAGAACAGGCACCTGA | 23317 & 23318 |
| CRYZL1 | AAGGAGCTCCCATGAACCA | CACTTGCCCCATTGGCA | 23213 & 23214 | CST8 | TGCCCGCAGTGATTGCAGAA | GAAGTGCTCTACCAAAAAGCTGCA | 23319 & 23320 |
| C5 | ACTTCCCATAGCCCGAGTGA | ACCCAGTTGGCCTCCAAACCA | 23215 & 23216 | CST9 | AGGAAGGTCTATGCCCTGGGCA | ACGCGCAACAGCCTGTAGGCA | 23321 & 23322 |
| C5AD | GCAGCGGTATTGGGGCCA | AAGGACAGGTTAAGGGTCGGA | 23217 & 23218 | CST9L | GCCTACAGACTGGGGCACA | CTCCCAGCCAGTAGCTCA | 23323 & 23324 |
| C5AG1 | GGAGCCGCATAGGTTGAAGGA | TGGCCAACCACCACGGA | 23219 & 23220 | CST5A | CTTCCCGGACAAAATGAGGA | GTAGCCAGTTGAAGGAATCAGA | 23325 & 23326 |
| C5DC2 | GGCCAACACTACTTGCAGCA | CCCAAGGAGACACTGGAGA | 23221 & 23222 | CST5B | ACATGCCGACCAGGTGA | CCTCGTCGCCGACGTGA | 23327 & 23328 |
| CSE11 | TGTGTCTGACATCCGAGGGGGA | GTGTGGGGGCCAGCTGA | 23223 & 23224 | CSTF1 | ACACAGAGAGGATGTTGGCCA | TGTTGGGTGGAAAGCAAGGCA | 23329 & 23330 |
| CSF1 | TAGAACGCGGTTCAAACACA | GTCAACTGATTCAGGAGGCA | 23225 & 23226 | CSTF2 | ATGATCACGGGGAGGCA | GGCTCATGGCCAGGGA | 23331 & 23332 |
| CSF1R | GGAGCACCAGGGATGACA | CCAAGCAGCAGGATGACA | 23227 & 23228 | CSTF2T | CAAATGACCTACGTGGAGGGA | GGCCACGAGTTGTCATGACCA | 23333 & 23334 |
| CSF2 | GAAACCCAGGAGCCTGGAGA | CATCCCAGACTGCAGCA | 23229 & 23230 | CSTF3 | CCACGGAGCAGGCAGCTGA | AGAATCTGCCAGAACTGGGGA | 23335 & 23336 |
| CSF2RA | GAGCCTGGACCTGCTACAGA | TTCCGGGGTTGGAGGGCA | 23231 & 23232 | CSTL1 | TTCCTGCCCCTTGCAAAGCAA | GCCCATGCCTCGGCCTCA | 23337 & 23338 |
| CSF2RB | GAGCTCCTGGAGTGAAGCCA | GCCAGGACGATGCCACA | 23233 & 23234 | CT45A1 | CTCTGCCATGTCCAAAGCAA | CTCCACAGGTCATTGCTA | 23339 & 23340 |
| CSF3 | TCCAGAACGCCACAGCA | CACAGAAGCGGAGGGCCA | 23235 & 23236 | CT47B1 | GCCGAGATGAGAAACCCCA | GTGACTTCCTCGGGGGCCA | 23341 & 23342 |
| CSF3R | CCCACCTTGGACACACTGCA | CGCGGTACGACACCTCA | 23237 & 23238 | C5S | CAAGGTTGACACCCAGTTGACAA | TAGAGGCACGTTGCCAGTCA | 23343 & 23344 |
| CSGALNACT1 | CACGCCACCATCACCAA | ACCAAGGTGGGGAGGCCA | 23239 & 23240 | C6T2 | GCCTACAGCCCACACCAGA | TCAAGTAGAAGCAGCCCCA | 23345 & 23346 |
| CSGALNACT2 | GACTGGCCTTACCCGCA | GGCCGTGTAAGGACGCGTGA | 23241 & 23242 | CT83 | GCTTTCAGAGAAACACTGGCGAA | AGAGAGGTCGTGAGCTGCAAGA | 23347 & 23348 |
| CSH1 | TGAGAAGATGCGGTCACTGCA | CTTCAGGATGGCGAGTGAGA | 23243 & 23244 | CTAG1A | TCAGCCTCCCTGGGCAGA | GACAAACAATCAGGCCCCACA | 23349 & 23350 |
| CSH2 | TGGGACAGATGCGGTTCAAGCAGA | GAAGCAGTAGAAGCAGCCCGTA | 23245 & 23246 | CTAG1B | GCAGACACCGCCAACTGCA | GCTGAGCCAAAACACGGGCA | 23351 & 23352 |
| CSK | TGACCACGCTATGCTCGA | GCTCCAGCACGACTCGA | 23247 & 23248 | CTAG2 | ACCAGGGGCGGTTCTGAAGGA | ATCAACGGAAAGCTGCTGGA | 23353 & 23354 |
| CSK | CGTGGCCAAGGTTCAGGCGA | CCTTCTCCACCCGAGGGA | 23249 & 23250 | CTAGE1 | GCTCCAGAGGCCCAGGGAA | GGGCCCAGCGTCAGAAGGA | 23355 & 23356 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| CTAGE15 | TCTGGATCAGCAGAACCCAGA | CTGACTGGGAGCAAGAGGTGGA | 23357 & 23358 | CTTNBP2 | ATGGGCAGCCCATGCAAGGA | GCATGCCCAAGGAACTACAGGA | 23463 & 23464 |
| CTAGE4 | TCTGGACCAGCAGAAACCCAGA | CAATGGACCGCTGATTGGAGCA | 23359 & 23360 | CTTNBP2NL | CTCCAGTCCAATGCCA | ATGGAGGGCTCTGTAGGCCA | 23465 & 23466 |
| CTAGE5 | TCTGGACCAGCAGAACTCAGA | TGGAGCAAGAGGTGGAGGA | 23361 & 23362 | CTU1 | CCCACCCATCCCCTCTGAA | GTCACGACCAGGCTCACACAA | 23467 & 23468 |
| CTAGE8 | TCTGGAGCCAGCAGAACCCAGA | CTGACTGGAGCAAGAGGTGGA | 23363 & 23364 | CTU2 | TGCAGACCCAGTTCCCCTCCA | CGGGTCTCAGTCAGGGGGA | 23469 & 23470 |
| CTBP1 | GGGAGATCCGCAGAGCGA | CCTTCCACAGCAGCTGGGA | 23365 & 23366 | CTXN1 | TGGACGCGGAGCAGCGCA | GTCGAACTGCCGGCGTCGA | 23471 & 23472 |
| CTBP2 | GGCAGGATACGAGGGGCA | CTGTACCAGGCAGTGTGAGGA | 23367 & 23368 | CTXN2 | CTAGCTTCCCAAGGTCACCA | CCATAGACCTGAGCAGTAACCA | 23473 & 23474 |
| CTBS | TGACGCTGCAGGACGTCA | ACATGCCAATGCCCGTA | 23369 & 23370 | CTXN3 | CTAGCATGTCCTGGAGCAGA | TCTCCAGGCCTTCAAGTCCA | 23475 & 23476 |
| CTC1 | CCTGGCCCCGCTACACCAA | AGCAGGTCGGTCAGTGAGGA | 23371 & 23372 | CUBN | GCTTCAGGACTCACCGA | ACTGGCACAGCGAAGGA | 23477 & 23478 |
| CTCF | AGTGCCCAGACTGCGACA | TACACTGGCGTAATCGCACA | 23373 & 23374 | CUEDC1 | CCAAGCTCGGGAGTGGAGGA | AATCGATCTCTTCCAGAGCGA | 23479 & 23480 |
| CTCFL | AACACGGCGAAAATGTCCCAA | AGTCTCGAGCGCTGTAAGCA | 23375 & 23376 | CUEDC2 | ATCAGAAGATTCACCGGCCA | CGGCTCAGGGTTCCGCA | 23481 & 23482 |
| CTDNEP1 | GGAGCCATCCAGACAGATGCCA | CGAACATCGCGGTGAACCTGA | 23377 & 23378 | CUL1 | AACATGCGAGGAAGACCGCAA | TGAACTCGGAGGACAGCCTGA | 23483 & 23484 |
| CTDP1 | TTGGAGAAGGCAGCGACGACA | TGGACGCAGGTGCCCCGA | 23379 & 23380 | CUL2 | TACCAGCAAGCTACATCGGA | AAGGAGCCTGAGTAAGAGGCCA | 23485 & 23486 |
| CTDSP1 | CCGGGGAACTACGTGAAGGA | ACTGAGTACACGTCGTCCACA | 23381 & 23382 | CUL3 | TAGCCAAACACAGTGTCGA | ACTTGTGCACCTCCAACACCA | 23487 & 23488 |
| CTDSP2 | GATTGAGGGGACCACTCACCA | CTTGGCCAGACGTGCAGTGA | 23383 & 23384 | CUL4A | ACGAGGAGCTGGAGCGGA | TTCAGCATCGACTGAGGCA | 23489 & 23490 |
| CTDSPL | TCCTCAGAGAGATGGCAA | GGAAGATGTATGAGGCAGGGGA | 23385 & 23386 | CUL4B | GATCAGACCACCCAGAAGTCA | AAGAACCTGAACTCCACTCGA | 23491 & 23492 |
| CTDSPL2 | ATCCACCCCTTACAGCACCA | CTTCTCTCAGTGCCGGGACA | 23387 & 23388 | CUL5 | AACCTCAAGTCAACTCACCCA | TAGTGAGCTGCAAACGTCCA | 23493 & 23494 |
| CTF1 | TCCCCACTTGGAGGCCAA | AGAAGCTGGGCAGCCCGA | 23389 & 23390 | CUL7 | GTGCCACGCTACTGTGAGCA | CTCCACCACCTCCCTGTGCCA | 23495 & 23496 |
| CTGF | ACACGTTTGGCCCACCAA | CATTGGTAACCCGGGTGGAGA | 23391 & 23392 | CUL9 | AGAGCGAAACCTCCAAGCCA | CGTCTCCTGCACCTGACGCA | 23497 & 23498 |
| CTH | GCCGAGAGCTTGGGAGGA | CTCATCCTCAAGGCCACAGA | 23393 & 23394 | CUTA | ATGAGTGGAAAGGGAAGATCGA | CGTAAGGGTGCACAGAACGA | 23499 & 23500 |
| CTHRC1 | TTGACCAAGGAAGCCCTGAA | CCAACCCAGATAGCAACATCCA | 23395 & 23396 | CUTC | ATCCAATGGCAGCTCTGGAGA | CTGTAGCACCTGAACCCTCA | 23501 & 23502 |
| CTIF | GACTTCACGGTCGCAGGGA | CATAGACGCAGAAAGGACAGCA | 23397 & 23398 | CUX1 | GCGAGAGCATGGAGAGGGA | CACAAGTCACCAGCCGCA | 23503 & 23504 |
| CTL1A4 | GCTGAACCTGGCTACCAGGA | GCTGTCAGCCTGCCGAA | 23399 & 23400 | CUX2 | CCCTGCCAGCAGACCATGA | CACCAACATCTCCGGCGCA | 23505 & 23506 |
| CTNNA1 | AGGTCAAGGCCGAGGTGCAGA | TTCACTGTCTGCACCACAGGA | 23401 & 23402 | CUZD1 | CCCCAATTACCCAAAGCCGA | AGGTGGGAGTCACAGCGCCA | 23507 & 23508 |
| CTNNA2 | ATGGGACGACACGCGGCAA | AATCAGGACACTGATCAGCCA | 23403 & 23404 | CWC15 | AGAGGTTGGAAGGGGAAAAGGA | TACGAACTCTTCAGGGGCA | 23509 & 23510 |
| CTNNA3 | CCAGAACCTCAGGCAGCAA | CATGAAGAATCCGCCAGCA | 23405 & 23406 | CWC22 | AACAGGGACCAGAGAAAAGCCA | GAATATATGCTCCACCAGTGCGA | 23511 & 23512 |
| CTNNAL1 | TAGAGGAGAGGGGCACTGA | TGGAGCTTGGTGGCATAGAGGA | 23407 & 23408 | CWC25 | CAGCGGGAGCTGCGAGAAGA | CACGGTTCACCATCCCACCA | 23513 & 23514 |
| CTNNB1 | CGGGATGTTCACAACCGA | TCACAGAGGACCCCTGCA | 23409 & 23410 | CWC27 | GGAGCCTCCCACGAATGGGAA | CTCCACCACTCCCTGTGCCA | 23515 & 23516 |
| CTNNBIP1 | CTCATGCGTGGGAAGATGGGA | TCTGCACCCTGGTCGATGGA | 23411 & 23412 | CWF19L1 | TACCTTGCCCTGCCCAAAGGA | GTAGAGCAAGCTGATTGGGACA | 23517 & 23518 |
| CTNNBL1 | TGCAATGCLCAGGTGGCGGACA | ATCCAGGCGCCGGAGGTAGA | 23413 & 23414 | CWF19L2 | GCTCTGATGGGAGGAGGAGACA | ACTCACGTCTGGACTGCCA | 23519 & 23520 |
| CTNND1 | GCGGAAGCTCAAGGGCA | ACAAGGCAGGCACACCA | 23415 & 23416 | CWHH43 | CTCAGGGACAAACCCTGGGAA | TAGCGTAGACACCTCCTGGGA | 23521 & 23522 |
| CTNND2 | CCCAGGAGGCCCAGCAGA | GCCGGTGGACTTGAGACCCA | 23417 & 23418 | CX3CL1 | TCACCTACGAGAGCCTCCA | CGGGCACCAGGACATATGAA | 23523 & 23524 |
| CTNS | GAGGGCTGGAGCATTGGCAA | GTCTCCAAGATCAGCGTCCA | 23419 & 23420 | CX3CR1 | CAACTCCATGAACAACGGCCA | ATTGCCGGACACGGCCA | 23525 & 23526 |
| CTPS1 | CCCGTGCGCTACCACGAA | TGCCAACTGCATCCCTAAGCA | 23421 & 23422 | CXADR | CAAAGAGCCCGTACGTCCA | GTGGAGAGTCCGGACTCTGA | 23527 & 23528 |
| CTPS2 | CAAGCCAAGGTGCCGGTGGA | GAGACAGGCGTAAACCCCTCA | 23423 & 23424 | CXCL10 | TCTGAGCCTACAGCAGAGGA | GAGAGGTTACTCCTTGAATGCCA | 23529 & 23530 |
| CTR9 | TCAGCAGGAAAGCCACTCAGA | TTCCAGACCCTTGGCCAGA | 23425 & 23426 | CXCL12 | CCCGTCAGCCTGAGCTACAGA | GGGCTACAATCTGAAGGGCA | 23531 & 23532 |
| CTRB1 | GCAGGAGGATTCACCGACGTGA | CACCAGGGTCCAGGCTCCA | 23427 & 23428 | CXCL13 | GGACCCTCAAGCTGAATGGA | CAGAGCAGGGATAAGGGAAGA | 23533 & 23534 |
| CTRB2 | GCAGGAGGATTCACCGACGTGA | ACAATGCCACCAGGGTCCA | 23429 & 23430 | CXCL14 | ATGAAGCCAAAGTACCCGA | CTGACCTCGGTACCTCGGACA | 23535 & 23536 |
| CTRL | CCTCAGCTGGCTGCACA | ACCTGCCCAACTGCACA | 23431 & 23432 | CXCL116 | GGACCCATGGGTTCAGGAA | CTGAGTGGACTGCAAGGTGGA | 23537 & 23538 |
| CTSA | TCCCTCAACCAGAAGAATGGA | GGGAGAACATGTGAAGGCA | 23433 & 23434 | CXCL17 | AAGACACCAAAGGCACCACA | GGAAGAGTGGGCGCTCAGA | 23539 & 23540 |
| CTSB | CGGATCTGCATCACACCA | CAAGCTTCAGCAGGATAGGCCA | 23435 & 23436 | CXL3 | GCTGAGCCCATGGCCA | GCAAGCACTGCAGCGCA | 23541 & 23542 |
| CTSC | TCTACCACCACTGTCTAAGA | CGGATCCGGAAGTAGCCA | 23437 & 23438 | CXL5 | AGCCAGGGCCCATGCCCA | CCTGGAGCACTGTGGGCCTA | 23543 & 23544 |
| CTSD | GTGAGGCCCATTGTGACACA | CGCCCTGAATCAGCGGCA | 23439 & 23440 | CXCL6 | ACGCTGAGAGTAAACCCAA | GGCTTCCGGGTCAGACA | 23545 & 23546 |
| CTSE | AACCGTGGTTGGCCAGA | ACATCGGCAAGTTCCACCA | 23441 & 23442 | CXCL8 | CCACACTGCGCCAACAAGGA | TCCACAACCCTCGCACCCA | 23547 & 23548 |
| CTSF | GCCTGGCTGGCCAAGAGA | CCCACAAGCAACACCGCA | 23443 & 23444 | CXCL9 | TCAGCACCAACCAAGGGA | AGGAAGGGCTTGGGGCAA | 23549 & 23550 |
| CTSG | GCAGGGAGAGATCATCCGA | CGCACCAGGACCCTCCA | 23445 & 23446 | CXCR2 | ATCTACGCCTTCATTGGCCA | GTGCCCTGAAGAAGAGCCA | 23551 & 23552 |
| CTSH | ACCTTCTCCGTGACTGGCGGAA | GATGGCCATCTGGCAGACTCCA | 23447 & 23448 | CXCR4 | GCCAACGTCAGTGAGGCAGA | ACAGGATGACAATACCAGGCA | 23553 & 23554 |
| CTSK | AACCCAAACAGGCAAGGCA | GGCTTCGCATCAATGGACA | 23449 & 23450 | CXCR5 | GAGAACCAAGCAGAAACGCA | GATGTGGTAGGGTGCAAGGTGA | 23555 & 23556 |
| CTSL | TAAGCAGTGAGAGCAAGCAAGCA | AAATCGCTAGCCAACCACCA | 23451 & 23452 | CXCR6 | CAGAGGCCCATGCATACCTGA | GTGAGACCTCAACTCTGGGCTGA | 23557 & 23558 |
| CTSO | TTGACTGAGAACGTCATCGA | CTGCCCCAGCCACGCTGA | 23453 & 23454 | CXorf21 | GATTGCAGGGGGCCAGGTGA | GGGGAAAGTCACTGGGCTGA | 23559 & 23560 |
| CTSV | GAAAGGCTACGTGACGCCA | CGCGAACAGTCCACCAGA | 23455 & 23456 | CXorf123 | TGGGCCCAAACTTATCGA | ATCAGAAAAGTCTGTCCCCA | 23561 & 23562 |
| CTSW | CATGGCAGCGGCAGGCAA | TGAACGCGTCCCAGACGA | 23457 & 23458 | CXorf36 | AATCTGGCGCCCTGTGGAGA | GCACAGGTCCGGCGTGA | 23563 & 23564 |
| CTSZ | CCGTGCGAACGTCATCGA | TGCAGGTCTCGTCAGGGA | 23459 & 23460 | CXorf38 | CTGGGTGAAGGCGGGCA | CGCCGGCAGTTTCCCA | 23565 & 23566 |
| CTTN | GGAGCAAGCCAGAGCCAA | GCCTTGAAGGAAGCCGCA | 23461 & 23462 | CXorf40A | GCAGCCAGCGGAACTGTACCA | AAGGCCTGAATCTGAGCAGGA | 23567 & 23568 |

| GeneName | Forward Primer | Reverse Primer | SEQ ID NOs |
|---|---|---|---|
| EFNA5 | CATGAGTCAGCGAGCCA | ATCGCCAGGAGGAACAAGTAGGA | 25265 & 25266 |
| EFNB1 | CCAGGAGTTCAGCCCAA | GGCGTCACAGCATTGGGA | 25267 & 25268 |
| EFNB2 | CCGCTAAGGACTGCGGACA | CCGGGCTCTGCGGGGGCA | 25269 & 25270 |
| EFNB3 | CTGGGAAGGAGAACCTGCCA | CTCCGCCAACACATGGCA | 25271 & 25272 |
| EFR3A | CCCGGGTTCGAGCAGGTA | GAATTCAACGCTGAGACGCA | 25273 & 25274 |
| EFR3B | GCTGTTCAGGACGTGGCCAA | AGGAGTCAATGACCACCCCA | 25275 & 25276 |
| EF5 | TGGGCAATGCCAGAGCCA | CCAGGGCGATGAGCAGCCA | 25277 & 25278 |
| EFTUD2 | AACCGAACCCGACCAAGCA | TGCGCAGGCATCAAGCA | 25279 & 25280 |
| EGF | GGCCTGCTGACCTGAGGA | GCCTGGCCATCTTCACCA | 25281 & 25282 |
| EGFL6 | TGGCATGGAGGAGAAGACCA | AGACGCCATCCACTGCGA | 25283 & 25284 |
| EGFL7 | CAACCCGACAGGAGTGTGGACA | TGTGCAGTGGGCGCAGCA | 25285 & 25286 |
| EGFL8 | CATGGAGGGGTCCCCAGA | GCAGCTCTTCAGGCGGCA | 25287 & 25288 |
| EGFLAM | CAGGCAAATCCCAGGCA | CCACGGCATCTTCCACGA | 25289 & 25290 |
| EGFR | GGGGTGCAGGAGGAGGAGA | TTTGCGCAGACCAGGCA | 25291 & 25292 |
| EGLN1 | TCAATGGCCGGGACGAAGGCCA | TCATAGGGTTGCGACGGTCA | 25293 & 25294 |
| EGLN2 | CTAGTGCAGCCAGAGGGCGA | ACATGGCCATGAGGGGCA | 25295 & 25296 |
| EGLN3 | TCAAGGAGAGGTTCTAAGGCAA | ATGCAGGTGATGCAGCGA | 25297 & 25298 |
| EGR1 | ACCCATCCCCTGTGCACA | TGTGGAGGCGGTCGAAGGA | 25299 & 25300 |
| EGR2 | GAGGAAGCGCCACACCAA | GAGAGGAGCAAGGGGTGA | 25301 & 25302 |
| EGR3 | CGCTCACCTCAGGCCA | TGCAGATCCGGCACTGGA | 25303 & 25304 |
| EGR4 | GCACCACCGGCGAGA | AGAAGCGAAGGAGGCCCA | 25305 & 25306 |
| EHBP1 | GAGCTGCTGAACCGGGAA | ACCAGGGCCACCAGTCA | 25307 & 25308 |
| EHBP1L1 | GCTGCTCATGAGAGGACAGGA | CTCGGTGCTGCTGAGCGGA | 25309 & 25310 |
| EHD1 | CCTCCGCAAGATGCAGGA | CCCTGACCACCTGGGAA | 25311 & 25312 |
| EHD2 | CCATGGAGGACGATGCGCCA | GAGCTTCCAGATGCGCCA | 25313 & 25314 |
| EHD3 | ACAAGCCCATGTACGACGAGA | CAATGTCGGCCAGCTTCCAGA | 25315 & 25316 |
| EHD4 | CCGAGGGCCCCTTCAACCA | CCCAGGACGCTGTTGGGCA | 25317 & 25318 |
| EHF | AACGGCCAGTGCAGTAGTGA | ATCAGGTGACTCTGCAACAGGA | 25319 & 25320 |
| EHHADH | AATGCAACAAGACGGGCA | GTGCCAATGACCAAGTGAGGA | 25321 & 25322 |
| EHMT1 | GCCGACACCAACAGGGCA | TTTTCCGAGTCGAGGGCGA | 25323 & 25324 |
| EHMT2 | CTGCTGCTGAGCACGAGGA | GCGTCAGTAGCATGCGGA | 25325 & 25326 |
| EI24 | AGCAAAGACCCCTGGCAAAGCA | TTCAGTTTGGCAGGCAGGA | 25327 & 25328 |
| EID1 | GGAAGGCCAATGGAGGAGGA | CGAAGTCTGCGCGCCA | 25329 & 25330 |
| EID2 | CTCCGTCTCGCCACTCA | GCTCTGCCAGGCTTCCACGA | 25331 & 25332 |
| EID2B | GGGATTTGCAGGAACGCCGCA | GAGGACTGAGGGCCTCGGA | 25333 & 25334 |
| EID3 | TGACGAGGAGAAGTGTGCCGA | CTCCAGAGCCTCGGTTAAGGA | 25335 & 25336 |
| EIF1 | GAGCATCCGGAATATGGCAA | CAATCTCTACCGAGGAACTGGCA | 25337 & 25338 |
| EIF1AD | GCATGCCTCAAATACCGCAA | CCTCCTTCACCACCTCTACCA | 25339 & 25340 |
| EIF1AX | AGCAAAGACCCCTGGCAAAGCA | GCTAGGAGAGCTGAGTGGCCA | 25341 & 25342 |
| EIF1AY | AGAAACTCTGGACAGCAGGGA | TCGCCGTATGCCTTCAGA | 25343 & 25344 |
| EIF1B | GGTAAAAACAGGCGCAGGGGTA | TGATAGTTCCCGTAGACCAACCA | 25345 & 25346 |
| EIF2A | AACCGGAACCGCAGAAAGACA | CAATGCCAACCTCCAAGAGA | 25347 & 25348 |
| EIF2AK1 | CGTCACGCGCCTTGACA | CCCCAGCAAACAAGGTCCCA | 25349 & 25350 |
| EIF2AK2 | CTGGACCAAACAAGAAACGGGA | GGATTCCGGCAACTGACCA | 25351 & 25352 |
| EIF2AK3 | CGATACATGAGCCCAGAACAGA | AGATGTGTTAGGTCGATCCTCA | 25353 & 25354 |
| EIF2AK4 | CCAAGCTTGAACACCGGGCA | GCTAGGAGAGCTGAGTGGCCA | 25355 & 25356 |
| EIF2B1 | AGAAACTCTGGACAGCAGGGA | TTATCCGAGACAAGGGCA | 25357 & 25358 |
| EIF2B2 | TAAACCAGCAAGACGTCCCAGA | AAGGAAGGGCAGTGTAGTCGA | 25359 & 25360 |
| EIF2B3 | AGAAGGTGCCTGCAAAGAGGAA | CTGCCAGTGAGCTGTGA | 25361 & 25362 |
| EIF2B4 | GACGCTGACATGGGAACTGCA | CCAATGAAGTCACGCTGCTCA | 25363 & 25364 |
| EIF2B5 | ATCTGCAATGTAAGCGGGGAGA | GGATCATCCCAGCTCCGTGA | 25365 & 25366 |
| EIF2D | CAATGCCTATTCCGGCAAGGAACGA | CATCTGGAGGGTGCAAAGAGA | 25367 & 25368 |
| EIF2S1 | ACAGCCCTATCACCCTCA | CGGACCTCACTGCCCTCA | 25369 & 25370 |

| GeneName | Forward Primer | Reverse Primer | SEQ ID NOs |
|---|---|---|---|
| EIF2S2 | ATCACCGGCACACAATCTGCA | CTTGCCCGTGACAGCCTGGA | 25371 & 25372 |
| EIF2S3 | CGGTGCAGCAGTGATGGA | AGCAGCCAGGTGTTCCGA | 25373 & 25374 |
| EIF3A | CGACAGGGACCGAAGAGGA | GCTGGGGGAGGAACTCGA | 25375 & 25376 |
| EIF3CL | AGCGCAACCAGGAGCGCAGGAGA | AGCGACCACATGTTCCCGCA | 25377 & 25378 |
| EIF3D | GTCATCTAGGCACCAGCA | CATGCAGATGTCAATGACGGA | 25379 & 25380 |
| EIF3E | TGATACCTGCGGGACAAGCA | TCTTCCAGATGCTGCATCCCAA | 25381 & 25382 |
| EIF3F | CCAACCCCATCACCTCA | GGCGTGAACATCACTCCA | 25383 & 25384 |
| EIF3G | TCCATGCAGCCCAACCGCAGA | TAGCCAGGTAGATGCGGGA | 25385 & 25386 |
| EIF3H | CCCGCTTCCCTGAGGAGGA | GCAATGAGCAGCCAGTCCA | 25387 & 25388 |
| EIF3I | ACTCCCGGACGATCAACGACA | GCTTCGTCGACCACCGCCA | 25389 & 25390 |
| EIF3K | GACCTGCTGAGACTCGCCGA | TACAGATGAAGATCTGCCCGA | 25391 & 25392 |
| EIF3L | AGCTGCGGGAGAGAATATGGGGA | CATAGTTGGGCACTACAGGCGA | 25393 & 25394 |
| EIF3M | CGTCCCGGCCTTCATCGACA | GGCATCAACTCGAGCCTGGA | 25395 & 25396 |
| EIF4A1 | ACCTGCTGGCCAGAGGCA | GCCACACTTTACGGCCA | 25397 & 25398 |
| EIF4A3 | GCCCAGAAAGAGCGGGA | GATGAGGAGACACCTGAGGGA | 25399 & 25400 |
| EIF4B | GGGAACCGGTTCGAGGACAGGAA | TCTGAGCTCTGAGATGAGCA | 25401 & 25402 |
| EIF4E | ATCAGGAGGTTGCTAACCCAGA | TCAAACTTGGAGATCAGCGCA | 25403 & 25404 |
| EIF4E2 | GACAGGCCACAGTGACTTCCA | TCCTGAAACGGCAGCA | 25405 & 25406 |
| EIF4E3 | CATCGGGAACAGTTCACAGA | TCTCGGTCCCGAACACTGA | 25407 & 25408 |
| EIF4EBP1 | CCGGGGACTACAGACGGA | GTTCCGACACCTCCATCAGGA | 25409 & 25410 |
| EIF4EBP2 | CACCTGCCCAATATCCAGGA | TGAGCATCATCCCCAACTGCA | 25411 & 25412 |
| EIF4EBP3 | AACGTCCACTAGCTGCCCGA | AGGGGGGTGTCGGGCAA | 25413 & 25414 |
| EIF4ENIF1 | GAGGATGCTGGCCAGGGA | AGATGCAGAGGTGTTCCAGGA | 25415 & 25416 |
| EIF4G1 | GCCATCGACACCGAGGAA | CCATGAGGCAGCGGCACA | 25417 & 25418 |
| EIF4G2 | CAGCAAACAACTCCGCAAACGA | CACATTGAGGAGCTCAAGGCA | 25419 & 25420 |
| EIF4G3 | GCTGGGGAAAAGGCAGCA | GCTGGAGGTTGCAGGGCA | 25421 & 25422 |
| EIF4H | CAATACGGTTCAGGGCGACA | CTGCCTTCGCAATGTCA | 25423 & 25424 |
| EIF5 | ATCGAGGCATGCTTGACACA | CACTGCTGGATACGGAGCCA | 25425 & 25426 |
| EIF5A2 | CTCAAAGGACGACCATGCAA | CAACAAGGTGAACTTGGCA | 25427 & 25428 |
| EIF5AL1 | ATGGGGACTTCTGACAGATAGCA | GACAGAACACGGATTTACAGGGGAA | 25429 & 25430 |
| EIF5B | CATGGTTTGGAGGCCCAGACA | AGTAGCAGCCACATCAGAGTCA | 25431 & 25432 |
| EIF6 | GGAGGGCCTGGTGCATCCAA | TGAAGACCATCCTCCACACTGA | 25433 & 25434 |
| ELAC1 | TCTGCACAATCAGCCTGCAGA | GAAGACCAGCTCCGTGTGAGA | 25435 & 25436 |
| ELAC2 | TCAGCCCCAACTTCAGCGAGCA | ATCTCCTCGATGTCGCAGCA | 25437 & 25438 |
| ELANE | GGGCAGGAACCGTGGGA | CCCGACGAAGGGCCGA | 25439 & 25440 |
| ELAVL1 | TGCAGCCAACCCCAACCAGA | GATGAAAATGCACCAGCCGGA | 25441 & 25442 |
| ELAVL2 | GACCATTGACGGAATGACCA | CATCTGCGTCAGGAGCCA | 25443 & 25444 |
| ELAVL3 | GCTACTCCCCAGCCCTACCA | CGCCAGCCTCCATACCA | 25445 & 25446 |
| ELAVL4 | CCCAGCCAGAAGTCAGCCA | ATCGGGGGACAGGTTGTAGACA | 25447 & 25448 |
| ELF1 | AGGGAGAAGCAGCTAGAACCA | TGATTCCTAGGAGACACAACCA | 25449 & 25450 |
| ELF2 | CATCCGGGCTGTGGAAGCA | ACATCTGGCCTCATAGCAGCA | 25451 & 25452 |
| ELF3 | ACGAGGTCAGCAAGGTCA | CACGTCACTTCCACCGGA | 25453 & 25454 |
| ELF4 | GATCCCACTACCTCCACA | GCCGTTGGAAACACTCTGGAGA | 25455 & 25456 |
| ELF5 | CCTGGCAAAGATGTGGGGACA | CTTCCTGCACCCGTGTCA | 25457 & 25458 |
| ELFN1 | GCTACTCCTCCAGCCCTACCA | TAGTCCAGGATGTGTCAGA | 25459 & 25460 |
| ELFN2 | CAGGAGCGGCCAGTCCAGTCA | GGTTCAAGGCCCTCAGAGGA | 25461 & 25462 |
| ELK1 | GGACCCCAGGATCGGGAA | ACGGGGGTCGAGAGGCCA | 25463 & 25464 |
| ELK3 | CGTTCCCTGTCCCCCAACTCA | AAGAAGGCCTGGGGTGAGGGGA | 25465 & 25466 |
| ELK4 | CTCCCCCTAAGTTCACGCAGA | AATGGCCAGGGGTGGAA | 25467 & 25468 |
| ELL | CCTGGCTCGATGTCAGCAA | AGTCCGTCAGCAGGGGCA | 25469 & 25470 |
| ELL2 | AAGGCCTACAAGAAACCGGA | CTGCAGCATTCTGAGACGGA | 25471 & 25472 |
| ELL3 | GCCACCGAGGGTATCTGAGA | GCGTTGGCACACAAGGTCCA | 25473 & 25474 |
| ELMO1 | ACCGCCTTGTGGAAGGGA | GCAAGGAATCGTGGGGGCA | 25475 & 25476 |

| GeneName | Forward Primer | Reverse Primer | SEQ ID NOs | GeneName | Forward Primer | Reverse Primer | SEQ ID NOs |
|---|---|---|---|---|---|---|---|

| GeneName | Forward Primer | Reverse Primer | SEQ ID NOs | GeneName | Forward Primer | Reverse Primer | SEQ ID NOs |
|---|---|---|---|---|---|---|---|
| FEM1A | AGAAAGTGGAGTGCACCCCA | CCACGTGCAGGGAGGGGA | 26961 & 26962 | FGFBP3 | AACCCTCAGAGAGGAAGACCA | GTGCCACTTCTCAGGCGCA | 27067 & 27068 |
| FEM1B | AGCACATTGTGGAGCCACAGCA | ATGGCGTCATCCATGGCCA | 26963 & 26964 | FGFR1 | CTGGACCAGTACTCCCCA | GCAGCGGCTCATGAGAGA | 27069 & 27070 |
| FEM1C | GGATGACACAGTCCCCTGCA | ATGACACGGAGCAGCAAGACA | 26965 & 26966 | FGFR1OP | CAAGGCTGAACTCCGAGCA | TCTGCCAACAAGACTAGCCA | 27071 & 27072 |
| FEN1 | TGCTGCGGCTACCGACGGA | TGGGCCAATACCCGGA | 26967 & 26968 | FGFR1OP2 | GAGACATGGGCCACGGTCCA | ATAAGTTCCAAGGCGGACTGA | 27073 & 27074 |
| FER | GTGCGGAGAGAGTCATGGGAA | TGAAAACCCAGTGCCTGA | 26969 & 26970 | FGFR2 | TCAACGGCAGACACCCCA | CTTCCAGGGGTTCGCCA | 27075 & 27076 |
| FERL15 | CATCAGGATGATGACGACGGA | ACCTTGCCCGACAAGCGCCA | 26971 & 26972 | FGFR3 | CGCCAACTGCACACACGA | GCTCGAAAGGGCCGACA | 27077 & 27078 |
| FERL16 | GAAACTCGGCCACTGTACCACA | TTGGGTCGCCTTGAGAGAGA | 26973 & 26974 | FGFR4 | GACCGGGTGTACACACACA | ACAGCTCCTCCACCGGGA | 27079 & 27080 |
| FERD3L | AAGGGTGATCACCTACGGCA | CTCGTAAGCAAACGTGGCCA | 26975 & 26976 | FGFRL1 | GCCTTGGCGCCAACACA | CAGGCTAGTTGGCCGAGGA | 27081 & 27082 |
| FERMT1 | TTCATCCAGGCGTGGCAGTCA | CTGGAATCCCGGTGGCTGCA | 26977 & 26978 | FGGY | GAGAAAGGCTGGGACGACA | CGACCGCAATCCCAGGGA | 27083 & 27084 |
| FERMT2 | GGAAGCCCTTGTCACCAA | AATACTTGAATGGAGCAGCA | 26979 & 26980 | FGL1 | TCAGCAGCTGGGACAGAGA | GAATACCACCACCATGCCA | 27085 & 27086 |
| FERMT3 | AAGGGCAGCAGGAAGACGAGA | AGTTGACATTCCACTGGCGCA | 26981 & 26982 | FGL2 | TAACTATAATGGCACAGTGGAGA | TACAGCCCAGGTTCCCAGA | 27087 & 27088 |
| FES | TGGGCCATTCACCGGCAGGA | ACGTCAGGTGCGGACCCA | 26983 & 26984 | FGR | CCCAGGTAGCTGAGGGCA | ATGAGACGCGCAAGCCA | 27089 & 27090 |
| FETUB | GGGAGGCGATGCGGGACGA | GAGTGCAGGCCCAAGCCGA | 26985 & 26986 | FH | CCCAAGTCATGGGGAACCA | CTGAAGCATCCCCCAGCA | 27091 & 27092 |
| FEV | CCACCGTCCTCCGGTGACACA | GGGTCAGAAACACACCGGGA | 26987 & 26988 | FHAD1 | AGATAGAACCGTCCACACTGA | GACCTCCTGTGCCGGGA | 27093 & 27094 |
| FEZ1 | AAGCAGAAGGACCAGCGAGA | TGAAGCGCTTGAGAGGCA | 26989 & 26990 | FHDC1 | CCAGGGACAAACCCACCA | GGTCAGGGTCCGCACAGA | 27095 & 27096 |
| FEZ2 | TGCAGCTTGGAGGAGAAGCTGA | AATCTCCTCCCCTGCAGGA | 26991 & 26992 | FHIT | CCCGCTGCGGCCASTGGA | GGAAAAGGTGAAGAGGTCCCA | 27097 & 27098 |
| FEZF1 | GCAACATGATGAGCACGTCCAA | GGGTAAGGCTCCCTGCAGGA | 26993 & 26994 | FHL1 | CAAGGGGACCGTTGGCACA | CATGGCAAGTCACGACGTAGA | 27099 & 27100 |
| FEZF2 | CATATGCACACCACCAACGGA | GTCCTTTGCAGGGGGCA | 26995 & 26996 | FHL2 | ACCAACCCCATACGAGGA | TGAGCAAGCCACCGCCCA | 27101 & 27102 |
| FFAR1 | TAGGACCCTACAACGCCTCCAA | TTCCCAAGTAACCGGTCACCA | 26997 & 26998 | FHL3 | CTGACACAGGGTGGAGTGACA | AAAACAGGCCACAAGTAGGGGA | 27103 & 27104 |
| FFAR2 | TGGTGCCGAGGCATTGGGA | GACCCACACCCTGTCCTCA | 26999 & 27000 | FHL5 | CTGCGTTGGACTGCTACAACCA | TCAGGAAGCCTTTACCCACCA | 27105 & 27106 |
| FFAR3 | GGGCCCTACAACGTGTCCCA | AGAGCCCAAGCAACCCTCTCA | 27001 & 27002 | FHOD1 | GCATCCCCAGAAGAACCCCCA | CCCTAGCAGCTAAGGCACGA | 27107 & 27108 |
| FFAR4 | ATCAAGGAGAGAGGCTCACGGTA | CTGGATCAGGATGAGGAGGA | 27003 & 27004 | FHOD3 | CGTCAAGTCAGCCACCA | AGGTGCCAACCAAGCCCA | 27109 & 27110 |
| FGA | GGGGGCTCCTATGACCCAA | GCGAACAGCCCTGAGGGA | 27005 & 27006 | FIBCD1 | CCTCCTGAAGCACCAGCGGCA | TGGCAGTTGCGGTACCACCA | 27111 & 27112 |
| FGB | GCTCGTTCCAGCCAAAGCA | GTAGGACACAACACCCCCA | 27007 & 27008 | FIBIN | GAGAGCAGGCTCAACGAGGA | GTCCCTGAGCCCACAGA | 27113 & 27114 |
| FGD1 | TACGCCCATTCCGGGAAAAGGA | CCCACAAACCACATGCCCCA | 27009 & 27010 | FIBP | GCGCCAAGCTGACCCCA | GTGCCATGTAGCGGTCCA | 27115 & 27116 |
| FGD2 | CCTGCAGCTCATCCGGGACA | CAACAGTCACCTGGTAGCCCA | 27011 & 27012 | FICD | GCCCATCACCATCCGCAA | CACTTGGCGATGAAGGGA | 27117 & 27118 |
| FGD3 | CATGCTGGAGCCCGTGCAGA | GCTCCAAGGACCTTCCCGA | 27013 & 27014 | FIG4 | TGATGCCAGGAGACAGTGCCAA | TGTTGACTCTGCCCAGCTGA | 27119 & 27120 |
| FGD4 | GTCAGAGCCCCAAAGCTGTGA | TGTCTCGCAAAGCTGTGCA | 27015 & 27016 | FIGLA | ATCCTCGGCAAGACACCTGTCA | GTAGCACTCACACTGTGGCGA | 27121 & 27122 |
| FGD5 | CAGAGCCCTGTCCACAGCAA | TGCCGAGAGATGGGACA | 27017 & 27018 | FIGN | GACGGCCTTACCTCGGAGCA | GCGACTAGTTCCAGAACCGGCA | 27123 & 27124 |
| FGD6 | GCCAGAGCAGTCTTCCAACAACA | TCCATGCCAAGTCACTGGGAA | 27019 & 27020 | FIGNL1 | CCCATGTTTGAGGCCAGACA | CTGACACTTGCAACAGCA | 27125 & 27126 |
| FGF1 | GAAAGGCTGGAGGAGAACCA | GAGACTGGCAGGGGGAGA | 27021 & 27022 | FILIP1 | GGGAGTTGCAGGCCAAGAGAA | ATCCGGTGCAGGACCCGA | 27127 & 27128 |
| FGF10 | GGGAAGCATGTGTGCGGGCA | TCCAGGATGCTGTACGGGCA | 27023 & 27024 | FILIP1L | GCCAGAGCACAGACCCAGA | GATGACTCCGATCTGGGGCA | 27129 & 27130 |
| FGF11 | TGGACAAGGAGGGCCAGGTCA | AAGGGGAGGCCTCGGGGA | 27025 & 27026 | FIP1L1 | CTATCAGCCGAGTAGAAGGCA | GACAGTCGGAGGAGGTGGA | 27131 & 27132 |
| FGF12 | CCTGCAGATGACCACCAA | GGATGGCCACTACAGCA | 27027 & 27028 | FIS1 | CAGAACAACCAGGCCAAGGA | CCAGGCCATGCCTCCA | 27133 & 27134 |
| FGF13 | TACCAAGCTATACAGCCGACA | TGGATAGCCACCACTCGCA | 27029 & 27030 | FITM1 | GCTTCGAGCCACTCTGA | TCAGCAGGAACAAGCGGCA | 27135 & 27136 |
| FGF14 | TGGGTGGGAAATGGCTCAAACACAA | CACACACAAAGAAACATAGAGGGGGA | 27031 & 27032 | FITM2 | AACATCGAAACACTACAGCGGCA | TCACCTCATGCAGCACAGA | 27137 & 27138 |
| FGF16 | TGGAGATCTTCCCAACGGCA | CCAGATTCCACTCCCCGGA | 27033 & 27034 | FIZ1 | ATCCTCTAGGGGACGAGGGGGCA | GGAGAGGGACGAGGGGGCA | 27139 & 27140 |
| FGF17 | GAAGCCCAACACCAGAGGCA | CGCGTGAAGGCCATGAACCA | 27035 & 27036 | FJX1 | CGACCGGCTCAAGCAA | GAACACGCACACTGACTGCA | 27141 & 27142 |
| FGF18 | GGATGGCACCAGCAGGA | TGGTGAAGCCCACGTACCA | 27037 & 27038 | FKBP10 | CAGCTACTCCGCAACCACA | CGTTCCCCATGCAGGGA | 27143 & 27144 |
| FGF19 | CAGTGCCAAACAGCGGGCA | CCTCTGGGAACATGGGGA | 27039 & 27040 | FKBP11 | GGCTATGGAAAACGGGGA | GTGCAATCAGCTCCACGTCA | 27145 & 27146 |
| FGF2 | GCCACTTCAAGGACCCCA | TAGCAGGTAACGGTTAGCACA | 27041 & 27042 | FKBP14 | AAACATAACAATGGTCAGCCCA | TCCATAGCCCAGAGGAGGA | 27147 & 27148 |
| FGF21 | GTTTACCAGTCCGAAGCCA | GCAGGCTGGTAGTGCCA | 27043 & 27044 | FKBP15 | CCTCTCAGGCCCTCACA | GAATTGAAGTGGGGGCCCTA | 27149 & 27150 |
| FGF22 | CACAACACCTACGCCTCACA | GGGCAGGAAGTGGGGCGGA | 27045 & 27046 | FKBP1A | GTGTGGGTCAGAGAGTCCAA | AAGCTCCACATCGAAGACGA | 27151 & 27152 |
| FGF23 | AAAACGGGTACGACGTCTACCA | CTCGGGGACAGGAACTGGGA | 27047 & 27048 | FKBP2 | CATCAAGGGCTGGGACCA | ATACCCTAGCTCGGATGGGA | 27153 & 27154 |
| FGF3 | GACCACACGTGGTACTGTGAAGA | GCCCAGTTCTCGAAGCTGA | 27049 & 27050 | FKBP3 | CTGGATGAGGGGTCCAGA | AGTCAAGAGAGCTTCATCCCA | 27155 & 27156 |
| FGF4 | CAACGGCAAAGGCAAGGA | GCTGCTCATGGCCACGAA | 27051 & 27052 | FKBP4 | TGGGGGAGGGTGTGCCACA | CCAGTGCAACCTTCCAGA | 27157 & 27158 |
| FGF5 | CCTGGGCTTCACGGGAGAGA | GAGGAGGAGGCAGAAGAGGA | 27053 & 27054 | FKBP5 | GTCATCAAGGACTGCAGCCGA | AGGGAGACTTGCCAGCCGA | 27159 & 27160 |
| FGF6 | GAGAAACCCTCTGCCCAA | GTGACAGTCATGATCGGGGGA | 27055 & 27056 | FKBP6 | CGGAAGGAGAGCTGGCCA | GTCGACTCAGCAACGTCCA | 27161 & 27162 |
| FGF7 | CGAACACAGTGGTACTGCCTGAGGA | GCCACAATTCCAACTGCCA | 27057 & 27058 | FKBP7 | CAAAAGGAAAGAAGAGCACCAGA | TCTTTAGCCAGGTAGCCGTCA | 27163 & 27164 |
| FGF8 | CAACGGCAAAGGCAAGGA | CCTTGCGGGTGAAGGCA | 27059 & 27060 | FKBP8 | CCAACAGCAGTCGCCCCA | GGCAACAGCAGTCGCCCCA | 27165 & 27166 |
| FGF9 | GGAGGCAGCTAGTACTGCAGGA | CACGGCCTGAATGCTGACCA | 27061 & 27062 | FKBP9 | CAGCTACTCTCGGAACCCGA | AGGTGAGGCGGGACCACA | 27167 & 27168 |
| FGFBP1 | CTGAGGCAGGAGGGCGA | GAGCGCAGATTCCGGCA | 27063 & 27064 | FKBPL | CGGAAGGGGACCCTTCCCA | CCTGAATGACCACCTTCCCA | 27169 & 27170 |
| FGFBP2 | GCCGCCAACACAGACCAGA | CATGGTGAAGGCGGCCTCA | 27065 & 27066 | FKRP | GACCACCCGGCAGGATGTGGA | GGGCCCGAACTTGAGCTTCCA | 27171 & 27172 |

FIG. 1 (cont.)

| GeneName | Forward Primer | Reverse Primer | SEQ ID NOs | GeneName | Forward Primer | Reverse Primer | SEQ ID NOs |
| --- | --- | --- | --- | --- | --- | --- | --- |
| FKTN | TGACAGGCCAGAGTTACAGCA | AAGTTCCACTGCTCAGCCAGA | 27173 & 27174 | FNTA | AGCAGCAGCACAAGGAAGAAGA | TACAGGACATAGGAGGCGA | 27279 & 27280 |
| FLAD1 | TGTCTGGAGGGGATGAAGGGA | CCAGCGATTCCCTGGGGCA | 27175 & 27176 | FNTB | TGACAAGCCGGCAGATGCGA | TCCAGAAGCCCCCCGCA | 27281 & 27282 |
| FLCN | ATCGTGGAAGTCCACGCA | GGCTCCCACTGGTCACCA | 27177 & 27178 | FOCAD | TGATGCCAATCGGATGGCCCA | TGTGCAGAATCATCCAGGCCA | 27283 & 27284 |
| FLG | CATGGGCAGCAGGATCCAGA | CTGGAAGCAGACCCCAGACCA | 27179 & 27180 | FOLH1 | ATGCTCCAAGCAGCCACA | TCTCTGCAGCTGCCTGCA | 27285 & 27286 |
| FLG2 | ACAAAGACAGCCAGGATCCACA | GCTGCCACCAGAAGGGCCA | 27181 & 27182 | FOLR1 | CAGCAACTACAGCCGAGGGA | GCCCCACTCATGGCTGCA | 27287 & 27288 |
| FLI1 | CCTCCCACACAGCAGGA | ACGCTGCAGTGCACCGGA | 27183 & 27184 | FOLR2 | GGCAACCCCAACGAGGAA | GTTGCAGCATCAGGGCCA | 27289 & 27290 |
| FLII | GGAAGCCTTCCACGGCAA | ACAGTGCGGCACTCAGCA | 27185 & 27186 | FOLR3 | GGAAGTGCCCAGCCCAGGA | CTGCCGTGCAGCAGGCA | 27291 & 27292 |
| FLNA | TGCCCAACTTCCCAGCA | CCCTCAATACCAGGCCA | 27187 & 27188 | FOS | CCAAGCGGAGACAGACCAA | AGGGTCATTGAGGAGGAGCA | 27293 & 27294 |
| FLNB | GTGTCTGAGCTGGAGCCAGA | TGCCATAGGCGGACACCA | 27189 & 27190 | FOSB | CCCTTCCAGACACCGCAA | GAGGGCGAGTTCAGGGGA | 27295 & 27296 |
| FLNC | GTCACCAGCCTCCAGGAGA | TCGATGGAGTGGACGCCA | 27191 & 27192 | FOSL1 | CCCCACACTCATGACCA | AAAGCGAGGAGGGTTGGAGA | 27297 & 27298 |
| FLOT1 | CCCCAGGCTTGCAGAGGAGA | CCACACTTCTTGCAGGCGA | 27193 & 27194 | FOSL2 | GTGAGGAGCCCTTGGAGCA | GCGGTGAGCCCTTGGAGCA | 27299 & 27300 |
| FLOT2 | CAAAATCGGGAGGGCGGA | GCAGGGCCTTCTAGCACCA | 27195 & 27196 | FOXA1 | CCTGAAAGGGGACCCCCA | CGGGCAACGTAGAGCCGTA | 27301 & 27302 |
| FLRT1 | TACAACCGGGCAGCAGGGAA | CTGCTGCCGTTGGAGGGGA | 27197 & 27198 | FOXA2 | AGGGCCACACAGATACCCCA | CTGCAACAACAGCAATGGAGGAGGAAA | 27303 & 27304 |
| FLRT2 | TCCTGGACTGGGATGGCAGA | CACGGTGAAGAGAGAGAGCCA | 27199 & 27200 | FOXA3 | GCTCACCCGCTTCTTCCACA | TCAGCCCGTTAGCCCCCA | 27305 & 27306 |
| FLRT3 | CAACCTACAACCACCCTCAATGA | GGCAATGGTAACCAGGGCCA | 27201 & 27202 | FOXB1 | GAGACATCATCGCGCGGGAA | GGAGATGGGAGTTGGCCCA | 27307 & 27308 |
| FLT1 | TCTGGCACCCCTGTAACCA | CACAACCAAGGTGCTAGCCA | 27203 & 27204 | FOXB2 | GAGTCCTGTAGGCCCGGA | ACGGTGGGATTGGCGCCGA | 27309 & 27310 |
| FLT3 | TGCAGAAGCATCGGCAA | TGCACAGCACTTGACCAGGA | 27205 & 27206 | FOXC1 | ACAAGCLAGGGGCTGGCAGA | GTTGTAGGAGTCCGGGTCCA | 27311 & 27312 |
| FLT3LG | GCTCGGGACTCAGTGGGA | CATCTTGCACCCAGCGACA | 27207 & 27208 | FOXC2 | CAGCGGGAGGACTGAACCA | AATCCCAGCGCCGTGGGA | 27313 & 27314 |
| FLT4 | CAACAAGGTGGGGCCAGGA | CTTGGCAGCTCAGGAGACA | 27209 & 27210 | FOXD1 | GCCAAGAACCCGCTGGTGAA | CGGCCGCTGATGAACTCACA | 27315 & 27316 |
| FLVCR1 | CTGGCCTACGTGCCCCTCA | ACCTCTTTGGGCCCAAACCACA | 27211 & 27212 | FOXD2 | GGTGGGGGTTGGAGTCGGCAA | CTTCACACAGACCATCAGACGA | 27317 & 27318 |
| FLVCR2 | TGAAGCTGGCAGCCTGA | CAGGAGGGACCAAGAACCCA | 27213 & 27214 | FOXD3 | GTTCAGGGGGCGGCTTGAGA | GTGGCAGTCGTCGCGGCTA | 27319 & 27320 |
| FLYWCH1 | GAGAAGGCTGCAAAGACAGCACCA | GGCGGGGTGGGCAGTGACCA | 27215 & 27216 | FOXD4L1 | CCTGCTGGAGAGCAAACACGA | CCAGGAAATGTGCAAATCCGGAA | 27321 & 27322 |
| FLYWCH2 | CAGGCTCCAAAGACAGCACCA | CGGGGTGGGTCTGGAGGA | 27217 & 27218 | FOXE1 | TCGCCCGGCCAGTTCGGA | TCCACCGGGATAAGCGGCA | 27323 & 27324 |
| C7orf55 | ATCGGAAACATGTGGCCCTA | CTCCCAGCCCTTCCCTCA | 27219 & 27220 | FOXE3 | CAAGCCGCCTCTTCCACCGA | CCAGGAAGAAGCTGAGGGCA | 27325 & 27326 |
| FMN1 | TCTGTCTCCAAGGTCTCCCA | GTGGCTCCAAGGTGCAGCA | 27221 & 27222 | FOXF1 | TCCACGCACTCCTGCAGCA | CGGTCACACATGCTGGGCGA | 27327 & 27328 |
| FMN2 | CCAACTCGCCCACCATGGACA | GGAGAAGAACAGGCCTGGGGA | 27223 & 27224 | FOXF2 | AGGGCAGAGACTTCAGGTGGGAA | AGGCAACGAAGATCCCACAGA | 27329 & 27330 |
| FMNL1 | AACAGGGCCAAAAATCTTGCCA | CATCAAGCATTCCACAAAGTCCA | 27225 & 27226 | FOXG1 | CTCGCTGGGCAACAACCA | AACTGGTCTGGCCCGCGA | 27331 & 27332 |
| FMNL2 | TACCAAGTCCACTGACCCGGA | CCTTCACGTCCAGGACCA | 27227 & 27228 | FOXH1 | AACCCTCTCCCAGAGCCTA | TAGGCAAGTAGGAGGTGGGCA | 27333 & 27334 |
| FMNL3 | ATGCTCCTAACGGATCACCA | CTGGGCCAGTCAAGCGGGA | 27229 & 27230 | FOXI1 | CAGTGACAAGACGGGCAGA | GGGCTGAATTGGCTGAGCA | 27335 & 27336 |
| FMO1 | CCGCAATGTACTGCCACGAA | CAGAGTAGACGACTTGGGACA | 27231 & 27232 | FOXI3 | AGGACCCATGCTCACCTCCA | TCTGAGATGGAGGTGCGGGA | 27337 & 27338 |
| FMO2 | CTCAGCCGCAGCAGAGAACA | CCAAATCGAGTGACGAGCAGCA | 27233 & 27234 | FOXI1 | CTACGCCACCAATCCCA | GCGTGGCGGAAGTAGCAGA | 27339 & 27340 |
| FMO3 | CATGGGCCCTGGAAATGGGA | TGAACTGGAGGCAGCCTTGGA | 27235 & 27236 | FOXI2 | CAGGACTGGAGAGGCCACA | GGACAAGGAAGACTCAGAGGA | 27341 & 27342 |
| FMO4 | GGCTCCAGGGAGGATGACA | CTAAGGGGTGAATCAAGCCTA | 27237 & 27238 | FOXI3 | CCACAGGCACTCAGCACTTCA | GATGTCATCTGGAGGCAGGGA | 27343 & 27344 |
| FMO5 | TCTCTTACAACCAGCTGCAGA | GCACCTGCAGCTTGGAGA | 27239 & 27240 | FOXK1 | GCCTGGAGGAGAAACCCACA | GGAAGGTGGTGCTGCCGA | 27345 & 27346 |
| FMOD | CAGCTGGAGAGTTCAAGGCA | TAGATCAATAGCAGTGACCCCA | 27241 & 27242 | FOXK2 | ATCATTCAGACGGCACAGACCA | ACCTGCGGTGCATCCGCA | 27347 & 27348 |
| FMR1 | CATCATCCGGGAGGACCACTGA | AATGGGCAGACATACCAGGA | 27243 & 27244 | FOXL1 | GGGAGAAGAAGGTCTGCAACGA | CCCGGAAGCTGCAAGCTGAA | 27349 & 27350 |
| FMR1NB | CCACCGGAAGATCCCCAA | TCGCATGGTGCCCAAGGA | 27245 & 27246 | FOXL2 | AGGAGAAAATGTGAAACCCGGCA | TTGGTCCCCCAAACAACAAGCTACA | 27351 & 27352 |
| FN3K | CCAGCCTTACTCCAGGGGGA | CTAAAGCCCCAAAACATGCCA | 27247 & 27248 | FOXL2NB | GGCTGGAATCCGTCTCCCAA | TAGAGTGGGCCCCGGA | 27353 & 27354 |
| FN3KRP | CCCTTCCTGCCATAGGGGA | CGAATGCGGGTCCAGCA | 27249 & 27250 | FOXM1 | GAGCTCCCGTTCCACAGCA | TGCTGAGATCATCAGCCCA | 27355 & 27356 |
| FNBP1 | AACAGGTGGGAGGAGGAGAGACAGA | ATCAAACTCATTGTGTGACCA | 27251 & 27252 | FOXN1 | TGGTGACCTCATCCCCGACA | CTGCCAAGTCACTGCCCA | 27357 & 27358 |
| FNBP1L | ACCAGCTCCCAAAATGCCACTCA | TCTCTGCCATGCCACTAACCA | 27253 & 27254 | FOXN2 | CATAGAGGGAGAGTGATGTGCCA | TGGAGAGTGCTCAATGGCCA | 27359 & 27360 |
| FNBP4 | GACTCGCAAGGCTCTTGAGA | CCTGACAGGCTCTGAGA | 27255 & 27256 | FOXN3 | GCACATCAGGTTCCACCA | CTCAGTCGCATCCGGCA | 27361 & 27362 |
| FNDC1 | CTGCCCGACGTGCACGACA | CGCAGATGAGCCGCCCA | 27257 & 27258 | FOXN4 | GAAGAACTCGGTGCGGCACAA | CGATGCGGGCCAGGTTCAGA | 27363 & 27364 |
| C1orf233 | TCACCATCCAGCCAGCCACA | GGTTGGGCAGCAGGTTTCGGA | 27259 & 27260 | FOXO1 | ACCTATGGCAGCCAGGCA | GGACGCCCGTTAACTGCA | 27365 & 27366 |
| C20orf195 | AGTGGGAGGTGCACATGCAAGGAA | AAGACAGGTCACAATGCCGGA | 27261 & 27262 | FOXO3 | CACCAATTCTAACGCCAGCACA | GCTGTAGAGCATGGGCGGAGA | 27367 & 27368 |
| FNDC3A | AGTACAGGTTGGAATGGGGAGA | AGAAGGTGAATCAGGGTAGGCA | 27263 & 27264 | FOXO4 | CCTTCCGTCCACGAAGCA | GAAGAGGTGAGATTGAGGCCA | 27369 & 27370 |
| FNDC3B | CCCCGGGTGCACTTCCGAA | CAGGCCAATTACAGCAGGCCA | 27265 & 27266 | FOXO6 | CCCGGCGCGTATCGTAGGCA | CTCGACACGGCACACACGA | 27371 & 27372 |
| FNDC4 | TCCAGGTGCAGGGCCATCTCCA | AGGACCACGACGATGATCAGCA | 27267 & 27268 | FOXP1 | GAAGAGCTGAACGGGGGCA | CAGGATGGCAGGCTTGCA | 27373 & 27374 |
| FNDC5 | GCCACGGGTTGACTGCAGA | GCCAGTAGATCCGGATGCCA | 27269 & 27270 | FOXP2 | TGAACACGCATTGGATGACCGA | TTGGGCTCGAGGGGTCGA | 27375 & 27376 |
| FNDC7 | CTGCCCGACGTGCACGACA | GCATCTCTCCGGCCGA | 27271 & 27272 | FOXP3 | CATCTGCCACCTGGAAGAA | CGGAACTCCAGCTCATCCA | 27377 & 27378 |
| FNDC8 | TCAGAGGGAGGAAGAAGACTTCCA | GCACCCGCATCAGGGGCA | 27273 & 27274 | FOXP4 | GGACTGTTGAGGAGGGGGA | GGGCTGTTGAGGAGGGGGA | 27379 & 27380 |
| FNDC9 | TAGGCAGAGACGACCACTCCA | CAATCCCAGAACCACTCCA | 27275 & 27276 | FOXQ1 | CCCCCTAAGTACATCCAGGAA | ACACGATGGGGCCCAGAA | 27381 & 27382 |
| FNIP1 | AAGTGGAGCTGCCTCTGCAA | TGTGTGGACAAGGTCGGCCA | 27277 & 27278 | FOXR2 | AACCAGACGACAACTCCCTCCA | ATCTCCTGCACACTGAGGGCCA | 27383 & 27384 |

| GeneName | Forward Primer | Reverse Primer | SEQ ID NOs | GeneName | Forward Primer | Reverse Primer | SEQ ID NOs |
| --- | --- | --- | --- | --- | --- | --- | --- |
| GATA4 | CATCTCACTACGGGCACAGCA | GTGGAGGACTGGCTGACGGGA | 27809 & 27810 | GDAP2 | GAATACAATCACCTGGACTCCGA | AGCTGGTGGAGGCTGTCCACA | 27915 & 27916 |
| GATA5 | CCACTTCGAAAGCCAAGCCCA | TCCAAGTGGCCGGGGGGCA | 27811 & 27812 | GDE1 | CAGGCGTGGAGTTGGACA | CACAATCGCCAGTCCCA | 27917 & 27918 |
| GATA6 | GAGAGCACCAATCCCGAGA | GGAATTCCGGTCGCACGGA | 27813 & 27814 | GDF1 | GGACACTTGGCGCAAGGA | GCCAAGGCATGCAGCCGA | 27919 & 27920 |
| GATAD1 | ATTGCCAGAAGAGTGCAGGA | GTCTGGTGGGAACTGTGGGAA | 27815 & 27816 | GDF10 | GCAGGAAGAAGGGCCAGGA | ATGGTTGGATGGACGAACGA | 27921 & 27922 |
| GATAD2A | AAGAAGACGCCCCTCAGCACA | CACGTGCTGACTGGGGGA | 27817 & 27818 | GDF11 | CGGCGGAACCTGGGTCTGGA | AGGTGCGATGATCCAGTCCCA | 27923 & 27924 |
| GATAD2B | CTCACAGGCTGCACGCA | TGTGCGGCACTGGGCACA | 27819 & 27820 | GDF15 | CCGTGCCAGTCGACCAA | GCCAGGTCTTCCAGGGA | 27925 & 27926 |
| GATB | GAAGAGGGAAGGCAAGACTCCA | TGAGGATGGGCCTTCCATCACA | 27821 & 27822 | GDF2 | CGATGTGACGCGACGAA | ATGGTACTTGAGGGTGGGCA | 27927 & 27928 |
| GATC | CGGGGTGGAGCCATGGAA | AAGTACTCTCCACGACGGA | 27823 & 27824 | GDF3 | AGCCATCCTGTCCCAA | AGATGGTCAGTGAGAAGGGACA | 27929 & 27930 |
| GATM | GCAATGCCTCGAGACATCCTGA | CACTTGGCGCCACGGTGGA | 27825 & 27826 | GDF5 | CAGGGCAAGCGACCCAGCAA | CCTCGTACTCAAGGGGTGCGA | 27931 & 27932 |
| GATS | GCCAAGTCAGTCATCGCCCCA | TGATGACAACGTGTGGGTGACA | 27827 & 27828 | GDF6 | TCGCCATGGCAAGCGGCA | GTCGATACACCCTCGA | 27933 & 27934 |
| GBA | GCCTGTTCCCCAACACCA | TCCAGTCGGTCCAGCCGA | 27829 & 27830 | GDF9 | CCGCACAGGTACAACCTTCGA | GTCTTGGGCATGAGGAGTCCA | 27935 & 27936 |
| GBA2 | TGGGGCACAGGACATCCAGGA | ATAGTTTGGAGAGCACGGACCA | 27831 & 27832 | GDI1 | GGGCGTGAAGTCTGAGGGGAGA | CTTGATGGGGTGGCTAAGGA | 27937 & 27938 |
| GBA3 | GAGGCTGGGATGCAGATGGAA | TCCACAGAGTGTAGCTGCCA | 27833 & 27834 | GDI2 | TGCGCACAATGTAGCAGCA | TGGTACCAGGAGGTCACTGA | 27939 & 27940 |
| GBAS | CTGTGCCAAGATCCGGACCTA | TGCACCATGTACAGCTGCCCA | 27835 & 27836 | GDNF | GAGAGGCCAGAGGGGGCAA | ATCGCAAGAGCCGCTGCA | 27941 & 27942 |
| GBE1 | AGGGCATCAGAAGATGAGGGCCA | ACATTCTGAAGGATGCTGGAGA | 27837 & 27838 | GDPD1 | CCGCGGAAGGTGCTGGAGA | TTGCGAAGTAAGGTGGGA | 27943 & 27944 |
| GBF1 | GTGCTATCCCGAGTCAGGCCA | AGCCGATGCACTCCAGCA | 27839 & 27840 | GDPD2 | AACAGAACCGAGAGGCCCCA | AATAAGCCAGATAGGGTAACGCA | 27945 & 27946 |
| GBGT1 | ATGGAGACCATCAGCCAGGA | GCCTGCCGTCATAGGGGA | 27841 & 27842 | GDPD3 | AGAACGAAGAGCTCATCCGTGA | AGCAGCCCAGGTAGTAGGA | 27947 & 27948 |
| GBP2 | GGCCTCATCGCACACACCA | GGGATAGGAGCACACCACA | 27843 & 27844 | GDPD4 | AGAATTTGGGGCCAAGCCAA | GTCTCCAATCATGGGCCTCA | 27949 & 27950 |
| GBP3 | CTGAAGCTAACGCAAGGTACCA | GCGGTGAATGGGCAGAATGA | 27845 & 27846 | GDPD5 | GGATCATGCCCCGGACGA | CGTATGCCACCCAGGCGCCA | 27951 & 27952 |
| GBP4 | GCCCACTCTTCTAAGCCA | GCTGCTTAGAAGCACAGCCA | 27847 & 27848 | GDPGP1 | GGTGCACTGAGGGCAGGGA | CGGGCAGTCTGTGGGCCA | 27953 & 27954 |
| GBP5 | TGGCTGGCAAGCAACAGA | CTGGGCGTGCTGGAGCTCA | 27849 & 27850 | GEM | GCGAGCTTCAGAAGGCA | TGTGCTGGACAGCTGCAGA | 27955 & 27956 |
| GBP6 | GATGTGGTGCGTGCCCA | GACAAAGGTGCTGCACGGA | 27851 & 27852 | GEMIN2 | GATGCCAACCCCGCCCTGA | CTGGTCCAACGAGCTCGTCA | 27957 & 27958 |
| GBP7 | ATGCCATCAACAGTGGAGCGA | CAAACTGCATGCACGTCCAGCA | 27853 & 27854 | GEMIN4 | CCGTGAAACCCCAAGGGA | CGGTCCAAGAGCTGGCACA | 27959 & 27960 |
| GBX1 | CAGGCGGTGACAGCGAGGA | ACCGGTCGCCCCTCCTCA | 27855 & 27856 | GEMIN5 | CATCAATCCCCTGCCACACCA | CTGCTTGGCTCAACAGAGA | 27961 & 27962 |
| GBX2 | CGGCGCGTAACTTCGACA | ACCGTCTCGGCCGTCGAGAA | 27857 & 27858 | GEMIN6 | TCCGAGTGCAGACCAGTCGAGA | CAGTCTGCACAGCATGTCCA | 27963 & 27964 |
| GC | AAAGAGCTGCCTGAACACACA | CATCTGGAAGCTCGGGGA | 27859 & 27860 | GEMIN7 | TGAGGCCAGAGAGTTCCTGA | TGAAGCTCACCTGATGACCCA | 27965 & 27966 |
| GCA | CTGGGCCAGCATATTCAGACA | TCACCATCCTGTCCAGCAA | 27861 & 27862 | GEMIN8 | AGAAGATCTGGGCAGCATCCA | TCTGCAAAGTACTGCTGGA | 27967 & 27968 |
| GCAT | CTATGCGTGCCAAGACCCAGA | TCTTCAGCATGTCATCGCCA | 27863 & 27864 | GEN1 | AAGGGGAACCACCAAAGCTGA | CAGCTTCCCACGTCCTGA | 27969 & 27970 |
| GCC1 | TGGACTTCAGGGACCGCACA | TTGGGTCAGGCTATCAGAGGA | 27865 & 27866 | GETA | GCACTCAGCGGACGGGGA | CGTCAGCTTCCCACCGTCA | 27971 & 27972 |
| GCC2 | TCCGAGATCAAGTCGGACA | TGTGCATGTCTAGAAGCGGGA | 27867 & 27868 | GFAP | TCGGGAACTCCAGGAGCA | GCATGTTGCTGACGCCA | 27973 & 27974 |
| GCDH | ACAGCGGAAGTGCACCCA | CATCTTCACACCGAGCCCA | 27869 & 27870 | GFER | ACAGCACCAAGACATGGCCCA | AGTCGAAGTCAGGCTTGCCCA | 27975 & 27976 |
| GCFC2 | CCCGGGTTCTGCGGAGGA | CTTTGGTGGCAGCCGGGA | 27871 & 27872 | GFI1B | GGCCACGCTGTGAGCCTGGA | AGGTGGGTGGCAGCCGTGGA | 27977 & 27978 |
| GCG | GGACTCCAGGCGTGCCCAA | CCTCGGCCTTTCACCAGCCA | 27873 & 27874 | GFM1 | GTGTGCAGGCCAGTATGGAA | AGCCAGAGAGCTTGTGACCA | 27979 & 27980 |
| GCGR | GCGGAACACCAGCAGCCA | CAGCCAATCTAGGGAGGCCA | 27875 & 27876 | GFM2 | TCATGGCCCAAGAGCGAGA | TCTGGGCCTCTACACCAGCA | 27981 & 27982 |
| GCH1 | CTCAGCAAACTTGCGAGGA | CAACCACTACCCCGACTCA | 27877 & 27878 | GFOD1 | CATCCCGCTGCTGAAAGACGA | CACACAAGGTCCACGTCCTGA | 27983 & 27984 |
| GCNIL1 | GTGGGCGATGAACAGTCGGA | TCTGGCCCACCCCGTCA | 27879 & 27880 | GFOD2 | CACGGGCTGTCTCAAGACA | CCTGCAGAGCCTACCACCA | 27985 & 27986 |
| ACRC | TCTGGACAGTCCAAGGCTCGA | TGCAACCTGGACATGGCAGGA | 27881 & 27882 | GFPT1 | CCGGTTGGAAGAAAAAGCA | ACAGCTCGTTCGGGGTGA | 27987 & 27988 |
| GCKR | GAGCGAGGACGGAAGTTAGCA | GAGCAACATGTGGGGCA | 27883 & 27884 | GFPT2 | GATGGTTCGATGAGCCACAGCCA | GTCACTCGCCAGTCGGAAGA | 27989 & 27990 |
| GCLC | GTGGGCACAGGTAAAACCAA | GGATAGCCACAGCGGCCA | 27885 & 27886 | GFRA1 | CCACTTCTCCCAGACGGGA | TCCCACAGGCTGGGGA | 27991 & 27992 |
| GCLM | ATGGCGATCTACAAGCGTGGA | GGAGAGAAGCTGCAAGGCCA | 27887 & 27888 | GFRA2 | GGCCTCAGGACCTTCCACGGA | GTCGGTCGAGGCCAAGCAGA | 27993 & 27994 |
| GCM1 | TTGCCGGCCATCAGACCCA | CGGAGCCAGCCCAGAACAGA | 27889 & 27890 | GFRA3 | TACGAGCATACCTGGGCCTGA | AGCAAAGGTAGGGTGTGGCCA | 27995 & 27996 |
| GCM2 | TCCAGTGTTGCGGAAGGA | CCACCTGAACCTGTCCCCA | 27891 & 27892 | GFRA4 | CTTGGACCAGCTGAACCCCA | GAGCCAGGACAGGAAGTATGGA | 27997 & 27998 |
| GCN1L1 | GTGGTCCAGAAGAGTCCGAA | GAAGACCCCTGGTGTCACCA | 27893 & 27894 | GFRAL | GGCAGAGGCATGTGTGAGGGGA | TGAGGCAAGTAGGGGGGTGGA | 27999 & 28000 |
| GCSAM | GGGCCACCATCCAAAGGA | ATGCACACTGAGCGCACA | 27895 & 27896 | GFY | CGGCTTCCGGACGACGGAGA | GGTGGGCGATGTGGGAAGGGA | 28001 & 28002 |
| GCSH | ACCACCGTGTTGGACGGA | TCTTGAGGACGAAGTTAGCA | 27897 & 27898 | GGA1 | GATGGTTCGATGAGCCACAGCCA | GTCACTCGCCAGTCGGAAGA | 28003 & 28004 |
| GDA | CCAACACCCCAAGTACGACA | TCCCCAGCCCCATAAACGCA | 27899 & 27900 | GGA3 | CCACTTCTCCCAGACGGGA | TCCCACAGGCTGGGGA | 28005 & 28006 |
| GDAP1 | CCAAGGAAGCACCCCCCA | ATCAGACACATCCTGGGCTGA | 27901 & 27902 | GGACT | GGCCTCAGGACCTTCCACGGA | GTCGGTCGAGGCCAAGCAGA | 28007 & 28008 |
| GDAP1L1 | TAAAGCCTTCTACAGACCCA | GAGAAGGCGACTGAATGAGCCA | 27903 & 27904 | GGCT | AAGGAGCAGAGAACTGACTGACA | CTCTGCCAGTAGACTACCAGCA | 28009 & 28010 |
| | CATATGCCTTCTACAGACCCA | TCAGAAGGGCCATAAGTGGA | 27905 & 27906 | GGCT | AAGGACGTTCACGGGTCTCAGA | AATCCTGCAGCGGGCCACA | 28011 & 28012 |
| GCSH | CACAGGAAGCGGTTGGGAGA | CAGTGTCATCTTGATCAGCCA | 27907 & 27908 | GGCX | GTGAGTGAAGACCTTGGGCA | ATGTACTTCACCAGCAGGCA | 28013 & 28014 |
| GDA | AGGAGCATCCATCGCACA | ATGCACACTGAGCGCACA | 27909 & 27910 | GGH | GTTGACCTCAGACGGCTCAGA | CCAGTGAAGTTCAGCGGCA | 28015 & 28016 |
| GDAP1 | CGGAAAGCGACCAACTGCAGA | ATGCTGGTCGCAGCACTGCAGA | 27911 & 27912 | GGN | CCTCTCAGACATGGGGCAGCTA | GGCCACCAGGAGCCGGA | 28017 & 28018 |
| GDAP1L1 | AGAAGAGGAAGCTGGAGAACGA | CCAGGAACTTGAGGGGGTGCA | 27913 & 27914 | GGNBP2 | TCACGCGAAGTTCCTGAGTGCA | TAGGGGTTCAAGAGCAGGA | 28019 & 28020 |

| GeneName | Forward Primer | Reverse Primer | SEQ ID NOs | GeneName | Forward Primer | Reverse Primer | SEQ ID NOs |
|---|---|---|---|---|---|---|---|
| GPR39 | TGCCGGCCAAACCAAGCAGA | GTCGGTGGTGGAGTGCGCA | 28657 & 28658 | GRAP2 | ACGAGCTGGGGTTCCACA | GGTCATGGGTGCCACGTA | 28763 & 28764 |
| GPR4 | CAACTGTGTGGCGGACCCCA | GGGTCTCCAGGGTGGAGCGA | 28659 & 28660 | GRAPL | CTCCGGGGTGTCGAGGGA | TCTCACTCTCCCGGATCAGGA | 28765 & 28766 |
| GPR42 | AGGGAGGGGGAGGAGCAGAGA | ACCTGGCCACAGTTCCACA | 28661 & 28662 | GRASP | AATGGCTCGAATGTGGAACGCA | GGTACTGCAGACGAGCCTCCA | 28767 & 28768 |
| GPR45 | AGACCAAGGCCTTCACCACCA | TGGAAGGTCTGGGGCAGCA | 28663 & 28664 | GRB10 | TACAACGCCCCTACAAGACCA | CACGAGGGAGTTCTCGCAGA | 28769 & 28770 |
| GPR50 | GCCTCCCATTGCCCGAGA | TAGGGTCAGGAAGGTCAGCGA | 28665 & 28666 | GRB14 | TCTCAGGCGCCAGAAAAGCAGA | GTGAAGAGGCAGTGGGGCTA | 28771 & 28772 |
| GPR52 | TCCACAGGTGTCACGAGTCA | AACCAGGTTTCCCCAGCCA | 28667 & 28668 | GRB2 | TAGCAAACAGCGGCAGA | CCAAACTTGCAGAGAGGAGA | 28773 & 28774 |
| GPR55 | TACCCGCTACTGGTGTGAGCCA | AGCCAAACACCTTCCAGGGGGA | 28669 & 28670 | GRB7 | CATCCTGCCGAGCGAGGA | GCGTGCAGCAATGGCGCA | 28775 & 28776 |
| GPR6 | TGCCTTCCGAAGCCAAGAGA | CACGGGCGAGCCCTTCAGA | 28671 & 28672 | GREB1 | CCCCAAGGTGGTGGGAACAGA | TGGTTCTCCAGAGGCCACCA | 28777 & 28778 |
| GPR61 | CCTGGCTGTGGGGGGGACA | AAGTAGCCAATCCAGGTGACCA | 28673 & 28674 | GREB1L | GTGGTCGACATGGAGCACGGA | AGTACTTGCCGGTACAGAGGCA | 28779 & 28780 |
| GPR62 | CTGGACGACTTCACCCCAA | GCAGCTGAGGTCCTGGAGGA | 28675 & 28676 | GREM1 | GCTGCAACAGTGCCACCA | GGGCTTGCAGAAGGAGCA | 28781 & 28782 |
| GPR63 | ATACTTCCCAGACGTCCCCA | TCTGCAGACTCATGAGACCCA | 28677 & 28678 | GREM2 | CACCGAGCGCAAGTACCTCA | GGGCTTGCAGAAGGCCA | 28783 & 28784 |
| GPR65 | CTGCAACCGGAAAGTCTACCA | ATGCAGCGAATCAGCAACA | 28679 & 28680 | GRHL1 | TGACAAGGGAGCTGAGCGGAA | AGACAGAGCCTTCACCCTCCA | 28785 & 28786 |
| GPR68 | TACCCCATCCAGGCATGGCA | GCAGCAACACGTGGTAGGGCA | 28681 & 28682 | GRHL2 | AGGGCCCATGACCTACTCA | ACCACCATCACCACACTCCTGA | 28787 & 28788 |
| GPR75 | TTCGAGCCATGGGAAAAGGGA | GGTCGAGCTGCTCTGACCACA | 28683 & 28684 | GRHL3 | GACCTGAAGGGGGCTGAGGAA | GCTCCCCATGTCCAGGA | 28789 & 28790 |
| GPR78 | GTGGCGACCGTTGGTGCACA | TCTTCAGCAGCTGGTGACCA | 28685 & 28686 | GRHPR | CAACATCAGCAGGGCGA | TCGTCACATCCAAGTCCAGGA | 28791 & 28792 |
| GPR83 | TGCCAGACTTCCCTGAGCCA | ACGAGCGTAGGCCACAGAGA | 28687 & 28688 | GRIA1 | ATGGTGGTCGACAAGGGCGA | GTCCAAGTCTCCGATCAGGA | 28793 & 28794 |
| GPR84 | CCCAGCCAATTAAAGGAGCCA | AAGGGATGTAGCTCAGGGCA | 28689 & 28690 | GRIA2 | ATGAGGAACAAGGCAAGGCTGTCAA | TCACGTAAGGGACAGCATGCA | 28795 & 28796 |
| GPR85 | AAAATGCAAACACCAACGACAGA | CACCAGGTAGGGGCCCA | 28691 & 28692 | GRIA3 | ACCAACCAGAACACCACCGAGA | CCTCTGCAAGACTGGAGCA | 28797 & 28798 |
| GPR87 | AATGGTCAGCCAACAGAGGACA | TCAGAATCAACGCACCGCCA | 28693 & 28694 | GRIA4 | ATTCAAGGGCTGCACAGGGAA | TAGCAGCTGTGTCATTGCCA | 28799 & 28800 |
| GPR88 | TACCACATCAAATCTGGCCCA | CCCAGGCGTGCAACAAAGCA | 28695 & 28696 | GRID1 | GCTGTGACCTCACCAGCCA | CACCAACTCAGGGCA | 28801 & 28802 |
| GPR89A | GGGAAGTGAGGCAGGA | GCAAACGTCACGGAGAAGA | 28697 & 28698 | GRID2 | AGGTGCTTGAGCACCGGA | ATTACCCAGATTGAGCCCCA | 28803 & 28804 |
| GPRASP1 | CACCTGTGAGTCCAAGCCAGA | CTCATCTCCTGCCCAGAACCA | 28699 & 28700 | GRID2IP | CAAGGTAGAGCAGAGAATGGGGA | CACCATCGTCAGGTGAGA | 28805 & 28806 |
| GPRASP2 | GGAACTGAGGAGGGGGCCA | ATCTCTGTCCAGAACCAGGA | 28701 & 28702 | GRIFIN | CTGGTCCAGGGACATGCTGA | CCACACAGTGGCGCTGGA | 28807 & 28808 |
| GPRC5A | TCACGGGCTGGGAAGAGACA | CCCAGCCATTGGCAGCCA | 28703 & 28704 | GRIK1 | GAAGTGGTGGCGTGGGAA | ACCAGTCGGCAGCCAGA | 28809 & 28810 |
| GPRC5B | TCCCAACGGCACGCTTGGGAA | CCGTTGACACACGGCCA | 28705 & 28706 | GRIK2 | AACGATTGCAGGCACTCCGAA | GAAACTGTTGAACGGCCACAGA | 28811 & 28812 |
| GPRC5C | TGCTCCTCACACAGCA | TAGAAGAGGACGAAGGCCCA | 28707 & 28708 | GRIK3 | CAAAGCCTGTCCACACGCA | CCATGCGCTCCACGGTCAGA | 28813 & 28814 |
| GPRC5D | TGCCCCGTCAGCCTACCAA | GGATCAACAGTCTGCGGCTGA | 28709 & 28710 | GRIK4 | TCGGGGGTTCATGCAGCAA | TCATCCACTGACTCAATGGCCA | 28815 & 28816 |
| GPRC6A | CTGCACCAAGATTACCACCA | GTCACTGGGAAGCAAGTGCAGA | 28711 & 28712 | GRIK5 | TGACCCTGGGGATTAGGCA | GCTGACGCCAAGGTAGGCA | 28817 & 28818 |
| GPRIN1 | GTCACAGTCTGGGCTCACAGA | ACACTGAGTGGGTCACAAGGGA | 28713 & 28714 | GRIN1 | ACGCACGGTGAAGCAGA | AGGGCCTCGAACTCAGCA | 28819 & 28820 |
| GPRIN2 | TGCAGGCTCAGCATGGGGTGA | CAGGCTCTGGGACTAACCCA | 28715 & 28716 | GRIN2A | CGCACAGTGAGACCAGCGA | GGCTGAATAGGTGGGCA | 28821 & 28822 |
| GPRIN3 | AGGTTCTGGCAAGAAGACCCCA | TGAGCAGCAGCTGCTGTCACA | 28717 & 28718 | GRIN2B | CCGGACATCACCACCA | TGGTGACAAGGGCCGGA | 28823 & 28824 |
| GPS1 | GGAGAGCGTGACAGTGACA | AAGGAGCTGCTGGAGATGACA | 28719 & 28720 | GRIN2C | CAAGAAGTCTCGGAGGCCCA | CTTGTCACTGAGGCCGACA | 28825 & 28826 |
| GPS2 | CAGATGCAGCCAGCAGGA | TGGATGAAGGGGAGCCGA | 28721 & 28722 | GRIN2D | ATGGCATCCGCCCTGCACA | TGTAGAAGACGCCCGCCA | 28827 & 28828 |
| GPSM1 | TGGACGACCAGCGGGGCCA | GGGCAGCCGCTGGTCATCGA | 28723 & 28724 | GRIN3A | CGGAACCACCAATGGGAAAGCA | CAGCTGCAGCTCTGCACGGA | 28829 & 28830 |
| GPSM2 | TAATGACAAGGTGCGAGAAGCA | CACAGCGCTGCTGCAGCA | 28725 & 28726 | GRIN3B | AACTCGCCGCTCACCTCCAA | CGCTTGCCGCAAGGCACCA | 28831 & 28832 |
| GPSM3 | ATCTTCAGTCACCAGTGCCA | GCTCCTCCATTTGCACCCCA | 28727 & 28728 | GRINA | GCCGTGGGCATCACCACA | GAGGAAGCAGGTGAAGAGCA | 28833 & 28834 |
| GPT | GCGGACGAGGGTGCTACCAGGA | TGGAGGTGGAGTGGAAGGA | 28729 & 28730 | GRIP1 | TACAGCCAAACACTCCTGGCCA | CCACCAAGATCTCCTGGCCA | 28835 & 28836 |
| GPT2 | GGAGGGCTCCCAGCCCCA | GCTTCTCCAGGTCGAGGGAGGA | 28731 & 28732 | GRIP2 | TGGGCCCGGGTGCGAATCCA | GGAAGCTCAGAGGGAAGCA | 28837 & 28838 |
| GPX1 | GCCAGCTCCCAGCCAGGGA | TCGTTGCGACACACGGA | 28733 & 28734 | GRIPAP1 | GCAGCCAACAGCAGACCGCA | ACTCCTTGCTGAGCCGCCA | 28839 & 28840 |
| GPX2 | CCTGAAGAGACAAGCTCCCCTA | CGGCACAGGGGCTCCAA | 28735 & 28736 | GRK2 | CCGGCAGCAACAAGACCAA | CCATCTGCCAGTCCAGGGA | 28841 & 28842 |
| GPX3 | TACAGGAAAGAGCTTGCACCA | GAGGCGGTCAGATGTACCCA | 28737 & 28738 | GRK4 | ACATCAACTTCAGGAGGCTGGA | TAGATCCCTTCACCACCGAGA | 28843 & 28844 |
| GPX4 | CCAGTGAGGACAGGAGA | CCCGAACTGTTACAGCGGA | 28739 & 28740 | GRK5 | AGCGGCTTAGAACGCGGA | GAGGCCCTTCACAGTGGAGA | 28845 & 28846 |
| GPX5 | CAAAGACGAGAAGCCACCA | ACCAGGATATTGCGCTGTCAGA | 28741 & 28742 | GRK6 | CCGTTCAAGCCTGACCCCA | TGGAAGCACCTCGGTCTCCA | 28847 & 28848 |
| GPX6 | AACAAAAGGGTGAACAAGGCACCA | CCAAGCCTCAATAGGCCGCCA | 28743 & 28744 | GRK7 | AGCTGGCCTCAATTGAACCCCA | TACCCCTCCACAACCCGTA | 28849 & 28850 |
| GPX7 | CTACCAGTACCGCGTGA | GGGCACCAGTACCGCTCA | 28745 & 28746 | GRM1 | TACTGTACCGGGACACCCA | ATGCAGAGGAGGCAGCA | 28851 & 28852 |
| GPX8 | GTGCCAGTGACTGCCAA | CCAACACGGCTGAAGTGGGA | 28747 & 28748 | GRM2 | CTTCGAACTGCCCCAGGA | GAGGAAGAACACCACCCAGCA | 28853 & 28854 |
| GRAMD1A | CTGGAGGAAGGCGGGAAGGA | GAGCAGGAGGTGAGGGCGA | 28749 & 28750 | GRM3 | CAGCCTGCTGACCAAGACA | TGCACCAGGATCAGACCCA | 28855 & 28856 |
| GRAMD1B | AGGTTCCACAAGGACGGCA | TTGGAGCCTTAGACCCTGCCA | 28751 & 28752 | GRM4 | GTGGTGGACTTCCAGGACCA | ACACGGTGCACGTGACCA | 28857 & 28858 |
| GRAMD1C | CAGGCCATTGAAGACCCTGGA | CCTTTGGCACCTAAGCCCACA | 28753 & 28754 | GRM5 | CCAAGGCACCTGGAGGA | AGAGGGCCGACTGGACA | 28859 & 28860 |
| GRAMD2 | AGATGCCGAACTGCTCTCCCA | ATGAGGACATGGACCACCACGGCACCA | 28755 & 28756 | GRM6 | GCGGTACAACAACACCCCA | AGGCTCAGCCACCATGAGGA | 28861 & 28862 |
| GRAMD3 | TTCTAGTGCCAAACGCCTGA | GAAGGGCGGTCTGCTCGGA | 28757 & 28758 | GRM7 | ATCGCTACAATGACACGCCA | AAGCCCAAGAAAACTCGCCGGA | 28863 & 28864 |
| GRAMD4 | CCACAGCCACAAGGACCTGA | AATTCTCCGTGACGTAGAGCA | 28759 & 28760 | GRM8 | AGCCTGCCGTGTAAGCCA | CACCACGGCCAGCAGGGA | 28865 & 28866 |
| GRAP | CTATGGAGACCAGGTGCAGCA | GGTGCGGTAGAAGTCGACCA | 28761 & 28762 | GRN | CTGCCGAGACAACCGACA | GCGAAGCCAGCAGGACA | 28867 & 28868 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| GRP | GGCCCTGGGCAATCAGCA | CACGTTGAGAACCTGAGGCA | 28869 & 28870 | GTF2E2 | TCAAGGCTTTGGGGGACCAGA | TCTACAGTGACACTCCTCCACA | 28975 & 28976 |
| GRPEL1 | GAACCCTGTCGGAGCCAA | GGTCTCAGAGTGCGCCCA | 28871 & 28872 | GTF2F1 | CGCAGGAGGAAGAAGCGCA | CGCCATGGAAGAGGGCTGA | 28977 & 28978 |
| GRPEL2 | CCGCGTGGGAGGAGCAAGGGA | GTTCAGCAAGAGGGGGGCCCA | 28873 & 28874 | GTF2F2 | TGGGAAACTGCGGATTGCCA | TCATGGCAGCTGGTCGGCA | 28979 & 28980 |
| GRPR | AGCTGTGCCCCATACCCACA | GATGACATGATTGGGGAGGCCA | 28875 & 28876 | GTF2H1 | GTGCGTCAAAAGAAGCAGGA | GTCCCTGCATGTAGAGACCA | 28981 & 28982 |
| GRSF1 | TGCCTAAGGAGGTGCCGA | CCTATGATGAACGTGGGACCTGA | 28877 & 28878 | GTF2H2C | CTAAGCGATGGGAAGGAGGCTA | CTACCATAAAGGTGGCGCA | 28983 & 28984 |
| GRTF1 | GGAGGACGCCATGCAGGACAGA | ATGGTGCCATATGCCAGCA | 28879 & 28880 | GTF2H3 | GCAGAAGACAGTGCGTTGCA | GAAGAGAAGGCATCTGAGGCA | 28985 & 28986 |
| GRWD1 | CACACACGCTCTGTGGAGGA | GGATGTCCAGATGCGGGA | 28881 & 28882 | GTF2H4 | AGCAGGCAATTGCCAGTGCA | CGGTGATGGTGGGGGGCA | 28987 & 28988 |
| GRXCR2 | ACTGCCGAGGGTGGGCA | TGCAGGCAGGGCACTCTA | 28883 & 28884 | GTF2H5 | TGAGTCCAATGCCCTGGGGAA | TCACCACTCGCTCTTGGA | 28989 & 28990 |
| GSAP | GTCTGCGGGCATACGTGAGGAA | GCTCAGACACATCAGCCCCA | 28885 & 28886 | GTF2I | ATGAGAAGATGCTGCGAGACCA | TACCATCACGACCACCTA | 28991 & 28992 |
| GSC | CCCTACATGAACGTGGGCA | TCCTGGAAGAGGTTCTCGAGA | 28887 & 28888 | GTF2IRD1 | CATCAACACGCTCCGGGA | TCCGCTTCAGCTTGGGGA | 28993 & 28994 |
| GSC2 | GAGCAGCTGCAGCGCTCGCGA | AGGAGCGCTCGCGGAAGCCGA | 28889 & 28890 | GTF2IRD2 | GCAACAGCGGTCCTGAAGAAGAA | AATGGAGAACAGCTGTTCGCA | 28995 & 28996 |
| GSDMA | GAGGAGCTGACCCTCACGGA | AAGAGCACAGAGGCGAGGGA | 28891 & 28892 | GTF2IRD2B | TCTCCTCAAGGACACTCCCAA | CAGGGTGGGAAAGTGGGCCA | 28997 & 28998 |
| GSDMB | GCAAGGAGGATATTCGGCAGGA | TTGCACGCGCTTCTACCAA | 28893 & 28894 | GTF3A | TGTCCAAGAGAAGGCTGTGGA | TATCCACTGAGATGAGAGGCCA | 28999 & 29000 |
| GSDMC | AACTTCAGATACCCCTGGAGCA | TCCAGCTCCATCCTAAGGCCA | 28895 & 28896 | GTF3C1 | AGGCAGCTCAGGGCAA | CAGACAGGTTCCGACCA | 29001 & 29002 |
| GSDMD | TGGGCAGCCTCTTGAGCAGA | CAGGGAGGCGTAGAGTGCA | 28897 & 28898 | GTF3C2 | TAACTCACCCCTGCAGGGAA | GTAGGGAAGCAGCCAGGGCA | 29003 & 29004 |
| GSE1 | GCTCCGTGCCATGAAGGCA | CCAACCGGCTTCTCCACA | 28899 & 28900 | GTF3C3 | CGCACTCACCCTGACGAA | CACAAGTGGAGGGAGCTCCA | 29005 & 29006 |
| GSG1 | GGTCCAGAAGACTGGAGACCA | TGAAGGTGGTGACAGCCGA | 28901 & 28902 | GTF3C4 | CTGCACACCTGGATCACAGA | GTTAAGAAGCACCCGGAGCCA | 29007 & 29008 |
| GSG1L | CATGCAGCGGCCTGACCTCAA | GAGGCTCACGGTGACCTGGA | 28903 & 28904 | GTF3C5 | GCAATGACGGGGCAAGGA | CAGGCCTCTTGGAGCGGA | 29009 & 29010 |
| GSG1L2 | GCACAGAAACGGCAGTCCGCA | GCTTGTTCAGCAGGGCAAGGA | 28905 & 28906 | GTF3C6 | AGACGAGGAAGAGGAGGAGGCA | CATACTCCCAGCAACAAAGACACA | 29011 & 29012 |
| GSG2 | ACCGAGACTTACACTGGGGGA | CCATCCCGTTCCAAGCGCGA | 28907 & 28908 | GTPBP1 | CAGCCTGGAGTTGGACCAAGA | GGCCTGTGCATGCCGAAGACA | 29013 & 29014 |
| GSK3A | GCGATGTCTGGGAACCCA | CTGGGGACCTCAAGTGAGGA | 28909 & 28910 | GTPBP10 | TGGGTTGTAGCCCAGAACAGA | TGCTTCCACTCCAGCCACA | 29015 & 29016 |
| GSK3B | CTCGGTACTATAGGGCACCA | CTACCAACTGATCCACACCA | 28911 & 28912 | GTPBP2 | CATGCAGCAGCTGACCGAA | GCCAGTGTAGCAGCCTGACTA | 29017 & 29018 |
| GSKIP | AACTCACTGAAGCAGGGCTCA | CTCGGTAGGCGGGGGCTGA | 28913 & 28914 | GTPBP3 | CTGAGGAAGGAGCTAGCTGCA | GTAGTGGCCGAGGGCATCCA | 29019 & 29020 |
| GSN | TGGGAGGTTACCCCTGTCCAGA | CAGTGCACCAGCCTTAGGCA | 28915 & 28916 | GTPBP4 | GCCATTACGGCAGTCCAGGCA | GGAGTTCGAGACCAACTCCCA | 29021 & 29022 |
| GSPT1 | CCGCAGAGAAGGCAGTGCCA | GCCAGCATCTACGTGCCCA | 28917 & 28918 | GTPBP6 | CCCTGGAAGAGGTGCCGA | TGCAGGCCACGCAGCGTGGA | 29023 & 29024 |
| GSPT2 | GCCCCAGAAGAAAGTGGCCA | GCCAGCGTCTACATGGCCAA | 28919 & 28920 | GTPBP8 | CTTCACGGCCACTGCAACCGA | ACACACCTCTGGCCGCGGAA | 29025 & 29026 |
| GSR | TACCCGATGTATCACGCA | CACACCCAAGTCCTGCA | 28921 & 28922 | GT5F1 | AAACTTACCACGCACTCCCTGGA | TGGTGGCGAGCATTGAAGGGA | 29027 & 29028 |
| GSS | GTGCACCAGGAGGTAAGCA | AACCGGCTAGGGGCAGCA | 28923 & 28924 | GT5F1L | CACCGAATCCCACCAACGTGGCA | TGATGGGACCAACGTGGCA | 29029 & 29030 |
| GSTA1 | ACGGGGCAGAAATGGAGTCCA | GTCTGCACCAGCTTCATCCA | 28925 & 28926 | GUCA1A | GACTGAGAGGAGTTCACCGA | GTGTCAGTGTGTCCAGGAGCA | 29031 & 29032 |
| GSTA2 | TACGGGGCAGAATGGAGTCCA | GTCTGCACCAGCTTCATCCCA | 28927 & 28928 | GUCA1B | CAGCTGCTCACACCGAGGA | CCCACTTGTCCCGACGGGCA | 29033 & 29034 |
| GSTA3 | AAGTTGGTACAGACCAGAGCCA | CCTCAGCTGCAATAAGGGCA | 28929 & 28930 | GUCA1C | CAAGCCTCCAATGCCCAGGA | CCTAGACCAGCTTCTGTCAGGA | 29035 & 29036 |
| GSTA4 | AATCAGCTGAGCCTTGCCA | GAGGCTTCTTCTGCTGCCA | 28931 & 28932 | GUCA2A | GGAGCCCAATGCCCAGGAGA | CGGAGGGAGGGCAGGGA | 29037 & 29038 |
| GSTCD | CAGCAGTCAGGCCCAAAGGAA | AACCTGACATGATGGCAGCA | 28933 & 28934 | GUCA2B | CCGGTTCAGCTGGAATCCA | GAAGCCTCCTGCGAGGCGCA | 29039 & 29040 |
| GSTK1 | GGCAGCCTGCAGATACGGA | AGCAGCTCATCCGGTCA | 28935 & 28936 | GUCD1 | CCAGCAGCTTCTACCACTGGGA | AGTGGTGCATCAGGTAGGCCA | 29041 & 29042 |
| GSTM1 | CAACCATATGCAGCCTGCA | TGGGAAGGCGTTCAAGCA | 28937 & 28938 | GUCY1A2 | CTGGTGATGTAGCACTGGGCA | GCATGGGACTATACTGGCA | 29043 & 29044 |
| GSTM2 | CCTGCAGGCACTCCCTGA | TGGAAAGGCATCCAAGGCA | 28939 & 28940 | GUCY1A3 | CAGCTGTGGCAAGGGCAA | GATGACCTGCAGCGGTGA | 29045 & 29046 |
| GSTM3 | TCGAAGCCAATGGATGTAGCGCA | TGCGAGGCGATGTAGCGCA | 28941 & 28942 | GUCY1B3 | GAATCACGCATCAGCCCA | CAGGCTGGACTGTGGGGA | 29047 & 29048 |
| GSTM4 | GTGGGAGACGAGCAAGAGGAGA | TCAAAGTTCAAGGGCTGTAGGCAGA | 28943 & 28944 | GUCY2C | AGAGGGACAGGGCTGACGATCACCGA | CCACATGTACGCATCACCGA | 29049 & 29050 |
| GSTM5 | GGGCTACATTGCCGCAGACA | TAGCACAGTCTGACCAAGCTCCA | 28945 & 28946 | GUCY2D | CGCGGACAGAATCGCCAACA | CCACGCTGCCACGCATGGA | 29051 & 29052 |
| GSTO1 | GAAAACAGTCAGGGTCAGCTGA | CATAGGGGTCATCCGGCA | 28947 & 28948 | GUCY2F | TGAGAGCTCAAAGAGGCAGCA | TGGAGACATTCTGGAGGGGCA | 29053 & 29054 |
| GSTO2 | CTGTCCTGGAGACCAGCCAA | TCCCACATCCAACGCTACCA | 28949 & 28950 | GLI1 | TTGCACACGTGGATCATGGCA | GTAAAACACCCTGGCAAGCAGA | 29055 & 29056 |
| GSTT1 | CCTCTTCCAGAGGCCA | TGGCCAGCACAGGGCCA | 28951 & 28952 | GLK1 | CGGCGACTTCATCGAGCA | GCACACCCTGCAGGTCCA | 29057 & 29058 |
| GSTT2 | GAAGGTGGAAGCGGAACAGGA | TCAGCTCCTCACGGGGCCA | 28953 & 28954 | GULP1 | CAGCACCTTCCAGCAGGCA | TGCCATTGCGAGTAGGCA | 29059 & 29060 |
| GSTT2B | AGCATGGCCTGCAGCGAGTGGA | TGGAAGGCAGCATAGCCTGA | 28955 & 28956 | LOC100507462 | TGACTGAGGGATGGAGGGAAGA | GATCAGAAGGTTGAGGAGTAGA | 29061 & 29062 |
| GSTZ1 | GTGTAGGGGTAGGGGGTGGACCA | ATGGTAGGGGCTAGGGGCGAGA | 28957 & 28958 | GXYLT2 | CCTGAGCACGAAATCCCA | CAACATGTCTCCCAAGCCA | 29063 & 29064 |
| GSX1 | AGAACCGCCGAGTGAAGCACA | TCGGAGCACTTGGCTGAGGA | 28959 & 28960 | GYG1 | GCCACCCCTCAGGTCTCAGA | AGCTTTGTCAGGTGACACCCA | 29065 & 29066 |
| GSX2 | GCAAGGCACGCAGAGGAACA | CTGAGGCGGCGACAGGGA | 28961 & 28962 | GYG2 | GTCGACCAGACATCCACA | TCTGGTAGACCGTCCACCA | 29067 & 29068 |
| GTDC1 | GCATCATCAACGGCCAAGTGCCA | GTCGGTCAGTATCAAGGCCA | 28963 & 28964 | GYPA | AAACGGGACACATATGCAGCCA | ATCAGTCGGCGAATACCGTA | 29069 & 29070 |
| GTF2A1 | CAGCAAGGCGCAGCCAGA | CACCTGAAGAAAGCTGGCCTGA | 28965 & 28966 | GYPB | ACCACTGAGGTGGCAATGCACA | ACTACAGGAGCTGGTACAGTGA | 29071 & 29072 |
| GTF2A1L | GACAGAGACTTCTGGAAGAGCA | TCTACTGGCCCAGAAGGTAGA | 28967 & 28968 | GYPC | CACCCCACCATATGGACA | GCCGGTACATGTAGCGCA | 29073 & 29074 |
| GTF2A2 | TGGGAAACAGTCTTCAGGAGA | TCCTGACCCTCGAGCCA | 28969 & 28970 | GYPE | TGCACTAACTTCAGGAGCCA | CGAGCCATGCCCACCAA | 29075 & 29076 |
| GTF2B | AAGAGCCTGAAGGAAGAAGCTA | AAAGGTTGGAACAGAACCTGGA | 28971 & 28972 | GYS1 | CGCAACATCCGTGCACA | GAGGTGCCGTGTCCACA | 29077 & 29078 |
| GTF2E1 | TCTCACCCCGTCCGGCA | TGTAGGAGAACGGACGGGCCA | 28973 & 28974 | GYS2 | CACCACCAACGACAGAAGGA | CTGAGGACTGGAGGCCTGA | 29079 & 29080 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| GZF1 | AACCTGGCTGCAGTCCAAGACA | ACTGATGGTGGTGGCCAGGA | 29081 & 29082 | HAUS2 | GTTGAAACCCATGTGCCAGGA | AAAGTCACAGCCAACTCCAGCA | 29187 & 29188 |
| GZMA | GAGGTGGAAGAGATCGAAAGTCGAA | CCCACGAGGGTCTCCGCA | 29083 & 29084 | HAUS3 | AAGAGCAAAAGCACAGCAGCA | GCGAGCTGCAGTCTAGCCA | 29189 & 29190 |
| GZMB | GCAGGAAGATCGAAAGTGCGAA | GTTACACAAGAGGGCCTCCA | 29085 & 29086 | HAUS4 | CAAAGGTGTGGAAACTCGCAGA | CAGCGGAGAAGCACCTGGGA | 29191 & 29192 |
| GZMH | GAGGAGGATCATCGGGGGCCA | TCTCACTAGGATGCCGCCA | 29087 & 29088 | HAUS5 | CAAGACCCGCCTGTGCCGGA | CTCCTCCAGACAGCGCAGCA | 29193 & 29194 |
| GZMK | GCCAAAGTTACTACACGGCGA | CAGATCAAGGGGCCCCCTGA | 29089 & 29090 | HAUS6 | GTTGGCCCCCATTGACCAA | ATAAACTTAGGACCACCAGGAGA | 29195 & 29196 |
| H1F0 | TCAAGCGCTGGTCACCA | CTCTTGGCTAGCCGGAAGGA | 29091 & 29092 | HAUS7 | ACATCAGCACCCTAGACCAGA | CCTGGATGATGGGGCCGCA | 29197 & 29198 |
| H1FNT | CCTGGGCCCAGTGGCGAA | TCTGAGCACGGAGCTTGAAGCA | 29093 & 29094 | HAUS8 | GCCCCTGTCTGAGGACGACA | GACAAGTTCCCTCCCTGAACGA | 29199 & 29200 |
| H1FOO | GCAGGGCCAAACACCAA | GCCTTGATGGGCAGCCCA | 29095 & 29096 | HAVCR1 | AACCCACGTCACCTATCGGA | CAATATACGCCACTGTCAGAACA | 29201 & 29202 |
| H1FX | GTAGGCTGGGCGAGCGCAA | TACTTGAGGTAGGTGCGCCCA | 29097 & 29098 | HAVCR2 | GGCAACGTGTGTGCTCAGGA | CCGCAGCAGTAGATCCCA | 29203 & 29204 |
| H2AFB1 | TTTCAGTGAGCCAGGTGGA | CCGGGACCTTGGCCGTCA | 29099 & 29100 | H8EGF | CTGGCCACCAAAACAAGGA | ACTGGGAGGCTCAGCCCA | 29205 & 29206 |
| H2AFJ | GTGGGCGAGTGCACAGA | CTCCGCCGTAAGGTACTCCA | 29101 & 29102 | H8M | ACGGTGTACCCCACGTGCAA | TGGCTGGGTCCACGTGCA | 29207 & 29208 |
| H2AFV | GGACAGTGGGAAAGGCCAA | TACACGGCAGCAGTGGCA | 29103 & 29104 | HBP1 | CCTATGCACGCCCTCCACCA | TTGAAGGCCAGGAATTGCACCA | 29209 & 29210 |
| H2AFX | GGAGTACGTCACCGCTGAGA | GATCGTCACGCCGCCCAGCA | 29105 & 29106 | HBQ1 | CCACCTGCACGGTGCCA | GGGCGAGGGTTACCAGCA | 29211 & 29212 |
| H2AFY2 | CACCCAACCAGCCCGAA | CGGAGCCCCACTGAGGGA | 29107 & 29108 | HBS1L | TGCCCTCAACACGCTGCTCA | TCATCTGGCACAGCATCTCCA | 29213 & 29214 |
| H2AFZ | CGCAGAGAGCCGGCTTGCA | TGCGGTGAGGTACTCCAGGA | 29109 & 29110 | HBZ | GCCCTGTCCAAGCGTGAGCGA | CCGTGAAGTTCGGCGGGGA | 29215 & 29216 |
| H2BFM | TACACCAAGCGCGTGACCA | AATGAAGTTCTGAGGGCCGGCA | 29111 & 29112 | HCAR1 | AGGCTCGATGGAAGAAGGCGA | TATGTGCAGGGCCCCATGGA | 29217 & 29218 |
| H2BFWT | CTACGTCCCAGAACGAGAGCA | CTGCTTCAGGACCGGCGGA | 29113 & 29114 | HCAR2 | ATGCCAAGATGAAGAAGAGCA | GAACGCCAGGTCACCGA | 29219 & 29220 |
| H2CE1 | CGCTTCCAGAGCCAGCTA | TTGGCATGAGATAGCACACA | 29115 & 29116 | HCAR3 | CAGAGACAAATTGGACCGGA | ACACCACGGGGTCCAGGA | 29221 & 29222 |
| H3F3A | CCGTCCGTGCGCTGCAGGA | TATCCGGCGAGCCAACTGGA | 29117 & 29118 | HCCS | AACAAGGACTACCAGTTCACCA | TCCAAGCGCACCAAGCGA | 29223 & 29224 |
| H3F3C | CAGGGCCAAGTACCGAGAGA | GGTCTGAGAGTGGGACGCA | 29119 & 29120 | HCFC1 | TCACTACCACGCAGGCCA | GGGGTGATGATGGCCGACA | 29225 & 29226 |
| H6PD | ACCATTCCCTCTGAGCACAGA | TAGGTGTCCCAAACAGGCTGA | 29121 & 29122 | HCFC1R1 | GGTGGACAGTGCCCTCCCA | CCTACTCTGAGGAGAGGGGA | 29227 & 29228 |
| HAAO | CTGCCACTGACCGACA | GGACCCATCAGGCAAGCA | 29123 & 29124 | HCFC2 | CTGCAGCTGTTAGAGGAGGA | AAGCTATGTCCAAGCGCGAGGA | 29229 & 29230 |
| HABP2 | GGAGAGAGGAGTCTCCAGCCAA | AATCACCACGGCTTTGGAAGGA | 29125 & 29126 | HCK | CGAGTACGGGCTCGGGAA | CACGGTCCAGAGCTCGGA | 29231 & 29232 |
| HABP4 | AGCGACGGAGGACGGCACCAA | CGATGTCGTAGAAGGTGAGCCA | 29127 & 29128 | HCLS1 | GAGGTGCTCGAGCCTGAAGA | AGCCACAGTGAGATCCCCA | 29233 & 29234 |
| HACD1 | TGCATGGACGATCACGGAA | CTGACAAAGGGCAGAGTCGCA | 29129 & 29130 | HCN1 | ACCTCATCCCACTGTGGGCGA | GTGACGCGCTGCGGACCA | 29235 & 29236 |
| HACD2 | TCAAGGACATGGTGCCAAAGGA | GTCTCTCCACCACTGACTCA | 29131 & 29132 | HCN2 | CGCTGTTCGCCAACGCCGA | GAGCAGGCAGATCTCCCGA | 29237 & 29238 |
| HACD3 | GCTCAGCCCAGGTATAGGAA | ATATGTGCAGTCAGTTCCAGGA | 29133 & 29134 | HCN3 | TGGTGGCATCATGGACAGCA | AGCAAGGAGGGTGCTGAGAGA | 29239 & 29240 |
| HACD4 | TGAACCAGAGGCAGCTGGTCA | ACAAGAATACTCCCACCCCA | 29135 & 29136 | HCN4 | CACTGAGCACCTCCAGAGACA | GCTGAGACCTCCTCGGAGA | 29241 & 29242 |
| HACE1 | ATCTGACAAGCAGGCCAGGA | TCTACAAGCTTCAACTGAGGA | 29137 & 29138 | HCRTR1 | GAGGCTCCGGCTCGGGGGA | GGGGACACAAGCTCAGACACGA | 29243 & 29244 |
| HACL1 | ATTAGGAGCCGGTTACCCA | CATGCCACCCATCCACGA | 29139 & 29140 | HCRTR2 | CCAGAAGGAAAACAGCCCGGA | CCAGTGTGAAAAGGTAAACCAGGCA | 29245 & 29246 |
| HADH | AGGAGGGTGTGAAGAGGAAGGA | TTGTCACCAGGCGAACTGGA | 29141 & 29142 | HCST | CAGAGACTCCAGGAGAGAGA | GTGGGCGTGCGCCAGAGA | 29247 & 29248 |
| HADHA | GGCCACTCTGCAGCGA | GAGGAAGGACGGATGCCA | 29143 & 29144 | HDAC1 | TGGCCCTGGATACGCAGGA | GGGATGGGTCTCAGGA | 29249 & 29250 |
| HADHB | GGTGTACGGGGGTGACGA | CATAGAACTTCCCGCAGCCA | 29145 & 29146 | HDAC10 | GAGGAGAACTCCACACCCA | TCCTCTGGGGAGGCCACA | 29251 & 29252 |
| HAGH | GTCCTGGCCTAAGAAGAGGGA | GACCAGGCCTTGCCGTGA | 29147 & 29148 | HDAC11 | GGGCATCGTGAAGCGGGA | CCAATGAGCCCCAGGCCA | 29253 & 29254 |
| HAGHL | CGCAGCCAGGAGGACCA | CCTTACACGAGAGCGACCA | 29149 & 29150 | HDAC2 | CCCATAAAGCCACTGCCGA | CAAGCAACTGAACCGCCA | 29255 & 29256 |
| HAL | CGAGACACCCACTTCCCA | GTCTTGCAGCACATCCCACA | 29151 & 29152 | HDAC3 | CCTCAGCATCCGAGGGCA | CGGGCAACATTTCGGACGA | 29257 & 29258 |
| HAMP | AAGAGAACCAGACGCAGGAAGA | GAACTAAACAGGAAGTGCAGCGACA | 29153 & 29154 | HDAC4 | CGGATCCACCAGCTGAGGA | GGGGCTCCTGCACAGACA | 29259 & 29260 |
| HAND1 | CCAACGTACCCGCCGACA | AAGGCCTCCGCTCGCCA | 29155 & 29156 | HDAC5 | GATGCCCAATTGCCCACGA | GGCGGTGACGAGTAGCCA | 29261 & 29262 |
| HAND2 | TGGGGCTCGACAACTGGA | AACACAGCCTGTTGGCGCCA | 29157 & 29158 | HDAC6 | CAGGACCTTGGAGCTAGGGA | AATGGGGACACCAGGGGCA | 29263 & 29264 |
| HAO1 | CGGGTCGGAACTGGCAA | GGCAGCCTGTAAGGGCCA | 29159 & 29160 | HDAC7 | GGACGTGCACCATGGCAA | ACCTCATCCACGCCCCA | 29265 & 29266 |
| HAO2 | AAGGGGTGATGGAAGAGGCAGA | GTCCAAGGTGTGAAGGGCCCA | 29161 & 29162 | HDAC8 | ACGATCACAGCTGCCCAA | TGTGCAGGGACACCGGTCA | 29267 & 29268 |
| HAP1 | TCAATTTTCACGAGGCAGCA | GCCAGCCGGCATTGCACCA | 29163 & 29164 | HDAC9 | CTGGAACCCACGCACCA | AACAGAGGCAGCAGGGCA | 29269 & 29270 |
| HAPLN1 | GGGGATCCGCAGCTACGGA | GCACTGGTCTAGCCCCGA | 29165 & 29166 | HDC | TCCAGTTCCAGGCTCAGGAA | TGCAACTGAGGGGAGCGCA | 29271 & 29272 |
| HAPLN2 | GATCGCCAAGGTGGGACA | GTTAGGATGCGGTGAACCA | 29167 & 29168 | HDDC2 | GAAATGTTCCAGGAGGCCGGAGA | CATGAACCAAGGGCTAGGCGTA | 29273 & 29274 |
| HAPLN3 | CGCAACTACGGGTATGCCA | CAGCGGGTCTAGCAGGTCA | 29169 & 29170 | HDDC3 | AGCTGGAGAGAAAAAGGCTGCA | TACCTCTGGGGTGCAGGGA | 29275 & 29276 |
| HAPLN4 | GCAGGGATGCCAGGGGTGA | TACTGAGGAAGACTGCTGCA | 29171 & 29172 | HDGF | AGGAGGCGGTTGAAGAGGAGAGCA | AAGGGGCCTTCAACCTCCA | 29277 & 29278 |
| HARBI1 | CGAACCCAAAGGGCGAA | CTGTGCAGATGCCACAAGCA | 29173 & 29174 | HDGFL1 | GCACATGACCCAGGCCAA | GGCTAATGGGCAGTCGGA | 29279 & 29280 |
| HARS | CAATCAGGCTGGGGAGGA | AACATGCCCACCAGCCA | 29175 & 29176 | HDGFRP2 | GCGGGCCCAGGCGAAGCAA | TCCCAGCCTCTTCCACCTA | 29281 & 29282 |
| HARS2 | CCAACCGCATGCTCAGCA | GGAACAGGCGGAGACCA | 29177 & 29178 | HDGFRP3 | GAAACTGAGGGAGAAAGGTGGAA | GCCCCATCTCCACCCTA | 29283 & 29284 |
| HAS1 | GTGGATGACCTACGAAGCGA | TCCTCTAAGGCAGCTGGCA | 29179 & 29180 | HDHD2 | TGGGGCTCAAGATGTCGGCA | TGTGGTCCACAGCATGAGGGGA | 29285 & 29286 |
| HAS2 | TCAGCCAAGTGACTGAGATTCAGA | AAGGCAGGAAGTGATGGTAGGA | 29181 & 29182 | HDHD3 | CACGGGGTCTGAGACTGGCA | CGAGGCCCTGGTAATGCCA | 29287 & 29288 |
| HAS3 | AGTGGAGAAGAACTGGCAGA | TGTTGACAGGGTACCAGCA | 29183 & 29184 | CECR5 | AGGCGTCTACAATCCAGGA | ACCAGTGCAAGCCTCA | 29289 & 29290 |
| HAT1 | AACAGGGTCCGGACAGGGA | GGCACCCGCACTGTCAACCA | 29185 & 29186 | HDLBP | GCCAAGGCCACCTTCCAGA | GGAGGGGTCTTGGGAGCCA | 29291 & 29292 |

| GeneName | Forward Primer | Reverse Primer | SEQ ID NOs | GeneName | Forward Primer | Reverse Primer | SEQ ID NOs |
|---|---|---|---|---|---|---|---|
| HSD17B3 | CAGGGCGATGGAATTGGGAA | CTCCCTGTAGTCTCGCTCGA | 29929 & 29930 | HTR1B | GTGGTGAACACCGACGACCA | TGCGGCCTATAGAGGGCGA | 30035 & 30036 |
| HSD17B4 | CCGCCTCAGTCGGAGACTGGA | GTAACACGCCTGGCAGA | 29931 & 29932 | HTR1D | CAGTGCCTGGAACGCAA | AGCAGGAGTCCCGGCAGA | 30037 & 30038 |
| HSD17B6 | GGAAAGAAGCCCCCAAGCA | AGTTCGCGGATGCACCGA | 29933 & 29934 | HTR1E | CTGGACAGGTACTGGGCCA | ACAGAGGGGCATGGAGA | 30039 & 30040 |
| HSD17B7 | GCACAGCAAAGGCAAGGAA | GCTGTACCTGGACAGGCCA | 29935 & 29936 | HTR1F | GAAGCTGCACCATCCAGCCAA | TGTCAGACCACTTGCCCCA | 30041 & 30042 |
| HSD17B8 | GCATCGTAGGAAAGGTGGGGAA | GGAGGACAGAAGTTACGACGGGA | 29937 & 29938 | HTR2A | ACAGGCAGGAGGACTATGCA | AGCAGGGCCCAATGACA | 30043 & 30044 |
| HSD3B1 | GCCCAAGCATCCGAGAGGA | ATTGGCCTGAGTAGGAAGCTCA | 29939 & 29940 | HTR2B | CACCGGAAAAGGTGGCAA | AAGAAGGGACCACCATAAGCA | 30045 & 30046 |
| HSD3B2 | TATGGGGAAGGGAGGCCCA | GCAGAGCCCTCAAGGCA | 29941 & 29942 | HTR2C | GTGCGTGTCAACGACCCAA | AACATCAAAGTCTGTGGGCGCA | 30047 & 30048 |
| HSD3B7 | CGACAAGGCTCAGTCGCA | CGTAGCGGCCTGTACCA | 29943 & 29944 | HTR3A | GCGGGATGAGATCCAGCA | CTGCCAGATGGACCAGAGCA | 30049 & 30050 |
| HSD1 | AGTTAGCAAGCCGAGGTCTCA | ACCATCAAACTAGTCGGCGGCA | 29945 & 29946 | HTR3B | GACAGAACCAACAGGAGGCGAA | CGCCCACAGTGCCCAGA | 30051 & 30052 |
| HSDL2 | GAACGTTGAACACCAGAGGCA | CTCCCAGCATATCCATAGCA | 29947 & 29948 | HTR3C | CCGGGAGGGGTTAGCAGGGAA | TGAAGAGCAGGTAGAGGCGGA | 30053 & 30054 |
| HSF1 | CCGAGGCAGAGAACAGCA | GCTCAAACAGACCCTGGCA | 29949 & 29950 | HTR3D | AGCACAGGGGTGCACCTGCA | CCAGATGGCAGACAAGGTGAA | 30055 & 30056 |
| HSF2 | TTCCAGGCCATGCTATCAGGA | AACAGAAGAAGCAGGGTTCCCA | 29951 & 29952 | HTR3E | CAGCACCGCGATGGACGCCA | GGTACTCAGGAAAGGGGGGA | 30057 & 30058 |
| HSF2BP | ATACATCAGCGAGAGTCCAGGA | ACATTATGCTCCAGAGTGCGGA | 29953 & 29954 | HTR4 | TCAACAAGCCCTACGCA | AGGCCTGCTCTGGAGGA | 30059 & 30060 |
| HSF4 | CCCAGTCTTCCAAGGCGGAGA | GAATTTAACCCTTGACCGCCA | 29955 & 29956 | HTR5A | CTGCCAAACAGCCCAGA | AGGGGATCCAGCAGAGCA | 30061 & 30062 |
| HSF5 | AAGGGCCACCATTCAGCACACA | GGCTTGCTAGCAGGCCCCA | 29957 & 29958 | HTR6 | TGTGCGACTGCATCTCCCA | GCCCGCTTGAAGTCCCCA | 30063 & 30064 |
| HSFX1 | CCTTCCACAGCGTCCCGTA | ATGGTGGTGCAGAGCTGGGA | 29959 & 29960 | HTR7 | CACTGTGGGTGGAGAGGACA | CGGTACTGGCACTGGAGCA | 30065 & 30066 |
| HSFY1 | ACATGCAAGCAAGGGGCCACA | GATATCGTGTGGGAACACAGCAGA | 29961 & 29962 | HTRA1 | GCACGGGACTTCCCAGA | CATCATTGGCGGAGACCA | 30067 & 30068 |
| HSFY2 | AAGCAAGGGCCACATTGTGA | CCTGGAATGAGGGGCAGTGA | 29963 & 29964 | HTRA2 | TGACCCTGAGTCCCAGA | TCACATCACCGAGCCA | 30069 & 30070 |
| HSH2D | AAGGAAGCCGTCAGCAGAGA | ACCGTGGATCTCCGGACA | 29965 & 29966 | HTRA3 | GCAAGAGGTTGCGCCGAA | CTGCAGCTCACTCCAGTCCA | 30071 & 30072 |
| HSP90AA1 | AGGGGTGGTAGGACTGGAGGA | AACCATTCTCATCACCAGAGGCA | 29967 & 29968 | HTRA4 | GCAGCCCGCTCAGGAGGAA | GGAACAAGCCTGCTGCCGTGA | 30073 & 30074 |
| HSP90B1 | CACCGGTGTAGGAATGACCA | CTGCTACAAGGAAGGCCGGA | 29969 & 29970 | HTT | ATCAGGCAGGAGGAGGAGGAA | ATGACCAAGGCAACAACGA | 30075 & 30076 |
| HSPA12A | TGAAGAAGCTTGCTGGGTGAAGGA | CTTCACCCCGGGATCAGTGA | 29971 & 29972 | HUNK | AAGACCCCTGATGCTGCAGA | GCAAAGGAGTATGGAAGGAGGCGA | 30077 & 30078 |
| HSPA12B | CTTGCACCCCACCCAGCCA | TCAATAGAGAGCCTGGGAACCA | 29973 & 29974 | HUS1 | GACAAGCTGGCTAATGGAGGA | TCTGCAGAGACAACCTCA | 30079 & 30080 |
| HSPA13 | AGCAGGACAGGAAGGAACCTCA | AACCCACTGTTCACGTCGA | 29975 & 29976 | HUS1B | GTGCGGGTGGACAATCGGAA | TGCACAGGGCGTCGTAGGA | 30081 & 30082 |
| HSPA14 | CGAACAGTGCTGAAGTAGTCGAA | GGGATTCGAGAAGACCCTCCA | 29977 & 29978 | HUWE1 | TCCTACGGCAGTCCACGA | GACGGACATGCACAGCA | 30083 & 30084 |
| HSPA1A | CTGCCCTGATCAAGCGCA | CTCGTACACCTGGATCAGCA | 29979 & 29980 | HVCN1 | GCAGAGCTGCAGCCCCTGA | TGATGACCTGAAACTTGTGGGA | 30085 & 30086 |
| HSPA1B | CGCCAACACCTTGGCGA | CAATGGTAGGGCCTGACCCA | 29981 & 29982 | HYAL1 | TGTGTCCGCCGCACAAGCCA | GTGAGAGGGGCACCCCGCA | 30087 & 30088 |
| HSPA1L | GCGAGCGGCTTCAGGA | AGCCCAGGCAGAGGGGA | 29983 & 29984 | HYAL2 | CGGGGTACACCACAGGGA | CGCAGCTGGGGTTCACCA | 30089 & 30090 |
| HSPA2 | CCATCCTCATGGCGCACA | GGGGTCATGACACCGCCA | 29985 & 29986 | HYAL3 | TCAATGTGACCAGGGCAGGGA | AGTAACAGTGGCAGCTGAAGGA | 30091 & 30092 |
| HSPA4 | TAGCTAGAGTGGAGCCACCA | AAGCAGGCGATAAGATGGCA | 29987 & 29988 | HYAL4 | CTTGAACCCTGCAAGTTACCACA | AGTGAACCAGGAGAAGGGGAA | 30093 & 30094 |
| HSPA4L | AAGAACCATCCTGCCCCA | TACTGATGCGCTAGCCACA | 29989 & 29990 | HYDIN | CTGGTGCAGGGAGACAGCGAA | TTCGGAGGGGCAGACGGA | 30095 & 30096 |
| HSPA5 | CATCATCGAGCTACGGCA | CGAAGGTTCCAGTCCCA | 29991 & 29992 | HYI | CCACTGATGGCTGCAGA | GATGGGTCCAGCAGTCCA | 30097 & 30098 |
| HSPA6 | CAAGGAGGAGGTTGGAGGGA | GCTCCAGCCAGGCAAGGA | 29993 & 29994 | HYKK | GTCAGAGGCTCTTAGCAAACCCA | GAAGTGGCCGGACTTGGAA | 30099 & 30100 |
| HSPA8 | AGTAGAGAAAGCCCTTCGAGGA | GAGGAGTGACATCCAAGAGCA | 29995 & 29996 | HYLS1 | CCGAAACCGGGGCAAGACAGA | ATCTGCTCTCGGACACCCA | 30101 & 30102 |
| HSPA9 | GGAGCTGCCATTCAGGGA | GACCATCAGCGGCAGTAGAGA | 29997 & 29998 | HYOU1 | GGGACAAGGTTCTGAGGCCA | ATCCTCTGGCAAGCTCAGGGA | 30103 & 30104 |
| HSPB1 | CCACGCAGTCCAACGAGA | GGCGGCAGTCTCATCGGA | 29999 & 30000 | HYPK | CGGCCTCCGGAGAAGCCA | TCACAGACATGGCCGTCTCCA | 30105 & 30106 |
| HSPB11 | TGGTACACACAGAGGGGCA | GCAGAACGCTATGCACAGA | 30001 & 30002 | HYPM | CAAAGCCAGAGTTCCTCCACA | CTCAGGCGTGTGGGGCTCA | 30107 & 30108 |
| HSPB2 | GTCCCGAGAGTTCTCCA | CCACCCGAGGTTGCTTCA | 30003 & 30004 | IAH1 | CAAGCAGCAATTCCCCTGGA | ACAAAGTGGGTCGCCGTGA | 30109 & 30110 |
| HSPB3 | TAAAAGCACAACACGGAACCAGA | TCATGACAGGAGCTGCAGACA | 30005 & 30006 | IARS | CCCACTGTGGGTCAGCGA | AATGAACCTGAGCATAGGGCA | 30111 & 30112 |
| HSPB6 | CACGGATTCGTTGCGCGCGA | TGCGGCCTGGATGGACAGGA | 30007 & 30008 | IARS2 | TGGCTCAGGAACCACGAGAGA | TCTGCACATCGAGGACACA | 30113 & 30114 |
| HSPB7 | CATCGAGGTGTCGGGCTTGAGA | CTGCCGTCTTCCCGCGA | 30009 & 30010 | IBA57 | CTACATTGGCCAGGAGCTGA | GCCAGCCTGGAACTTGCCCA | 30115 & 30116 |
| HSPB8 | CACAGCTTCAAGCCAAGA | CACCTTGCAGGAAGTGGA | 30011 & 30012 | IBSP | TGAATACGAGGGAGTACGA | GCCGATGCCAAAGCCAA | 30117 & 30118 |
| HSPB9 | CCAACTCGAGTCCTACGCA | AGGTTGGAAGCCTTAGAGCCGA | 30013 & 30014 | IBTK | TCCTGGAGGGCGATTAGGACA | TACAACTGGAAGGCCGTGA | 30119 & 30120 |
| HSPBAP1 | GGTTACACTGAGCCCAGGACA | TCTTCTACCCGGCTAGGTGA | 30015 & 30016 | ICA1 | GACCCAAGGCCCAGACA | GGCAGTCAGCTCAGCTGAGGCA | 30121 & 30122 |
| HSPBP1 | CGGAACTGGGCCTGGAGA | CGTCCGTGGGCTGGAGA | 30017 & 30018 | ICA1L | TTGGGCAACCCAGACACA | TCCAGTTCAGCATCCACGACCCA | 30123 & 30124 |
| HSPD1 | TGTGGCAGTCAAGGCTCA | CACTGCACCACCAGTAGCAA | 30019 & 30020 | ICAM1 | CAAGAACCAGACCCGGGA | GACACTTGAGCTCGGGCA | 30125 & 30126 |
| HSPE1-MOB4 | CGGAGGGAGTAATGGCAGGA | GAACCCGATCCAACAGGGA | 30021 & 30022 | ICAM2 | CACAAACACTTCAGCCCCGAA | GAGCAGGACAGATGTCACGA | 30127 & 30128 |
| HSPG2 | GCAGAAGCGAGTCCCAGGGA | TCAGGTGTGGAAATGGCCCA | 30023 & 30024 | ICAM3 | GTCCAGCTCACGAGGCAA | CGATAGTCACCAGCCCA | 30129 & 30130 |
| HSPH1 | CTAGGACAGAGGATACAACTGGA | CCTGAGCCATTACACTGA | 30025 & 30026 | ICAM4 | CTCGCACCCATTACAGTGA | ATAGGTACGCACGCCCA | 30131 & 30132 |
| HTATIP2 | AGGCAAGAATCTCGCCCA | ATTGCTCTAACCACGGTCACCA | 30027 & 30028 | ICAM5 | TACCTGCCCAAGTCACCAGA | CGCATTGGTTGGCCACACA | 30133 & 30134 |
| HTATSF1 | CTACGAGTGGGACCTCGGACAA | GCGGTAGAACTAAGTATCATGAGCCA | 30029 & 30030 | ICE1 | CTGGACTCCAGTGTGGAGACACA | ACAGCCAGGGCCTCACCA | 30135 & 30136 |
| HTN1 | CATCATACCGCATCATCACATACCA | GGAAGGGAAGTATCATGAAAACACA | 30031 & 30032 | ICE2 | CTGCAAAGAAATGTGCGCAGGA | TACATCGCCAATGCGAGAAGA | 30137 & 30138 |
| HTR1A | CAGTGAAGAGACTGGGGCA | GAGTTGGAGTAGCCCAGCCA | 30033 & 30034 | ICK | ATCTCCAGGAGGACAAGCCA | CAAGTCATCCAAGTCAGCCCA | 30139 & 30140 |

| GeneName | Forward Primer | Reverse Primer | SEQ ID NOs |
|---|---|---|---|
| KCNAB1 | GGCCTGTGCCAGTACGAA | GACAGGAGACACCTCAAAGAATCCA | 31201 & 31202 |
| KCNAB2 | TCCAGCGTGGAGAAAGTGGA | GCCGGCCCTCTCACTGA | 31203 & 31204 |
| KCNAB3 | GGCTCAAGGACAAAGTGCAGA | ACGCAATAGCAAGCTGGGCCA | 31205 & 31206 |
| KCNB1 | TCTTCATCGAGAAGCCCAA | TGTCCAAAAGCGTGGCACA | 31207 & 31208 |
| KCNB2 | AGTCTGACAATGTCCACCGACA | GCTGCGGGGTAGTGAGCGA | 31209 & 31210 |
| KCNC1 | CTCCGAGCCAGCACCAACGA | TCCATAGCCCAGGGTCGTCA | 31211 & 31212 |
| KCNC2 | CCCAAACATGGTCAGGCA | GTGAGCTTGCCTGAGGAGCA | 31213 & 31214 |
| KCNC3 | GGACTGCCCAGCCATTGACCA | AAGGGGCATAGTCGGTGAGGA | 31215 & 31216 |
| KCNC4 | CGACCGCAACGTGACAGAGA | CAGCACACATACGCCCTCGA | 31217 & 31218 |
| KCND1 | GGTGCCCAAGAAGACGA | AAGCCCAGTCAGAGGCA | 31219 & 31220 |
| KCND2 | TACCGACTGGGAAGTCGCCA | CCTCATAACAGCAGTGCCTCCA | 31221 & 31222 |
| KCND3 | CCTCGGCCAGCAAGTTCACAA | GGAGCAGATGGAGCCGAAGA | 31223 & 31224 |
| KCNE1 | GACAGTTCAGCAGGTGGTGGCAA | TGCCCAGGGTGAAGAAGCCGA | 31225 & 31226 |
| KCNE1b | CGGCCCTGTGTAAGCCAGA | AGTGCGTGCCAGGGATCACA | 31227 & 31228 |
| KCNE2 | CTTCAATGACCCTACCACCA | TTTGAACCAGCCGCACCA | 31229 & 31230 |
| KCNE3 | TGGGGCCAGACAACCAGA | AGCGGGTGTATTCCAGGA | 31231 & 31232 |
| KCNE5 | TGCACCACGGCGGGTAATGCA | GGGAGCGGGTGTAGGCA | 31233 & 31234 |
| KCNF1 | ACCATGACCACCGTCGGCTA | TGATGATGGGGTGGATGGGCA | 31235 & 31236 |
| KCNG1 | CGGGCAACAGTCACCTGGACA | CAGCCCACCAGTAGCAGGCA | 31237 & 31238 |
| KCNG2 | CCGTGGGCTACGGCGACA | GCTCGGAGTAGGAGCCGCGA | 31239 & 31240 |
| KCNG4 | GTCTACGTGGCCGAAGGGA | TGAGGATCCCGTCAGGA | 31241 & 31242 |
| KCNH2 | CTGTCCTACACACAACGGA | GAAGTACAGGGCCGGTGAAGCA | 31243 & 31244 |
| KCNH3 | CTTCGGCAGGGCGGTGACAGA | AGGATGCCCAGTGTCCACA | 31245 & 31246 |
| KCNH4 | TGTGCCGTCCAGCACCA | CTCAAGTCCAGGAGCGCA | 31247 & 31248 |
| KCNH5 | TGTGGCTAGGAACCTGGTAGAGCCA | CAAAGCCAGCTGGTAGAGCCA | 31249 & 31250 |
| KCNH6 | AAGCCCTCCAGGAAGCACCAGA | AAGGCCAAGGTCATTGGAGGCA | 31251 & 31252 |
| KCNH7 | TACAAACTGCAGACACCACGCA | TCATTGAGGAGGAAGGCTGCA | 31253 & 31254 |
| KCNH8 | TCTCCAGGTCAAATTCCCCA | GAGGTCTGGGGGTCCAGA | 31255 & 31256 |
| KCNIP1 | CACTCCAAGGCAGCAATGTGAGA | TGAAACAGCTGGAGAGACCTCA | 31257 & 31258 |
| KCNIP2 | TCCTCAAGGAGAGCTCCAGCA | CTCCGGAGTGCAGGGTA | 31259 & 31260 |
| KCNIP3 | ACGGTGCGCCACCAGCAGA | TCCACCAGGCGCCGTGGGACA | 31261 & 31262 |
| KCNIP4 | GAACAGCACAGTGTGGCCA | CCGATGCTGACGGTGGCCA | 31263 & 31264 |
| KCNJ1 | ACCTGCCAAGTCCGGACA | AAAGGCATGATGCCACAGTGA | 31265 & 31266 |
| KCNJ10 | CCACCAAACCAAGGAAGGGGA | TGGCAGGGTAGGAAGTGCCGCA | 31267 & 31268 |
| KCNJ12 | GCTGGACCAGAGTCGCGAAGA | CTGCGGCATCCAGTTGAGGA | 31269 & 31270 |
| KCNJ13 | CCGACCTAGCCCCTTAACCA | GGAGCAGAGTAGCCAGAGGA | 31271 & 31272 |
| KCNJ14 | AGTATGAGGTGCACTATCGCCA | GCAGTTAGAGAGCCGGGGA | 31273 & 31274 |
| KCNJ15 | CCAAAAGCCGGAAGGGCTCTCAGA | GAATGAGGAAGGGCTCTCAGA | 31275 & 31276 |
| KCNJ16 | CTGGAAAGACCAGCAGTTCCA | TACAGCGTCCACAATGGCA | 31277 & 31278 |
| KCNJ18 | ATCGTTGGTCATCTGGAAGGCA | TCCTCGAAAGAGCACGGGCTCA | 31279 & 31280 |
| KCNJ2 | GCCAAGATGGCAAAGCCA | CTCGAACATGAGCTTCACCA | 31281 & 31282 |
| KCNJ3 | CACGGCAACCTGGTGATGGAGA | AGGCCACGGTGTAGGTGAGA | 31283 & 31284 |
| KCNJ5 | CAGGCTTCAGCTGCATCAGGAA | TGGTGTGAATCCGTTGGCCCCA | 31285 & 31286 |
| KCNJ6 | CTGGAGGACGGGTTCTACGAA | GATACAGACCAACTCAGGGGCA | 31287 & 31288 |
| KCNJ8 | CAGGCTCACAGAAGGGCGCA | ACCACCTGCAGTGCGCACA | 31289 & 31290 |
| KCNJ9 | GGAGTAGCTGAGGAAGGAAGATGAAGA | CACACATAAAACCCCACCCTTCACA | 31291 & 31292 |
| KCNK1 | TCCACCAGGTTATGGCCACA | GAGAAGACAGCGGCCGGGA | 31293 & 31294 |
| KCNK10 | GACATCAACAACCGGCCCAA | GAGTCTGGAGGTGGACCCGA | 31295 & 31296 |
| KCNK12 | GGGCTTCACCGCTTGAGCA | GCGCAGCATCCAGTTGAGCA | 31297 & 31298 |
| KCNK13 | CCGGAGCTCCGCAAGCA | CAGGCCCCCATCCCTGGAA | 31299 & 31300 |
| KCNK15 | CACCATCGGCTTCGGCGA | AGGTTGAGGAAGGGCGCA | 31301 & 31302 |
| KCNK17 | CTGTGTCCACCATCACCACA | GCACCAGGGTTGAGTGGGA | 31303 & 31304 |
| KCNK18 | TTCTCACGGACACAGGCGACA | TGAAGAGAGATTTGGGGCACCA | 31305 & 31306 |

| GeneName | Forward Primer | Reverse Primer | SEQ ID NOs |
|---|---|---|---|
| KCNK2 | GGAGTGCCCTGGACGCCA | CATGCTCAGGACACGCAGCA | 31307 & 31308 |
| KCNK3 | CAGCGCGCACACTACGTGCACA | GCTCTTGTACCACAGGCACGA | 31309 & 31310 |
| KCNK5 | GCCAGATCACGTGCACA | GTAGATCCAGAGCTCCACGA | 31311 & 31312 |
| KCNK6 | CACGGCCTCACGAGAGTCA | GTCGGTGTGGGAGCTGGCA | 31313 & 31314 |
| KCNK7 | TGCAGGGCAGTTGCACTGGGA | AGCAGAAGTAGAGCGGCCCCA | 31315 & 31316 |
| KCNK9 | TACAAGGGGACGTCCCGGA | GCAAGCTTGGCGCTGAAGGA | 31317 & 31318 |
| KCNMA1 | CTGGGGTCAACATCCCA | TCCAGGACATGACGGGA | 31319 & 31320 |
| KCNMB1 | CTCGAGGGAACGAAAACA | CCGCCAGGATGGACAGGTA | 31321 & 31322 |
| KCNMB2 | TCTGACCCAGAAGGAAACCAGAAGA | GTTGGCCAGAAGAGTGAATGGAA | 31323 & 31324 |
| KCNMB3 | GGAGAGGACCGAGCCGTGA | CCCTGACCGTGGCAGTGCA | 31325 & 31326 |
| KCNMB4 | CCAGCTCCTGACCAACCCAA | AGGACACAATGAGAAGCCCA | 31327 & 31328 |
| KCNN1 | TCGGAAGCTGGAGCTCACCA | GAGCCACGTCTCCCTGAAGA | 31329 & 31330 |
| KCNN2 | CATCAGGCAGCAGCAGAGAGA | GGTGGTGCTGTGGAAGAGGA | 31331 & 31332 |
| KCNN3 | CTCAGCTCACCAAGCGGA | AACTGGTGGATAGCTTGGAGGA | 31333 & 31334 |
| KCNN4 | ACGGTTCCTACCGCACCA | CCAGTCCACCATAGCCGA | 31335 & 31336 |
| KCNQ1 | ACAGCTGCGGGAACACCA | GCTCAATGACGTCCCGCA | 31337 & 31338 |
| KCNQ2 | GCAGCACAGGCAGAAGCA | GCAGGTCTGTGCGCGAGA | 31339 & 31340 |
| KCNQ3 | AACGTATGTGGAGAGGCCA | GTTGACCGACATCAGGGACTA | 31341 & 31342 |
| KCNQ4 | CTGCAAACTCGGGTGGACCAA | AGAAGCCCAAGACAGGTCCA | 31343 & 31344 |
| KCNQ5 | GTGGGTCCGAAGAGACAGA | TGAGGCAAGCTGAGGGCA | 31345 & 31346 |
| KCNRG | AAACCCATACCTGCTTACAGCCA | GTAAGGTCATCTGAGGAGGGA | 31347 & 31348 |
| KCNS1 | TGGTAGCACTCCCCATCACCA | TGTCTCCAGAGATGCCTGCGA | 31349 & 31350 |
| KCNS2 | CAACGACGCCTCCAAGTTCGA | CCATCACCACCAGGATGGACA | 31351 & 31352 |
| KCNS3 | ACATGGGCAAGGTGGTCCAGA | AATGCCCACAGGAGGAAGAGA | 31353 & 31354 |
| KCNT1 | CGAGATGAACGACCACCAGA | CGGGGTTGCAGGACGACA | 31355 & 31356 |
| KCNT2 | ACTCACCCGCCAACATGAGA | TGTAGTGTCCAGTCCCAACAGA | 31357 & 31358 |
| KCNU1 | GTGATCACCCGGCCAGCCAA | GCTGAAGGGTATTGGCACAAAACACA | 31359 & 31360 |
| KCNV1 | TAAGCTGGCTGGACTCGA | GAAGCGACACCTGTCCCGA | 31361 & 31362 |
| KCNV2 | CCATCCTGGAGCACGTGGAGA | TGAGGATGCGGAAGATGCGCA | 31363 & 31364 |
| KCP | TAAGGGTTCATCAGGCTCCAGGA | CAGGCTCCAGTGTCCAGGCA | 31365 & 31366 |
| KCTD1 | ACTCAGTCCAGGTCCTGCAGA | GCCTCAGTTGCCGCCGA | 31367 & 31368 |
| KCTD10 | TGCTGTATGAGGCCCAGGA | TCCTCCGACCGCCTCGA | 31369 & 31370 |
| KCTD11 | GACGCGCTGCCGGAACTGGA | CCGGCGAGCAGAGAAGTGCA | 31371 & 31377 |
| KCTD12 | CTACCGCGGCTCTCTACACCA | CCCAAACCCTTCCTTGGCCA | 31373 & 31374 |
| KCTD13 | TGAAGCTCTGCACAACCGA | CATAGACAACGGTGCAGCA | 31375 & 31376 |
| KCTD14 | TGAGCAGGTGTCTCGGAAGCA | CTCAGTTTCCACCAGGCACA | 31377 & 31378 |
| KCTD15 | GGTCTTCCCGAGACCGGA | AGTTGAGCCGGCAGTAGCCA | 31379 & 31380 |
| KCTD16 | GACCCTGATCGGACCCAGA | AGTTACAGCCACCATGTGGA | 31381 & 31382 |
| KCTD17 | CCCAGGTCCACCCAAGCA | CGTAGTTGTAGGAGGAGCCGA | 31383 & 31384 |
| KCTD18 | CGACAAGAAGCCTACACCCA | CGGGAAGCGGCTTGAGGGA | 31385 & 31386 |
| KCTD19 | CACCCACAGCCAGTCCCA | TGATGATGTCAGCCAGGAAGCA | 31387 & 31388 |
| KCTD2 | ACAAGGGATGAGACAGGAGCCTA | AACTCCGCTTCCTCCAGCAGA | 31389 & 31390 |
| KCTD20 | GCGGGCCGGTCTGAAGTCA | ACATCATCTCAGCAGCTACCA | 31391 & 31392 |
| KCTD21 | TCCAAGGGCTGGAGAAGAATGCCA | ATGTTGGCGTTGAAGACCTTCA | 31393 & 31394 |
| KCTD3 | AGGAGGATTTGAAGGGGGAGGA | TGTAGGAGATGGGAGCGA | 31395 & 31396 |
| KCTD4 | GTGTCCAAAAGCAGGCTGGA | AACATCCAGGCTGGTCAGCA | 31397 & 31398 |
| KCTD5 | TGAGACACGGCAAGCTGGTGA | CAGCCGTCGGACATGGTGA | 31399 & 31400 |
| KCTD6 | GATGGAACCAGAGACTGCCA | GCACCCGGGTGTTGCGA | 31401 & 31402 |
| KCTD7 | ACTTGGACGGATTGTTGGAGA | TCTCACTCCGTCAAATGCGA | 31403 & 31404 |
| KCTD8 | GCTCAACCAGAGAGCCCGA | CCCGAGGAGTTACACGCA | 31405 & 31406 |
| KCTD9 | TGGCCAGCAGTAAACTCGGCA | TGTAAAGTACCGCCCTCA | 31407 & 31408 |
| KDELC1 | CAGCCGCAAAGAAGAGACTCGA | GGCAGCCGATAAGCTGCTACA | 31409 & 31410 |
| KDELC2 | GTAGAGACAGCCGAGAGGAGA | CCGAGTGTCGCCCAGCA | 31411 & 31412 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| KDELR1 | GCGGAGACCATCACCAGCA | AGTAGAGGACTGTCTGGACCA | 31413 & 31414 | KIAA0825 | GGACCTTCCTGCCACAGCA | GAGACGTCCTAGAGAGGAAATGGAA | 31519 & 31520 |
| KDELR2 | GGAGGCCGAGACCATCACCA | GGTCTGGACTACGCCGGCCA | 31415 & 31416 | KIAA0895 | CAACCTTCAGCAGCCATGGAA | AACAGTGTAGTAGAGGAGGGCA | 31521 & 31522 |
| KDELR3 | CATCTCTGGGAAGAGCCAGA | GGCCAATGACTGGGACCA | 31417 & 31418 | KIAA0895L | GCTACGTGCAGGAGCGCCGA | CTCATAGGACACCTTGCCCA | 31523 & 31524 |
| KDF1 | CTACCACTGGATGAGCAGGA | CGAGTTGAAGAGACCCTCCGA | 31419 & 31420 | KIAA0907 | CCCCCTCCTACTCACAGCA | TGGCAAGGTGGGGACTCA | 31525 & 31526 |
| KDM1A | CTGAAGCAGCAGCCACCA | GGATCCAGAACACCCGA | 31421 & 31422 | KIAA0922 | CCGCCTACCTCACAGCA | GGGGTTGATGGGGCAGCA | 31527 & 31528 |
| KDM1B | AGCACAGACCATGGATCCAGA | TTGTTGCCTCACCAGCGAA | 31423 & 31424 | KIAA0930 | ACTGAAGAGGACTCCAGCCA | CCTCTTGAGGGATGGGGAGA | 31529 & 31530 |
| KDM2A | CTTCGTCAATAGGCTGCCAGGA | ATCAGCCGGTGGAGTAAGCA | 31425 & 31426 | KIAA1024 | TGGACTGCAAGGACTGCCA | CAGGGCCTGCAACCTGTCCA | 31531 & 31532 |
| KDM2B | CAGGCCAGGTCAGATGAGCA | GATGATGAGCCGCAGGGA | 31427 & 31428 | KIAA1107 | CCAGAGAGCCATGAAACTCCAGA | CTCTCGTGATGCAGAACACCA | 31533 & 31534 |
| KDM3A | AAGAGGCCTCAAGGACTAACCA | GGGTCTTGCAAGCACAGCA | 31429 & 31430 | KIAA1109 | CAGACCTGACCAGTTCCAGCA | CTGATCCAGGTGTGCAGGCCA | 31535 & 31536 |
| KDM3B | GGCCAATGTTGGGGACCA | TCTCCGTACACCACGCA | 31431 & 31432 | KIAA1143 | GCAAGCGGAACCAGGTATCGTA | CATCTGGGGCTGAGGCTGA | 31537 & 31538 |
| KDM4A | GTCCGGTGGATGTGAGCA | TGCATCATCACCGGCA | 31433 & 31434 | KIAA1147 | ATCAACAGTGCTGACAGGGAGA | TGACTGGGAGACACCTTCA | 31539 & 31540 |
| KDM4B | CGACGATGGTCCTACAAGCGA | GTCAGTCCACCGGAGCTCCA | 31435 & 31436 | KIAA1161 | CGCGACTGGTTCCAGGGACA | AGGTCGTAGCCCACACAGA | 31541 & 31542 |
| KDM4C | GGTCACGGGCAGTCAGGA | TCCAGTACTTGCGCTCCAA | 31437 & 31438 | KIAA1191 | CCAGTCCACCCAAGCACCA | ATCCCCACTTCCAGAGTCCA | 31543 & 31544 |
| KDM4D | TGCTCTTCACTTCCACGCGA | TCTGGAGGTCAGTTCCTGA | 31439 & 31440 | KIAA1210 | GGAGGCCTGAAGACCCACAGA | AGAACTGGCAGAAACAGGGGA | 31545 & 31546 |
| KDM4E | TACCCTGGGGATGTCAGCA | ACAACAACATGACCACGACCA | 31441 & 31442 | KIAA1211 | ACCAGTCAGACCCCACAGCA | CAGGCAGAGGTGGGGAAGCA | 31547 & 31548 |
| KDM5A | CGGCAGGTCTAGCCACAGA | GAGCCGCCTGTTCCACCA | 31443 & 31444 | KIAA1211L | GCTTCACGGTCCCGCACCA | GGTGATCCAGGGTGGCGCA | 31549 & 31550 |
| KDM5B | GCTCACCAGTGAGACCAGCA | TCCCACGGCTCACTGGAGA | 31445 & 31446 | KIAA1217 | GGGAGATGCCCAGTGGACA | TTGCAGAGGAGGTGGCGGA | 31551 & 31552 |
| KDM5C | GCCCTCACTTGCAGCAGA | GTGCGACAACTTGGACCA | 31447 & 31448 | KIAA1257 | CTGGGTGTCGTGAAGCGGA | ACGTGCTGTGTGAAGCGGCA | 31553 & 31554 |
| KDM5D | ACAGGCCAAACCCAGACCAGA | ATCATGAGCTCCTCCAGGGGA | 31449 & 31450 | KIAA1324 | GCAGTCGGTGATGGCAGA | GGTCCTCTGGAAGGCCCA | 31555 & 31556 |
| KDM6A | GTCCACTCCAAGACCACCA | AGAGCTCCAGCAAGGCCA | 31451 & 31452 | KIAA1324L | TCCCAGTTCCAACAAGCCA | ATGCTCCGTACACAGAGGGGCA | 31557 & 31558 |
| KDM6B | GGGTAACATCCAAGGGCA | CTCCGTGCCACCGGAACCA | 31453 & 31454 | KIAA1328 | TGTCACCACAGCCTCACCA | CTCTGGAGGGATAGCGCTGA | 31559 & 31560 |
| KDM7A | GAGGCAGGCAGACAGCA | CTATATCAGGGACCTCCACCA | 31455 & 31456 | KIAA1429 | CAAAACAAGACTCCTTGGCCA | TGTAACTCCTTGAGCCCCA | 31561 & 31562 |
| KDM8 | AGATCCTGGCTGCCGAA | GGCTGCAGTAGTCGGGGA | 31457 & 31458 | KIAA1456 | CTGTGGGGCCACTGGTAGAGA | CGGGAACTAAGACCCTGGCCA | 31563 & 31564 |
| KDR | GAGCCCAGTCAGAGACCCA | GGAAACAGGTGAGGTAGGCAGA | 31459 & 31460 | KIAA1462 | CGGAGAGCGGGACAGAACCA | ATCAGTGGACACCCTGGGGA | 31565 & 31566 |
| KDSR | ACCCACAGCACACAGACACA | GTTACTGGAGCCATCCACA | 31461 & 31462 | KIAA1468 | AAGAGGCCAGATGATGAGGA | GAAAGAACCAAGGAGCCTACGGA | 31567 & 31568 |
| KEAP1 | CCATGAAGCACCGGCGAA | GCTCCATGGTGACAGCCA | 31463 & 31464 | KIAA1522 | CAGTGGATGAGCACCAGGACA | TGTCTCCATGGTCCCAGCCA | 31569 & 31570 |
| KEL | AAGAGGCTGTTACGGCCACCA | CACCACGTGCACAGCGGA | 31465 & 31466 | KIAA1524 | GCGCCACTCTGGGAAGCCA | ATCAGCCGGAGAACAGTTAGCA | 31571 & 31572 |
| KERA | AGGTTCCCGAATCAGTGCTCA | TCGTTCTGCAGGCAGCAGTGCCA | 31467 & 31468 | KIAA1549 | GCAGGGCACAGATGCAGA | CTCAGCGTCGGCAGGGACA | 31573 & 31574 |
| KHDC1 | ATCATGCTCGAGGCTGGAGA | TATCCTGGGAGCCAAAGACA | 31469 & 31470 | KIAA1549L | AGGAGCCAGGAGTCATCGGCA | GCTCGTCTCACTGCAGGGGA | 31575 & 31576 |
| KHDC1L | CATTGCTGGGAGCCAGGA | TACGGTGGCAGGCTAACGGA | 31471 & 31472 | KIAA1551 | CCAGTGTGACCTGCAGGGCA | CCCAATGCACAGCAGTGGA | 31577 & 31578 |
| KHDC3L | ACTCAGAAGGCCGAGACCCA | CGGAGAACCCTGTGTCCCGA | 31473 & 31474 | KIAA1586 | AGTGGCCCTGAGGCATCTGA | TCATCACCAGACCAGATCGA | 31579 & 31580 |
| KHDRBS1 | CCAGCACCAAGAGCCAGGACA | ATCCTTGAACCCTCCCATGTCA | 31475 & 31476 | KIAA1614 | AGGGAAGCCTGCAGAGGACA | TCCACTACTGTAGCTGCGGGA | 31581 & 31582 |
| KHDRBS2 | CCCCCACCACCTGGACGA | GGGCTCCAGGGGTAGGGA | 31477 & 31478 | KIAA1644 | AGCTCCGAGGGTTACATGCACA | GGATGCCCCACCGTGCCA | 31583 & 31584 |
| KHDRBS3 | GAGGAGTTACAGACCGGCCA | TCTGTACCCAGTTGGGGGGA | 31479 & 31480 | KIAA1671 | CCCCCTGCCAACATCCGAGA | TCCAGTCCCTGACTCCCACCA | 31585 & 31586 |
| KHK | AGACGACACACAACCAGGCA | CACGACCATACAAGCCCTCA | 31481 & 31482 | KIAA1683 | GCGCTCTTGGGACCCAGGA | CCCACGAAGCTCCCACTGGA | 31587 & 31588 |
| KHNYN | GCGCTCCACAATGGGAA | GTCACCCCGGTCTCCACA | 31483 & 31484 | KIAA1755 | TGCAGAGGCTGAAGACGGGCA | CTGAGGAGAAGCTGCCCCA | 31589 & 31590 |
| KHSRP | TCGTAGAGATCTCCCGGCA | GCCTGGTTCCAACTGGGCA | 31485 & 31486 | KIAA1841 | TGATCAAGGTGAAGGCGGAGA | TCATACAGAGGCCAACCCA | 31591 & 31592 |
| KIAA0040 | GACCCAGGCGCCTTGCAGCA | ATGTGCACACACTTGCACCCA | 31487 & 31488 | KIAA1958 | ATGAGCATTCCCAGGGGACACA | CAATTCCCGAAGAGAGGCCA | 31593 & 31594 |
| KIAA0100 | TGGGAAGGGTGTGGCACA | GTACTCCAGACAGGGACGCA | 31489 & 31490 | KIAA2012 | AAACAAGCCAGGAACAAGCA | AGCACTAGCACTTGGACAGTGAA | 31595 & 31596 |
| KIAA0141 | AGGAACCTCACGCTACCACA | GGGTAGGGGTGTGGGGGA | 31491 & 31492 | KIAA2013 | GGGGGCTGCAGTTCACAGAGA | CCACGGGACTCCACGGACA | 31597 & 31598 |
| KIAA0232 | TGTGGGAGGGACAGAAAGAGA | ACTAGGTGGTACGACTGCCCA | 31493 & 31494 | KIAA2022 | GGGGAGAGGAAGCAGCCA | CCAGAGGCAATGTTGGACAAGA | 31599 & 31600 |
| KIAA0319 | CTGCTGAAGTGGGCCGA | AGGGGGTCCAGTGCACACCA | 31495 & 31496 | KIAA2026 | CGTCTACAGTTGGGCACACCAA | ATAGCTGGCACAGTGCCTGA | 31601 & 31602 |
| KIAA0319L | AAACGAGCTCTCCCACCAGGA | TCACAGTGGCCATGGTCGGA | 31497 & 31498 | KIDINS220 | TCCAGTCCCAACCCAACCA | CTGCTGCATGGAGCCTCCGGA | 31603 & 31604 |
| KIAA0355 | GGTCGGTCGTCAGGGAGA | GAGGAGAGGTGGTGAGGGCA | 31499 & 31500 | KIF11 | GGATGGCAGCTCAAAGCAA | CAGAGACTGGAAGACAGCA | 31605 & 31606 |
| KIAA0368 | TGGACCGAAGTGTGGCAGGAA | CCAGCCGAGGCCTTGCAGCA | 31501 & 31502 | KIF12 | AATAGCCGAGCCCTTGGCCA | GCAGAGTAGAGGGGTGGCA | 31607 & 31608 |
| KIAA0391 | GTGGAGTCGGATGATGGA | GGTCTTGGCATCAGGCAGACA | 31503 & 31504 | KIF13A | CTCCTGGCAGCAAGGAGTGAA | CCTGCCGGAGCCGTTCAAGA | 31609 & 31610 |
| KIAA0408 | AGGTCAGCTCAGTCCAGGTCA | CTTCCTGTCCCCCACACA | 31505 & 31506 | KIF13B | CCTGCCAAAGTGCCTTCCCCA | GACAGGGTCGCGGTGGAGA | 31611 & 31612 |
| KIAA0430 | GAATTGCACAGCAAGCTCGAA | GAGGGGACAAGGCGCACACA | 31507 & 31508 | KIF14 | TGATGACCCAGACCCAAGAGACAGA | GCCATAGAGCAGCGCTCA | 31613 & 31614 |
| KIAA0513 | GGAGGAGCTTGGATCAGGAGGA | TGATGACACTGGAACAGCACCA | 31509 & 31510 | KIF15 | AGAAGGAAAGCCCTGATTCAGGA | TCTGGGAGTCTGCAGCAGGA | 31615 & 31616 |
| KIAA0556 | GGGTGAACAGGACCGAGGA | CTTCACGCCTCGGAAGGA | 31511 & 31512 | KIF16B | TTCCCCTCATGATGTCCAGGA | GCAGAGGACGTAGGCTGGGGA | 31617 & 31618 |
| KIAA0586 | GATGGAGACCTGCCACTGGA | ACCTGCATCTGTGAGGGGGA | 31513 & 31514 | KIF17 | CCGCCAGGAGGCCGTGACTCA | CCAGGACCTGCAGTGCCTGA | 31619 & 31620 |
| KIAA0753 | GTAAAAGCAGAGTGCAGCAGACA | TAGGAGACGCTGCTGGGGGA | 31515 & 31516 | KIF18A | ACACACCCCAAATCCTCAGA | GGGTCCCTTAGCACCGGA | 31621 & 31622 |
| KIAA0754 | CTGCTCAGGGGGTTAGAGGGA | TGCAGCCAGCCCTTCAGA | 31517 & 31518 | KIF18B | CCTGCTCCAAGCAGCCAA | AACACAGCTCCTGAGCCGGA | 31623 & 31624 |

This page contains a large data table of gene primers that is not reasonably transcribable at this resolution.

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| KRT6A | CAGGCAGTATCCATGAAAGCACA | ATTGCAAACAGCGAAGAGCACA | 32049 & 32050 | KRTAP2-4 | TCCATTACCACCCTCACCACA | TTGCAAAGTCCACCCCAGGAA | 32155 & 32156 |
| KRT6B | GGTCCAGTCGCAGATGAGGA | GAGAAAGCAGTGCAGGAATGCA | 32051 & 32052 | KRTAP24-1 | CTGTGAGCCCAAGACCTGCA | TGATGGGAGTTGCAGGGCA | 32157 & 32158 |
| KRT7 | GGGAACCATGGGCAGCAA | ACTCCTGCGACTGGCGGA | 32053 & 32054 | KRTAP25-1 | TAGTTGCCACCCCAAAACCA | GAAATGGAGATTGCCAACCCACA | 32159 & 32160 |
| KRT71 | ATCTCCATCATCAGCAGCACCA | CCGCCTCTCACGCTGCACA | 32055 & 32056 | KRTAP26-1 | TCCAAGAGTTGCCAGCCCCAA | ACATGGGTCAGAGGTTGGCAA | 32161 & 32162 |
| KRT72 | GAGTGCAGGATGTCTGGCGAA | GCTATAACTGCTTGAGGCGCCA | 32057 & 32058 | KRTAP27-1 | ACCACCAGCTGCCAAATGACCA | TCGCAGGGCCTGGAATTGGA | 32163 & 32164 |
| KRT73 | CCAGTCCACATCAGCGA | CTCCTCATACTGGGCACGGA | 32059 & 32060 | KRTAP29-1 | CCCGTCAGTGCGTGAAGGCCA | AAGTGAGTGGCTGGCAGGGA | 32165 & 32166 |
| KRT74 | AGGGCTGGCCGACACAAGGA | AGCCCAGAGAGACTGTGGA | 32061 & 32062 | KRTAP9-1 | AGATCAGCTCCTTCAGGCCA | TTGATCCCACTCAGTCCGGA | 32167 & 32168 |
| KRT75 | GCTATGAAGTGGGCAGCAGCA | CAGAACCTCCAGGCTTGCA | 32063 & 32064 | KRTAP9-2 | CCGGGCCTGAGAGACCCTCAA | CACTGAGCAAAGTAGCCATCA | 32169 & 32170 |
| KRT76 | GCACGGCCAAGATCTCCAGA | GCTCAGGGAATTAGGGACAGAA | 32065 & 32066 | KRTAP9-3 | TACCACAATCACCCCTGCAA | CTTCAGGAAGCTATAGGCATCCA | 32171 & 32172 |
| KRT77 | TGCTGAGGAGAGGAGGCAGGA | GCATGGCCTGGTAGTCACGCA | 32067 & 32068 | KRTAP4-1 | CCACTAAGTAACTGGTGAAAGGGCA | GCTGGGAAGAGATCACTGGGA | 32173 & 32174 |
| KRT78 | GGGTGCTGCTGCACCAGCA | GAGCCAGCGCTGGAGCCA | 32069 & 32070 | KRTAP4-11 | GCAGGCCCACAGTTGTAGACCA | GAAGAGAAAGAAGCAAGGGAGGGA | 32175 & 32176 |
| KRT79 | CTGCAGTAGGATGGAGGGA | GGTCACCCCAAGTCACCCA | 32071 & 32072 | KRTAP4-2 | TGGCCAGACCACCTTGCTGCA | CAGCAGCAAGAGCCACCTAGAGCA | 32177 & 32178 |
| KRT8 | GGCTGGAGTCTGGGATGCAGA | TGGAGCCCAGGCTGCTAGCTGA | 32073 & 32074 | KRTAP4-3 | CCACCCCATCTGCTGCGCA | GAGAGCAAGAAGGTGCACAAATCCA | 32179 & 32180 |
| KRT80 | CAGCTGCCAAGTACCACGGA | CCAGTGGCTGAGGGCGA | 32075 & 32076 | KRTAP4-4 | CCGCCCAACTGCTGCCAGA | GACAGCCTCAGCAGCAAGAAGCA | 32181 & 32182 |
| KRT81 | CGGGAACGTGGCGTGATACCA | CACCCAGGCTGTGATACCA | 32077 & 32078 | KRTAP4-5 | CAGGACCACCTGCTGCAGGA | TCACAGCAAGAGGGGTGCGA | 32183 & 32184 |
| KRT82 | CAGCACGCCTGTCCTCAGCA | GATTTCCGCCCGCTCCACA | 32079 & 32080 | KRTAP4-7 | CCGAGTCCTCTGCCACACCA | CAGCAAGAGGAGGCACAGCA | 32185 & 32186 |
| KRT83 | AGCCGAGGTGAGAATGCCAA | GCTCCTCGCCCTCAGCA | 32081 & 32082 | KRTAP4-8 | CCGAGTCTCCTGCCACACCA | CAGCAAGAGGAGGCGCAGCA | 32187 & 32188 |
| KRT84 | CCCAGAGAAGAACCAGCTCCA | CAGGCAGAATAATCGGGGGA | 32083 & 32084 | KRTAP4-9 | CTTCCACCACTGGCCACAGA | TTGGTGCCACAGCCAGCA | 32189 & 32190 |
| KRT85 | GCGGGACAGAGAGTTAAGCCA | CCCAGAAGGCAATGCACCCA | 32085 & 32086 | KRTAP5-1 | CTTGCGCGGGGTCTAAGGGA | GCACTGGCAGCACACGGGGA | 32191 & 32192 |
| KRT86 | ATGGAGACCGACCTGGA | TCTTGAGGGCAGCCCCGGAA | 32087 & 32088 | KRTAP5-10 | CCTTGCTGGACGCGGGCA | CTCAGTCAGCCGAGGGAGAA | 32193 & 32194 |
| KRT9 | CCAGATGGGGACTCCTGGA | ACCCTGAAGGCATCAAAGCCAA | 32089 & 32090 | KRTAP5-11 | CCAAACCCTGCTGCTCAA | CAGCAGGGCTTGAAGCA | 32195 & 32196 |
| KRTAP10-10 | AGCTACTCCCCAGACTCCGA | GGGTGCTGCCCAGGGTGGAA | 32091 & 32092 | KRTAP5-3 | CAAGGGGGCTGTGTGCTCA | CCACAGCTGAGGGCTGAAGCA | 32197 & 32198 |
| KRTAP10-3 | TGCTCACTGCCAGCCCA | CCTGAGGAGAGGCCGCAGCA | 32093 & 32094 | KRTAP5-4 | TCCAGCTGCTGCAAGCCCTA | ACAGCAACTAGACTGGGAGCA | 32199 & 32200 |
| KRTAP10-4 | GGGAGGGCGGGCCTTCTAGA | GACAGACCACCTACGGTCAA | 32095 & 32096 | KRTAP5-5 | GCTCCGAAAACTGACTGAGGA | GTGAGGAGCAGGGAGAGGAA | 32201 & 32202 |
| KRTAP12-4 | TATCCACCTGCTGCCAGA | GGCAGGAGGGAGACACGA | 32097 & 32098 | KRTAP5-6 | CTTGTGGGGGCTCCAAGGGA | GCACTGGCAGCAAATGGGGA | 32203 & 32204 |
| KRTAP10-7 | GAAATGAGGGTAGACAGGTACCA | GGGAAGACAGAAAGAGGCCCA | 32099 & 32100 | KRTAP5-7 | TGTAAGCCCTGCTGCTGCCA | CACTGGCAGCACACGGGGA | 32205 & 32206 |
| KRTAP10-9 | CGCCACTGCTCTGAGGA | GCAGCAGACAGGCTTACAGCA | 32101 & 32102 | KRTAP5-8 | CTGAGCTGCCACAGCTCCGA | CAAGGCCAGGTCAGAGGTAGA | 32207 & 32208 |
| KRTAP11-1 | CCAGCCAGCGTGCTGTGAGA | CTGGCAGGCAGTAGAGTCACAA | 32103 & 32104 | KRTAP5-9 | CTGCCAATCCAGCTGCCAA | GCACTGGTAGCACAGGTGCACA | 32209 & 32210 |
| KRTAP12-1 | CCCTGGAGGCATCTCA | TGATACGTCTCTGGAGACCCCA | 32105 & 32106 | KRTAP6-1 | GTGTGGCAGCTACTACGGAA | GCCAGAGCCAGAGCCGCA | 32211 & 32212 |
| KRTAP12-2 | AGATGAGGCCACACTCTACA | CAAGTTCAGCCAGGGCTCA | 32107 & 32108 | KRTAP6-2 | CTAGGAAACTACTACGGCCA | ACAGCCACAGAAGAAGCGGGA | 32213 & 32214 |
| KRTAP12-3 | AGATGAGGCCACACTCTACA | GGGATGGCCAGGTCAGCAA | 32109 & 32110 | KRTAP6-3 | ACAACCAACACTGTGTGGCA | GTAGCACAGCCAAGAAGAAGGA | 32215 & 32216 |
| KRTAP12-4 | CTTCTGCAGTCCCCGGCGA | CTATAGACCAGGGTGGGGCA | 32111 & 32112 | KRTAP7-1 | CTGCAAGAGAACAACCTGAAGAGCAA | AGACCAGCAAGAAGTCAGCAAGA | 32217 & 32218 |
| KRTAP1-3 | AGCGCCGACGAGCAGCATGGA | CAGGACCGTGGGATACAGGA | 32113 & 32114 | KRTAP8-1 | CCCAGGATGCTACTGGGGCA | TCCTGTAGCCCGAAAGCCCCA | 32219 & 32220 |
| KRTAP13-1 | ACCTCCTGCCTACCGTCCCAGA | ATAACCCAGGGATCTGAAGCCA | 32115 & 32116 | KRTAP9-1 | AGATCCACCTGCTGCCAACCA | TAGCAGGTGGTCTGGCAGCA | 32221 & 32222 |
| KRTAP13-2 | ACCAGCTGCCAGACGTCCTA | ATAACCCAGCAGTAGAGTCACAA | 32117 & 32118 | KRTAP9-2 | CACACCTGCTGCGACACCA | CTGCAGTACAGACGTCACA | 32223 & 32224 |
| KRTAP13-3 | GAGTCCAGCCCCTGCCACA | AAGCCATTGGATCCACAGCCCA | 32119 & 32120 | KRTAP9-3 | CCAAGAGAACTACCATCCTCACACA | CCACAAGGTGTAAGGAAAGAGGGAA | 32225 & 32226 |
| KRTAP13-4 | CTACGCCAGGACCTCA | ATCCATAGCCTGGGAGCGA | 32121 & 32122 | KRTAP9-8 | CACACCCTGCTGTCAGCCCA | CTGAGTACAGAGGTGCACA | 32227 & 32228 |
| KRTAP1-5 | GAGCCACTTGCTGAAAGCCA | GTCCAGACCAGCTCAAGGGA | 32123 & 32124 | KRTAP9-9 | CCCCGCCTGCTGTGAGACCA | GAAGGCTGCAGCCAGCTGGA | 32229 & 32230 |
| KRTAP15-1 | CTTCTGCAGTCCCCGCTGGA | GTTGGGTGGTTAGAAGCTGGA | 32125 & 32126 | KRTCAP2 | GGATGCAGATGTACAGCCTGTCA | TGGTGACAGAGTCCGGTGGA | 32231 & 32232 |
| KRTAP16-1 | CGTCCGATCTGCCGCCAA | CGGAAGTAGACTGGGCGGCA | 32127 & 32128 | KRTCAP3 | ACTGCCCTTTGACCCCACA | GTCCTTCCTGCAGGGCCCA | 32233 & 32234 |
| KRTAP17-1 | ACCTCTGCACCCAGGAGCAA | AGGGCCACAGCACCCGGA | 32129 & 32130 | KRTDAP | ACTCTGCCAGGGAGCCA | GCCTCGGGTCTGTGACGA | 32235 & 32236 |
| KRTAP19-1 | CACTACGGCAGCTACTACGGA | TAGCCTCCAAAGCCAGCAGCA | 32131 & 32132 | KSR1 | CCTGCATGAACCGCCCA | CTGAGATCCCAAACAGCCCGA | 32237 & 32238 |
| KRTAP19-3 | GTGGCTATGGAGGGCTACGGA | ATGATGGGCGGTAGCAGCCA | 32133 & 32134 | KSR2 | TGAGGCCGAAGAGTCAGAGGA | CCTTTCCAATGAGCTCCCGA | 32239 & 32240 |
| KRTAP19-4 | GCTATTACAGAGGCCTGGGCTA | TCCATAGCATGATGGGTCGGCA | 32135 & 32136 | KT112 | AGGCCGACGTACCCAAGGAA | CTCAAACAGGGCAGAGCGGA | 32241 & 32242 |
| KRTAP19-5 | GCCTGGGCTACCGGCTACGGA | GTAGCCACCCGCCATAGCCA | 32137 & 32138 | KTN1 | TGCCCTCCACCAAGAGA | TCTACCACGACTTGAGTCA | 32243 & 32244 |
| KRTAP19-6 | GCTACTACAGAGGCCTGGGA | TCACGGCCATGATGGGCGCA | 32139 & 32140 | KXD1 | ATTGCCACCTCAGAACAGAGCA | CGTTGATGGCTGGGGAGCCA | 32245 & 32246 |
| KRTAP19-7 | TACTCCGGCAGCTACTATGGA | CATAGCATGATGGGTGGCAGCA | 32141 & 32142 | KY | CACGGGAGGAAGCAGAGACGGA | GCTCTCAGGGAACATGGGCCA | 32247 & 32248 |
| KRTAP19-8 | GCTGAACTACTAGAGCTACTACAGA | AGCCACAGCCATAGCCCA | 32143 & 32144 | CCBL1 | TGCTCTTCCGCACCAGCA | ATGAGGAAGTAGCTGCCCTGA | 32249 & 32250 |
| KRTAP21-1 | GTGTTGCAACTACTACGGCAA | GAGCCAGCCCACAGCA | 32145 & 32146 | CCBL2 | ATGACACTCTGCATCAGTCGA | TGGACCAATGGACCAGCCA | 32251 & 32252 |
| KRTAP2-2 | AAGGTGCTGCCGCCCA | CCGCAGGGGGACTGCACA | 32147 & 32148 | KYNU | CGACAATGAAGGCATTGTGGGAA | GAGGAACTGGAGCCACTCGA | 32253 & 32254 |
| KRTAP22-2 | GACACCATGTGCTACTACCACAA | GAATCTTCCATAGGAGCACGGA | 32149 & 32150 | L1CAM | GGAGAGGATGTTCCGGCA | GATGATGGAGCCAGGACGAGGA | 32255 & 32256 |
| KRTAP2-3 | CCTAGTCGATCCTCAAGACGAA | GAGGGCCAGGATTAGCTGCA | 32151 & 32152 | L2HGDH | CAGCAGCACTCATCCTGGCA | ATAGGCCTGAAGTCTGGGA | 32257 & 32258 |
| KRTAP23-1 | CCCCAGCAACCTGGTCTACA | GCCCTTGCAGAGAGGAACCCA | 32153 & 32154 | L3HYPDH | GTGCAGTGACAGAGAGGCAGTGA | TCACTCCTGAGCCAGTGGGA | 32259 & 32260 |

| GeneName | Forward Primer | Reverse Primer | SEQ ID NOs | GeneName | Forward Primer | Reverse Primer | SEQ ID NOs |
|---|---|---|---|---|---|---|---|
| MACROD2 | CAAAAGGCGTGAAGTGACAGA | GTTGCTCCACAATCACGGCA | 33321 & 33322 | MAGOHB | TGATAGGGTTGGCCGACAGGA | AAAATACTCGAAGGCCTTCAGGA | 33427 & 33428 |
| MAD2L1 | AAGATGACAGTGCACCCAGAGA | GAACGAAGGCGGACTTCCTCA | 33323 & 33324 | MAGT1 | TGGAAGCAGTCAAGCCCA | ACAACAAGTCCAATACCAGCCA | 33429 & 33430 |
| MAD2L1BP | GTCCTCAGCCACCTGGAGGA | GCCATGACGACGGTGCCA | 33325 & 33326 | C2orf47 | GAAGCCGTAGGGCCTTGGCA | CTGTAGCTGCCCTGAGGGCA | 33431 & 33432 |
| MADCAM1 | TGCACACGAGAAGAAGCCGCCA | GTGGTATCAGCCGGGGGTCA | 33327 & 33328 | C11orf85 | AAATGCAGCGCTGGAAAGAGGA | CAGAGGACTCAGCATGGGGA | 33433 & 33434 |
| MADD | TCCAAACTGCGGGTGACCA | GTGCCGGCAGCGTTTCCAGA | 33329 & 33330 | MAK | CAGCTGGTTCCCCAAGCCA | TGCCCAGCAGCTGAACGCA | 33435 & 33436 |
| MAEA | GCACCAAGTGCCAGAGA | TAGACGTCAGGCTCACACCA | 33331 & 33332 | MAK16 | AGAAGGTGGAGCGTAGGGAGA | GTCGAAGGCATGAATGGGGA | 33437 & 33438 |
| MAEL | GGAGGACGGCAGCTCCAAGA | ATCTTGCAGACCAGGCGGGA | 33333 & 33334 | MAL | CTCCGCGGAGCCAGCGA | GGTGAAGACCGAGAAGCCA | 33439 & 33440 |
| MAF | TGGGCCTCAGAGAACAGA | CAATGAGGAGGTAGTCTGCCA | 33335 & 33336 | MAL2 | TGGAAGCAGCAGCACCA | CCAGACCAAACTGCAACCA | 33441 & 33442 |
| MAF1 | TGCCGCTTCAAGAGGGTGCA | CTCTCGCGACCAGCCTGGA | 33337 & 33338 | MALL | GCCTGTACCACGGACCA | GAAGAACGAGGCTGCCGA | 33443 & 33444 |
| MAFA | TACAACAAGCGGCTCAAGCGAA | CCACTTCCTCTCCCCCA | 33339 & 33340 | MALRD1 | TCCCGTGCTCTACAGACGA | GATACAGCTGTTGGAGGAGGCA | 33445 & 33446 |
| MAFB | CTCAGGCGCCTTCCACTCGGA | GGCGCGCCTTCACTCGA | 33341 & 33342 | MAL5U1 | CTACCCGACACTTACATGCCA | CCATGCTGCCAAAATCCAGGA | 33447 & 33448 |
| MAFF | TCGACGTGAAGAAGGAGCCA | AGCTGGGCGACGAGGGCA | 33343 & 33344 | MAUT1 | TTACCGGGAGCACCCCA | CTCATCCACAGCATTACGCA | 33449 & 33450 |
| MAFG | GGTGACACGGCTCAAGCA | CTCGGCTCCAGCTCGA | 33345 & 33346 | MAMDC2 | AACTCCCACTTCCTACACAGGA | TCCAGAGACTCCTCGCAGA | 33451 & 33452 |
| MAFK | CAGAAGGCGGAGCTGCAGCA | CGTCCGGGCGAAGGTCTGCA | 33347 & 33348 | MAMDC4 | ACAGGCTGCAGGTCTCAGGA | TTCACAGAGCAACAGAGTCAGGACA | 33453 & 33454 |
| MAG | GGGCGGTGAGAACAGCACGA | CCACCTTGGAGGCGGCCACA | 33349 & 33350 | MAML1 | CCTGGCAGCATCAGGAGCA | CTGAGCTCATGGGAGCCA | 33455 & 33456 |
| MAGEA1 | GGAACCTCTATGCGCCCA | GCTGCTGAACAGGACGGGA | 33351 & 33352 | MAML2 | GCCACCTACCTTAGGGCCA | GGAAGCGGACTCCTGCAGA | 33457 & 33458 |
| MAGEA10 | TGCCGGACAGTGATCCCGA | CTTCACGCAGGGATGGGAAGA | 33353 & 33354 | MAML3 | CAGGGCATGCTCGGGAGGA | CATCCACGACTGCAGCTGCTCA | 33459 & 33460 |
| MAGEA11 | TGATGTCCAGACATGCAGCCCA | TCCATCCAGCATCAACAGCCCA | 33355 & 33356 | MAMLD1 | AGCCCAGCATCAACAGGGGA | CTCTGAGGTGCTGTACGAGGA | 33461 & 33462 |
| MAGEA12 | GAAGTGGACCCCACTAGCCA | CTTCCAGCATACACCCCA | 33357 & 33358 | MAMSTR | TTCACTCCGTCTCCCACGAA | GGTGGGGACCAGAACCCA | 33463 & 33464 |
| MAGEA2 | AGATCAGTGGAGGACCTCACA | GGAAGGTGCACTGGCCCAGA | 33359 & 33360 | MAN1A1 | CGCAAGTCTAGCACGCGA | CATCAGCCCGAGTGCGA | 33465 & 33466 |
| MAGEA2B | GGGGTCCAAGGGCCTCA | TTCATGCAGGGATGGGCTAGGA | 33361 & 33362 | MAN1A2 | GTCGGTGGCCTGGCAGACA | GTGCAAACATTCCCCAGCA | 33467 & 33468 |
| MAGEA3 | TGGCATCGAGGTGGTGGAA | TTGGGATTATGGCCAGGACGA | 33363 & 33364 | MAN1B1 | AGATGAACCGGGCAGATGAAGA | TGCAGAATCCCAGCCCA | 33469 & 33470 |
| MAGEA4 | GCCGGTCACAAAGGCAGA | TTGTCACCAGCAGGCCA | 33365 & 33366 | MAN1C1 | TACGCCCGGTCAGACAACAA | CACCACCTCCAGCCCCA | 33471 & 33472 |
| MAGEA6 | GAGGGTTCCAGCAGCCAA | TGGCTCGATACTTGCGGA | 33367 & 33368 | MAN2A1 | CTGGGGAGTTCCCCCAGA | CTCCTAGTTGGAGCCAGGAGAA | 33473 & 33474 |
| MAGEA8 | CTGATGGAAGTGCACCCA | TTGTCACCAGCAGGCA | 33369 & 33370 | MAN2A2 | GCTTTCAGGTGCAGCCCGA | AAGATCACCTCCAGCTGGCCA | 33475 & 33476 |
| MAGEA9 | CACCGACAGCACTCTGTGGA | AGTGCTTCCCGGAACAGGGA | 33371 & 33372 | MAN2B1 | AAGGACGATGGACGCGGA | GGGCTGTGTCCAGCAGCA | 33477 & 33478 |
| MAGEA9B | GGTCAGGGCCCCATCCAGCA | CACCCACTGCCACTGAGAACA | 33373 & 33374 | MAN2B2 | GAAAGGCCATGCAGGGGA | TGCAGCACAGCCTCCAGA | 33479 & 33480 |
| MAGEB1 | CACCCAAGATTGGGTGGCAGGA | TTCAGCGTGGGGCTTGGAA | 33375 & 33376 | MAN2C1 | CACCTTGCAGCGACCTACCCA | GGAAAGACCCTTGTGCGGCCA | 33481 & 33482 |
| MAGEB10 | CAACAGTGATCTCCCCACGCTA | TGGGATGGGAAGTTCACGGGGA | 33377 & 33378 | MANBA | GCCGTAGTGCAGCGAGAA | CGTACTCAAGAGAAGCCCAGGA | 33483 & 33484 |
| MAGEB17 | GTGCCAACAGTGATCCTCCA | TAACGCGAGCCTTGGCTGCA | 33379 & 33380 | MANBAL | AGAACCTGCTACGGTACGGA | GGGCTTCCTCGTCACCTCA | 33485 & 33486 |
| MAGEB18 | GCCCAGGAGCTTGTCACCAA | TCAGCAGGGGCTGTCCGA | 33381 & 33382 | MANEA | CGTCATGGAACACGCAA | CTGAAGTGCGGCACTCAGA | 33487 & 33488 |
| MAGEB2 | GTGCCACAGATGATCTCCA | TTCATAGCAGGATGGGAAGGCA | 33383 & 33384 | MANEAL | TACTATGAGACGGCCCTGCA | CTGGTGAGGCAGGTAGTCA | 33489 & 33490 |
| MAGEB3 | AGTCAACCCAAGCGGCCA | TCAACCCAGGAGGAGGCA | 33385 & 33386 | MANF | TGAGCTGCTGCCGGGCA | TGTGGCCCGATATAGTAGCA | 33491 & 33492 |
| MAGEB3 | TGGAGTTACCGACAAGTGCCCAA | TTGACTTGGCCCAAAACTCCA | 33387 & 33388 | MANSC1 | GCAGTTCCTCCCAGGGCA | GATTCCGAGGAGGATTCTACCCA | 33493 & 33494 |
| MAGEB4 | TGAAGAGGTCAACCCACCA | AGTAGAGGTAGCAGAAGCCCA | 33389 & 33390 | MANSC4 | TAAGCATGGGGTGGACATCAGA | TTCCAGACAGCAGCTCTCTA | 33495 & 33496 |
| MAGEB6 | CTGAAGTGTCCGCAGAGA | TGAAGATCACAACAGGAGGCGA | 33391 & 33392 | MAOA | TCGGGAAGGTGACCGAGA | AATGATCTTCAGCAGGCCAGA | 33497 & 33498 |
| MAGEC1 | GTGAAGAGTCAGCAGCCA | GGAGAAGAAACCGCGCCA | 33393 & 33394 | MAOB | CACAGCCATCACCACCA | TTGTGGGCCAGGAGGCCA | 33499 & 33500 |
| MAGEC2 | AACACAGTAGGCCTCACGA | AGGTAATGTCCCTGCACCA | 33395 & 33396 | MAP10 | AAATCCCAGAGGCACAGAAGGA | CTCCCATTGCACCACCTGA | 33501 & 33502 |
| MAGEC3 | ATGAGGAGTCCAGCAGTGAAGA | AGAAACTGCACCAACTCAGCCA | 33397 & 33398 | MAP1A | AGACACCCCTACATCAGCCA | GGTCTGGCTGTCACAACAGGA | 33503 & 33504 |
| MAGED1 | GGGTTCTCCAGACTGGCAA | GGCACGCGAGTTGGGAGA | 33399 & 33400 | MAP1B | ACACCAAGTCACCCCA | CCCACACAGCTCACCCA | 33505 & 33506 |
| MAGED2 | CAGTGCCAGTGCCAGCACCA | GCCACTGGTTGCTGGCACCA | 33401 & 33402 | MAP1LC3A | CTGCAGCTGAACCCACGCA | TCTGGGAGGCCGTAGACCA | 33507 & 33508 |
| MAGED4 | CCAGAGCCGCCTTGCAGA | CCACCTCCGACTGAAGACCAGGA | 33403 & 33404 | MAP1LC3B | GCAGCCCGCCACCTTCGAA | TGTGTCCGTTCACCAACAGGA | 33509 & 33510 |
| MAGED4B | AGCCCGCCATGAGACCAGCAA | CAATCAGCGCTTCATCCCCGA | 33405 & 33406 | MAP1LC3B2 | GCAGCGGCCGCCACCTTCGAA | TGTGTCCGTTCACCAACAGGA | 33511 & 33512 |
| MAGEE1 | CAACCGAAGGAGGATGGAAGA | CCCGCAGAAAGCCCAGA | 33407 & 33408 | MAP1LC3C | GAGCGCAACCATGGCAGAGA | TGTCCTTCAAGGCTGCTCCA | 33513 & 33514 |
| MAGEE2 | CCTCCTTGTCCGCAACCAGA | TGACAGGTTGCCCATCAGGA | 33409 & 33410 | MAP15 | GCCTCACCCACAGTGACCA | ACCAGCACCAGGTCCACA | 33515 & 33516 |
| MAGEF1 | GTGCCTCACCAATCCACCA | TCTGCTAGGGCCTCACGGTA | 33411 & 33412 | MAP2 | ACCCGACGACTCAGCAA | AGCAGTGACATCCTCAGCCA | 33517 & 33518 |
| MAGEH1 | GTCTGGAAAGTGTGGGGAA | TCATACTCCACGGACTGCTA | 33413 & 33414 | MAP2K1 | CCCCGCAGAGAGAGCAGA | GAGCAGAGCCAACTTGCA | 33519 & 33520 |
| MAGEL2 | CCTGTCCAGCGCTCGGAGA | AAGATGAGGCTCAAGACCACCA | 33415 & 33416 | MAP2K2 | CTTCCGGTGAGCGGCCA | CAGATGCCGACTGCCACGGA | 33521 & 33522 |
| MAGI1 | AAGCTAAAGTAGGAGCAACGGA | CGAAGCTCATCCCCAGGA | 33417 & 33418 | MAP2K3 | GGAGCCTGGGCATCACCA | GGGACGCCTCCACCA | 33523 & 33524 |
| MAGI2 | GACATGACATATGCCAGAGCAA | GCGGCAGCGGGAGAACTTCCA | 33419 & 33420 | MAP2K4 | GACTTCGGCATCAGTGGACA | TCCAACATCAGACGGGACA | 33525 & 33526 |
| MAGI3 | AATGCAGGAAGTTGGAGGGCA | CTCCTAGCACCTGCAAGCCA | 33421 & 33422 | MAP2K5 | GCAGCCCAGCAGTCTCAGA | ACTGTGCCCCGTTGCCA | 33527 & 33528 |
| MAGIX | CGTGCAGCGCGTTGGTACGCA | CCAACAATAGTGCCATGAGGCA | 33423 & 33424 | MAP2K6 | AGCGGGCAGATCATGGCA | TAAAGGTGCAGTGAATGGACA | 33529 & 33530 |
| MAGOH | TGAGTTTCGACCGGACGGGAA | CAAGCTCCTGCCGGCCA | 33425 & 33426 | MAP2K7 | CGCTTCTGCCCGGACACA | CTTGAACCAGGACGCCA | 33531 & 33532 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| MAP3K1 | GCAGTGGAAGCAGCCCGA | TGTAGACAGGGTCAGCACA | 33533 & 33534 | MAPRE3 | ATGTGGCCCCCCCTGCA | CTCCAGCCATCCACTGTCA | 33639 & 33640 |
| MAP3K13 | CTTGGCAGAAGAAGCTAGAGGA | CACAGCTTGCCAGGAGGACA | 33535 & 33536 | MAPT | GCGAGAAAGCGCAAAGCCA | GCTGGGGCGAGTCTACCA | 33641 & 33642 |
| MAP3K14 | CCGGCCAGCTGAGGAGACA | GCTGGCTCCAGGGAGGACA | 33537 & 33538 | MARC1 | GGGACTGTGGCGAGGCCA | ATGAGGACGTCTCGGTCGCA | 33643 & 33644 |
| MAP3K15 | GGGAGAGACCGATGGAGACA | CAGATCTCGGCCAGCATTACACA | 33539 & 33540 | MARC2 | TAAAGGCAGAGACTGTGGCCAA | CATGATCAGGAGCGGGGCA | 33645 & 33646 |
| MAP3K19 | TGGAATGGCCCCAGAAGTCA | AAGTGGTCTGTAAAGGAGGCA | 33541 & 33542 | MARCH1 | GCAGCCCAACAACAGGGACA | AAGGCAGTGTCCCAGTGCA | 33647 & 33648 |
| MAP3K2 | CTGGATGAGCCTGAAGTCA | GTCTGAGACATGAGGGTGGCA | 33543 & 33544 | MARCH10 | AATCGCACAGCCCGAGAGCA | GGCTGTGACGATGGGACCAA | 33649 & 33650 |
| ZAK | TACACAACAAGGCCGGAGTGGA | CAAGAGAAGCGGGGTGTTGGA | 33545 & 33546 | MARCH11 | CAGTGTGGCAGGAGGAAGGACA | CCGCAGAGCTGTCAATGGCA | 33651 & 33652 |
| KIAA1804 | CAGGAAGTGTCTGAGACCA | GGCAGAGTGGCAGTGCAGA | 33547 & 33548 | MARCH2 | GCCTCGACCCTCACAGA | ATAGATGGTGAAGAGGGCGA | 33653 & 33654 |
| MAP3K3 | GCAAAGCCTGCAGACGA | CCACCAGTGCAGCCCA | 33549 & 33550 | MARCH3 | GGGCAGCAGCCAAGAGGA | ACCTGAAGTGGCAGAGTTCACA | 33655 & 33656 |
| MAP3K4 | TCAGCCGGTCATCGCCAA | TCCACGCGGTCAATGGCA | 33551 & 33552 | MARCH4 | AGGTTCAGGTTGCAGCCGCCA | CACACCACGTCCATGAAGCCA | 33657 & 33658 |
| MAP3K5 | GAAGGCGGTACAGACAGCCA | TCACGCCTGAGGTAGCCA | 33553 & 33554 | MARCH5 | CTGTCTACAACGCTGGGTTGGA | AAGACGTAAACCTGGACCCA | 33659 & 33660 |
| MAP3K6 | GCACCAGGAGCAGAAGCA | GGTCTGTGCAGAAGCGCA | 33555 & 33556 | MARCH6 | TCCATGGGGGAGCACCAA | GCAGGCTGATCAGCAGCA | 33661 & 33662 |
| MAP3K7 | GAAGTGATAACGCGTCGGAA | CATTGAAGGGCGCCTGGGA | 33557 & 33558 | MARCH7 | AAGGAGGCGAGAGGGAAGAGA | GTCTGTTGGCAGCAGCTCCAA | 33663 & 33664 |
| MAP3K7CL | ATGACTCCGAGGAATCCATGGA | TGAGACTGGGCCAACCTCA | 33559 & 33560 | MARCH8 | TGGAGACAAGCTGAAGCCA | CACATACAAGGACCAGACCACA | 33665 & 33666 |
| MAP3K8 | GAGGCTGCTGAGTAGGAAGGA | ACAAGATTGAAGTAGCCAGCA | 33561 & 33562 | MARCH9 | GAGGGACGGCAGGGAAGTCA | TGTATAACCGACGCGCTGA | 33667 & 33668 |
| MAP3K9 | GCAATGGGTTGAGCCCCA | TGCCGTTGGCAGAAGGA | 33563 & 33564 | MARCKS | CCAGGCGAGGGCGGCGA | CAAAACCAGTACTCGGCACCA | 33669 & 33670 |
| MAP4 | GAAAACCGGGAACTGGCTAGGA | CATGACCACCATGGCTAGGA | 33565 & 33566 | MARCKSL1 | CCCCAAGGGTGAAGGGGA | CTCCCCTTGGCCTCAGCA | 33671 & 33672 |
| MAP4K1 | CGCACACCTGAGATCCCA | CACTACAGGGTCTGGGGGA | 33567 & 33568 | MARCO | CAAGAAGGGAGAGCAGGGAA | GTAACCAGCATGCCAGGA | 33673 & 33674 |
| MAP4K2 | GATGGGAAGGAGCTGCGCGA | GATGTCCGGCGTCAGGCCA | 33569 & 33570 | MARK1 | GTCAGAGGTTCCCGGCCCA | TACAGCAGGAGGAATGGATGGA | 33675 & 33676 |
| MAP4K3 | TCCAGATTACCCCACACA | TAGGTGTTGGAGGGAGACCA | 33571 & 33572 | MARK2 | GAACAGCTGCCAGAGCGA | AATCGAACCCGTTGAGAGA | 33677 & 33678 |
| MAP4K4 | TCAGGGTCCAACTCAGGA | TTCCAGGCCTGAGATGGA | 33573 & 33574 | MARK3 | CTGGACTATGAGCAGAGGGA | TAAACAGGACCCGTTCAGA | 33679 & 33680 |
| MAP4K5 | TGTGGGCTGTGGCAAGGCA | GGGGTGGGTGGAAGGCA | 33575 & 33576 | MARK4 | CAGCCACAGCAAAGGGCA | TGCAGGGATGGGCCA | 33681 & 33682 |
| MAP6 | AGTGCCATGGCCAGGCA | TCACGGACTCGGGGACCA | 33577 & 33578 | MARS | TGAATGAGCCCTGGAAGCGCA | TTGTGGCACTAACCGTGGGCA | 33683 & 33684 |
| MAP6D1 | CCCACACTTCGGGATGGGACA | CGGGGAGCTGAGGCCTGA | 33579 & 33580 | MARS2 | TGTCAAAGGCATGGCACCA | AGAGACCCCCAGCCTAGACA | 33685 & 33686 |
| MAP7 | TTCTGCAGGCACCCGA | CAGCCACACGTTGAGCCA | 33581 & 33582 | MARVELD1 | CCACCCGACTGCCCCA | GGCCCAGAATGGGATGGGA | 33687 & 33688 |
| MAP7D1 | GCCAACGGTTCCAGCCCAGA | GTGTGCTGGGAGAGGCTGCA | 33583 & 33584 | MARVELD2 | ATAGCGCCAGATCTCAAACCA | TCCCGGGAAACACTGCGTCA | 33689 & 33690 |
| MAP7D2 | CAGACCGAGCTCATCACATGCA | CTGCCCAGAGAGCATGACTGAA | 33585 & 33586 | MARVELD3 | ATATCTGCCCTCGACCCCA | ACCACACTCTCCAGTGCA | 33691 & 33692 |
| MAP7D3 | ATCTCCGAGGCAAAAGCGAGA | AGTGCTGTATGGAGGACGGCA | 33587 & 33588 | MAS1 | GTCGGGAATGCACATGGAGGTA | TCTCATCCGAAGCACAAGGAA | 33693 & 33694 |
| MAP9 | AACCATCACTTCGGCCAAGGA | CCATTCGGCGTTGGAAGGAGAA | 33589 & 33590 | MAS1L | GTACAGATGCCACCGCCCAA | GGATAGCATGGAAGAGCCCAGA | 33695 & 33696 |
| MAPK1 | ATGGAACAGGCTGTTCCAA | CCAGATATGGGTGGGCCA | 33591 & 33592 | MASP1 | CCACCAGACTTCAACATCCAA | CTCAAGCCTTGGCAGGCAGA | 33697 & 33698 |
| MAPK10 | TGACCAGCCGAAGTGGA | TCACTGCTGCACCTGAAGGA | 33593 & 33594 | MASP2 | TGCAGAGGTGACAGCGGA | ATTCATGGAACCCAGGACA | 33699 & 33700 |
| MAPK11 | CTGGTACGCGGGACCTGAGA | GAAGAGGCCTTGCCCTGGA | 33595 & 33596 | MAST1 | CCCCACCTAGAGTCGGAA | CGCGGAGGCAGGAGAGA | 33701 & 33702 |
| MAPK12 | ATGAAGGGCCTCCCCGAA | CGAAGTAGGGATGGGCCA | 33597 & 33598 | MAST2 | TCAAAGGCCGAGACCGGA | ATCCAGGAGGGCCTGAGCA | 33703 & 33704 |
| MAPK13 | GCTGGCGGACATGCAGA | GTAGTGCATCCAGCTGAGGA | 33599 & 33600 | MAST3 | CTCACCGGTCAGCAA | CTCAGCCGGATGTCAGCA | 33705 & 33706 |
| MAPK14 | ACTGGCTGCCAGACAGA | CAGTCAACAGCTCGGCA | 33601 & 33602 | MAST4 | GGAGCCTGACTGGCAGGTA | CATGCGCACGAGGTTGGA | 33707 & 33708 |
| MAPK15 | CGAGAGAGAAGGGCCCGGA | CCTAGGAGAGCAGTTTGGAGCA | 33603 & 33604 | MAST1 | GTGCCTTTCCCACCACTGGA | CCCACCAGAATCCAGAGCCCA | 33709 & 33710 |
| MAPKIP1L | ACCATATTCCTGCCCTACAAGGA | GGCCACCAGGCATTGGTTGGA | 33605 & 33606 | MAT1A | TTGTCATCGGAAGGTCCCA | TGGACAAGCACTCTCCGGCA | 33711 & 33712 |
| MAPK3 | AAACGGATCACGTGGAGGAA | GCTCCATGCCAAGGTGA | 33607 & 33608 | MAT2A | GGTTGGGGTGTCATGGAGGA | CTGAACAAGAACCCTCCGGCA | 33713 & 33714 |
| MAPK4 | GGCACGCTGCTGGAGCA | CGTGTCAGCACCGTTGGCCGA | 33609 & 33610 | MAT2B | GGAAGATGACCAAGAGAGCA | CTCTGCTAGCTGCCGGCACA | 33715 & 33716 |
| MAPK6 | TTCCAGCATGAGCCTACTGA | GAAAAACAGTCCTCCCCACCA | 33611 & 33612 | MATK | CCGTGCACGTCCTCATGAGCA | GAGACGGAGGCTGGGGCA | 33717 & 33718 |
| MAPK7 | GAAAGTGACCTGCACCAGA | GCACAGGCCACGAGCCA | 33613 & 33614 | MATN1 | ATCAAGGCGGGCGTGTGCGGAA | GGCTAGCCCACTGGACA | 33719 & 33720 |
| MAPK8 | GCAGAAGCTGCAACAGA | CAGACGACGATGATGATGGA | 33615 & 33616 | MATN2 | GGCTGGCCCTGAAACACA | CGTCCGTCCGTGAACACA | 33721 & 33722 |
| MAPK8IP1 | CCCAGGAGGCCAAGGGGGAA | TGTGGGGCAGGTGTACTCCA | 33617 & 33618 | MATN3 | AGTGAGCCCCTAGAGGAGCA | TTCCAAGCACACAGGGGTCCA | 33723 & 33724 |
| MAPK8IP2 | TCAACATGCCACAGGGGGA | AGAGATCTGCAGGTCACAGGA | 33619 & 33620 | MATN4 | ACCAGCCAGGCGAGGTGAAGCA | TGCACCCTCGGCCTTCGGAGA | 33725 & 33726 |
| MAPK8IP3 | GCACGTCATCCAGCCCA | AGTGCAGGGTCTGGACA | 33621 & 33622 | MATR3 | CAAAGGATGACCAGACGAGCA | TCGTTCTCCCACTGGAACTGCCA | 33727 & 33728 |
| MAPK9 | ACCGGGCGTCCGAAGTCA | GTCTTCTTCCCGGGAACAGGA | 33623 & 33624 | MAU2 | CTGCACTGCCTCCGAGCA | ACGACCACAGCTGTACCGACA | 33729 & 33730 |
| MAPKAPK1 | GAAGCAGCGCGAGAGGCAA | GTTCTGCGCGGACCAGGCA | 33625 & 33626 | MAVS | CGACCGGAAGTTCCAGGA | GCCGGTACAGACACCACA | 33731 & 33732 |
| MAPKAPK2 | CAGAAGTGCTGGGTCCAGAGA | ATGGCAAGGCCGTGGTTGGA | 33627 & 33628 | MAX | GAGGCGACGAAGAGCAACCGA | ACTGACTCCCGCAAACTGTGA | 33733 & 33734 |
| MAPKAPK3 | CCACAGACCCCACTTCCACA | CGCATAGTGGCTCAAGGCA | 33629 & 33630 | MAZ | CAGCCAGGGTCTCTCACA | GGCTGAGAGCTCACAGGCA | 33735 & 33736 |
| MAPKAPK5 | ATCGAGGAGTGTGGACCA | ATCATCAGCTGAGCAGAAGAACGGCA | 33631 & 33632 | MB | ATCCCCGTGAAGTACCTTGGA | GCCCCTGGGCATCAGCA | 33737 & 33738 |
| MAPK8P1 | TGAGCAGCCGAGAGGCAA | CTGTCAGGGTTGGAGACGGCA | 33633 & 33634 | MB21D1 | GAAGTTGAAGCTCAGCCGCGA | CGAGCCTCTGAACGCGGA | 33739 & 33740 |
| MAPRE1 | GCAGCTGAGTTGATGACGA | CCCGCCTTCTCTGGCA | 33635 & 33636 | MB21D2 | GCTCTGGGCCTGCACAGA | CTCCGGGTCTGAGCGCA | 33741 & 33742 |
| MAPRE2 | TTCTCGACCCTCATCAGCCAA | TTCCACGCCTTCAAGGGCA | 33637 & 33638 | MBD1 | CCCCATCACAGTCCCCAGA | CTCTGACCAGACACTGGGCA | 33743 & 33744 |

(Table content omitted - large sequence data table with columns: GeneName, Forward Primer, Reverse Primer, SEQ ID NOs, GeneName, Forward Primer, Reverse Primer, SEQ ID NOs)

| GeneName | Forward Primer | Reverse Primer | SEQ ID NOs |
|---|---|---|---|
| PRELP | CCTGGGAGAACGTGCCACA | TCATGAGGTCCAGCGGGA | 40105 & 40106 |
| PREP | CATCAGAGGAGGTGGCACGA | CAGCCACTAAGAGGCCTTCA | 40107 & 40108 |
| PREPL | GCCTTCCAGTGGCACGCTGA | CTCCTGCAAGACACCCTTCCA | 40109 & 40110 |
| PREX1 | TGGCGAGTACGAGGAGAGCA | GCTCTGCACAGCGTCACCCA | 40111 & 40112 |
| PREX2 | CTTCCAGCAGCGTCGGCA | ACATCTGGTTCAAGGCCGCA | 40113 & 40114 |
| PRF1 | ATCTCCAACTACGGCACCCA | GGCCTTGGCTTCGGCAGA | 40115 & 40116 |
| PRG2 | GGAGGTGCTACAGGGGCAA | AGCGACCCGAGCCTGTGA | 40117 & 40118 |
| PRG3 | AAGCCATGGAGTAGGCGGCCA | CCGACCAATAGGTAGCGGGA | 40119 & 40120 |
| PRG4 | GACACCAACTCCCCGCAA | GTCGGGAGTAACTTCAGGCA | 40121 & 40122 |
| PRH1 | CACCCAACAGGGAGGCCA | GAGGAGACTGCCCTGTGA | 40123 & 40124 |
| PRH2 | CATAGATGAGGAGCGTCAGGGA | CTGGTTCCATCACCAGCAGA | 40125 & 40126 |
| PRICKLE1 | CTGGGACTCTACGGCGAGGA | TGACCAAACTGAGGGGTGGGA | 40127 & 40128 |
| PRICKLE2 | GGCACTTCGGCAAAGTGA | CTACCACATCAAGGCTCCGA | 40129 & 40130 |
| PRICKLE3 | TCCAAACTGCAGAGAGCA | GTGTGACTGCCCAGGCCA | 40131 & 40132 |
| PRICKLE4 | CTGAACAAGGACACGGGGA | GGGTTGCGCTGAGCACCA | 40133 & 40134 |
| PRIM1 | CCTGGCTGGAGTGGGGAGA | GGCATCCAATTCACGGCA | 40135 & 40136 |
| PRIM2 | TGGAGAGTGAGCTTCGGAA | ACTGGCAATAAGCAAGCCGCA | 40137 & 40138 |
| PRIMA1 | TCCGAGCCCTGAGCGTCAAGA | TCAACTGTCAGACGGCTGAAA | 40139 & 40140 |
| PRIMPOL | TCCAGAGACAACAGGCCATGGA | GCTGACCCCAGCCTCTCA | 40141 & 40142 |
| PRKAA1 | GGCACTTCGGCAAAGTGA | CTACCACATCAAGGCTCCGA | 40143 & 40144 |
| PRKAA2 | TCCAACTGCAGAGAGCCA | GTGTGACTGCCCAGGCCA | 40145 & 40146 |
| PRKAB1 | CTGAACAAGGACACGGGGA | GGGTTGCGCTGAGCACCA | 40147 & 40148 |
| PRKAB2 | TGGTCTGAAGGAGGCAAGGA | TGCAAGCTGACTGGTAACCA | 40149 & 40150 |
| PRKACA | TGAGTACCTGGCCCTGAGA | AGAGCTGAAGTGGGAAGGGA | 40151 & 40152 |
| PRKACB | CAAGGCTATATCCAGGTCACGA | GGGGATAGGCAGCCTGCCA | 40153 & 40154 |
| PRKACG | CACATACTGAACGAGAAGCCA | CCCACCCGGCACGTACTCCA | 40155 & 40156 |
| PRKAG1 | TGGAAGCAGAGGTTCACGGA | CTCTCCACCTGTGAGCACCA | 40157 & 40158 |
| PRKAG2 | ACCTGTGAGGCCCAAGACGA | AGGAGAGCGCCAAGGATCCA | 40159 & 40160 |
| PRKAG3 | CAAACCTACAACCACCTGACA | CTCCGAGCAATCTGTGA | 40161 & 40162 |
| PRKAR1A | GGGGCATCGACCGAGACA | CTGACCGACGTTGTAGCACA | 40163 & 40164 |
| PRKAR1B | GGGAGAGCCTGGGGACGA | GGGCCGGTTCAGCAGCA | 40165 & 40166 |
| PRKAR2A | GGGAACCAGGAGGTGGGAGCA | TCCAACTGCATAAGCTGAGGCA | 40167 & 40168 |
| PRKAR2B | TGGTCAAAGATGGGGAGCA | TAAGGCCAGTTCGCCGAA | 40169 & 40170 |
| PRKCA | GATGACGTTGGAGTGCACCA | CCATGACGAAGTACAGCCGA | 40171 & 40172 |
| PRKCB | TCCAGACATACTGCCCCGA | AAGGGTGCCTGCCCAGCCAA | 40173 & 40174 |
| PRKCD | AAGCGGAGGTTGGAGCCA | GAGAAGGCAGCGAATGCAGA | 40175 & 40176 |
| PRKCDBP | TCACGCCTAATAAGGAGCGA | GGACTGGGCTTAAGGAAGGGA | 40177 & 40178 |
| PRKCE | GGCCGACATGAGGAGACGA | GCGATGCCACACAGCCA | 40179 & 40180 |
| PRKCG | GTCCAGGACGCCTGTCCA | ACCAGCCGTGCAGTCCA | 40181 & 40182 |
| PRKCH | GGTGTCACCACCGGCACA | TGGAGCCAGGTAGGGTAGGACCA | 40183 & 40184 |
| PRKCI | GAAGGATTACGGCCAGGAGA | ATGAGCACTCCAAGAGCCA | 40185 & 40186 |
| PRKCQ | TAGGAGATACGGCCAAGCCA | GGCGAGTTGACCAATCAGCA | 40187 & 40188 |
| PRKCSH | AAGCGGAGGTTGGAGCCA | GAGACAAGCTTGAAGGGGCA | 40189 & 40190 |
| PRKCZ | TCACCGACAACCGGACA | GGGAGGCTTTGACGGACA | 40191 & 40192 |
| PRKD1 | CCTTCAGCCATCCA | CCTTGGGAATGACGGGCA | 40193 & 40194 |
| PRKD2 | GGAGCCACATCTCAGCTGGA | CCAGCTCTCGGAGGTTCA | 40195 & 40196 |
| PRKD3 | ATCTGTGGTTAGGAACTTCAGCA | AAATGTGCCACTGAGGCTCACA | 40197 & 40198 |
| PRKDC | ATGACGGTAGGGGAGGAAGA | GTCCTGCACCCTTCACCA | 40199 & 40200 |
| PRKG1 | TACAGGAGCAGAGCAGCA | GTGGGCTGCCAGTCAGGA | 40201 & 40202 |
| PRKG2 | GAGGAGCTCCAGAACAAGTGCA | CCGGTGACCTCAAGAGGCA | 40203 & 40204 |
| PRKRA | GCTAAGCCAGGGAGAAACACCGA | TCAGGCATTAAGGGGTCAGGA | 40205 & 40206 |
| PRKRIP1 | CGCCGAAGAGGCCAGA | GCCCATGTGAAACTGGGCA | 40207 & 40208 |
| PRKX | CTGGACCGTGGCATGACGA | TGCAGGTACTCCGATGGCACA | 40209 & 40210 |

| GeneName | Forward Primer | Reverse Primer | SEQ ID NOs |
|---|---|---|---|
| PRL | CCAAACGGCTTCTAGAGGGCA | AGGGATGGAAGTCCCGACCA | 40211 & 40212 |
| PRLH | CTTCGGTCGGAGGAGGGCAA | CCGCCTTCCAGGGGGAAGCA | 40213 & 40214 |
| PRLHR | GGTGTCAGTGAAGCTCCGCAA | AAGGGGTTGTAGCAGGCCGA | 40215 & 40216 |
| PRLR | CGCTGCAAACCACAGACCATGGA | AAAGGACAGCCACAGAGATCCA | 40217 & 40218 |
| PRM1 | AGCCAGAGCCGGAGCAGA | GTACCTGGGGCGGCAGCA | 40219 & 40220 |
| PRM2 | GGCTGCACCGGATCCA | CCTCCGGTCCTGCCAGGA | 40221 & 40222 |
| PRM3 | CGGGGCCACGAATCCTCCA | CCTGCCGCTCAGGCTCCA | 40223 & 40224 |
| PRMT1 | GCCTGCAAGTGAAGCGGA | CCAGTGCGTGTACGGGGA | 40225 & 40226 |
| PRMT2 | CTTCCACCCACCACACA | CAGCCCAGCTCAGAGGCCA | 40227 & 40228 |
| PRMT3 | CATCCATGTGCAGGGCAA | GGGCCCTGTAGAGAACACGA | 40229 & 40230 |
| PRMT5 | GTGGCTCCAGAGAAAGCAGA | GGAGGAAGGAACTGAGGAGGCCA | 40231 & 40232 |
| PRMT6 | GCTACGGACTCCTGCACGA | CCGACAATCCTGCACA | 40233 & 40234 |
| PRMT7 | AATGAGGACTTACAGGGCAGAA | CTGGTCCACAGCGGTCCGGA | 40235 & 40236 |
| PRMT8 | CATGACCTGCATCCGGGA | ATCTGCAGGGCAGAATGCAGA | 40237 & 40238 |
| PRMT9 | GCGCCGAGCTGCCCTGGAACAACA | ATTCTGAAGAGATGCTCCCCA | 40239 & 40240 |
| PRND | CACCCAGGCGGCGGAACCA | GTCCTGCGCCCCTCTCCAA | 40241 & 40242 |
| PRNP | CAGTCAGTGGAACAAGCCGA | CCAAGCATGTAGCCGCCA | 40243 & 40244 |
| PROB1 | GAGAGTGGGCAGTGGCAGT | CCCATAGCGGGGCGGGTAGA | 40245 & 40246 |
| PROC | CCTGGAAGCGGATGGAGA | GGCTGTCAGLACCCAGGA | 40247 & 40248 |
| PROCA1 | GAGGGAAAGGAAGGGGGCACA | TCTGGCAGCAGAGAGGGGAA | 40249 & 40250 |
| PROCR | CTCGGTATGAAACTGCGGGAA | GATGCCTACAGCCACACCA | 40251 & 40252 |
| PRODH | CCGCTGCCTGCCAGGAACA | GGCGATGGAAGAGGTTGCCA | 40253 & 40254 |
| PRODH2 | CGCCAGGCAACCAAGCGCA | GCCTGCCCAGTGCTAGAGA | 40255 & 40256 |
| PROK1 | GGAAACGCAAGCACCCA | AAGTCCATGGAGCAGCGGTA | 40257 & 40258 |
| PROK2 | CACCACCCAAGCCCA | GAGGAGGGAAGAAGAAATGGACA | 40259 & 40260 |
| PROKR1 | TGGTCAAGGCGGTCCCCTGGA | GGTGGGGAAGAAGAATCGGGCA | 40261 & 40262 |
| PROKR2 | GAAGTTGCGCAACCTCACCAA | AGCACGTGGCCATGCTCCCA | 40263 & 40264 |
| PROM1 | GACCAAAGAGGCGTTGGAGA | ATGATGCCACCAAGGACAGA | 40265 & 40266 |
| PROM2 | GAGGAGGTGACTCAGCGCA | TGCACCATGCCAGGCAGA | 40267 & 40268 |
| PROP1 | AACCGCAGAGCTAAGCAACGGA | AAGAATAGGGCAAGCAGTGGA | 40269 & 40270 |
| PRORY | CTGGGATCGGAGCCGCACA | GGAGGAGGATCAGCGGGCA | 40271 & 40272 |
| PROS1 | AATCTGGAGTTGTCGACACA | CATCTGGAAGGCCACCA | 40273 & 40274 |
| PROSC | ACCATAGCCATCGTGGAGCACA | CTCAGTCAACCTGGTCAGCA | 40275 & 40276 |
| PROSER1 | CCCCACCCAGGTACTTCAGA | AGATAGGACCTTGAAGGCCGA | 40277 & 40278 |
| PROSER2 | CTTTTCCAAGAACTGAGAGA | CCTACTCTCCAAACCCCA | 40279 & 40280 |
| PROSER3 | TCGGCAGAAAAGGGAAGCGGA | TGGGACCTTAGGGGGCGA | 40281 & 40282 |
| PROX1 | GCCGAAGCGAGAAGGCAA | GAGGTGGGAAGACCTGAGGA | 40283 & 40284 |
| PROX2 | GTCACCTCCAGGGCGTCAGA | CTTCCGGAAAGACTGCAGTACA | 40285 & 40286 |
| PROZ | GATGGAAGTGTTGGGTCACCAGA | GACCTTGGTGACAAGGCACCA | 40287 & 40288 |
| PRPF18 | TGCGACCCAGGAAAACAGACCGA | CCGATGGGCCAAGGGCCA | 40289 & 40290 |
| PRPF19 | TGGGGTTGCACAGTGCCAGCA | TGTACAAGAGGCATTGGGGA | 40291 & 40292 |
| PRPF3 | GGGTACAGCCAAAGACCCGA | ACACAGATTCACTCAGCGCA | 40293 & 40294 |
| PRPF31 | CGGACCCTGCAGAAGCAGA | GGAGTGGGGTGAAGGCCA | 40295 & 40296 |
| PRPF38A | CACACTGCGCTCAAGGAGGA | CGGATCTGTGCCGCCGA | 40297 & 40298 |
| PRPF38B | ATGGGAAGGAAGGTGCTGAGGA | GACCCATGGCCCTCCGA | 40299 & 40300 |
| PRPF39 | ACCTTCCAGTGACGCTGACAGA | TTCCTGGCAGCCATCAAGTGA | 40301 & 40302 |
| PRPF4 | GACTGGGGGACTGGATGCA | CGCTGTCGGAGGTCCCACA | 40303 & 40304 |
| PRPF40A | CGATGCTGAGCGAGAGAAGGA | TTCCGCTGCCAAGGTATCCA | 40305 & 40306 |
| PRPF40B | GAAAGCTGCCAAGGAGGGGA | TCTCCAGCTTCACCCTCACTCA | 40307 & 40308 |
| PRPF4B | CTCCTCGGAGAAGGGACAGA | TCTACGACCACCGCGTGA | 40309 & 40310 |
| PRPF6 | ATGATGGAGAAGGGCGGGAA | GACAGGTACTTCCAGCCGCA | 40311 & 40312 |
| PRPF8 | GGGAGACGAGTGAAGGCGA | GCACAGCCTGTTGACGA | 40313 & 40314 |
| PRPH | CAAGCCCTTACCCCGGCAGCA | ATCGGGACATGAAAAGGGAAGCACA | 40315 & 40316 |

| GeneName | Forward Primer | Reverse Primer | SEQ ID NOs | | GeneName | Forward Primer | Reverse Primer | SEQ ID NOs |
|---|---|---|---|---|---|---|---|---|
| PTPN12 | AACCACCAAGGACCCGCA | TGAAGGGGAGAAGGTGTCA | 40741 & 40742 | | PUS1 | GACGCTGCAGCAGGTCAACA | CCAGGATGTAGCGGCAGGCA | 40847 & 40848 |
| PTPN13 | GACGAGCAATCAGCACTGGCA | AGCGACAGCTCTGAGCAGGA | 40743 & 40744 | | PUS10 | CAGCTTGTCACAGAGAGGCA | GTGAATGACGCGAGCTCGCA | 40849 & 40850 |
| PTPN14 | GGTCCGTCGCCATACCAA | GCCTCAGCATCATGGGCA | 40745 & 40746 | | PUS3 | ATCACCGATGTGGGAGAACAGA | CGGTAAGTCCGCTCAAGGCA | 40851 & 40852 |
| PTPN18 | CCCAGCTGGTACGATCACACA | CAGTGAACACAGCAGCCAGAACA | 40747 & 40748 | | PUS7 | TCAAAAGGTGTGTGGAAGGGCA | TGAGAACGAGGTCCCTGGA | 40853 & 40854 |
| PTPN2 | TGGAGTCCCTGACAATGACCA | TCTACCAGAGAGAAGGTGCA | 40749 & 40750 | | PUSL1 | CCAAGATCCCTGGGCAAGCA | CCGAACTGTGGCCCTGCA | 40855 & 40856 |
| PTPN20 | AGTGATCCAGCATGTGGACA | TAGAGGGGAGAGAGCCTGTGA | 40751 & 40752 | | PVALB | CGAGGAGGATGAGCTGGGA | CTCCAGCAGCATCAGCA | 40857 & 40858 |
| PTPN21 | AGGTGCTGGACAATCCCGA | CTGGCAGAGAGTCTGCACCA | 40753 & 40754 | | PVR | AGCAACCCAGAGCCCACA | TGGCGAGCTCCTAGGGCA | 40859 & 40860 |
| PTPN22 | ATGCCTCCAAGTGGTATACCA | TGTAGAGGATGTTGGCAACAGA | 40755 & 40756 | | PVRIG | CCCCACCACGCTGCACA | CCGGGACCAGTGTGAGGA | 40861 & 40862 |
| PTPN23 | GAGCAGGTCCTGCAGCGCA | CCGAGGACCAGGTCCTGGGA | 40757 & 40758 | | PWP1 | GGCGATTCAGTGGGCAGA | GTCAGCTGAAGCAGTCACGA | 40863 & 40864 |
| PTPN3 | AGAGGACTGCACCATCGCCTA | GTCGGAGGAGTCATCGGGCA | 40759 & 40760 | | PWP2 | GCAGGAGGATTGGAGTCGCGA | TGTCAGGGAGTAGATGAGGA | 40865 & 40866 |
| PTPN4 | GCCTGGCTGCACATGGACA | TCCAGCACTGCAATGGACA | 40761 & 40762 | | PWWP2A | CCACGGTGTCGCAACTGA | ATCCATGAGGACCCCGGA | 40867 & 40868 |
| PTPN5 | AAGAGTGGGACTGAGGAGCGA | AGTGGACACGATGATGGGGGCA | 40763 & 40764 | | PWWP2B | CTGTCCCAGGGTCACA | CGCCGACTCACTGGCACA | 40869 & 40870 |
| PTPN6 | TGTGACCAACTGCTGGGGA | AAGCTGAGGACACACCCCA | 40765 & 40766 | | PXDC1 | CCGCACGAGTGGTCGGA | TCGGACCCGTCCTCGGGA | 40871 & 40872 |
| PTPN7 | AGCGCCGGTCAGTAAAGCACA | CGTCCGGCCAATTCCTGCA | 40767 & 40768 | | PXDN | CTGTGACGCCTCAGGACAGA | CAGTCAGGTGGGCCACGA | 40873 & 40874 |
| PTPN9 | TGGTCATTGCACACCGTCTGGA | TCATGCGTGACACGTCTGTGGA | 40769 & 40770 | | PXDNL | GAGCGCTGGATGAAAGAAGACTGCA | GACAGGGAGCCGGGGACAA | 40875 & 40876 |
| PTPRA | AGTCAGGGAACCACCCCA | CTGACCACCTTGTAGCAGA | 40771 & 40772 | | PXK | CCACATGGATCTGAGGAGGA | TGTAGAGGGTGGAGTTGGCGA | 40877 & 40878 |
| PTPRB | AAGTCACAGCGGAGAGCAGA | CCACGTGATGGCCAAGGA | 40773 & 40774 | | PXMP2 | GGAGGGGAAAGACACGCTCA | TGGCGAAGAGCACCGGA | 40879 & 40880 |
| PTPRC | CACCAGCTGGCCACACGA | GTGCGCCAACACCAGGA | 40775 & 40776 | | PXMP4 | GCGCAAACGGCGCTGACA | GGGCAAACGGACGCGTGACA | 40881 & 40882 |
| PTPRCAP | AGGAGGATGAGCAGGACACAGA | GCTGGACCCTCCACA | 40777 & 40778 | | PXN | CGCCATTCGTGAACGGCA | GCTTGAGGCAGAAGGCACA | 40883 & 40884 |
| PTPRD | GGGAGCATGGAGGAGGAGCA | ACCCAGGCCTTGAGGGGGA | 40779 & 40780 | | PXT1 | ACCACTCGACCCTGCTCGAA | GCAGGACTGTTGGCCAAGGA | 40885 & 40886 |
| PTPRE | AGGCCAGGGTCATCCAGA | CCTCCGTCAGCATCACGA | 40781 & 40782 | | PXYLP1 | TCAGAAGCCAGGTTCCCAA | GCACATGGGCTTGGGAGA | 40887 & 40888 |
| PTPRF | AGACCCTTGCCCAGAGCGA | GTAACGTGTGCCTGCCGA | 40783 & 40784 | | PYCARD | CTCAGTTGGGCAGCCAAGCCA | GGACTTCCCGTACAGAGCA | 40889 & 40890 |
| PTPRG | GATCCAAGAGGCCCGAA | GAGAAGGATGAGGCACAGGA | 40785 & 40786 | | PYCR1 | AGAACAGCACCCAGGCCA | GCAGCTCCCGTGTGCGGA | 40891 & 40892 |
| PTPRH | GGGTCCCCTGCCACAGACA | GTAGTGGAATTGGCGCACAGA | 40787 & 40788 | | PYCR2 | CGAACACGAGAGCTACAGTCCA | CTGGGCTGGAGGGGGTCA | 40893 & 40894 |
| PTPRJ | CAGCGAATGGCACGAAGGA | ATGACAGCGCGAGGCTCA | 40789 & 40790 | | PYCRL | AAGCCTACGTCGACAACTGCA | CATCTTGGCCGTCCCAGGA | 40895 & 40896 |
| PTPRK | CAAGAGAAGCCGGAGCCA | CCCACAGTGAACGGGGCA | 40791 & 40792 | | PYDC1 | CCAGTCGCGTAAGACAACAGCA | CAGGTGCAGGGGCTGGAGGA | 40897 & 40898 |
| PTPRM | CGATGGGGAGAGCAGCAA | GTGAGACAACTGGGCAGGA | 40793 & 40794 | | PYGB | CCCCAAGGAGTGGACCAA | AGGTCGGAGGGGCTCCACA | 40899 & 40900 |
| PTPRN | GTGCCTACCAAGCAGAGCA | GGGCATGGTCATAGGGCA | 40795 & 40796 | | PYGL | GAGAAGCCTCTCCCTCGACA | GCCACGCCATTCACAGCA | 40901 & 40902 |
| PTPRN2 | TGGAAGGCGCAGCGCAA | TGTGGGAAGGGCCGGGATGGA | 40797 & 40798 | | PYGM | CCAAGAGAGTGGACGGCGGA | GGAAGGCTCCACACCCA | 40903 & 40904 |
| PTPRO | GTGCCACAGCAAATGCTGCA | CGTCCGTCCACGCAGCA | 40799 & 40800 | | PYGO1 | GACGCAGAATAAGCACGACA | GAGGCCTCACATAAGATGGCA | 40905 & 40906 |
| PTPRQ | GGCCAGAGGACAACAAGCCA | AGGAACCCATGCTCTGGCCA | 40801 & 40802 | | PYGO2 | ACCGTGAGTGCACAGGCA | GCAGAATGCCAGGCCCA | 40907 & 40908 |
| PTPRR | TTGTTGCTGCAGTGCAGGAA | ATCCATAGAAGCTGGCAGACA | 40803 & 40804 | | PYHIN1 | CCAACCGTCACGCAACTGCA | GTCTGCAGGTCACTGTAGCA | 40909 & 40910 |
| PTPRS | CAGTTCACAGACTGGCCGGA | CCACGCCTTCATACCGCA | 40805 & 40806 | | WIBG | TGCATCTGACCAGCCTGACTCA | GCTGACTTCCCAGCCTGGA | 40911 & 40912 |
| PTPRT | TCACCAGCTGGCCTGACCA | AGTGGACCACTATGGCCCA | 40807 & 40808 | | PYROXD1 | AAGATGGTGGCCTGAAAGTGGA | TCCTGAACTCGCTGCAGCA | 40913 & 40914 |
| PTPRU | GGTGTCAGCCGCTACACA | CTGCAATCCACTGGGGA | 40809 & 40810 | | PYROXD2 | AGACATCCTCACACACCAGA | GCTCCCATCACACCTCTCCA | 40915 & 40916 |
| PTPRZ1 | GGAGGAGTGACGGCAGGAA | TCAGGCAATGCTGCACCA | 40811 & 40812 | | PVURF | CCTCAGCGCTGCGGGGA | GAACTCCAGCAGCGCCGGA | 40917 & 40918 |
| PTRF | GCGGGACAAGTTGCGCAA | CCACTTGGCCCTCGCGA | 40813 & 40814 | | PYY | TGGCCCGCCTTGACCA | CAGGTTGAGGTAGTGGCGCA | 40919 & 40920 |
| PTRH1 | TTGGAGGCCCGGACCGGA | GTCCAGGACCCAAGGCACCA | 40815 & 40816 | | PZP | CTCAGAGACCCAAGGCACCA | GGGCCGTGAGATAAGCGA | 40921 & 40922 |
| PTRH2 | GACGAGCAAGACACACAGA | GCATGAGAGCACTGGGCA | 40817 & 40818 | | QARS | CAAGGAGGAGCCAGGAGA | GTCTGCAGGTCACCTCCAGA | 40923 & 40924 |
| PTRHD1 | GCCCAGATGAGAGCAACCCTA | CCTTGGGGTAGGGCCGGA | 40819 & 40820 | | QDPR | CATCGACCATCTCCAGCCA | TGGCCATGCCGTACCCGA | 40925 & 40926 |
| PTS | AGATTGACCCTGCTGCGGAA | TTCAGTCGTGCTCACCACA | 40821 & 40822 | | QKI | ATGGCACCTACAGAGATGCCAA | CTGGTGGAGAACCGGCGCA | 40927 & 40928 |
| PTTG1 | TGATCTTGACGAGGAGAGA | CCCATGTGGAGGCAGA | 40823 & 40824 | | QPCT | TCAGCACCCTCAATCCA | TAAGGCACGCAAGTTCCA | 40929 & 40930 |
| PTTG1IP | GGCCGAGCCGGTACTGGA | AACTCCCCAGGTGCAGA | 40825 & 40826 | | QPCTL | CTACAGGCCACTTCCCTGCA | AGATGAGATGGACACGGGGTA | 40931 & 40932 |
| PTTG2 | TGAAGAGCCAGATTGCACA | TCCCATGTGGAGAGGGGA | 40827 & 40828 | | QPRT | ACGAGGAAGACCACGGCA | ACGCCTTCTCCACGCA | 40933 & 40934 |
| PTX4 | AGAGTTCCCGGCCCTGCACAA | GCAGTTGGCCCCCTGCACAA | 40829 & 40830 | | QRFP | AAGAGAGCCCACAGGCACCA | GTGAAGCTCTCAGCCACGGA | 40935 & 40936 |
| HDHD1 | CAGCCCGTCACCACCTCA | TCATATGCAAGGACGACGGA | 40831 & 40832 | | QRFPR | ACCCTGCGTCTACACCCAGA | CCCCAGCCAGTTGTCGGA | 40937 & 40938 |
| PUF60 | AGGCGAGGAGGAGGATGCAGA | GTCGTACACTTCAGCCACCA | 40833 & 40834 | | QRICH1 | TTGAAGACAGTGGACCAGCACA | CAAGGGCCTTCAAGTACCGGA | 40939 & 40940 |
| PUM1 | CCATGAACGACGGTCCCCACA | GTTGCGATGTGGGGCCGGA | 40835 & 40836 | | QRICH2 | CTGGACAGGCGTCCTCAGA | CCGGTCACATGAGGCA | 40941 & 40942 |
| PUM2 | AACACGTGACCTGAAGACA | ATAAGGCACTTGGTAGGACCA | 40837 & 40838 | | QRSL1 | AAGCAGAATCCCCACAGCCGAGA | ATTCACCAGGGAATGACACCA | 40943 & 40944 |
| KIAA0020 | GAAAGATACAGAGGTCCGACAGA | GGCTGAACGTCTCCAGTGGCA | 40839 & 40840 | | QSER1 | AAGCCCCTTCCGTGAAACCCAA | CGAGTAGACAAAGGGACGGGGTA | 40945 & 40946 |
| PURA | ACCATTGCTGCATCCGCGA | CAAGGAGGTGCCCTGGGGA | 40841 & 40842 | | QSOX1 | CGCTAGCCACTTCGAGCA | ACGCCTCACGCAGCGCA | 40947 & 40948 |
| PURB | TACCGCAATGCTCACCGTA | CCCCACCAGTCGCTCA | 40843 & 40844 | | QSOX2 | CAAGGGGTGAGGAGGAGGAGA | GGCTGGAGAAGTCAACCCGA | 40949 & 40950 |
| PURG | TCGGCACCCTCCCCACCA | TATCATGCCAGTCCCCCGCA | 40845 & 40846 | | QTRT1 | GTGGAGAAGGCGCTTCCCGGA | GTGTGAATTCCCACAGAGGCCA | 40951 & 40952 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| Q1RTD1 | GTCAGCACGAGAGACAGCCAA | TCGAGCAACCTCATCTGGCCGA | 40953 & 40954 | RAB31L1 | CCCACAGTGAAGGTGGCCGA | CGCACCAGGCCTTGCTGGA | 41059 & 41060 |
| R3HCC1 | ACCAGCGGCTCAAGACGGAGGA | CACCGAGAACTTCCCGGGTCA | 40955 & 40956 | RAB31P | ATGAGCCCACAATGGACAGGA | TACTTCGGCCAGTGAGAGCA | 41061 & 41062 |
| R3HCC1L | GAGCAGCCAAGGCCAAGCTA | TACTTCGAACCCAAGGGCA | 40957 & 40958 | RAB40A | TTCACGGAGCTGGCCAGGA | TAAGGTACTGGGGAGCGGGA | 41063 & 41064 |
| R3HDM1 | CCAGTCCCAACCACGTCGTCA | GTGCAGCTGAAATGGAGGGGA | 40959 & 40960 | RAB40AL | TTCACGGAGCTGGCCAGGA | TAAGGCAATGGGAAGCGGGA | 41065 & 41066 |
| R3HDM2 | AACCGGGGCAAGAGACAAGCA | CGGGTGATGCCTCAGGGA | 40961 & 40962 | RAB40C | CCGGTGCACCTGGTGGACAA | GGAGTAGGAACCGCCGTGA | 41067 & 41068 |
| R3HDM4 | GGAGAGGAGGACCCGCCTA | GTACACGGCTGGGGGGA | 40963 & 40964 | RAB40C | AGATCTGGAGGCCCAACCGA | GATGGTGACGGGCAGTGGAA | 41069 & 41070 |
| RAB10 | GGAAGCATGTGCAGGAGACA | GGAGGGAGACGCAAGGAA | 40965 & 40966 | RAB41 | TTCGAGGAGTCAGGCAACAGA | GGGAGGAGAACTTGGTATGGCA | 41071 & 41072 |
| RAB11A | CCCGGACGACGAGTACGA | CAATAAGGCACCTACAGCTCCA | 40967 & 40968 | RAB42 | ACAAGAGTGACCTGCAGAGCA | AGCGAGGGTGTCAAAGGCA | 41073 & 41074 |
| RAB11B | CATGCCCAAGCACCTGACCTA | CAGTGGCACAGCCCCA | 40969 & 40970 | RAB43 | GACCCGGACGAAGCAGTACGA | CATGGTGAAGTGCACGCCGA | 41075 & 41076 |
| RAB11FIP1 | GCAGCTTGGGAACTTGCCACCA | TCCATGACCCTGACAAGCA | 40971 & 40972 | RAB44 | TCCCAGGAGAGCTTTGCCCA | ATGTTGTGACCCAAGGCGGCA | 41077 & 41078 |
| RAB11FIP2 | CCAACCCACGTGCAGGTCACA | TAGCAATCCAGGTAGCTCGA | 40973 & 40974 | RAB44 | ACAAGAAGGACATCTGGATGCAGA | TCTCAAGGCAGCATCTCCGTA | 41079 & 41080 |
| RAB11FIP3 | CTCAGCATCCAGGGCGCCAA | CGATGTAGTCCTGCAGGCGGA | 40975 & 40976 | RAB4A | ACAGGCGAGAACGTGGAGGA | GCACTCCGAGGCTGCGGA | 41081 & 41082 |
| RAB11FIP4 | GCTGCCCAGACTAAAGCCCA | GATTGTGGTCCAGGATGGCCGA | 40977 & 40978 | RAB5A | CCCAACAACCAACCAGGA | AGTGAGAGGGACCCATGCA | 41083 & 41084 |
| RAB11FIP5 | GTACTACCACCTGACCCACGA | AGGTCTCCATGATCCGCACCA | 40979 & 40980 | RAB5B | GGCAACCCCAGGCCAGCAA | GGGTGAGGAAGGCCGCTCCA | 41085 & 41086 |
| RAB12 | GGAGGAAGCAGCCCCCA | GAAGTTCAACACCCAGGTGGA | 40981 & 40982 | RAB5C | TCCAGGAAGCACAAGCCTA | GGTTTCGGCCTGGAGCACGA | 41087 & 41088 |
| RAB13 | GTGCAGAAGGGAGCAGGCCGA | GAGCAAGATGTCCCGGGCCA | 40983 & 40984 | RAB6B | CCATCGAGGAGGGGGAGCA | TCCATTCCGGGTAGAGCCGA | 41089 & 41090 |
| RAB14 | AGTCGGTTGCAGATGCAAGGA | TCTTGGCAGCCTCAAGGAA | 40985 & 40986 | RAB6C | TCAGGAGCAAACAGTCAGCGA | CCTCACGAGACAAGCAGCAGCAA | 41091 & 41092 |
| RAB15 | ACTCTCTGCCACATCTCCA | CTGCCCCAGTGTCCCAGA | 40987 & 40988 | RAB7A | TGGAGCAGGCGTTCCAGCAGA | GAGGCCTTGGCCCGGTCA | 41093 & 41094 |
| RAB17 | TTCGGCCAAACTGAACCACCA | TTGTTCAGAGCCACAGCTGCA | 40989 & 40990 | RAB878 | GGGGCCAGCATCTCTCCAA | CCAGGACATCACCCCGCCA | 41095 & 41096 |
| RAB19 | CTGTTCGAGGATGCCTGCACA | CCTTGGCCATGAGCACGAAGA | 40991 & 40992 | RAB8A | GTCAGGGAACGGTTCGGACGA | ATGTTGCGAATCCAGTTCCGGA | 41097 & 41098 |
| RAB1A | CATGACGGATGCAGCTGAGA | TGGACTTCTCAGCACACCCA | 40993 & 40994 | RAB8B | CAGGCTACTACAGAGGAGCCA | TTCGACATCGGAAGGAGCGA | 41099 & 41100 |
| RAB1B | TGGACAACAACACCACAAGGA | CCCCAGAGGCTGCTCA | 40995 & 40996 | RAB9A | ACGGCAGGTCAGGAGCGA | TAAAGTAAGCAGGCAGCAGTCA | 41101 & 41102 |
| RAB20 | AGAAGGAAGAGTGCAGTCCCAA | GGCCGGCACATCCTGCTCA | 40997 & 40998 | RAB9B | CTGGTGCATGGAGAATGGGGA | CAATGGTGTGACCAACATGCA | 41103 & 41104 |
| RAB21 | ATGCAGAATCTGTGGGAGCA | TCCAGAAGAACAGCACCCTCCA | 40999 & 41000 | RABAC1 | GAGAGGTGAGCCCAGCGCA | GCAGCTCCTCCGTCA | 41105 & 41106 |
| RAB22A | GAGATGCAAAGGACTACGCCGA | AGGTTGGCGTCAGTGGATGGAA | 41001 & 41002 | RAB8FP1 | TGGGTCACTCCAGATGCAA | ACCATAGGGGACACATAGGCA | 41107 & 41108 |
| RAB23 | TGAGGATCCAGAACTAACGCA | GACCGGAGTGACTTCCACCA | 41003 & 41004 | RAB8P2 | GCAAGGCCAGCTCCAGA | GGGTCTCAGCCTGGCGGA | 41109 & 41110 |
| RAB24 | GAACTGCAGCCTAGAGGA | GTGGAAGTCCACATCGTCGA | 41005 & 41006 | RAB8PK | GCCGAGAGAGAGGTGCCCA | CATAGAATCTGTCCCCGCCA | 41111 & 41112 |
| RAB25 | CTCAGCCTGGACTCTACCAA | CTGCCAGAGTGATGGCA | 41007 & 41008 | RAB6AP1 | GACAGTGCTATCACCGGGA | TATGGAGAAGGAGCACAGCA | 41113 & 41114 |
| RAB26 | GGCTGACCGAGATCACGA | CCCTATGGGCGAGAGTCA | 41009 & 41010 | RAB6AP1L | ACCGGACTTGCATAGCCA | GAACACCATGCAGAGTGGGA | 41115 & 41116 |
| RAB27A | GAAGCCATAGACTGCAGA | GATCCGTAGAAGGCATGACA | 41011 & 41012 | RAB6EF1 | TGATAGCTGGAGGAGGATGGCTA | CCTGGGAGAGGTCTTGGCCA | 41117 & 41118 |
| RAB27B | CAGTAGCCAAGCAGTCTCCCA | TTCTCACTAGGAACCCGGGCA | 41013 & 41014 | RAC1 | AAGGAGGAAGAAGCTGACTCCCA | TGAGCGCCAAGCACTCCA | 41119 & 41120 |
| RAB28 | TCCCGCAAAGCATGGTCA | TCAGGGCTAAGTTGGAGGGGCA | 41015 & 41016 | RAC2 | GGTGGGCACCAAGCTGGA | GGGTAGGTGATGGGAGCCA | 41121 & 41122 |
| RAB33A | GTCCAGCGGGGCAGTGTCA | GGGAAGCGGCCAGCGCAGAA | 41017 & 41018 | RAC3 | ACTCTCTACCCCAAACTGA | CTTGTCGTCGCGGAGGTCCA | 41123 & 41124 |
| RAB33B | ATGGAGAAAGACGCCCTCA | CAAAGGTCAGTGCTGCCACA | 41019 & 41020 | RACGAP1 | CAGGCCAACAGGGACACA | TGGGCACAGCATGGGGCCA | 41125 & 41126 |
| RAB34 | CAGGCAGGTACATCACCACGA | ACGTGCAGGTTGATGGTGCGGA | 41021 & 41022 | RAD1 | CAATACACAGGGAACCTGAGGAGA | GGAGCCCTTGACTGCA | 41127 & 41128 |
| RAB35 | CTCTGAGGGAGAACGAGGGA | CTTGGCCGACACTTGACCA | 41023 & 41024 | RAD17 | CTCAAGCCACTCGTGCCGGAA | CTGGGGCTGGCTTAGCAGGCA | 41129 & 41130 |
| RAB36 | GGACACCGCTGGGCAGGAA | CCAGTGAGCCAGGCCCTGA | 41025 & 41026 | RAD18 | TACTTCTGTAGCCTCCAGA | CCTCTGAGGGATCTGGAGCGA | 41131 & 41132 |
| RAB37 | ACCAGGGGAAGGATGTGCTCA | ATGTGAGATGGGGCTTCACGA | 41027 & 41028 | RAD21 | GGGGGCATCAAGATCAGGA | GTTTTAGCAAGGCACGCTGA | 41133 & 41134 |
| RAB38 | GGGGACTCACCCGTGGCCAA | GCAGGGCGGAGAAGAAGTCCA | 41029 & 41030 | RAD21L1 | AGCTGAGAGCTTTGGGAGGGGAA | TTCTCCAGTGAGGCTTCAGA | 41135 & 41136 |
| RAB39A | CTGATCGCCGCTTCACCGA | CCTGTAGGAGGCGCAGTGA | 41031 & 41032 | RAD23A | CCCTGGGCTTCCCAGAGA | GGAGGAAGTTGGCAGCCA | 41137 & 41138 |
| RAB39B | CCGGACCTCACCACCGA | CTGATGACACGCGGCTCA | 41033 & 41034 | RAD23B | AACCCTGCACAGAGCAGTGGA | CTGAAGGTGAGGAGGCCCA | 41139 & 41140 |
| RAB3A | CTGATGACGTTCGTGCCA | CGGTACCGCTTGCCA | 41035 & 41036 | RAD50 | CCAGGAAACAGACTTGCCAA | CTGTGGCTCCAGCCAGCA | 41141 & 41142 |
| RAB3C | GAAGACGAGCGGGTCATCTCA | TGCAGCAGTGATGGCAGGA | 41037 & 41038 | RAD51 | CCGAACTGGGAAGAACCCAGA | AGAACCATACCTCTCAGCCA | 41143 & 41144 |
| RAB3D | AAGTGTGACCTGGAGGACGAA | CCGCAGATGACATCCACCA | 41039 & 41040 | RAD51AP1 | GCAGAAGTAGGCAGCAGCCA | TGGACAAGCCAAGGCGGA | 41145 & 41146 |
| RAB3GAP1 | GGAGGGAAGGTACCAGGACCA | CCCTCCAACAAAGCAACGACCA | 41041 & 41042 | RAD51AP2 | AGGACCCGGAGTTCCCAACCA | CGCTCAGACAAGCCAGGCA | 41147 & 41148 |
| RAB3GAP2 | CAGGCCCAACATTCAGCCACA | CCTTTGCCCCGTGAGCACCA | 41043 & 41044 | RAD51B | TGTGTGATTAGCCGCACTAGGA | ACAAATGAGGTGAAGGGACCCA | 41149 & 41150 |

| GeneName | Forward Primer | Reverse Primer | SEQ ID NOs | GeneName | Forward Primer | Reverse Primer | SEQ ID NOs |
|---|---|---|---|---|---|---|---|
| ROM1 | GGTACTGCAAACAGCACTGGA | GCAACCCTCCCTGTAGGCA | 42225 & 42226 | RPN2 | GAGGAGACTGTGCTGCAACA | CGAGTTCATCCAGGCGAGCA | 42331 & 42332 |
| ROMO1 | CCTACGGACAGTCCCAGCCAA | GCCGCCCATCAGCTCTCGA | 42227 & 42228 | RPP21 | CAGAGACGCTGCAGGGGACA | CTCCCGAGCTGGGCCTCA | 42333 & 42334 |
| ROPN1 | CCGGTGAGAGAGCCGGTCTGA | TCCGTGAAGCGACCCACA | 42229 & 42230 | RPP25 | GAGCCGGCCGCTAGTCTCA | GGGGACGAGGGGACCAGGA | 42335 & 42336 |
| ROPN1B | CTGGGCAGAGCTAACACCTGA | GTAACTCCCAGAGCGCTGCA | 42231 & 42232 | RPP25L | GGGCTGCAGAAAGGCTGTCA | CTGGGACCCAGCTGCCTCA | 42337 & 42338 |
| ROPN1L | TTAGCGCTTGGATGCACCA | CTAATCTGGCCAAGTAGCGGTA | 42233 & 42234 | RPP30 | GAGGGCCATATGACGTGGCAA | TGGAGAAGCGCTGCTCGGCA | 42339 & 42340 |
| ROR1 | CTGAAGACTGCCACCCAGA | TGGGCTGGCATTGAGGGA | 42235 & 42236 | RPP38 | GCCTGCACGTCAGGAGGAGCA | CTCTCACTGAGCCGGGGGA | 42341 & 42342 |
| ROR2 | TGACACAGAACGCCTCCAGA | GGCCTGGTCCACCTGCAGA | 42237 & 42238 | RPP40 | AGTAGCACTTGAGCACGTTGAGA | CATTACTGAAGACGGCGCCGA | 42343 & 42344 |
| RORA | CGGGAGGTGATGTGGCAA | AGGCACGGCACATTCTGA | 42239 & 42240 | RPRD1A | TACAAGCGCAAGCTAGCACGA | CCCGCAAAGGGCAGGTGCA | 42345 & 42346 |
| RORB | AAGATACCAACCATCACGGCA | CCGGTGGCACAGTCAGGA | 42241 & 42242 | RPRD2 | TCCTCCACCCCTGTTGACCA | AGTACCCAAAATGCTCAGCCA | 42347 & 42348 |
| RORC | GGAGCCTGTGTAGCCAGCA | AAGCGGCTTGGACCACGA | 42243 & 42244 | RPRM | GGGAGGGGGAGCCTGCTGA | GGAACGCTAGACGCTCCCA | 42349 & 42350 |
| ROS1 | TGCGAGGTCTGGACAGAGCA | CACTTCCCACAAGAGACGCA | 42245 & 42246 | RPRML | ACACGGTGCGAGTGGGTGAA | TTCCAAACGCAAGATCAGGCCAACA | 42351 & 42352 |
| RP1 | GAATGGCGACCCGAAGACGA | CTTGACCACAGGGCGGCTGCA | 42247 & 42248 | RPS12 | GCACGTGGAATTCGCGAA | CATCACAGTTGGATGCAAGCA | 42353 & 42354 |
| RP1L1 | CAGTGAAACCAGTGCGGGCA | GCCAGCAGGGCCAGCTGCAA | 42249 & 42250 | RPS13 | GACGACGTGAAGGAGCAGA | CTTCAGGAAGATCAGGAGCAA | 42355 & 42356 |
| RP2 | TCAGAGACAGAAGAGCAGCGA | CTTCTACAGACACCATTCCCCA | 42251 & 42252 | RPS14 | GGCCCAAGAGGTGCAAGGA | AAGGGCTCTGAGGGCCGA | 42357 & 42358 |
| RP9 | GCAGCAGTCAAGCACCTGA | CTTTCCCAGTGGCATCAA | 42253 & 42254 | RPS18 | AATACAGCCAGGTCTTAGCCAA | GTGCTGGCCTCGGACACGA | 42359 & 42360 |
| RPA1 | TGCAAGAGCTATGAAGACGCCA | CCCACAGTGTAGCAGTCACCA | 42255 & 42256 | RPS19BP1 | ACGAGAAGCACGGTGCCTGA | TCGGTGAACACGGTGCCCTCA | 42361 & 42362 |
| RPA2 | GAGCCGAGCCAGCACA | CCCATGGCGAACGTCA | 42257 & 42258 | RPS20 | GCCAGGAGTTGAGGTGGAA | CAAACGACAACGAAAACAGGA | 42363 & 42364 |
| RPA3 | GGACTTGCCCAGGTCGCGA | TCCAGCCTCACATCAGAAGCA | 42259 & 42260 | RPS24 | GTCACCCCACATCACGGGA | GGCCCAGCAAGCAGAGGA | 42365 & 42366 |
| RPA4 | GATAACGATGGAGTGAGCCGCAA | GTCGCAGAGCTGAGCCCGGA | 42261 & 42262 | RPS27A | GTGGTGGTGCTAAGAAAAGGA | ACCACATTCATCAGAAGGGCA | 42367 & 42368 |
| RPAIN | GGGCTCGCCGCCTTGGAA | TCTGAGAATTCCCTGGCCCA | 42263 & 42264 | RPS27L | CATCCGTCCTTGGAAGAGGAA | GCATGGCTGCAAAACCGTGGTGA | 42369 & 42370 |
| RPAP1 | AACCTCAACCTGGACTGCCGA | AACACTCCAGGGACACAGGCA | 42265 & 42266 | RPS3A | CACCAGGACCCAAGGAACCAA | TCAGGGTAAGATCCATGCCA | 42371 & 42372 |
| RPAP2 | TAGGGCTCAGGTACAGCCA | TGAAGAGGAACCAGAAGCCCA | 42267 & 42268 | RPS4Y2 | GTGGGACAAAAGGGAATTCCACA | GACCGAGGTTAGCTCCAGGA | 42373 & 42374 |
| RPAP3 | CCAACGAACAGAGCGTCAGCA | TCGAGCAGCACCTCGTCTGGA | 42269 & 42270 | RPS6KA1 | GGACCTGAAAGCCCAGCAA | AGCCCTGGCGCTTCAGCA | 42375 & 42376 |
| RPE | GGCACCATGGGCTAATCAGA | CATAATAGCACTGCCAGACACA | 42271 & 42272 | RPS6KA2 | CCGTGGGTGGTCAACAGA | ATGACACGCGGCTCCA | 42377 & 42378 |
| RPE65 | TTGACAAGGCTGACAGAGGCAA | CAAATGCTTGACGAGCATGCCACA | 42273 & 42274 | RPS6KA3 | AAACAGACAGGATGCACCACA | TCTCCGCTGAGCAAGAGTAGA | 42379 & 42380 |
| RPEL1 | ATGCTAGACTCTGGGGCCGA | TCAAAGAAAAGGGTCCTGGCCTA | 42275 & 42276 | RPS6KA4 | CGCGACCTCAAGCCGGAGA | GGCTCCAGAGGTCGCAGGA | 42381 & 42382 |
| RPF1 | GCAAGGACCCCACAGAACACA | ATGTGGCAACCTGCCTTCCA | 42277 & 42278 | RPS6KA5 | AACACATTAGGCAGTCGCCA | GTTGGAGATGTTGAGGGCAA | 42383 & 42384 |
| RPF2 | GATTTCTTCAGAGGCCCCA | TGTGTCCTCTCAGAACCAGA | 42279 & 42280 | RPS6KA6 | ACTCCACAGAGACCAGTTGCCA | AAGCAGTACAGGCTCTAGGA | 42385 & 42386 |
| RPGR | CTCTCTGGGCAATCACAGAACA | TGCCAAGACCCAGTGACCA | 42281 & 42282 | RPS6KB1 | CTGACTGGAGCACCCCA | TGTGTGAGGTAGGAGGGCA | 42387 & 42388 |
| RPGRIP1 | GGACCACAGACAGCAGCA | TGACTCCAGGATCTGCCACA | 42283 & 42284 | RPS6KB2 | TCAGAGGAGGACGTGAGCCA | CCAGGACAGAGCGGCGCA | 42389 & 42390 |
| RPGRIP1L | CCATCCACTTAGAACGAGGCGA | TGGGGATGAAGGCCTCGCA | 42285 & 42286 | RPS6KC1 | TGTGCCGCGATTTGAACCGA | TCAAAGAGGACAGCACCCA | 42391 & 42392 |
| RPH3A | AGCCCACCTCCCTCACCA | CCAGCATCAGGCTTGGGCGA | 42287 & 42288 | RPS6KL1 | TGGGAAGAGGGAGCCAGCCA | GATGAAGCCTCCACATGGTGGA | 42393 & 42394 |
| RPH3AL | CTACACGTGGCCCGAGGAA | CCATCCTGGGGCCTCCA | 42289 & 42290 | RPS7 | CAAGTCCGGCTAGTACGCGAA | TGGGAAGACCAAGTCCTCA | 42395 & 42396 |
| RPIA | CAATCTCATCAAGGGTGGCGGA | CGAAGTTCAACCACGCCCCCA | 42291 & 42292 | RPS9 | GGCCAAGTCCATCCACCA | TCTGGGAATCCAGGCGGA | 42397 & 42398 |
| RPL10 | GGCCCTTGCGCAGGCCAA | TGAACTTGGTGAAGCCCA | 42293 & 42294 | RPTN | CACAGACAGAGGCACGAGGA | TCAGCTGACCATGGTGGGA | 42399 & 42400 |
| RPL10A | ACATGGACAATGAGGCGCTGA | ATTTAAACCTGGGCCGAGGA | 42295 & 42296 | RPTOR | CGTCCGGATCTGGGACACA | GTACGTCATGACGCGGCA | 42401 & 42402 |
| RPL10L | TTCAGAACGAGGAGCATGTGA | AAGGGGCCATGACTGGGA | 42297 & 42298 | RPUSD1 | GGCGACCTGACCTACGGAGA | GGAGGGCCAGGAAGGGGTCA | 42403 & 42404 |
| RPL11 | GTGTTGGGGAGAGTGGAGACA | TTCTCCGGACCCAAAGGA | 42299 & 42300 | RPUSD2 | CAAACAGGAGTTGCTACGGGA | CTCTGAGCGAGGGCCGTA | 42405 & 42406 |
| RPL14 | TCAAGTGAGGAGCAGGGA | GGTGGGCACTGTGCGGAA | 42301 & 42302 | RPUSD3 | TCCAGCTGCAGCCACTGACA | CCTGGTGCCTGGGAGAAGGA | 42407 & 42408 |
| RPL18 | CCGAGAGGTGTACCGGCA | GCCCTTGGAGCCGACGTA | 42303 & 42304 | RPUSD4 | CTTCACTGCACGGCCGGCA | CAGGCGGTGCAGGGAATGCA | 42409 & 42410 |
| RPL22L1 | GCAGGAGATTAGGAGGACAAGA | ACCTGAAGTAGTGGCACCACCA | 42305 & 42306 | RRAD | CACGGCCAAGCAGGCA | AACCGAGAGGTGTGGCA | 42411 & 42412 |
| RPL24 | AAGAACCCGCCGGAGACGTCA | CCACAACCCAGGGAGCTGA | 42307 & 42308 | RRAGA | CTTCACCAGCCAGCGAGACA | CGTCAGGAGAGTTCTGGAGGA | 42413 & 42414 |
| RPL26L1 | CCTTCGTTACCTGGGAGCCGA | CGGATGGGCATGGAGTGGA | 42309 & 42310 | RRAGB | CCAAGGGGACAAACATCTTCCGA | GAATTCTGCAGAATGGCCTCCA | 42415 & 42416 |
| RPL28 | AACGGACTGATTCACCGCAAGA | TCCGCACATAGGAGGTGGCA | 42311 & 42312 | RRAGC | CACTCCAGGGTCCGATGCCA | GTGAACAGGGCACCAGATTCCCA | 42417 & 42418 |
| RPL35 | GACCTCGGCCTAAGAAGACA | CCTTGACCGGTACTTCCGCA | 42313 & 42314 | RRAGD | TGGAGCAGGGAACCCCTA | AATGGCCTTCCGGAAGCA | 42419 & 42420 |
| RPL36 | TGAGCAAGCCCAGGCACA | CCCGAATCATGTCCCGCA | 42315 & 42316 | RRAS | GCGTCTCAAGCGTGGACGA | TGGGAGGGCTCCGGTGGGA | 42421 & 42422 |
| RPL35AL | GTGGCAAGCATCAGCTCACA | TGTCTGCCCACCTAGCCA | 42317 & 42318 | RRAS2 | ATGACAGGAGCAGCCCGGCTA | ACCAACAGGAGGAAGCCTTCGCCA | 42423 & 42424 |
| RPL37 | TACCCTGCAAGCCGCAAGAGA | TCACGAAATCCATGCCTGA | 42319 & 42320 | RRBP1 | GCAGAAGAGCGCTGGAGGAGGA | TGCTCCCTCCACCTGGTCCGAA | 42425 & 42426 |
| RPL3L | CTATCACCACCGTGTGATGGA | ACCCAGCGGTGTTGATGGA | 42321 & 42322 | RREB1 | CAGGAGATCACAGAGGGGGGA | CGGCGATGTAGTCGCAGGA | 42427 & 42428 |
| RPL7 | TGGAGTGAGCCCAAAGGTTCGA | TCAGATTGGGGTACCCCA | 42323 & 42324 | RRH | CTGTGGACCGATACTTGACCA | GTACACGTAGCACCAGTAGGA | 42429 & 42430 |
| RPL7L1 | AAGACATCCCTCTGACACGACA | CCGATAGCCAGGTGTGCCCA | 42325 & 42326 | RRM1 | TGACCTTGCCAAGAGACA | GCTAGGCATCGGGGCA | 42431 & 42432 |
| RPLP1 | GTCTCGAGCTGCCTGCA | CTCCTGCTGGTGCAGCACGA | 42327 & 42328 | RRM2 | CATCACGGACCCCGCTCA | GGACGCGGTCCGCCTCA | 42433 & 42434 |
| RPN1 | CAGCCGCAGAAGCCAGGA | GGTGGAGAGTGTCCCGGGA | 42329 & 42330 | RRM2B | CAGGAGGGTGCAGGTTCCAGA | TATCCATCGCAAGGCCCA | 42435 & 42436 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| RRN3 | ATGAGCCAGCTAAATCCCTGA | GACCTCTTCAGCACACAGGGA | 42437 & 42438 | RTN4RL2 | GCCGGCTGCTCACAGAGCA | TAGCGTTGAGCCGCAGGA | 42543 & 42544 |
| RRNAD1 | TGAATTTCACAGGCTGCACCCA | TCTTTCTCCAGAGCCTGCAGA | 42439 & 42440 | RTP1 | CAAAGCACAAAATCTCTGGGAGGCA | GCAAAGAACCCAGGAGGAGGCCA | 42545 & 42546 |
| RRP1 | AGACGAAGAGGAGGCAGGAGGA | CGAGCCCTCTCTGGCCA | 42441 & 42442 | RTP2 | TGGGGAGGACGACAGTCTGGA | GGCCCAGAGAGGTGACCGGA | 42547 & 42548 |
| RRP12 | CACCTCCTCACCCGCCAAGA | GCAACAGGATCACCTCTGGGA | 42443 & 42444 | RTP3 | TGAGGACCCTGAGTTCACACA | GGGGTCTGAGATGGGGGAGA | 42549 & 42550 |
| RRP15 | TGAAGGAAGCTGTGGATGGAA | TAGCCATAGCATCTGCCCA | 42445 & 42446 | RTP4 | GGATCCCATGACACAGCCA | TGCGAGGTACACAGCACCA | 42551 & 42552 |
| RRP1B | TTCAGAAGAGCCAAGAGCAGAGCA | GGTCTTCAGCACCCCGTGGA | 42447 & 42448 | RTP5 | GAAGGCAACGGGAAGGAAGGA | GGAAGGGGAGGGCAAGGGA | 42553 & 42554 |
| RRP36 | GAATTGCAGAGCCAAGTGGGGA | AGCGAGGGTCCCGGGCTA | 42449 & 42450 | RTTN | GGCCATGCTCCTGAGGAA | GGCAGACAAGCCTGGACA | 42555 & 42556 |
| RRP7A | GTGGAACACTGCATGGAGGCA | CTGCCTCAGTCCGGGGGA | 42451 & 42452 | KIAA0226 | CCAGCCGGGTTCTTGTGCGA | GAATCCAGAAGCTCCTTGGCCA | 42557 & 42558 |
| RRP8 | AAGTGGCCACTGCAGGCA | CCTGGGCCATGTCACACA | 42453 & 42454 | RUBCNL | GCATCCTGCCCGAATCCTGA | GCTTTGGCCGATGCTCAGCAA | 42559 & 42560 |
| RRP9 | CCTTCACAGGACACCCGGGA | CCCAGCCGTCAACAGCA | 42455 & 42456 | RUFY1 | GCCGGAACTGTGGCCACA | AGCTGTCGCACACTCGCA | 42561 & 42562 |
| RRS1 | AAGAGAAAGGAGGAGGCCGCA | TCTCTTGCCCAAGCCA | 42457 & 42458 | RUFY2 | GCCAACAAAGGCATTGCAGGGA | GCAGTGCATGACGAGGAATCACA | 42563 & 42564 |
| RS1 | CGATTGCCAAGGAGGACCCAA | TGTGACCTCCCTGACTCGA | 42459 & 42460 | RUFY3 | AGAAGCCGCAGAGATAACAGCA | ATTCAGACCCACCACAACAGACCA | 42565 & 42566 |
| RSAD1 | GGCACCGCACTCTTCGCCCA | GAAGCCAGCTCCTCCCGAAGGA | 42461 & 42462 | RUFY4 | TCACCCAGCAGGGTGCCA | CCAGACAGGAGCTGCTGGAGA | 42567 & 42568 |
| RSAD2 | GAAGAGGACATGACGGAACAGA | GTTAGATTCAGGCACCAAGCA | 42463 & 42464 | RUNDC1 | GTATGCTCTCCCCCAGGGA | ACAGTGCCTCCCGTAACAGGA | 42569 & 42570 |
| RSBN1 | GTACCTACCTCGGGGCAGTGA | CAAAACTCCAACAGCAGCCGTA | 42465 & 42466 | RUNDC3A | GACTCCCAGGGACTTGCA | AAGCTCCCAGGGACTTGCA | 42571 & 42572 |
| RSBN1L | CAGAGCTGGCCAATGAGAGA | TGGCATATCAGCCACAGGGA | 42467 & 42468 | RUNDC3B | TAGAGCCTGGATCAGAGTAGCA | AGTCCTAGAAGCATGCCAGCA | 42573 & 42574 |
| RSC1A1 | GACAGGCCTGAAAACAGGA | CTGCATTCCACCAACTCGA | 42469 & 42470 | RUNX1T1 | CTAGACGCGCATGGGAA | TCCGCTCCGCCTCAGACA | 42575 & 42576 |
| RSF1 | GCAAACGCTACACCGGA | GTTCTGAGGGAGGACCCTA | 42471 & 42472 | RUNX2 | ACCCTTCCAGACGACAGCA | TCCATCAGCGTCAACACCA | 42577 & 42578 |
| RSG1 | GACCACCGGCATCCAGACCA | GACGACACCAGGGGCCTA | 42473 & 42474 | RUNX3 | CCTTCCCCACGCTGCCAA | CTGTAGGGGAAGGCAGCTGA | 42579 & 42580 |
| RSL1D1 | TACTGGAACCTCCACCTGA | GCGTCAAGAGAGCGTCA | 42475 & 42476 | RUSC1 | TCTCCAAACCTTCCACACCA | ATGACGCCCGGTGCCCA | 42581 & 42582 |
| RSL24D1 | GCATTCCGAAAGACGCTGGTA | GAGGGGCTCGGATAAGGATGGA | 42477 & 42478 | RUSC2 | CCTGGAGGCATCAAGTCGGGA | CACGGAGGACTGGGAGGGCA | 42583 & 42584 |
| RSPH1 | CCAACTCTCCCAAAAAGCCGA | CTCACCCTCCAGAAGCCTCCA | 42479 & 42480 | RUVBL1 | AACAAGTACATCGACCAGGGGCA | AGACTCCAGGGCGCGGTGCA | 42585 & 42586 |
| RSPH10B2 | TTGCCCAAGACTGTCCAGGA | TCTCAGGGTACATGTCCAGGA | 42481 & 42482 | RUVBL2 | CGTCACTGCGCTACGGCA | AGCGGGACTCGTCCAGGA | 42587 & 42588 |
| RSPH14 | TCAGCATATCTCGAGAGGGCA | CTATGGTCATGGGGGAGTGCA | 42483 & 42484 | RWDD1 | GAGCAGCCCAACGAGCGAGCTCCTA | TCTCCAGCCTCAGACGTCA | 42589 & 42590 |
| RSPH3 | GCTAACCTGCGGGGCAGTGA | CAAAACAGACGGGAGAAGGTCA | 42485 & 42486 | RWDD2A | CATGCCTCACAGCTACCCTA | ACATACACAGGCACTCACCTGGA | 42591 & 42592 |
| RSPH4A | AAGGCGGCCATGGAGAAGAA | TAGACTGCCGGGCTCCAAGGA | 42487 & 42488 | RWDD2B | TGAGGGGGCCACGGCTCA | CTGCTACAGGCAGCTGGTCA | 42593 & 42594 |
| RSPH6A | GCAGATGAGGGGCCAGAGGA | GCCACTGAGTACTGCGGGCA | 42489 & 42490 | RWDD3 | GCCGCTCAGAGACAGATGGGA | TCATGAACCATAGGCTCCGACA | 42595 & 42596 |
| RSPH9 | CTGTGGCCATCATCCCCGA | TGAAATTCAGGGAGGGGGTCCA | 42491 & 42492 | RWDD4 | GCCAACGAGGGACTCAGGAGA | AGAAGGCTTTGGGACTACCA | 42597 & 42598 |
| RSPO1 | GGCCGGAGAATGCTCAACAAGGA | TGCAGATGTGAGTGCGCCCA | 42493 & 42494 | RXFP1 | ATGGGGGTGGACAGGAGTGTCA | TGATTCCGCAGTCGTCCACA | 42599 & 42600 |
| RSPO2 | GCAACCGATGGAACGGA | GTTGACATCGGCTACACCA | 42495 & 42496 | RXFP2 | ACCCACATGCTGAAAAGCA | TGTGAAAGACCACACAGTGCCA | 42601 & 42602 |
| RSPO3 | CAATTGCCCAGAAGGGTTGGAA | TTCGTGCATGGACTCCAAGGA | 42497 & 42498 | RXFP3 | CGCTCACCTGGGAGCA | GAGGACGGGGTTGAGGCA | 42603 & 42604 |
| RSPO4 | CCAGGAGGTCAACAGGTGCAA | CGGGCAGGTGGCAGACA | 42499 & 42500 | RXFP4 | TGGGGACGGTGGCCGTCAGA | TGAGACGCAGCTTGGCCA | 42605 & 42606 |
| RSPRY1 | TGGAAGATCCACTGGGACCA | TCTCGCCCAAGCAGCCTA | 42501 & 42502 | RXRA | TGGAGGCCTACTGCCAAGCA | TGAGCCCGATGGAGCGCA | 42607 & 42608 |
| RSRC1 | TAGACGGTCCTCTCCGAGCA | TCCCTGCGACCCTTGAACGA | 42503 & 42504 | RXRB | GCAGCAGGGAGACGGTTGCCAA | TGTCGATGGGGTGTCACCA | 42609 & 42610 |
| RSRC2 | CAAGATCACAAACCCACACACAA | GGTGAACAAGGAGCGTGACATCAGAA | 42505 & 42506 | RXRG | TGGGATGCTGCGAGCCA | GCAGCAGCAGCTTGGCA | 42611 & 42612 |
| RSRP1 | CCGTTACGAGAGAGGCGCTA | TCCCCGCGCGATCGCGTA | 42507 & 42508 | RY8P | CTCATCCACAGTGACCTCCA | TTGGCGTGGAGGAACGGGA | 42613 & 42614 |
| RSU1 | GAGGAGCTGCCCACACAGA | CCAATATCTGGCGGCAGGA | 42509 & 42510 | RYK | GCCAGACTCCTCCTCGTGGACA | CTCTGGATCTAAGGCCCAGCA | 42615 & 42616 |
| RTBDN | CCGAGCCTGAATGCGAA | CGAACCAGGCCTGAATGGGA | 42511 & 42512 | RYR1 | CCACTAGCAACGCCACGCA | TGGGATGACTCCACGCCA | 42617 & 42618 |
| RTCA | CATCAGAAAAGGAAGGAGTTGCACGGA | TACCAAGGCGATGATCCAGCA | 42513 & 42514 | RYR2 | CTACACGGAGTTCAGAAACGGAA | GACGGCGACGTTGAAGCCGA | 42619 & 42620 |
| RTCB | TGCTCGAATCGCTTCCCAGA | GAGGGGAAAGCGCGGGTGGA | 42515 & 42516 | RYR3 | CTCTGGCAGTCACCAAGCAGA | AAGCAACCACTGCGTCCCA | 42621 & 42622 |
| RTEL1 | TCTGAGAAGAGGCCGGCCA | CTCAGCAAAGAGGGGGCCGA | 42517 & 42518 | S100A1 | TGATGAAGGAGCTAGACGAGA | TACAGGCCACTGTCGAGAGCA | 42623 & 42624 |
| RTF1 | ATCCCTGCAAATCCAACCA | ACAACACCCGTAATTCAGCGA | 42519 & 42520 | S100A10 | ATGGAAAAGGAGTTCCCTGGA | AAAGAAGCTCTGGAAGCCCA | 42625 & 42626 |
| RTFDC1 | TGACAAGCACGATGACCTCA | CTCCTGGAAGGCAGCCCCA | 42521 & 42522 | S100A13 | GGCCGGAAGGATAGCCTCA | TCTCATCAAGAGAGCCCACA | 42627 & 42628 |
| RTKN | ACGGCCCTTCACCTAAGCA | GTGGTTTCCGGGAGGAGCAGGA | 42523 & 42524 | S100A14 | AGCAACTGTGGCCTGGAAGAGA | CCCGACCTATCAAGGTCCA | 42629 & 42630 |
| RTKN2 | CCCACCCAGGAACTGCAA | TAGTCGAGCATTGCACACA | 42525 & 42526 | S100A16 | GGACACAGGGAACCGGAA | GCCGCTTATCAAGGTCCA | 42631 & 42632 |
| RTL1 | GCCCACTTCAGCATGCCCA | GCGGGCATCTGGGTGAGCA | 42527 & 42528 | S100A2 | CAGCAGGTGGACTTCCAGGA | GTCTGGGCAGCCCTGGAA | 42633 & 42634 |
| RTN1 | GAAAACCGACGAAGGGCA | CCAGACCATGAAGGCA | 42529 & 42530 | S100A3 | GAAGGAGCTGGCCACCTGGA | AGTACTCTGGCAGTAGAGACA | 42635 & 42636 |
| RTN2 | CACCAGGCTTCAGATCGACCAA | GGAGACTTGCGGCTGCTGGA | 42531 & 42532 | S100A5 | CCCTTCCACCCTGACCCCA | CTGGGAGGGAGAGGAGGGCA | 42637 & 42638 |
| RTN3 | AGTCAGAAGAAGGTTCATCAGCCACA | CCAACATAGGTCATCAGCCACA | 42533 & 42534 | S100A7 | GATGAGCAACACTCAAGCTCGAGA | CAGGCACTCAAGAAGTTGGGGA | 42639 & 42640 |
| RTN4 | AAGGCCACCCATTCAGGGCA | TCAACTAAGAAGAAGGCGCCTGA | 42535 & 42536 | S100A7A | GCAGGGACACATGTGTGGCA | CGACCTGCCATGCAAATCAGCA | 42641 & 42642 |
| RTN4IP1 | TAAGGAAGCTTGGTGCAGACGA | TTCAGGAGGAAAGGAGTCACCA | 42537 & 42538 | S100A7L2 | CAGGCCGAGCCTTATAAAGGGA | AGTCGGGAGCAGTAGTAACCA | 42643 & 42644 |
| RTN4R | AGGCCAGGCTGTTCACGAA | GCTGCAGGGTGAGGCTGGGTA | 42539 & 42540 | S100B | CAATGATGGAGACGGCGA | GTGGCAGGCAGTAGTTAACCA | 42645 & 42646 |
| RTN4RL1 | CCTCGGCCTCAACGGGCAA | AGTCCTCGCCCCTCAGCA | 42541 & 42542 | S100P | TCAAGGTGCTGATGGAGAAGGA | TCACTGAAGTCCACCTGGGCA | 42647 & 42648 |

| GeneName | Forward Primer | Reverse Primer | SEQ ID NOs | GeneName | Forward Primer | Reverse Primer | SEQ ID NOs |
|---|---|---|---|---|---|---|---|
| SLC2A14 | AACAGCCCATCTATGCCACCA | AAGCCATCCTCCAAGGCCTA | 44133 & 44134 | SLC35G5 | CCGGAACCTCAGCTGTGAGA | CCCAACCCCGGGCTCCCA | 44239 & 44240 |
| SLC2A2 | AAATTGGGCCAGGCACTCCA | AAGGCCAGGAGCACTCCA | 44135 & 44136 | SLC36A1 | TGGCACAGGACTCCTGGGA | CCAGGATACCCATGCAGTGCA | 44241 & 44242 |
| SLC2A3 | AAGAGCCCATCTATGCCACCA | AAGCCATCCTCCAAGGCCTA | 44137 & 44138 | SLC36A2 | CCCGCCACTTCCAGCCA | CAGCGTGTTGACACCCGGGA | 44243 & 44244 |
| SLC2A4 | CCTGGGGACGCTCAACCA | AGAAGGGCAGCAGGGACCA | 44139 & 44140 | SLC36A3 | AGTTCCACGTCCCAGCTGAGA | GGGCTGGGGATGATGAGAGCCA | 44245 & 44246 |
| SLC2A4RG | GACGGGCTGTCCAGCCTGA | GCCGCAGGGGACTAGGCA | 44141 & 44142 | SLC37A1 | TGGTCAGTGGGCCTCACA | TGGCCGTCACGGTGGAGA | 44247 & 44248 |
| SLC2A5 | CTGCTGTCAACTCCCAGCA | CGACCAGGAGGGATCCGA | 44143 & 44144 | SLC37A2 | GCCCATACGCGTCATCACCA | GCAGGCTAGGAGTCGGCA | 44249 & 44250 |
| SLC2A6 | CGCCTTCGTCTTCACCAA | GTCCCTTGGTCTCGGGCA | 44145 & 44146 | SLC37A3 | GTGCTAAGGAGACAGGCTCA | GGCAGACTGGAAGCCCA | 44251 & 44252 |
| SLC2A8 | AGGGCGTGGCGACAGGCA | AAGCGGAGGCAAGCCAGA | 44147 & 44148 | SLC37A4 | GGGCTGCCCTTCAGCACCA | TCGTAGGAGGAAGAAGGCA | 44253 & 44254 |
| SLC2A9 | ATCCCTCCGCAAAGATCCCA | CCACGATACTCAGGTAGGGGA | 44149 & 44150 | SLC38A1 | TGACAACGTGCAGTCCGA | AGGTAACCACGTATGACGACA | 44255 & 44256 |
| SLC30A1 | CAGAAGAAACACGTTCGGCTGGA | CGGCTGATGAAGCGCTCGA | 44151 & 44152 | SLC38A10 | AGGGCGGAGATGCTGGACCA | CTCCTCGATCACCGCCAGCA | 44257 & 44258 |
| SLC30A10 | GAGGAGCCGTGTAACTGGCA | CTTGATAAGCGGGAAGGCAGA | 44153 & 44154 | SLC38A11 | AGAACCAAGGACACACTCCGA | AAAACATCACCACGACACCAA | 44259 & 44260 |
| SLC30A2 | GGAGAACCCCAGCGTCCGA | TCTACCCCTCCACGGACA | 44155 & 44156 | SLC38A2 | AACACCACCTTAACACACGCCAA | AGATGGGAAGAACAGCAGGA | 44261 & 44262 |
| SLC30A3 | ACAAGGCAGCCGACCCA | GATGGCCAGGTGTGCAGA | 44157 & 44158 | SLC38A3 | CCACGGAGAAGGAGCCTGCAA | GCTGGTCCTGAGGCCCA | 44263 & 44264 |
| SLC30A4 | GACCCTAGCCATGCCGACGA | TACGAACGGCAGCAATGGTCA | 44159 & 44160 | SLC38A4 | GCTGGATGAGAACCAGGCCAA | ATTGCATAGGCCGTCCGGGA | 44265 & 44266 |
| SLC30A5 | GCCCATAGCCATGCCATGGA | GCATTCATGCCTCCACCGCA | 44161 & 44162 | SLC38A5 | GCAGTGTGAAGGCGAAGA | GGGGATAGGGAACAGCA | 44267 & 44268 |
| SLC30A6 | CTCCAGACAACACCACCCA | TAAGGCAGGCCTAATCCAGTCA | 44163 & 44164 | SLC38A6 | AACGAACTTCACAGACAGCGA | GAGTAAGAAGCCAGGAGAGCA | 44269 & 44270 |
| SLC30A7 | CCTACGGCATCTGGGAGCAA | GTGGACATCTGGAGGGGCTA | 44165 & 44166 | SLC38A7 | TACACAGACCGCAAGTTCACCA | ATCCGAAGCAGATGGTGGGCA | 44271 & 44272 |
| SLC30A8 | CCTCCCTAAGCGCTCACATGCCA | CAGCAGCGCTCACATGCCA | 44167 & 44168 | SLC38A8 | ATCTACTGCAGCATGCGCA | AGATGAGGGAGCAGGCA | 44273 & 44274 |
| SLC30A9 | AAGCCACGCTCCAGAACACGA | AAAATCCGTACGGATGAGAAGGA | 44169 & 44170 | SLC38A9 | ATTCAGGAGCAGCATGTGGA | CAATCAGGTTAGCCACGCCCA | 44275 & 44276 |
| SLC31A1 | ATGGTGGAGGAGAGCAGCAGCA | CTGCACAAAAGCTCCAGCCA | 44171 & 44172 | SLC39A10 | CCAGTGCACCACAAGCA | GCACAATTGCGAGCCCA | 44277 & 44278 |
| SLC31A2 | CGCAGAGACAGAGGGGA | ATGATGAAGTAGCCGATGACCA | 44173 & 44174 | SLC39A11 | CGTGGTGTGGCTGAGCCA | CGTCCATGACCACGTAGACCA | 44279 & 44280 |
| SLC33A1 | GCAACGGCTGGCCAGGGAA | AAGAAGTCCAGTGCCGGTA | 44175 & 44176 | SLC39A12 | TGCCACTTACCACTCTGGAGA | GTGAGCGAGAGCGTCCCA | 44281 & 44282 |
| SLC34A1 | GCACCTTCTGTCACCAACACCA | CCATGGATGTTGAAGGAGGCCA | 44177 & 44178 | SLC39A13 | CTCTGCATGAGATCCCCA | CGATGTAGAGAAAGCCGCCAGA | 44283 & 44284 |
| SLC34A2 | CTTGGAGGAGGGCCAGGA | TTGAGTCCGAGGCAGGGA | 44179 & 44180 | SLC39A14 | GAAGCTGCAGAACCGGGA | GCGGACACCTTTCAGCCA | 44285 & 44286 |
| SLC34A3 | GGCACATCCATCCATGTGAGCA | GGACCAGCACTGTGAGCCA | 44181 & 44182 | SLC39A2 | GTACCAGCTCACGATGGGCA | GCTGCCACCCCTCTAACCA | 44287 & 44288 |
| SLC35A1 | TCTTGGGGAGCCCAAGGAA | ACAAGCTAACTCCAGCACACA | 44183 & 44184 | SLC39A3 | CTCCCGTGAAGATCATCGA | CTGCTGCTAGTGCCCAAGGA | 44289 & 44290 |
| SLC35A2 | TGGTCATGGCCGGAAGTGCTCA | GTCACATACTGCCACCAGGACA | 44185 & 44186 | SLC39A4 | GAGTCAGCGAGGAGAGCGA | CCAGTTGTGCAGCAGGA | 44291 & 44292 |
| SLC35A4 | CGTGTGTCTGAGCCGGGTA | TGAGAGCCGGGTGAGGCTGGA | 44187 & 44188 | SLC39A5 | GGCGGACTACCAAGAAGGA | CTGAGCCCTCGGTGCCGAA | 44293 & 44294 |
| SLC35A5 | TCTTGATGGCCAGGTTACCA | CCCACTGGAACGCTCCA | 44189 & 44190 | SLC39A6 | CAGGCTACTCTCGGGAGGA | AGCAGCACCAATTGCTAGGCA | 44295 & 44296 |
| SLC35B1 | GGACCATCATCGGGGCTCA | AAGTCTGACCCAGGGCA | 44191 & 44192 | SLC39A8 | CTCAATGCAGGGATGAGCA | ATGCCTCCAGCAAGTGCA | 44297 & 44298 |
| SLC35B2 | AGTCTCCCAGCCACCACA | GAGCCACTGTGAAGAGGCA | 44193 & 44194 | SLC39A9 | TGCTTTGGGAGCAGCAGCA | CCGCTCAAGCCAGCATGCA | 44299 & 44300 |
| SLC35B3 | GCTGACAAGCACAACTGCACCA | CATAACCATAGGTCCGAACTGGA | 44195 & 44196 | SLC3A2 | CTGCTCAGCACCCAGCA | CGTAGGGGAAGCGGCAGA | 44301 & 44302 |
| SLC35B4 | GCGCCTTCCCTCACCGTCA | GACAAACAAGGTGCCCAGCCA | 44197 & 44198 | SLC40A1 | CTGGGAGCCATCATTCGGTGA | ATAGCAGGAAGTGAGAACCCA | 44303 & 44304 |
| SLC35C1 | CAGGAGGGCGGCAGAAGGCA | CCAGCGTCATCATCCCCA | 44199 & 44200 | SLC41A1 | ATGAATGGAATGCCCGGAGAGA | AGGAGAATCAGCACCTGGAGCA | 44305 & 44306 |
| SLC35C2 | CGGCCTTCAGAATCCCATCGA | CAATGGAGAGAGTGAGGCTGGA | 44201 & 44202 | SLC41A2 | CATGCCAATAATGGGACCA | TATCAGTACCATCCAGCTGA | 44307 & 44308 |
| SLC35D1 | CGTCGGCCGAAACGCTGA | CCCACCCAGAGAACTGCCA | 44203 & 44204 | SLC41A3 | TGGGCATTCAGACCAGCCGAA | CTGGATCAGGCCTGCCAGCA | 44309 & 44310 |
| SLC35D2 | TCCTTCACGTTCGGAAACACA | GCTGCTATGAAAGCCCGA | 44205 & 44206 | SLC43A1 | GTGGGACCCCTGAAAGGAGA | CGGTCACTTCAGAGCCGCTA | 44311 & 44312 |
| SLC35D3 | CAATTCGGTGCCACCACA | CACCACGCCGGCAATGAACA | 44207 & 44208 | SLC43A2 | CCGTGTACCCCTCCACCA | GCACCCCAGGCTTCACCA | 44313 & 44314 |
| SLC35E1 | CAACCAGTCACCAGGAGCCA | GCTGTGGTGACGGCAGGAGGA | 44209 & 44210 | SLC43A3 | GCACGAGTCAGCACTACACA | AAGGTGAGGTACTGGAGAGGGA | 44315 & 44316 |
| SLC35E2 | GTGAAGAGCTCCGCCCCA | CGTACGCCGTGACGCTCGA | 44211 & 44212 | SLC44A1 | TAGGTACGGTGGCAAAAGGA | TCAGCACACATGTGCACA | 44317 & 44318 |
| SLC35E2B | AGTGGTCGAGGGAGTGGGAA | TGTTGTAGAAGCAGGACCCCA | 44213 & 44214 | SLC44A2 | GGTGGTTGAGTCGGGCTACCA | ATGATCTGCAATGGCAGGA | 44319 & 44320 |
| SLC35E3 | CGCCGGTGATCATCAGCA | ATCGGAGCCTGGTAGTACAGCA | 44215 & 44216 | SLC44A3 | TCCACAGGCATCACGGCA | GCAGTTCCCAGGCTCAGCA | 44321 & 44322 |
| SLC35E4 | ACCGTCCACGTTCTCGGGCAA | GAAAGAGTGAGTGCGCAAGGAGA | 44217 & 44218 | SLC44A4 | CATGCAACCCCACGGCCCA | GAGTGTGCGGATGAAGGCAGA | 44323 & 44324 |
| SLC35F1 | CGAACTCTGAGCCGAGTGAA | AAGTCTGCTGTGAGCAAGGAGA | 44219 & 44220 | SLC44A5 | ATCACACAGGATCCCTAGCA | ACCAAGCAGCATCTCAGGGCA | 44325 & 44326 |
| SLC35F2 | CTGGGACTAGCAGATGTGGA | CACCCAACAGACAGAGTGGA | 44221 & 44222 | SLC45A1 | ATCCTGAGAAGCTTGGAGGA | GCAGAGAGATGTTCAGCCCA | 44327 & 44328 |
| SLC35F3 | AGTGGAGGATTGTGGCCGCA | TGTAGAGGGCAGACATGGA | 44223 & 44224 | SLC45A2 | CAGACTCGCAGGGCAATGACA | GACAGGAAGGCTGTCATCCA | 44329 & 44330 |
| SLC35F4 | AAGAAGCTGACGGCCACGGA | CAGATGTAGAGGCTGAGCCCA | 44225 & 44226 | SLC45A3 | AAGGCGTTGCAGGGATGGGCA | AAGCTGTCACCACGGCA | 44331 & 44332 |
| SLC35F5 | GGAAGGCCAGGGGTGCTGA | CGCCTGCGTGAGTGAAACCA | 44227 & 44228 | SLC45A4 | CTACACGGACTTCTGGGGCCA | TAGACGTTGGGAAACATGGCCA | 44333 & 44334 |
| SLC35F6 | TGAGCGGCACCCCA | CAGCGGACGGTGTAGCCCA | 44229 & 44230 | SLC46A1 | CGGGCCCAGGGGTTATGCCAA | TAAGATGTTCCTGCCCCA | 44335 & 44336 |
| SLC35G1 | AAGAAAGACACCCTGTCCTGGA | AGAGCCCACTGAGAAAAGGAAGGCA | 44231 & 44232 | SLC46A2 | ATCCCGTTCACAACCATCCGA | GAAAGGAGGAGAGCAAAGCA | 44337 & 44338 |
| SLC35G2 | CCTCACCAAGAAGACCCA | GTCCAAAGGGGCCTTCTGA | 44233 & 44234 | SLC46A3 | GTTGGTGTCCTGTCAACCA | GGCAAAGCAAGCTCCCA | 44339 & 44340 |
| SLC35G3 | AGGCCCCCGTGTTGCCA | CTCGGAATGTAGGGCACGGCA | 44235 & 44236 | SLC47A1 | AGACATGGAGGCAGCACGAA | CCACTCCCCCTCAGAACACCA | 44341 & 44342 |
| SLC35G4 | CAGACCCCTGCTGTTGCCA | GGGCCATCACCACCTCGGA | 44237 & 44238 | SLC47A2 | CATCGGCCTACCACTGGGCA | CTTCCAGTCCAGCCGGGCA | 44343 & 44344 |

| GeneName | Forward Primer | Reverse Primer | SEQ ID NOs | GeneName | Forward Primer | Reverse Primer | SEQ ID NOs |
|---|---|---|---|---|---|---|---|
| SLITRK1 | TGTACGCTAGGATCTCGCCCA | CCAGCAGCAGTTCCCGGGA | 44557 & 44558 | SMCR8 | TCCTGGGGGAAGATGAGGCCA | TCTGTAAAGGGGGCAGCGCA | 44663 & 44664 |
| SLITRK2 | GCTAGAAAAGCAGGCCACACA | GACTAGGCCTGCGCTGGGAA | 44559 & 44560 | SMDT1 | CCGGAGCCTGGTACCGTCGA | GGGGATCACAATGGAGAACACA | 44665 & 44666 |
| SLITRK3 | GGCATCCAAATGCAATGCCACA | CTCATACACATGACCCACGGGA | 44561 & 44562 | SMG1 | GCAGAATGCTGGTCAGGCCCA | CCTTCGGATACTGCAGGGCCA | 44667 & 44668 |
| SLITRK4 | TCCGGAGCACCCTTAGCTA | TCACAACAATCCCGTCGCTCA | 44563 & 44564 | SMG5 | GGAGGAAGCTCGTCGGAA | TGGCGGATGACAGGGAGA | 44669 & 44670 |
| SLITRK5 | ATGAAGCTGTGGGTGGAGA | GCTATTCAACGGGACCGGA | 44565 & 44566 | SMG6 | GCCAGCAAAGAGGAGCCA | CTGGGATGTCCGTACAGGA | 44671 & 44672 |
| SLITRK6 | CCCCGGGCATCTCGACA | TTGTTGCAGGAGTGGTGACCA | 44567 & 44568 | SMG7 | ATCATTCAACACCAGCCAGCCA | AATCAATGCCAAACCCACCCA | 44673 & 44674 |
| SLK | AAGTGGTCGAAGTAGGCCAGA | TGGTCAGTATCAGCCACCA | 44569 & 44570 | SMG8 | AGGAACCCACAGCCTTCCA | CTCTCCAGTGCGGTGACCCA | 44675 & 44676 |
| SLMAP | CAACCTGAAGCTGCTCGAGA | GGCCAGACCTGGCACGTACA | 44571 & 44572 | SMG9 | CAGGACCTTGGTTCCAGCCA | CGGGCAGCGTAGTGGAACCA | 44677 & 44678 |
| SLN | GCGAGGAGAAACCTGCCA | GGACCTCACAAGGAGCCACA | 44573 & 44574 | SMIM1 | AGCAGGGACGGAGTCAGCTA | GCCCAGCACCTTCATGGCGA | 44679 & 44680 |
| SLPI | AGAAACCTGAGTGCCAGAGTGA | TGGGGTGTCAACAGGATCCA | 44575 & 44576 | SMIM10 | TGGGAGGCAGCATCAGTTCCA | ACGTTGAGAATCACCGAGGCCA | 44681 & 44682 |
| SLTM | GCCCGAGAAGGAAAGCA | GCTTGACCAGAGGCCCA | 44577 & 44578 | SMIM10L1 | TCAAGCCCCGCGTCGACA | CCGCGACGTAGAAGTACGGGA | 44683 & 44684 |
| SLU7 | GATGACCAGAGAGGACTGGAGA | TCTGCAGGAGCATTGCCCAA | 44579 & 44580 | SMIM10L2A | TGCGGCCCGAGGCTCGTA | AAGTAGGGGGAAGTTCATGCCGA | 44685 & 44686 |
| SLURP1 | GCAAGGAGCCCATGACCA | CTGCCTCACCGTCACCA | 44581 & 44582 | SMIM10L2B | GGGCTGACTGGGGAGGAGGCA | CATGGAGACCCCATCACGCA | 44687 & 44688 |
| SLX1A | GCCTCTAAGGGGCCCATGTGA | TGACTTCTCACAGGAAGGGCA | 44583 & 44584 | SMIM12 | CCAGCCGTGGGAGGAGGAA | TTCAGCACAGCTTTCCGGGGCA | 44689 & 44690 |
| SLX4 | ACCACTGGAACCTGGAGCGGA | GATGGGGGTGGTCTCCAGGA | 44585 & 44586 | SMIM13 | CAAGAGGCTTGGTGTGACCGA | GGGGAGCTTGGGACAAAACGA | 44691 & 44692 |
| SLX4IP | CCCAGTGCAAAGCTCCGGAGA | GAAGCCCCAGTGGCCTCTCA | 44587 & 44588 | SMIM14 | TACCGGGACCCTCTGGTGA | TCCAAGAGGAGGACTGGTGGA | 44693 & 44694 |
| SMAD1 | CCAGCAACCCAACAGCCA | GGGGGCTATGAGCTGGCA | 44589 & 44590 | SMIM15 | GCAGCCCGTAGGGCAA | CCACAACATACTCAGCCCAA | 44695 & 44696 |
| SMAD2 | GAGCAGAATACCAAGGCAGA | GCAACAGCTTGCACGTACA | 44591 & 44592 | SMIM17 | GCCTGCACCAAAGACTCTGGGA | ACCGAGCTCCACTCCTGGGA | 44697 & 44698 |
| SMAD3 | GGGGAGGGAGTACAGGGAGA | ACAGCGGATGCTTGGGGA | 44593 & 44594 | SMIM18 | GGCTTCCAGCCACTGGA | CAGCAGCAGTCAAGCA | 44699 & 44700 |
| SMAD4 | GTCCACAGGACAGAAGCCA | CTGTCGATGACACTGACGCA | 44595 & 44596 | SMIM19 | AGTACGACTATCAGCACAGCACA | GGCAAAACAATGCACAGAACA | 44701 & 44702 |
| SMAD5 | GCAGTCCAGGACAAGCCGA | ACTCTGCAAATCCGGCCA | 44597 & 44598 | SMIM2 | GCCAGCCAGCTGCCTCACA | TCTTGCTGCATCCAAGCGAGGA | 44703 & 44704 |
| SMAD6 | TCAACCTGGAGCAGGCGA | CGCGGTTGTAGGCCACA | 44599 & 44600 | SMIM20 | CATGTCCCGGGAACCTGCGA | GGGATAGAAGGCGGCGGA | 44705 & 44706 |
| SMAD7 | CACACTGGACAACCCGGA | CTCAGCCAGCACGGGCA | 44601 & 44602 | SMIM21 | CTGCAGGAATGGGACGGA | CCTCAGCACAACATCACA | 44707 & 44708 |
| SMAD9 | TCCAGGCTTCCTCCGAA | GCTGTCGTCACTCAGCGA | 44603 & 44604 | SMIM24 | GAGGAGGAGGACCACGTTCAGA | TCCTCCAGATCCAGTCCA | 44709 & 44710 |
| SMAGP | AGAAGAACTGATGACGCAGA | CTCTCCATCTGACGATGGCA | 44605 & 44606 | SMIM3 | CTTCCCAAGCACATCCTCGGA | ACAGCCCCACTAAGGATCGGA | 44711 & 44712 |
| SMAP1 | ACCAGTGCACCAAGCGGGAACACA | GTGCAGAGGGTGTCCCCTGA | 44607 & 44608 | SMIM4 | GGGCCCAGGTGAGACGGA | CATAGAAGGGTCTCCTGGCCCA | 44713 & 44714 |
| SMAP2 | CATATCCACAGCCTACCCA | TTGATGCCTGCATGCCACCCA | 44609 & 44610 | SMIM5 | CAGGTGAGCCCGTGGAGA | GCCTCTCCGCCTCAGGGCA | 44715 & 44716 |
| SMARCA1 | GGGCTGGAGGTCTCGGAA | TGTTGTCAGTGATGAGACGGA | 44611 & 44612 | SMIM6 | AGGGGGGCCTGGCACTGA | TCTTCACCCGCCTTCACCTCA | 44717 & 44718 |
| SMARCA2 | GCCTTGATGGGCACCACA | TTTAAGCCAGGCACCA | 44613 & 44614 | SMIM7 | CACAGGTGACAACATCCGGAA | GAAGATGTTCCACAGGGCGA | 44719 & 44720 |
| SMARCA4 | TACGTGGCTAACCTCACGGA | GGATCACCTTCACCGGGA | 44615 & 44616 | SMIM8 | GCAGTCCAGGAGGGCAACA | ACATCAAACACATAGGCCAGGCA | 44721 & 44722 |
| SMARCA5 | GCAAGAGCTCCAGGACA | TGCGAATACACTGTCGCAA | 44617 & 44618 | SMIM9 | GGAGTCCATGGAACCCCAGA | AGGCAGAGACAAAGGCAAAGGAGA | 44723 & 44724 |
| SMARCAD1 | GTCCCAGAATACCAGGCCA | CTGGGCCCACACCTGCA | 44619 & 44620 | SMKR1 | CCAGGGCAAGTCTCATGGGAA | CTTTGGGAGCCAAGTTGGA | 44725 & 44726 |
| SMARCAL1 | ACGTGCAGCACATCCGCA | TGATGGACAGCACGGCA | 44621 & 44622 | SMLR1 | CAAAGGCCGGAGCCCCAGA | TGAAGTAGGCGATGAGGAGGA | 44727 & 44728 |
| SMARCB1 | CTGGAGGCACAGTCAGACCA | GCCAAACCCAGCTCGA | 44623 & 44624 | SMN2 | GCCAAGACTTGGGACCAGGAA | ATATGGGAGGTGGTGGGGGA | 44729 & 44730 |
| SMARCC1 | CAGGTCAGATACCAGGCCCA | GGGTAGGGCACTTCCAGA | 44625 & 44626 | SMNDC1 | AGTCTTGGAGTGAAGATGGACA | GGCTTGGCGTTCAACAGTGGA | 44731 & 44732 |
| SMARCC2 | CTCACCGTTCCCCAACCA | GGTTAGGAGGAGCGGGGGA | 44627 & 44628 | SMO | GGCTTCTCTAAGCGCGCA | TGCCACAGGGGTGACAGA | 44733 & 44734 |
| SMARCD1 | CCTGGGCATCCATACCCA | CTGGTGGCATAAGCAAGGCA | 44629 & 44630 | SMOC1 | CAGCCAGCTGGACAGCAA | AGGCAGCCCTTCAGCTCA | 44735 & 44736 |
| SMARCD2 | TCTACCACCAATCAGCAGGAGA | GAGGTCTGGGCTGCTGGGAA | 44631 & 44632 | SMOC2 | CCAGTGGAGACATCGGCA | TTTCGCCACGCCCAGGCA | 44737 & 44738 |
| SMARCD3 | AGATTCCCAGGGCCTTACA | GCTCCTCCACCTCCAGGTCA | 44633 & 44634 | SMOX | GCTCAAAGACAGCGCCCA | TGGCCGGACAGAGAGCA | 44739 & 44740 |
| SMARCE1 | TGAGCGCAGTCAGAGCAGGA | TCGACCCCTCCTGCCCA | 44635 & 44636 | SMPD1 | GGAGCCATACCGCACTGGCA | AGCTGGGCACAAAGAGTAGCCA | 44741 & 44742 |
| SMC1A | GCCAGGGTGAGGAAGAGA | CGGCAATACGCTGAAGCA | 44637 & 44638 | SMPD2 | CCCCACAGCAGAACCCA | GCCAGGAGAAGCAGCCCCA | 44743 & 44744 |
| SMC1B | CTGCAGAAACAAACTGGCTGA | TCTAGGGTCAAAACTGGCTGA | 44639 & 44640 | SMPD3 | GGGTACGTACGCTGCACA | GTTGGCTGCGTGACGA | 44745 & 44746 |
| SMC2 | GGTGCTTGATCCCAGGGA | CTCTAGAGCCCGCAGCTCA | 44641 & 44642 | SMPD4 | CTGTCGCTACCACCTCACAGA | GGACATAGCCCAGGGTGAGCA | 44747 & 44748 |
| SMC3 | GAAAGGAGATGTGGAGGGCA | GAGCAAGGGCTACCAAGGA | 44643 & 44644 | SMPDL3A | AAGACTGACCAGCCTGACCGA | TGAAGATGGCAGATCCCCA | 44749 & 44750 |
| SMC4 | TCGGTTCTAAGCCACCAGA | ACTCTGCGATGGCACCGA | 44645 & 44646 | SMPDL3B | CTCGAGTACCAGCTGACCGA | CAATGTCCACCTGGCCGA | 44751 & 44752 |
| SMC5 | CAAGAGAGCTCCCGAGAGA | GGACGATAGAGCCTTCCACGGA | 44647 & 44648 | SMPX | GAGCAGGTCAACCCCCAGA | GATTGACTGGCAGGTCCTGGAA | 44753 & 44754 |
| SMC6 | GGACCTTCACGGCCACCGA | GGGACTGCATTACTGCACGA | 44649 & 44650 | SMR3A | GTCCAGGAGAATCCCACCA | GTTGGGAAGGTGGCTGTGAA | 44755 & 44756 |
| SMCHD1 | AAGAAGAGAGGGCTTGCACCAA | TCATCAGTCCTTCAGCCACA | 44651 & 44652 | SMR3B | CGCAACCTATGGTTCAGGGA | GTCGGGGAAGGAGGCTGTGGA | 44757 & 44758 |
| SMCO1 | GTGGGCTGCAAGAAGGAAGCA | TAGGAACGTGACATCCCTGA | 44653 & 44654 | SMS | GGTACGCCAAAGAAGGGAGA | CTGGAGACGTGGAGATTGGA | 44759 & 44760 |
| SMCO2 | AAATGGAGGCAGAGGAGACACTGA | ATGCTGTATTGCGGGGGAGGAGA | 44655 & 44656 | SMTN | CCTCAGAACCGACGCCAGA | ACCTCCACCAGGGGGCACA | 44761 & 44762 |
| SMCO3 | AGAGAAGAGGAAAAGGGGGA | TCAATGGAGGCCAGCCTGCA | 44657 & 44658 | SMTNL1 | TGCTCAGTCTGCTGGACGTGGA | TCTGCACAAGGCTGCGGTA | 44763 & 44764 |
| SMCO4 | AAAGGGAAGCCCAAGAGGAGA | CAAGAGCACCACGGCCA | 44659 & 44660 | SMTNL2 | CGCCAGCAGCATCAGCAGA | AAGGCCATGCCTGCCTCCA | 44765 & 44766 |
| SMCP | CAAAACAGAAACCAGTGCTGCCA | TGGTCTCCAAACCACAGCA | 44661 & 44662 | SMU1 | AAGTGGGCAGCAGCATCAGGGA | CATCAACACGACCCAGTGACCA | 44767 & 44768 |

| GeneName | Forward Primer | Reverse Primer | SEQ ID NOs | | GeneName | Forward Primer | Reverse Primer | SEQ ID NOs |
|---|---|---|---|---|---|---|---|---|
| SPTSSA | CGCGGGCTGGAAGCAGA | GTGCTGGGGCATGAAGACGTA | 45405 & 45406 | | SRSF11 | CAGCAGTTGTGGCACAGCA | CCAGGAAGCCCAAGTGCA | 45511 & 45512 |
| SPTSSB | TTTAGAGCCTGGGAGCGA | GAAAAATTCCCAAGCCAGGCGA | 45407 & 45408 | | SRSF12 | TAAAGAGTCTGACACAGGCGA | TGACCGTCCTCTAGAGCCA | 45513 & 45514 |
| SPTY2D1 | GTGGGTCCAAGAAGCCAACCA | GGCCACGAGAGCTGCCA | 45409 & 45410 | | SRSF2 | ATCCCCACGAAGGTCAA | CCTGGACCGAGACCGGGA | 45515 & 45516 |
| SPX | GAGAAGGAACTGGACTCCTCAA | GGTCGGAGATGAAGCGGCGA | 45411 & 45412 | | SRSF3 | CCTCCACCTGTCGCAGA | TTCTCTCCCGAGACAGCGA | 45517 & 45518 |
| SPZ1 | AGTCAGCTGAGATGCCACCA | GCCCAGGAGGATGAAGGGGA | 45413 & 45414 | | SRSF4 | GCAGTCGCAGCCGCAGCAA | ATCTGGACTGGGAGCGGTCA | 45519 & 45520 |
| SQLE | AGCAGCTCGAGGCCAGGA | GCAGAGCCAAGCACGCCA | 45415 & 45416 | | SRSF5 | GAGCCGAGCGGGAGCAA | GGCGATCCACAGATGCTGGA | 45521 & 45522 |
| SQRDL | GAGATCATCCAGGAGCGGGAA | TCCACATCCACCCAACCA | 45417 & 45418 | | SRSF6 | TGGAAGCAGATCCAGGTCTCGA | CTCCGCGACCTGGAACGGGA | 45523 & 45524 |
| SQSTM1 | TACCCACATCTCCGGCA | CAGGAGCCTGGTGAGCCA | 45419 & 45420 | | SRSF7 | GAGTGTGGCGAAAAGGGACA | CCTGCTGCGTGAGCGAGA | 45525 & 45526 |
| SRA1 | AGGAACAGTGGGCTGGAGGAA | AACCATGAGGGAGCGGGTGGA | 45421 & 45422 | | SRSF8 | AGCCGCTTCCCTACAGCAGA | TGGAGGTTGATGCAGAGCGA | 45527 & 45528 |
| SRBD1 | ATGCCTGGAAGATCTGCAGA | TAACACCCGAATGAGGTCCAGA | 45423 & 45424 | | SRSF9 | AGTGCCAGGACCTGAAGGA | TCATCCAGTTTACGCCAGGGCA | 45529 & 45530 |
| SRC | TGGGATGGTGAACCGCGA | CTCAGGCTCCTTCCGCCA | 45425 & 45426 | | SRXN1 | TCCGGGAGGACCCAGACA | TAGCGGTGCAGCCCCGA | 45531 & 45532 |
| SRCAP | TCACCCCACGTGGCTGGGCA | TGTGTGAAAGACAGCTGGGGAA | 45427 & 45428 | | SRY | TCTGCGGATCAGAGGCGCAA | TGCCTCTGGAAGAATGGCCA | 45533 & 45534 |
| SRCIN1 | TGAGCGGGCCAGCTGAAGGA | CTCTGCAGCCTCAACAGACACA | 45429 & 45430 | | SS18 | GCAGCAGTACCCAGGGCA | GACCTGGACCACCCTGTGA | 45535 & 45536 |
| SRD5A1 | GAGGAGGAAAGCCTATGCCA | ATCAACATGCCCGTTAACCA | 45431 & 45432 | | SS18L1 | GGCCAGCAGTACTACCCCGA | GCGTGGACTTCCTCGAAGGA | 45537 & 45538 |
| SRD5A2 | CAGCTCAGGAGCCTGGAGA | AGCTCGCAGCCAAGGAA | 45433 & 45434 | | SS18L2 | CAGTAGGTGTTGCGGCAGA | GCAGTCAGGGGGACCACA | 45539 & 45540 |
| SRD5A3 | CAGGGAGGGGAGCTGGCA | GGCTCAGCACAGTTAGGCCA | 45435 & 45436 | | SSB | GTCAGAGGAGCAAAAGAGGGGA | TACCAGACCCAGGCTGGGCA | 45541 & 45542 |
| SREBF1 | GGGTCAGCTGATGGGGACA | CAGCTGTCAGAGAGGCCA | 45437 & 45438 | | SSBP1 | TGGGATCAGGGGATAGTGA | CTCGAGGCCTGGCCGGA | 45543 & 45544 |
| SREBF2 | CAGTGGCCACCTATGAAGCA | TAGCAGTCAGAGGTGAAGCA | 45439 & 45440 | | SSBP2 | GTGCAATGAGACCCCCACTGA | TCCCAAGAGATGCTTGAAGGA | 45545 & 45546 |
| SREK1 | GCTTCGGCCTCACCCCA | GTAGAGCGCAGCTCCTCGA | 45441 & 45442 | | SSBP3 | CATTATGCCCAGTCCCGCAGA | AGCCGGGACCCATCGGGA | 45547 & 45548 |
| SREK1IP1 | CCCAGGCAGTATGTACCAGAA | CGAAAGACACCAAGGCCCA | 45443 & 45444 | | SSBP4 | AGATTCCACCAACTCCAGCGAA | CCGGGGACTCTTCGGCA | 45549 & 45550 |
| SRF | ATGATGTACCCTAGCCCGA | TCAGGAACACTCGGGGGA | 45445 & 45446 | | SSC4D | GTCAATGGAGCCCACCGA | AGCTGGCGGCAAGGACA | 45551 & 45552 |
| SRFBP1 | AGCCCGGGAACTCTGAACCTA | TCAGTCGGCCAACACTCCTGA | 45447 & 45448 | | SSC5D | GCCAAGCATGGACCCA | AGGGGGTTCAGGAGACA | 45553 & 45554 |
| SRGAP1 | CCTGCACTTCACGGAA | GCTTCAGTGCACGCCCA | 45449 & 45450 | | SSFA2 | ACACTTGAAGAGGAGCAGGAA | GGTGGTGGAGCAAGCCGTGA | 45555 & 45556 |
| SRGAP2 | CACCACGCAGCGGATGACGAA | CGGAAGCCCCTGGTAAAGCA | 45451 & 45452 | | SSH1 | TCCAGGGAGCCATGTGAGGA | AACACGGGACCTGCTGCCA | 45557 & 45558 |
| SRGAP2B | ACAAGCAGCGGCTCATGGAGA | TGTAGCAGCTCACTCTGACA | 45453 & 45454 | | SSH2 | GCAGGGCTCACCAAACCA | GGGGATTCACAGGAGGCA | 45559 & 45560 |
| SRGAP3 | TGGAGAACCCAGCCAGCGAGA | GCATGAGGGTTAGGCCCGA | 45455 & 45456 | | SSH3 | TGTAGGCATGGAAGAGAGGCCA | CTCCAAGAGAGGGCTCCAGAA | 45561 & 45562 |
| SRGN | ATCCCCGTTCGAGGACTGA | TCCAGAGCCGGAGCCGGA | 45457 & 45458 | | SSMEM1 | AACACCACCATCACCAGACA | CTGTCGGGAATGGTGCCCA | 45563 & 45564 |
| SRI | GGCCTGACAACAATGGGA | AAGCTGTCTGTAAGAGCCCTCA | 45459 & 45460 | | SSNA1 | AGGGTGAGGCAGCTGACAGAGA | AAGTCTGGGAGCTCTCCAGGA | 45565 & 45566 |
| SRL | AGGGGGCTGTGAATCCAGA | GACATTGATGAGAGGGGCCA | 45461 & 45462 | | SSPN | CGGAGCCGCGTCAGCAGGA | AGCAGGCCAACAAGCACA | 45567 & 45568 |
| SRM | CACTGACTCTTCAGACCCCA | CATAGGCCACCACGGGGA | 45463 & 45464 | | SSR1 | CCCATGGGCGGACAGACCA | CTAGGAGTTGATGAAGGCCA | 45569 & 45570 |
| SRM5 | ACATATTCTCCCCGAGCAGCA | TGAAAACCTCGTGCAGCAGGA | 45465 & 45466 | | SSR2 | GCACCTGGACAGGGAGGAA | CGATGGAGGGAAGGGTCA | 45571 & 45572 |
| SRP14 | TATGACGGGTCGAACCAAACCA | ACTTCCTTGGAGTCACACA | 45467 & 45468 | | SSR3 | AAAGGCAGCTCCAAACAAGCA | CGCGGAGGACTTGGCCGA | 45573 & 45574 |
| SRP19 | AGGGAAGGCGAATCCCA | ACAAGGCAGAGGCTCCCA | 45469 & 45470 | | SSR4 | ACATGCAAGAACAGGGTCCAGA | CCCGTTCCAAGTGCCCCGA | 45575 & 45576 |
| SRP54 | GTAGACCCTGGAGTTAAGGCA | GTCAAAAGCCCCTGCTCTGA | 45471 & 45472 | | SSRP1 | CTAAGGCGAGAGCTTCAAGAGCA | GTCCTCTGAGCTGGGGGGA | 45577 & 45578 |
| SRP68 | ACAGAGACCTCCTCTCCAA | AAGCCACATGGTTGAGGGCCA | 45473 & 45474 | | SSSCA1 | CACAGACAGCCCTCTTGCAGA | CCTCCGCACAGTTGGGAGA | 45579 & 45580 |
| SRP72 | AAGTGAACCGGTATGGCCAGA | ACAATGCAGGGCAGTTACGTCA | 45475 & 45476 | | SST | GGACCCCAGACTCCGTCA | GATCTTCAGGTTCCAGGGCA | 45581 & 45582 |
| SRPK1 | CTGGCTGAGAAGCAACAGA | AGGCTGGGGAGCAGTACTGA | 45477 & 45478 | | SSTR1 | TCATGCCAGAGCCCGCTCAA | GCAATGATGAGCACGTAGCACA | 45583 & 45584 |
| SRPK2 | AGACAAGACAACATAGCCCA | GCATCTTCATGGGCCAGGA | 45479 & 45480 | | SSTR2 | CCCCAGCCCTTAAAGGCA | CGCTCACCTTGACCAAGCA | 45585 & 45586 |
| SRPK3 | TACAGTCGTGATGAGGACCACA | TACAGGCCCCAGTGCTTGAGA | 45481 & 45482 | | SSTR4 | CGTGACCAGCCTTGATGCCA | GAATCGGCGGAAGTTGTCGGA | 45587 & 45588 |
| SRPRA | AGCATGGTGGCCCACCA | CTGCCTGTCCACCAGCA | 45483 & 45484 | | SSTR5 | CTACGCCAAACAGCTGTGCCA | TCAGCTGCCTTGGCCACCAGA | 45589 & 45590 |
| SRPRB | GCAACTGGACAGTTCCAGCA | TCTTCCACCCTTGGCACTGCA | 45485 & 45486 | | SSU72 | GCCCCGGCCAGCGAAAAGATTCCA | CTCCTGCAGCAGCTCGTCGA | 45591 & 45592 |
| SRPX | TACATGAAGTCTGGCAGGA | GCCGTTCTGCAGCCACA | 45487 & 45488 | | SSUH2 | CTGCAGCAGCCGCAGCGA | CAGCCACGCAATACCGCTCA | 45593 & 45594 |
| SRPX2 | CTGTCAGTCCAGCCGCCA | ATCGGTTGGAAGGATCAGGA | 45489 & 45490 | | SSX1 | AAGAGACCCAGGGATGATGCTA | ACATGAAAAGGTGGGAGGGTGA | 45595 & 45596 |
| SRR | AATACAAGCCTACGGAGGCGTCA | TGGTTCAGCACTTCCAGGGCA | 45491 & 45492 | | SSX2B | AGAGAGCGCCGGAACAGCTCA | TGGGGGTACCATTGAACTGCA | 45597 & 45598 |
| SRRD | CGGCCTGGAATCCTGGCA | TTCTCAGCCCCAGATGCGA | 45493 & 45494 | | SSX2IP | GCAGCCGCAAAAGAAGCCTCA | ATGCAGGGAACGTGTCTTGGCA | 45599 & 45600 |
| SRRM1 | CCACCGTTCGAAGAGGA | TGGCTCAGGAGACCCGGA | 45495 & 45496 | | SSX5 | CACACCAAGTACCAGTATAGGCA | TGAGGGGAGTACATGCTGAACA | 45601 & 45602 |
| SRRM2 | AGCCAACCCCAGCAAACGGA | AGGCTTAGCAGGGGAAGGGGA | 45497 & 45498 | | SSX7 | ACACACAGACACCAAGTACCA | GGGGAGTACATGCTGAACAGGA | 45603 & 45604 |
| SRRM3 | CGGGCTCCAAGTCGGGGGA | AGAAAGAGGAGGGGGGACA | 45499 & 45500 | | ST13 | CAGACGACAGTCAGGAGCTCA | ATGGCTGCAAGAACCTCTGGA | 45605 & 45606 |
| SRRM4 | CTCCAAGTCTGGCAAGAGGA | CTCATAGGCGAGTAGGACCGA | 45501 & 45502 | | ST14 | GAGTGTGACGGGCAAGAGGA | GAGACCAGCCAGTTGGGAGGA | 45607 & 45608 |
| SRRM5 | GGCCGGCCTAGAACCAGCAA | GGAGTTACAGCCAGCTCGGA | 45503 & 45504 | | ST18 | ACATCCTTCCCAACAAGCCACA | AGACGAAGTTAGGGCGTGCAGA | 45609 & 45610 |
| SRRT | TACCCACCAGACTCCCA | ATCATAGTTCCCTGCAGCCAGGA | 45505 & 45506 | | ST20 | CAGTAAATCATTGGCACCAGGA | GGGTCAGCACGGACACGA | 45611 & 45612 |
| SRSF1 | GGCCGTGGAACAGGCGCA | TCCACTTGGAGGCAGTCCA | 45507 & 45508 | | ST3GAL1 | CAACTGGCTGCAAGGGCA | CAAGTCCACCTCATCGCAGA | 45613 & 45614 |
| SRSF10 | GTCTGAAGACTTGCGCGGTGA | CAATCTGCCGTCCACAAATCCA | 45509 & 45510 | | ST3GAL2 | GATTCACCTACGCCCCAGTGA | TCATCACACATGCAGGGGCA | 45615 & 45616 |

| GeneName | Forward Primer | Reverse Primer | SEQ ID NOs | GeneName | Forward Primer | Reverse Primer | SEQ ID NOs |
|---|---|---|---|---|---|---|---|
| TAF1C | CTACCACCCAGAGGAGGACA | GGAGGGGCTGAGGAGCTAGAGA | 46253 & 46254 | TAS2R3 | ATCCAACCACTGAGGGCCACA | GATGACCAGACTCACACCGGA | 46359 & 46360 |
| TAF1D | AGCTCTAGGACACCAGGCCA | CAGTGGCCCCAACCAGCGCA | 46255 & 46256 | TAS2R30 | ATGTCTGGGCAGTAACCAACCA | AAAGGCCCAACAGTATCACCA | 46361 & 46362 |
| TAF1L | GACAGAAGAGCAGGAGGAGGA | TCTGCGAACCTCATGCACA | 46257 & 46258 | TAS2R31 | GTCTGGGCAGTAACCGGCCA | AAATAGTAAGGCCCCAACAGCA | 46363 & 46364 |
| TAF2 | AATCCAAGCAGTCACCCACA | CGGGAGCTAGCTGGCCGA | 46259 & 46260 | TAS2R39 | CCTATCCACTTCCTCCAACTCCA | GCCCCCATGTGAGCCTCCA | 46365 & 46366 |
| TAF3 | CCGAGATGAGTGGGGCAA | TCGCACACTTGGGCAGA | 46261 & 46262 | TAS2R4 | TGTTCAGCCTGGGCATTCACCA | CCAGCAGCAGCCTGGGGA | 46367 & 46368 |
| TAF4 | ATCGGGCCCAGGAAAAGAGGA | CCTGAGGTTGACCGCGTGA | 46263 & 46264 | TAS2R40 | CTCCCACTGGTGACCGCA | AAGACTTTGAGCCAGGCAGCA | 46369 & 46370 |
| TAF4B | ATCCAGCCTGACAGCCACCAA | AAGGGCCAGGTATAGAGCTCGA | 46265 & 46266 | TAS2R41 | TGGGGGTCTCGGCCGACA | AAGGAGATCAGGACAGAGCCCA | 46371 & 46372 |
| TAF5 | CAATGCTCCACCTCAGAACAGA | TACGACCACACTCTGACA | 46267 & 46268 | TAS2R42 | GGCTCTAGAGACTCACAGACA | AGTGGCACGAGGGAAAGGCA | 46373 & 46374 |
| TAF5L | GGTTTGGAGCCCCCGACA | AGAAGCAGATGGTAGTGAGGGGA | 46269 & 46270 | TAS2R43 | ATCTGGGCAGTGAATCAACCA | AAAGGCCCAACAACATCACCA | 46375 & 46376 |
| TAF6 | GGCTCAGGTTCCACCACA | CGGGGAGGAAGTGGAGA | 46271 & 46272 | TAS2R46 | ATCCCAGCATGAAGGTCCACA | CACCCAGTACCTCACATGCCA | 46377 & 46378 |
| TAF6L | CTAATGCCCAGGTCAAAGGAGA | AGAAGAGGGTGTCCCATGGCA | 46273 & 46274 | TAS2R5 | TCCATTCAGCTGGTAGGAGGGA | ACACTGGTGAGATGCAGGAGGA | 46379 & 46380 |
| TAF7 | AGAAGGTTCCGGAAGACAGCAA | CATGGCCCTGCCTGTGACCA | 46275 & 46276 | TAS2R50 | AGCTCCATGGAGAAGGATCGJA | TCATTCCGCAGCCTCCTAGGA | 46381 & 46382 |
| TAF7L | GACCCACTCGACCATGAGA | AAGGATCCCTTAAGCCCAGGA | 46277 & 46278 | TAS2R60 | ACAACCTCAGGATTCCGAGA | GGGGTGAACTGCTGCACA | 46383 & 46384 |
| TAF8 | AGGATTCTGGAGCCGAGAAGAGGA | GCTTCTTCACCGAGCCGCAGA | 46279 & 46280 | TAS2R7 | TAGCCTTCCAGCCACTGAGA | TCTGCACCCTGTGGCACTGA | 46385 & 46386 |
| TAF9 | TTCTCCAAGAGCATGCGAA | AGCGCGGCACTGAGATTGCCA | 46281 & 46282 | TAS2R9 | GACCCAGTACAGAAGCATCCA | TACACAGTGAGGAGGAGCAGA | 46387 & 46388 |
| TAF9B | CCAAGGGAGACTAGTTCCACGA | TGACAGGTGTGGACTGAGA | 46283 & 46284 | TASP1 | GGCTTGAAACATCCGGGGA | CACTCCGCCAAGCACGCCA | 46389 & 46390 |
| TAGAP | GGAGATGGAGGACGAGGAGGAGGA | CTTGCTGATGAGGTGCAGCA | 46285 & 46286 | TAT | CCATCCTGGACTCCGGCCA | CTAACCGCTCCGTGAACTCCA | 46391 & 46392 |
| TAGLN | GCAGCTTGGCAGTGACCAA | CTGCCCATCTGCCTGTGACCA | 46287 & 46288 | TATDN1 | GATGGTTACCAAGGAAGCAGCA | TGACTCCACCAAGGTGCA | 46393 & 46394 |
| TAGLN2 | AGATCCAGGCCTCACCA | TCCGCTGCACACAGGCCA | 46289 & 46290 | TATDN2 | GCCTGTCCCAGAACAGCA | GGTAGCTGCCGGTGAAGCA | 46395 & 46396 |
| TAGLN3 | TGGGAAGGGAAGGAACATGGCA | TCCTTCGGAAAAGCCTCTCCGA | 46291 & 46292 | TATDN3 | CCCGGACTTTGACCGCGA | GATGAACACCCAAGCATGGCA | 46397 & 46398 |
| TAL1 | GCAAGCTGATCCCCACACA | ACTTCATGGCCAGGCCGGA | 46293 & 46294 | TAX1BP1 | CCTCTTGGGGACTGGAAGACA | CAAAAGCTGTCCCATGCCCA | 46399 & 46400 |
| TAL2 | CTGAGGAAGCTTATCCCA | TGTCTCCAGGCCTGGCA | 46295 & 46296 | TAX1BP3 | GAGGTGGAAATCGACCAGGA | CAGCAGGGCCTCCTTCAGA | 46401 & 46402 |
| TALDO1 | GGAGCTCGAGGAGCAGCA | GCCACATGCCAATCAAGGA | 46297 & 46298 | TAZ | GGCGTCTACCAGAAGGGGA | CATGCCACAGAGGGCAGGA | 46403 & 46404 |
| TAMM41 | TCACTTCCCCGAGGAGCTGA | GAATGCCATGCCGACAGGGTCA | 46299 & 46300 | TBATA | ATCTCCACCAGGCCAGCAGA | GGAGACTTAGGGCGTCGGGGA | 46405 & 46406 |
| TANC1 | AGCCAGAATGTCGCCTGCA | GCGTCACAGGCCTCTGCAGGA | 46301 & 46302 | TBC1D1 | CTACCGTAATGCCCTGCGAGA | GGGGTGGCTACTCGGAGGA | 46407 & 46408 |
| TANC2 | AGCAGAATCGGACCTGGGCA | TCACGTCGGGATAGGAGGGA | 46303 & 46304 | TBC1D10A | CCCCAGCCCAAATCAAGCCA | GTGGGCTGAGACCTGGGGA | 46409 & 46410 |
| TANGO2 | GAAGGCAAGGAAGGAGGGCACA | CCCACCCTGGTCCTCGA | 46305 & 46306 | TBC1D10B | GGCAACAGGACCTGTACCGAA | CGCAGGCATGTGCATGAGCA | 46411 & 46412 |
| TANGO6 | AAGGAGTCAATGAGCGCAGGGGA | TGGGAAAGAAGTACGCAGGGCA | 46307 & 46308 | TBC1D10C | CCCCCAGGCGCCAACGA | GAAGGAAGCCAAGTCCCCGA | 46413 & 46414 |
| TANK | CCACCTGAGAGAACCCATAATGCA | CGGGGAATCGATGAGTGAGGGA | 46309 & 46310 | TBC1D12 | CTGCAAACAGTTCCAGGTGA | TCTGGTGAAGAAGTCGCGA | 46415 & 46416 |
| TAOK1 | AAGGAGGGAACAGACCCGGAA | ATACGCATTCAACAGCTCCA | 46311 & 46312 | TBC1D14 | AAGCCCAGCGAGGAAGGAAGAAGCA | ATGTCAAAGAGCTCGTGGGTGA | 46417 & 46418 |
| TAOK2 | GGGGCAGTACGATGGCAA | TGACTGGAGCACGGGGGGA | 46313 & 46314 | TBC1D15 | TAGAATGGACTCAGGCCCCAA | GAATACCAAATAGGACCAGCCCA | 46419 & 46420 |
| TAP1 | GTCCGCGGATAGCACA | GCCTAGAAGCCGACGCACA | 46315 & 46316 | TBC1D16 | CGTGGTCGGACAGATCGGAA | CCCGGGCGTGAGCTGACGA | 46421 & 46422 |
| TAP2 | ACATGACCGACCAGCCAA | AGCGCCGTCACCTCACCA | 46317 & 46318 | TBC1D17 | CAGGAGACCCATGAAGCGGCAA | TCCATGTCCAGGATGCGCCGA | 46423 & 46424 |
| TAPBP | AAAGTGTCCCTGATGCCAGCAA | TCCACTTCCAGGCCCCCA | 46319 & 46320 | TBC1D19 | TTGGGGCTCAACCACTTCGCA | TGCTTCAGCTGCAGCCAGTGA | 46425 & 46426 |
| TAPBPL | CCCAGGTTGTCCCAACGA | GCCGTCTCTGAAGCCCCA | 46321 & 46322 | TBC1D2 | TCCAGGACTGTCCTCGGAGA | ATGAGACTGTCCCCAAAGACCA | 46427 & 46428 |
| TAPT1 | AAGCTGTCGAATCCTCCGCAA | TTGGTGATGGAGGCAGACA | 46323 & 46324 | TBC1D20 | CTGACCAAGCCAAGGACCAA | CAGCTGAAACTTAGGGCCCA | 46429 & 46430 |
| TARBP1 | GGACAGTGGACAGGAGGCA | GGGCCCAGCATGGAGAGA | 46325 & 46326 | TBC1D21 | CGGGAAGCCTGCTGACGGAA | GGTTGTTGCAGGCCAGGAGGA | 46431 & 46432 |
| TARBP2 | CGGTTGCCGGAGTACACA | CCGTGTGCACTGCAAGCA | 46327 & 46328 | TBC1D22A | TGAAGACCCTGTCGATGAGGGA | TGTGGGCAGGTTCTGGAGGA | 46433 & 46434 |
| TARDBP | GCAGAACCAGTAGGACGCCA | CTGACCAGAATTAGAGCCA | 46329 & 46330 | TBC1D22B | CCCAATGACTGTCCGGAGAA | CCTGGGAACCCTGGCCA | 46435 & 46436 |
| TARM1 | TGGGCCTCAGAACCCAGTGA | GATAACCACAATTACGGCCAGCA | 46331 & 46332 | TBC1D23 | TATGGCACTGCAGCAGCA | CCTTGAGCCTGAGGTACTAGCA | 46437 & 46438 |
| TARS | CCCATGAACTGCCCAGGA | CAGCTAGCCGCCAGGA | 46333 & 46334 | TBC1D24 | CAGCGTGAGGGAGGATGAGAGA | TCCGGTCCCAAAGAAGCCA | 46439 & 46440 |
| TARS2 | TGGAGAACCCTGGACCTCA | TGGAGGTTCAAATCTCAGGGGA | 46335 & 46336 | TBC1D25 | AACATGGCTCCAGGAGGGA | GAGAGCAGTGGGTCTGGGGA | 46441 & 46442 |
| TARSL2 | TGGTCATCCTGTGGGCCAA | TATACTGAGCCAGCTGTGCA | 46337 & 46338 | TBC1D26 | TTGGACCAGGGATGCCCCA | AACGCAGGCAGCCGAAGAGA | 46443 & 46444 |
| TAS1R1 | CCCTGTGGTGAGGTGAGCA | GCGAACTTCCAGGCAGGA | 46339 & 46340 | TBC1D28 | GGCTTCGGAAAGGAAGGCGA | GTCCAAGAGATCATGGCCCA | 46445 & 46446 |
| TAS1R2 | CCACCAACTACAACGAGGCCA | GCGCTCCGGTAGAAGAGGCA | 46341 & 46342 | TBC1D29 | GCATGGAAGACCAGGACCCA | GTCCTGGCACCCTTGGAGGA | 46447 & 46448 |
| TAS1R3 | CTCAGGCCCGTGACAGA | CCCTGGCCTGCGCATGAGCA | 46343 & 46344 | TBC1D2B | AGAAGGCGCTGCGGAGAACAGA | TAGGCCTTGACGTAGCCGA | 46449 & 46450 |
| TAS2R1 | GCCAGCTGTCGTCACCA | CAATGGCACTGAGAACTTCAGCA | 46345 & 46346 | TBC1D30 | CTGAGCTCAGGGTGCACCA | CAGGGGCTTGACGCTGGGA | 46451 & 46452 |
| TAS2R10 | CTTTGGAGCACAACAGGCAGA | GATAAATGAGTGACCCCAGGGA | 46347 & 46348 | TBC1D31 | TAGGCAACAAGGAGGAGCGGCAA | TAAGCAGTGCCCTGTGCA | 46453 & 46454 |
| TAS2R13 | GACCCAGGACCCAAGGTCA | GAAAGGAGTGGCTTGAAGGAGA | 46349 & 46350 | TBC1D32 | CCAGCAGGACCAGGGCA | CACTCAGGGAAGGGGCA | 46455 & 46456 |
| TAS2R14 | AGCACCAAAGCCCACAGAGGA | GTGACCTGAGGGCTCCCA | 46351 & 46352 | TBC1D38 | TGGGGCTGTCCGGGAAGACA | CCAAGGCCCCTCTACGTCCA | 46457 & 46458 |
| TAS2R16 | ATGGCATCACTGACCAAGCAGA | CAACGTAGGGCTGCTCAGCA | 46353 & 46354 | TBC1D5 | AGAAACGCCAGGGTGCACTGA | ATCTGAGAACACCAGTGGGGA | 46459 & 46460 |
| TAS2R19 | AATGCTGGGCGTTAACGAA | GGGCCCAACAGTATCACCA | 46355 & 46356 | TBC1D7 | TGTATCAGCTGGAGTCTGGGAA | GATTCAGGCAAACATCCCGCA | 46461 & 46462 |
| TAS2R20 | ATCCCAGCACCAAGGATCCACA | GCCCAGCAAGTCACCTGCCA | 46357 & 46358 | TBC1D8 | AAGCCATCGCCACAGTCACCA | AGAAGGAGCTGAAGCCCTGCA | 46463 & 46464 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| TBC1D8B | GCTCTCTGCCTGAGCACCA | TCAAAGACTGCCTGATCCACCA | 46465 & 46466 | TCERG1 | CTACGACCAGTAGCCTCAGCA | GTGTGGCTGTGAGGCAGGA | 46571 & 46572 |
| TBC1D9 | GACACGGTCTGTGGTGTCGGA | GTAATCCTGGCCATCATGCACA | 46467 & 46468 | TCERG1L | AACCAAGAGGAACCGGACCGAA | GGGTCACGCTCCTCCAGA | 46573 & 46574 |
| TBC1D9B | GGAGGACACGGCCAAGAGGA | AGCAGAGGTGTGTGGGAGCCA | 46469 & 46470 | TCF12 | CAGGTACCAGTTCAGTGGCCAA | GGTGGAAGGTCCACAGCA | 46575 & 46576 |
| TBCB | CCTACGACCAGAGGCAAGACA | CCTCACAGCGGCTGCCCA | 46471 & 46472 | TCF15 | CGTGGACATGGAGGTCAGA | GCTCAGGGCAGCCCCAGAA | 46577 & 46578 |
| TBCC | TGGGAGAAGAGCAGCAGGA | AGTCACTGCAGTCCTCCAGGA | 46473 & 46474 | TCF19 | CCGTCTCGGAAGTACCCA | TGCAGCCAACACAGGCCA | 46579 & 46580 |
| TBCCD1 | AAGAGTGGCCCAGTCCCAGA | TCAATAAGGAAGCTGAGCGCCA | 46475 & 46476 | TCF20 | TGCAGGCAGCACAGGGCA | GACATTAGGCAGCGCCCA | 46581 & 46582 |
| TBCD | CGCTGATCGGAAGACA | CGCCGAAGGTCACACA | 46477 & 46478 | TCF21 | TGGCCACTTGAGGCAGA | ATAAGCGGCTCGCGGTCA | 46583 & 46584 |
| TBCE | CACAGCCCATCCAGATACCA | GAATTGTCATGGAGCCGGCA | 46479 & 46480 | TCF23 | GCCCACTTCACCCGCACA | AGTCAAGATCGGAGTACCCA | 46585 & 46586 |
| TBCEL | TCCAGGAAGAAGTGCCA | TGGTCCAGACGAATGCTCA | 46481 & 46482 | TCF25 | CTCCTACGTCAAGGCCCAGAGA | AGTTGGCCATCATGTCGCGCA | 46587 & 46588 |
| TBK1 | CAACCTGGAAGCGGCAGA | CTGCCAGTGATCCACTGGA | 46483 & 46484 | TCF3 | GCAAGTGCGAGAGCGGAA | TGGGGGTCCAACCACA | 46589 & 46590 |
| TBKBP1 | GAAGCGGCCACTCTTCCCAA | GCGACTCGGGGATGGGGA | 46485 & 46486 | TCF4 | CTGGAGCAGCAAGTCCAGA | GCCAAGGAGAGCAAGGGGA | 46591 & 46592 |
| TBL1X | TCCAGGGACACACAAACGA | TTGCTGGTGGCGGCCCA | 46487 & 46488 | TCF7 | GCGGTCGAGGGAAAAGGA | GAGCACTGTCATCGGAAGGAA | 46593 & 46594 |
| TBL1XR1 | GGGGAGGAGAATGGAGCACA | CTCAGACCCTGATGCTAGGA | 46489 & 46490 | TCF7L1 | CCCTCTCCCTCCACCACCA | GCTGTGGGCATGGACCCA | 46595 & 46596 |
| TBL1Y | GCAAGTCTCGGCTGTGACCA | AIGTCAIGTCATCCGAGCAGGA | 46491 & 46492 | TCF7L2 | CGCTACACACGACGGGGA | TGAACTATGGAGTGAGCGACA | 46597 & 46598 |
| TBL2 | CTTCAAGGACTCACGGAGGA | TGCCACTGGCCAAGGCA | 46493 & 46494 | TCFL5 | GTGGGCCCCAGGAACGGA | TCTCGGCATTGCAGAACGGCA | 46599 & 46600 |
| TBL3 | TGGAACACCAACTCGCGGGA | GTGCCGCTCAGTGTAGGGGA | 46495 & 46496 | TCHH | GGAGCAGAAACGTCGCA | AGAGAGGGGCTGGAGCGCA | 46601 & 46602 |
| TBPL1 | GCTTAGCCGTAGTCGCAGA | ATCCGATAGCACAGCAGGA | 46497 & 46498 | TCHHL1 | GCAAGGTCAACCTCAGGAGAGA | TTGGAGAAGAACAGGCCAAACCA | 46603 & 46604 |
| TBR1 | CAGCGATTCCGACCGCCA | GACGCGCTGGGTGGGTCCA | 46499 & 46500 | TCHP | TGAGCGAGGTTCTGACAGGGA | CTCTTTCTGCGAGAGCCTTGGGA | 46605 & 46606 |
| TBRG1 | AAGATGACCCCCAGAATGCCA | CAGCTGGAAGCAGGTTAGGCA | 46501 & 46502 | TCIRG1 | GCTGACCTTGCCTGACGCA | CATGAGCACCTCGAGGGGA | 46607 & 46608 |
| TBRG4 | CCTGAACAGAGCGCAGGA | GCAACACAGAGCCCACA | 46503 & 46504 | TCL1A | CCTATGACCCCACCCAGA | ATGGTACACTAAGCGCCAGA | 46609 & 46610 |
| TBX1 | TGGCAAAGGCTTCCGGGA | AGCCACGGGTTCCCGGA | 46505 & 46506 | TCL1B | CCAGAGCCTCAGTGAGCCCA | TAAGCAGAAGACACAGGCCAAACCCA | 46611 & 46612 |
| TBX10 | TCACAGCAAGGCTGGGAGCA | CCCCAAAGCAAGAGGGCACA | 46507 & 46508 | TCN1 | TCCAAACGCTGACCCA | GTTATAGCGGCTCATCAGCGGAGA | 46613 & 46614 |
| TBX15 | GGGCAGGCACATGCAAGAGA | GTGCTCCATCCTGACGGCA | 46509 & 46510 | TCN2 | CAGACTGTCTGGCACCACGA | CGGCGGCAAGAGACTAAGCA | 46615 & 46616 |
| TBX18 | GCCATCACCCTCCAGCAA | CACTCGGTGAGGACCCCA | 46511 & 46512 | TCOF1 | CAGTGGAGGACAGCAGCGGACA | GAGAGCTGGGATGGCGCCA | 46617 & 46618 |
| TBX19 | GTCTCCGAGCACACCGA | TGCTGATGGTCCACAGGA | 46513 & 46514 | TCP1 | GTGGGGGTGCTGTAGAAGCA | CGCAAGCTGTTCCGAGA | 46619 & 46620 |
| TBX2 | TCCACATAGTGCGAGCCAA | GTACAAGCGTAGAGACGCCA | 46515 & 46516 | TCP10 | GAAATAGCACAGGCCATGGACA | TGGAGGGAGGCGGCGTGCA | 46621 & 46622 |
| TBX20 | CAACACCATTCCTCACCCCA | GAATGAAGGAATGTGGGCCA | 46517 & 46518 | TCP10L | GCAAGAATCGCACATTCTGGCA | TTGTCCCAGGAGAGAGTGCA | 46623 & 46624 |
| TBX21 | GGACTGAGATTGCCCCA | GAGGAGTGTCACCACTGGA | 46519 & 46520 | TCP10L2 | TCCCGGTGCAGAAAGACGGGA | AGCGTGGCGGCCTGGGAA | 46625 & 46626 |
| TBX22 | GGAAGCAGTAGTACCATGTGGCCA | GCAGGGTGAGTCGGTGAA | 46521 & 46522 | TCP11 | GGCAGCCAACAACCCAGA | CACCAGCAAGACTGAGGCCA | 46627 & 46628 |
| TBX3 | CCGACCCGAAATGCCAA | CTGGTATGCAGTCACAGCGA | 46523 & 46524 | TCP11L1 | CCGATGACCCCATTCGCAGGA | TATAGTTGACCAGGCGAGCA | 46629 & 46630 |
| TBX4 | CTCAGGTTCAGGCCCGAGA | GCGGTGAAGTGCGTGGGGA | 46525 & 46526 | TCP11L2 | GGCAACCGCTTCGCAACCAA | TGTCTCAGCCACCTCCACGA | 46631 & 46632 |
| TBX5 | CCCAGATGCTGGGGCCAGGGA | GCTGAAGGGTGCCAGGGGA | 46527 & 46528 | TCP11X2 | CACCAAGGCCCTAACTGAGGA | TGCTCAGATGTGAGGCCCA | 46633 & 46634 |
| TBX6 | CCAAATGGGGCCAAGACCA | GGGGATTGAGCCCTCCAGA | 46529 & 46530 | TCTA | GAGTGGGAGGCGCCAGGACA | CCAGAAGGGAAATGCGTGGA | 46635 & 46636 |
| TBXA2R | GATGGTCAGTCTGCGGGGA | TCCAGGTGGCCACGCGCA | 46531 & 46532 | TCTE1 | GCATCAACCTGTCCTGCAACCA | TCCTGGCCACATCTGACA | 46637 & 46638 |
| TBXAS1 | ACCAAGCCTGACTTGCCAAGAGA | TGAATCTGAAAGCTGTGGGGTA | 46533 & 46534 | TCTE3 | CCGAACCAGACCCTCAGCA | CAAAAGAGGCTCCACATACTGA | 46639 & 46640 |
| TC2N | CAGTTCATCCAGCACGGA | AACTACTGGGTACACTGGACAA | 46535 & 46536 | TCTEX1D1 | TGGAAGAACCCAGTCAGCGTGA | ATGATTGACGGTGACCACAGGA | 46641 & 46642 |
| TCAF1 | GGAGAGCTGGCCACGGACA | ACTGAGATTCTGCACGTCGGCA | 46537 & 46538 | TCTEX1D2 | CATGCTGTCTCAAGGAGGAA | TCAGATCCCAGAAACAGGA | 46643 & 46644 |
| TCAF2 | AGAGAGGAGAATCACAGGCCCA | CCCCAGCCTCAAAGAAGGGA | 46539 & 46540 | TCTN1 | CTGCTGAATCCACAGGCCAA | CAGGTGCACACATTCCACA | 46645 & 46646 |
| TCAIM | TAAGCCGTTAGCACAGAGGA | TTCCTAGCATCACATGCCCA | 46541 & 46542 | TCTN2 | CAGTTGCAATGAGAGGCA | CGGATGCTCAGGTGGCCA | 46647 & 46648 |
| TCAP | CCCATCCAGCTTCAGGA | GCACCGGGCTTGCTGACA | 46543 & 46544 | TCTN3 | TCAACAGGCACTGCGAGCA | TGCGGGTTGGACAGGAGA | 46649 & 46650 |
| TCEA1 | GAAAGTACTTCCAGCGCAA | CTCCTACACTTCAACCGCA | 46545 & 46546 | TDG | ATGGCTGCTTACAAAAGGGCA | TGGAACTTCACTGAGCCCTGA | 46651 & 46652 |
| TCEA2 | CCATCGTCGGACATGCGA | GTGTTATGGCCCACACAGCA | 46547 & 46548 | TDGF1 | CGGAACGAACTGTGAGCACGA | TCTGAGTCCTTGGAAGCCA | 46653 & 46654 |
| TCEA3 | TGACTGGCAGAGGAAATGGCCA | TGCTGCACTGGAAGAGGTCA | 46549 & 46550 | TDO2 | GACGGCTGTCATACAGAGCA | GAGGAACCACCGGTGCCA | 46655 & 46656 |
| TCEAL1 | GGCGCCTCCACCATGGAGCA | TCTAAATTGCCGGCGAGAACGA | 46551 & 46552 | TDP1 | TTGAGCCCTTATACCCACGAA | CACTCCTTGAGAAGGGGCA | 46657 & 46658 |
| TCEAL3 | AAAGGCATCTGAGCAGTGAGGA | CCCTACCTCACCCCTCA | 46553 & 46554 | TDP2 | GAAATGCAAGAGGCCTCAGA | CAAAACTCCAGACATCCACA | 46659 & 46660 |
| TCEAL4 | AGGAAAGGCGCCAGTGAGGA | GCATCCACAAAAACGCCCCA | 46555 & 46556 | TDRD1 | CAACTGCAAAGTGGCCGA | TCTTCAGAAGCGTAAGCCA | 46661 & 46662 |
| TCEAL5 | AAAACCGACAGGGGGACGGA | TCCTCTGAGCCTTGACACA | 46557 & 46558 | TDRD10 | CCACCCTGACTCAGCCA | TAGGATGTGCAACGCCGA | 46663 & 46664 |
| TCEAL6 | GAAAAGAGCAAACAGGAGGGA | TCCTCCTGAGCCTTGACACA | 46559 & 46560 | TDRD12 | CAACAGCCACAGCACAGGACAA | GCTGGCCAGTACACTGAGGA | 46665 & 46666 |
| TCEAL7 | AACGCAGCAAACACCCGTTAGGCA | ATGGGATAAGGACAGCTTCCGA | 46561 & 46562 | TDRD15 | ATGGCAGAGAAGAAGAGTCATGAA | GAAGCAATCTGTAGACGGTCATGAA | 46667 & 46668 |
| TCEAL8 | AGAGGACACACCCGTTAGGCA | AGGATAAGGACGGCTGTCGTGA | 46563 & 46564 | TDRD3 | TGGAACTGAAGGTGGACCA | CCACACCACCTCCTCCAA | 46669 & 46670 |
| TCEAL9 | CCCTGAGGCGTGGAAGGA | GCTGAAACAACAGCCCTGCAGA | 46565 & 46566 | TDRD5 | ATGCCTGGAGTGAGTGACCA | AAGGCTGAAGGCTGCCA | 46671 & 46672 |
| TCEANC | AGACTACTTCCAAAGCGGGA | GAATTGCAGCTGCAGATGCCCA | 46567 & 46568 | TDRD6 | TGTGCCATCCCACCGCA | CCCGGTATACCTGGGCCA | 46673 & 46674 |
| TCEANC2 | CGTACCGGCGGACGGTGAGA | GTACAAACGTGCCGACTGGCA | 46569 & 46570 | TDRD7 | GAGCTGACTTCTCCAACAGCA | AGGCCACAGGCACATACACA | 46675 & 46676 |

| GeneName | Forward Primer | Reverse Primer | SEQ ID NOs |
|---|---|---|---|
| TGFBR1 | TAGGACTGGCAGTAAGACA | CGAGAACTTCAGGGGCCA | 46889 & 46890 |
| TGFBR2 | AGCCCAGTGTGTGCAGGA | TAGGGAGCCGTCTTCAGGA | 46891 & 46892 |
| TGFBR3 | TCCTGCTGCAACTCCCCACA | TGGACCACAGAACCCTCAGACA | 46893 & 46894 |
| TGFBR3L | CCAGGACCAACAGGAGACCGGA | TGGGAGGGACAGGGGTGGAGGA | 46895 & 46896 |
| TGFBRAP1 | CAGTGGCAAGGGTGGCAGA | CCTGCAGCTCGTGACACCA | 46897 & 46898 |
| TGIF1 | CCAACCCTAGGGAGGGCCA | TTGTCCACACCGACCGA | 46899 & 46900 |
| TGIF2 | GCCGCTTCACTCAGGCCA | GGGGCTTGGGGAGACTCCA | 46901 & 46902 |
| TGIF2LX | TAGCCAGCCGAAGAAAAAGGTCAA | TGCATCGACTAGCAGCAGGAA | 46903 & 46904 |
| TGIF2LY | TAAGATCCTCCGGACTGGA | CAGGTGGGTGGCATGGGCA | 46905 & 46906 |
| TGM1 | TCCCGTCACCTACCAA | CCTGGTCGCACAGGCACA | 46907 & 46908 |
| TGM2 | GGCCGAGGAAGGAGGAGACA | ACAGAGCGAGGACGGGCA | 46909 & 46910 |
| TGM3 | AGGAACAGGAGCCCAGGA | CCAGGACATTGTGTGCAGA | 46911 & 46912 |
| TGM4 | TGAGGAGGAGGCAGGTCATGGA | TAACAGAGTTTCCAGCAGCA | 46913 & 46914 |
| TGM5 | CAACCTTCCAGGCCCAA | TGCAGGAGAGACTGGGCA | 46915 & 46916 |
| TGM6 | AGGGTCCCGGAAAGAAGAGGCA | CCAGAGACAGCCGACCCCA | 46917 & 46918 |
| TGM7 | ATTCAACTGGACCTCTACCCGA | GCCCCAGCCACAGTGACGA | 46919 & 46920 |
| TGOLN2 | GCAAGTGGGGTGCGGAGGA | CTGCTCCTCCGCACCCGA | 46921 & 46922 |
| TGS1 | GAAGTGCCAGGAACTCCGCCA | TGCCAGCTCAGGAACACGCA | 46923 & 46924 |
| TH | GTGCAGCCCTACCAAGACCA | CGCTGGATGCGTGAGGCA | 46925 & 46926 |
| THADA | GCATGGGTCGGAGTGGGGA | TGTCCGGTTAGGCTCGGGGAA | 46927 & 46928 |
| THAP10 | GGCACCTAAGAGGGGAGAGGA | GGCGTTGTAAGAGAGACTGGA | 46929 & 46930 |
| THAP11 | CTGGAGAAGACCTGAAGCCA | GTCGGAGCCAGTATGAGGGA | 46931 & 46932 |
| PRKRIR | CATAGCAGGGGAAGAGCACCTA | ACAATAGTCAGACGAAGCAGCTGA | 46933 & 46934 |
| THAP2 | GTAGAGACCTAAGGGCGCTGAA | TAGTGGCACAGCCCCGCCGCA | 46935 & 46936 |
| THAP3 | AGCCCAAGCAGACTCAGGA | TGTGGGGTGCTGAAAGGCGA | 46937 & 46938 |
| THAP4 | CGCCTCAAGCCCGACACCAA | GGGGCTCCTTGGCGAAGGA | 46939 & 46940 |
| THAP6 | TGTGATCGGCGAGCTAGAGGA | CTCTCTGCACAACAGTCCA | 46941 & 46942 |
| THAP7 | AACACAGTACCAGGGTGGGCA | AGCCTTGGTCAGTCTCAACGCGA | 46943 & 46944 |
| THAP8 | CAACAGCCCAGACCCTTGGA | GCATCCACTGTGGCAGGTGA | 46945 & 46946 |
| THAP9 | AGTGGGATCCTAGCAGTCACA | CAATAGTCAGACGAAGCAGCTGA | 46947 & 46948 |
| THBD | GCAGCGTTGTCCAACACA | GCTGGCACTGGTACTCGCA | 46949 & 46950 |
| THBS1 | ACTCGTCCCAAGTCCGA | TAACCTACAGGGAGTCCAGGA | 46951 & 46952 |
| THBS2 | CACTGTTGAGGACCTGGACGA | GGCAGGCAGTGGAAGCCA | 46953 & 46954 |
| THBS3 | GGGATGGGTACCAGGCGGCA | ATTGGGTACCAGGCGGCA | 46955 & 46956 |
| THBS4 | CTGCCCAGAGAACCACCA | CCTGGTTCAGGAACCACCCA | 46957 & 46958 |
| THEG | CCCAAATGGCAGTCCCA | GATCTCGGTCAGGAACGCA | 46959 & 46960 |
| THEGL | TGAGAACTTGCCCAGCCA | ATGCAGGAGGAGTGATCTCCA | 46961 & 46962 |
| THEM4 | GGCCCTTACCTGGAAGGACCA | CCCCAGCCATCATTGCA | 46963 & 46964 |
| THEM6 | GAGCCTTCAGGGGCTCA | GCAGCTCAGGGGGCTCCA | 46965 & 46966 |
| THEM5 | TGTTGGCTGCCACACCAGGA | CATATTCAAGCAGGCCACAGGA | 46967 & 46968 |
| THEMS2 | GCCTAGACTCTGAGCCTGGGA | CACTGTGGCTATGGGGAGAGA | 46969 & 46970 |
| THG1L | TGATCGGTATGGACAGGTGAGA | TCCGTCAAAGCCTGGGGCA | 46971 & 46972 |
| THNSL1 | CCCCAGAGGAGGTAGCTGACA | AGAGGCCACCATCAGAAGCCA | 46973 & 46974 |
| THNSL2 | CGTGGCAGTGAACCGCAA | CAGAGCCAGAGAGCAGCCA | 46975 & 46976 |
| THOC1 | AGACAAGGGAACACATGCCCA | GTCTCAGGAGCTCTCCAACCA | 46977 & 46978 |
| THOC2 | GAAAGGGAACAAAAACGCCGCA | CTCTTGGACAAGTTGGTGAGGA | 46979 & 46980 |
| THOC3 | TTGCACAGGAAGTGCAGA | CCGATGCTGACGGCAGA | 46981 & 46982 |
| THOC5 | CGAAAGGGGACAGCCAA | AACATTCAGCAGCACACACA | 46983 & 46984 |
| THOC6 | TCCGATCCTCCACCACCA | GTGAAGACATTCACCCGGCA | 46985 & 46986 |
| THOC7 | TATACGGAAGCCGTCTCTCTCA | TTCCTGGGACCCAGAGTTTGCA | 46987 & 46988 |
| THOP1 | GTCCCGGCAGGCCAACACA | CGTGTAGCCACCTGCCACA | 46989 & 46990 |
| THPO | AGGCTCCCTGCCACCA | GGTGGCGTTGGAGCAGA | 46991 & 46992 |
| THRA | CAGCTTGGTGAAGCGGGA | ACCGCTCGGGACATGGAGA | 46993 & 46994 |

| GeneName | Forward Primer | Reverse Primer | SEQ ID NOs |
|---|---|---|---|
| THRAP3 | TGAGCAGGAGGCAGCCAA | CAAGGCGGAGATCAACAGGA | 46995 & 46996 |
| THRB | GGGTGGGTGTCAGACGCCA | CAGGCAAGCCCCGGGCGA | 46997 & 46998 |
| THRSP | GAACCCCAGAGACAGAGGAA | ATGGAGGCTGGAGAAGTGCA | 46999 & 47000 |
| THSD1 | CCTCAGAGTCGAGGTGCCCA | TTCCTCAAGGGGTGCCCA | 47001 & 47002 |
| THSD4 | GGAACAACCGGCCGGCAGA | CCGCTCCACACTCGATGGA | 47003 & 47004 |
| THSD7A | CAGGATCTGTGCCCAGAGCA | GACACACATTGTTCGGGAAGA | 47005 & 47006 |
| THSD7B | TGCAGCTGGACGTGTCGAGGA | TAAATGGCAGTCTCCTGGGCAA | 47007 & 47008 |
| THTPA | GGTCACTTCCGAGACACCTA | CTAAGACACTTGCTGCTCA | 47009 & 47010 |
| THUMPD1 | GAAGCGCAAAGGCAAGGCTCA | CTGTAGGCCTCCTCCACGCA | 47011 & 47012 |
| THUMPD2 | ATAGCGTGGCAAGCA | GTGAGTGCTGACATCAGCA | 47013 & 47014 |
| THUMPD3 | ACTGAAGAGAGTCTTCCACGA | GTATTGCCCCAGTTCCACACA | 47015 & 47016 |
| THY1 | GACCCGTGAGACAAAGAAGCA | TGAAGGCGGGATAAGTAGAGGA | 47017 & 47018 |
| THYN1 | GAGGACAACCTAAGTTGGTCCA | CTCTGGCGAGTGAAGAGAACCA | 47019 & 47020 |
| TIA1 | GATAAATCCGTGCAACAGCAGA | ATGCAGGAACTTGCCAACCA | 47021 & 47022 |
| TIAF1 | GGTGAGGAGAGCGTGGCTCA | GGAGGTGCGATGGTCCACA | 47023 & 47024 |
| TIAL1 | ATGGCAAATGGGTGGCAA | CCTTGGGGAGGCTGAGCA | 47025 & 47026 |
| TIAM1 | CCAGAACCCGAAGCAGCACA | CTCCGCATGGTCAGGGCGA | 47027 & 47028 |
| TIAM2 | GAAAGAGAGACTGCAGCCAA | TGTCAAGGACGTCTGGTAAGGA | 47029 & 47030 |
| TICAM1 | CTGCAGGACGCATAGACCA | GTGCAGCTCAGGGCACA | 47031 & 47032 |
| TICAM2 | GATGAAGCCTCAGAGTCA | CATGCAGACCCATTTACAGCA | 47033 & 47034 |
| TCRR | TAAAGACTTGCCCAGGAGAA | CTGGTGGGAGCTGGCACA | 47035 & 47036 |
| TIE1 | GGCCCTTCAGACTCGAGA | GCCACTGCACCTCCA | 47037 & 47038 |
| TIFA | TGATGGAGAAGGAAGATGGCGA | AACTGCTTTGGGAGGAGGAGGA | 47039 & 47040 |
| TIFA8 | GTCCCCTGAGCACCTCA | TAAATCAGGGGGTGAAGGGCCTGA | 47041 & 47042 |
| TIGAR | TTCAGACAGCCGGTATTCAGGA | CTCAGAGTGGCTGGTAAGGA | 47043 & 47044 |
| TIGD1 | CAAAGCCCGGATGAAGAGCACA | CCTTGATCCATGGGCTGCAGA | 47045 & 47046 |
| TIGD2 | ATCGTCAGGCTGGCTAACTCGA | TCTGCTTGACCTACCACCCAGA | 47047 & 47048 |
| TIGD3 | TGCCATCCAAAGCGAGGAGGA | TCCAGGTGCCACAAAGCGAGA | 47049 & 47050 |
| TIGD4 | GGAGGGCTTGTAACCCCAGAGA | CAAATCATCATCCAGGGCAGCA | 47051 & 47052 |
| TIGD5 | GCGAGGACAGTGCTGGGCA | ATCATCGTCCAGGTGCAGCCA | 47053 & 47054 |
| TIGD6 | GCCAGGATGAAGAGGGGGGAA | CAGCAGTACAGTTGGAGGGGCA | 47055 & 47056 |
| TIGD7 | GAAAGAGGACAACCGGGAGCCAA | TGCCCAAAACCGTGA | 47057 & 47058 |
| TIGIT | AGGAGGAATGAGGCCCA | GTCATGCAGCTCGGCACA | 47059 & 47060 |
| TIMD4 | CAACCGGAACCACCACTCCAGA | CCTTCCTTAGAAGGCTCGGGA | 47061 & 47062 |
| TIMELESS | CTGCCTGAGGAACACCA | TGGAACGGCCTGGGAGGCA | 47063 & 47064 |
| TIMM10 | CAGTGCCTGCCACCGGAA | CTTAGAGACAACATCGGTCCA | 47065 & 47066 |
| TIMM10B | ATCCATTCCAACCACCGCCTCA | TGCCTGATGGGAGAGACCCCA | 47067 & 47068 |
| TIMM13 | CGTGGCCAACCGCAGGA | TTGTCCAGGGAGCCCCA | 47069 & 47070 |
| TIMM17A | AACAGGGCTCCACAGTTAGGA | GCTCCGTTAAGGCACA | 47071 & 47072 |
| TIMM17B | GGGCAAGGAGGATCCCTGGAA | CTGTGTAGGGAGTGAGGAGGA | 47073 & 47074 |
| TIMM21 | CGTGCTTGAAGACTGAGGCCA | CTCGGTCCCTGCGTCAGA | 47075 & 47076 |
| TIMM22 | CAGCCAAGAGTGAGAGCAGA | ATGCAGGGGTAAACACCCA | 47077 & 47078 |
| TIMM23 | GATACCTCGTGCAGGATACAGA | ACCAAACGCAGCCCTGTCA | 47079 & 47080 |
| TIMM23B | GGAAGCGGCGACAAAACCACA | GGCCAGCTCAAATTGCCCCA | 47081 & 47082 |
| TIMM44 | GTCAGGAACCCCAAAGGCGCA | GAGATGTCAAGGCGCCA | 47083 & 47084 |
| TIMM50 | GAGCACTATGCCCTGGAGGA | CAAGCGCTGGTGAGGGA | 47085 & 47086 |
| TIMM8A | GTGGACCGCAGTTGCAGCA | ACAAAACAGGCCTCAGCCGA | 47087 & 47088 |
| TIMM8B | CGAAGCAGAGAGGGCGCA | AAGGGCTTCACACAGTGGA | 47089 & 47090 |
| TIMM9 | CTGGCAGCCAAAGCAGGA | GTGGCTACTGCTTTCAGGGGGA | 47091 & 47092 |
| TIMMDC1 | TACCCGGAATCTGGATGGGA | TCCCCATACACCCAGCCA | 47093 & 47094 |
| TIMP1 | CCGGGCTTCACCAAGACCTA | TGGCTCCGAGGCAGGCA | 47095 & 47096 |
| TIMP2 | GGGACGGCAAGATGCACA | GCACGGGATCATGGGGCA | 47097 & 47098 |
| TIMP3 | GAGAGGTGGGACCCAGGCTCA | TGGAGAGCATGTCGGTCCA | 47099 & 47100 |

| GeneName | Forward Primer | Reverse Primer | SEQ ID NOs | GeneName | Forward Primer | Reverse Primer | SEQ ID NOs |
|---|---|---|---|---|---|---|---|
| TMEM88 | GGCACTGCTACCCACCCA | GGCAGGAAGCCCACCA | 47737 & 47738 | TNFAIP3 | ATCGAGCCAGCGCAGAGA | GATGCTGACACTCCATGCAGA | 47843 & 47844 |
| TMEM9 | GCGAGTGCAGGTACGAAGGA | CGGATCAGAAGGGTCCACCA | 47739 & 47740 | TNFAIP6 | TGAAGGCGGCCATCTCGCAA | TAGCCATCCATCCAGCAGGA | 47845 & 47846 |
| TMEM91 | AGAATGTGAGACCCCTGCCCA | CGGAGGGAAGAGGCGGTGA | 47741 & 47742 | TNFAIP8 | AAGACAGTCATCAAGCTGCCA | GGCAGTGAGGTGGCGCCTGA | 47847 & 47848 |
| TMEM92 | AGCTGCTGCCAGGAGACAGA | TCTGCCAGTTGCGACAGAAGCA | 47743 & 47744 | TNFAIP8L1 | ACCCCACGCTTCCAAGGCAA | GACAGCCCAACAGGGACACA | 47849 & 47850 |
| TMEM94 | CCGCTACCAGAGAGCACGA | CCACGGGTGCAGGGAGCAA | 47745 & 47746 | TNFAIP8L2 | GGAACACTACCTCACGCCCAA | ATCTTGCCAAGTGCTGAGTGA | 47851 & 47852 |
| TMEM95 | GACTGATGGGGAATCGCGGGA | GAGGGAGGGCATGCCCGGA | 47747 & 47748 | TNFAIP8L3 | CACTGCACGCCCAGGACCCA | GAGGGTGGAGGAGAACTCCA | 47853 & 47854 |
| TMEM97 | CTGCTACAGGGAGCCCCA | TGAGGAAGGCATACGTTGCA | 47749 & 47750 | TNFRSF10A | GAGCTGGTACAGCAGGCCCA | TCTTCCATCCTCTCCAAGGCA | 47855 & 47856 |
| TMEM98 | ATGTCGTTATCACCAACCCCA | GCTGATCCGCTTGGCCACCA | 47751 & 47752 | TNFRSF10C | CACAGCTTCAAGGGGAGGGA | TGCACGGGTTACAGGCTCCA | 47857 & 47858 |
| TMEM99 | GAGTCCACCTCAGCTCAGCAA | TAAGGTAAGCCTATCACCGCCA | 47753 & 47754 | TNFRSF10D | CCCGAACGTGTGCACAGA | AGACCTTGGGTGGGCTTGCA | 47859 & 47860 |
| TMEM9B | CGGGGGCCTGATGTAGAAGCA | GACTGCCGGGAGCGGGGTA | 47755 & 47756 | TNFRSF11A | CTGCACAGGCTGCCGGAA | AGCTCCCATCAGCCCCA | 47861 & 47862 |
| TMF1 | CAAAGGATAGTGCAAGCCAAGGA | TGTACGCTGCAATGCAAGCCTA | 47757 & 47758 | TNFRSF11B | AGAAAGTGGGAGCAGAAGACA | ACAAACTGAGCAGCTTCAGGA | 47863 & 47864 |
| TMIE | CTGTGGCACGTGGTGGGCA | AGCTCATTGAGGGGGTGGGCACA | 47759 & 47760 | TNFRSF12A | ACGATGCGCCAGGAGAGAGA | ATCAGCGCCAGCTGGGCA | 47865 & 47866 |
| TMIGD1 | CGAAGGAGGGGAGAGTGGA | GTAACATTCAGCACCACGA | 47761 & 47762 | TNFRSF13B | ACGCGATGGAAGCCGGCA | GTGGGCAAGGCTGCAGGA | 47867 & 47868 |
| TMIGD2 | CAGGGACGGCTCTCCTGGCA | CAGCCTCCTCAACTCAGGAA | 47763 & 47764 | TNFRSF13C | AGCCCTGGACAAGGTCA | CCAGGAGGAGGGCCAGGCA | 47869 & 47870 |
| TMIGD3 | TTGCCAGGGATGATCATGGA | GGACGTCTGGAGCGGTCA | 47765 & 47766 | TNFRSF14 | TGCAAGGAGGACGAGTACCCA | AGGCCATTGAGGTGGGCA | 47871 & 47872 |
| TMLHE | CCTCCCACTCAAGAGCACACA | GTGTCAGTGTGCCCATCCAGA | 47767 & 47768 | TNFRSF17 | CTGCATCAAGAGCAAACCGA | GCACTCAAAGCAGCTGGCA | 47873 & 47874 |
| TMOD1 | CCATCCCCACCCTGAAGGCA | CTCAGCCAAGGGCATACGCCA | 47769 & 47770 | TNFRSF1B | CAGGAGGAGAGAGAGACACA | GCACTGCACCCACGGACA | 47875 & 47876 |
| TMOD2 | GACCGCGAGCACCTCTCA | TGTACTCCAAGGACACAGCTGCA | 47771 & 47772 | TNFRSF19 | AGGCAAGAAAACGCAGGGCA | ATGTTGTCACCACCCATGGA | 47877 & 47878 |
| TMOD3 | CTTGCAGCCACCCGGAGCAA | CCAGAATCCCAACTCCCGTGA | 47773 & 47774 | TNFRSF1A | AAGAGGGGGAGCTTGAAGGA | TGAAGGTGGAACTGGGCA | 47879 & 47880 |
| TMOD4 | ACAAGGAGCTGGAGGAAGGTGA | CCAGGTCAAGCTCCGACA | 47775 & 47776 | TNFRSF1B | CCATGGGACCCAAGGTCAA | TCTCCTTGGAGAAGGGGA | 47881 & 47882 |
| TMPO | CCTCGGTCTGACAAAAGACA | GCCGGTTGAAGCCCGTGA | 47777 & 47778 | TNFRSF21 | AGAAGTTCCAGACCCGTGA | TCCGGATACTGCACCACA | 47883 & 47884 |
| TMPPE | GGAGTGAGGATGAGGACTGGA | GCATGTGTGCCCAGAAAGGA | 47779 & 47780 | TNFRSF25 | CCTTGGACAGCGCCCCA | ATGTCACCTGCCAGGAGA | 47885 & 47886 |
| TMPRSS11A | GTAGTCAGATGCTGACTCCAGAGGA | GTAGAGGGGAACTGGAACACCA | 47781 & 47782 | TNFRSF4 | GCCCAGAACCTCACAGGGA | GGAGCAGGTACAGGGCCA | 47887 & 47888 |
| TMPRSS11B | TGTGGGAGACAAGTAGCCA | CTGCTGATCAGAGAGGCTCCA | 47783 & 47784 | TNFRSF6B | CGCTGCGGTGGCCAGGA | CCAGGATCAGTGCACAGGGA | 47889 & 47890 |
| TMPRSS11D | CTGCACACAAGTTCCAGA | CACCCTGACATGGTCCA | 47785 & 47786 | TNFRSF8 | CTGCATCACCCACAAGGCCA | CTCCCATCATGGGCCCAGA | 47891 & 47892 |
| TMPRSS11E | CCTGCAGTTGGGATGGGAGTCA | AAAGGAAGCAGTCCATCTGGCA | 47787 & 47788 | TNFRSF9 | TGGGACGAAGGAGAGGGA | GCAGTCGACGTCAGCGCA | 47893 & 47894 |
| TMPRSS11F | CACCACCCGAGTGAAACGA | CCAGTAGAGAGTCAGTGAACCAAGCAA | 47789 & 47790 | TNFSF10 | GACCCAGCTGGGACAGA | CGTAAGTTACAGCCACACAGAGA | 47895 & 47896 |
| TMPRSS12 | CGCCCTGCAACCACAGGGA | CCGAGACCCTTGCAAACA | 47791 & 47792 | TNFSF11 | ACATCAGGACGAGAAAGCGA | ATCATGGTACCAAGAGGCAGA | 47897 & 47898 |
| TMPRSS13 | TGCACTTCGGCACCACCACA | CGTACACCTTCCAGCCCTCCA | 47793 & 47794 | TNFSF12 | TCTCAGCCACTGCGGGCA | AAGAGTCCGAAGTAGGTGAGGA | 47899 & 47900 |
| TMPRSS15 | AGGGGATTCAGGAGGACCA | GGTAAACCTTGAGACCCTGGCA | 47795 & 47796 | TNFSF13 | CAGAGGTGATGTGGCAACCA | CTTCTCGAGACACCACCTGA | 47901 & 47902 |
| TMPRSS2 | GAACTCAAGCGCCAGAGCA | GATGATGGAGCCTCCGCACA | 47797 & 47798 | TNFSF13B | GTCCGATCCTCCAAAGCACGGA | CTGGCCAGGTCCCTTGCA | 47903 & 47904 |
| TMPRSS3 | CAAGATCTGCAACCACAGGGA | TGGCAGCTTGTCACGCCA | 47799 & 47800 | TNFSF14 | ACCCCGCTACCCGAGGA | ACCGGTACCATCACGGA | 47905 & 47906 |
| TMPRSS4 | CTCAGGCACAGTCAGGCCA | GACCTGGACTGACGCCTGA | 47801 & 47802 | TNFSF15 | CTGGCCTTCACCAAGAACCGA | CTCAGAGGTTCATCCCACGGA | 47907 & 47908 |
| TMPRSS5 | GGGAGTGCAGGACCCTCCA | TCCAGTGTACCCACCCCA | 47803 & 47804 | TNFSF18 | GGCAAGTGGCTCCCAATGCA | TCTATGGTGTCCCAACATGCA | 47909 & 47910 |
| TMPRSS6 | ACTGCTTCCAGGAGGCACCA | AGGCGGCTCATCTTGAAGGA | 47805 & 47806 | TNFSF4 | GAATGTGGAAATGCAGCCA | CCTGAAGAGCAGAAGTGCA | 47911 & 47912 |
| TMPRSS7 | AGGGCTGTCAGATCCCACACA | TACCCACGACTTCTCCCCA | 47807 & 47808 | TNFSF8 | CGTTCAGAGGACGGACTCCA | CCACTTGGAGGTAGGCCCA | 47913 & 47914 |
| TMPRSS9 | CCTGAGGGAGCCCTCTGA | CTGGGAAGTGGGGCCGGCCA | 47809 & 47810 | TNFSF9 | GCAGCCACCTGGACAGA | GGAGGTCAGCAGCAGGGA | 47915 & 47916 |
| TMSB10 | GCAAGAGCCACCCACGGA | CGGGCAAACCGGAGAA | 47811 & 47812 | TNIK | AGATAATGGCCTGGGCGCGAGA | CTTCCCAGATGCGACGGA | 47917 & 47918 |
| TMSB15A | GGCTAAGAAGTCAGAGGTAGCCA | GAAGCAATGAAGGACACCA | 47813 & 47814 | TNIP1 | CCGGTCCATGAAGCAGGA | TGGACTTGGCGACAGGAGGA | 47919 & 47920 |
| TMTC1 | CCCAGTCATCACGTGGCCA | CTGAGCCAGTGCCAAGCGGA | 47815 & 47816 | TNIP2 | GCCGAGTCTGATGAGGAA | GCATCTGCACCCGCTCCA | 47921 & 47922 |
| TMTC2 | ACAGCTCCTTCACCGA | TTTGACCAAGGAGGCAAGCA | 47817 & 47818 | TNIP3 | GACAACAGGCAACGAAGGGA | GGAAAACATGACAGGCACA | 47923 & 47924 |
| TMTC3 | AACAGAGGTTGTTGGAAGAGGA | GGCAAAGTATACCCCTGGAGGCA | 47819 & 47820 | TNK1 | AACCCCACACAATCACCCA | GCAGAAACCACATCTCCCCA | 47925 & 47926 |
| TMTC4 | GGATTCGGAGCCCTGAGCAA | TAGCATTGAGGGGACACACA | 47821 & 47822 | TNK2 | TGGGAAGACCATGCCCACCA | ACGATGGGCAGGATGCAGGGA | 47927 & 47928 |
| TMUB1 | ACACCAGACTCTGGGCA | CTGGATCTGCCAGTACCACA | 47823 & 47824 | TNKS | AGGAGCCTCCAATGCAGGGGA | TCCGAAGGTGTTCAAGGCCA | 47929 & 47930 |
| TMUB2 | CCCCCTGAGATCTGAGGA | TTCAGGCCACCCACGGTA | 47825 & 47826 | TNKS1BP1 | CGAGATCTCCGACAGTGCCA | TGCTGCCTCGACAGGCCA | 47931 & 47932 |
| TMX1 | GGCCTATCGGGTCCAAGGA | ATATGATTCCCCACTACTGGCA | 47827 & 47828 | TNKS2 | GCTGCAAGCTGCACGAGA | ATGGAGATGCAGCAGCA | 47933 & 47934 |
| TMX2 | GTGTATTCGGGTGGTGGGA | CTTCGCGTTGGGTGGGGA | 47829 & 47830 | TNMD | TCAGCGCAGACGAAGCAAGTGA | GTTCAGAGCGCGGCGGCA | 47935 & 47936 |
| TMX3 | CTGCGGCTCTGCGCCACA | TGGCCACCATGGCGGA | 47831 & 47832 | TNN | CATGCCACCACGACGAGA | TGAGCACTCCCACAAAACCCA | 47937 & 47938 |
| TMX4 | TTGCAGGATGCGGAGGAGGA | CTCTCCTCATCCACCAGCA | 47833 & 47834 | TNNC1 | AGGTGGACGAAGACAGGA | AACATGCGGAAGAGGTCAGA | 47939 & 47940 |
| TNC | AGGGGTACAGTGGGAACAGGA | GCCCTTCCAGTGGAACCA | 47835 & 47836 | TNNC2 | GCACATGCGACTTCCGAGGA | TCCTGTCCAAGCATGCGGAA | 47941 & 47942 |
| TNF | CAATGGCGTGGAGCTGAGA | GTGAGGAGCACATGGGTGGA | 47837 & 47838 | TNNI1 | CATGGATCTGCGGGCCAA | GTCGAGACTTGAGCATGGCA | 47943 & 47944 |
| TNFAIP1 | GCCAGGCTTCCCCAGTGA | ATGGGTAGAACTGGTGGCCGA | 47839 & 47840 | TNNI2 | GGGTGCAGAAGACACCAA | AGGGCCTTGAGCATGGCA | 47945 & 47946 |
| TNFAIP2 | GCAGCCAACCAGGCAACCA | CCACCCACGAGGAGGACAG | 47841 & 47842 | TNNI3 | GAGACTGGCGCCAAGAACATCGA | GCAGGGCAGTAGGCAGGAA | 47947 & 47948 |

| GeneName | Forward Primer | Reverse Primer | SEQ ID NOs | GeneName | Forward Primer | Reverse Primer | SEQ ID NOs |
| --- | --- | --- | --- | --- | --- | --- | --- |
| UGT2A2 | TGTAAAGCCCCTGGATGAGCA | GTTGTCACACAGACCAGCAAGA | 49221 & 49222 | UPF2 | TGTAGCCAACCTCTTAGCAGGA | GCTCAGGTGGGTCCAGGGA | 49327 & 49328 |
| UGT2A3 | TGGCCCTGTGACATGAGCA | TGTGGCATATGAGGACCACCTCA | 49223 & 49224 | UPF3A | AGGCCATGGAGAGACTGGGAA | CTCGGAAGCGAGCTCCTGGA | 49329 & 49330 |
| UGT2B10 | GACTCCACTGCAAACCTGCCAA | TACTGACCATTGACCCCAGA | 49225 & 49226 | UPF3B | GAGAGGCTGAAGCGCGGCA | AGCTGCATCGCTGACGA | 49331 & 49332 |
| UGT2B11 | GTAAAGCCCCTTGGATGGAGCA | GGTCATGGGCTGCAACTCGA | 49227 & 49228 | UPK1A | AGGTGTGCCCTGAAACCCA | GCCATGAAGGAGGAGGTCAGAGA | 49333 & 49334 |
| UGT2B15 | ATGAAGCCCCTTGGATGGAGCA | CACAGTTGCCAGGCAGGGCA | 49229 & 49230 | UPK1B | ACAGGCTCATGCTCCAGGACA | TCCAAACCAGGGCAACCCCCCA | 49335 & 49336 |
| UGT2B17 | CCTTGCCCAGATCCCACA | ACAAGGGAATGCCCACA | 49231 & 49232 | UPK2 | AGTTCAGCAGAGAGATCCCAA | CCAGGGCAATGATGAAGCCA | 49337 & 49338 |
| UGT2B28 | AGTAAAGCCCCTGCATGGAGCA | CACAGGCCAGCAGAAACCCA | 49233 & 49234 | UPP1 | AACAAGAAGCTGGGTGCAGGA | GTAGGAGCAGAGAGCCCCA | 49339 & 49340 |
| UGT2B4 | AAGCCCCTTGATCGAGCA | CGTGGGCTGCAACCCGAA | 49235 & 49236 | UPP2 | ATCTGTGCTGGGACACGACAGA | TGACATCGACACCGTGTCA | 49341 & 49342 |
| UGT2B7 | CAATGGGGAAAGCTGACGTA | TACTGACCATTGACCCCAGA | 49237 & 49238 | UPRT | GAGCAGCTGTGCGACCTGGCCGA | AGAGTCCAGCTCGGCCGGCA | 49343 & 49344 |
| UGT3A1 | GACTGGGGGAGTCGACGA | ACCCAGCAGCTTCCCACA | 49239 & 49240 | UQCC1 | GCCGCTGCCCTCTGGAGA | TCCGAGAATGGGGCTTCAGGA | 49345 & 49346 |
| UGT3A2 | CAGCAGCCCTCAGTGCATGAGCA | ACGCAGCCACCAGACAGCCA | 49241 & 49242 | UQCC2 | AGGAATGCCAGTGCACGAGA | CACAGGCTCAGGCTCTGCA | 49347 & 49348 |
| UGT8 | ACCAGAGTACAGGCAAAAGGCA | TCGATTGACAGGGTGACCA | 49243 & 49244 | UQCC3 | GACCCAAGGAGCAGGGAGGA | CGCCTTCGCCGCCAACCA | 49349 & 49350 |
| UHMK1 | GCGCGTGTGGCAGGTACAGA | CGGAAACCTACTCGGCGGCA | 49245 & 49246 | UQCR10 | CGCGAGTTGACTTCGAA | CCCTCGTTGATGTGCGTGTA | 49351 & 49352 |
| UHRF1 | CTCACGGCCCAGCAGAGCA | AGCTGAACACTTGTGCCGA | 49247 & 49248 | UQCR11 | GTCCCGACGGCCTACACA | ATGTAAGGTACCCAGTCAGGA | 49353 & 49354 |
| UHRF1BP1 | CCAGCTGCATTGAAGCGCCCA | ATCTCTGCCCAAACTGAAGGCA | 49249 & 49250 | UQCR8 | TGCCTAAAGAGCAGTGGACCA | CATAACAGCTGCATCCACAGA | 49355 & 49356 |
| UHRF1BP1L | ATTACTGGAGGGGCAATGCAA | GTGTGTGCTGGGAGAGGGA | 49251 & 49252 | UQCRC1 | CCCTGCTGCTGAATGGGAA | AGCTGCTCAATGGGGCCA | 49357 & 49358 |
| UHRF2 | GCGGATGAAGTGCACGGA | GATCAGCTGAAGATGCACA | 49253 & 49254 | UQCRC2 | ATACTATCTCCCAGGCCACA | AACCAGCAACTAGAGCCTGGGA | 49359 & 49360 |
| UIMC1 | CAGTGGACAGCCTGCCAGA | TGCTGCCACTTCCCTCCACA | 49255 & 49256 | UQCRFS1 | GAAATTGAGCAGGACAGTGCA | TGCAATGCGACACAGCCA | 49361 & 49362 |
| ULBP1 | CTTGTGAGCATGAAGCCCA | GTCATCTTCTTGGCTCCAGGA | 49257 & 49258 | UQCRH | GAGAGCAATGCGAGCAGTTGGA | GTCAAAGAGCTCTCCGTGCA | 49363 & 49364 |
| ULBP2 | CAGCTGGAGAATTACACCCA | AAAGAGGAGAAGATCTGCCCA | 49259 & 49260 | UQCRHL | AGAGAATGCCAGGCCACA | GTCAAAGAGCTCTCCGTGCA | 49365 & 49366 |
| ULBP3 | CTGAGAGAGGTGGGGCAGA | CGAAGCTGAACTGCCAAGA | 49261 & 49262 | UQCRQ | CGCGGATGCGGCATGTGA | AACTGCGGCACCACGGCA | 49367 & 49368 |
| ULK1 | GTCGGCTGCCCTGGACTGAGA | GTCGGCCTTGGTCCGAGAGCA | 49263 & 49264 | URB1 | AGGAGCCTGTGGGACTCAGCA | AGGAGGTTCAGCCACGACCACA | 49369 & 49370 |
| ULK2 | ATGGAGCGGGAACACAGACA | CCACACGACACTCTCCTGGA | 49265 & 49266 | URB2 | CACGCTCTTGGAAGCCGA | AAACACCCTGGTTAGAGGGCA | 49371 & 49372 |
| ULK3 | CGTGTCCCGGCTGAGGA | GCTGAAGCCACTTCCAGGGCA | 49267 & 49268 | URGCP | AAGTCCACTCTCAACACA | ATCTGTCCCCAGCTGACGTCA | 49373 & 49374 |
| ULK4 | GCTGCACGAATCCTGGGTGA | ACGAGGTGAAGCACTACAGGCA | 49269 & 49270 | URI1 | AAATGAGCAGGATGCTGCAGGTGA | TCTTCAAGTGAGCCAGA | 49375 & 49376 |
| UMAD1 | TCATTAATGGCCGAGCTCCTGA | ATAGGAGAGTAAGTGGTCGGGA | 49271 & 49272 | URM1 | AACGATGCCGACTGGGAGCTA | GTGCCTGAGGAGAGGCCA | 49377 & 49378 |
| UMOD | CCAAGGACGATGCCCACA | CCGAACATCTGGACGGA | 49273 & 49274 | UROC1 | CCGGTGGTCTCAGCCGAGA | CCAGAAGTTCTGCCAGCCA | 49379 & 49380 |
| UMODL1 | AGGAACACGCTGAGGAACGA | GATGATGGTGTAAACCCCCA | 49275 & 49276 | UROD | CCGTGATGTGGCCAAGCA | GCCCAACCACCTCATAGCCA | 49381 & 49382 |
| UMPS | GATGCTGAGACAGTTGGGAGA | GCTCTGACGTGCACCGA | 49277 & 49278 | UROS | CAGAGCAGTTGGAAGCACGCAGA | ATAGAAGAGGCAGTGCTGGAGGA | 49383 & 49384 |
| UNC119 | GGCACTACTTCCGCAACCA | CTGATCAGCTCCTCGGAGAGA | 49279 & 49280 | USB1 | GCCAAGGAGGAGTTCTTCTGGA | GAGGATCCAGTGGTGGCGCA | 49385 & 49386 |
| UNC119B | GTGGACATCAGCGCAGGA | ACTCCACGTAGCCCGA | 49281 & 49282 | USE1 | AGAACCTGGAGAAAACTGAAGAGCGA | ATAATGAGCATGGCCCAGAGCA | 49387 & 49388 |
| UNC13A | TCCAGCAGACCTCAGGCA | CCACGATCTGAGGGTCGGGA | 49283 & 49284 | USF1 | AGAACTGCAGGGAGCTTGACCA | CTCTAATCCGGTGTGCCGCCA | 49389 & 49390 |
| UNC13B | ATCCCTGAAGCTCGAGGAGA | ACTGCTGGCACACAGGA | 49285 & 49286 | USF2 | TACCAGTTCCGACACAGAGACAA | ACACGACGCTGACGGCCGCCA | 49391 & 49392 |
| UNC13C | AATCATGGTGAGGGAAGGAGCTAGA | GACGCTGAGCTCATCCAGGA | 49287 & 49288 | USF3 | AGTLCATGCCACCAAGGGCCA | CAGAGGGCCTTGATCGCCA | 49393 & 49394 |
| UNC13D | TCACCGTGCTGAGGCACCTCACGA | GGGTCTGAGGCACCTCACCA | 49289 & 49290 | USH1C | GAGATCATGGCAATACAAGGCA | GGCAACCACAAGGTCGATCCA | 49395 & 49396 |
| UNC45A | ATGAGATGATCCCGGGGCA | TGGGCCGCATGGAGGGTAAGCA | 49291 & 49292 | USH1G | GGCCACCCCCAAGTGCCGA | GGTACAGTGGTGGGAGCACA | 49397 & 49398 |
| UNC45B | GTGCTCAAGGTGGTGGCAA | ACCTCATACACCCGCTCCCCA | 49293 & 49294 | USH2A | TTCAGTGTGACACCTGCAGAGA | GTTGCAAGGCAGAGAGGA | 49399 & 49400 |
| UNC50 | CCTTAGTGCGAGCAACGGA | TGAACAGGTAGAGCATCTGCCA | 49295 & 49296 | USHBP1 | GCAGGAAGAGAAGGGCCGAA | CAAGCTGGGAGGCGGGA | 49401 & 49402 |
| UNC5A | CCACAACTGCGCTATCCA | GCAAGTACTGCTGCGTGCCA | 49297 & 49298 | USMG5 | CCAGAAAGTGATGCGCAA | AGTTCTCCAGGCATGGGA | 49403 & 49404 |
| UNC5B | TCCCACTGTCCATCGCTGCAGA | AGCTTCCCAGAGGTCAGGGCA | 49299 & 49300 | USO1 | AGCACAGAGGCGAGAGA | ATACCACTTCCAAGCGGTA | 49405 & 49406 |
| UNC5C | CAGCTGTGAACATCAAGGCA | CTGAGACGTCATGCAGGGCA | 49301 & 49302 | USP1 | GAAACAAGGAATCCAGTGACCA | AAAGCAACCACTTCCCCTCA | 49407 & 49408 |
| UNC5CL | CTGACAACGAGGAGGGGCA | CAGAAGGACAGGGGCCA | 49303 & 49304 | USP10 | CCTTCCTGTCAGCCAGCCAA | TACAAGGATCCTCTGAAACCGGA | 49409 & 49410 |
| UNC5D | CAGGAATCGTGAAGGAGCTGAGA | GAGGAAACAATGACAATGGGCCACA | 49305 & 49306 | USP11 | CAACAAGGACAGGGGCCA | CTCAGAGTCTGGGTGGGGA | 49411 & 49412 |
| UNC79 | GAGATCCTGAGCGCCGAGGA | TTGACACTGAGCGCCGAGGA | 49307 & 49308 | USP12 | ACAGGAAGCACACAACAACGGA | ATTGGGACCACTTCCACAGTGA | 49413 & 49414 |
| UNC80 | CCAGGGTTCTCAGGGTGA | TGGCCAGACGAAGGTGA | 49309 & 49310 | USP13 | CCAGACATCAGCCCCCCA | CAGGCATGGTCAGGGCTCA | 49415 & 49416 |
| UNC93A | AGGTCTCGAGTACAGGGCA | CGAAGGCAATGACGAAGCCCA | 49311 & 49312 | USP14 | GCCGAGAAAGGTGAACAAGGA | GCTGCCGATGCAGATGAGGA | 49417 & 49418 |
| UNC93B1 | GGAGGAGATCGATCTGCGCA | CACCTCGAAGCCGCTGTAGA | 49313 & 49314 | USP15 | GAAAGGGGACACCTGGTACCTA | TAAGTGACTGGGCATCACCA | 49419 & 49420 |
| UNCX | ACCAACTTCACCGGTGCCA | CTCGACCAAGGTGTAGGCGCA | 49315 & 49316 | USP16 | CCAAGGCAAGAACCGCAA | TGTAGGCACAGCTTGCACA | 49421 & 49422 |
| UNG | GGTTCGTGCCCATCAAGCCAA | TTAGCCAGGACACAACTGCA | 49317 & 49318 | USP17L15 | GGCCAGGAGATCCAAAGGGA | CTTCCACTGAGACCACTGCA | 49423 & 49424 |
| UNK | TGGACAAGGCCGTGTTCCACA | CAGGCTGGCAGATGGGGCA | 49319 & 49320 | USP17L4 | CCGTGAAGACACAGACAGGCCA | ACTCGGGTACCTGCAGGGCAA | 49425 & 49426 |
| UNKL | GGGCAGAGGCCAAGGA | GGTGCTGACAGGGCGCA | 49321 & 49322 | USP17L7 | AGTGCCGTGACATGCCAGCCA | CAGGAGAGGTGATGCCAGA | 49427 & 49428 |
| UPB1 | CGAGCACTTCCCGGCTA | AGCAGTCCATCCCGGCTA | 49323 & 49324 | USP18 | GCACGTGGGAATGCGAGA | GATGTCTTCCAGGACACCAA | 49429 & 49430 |
| UPF1 | GCCCGCTTCATGACCACA | GCATGGGGTGGCATGACCA | 49325 & 49326 | USP19 | CCACTGGAGCTGGGGTGACGA | GCAGAGCCTGGATCCTCAGCA | 49431 & 49432 |

| GeneName | Forward Primer | Reverse Primer | SEQ ID NOs | GeneName | Forward Primer | Reverse Primer | SEQ ID NOs |
|---|---|---|---|---|---|---|---|
| YARS2 | AGCTGGGAAAGTCTGCTGGCAA | TGATCAATCTCTGGAAGGGGCA | 50281 & 50282 | ZBED9 | GCTCTGAGTCAACTGCGGGAA | CTCCCGCCACCCAAGACTGGA | 50387 & 50388 |
| YBEY | CGAGTCATCCCCATCAGGAGA | AGAAAGCACATGGGTTGGGACA | 50283 & 50284 | ZBP1 | GGAGTCGCAGGGTCTGAGA | GGGAGTGATGGGCTGACCAA | 50389 & 50390 |
| YBX2 | CAGCAGGGAGATGACCGA | CGGAACCATCAGCGGGA | 50285 & 50286 | ZBTB1 | GCCAGCCCAAGATCTGACCA | AGGACATCGAAAAGGCAGGCA | 50391 & 50392 |
| YBX3 | TGCCCCAGCAGTTGGGACA | TAGGGACGGCCGGTATCCA | 50287 & 50288 | ZBTB10 | GGGGCCAGATGGTGATAGGA | AAGGACCAGGCATCAAACCA | 50393 & 50394 |
| YDJC | CGGGCTGCCGGTGACAGA | GTGGGAGGCACACTGGGGTA | 50289 & 50290 | ZBTB11 | AAGGGCAGAACCAAGCGGGAA | TCCACAGACCTGGCATGCA | 50395 & 50396 |
| YEATS2 | CCTCAGCCTCTCCGAGCCA | GATCATGTCCTCCACCACGGA | 50291 & 50292 | ZBTB12 | TCAAGTCACTCGTGCGGCA | CGCACGTGGCAGTAGGAGCA | 50397 & 50398 |
| YES1 | TACACAGCAAGACAAGGTGCA | AGCCCTGAGGGCACGGCA | 50293 & 50294 | ZBTB14 | GTGGCTTCCTGCACCAAGGCA | CCATCGCTGCCGCTGCA | 50399 & 50400 |
| YIF1A | CAGAAAAGGTTCTCCCGGA | ACAGCAGCCCCGTGAGTCA | 50295 & 50296 | ZBTB16 | GCATCAGCTGGAGACGCA | GGTGCACTGGTAGGGCGA | 50401 & 50402 |
| YIF1B | CCCTGGAGGTGCTGGLCA | CTGCCAAGATCTTCAGCCGCA | 50297 & 50298 | ZBTB17 | GTGCAGCGTGTGCAGCAA | CGGTTGAAGCCACGCCCA | 50403 & 50404 |
| YIPF1 | GATCCCCAAGAGGCTCAGGAA | AAAGGGGCCATAGAGAGATCTGGA | 50299 & 50300 | ZBTB18 | TGGAGGGAGGCATGGAGAGCA | TGCCGTCCTGCTCGCGGA | 50405 & 50406 |
| YIPF2 | CAAGGGTGTCCAGGAGCGCA | CCAGGAGGGGTGGAGCA | 50301 & 50302 | ZBTB2 | CAATGCAGCTGACCTCGGGAA | TTCCGACTGTGCTGCCCA | 50407 & 50408 |
| YIPF3 | TGGTAGAGGGGGATCCTGGACA | GGACGGTGTGTGGGAAGCGA | 50303 & 50304 | ZBTB20 | ACACACAGAGGAGTGAGGGCA | GCCACGTGTCGCTCCAGGA | 50409 & 50410 |
| YIPF4 | CAGCAGACCGCGGAAGATCTCA | TTCAACTTCAGAAGCCAGCCA | 50305 & 50306 | ZBTB21 | GCCCTGCGAGAAGTGTGGGAA | CGGTGGCAGAGGTGGTGGA | 50411 & 50412 |
| YIPF5 | TTACCAGCCAACTCAGGCA | AIGTGGCTCCAAAAGCAAGGCA | 50307 & 50308 | ZBTB22 | CTGGCAGTGGGGACGGGAA | TGTTGCACACGGGGCAGTCA | 50413 & 50414 |
| YIPF6 | CGGGACAGCATGCCCA | CCCGGATGCAGAGATCTCA | 50309 & 50310 | ZBTB24 | GGGCCTCACAAACAGCCA | AGCTGCAGGTGCTGAGCTGGA | 50415 & 50416 |
| YIPF7 | AACGGACCTCACTGGACCCA | CCCAGACACGCTGGCCACCA | 50311 & 50312 | ZBTB26 | TTCAGTTGGGAGATAAGCCCA | AGTTCAGGACAGCTTGGGCCA | 50417 & 50418 |
| YIEFN3 | CACCCAGTGCGAGAAGATGGA | CAGCAGTGCAGGCCGCA | 50313 & 50314 | ZBTB3 | GGACCTGGCCAAACGCAGCAA | TCTTTAGGTGGCCCTCCACCA | 50419 & 50420 |
| AGAGATCCAGCGTTCAGGAA | AGAGATCCAGCGTTCAGGAA | CAGCAATGACCACACTTGCA | 50315 & 50316 | ZBTB32 | CAGATGGAGACGCACTAGGA | GGCCTCCAGGAGGCAGTAGGAGA | 50421 & 50422 |
| YKT6 | CCATGGAGAAAGAGCGAGGGCA | TCTCTCCAATCATCCCACCA | 50317 & 50318 | ZBTB33 | CATCTCAGGTACAGCGCAGGA | TTGTGGGCAGAATCTCGGA | 50423 & 50424 |
| YLPM1 | AATAGGAGCCACAAACTTCCA | ATTCTCCAACTCTGCTCCGGAA | 50319 & 50320 | ZBTB34 | CCACATCCGGGGCCATACAGA | TCTGGGGGACTCAATGCGA | 50425 & 50426 |
| YME1L1 | AAAATCTCCTTCCCAAGACCAA | CAGCAGAGCCCTGCTCCTGA | 50321 & 50322 | ZBTB37 | AGGAGATCCAGCCTCCAGA | TCATCATCCACTCCGACCCA | 50427 & 50428 |
| YOD1 | GTGTAGCACAGAGACACGGCA | ACTTCATCTCGGCCACCCA | 50323 & 50324 | ZBTB38 | TGAGATGTCACAACGGGGAGA | AGACAAACTTCCTTCAAGCCCA | 50429 & 50430 |
| YPEL1 | CCTGGCCAATCATGACGA | TGGGACCACACACTTGCA | 50325 & 50326 | ZBTB39 | GAATTCAACTACCACCGCGGA | GGTACATGAGGGGCCCGA | 50431 & 50432 |
| YPEL2 | CCACGGACCTACAGCTGCA | CCTGGTACGAGGAGCTACCCA | 50327 & 50328 | ZBTB4 | AGGAGCCCCAGTAGTGGCAA | ATTTTCCCTGCCACGCCA | 50433 & 50434 |
| YPEL3 | TCTCCAAGTCCTTCCAGGGCA | CGCAGTGGATGTCGGCGACA | 50329 & 50330 | ZBTB40 | CACCTGGAATCTGAGCACCCA | CAAACACTGCGACCCGGCA | 50435 & 50436 |
| YPEL5 | TGAACACTGCTCAGAACTCA | CATGTGGCGGCCAGTGAGCA | 50331 & 50332 | ZBTB41 | TCGAAGACCACACTTGGAGGAA | CCAGTGTCGTTAAACTGGCGA | 50437 & 50438 |
| YRDC | TGCCAACTTCAGCTCCCA | CACAGTTGAGCCAAGGGCGA | 50333 & 50334 | ZBTB42 | ACTTCCGTGAGLGGAGACAGCA | GCGCTCACACACCTGGCA | 50439 & 50440 |
| YTHDC1 | GATGGACGTGATGGACAGGA | ACGCCTTCCCACATCCCGGA | 50335 & 50336 | ZBTB43 | AGAGAGATGGGCACATGAGCA | AAGAAGTTCACATGCCGGTGGA | 50441 & 50442 |
| YTHDC2 | AAAATCTCCTTCCCAAGACCAA | CAGCAGAGCCCCTCAAAGCCAA | 50337 & 50338 | ZBTB44 | TGATCAGCAGAGACAGTTCCAGGA | GAAGTGTAGGCAAGCCCTCCAGA | 50443 & 50444 |
| YTHDF1 | GTGTAGCACAGAGACACGGCA | ACTTCATCTCGGCCACCCA | 50339 & 50340 | ZBTB45 | CCCAGGTGCTGAGCCACCTA | GAGCAGGTAGTGCGCGTAGAGA | 50445 & 50446 |
| YTHDF2 | CAGCCTCAACCACCACAACCA | CCTGTTACGAGGAGCTACCCA | 50341 & 50342 | ZBTB46 | CTGCTGCGTGAAGGCCGA | CCGAGATCTCGCAGGGGTA | 50447 & 50448 |
| YTHDF3 | AGCCTGGCAAAAAGGGCA | TCCGATGTCACAGAGTGA | 50343 & 50344 | ZBTB47 | CATGCCAGAGTGCCACGA | AGCAGGAAGGCTTGCCGCA | 50449 & 50450 |
| YWHAB | GGCTGCGGAGAACAGCCTA | AACTTGCAGGCACGGTCA | 50345 & 50346 | ZBTB48 | CCAGCTCCCCGGCCAGAGA | TGAGGAGGGCTCCAGGACA | 50451 & 50452 |
| YWHAE | CCGAGAAGGCCTACAGCGA | AGTAGTTAAGAGCCAGGCCTA | 50347 & 50348 | ZBTB49 | ACTCGGATGTGGACACCCCA | TGGAAGATGCTGACTGCCCA | 50453 & 50454 |
| YWHAG | TGAGCTGGACACCATAAACGA | CGCTCGTCCAGAGGGTGA | 50349 & 50350 | ZBTB5 | TTCAGGCTACCAAGGAGGAGA | TGGGAGCCTATGCGGCGGTA | 50455 & 50456 |
| YWHAH | CATCGAGCAGAAGACCGACA | CAACTTCAGCAAGGTACCGGA | 50351 & 50352 | ZBTB6 | GTGCCCAGGTGTCTCGA | ACTGAAAGGGCCGTATGCCCA | 50457 & 50458 |
| YWHAQ | CGGACAAGAAGAGAGCGGCAA | GGACCACATGGTGACCGA | 50353 & 50354 | ZBTB7A | CTCACCGTCAGCACAGCCAA | CGCAGGGATCTGCCGGTCA | 50459 & 50460 |
| YY1 | TGGGGGTCAGGTGGAGGTGGA | GAAACATGGAAAGGGCAGGGGGA | 50355 & 50356 | ZBTB7B | CGCCACCTCAAAGCCAGAA | CCAGCGGGGCAGTGCAGCA | 50461 & 50462 |
| YY1AP1 | GGGCAGTTGGGTGAAGGCCA | CATGGCGCGTAATCCAGGA | 50357 & 50358 | ZBTB7C | CACCACCCAGATGTCCACGA | GAGAGGCGGCTGCCAAGGCA | 50463 & 50464 |
| YY2 | AGTGCCCTCAGTAGAAACCGA | CAAACTGGCCGTTCCCCA | 50359 & 50360 | ZBTB8A | GAGTCAGCCAACCACAGCTACA | GAAGGAAGCTAGCAGCCGACA | 50465 & 50466 |
| ZADH2 | CGGGGCCTCCAAGTGTCCGAA | CCACCGTTCGGTGACAGGCA | 50361 & 50362 | ZBTB8B | TCACGAGTTCACCTGTCCA | TCAGATGAAGCCTCCACCA | 50467 & 50468 |
| ZAN | CCTTCATCGAGCAGCAGGA | GCTCGTCCACGGTCAGGA | 50363 & 50364 | ZBTB8OS | TCCAGTTACACGCATGGGGAGA | GAGGGGTTCCACTGTCCCA | 50469 & 50470 |
| ZAP70 | TGTGCGTAGATGCAAAGGCA | GGTGGAGGAGGAGCACGGAA | 50365 & 50366 | ZBTB9 | GGACACCCCTGCAGATGGAA | CGACGGCCACAGTGGGGA | 50471 & 50472 |
| ZAR1 | AGGAGTCAGGCAGGGAGGA | TCGGAGGCGGCGTCTCA | 50367 & 50368 | ZC2HC1A | CAAACCCGAAATTCCACACA | AAGGAGAATGCACAGTCCCA | 50473 & 50474 |
| ZAR1L | CGCGTTCACATGCACCCA | GAGCAGGCTGAGGAAGACGA | 50369 & 50370 | ZC2HC1B | ATCCAGCCTCAGACAGCCAGCAA | TCATTCGTGGCCACCAGGA | 50475 & 50476 |
| ZBX | TCCGTGGTGGAAGGAGGCCAA | AGTTGCTTCAGTTCCTCCACCA | 50371 & 50372 | ZC2HC1C | TGGCACTGATGGGGACCA | TCCGCCCTGCGTGGGCAGCA | 50477 & 50478 |
| ZBED1 | TCCCCACAGGCATTGAGGGTA | CACAGCCCTTCTCCGCA | 50373 & 50374 | ZC3H10 | CCTCGTCCAGTGTCCCAGCAA | CAGATACAGGCACAGGAGGCCA | 50479 & 50480 |
| ZBED2 | TCGAGCAGAAGGCAGAACCAA | TGCCCACGAAAAGGCCGCCA | 50375 & 50376 | ZC3H11A | CCCCAGCCAAAAAGGCA | TGGGATGAGGAGGGCA | 50481 & 50482 |
| ZBED3 | CCGGAGGATGAGCACGCAGA | GGTCGTGGAGGTGGCAGA | 50377 & 50378 | ZC3H12A | CTGGAGGACCCAGATGTCAAGGA | TGGCTGGGAGCTCAGATCCA | 50483 & 50484 |
| ZBED4 | CACGGGACTATGAGAGCCTGA | CACGCACTGCACGCCTTGCA | 50379 & 50380 | ZC3H12B | CCCAGACACCCATCAACTGGA | TCCAGTCATCACCAGGGCA | 50485 & 50486 |
| ZBED5 | TGACCAGGTTGCCATCCA | CTGCTCAGGATCCCAGTCTA | 50381 & 50382 | ZC3H12C | AGGTCCTTTGGTGGCCAGGAGA | TGTGGAGTTATGGGGCAAGGA | 50487 & 50488 |
| ZBED6 | CATGGGGGTGAGCGGCAGA | GGCTGACAACCATCCAGGA | 50383 & 50384 | ZC3H12D | GGAGAAGGACCCCACCAGA | GACCAGGGCGTTGCCGTGCA | 50489 & 50490 |
| ZBED6CL | TAGATGGCAACTCAGCGTCACA | AGATCATGTCCAGCTACACCA | 50385 & 50386 | ZC3H13 | ACAGGGACGAGAGAGAGACA | AAATCCCTGCACAGATCCCAGA | 50491 & 50492 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| ZC3H14 | CCTGCAAAGGCTTCCCCA | CAAGCAGGGAAGTAACGGCA | 50493 & 50494 | ZDHHC6 | CATACAAGGCACCACGTTCACA | TTCCACCCAAAGGAGGAGCCGA | 50599 & 50600 |
| ZC3H15 | AAGAAGCACGGTGAGGCGAA | TCCAGGAGGAAGTGCATGACGA | 50495 & 50496 | ZDHHC7 | ACCTGAGAACCATGCTCACCGA | AATACAGCAGCACCTTGGGGCA | 50601 & 50602 |
| ZC3H18 | CTCGACACCCAGCAGGCA | ACCTGACTTCCGGTCCCAGAGA | 50497 & 50498 | ZDHHC8 | GCCCTATGGCTCCAGAGACGA | GCCTGATCAGCCTGCAGGGA | 50603 & 50604 |
| ZC3H3 | CCACCCTACCCAGAAACGCCA | GAAGCGGGAGGGGATGAAGGA | 50499 & 50500 | ZDHHC9 | AGAATCCCTACAGCCATGGCAA | TCTTGAGTACTGGGAGGTCGA | 50605 & 50606 |
| ZC3H4 | CCACGGTCACAGCTGCAGCA | CTTGGGGATGGGTAGGGGGA | 50501 & 50502 | ZEB1 | CACCAAGTGCCAACCCA | GACTGCAGGGGCTGACCGTA | 50607 & 50608 |
| ZC3H6 | TAGGCTTCACAGACTGCCCAA | TTAGGGGCATATGGAGGGCA | 50503 & 50504 | ZEB2 | GTCCCAACAAAGCCGGA | TGAGGAAGGCCACAGCA | 50609 & 50610 |
| ZC3H7A | TGTGCGCCCAGTGTCTGAGA | CTTTGTGGGGAGGAGGACGGA | 50505 & 50506 | ZEB3 | CCTGTTGGAGAGCAAGGCGA | CTGGGGAAGGAGGGCGGAGA | 50611 & 50612 |
| ZC3H7B | AGAAGCAGTGGCAGCAGCACA | GCAGCGGCACTTGTCCCA | 50507 & 50508 | ZFAND1 | AACACAGAAGCAGGGAGTCTCA | TCTGAGTGGCAGCCATTCGA | 50613 & 50614 |
| ZC3H8 | GATGGGACAGAGAGCTGGGA | ACCAGCCATCACCTCTGCCA | 50509 & 50510 | ZFAND2A | TCACGTCCCAGTATGCCCA | TGCCGTTGACATTGGGCACA | 50615 & 50616 |
| ZC3HAV1 | ATGACCAAGGCGGTCAGGAGA | TAAAAGAGGGCCAGGCTGGA | 50511 & 50512 | ZFAND2B | TCCCAGCCCAAGTCAAACCA | CATTCCAGGGCCCGCTGCA | 50617 & 50618 |
| ZC3HAV1L | TCAGACCTGCAGCGCAGCA | CTTGGCCAGGCAAACAGTCGA | 50513 & 50514 | ZFAND3 | CGGTCCGAGGAAACCAGTCGA | TGCTCGCTCGGGAGGCGA | 50619 & 50620 |
| ZC3HC1 | GCTGGAAAGCAGTGCTGAACA | CACAGAGATTCCCACTGCCGA | 50515 & 50516 | ZFAND4 | TTGAGGCTCGGGATATCACAGA | GTAGACAGCCCAGTTCAGA | 50621 & 50622 |
| ZC4H2 | CCGACTGATCACGCTGACA | CAGGCCAGAGTCATGCGCA | 50517 & 50518 | ZFAND5 | TGCTGCTGGCAGCACATCTGA | GATGGACTGGGCTGAGTGACA | 50623 & 50624 |
| ZCCHC10 | CTCCTCAGAGAAGCAAGTGACA | CTGCTACTGGAAGAGCTGGA | 50519 & 50520 | ZFAND6 | CACAGCACAGCAGCCATCTGA | CCACACCGGCATTCAAACCCA | 50625 & 50626 |
| ZCCHC11 | GAACATGCACCGCGTCCCA | GGACAACGCTCTTACACGGA | 50521 & 50522 | ZFAT | TGTGAAGTGTCCCACGA | CAGTGAACCTCTTCCGA | 50627 & 50628 |
| ZCCHC12 | ATGCGTAGAGCCAGGAAGCGAA | GTATGGGTCAGCTCCTGGAGA | 50523 & 50524 | ZFC3H1 | TCAGATCCTGACCTGAGCGCA | CACTGGTGAAGGAGCTGGAGA | 50629 & 50630 |
| ZCCHC13 | TGCGGCAAACTTGGGCACA | GGATTTGCCGCCAGGCTGGTAGCA | 50525 & 50526 | ZFHX2 | CCAACCTTCCACAGCAGGCA | AGGGGCAATGGAAAGGGCA | 50631 & 50632 |
| ZCCHC14 | GGCTACGTCAGCGCCAGCA | CTGCATGGGTGGCACGGGA | 50527 & 50528 | ZFHX3 | CACAGCATTGCTCACAGCCA | GGAACAGGCTTCCATGCGA | 50633 & 50634 |
| ZCCHC16 | CCCTCACCCCAGCCAAACGA | GTCGTTGCCGGAGCTCAGA | 50529 & 50530 | ZFHX4 | GCAGGAAAACGTCCAGCA | ACGGTTTGGGCAGACCA | 50635 & 50636 |
| ZCCHC17 | AGGAAGGCCTGAGACCATGGAA | TCAGAGGGCTTATCCACCCGA | 50531 & 50532 | ZFP1 | TCACACGGGGAGAAAACGCTA | CTGATGGACACTGAGTCGGGA | 50637 & 50638 |
| ZCCHC18 | CGGCCGAAAAGGTCTGAGCCA | AAGGGTACAGAGACACACCA | 50533 & 50534 | ZFP14 | CAACTGGCTGGACATCAGAGA | AAGGCTGAGCACCAACATACA | 50639 & 50640 |
| ZCCHC2 | AGTGTGGGAGCCCAAGCCAA | TTCTTCTTGGGCCCCGAACCA | 50535 & 50536 | ZFP2 | GGACTTCCCAGCTGGAACGA | AGAGCTGAGCAGCACTCAGTCAA | 50641 & 50642 |
| ZCCHC24 | GCAGGAGTGCATCAAGTGCCA | GCGACGGCAGTAGTAGCCCA | 50537 & 50538 | ZFP28 | GGAAAGCTATCCCAGGCAGTGA | TGTAGCTGCTGGCGGAAGTCA | 50643 & 50644 |
| ZCCHC3 | CTTCTTCCTGGGGGCCGAGA | CCTTCCGGCAGTAAGGGCTCA | 50539 & 50540 | ZFP3 | GTGGAAAGGCTTTCAGGCGGA | TCTGGTGGAGAAGCAGCTCA | 50645 & 50646 |
| ZCCHC4 | CTGGGGCAACATAGTGAGCA | AACTGACAGCTCCGATCAGCA | 50541 & 50542 | ZFP30 | TGTGCCCACTCAGTCGACA | ATACTGCCTAAAGGCTTCCA | 50647 & 50648 |
| ZCCHC5 | CTGCAATCAACTGCCCACACA | TTGACAGGGCAATCTCTGGCA | 50543 & 50544 | ZFP36 | CGAAGAGACCCCACCCCA | GGATCCCAGGGACTGTACAGA | 50649 & 50650 |
| ZCCHC6 | GACGGTCGGCGAGATCAGGAA | GGTCAGCAGCCTGCCGCA | 50545 & 50546 | ZFP36L1 | CCTGCCCGATGGCACCAA | AACATGTGAGGGGACTGGA | 50651 & 50652 |
| ZCCHC7 | GGAAAAGCAACAGCGGTGGCCTCA | GGGCCCTGGGAAAATCCTCA | 50547 & 50548 | ZFP36L2 | CGGACCGTGACAGCTACCTA | AGATGGAAGGCGGCTGA | 50653 & 50654 |
| ZCCHC8 | TCACCCCAGACGACAGAACAGCA | GCCTGCTCAAGAGTGCCCA | 50549 & 50550 | ZFP37 | ACCGGAGGAGAAGTGCGGAA | AGGTTGCTCTGAGCAGGATCCA | 50655 & 50656 |
| ZCCHC9 | AATCAAGACATGGGCACTGGGA | TGCAACGCCACCATCAGCA | 50551 & 50552 | ZFP41 | GTGCAGTGAGTGTGGGCGGA | GACGTCAGAGCTGTGCCGA | 50657 & 50658 |
| ZCRB1 | TCGGAACGTGAGCCTCCA | TGACTGAGGCTGTCAAGAGCA | 50553 & 50554 | ZFP42 | AGACCACGTGTCGTCGGA | TGGATGCGCACGTGCGTA | 50659 & 50660 |
| ZCWPW1 | ATGCCTCTACACTCCAGGA | CATGACTGATAGCTCCAGGGA | 50555 & 50556 | ZFP62 | CAAGGCAAACGTGTCGGAGAAACA | AAGGCTGGGCTTCCCGAGGCA | 50661 & 50662 |
| ZCWPW2 | AAGCACTGCAACCCACCAGCCA | TCAAACAGACTGCTGCAGGA | 50557 & 50558 | ZFP64 | GGCCAAGATCGTGACGCA | CTGAGCTGTCCCGAGGCA | 50663 & 50664 |
| ZD8F2 | GAGGCAGACCCTCAGAAGGA | CACTATCACCGGGCACCA | 50559 & 50560 | ZFP69 | GAGGATGAAGTGACCCCTGGA | GATTCTGGTGAGCAGGAGGCCA | 50665 & 50666 |
| ZDHHC1 | TCATGTGCACGGATGTCACCA | GGGGCCGCATCTTGGGAGGA | 50561 & 50562 | ZFP69B | TGCCCACCGAGGCCAGA | CTGTCAGGGATCCAAGGGTCA | 50667 & 50668 |
| ZDHHC10 | CCCTCAGAGCCCAGCATCCA | GCCTGCTCAAGAGTGCCCA | 50563 & 50564 | ZFP82 | CACACCTGACTCGGCATCAGA | CACTCTAAAGGCCTTCCCGA | 50669 & 50670 |
| ZDHHC11 | CCGCACGGAACGTGAGCCTCCA | GGAAGATGAGCAGCTGGCCCA | 50565 & 50566 | ZFP90 | CGCCCAGGAATCAGTGACA | GCTCCTCTGAGGAGGGTCGA | 50671 & 50672 |
| ZDHHC11B | TCCTCACCAGCGATCCGCTA | TCCTCCTCCAGCCCAGA | 50567 & 50568 | ZFP91 | GAAACCCAAAGCCACCGGAGA | AAATAGCGAGGATGGGCAAGGA | 50673 & 50674 |
| ZDHHC12 | TTCAGCAGCATCCACCTGCCA | TTCCTCGTCCAACTCGCA | 50569 & 50570 | ZFPL1 | CCCAAAGCCAAGTCACCAGA | AGGCTGGAGACCCGGGAGGTCA | 50675 & 50676 |
| ZDHHC13 | CACCAGTTCTGACGCCCGA | GCTTCACCAGGCCGCCGCA | 50571 & 50572 | ZFPM1 | CCCCCTCTACTCGGACA | TGAAGGTGGACAGGGCTGCCTGA | 50677 & 50678 |
| ZDHHC14 | CTACACAGACAAGGAGCGCTA | GATCAGATGACACCGGTCACA | 50573 & 50574 | ZFPM2 | GGACGACCACGTCTCCAA | GATGGCAGTAACCGGGCA | 50679 & 50680 |
| ZDHHC15 | CTGTAGGTGCAGTGAACACGTGGCA | ATCCAAGGTGAACACGTGGCA | 50575 & 50576 | ZFR | CCGGACGTCTTGAGCAGGCAA | CCCAGGGCTTGTGAGGGCTA | 50681 & 50682 |
| ZDHHC17 | ACCTCGTCGCCTCCAACCTGA | CTGGGAGGTAGGGGGGCCA | 50577 & 50578 | ZFR2 | ACTCCCTGGGCCCTTGCA | TAAGATGGAGAGATGCAGGCA | 50683 & 50684 |
| ZDHHC18 | TGTGCACCACTGGGACCCAA | GGCTGGGGGGGTTGAAGCA | 50579 & 50580 | ZFX | ACCATCCGAACACTTGCCAA | GTAAACAAAGCCCCTGCATGAGA | 50685 & 50686 |
| ZDHHC19 | CGAGCAGCCAAGGATCTTCCCA | CAGACGAGCAGTGATGCCA | 50581 & 50582 | ZFY | TGGCAGCAGCTGGCTAAACAGAAACCA | AAGGATGCCATCAGGGCCAA | 50687 & 50688 |
| ZDHHC2 | CTCCCGTTCCCCTCAA | TACATGAGTCACAGGCTGAGCA | 50583 & 50584 | ZFYVE1 | TGAGCTGCAACAAGTGTGCGA | TAGCAGTTGTCACAGAACCGCA | 50689 & 50690 |
| ZDHHC20 | TGAGAACCCAAGATCCCACA | CTCTCACACAGTGGCCGA | 50585 & 50586 | ZFYVE16 | GATGAGGACAGTTTGCCCCCA | TTCTGCCTGTCCAAGCA | 50691 & 50692 |
| ZDHHC21 | CCTAGCACCACTTGCGCCGA | CTGGCTGATGGAAGGTGGGGA | 50587 & 50588 | ZFYVE19 | CCATCCAAAGAGTCTGCAGCA | GGGGACAAGAAGAGGTCCCCA | 50693 & 50694 |
| ZDHHC22 | ATCACAGAGTACCACACGGA | TGATCAAGAGTACCACACGGCA | 50589 & 50590 | ZFYVE21 | GACGGAGGGTGTGACCCA | TGGCCACTAGCCACGCCA | 50695 & 50696 |
| ZDHHC23 | CTCGGGGCCAGCACTCTA | TGGAAGGTGATCCCATCCCCA | 50591 & 50592 | ZFYVE26 | GAATCCTTGACCCCACCA | TCACGGTGTCGGACAGCA | 50697 & 50698 |
| ZDHHC24 | GACCGAGCCACCACTGCA | TGTGGTTGGGGTGGAGAAGAGGA | 50593 & 50594 | ZFYVE27 | AGGAACAGGGTTCCTGAGCAA | AGCACTGAGAAGGTGGCCGA | 50699 & 50700 |
| ZDHHC3 | CCGTCGCCATTGTCGCGCAGA | CTGGTTGGTGGCGCAGA | 50595 & 50596 | ZFYVE28 | GCTGCGGGACTGAACACCTA | CCTCTCACCGTCGCAGA | 50701 & 50702 |
| ZDHHC4 | GCAACGGGAAGCTGAGAGGCA | TCGTTCCTGGAGAGAGGCCA | 50597 & 50598 | ZFYVE9 | CCCAGAGAGCAGAGGCGA | GGGTCGTGTGTGACACGGA | 50703 & 50704 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| ZG16 | GGAGGTGGTGGTGGAAAGGGA | ACCACCTCACATAGTCGGCTCCA | 50705 & 50706 | ZNF132 | GAAGGAGCACAGTGGAGGGAA | GAGGAGGTCAGAGCTGCCCA | 50811 & 50812 |
| ZG16B | GGGAAGCTTGATGGCCAGA | TGGTCGGCTCCTCTAGTGGA | 50707 & 50708 | ZNF133 | GAAGCCTACATGTGCAGGGA | TTGGAGAAAGCCTTGGCCA | 50813 & 50814 |
| ZGLP1 | AGTGGGAGAATGGGCAGAAGCA | GGCCAAGGCTGACTGGAGAA | 50709 & 50710 | ZNF134 | CAGCACGAGGGGCTTGGACA | AGATGGGGCCACATATGTCACA | 50815 & 50816 |
| ZGPAT | GGGGAGGAGGAGCAAGGACA | GCCACGCTATGCCGGCCA | 50711 & 50712 | ZNF135 | TGTGGGAGGACCTTCAACCAA | TCGTGCTGGCTGAAGAGAGA | 50817 & 50818 |
| ZGRF1 | ATAGCCCTCCTGAAGTGAGGAA | CTTCCCGAGGAAGAGAACTGCA | 50713 & 50714 | ZNF14 | GAAAGGTCACACACTGGAGAGA | GAACGAAGGAAGGCCTTACCA | 50819 & 50820 |
| ZHX1 | TGATGAAACCACGACAATCCCA | GAAAACTTGCCTGAAGGACACGA | 50715 & 50716 | ZNF140 | TGCCTCCAACCTCACTCGACA | AGTAAGGTGTGAGAAACGGCGA | 50821 & 50822 |
| ZHX2 | GTGACCGCAAGAAGACAAAGGA | GGCAAGGCCAGTCACCTCGA | 50717 & 50718 | ZNF142 | AGACCCGGCATCGAGAAGCA | GTCGGTGTGGGTGAGGGCA | 50823 & 50824 |
| ZHX3 | GGAAGAGGAGGCTGCTGAGGA | TCATCTCCAGGGTCACAGGCA | 50719 & 50720 | ZNF143 | GCAGGCTGTGGGAAGGCA | GTTGTAAAGGACCGACCGA | 50825 & 50826 |
| ZIC1 | CGCCAGCTCTGGCTACGAA | GTGGACTGCGGAGGAGGA | 50721 & 50722 | ZNF146 | GAAAACCTCCTTACGCACCAGA | TTCTGGCCAAAGGCTGTTCCA | 50827 & 50828 |
| ZIC2 | CACAGTCGGCCTCTTCCTCA | TGGGGACAGGGAGGAGGGGAGA | 50723 & 50724 | ZNF148 | TCTGAAACAGCCACTGGAGCA | TTACTGGCCCCTCCTGCA | 50829 & 50830 |
| ZIC3 | CAAGTCCTACACGCACCCGA | CATAGCCTGTGAACTCCCCGA | 50725 & 50726 | ZNF154 | TTCACAGTGTGAACTCCCCGA | TCCCCAGTGTGAATCTCCCGA | 50831 & 50832 |
| ZIC4 | AGCATTCGCACGTGCACA | GGCAGACGGTGTAGCCGA | 50727 & 50728 | ZNF155 | TGGTCCCCGGCCAAGCTGAA | GGACCTTGGCCGGGACCA | 50833 & 50834 |
| ZIC5 | CTTTCCCGGCTCGGGCAA | GTGGCGGGGACTTGCAGTGA | 50729 & 50730 | ZNF16 | ACTCGCCGTGGAGGAGGCAGA | GTACCACAGGCTGCAGATCCA | 50835 & 50836 |
| ZIK1 | ACCATCACCAGCACCAGAAGCA | ACTGCGAATGTCCTCCCACA | 50731 & 50732 | ZNF160 | ACAAATGCAGTGAGTGCGGCAA | ATTGTGCCTGAAGACCTTGCCA | 50837 & 50838 |
| ZIM2 | GAGGGGCAGAGAGGAGACA | CCAGGAGACCACGTTCCGA | 50733 & 50734 | ZNF165 | TGGAGAGGAGGCAGTGACCA | GCTGGTCCAGGAGGTGACA | 50839 & 50840 |
| ZIM3 | CACCCCTGATGGACACAGCA | CTGGAAGCTCCTCAGCTGGA | 50735 & 50736 | ZNF169 | AGCGGACCCATTCTGGGAGA | GGGGTAGGAGCTGATGACCA | 50841 & 50842 |
| ZKSCAN1 | AATAAGGAAACGCTGACTACGCA | TGAACAGGGCATGCCTCCTCA | 50737 & 50738 | ZNF17 | TACCTGCACCAAAAGGAGCA | TTGAAAGGCCTCCACACCA | 50843 & 50844 |
| ZKSCAN2 | GCCTTCAGCCCAGAAGCTCGGA | CGGGTGAAGGCCTTGCACGA | 50739 & 50740 | ZNF174 | CCATCCTGCCCCCGGAGA | CCTGGGAAGACCTGCCCA | 50845 & 50846 |
| ZKSCAN3 | GAAAGATGTCCACCTGCCCAGA | CCAGGAGACCACGTTCCGA | 50741 & 50742 | ZNF175 | ATGATTCGCACGAGGGCCCA | TGACCAGCCCAACAACGTCA | 50847 & 50848 |
| ZKSCAN4 | ATGCATAGGGAGTAGGCGACA | ATGACAAGGGCAGAGCTCCCA | 50743 & 50744 | ZNF18 | AAGAACTCACACCGGAGAGACA | GTGGTGGCGCCATCCTGAGA | 50849 & 50850 |
| ZKSCAN5 | CATCACGCGTCCACACA | GAGTCGAAGATGTCCAGCCA | 50745 & 50746 | ZNF180 | GTGGAAAACCCCTCAGAGCA | TGGGGTTCAAAACTGCCCA | 50851 & 50852 |
| ZKSCAN7 | TCACCCTGAGAGTGGTGAAGGA | AGTACATTGAGCGAAGCTTCCCA | 50747 & 50748 | ZNF181 | AATCCTCAATGCCACTGGAGA | ACATGGCTAAAGGCCTTCCA | 50853 & 50854 |
| ZKSCAN8 | CCCGAGACCTTCTGGGCAGA | CCAGTGGGCAACAAGGCTGA | 50749 & 50750 | ZNF182 | AGGAGGAGTGGCAGTACCTGA | TTGGTAACCTGCTGCCCA | 50855 & 50856 |
| ZMAT1 | CCCGTTCCCACATAGGAA | GTCTGGGTTCTGGAATGACCA | 50751 & 50752 | ZNF184 | CTGGACCCTGGCCAGAGAGA | GTCAGGCCTGTGGGCTGACA | 50857 & 50858 |
| ZMAT2 | GGAATCCAAGCTTGGGAGAACA | CCACAGCCATAGACATGCCCA | 50753 & 50754 | ZNF185 | CTGCTCCAGAGAGCTCCACA | GTGGCCTCCGGATCCTCACA | 50859 & 50860 |
| ZMAT3 | TCGAGCCTGCAGCTACTCCA | CTTGATAGTGAGCCTGAGGCA | 50755 & 50756 | ZNF189 | GCCCCGCGCGGGAGTTGAA | CCATCCTCTCGGGTAAAAAACACA | 50861 & 50862 |
| ZMAT4 | AGTGCACAGCTGATCTCGAA | CTGACCGGAGCCTCTTGGCA | 50757 & 50758 | ZNF19 | CAAAACTAACTCGGCACCAGAGA | ACCTAGCTGGGAAGAAGTCCA | 50863 & 50864 |
| ZMAT5 | TAGCAGGGCTGAACCCATCGA | ACTGGACTCTGGCCTGCAGA | 50759 & 50760 | ZNF195 | CCTGGACCTGCCTCAGCAGA | GATCAGGCCTGGCTTACAGA | 50865 & 50866 |
| ZMIZ1 | CAGCCATCCACAGGCGA | CGGGAAGGAGATCCAGGGA | 50761 & 50762 | ZNF197 | TCCTGGCCAGCACATAGCA | AGGGCAGAAGCTTCAGGGGCA | 50867 & 50868 |
| ZMIZ2 | CACCATTCAAACCCTCCCCA | GGTTGGTCAGTTCCGGGAGCA | 50763 & 50764 | ZNF2 | CATCCTTACTCGACACCAGA | TGTGTAAGGGATGAGGCGGTCA | 50869 & 50870 |
| ZMPSTE24 | TACCACCGGAGTTAGGACAGA | CCAACAGGAAACACCAGGGGA | 50765 & 50766 | ZNF20 | GAAGAGAGACTTGCGATAGGACA | GCTGGAAGCCGGGTAGCCACA | 50871 & 50872 |
| ZMYM1 | TGACAAGGGAGTGGACGATGA | ATTCACGCCAGATGATGCCA | 50767 & 50768 | ZNF200 | TCATGGAGTGCTCATGAAGGA | GGTACAGTTTGACCTGCCACCA | 50873 & 50874 |
| ZMYM2 | CCAGCCGTCTGTCCAACAGCA | GCAGGCTTGTGGGAGAAGGA | 50769 & 50770 | ZNF202 | TCACATCTTGCCAGGCACCAA | CAAGGTCTGAAGTCCAGCCGGA | 50875 & 50876 |
| ZMYM3 | GGCTGCAGACAGCAGCTGAGGA | ACTTGACAGGGCCAGCGGA | 50771 & 50772 | ZNF205 | CGGAAAGAGCTTCAGCCACCA | AAGTCCGAGCGGCGGGTGAA | 50877 & 50878 |
| ZMYM4 | GCCGGAGGAGGTAGCACA | ACATGCTGGGACTGGGCA | 50773 & 50774 | ZNF207 | CCCCATCGGTAATCACCA | ATGATGACCACCATACTGACCA | 50879 & 50880 |
| ZMYM5 | GAATTTCCAGCAGGCTCACCAA | AAGAAAGGCAGGTTGGTAGAGCA | 50775 & 50776 | ZNF208 | TTCATGCTGGAGAGAAGCCCTA | GATAACTAAGGGTTGAGGGCCA | 50881 & 50882 |
| ZMYM6 | AGTCCATAAAGTGGCGAGGGA | TTGCAGAAGGGAGCTCCGTCA | 50777 & 50778 | ZNF211 | ACCTGCAGGGAGGATCAGGAA | CCACTGTAAAAGGCCACCGCA | 50883 & 50884 |
| ZMYND10 | GCTGCTCACGATGCCAGA | CTGGGCTGCCGGACACA | 50779 & 50780 | ZNF212 | CAGGTACAGCTGGCAGGGAA | CACCCAGAGTGGCGTCACGA | 50885 & 50886 |
| ZMYND11 | CCACGATGCCTCACAGGCCA | GGGTGCTCCGATGCAGCA | 50781 & 50782 | ZNF213 | TCCATTGGCAACGCCCA | GAGGCAGCAGCAAAGTGCCA | 50887 & 50888 |
| ZMYND12 | TACATCTGACAAAGCCCCCAA | GGCTAGACTGAGGGCCCTCA | 50783 & 50784 | ZNF214 | CTACTGGCAAGGCTTGGTGGAA | CCATTCCTGACACTGGGAACGA | 50889 & 50890 |
| ZMYND15 | TCTTTCACCGAGGAGCAGCGA | GCTCTCGAGGCGAAAAGGGGGA | 50785 & 50786 | ZNF215 | AGCCAGGGGACCACTGTGTGGA | CTCAGGGCAATGGTGGGAACA | 50891 & 50892 |
| ZMYND19 | TCCAGCAGGAGGCACAACGTGCA | CACCTGGCAGCCGCCA | 50787 & 50788 | ZNF217 | ATGCACCAGAGGGAGGCA | AGAAACTAGAGAGGGGAGGCA | 50893 & 50894 |
| ZMYND8 | CGCAGGCTGAGGATCGAGA | CTTGCAGTTGGCGCACCA | 50789 & 50790 | ZNF219 | GCCCCGCAATCTGGAGGCCAA | GCAGAAGAGGCAGGCGGTGAA | 50895 & 50896 |
| ZNF10 | CCATGTGAGAGTGAGGCCCTA | ATAAGGGCAGAACTCTGGCTGA | 50791 & 50792 | ZNF22 | TCCATACGGGGAAAAGCCCTA | TCTGGCTGAAACACCGGCCA | 50897 & 50898 |
| ZNF101 | CGCGCTGAAGAAATCCACCA | TGTGCTTGAAGGGACGGTGGGA | 50793 & 50794 | ZNF221 | TGAGCAGTGTGGAGAAGGGGTA | CAAAAGACATGAAGGCCAGCCA | 50899 & 50900 |
| ZNF106 | TACGGGATGCCCGGAATGGA | ACTGACTGATCACTGGAGCCA | 50795 & 50796 | ZNF222 | ATCAACGAGTCCACACTGGAGA | TGTCTAAAGCTCTTCCCGCA | 50901 & 50902 |
| ZNF107 | CAAGACCTTGGCCAGAGCAGA | GTCCCCGTACACTCATCA | 50797 & 50798 | ZNF223 | TTAGTGCTGCAGAAGCAGAGA | GAAGGGTAAGGATAGGTGGGA | 50903 & 50904 |
| ZNF112 | CACATCAGCCCTTCAAGCCGA | TGCCAGGTTCGACGGGAGGA | 50799 & 50800 | ZNF224 | CAGAGGGTCCACATGGAGGA | GCTTAGGCCTGACTAAAGCACA | 50905 & 50906 |
| ZNF114 | CCACACAGGAGGGCCA | CACCTGGAGCCGGCCA | 50801 & 50802 | ZNF225 | CCAGAGCGCACAAGTGAGA | GCCCAGCCAAAGCTCTTCCA | 50907 & 50908 |
| ZNF12 | TGCCAGAAGACACACCTCA | CTTGCAGTTGGCGCACCA | 50803 & 50804 | ZNF226 | GCTGTGGCCTTCACGGAGGA | TTGAAGGGTTGGATGCCCA | 50909 & 50910 |
| ZNF121 | ACAATGGAGGAACTCTGTGA | GTGTCTTCTCCAGCAGGGGCA | 50805 & 50806 | ZNF227 | GCAAGGGATTCAGTAGCACGA | GACCCTTCTGGTGAACACGGA | 50911 & 50912 |
| ZNF124 | GGAAAGCCTTCAGATACGCA | CATGGTCACGAAGGGAACTGGA | 50807 & 50808 | ZNF229 | AAGGTCATCAGAGGGTCCACA | AAGCCTTTCCCACACACCA | 50913 & 50914 |
| ZNF131 | TTCCAGAGCAGGTCCAAGTGA | TCTGGGGTCACGTGGTCCAA | 50809 & 50810 | ZNF23 | CAGGAAGTCCATTCAGCAGGAA | CCCCAATCCTGTACACCCAGA | 50915 & 50916 |

FIG. 1 (cont.)

| GeneName | Forward Primer | Reverse Primer | SEQ ID NOs | GeneName | Forward Primer | Reverse Primer | SEQ ID NOs |
| --- | --- | --- | --- | --- | --- | --- | --- |
| ZNF230 | GAAGACTGCCCTTGCCAGCAA | TAGTCCTGCCTCAACCTGGGA | 50917 & 50918 | ZNF329 | TCACACTAAGGAGAGACCCCA | CTGAGGACCACCGGCTGGGA | 51023 & 51024 |
| ZNF232 | GGATCATTGCCACAACCACCCA | CTTTCCTCCTGGGCAGGGGA | 50919 & 50920 | ZNF330 | ACAAGTGTCAGAGGCGGCAGA | CTCAGCATCGGTAAGAGGGCA | 51025 & 51026 |
| ZNF233 | AATGTTGAGTACGGGAAGGGCA | CTGGTTGAGCTCCGGGCA | 50921 & 50922 | ZNF331 | ATAGTGGGGAGAAGCCTTACGA | ACTCGAGTAAAGGCCTTCCCA | 51027 & 51028 |
| ZNF234 | ATGTGAAGAGTGCGGAAAGGGA | GAAGATGCGGAGGCCTGACTGAA | 50923 & 50924 | ZNF333 | CCGGCCAGCTCTCAGGA | GCACAGCAGAATCCTCGGCCA | 51029 & 51030 |
| ZNF235 | GCCTCACACCTTCAAGCCA | GATGGGCACTGAGACCACGA | 50925 & 50926 | ZNF334 | ACAGGGGAGAAGCCTTACGAA | CTGATGCGCAGTAAGGGCTGA | 51031 & 51032 |
| ZNF236 | TGACCTCTGCGAACTGACCA | AATTCCTGTGGAGACCCCGA | 50927 & 50928 | ZNF335 | TGGTGCCTTCAAGTGCCCCGA | ACGGTTGAAACGCTGCCGCCA | 51033 & 51034 |
| ZNF239 | TGTGGCAAGTGTGGGAAGGGA | CTTGTGAACCCGCTGGTGGA | 50929 & 50930 | ZNF337 | TGTGCAAGGAGTGTGGGGCA | GCTTACACTGCCTGCACGA | 51035 & 51036 |
| ZNF24 | GATCCTGATGGCGAAGTTCTCGGA | ACAGAGCGCAAAGTTCTCAGGA | 50931 & 50932 | ZNF33A | TAGCCATAAGTCAGCCCTCA | TAAGGTGCGAAGTCACGAAGGA | 51037 & 51038 |
| ZNF248 | ACGTGTTAGAGAGCAGCCAGGA | AAGAAACAGGGTCTGTGCCCAA | 50933 & 50934 | ZNF338 | GAGAACACACAGGGCAGA | AGGATTTCCACACTCAAGACA | 51039 & 51040 |
| ZNF25 | ACTGACCCTGCTCAGAGGA | AGGTCTTCAGGGAAGCCCCGA | 50935 & 50936 | ZNF341 | CCCTGCCCACACTGCCAGA | GGTTGAACGCAGACTCGCACA | 51041 & 51042 |
| ZNF250 | AGCGGATCCACACCGGAGAA | GTGACTGAAGGCGTGCCCA | 50937 & 50938 | ZNF343 | CAGAGGACCGCACTCAAATGAGA | CCTCGGCCACTCACTGCA | 51043 & 51044 |
| ZNF251 | TCACACTGGAGAGAAGCCCCA | TAAAACCAAAGGCTCTGCCGCA | 50939 & 50940 | ZNF345 | TACTCCTGAAGACATGCCCA | ACCACTACCAAAGGCCTTGCCA | 51045 & 51046 |
| ZNF256 | TACAGACGGGGGCATGTAGGAA | TTGCAAGTGAAGGGCTTCCCA | 50941 & 50942 | ZNF346 | CACTACCTGGGGAAGACCCA | TGCATGGCAGAGGCTGCA | 51047 & 51048 |
| ZNF26 | GAAAGAGCCTTCAGTGCCAA | CCCACATTCACTGCAGCCA | 50943 & 50944 | ZNF347 | TCAGGCAACCCACAGTGGAGA | ACGCCTAAAGACCTTGCGGCA | 51049 & 51050 |
| ZNF263 | CGCCACCAACGCACCCACA | GACGAGGTGTGAACTCCGAGA | 50945 & 50946 | ZNF35 | CAACAAGTGCACTCGAGAAACA | CAGGACTACCGCCTATATCCA | 51051 & 51052 |
| ZNF264 | ATAAAAGGGCCACACTGGAGA | GTGCCTCGTGAGGCCCGA | 50947 & 50948 | ZNF350 | TGCTAACGGGGCGACTACACA | CTGAGGCTGCACATCTGACCA | 51053 & 51054 |
| ZNF266 | ATGGGAACCCACACTGGAGACA | GGAAACAGTGAAGGCTCTCCCA | 50949 & 50950 | ZNF354B | GAGGCCCAGGTGTCACTGA | TTCTCCTTGCTGCAACAGGGA | 51055 & 51056 |
| ZNF267 | AACACTGGAAGCACCTCCTAGAGA | TGATCAGGTCACCGCTTAGAGA | 50951 & 50952 | ZNF354C | TCTGCTCAGGAGCCTGTGACA | AATGGAATCCCAGTGAGACCA | 51057 & 51058 |
| ZNF268 | TGTCCTAGGGTACCAACACA | GAACTTGGGCTTGCACCA | 50953 & 50954 | ZNF358 | GGCTCCAGATCCACCCCA | GGCAGGACACAGGGTTGGGA | 51059 & 51060 |
| ZNF273 | GCCTGGACACTTCACAGAGA | TTAGAGACAGCAATACCCAGGA | 50955 & 50956 | ZNF362 | ACACCTCGGACGACTACTGA | TGAGAGAGATTGCACCGGGA | 51061 & 51062 |
| ZNF274 | AAGGGGAGCCAAGTTTGCCGA | TGCTGGAGATGGCTCAGCGA | 50957 & 50958 | ZNF365 | CAGAACTCTGAAGACCGGGA | GGGCAGTTCAGGACCCGA | 51063 & 51064 |
| ZNF276 | TGCAGGCCCAGTGAAGTTCA | TGCAAAGGCTTGGCTCCCGA | 50959 & 50960 | ZNF366 | CACCTTACTCCAAGCAGTCAA | AAAACAGGCCTGGAATACACTCCA | 51065 & 51066 |
| ZNF277 | GATGGGAGCTGCAGCGA | AAAATACAGGCACAGATGAGAGA | 50961 & 50962 | ZNF367 | CCACTGTCCGAAGCACCCTA | TCCAATACCTGCCAGCCA | 51067 & 51068 |
| ZNF28 | ACCATGCAGCACCCATGACAGA | GTGCAGTTCAGGCAGATGCGA | 50963 & 50964 | ZNF37A | AGAAAGGTCGAGGAGCCATGGA | ATTCAGCCAGAAGCTGTTCCCA | 51069 & 51070 |
| ZNF280A | AGGACATCTATAAGCTCGGGGA | TAGCCGGCACTTGGAACACTGA | 50965 & 50966 | ZNF382 | CCGTCGAAGAACAGCCCTA | AAAGGCACTTCCACATGAGGA | 51071 & 51072 |
| ZNF280B | GGAACGACAGCTGGGAAAACCA | CAGTAGAGGGCTCCTGGGCA | 50967 & 50968 | ZNF383 | AACAAGGGGAAAGAGCCCTGGA | CAAAACTGGAGTACTCAAGGCCA | 51073 & 51074 |
| ZNF280C | AACAGAGGCCACTCCAGCTCA | GGCGAGGCAGCCACTGGA | 50969 & 50970 | ZNF384 | CTTCAGCAGCACACCCGA | GTGGGACTGCAGATTGGAGA | 51075 & 51076 |
| ZNF280D | TGAAGAAGAGGAGTGCGACCA | AATACCTCCGTCGAGTGCACCA | 50971 & 50972 | ZNF385A | AACCCACTACTGACGCCGTCACA | TGGAGAAGAGGTTGCGGCTGCA | 51077 & 51078 |
| ZNF281 | CAGCGGCAGGAGGGCAGAGA | GCTGCGGAGGTAGAGGAGGA | 50973 & 50974 | ZNF385B | TCCTCAGCGCTGTCACTCCCA | GTACGGAGGCAAAGAGGATGGA | 51079 & 51080 |
| ZNF282 | GAATCATTACGGACTCCCCA | ACTAGGGCCAGAGTCTAATCCA | 50975 & 50976 | ZNF385C | CAACTCACCAAGACGTGTTGGCA | CTGTAGGGGCAGGGCGGA | 51081 & 51082 |
| ZNF283 | CAATAGAGGAATCCCATGGAGCA | TCCCTGAATGTCACCAACCCA | 50977 & 50978 | ZNF385D | AAGCCCGGAATTGAAGTGGCA | TTCCGAGTTGACGTGCACA | 51083 & 51084 |
| ZNF284 | TGTGGTCTTCACCGACGAGGA | GGTGGGAAAGTTGATGCCCCA | 50979 & 50980 | ZNF391 | AGTCAGCATCAGGAGATCCAACTGA | GTAAGCGATAGAGTCCAATGA | 51085 & 51086 |
| ZNF285 | TAGACATCCCAGCTGTGGGAA | TCATCTGCAAAGGCCACCCCA | 50981 & 50982 | ZNF394 | TAAATGTGAGGAATGCGGGGGA | GAAGGTTTCCCACAGACGGA | 51087 & 51088 |
| ZNF286A | CACGCCAGATCCCAGGA | GGTTTGGAAACTGGAAGGCA | 50983 & 50984 | ZNF395 | CTTCAGCGAGCCCCAGCA | GCCATACACCTTGCGGCA | 51089 & 51090 |
| ZNF286B | GTGCCAGAGCATCCGTCAGATAGA | TGTGCAGAAACAGCACCAGATGGA | 50985 & 50986 | ZNF396 | GAATGGCCTCCAAGCTTGCACA | TGCACACTCGTCACATGCA | 51091 & 51092 |
| ZNF287 | TGGTGGTCCTTCGAAAAGGCA | AAGTCCTAACCTCACCAGGCA | 50987 & 50988 | ZNF397 | GATACCTTCAGGATCCTCCGGAA | GGAACTGCTCCAGTACCAGCA | 51093 & 51094 |
| ZNF292 | AACCCACCGAAAGGAGCA | GGGCTTCAGGAGGGCAGCA | 50989 & 50990 | ZNF398 | TCGGCCTGATCCGCCACCA | CAGCCGCCGGTGTTCAGCA | 51095 & 51096 |
| ZNF296 | ACGCCTGGGCCAGCA | GCTCCCAGCTGTCTCCACCA | 50991 & 50992 | ZNF407 | CAAGGACCGGTGTCACCA | GCACCATGGCCTGGACCA | 51097 & 51098 |
| ZNF30 | GGAAGACTTCACACTGCGAGA | ATGTACGGGTAAGCTGATGGCGA | 50993 & 50994 | ZNF408 | CCAGGCGAGACCTCAAAGAGCA | TTGCGATGCAGCCGCAAGGGA | 51099 & 51100 |
| ZNF300 | ACCTTCCGGGACAACAGGCAA | TTCTGATGAAGGCCTTCCCA | 50995 & 50996 | ZNF41 | ATGAATGCAAGGACTGCGGGAA | CTGGATAAAGGCCTTCCGGCA | 51101 & 51102 |
| ZNF302 | GGGCAGCCTTCAACCAGAGCA | TTCCTCCAGTGGCGACTGAGGA | 50997 & 50998 | ZNF410 | CAGCCCAGCCTTGCGACCA | ATCAGGCGTCGAAGACAGGGA | 51103 & 51104 |
| ZNF304 | ACCTGCGTGAACCGGGCA | TTCCTCCGCACGTAAAGGA | 50999 & 51000 | ZNF414 | CACACAGTCTCCTGGAAGGCA | GGTGCGTGCGGAAGCCGA | 51105 & 51106 |
| ZNF311 | ATGAATGTCAGGAGTGCGGGAA | TCCGACTGAAGGCCCTTCA | 51001 & 51002 | ZNF415 | TTGTAGGAGAGACAACGCGA | TGGGGTGGTGAAACTGAGGA | 51107 & 51108 |
| ZNF316 | TGTGAGTTCACGAAAGGTGGCA | TGGGGAAACCCGCTAAAAGAGA | 51003 & 51004 | ZNF416 | ATACCCTCGTTGAACATCGCGA | TCGGTGGAGAATTGAGGGCA | 51109 & 51110 |
| ZNF317 | AGTCAACGCTGAGACGACA | TGTGGATCCCCCTGTGCACA | 51005 & 51006 | ZNF417 | AACAGGAGTTGGAGCATGTGGAA | CGTCTTCCAAACTCGCGGA | 51111 & 51112 |
| ZNF318 | ACTCGGGTAAGCTCCAGACA | TCGAAGTCAGCGGGATCGGA | 51007 & 51008 | ZNF418 | AGGGTGTGAGGCATGGGGGAA | GTGAGTGGCCTCCTGCAGCA | 51113 & 51114 |
| ZNF319 | TGGTGCACCAAGCGCA | GCAGCAGCTCGCAGGA | 51009 & 51010 | ZNF419 | GCAAAGCAGGGAGGTTGGGAA | CCAGCATGAAAGGCCTCCCTA | 51115 & 51116 |
| ZNF32 | TTCACAGTGGTGAGAAGCCCTA | TTCCTGCACTGGGTACAGGCA | 51011 & 51012 | ZNF420 | TGTCAAGAGCCCAGGAGGAGA | CAGAGTCCAGGCATTCCCA | 51117 & 51118 |
| ZNF320 | GCAACGAGCAACTCTTGCAGGA | GCAAGACGTGAATCACTCCGGA | 51013 & 51014 | ZNF423 | AGCACAGCTTCGAGGGCA | TCTCAGGCCACTGTGAGCA | 51119 & 51120 |
| ZNF322 | TCACACCAGAGGATCCACA | GGCTTCGCTGGTGGACAAGCA | 51015 & 51016 | ZNF425 | CGAGTCCACACGCGGGGAGA | CCTCTCCCACTGCTGAAGGCA | 51121 & 51122 |
| ZNF324 | GCTCCAACCTGCAGCAGGA | CAGGTGCGAAGCCTTGCCA | 51017 & 51018 | ZNF426 | ATAGATACCCAGCCTACCTCA | CATACTAAGGCCCGAGTACTGA | 51123 & 51124 |
| ZNF324B | TCGCACCAGATCACTCAGAGA | TGGCGAAACCCTTGCCACA | 51019 & 51020 | ZNF428 | AGGAGACCACTTGACGATCCTGA | GAGCGGCCACAGAGCTGCCA | 51125 & 51126 |
| ZNF326 | AGGGCGGGTCTAGTGGGAA | CCCGAGAGCCTACAGGGTGCA | 51021 & 51022 | ZNF430 | TGGATGCCCTGGGGCTGACA | GCATTGCCCACTCCTCCAGAGA | 51127 & 51128 |

FIG. 1 (cont.)

| GeneName | Forward Primer | Reverse Primer | SEQ ID NOs | GeneName | Forward Primer | Reverse Primer | SEQ ID NOs |
|---|---|---|---|---|---|---|---|
| ZNF431 | GCCCTGGGGCTGAGAGGAA | TGCTGAGCAGGGTTCAGGCA | 51129 & 51130 | ZNF519 | GCCTAGACCCTGCCAACAGA | TTCAAGGCCACAGCTCCCA | 51235 & 51236 |
| ZNF432 | CTGGCTACCCTGGGAAGAGA | CACCAGTGAAGGGTGTCCACA | 51131 & 51132 | ZNF521 | CAGTCACCAGCAACCGGA | TGGAGTCGTACTGACACGGA | 51237 & 51238 |
| ZNF436 | AGTCCACACAGGCATCCGCTA | CAGTCATAAGGCCTTCCCCA | 51133 & 51134 | ZNF524 | GCCGTACCAGTGCCCA | CGTCCACGGCCGGTTCAGA | 51239 & 51240 |
| ZNF438 | TCAGGAAGAGTTGGTGCAGCA | AAGAGAAACGTGTGGAGGCCA | 51135 & 51136 | ZNF526 | AGCTGACCCATACGGGTGCA | GGCGACTGGCCGCAAGTGCA | 51241 & 51242 |
| ZNF439 | ATCACCCTCCTTGAGAACACA | CATCCCACTGTGCACTACCA | 51137 & 51138 | ZNF527 | GGAAAAGCCTTCAGCAGACGCA | ATTCAGGTGTGAGCGATAGCCA | 51243 & 51244 |
| ZNF44 | ACACACTGGAGATGGCCCTCA | CGAAGGGAACTGGAAGTACGGA | 51139 & 51140 | ZNF528 | CTGGACCCTGCGCAGAGGA | TCACTCTGCCAGTCAGGGA | 51245 & 51246 |
| ZNF440 | GAGGACCAAACCCAGGAGA | CCTAGGCCAACTTCTCCACACA | 51141 & 51142 | ZNF529 | GAACTGGTGACACTCAGGGA | AAATGGAACCTTCAAGGCCACA | 51247 & 51248 |
| ZNF441 | GAGGAACTGGACGCGCGAA | CAGCAAAGCCCACTCTCTCA | 51143 & 51144 | ZNF530 | TCAAACCTTCACCAGCTCCAGA | TGGCTGAAAAGTCCCTCCGA | 51249 & 51250 |
| ZNF442 | AACTCACACTGGAGAGAAGCCA | GCAGAAGGCAAGTGAGCA | 51145 & 51146 | ZNF532 | AAGAAACACCCCTGCCGCCA | GAGTCTGGGCAGTGCGAGCA | 51251 & 51252 |
| ZNF443 | TGCACACTGGAGATGGACTCA | ATGCCTTGAAGGGAACTGGA | 51147 & 51148 | ZNF536 | CAAGGAGACTCTGGGAGACGA | GGGATCAGGATGGGGACA | 51253 & 51254 |
| ZNF444 | AAACGTCCCTGAAACCAGCTCA | GCTTCTCACGGCGGGCA | 51149 & 51150 | ZNF540 | AGTGCCTGGACACTACCAGA | CATCCTCGCACCACGCA | 51255 & 51256 |
| ZNF445 | GAAAACCTGAGGCGGGCCA | TGATTGCGAAGGCCTTGCCA | 51151 & 51152 | ZNF541 | CTGGCTGGAACTGACGAGCA | TCCTGGCATCACGCTGGAGCA | 51257 & 51258 |
| ZNF446 | CTTTCCGCACCACCCGA | GCGGCCACAGTCACTGAGA | 51153 & 51154 | ZNF543 | CATACCTCACGTGGCACCAACA | GAACGCTTCCCACACTCCA | 51259 & 51260 |
| ZNF449 | GCAGAACCCCACTCTGGGAGA | CCACATGAGGGACATCCGGTGA | 51155 & 51156 | ZNF544 | GAGTGGACCGGAGGAGGCA | ACTTCCCCAAGTTCAAGCTCA | 51261 & 51262 |
| ZNF45 | TTCAGGGCCATCAGATAAGCCA | GCTACGACTGAAGCCTTACCA | 51157 & 51158 | ZNF546 | TTCACACTGGTGAGAGACCCTA | TCATAGGGTCTCTCCCAGGA | 51263 & 51264 |
| ZNF451 | ACAGCATGACCGGATGCCA | TAGAGGTGGAGATGTCCCA | 51159 & 51160 | ZNF547 | GAGGAGTGGGGGCATCTCGA | TTGGAGCCATGACCTGTGA | 51265 & 51266 |
| ZNF454 | CACCAAAGAATTCACACTGGCGGAGA | GTAAGTGAGGAGCTCACTGAGAA | 51161 & 51162 | ZNF548 | TCAGCACCCAAAGCAGCAA | GAGGGCCCTTGGTGCTGA | 51267 & 51268 |
| ZNF460 | ACGAACCCATCCAGAGTGGGAA | TGATGTCCGAGAGAGA | 51163 & 51164 | ZNF549 | GACCGCATTCAGACAGCAGGAA | GCATGTAGTCAGACGACGGA | 51269 & 51270 |
| ZNF461 | CCTGCGACTCCATACTGAGAA | GATAGCTAAAGGCCTTCCCACA | 51165 & 51166 | ZNF550 | GACGAAGGACGCAGCGCAGA | GGAACCCGATGCCTAGTGAA | 51271 & 51272 |
| ZNF462 | CGGGACAAGCATGGTGGGAA | TCGGGAACTGCTGAGTGCCA | 51167 & 51168 | ZNF551 | ATTCGACACCGCAGCATTCACA | TCCGGTGCTGAATGAGGCCA | 51273 & 51274 |
| ZNF467 | AAGAACCTGCCACGCACCA | GCAGTCCGGGACGAAGAAGGA | 51169 & 51170 | ZNF552 | CATGTGGCAGATCATCAGGGA | TTCGAAACAACGCCTCCTCA | 51275 & 51276 |
| ZNF469 | TCATGCACCGACCCAACCA | ACCCACCTTCACAGGCACGA | 51171 & 51172 | ZNF554 | GAAGGTGTTCAACCGAGGGA | AGATGGCGCGTGAGGGTGGA | 51277 & 51278 |
| ZNF470 | AAGGCATTCAGGCAGAGGGCA | GTAAGATGGGCAACCTGGCTGA | 51173 & 51174 | ZNF555 | GCCCTCAGCCAGATTCCACA | TCTTGAGGGGATGTGCGGCGA | 51279 & 51280 |
| ZNF471 | AAGCCTTCAGACAGCCTGACA | ATGTCGAGCAAAAGACGAGCCA | 51175 & 51176 | ZNF556 | GCCCTCGCCCTTCACAGA | GGAAGAGCAAAGCCCGCCTGA | 51281 & 51282 |
| ZNF473 | GAAGGCTTCCACCGACTCA | AGATGTGAGGGCCGGCTGAA | 51177 & 51178 | ZNF557 | ATACCTCAGACCGCCACTTGAGA | GAAAGAGATGACCTCTGTCCGA | 51283 & 51284 |
| ZNF474 | CCCCAGCCCGACCAAGGA | TGTGCATTCGGAAGGGGCTGA | 51179 & 51180 | ZNF558 | AGGGACACACACAGGGCGGAGA | TAGTGAGGCCAGGTTCCTGCA | 51285 & 51286 |
| ZNF479 | CTCAACCCTCACTGACCACAAGA | GATAAGCTAAAGGCTTGGCCACA | 51181 & 51182 | ZNF559 | CATGCGCATAACGGCCGCCA | GGTTGCTGAGGCCAGGAGGA | 51287 & 51288 |
| ZNF48 | CCACTCGGCCACTGAGA | CAGATCTGAGGCCTCCGGGGGA | 51183 & 51184 | ZNF560 | AGCCTTCACAGAACGCTCGA | AGGAGAACAACAAAGGCTTTCCCACA | 51289 & 51290 |
| ZNF480 | GAATTCTCTCAGGCGGAGTGGA | GAGAGATTCCCAGGGAGGACCA | 51185 & 51186 | ZNF561 | TGTGGACTTCACCCAGAGGA | TGTTCCCTGAAGACCTCTCA | 51291 & 51292 |
| ZNF483 | CTGACCCAGGAAAGCCTTCACA | CAAATCCTGATCTCCCCAGGGCA | 51187 & 51188 | ZNF562 | ATGAGAGCTTCAGATGGAGGGA | AGATGCACAGAAGGCTGAA | 51293 & 51294 |
| ZNF484 | GAGTGTGGAAAGGCTTTGGGA | CCTTCGAGTCCCCACACA | 51189 & 51190 | ZNF564 | GACCCGGGACACCCTGGA | CCAGCAAAGCCACTCCTCAA | 51295 & 51296 |
| ZNF485 | CCCTGGACTGAGGTGCAGA | GTTCGCTTCCCAGAACAGA | 51191 & 51192 | ZNF565 | AGAGCAGGGAGACTGGTGAGA | AGGTGTGAGCAGCCGGCTGAA | 51297 & 51298 |
| ZNF488 | TCACATGCCATCCACCACACA | AGGTGGTGGCGTCCCGGAA | 51193 & 51194 | ZNF566 | CTCGGCTCTCAGGGGGGACA | GATGGTGACTCAAAGTGGGCA | 51299 & 51300 |
| ZNF490 | AAGGCGCGACAGGAACAGGA | CACAGCCACATCCTCAAGGGA | 51195 & 51196 | ZNF567 | ATCACCGAACTCACACAGGGAGA | TCTGGCGAAAGGACTTCCCA | 51301 & 51302 |
| ZNF491 | GAAAGGACTCACGCTGTGAGA | CGAATGAAGGCTTTCCCACA | 51197 & 51198 | ZNF569 | CAGCCAGAAGACAAAGCCTCA | GAGCAAGGGATGCAATTCGA | 51303 & 51304 |
| ZNF496 | GAGCAGGAGAAGCCCCACGA | CAGGTGGGAGTTCAGGCGGA | 51199 & 51200 | ZNF57 | TCACACCTACACAGTCACGGA | TCTAGTGAAGCTTGCGAACCCA | 51305 & 51306 |
| ZNF497 | CACTGCACCCGGCATCTCCA | GGGATAACTGGGCAAGGAGCA | 51201 & 51202 | ZNF570 | GTAGGAAAGGATTCAGGCCAGA | TTGGGCAAGGGATCCA | 51307 & 51308 |
| ZNF500 | GCGACGCCCAACTTCAGCA | TGTCCTGGTGGATGACCA | 51203 & 51204 | ZNF572 | CGGAGGACCCACCAAGTAGGA | CCCAACGTGGGAGAGCTCAA | 51309 & 51310 |
| ZNF501 | TTCACAGAGGAGAGGCCTTGACA | AATAAGGGATGGGCTTCTGACA | 51205 & 51206 | ZNF573 | TTGGAACCCACCAAGTAGGA | TCCCACTCCTGCCGAAGA | 51311 & 51312 |
| ZNF502 | TACTGGAGAGAGAGCACCCTACACA | GATTGCGGAAGGAATTCCCACA | 51207 & 51208 | ZNF574 | AATACCCCTACAAGTGTCGGA | TCGTGTGCCTGCAGTCGAGCA | 51313 & 51314 |
| ZNF503 | TGCAACTGGGTGTCGGCCAA | AGAGAACGACGAGCTGGGGTA | 51209 & 51210 | ZNF575 | GAGCTCAGAAGCCCGAGGAA | AGCAGAGCCAGCGCTGTCAA | 51315 & 51316 |
| ZNF506 | CTGAGCAGTGCACCCGGGA | CTGACCAAAGTCTTGGGCA | 51211 & 51212 | ZNF576 | AACCACTACTTGCCAGCCA | CTGAGCAAAGTCTGACGCGA | 51317 & 51318 |
| ZNF507 | AGGACAACGCCCAGTGCCAA | GTGTAGTGACAGGGGCGGCA | 51213 & 51214 | ZNF577 | TCATGGTCCATCAAGAGAACCCA | TCCCACACACTGCACCCA | 51319 & 51320 |
| ZNF510 | CACTGTGGGCTTAGCCACGA | TGAAACAGCAGTACCCCACTGA | 51215 & 51216 | ZNF578 | GAAGCGATACTTGCACGCCA | CTACATGCGATGTCAGGGA | 51321 & 51322 |
| ZNF511 | CATCTGGGCCTTACCACGA | GTGCAGCCTTCACAGA | 51217 & 51218 | ZNF579 | CGGACAGTTGGCACGGGA | CCAGTGTGTGAAACGGGGA | 51323 & 51324 |
| ZNF512B | CTCCCTACCTTCAGCCAGGAA | ACAACGAACCAGTCCTCAGA | 51219 & 51220 | ZNF580 | CGTGTCGCACTCGGACCTCA | CTCCGCGGCGTCCTGGAA | 51325 & 51326 |
| ZNF513 | GGTGTGGAGCGGACCCAA | CGGTCTCGGGCACAAGGTCA | 51221 & 51222 | ZNF581 | AGCATCACCACTCGGAGGTA | GCATCCCGGAAGCGGCGA | 51327 & 51328 |
| ZNF514 | GCGCTATACCAGCGGGCCA | GGCTATGAGGTGGGGCCCA | 51223 & 51224 | ZNF582 | TGGCACCTGCTCAGGAGGA | CAATACTGGACACAGGCCTCA | 51329 & 51330 |
| ZNF516 | ATCAGGATGTCACACTGGAGA | TCTGGCTGAAGGCTCCCA | 51225 & 51226 | ZNF583 | GGAGCTGAAGGAGTAGGACAGAA | CAGCCACATCCCAAATGTCACAA | 51331 & 51332 |
| ZNF517 | AGAGGGACACTCCGACGGA | CACCACTGAGTGTGCCCGCA | 51227 & 51228 | ZNF584 | AAAGGCCTTACGAGTGCAGCAA | GATAGAGGCCTGAACGGGTCA | 51333 & 51334 |
| ZNF518A | AAAGCCGACTAACAGGGTACAGGGA | GACTACAGCGTACAGGCACAGA | 51229 & 51230 | ZNF585A | ATGAATGCAGCCAGTGTGGGAA | TGGATGAAAGCCTGTCCGGA | 51335 & 51336 |
| ZNF518B | TCAAATGTGGCACATCTGGGTGGA | TGTGCCAAACATCCTGGGTGGA | 51231 & 51232 | ZNF585B | CAGCTCCAAGTGCATCAGCGA | TGAAGAAAGCCTTTCCCACAGA | 51337 & 51338 |
| | ATAGATCTCAACAGCCTGGGGA | CCAAAGATGACGGCTTCCCACA | 51233 & 51234 | ZNF586 | TCCTGCCTCACTGAACCCAGA | TGTCTGACGCGTCAAGAGTGA | 51339 & 51340 |

| GeneName | Forward Primer | Reverse Primer | SEQ ID NOs | | GeneName | Forward Primer | Reverse Primer | SEQ ID NOs |
|---|---|---|---|---|---|---|---|---|
| ZSWIM1 | CTGCGCACATCCTAGCCA | ACTCCACTTGCTGCCAGGA | 51765 & 51766 | | GPR33 | TGCAAGCATCAAGGCAGTGGA | AAGGCAGAAGAAAGCCCAGCAA | 51871 & 51872 |
| ZSWIM2 | GAGAGGCTCAGCTGGCACCA | CCTCCCTCAGCAGGAAGCCA | 51767 & 51768 | | CXCL1 | CCTGCCTTATAGGAACAGAAGA | GATGCTCAAACACATTAGGCACA | 51873 & 51874 |
| ZSWIM3 | TGATTCAGGGACCTAAGCAGGGA | AGGGGCAGCCCAGATATCCA | 51769 & 51770 | | CXCL2 | TCTCAACCCGCATGCCCA | CTCCTTCAGGAACAGCCACCA | 51875 & 51876 |
| ZSWIM4 | TGTGGCCCGCTATATCGGACA | AGCGGCGCAGAATATCGGACA | 51771 & 51772 | | GTF2H2 | CTGCCCACAGTGTTCGGGCAA | AAGACGTGCCAAGTGGGGA | 51877 & 51878 |
| ZSWIM5 | CCACAGCGCGTATCCACACA | GAGCTCATGTAGCGGGCGA | 51773 & 51774 | | GZMM | TCAGGAAGGTACCGGCCAA | CACCCACTGCACCCTGGA | 51879 & 51880 |
| ZSWIM6 | CCACCTGGCCATGACCA | TCTCCCATGAAGTCCACCA | 51775 & 51776 | | HCRT | CCGTCGCCCGAGAGACA | GGCTGACGCTGGGTGGGCA | 51881 & 51882 |
| ZSWIM7 | GCCGGCGGGTTGTGGAGGA | CCAAGGCTTGGGTGGCTGA | 51777 & 51778 | | HHEX | GGAAAGGCGGCCAGGGTGAGA | TCTTCCGGGCGGAGAGAGA | 51883 & 51884 |
| ZSWIM8 | CATCCTACCACACAGAGCA | GTGGTGCAGCTGTGGGGA | 51779 & 51780 | | HLA-DRB4 | CTCTGGACTTCAGCCACCAGGA | AGCTAAGGAAGCCACAAGGGA | 51885 & 51886 |
| ZUF5P | AAAACAGTCCAGCCTGACCGAA | ATGAGCCCACACATAGGACA | 51781 & 51782 | | HLA-G | CCCACCCTGTGCCACCA | GAGACAGAGACGGAGACATCCCA | 51887 & 51888 |
| ZW10 | GTGATGGATGAAGGACCCA | CTTCACTGGAAGAGAACGCA | 51783 & 51784 | | HMX1 | GGTGGAGAAAGGACCCTTGGA | CAACAACCCGAGGCTGCGA | 51889 & 51890 |
| ZWILCH | AGTTGGGAAGGCAAGGCAA | TGATAAGCTCAGCTCTAGCCA | 51785 & 51786 | | HOXB8 | AGCATGCGCGCTGTGGGCAA | CTTTTCAGGCGCAGCAACAGA | 51891 & 51892 |
| ZWINT | CGAGCCGACAGAAGGCAA | AGGGCCTTGGTGAGGCCA | 51787 & 51788 | | IRF8 | CCCGCATTCAGAACTCCCA | GGCATGGTGCTGGGAAAAGGA | 51893 & 51894 |
| ZXDB | GCTCGACTCTGGCAGGGCA | CATGGCCAAAGAGTCCAGAGA | 51789 & 51790 | | IFNA6 | CCAGTTCCAGAAGGCTGAAGCCA | CATCAGGGAGAGTCCCTCCCA | 51895 & 51896 |
| ZXDC | CTTCGAGCACCCCCGAGA | GGCAACGTGGACTGGGGCA | 51791 & 51792 | | IFNA10 | GAGGTTGGGGTGGAAGAGA | GACAACCTCCCAGGCACA | 51897 & 51898 |
| ZYG11A | ATAGCCCACTTGACATCTGACA | GATACATAGCCATAGTGCCCA | 51793 & 51794 | | CXCR1 | GCTCACCAGTCTCCTCCAA | CCGACAGGGCCTGTCTTCCA | 51899 & 51900 |
| ZYG11B | AAGCGTTACAGTGAACGGGCA | AAATGGGTCACATCAGCCAGGA | 51795 & 51796 | | IRF6 | TGGAGGTAAACTGGGAGCA | GGTGCTATGGGAACATACAACCA | 51901 & 51902 |
| ZYX | CAAGGCCTATCACCCGCA | TGTGGTAGTCGGGGACACA | 51797 & 51798 | | KCNH1 | GCACACTTGATGCCCAGACA | TCTCCCCAGGTGGAGGGCA | 51903 & 51904 |
| ZZEF1 | CTGAGCCAGTACTCCAGA | CTTTCAGGGAGCCAGGGACA | 51799 & 51800 | | KCNJ11 | GGCTGGAGTGCCCAGAGA | CCCAGGCAGGGCTCTCCA | 51905 & 51906 |
| ZZZ3 | GGCAGGCACCAGAGAGAAGCA | GTCCATACGATCTCAGGCA | 51801 & 51802 | | KIR2DS3 | ATTCTGACGAACAGGACCATCAGGA | TGGGCCTGGAGAAGGGGA | 51907 & 51908 |
| ADR8K2 | CCCCACATCAGCCTTGCCA | GAAGGGGGAAAAAGTCACACTCAA | 51803 & 51804 | | KIR2DS4 | CTGCCTGCTGGAGAGAAAACACA | GCAGCTCAGGTAGACTCAGGA | 51909 & 51910 |
| ALDH2 | CTGCAGGCACTGAAGTGCCA | CCATAATGGCTGAGGAGGA | 51805 & 51806 | | KLRC3 | TCCAGAAAGCTCACTGCCGA | TCCTCAGGCAATGGCCACAA | 51911 & 51912 |
| AMELY | CCACTTGTGCAACCATGCA | CAGGGGCCTGCAGGGGAA | 51807 & 51808 | | KRT14 | AGGCCCCCGTGTGACACA | GAGGGGTGAGGGTGAAGCA | 51913 & 51914 |
| AQP1 | CTGGCTACTACCGACCGGA | GTGTGTGATCACCGCGGA | 51809 & 51810 | | LGALS9 | CACCTTGCACCGTGCACCAA | GAGCCAGTCTCTGAAGAGAACA | 51915 & 51916 |
| AQP2 | CAGCTGTCGTCACTGGCAA | CGAGTGCAGCTCACCGA | 51811 & 51812 | | MAGEA5 | CTGAGCATGAGCTGCAGCCA | TAGTGGACCGAGCCTGGAA | 51917 & 51918 |
| AQP5 | CAGAGCTCCTTAGGAGAAGACAGA | GTAGCCCACTCTAAACACCA | 51813 & 51814 | | MLN | CGCTGGGGAGAAAGGTGGACA | CCTTCCAAGCCCAGCTGGA | 51919 & 51920 |
| ATOH1 | CTGACAGCGATGATGGCGCAA | GCAAGATGCTCCCGGGGAGA | 51815 & 51816 | | MAP3K11 | GGCCTCAGCTGTCACCAGCA | GGATCCGAGGCTAAGACTCCA | 51921 & 51922 |
| ATP4B | TCCCTGCCAAATCATCCCAA | AAGGAAGAACTGATACTCGCGAGCA | 51817 & 51818 | | MT1A | AAAGGGCCATGCAGAGAAGTGCA | CGAGCAGGGCTGTCCGGACA | 51923 & 51924 |
| BNIP3L | GGGGGCTGAGAACAGGGTGTCA | CTTGTGGGGAAGGGGTGTCA | 51819 & 51820 | | MT1B | GCCGGCTCTCGAAGTGCAA | CTGGAGCGGGGCTGTCCCA | 51925 & 51926 |
| BSG | CATCCGGGGCAGCTCTGGA | CTCCAGGGGTAGGGGACACGA | 51821 & 51822 | | MT1E | GCTGGTCGTGCAAAGGGGCA | TGTTCCACATCAGGCACAGCA | 51927 & 51928 |
| C4A | GCAGCTGTGCCCAGCTCAA | TCCTCCAGCGGAGGTGGGA | 51823 & 51824 | | MT1F | CACGCTTCACCTGCCCA | GGCACACTTGCTACAGCCA | 51929 & 51930 |
| C4B | CTCGAATAGCTGGATCGAGGAGA | CTGGCACCCTGAGTGCCA | 51825 & 51826 | | MT1G | ACCTGCGCCAGCTCCTGCAA | CTGTCCGGACATCAGGCGCA | 51931 & 51932 |
| S100G | AATAGAACCCTTAGGAAGAAGACAGA | CCACATAGGATAAGACCAACAGCACA | 51827 & 51828 | | MT1H | CTGCAAAGGCGCCTTCAGGAGA | TGACAGCGCAGTGTCCGCAA | 51933 & 51934 |
| RUNX1 | GTCCACAGTTCCACGGTACACA | CTCAGGCTGGGCACGACGAA | 51829 & 51830 | | MT1M | ACCGGCTCCTGCAAGTGCAA | TGCAGACACAGCCGTGGGCA | 51935 & 51936 |
| CDH11 | TCTGAACGCCGGCCTGAGCA | CAATGACCAGGAAGAATGACGATGCA | 51831 & 51832 | | MT1X | AAAGGGACGTCAGAGAAGTGCA | AGAGCAGGGCTGTCCGGACA | 51937 & 51938 |
| CHI3L1 | TTATACCCCTGTCAAAGCCCA | GGGAAGTAGGATAGGGGACACGA | 51833 & 51834 | | MT2A | AGGGGCGTCGGAACAAGTGCA | CTGGAGCTGGGGCTGTCCCA | 51939 & 51940 |
| CHM | GTCACACAAATCAGGGACAGTAGGA | GGGCAAGGCCAATATCCGGTACA | 51835 & 51836 | | NEK1 | AACAGGCCCATCAAACTCCAGA | CTATAGTCCTCCACTGCCCA | 51941 & 51942 |
| CHRNA5 | GACCAGGTAGCAACACTGACAGAA | CCTCCGCCTTCCAAAGAGCA | 51837 & 51838 | | NEUROD2 | CTGGTGGGGTGGGCCGGGAGGA | CCTGCCTCCGGTGGGCAGA | 51943 & 51944 |
| CRYBA2 | GGGTGCTACCACTCACCCA | GCCGAGCTCACCGTAAGTACA | 51839 & 51840 | | NHLH2 | CAAGTAGACACACTTGGGAGGA | AAAGGGCCTTCGCTGCA | 51945 & 51946 |
| CRYGD | GAGCTGTCCAACTACCGGCA | TCAGAGAGCCCACTTCTGGCA | 51841 & 51842 | | NOVA2 | CACCCACTCACCACCTCCA | AGGTGAAGTGCCGAGGGGA | 51947 & 51948 |
| CSHL1 | CTCATCGAGTCGCGGCTGGA | CTTGAGGGTCTGCCAGTCA | 51843 & 51844 | | NRD1 | GGGGAGGAGGTGGATAGGAA | CTCGTGGGCAAGGCGGTCAA | 51949 & 51950 |
| CTSS | AGCTGTGGCCAATAAAGCCCCA | TTCACCAAAGTTGTGGCCCA | 51845 & 51846 | | PC8P2 | TGCGAACCCAGTGGAAGGA | CATGCCACCCGTCTCCGA | 51951 & 51952 |
| CYB561 | CCTACACAGCCTCAGGGAGA | GTAGCGGCTTGCGGGA | 51847 & 51848 | | PCK2 | TGACAGGCAGGTCAACCAGGA | GACTAGGGCCTCAGGTCACA | 51953 & 51954 |
| CYP24A1 | CATATCCAACTCAAGGGAAGCGGA | GACACAGGTGAAGTGTAAACCAGCA | 51849 & 51850 | | PDGFRL | TGGCCTCCCCAGTCAACCA | CTCCACATGCGGCTCCCCA | 51955 & 51956 |
| DCT | AAACTTCCAGGTTGGCCACAA | CAACAGCACAAAAAGACCAACCA | 51851 & 51852 | | SLC26A4 | AAGGCAGGAGAATGGCGTGAA | GCTGGAGTGCAGTGGCACGA | 51957 & 51958 |
| DUSP4 | AGCCTGGTCAGGGGTTCAAAGAGA | GGAAGCGGGGGTTCAAGAGGA | 51853 & 51854 | | PFDN4 | AAGAGGGACGGAATGTGGAGACA | ATGCCGCGTTCGCCCCCGA | 51959 & 51960 |
| EVX1 | GGGAAGAGAGTTTAGGAGGTGGGAA | ATACCAATGCAAAGGGTAGGGCA | 51855 & 51856 | | PHB | GGGCTGAACATGCTGCCAA | AGAAGGGCAGTCTCTGAACGA | 51961 & 51962 |
| PKBP1B | GGAACTTCAAGGTGGCTGGAGA | TACAGAGCAACTTGGGCAGAGAGAA | 51857 & 51858 | | PIM1 | GTGGGTTGATGGGAGGGGGCA | AAACACAGCCCAGAGAGGA | 51963 & 51964 |
| FOXD4 | AAAACACAGCCTCCGATGCCAA | CATCCCTATCAGGAAGACACAGAGA | 51859 & 51860 | | POU1F1 | CAAGCAGGAACCTCAGGCGGA | AGAGCATGCACAGCTGCCA | 51965 & 51966 |
| FUT6 | CGCTTGAACCAGAGAGTCGGA | GCTGAGCTAGGAGTGCGCGA | 51861 & 51862 | | POU5F1B | AGGAGCTAGGGAGGAAGAAAACCTGGA | CCCAAACTCCCCTGCCCA | 51967 & 51968 |
| GCK | GCTCTGGAGAAGTGGTGGGGAA | GCGTTCCACTGACAGGAGCA | 51863 & 51864 | | PSG11 | ATGGGGAACAGGGGAGGGGA | AACTTAATCCCAAAAGCCCTGCCA | 51969 & 51970 |
| GFI1 | CACCGGCTACCAAGGTACCA | CCAGCCACTTGGAAGTGCAA | 51865 & 51866 | | TAS2R38 | GCAAACTCTACCCACCAGCACA | GGCTGAGTTACGAGCAGAGCA | 51971 & 51972 |
| GNB2 | GGGGATGGAATGGGGAGAAGGGA | GGGTGAGGCCCAACCCCA | 51867 & 51868 | | PTM5 | GTTGAGGAGGCTGTGATGACCA | CTCAGCAGTGTCCGGGAA | 51973 & 51974 |
| NPBWR1 | CACCACCGACCTTCCCGCAGA | CCTGCGAAGCTGGCGTCCA | 51869 & 51870 | | | GCTCTCCAGCTGCCCCCAA | GGATCTGAGGGAGGATCCAGGGA | 51975 & 51976 |

| GeneName | Forward Primer | Reverse Primer | SEQ ID NOs | GeneName | Forward Primer | Reverse Primer | SEQ ID NOs |
|---|---|---|---|---|---|---|---|
| ELMOD3 | CCCCCTGACCCCGCTCCA | GTGGGGGCTAGGATGGAGCA | 52401 & 52402 | SLC25A29 | TTGGGGCTGGGCGCAGAGGA | CAGCGACACCAGGCTGTGCA | 52507 & 52508 |
| MFSD14C | GAAAAGCAGAAGATGGAGTAGGA | CAAGGCACAAATCACACAAACCA | 52403 & 52404 | HIGD2B | CCACTGGCCCTACCATGGGA | TAAGCAGGGGAGTGGAGGGA | 52509 & 52510 |
| ZDHHC16 | CCCAGACTAGGGGTCAGGCA | AAGTAGAAGAGGTTGTGGCCAA | 52405 & 52406 | FO:PNL | TGAAGAGACAGGCTTTGGGAGA | AACCGAGGGCCACAGGAGA | 52511 & 52512 |
| LCE3D | AAGGGCCCAGGAAAACCCA | GTCAGCGCAAAGCCACTGCCA | 52407 & 52408 | HEXIM2 | GGCTTCGTCAGGAGAACCAAGA | GTCCACCAGGCTGGGAGGCA | 52513 & 52514 |
| ZNF607 | AAGCTGGAAGCTGCAGAAGACA | GCTGGGGCCTCACTAGGGCA | 52409 & 52410 | C17orf49 | CTGCACGAGAGAGGGCTGAA | TCAAAGGGGTTGGGGGCAGA | 52515 & 52516 |
| TUBA3C | GACCTGGCCAAGGTACAGAGA | CCACGTACCAGTGAACAAAGGCA | 52411 & 52412 | MBD3L2 | GCCAAGGCCTTGCAGGCGA | AAAGAAAGGGACCGAAAGCCAAGCA | 52517 & 52518 |
| AGBL4 | GACGAGTTCCACCCAGGGGAA | TTGAAGACCAGGTATTCCGGA | 52413 & 52414 | PLK5 | TGCCAGGGACCCAGGCTCA | TGAACAGTCATGCCACAAGGCA | 52519 & 52520 |
| ZSCAN10 | ACAGCGGAAGGCAATGCTCAGGAA | CCAGAAAGCAATGCTCTGGCCA | 52415 & 52416 | C2CD4C | GTGCCTGCATGGAGAGAGA | GGGGGCTACTAAACGGGGGA | 52521 & 52522 |
| MEDAG | CCATGTAGAAGGAAGCCAGGAGA | GAGGACGCTGCCGTGTCCAA | 52417 & 52418 | OR2AJ1 | TTTCAACTCCACAGTCCACACA | GAAGCAGAGATCAAGGAGGAAAGGGA | 52523 & 52524 |
| FBXL20 | GCCAATCTCTGGAGCCGACA | CAAGCGCCAAAGTACTGGGTGGAA | 52419 & 52420 | BHLHE23 | CTGGGGCCCTGCCCTGACAA | TCACAGGGGCGATGGGAGGA | 52525 & 52526 |
| HIST1H2AH | CAACTGGCCATCCGCCGCA | CAAGACACCCACCCTGCGCA | 52421 & 52422 | MIR1-1HG | GGGCAACAGCTCAGCGGGAA | TAGCAGGAGGGGCGTTCCA | 52527 & 52528 |
| KRTAP9-4 | TCTACTTGAGGGAGGGCAGAA | ATTGAGAACACGAAGCTGGGTGGCACA | 52423 & 52424 | NMS | CGCCAACAGGCGGGATGAAGAAGAA | AAAGGAAAAGGGTGCGTCCCA | 52529 & 52530 |
| BAGE5 | AACAGGGCGTGGGTCTGGA | CCCAAGCAATACACAGCTCCA | 52425 & 52426 | TRIM43 | ACAGGCTCAACGCCTTCCGA | GAGAAGACCCTGGCTCCCA | 52531 & 52532 |
| BAGE4 | GGCGAGGGTGGCCTGCAGGGCAA | AGTAGACACCCCCAGGCAATACAACA | 52427 & 52428 | TMEM19B | GAGCTTCCGAGACCGGCCAGA | GGCCTGAGCAGGCTGTCAGA | 52533 & 52534 |
| BAGE3 | GGGGTGAGGTGGCCTGGAGGCA | AGTAGACACCCCCAGGCAATACAACA | 52429 & 52430 | C3orf49 | GAAGTCTTTCCCACCCCCA | TAGGGGGACAGAAGTTACAGGCAGA | 52535 & 52536 |
| BAGE2 | TTGGAGCATCAAAGTGGGGCCA | CCCAGGCAATACAACAGCTCCGA | 52431 & 52432 | OCIAD2 | CATCCAGAGAGCAGAGATCTCAA | AAATCCCAAGAGACACGAAGTGCA | 52537 & 52538 |
| CFAP74 | TAGAGCCTGGGAGCCTGGCCA | GCTGCGGGGTGCAGGGCA | 52433 & 52434 | PDCL2 | GAGAAGGTGTGGGGTCTCCA | AGAGCCCGGTCGTCTGCA | 52539 & 52540 |
| DISP2 | CCAAAACCGGGCCAGGCA | CCAGGGTTGTCGCTGAGGA | 52435 & 52436 | AS810 | CCCAATGCAGAAGAAGCGACCGA | GCTAGAAGGGGGCTGTCTGGGA | 52541 & 52542 |
| GALP | TTGCCAAACCAGAGATTGGAGA | AAAGGTTTCAGAGGGGAGCAGGA | 52437 & 52438 | TMEM71 | GAGTCAGGGAAGATGAATGCAGA | AAGCTGTCAACTGGGACTGAAGAGA | 52543 & 52544 |
| ARHGAP11B | GCAGAAAAGAAGGGCGTGTACCA | TCCAGTGATGGAGTAGCACAGA | 52439 & 52440 | PRSS47 | CCTTCACATACCCCACCCA | ACAGCAGCTAAAGGCCCGA | 52545 & 52546 |
| UBE3B | CAGTGAGGGCTGGGAGAGA | ATCAAGGTGTCAGTGAACACCA | 52441 & 52442 | PPP4R3C | AAGGCAAGGTAGACTCTCCA | CTAAACGAACCACACTCTACCA | 52547 & 52548 |
| SAPCD2 | GAGCAGAGCCAGCGCCGA | CGGCTGGCACAGGCTGCA | 52443 & 52444 | MAGEB16 | GAAGAAGAAGAGAGTCTAGAGCCAGAA | TAGGTATGGGAGAAGTACAGACA | 52549 & 52550 |
| C19orf52 | GACAGCAGAACGACTTGACACA | CATGCCAGGCACAACCCAA | 52445 & 52446 | TCEAL2 | CCACGAAGGGACACTGAAGACA | CAAAACGCTACTGGTAGCAGGA | 52551 & 52552 |
| ERVH48-1 | GGAGCCCAAAGATTGTGAGAGGAGA | AGTGCGATAACCCATGAACCA | 52447 & 52448 | SLC32A1 | CGTGGTGGTGAGTGGCAA | AGTGGGCCAGAGTGCACA | 52553 & 52554 |
| ZNF486 | AGGCTGAGGCAGAGAATTGAA | CCAGCTGGACAATGGTGCA | 52449 & 52450 | MOL4L | AGTCTCACAGGATGAGCCCA | GCGTACACAGGGTCTGGGA | 52555 & 52556 |
| SCARF2 | CGGGACCTCAGGGGCGA | GCCAAGCCCCGCCGGGA | 52451 & 52452 | R3HDML | ACACCTGGCATCCGGCGGCA | TAACTGGGGGACAGGAGGGA | 52557 & 52558 |
| RNF185 | ATCCTCGGCAAGCTCACCA | GGTGCAGGAGGAGGGTGGA | 52453 & 52454 | FRMPD2 | CCCATACCAGGAACCCAGA | CAGACTCGTCACATGGCAAGCA | 52559 & 52560 |
| TPGS1 | CGCCCATGACCCGCGAGGA | CAGGGCCTCACAAGGCCGA | 52455 & 52456 | GLIPR1L2 | CCAGACGAGGAGGACGTAGA | GGGAATGACGCTGCCCCCGA | 52561 & 52562 |
| RIPPLY1 | AGGGAAGGCAGTGTGTAGAGAA | CAACACACAGACTTCAATGGACA | 52457 & 52458 | GCOM1 | TCTGGTACAGGAGGAAGCCCAA | CAAGGAACTCAAGCCAGGTGATGCA | 52563 & 52564 |
| SCGB3A1 | GGAGCATCTACACCTGAGGACAAGA | ATTGAGAGGGGCCGGGGGAA | 52459 & 52460 | TOM1L2 | CCTCCAGGCTCTCCGGAGA | TCCAGAACCAGCTCTGCCCA | 52565 & 52566 |
| HIST1H2A | CTGCAGCTGGGCATCCGCAA | CAGGAGCCACCCTGCGCAA | 52461 & 52462 | C19orf84 | CCATCCCCACAAAGAACCGA | AGCAGGCAGTGGGGTGGGGA | 52567 & 52568 |
| TBCK | GCCTTCACTTGCAGAGAATTGAA | CCACATGCCCACGATGACA | 52463 & 52464 | ZNF534 | CAGAGAAGCTTACAAATGCAGCGA | CAAGATGGCGGCTAAAGCCTGAACA | 52569 & 52570 |
| ACP4 | CTGCATCCCCCAGCTCCA | CTCACACGGGGCCCCCA | 52465 & 52466 | LYPD4 | GTGGGCGAGCACATGAAGGA | GTAGAAGCAGCCAAGGGGGCA | 52571 & 52577 |
| ATPIF1 | AGCACAGAGTAGAGAAACACTGGCA | CTACACAGAAGTTGGGCAATGACA | 52467 & 52468 | CDC42EP5 | GCCCAACGCGGACCTGA | CGGAAGGGGCGGGGGAA | 52573 & 52574 |
| CMTM1 | TACCCCGAAACCGGCCCGA | GTGGGCTCGGAGCAGCGA | 52469 & 52470 | ZNF98 | GGACCCTTGGAAGCCTAGA | TTGCCACTCTTCGAGAGAGA | 52575 & 52576 |
| ZNF257 | GGGATTACAGGGACCACTGACA | GACAGGCAATACCCAGGAAGACCA | 52471 & 52472 | SYT6 | CCCAGCACCCTCAAGGTAGA | CAAAGCTCACAGCAACAACCCGA | 52577 & 52578 |
| PTPMT1 | AAGCACTGGATGAGTTGCGGAA | TGGTGCCAACTTCAAGGGGA | 52473 & 52474 | GCSAML | ACAGAACACGTACATCCTCCAGAA | AGGACTGGTGAAACTCAGGGAA | 52579 & 52580 |
| PCMTD1 | AACTGGCAGAGAACACTTGGGAA | AGATTCCTGCAGACAGGGA | 52475 & 52476 | CCDC27 | GTGGCCCTGGAGAGCCCCA | GCCAAGACGTTGGTCCCGA | 52581 & 52582 |
| ARHGAP33 | GAGGGCTAGGGTGACCCA | TGTGGGAAAGGGGTAGGA | 52477 & 52478 | NBPF12 | AGGACCTATAGGCACTCTGAAGA | AGCACAGGTTGCCACTGGCA | 52583 & 52584 |
| TM4SF19 | GAACTGGGCTCTGGGAGGA | GCTCCAAGTAAAGCCAGGCCA | 52479 & 52480 | LIP1 | AAGGTTCTCAGAAAAACACCA | GGAGTCAGAATGGATGACATCCACA | 52585 & 52586 |
| TLCD1 | GACAAGAAAAGCGGACAAAGGCCA | GTGAGAGGGCTGGCCTCAGA | 52481 & 52482 | LOC150051 | TTCGCCCCGGGAGCTGGGAA | GATGGGAGACGGGTTAAGAAGAAGGA | 52587 & 52588 |
| SLC26A8 | GACCTAGACTGGATACGAACTAGCA | GTATGATCCCAGCGCAGAGA | 52483 & 52484 | CBWD2 | ATGACGTCAGGCCCCGGGCA | CCTCAGCTGAACGCTGGGA | 52589 & 52590 |
| ZNF837 | AACGAGCACCGGAAGCGGCA | AAAGGCCCCTCCTCGACGCA | 52485 & 52486 | OTO5 | CCACTTCCCCTGGGGAGCA | CCATGCCTGTGGAGGCCCGA | 52591 & 52592 |
| MRGPRE | GCCAGCCGGACCCTGGAGGA | TCCAGCTGCCTCCCAGGGGA | 52487 & 52488 | WTH3DI | TCAGGAGCAAACAGTCAGCGAA | TCTCCACGAGACAGGCAGCA | 52593 & 52594 |
| WFIKKN1 | GCGAGAAGCGGGTCAAGAAGA | CACCAGGCGGGGTGCGCGCA | 52489 & 52490 | GDF7 | GCTGGTGTAGCCACAGCAGA | AGCTGGCCTGGGGCATCGGCA | 52595 & 52596 |
| MMP21 | ATCAGGGCCCTCACAGAAGATGAACA | TAAAACGCCTGTGTCTAGGGGA | 52491 & 52492 | C3orf79 | GAGCCTCAGTAGGAGCAGA | AGGAGTAGGCAGAAGATGGCA | 52597 & 52598 |
| FRA10AC1 | CAAGGGGGGCGGTTTCCCCA | ATGGCTCGGAAAGCTCAGAA | 52493 & 52494 | PYDC2 | TACAGACGCTCTCCCCAGACA | CCTGCCCAGTAGCTGCAGGA | 52599 & 52600 |
| SLC36A4 | GTCAGAGGAAAAGAGGGCCTAGA | CTGGCCTGGAGTCAGAAGGA | 52495 & 52496 | CCDC27 | CTGGCGTGCGGGGCCGA | GGGATGTCTGCAGGCCAACA | 52601 & 52602 |
| CCDC38 | GAAATGGCAGCAAGGAAACGGA | AATCTAGGAATGGAGCAGGA | 52497 & 52498 | NCBP2-AS2 | CACCGAGACCTTGAAGCCA | GCTCCAAGCCTTCAGCAGCA | 52603 & 52604 |
| TPH2 | GTGCAGGAGCCTTCGACGGA | AAGCCCAAAAGATCATGCTGGCA | 52499 & 52500 | PPP1R2P3 | GCAGTGCACTGGCTCACCAA | GTAAATCGCAGTGAGGAGGCAGA | 52605 & 52606 |
| ASCL4 | CATCCAGTGGCCACGTGGAA | GGGGGCCGGGGGTATGCA | 52501 & 52502 | SLC2A7 | ACAGCAGGGCTCTGAAGGGGA | GGCTGACCAGCTGGGAGGAGACA | 52607 & 52608 |
| PLD4 | CAGCCCCCCTGAGCCCA | TGTGGGCCAGGAGTCAGGGA | 52503 & 52504 | MCMDC2 | CTTTCGCGGCCAACACACA | TGAATGCAGGCAGCAAAGTCCA | 52609 & 52610 |
| NOXRED1 | AGGGCCAGAGACTCTGGGTGA | GGCAGCTGAACGGCAAGCA | 52505 & 52506 | C9orf163 | CGACGGGGTCAGCTCTCCCA | AGTCTAGTCTCACAGCAAGCA | 52611 & 52612 |

| GeneName | Forward Primer | Reverse Primer | SEQ ID NOs | GeneName | Forward Primer | Reverse Primer | SEQ ID NOs |
| --- | --- | --- | --- | --- | --- | --- | --- |
| LCE3A | CCTGCAAAGAGCCCAGCACA | TGGCAACGGCAACGGTGAGA | 52825 & 52826 | HELT | ATCGGCCACGCGCCACCCCA | GGCGAGTGGGCGTCAGAGCA | 52931 & 52932 |
| LCE3C | TGCCGGCCGCAGAGATCCAA | CAGGTCAGCAGCAGCCCCCA | 52827 & 52828 | OR10AC1 | GATCACCGCCGCCCTGAGCA | GGTACGGCGCTGCCATCAGA | 52933 & 52934 |
| ZACN | CCCATGGCACGCGGCCTAGA | CTGTCATGGCCCGCCCCCA | 52829 & 52830 | FLJ44635 | GCACCTTCCGACCATGACCA | TGGAGCAGAAAGGGAGGGCA | 52935 & 52936 |
| XKR Y2 | GCCATCGCACTGGCAACGA | AGGGAAGAAATGCCAGAGTCACTACA | 52831 & 52832 | EEF1AKMT2 | ACAGTAACAGGATGGAGCCAGGA | AGACTAAGCACCTGTGAGGCA | 52937 & 52938 |
| PRSX1 | AATGGACTGCGTCAACCCAA | ACCCTCCGGATCCAGTGGAA | 52833 & 52834 | FOXJ2 | AGCAGGTGAGCAGAGTGCCA | TGGGGAGTGTCCCCAAGGA | 52939 & 52940 |
| RBM43 | TACACCCCACCACTTTCAGA | GCTGAGGTCAACAGGGGGAA | 52835 & 52836 | TRIM49D1 | AAGACCTACCAACCATGTAGGA | TAAAGGGGTTCCACAGCAGA | 52941 & 52942 |
| TRIM73 | TAACCAGGGCGTCCCAAGCA | GAGACCCTTGAAGGCAGGGA | 52837 & 52838 | COLCA1 | CCAGTTCCATACCCAAAGTGATGGAA | GGGGGAGAAAACAATGCTCTGCA | 52943 & 52944 |
| NAT16 | GCAGCCGCGCTTTGCCA | CGTGGTCACCGTGACAAGA | 52839 & 52840 | ATP11AUN | TGGGGTGACAGGGGCAGAGA | TTGGGGGAACCTACAGACAGAAGCA | 52945 & 52946 |
| ENTPD8 | AGGGAGCTGCCCACTGGA | GGAGGCGCGGGCTGGCCA | 52841 & 52842 | C17orf102 | AAGCTCCCCAAGGGCAAGA | GCCAGGCACCATTCTGGGCA | 52947 & 52948 |
| CENPS | ACAGGTAGAGCCACCTAGAAATGCA | TCAGCAGAAAAGCACCTAGGCCA | 52843 & 52844 | SIGLEC16 | ACCTGGAAGCCCCCTCCCA | GCCGTGACACAGCCTCAGGA | 52949 & 52950 |
| KRTAP10-6 | CAGCTGCTGACAGCCCTGGA | TGAGGGTGTCAAAGCCAGGA | 52845 & 52846 | PRAMEF13 | GAAAACATAACAGCAGGGGGCA | GTAGGACACGGGTGCCTGAA | 52951 & 52952 |
| KRTAP10-1 | GGCACCCGCCCTGGGCA | GGGGGAAGCACCTAACCCA | 52847 & 52848 | RGPD1 | CCCACCTGGGTCACATGCA | TCACGTGGGGGGAACAGACA | 52953 & 52954 |
| KRTAP10-11 | GAGCTGCTGCCTGAAGGGGA | TTGAGAAGGGGGCTCCAGA | 52849 & 52850 | LOC401052 | AACTGACAACCCCCTCCA | TCCACTACCTCAGAGAGACCA | 52955 & 52956 |
| KRTAP10-2 | CCAGCCCGGGGTCTCAGA | GCTCCTGGGGGTGAGACCCA | 52851 & 52852 | C3orf85 | AGCTCAGGAGGGCTTCCAGGA | CTTCCAATGCTCCGATAAGCAA | 52957 & 52958 |
| KRTAP10-8 | TGCCAGCCAGCTGCCCA | CCTGGGGGACGTGCCCA | 52853 & 52854 | C5orf85 | AAAATCTGCACCTGGACAGA | AAGACGATCGAATGAGGCCA | 52959 & 52960 |
| MRGPRG | TTGGGCCGACAGCCCGGGAA | GGACTGTCCCTGGCACCCA | 52855 & 52856 | C7orf65 | AGCCCCTTCCAGCTTCAGGGA | AGCAGACATGCCCACCCCA | 52961 & 52962 |
| C10orf143 | CATCACTTCAAAAGAGCCCCAA | GGGTGGGCCTCCATAGGCCA | 52857 & 52858 | SMIM30 | GAAGCAGTAGAAGCCGGTGATGCAA | TGCATATACCCCAAGCAGGCA | 52963 & 52964 |
| IFITM5 | ACCTAAGGCTGAACCAGTAGA | GTGGAACCGAGGGGCCTGA | 52859 & 52860 | USP17L1 | CCACTGGAAATTCTCAAGAGCAA | CACAAGTGCGTTGGGAGCGA | 52965 & 52966 |
| LOC388282 | CACTGCCACAGGGACAGCCA | TCACAGGGAGACCCCTCCAA | 52861 & 52862 | C9orf170 | AACCCCTTCCCCTGCCACA | CACATTACTGCAGGAGGAGGAA | 52967 & 52968 |
| C16orf47 | AGGAAACCAAGACTGCTGCGGA | CCTGAGGTGGTGAGAAGACCA | 52863 & 52864 | SERTM2 | GCCAGAGTAACCAGACAGGCACAA | GAGGGAGTGGGGGTGGGGGA | 52969 & 52970 |
| CCL4L1 | GAAGGTCACTGAGCCTGGA | GAAAGACAGGAACTGCGGAGA | 52865 & 52866 | FIGNL2 | CAGGGGCCAAGGAACTGGGGA | CACAACTGCAGAGCATGTCAGA | 52971 & 52972 |
| C17orf82 | CTTCAGGGTTCGAGGGCAGA | CCCACCACCTTCCGCTGAA | 52867 & 52868 | OR2T5 | TCCAAGGATGAAACTLAGCAGA | GGCAGCCCATAGAAGAGGA | 52973 & 52974 |
| RPSAP58 | GAAGGCAGTGACCAAGAGAGAA | CAGTGGCCTGAGCAGTGGGA | 52869 & 52870 | IGLON5 | GACTGCTGAGCAGCGGCA | CCAGGGATCCTGGGCGCA | 52975 & 52976 |
| C1orf137 | CAGGCCCCAAAAAGTTGGATCCAA | GGAACCTGAGCTCCACAGGA | 52871 & 52872 | OR4C45 | GGCCTGCACAGACACTCACA | TAGGGAGCACCAAGATGATGACA | 52977 & 52978 |
| NOTCH2NL | TCACAGGCTTCAGAGGCAGA | CAGGGCACATACAGGCTGTCA | 52873 & 52874 | LOC403312 | GAGGCTGAGAATGGCGTGCA | GCTGGAGTGCAGTGGCGCAA | 52979 & 52980 |
| OR14A2 | CTGGTACAGAGCTGGCACA | AAACTGTGGAATCACACTGGAGGCA | 52875 & 52876 | SPINK6 | CTGATGGCCAGACATATGGCAA | TGCAAAGCTGGCAAGTCACCA | 52981 & 52982 |
| LOC388780 | GGAATGGCCCTGGTACCACA | GAGGACACACTCAAGCCCCA | 52877 & 52878 | C2orf278 | CCTCTGCTCCCAGAGGCGA | TGGGCAGCACGTTAGGGGCA | 52983 & 52984 |
| SMIM26 | CACGGCCTGGTACCGGACA | AAAGCAGTGAGCCCAACACAGA | 52879 & 52880 | DNAJB3 | GCTGGGGAAGCAGAAGCAGA | CAGAAGGAAGAAAGCCCCCA | 52985 & 52986 |
| LOC388813 | CAGAGCAGAGGATATTACGCAGGAA | GAGTTGCCAGGATTCACAAACCA | 52881 & 52882 | C10orf105 | GACCCCTTCCCCATGCTCA | GGAGCCCAGGGCTTCA | 52987 & 52988 |
| PLEKHM3 | AGTCTGGGCAAGATGCGAGA | GGCATAGACCTGACCCAGGA | 52883 & 52884 | AGAP6 | GAATGCTCAGGTATCCACCGCA | CCCAGGGACAGCTCAGTGCA | 52989 & 52990 |
| C2orf82 | GAGGCCAAATCCGTTCCA | CCAGTAGTGAGAGAGAGGAGCA | 52885 & 52886 | PRR26 | GTTCTCACAGACTCCTGAAGGAA | TCCTCAGCACCAGTCAGTGGA | 52991 & 52992 |
| C4orf50 | TGCAGCGTGGTGCCACGA | GAGCGCCGCAGAGGGGGAGCA | 52887 & 52888 | C9orf106 | GCAGGGGTAAACATGGTCCA | GCTCACCCACTGTCCAGA | 52993 & 52994 |
| LOC389199 | GCCTCAAAGAGCCCGGCCGA | AGCAGCGTCTGTAGAGCCGA | 52889 & 52890 | DEFB103A | TGAAGCCTAGCACTGCTATGAGGA | ACCGCTGCAGACTTGCCGA | 52995 & 52996 |
| GRXCR1 | GCCATGGAGCAGAAGATGTCCA | GTAGAAGCTCCAATTAACCAGCA | 52891 & 52892 | BUD | AAAGCACGCGCTGCCACTGGA | TCCGCTTCATGGCAGAGGA | 52997 & 52998 |
| SMIM32 | CGCCTGGGTCTAAGGACCA | GCGCCCCTGAAGATGTGAGA | 52893 & 52894 | RGS21 | GTCACCAACTGCTGGAAACAATGACA | TTCACAGGCAAGCCAGAACTCAACA | 52999 & 53000 |
| PSMG4 | CGCAACCTGCGCGTGGCA | GTGTCTCCAAGGAGGGGAGGTAGA | 52895 & 52896 | KRTAPS-2 | ACCCCACAAGGCCAGGCGA | GGGCCACAGGGAGAACAGGGA | 53001 & 53002 |
| LOC389602 | ACTCTCAAGGAACCCTGAGTAGACA | CCAGAAAGTGTGAAGCCTCCA | 52897 & 52898 | CCDC196 | ACTACCAGAAGGCCAATGACCTGAA | TAGTACCTTGGGACCCAGGAA | 53003 & 53004 |
| C8orf87 | GAATATCTGGTCAAGATACA | CCCACATGTTGGTTCACAGGCA | 52899 & 52900 | SMIM22 | GGGGAGACTTGAAGAGCCACCA | GCACAGACAGTTGGCGACGA | 53005 & 53006 |
| SPATA31D4 | AGCCCCAGGAAGTTGAGGCA | CACAGGATCCTGTGGGGCA | 52901 & 52902 | NUDT4P1 | GAGGAAAGGCCCTTAGGGAGA | TGACAGTCCCAACACTCTGA | 53007 & 53008 |
| SPATA31D3 | CAGAACTGCAGGTCAGAGCAGA | CACTTTGCAGGAGGGGAGCCA | 52903 & 52904 | HIST2H2BF | ACCCAGAGTTACCACAGAGAGACAA | CTCCACCAGCTTGGAGACA | 53009 & 53010 |
| MYMK | GGACCCGGCCAAGCTGGA | CAGAGCCGGCTGGGCGCA | 52905 & 52906 | C5orf56 | AGAGGCATCGCCTGTGGACA | AAAGCCACCTACGATATACCACCCA | 53011 & 53012 |
| CENPVL1 | GTAGGACGCAACACACAACCA | CTGAAACTCACAGGTGCGGGA | 52907 & 52908 | TMEM151B | GCCTGGCTGGGGCAGAAGCAA | CAAAAGGCACAGTGTGATGCA | 53013 & 53014 |
| LOC389895 | GCGCACCTCGGCCAATGCA | GGCAGGCAACCAATGAGGGCA | 52909 & 52910 | SPDYE2 | AGGCAGGAGGGAGAGGAACCA | CCCACCCCCTCCCCCA | 53015 & 53016 |
| C5AG3 | ATTGTCCAACAACCACCACCAACA | CTGGGCAGGGTTGAGAGGA | 52911 & 52912 | SPATA31C1 | AAAGTGTCCGGTGCAACAATGAGCA | CGGCCGGTGCTGAGGGGGA | 53017 & 53018 |
| OR52I1 | CGGCCTGGTTGGCGCCGA | GTGGTCAAGAGGAAGTGCATCAGA | 52913 & 52914 | NUTM2G | GAAGCCATGGCCTCCTGAGA | GTGCAGCTACAAAGGGCAGCCA | 53019 & 53020 |
| ACC5L | TCCGGGAAGCTCAAGATACA | AAGTTGATCCAGACATAGAGGCCA | 52915 & 52916 | FTH1P18 | CCGGAAGCAGGCCTGGCAGA | GCGGAGCAGGGGAAGGCA | 53021 & 53022 |
| BSX | GCCAGAAGCCCGAGGGGCA | GCTCGGTCAGCACGAAGGGA | 52917 & 52918 | CENPVL2 | GTAGGACGGCAACACACACCA | CTGAAACTCAGGTGCGGGA | 53023 & 53024 |
| OR10G4 | GAGGGCGAGCCTTTCAGA | GTTGAGGAGCAGGTTGCCA | 52919 & 52920 | CT45A5 | GGCCTGGCAGGATGCATCAA | GCAACCCCATCCAGGCAGGA | 53025 & 53026 |
| SKOR1 | CGCGCTATGCCGTGCCAGTGA | GAAGGAGCAGTTGGCCATCGA | 52921 & 52922 | FRG28 | GTGTGGGCACAGCAGTCA | AAGCCAGCTCTTCAGCAGGA | 53027 & 53028 |
| LOC390877 | GCTCTGAAACATCCGAGCAGAA | GACTCTCAATGACAGAGCAGCA | 52923 & 52924 | OR2W5 | AGAGTGCAACGCGCGGTGGGAA | CCTGAAGCAGGCAACTTCAAACAGA | 53029 & 53030 |
| PLA2G2C | AGGATGAGAGCCCACCTGGA | CAGCCAGGTTCCCTCACACA | 52925 & 52926 | SULT1A4 | GTAGGATCACAATAGGCCACGAA | ACTACAGGTAAGTGCCAGCACA | 53031 & 53032 |
| OR2M2 | CTTCAATCAGAGGCCACCACACA | GAGGGACAGTTGGCTGAGGA | 52927 & 52928 | TARP | ACGGCGATCTCCAGCACAA | AGAAGCCGCAAGGATGTCTACA | 53033 & 53034 |
| OR391322 | CAGGGCCGTTCGAGCGGGTCCA | GCGGTGCCCACTACGCCGA | 52929 & 52930 | RNASE12 | GCAGACCTTGGACCGTGGACA | CCAACCCAGCAATACAGGAAGGA | 53035 & 53036 |

| GeneName | Forward Primer | Reverse Primer | SEQ ID NOs | GeneName | Forward Primer | Reverse Primer | SEQ ID NOs |
|---|---|---|---|---|---|---|---|
| GOLGA8F | ACAAAAGGGCACTGGTTGGCA | AAGCTTCCATGAAGACAGGGAATGCCA | 53249 & 53250 | LOC101928120 | GCTGGGCCTGGGCCTGTAGA | GAGGCAGAAGTCAGCCCGAA | 53355 & 53356 |
| LOC100132813 | CCTGACCCACACATAGCATAAACCA | AAGAGGCAAGGCTGAAAGCAAGAGA | 53251 & 53252 | ETDA | GGCAGGCACAGAAGTGACATCGA | GGCTTCAGCACGTAAGCCACA | 53357 & 53358 |
| DPH3P1 | CCGAACCCTGAACAGCTGGA | GTGTCTCCACGAAGCCAGGA | 53253 & 53254 | LOC101928841 | TCAGACACTCGCTCAGGGA | AAAGACCGTAACTCCAACAGCA | 53359 & 53360 |
| CXorf51B | TTCGAGAGGAGTCGAGCCAA | CCGGTGATAACGACCACGCA | 53255 & 53256 | LOC101928917 | CTTGATGGAAGGCACAGGGA | CTGAGAGGGAGCCCAAACAGA | 53361 & 53362 |
| LOC100134391 | CTGCTGAGGAGAAGAGCAGAGCA | CAGGCATGGACAGGAGGGCA | 53257 & 53258 | CCDC928 | GCAGAGGGACCCTGCTCAA | TATGACAGTCACCCCTAAAGCA | 53363 & 53364 |
| LOC100287036 | GCCTTCGGCCACAGACTGAA | GCAAGCTGAAGGAGCCAGGAA | 53259 & 53260 | LOC101929372 | ACAGAGGCTCATCAGGAAGGA | GAGCGTATGGGACATGGGGAA | 53365 & 53366 |
| USP17L10 | GAAGGTACGGTGCCTCCCGA | GTAGGGAAGCGAGTGTGCCA | 53261 & 53262 | LOC101929726 | GCCTCTCCACTCCCAACAGA | TGGGAGGGAACTGCTGGAGGA | 53367 & 53368 |
| USP17L13 | TCGACCCGACAACATCAGGA | CTGGCCCTCCCTCGCAGGGA | 53263 & 53264 | LOC101929926 | CTGGGTCTGGGGCCCAA | GTGTAGGCAGTAGGCAAACACGA | 53369 & 53370 |
| GLYATL1P3 | GGACACGGCTGATCATGCGA | CCACTGACAGGAGGCCTCAA | 53265 & 53266 | CT45A10 | CCCAACTTCCAGAGGGCA | CTGGAGGAGAGACGCGGCA | 53371 & 53372 |
| LOC100287896 | GCATGCGTCCAGGCTGGACA | GCACACAGGTCTTGGCCCCA | 53267 & 53268 | SPDYE7 | TGGAGGAGTTGGAAGAGATCCA | TCTAGGAAAGGTGGGCGCGA | 53373 & 53374 |
| ERVMER34-1 | CCCCACCTGGTGGCCCA | ACCCAAGTCCACATCGCCA | 53269 & 53270 | LINC00694 | TCCTGAGCCACCCGTTGGCCA | AGGGAAGGTAGATGGGCCA | 53375 & 53376 |
| TMEM225B | AACAGTCATCTAGCCCAGGACA | AGAAGCTCCTCAAAGGCACAGA | 53271 & 53272 | LOC102724265 | ATGAGGAACAGGGGCAAGGAA | GGCTGCAGTCAAGGTGCCAA | 53377 & 53378 |
| LOC100289561 | AGAGGAGCCGTGGATAATGGAA | GCCGGAACAGTCAGAGCCACCA | 53273 & 53274 | LINC01835 | TGACCTAGGCCCCTACCCCA | CCAGAGGGGCAGGGATGGA | 53379 & 53380 |
| TRPC5OS | CCCCCGGTCCAAGGAATGGA | CTCTGAAAAACCGTCCCCA | 53275 & 53276 | GAGE10 | GCCAGGAACAGGTTCACCCAA | GCAGGCCATCTCCTCGGCCA | 53381 & 53382 |
| MTRNR2L2 | GCACCCTGCCCGTGCA | GACAGTCAACCCTCGTGCA | 53277 & 53278 | U2AF1L5 | GGCCGCGTCGCAAGAAGCA | CTCCACCACGGCCACCGCCA | 53383 & 53384 |
| MTRNR2L3 | GACGAGCTACCAAGAATAGCTGAA | TAAGCCAGCCAGCTATCACCA | 53279 & 53280 | LOC102724957 | ATGGAAGGAATAGAGGGAGAGCAGA | CTGGAAAACTGGAGGGTGGGA | 53385 & 53386 |
| TEX48 | CCAGCATGCCTCACTGGGA | CTCATGGAGATGCCCCAGCA | 53281 & 53282 | HOT5 | GGGCAGCCATAGTGTGCCGA | GCTGGTGGGGCTGGGGCAA | 53387 & 53388 |
| LOC100505549 | GGATCAGGAAAGGATCAGGAAGA | GCCCAACAGCAGCCTCTCAGA | 53283 & 53284 | CPHXL | CTGCAGAGTCAACTGCCTCAGAA | GCAGAAGGGGTGAGGCCAGGA | 53389 & 53390 |
| INAFM2 | ATCAGAGAGTCTAGAGAGGGCA | GGGCTGGGACAAATGTCCCAA | 53285 & 53286 | LOC105372280 | TGTCCAAAGATGGCCGCCGA | GGCCGGGATGCCCACAAGGA | 53391 & 53392 |
| UBE2Q2L | GTACCCTGGATGCAGCAGGAA | TGGCTCATCAGAGTCCACAGA | 53287 & 53288 | LOC105372977 | GAAACAGGATTTAAGAGGGGAGGGA | CCTAGCACATAAGGAGTGGTCAA | 53393 & 53394 |
| KRTAP5-7 | CAGCCGTGCCTGCCCCA | GGTCACAGGTGGGCTGGA | 53289 & 53290 | PNMA6F | TCTTGCCAGGAACCCCAGGA | GAAACTGCAAATTGCCACCAGGA | 53395 & 53396 |
| SPATA1 | GGGGAGGAAGGGGGGGA | TCGGCCCCTTCTGGAGAGGAA | 53291 & 53292 | LINC02054 | CACAGCTTCCAGCTTCGAA | AGCCAGGTGAGTTAACGACGA | 53397 & 53398 |
| LRRC72 | CCGCTGCTTCGGCCGCCA | GATGCCTCCGTAGGGCGCA | 53293 & 53294 | UPK3B | ACCACGGCTCCCGGCATGCA | CCAAAGAGGGGCTGCAGACCA | 53399 & 53400 |
| EDDM13 | GGGGCCATGCCTTAGGGGGA | GTTCGAGAACGATCTGGAGGAGA | 53295 & 53296 | LOC105375787 | GAGAAGACTTCCGCTTGTACAGGA | GAAGATGTAGGGAAGAGCTGGGA | 53401 & 53402 |
| LOC105206388 | GAGAAGGCCATTAGAGTCCACA | ATATCTACCGCCCACCCCA | 53297 & 53298 | TEX53 | ATGACAACCGCACATGATGTCAA | GGAAGCCCAGCAGCTGTGCA | 53403 & 53404 |
| LOC105206422 | GCAAGCCCAGGAGTCAAGA | CCAATGCATGTGGAGCGCCA | 53299 & 53300 | POP3 | CTGGATAACATCACCGATGAGGA | CTCACTGCAGACACCATGCCA | 53405 & 53406 |
| SPTY2D1-AS1 | AACAGAACATGGAGGACCTCTACCAA | TCAACTCTGGAAACGTGCCA | 53301 & 53302 | LOC107984640 | GGGCCTGCCCAGCCTGGA | GACCTGGGCCATGGGCAGAA | 53407 & 53408 |
| C17orf112 | CACAGAGACATGAGCACCAGCAA | GATGCCGTTGAAGAAGGGAGGA | 53303 & 53304 | HTDZ | TCACCCCCAAAAGAACCTCCA | TGTCCAGAACAGGGAAACCCA | 53409 & 53410 |
| TPBGL | GCTGCGTGCACACAGGAA | ACTGCTCAAGGGAGATCCAGA | 53305 & 53306 | FAM236C | CAGGCGTGAACGGTGACCGA | TTCAGGCCCGGTGACCGGCA | 53411 & 53412 |
| LOC100507507 | GCCACAGGCATGTGTGCCA | GACACAATCTCCAACATGCACAGGA | 53307 & 53308 | ASDURF | GGCGCGCTGGAAGCGCGCA | GGGCATTTCCACGAGCGCA | 53413 & 53414 |
| THEG5 | GCGAGGCATAGGCATTCCCA | CAGGCGAGGGGCTTGCATGGA | 53309 & 53310 | ACTB | CCACACAGGGGAGGGGTGATAGCA | ACCCACTCCAGGGAGACCA | 53415 & 53416 |
| KRTAP9-6 | GGCTCAACCAGACGTGTGGA | GACACAGCAGGCGTGGCA | 53311 & 53312 | ACTG1 | TCAAGATCATCGCACCCAGA | GGTGGACAGTGAGGCCAGGA | 53417 & 53418 |
| TBC1D31 | CGAACAGCAGTGTGCTCCA | CAGCCATGAGCCGTGCCCA | 53313 & 53314 | ALAS1 | GTGAACCGGCGAGCAA | CCACTGCCCCAGCACCA | 53419 & 53420 |
| 5MIM35 | CAGGCGGGTACTGCTGAGGA | GATGGTGAAGGGTGGACCCA | 53315 & 53316 | ALB | TTGGTGAACAGGGGACCA | TCAGAGCTCAACAAGTGCA | 53421 & 53422 |
| FAM187A | CCAGCTGGATGACCGGGCA | ACAGAGCTGGTAGTGCCCA | 53317 & 53318 | ALDOA | GGAGGCGTCCATCAACCTCAA | CCCCAGCCTTCCAGGGCA | 53423 & 53424 |
| FTCD-AS1 | CGTGGGGCCTGCGTGGGA | ATACCCACCCTAGGCTGCA | 53319 & 53320 | APP | GAGGACTGACCACTCGACCA | TGACAACACCGCCACCA | 53425 & 53426 |
| MED14OS | CGGGAATGCGGGGGGGAAGCA | TCCGCCTCGGGCAGTCAACA | 53321 & 53322 | ATP5A1 | CAAACCAGGGCTATGAAGCA | CTCAGTTAGACGCACGCCA | 53427 & 53428 |
| APOBEC3A_B | TGCGGGATGCTGGGGCCCA | GTCCAGAAGGGTGTCCCACA | 53323 & 53324 | B2M | ACGTCATCCAGCAGAGAATGGA | TGGTTCACACGCAGGCCA | 53429 & 53430 |
| C5orf66 | CATAGATACTGGAGAAGGGAGCGA | AGCAGAGCCAGGACTCAAATTCACA | 53325 & 53326 | BOLA2B | GCCATGGAACTTCAGCGCCGAA | TCCCCTGAACTTGCCGA | 53431 & 53432 |
| CTXND1 | CCATGAGGGCGGAGTGAATGGA | ATGGTGGAAGGAATCACATGGGCAA | 53327 & 53328 | CALM2 | TGGGCAGAATCCACAGA | ATGGCGAAGTTCTGCAGCA | 53433 & 53434 |
| LOC100996634 | ATGACAGAGAAGCCAGAGAGGCA | GGCACGGGGAGAAAAGAAAGGGA | 53329 & 53330 | CALR | GGCACTTGGATCCACCCAGA | GTGCGAAGACTTGACCTGCCA | 53435 & 53436 |
| LOC100996693 | CAGGACAGCGGGCAAGTACGA | GCCACGTGCAGCAGGGA | 53331 & 53332 | CANX | GACGCAGAGAAACCTGAGGA | AATCACAGGTGCGTGCCA | 53437 & 53438 |
| LOC100996842 | ACCCAACACCAGCTGTGCCA | CTGGGTCTCAGGGAGCCTGGA | 53333 & 53334 | CCL7 | GAGACCAAACCAGAAAACTTCCA | TGAAAGCAGCTGCTGTGAGCA | 53439 & 53440 |
| LOC101059915 | CCTTAGAGACCTAAGCTGTGCCA | GGGGAGCAAATGCAGCAGAAGA | 53335 & 53336 | CHCHD2 | TGGGGGCTTCAGTGGAGGAA | TGGTTCTGGCCACTCCAGA | 53441 & 53442 |
| TBC1D3L | CGAACAGCCGTGTGCTCCA | GCCATGAGCCTGTCCCAGA | 53337 & 53338 | CIAO1 | CTCGGATCCACAGCAGGCA | CTCCCATCATCATGCAGGA | 53443 & 53444 |
| MMP24-AS1 | GACCCAGCAGTCCACTGGA | GTTAGGCCCTTGGGAGGCCGA | 53339 & 53340 | CLIC1 | CCCCATGGCACTGAGAAGAAGTGGA | GTACCGATGCACTCCCGGA | 53445 & 53446 |
| LOC101927322 | ATCTTAGCAACATCCAAGGCCA | AATGGCAACAGAAATTGGGCCAGGA | 53341 & 53342 | COL1A1 | GAGGGCCTAGTTGGCCACA | CCAGCAGGACCATTACAGGCA | 53447 & 53448 |
| LOC101927503 | CAGCAGAGTGTTGTGCCCA | AGCCTGGAGTGGGGACAGGA | 53343 & 53344 | COL1A2 | GAGGTCCTAGTGGCCACA | GTGACCAGCGGATACCAGGCA | 53449 & 53450 |
| LOC101927572 | TCCAGCTCCAGCCCACCCA | TCTCTCCCAGAAGCAGCACA | 53345 & 53346 | COX7B2 | AGGCCTAAAACGGCAGGTAACAGGCAA | CAAGGACGTCAGGTAACAGGCAA | 53451 & 53452 |
| ZASP | GTGGCCTGGGGCTTGGGCA | CTGACACGACACCCTGGCACA | 53347 & 53348 | COX7C | CCGTAGGAGCCACTATGAGGA | GGAAGGGTGTAGCAATGCAGGA | 53453 & 53454 |
| HSFX4 | CTGGATGGAAGGCACAGGGA | TGGAGACATGACTGAGAGGGGA | 53349 & 53350 | CSDE1 | CAGGGTTCTGGCCAGTGGA | TAAACCGCCTCCCCACA | 53455 & 53456 |
| LOC101927844 | GAAGTGAAGGCAAATGTGGAGA | AAGAGCAGGAAGCAGTGGAGAA | 53351 & 53352 | CXCR3 | CAGCCTGAGGACTGCACCA | AGTGGGGCCTCCAGGCAGCCA | 53457 & 53458 |
| LOC101928093 | CAGCACAACCAGTCCTCCCA | TGTCCAAAGAGAAGCCCAGGA | 53353 & 53354 | CXYC1 | CGGACCCCTTACACCCTGCA | CAAGGATGAGTGGACTCCGCA | 53459 & 53460 |

FIG. 1 (cont.)

| GeneName | Forward Primer | Reverse Primer | SEQ ID NOs | | GeneName | Forward Primer | Reverse Primer | SEQ ID NOs | |
|---|---|---|---|---|---|---|---|---|---|
| DCN | TCTGGCCAACACGCCTCA | GTCCAGGTGGGCAGAAGTCA | 53461 | 53462 | MZT2B | CCCGAGGGAGGAAACAAAGGCA | GCGCTGGGCTGGCGTGGCA | 53567 | 53568 |
| DDX31 | CTGGACAAGAGCCATGACCA | TGTAGGAAGAGGCTGTAGTGGA | 53463 | 53464 | NACA | CACCCACAACTACCCTAGCCA | AAAGGTGCAAGATGAGAGCCCA | 53569 | 53570 |
| EEF1B2 | CAACGATTACCTGGCGGACA | TACCAACGTAGGGCATGACACA | 53465 | 53466 | NBPF20 | AAACAGCCCTTACTAAGCCGAGAGA | GAATAGGAATACAGCCATGCCCA | 53571 | 53572 |
| EEF1G | TGCTGAGCCCAAGGCCAAGGA | GAAATATGGCAGTGCCACAGAGA | 53467 | 53468 | NDOR1 | CACCCTCACGGCTGCAGA | GTGTCTGGGAAGGCCAGA | 53573 | 53574 |
| EEF2 | CCCCAACATCCTCACCGA | CGTGGACGTCGAAGCGCA | 53469 | 53470 | NONO | GATGGAAGCTGCAGCCA | GCCATCTGACCCATCCGA | 53575 | 53576 |
| EIF3B | TCAGTCCAAAGCCTCAAAGGA | CCCCTCCTGCAACTCCA | 53471 | 53472 | OAZ1 | CCCGAGGGGAGCAAGGACA | CAAAAGTCGAAGGTTCGGAGCA | 53577 | 53578 |
| EIF4A2 | TACGAGGCGCAAAGGTGGA | CGACTTGACCCTGACGGGA | 53473 | 53474 | OR2A1 | CATCGCTACACCCGCAACA | GAGAGGGTGGCAGATGGCCA | 53579 | 53580 |
| EIF5A | GAGGAGGAGGAGGGGAGGGGA | GCAGGAAGGGTAAAGCCCA | 53475 | 53476 | OR2A7 | CCATCTGCCACCCCTCCGA | GATAAAAGGACTCCAGTGGTCA | 53581 | 53582 |
| FAU | CCAGGAAAACGGTTGCCCAGA | ACCCCGACTGGCCCAGA | 53477 | 53478 | OST4 | GTCGGAGCCGAGCCGGA | GGGCGGAGAAGAGCCCA | 53583 | 53584 |
| FGG | GGTCCTTGCACCCCGGAA | CAATGCCACCAGGTAGTTGGACA | 53479 | 53480 | PGK1 | CTGCTTGGACAATGGAGCCA | GAACATCCTTGCCCAGCAGAGA | 53585 | 53586 |
| FN1 | GAGGAAATAGCCCTGTCCAGGA | CGGCCAGTGACAGCATACACA | 53481 | 53482 | PLP1 | CACCTGGACACCCTGCCA | TGGACAGAAGGTTGGAGCCA | 53587 | 53588 |
| FTH1 | AACTGCACAAACTGGCCACTGA | AGTTGGTCACGTGGTCACCCA | 53483 | 53484 | POLR2L | TTGTGGCAAGATCGTCGGCAA | CAGCAGCATCCGGCGGCA | 53589 | 53590 |
| GAPDH | CTGGCTACACTGAGCACCA | CCACCTGTTGCTGTAGCCA | 53485 | 53486 | PPIA | GCAGAGGGTTAAGGCGCAGA | TTGCAAACCTCAAAGCTCCA | 53591 | 53592 |
| GBP1 | CCAAGAAGCCAGGCACCA | CCATGCACGGCAGATCCCCA | 53487 | 53488 | PPIH | CTGCACCGGAGAATTCAGGA | GCCATGGAAAGCAGGCCTGGA | 53593 | 53594 |
| GNAS | CTGACTATGTGCTGAGCGA | CTGGCCACCCACGTCAA | 53489 | 53490 | PTMA | ACCAGCTCCGGAAATACCACCA | GTCAGCTCCTGCTCCCA | 53595 | 53596 |
| GSTP1 | CTATGAGGCGGGCAAGGA | AACGCATCCAGGCAGCCA | 53491 | 53492 | RACK1 | CAAGGCAGAACCCACCCA | CCAATGGTCACCTGCCACA | 53597 | 53598 |
| GUSB | GCAAGACTGGGCTGGTGAA | CCCAGTCCATTCGGCCACGA | 53493 | 53494 | RHOA | CAGCAAGGAGGACCAGTTCCCAGA | CTGCCAGCTGTGTCCCACA | 53599 | 53600 |
| H3F3B | TCGGTAAGGGTAAAGGACAGA | TCAAGGGCATAGGATACCTGCA | 53495 | 53496 | RPL12 | CATTGCTCGACAGATGGGCA | ATGTCATGAAGATGTGGGCCA | 53601 | 53602 |
| HCG22 | GCTGGCCCTGGAATAAGCA | GAAGTAACCAAGGTCAGGCAGAA | 53497 | 53498 | RPL13 | CCATCGTGCGCTGCCCA | CGGTCAGCTGGGTGGCCA | 53603 | 53604 |
| HIST1H2AC | ATCTGGAGCTGGCCGGCAA | CAGCTGCAAGTGGCGCGGGA | 53499 | 53500 | RPL13A | CCACAAAACCAAGCGAGGGCA | TTGTAGGCTTCAGACGCACGA | 53605 | 53606 |
| HIST1H2AD | ATCATCCCCGAACCTGCA | CAGAACAGCCCTGAAGCAA | 53501 | 53502 | RPL15 | AACTTAGCCAAGCCTGTCA | TTCAGGACTCTCAGAGCCCA | 53607 | 53608 |
| HIST1H2AE | CTAAGAAGACGGAGAGACCACCA | GACTCGGGATCATCGACGGA | 53503 | 53504 | RPL17-C18orf32 | ACACAAGGTCGGTGGCCAA | TCATCTCAATGTGCAGGGAGA | 53609 | 53610 |
| HIST1H2BD | TTCGAGCGCATCGCAGGGGA | CAGCTCCCGGAAGCAGCA | 53505 | 53506 | RPL18A | CGGGACCTGACCACGCA | GGCACTTGCTGGCCGGA | 53611 | 53612 |
| HIST1H2BN | CCAGGGAGCTGGCCAAGCA | GTGGCCGAGACTGACCGAA | 53507 | 53508 | RPL19 | ATGCCGAATGCCAGAGA | CAGCTGGTCAGCCACGA | 53613 | 53614 |
| HIST1H3A | GTCACTATCATCGCCAAGGACA | GGACCGTCAGAGAGGACCACA | 53509 | 53510 | RPL21 | GGAAAGGAGGAGGCACCCGA | AATGCCAACACGATGCTGGGTA | 53615 | 53616 |
| HIST1H3B | CGAGAAATCGCCCAAGACTTCAAGA | GCCCTACCAAGTAGGCCTCACAA | 53511 | 53512 | RPL22 | CATCGAAAGGAGGCAAGAGCAA | GCTGTTAGCAACTACGGCCA | 53617 | 53618 |
| HIST1H3C | GTGCGAGAAATCGCCCAGGA | CCACCAGGTAGGCCTCACAA | 53513 | 53514 | RPL23 | GAAAGGCAAACCAGCTCAGA | CCGGGCCACAAGTCTGCA | 53619 | 53620 |
| HIST1H4B | AGGCATCACCAAACCGGCA | GCGCGTAAACCACATCCATGGCA | 53515 | 53516 | RPL23A | TCCTGCCCCTCTAAAGCTGA | GGGAAGCCTCTTCCGAGGA | 53621 | 53622 |
| HIST1H4E | CACCGTAAGGTCTGCGAGA | TGCGCTTGACACCCCGGGA | 53517 | 53518 | RPL26 | GTGACTTCCGACCGAAGCAA | TCGGATGGGCATGGATCGCA | 53623 | 53624 |
| HIST1H4H | CGCGATAACATCCAGGGCA | GTGTAAGTGACAGCGTCACGA | 53519 | 53520 | RPL27 | GGACGCTACTCCGGACGCAA | GGTAGGGGTCAATTCCAGCCA | 53625 | 53626 |
| HIST1H4J | AGAGCACGCCAAGCCAAGA | CGCTCAACCACCGAAACCGTAGA | 53521 | 53522 | RPL27A | CAGACTGAGGAAGACCCCGAA | ATCCGGTGGTGATGCAGACCA | 53627 | 53628 |
| HIST2H3A | GCAAGGCCCGGAGGAAGA | TACGGTGCCGGGCGGTA | 53523 | 53524 | RPL29 | GCCTACATTGCCACCCCAA | GGAACTGAAGCTGGGGCTGCA | 53629 | 53630 |
| HIST2H4A | GCAGTCACCTACACCGAGCA | GCGCTTGAGCGCGTACACCA | 53525 | 53526 | RPL3 | AGGCTACAAAGGGGTCACCA | CAGCGCGTGCCACAGAGA | 53631 | 53632 |
| HIST3H3 | CCTAAGGACATCCAGTTGGCA | CAACCTCTCAGGTGGCGAGA | 53527 | 53528 | RPL30 | GTGGCCGCAAAGAAGACGA | GATTTCCTCAAAGCTGGGCA | 53633 | 53634 |
| HLA-A | CCCCACCCCATGTCACCA | AACAGGAAAGATGATTGGGGAGGGA | 53529 | 53530 | RPL31 | CACCTTCGGGGCACTCAAAGAGA | CTGGACGCCCATCCAGGA | 53635 | 53636 |
| HLA-B | AGGCTGCGTGCAGTGGACA | GCTAACAGGGACCGCAGACACA | 53531 | 53532 | RPL32 | CAGACCCCTTGTGAAGCCCAA | CTTCGGAAGGCCACTGGGCA | 53637 | 53638 |
| HMBS | TCTGCAGTTCAGACGCCTCAGA | TACGAGCAGTGATGCCTACCA | 53533 | 53534 | RPL34 | GGTGTGTGCCCAGGCAGA | TAGCAACATGAACCACCA | 53639 | 53640 |
| HNRNPA1 | AAAGCCCTGTCAAAGCAAGAGA | TAGCCATCCCTCCTCCA | 53535 | 53536 | RPL35A | TACGCCCAGGATGAAACAGA | GAATTGGCACGAACCATGCCA | 53641 | 53642 |
| HNRNPA1L2 | TGATGAGAGGCTGAGGGACCA | GCTGCATCCACCTCCTCACA | 53537 | 53538 | RPL36A | GAAAGCGGCGTTATGCACGGA | TCTGCAGTTGGGCTCAACGCA | 53643 | 53644 |
| HNRNPC | GGATGACAGAGACAGGCGCA | AGGATGGGGAGAACAGTGAGCA | 53539 | 53540 | RPL37A | CAGCCAGCACGCCAAGTACA | TCCAGGCACCGCCAGGCA | 53645 | 53646 |
| HNRNPH1 | GCACGGAAGGTCAACAGGAGGA | GAAACGAATACCTTGAGCCCCA | 53541 | 53542 | RPL38 | AGCCGACGAAAAGGATGCCAA | CTGCCAAACCGGGGGGCA | 53647 | 53648 |
| HPRT1 | ATGACGGGTCGACCAAGGA | TATACTGCCTGACCAAGGAA | 53543 | 53544 | RPL39 | AAGCGATTCTGGCCAAGA | GATCGTGACCTTCAGACAGCA | 53649 | 53650 |
| HSP90AB1 | CCAGACCCACTCCAACCGCA | AGAGGGGGGATCTCATCAGGA | 53545 | 53546 | RPL4 | GACCATGCGCCGGAACACCA | CTGCAACCGGCGCCTTCTCA | 53651 | 53652 |
| IFITM1 | TAGCCGCCCATAGCGTGCAA | CCAAGAGGGCAGGGCAACA | 53547 | 53548 | RPL41 | GGAGGCCACAAGGAGCAGA | CCAGGAGGAGGACCAACA | 53653 | 53654 |
| IFITM3 | AGGCATCACTGAGGCTGCAA | GGGCAGGGCGGAGGAATGGAA | 53549 | 53550 | RPL5 | AGATCTATGAAGGCCAAGTTGGA | TGGCAAGGCCTGCATCCA | 53655 | 53656 |
| LDHA | AAAATACAGCCCGAACTGCAA | CAAGGACCCACCCATGACA | 53551 | 53552 | RPL6 | GAAGCCCAGAACAACCAGGA | CAGGTAGCCCTGGAGCTGA | 53657 | 53658 |
| LPL | GCTGGGAACCCGACTGTGAA | TGCTGAAGGACAACAACACATGCAGA | 53553 | 53554 | RPL7A | CTGGCCCACAAGTACAGACCA | TTACGACACAGGGGCAGGCA | 53659 | 53660 |
| LYZ | GGCAAAACCCCAGGAGCA | CACAAGCTACAGCATCAGTGA | 53555 | 53556 | RPL8 | CTCCCACAACCTCGAGACCAA | GATGGTGGACGGGCTTGCCGA | 53661 | 53662 |
| MIF | AGCAGCTGGCGCAGGCA | TGCAGCCTGCAGAGGTGCGCA | 53557 | 53558 | RPL9 | GAGGAACCCTGCGAGGGGA | CAAATAGTCCGAACGGTAGCCA | 53663 | 53664 |
| MRPL30 | ACAGACTAGCAAGATGGGCACTACA | CAAAAAAGGTGACACGAGCGGCACA | 53559 | 53560 | RPLP0 | TCACTGTGCCAGCCCAGA | TGCTGATGACCAGCCCA | 53665 | 53666 |
| MUC2 | CCAGGGTGCCCTGCTCA | TGTCCCGCAGGACCCGGA | 53561 | 53562 | RPLP2 | GGTATCGAGGCGGCGACGA | CACCAGCAGGTCACTGGCA | 53667 | 53668 |
| MYADM | TGCTACCCATCCCTTCCCA | CGGTCCGAGGCACACGTA | 53563 | 53564 | RPS10 | CCCGAGCTACGTGAAGGAA | CAGGTAGCCCTGGAGCTGA | 53669 | 53670 |
| MYL6 | ACCAGACCCAGAGTTCAAGGA | GGTTCCCCAGGACCTTGAGCA | 53565 | 53566 | RPS11 | ACCGGCTTCGAGAAGGCCACA | GTCTTGCTCAGAAGGCCGGCA | 53671 | 53672 |

| GeneName | Forward Primer | Reverse Primer | SEQ ID NOs |
|---|---|---|---|
| TRPM5 | CCAGATCCCACTGGACGAGA | GGATGACCAGCCAGTTGGCA | 54097 & 54098 |
| TSSC4 | CAGGGGCGGCCTTGGGAA | CTCCATGGTGGCTGCCCCA | 54099 & 54100 |
| UPK3A | AGACCCCATCCGCACCAA | CTGAGGGCAATGGCGGCA | 54101 & 54102 |
| UTS2R | GTCAACTGGGCTGGCCGGA | AGGCCGAAGAGCACGCGGCA | 54103 & 54104 |
| VAX1 | CCCAAGGGCCTGGACTTGGA | CGGCCCACCACGTACTGGCA | 54105 & 54106 |
| VCY1B | AGACTACCAAGGTGGCCGAGA | CCGCCTCAGGTGCCGTCA | 54107 & 54108 |
| WDR97 | CCGCGAGGTCCGCGATGAGA | CTCCACACGCGGCAACGGCA | 54109 & 54110 |
| WFDC11 | GAGGCAAGGAAGAAGAAGCCA | TCCCAGCACAGACAGTAGCA | 54111 & 54112 |
| WFDC8 | GCCAGGGCCTGGACAGTCAA | CAGTCCACAATGTGAGCAGCA | 54113 & 54114 |
| WNT6 | GCAATAGCAGCGCCCCGGA | CAGTGGAAGCCGGCACAGGCA | 54115 & 54116 |
| XAF1 | AGCCCAAGCCCAGGACCA | ATTTAGGATCGGGCAGGGGAA | 54117 & 54118 |
| XAGE5 | CTTGAGCCCAGTGTGCCAGA | TGACTGAGACAGCTCCTGGA | 54119 & 54120 |
| ZFP92 | GCCTTCAGCCGCAGCTCCAA | GGTGCTCCAGGAGCGCGAA | 54121 & 54122 |
| ZNF141 | GAAATGCCTGGGACCCTGACCA | TGCTCCAGACAGGTGACCA | 54123 & 54124 |
| ZNF253 | TACCTGTCTGGAGCAAGGAA | CTGGCCAAAGGTCTTGGGCA | 54125 & 54126 |
| ZNF34 | AGAAACCCTACAGATGCAGCGA | GTGCCGGAAGGCCTTCCCA | 54127 & 54128 |
| ZNF563 | CGGGAGGCAGAGGGGAGGA | TGGACCCAGCAAAGCCA | 54129 & 54130 |
| ZNF676 | GGGAGACCATTGACATTTAGGGA | CAGCAATACCCAGGAAGACCA | 54131 & 54132 |
| ZNF69 | GACAGGCTGAACTTCCAGGA | TAGGCCAACTTCTCCACACACA | 54133 & 54134 |
| ZNF695 | TCATCTGTCTGGAGGCAAGGAA | GCAGGCCCTGCTCTGGCA | 54135 & 54136 |
| ZNF716 | AAGACCGGACCCCCTGGAA | GCATTGCCATTCCGCCAGAGA | 54137 & 54138 |
| ZNF730 | GTGGCAAATGTCTGGACACCGA | CTGGCCAAAGGTCTTGGGCA | 54139 & 54140 |
| ZNF74 | CAAAGAAGAACCGGCCCAGGA | GGGGACACCTGAGGGGGA | 54141 & 54142 |
| ZNF90 | CACCTGTCTGGAGCAAGGAA | CTGGACAAAGGTCTTGGGCA | 54143 & 54144 |
| ZNF92 | TCACAGCTAAGACGCCAGGA | CAGCAATACCAAGGAAGAGACCA | 54145 & 54146 |
| ZNF99 | CCTGGACATGGCTCAGCAGA | TAGAGACAGCGATACCCAGGA | 54147 & 54148 |
| ZNHIT2 | CGTGGCTAGAGAAGAGCGAGA | CCTGGCGCAGTCTAGGGCCA | 54149 & 54150 |
| ZNF680 | CACCTGGAAGCCTAGAAATGGGA | TTGCCACTCCTCCAGAGAGAA | 54151 & 54152 |

FIG. 2

```
                    SeqDNA-FwdAnc6                                                      SeqIND-FwdAnc7
                    AGCAGCAGCACCGACCAGCAGACA           F                                TCTGTGCTGCTGGTCGGTGCTCGTCGT
FP7-Ind-A                                                                                                                                                  RP5-Ind-A
AGCAGAAGACGGCATACGGCATACGAGATGCATACGAGATGCATACGAGATGCA...GSP-DNA-GSP-TCTGTGCTGCTGGTCGGTGCTCGTCGTGTAGATCTCGGTGGTCGCCGT
TCGTCTTCTGCCTGCCTGCCTACGTATGCTCTACGTATGCTCTACGTATGCTGT...GSP-DNA-GSP-AGACACGACGACCAGCCACGAGCACGATCTAGAGCCACCAGCGGCA
                    TCGTCGTCGTGGCTGGTCGGTCGTCTGT         R        AGACACGACCAGCCACGAGCACGA
                    SeqIND-RevAnc6                                SeqDNA-RevAnc7
```

EXPERIMENTALLY VALIDATED SETS OF GENE SPECIFIC PRIMERS FOR USE IN MULTIPLEX APPLICATIONS

CROSS-REFERENCE TO RELATED APPLICATIONS

This application is a continuation-in-part of U.S. application Ser. No. 15/133,184 filed on Apr. 19, 2016, which application claims priority pursuant to 35 U.S.C. § 119(e) to U.S. Provisional Application Ser. No. 62/150,166 filed on Apr. 20, 2015, the disclosures of which are herein incorporated by reference in their entirety.

INTRODUCTION

Multiplex polymerase chains reactions (multiplex PCR) include the simultaneous amplification of many DNA sequences in one reaction. Applications of multiplex PCR include but are not limited to the identification of mutations, gene deletions, and polymorphisms and the production or quantitation of amplicons for high throughput sequencing and genotyping. Multiplex reactions may include two or more target sequences with primer pairs or one template selectively amplified with primers designed to target specific regions. Additionally, such reactions may include multiple templates with regions multiplied by multiple primer pairs.

During multiplex PCR, proper amplification requires optimal conditions. It is important to maintain controlled cycling and annealing temperatures and fine-tuned relative concentrations of primers, buffers, dNTP's, Taq DNA polymerase, template and other PCR reagents. Common problems associated with multiplex PCR include: i) mispriming due to nonspecific primer binding to non-target templates; and ii) the formation of unwanted side products due to the presence of multiple primer pairs. In conjunction with several other sensitive procedural variables, these issues may lead to cross hybridization, and uneven or no amplification of some target sequences. Unwanted multiplex PCR side products form in the presence of multiple primer pairs. These side products may include homodimers, formed by inter-molecular base pairing between two similar primers, and heterodimers, formed from inter-molecular interactions between sense and antisense primers. Another undesirable occurrence is the formation of hairpins from intra-molecular interactions.

SUMMARY

Sets of experimentally validated gene specific primer pairs are provided. Embodiments of the sets include 10 or more gene specific primer pairs of forward and reverse primers. The forward and reverse primers of each primer pair include gene specific primers that are experimentally validated as suitable for use in a multiplex amplification assay. In some instances, each of the forward and reverse primers includes an anchor domain that includes a universal primer binding site. The sets find use in a variety of different applications, including high-throughput sequencing applications.

BRIEF DESCRIPTION OF THE FIGURES

Figure 1:
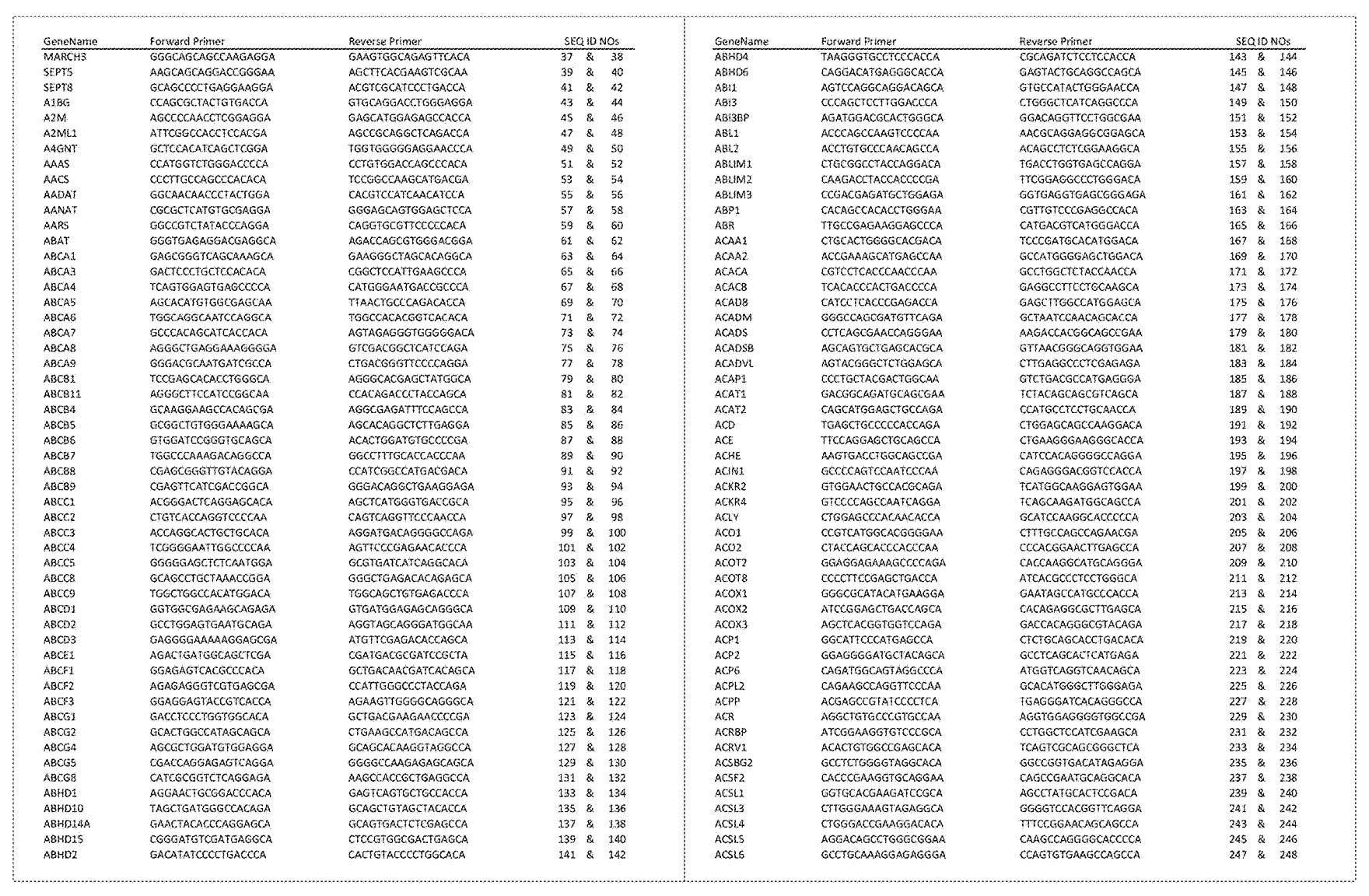
Figure 1:
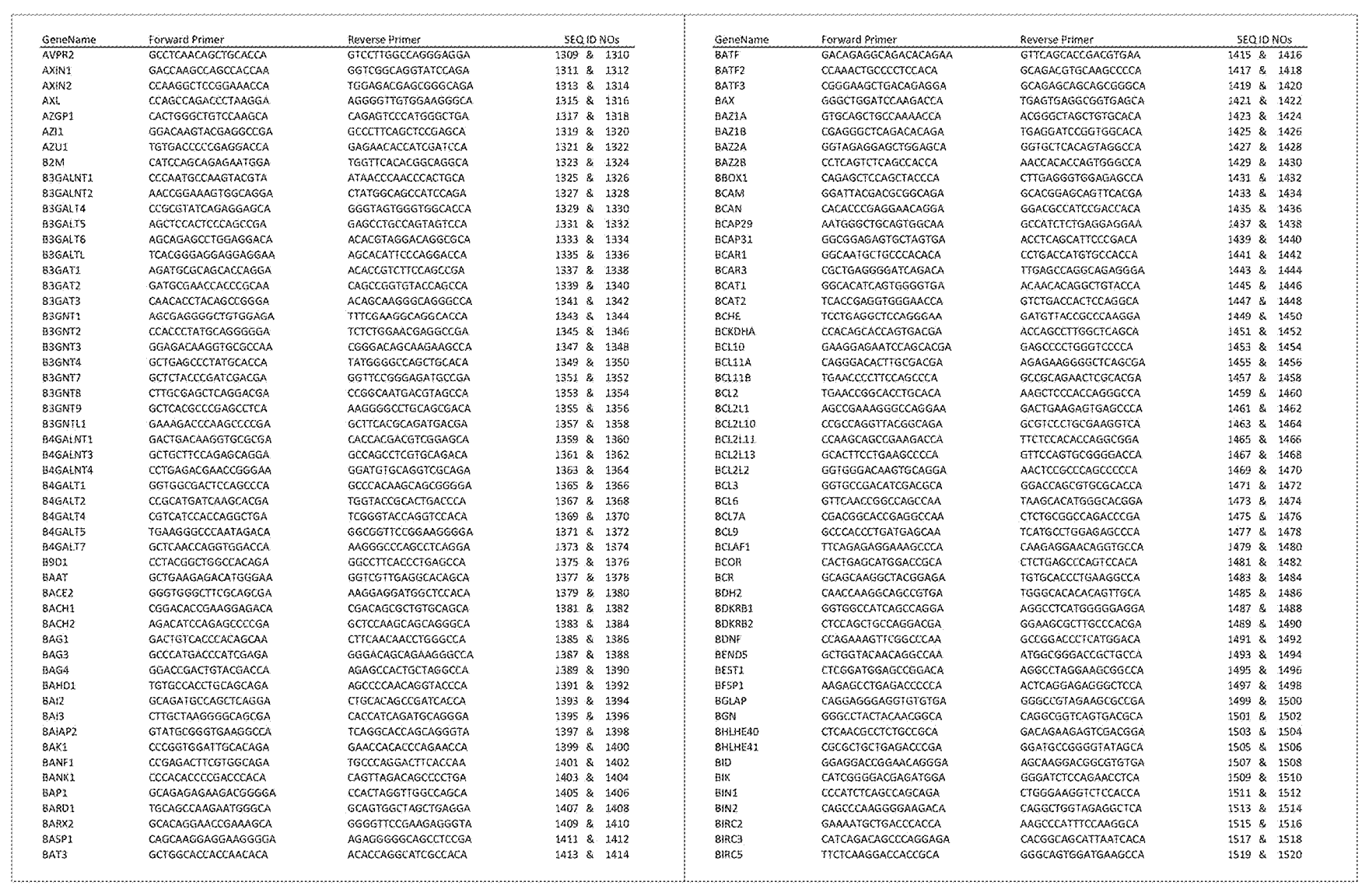
Figure 1:
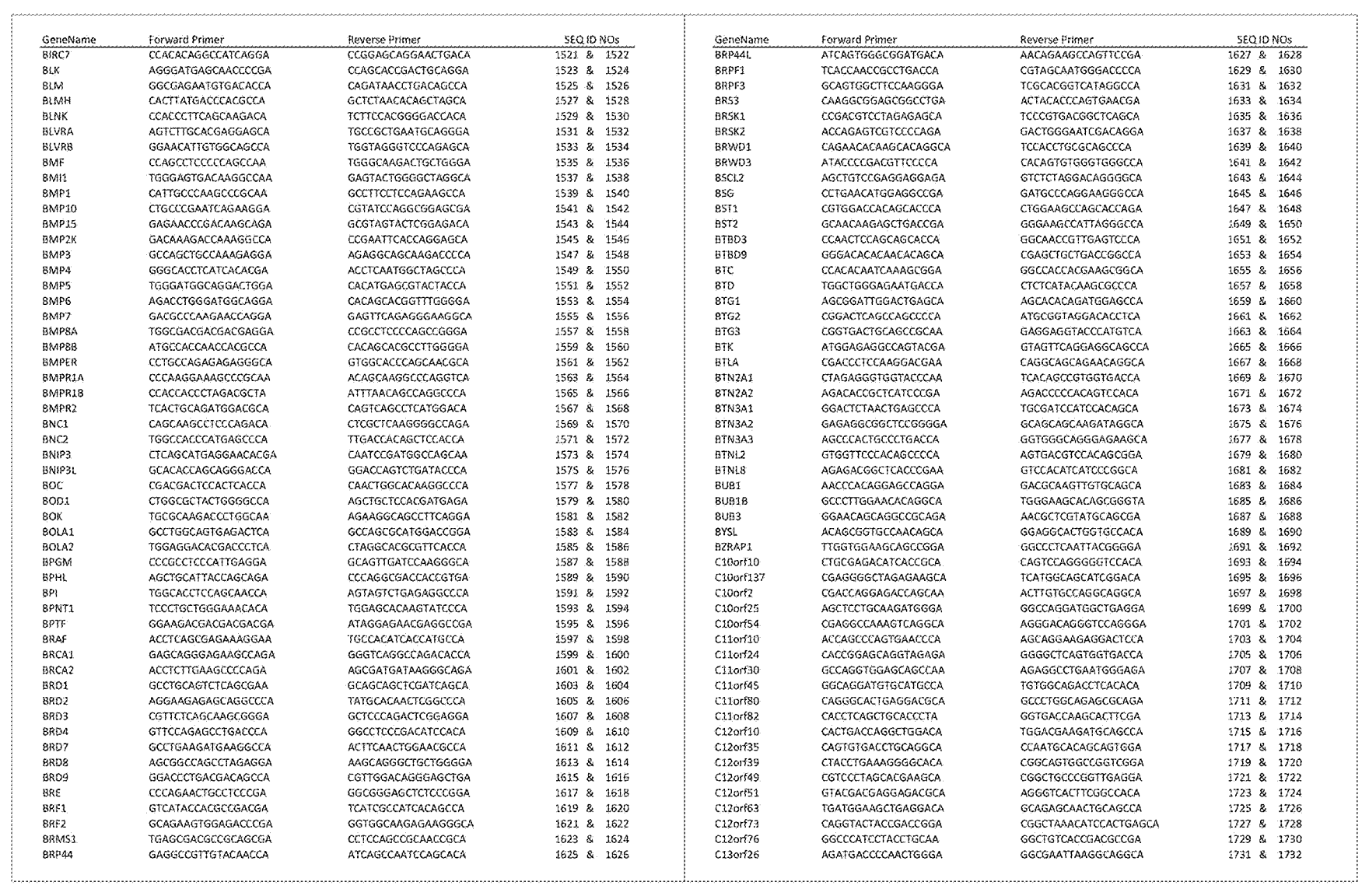
Figure 1:
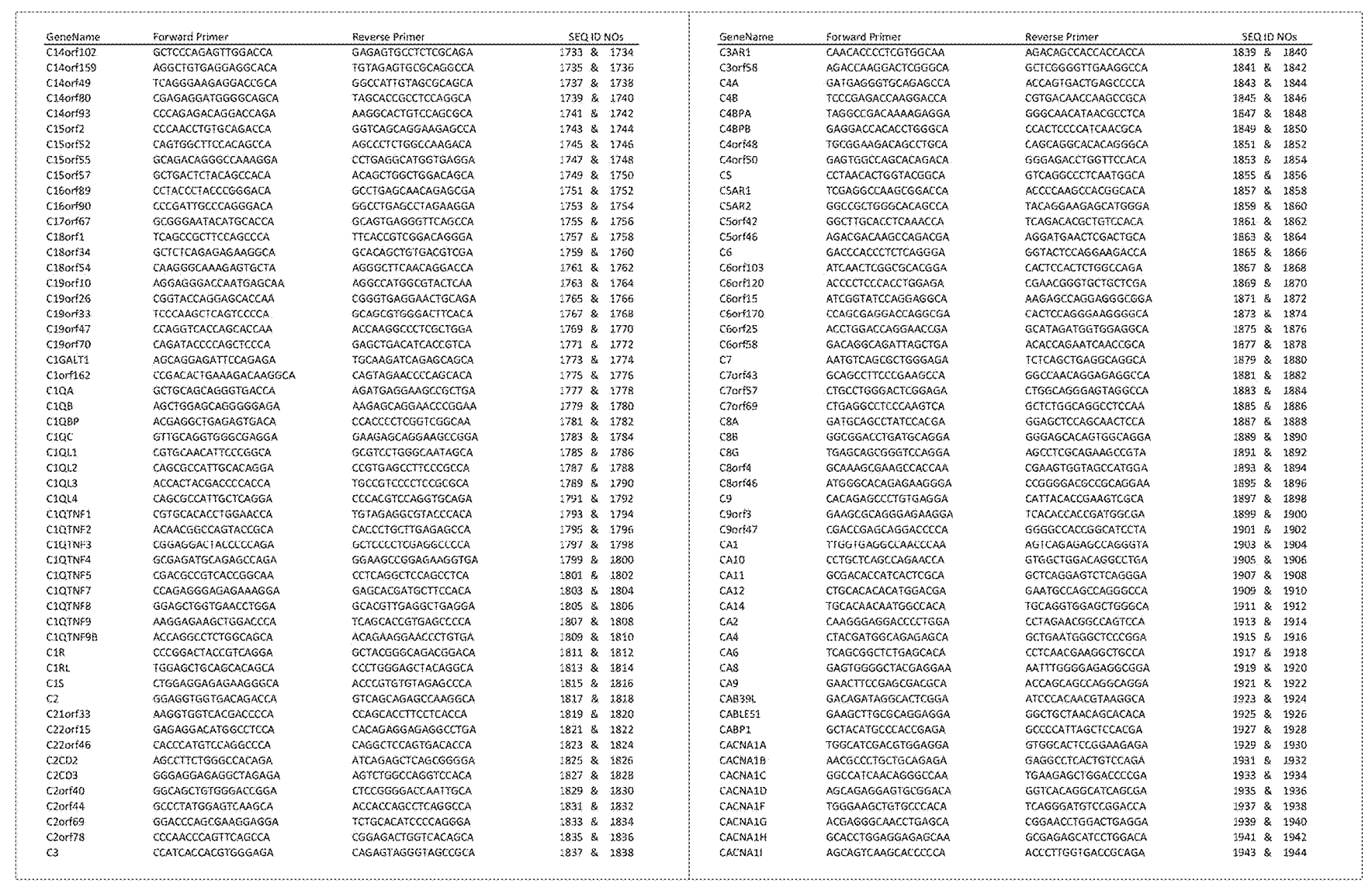
Figure 1:
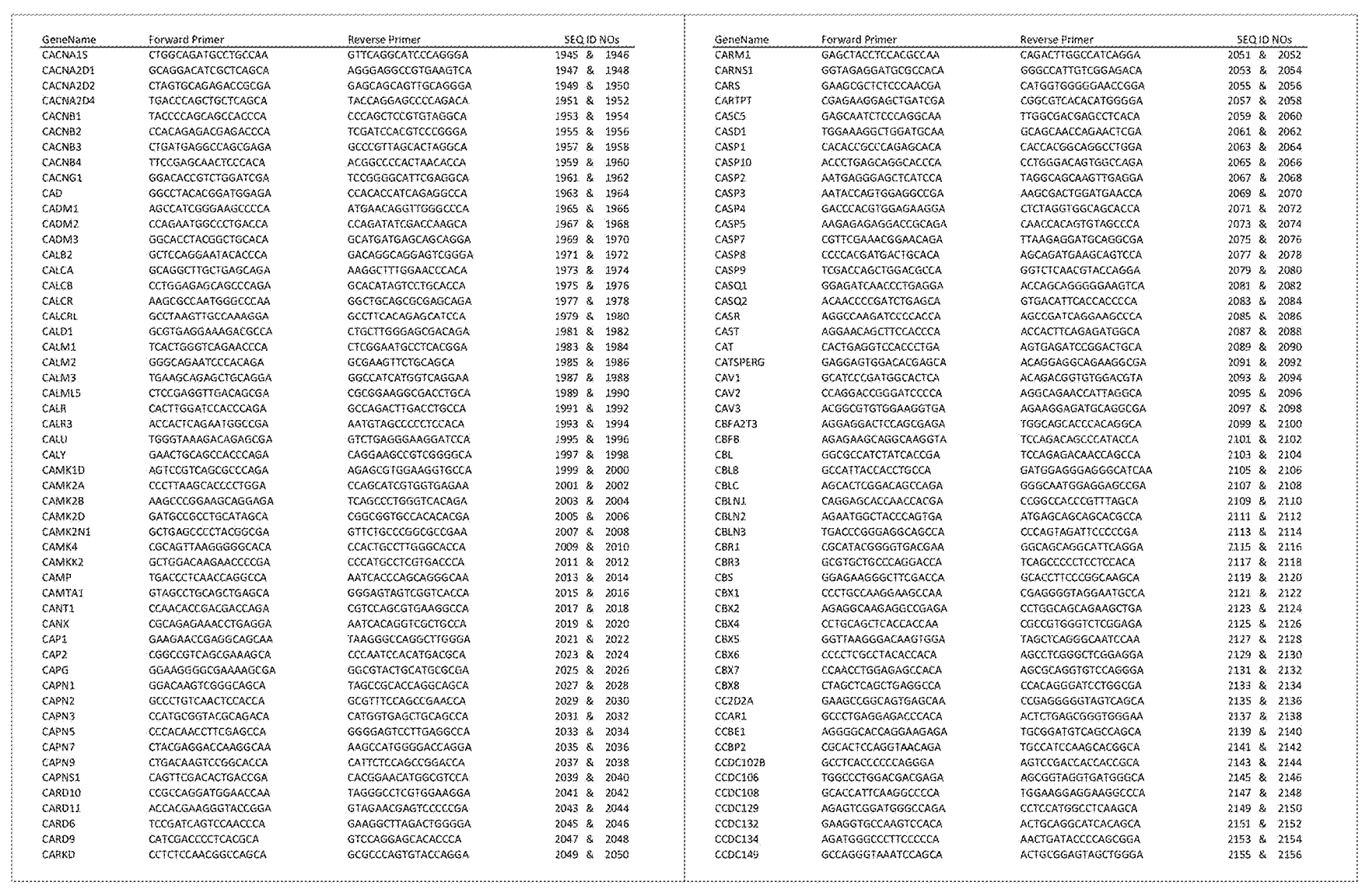
Figure 1:
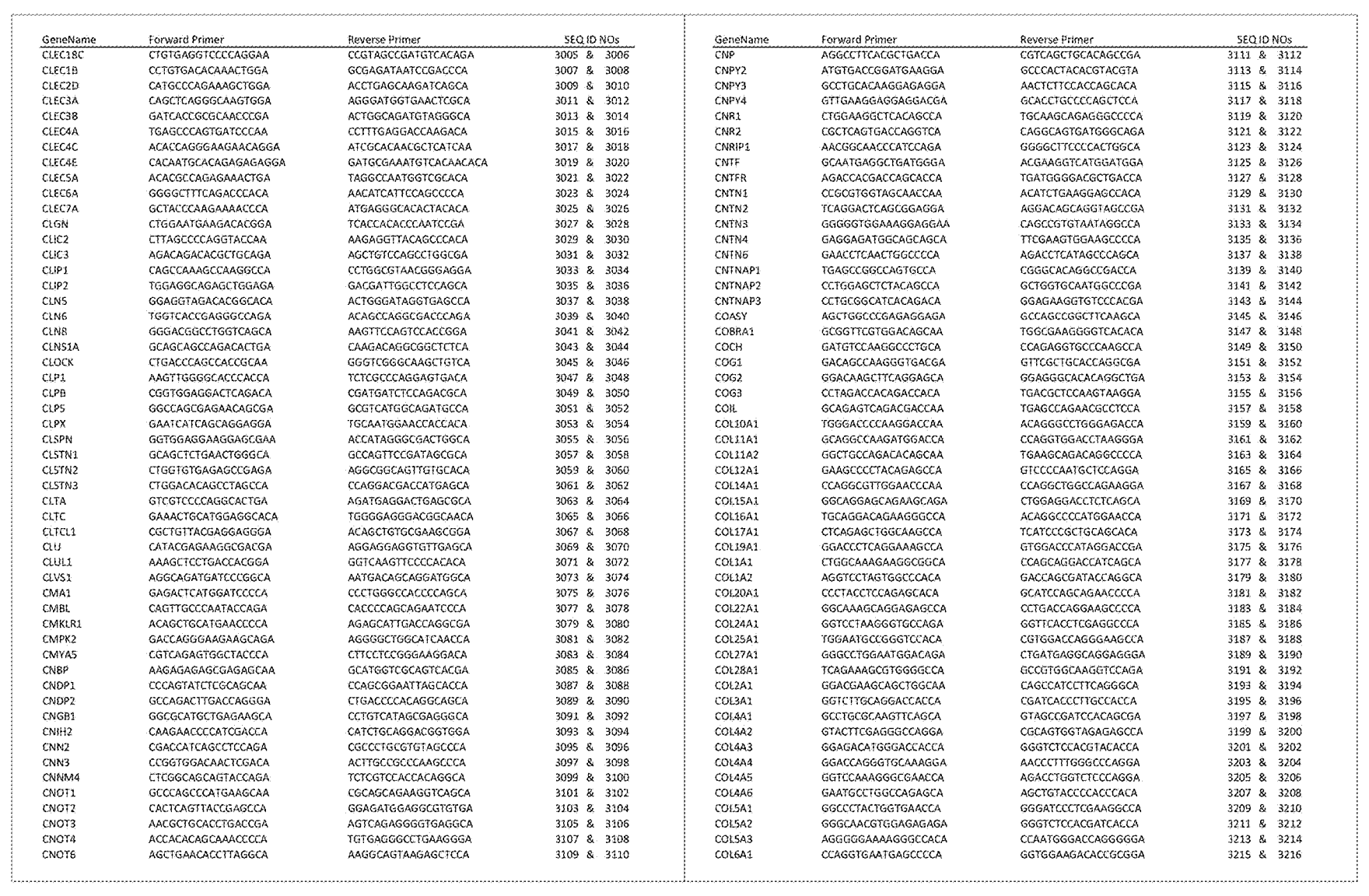
Figure 1:
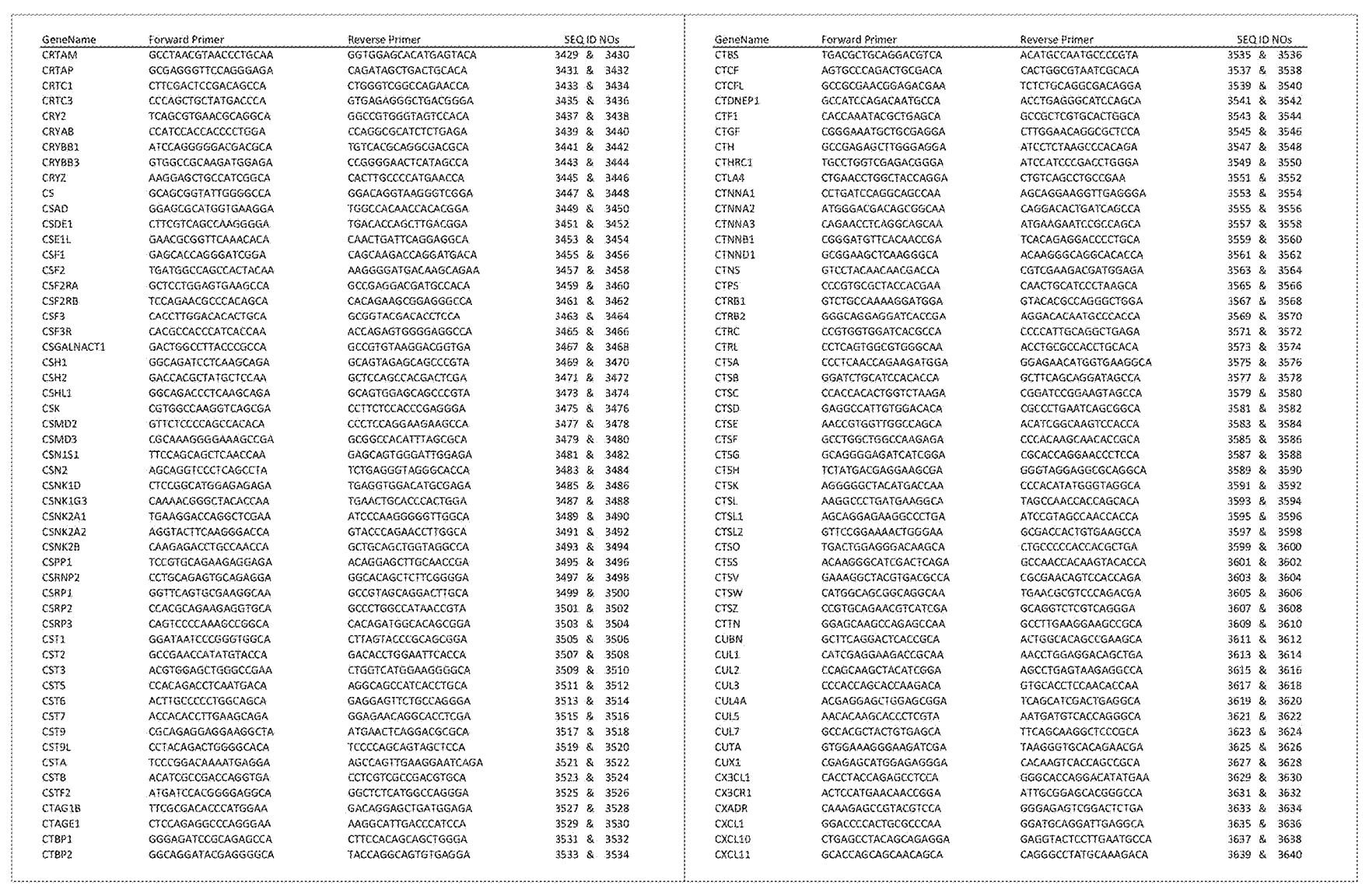
Figure 1:
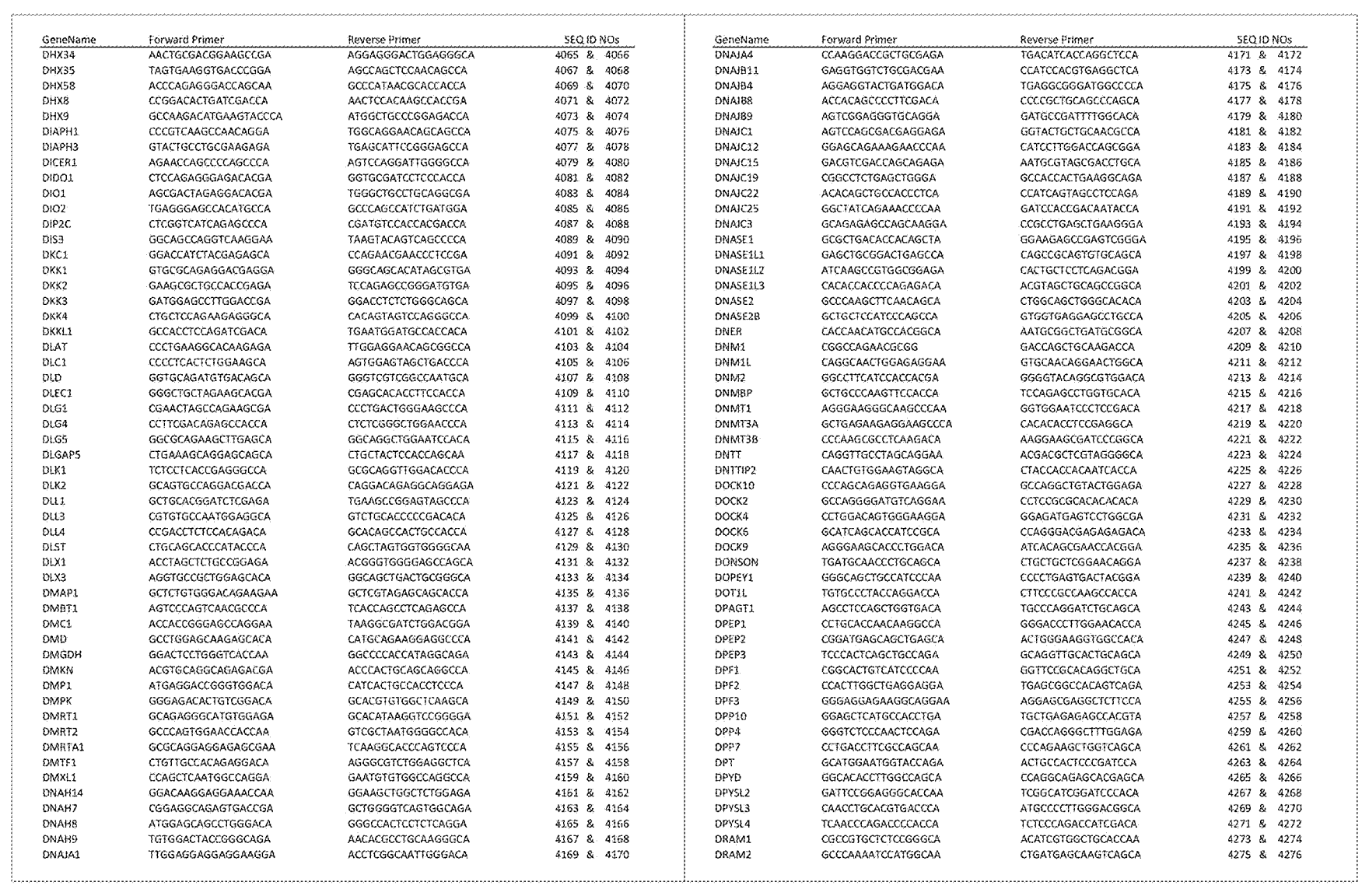
Figure 1:
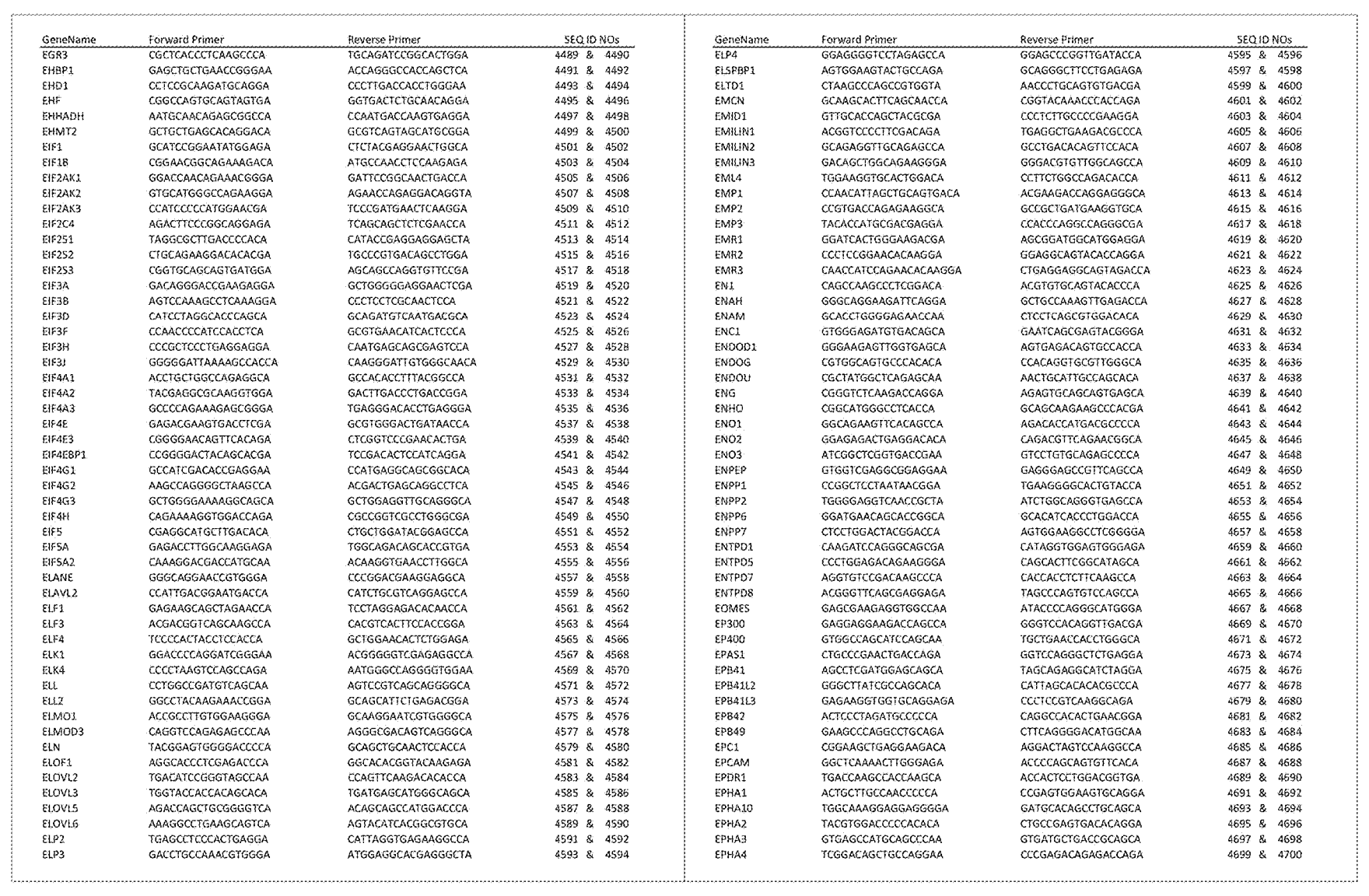
Figure 1:
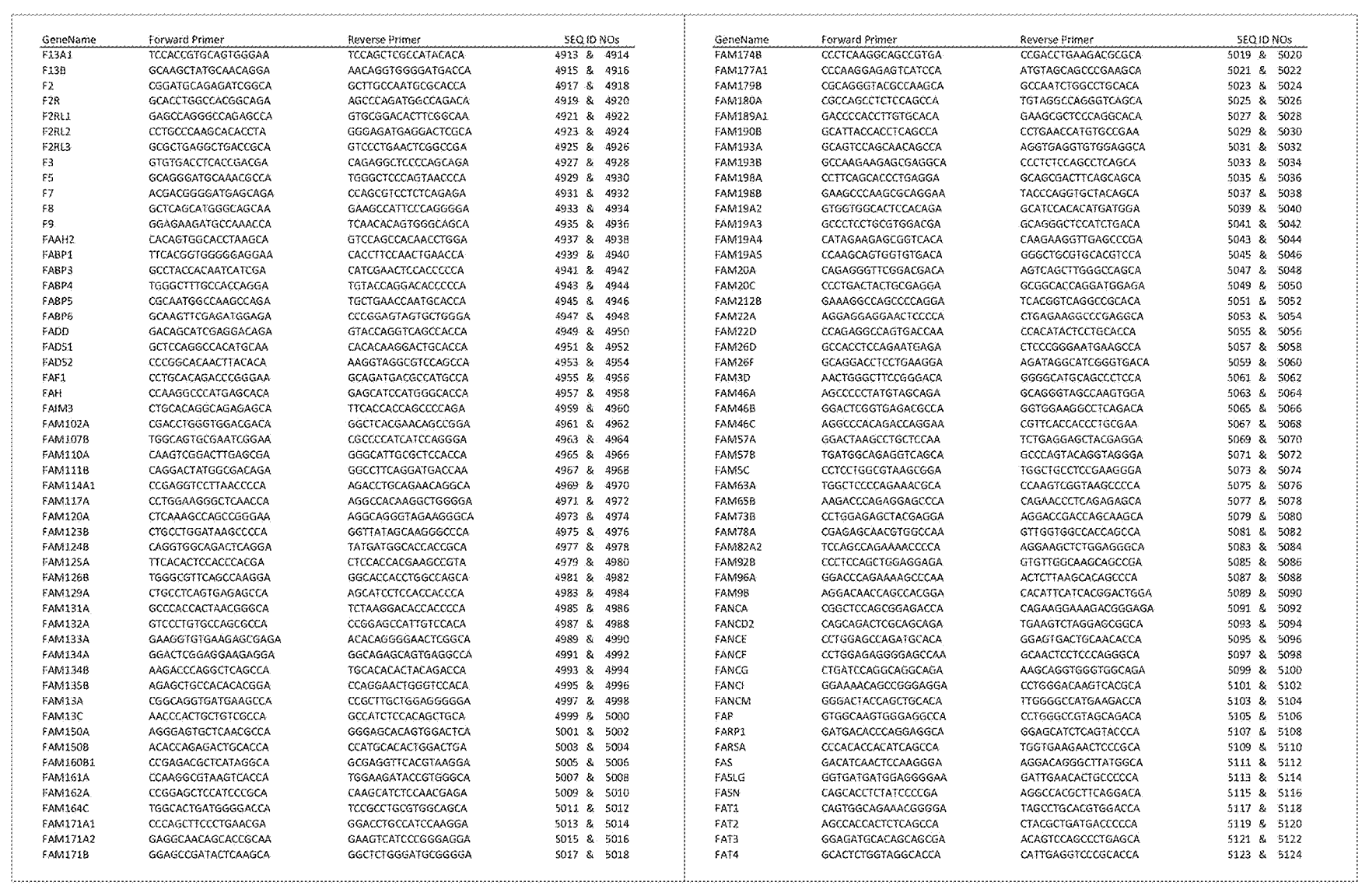
Figure 1:
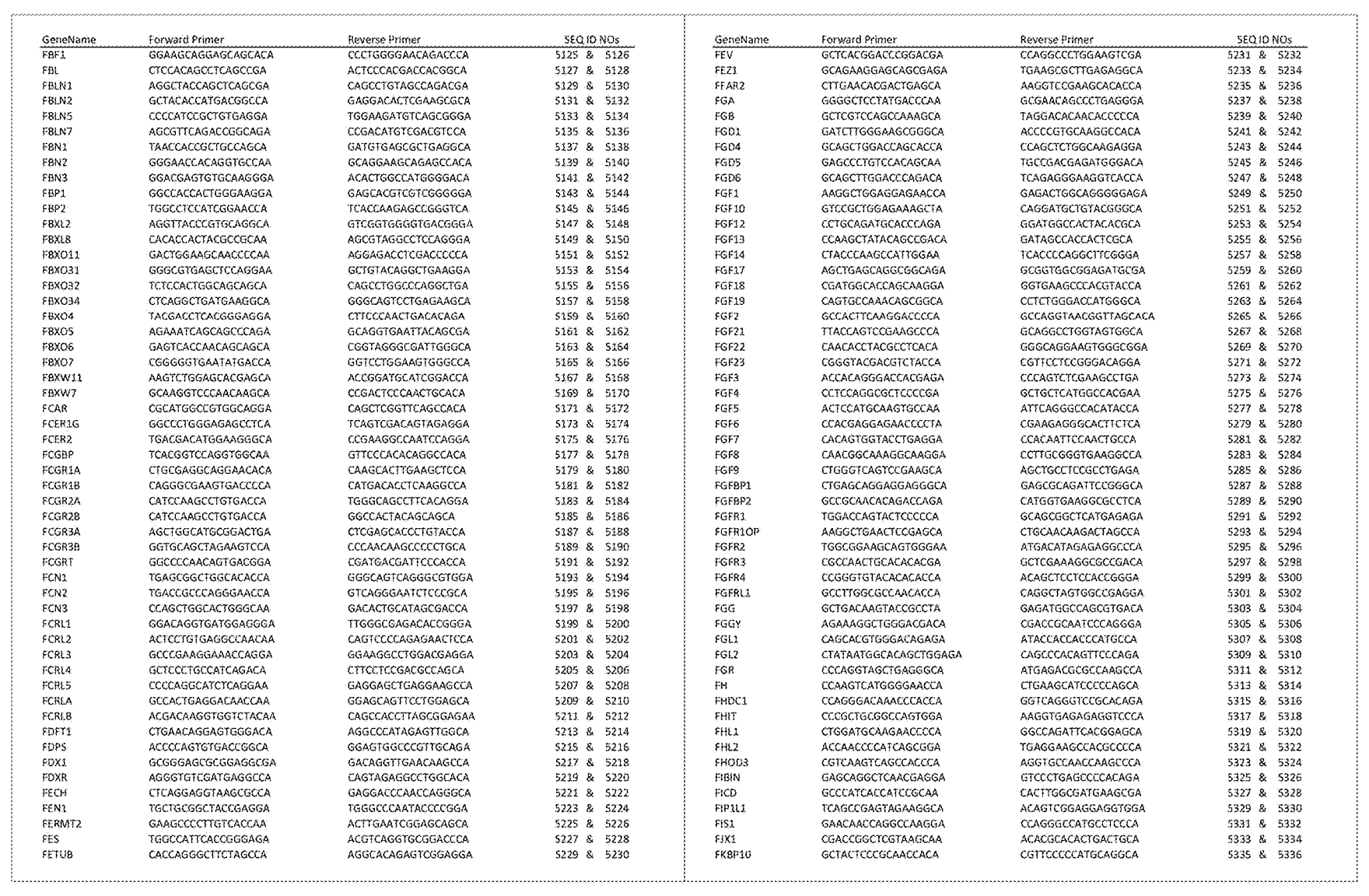
Figure 1:
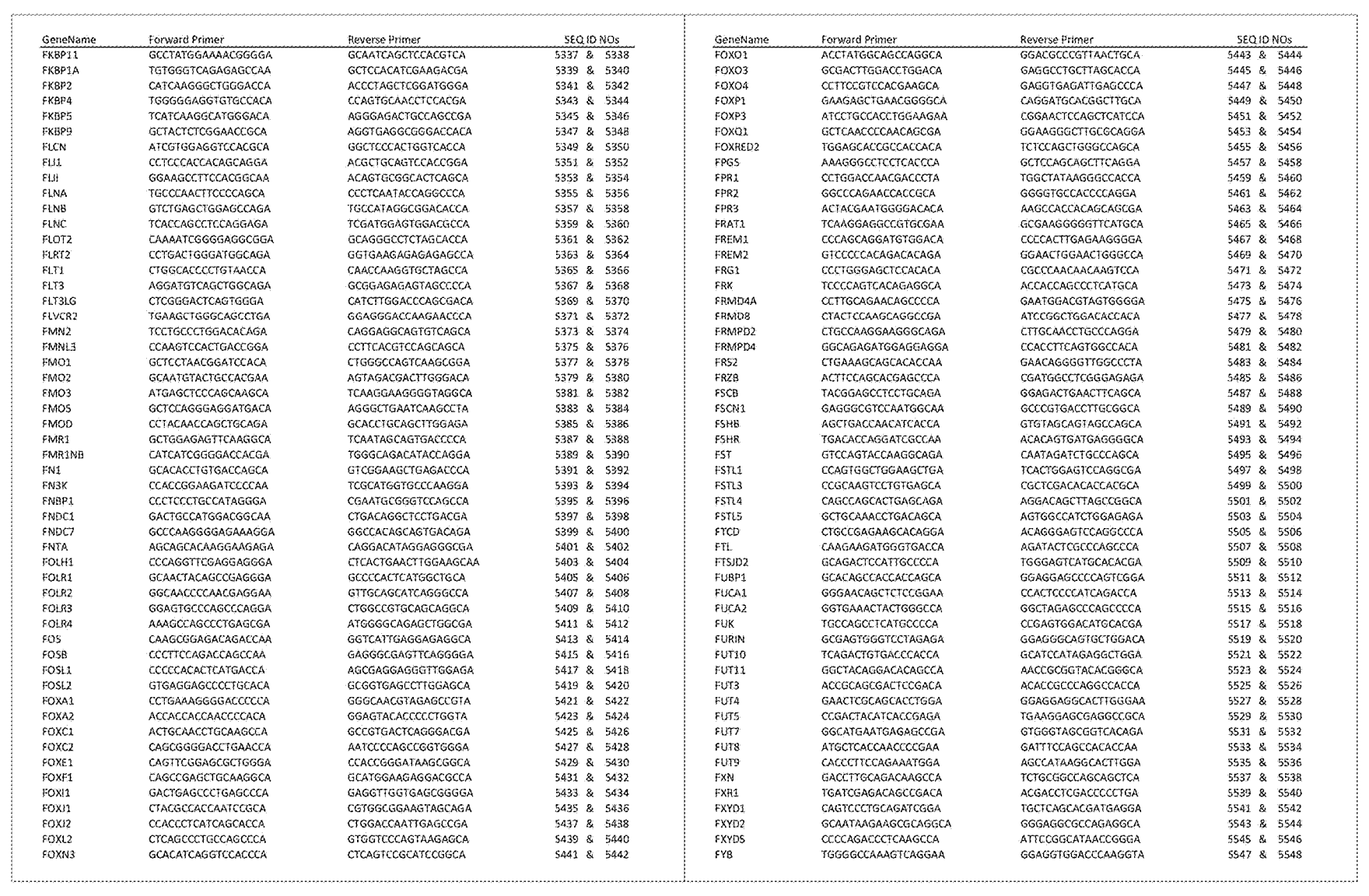
Figure 1:
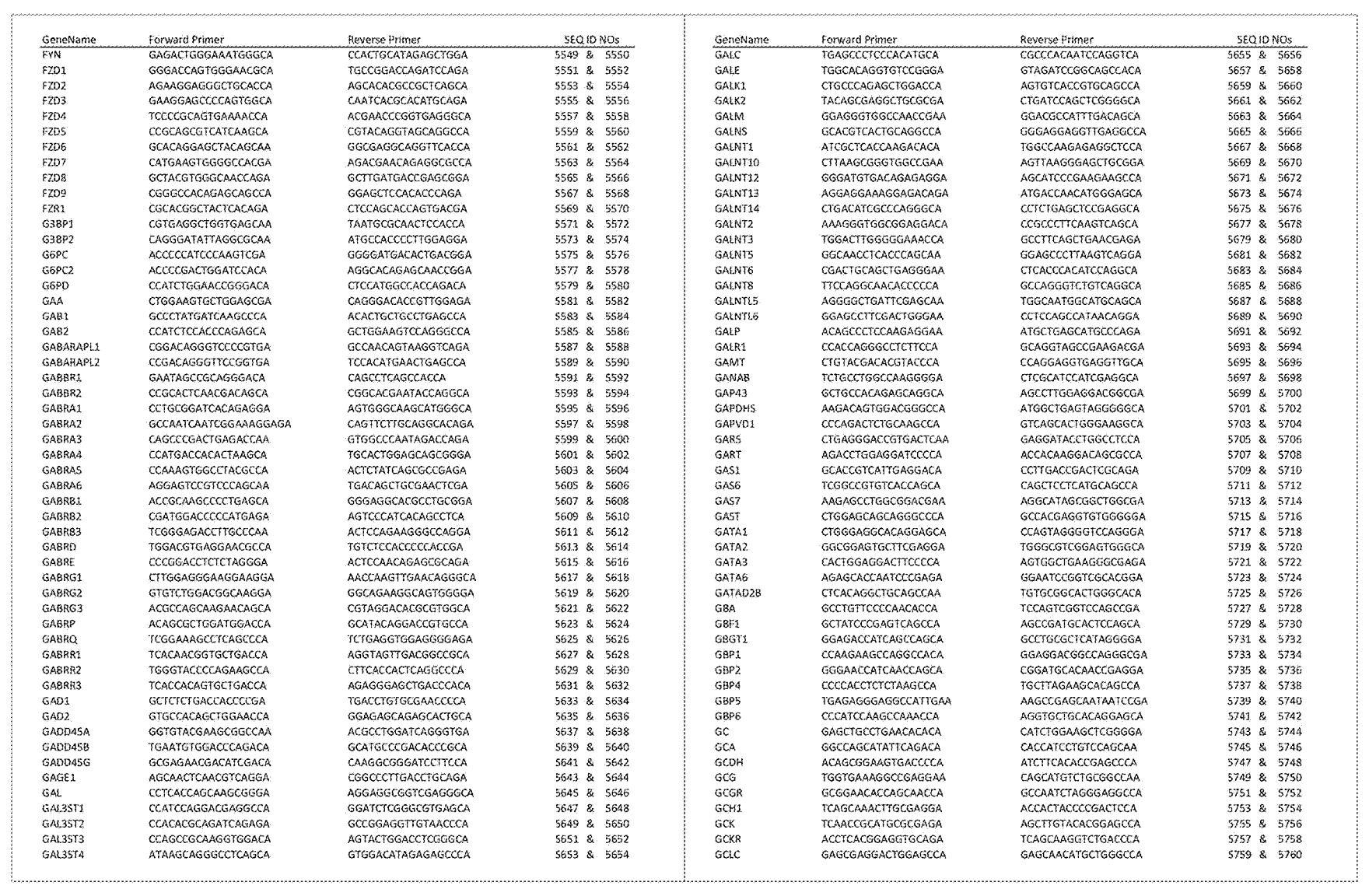
Figure 1:
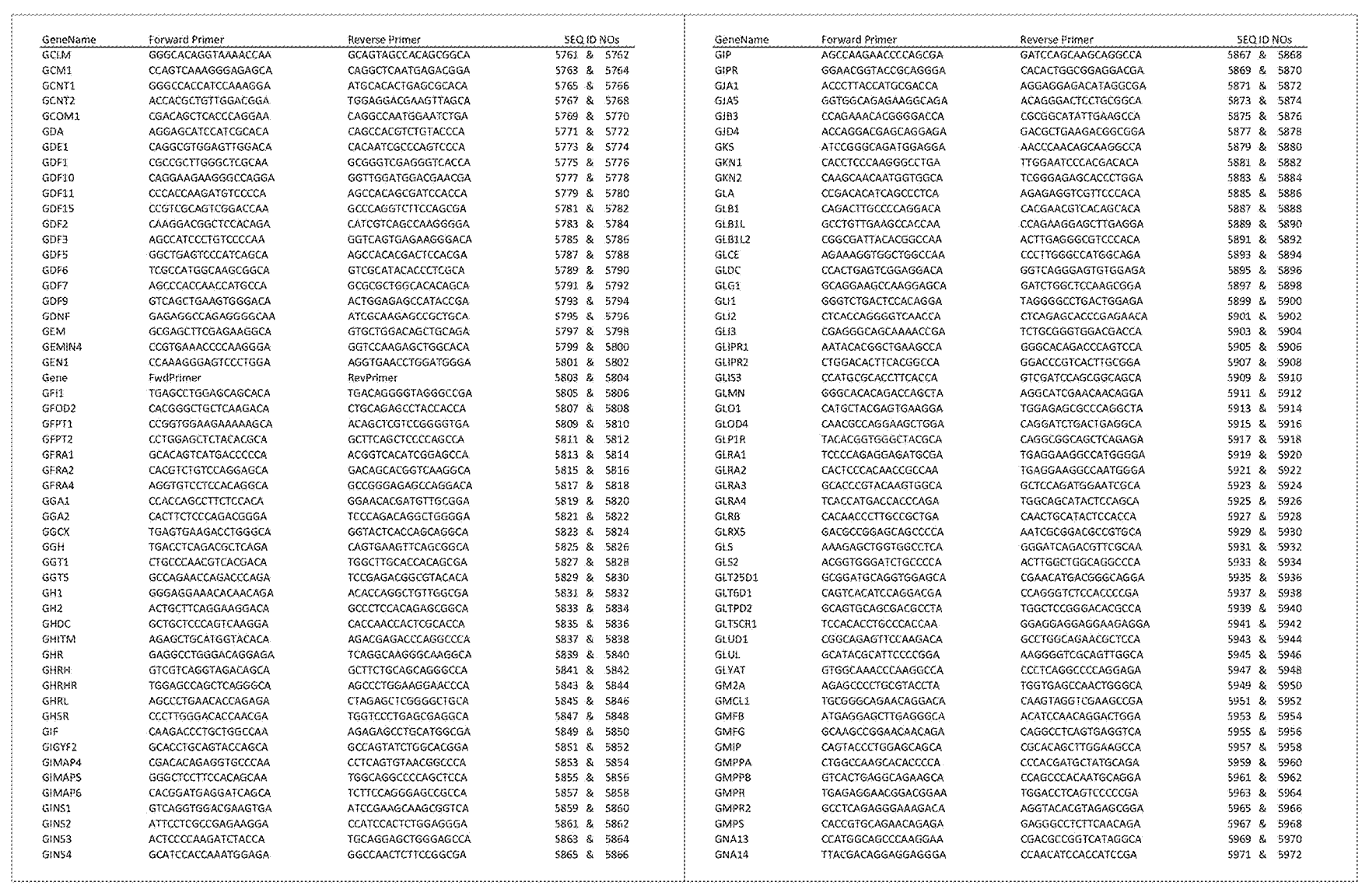
Figure 1:
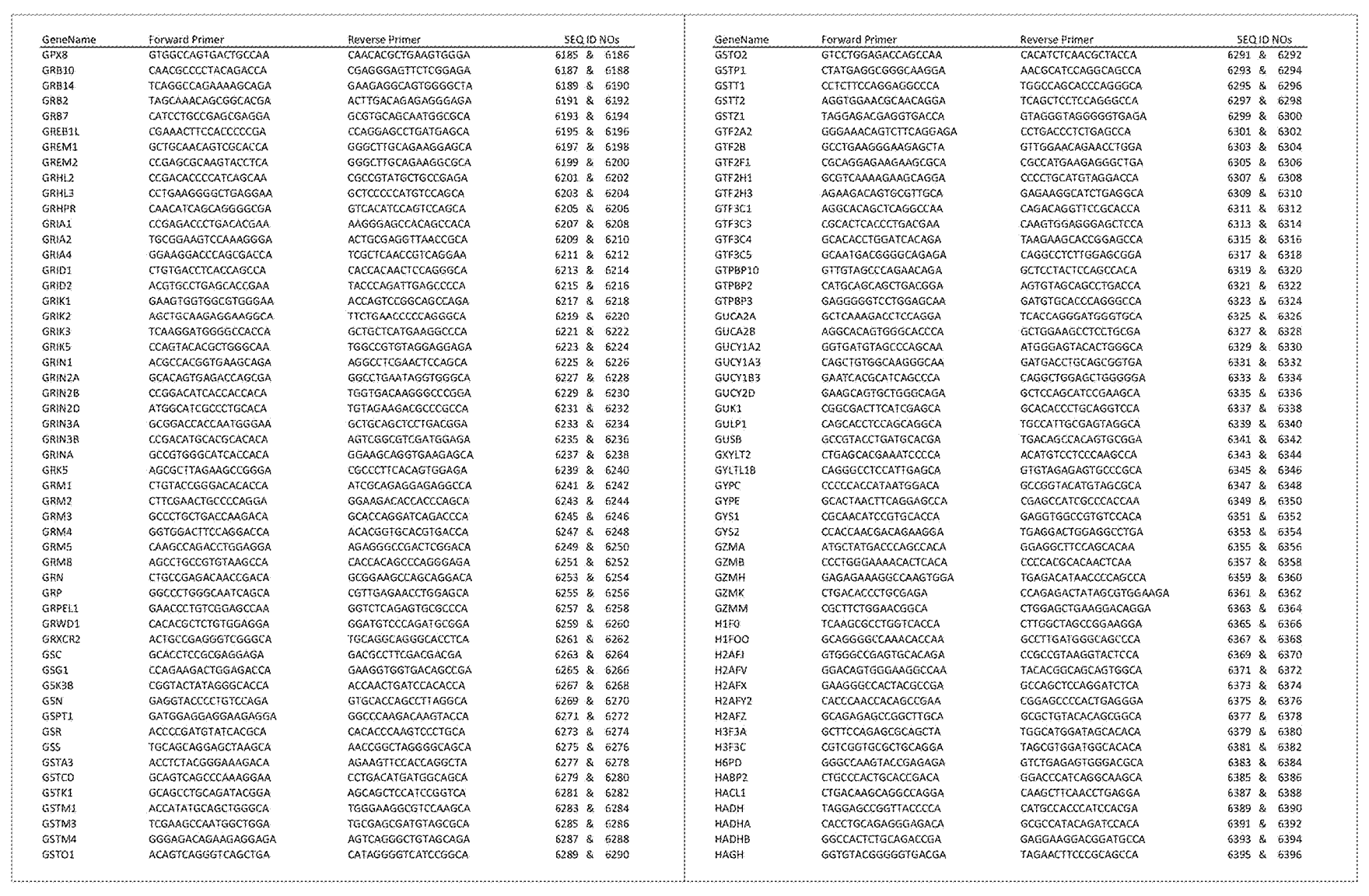
Figure 1:
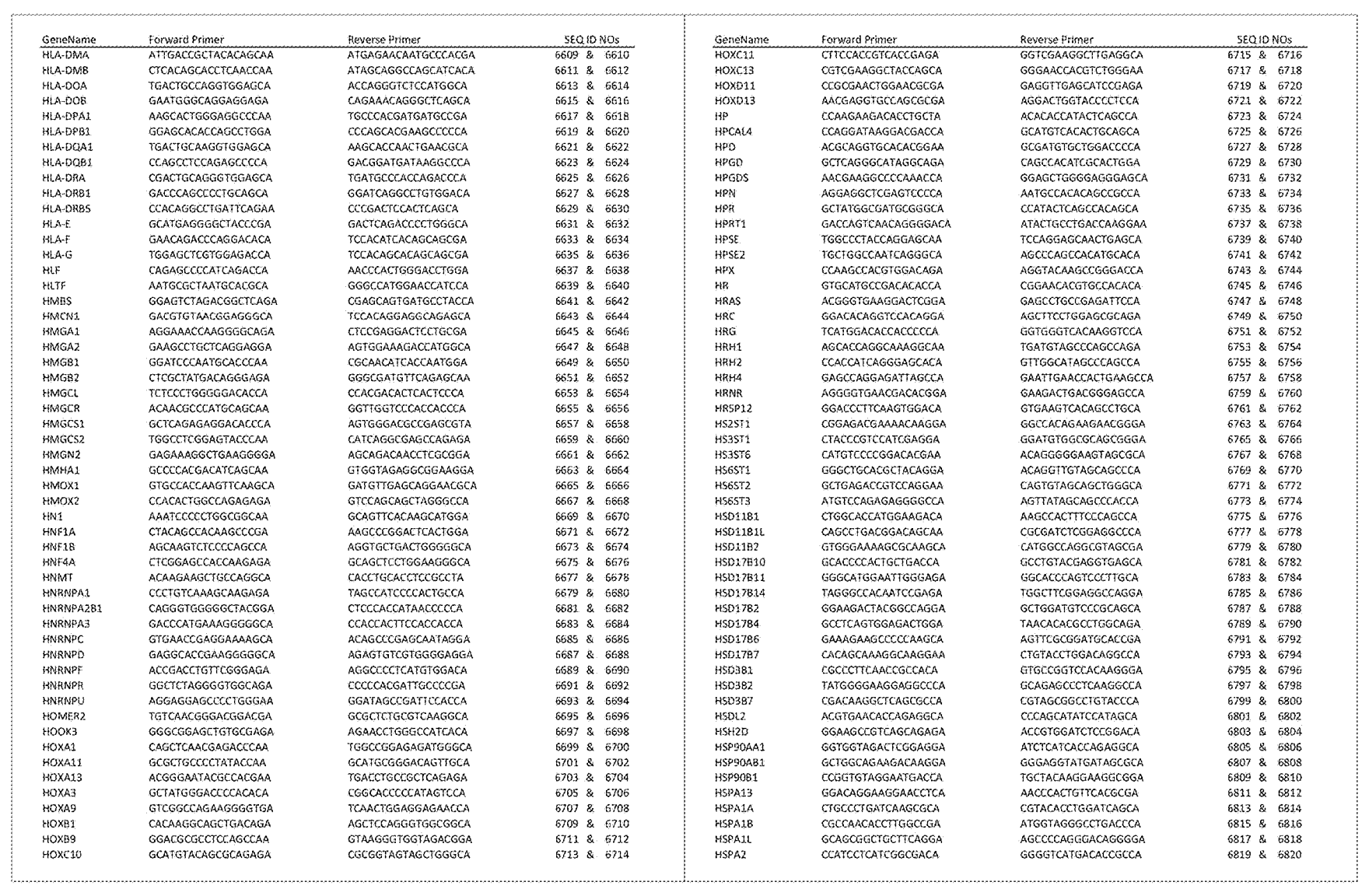
Figure 1:
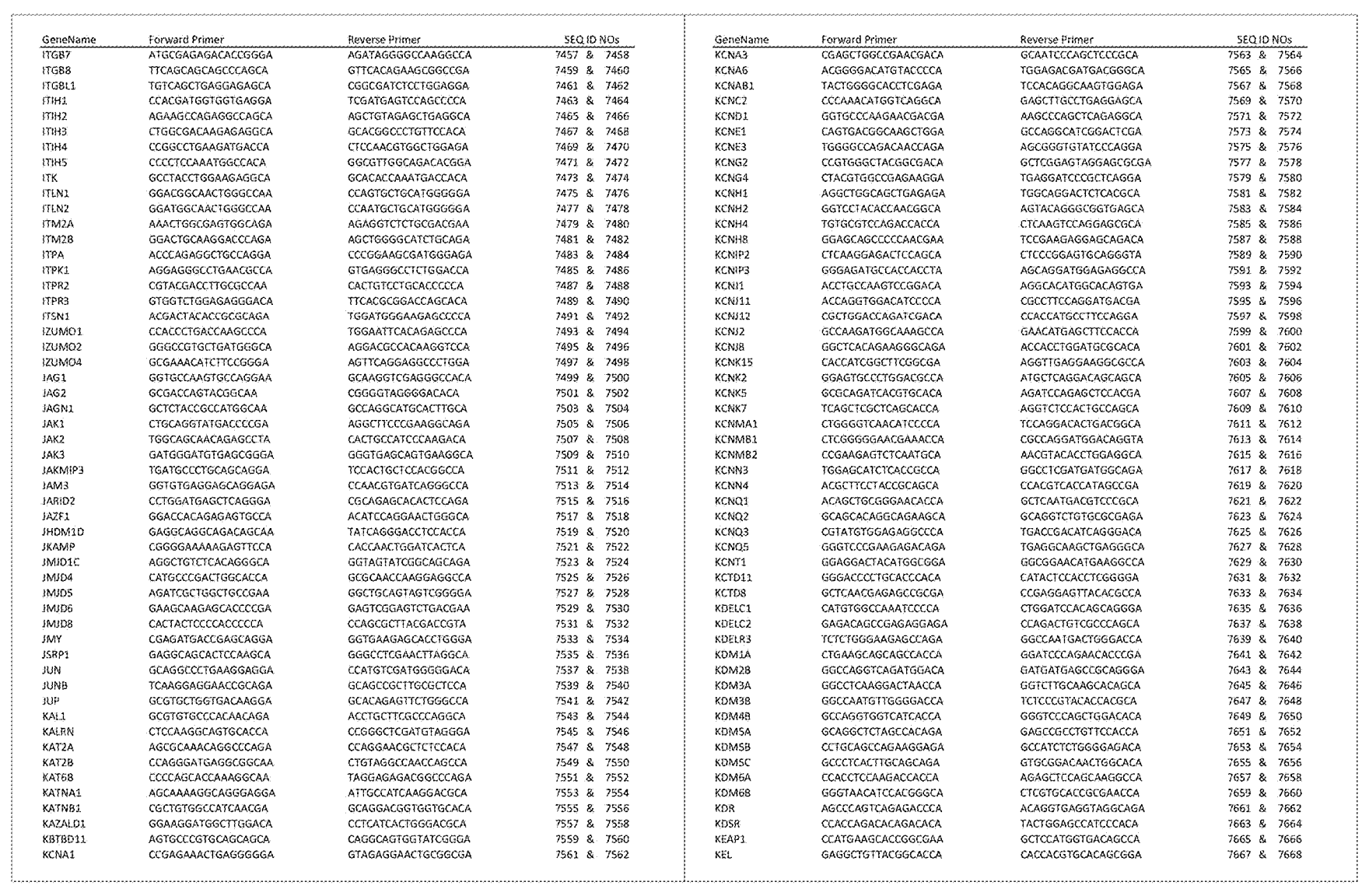
Figure 1:
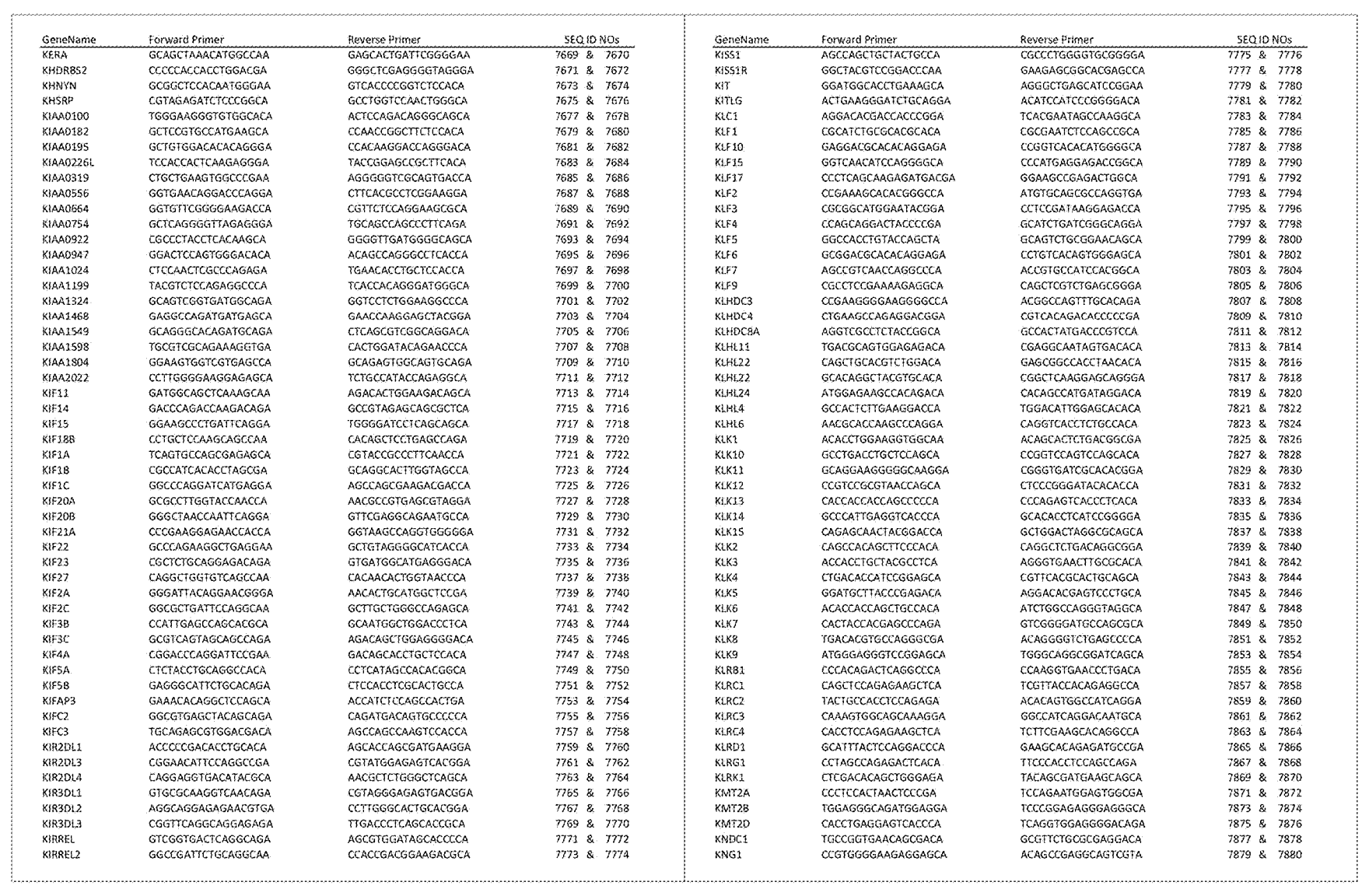
Figure 1:
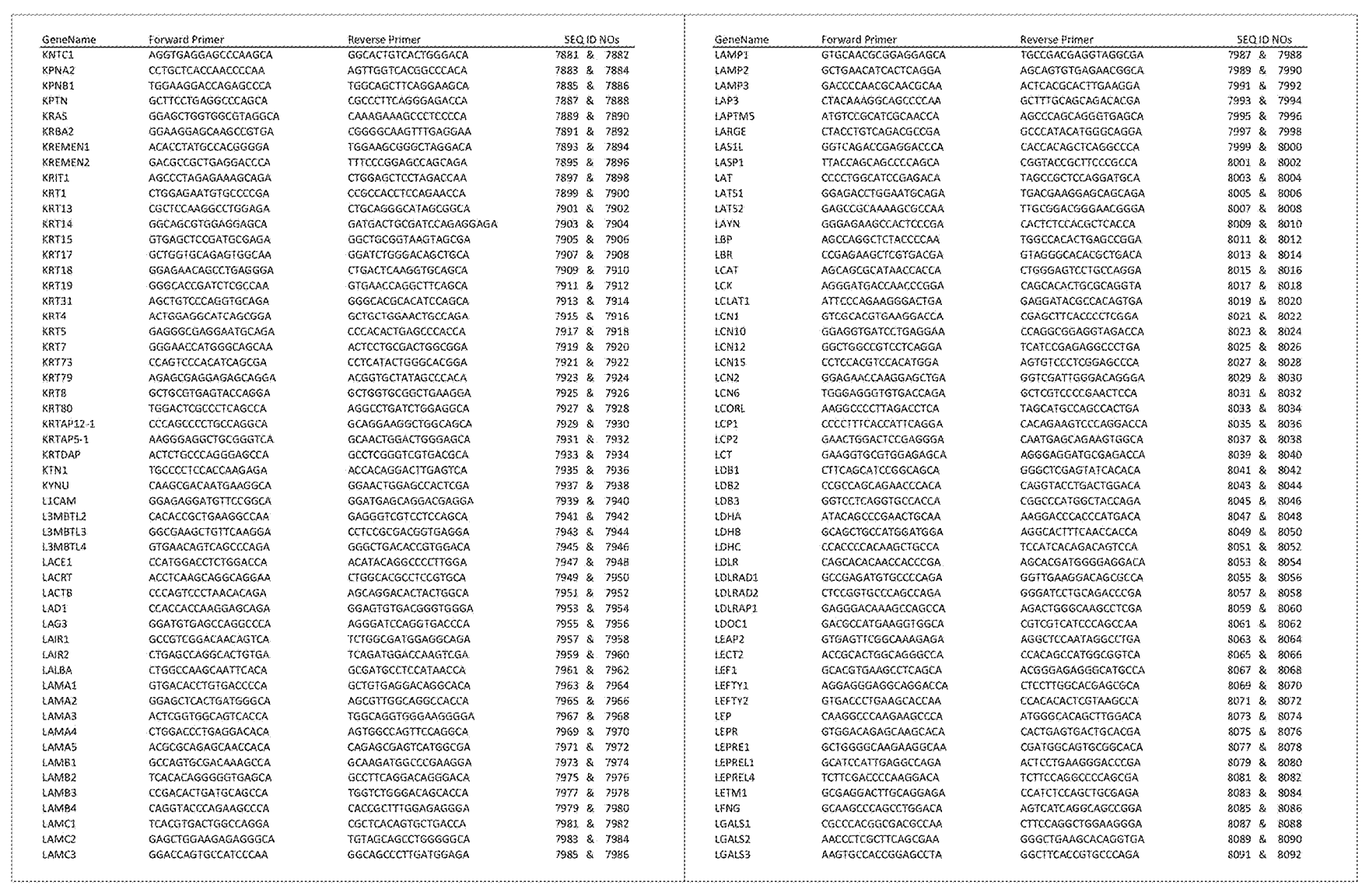
Figure 1:
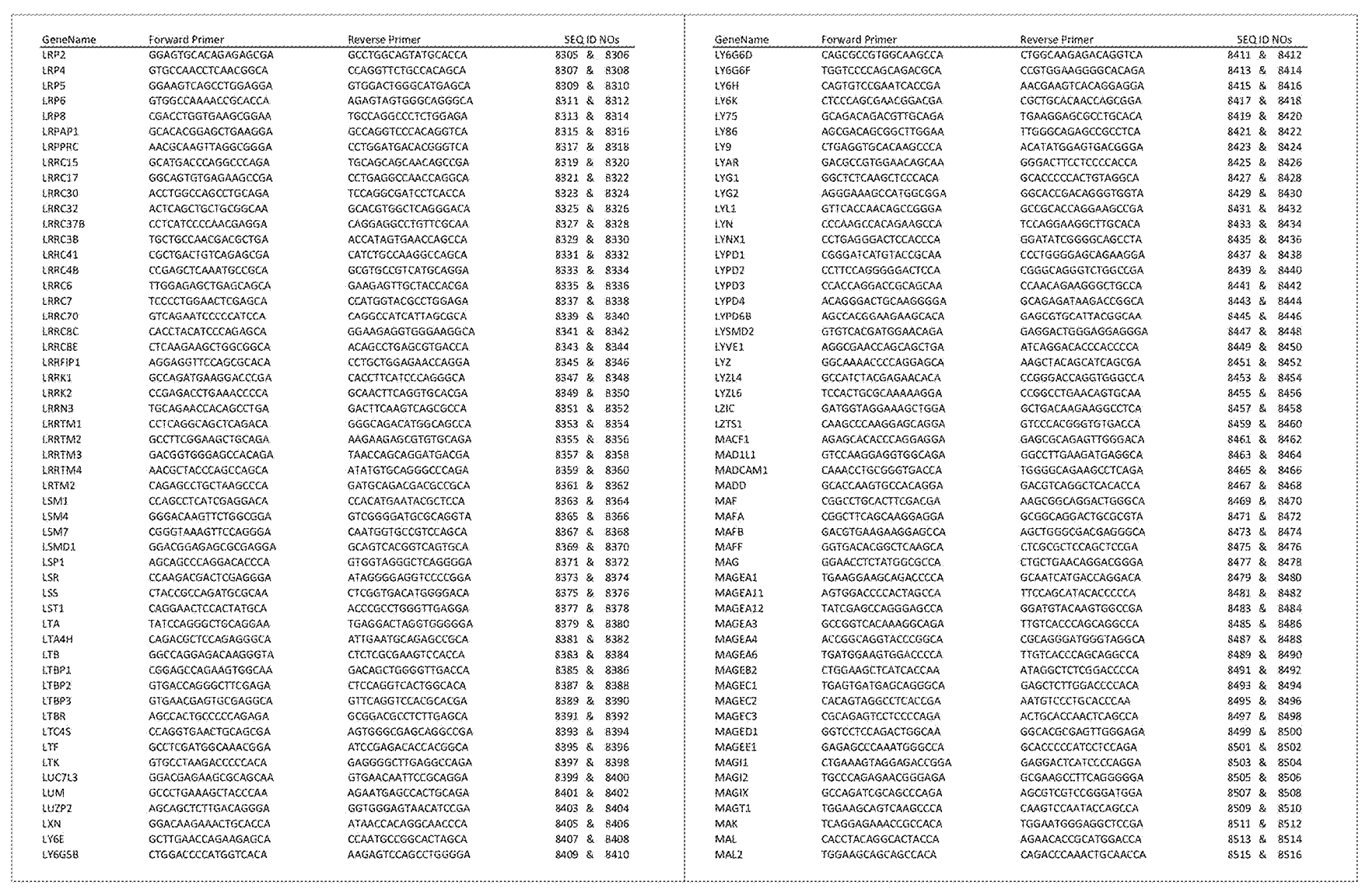
Figure 1:
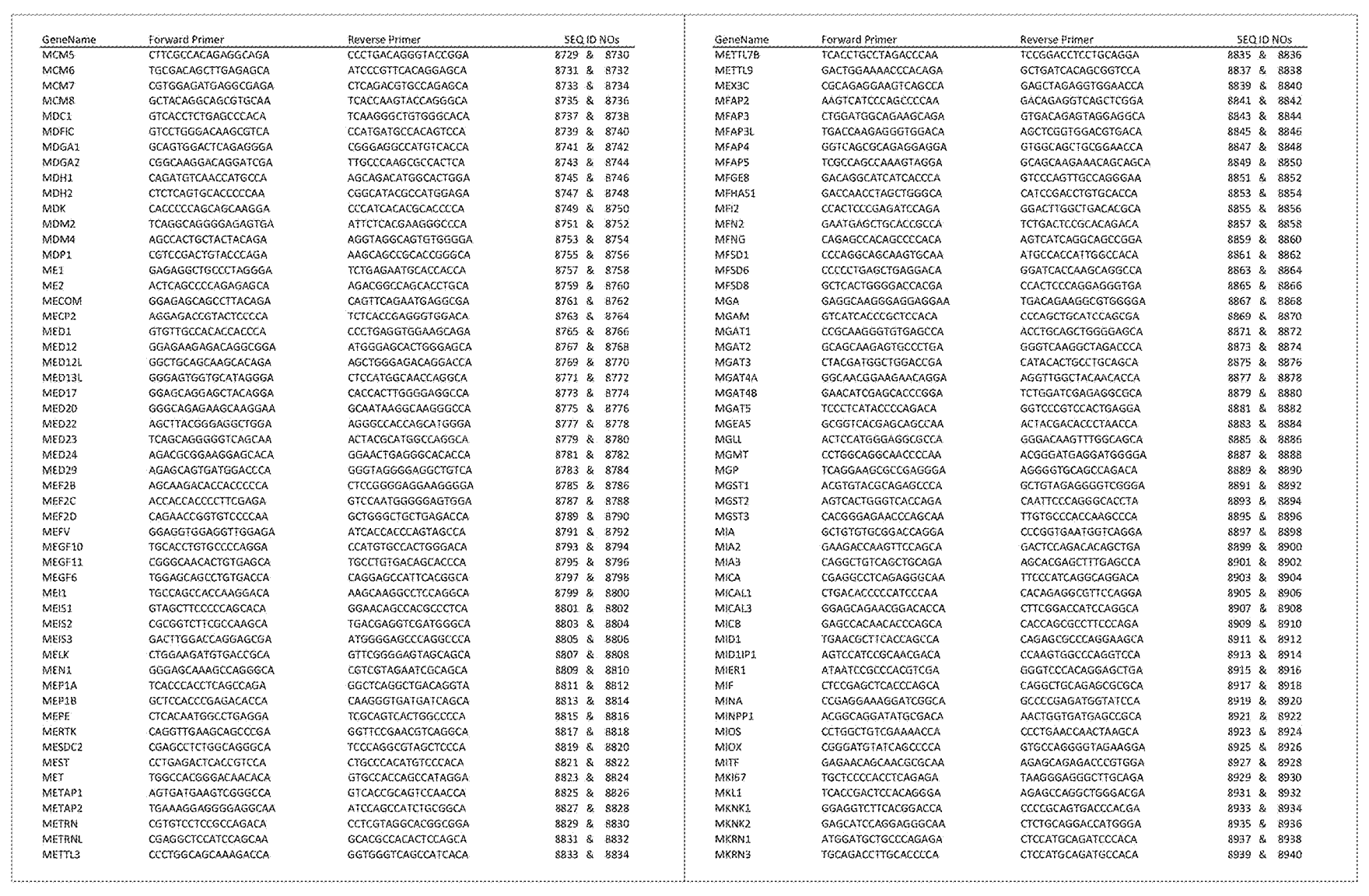
Figure 1:
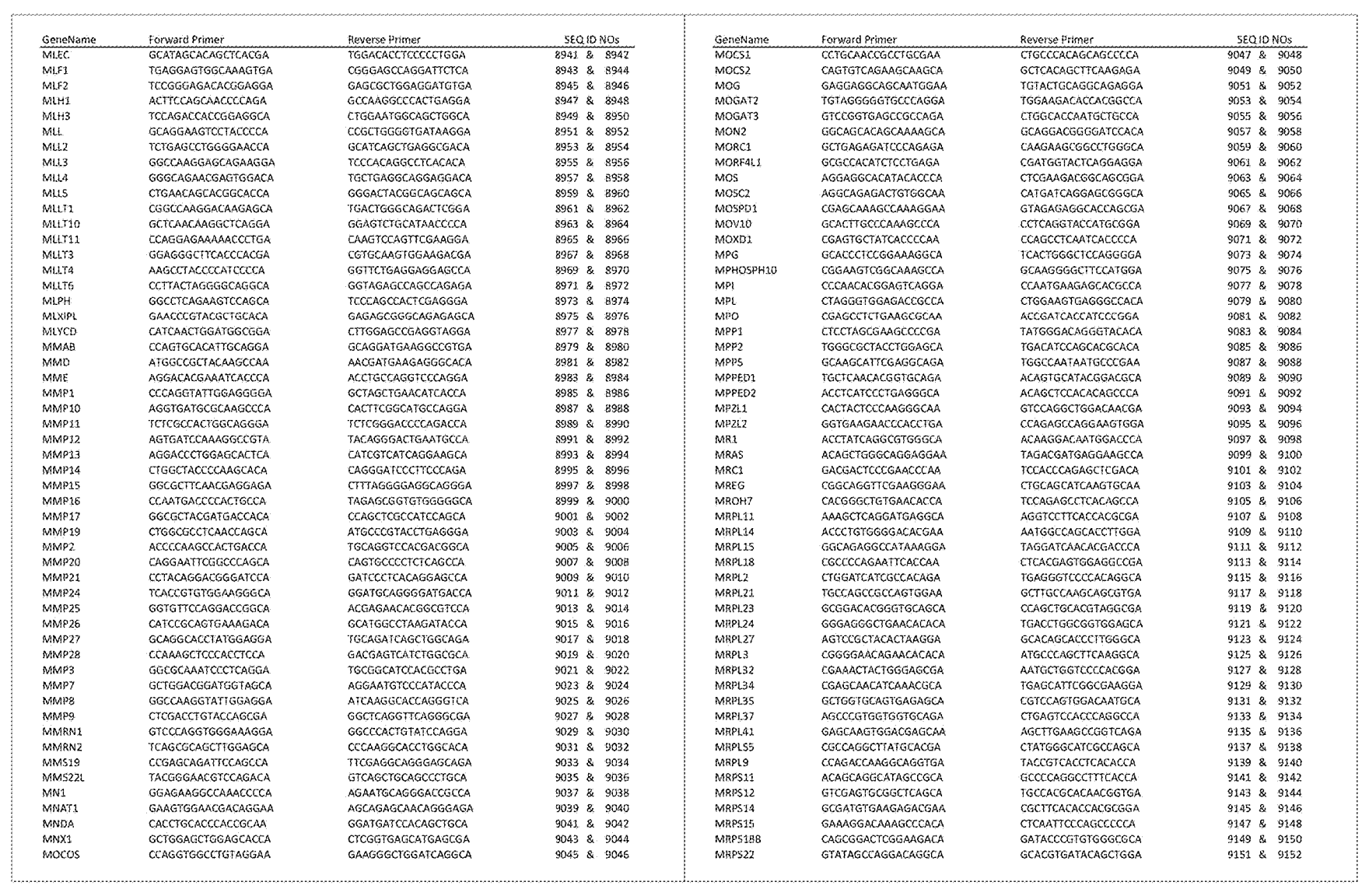
Figure 1:
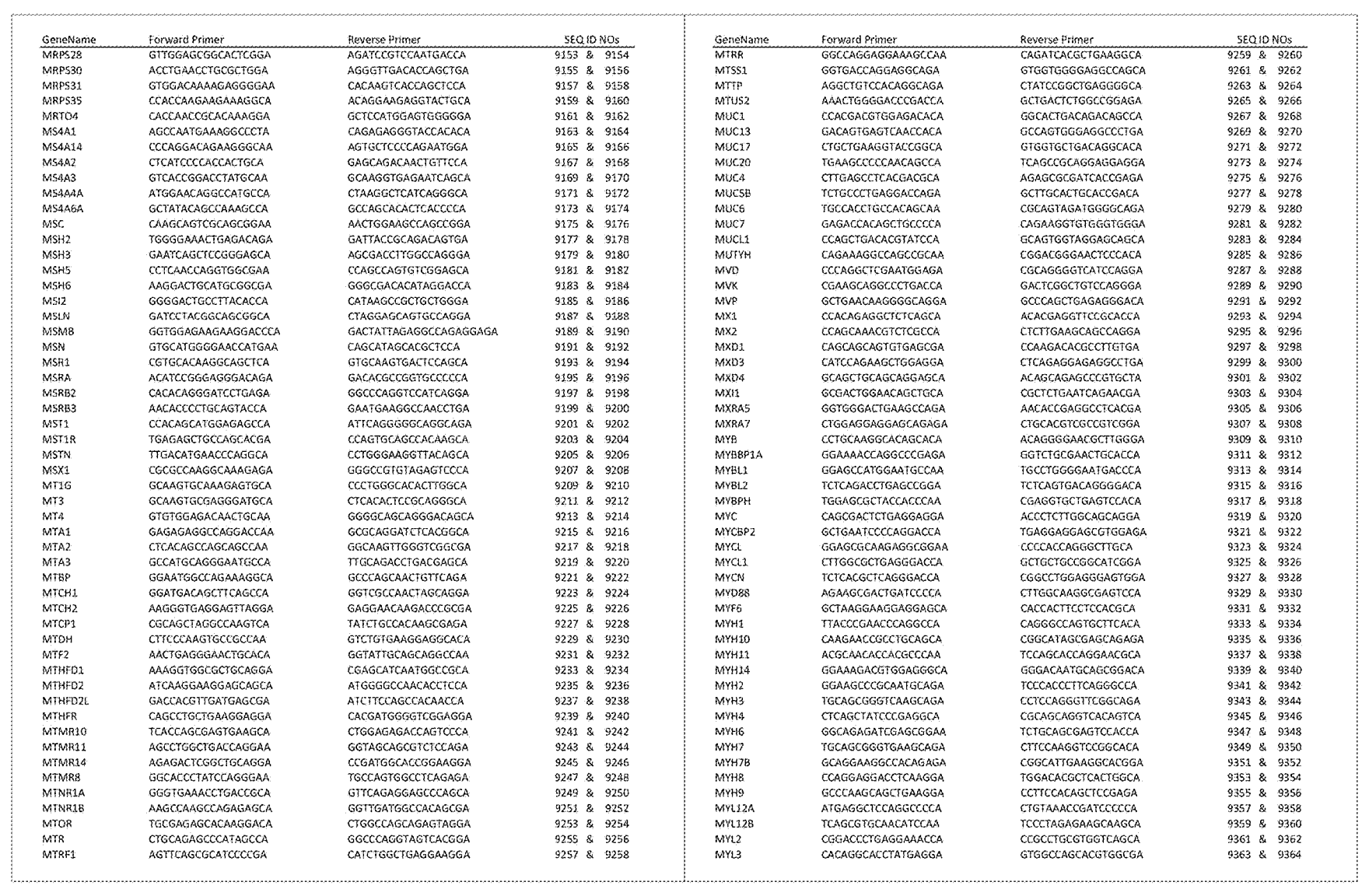
Figure 1:
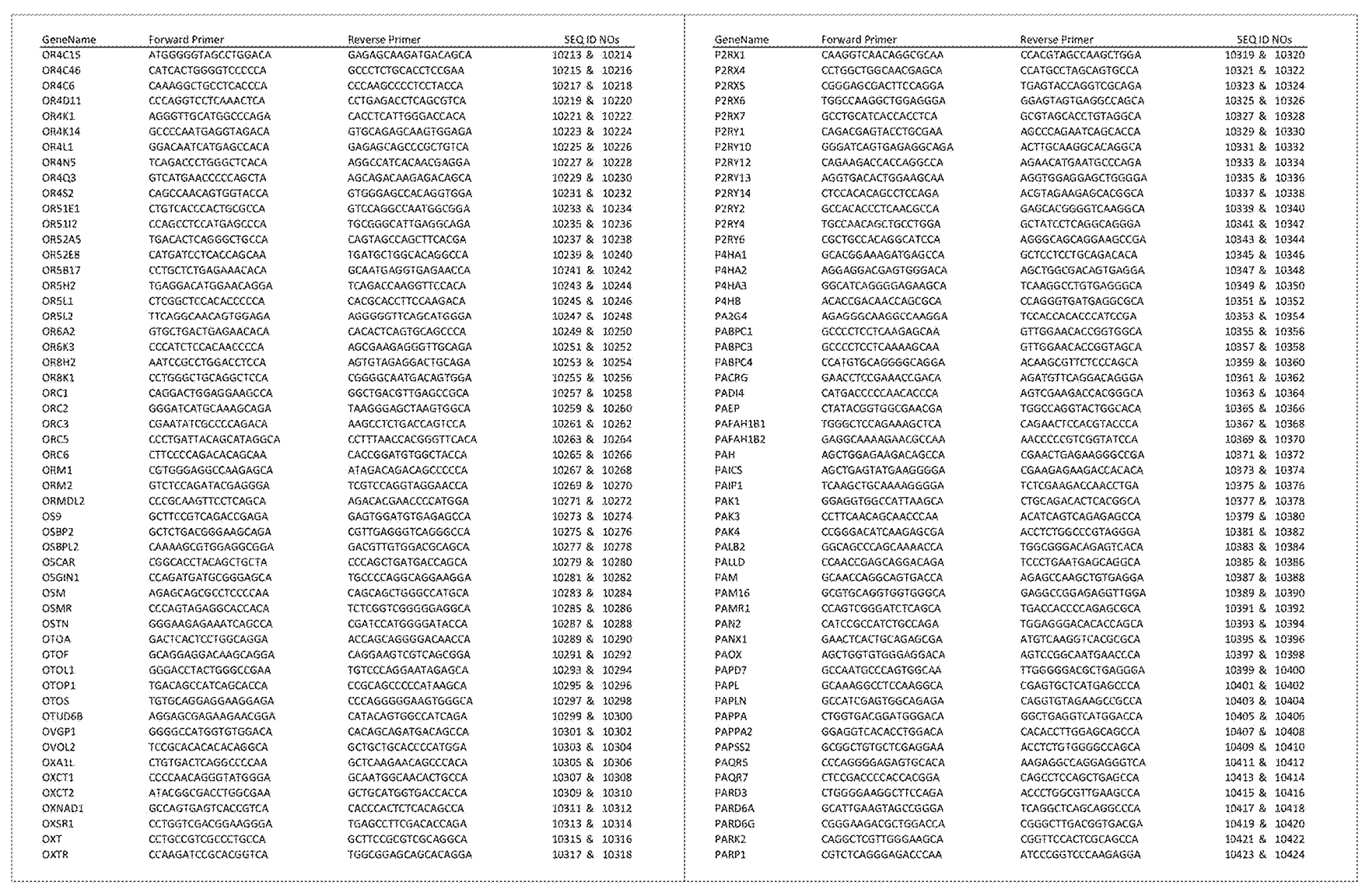
Figure 1:
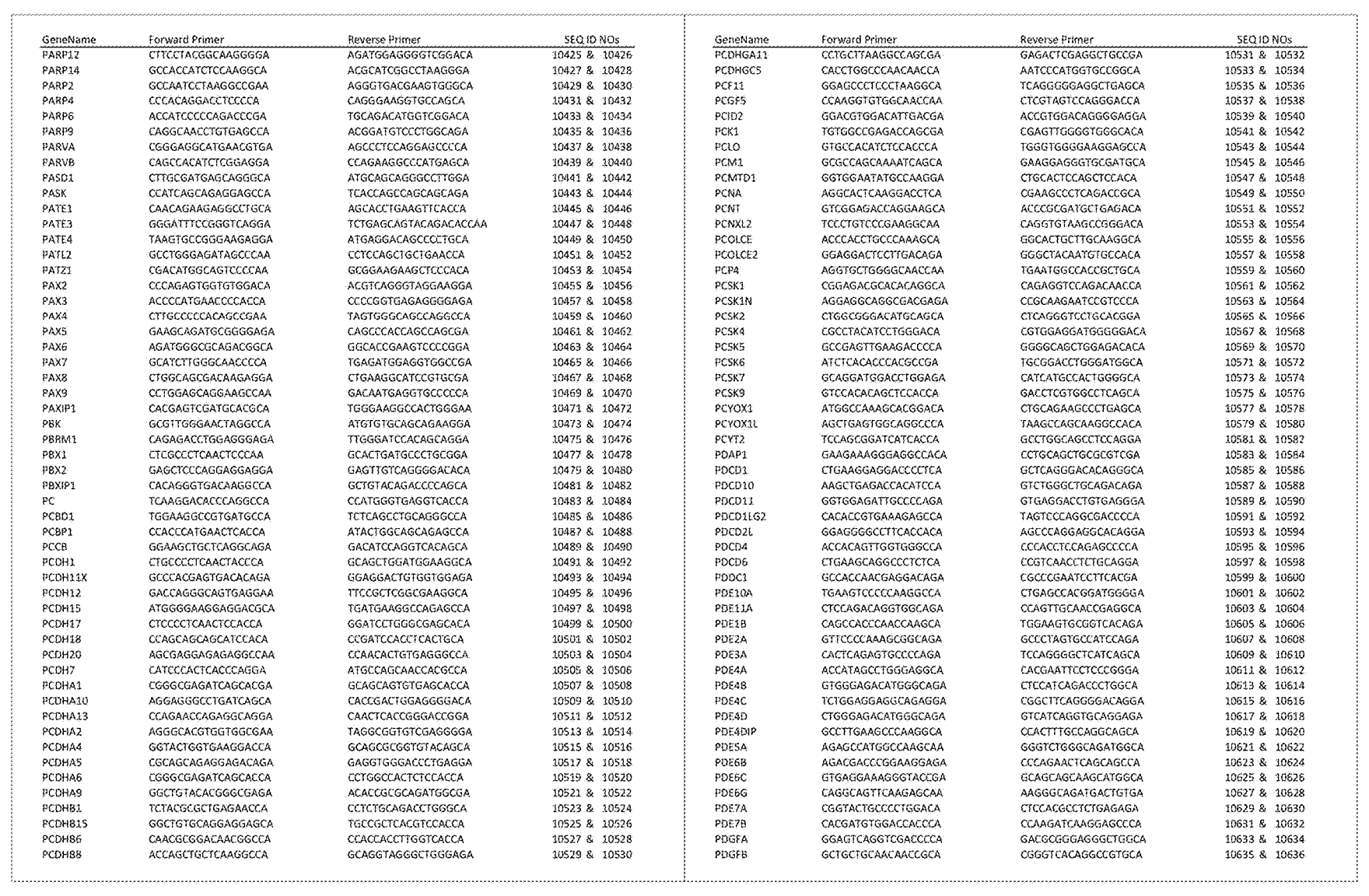
Figure 1:
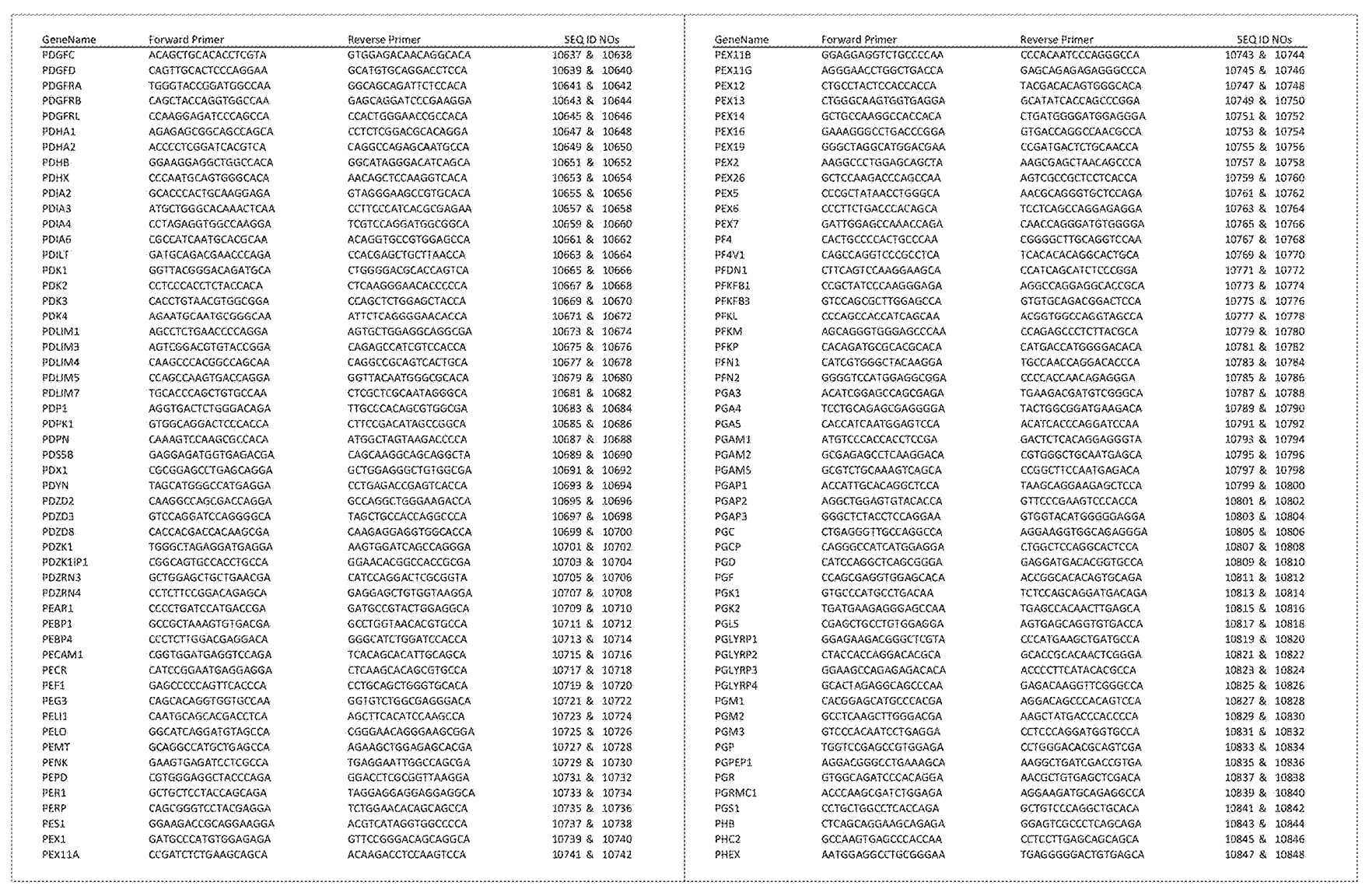
Figure 1:
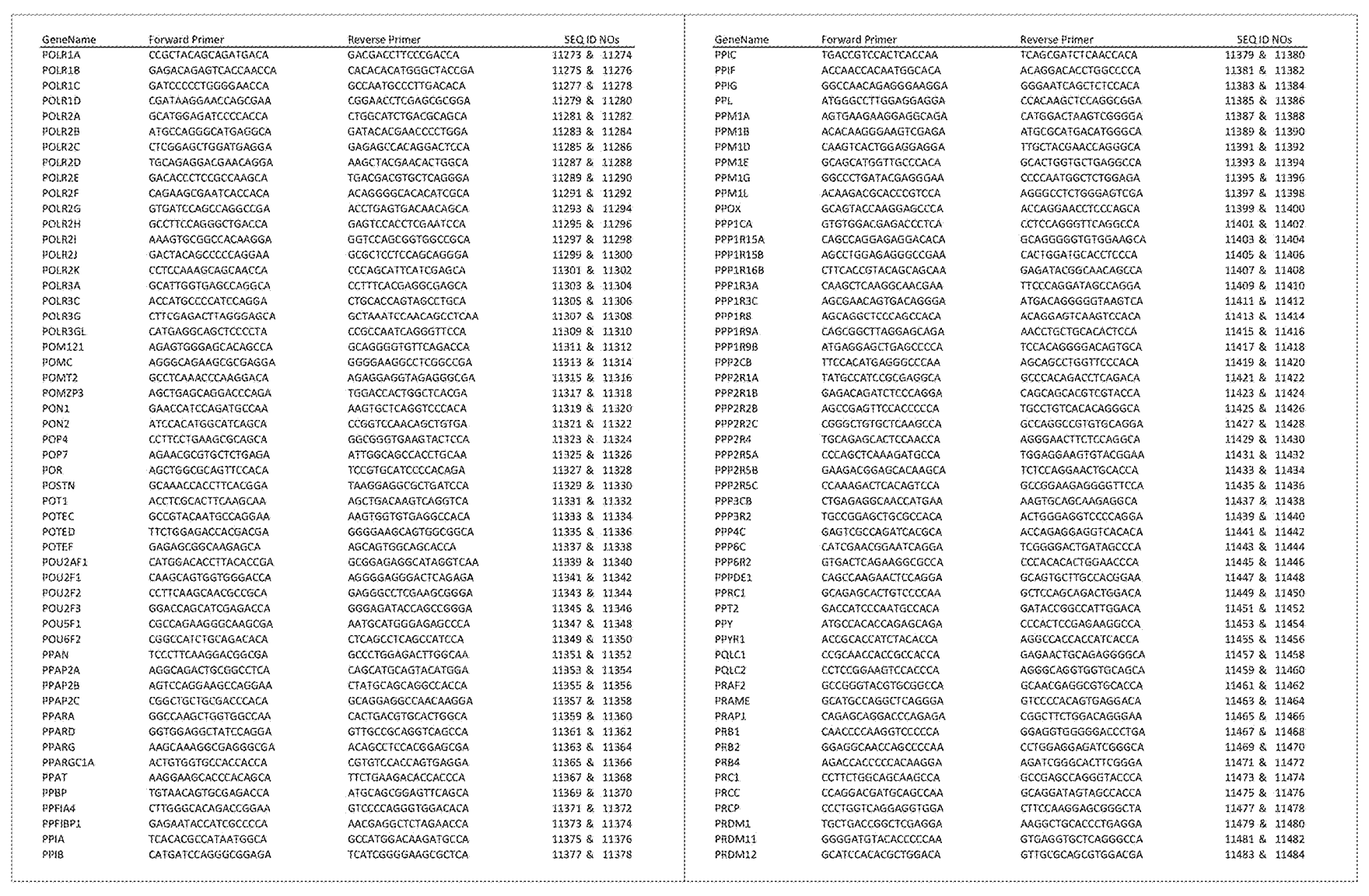
Figure 1:
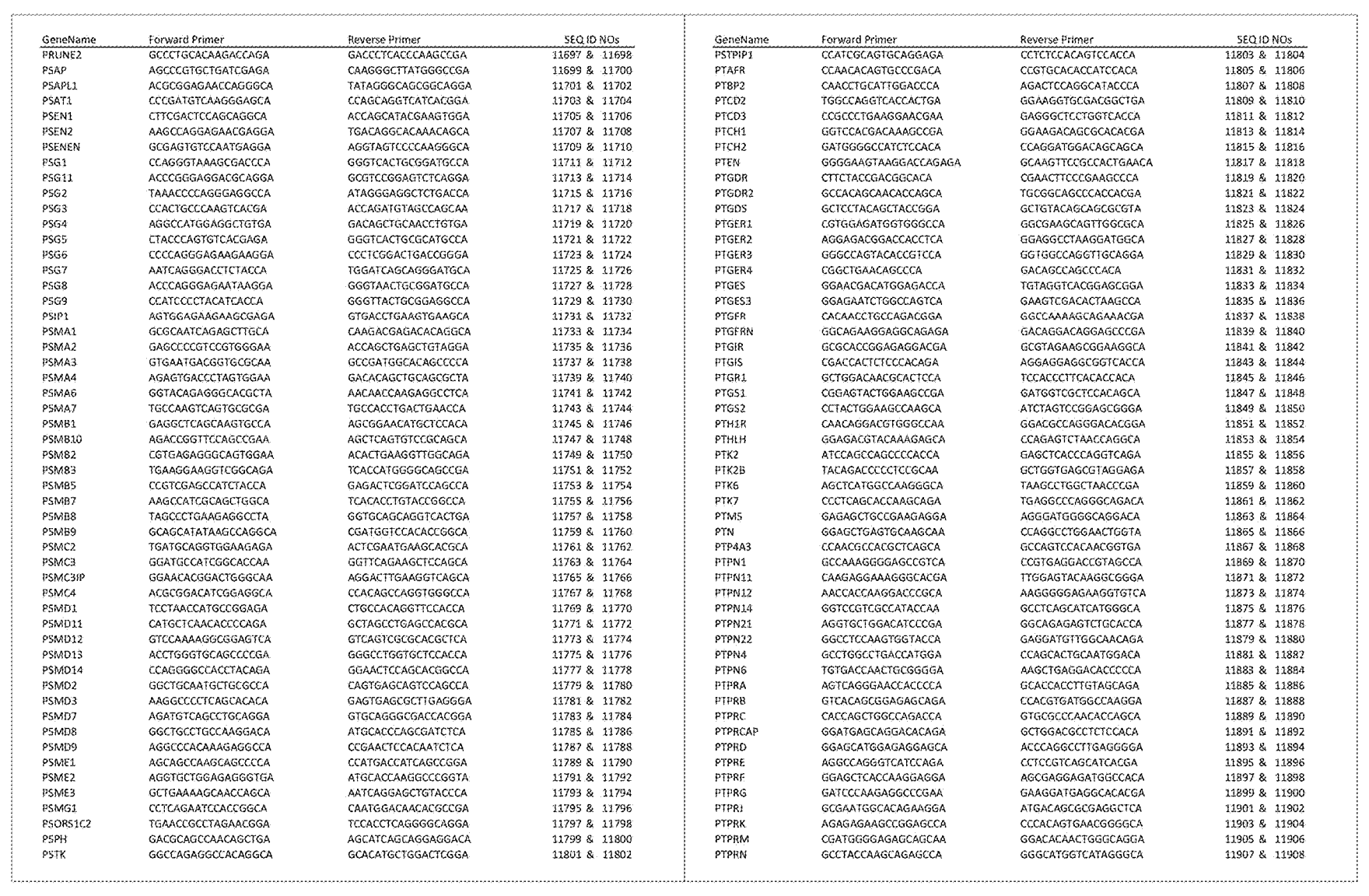
Figure 1:
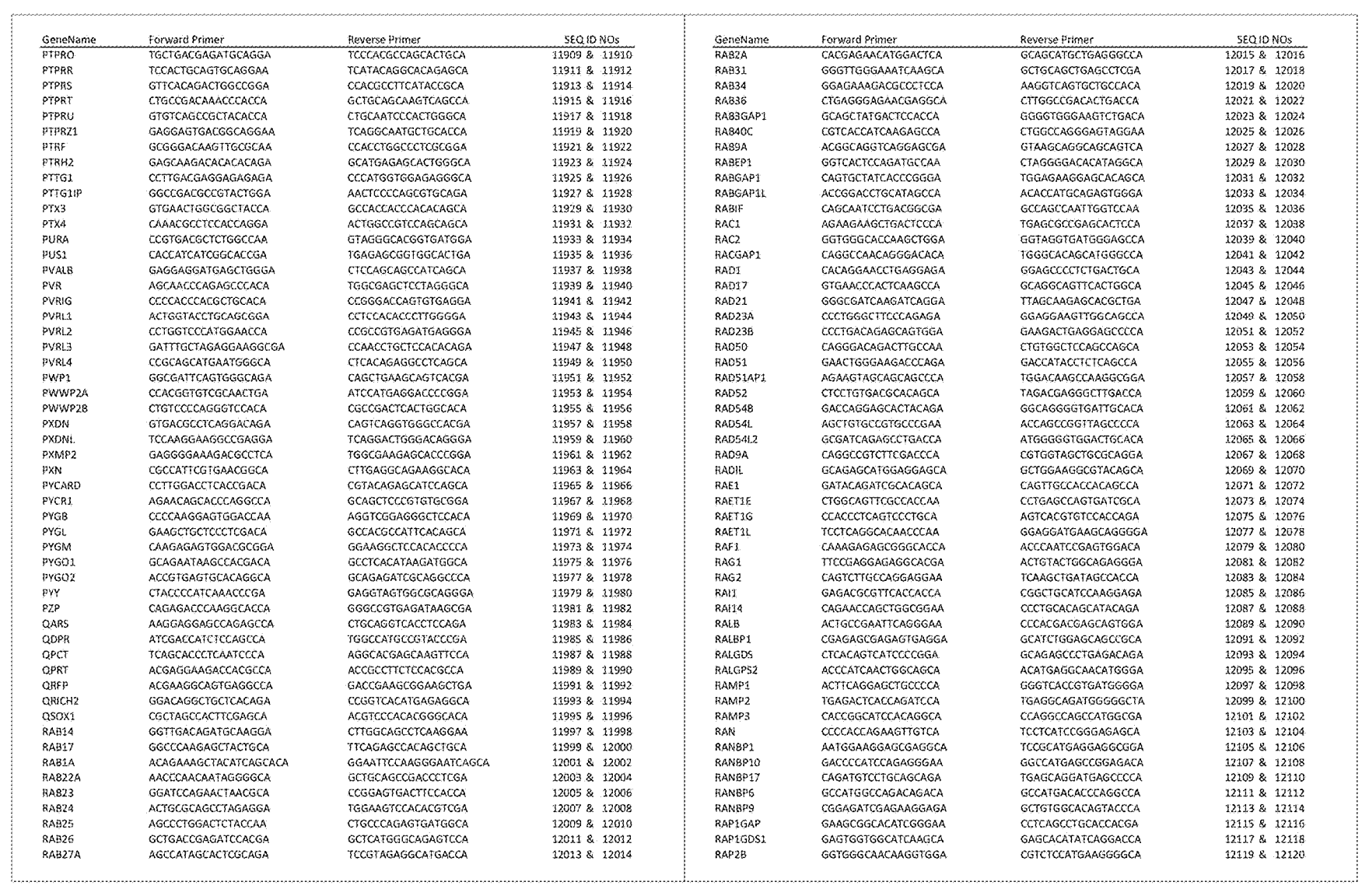
Figure 1:
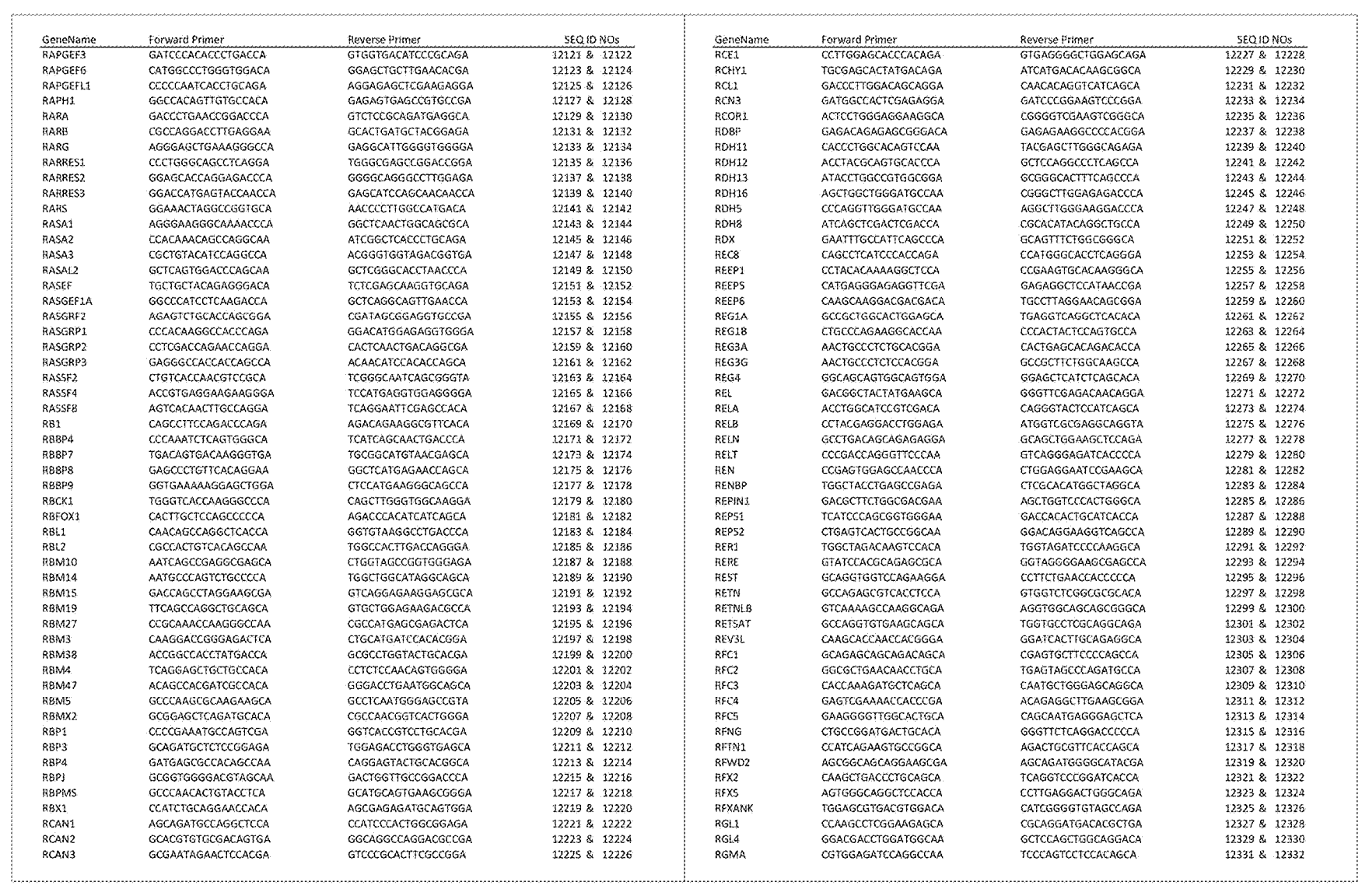
Figure 1:
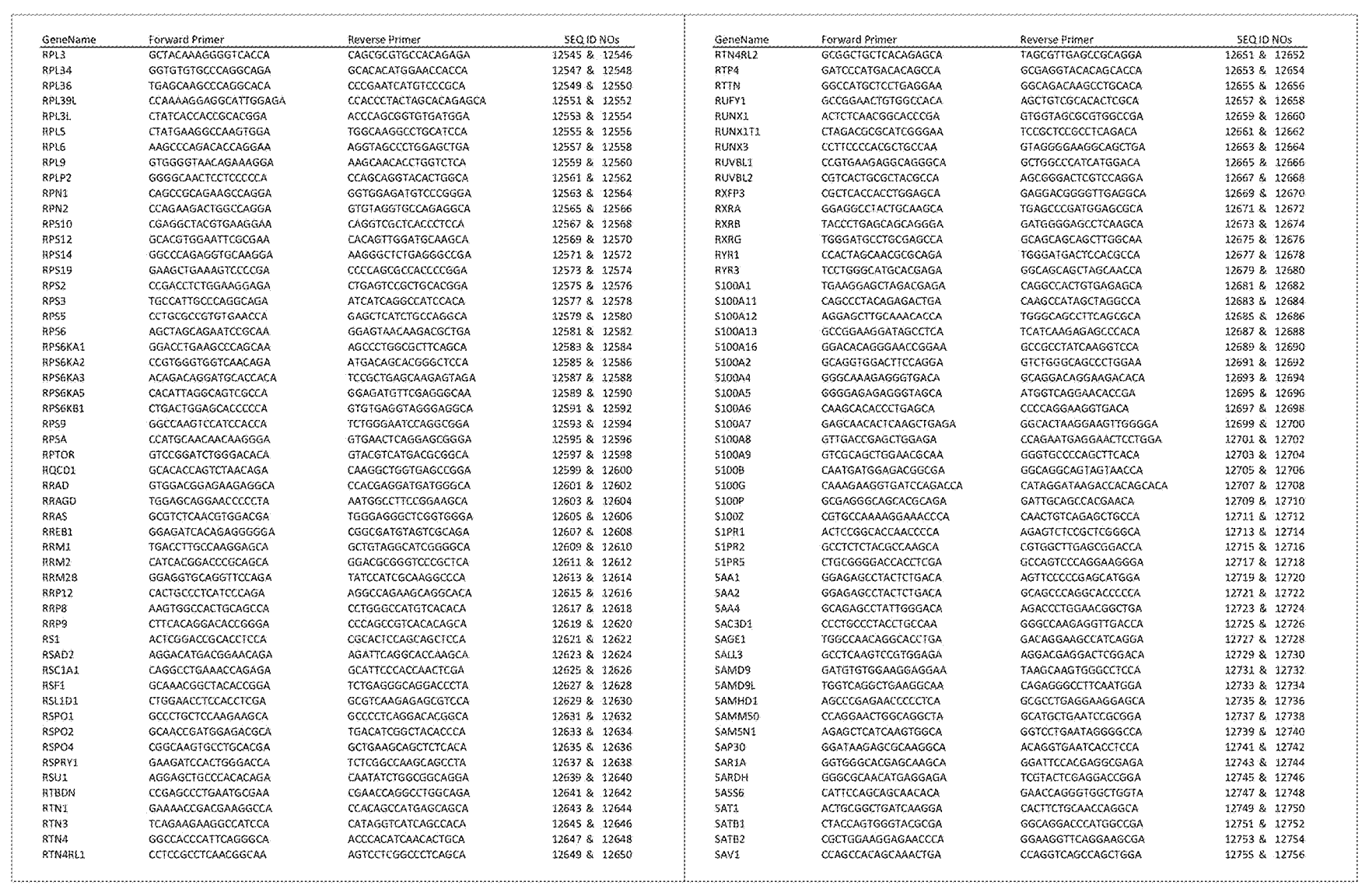
Figure 1:
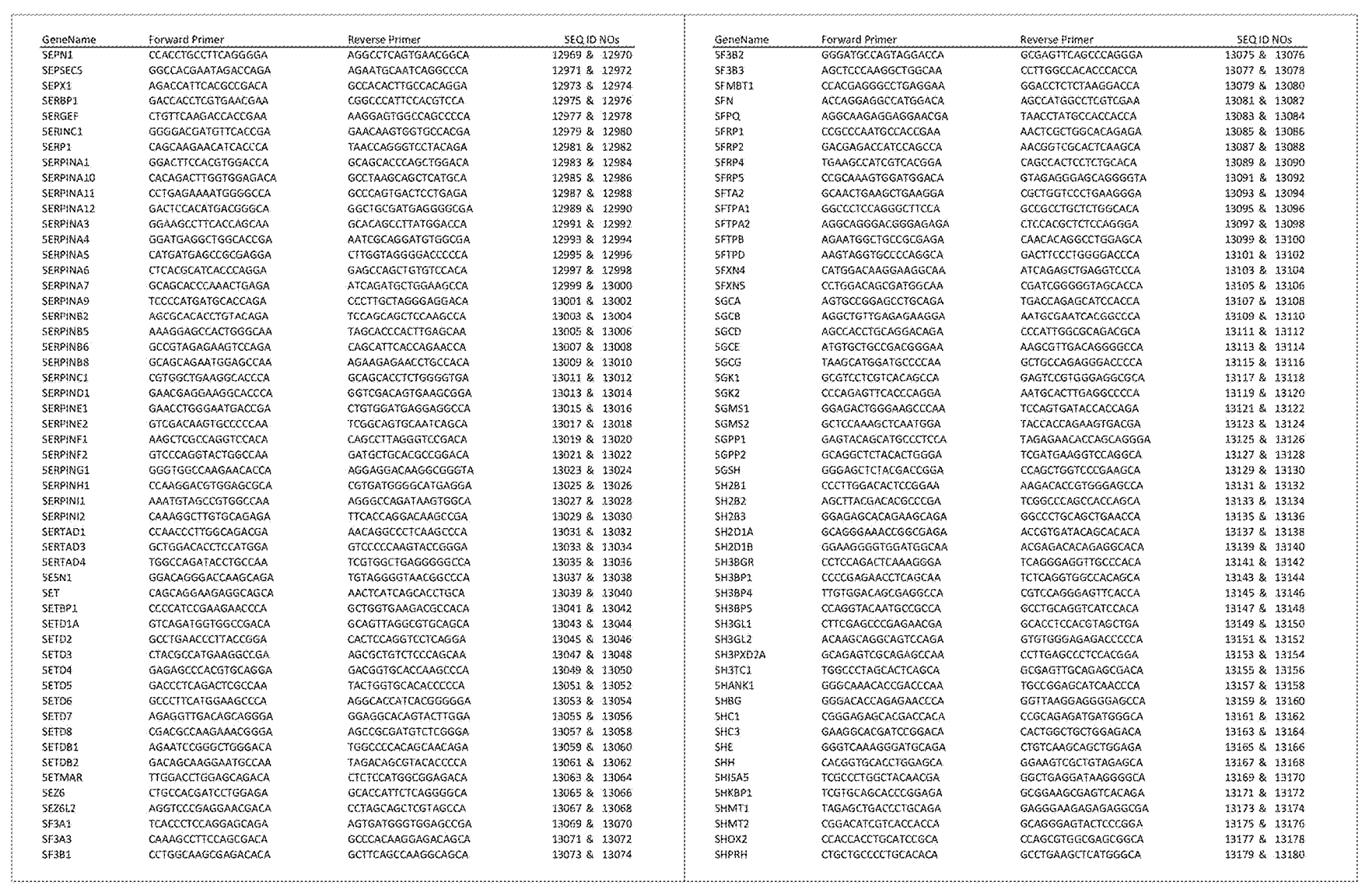
Figure 1:
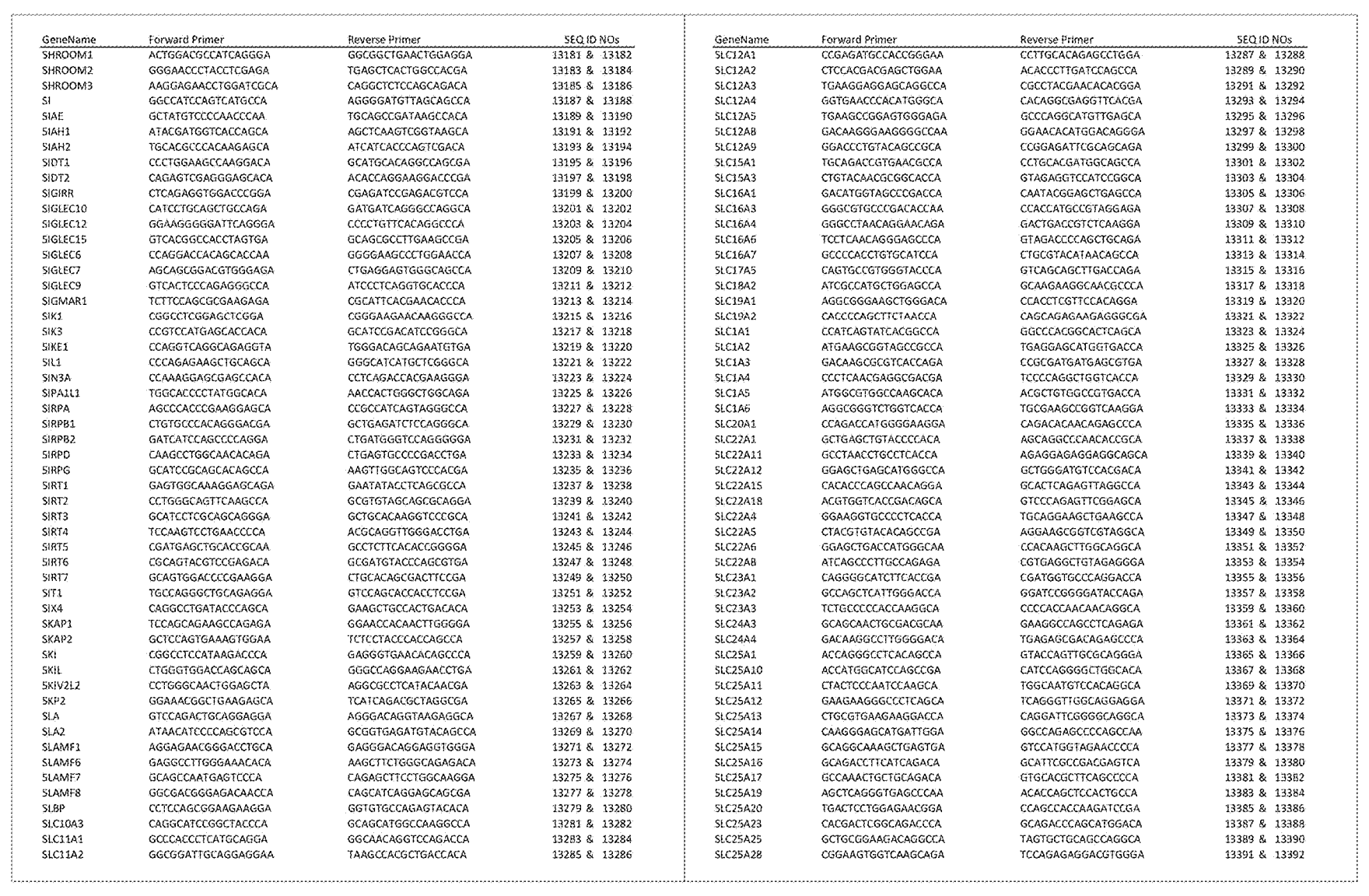
Figure 1:
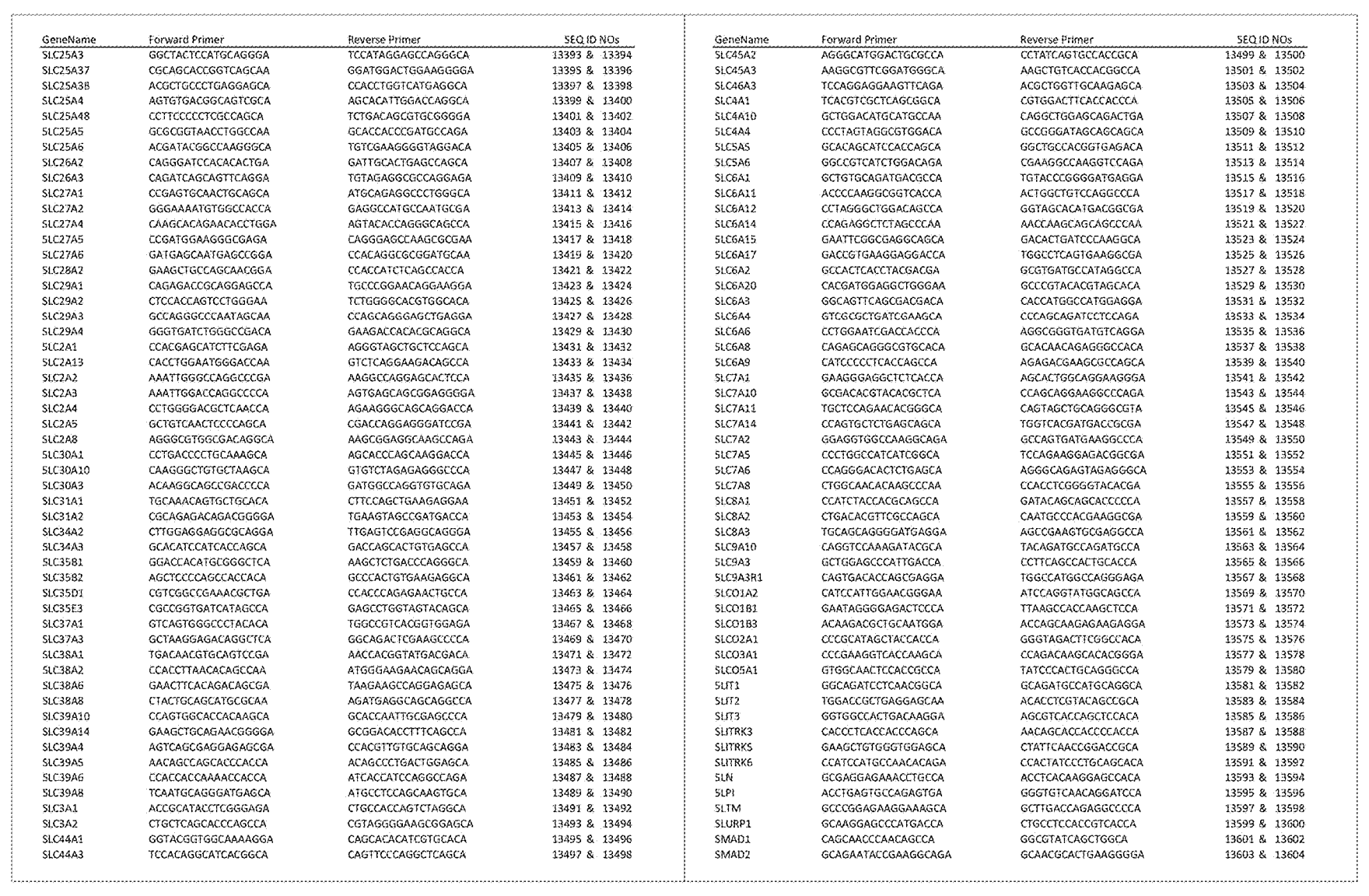
Figure 1:
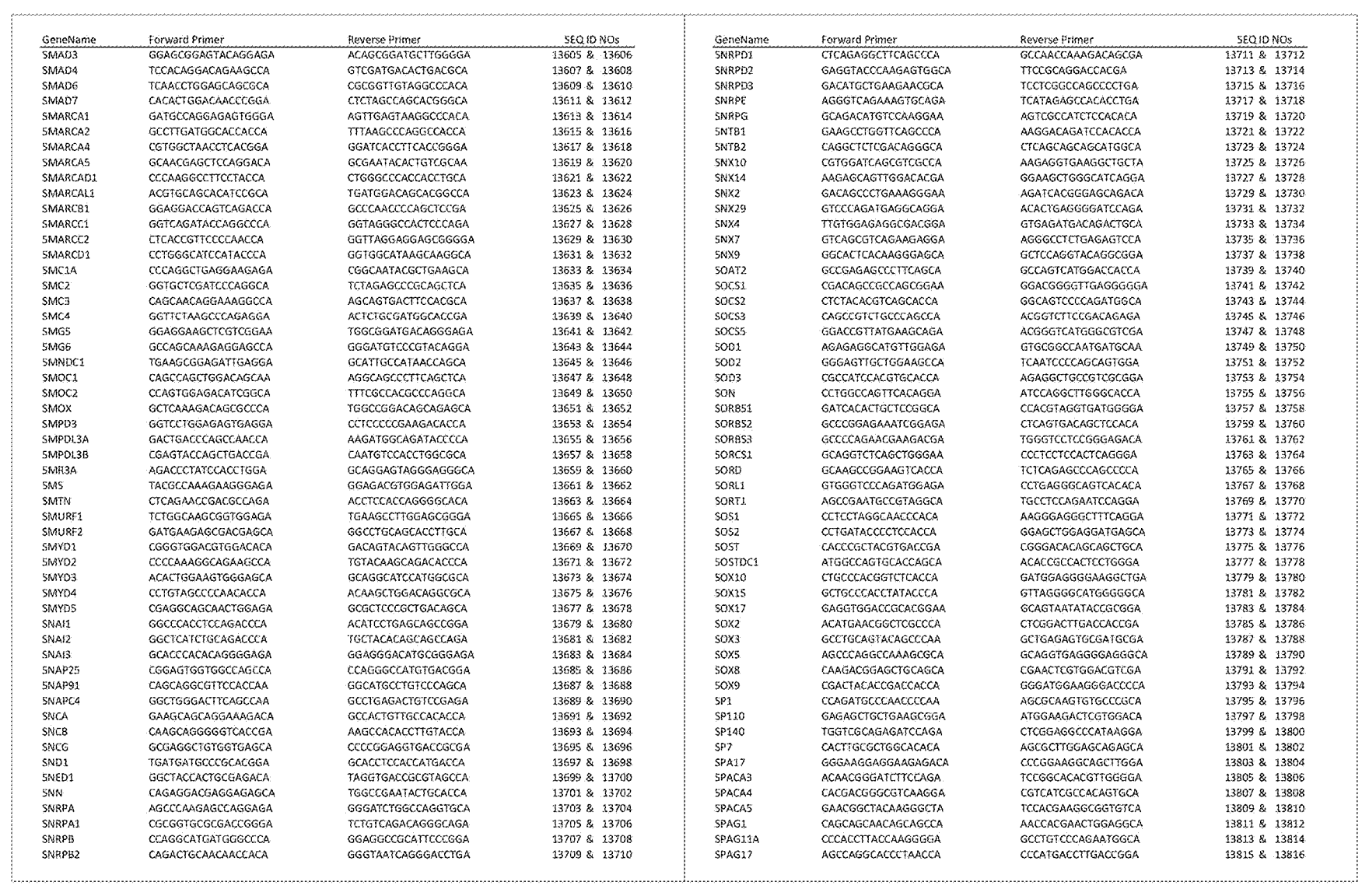
Figure 1:
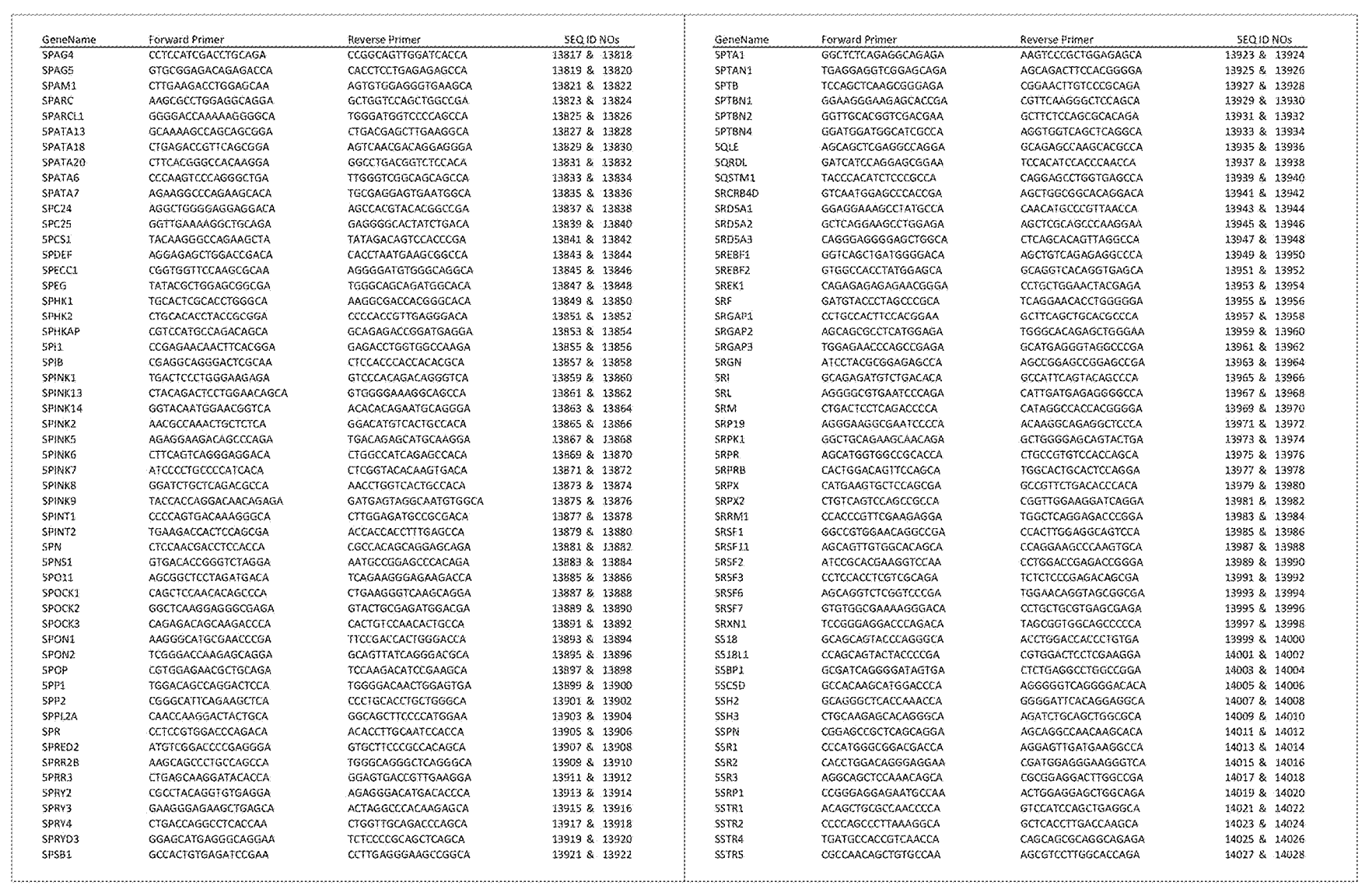
Figure 1:
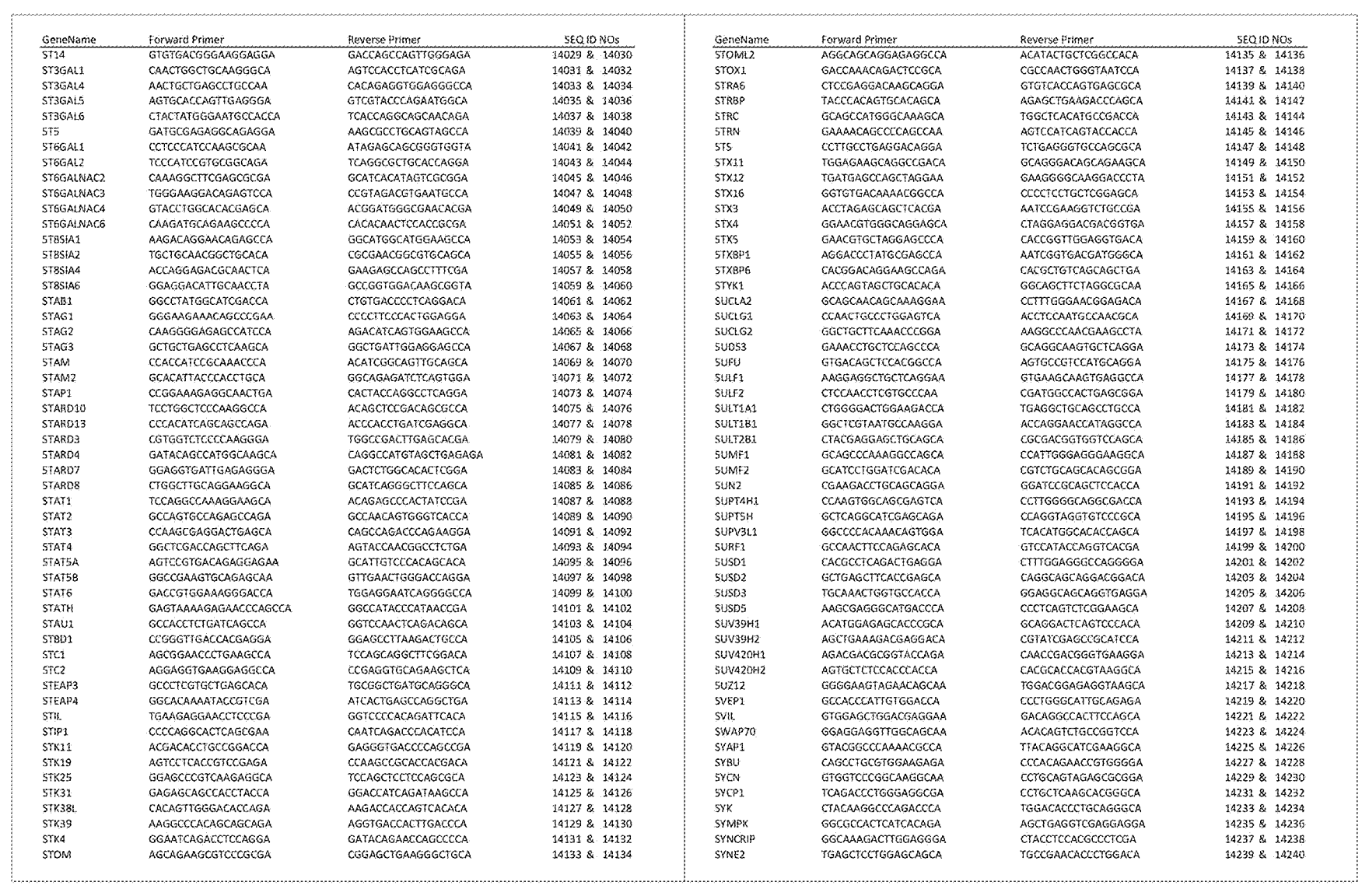
Figure 1:
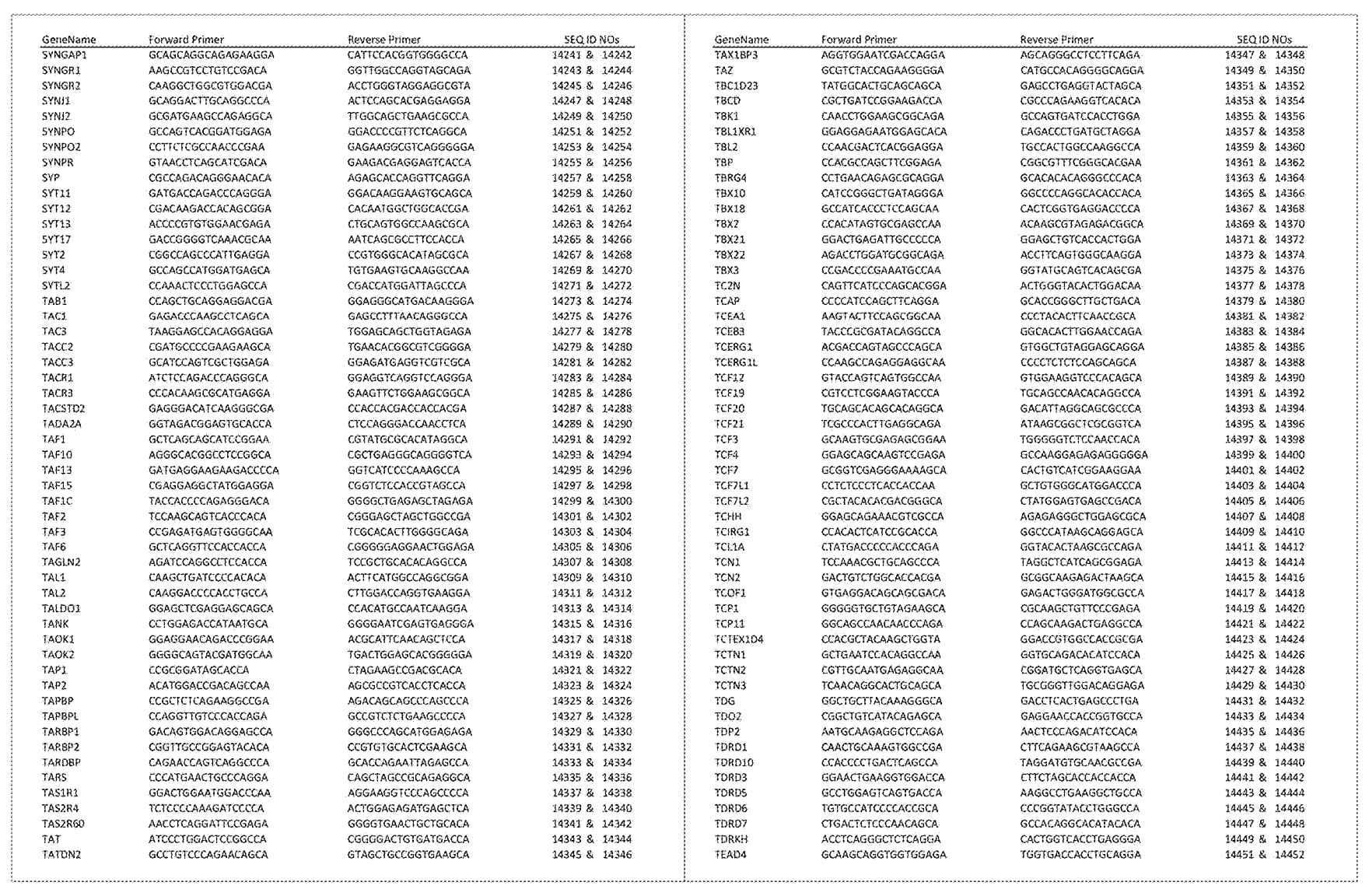
Figure 1:
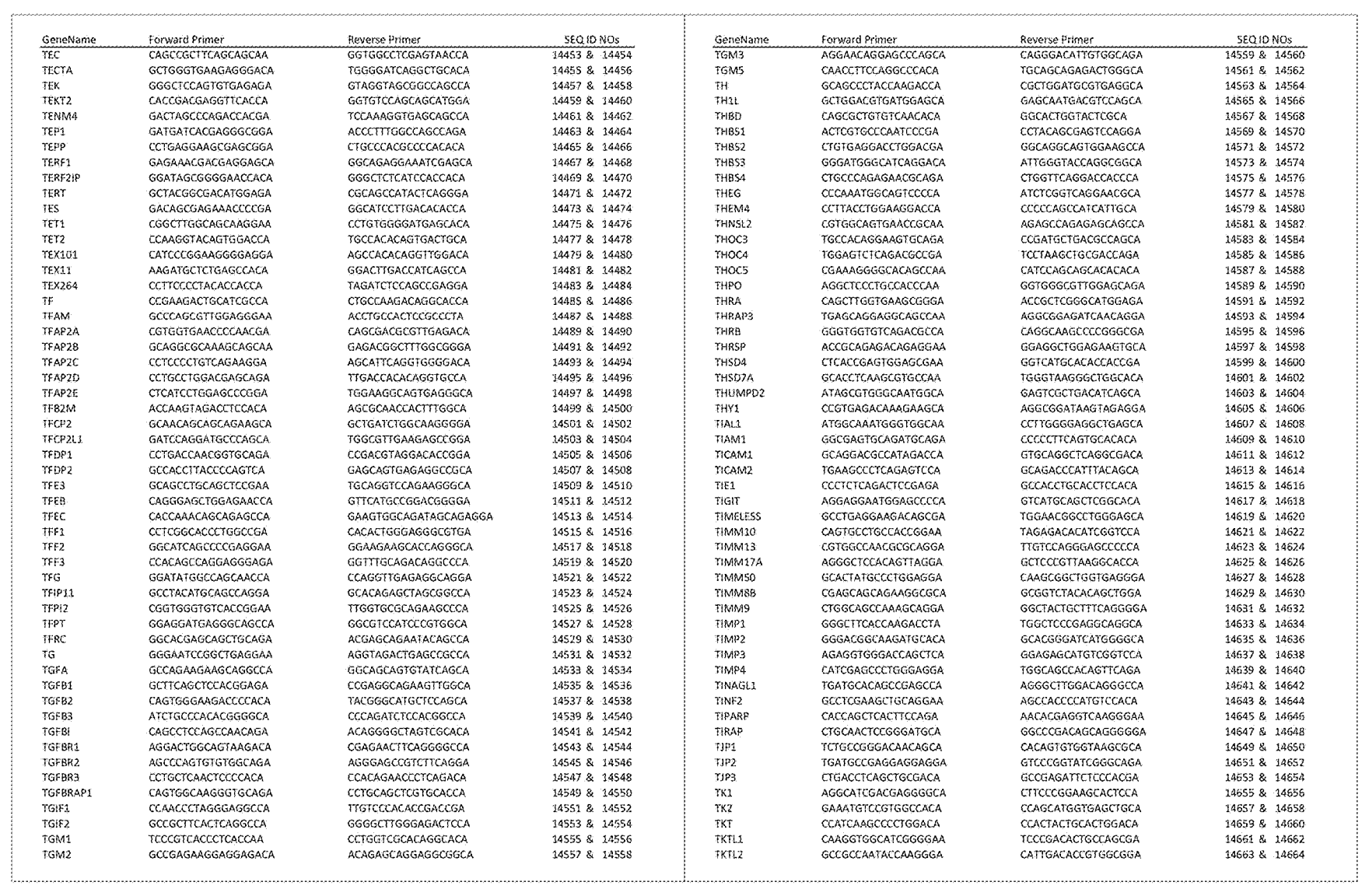
Figure 1:
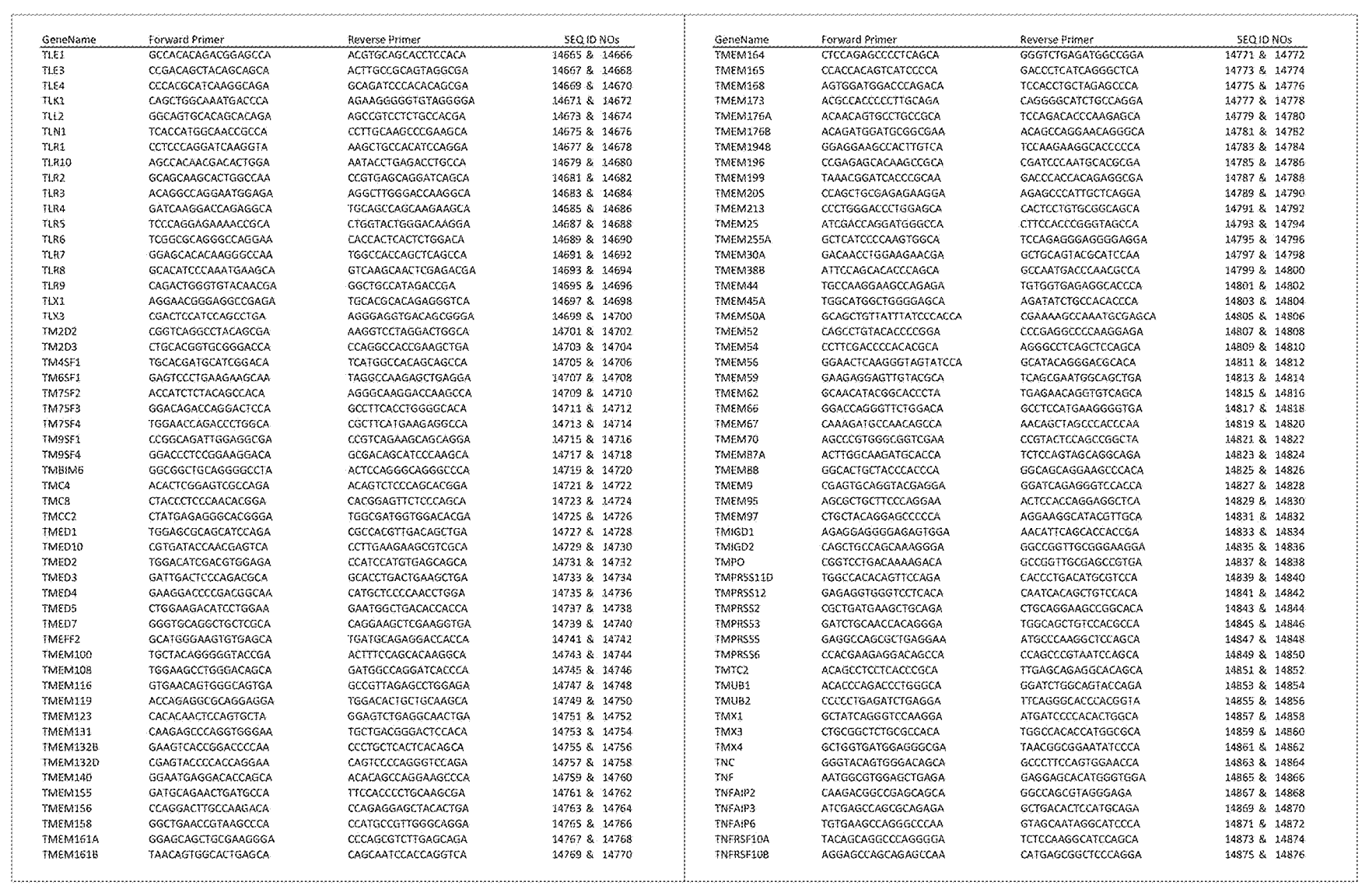
Figure 1:
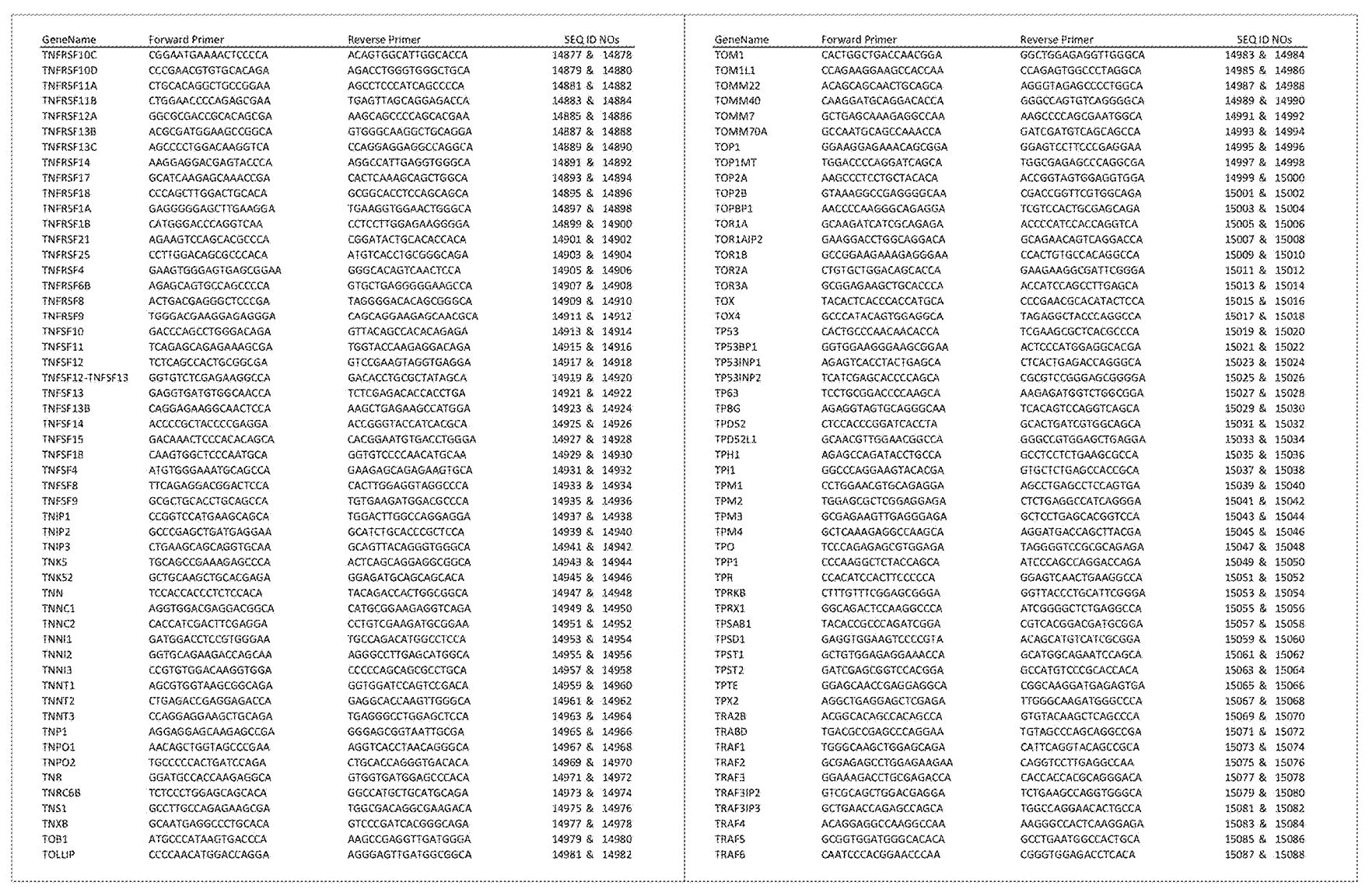
Figure 1:
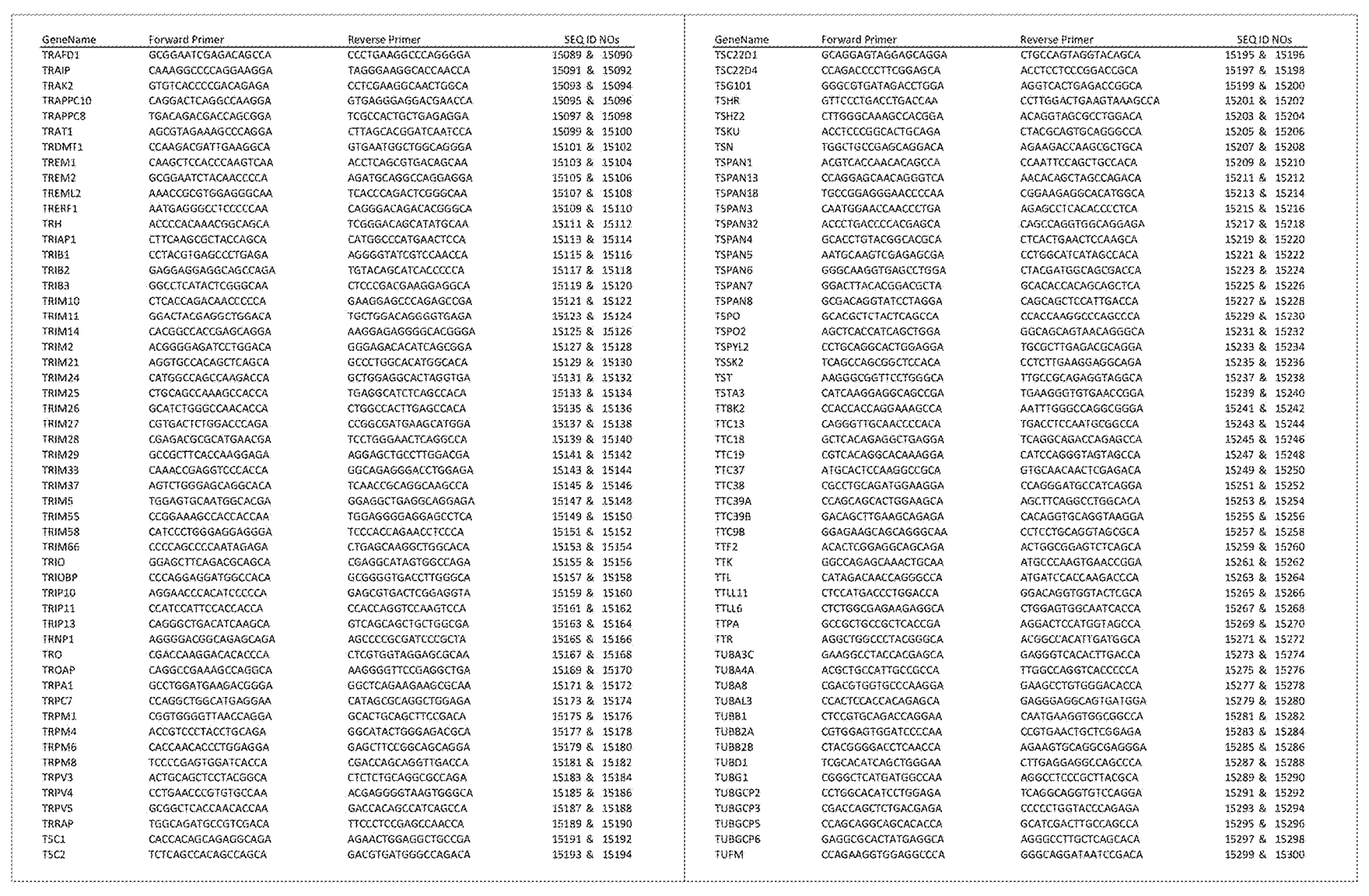
Figure 1:
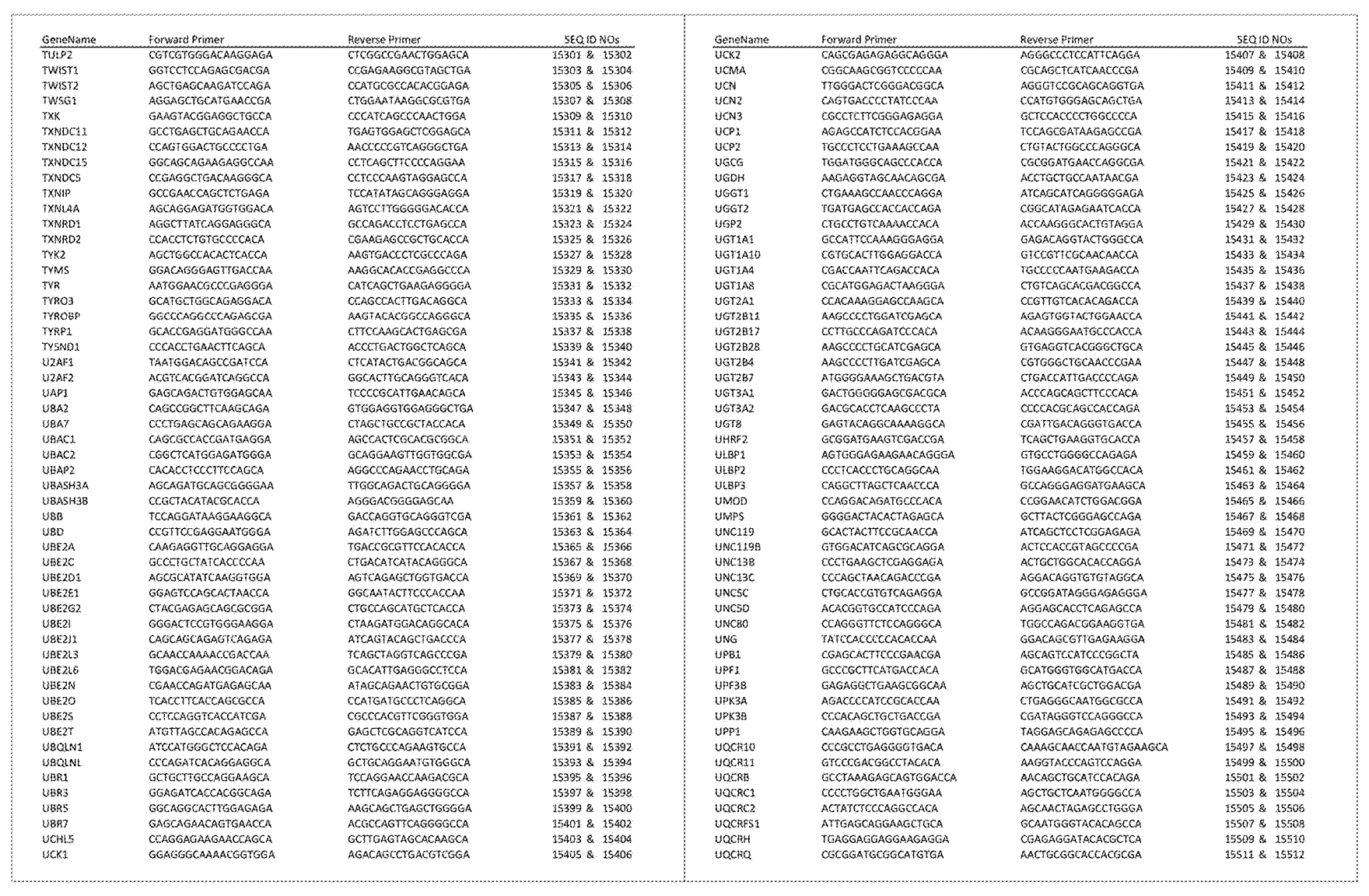
Figure 1:
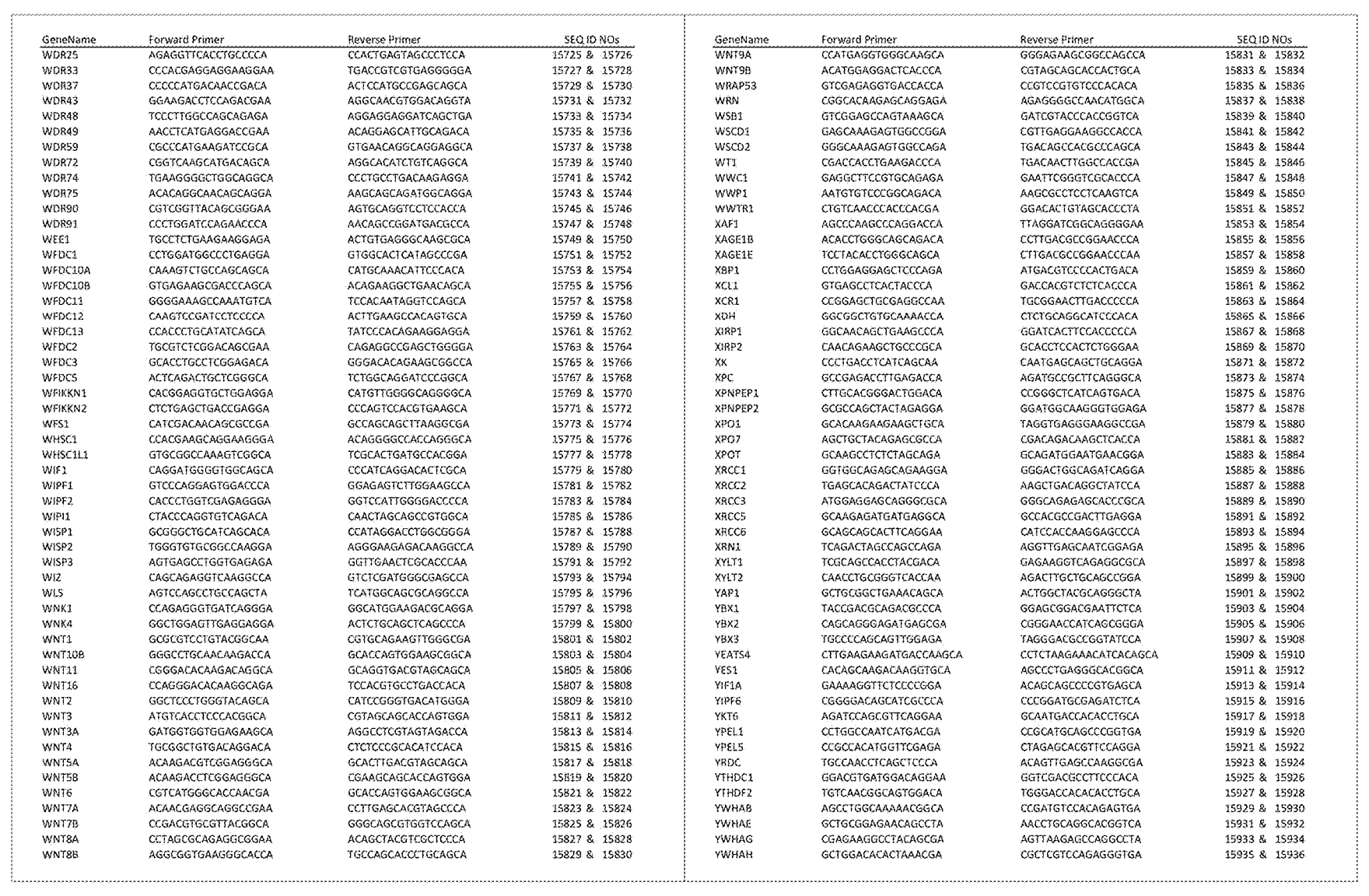
Figure 1:
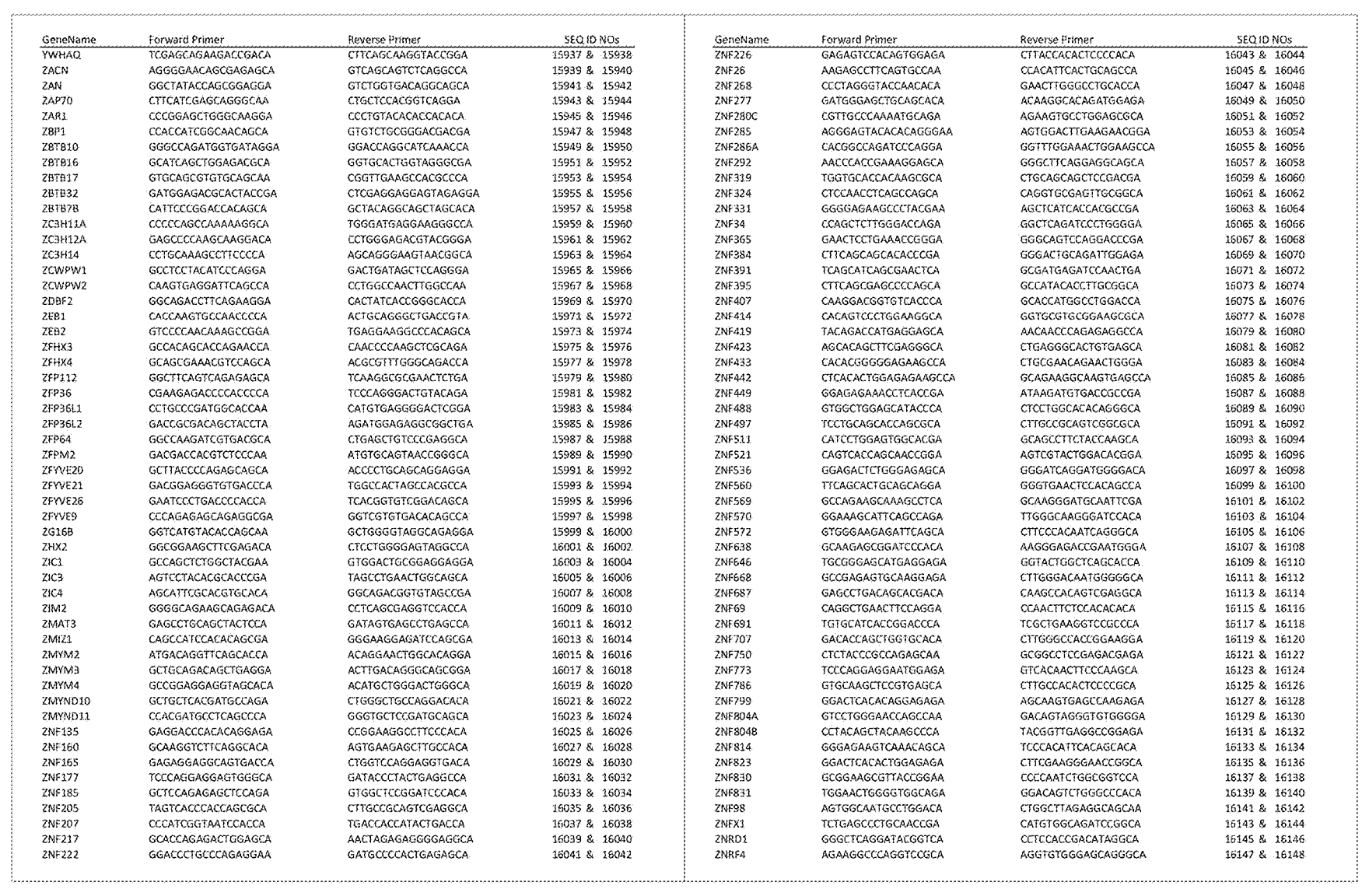
Figure 1:
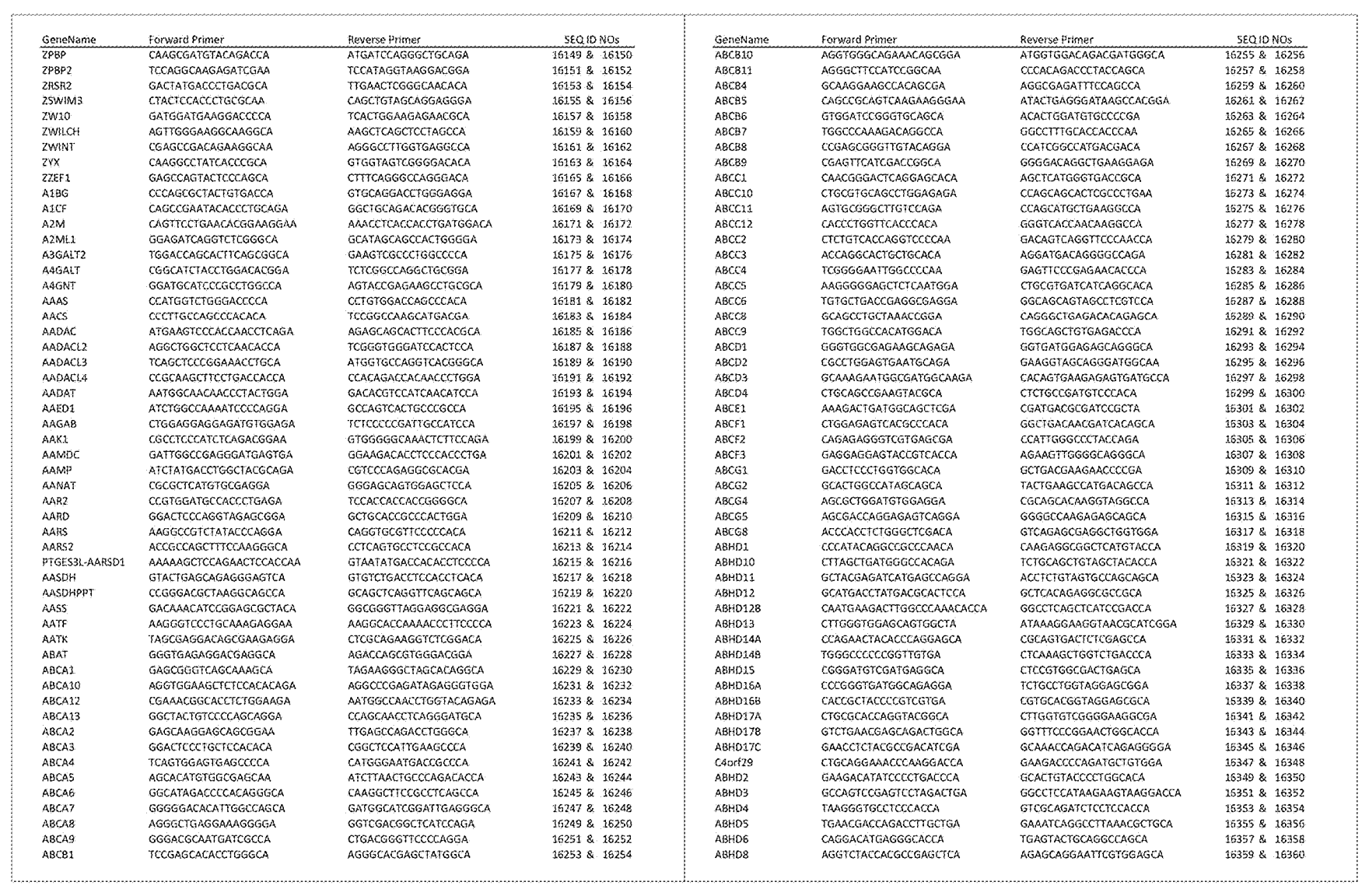
Figure 1:
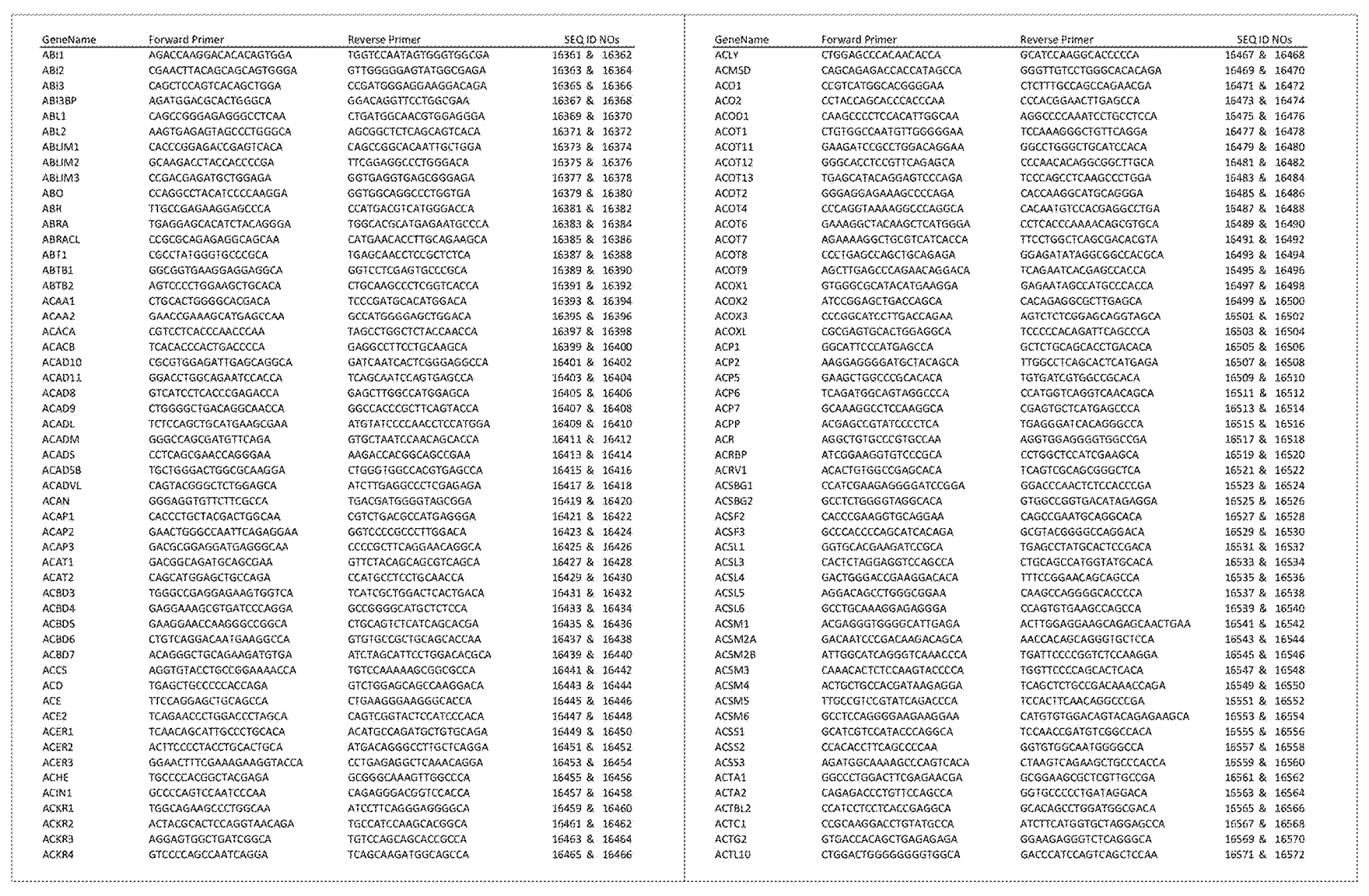
Figure 1:
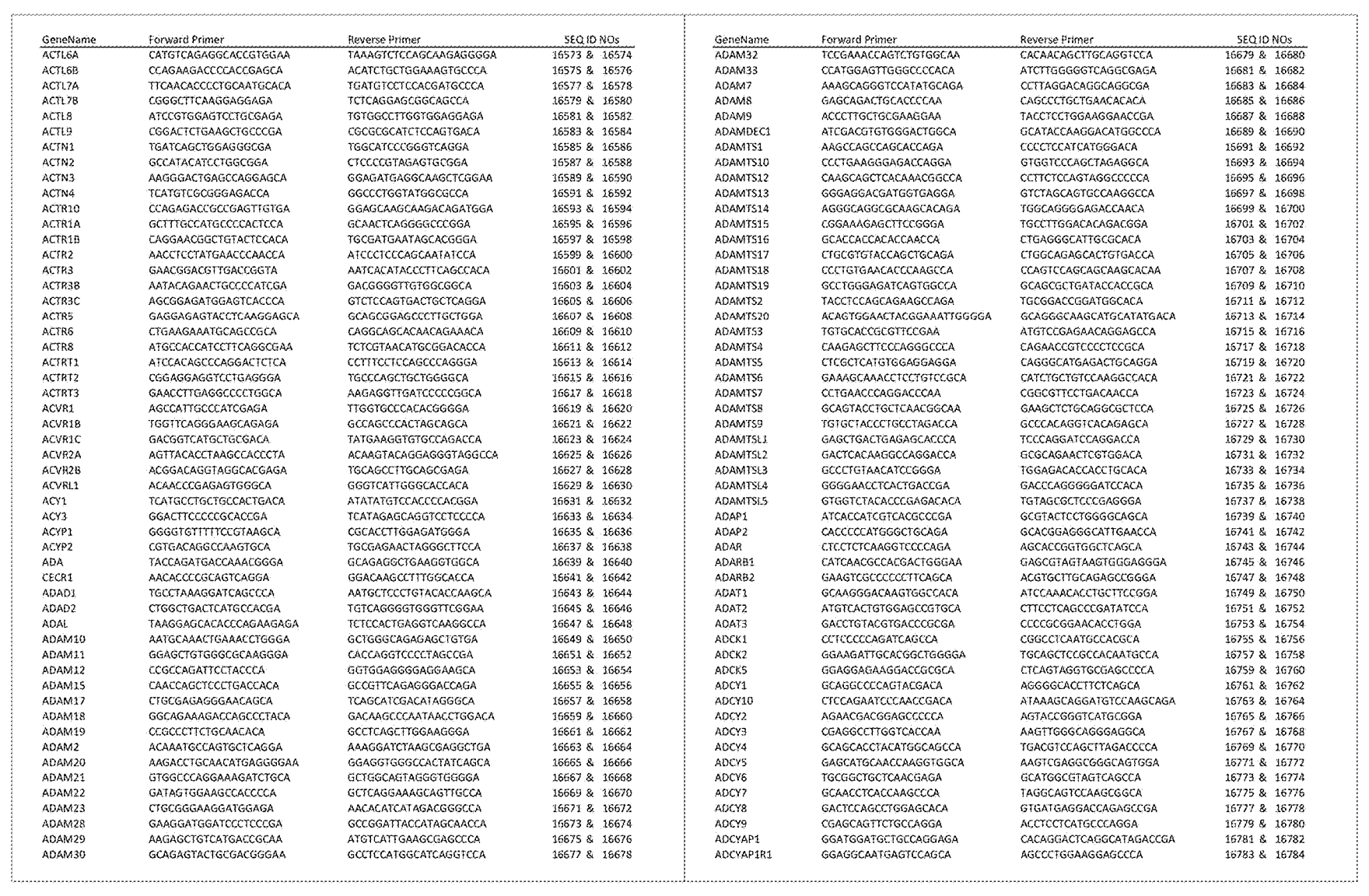
Figure 1:
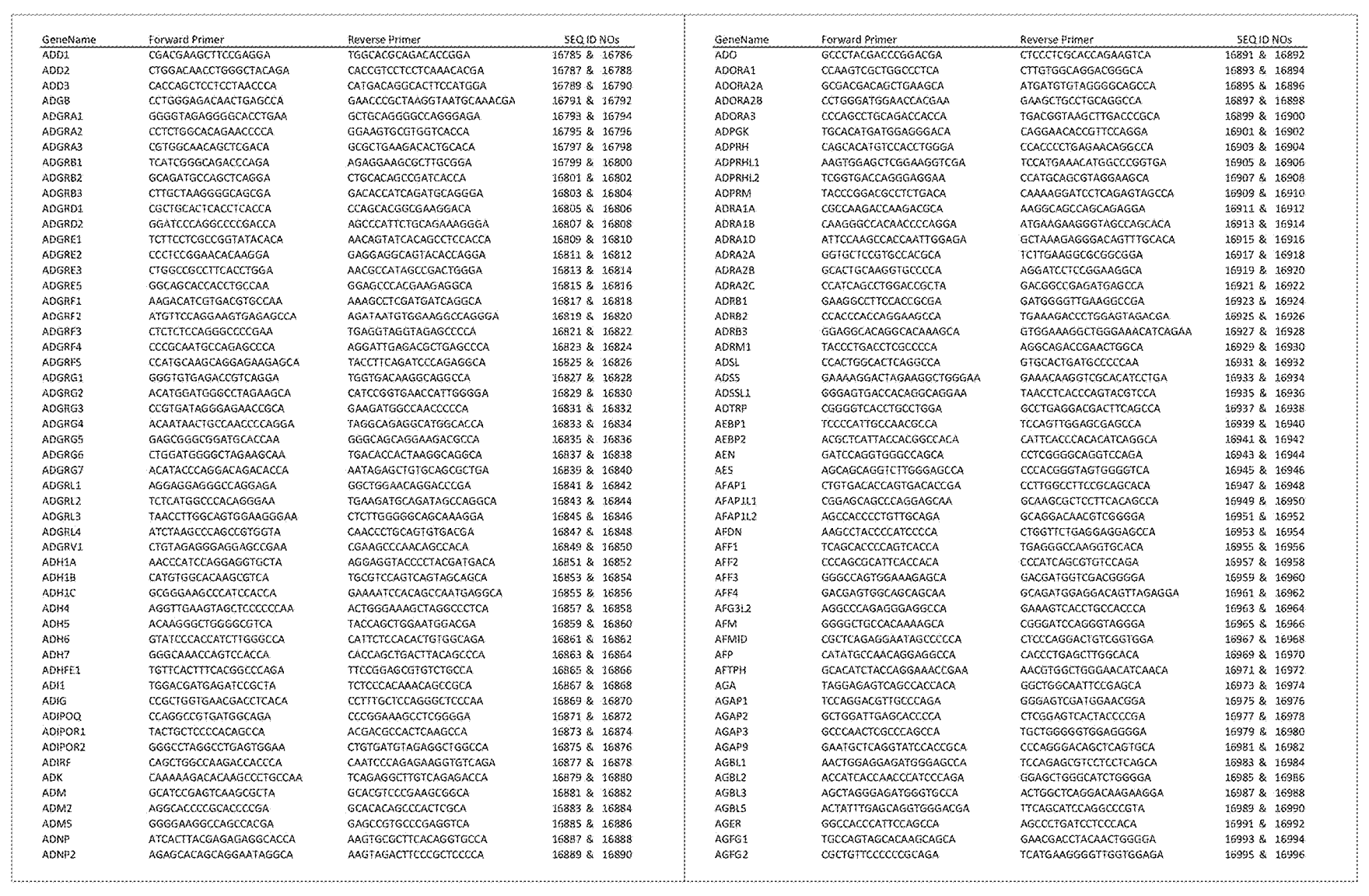
Figure 1:
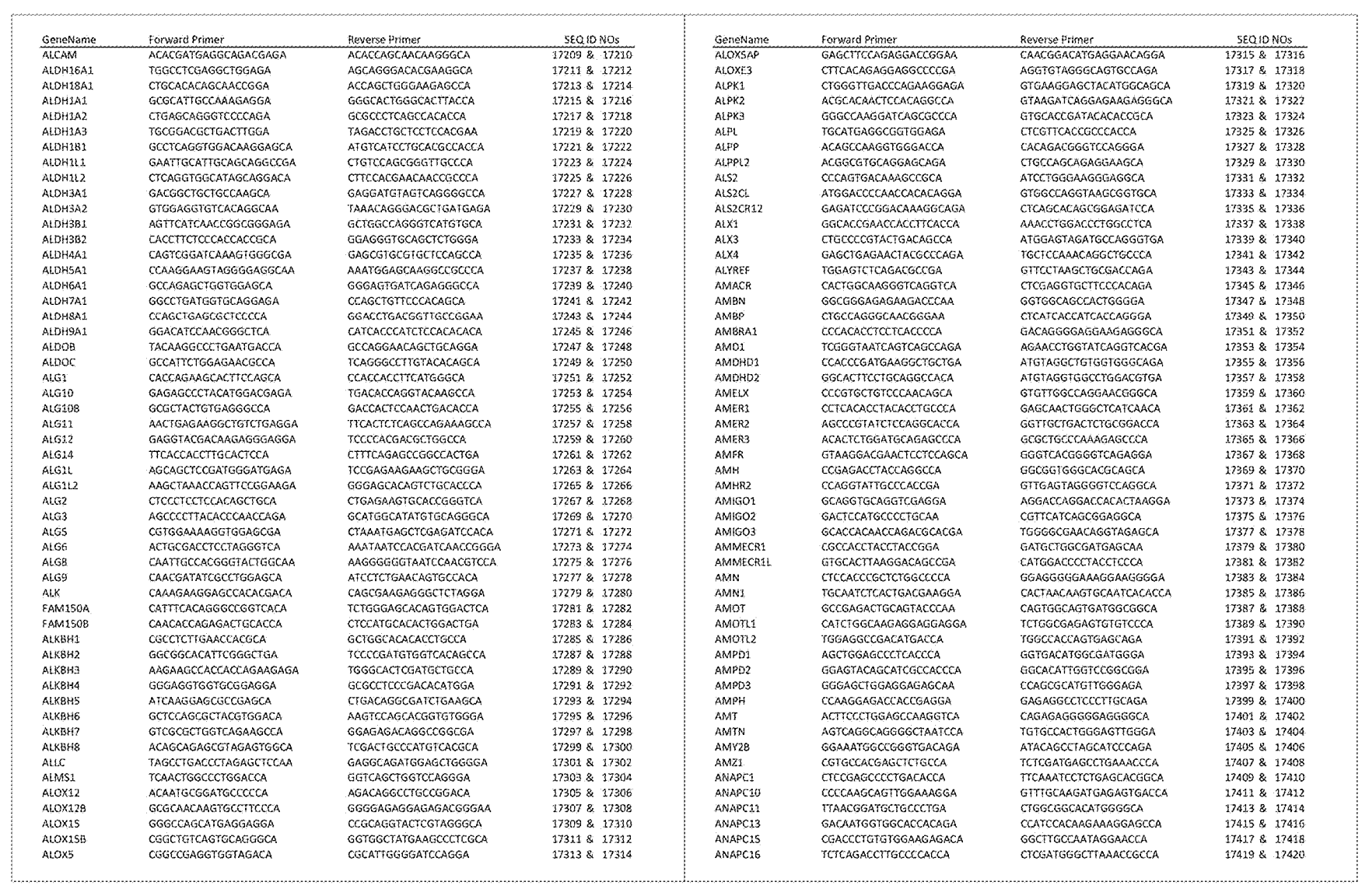
Figure 1:
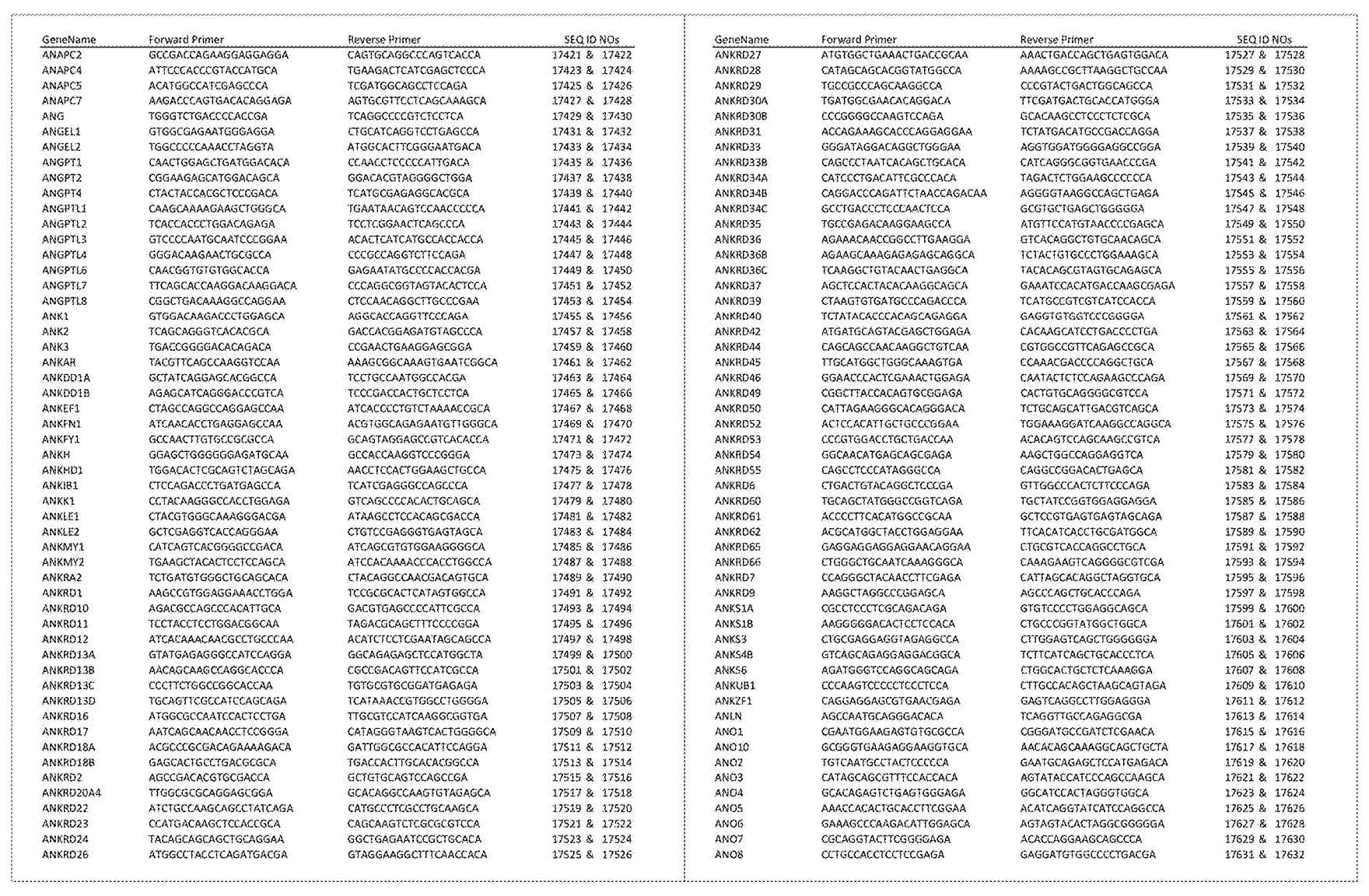
Figure 1:
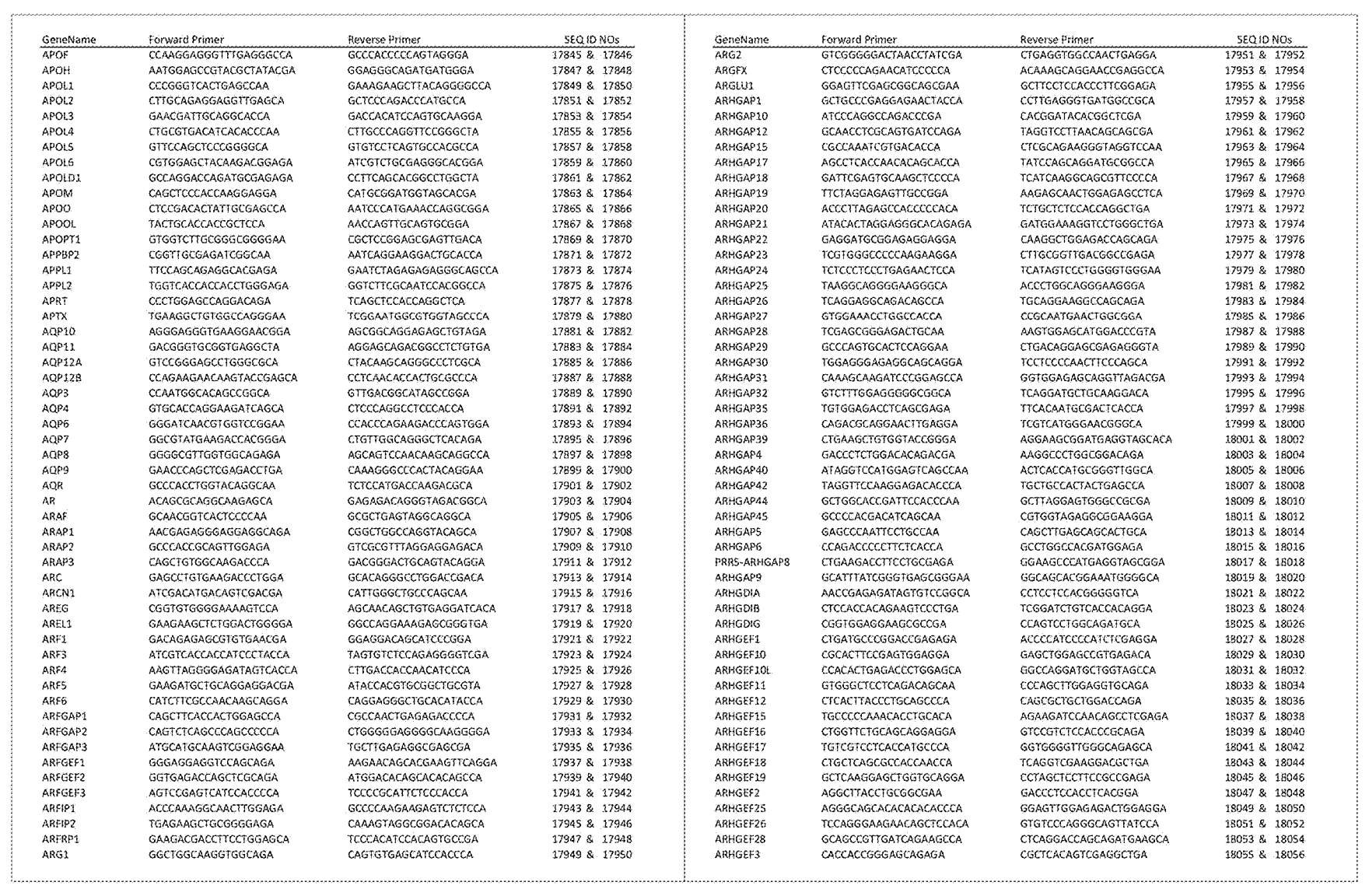
Figure 1:
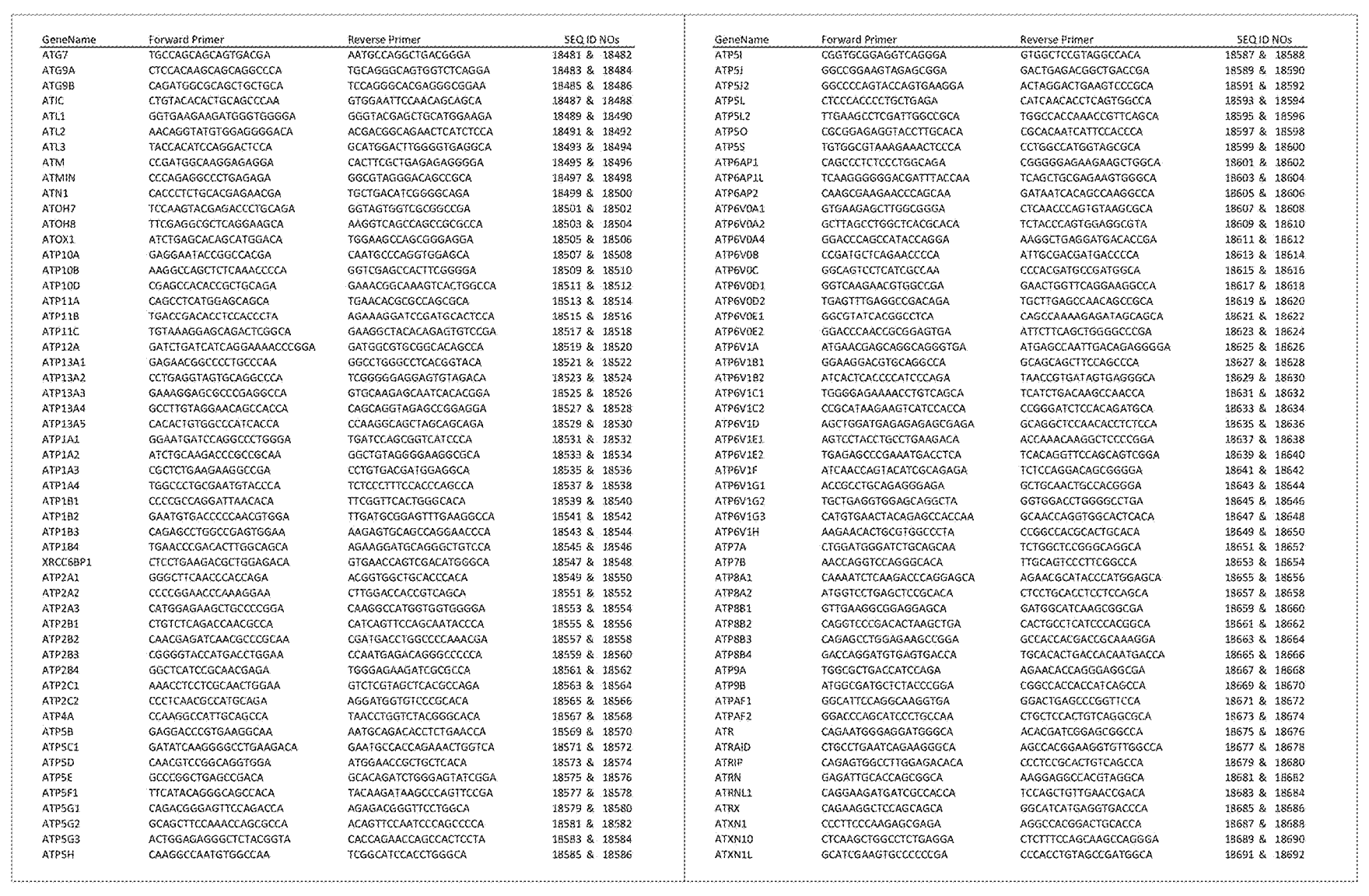
Figure 1:
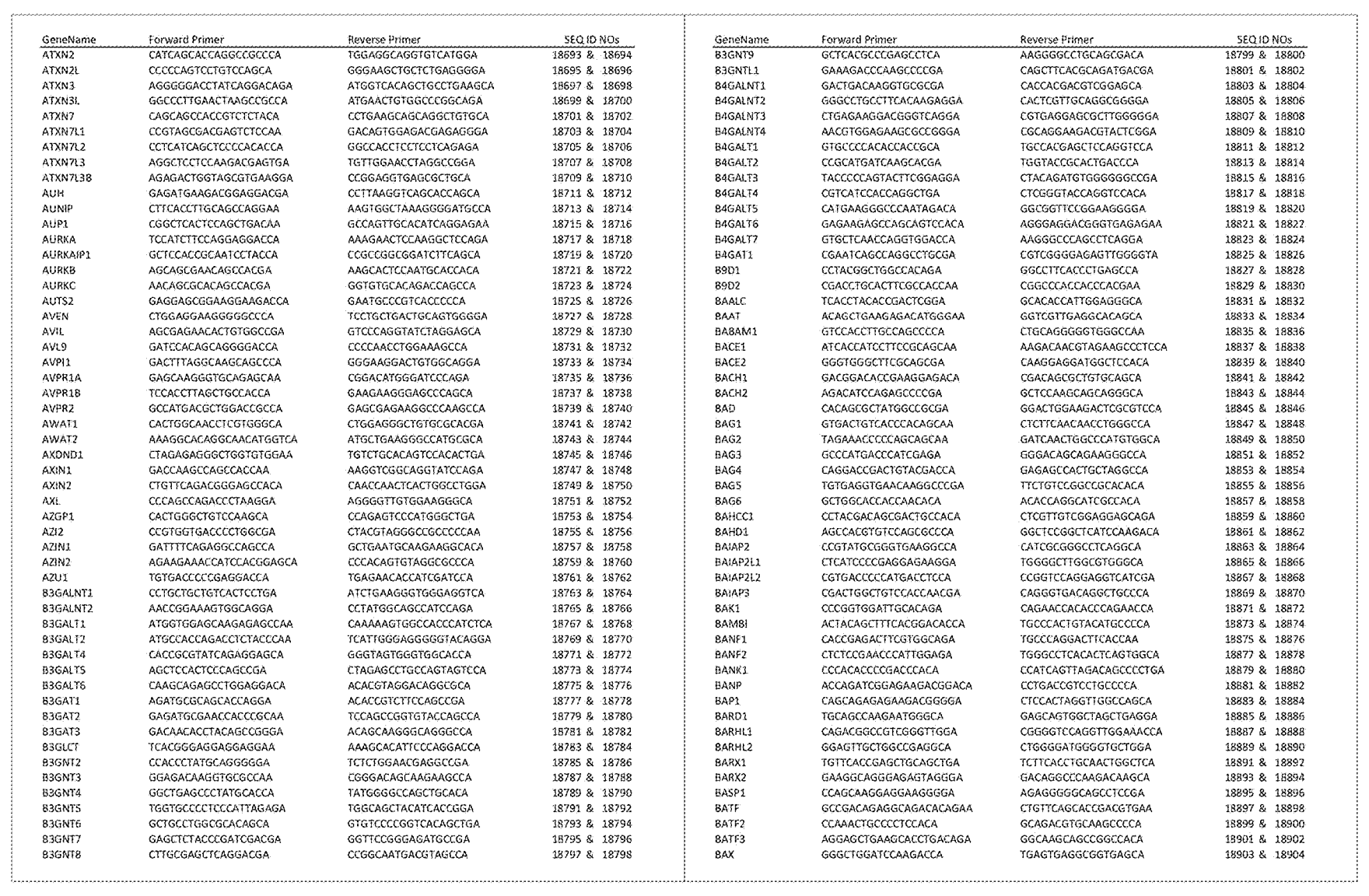
Figure 1:
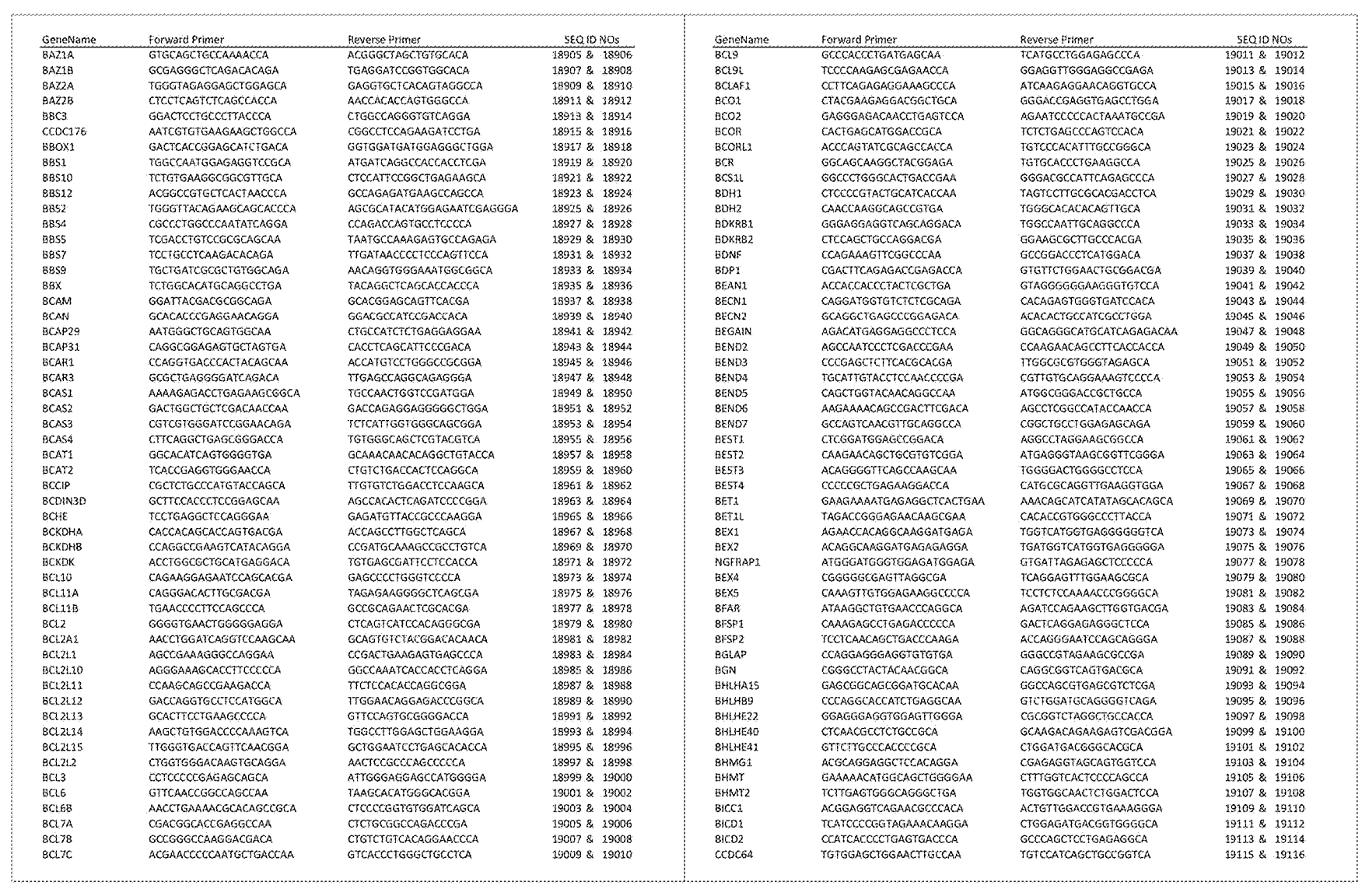
Figure 1:
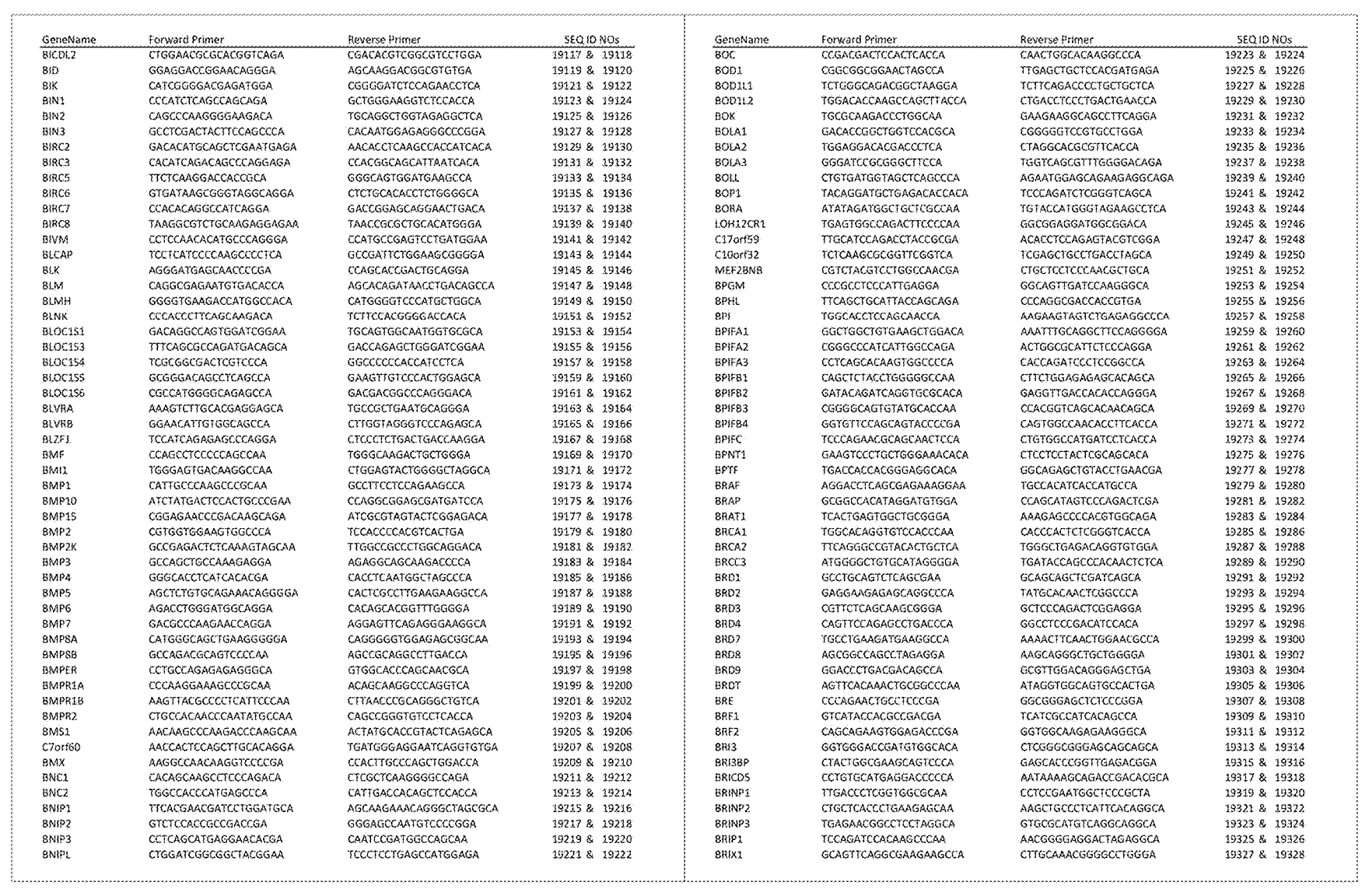
Figure 1:
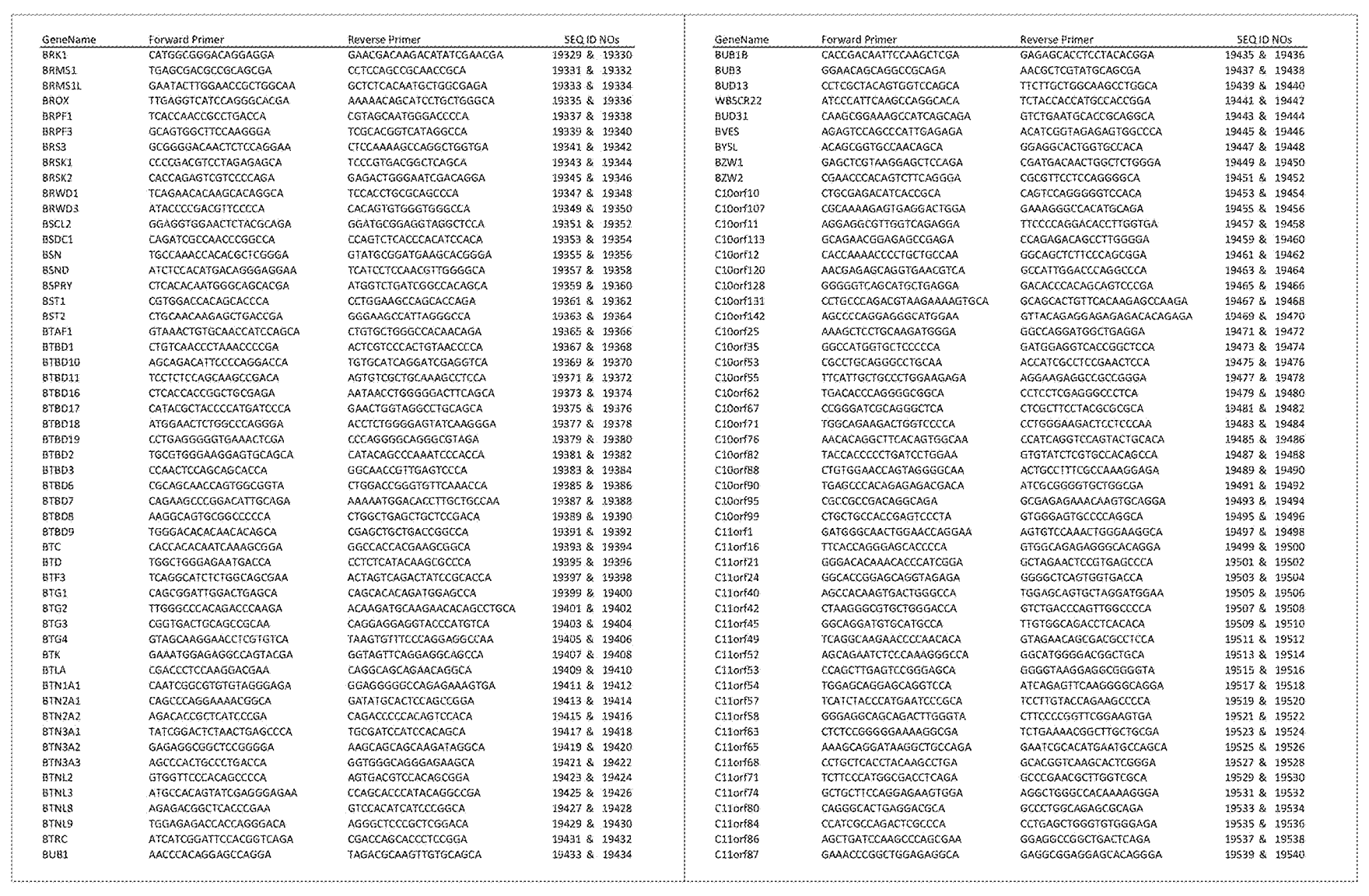
Figure 1:
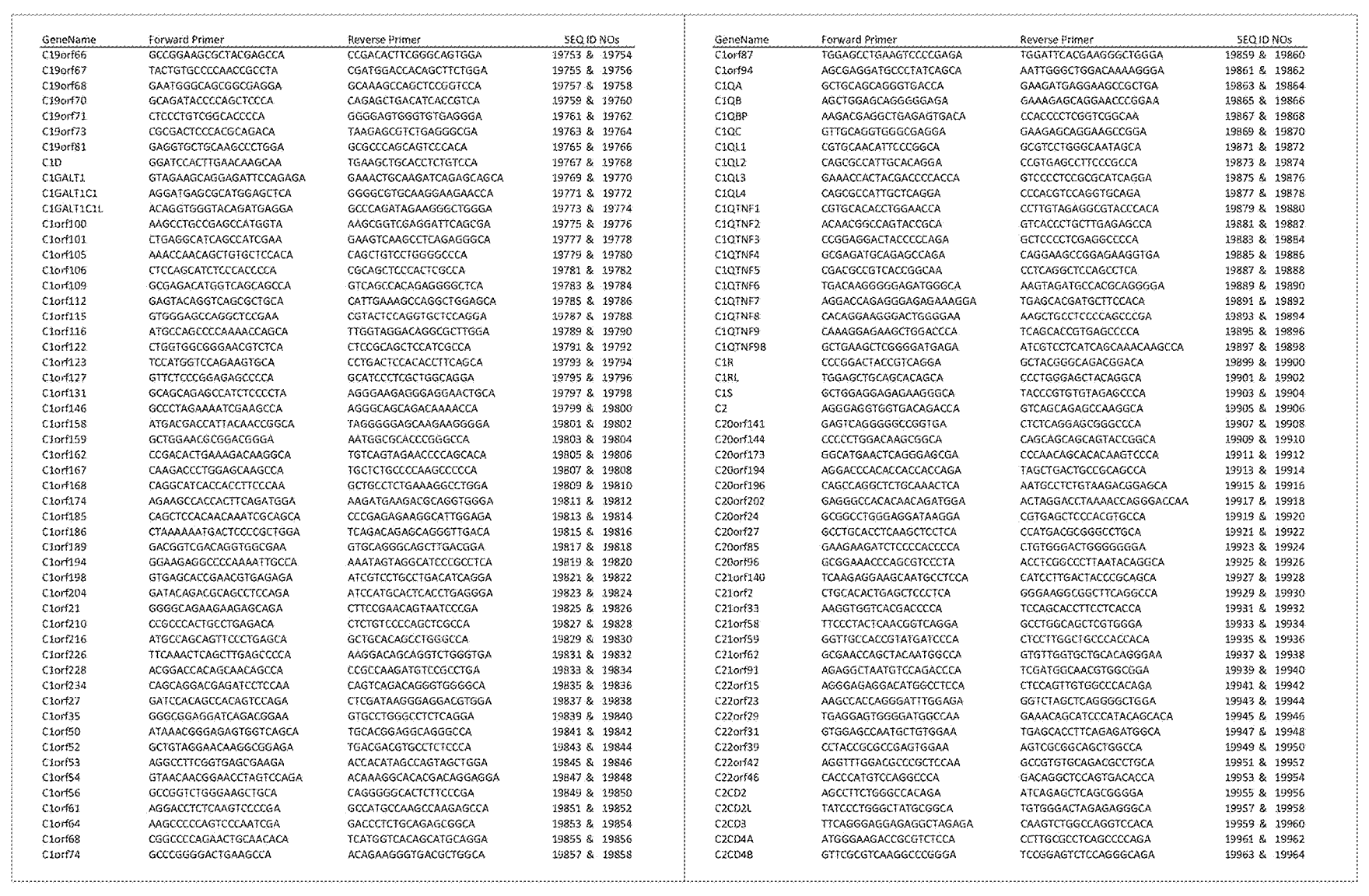
Figure 1:
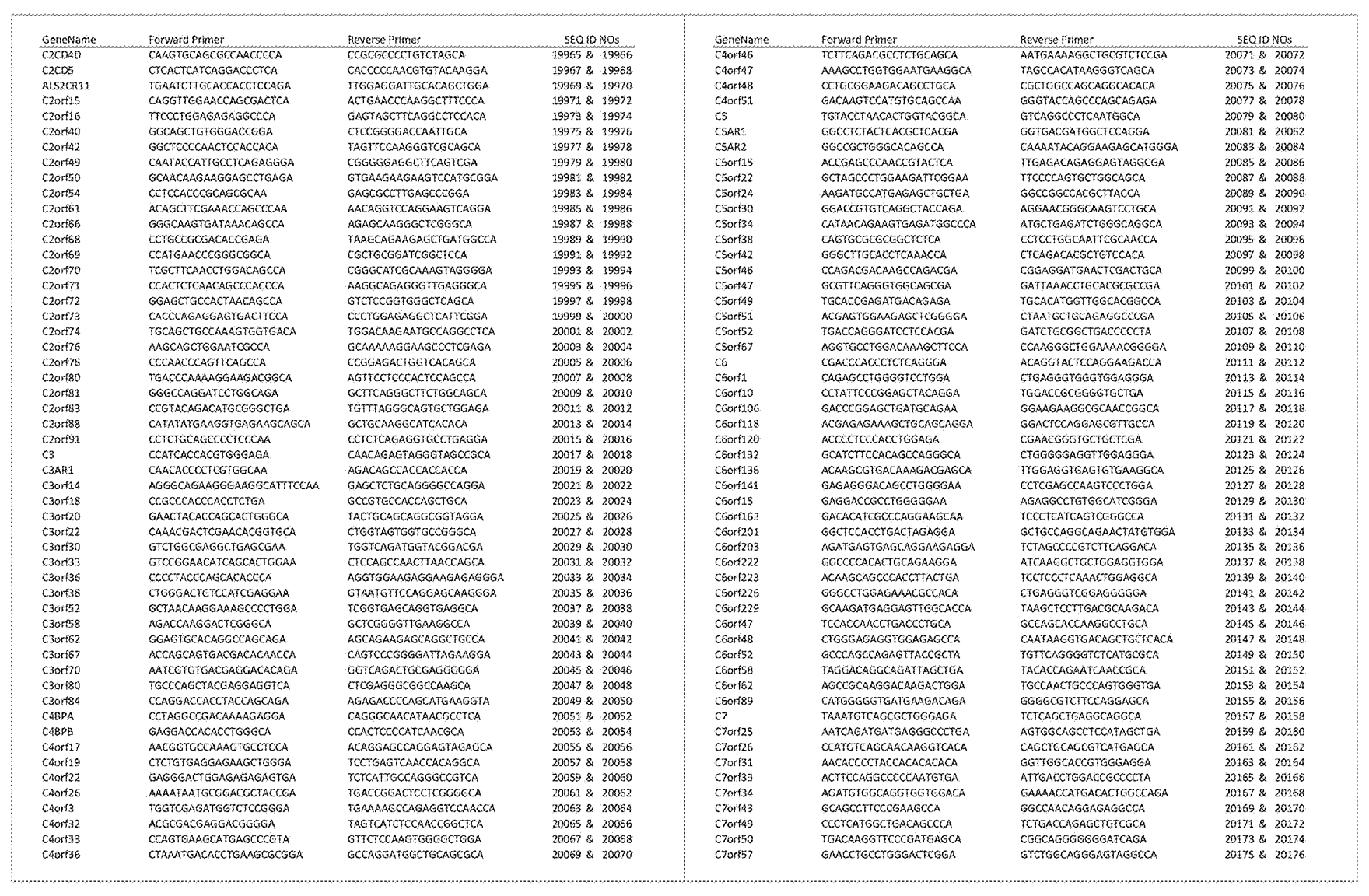
Figure 1:
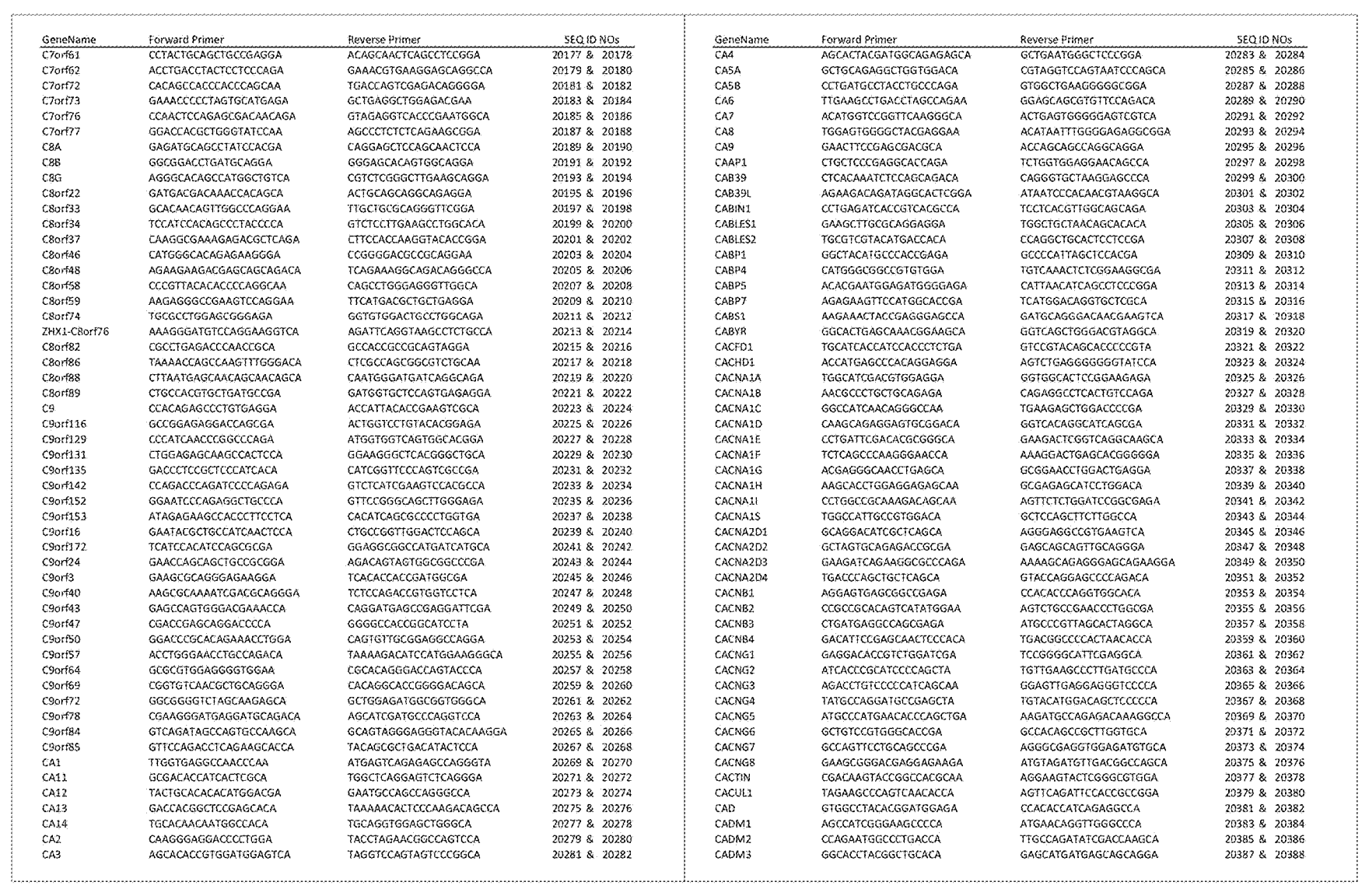
Figure 1:
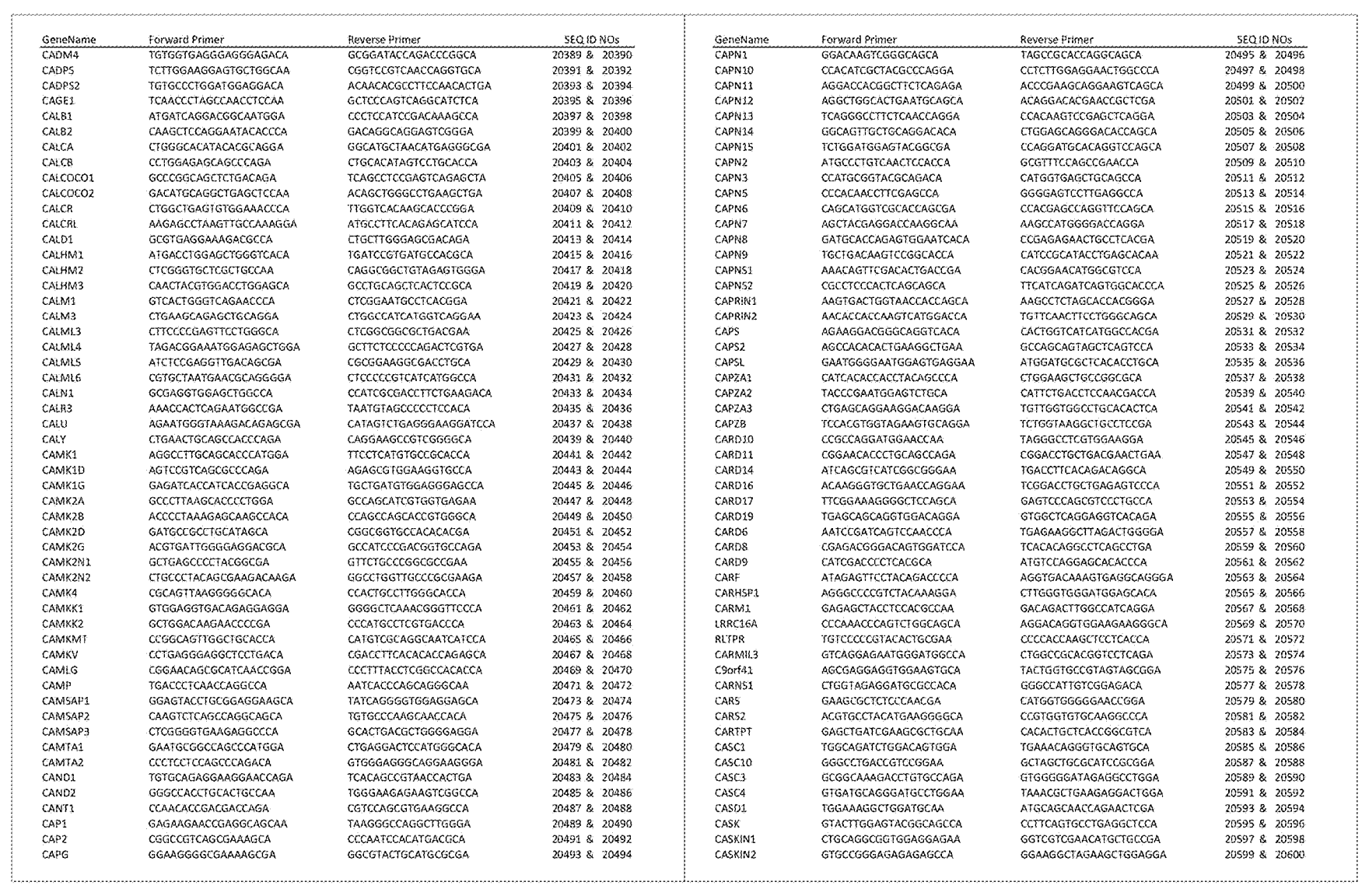
Figure 1:
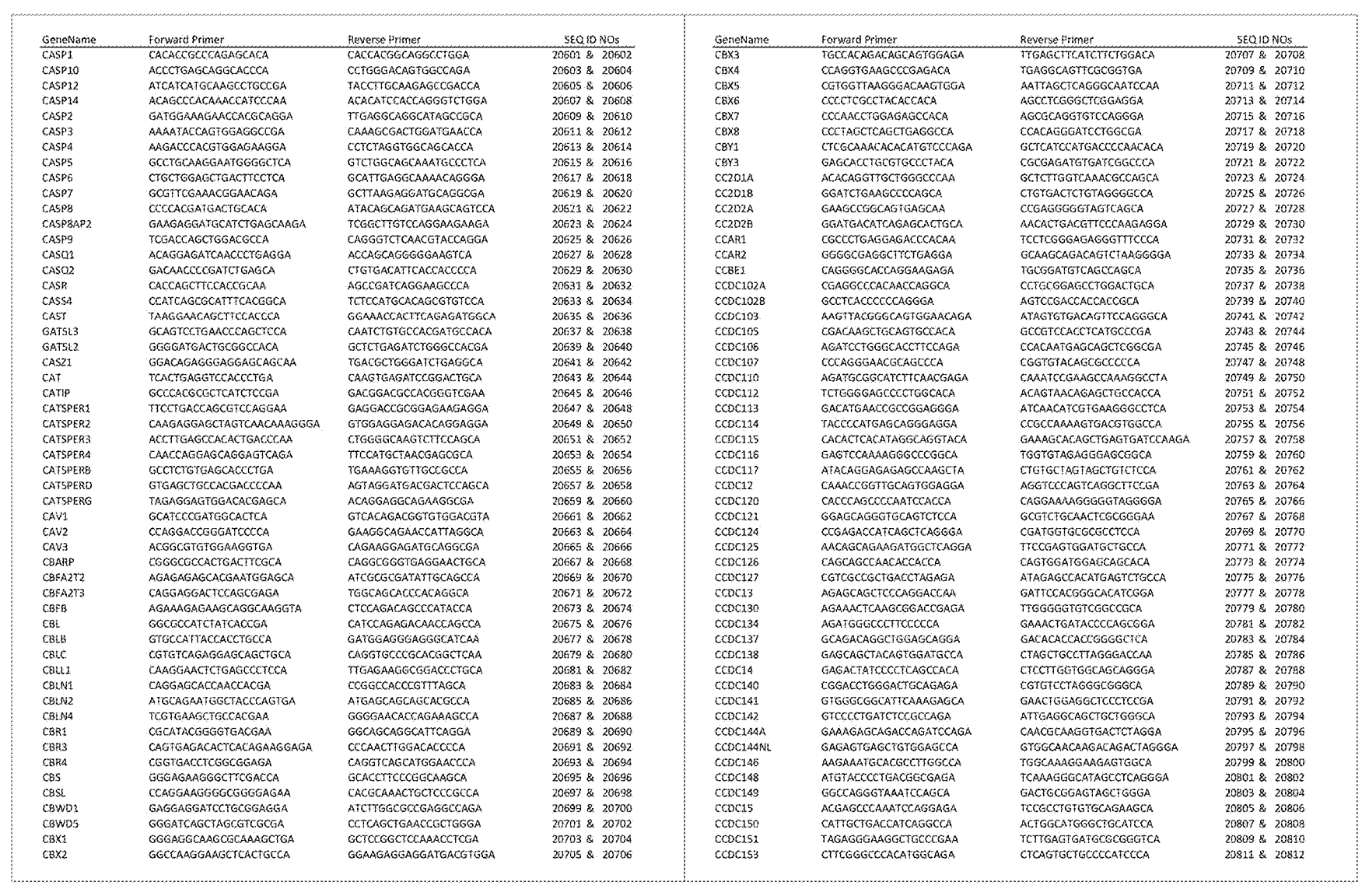
Figure 1:
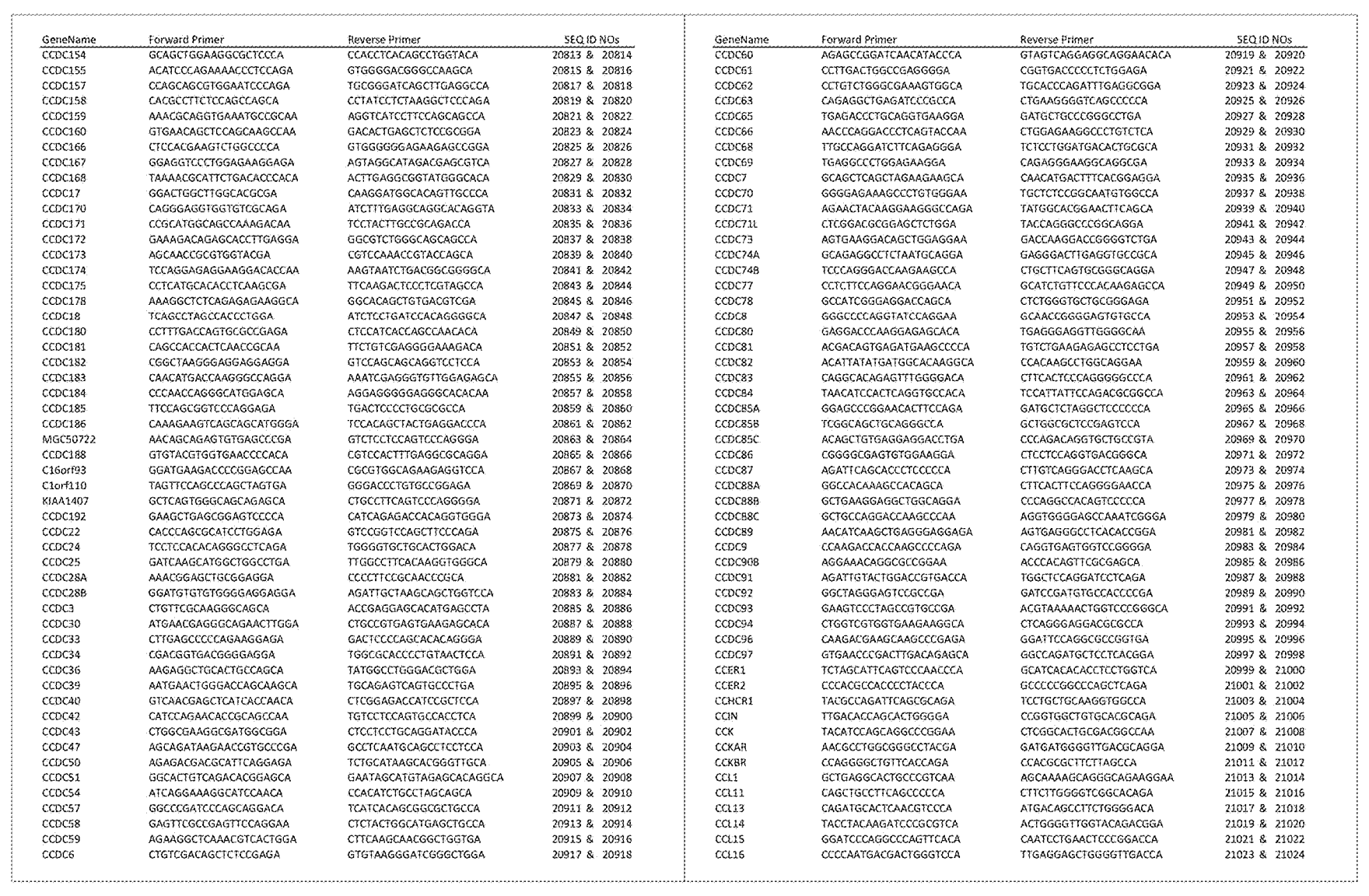
Figure 1:
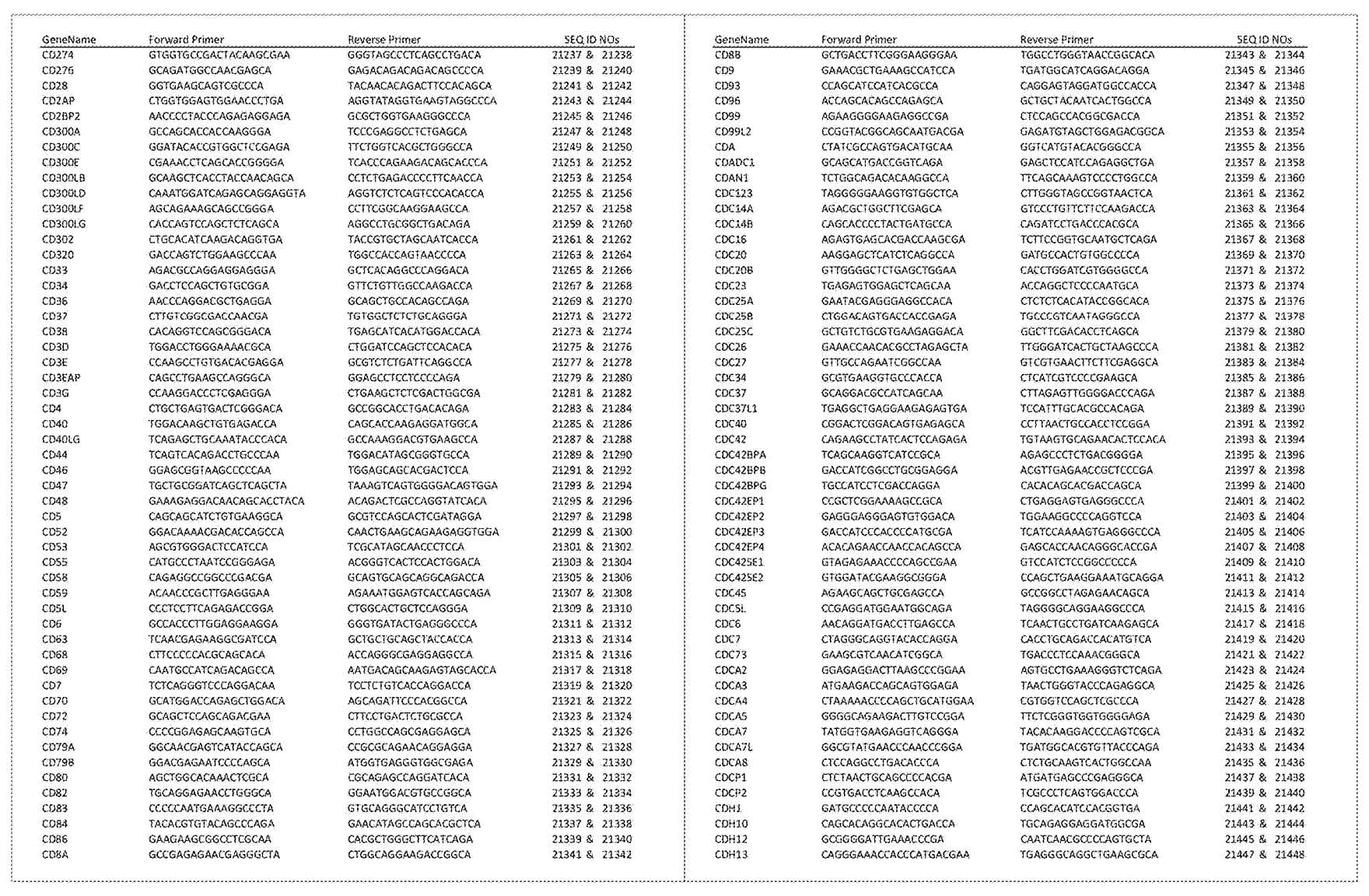
Figure 1:
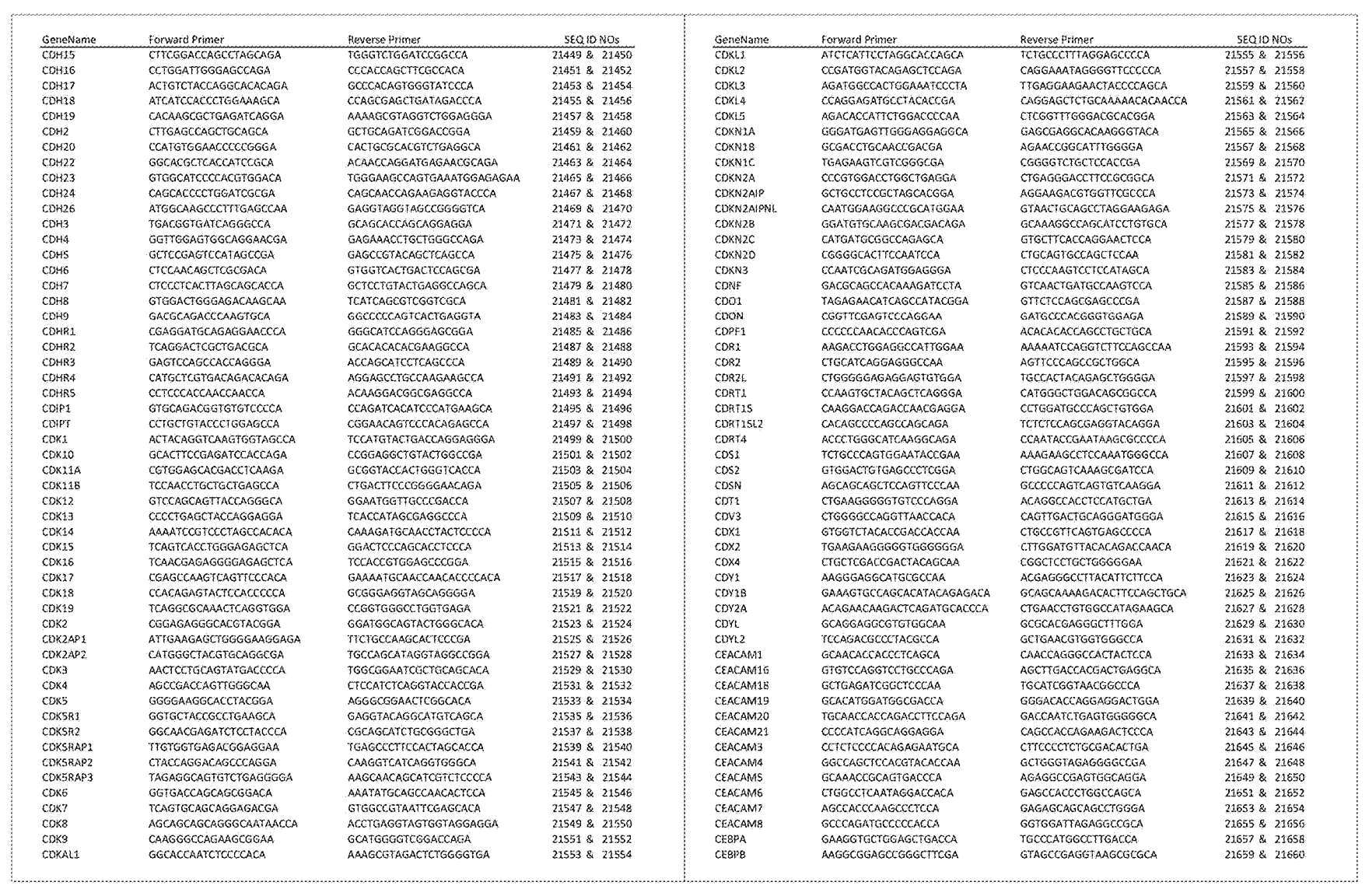
Figure 1:
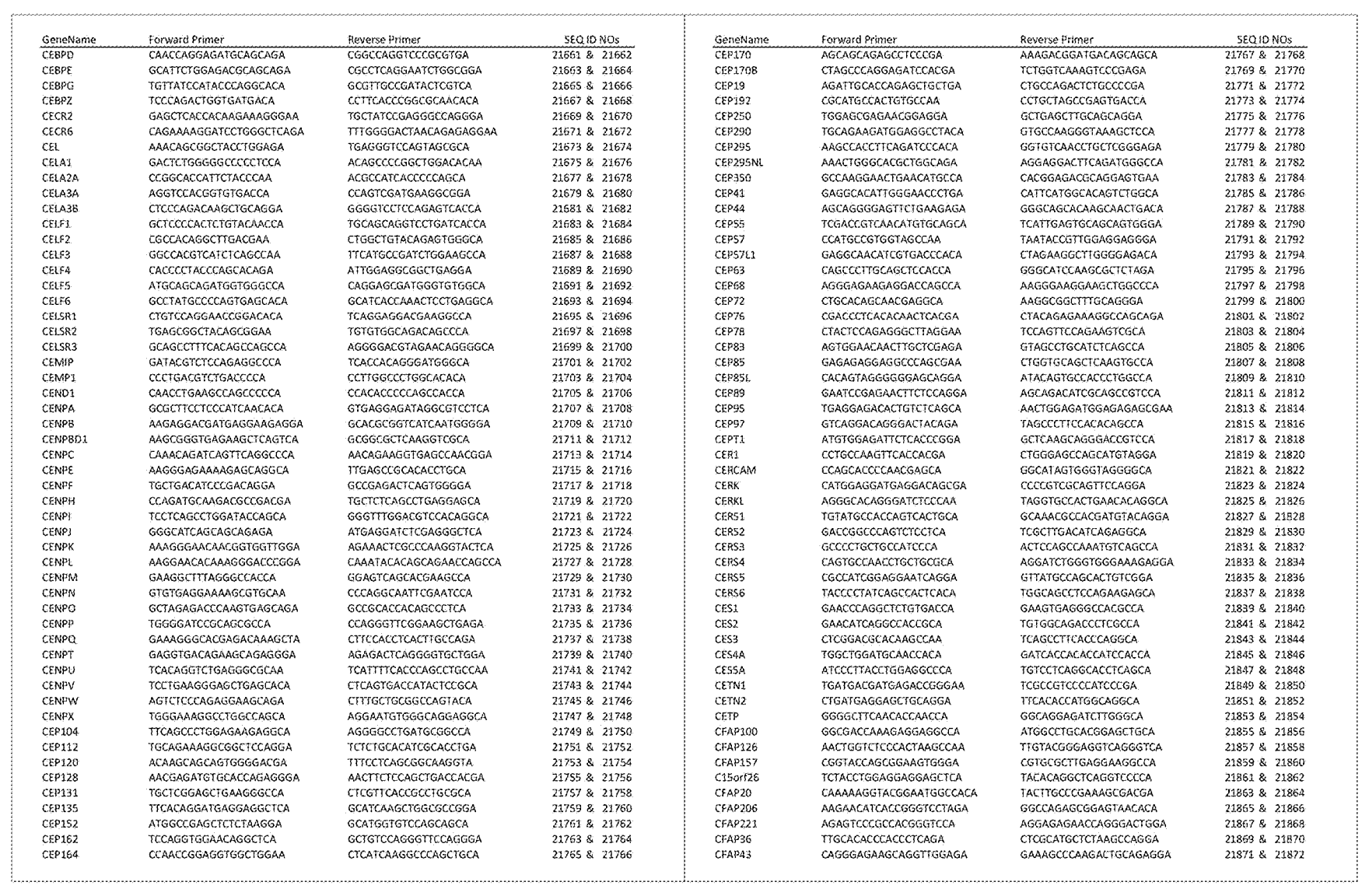
Figure 1:
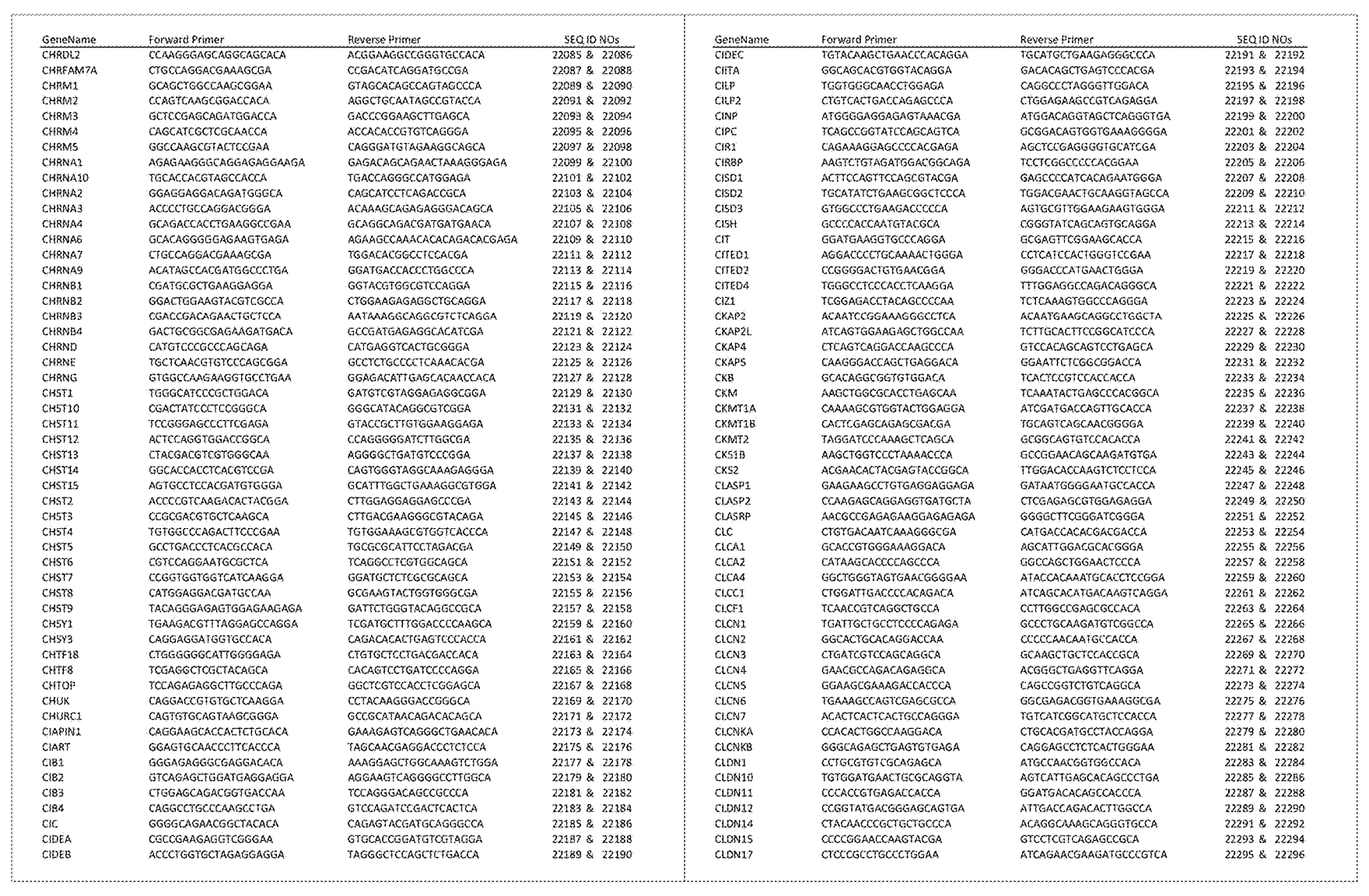
Figure 1:
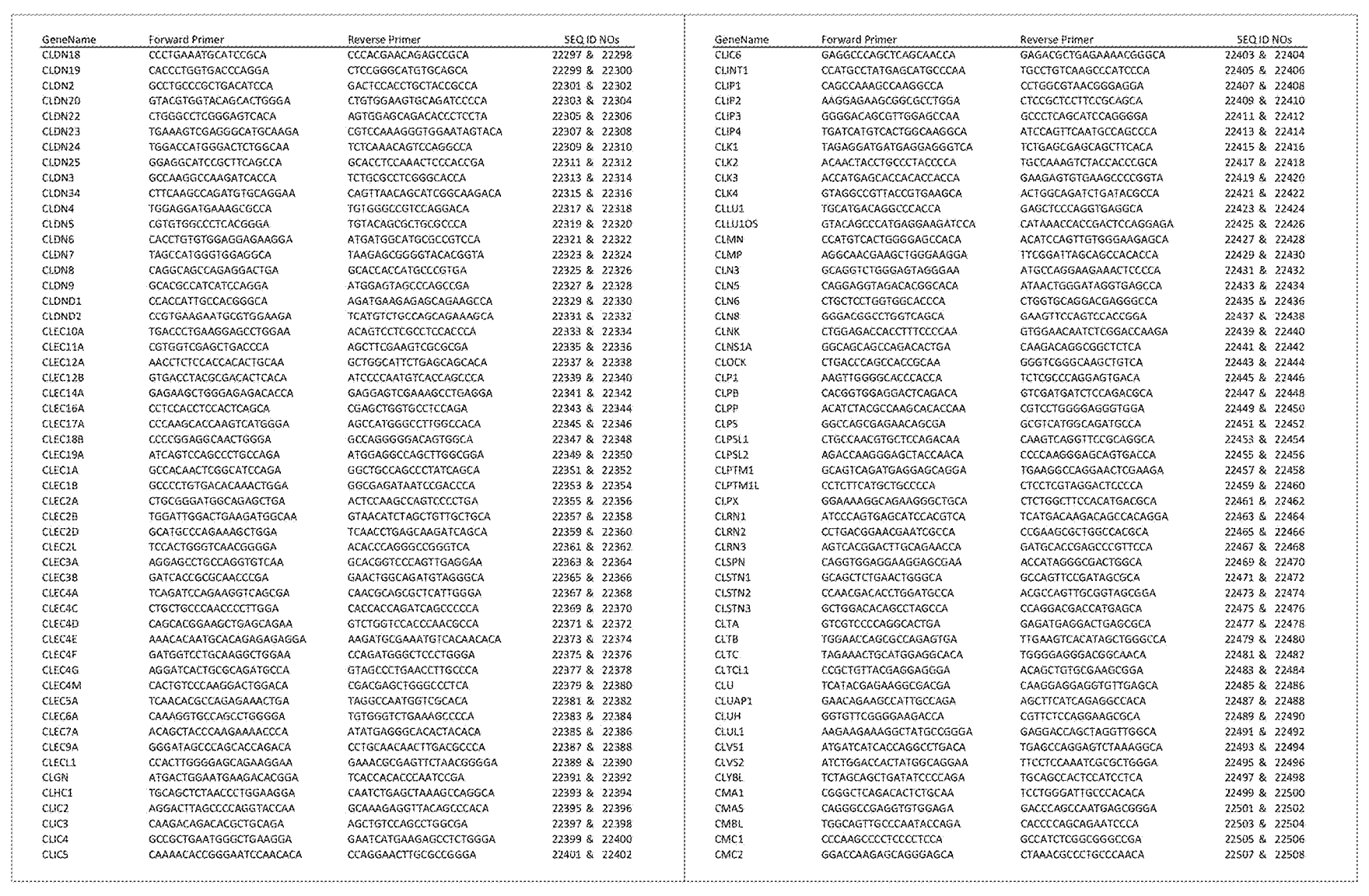
Figure 1:
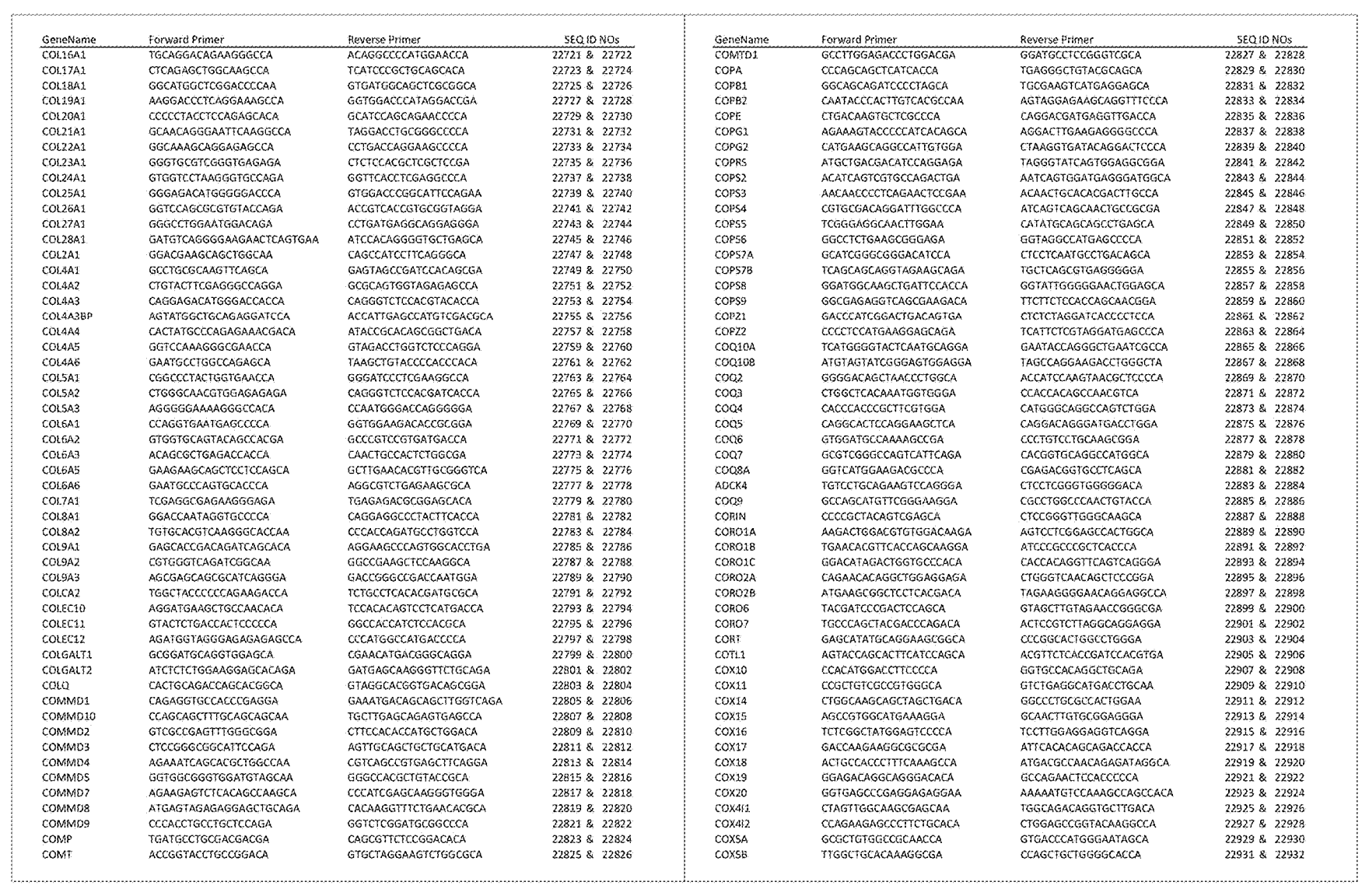
Figure 1:
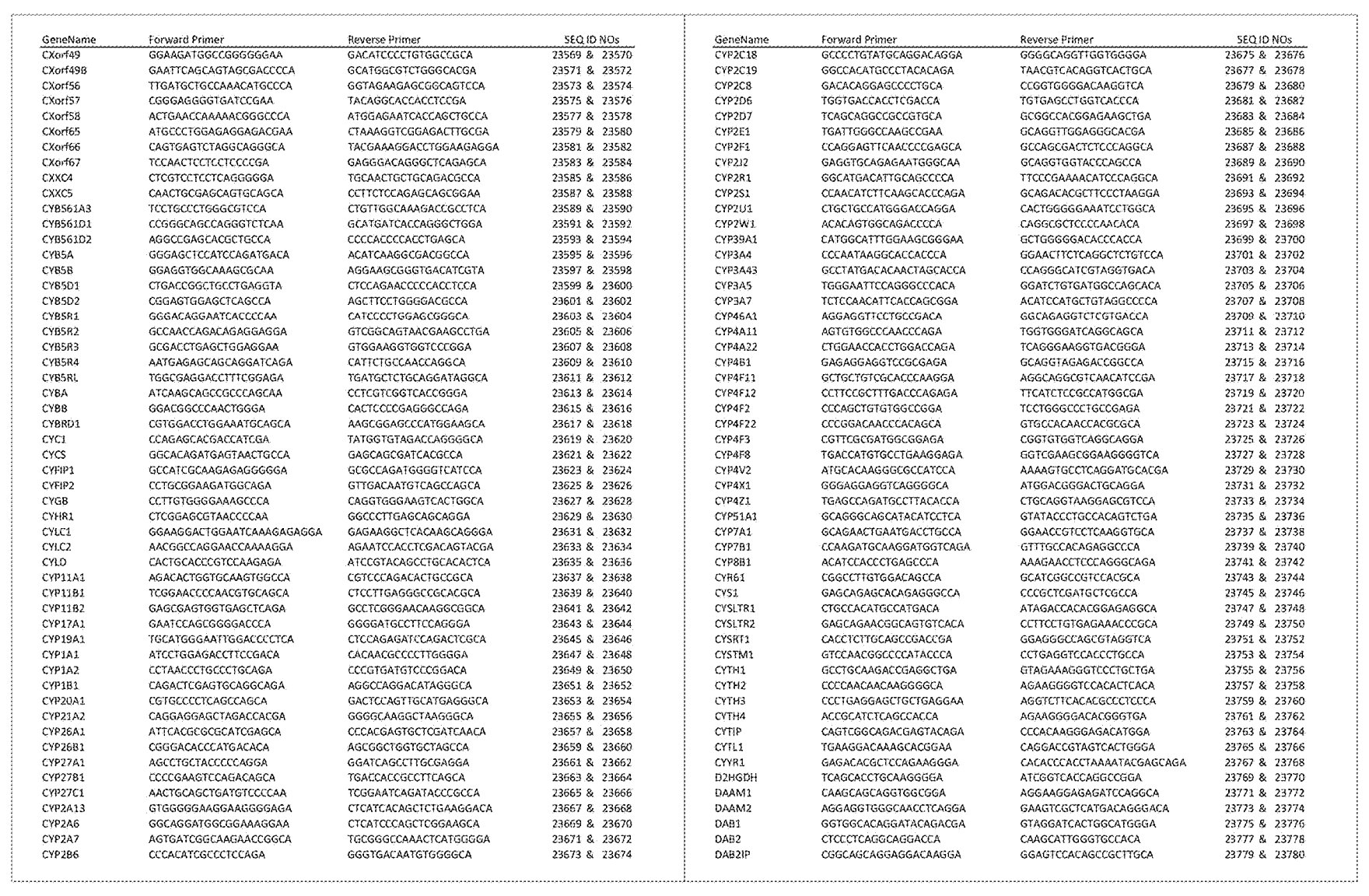
Figure 1:
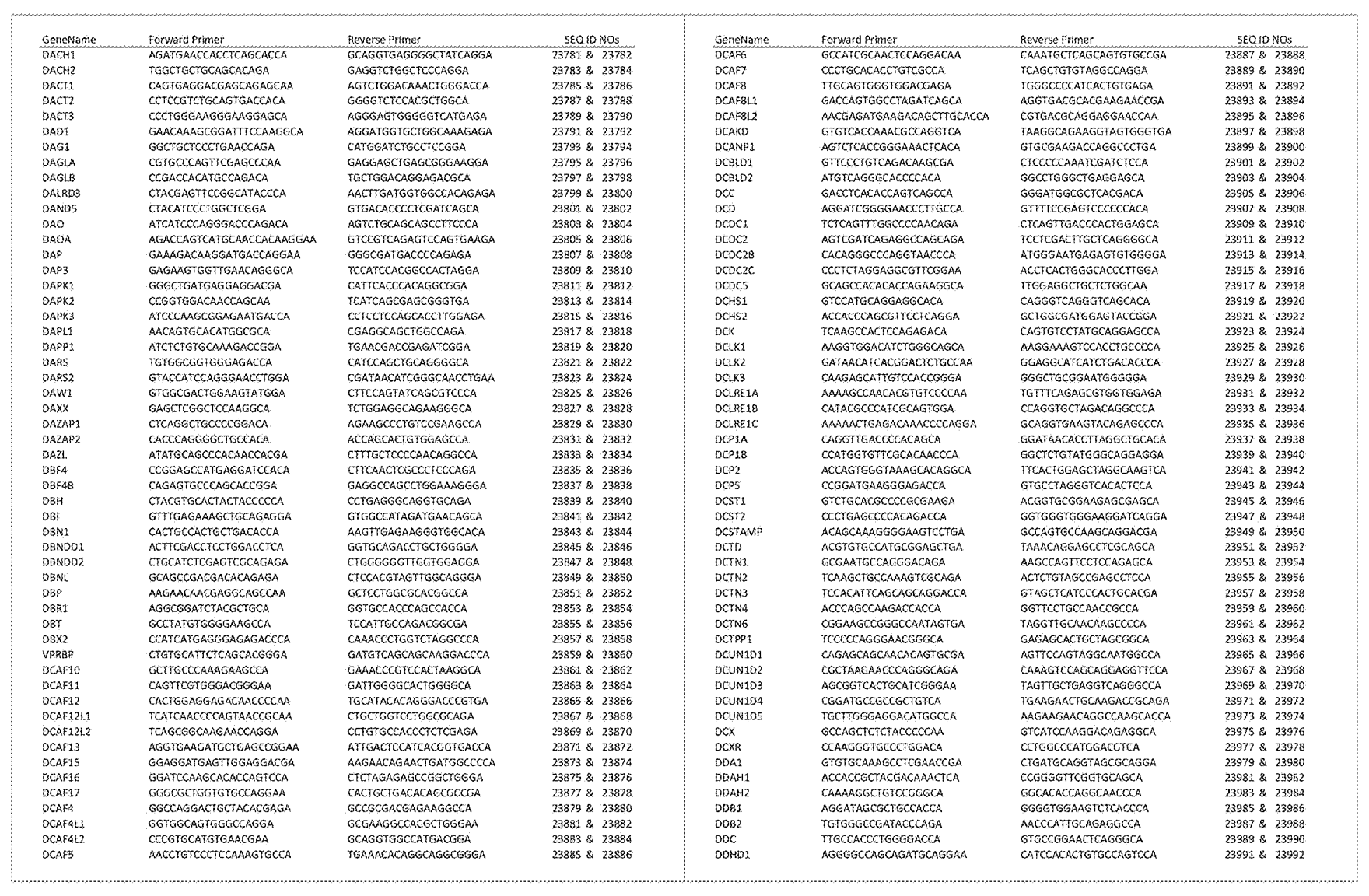
Figure 1:
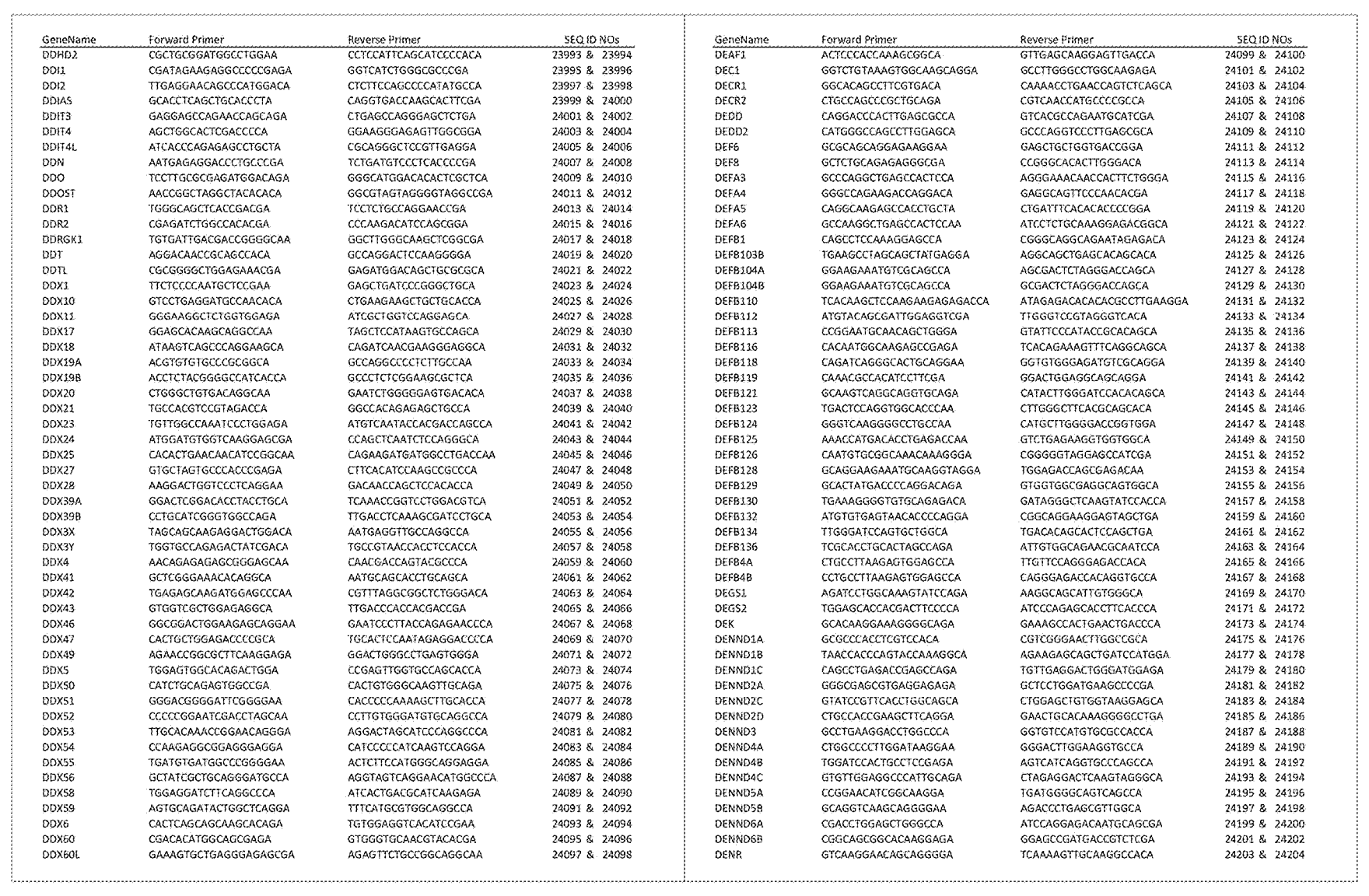
Figure 1:
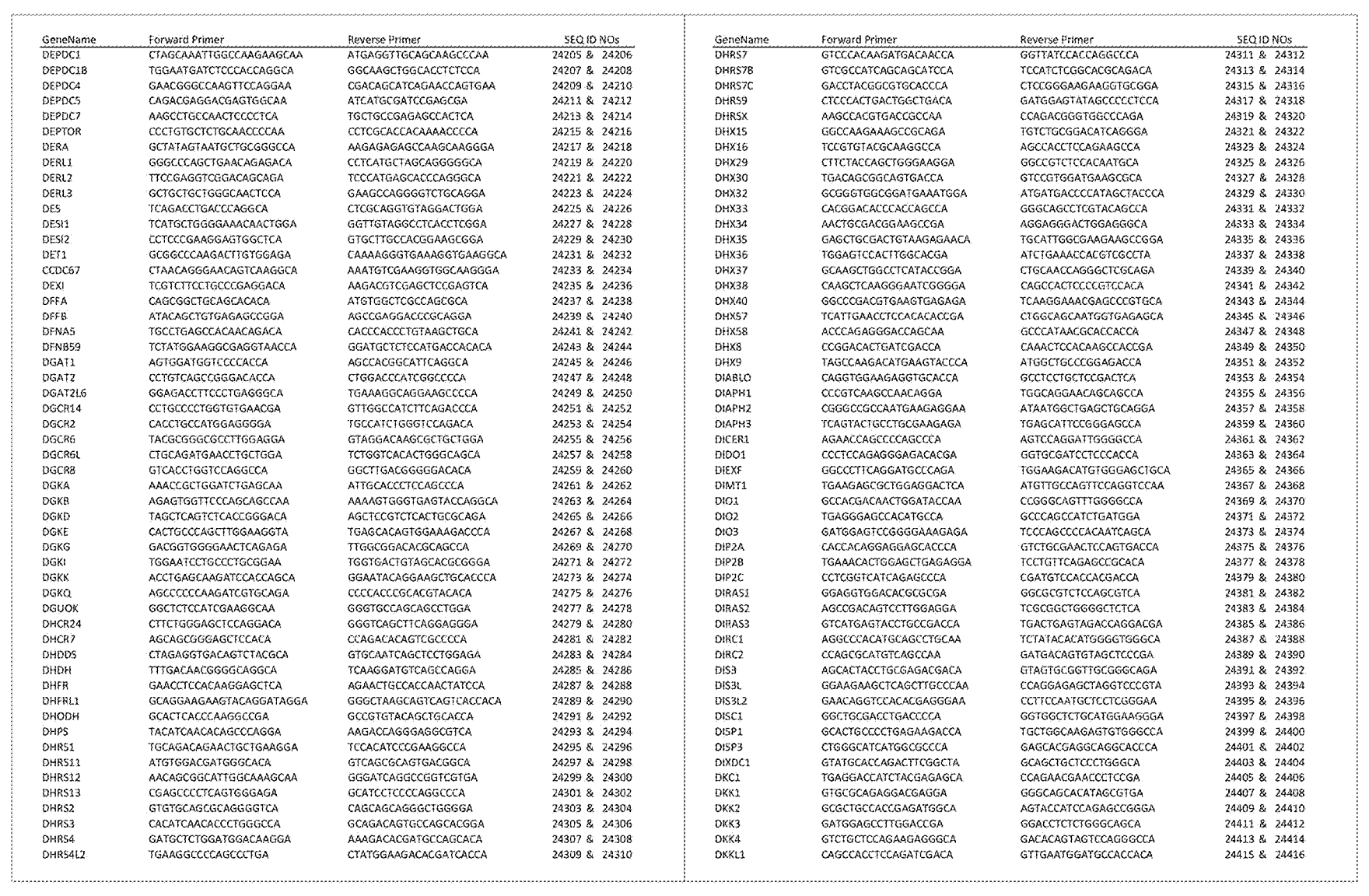
Figure 1:
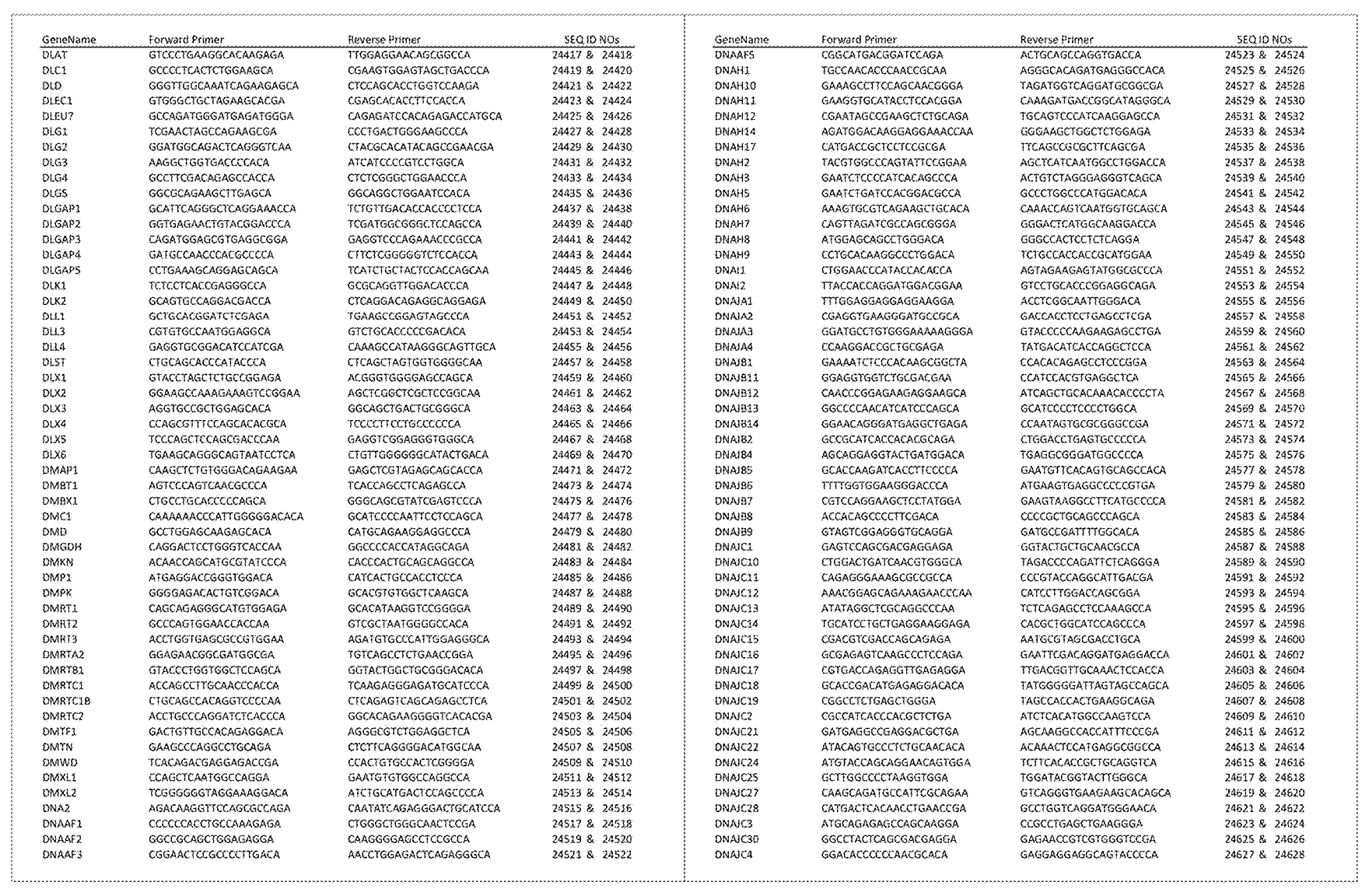
Figure 1:
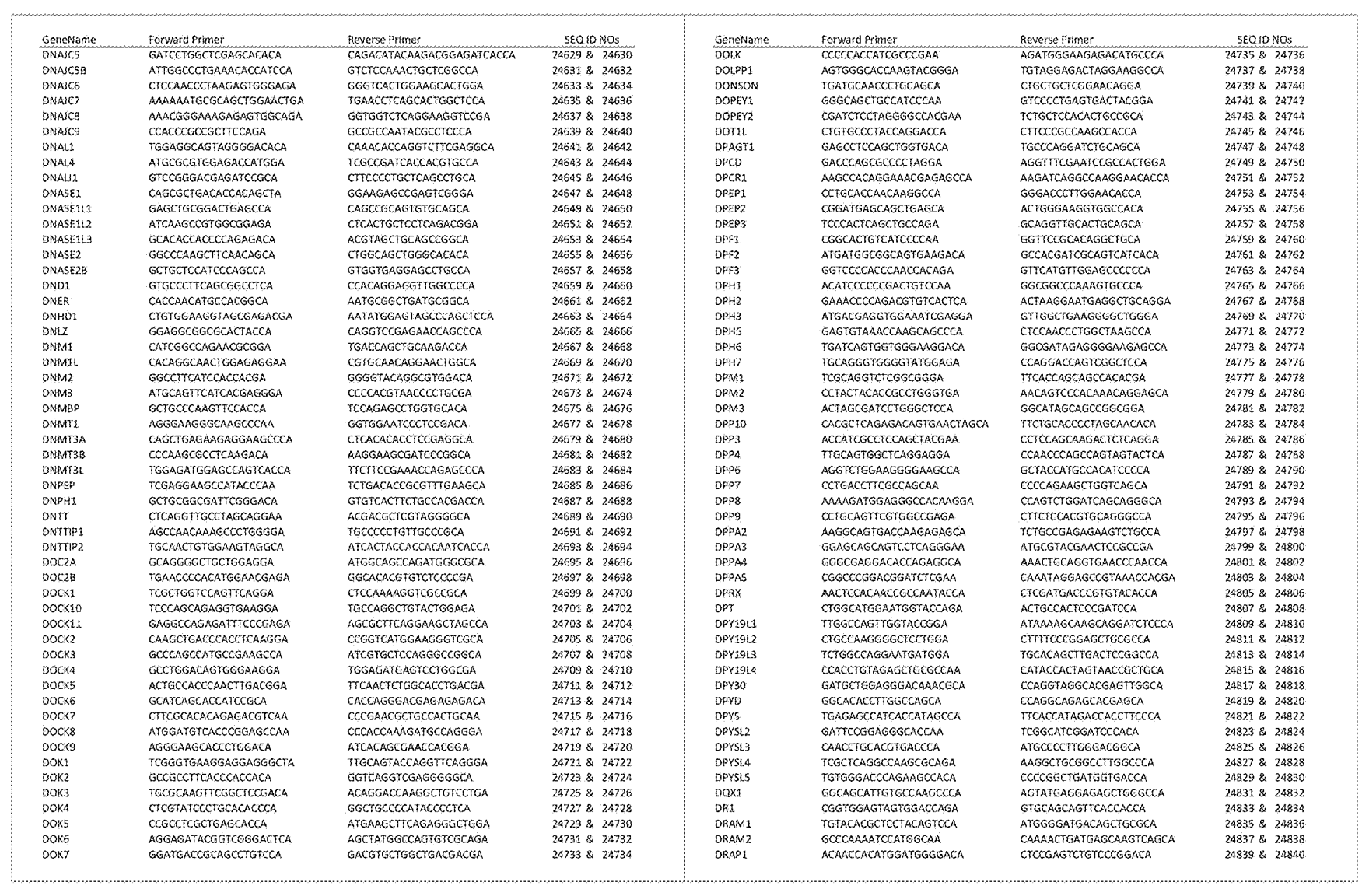
Figure 1:
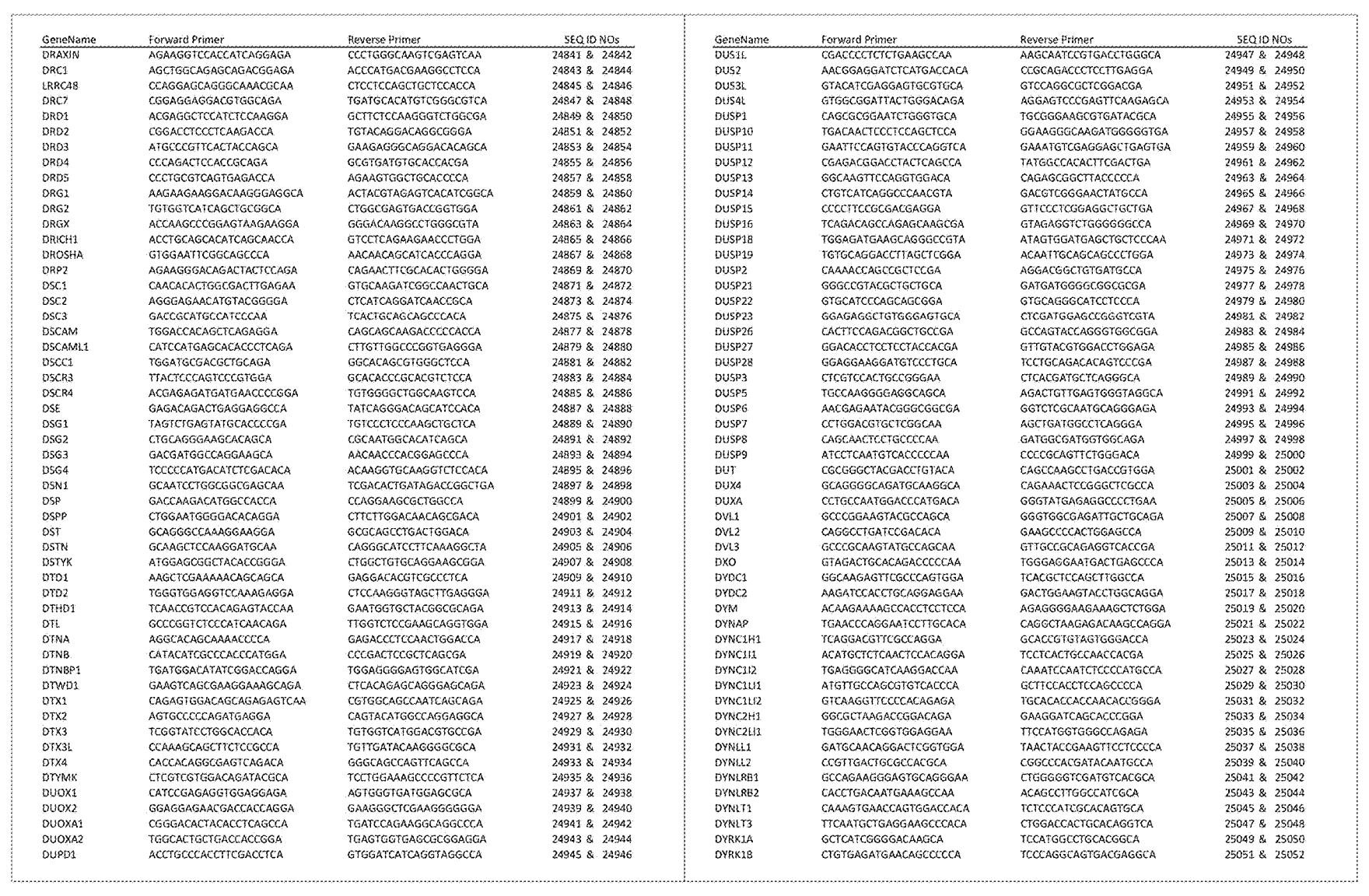
Figure 1:
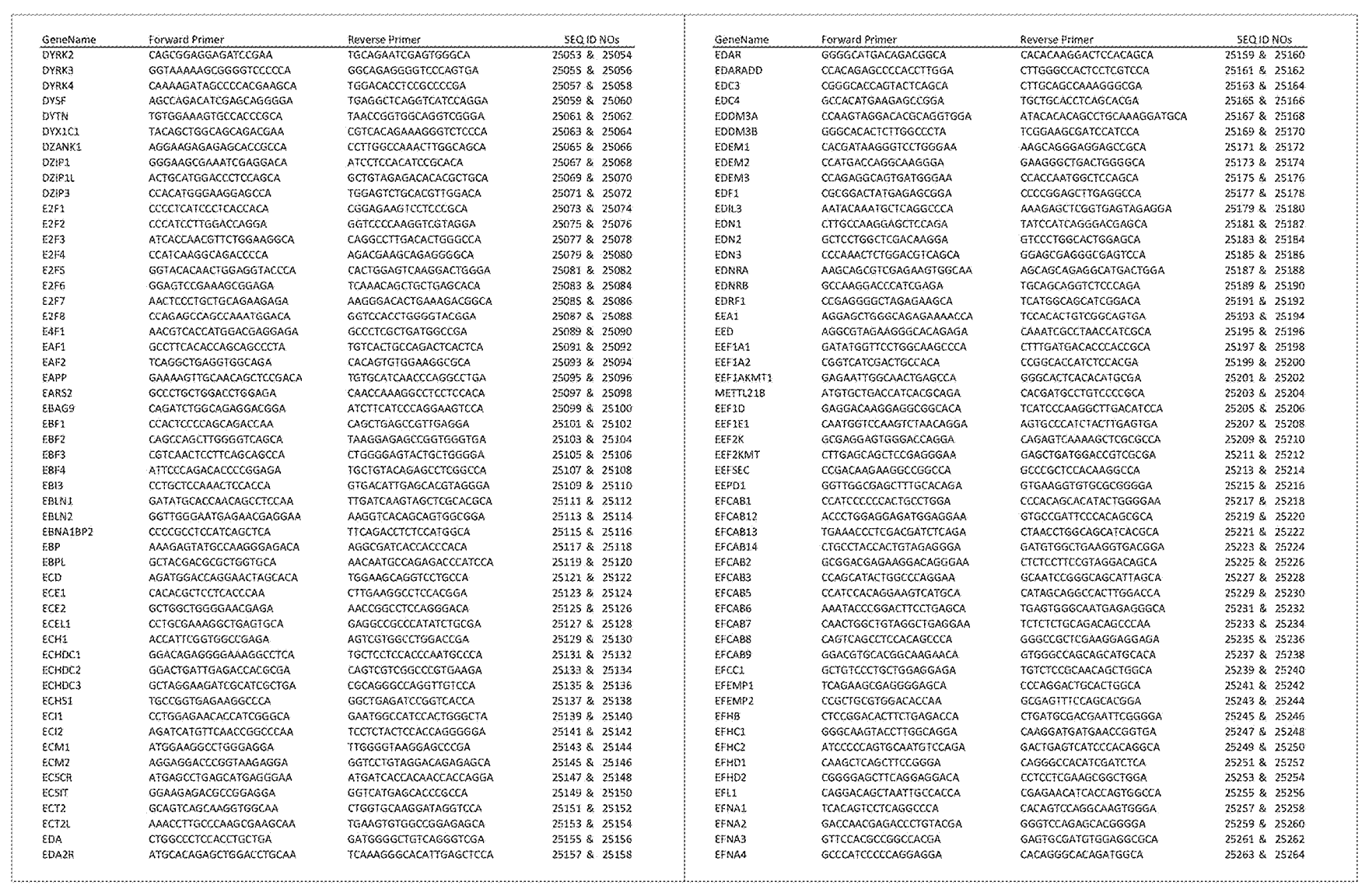
Figure 1:
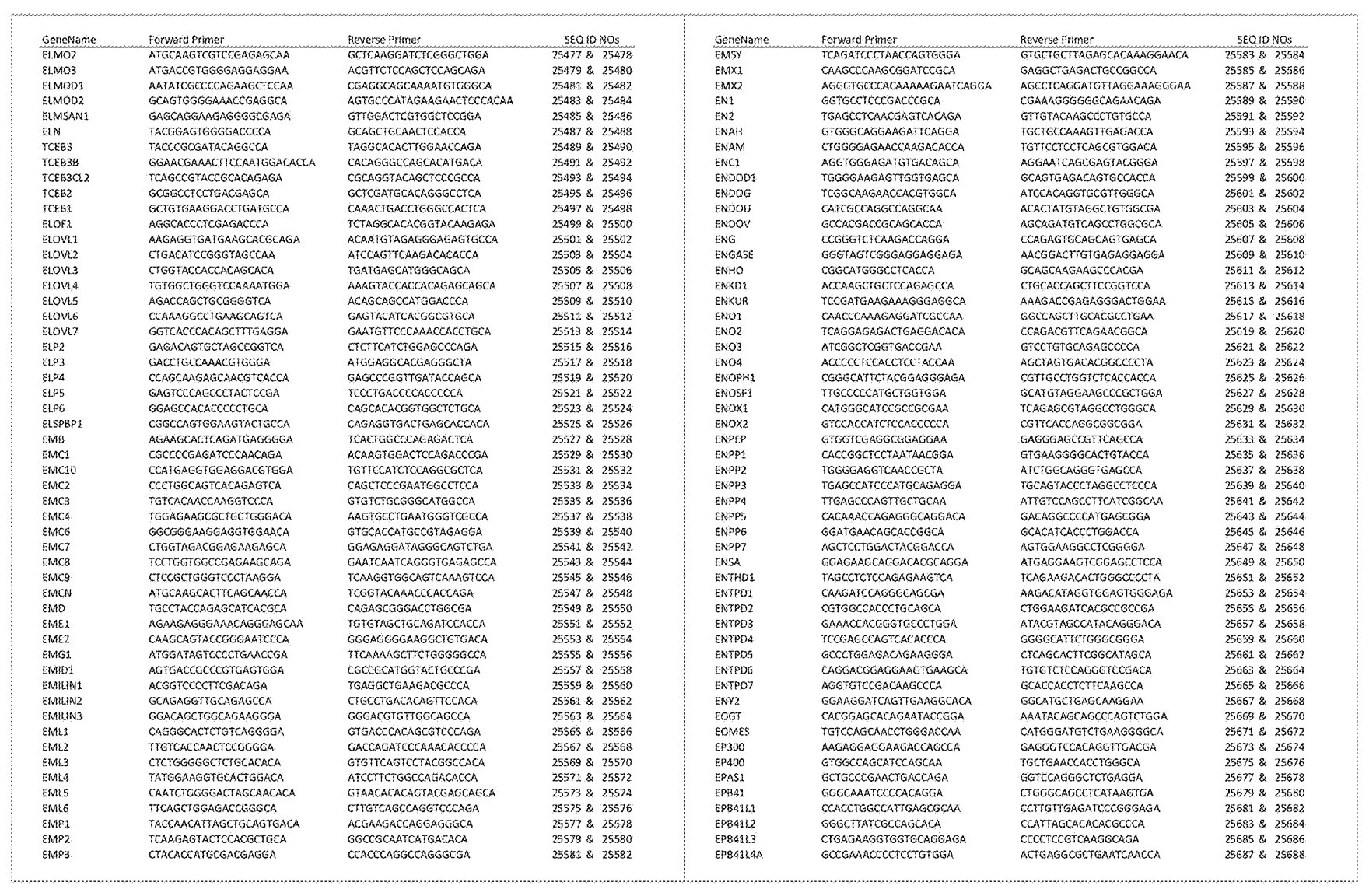
Figure 1:
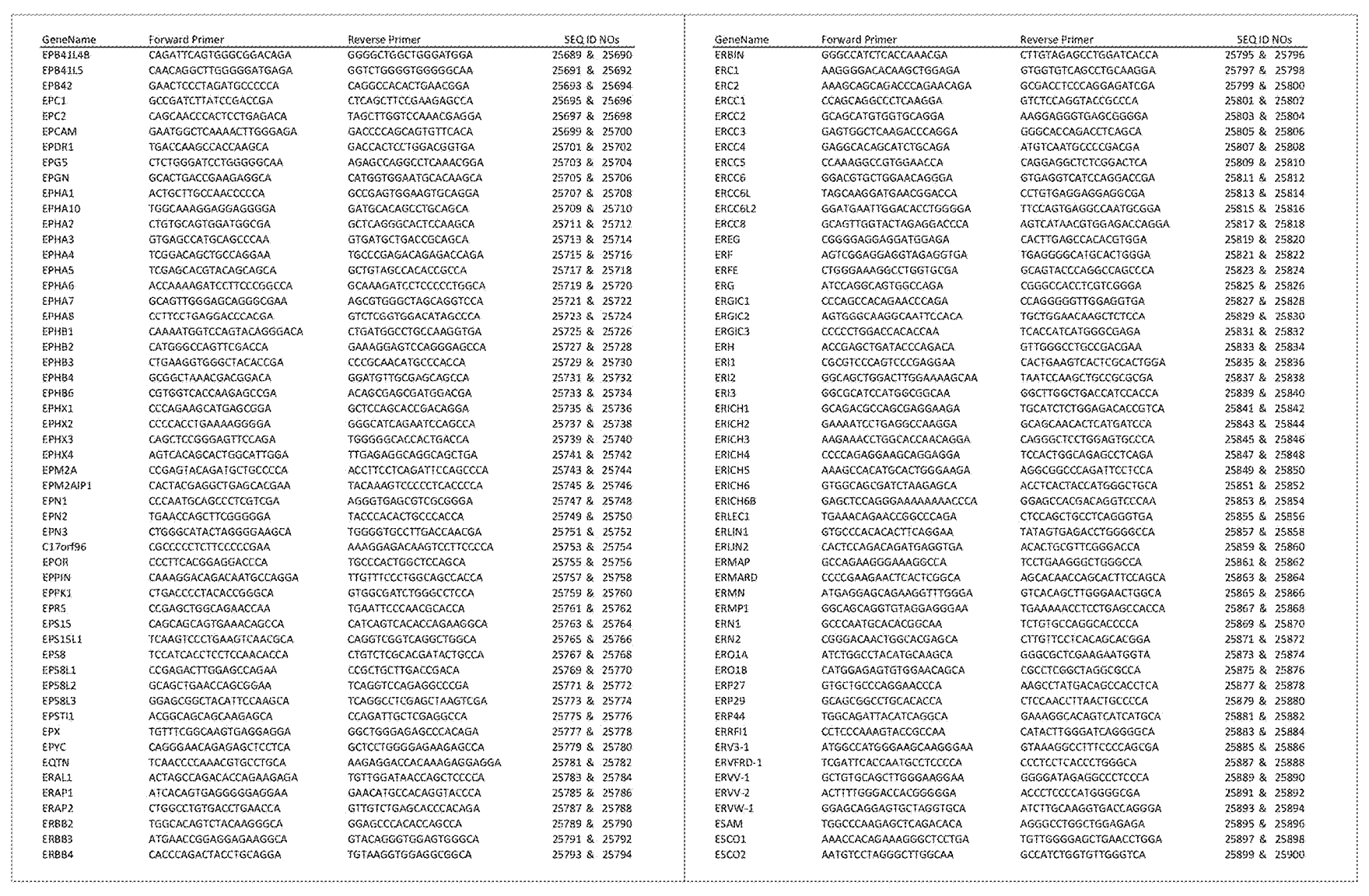
Figure 1:
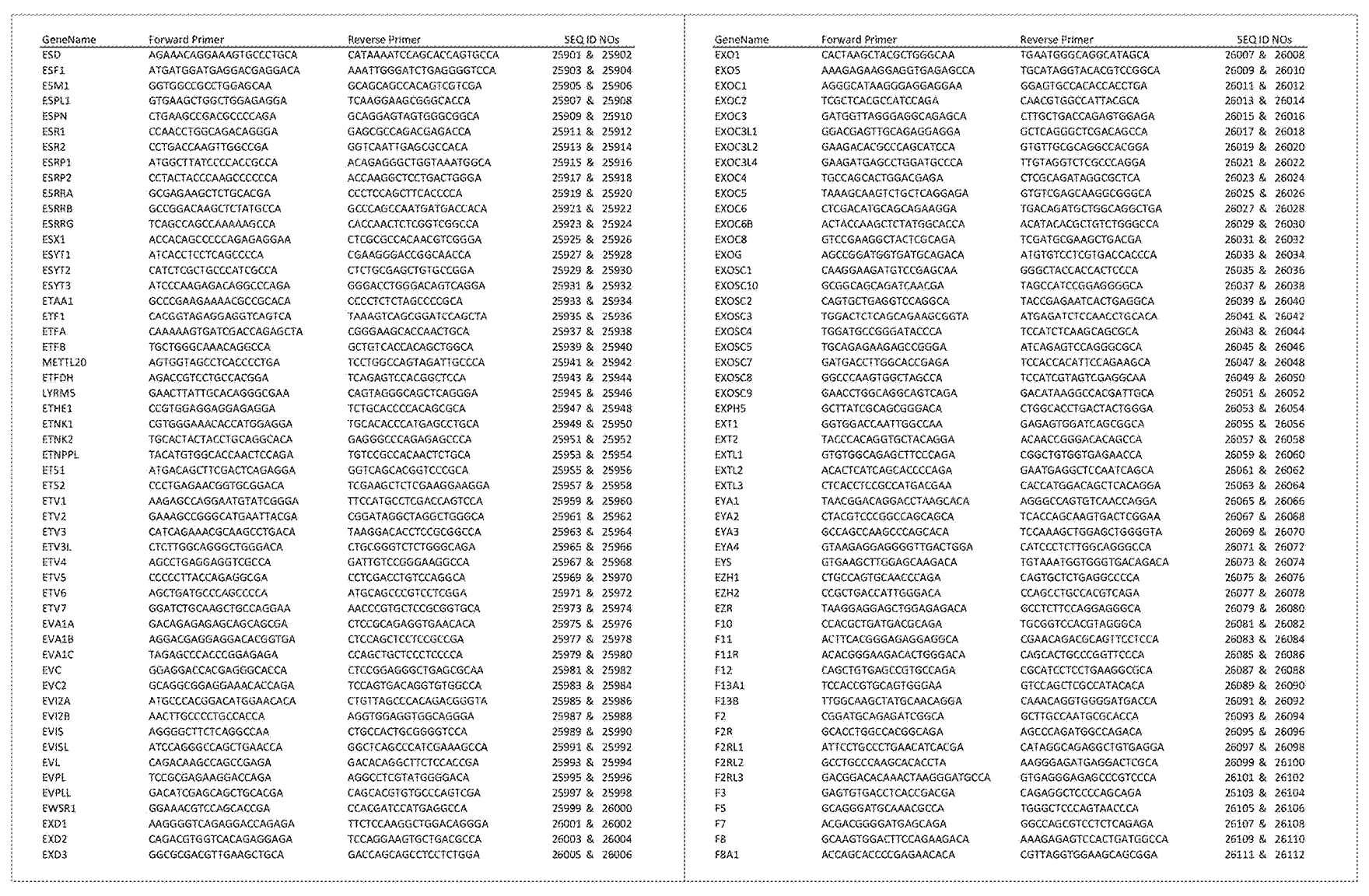
Figure 1:
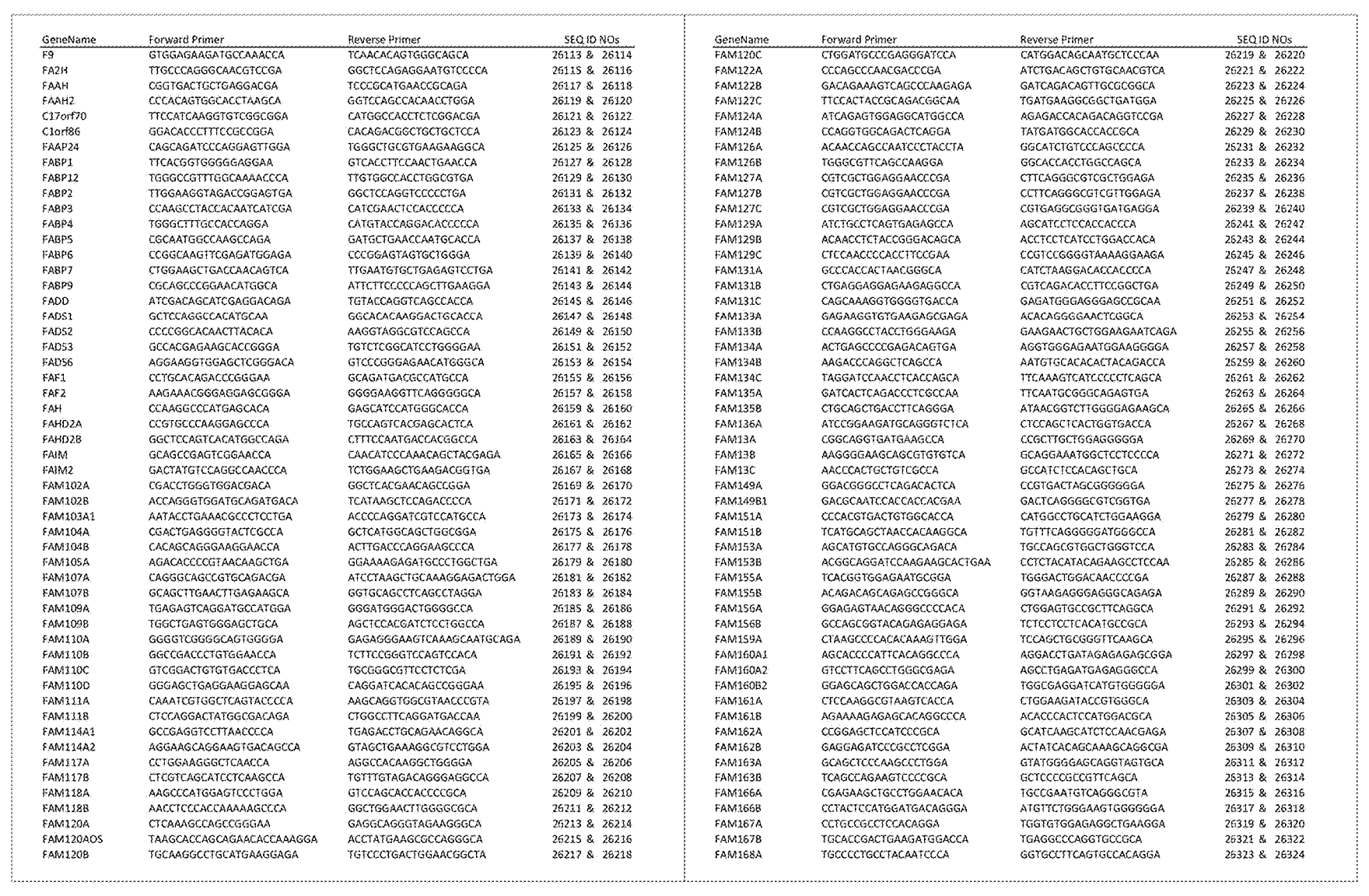
Figure 1:
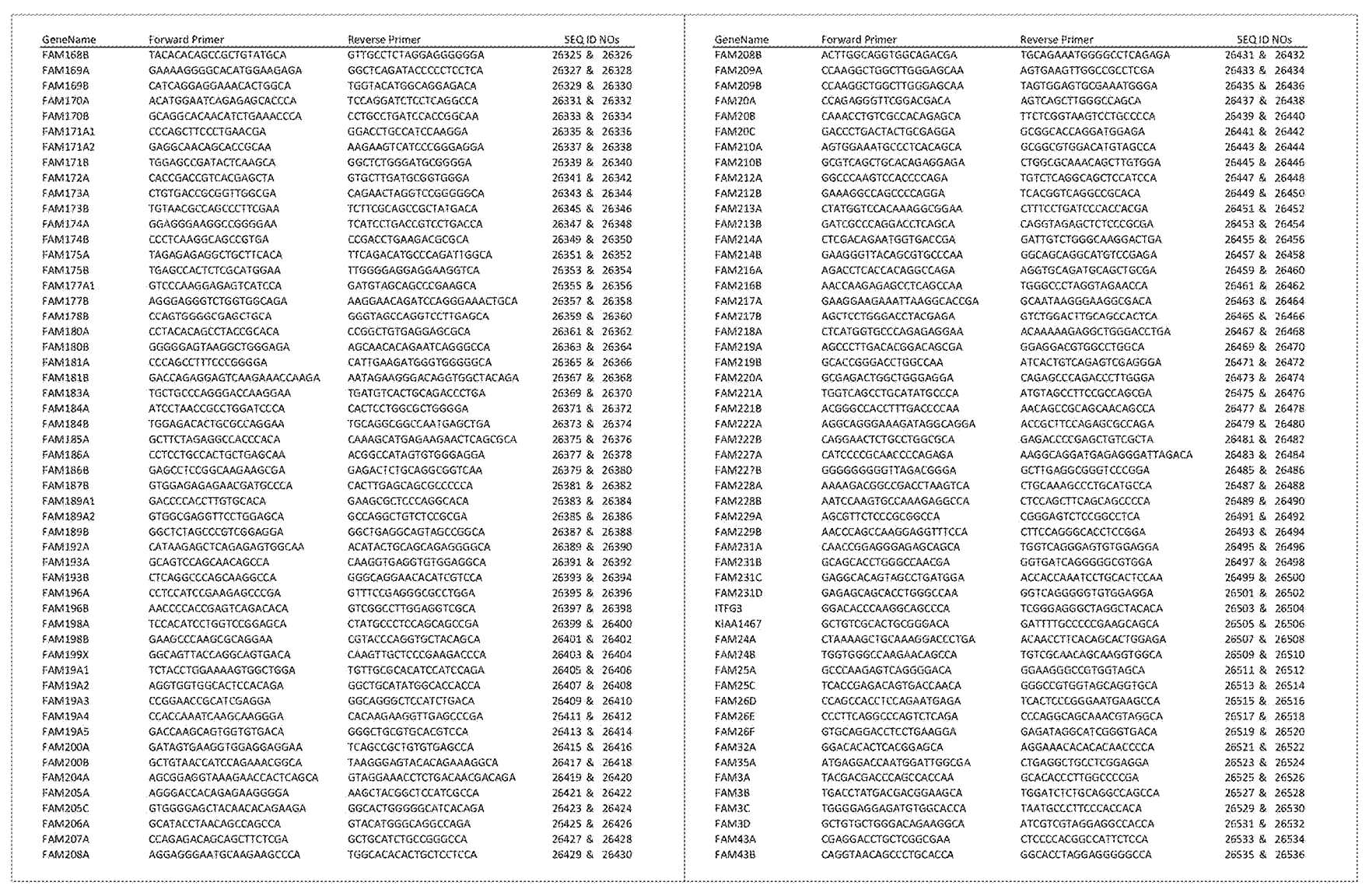
Figure 1:
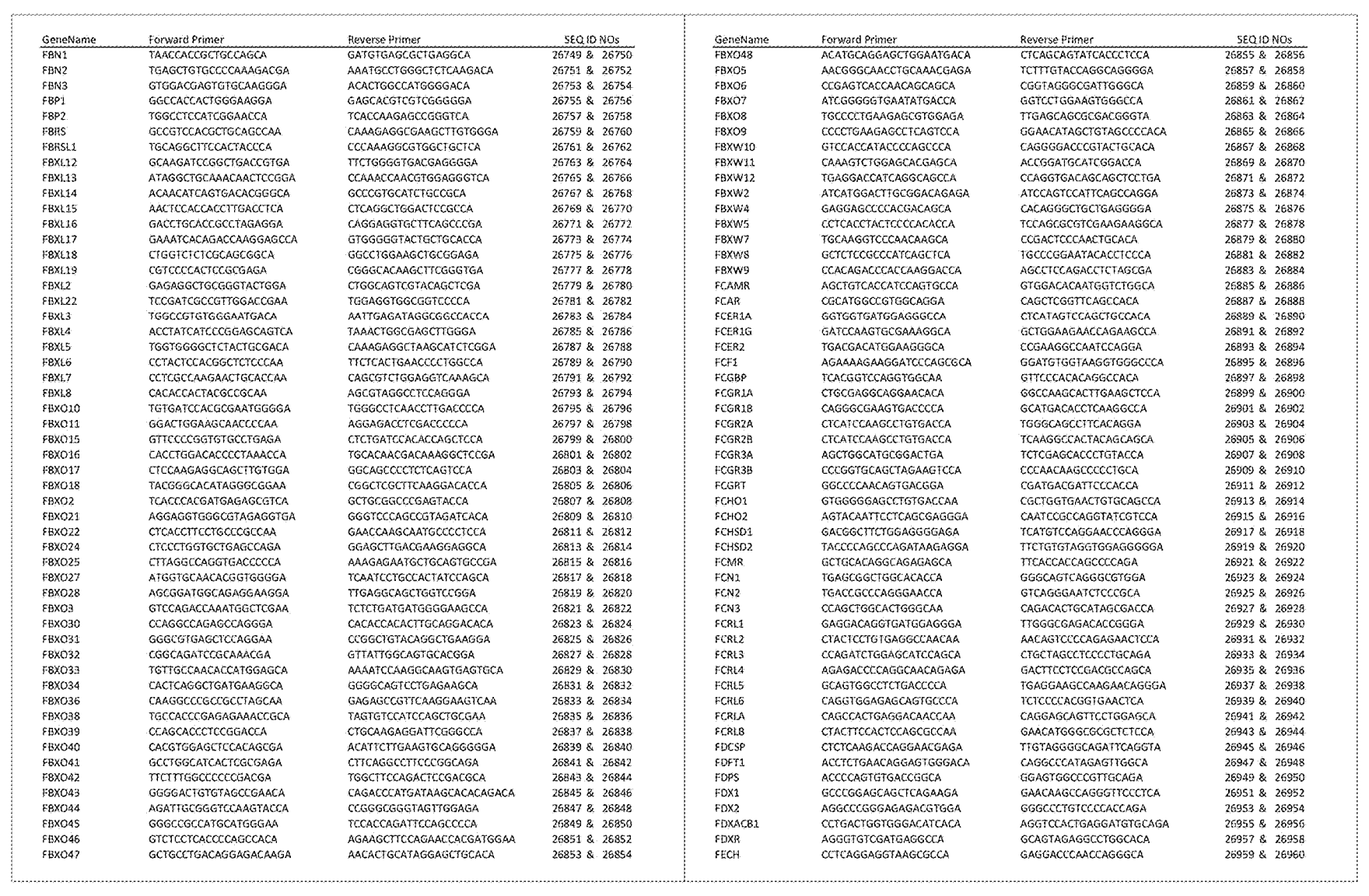
Figure 1:
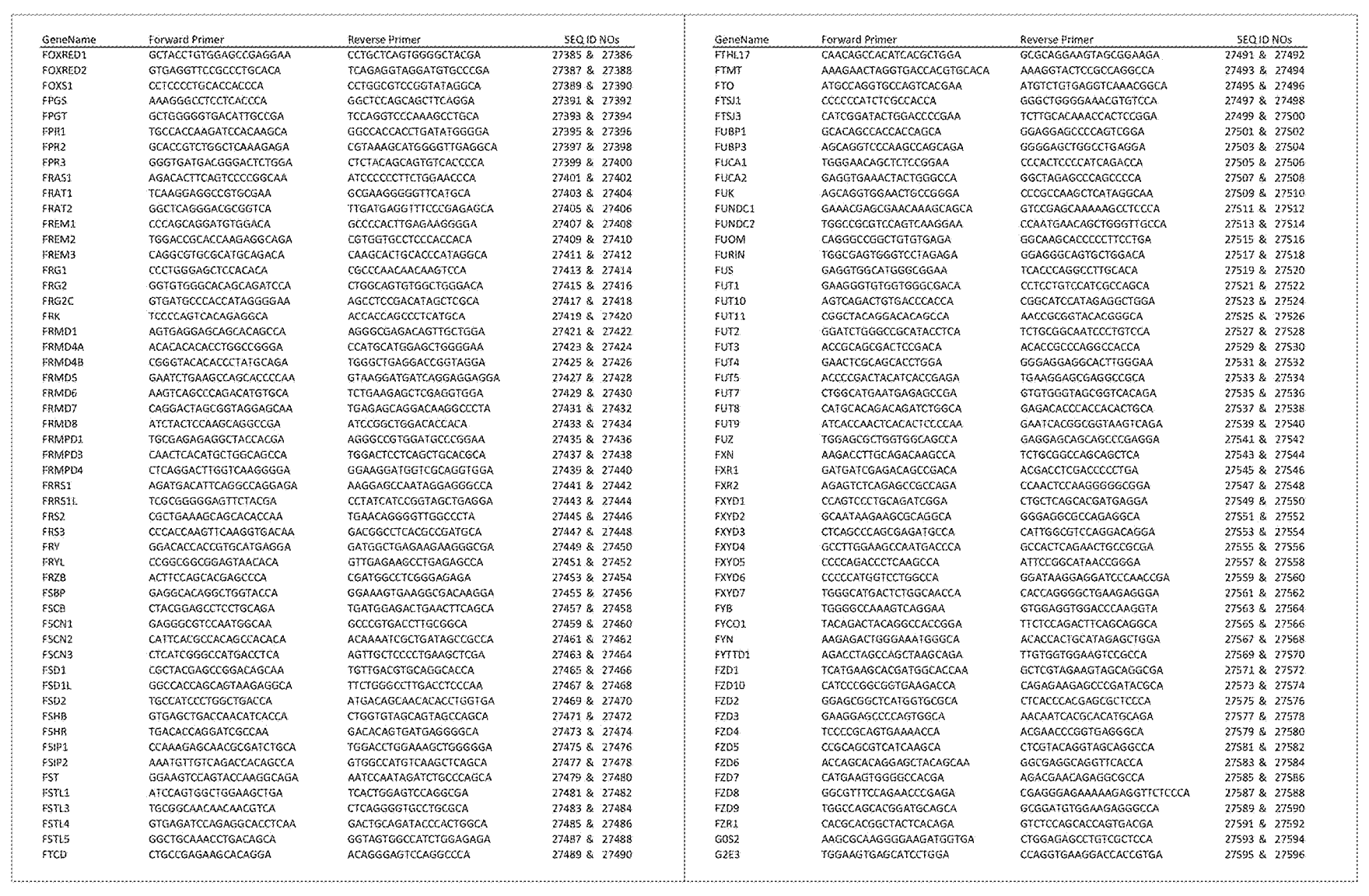
Figure 1:
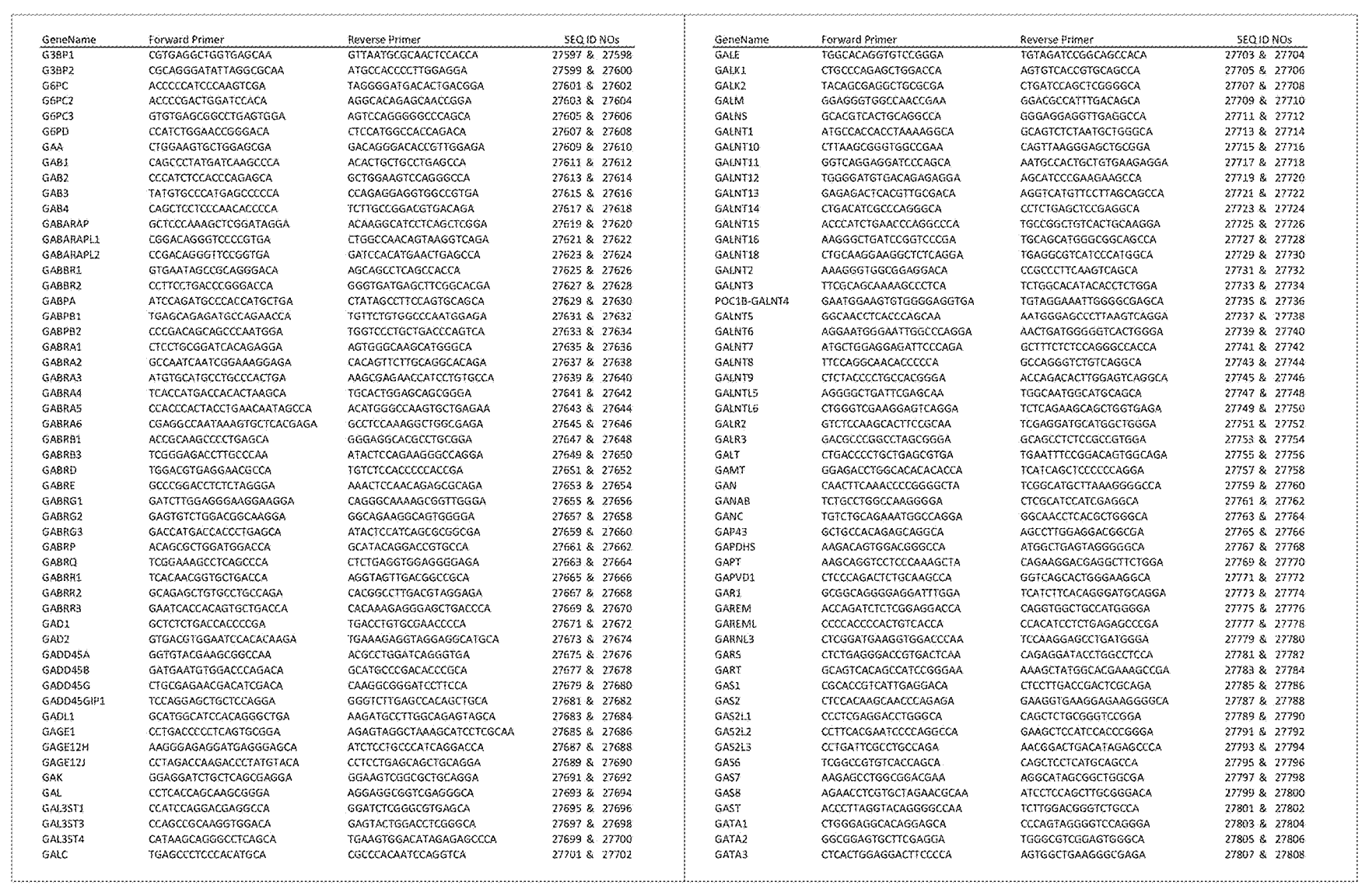
Figure 1:
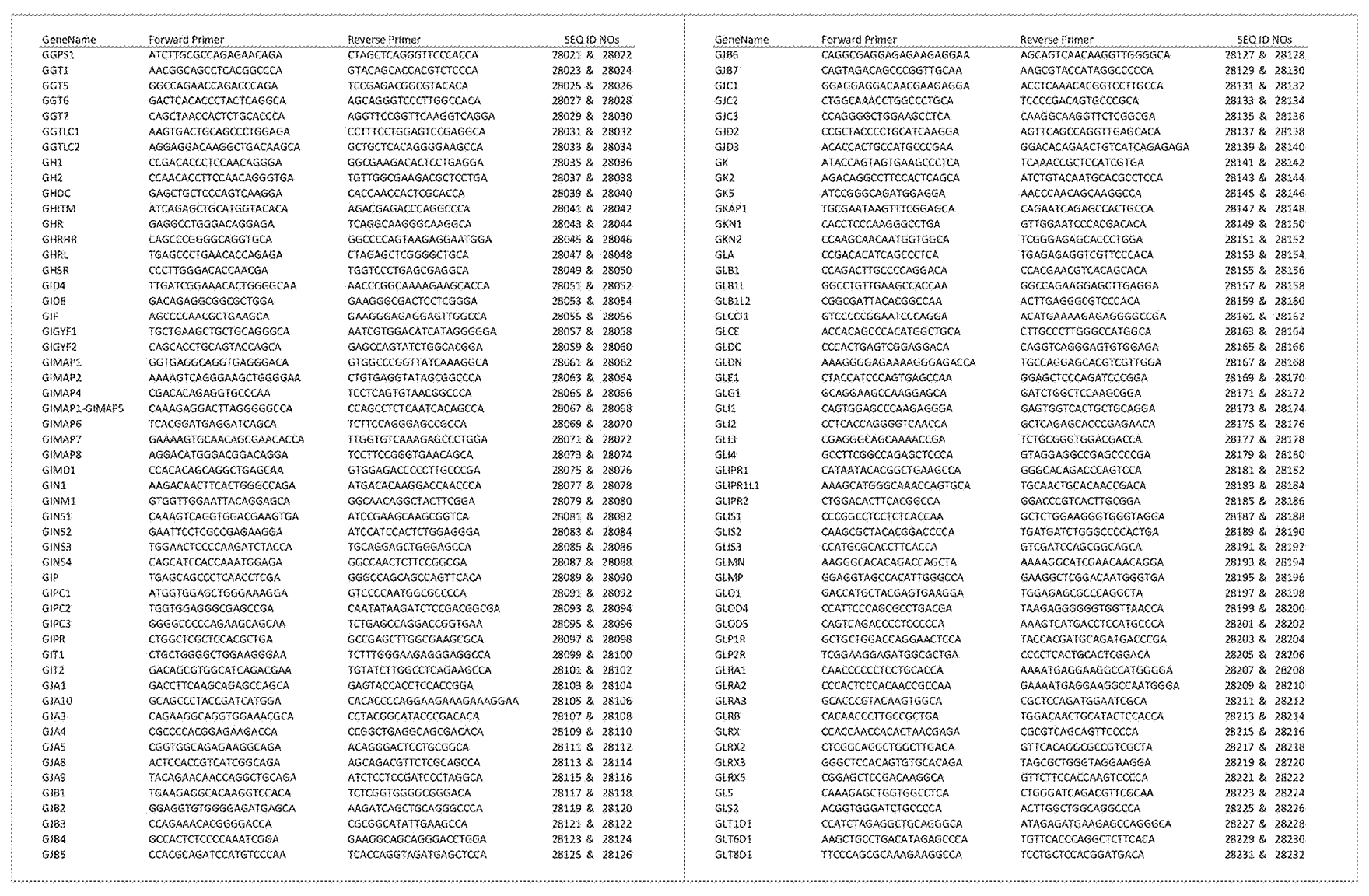
Figure 1:
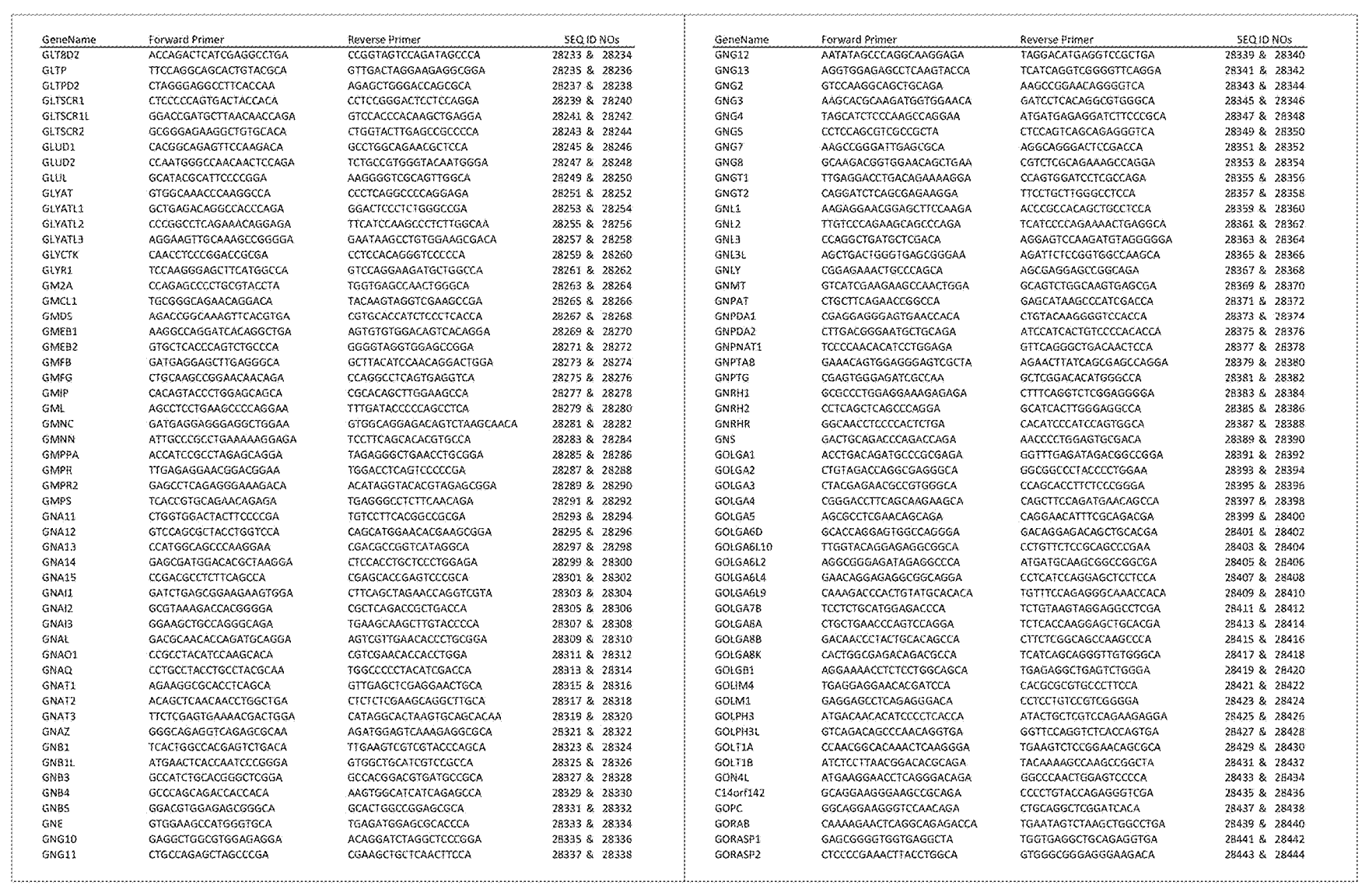
Figure 1:
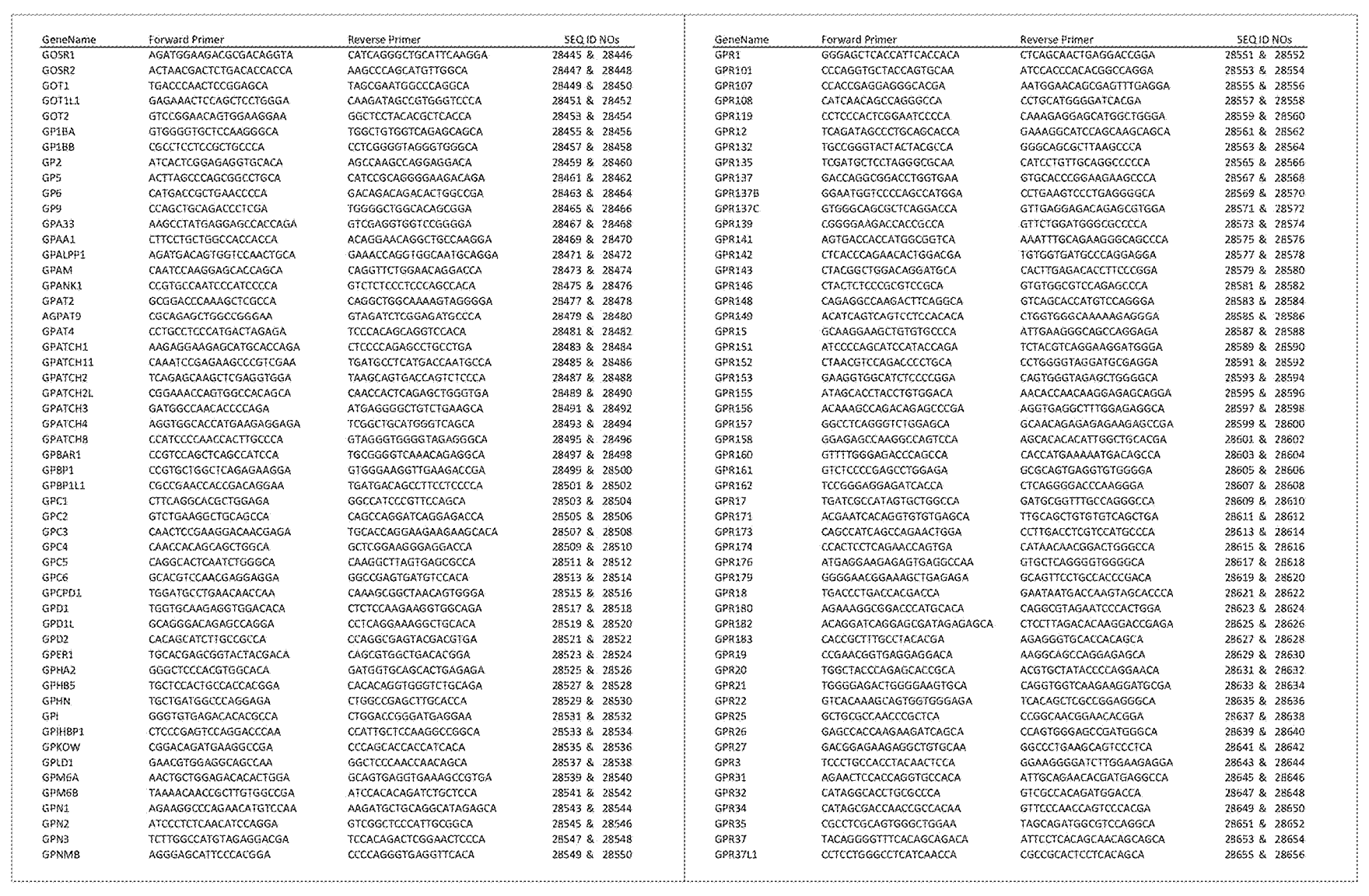
Figure 1:
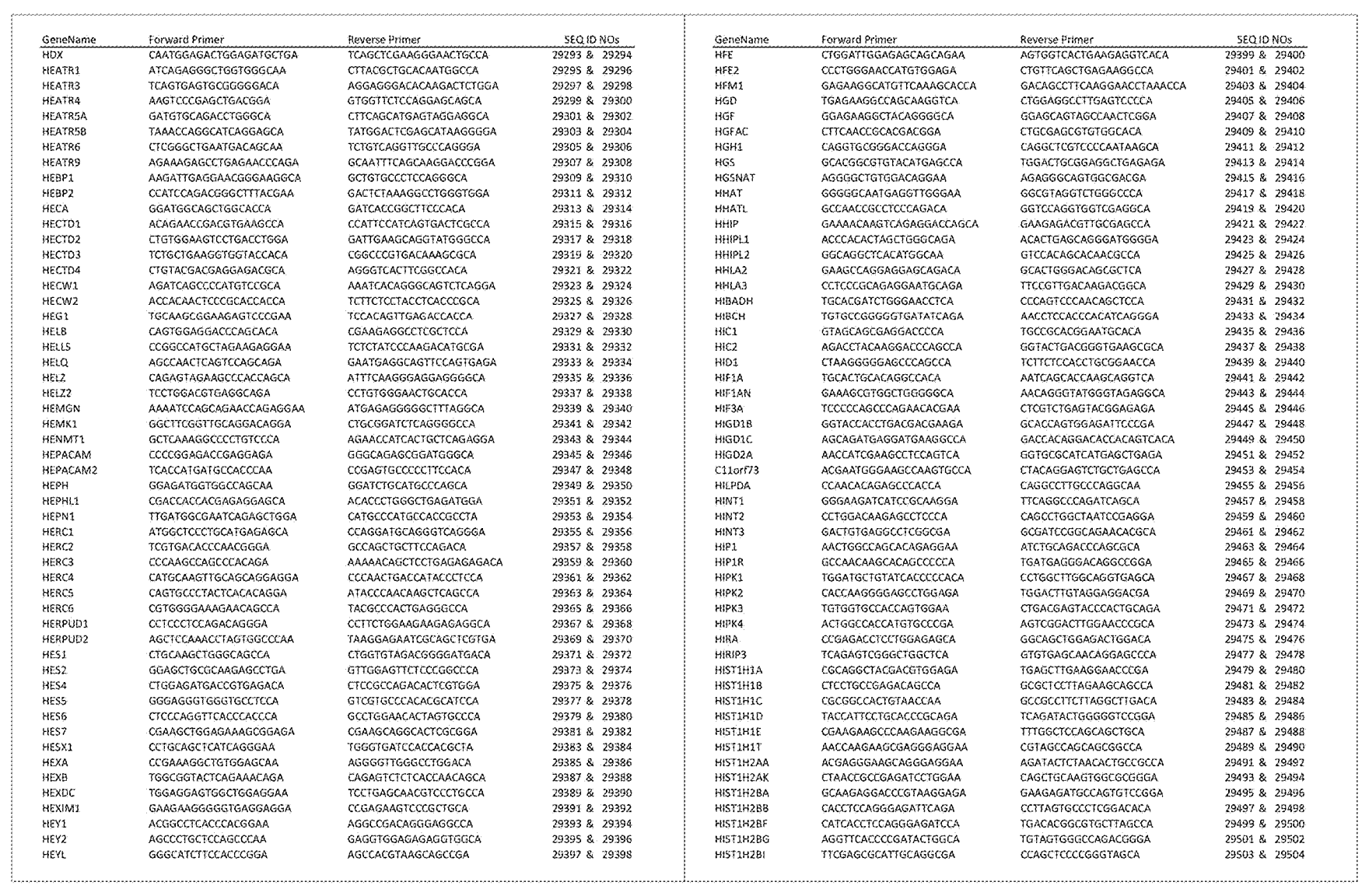
Figure 1:
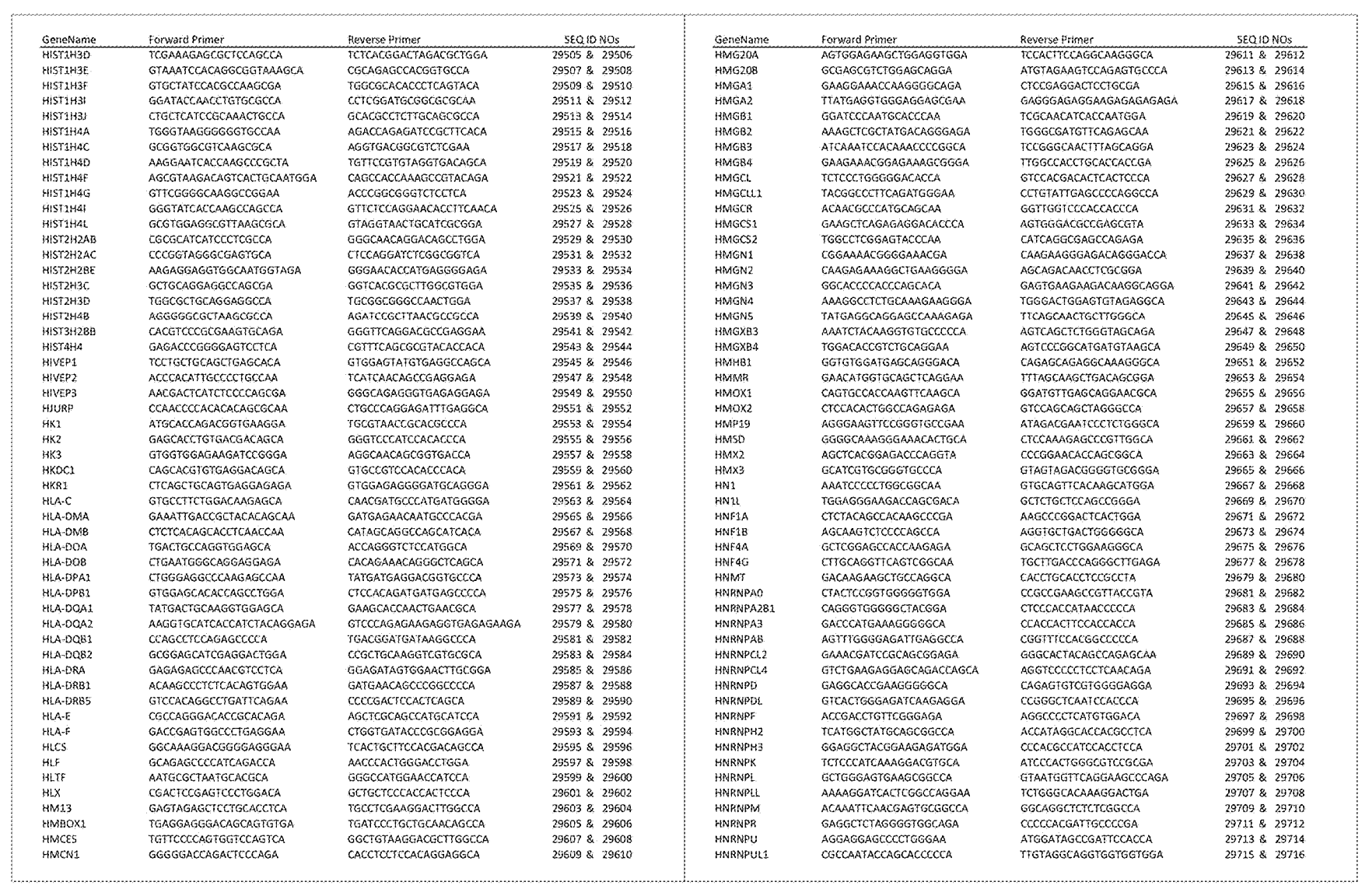
Figure 1:
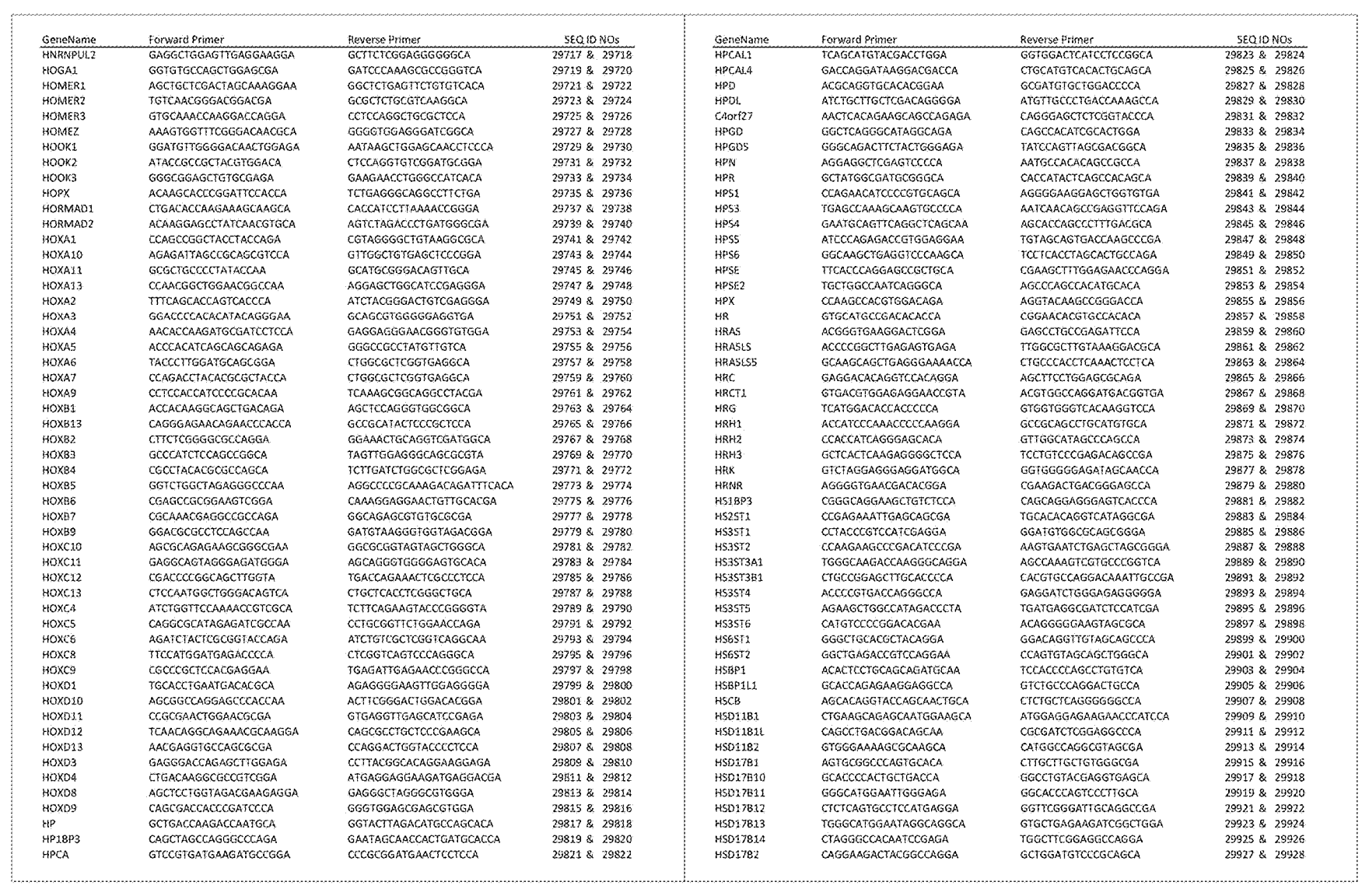
Figure 1:
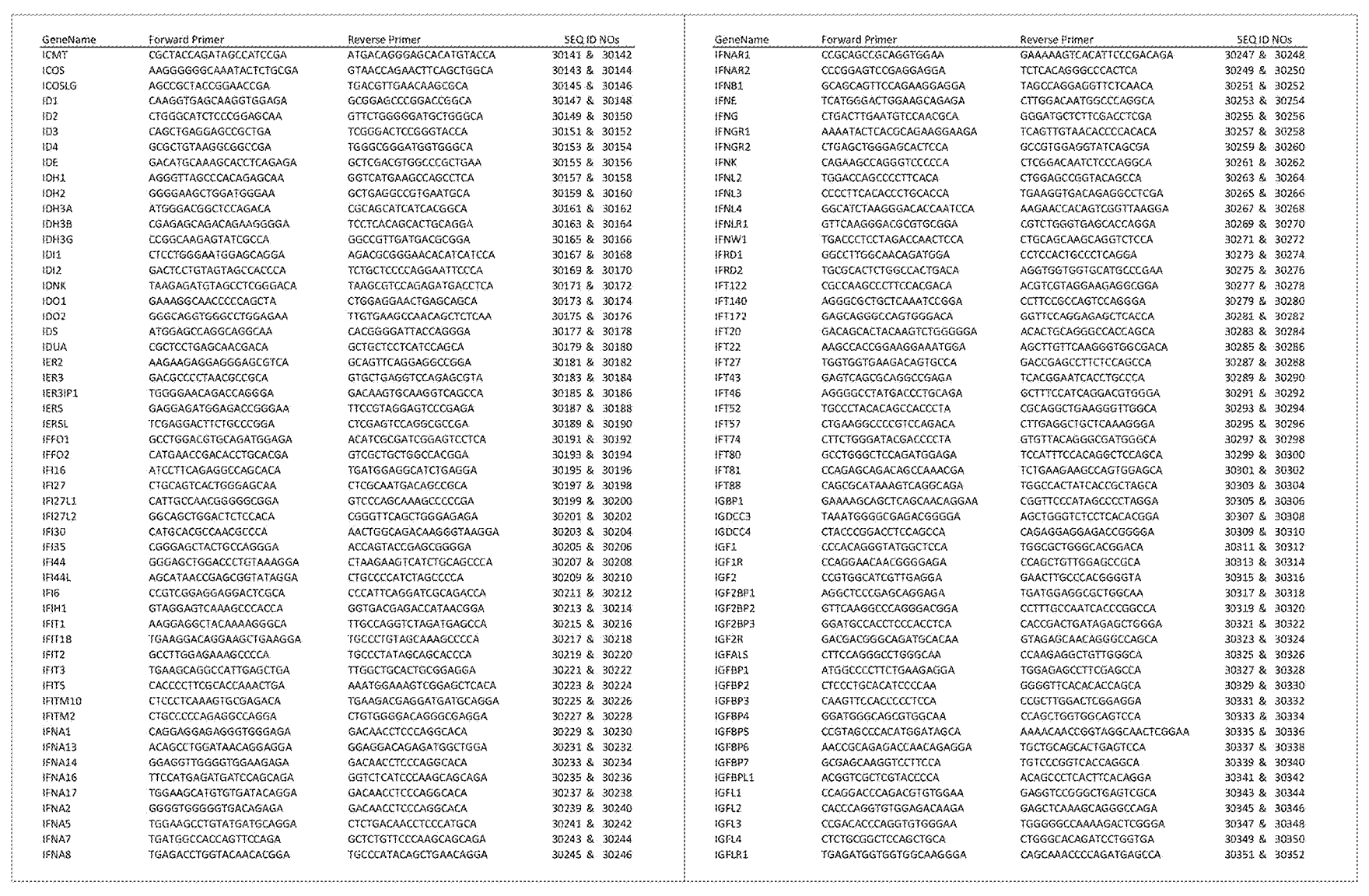
Figure 1:
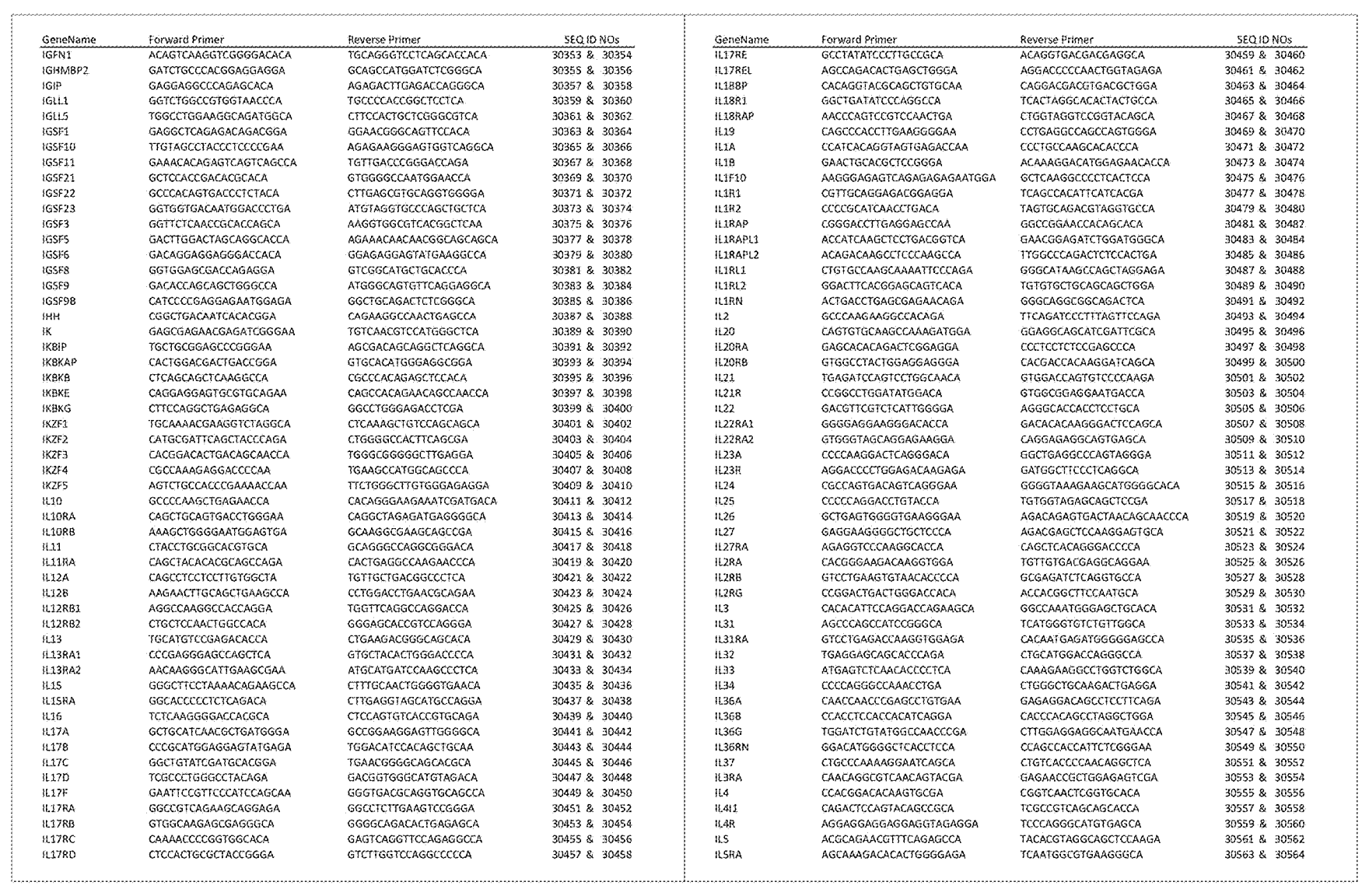
Figure 1:
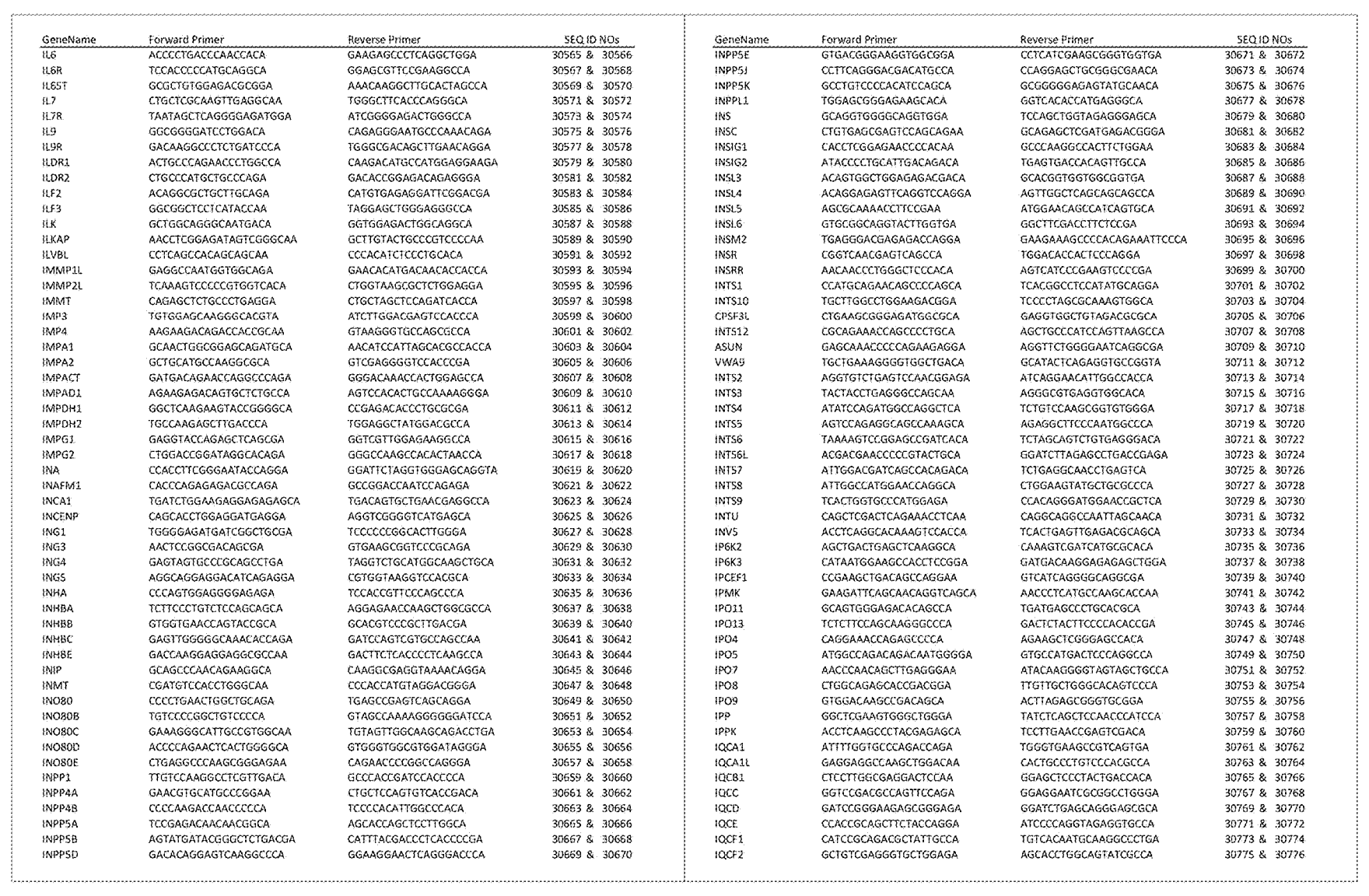
Figure 1:
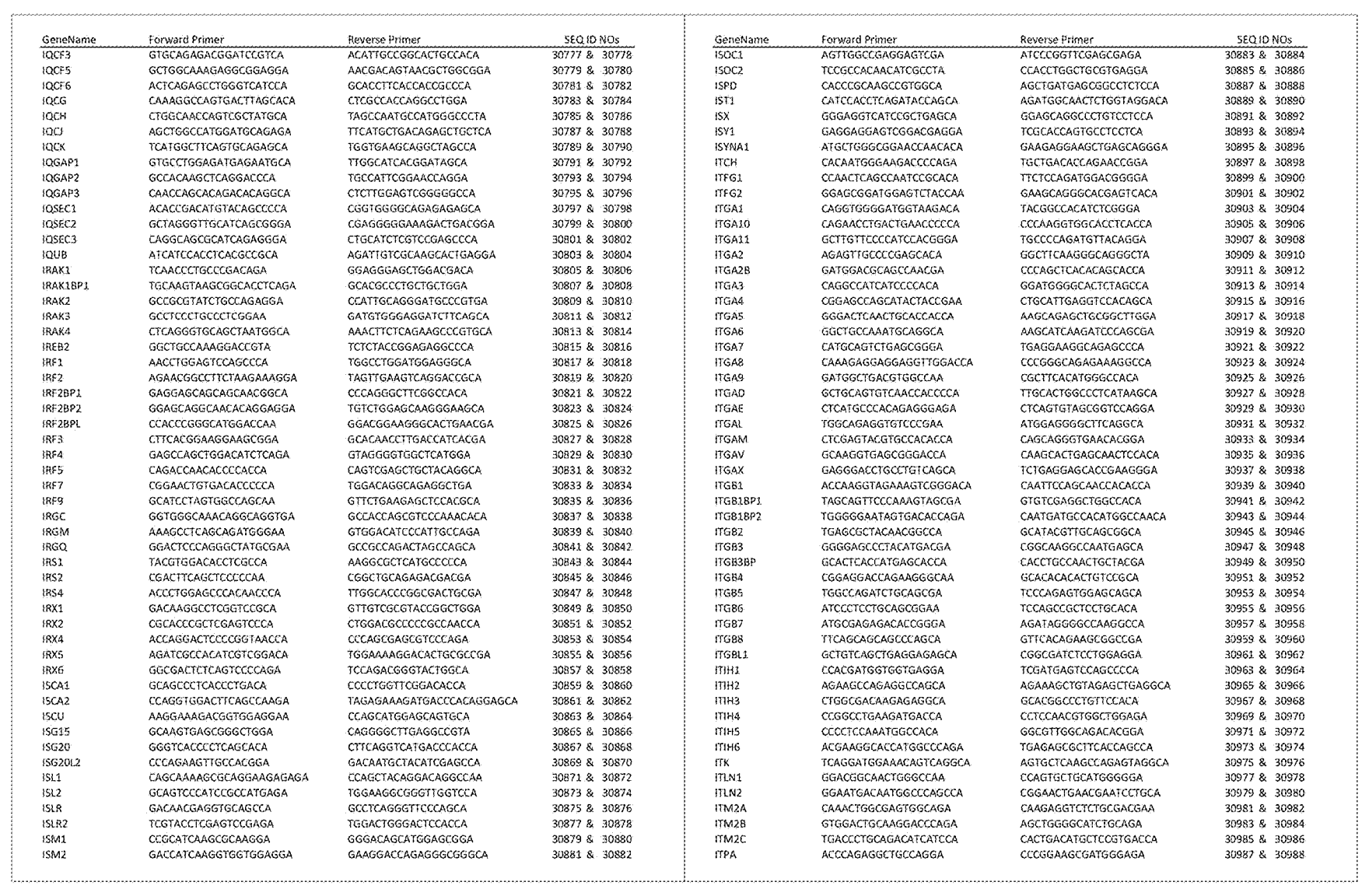
Figure 1:
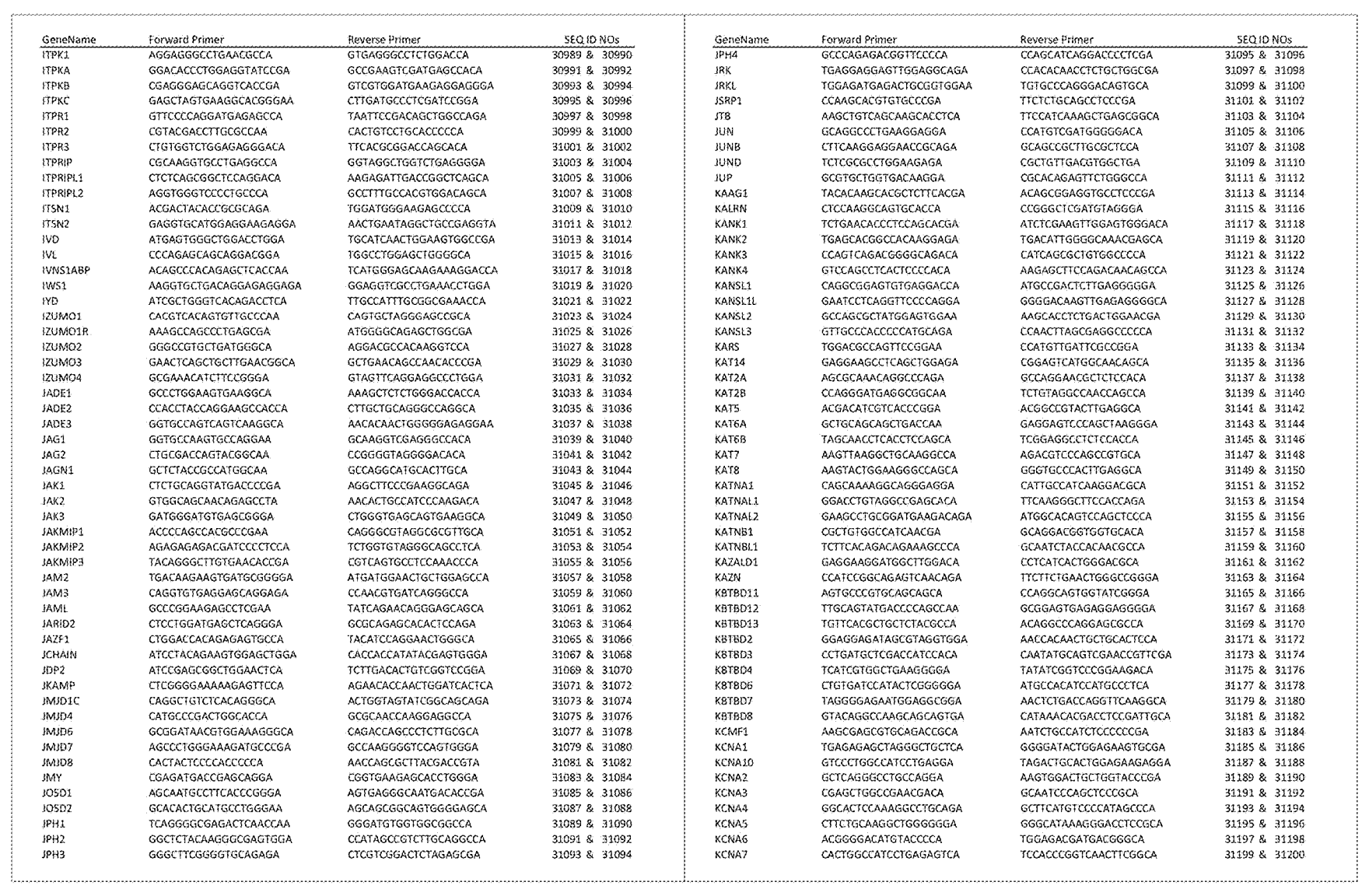
Figure 1:
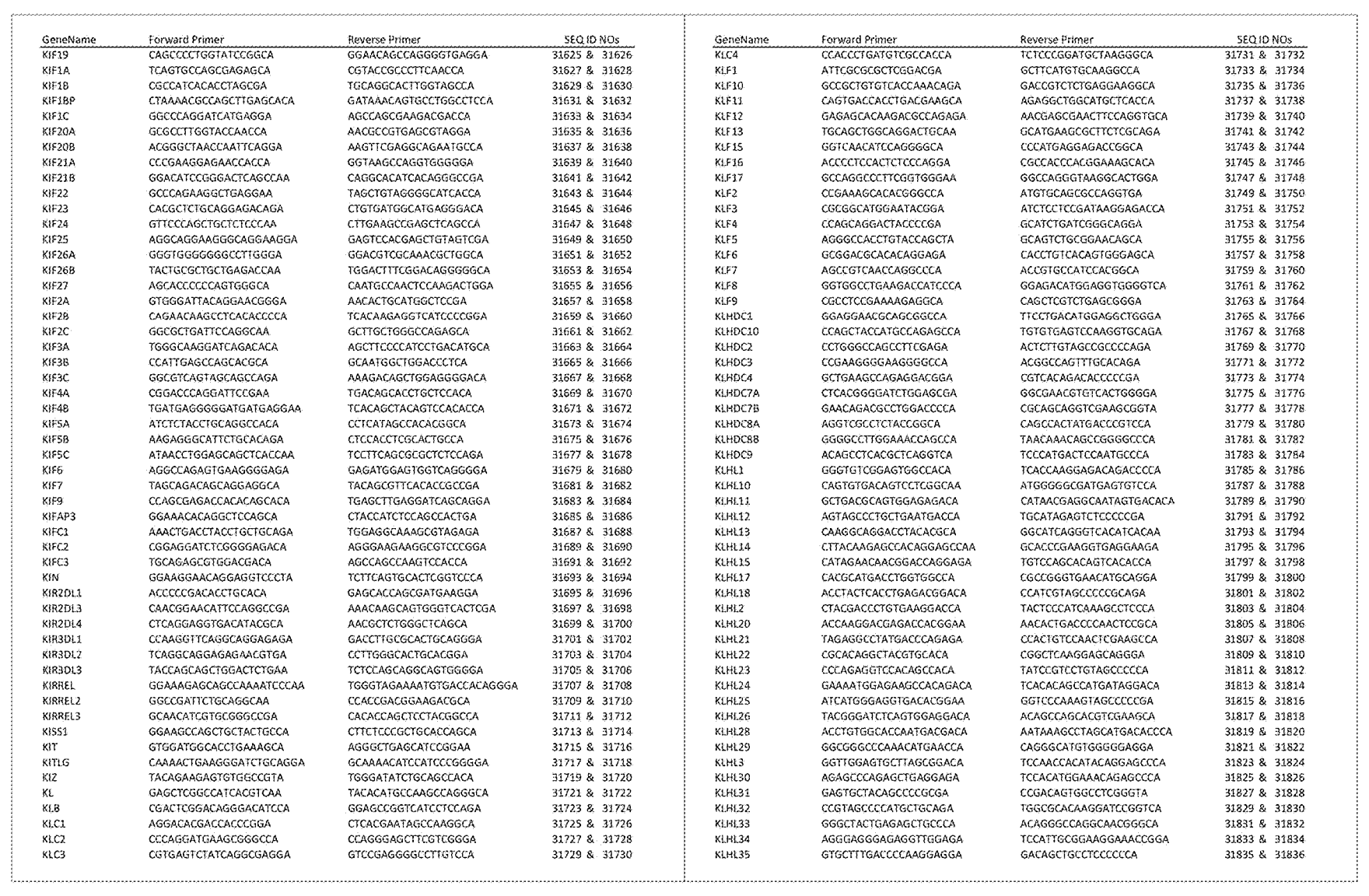
Figure 1:
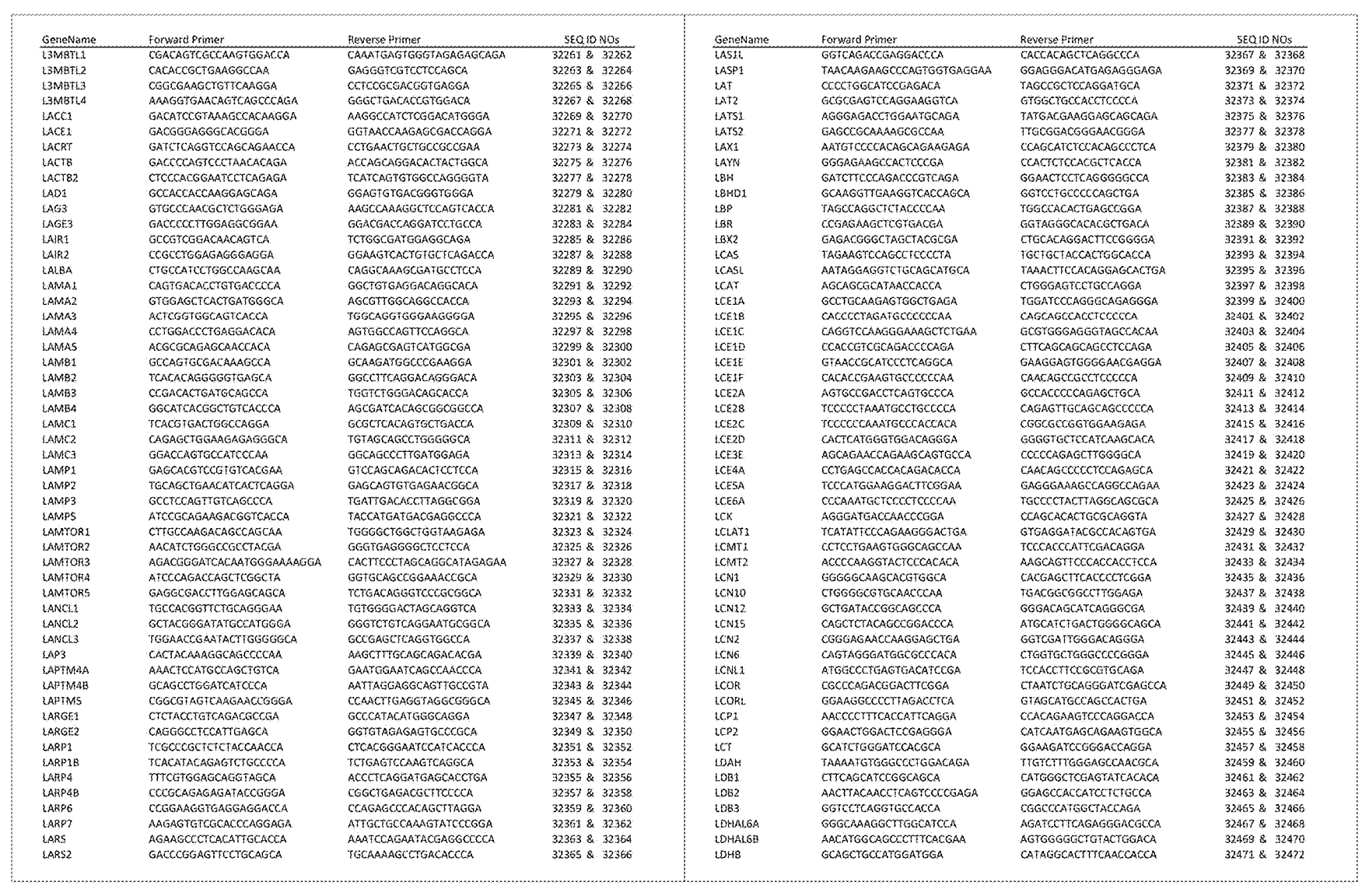
Figure 1:
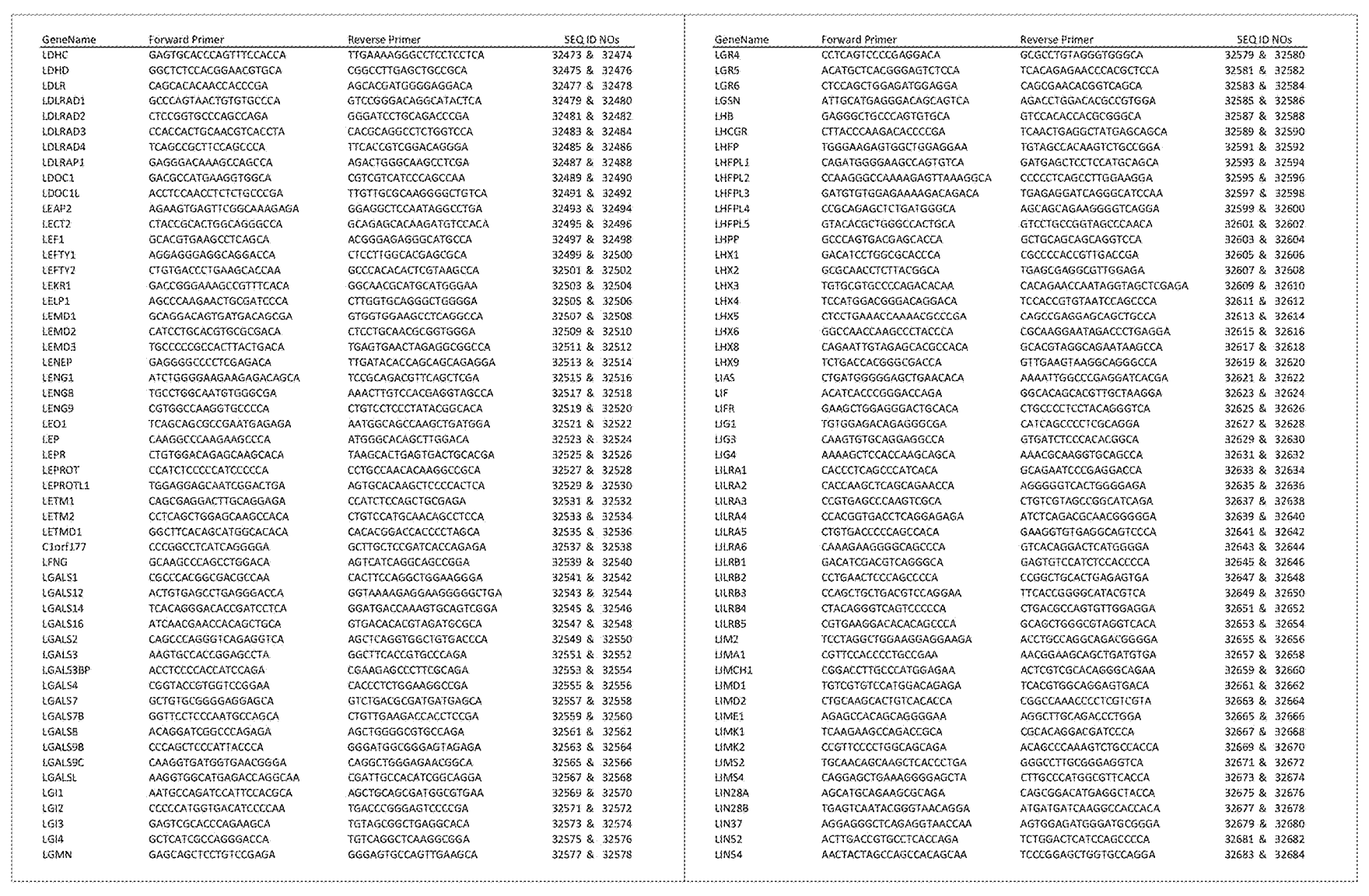
Figure 1:
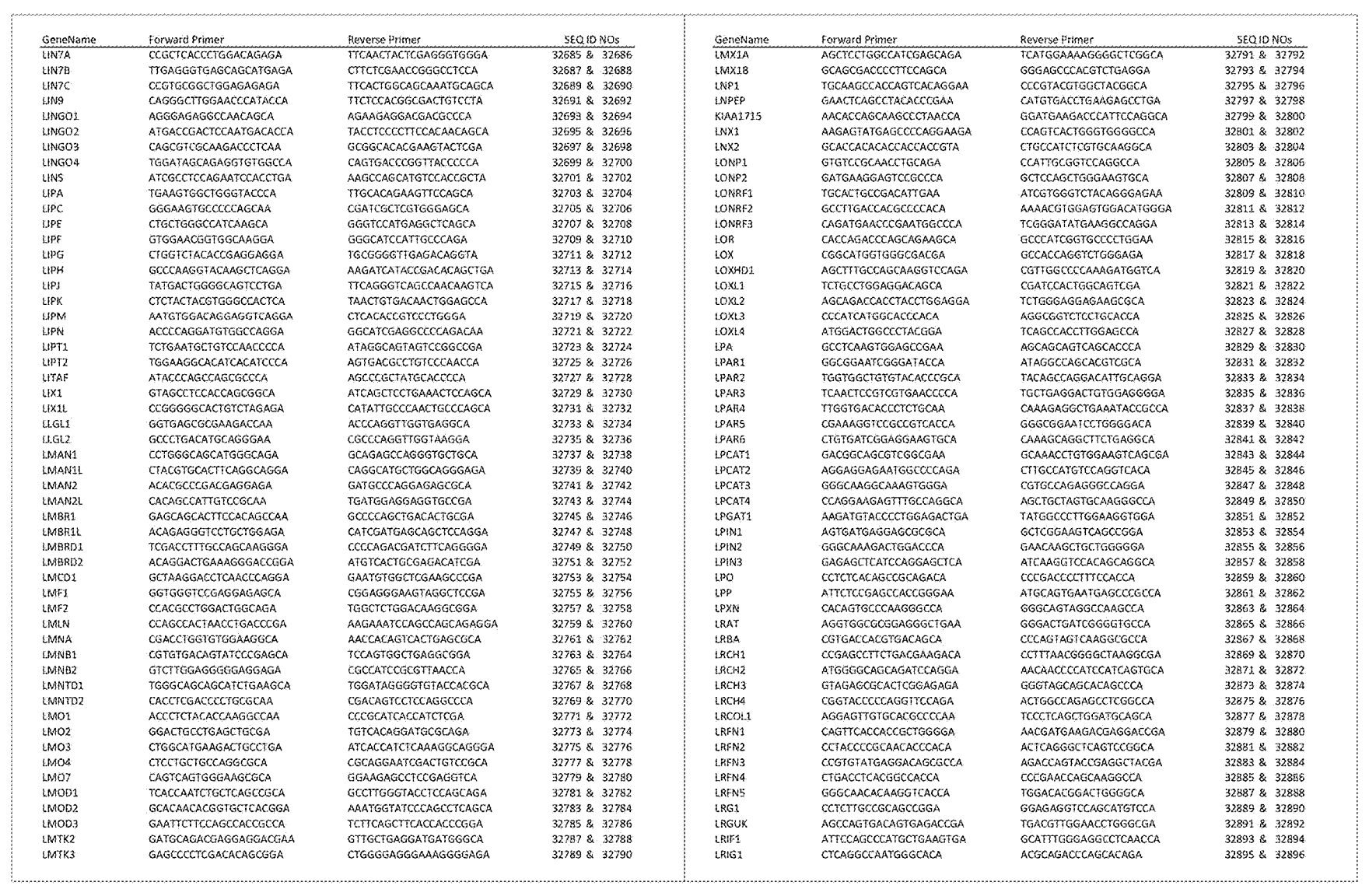
Figure 1:
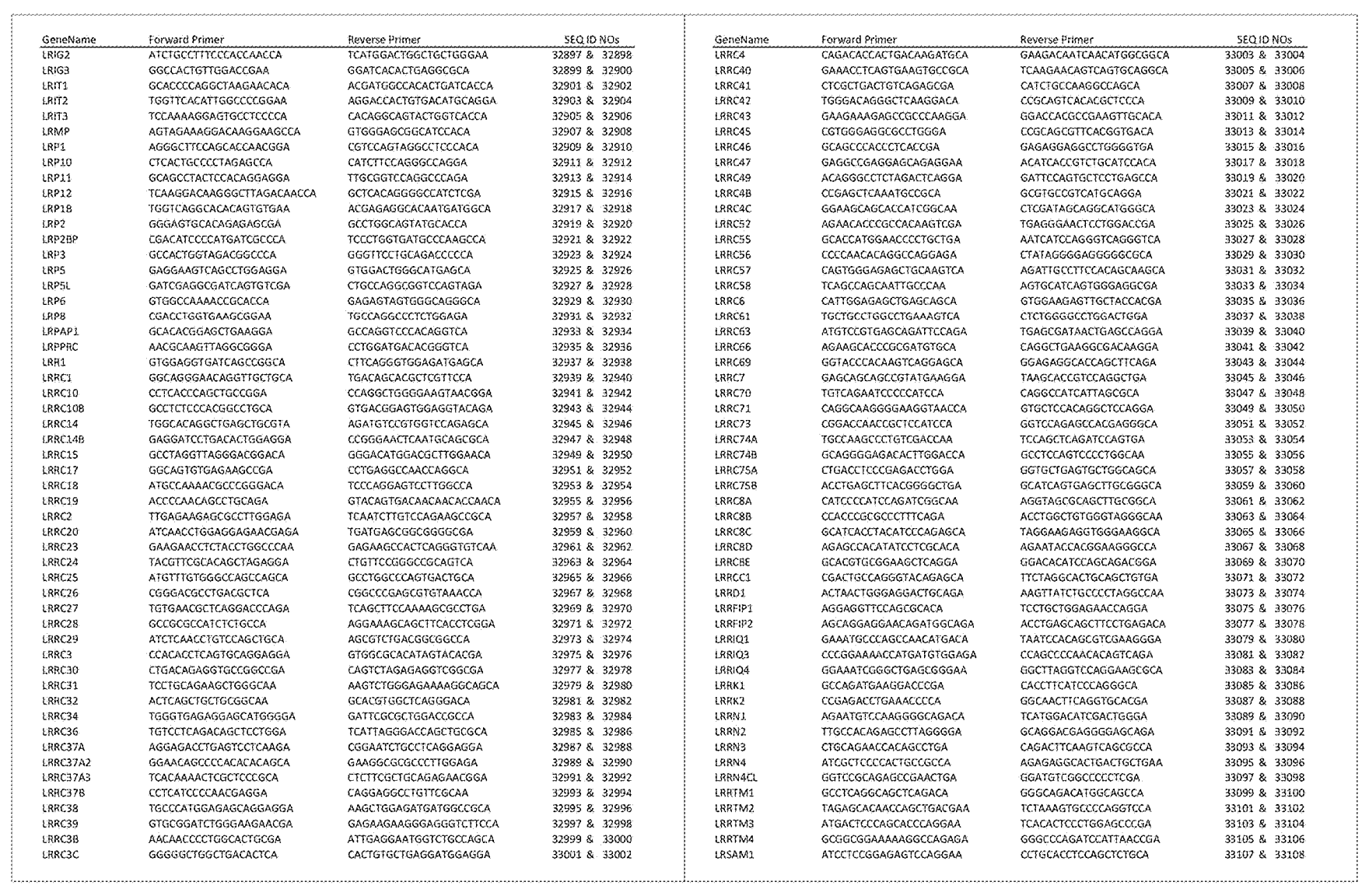
Figure 1:
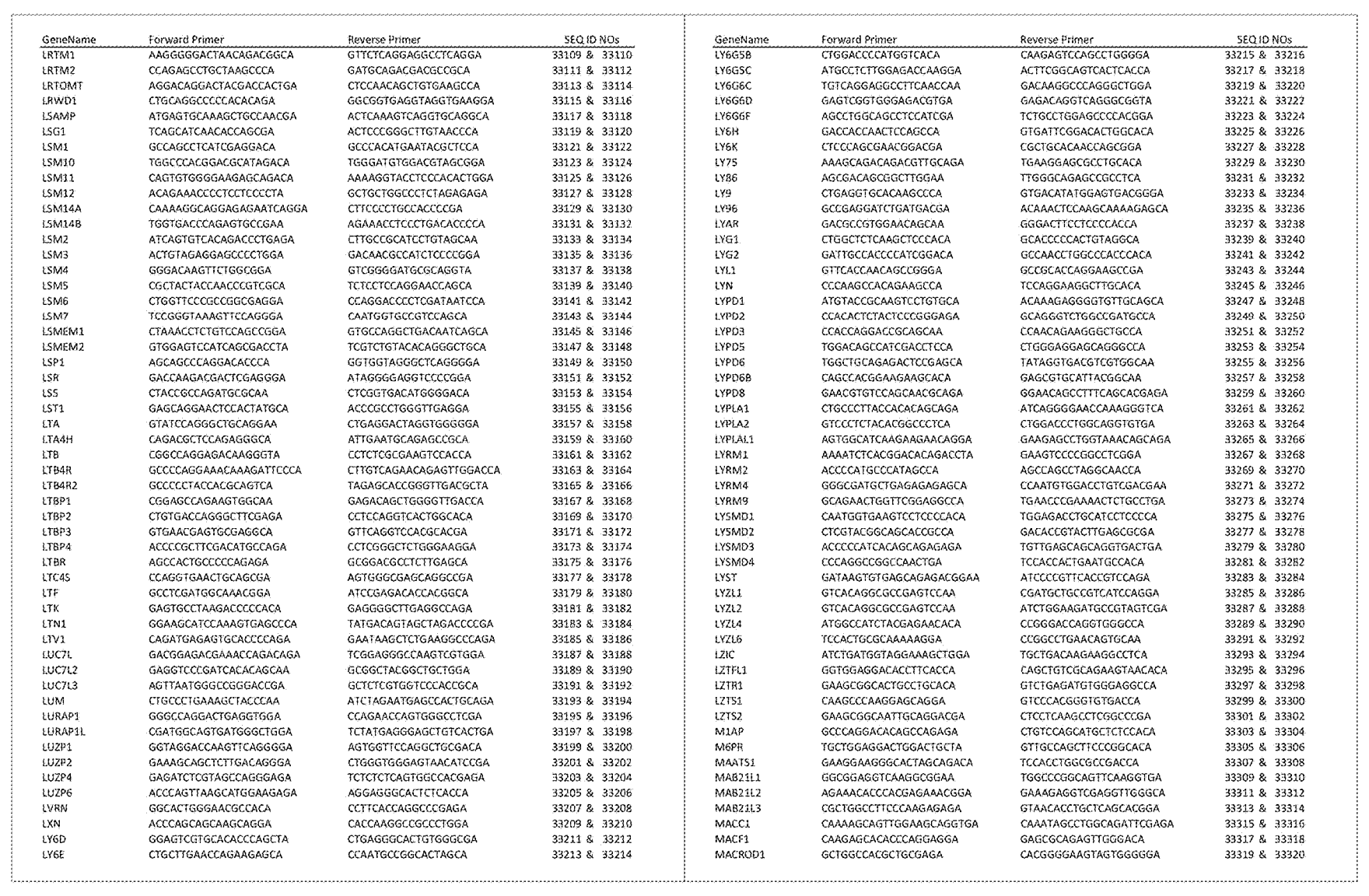
Figure 1:
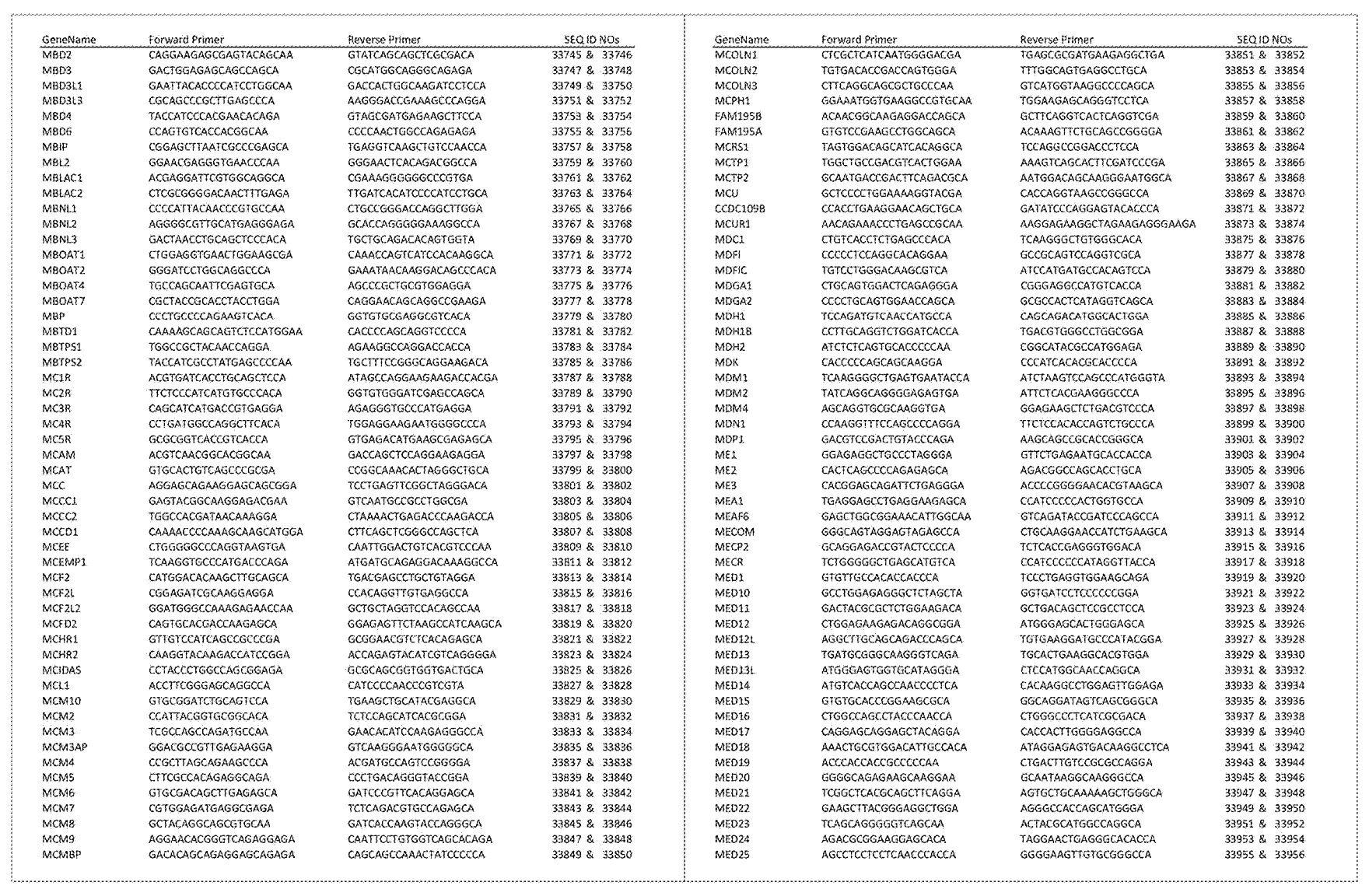
Figure 1:
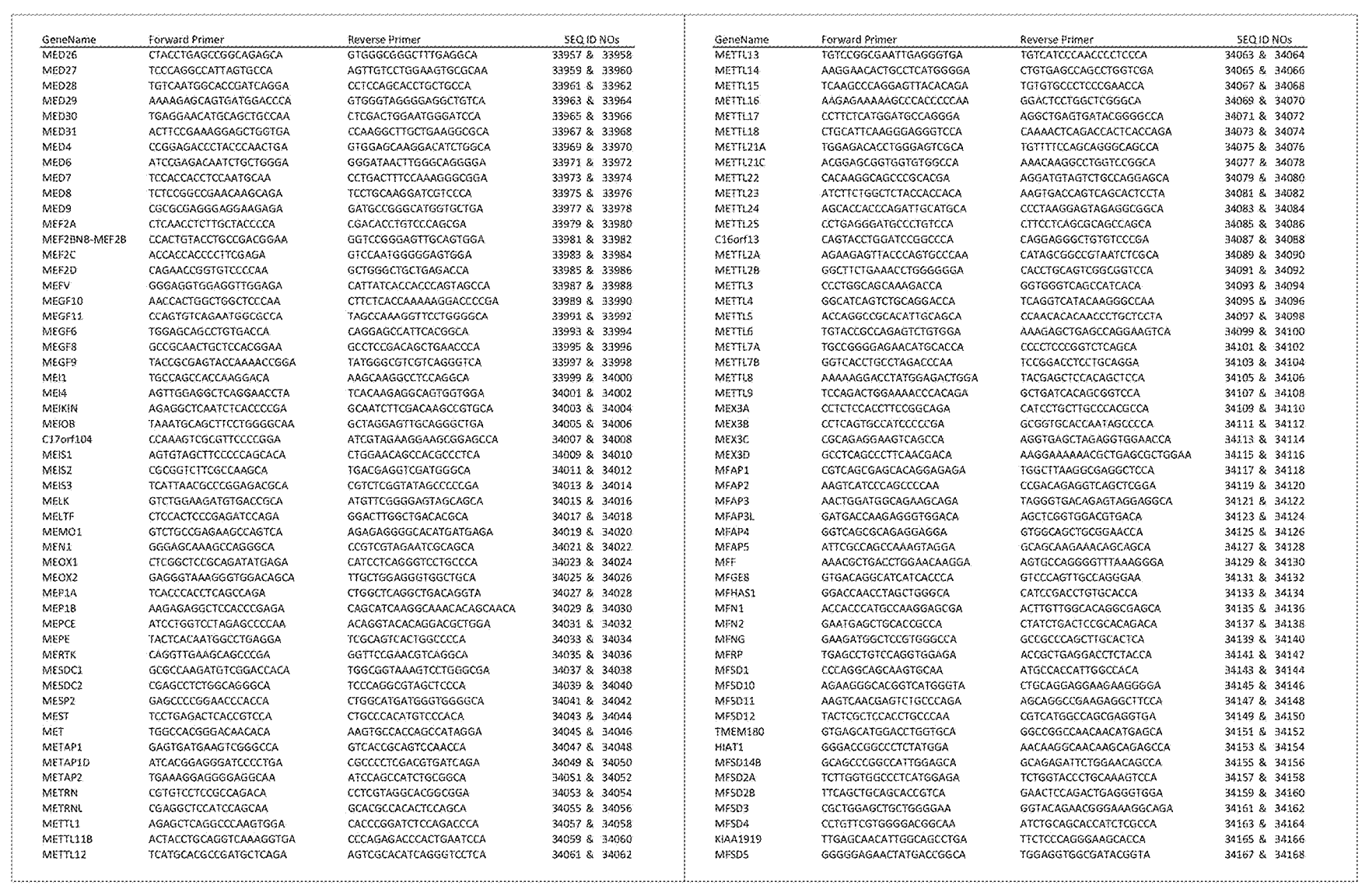
Figure 1:
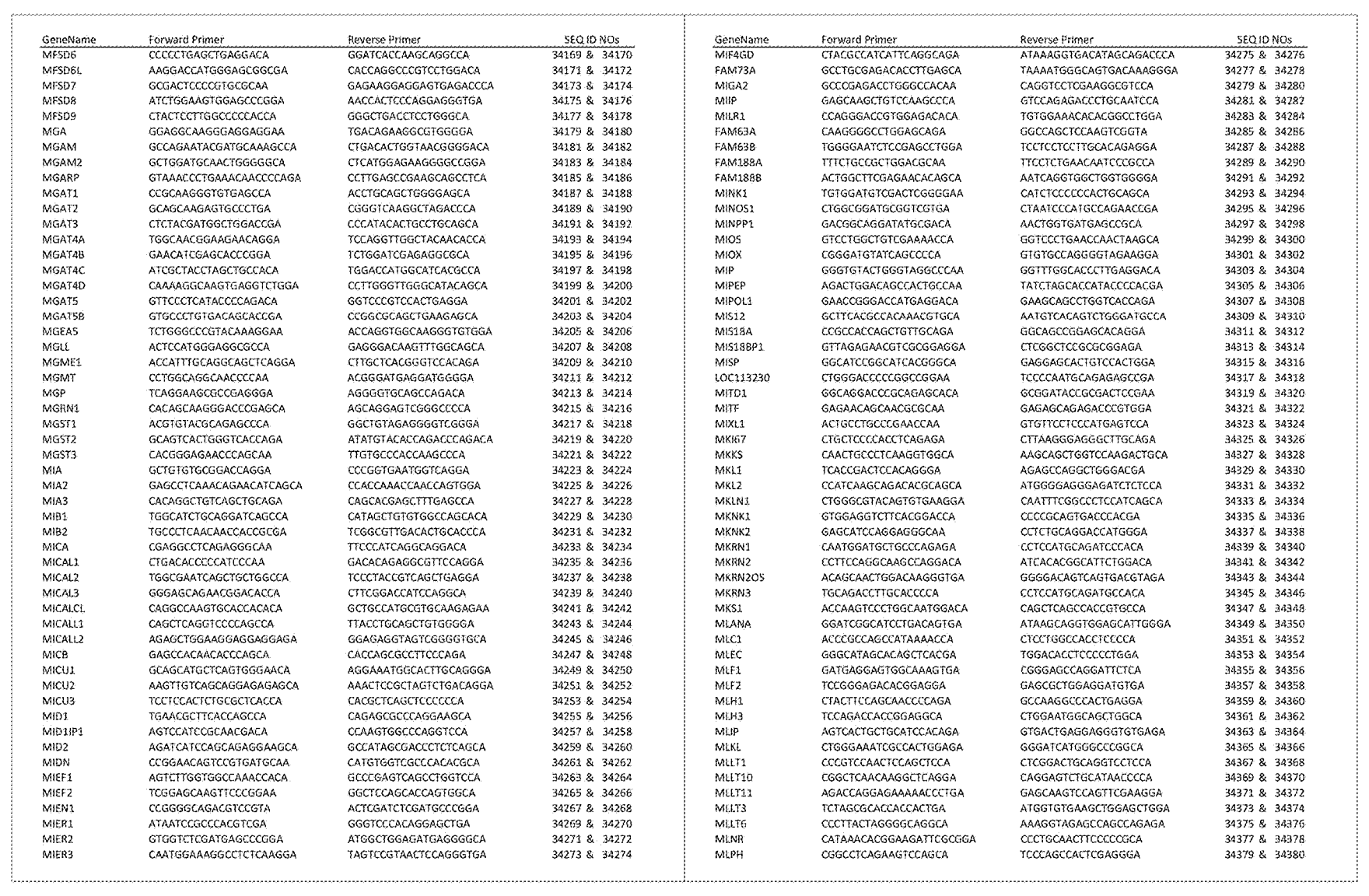
Figure 1:
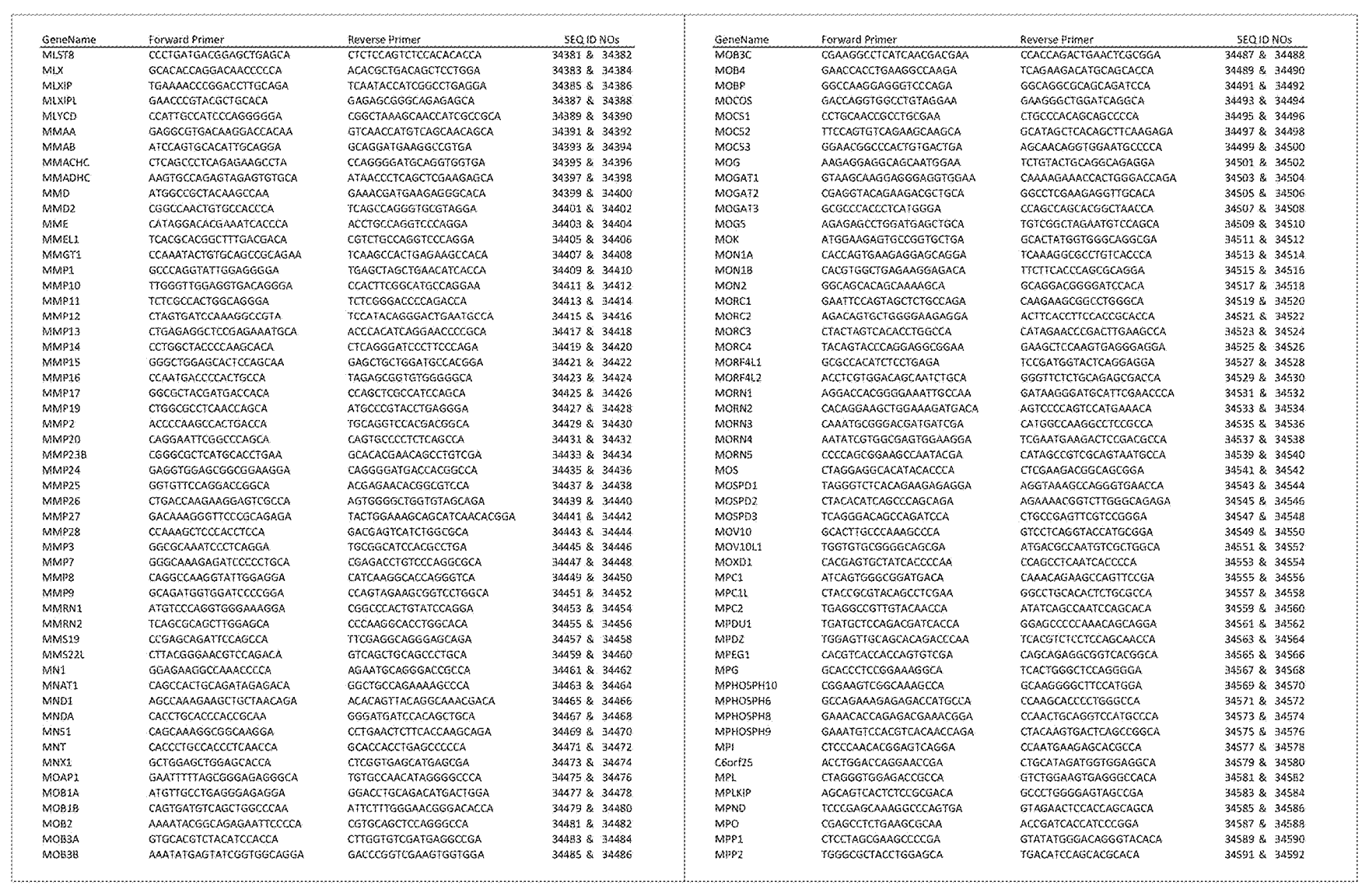
Figure 1:
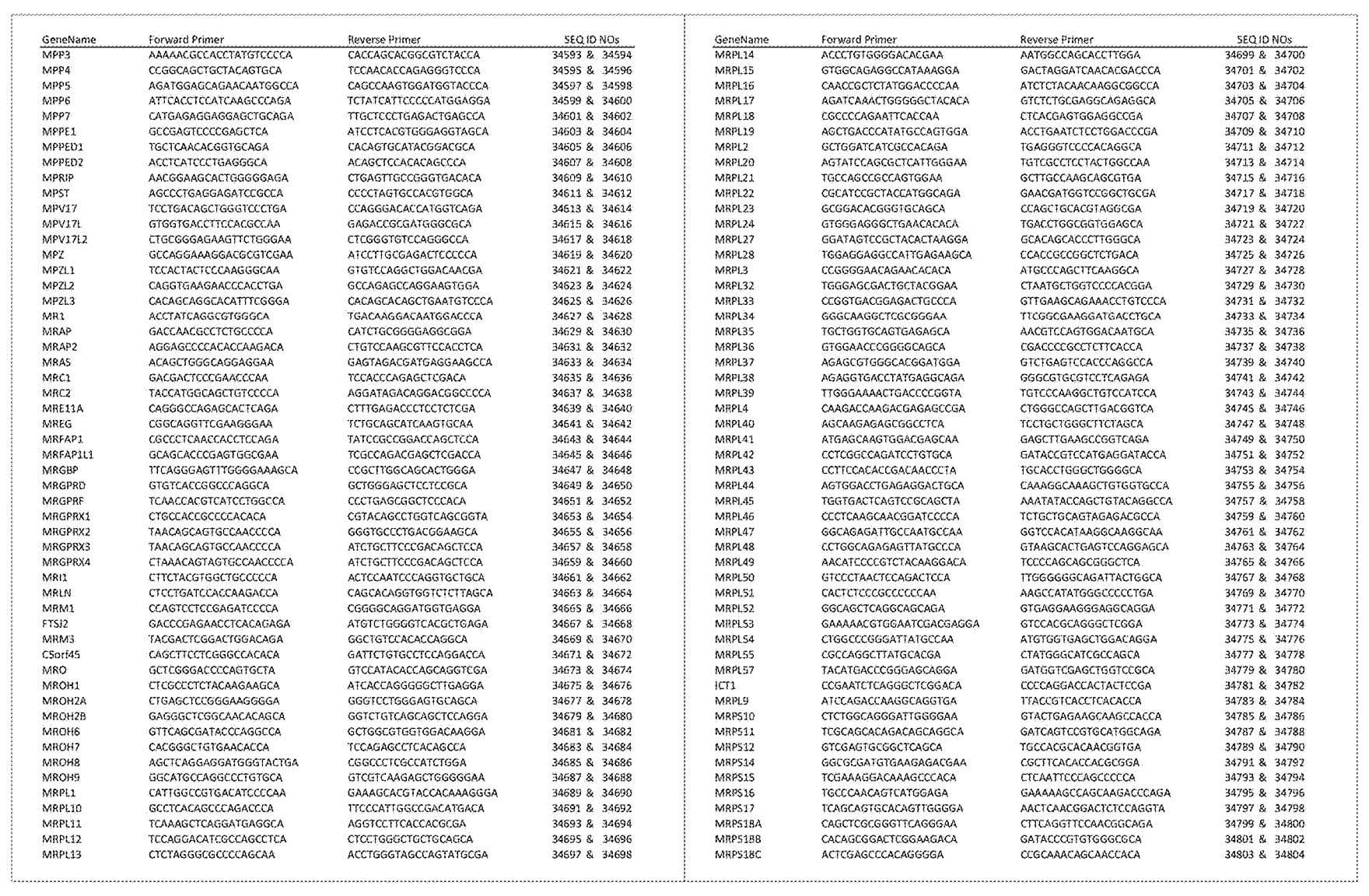
Figure 1:
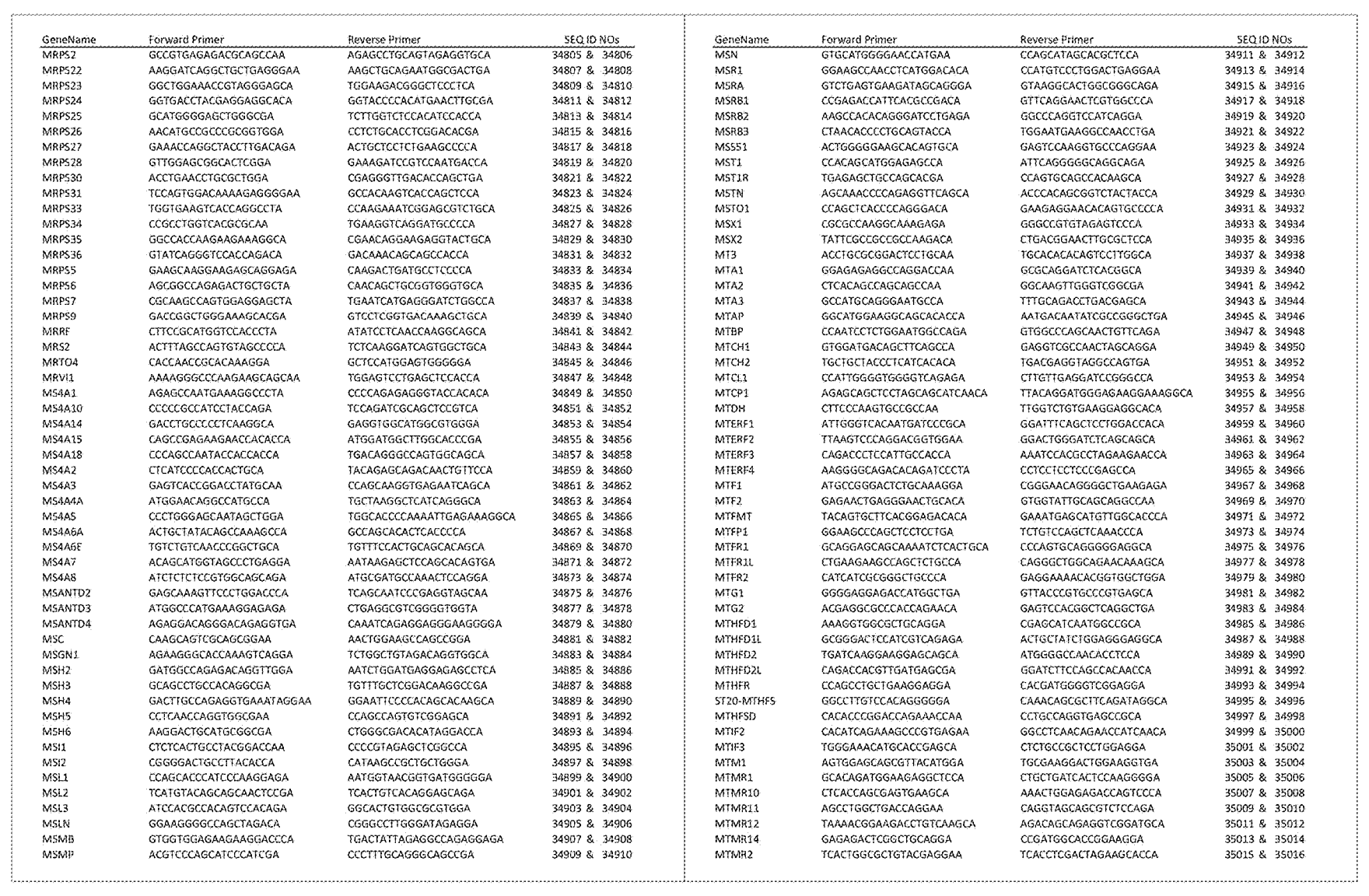
Figure 1:
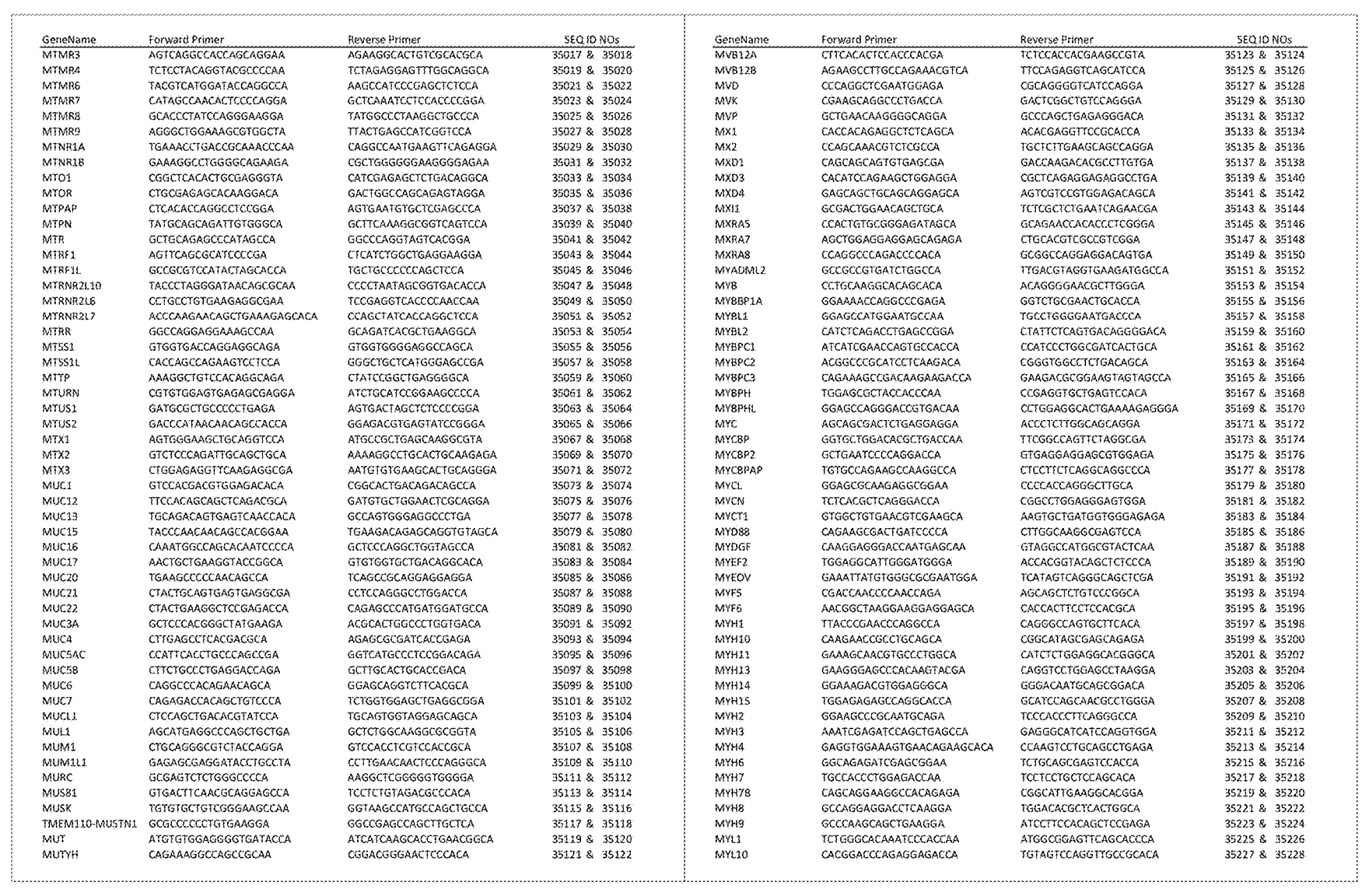
Figure 1:
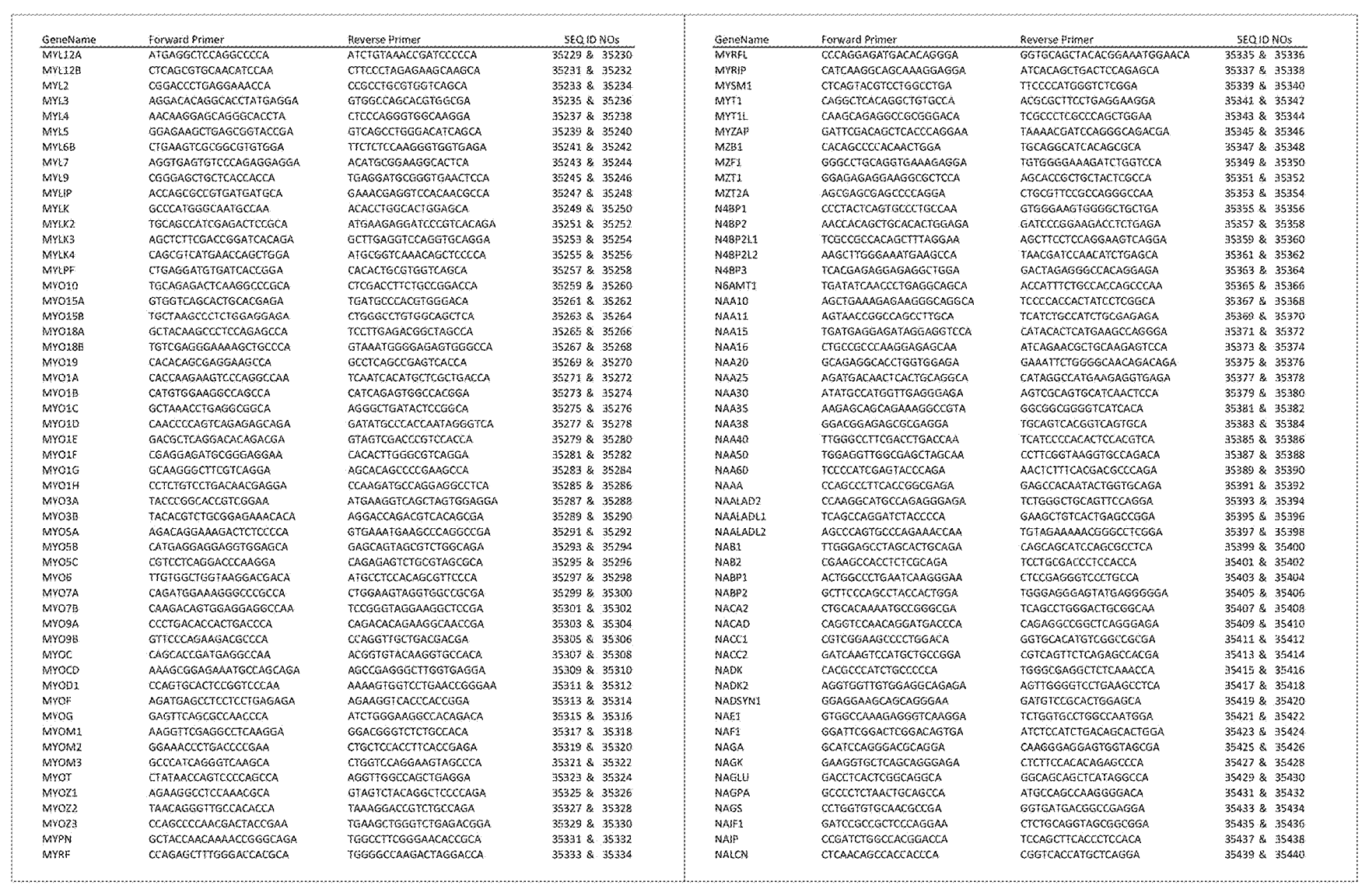
Figure 1:
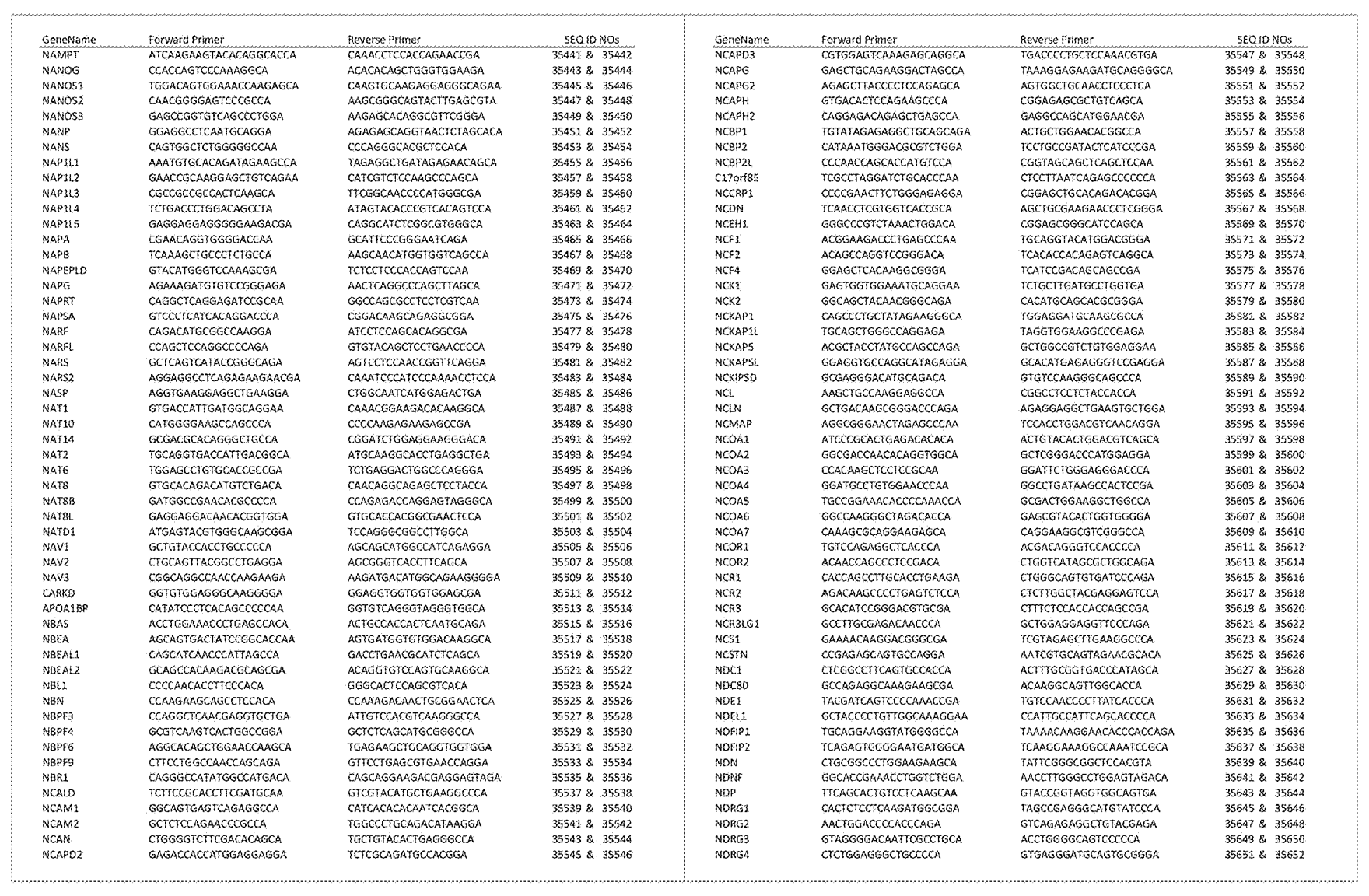
Figure 1:
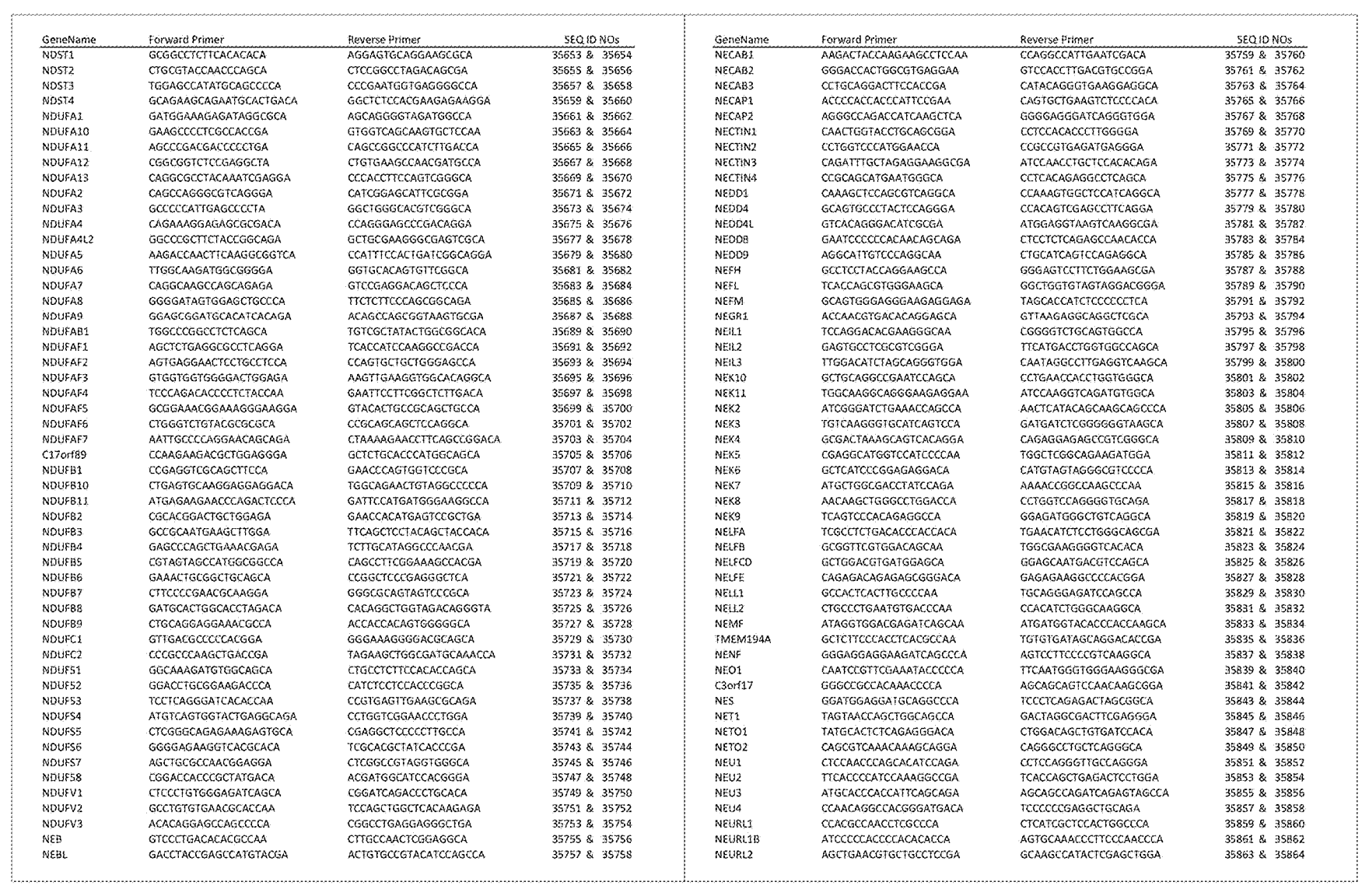
Figure 1:
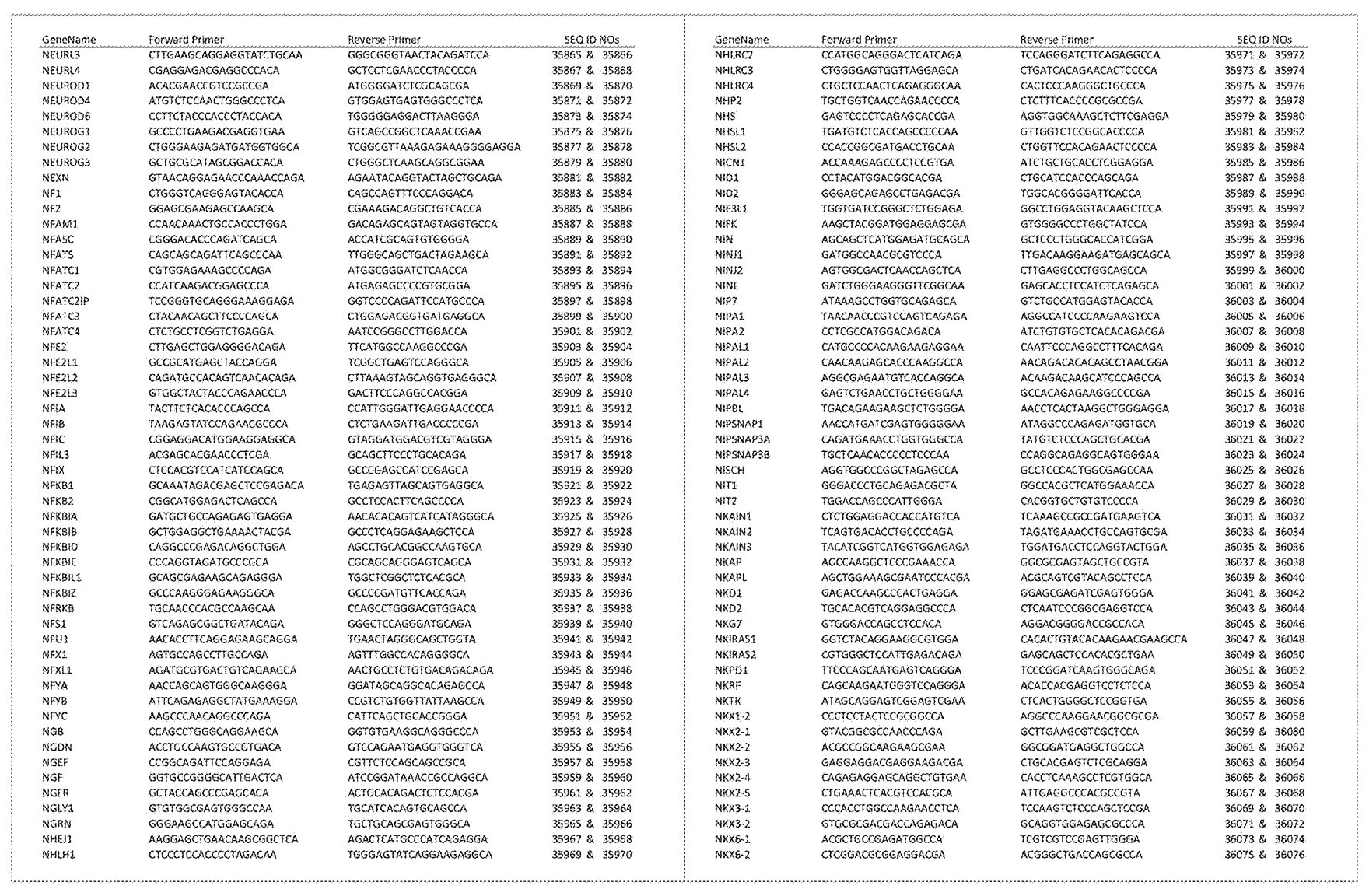
Figure 1:
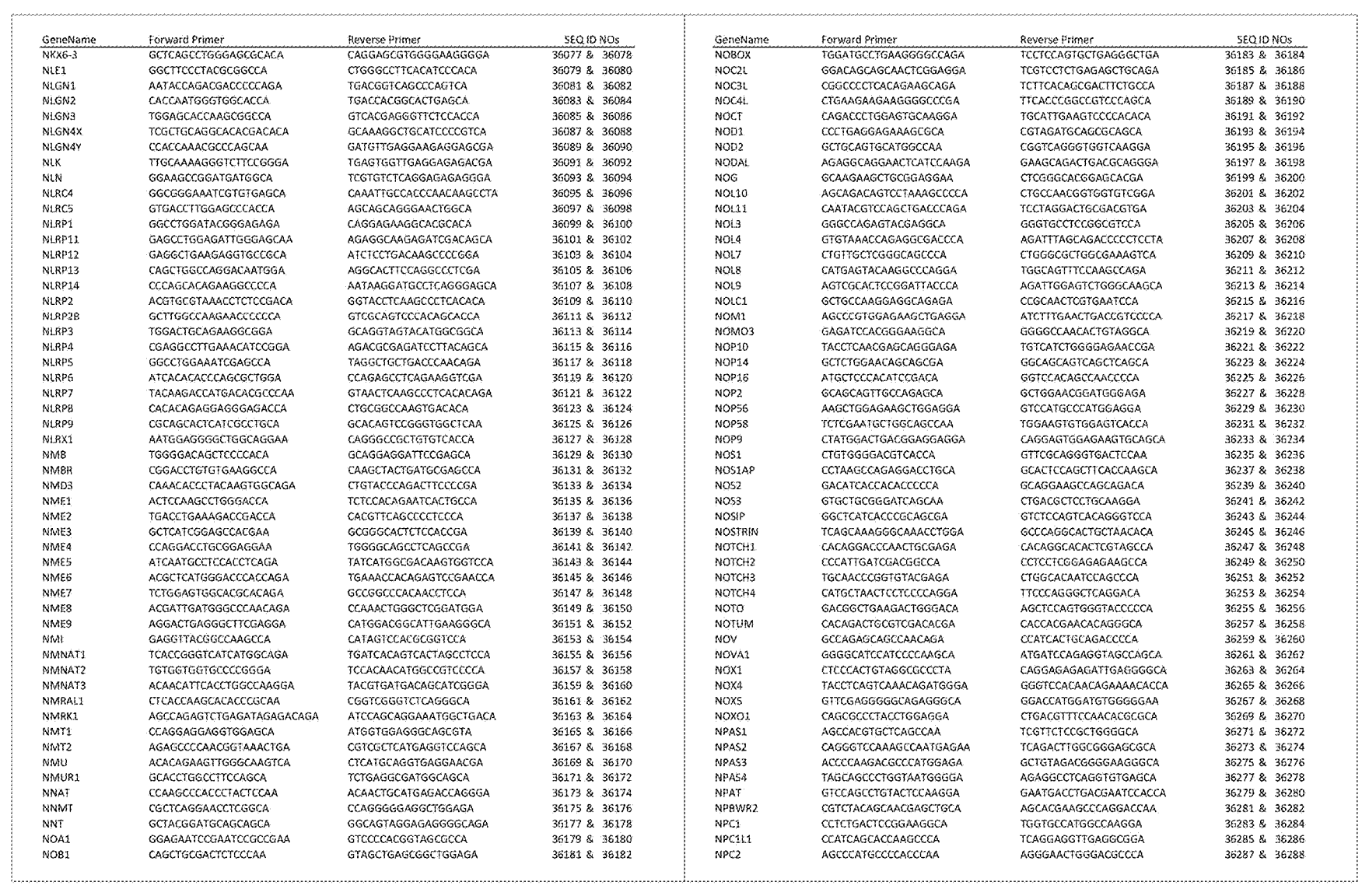
Figure 1:
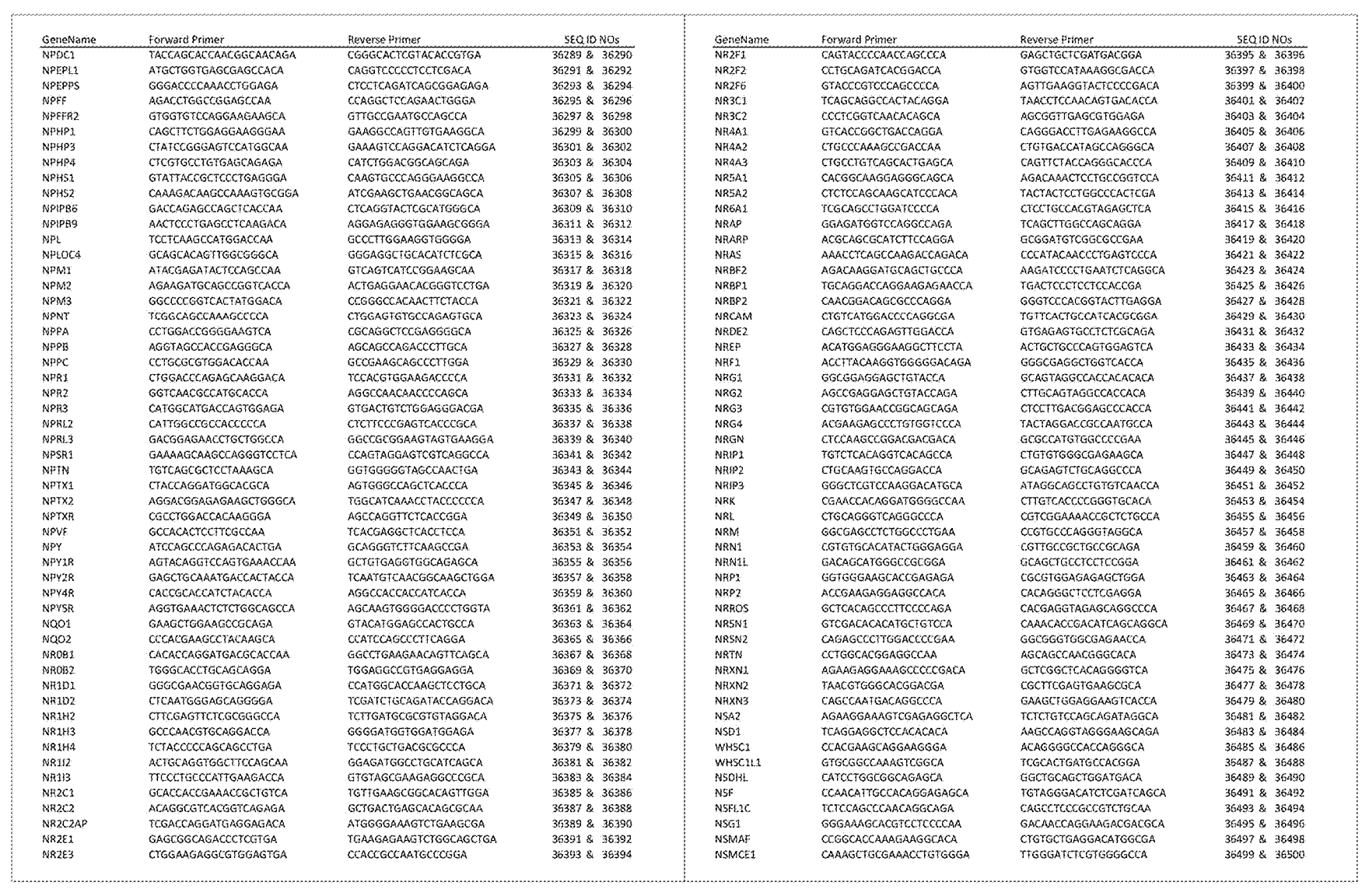
Figure 1:
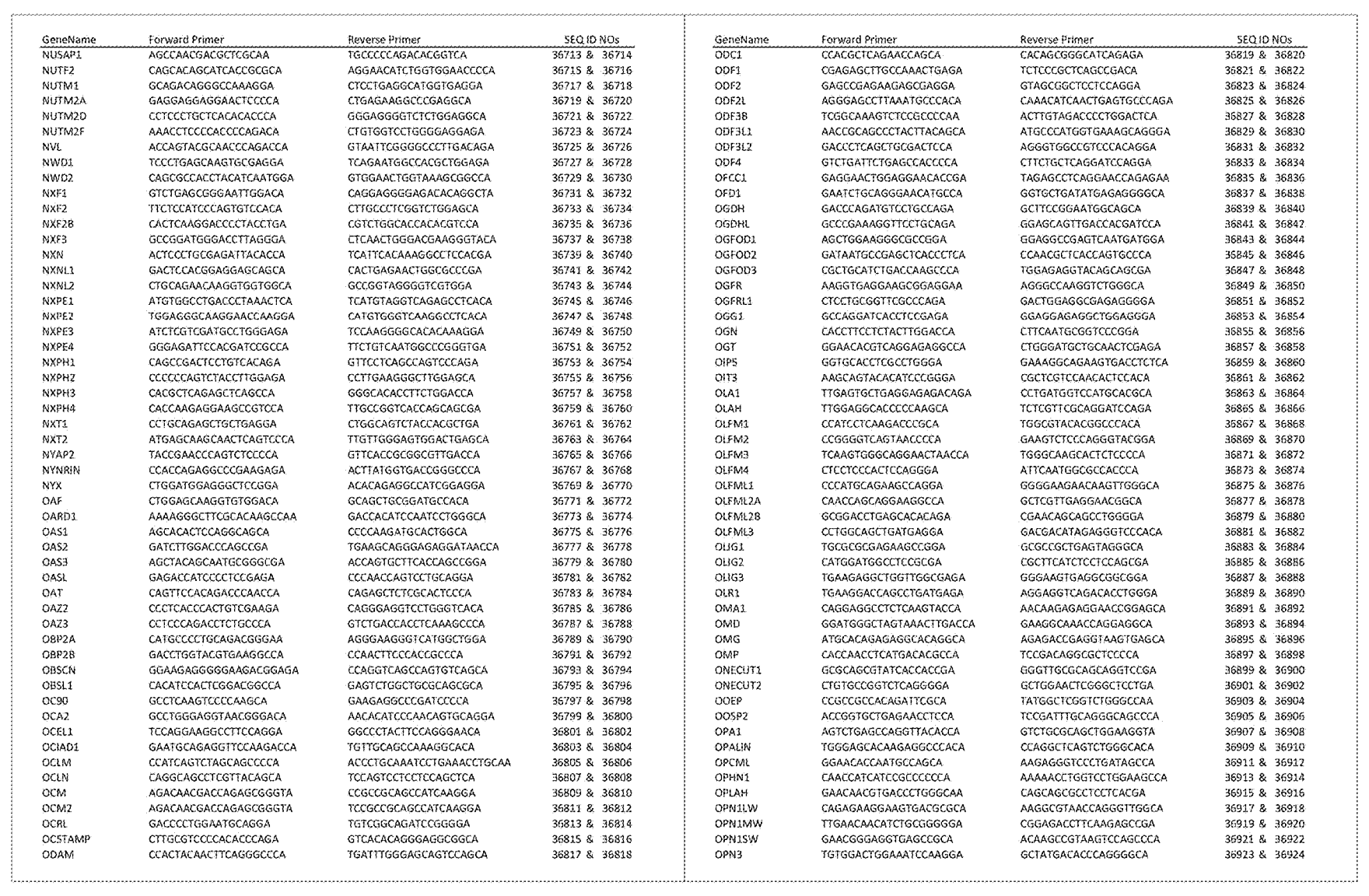
Figure 1:
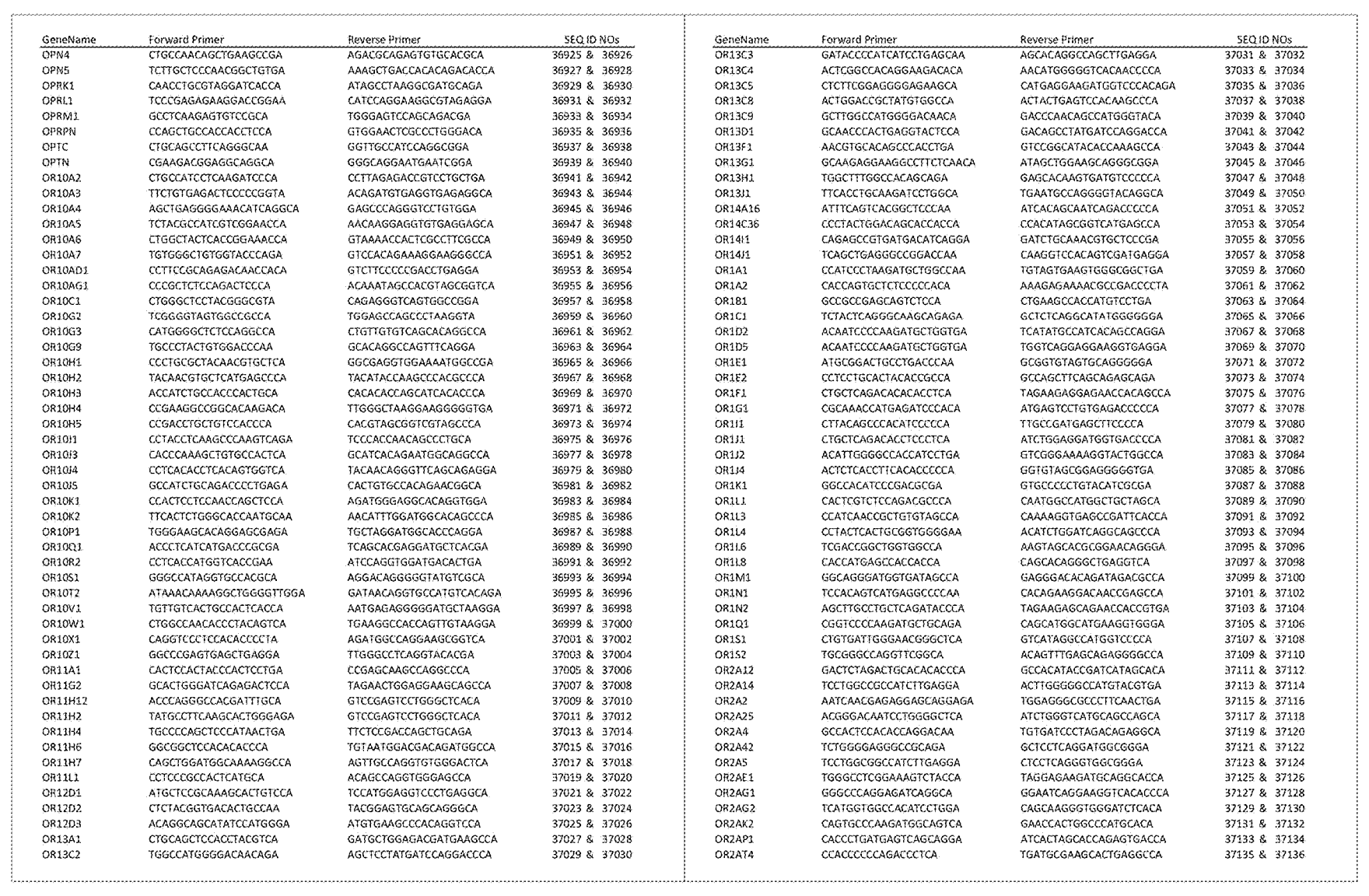
Figure 1:
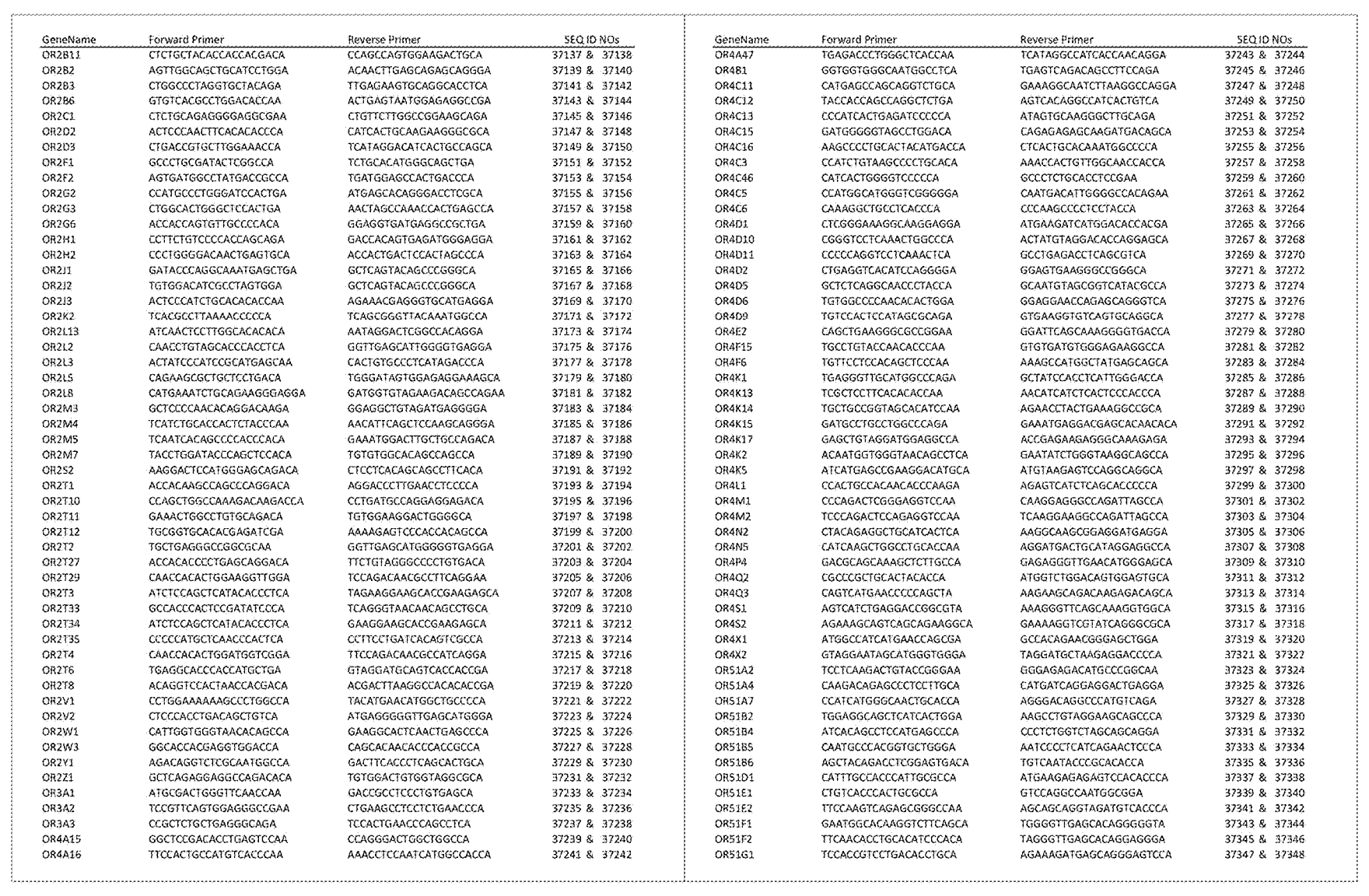
Figure 1:
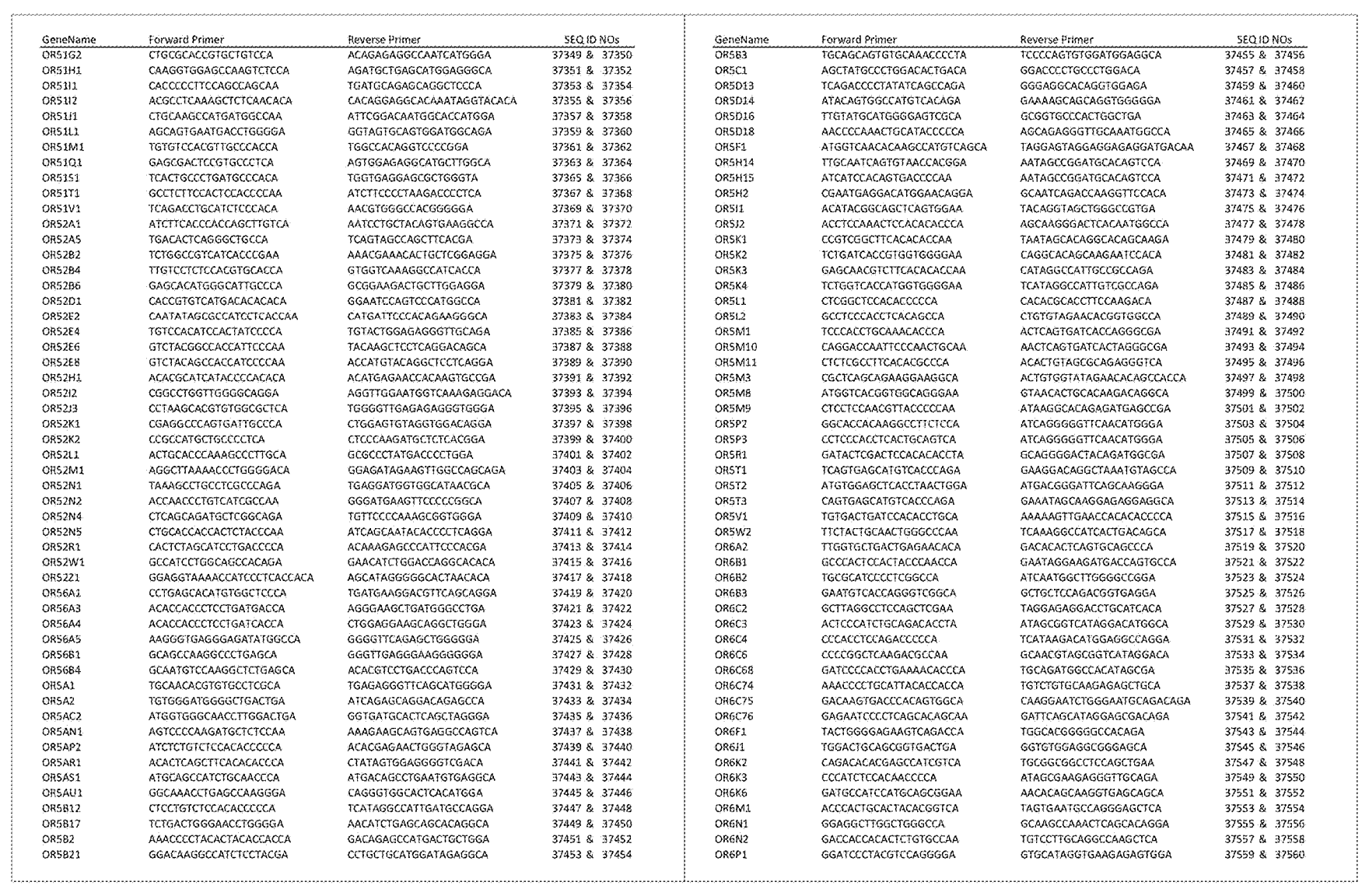
Figure 1:
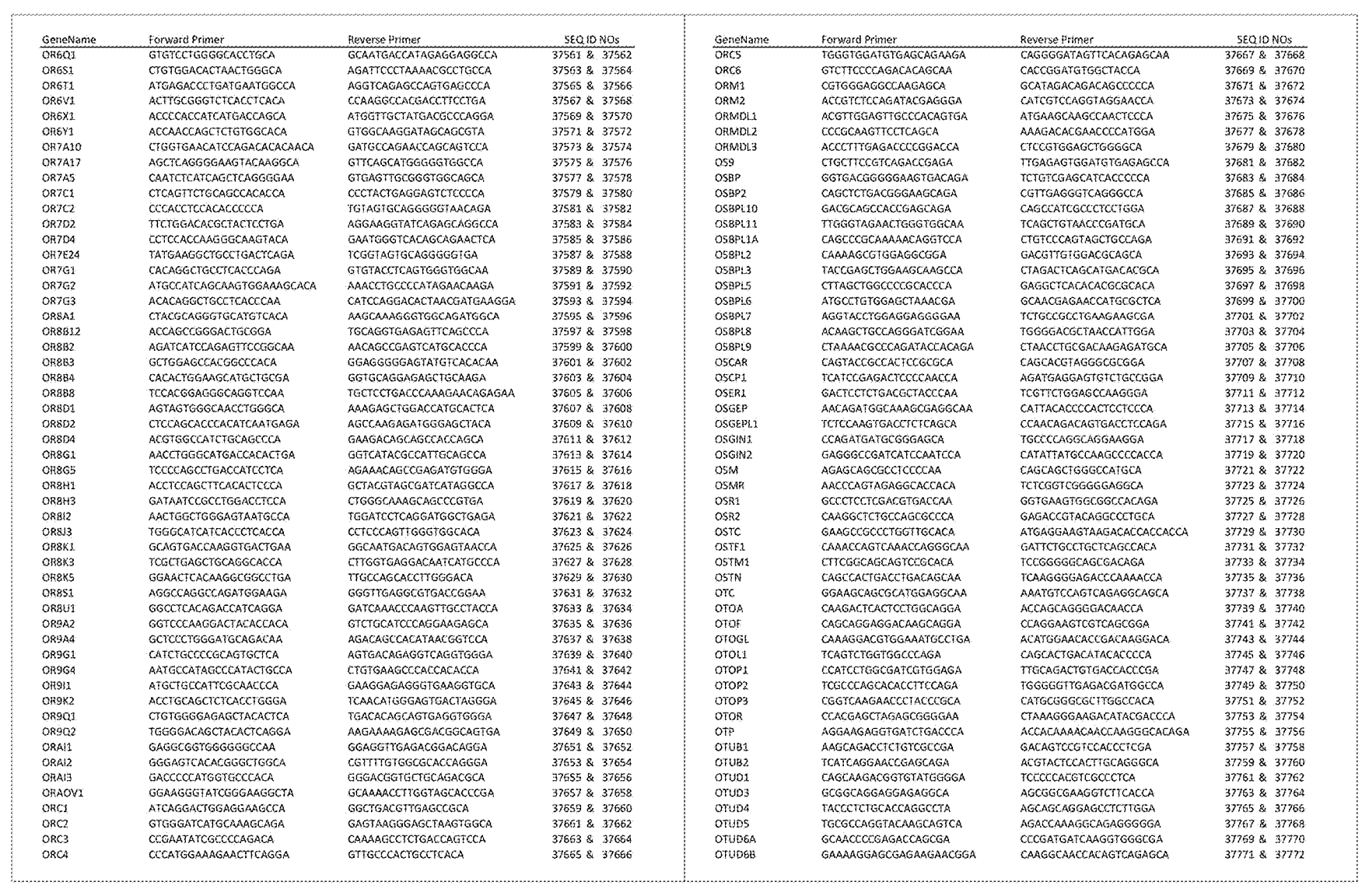
Figure 1:
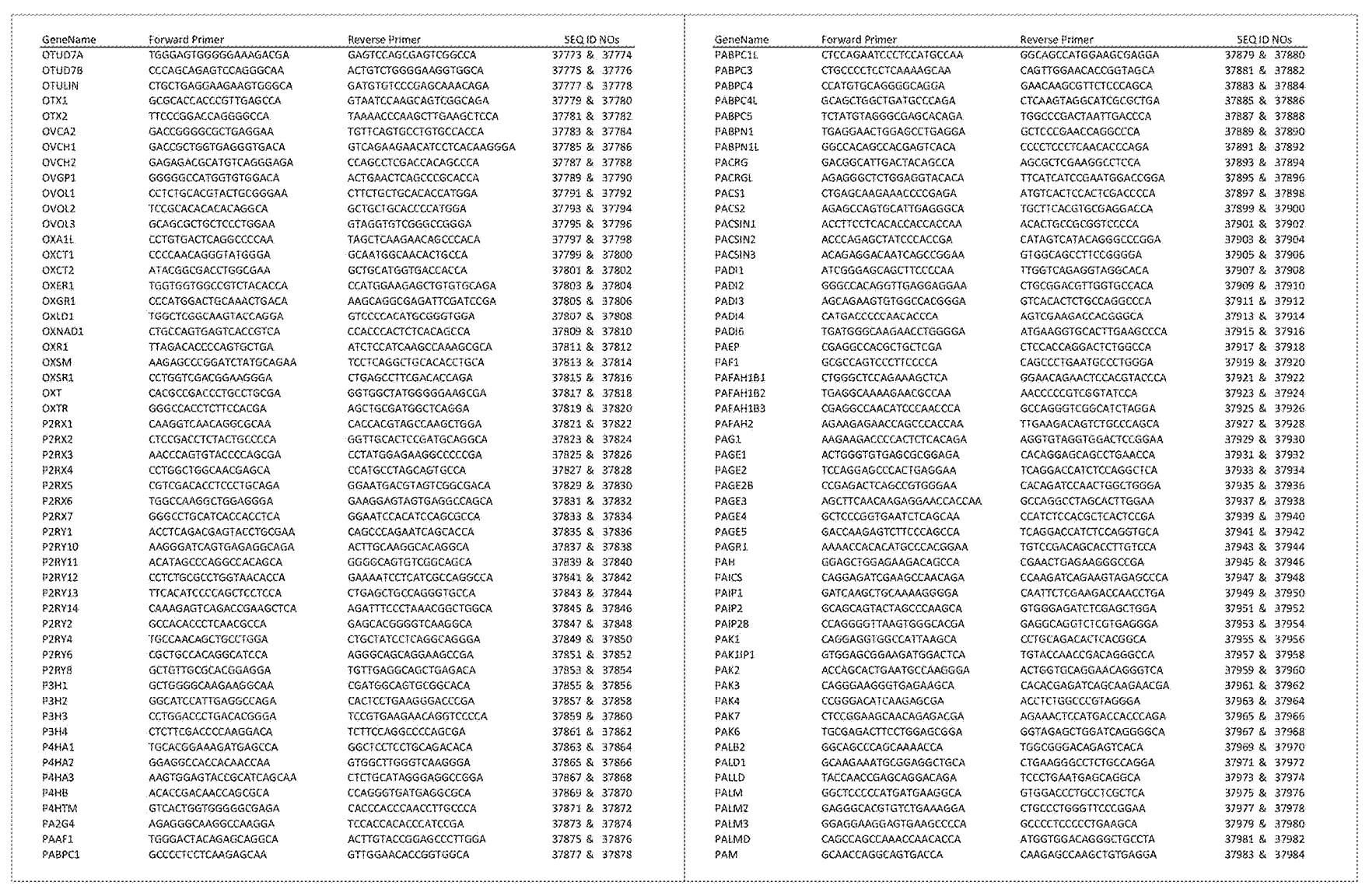
Figure 1:
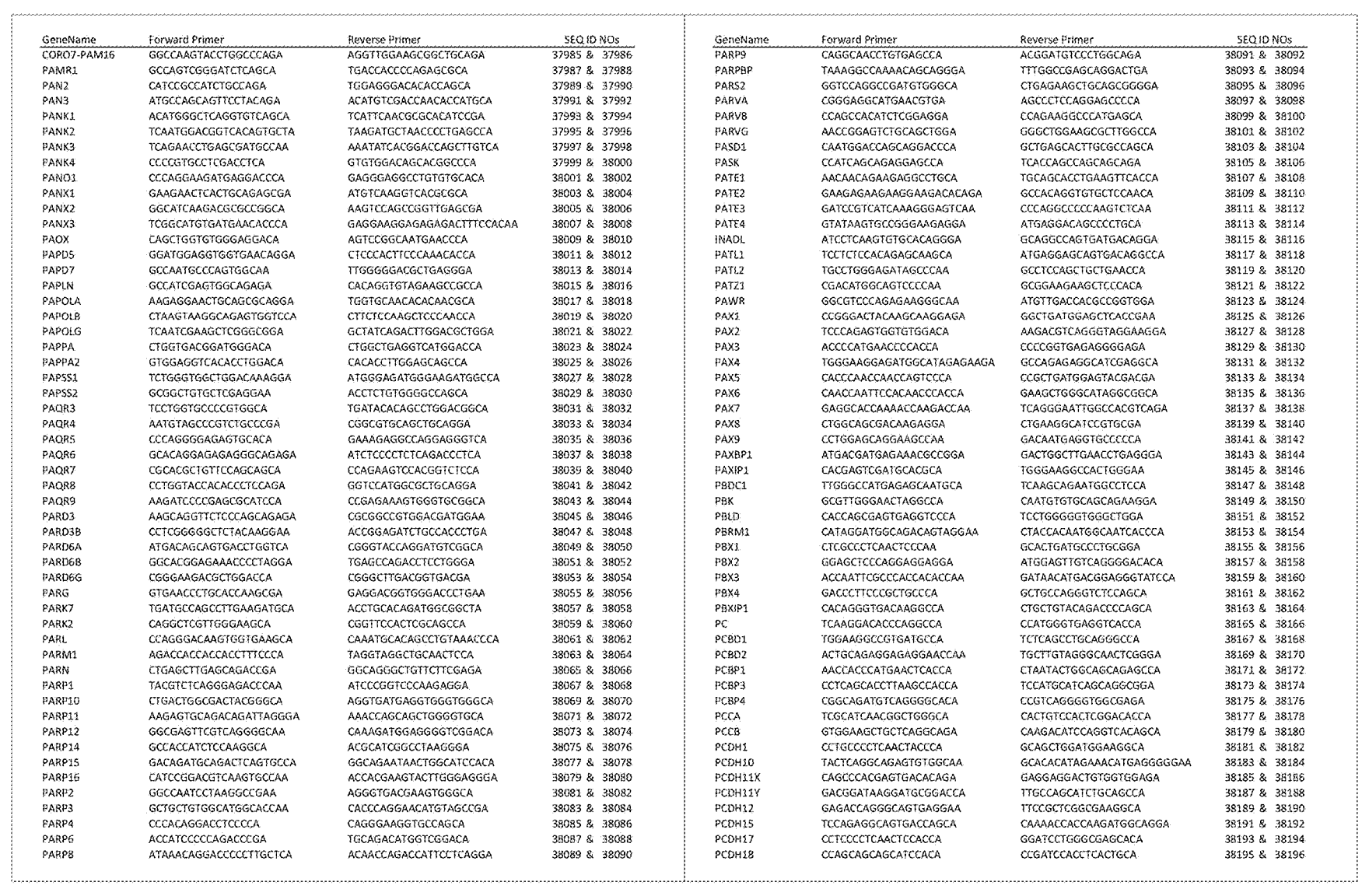
Figure 1:
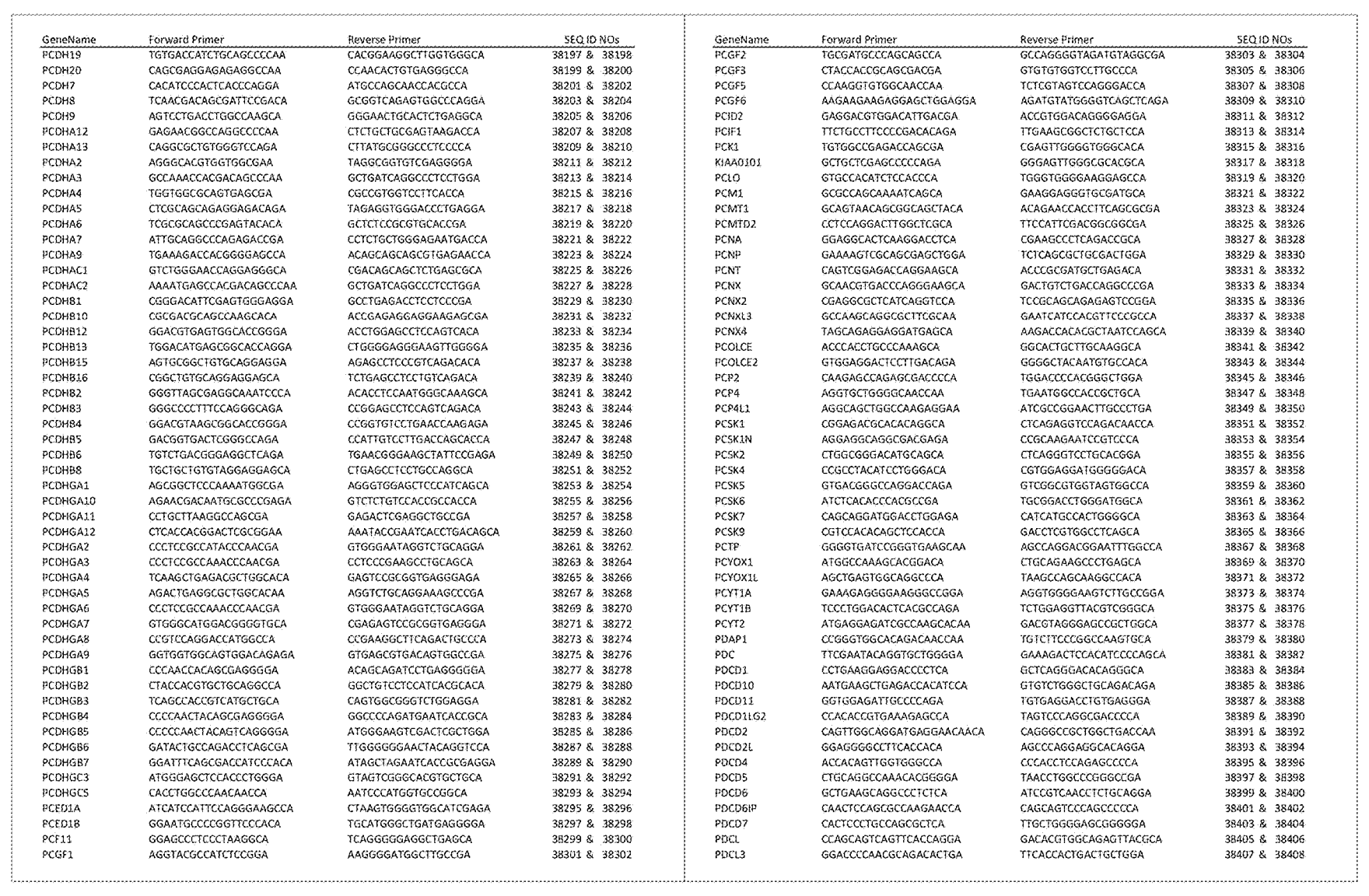
Figure 1:
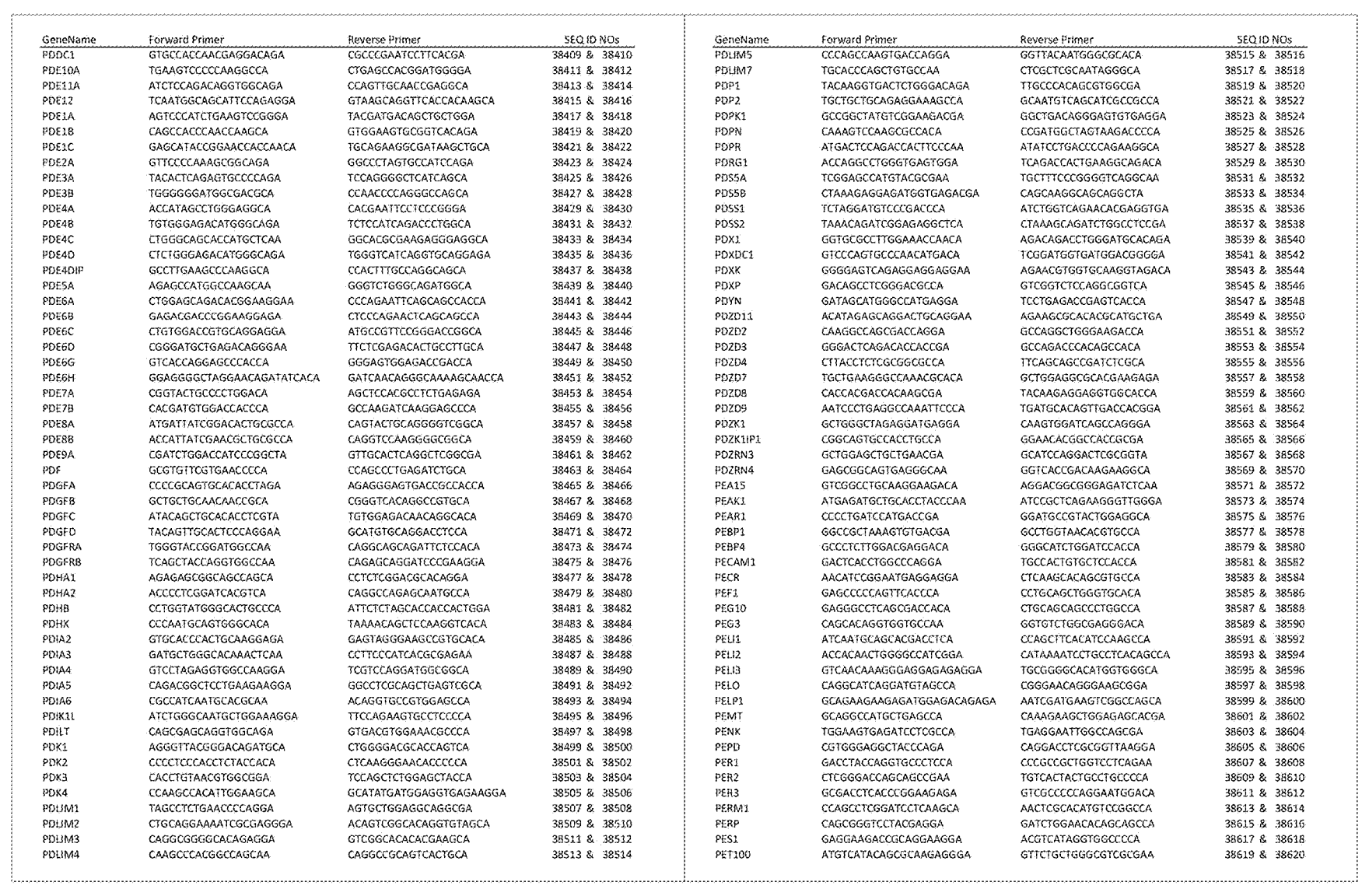
Figure 1:
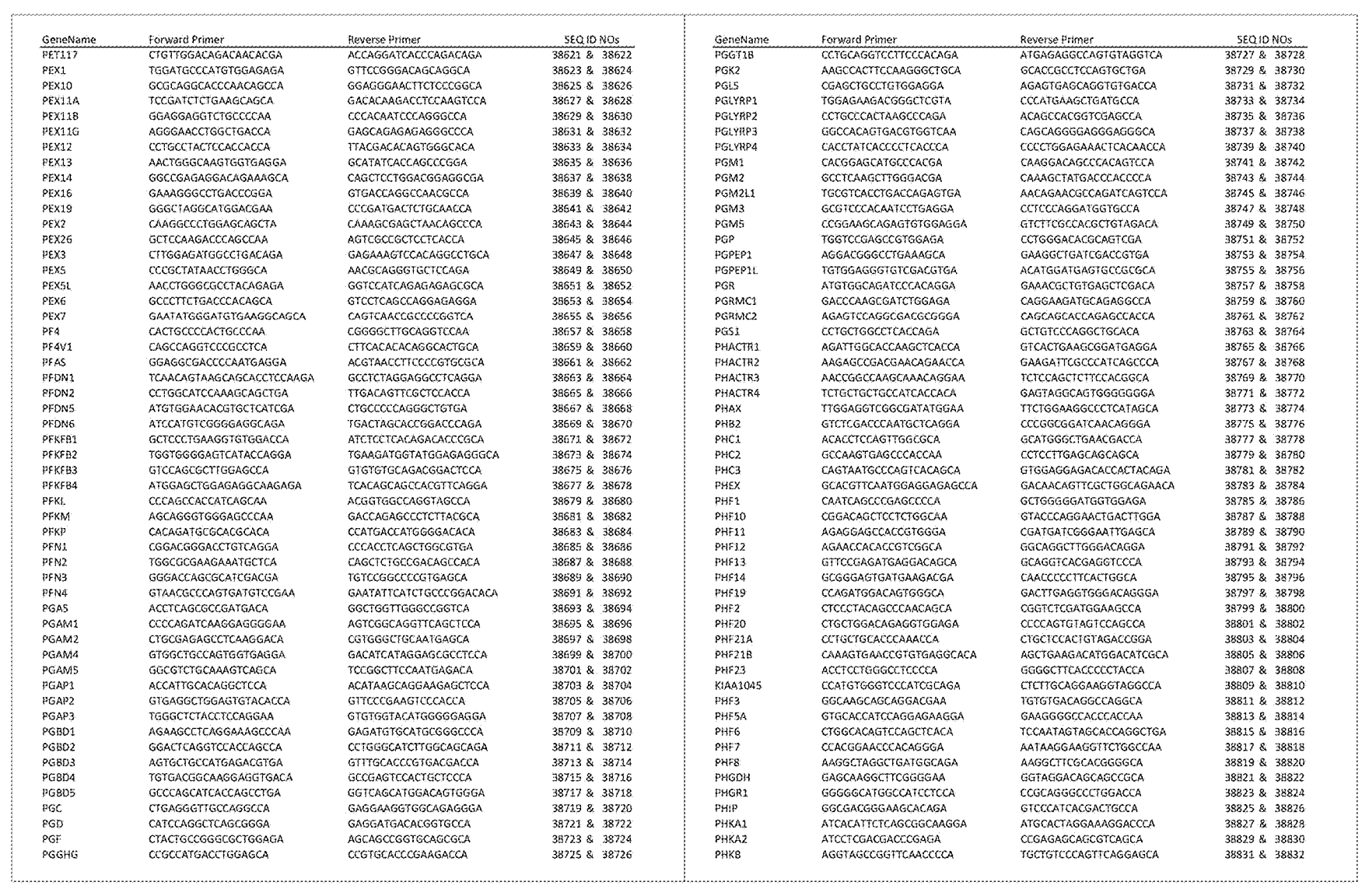
Figure 1:
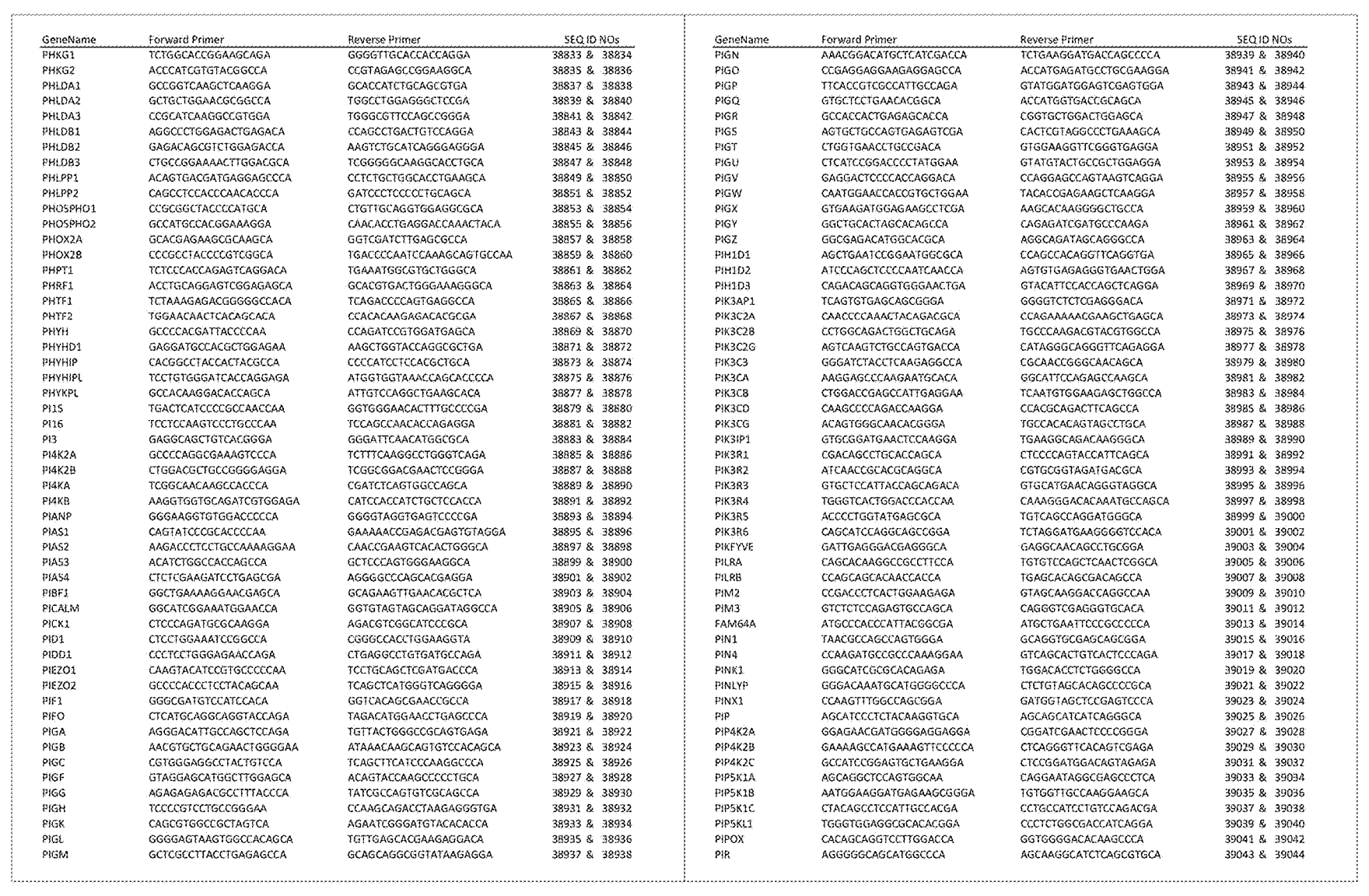
Figure 1:
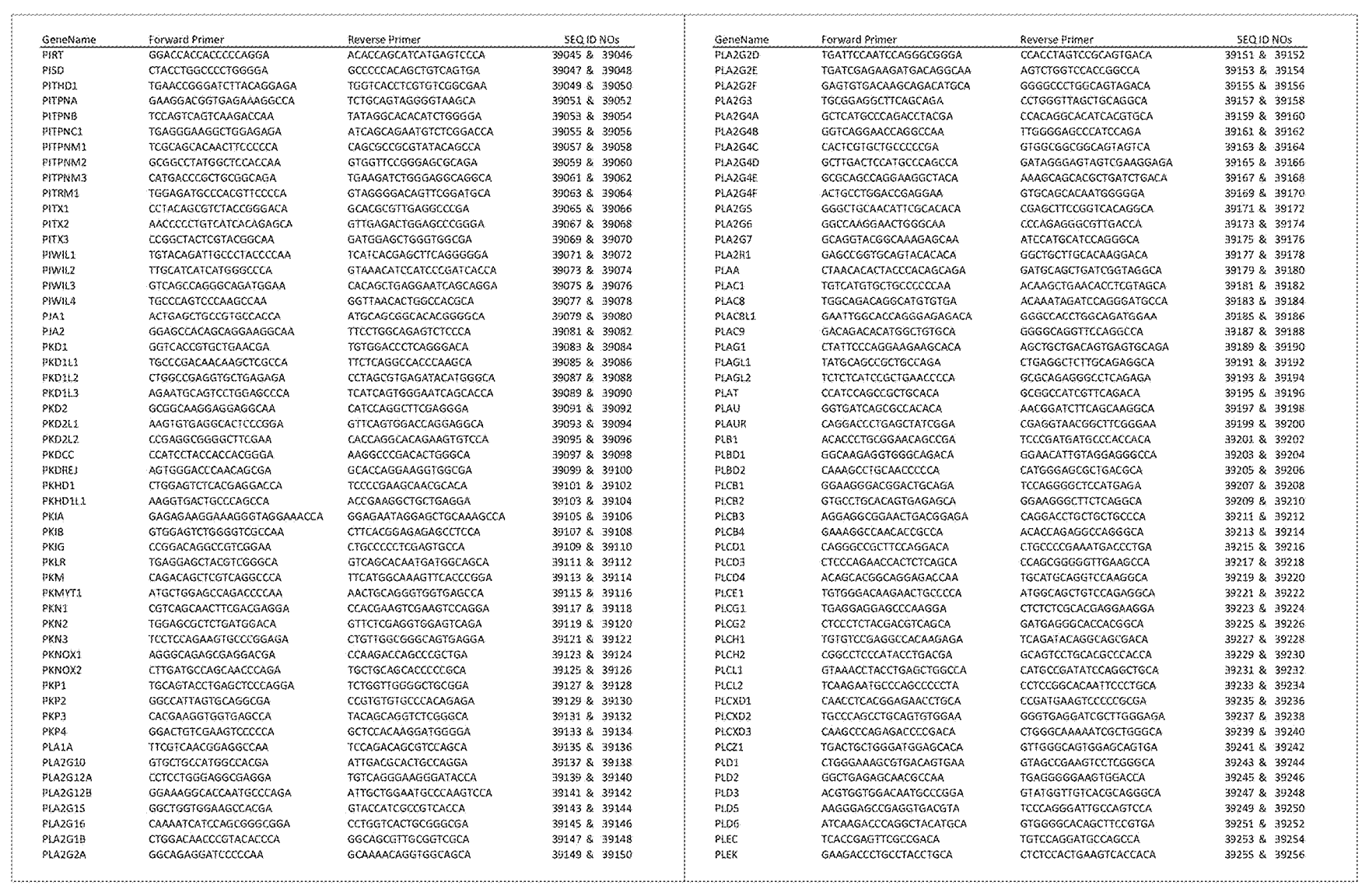
Figure 1:
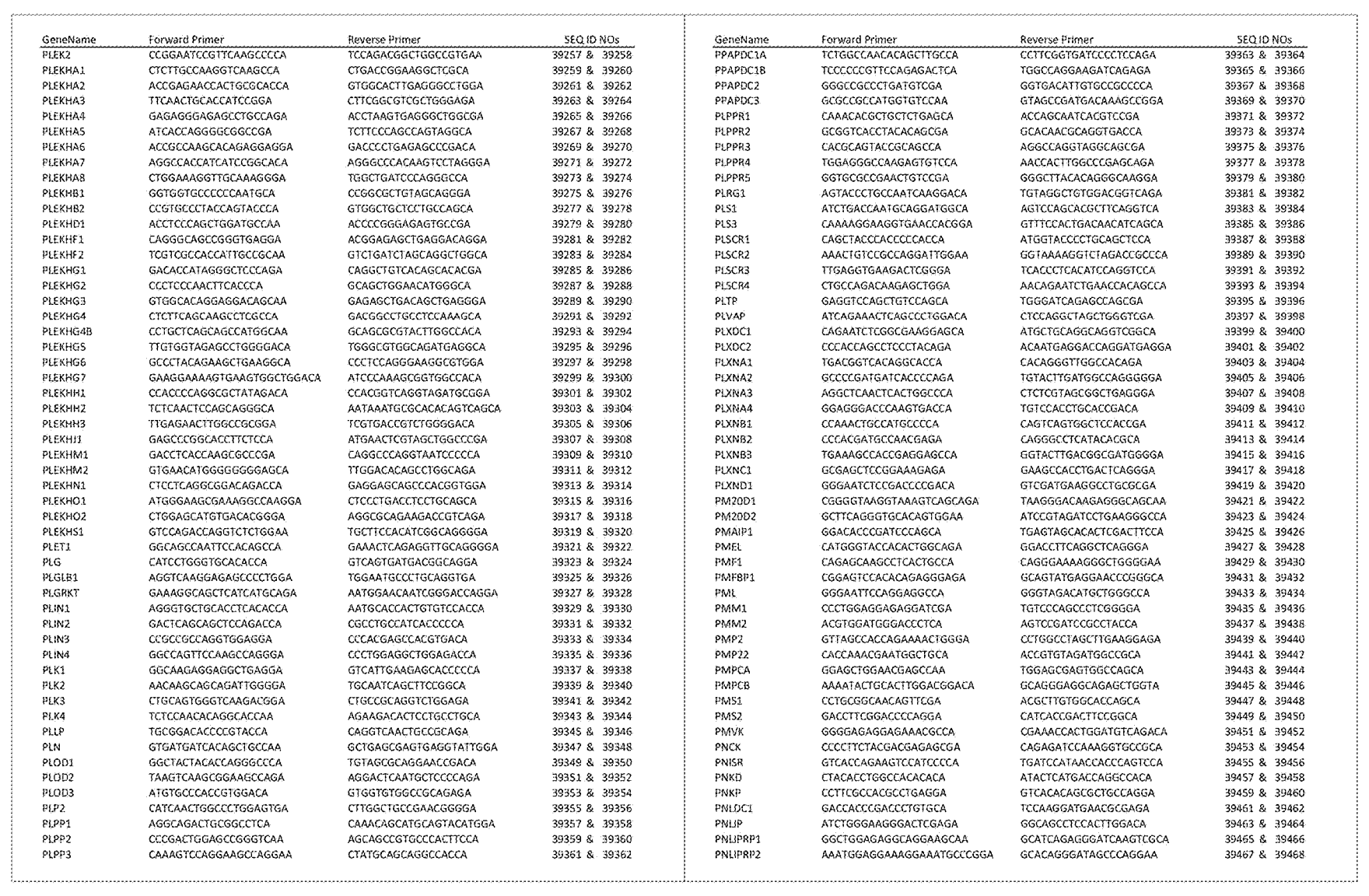
Figure 1:
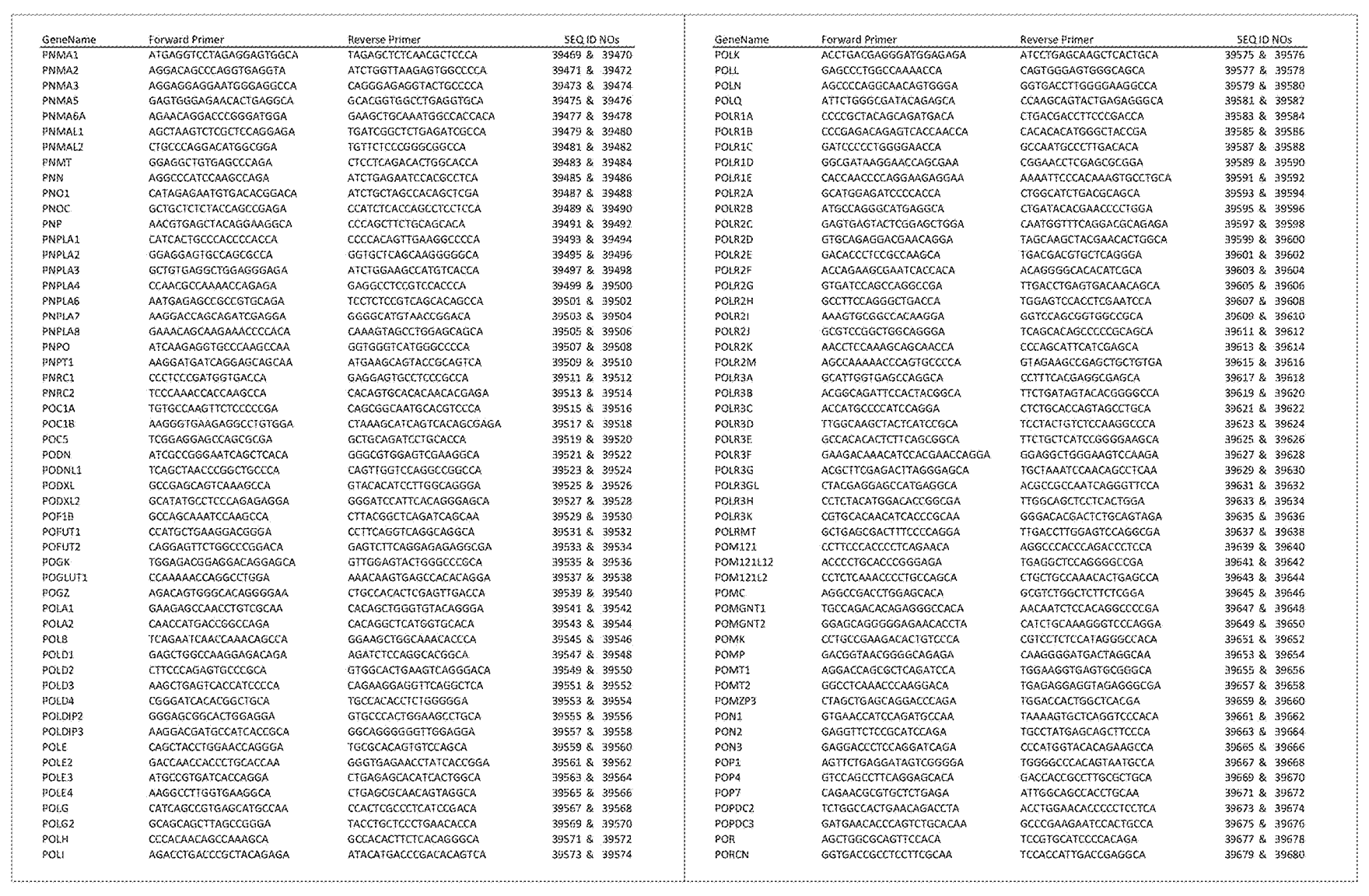
Figure 1:
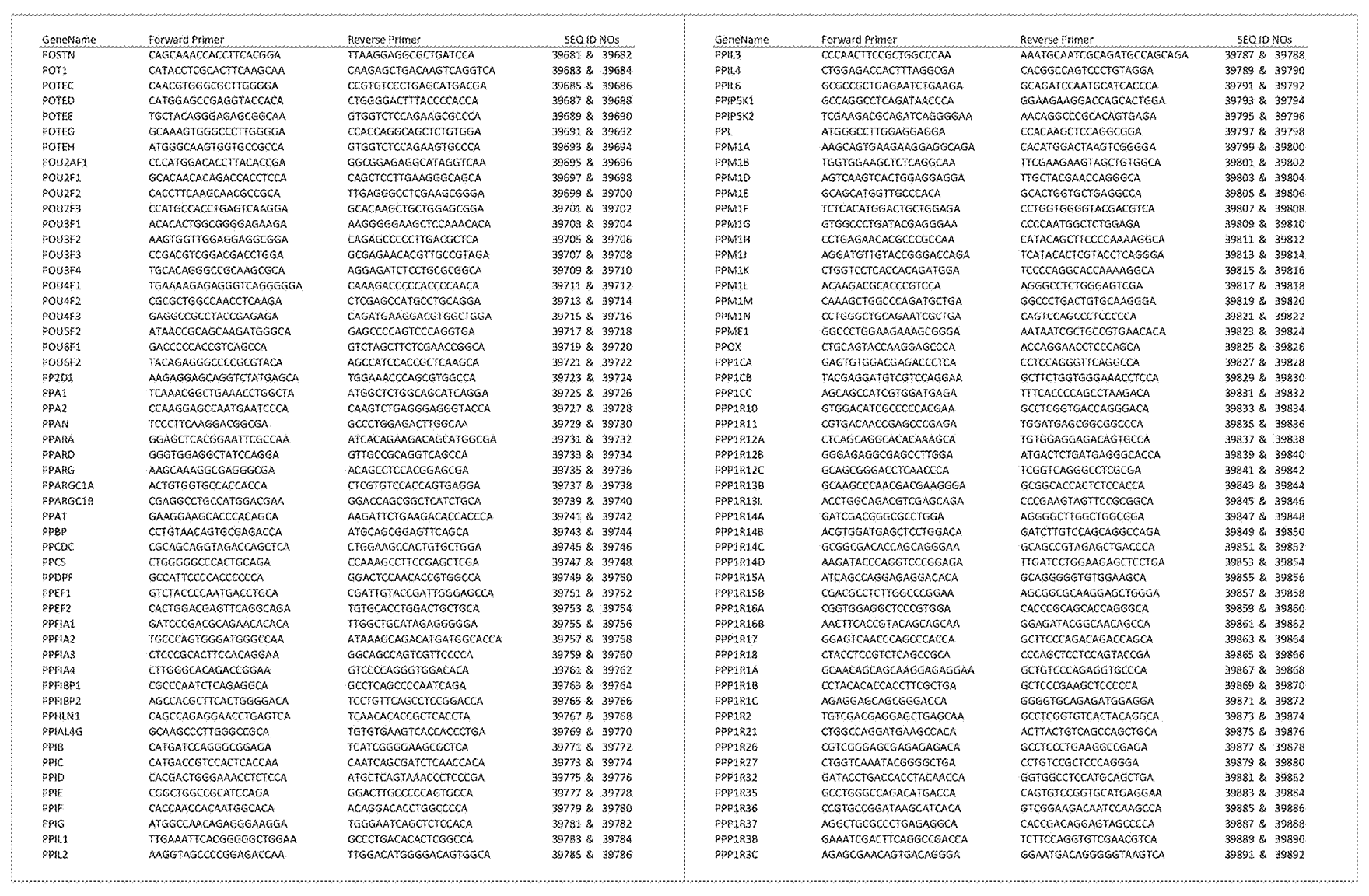
Figure 1:
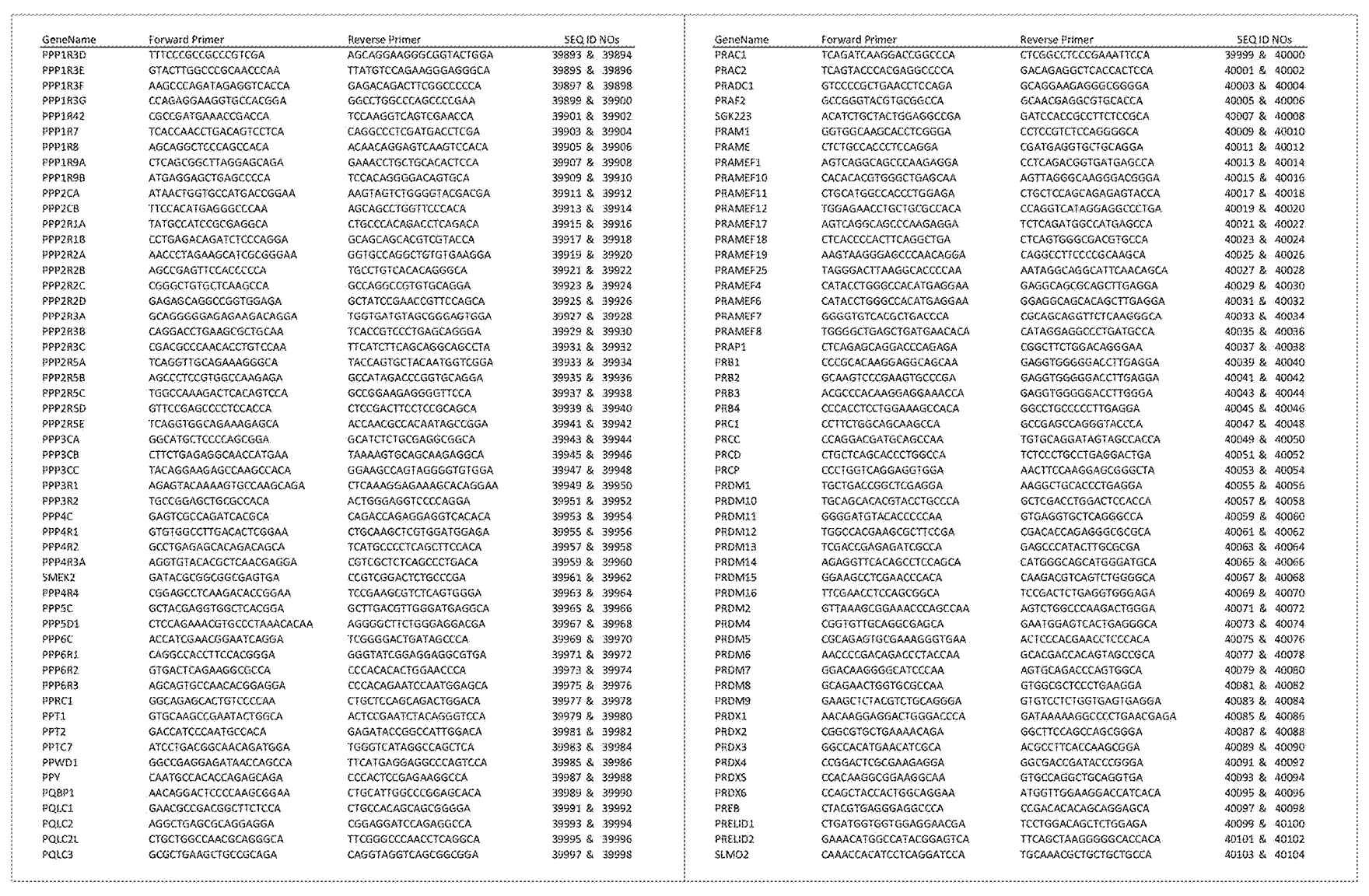
Figure 1:
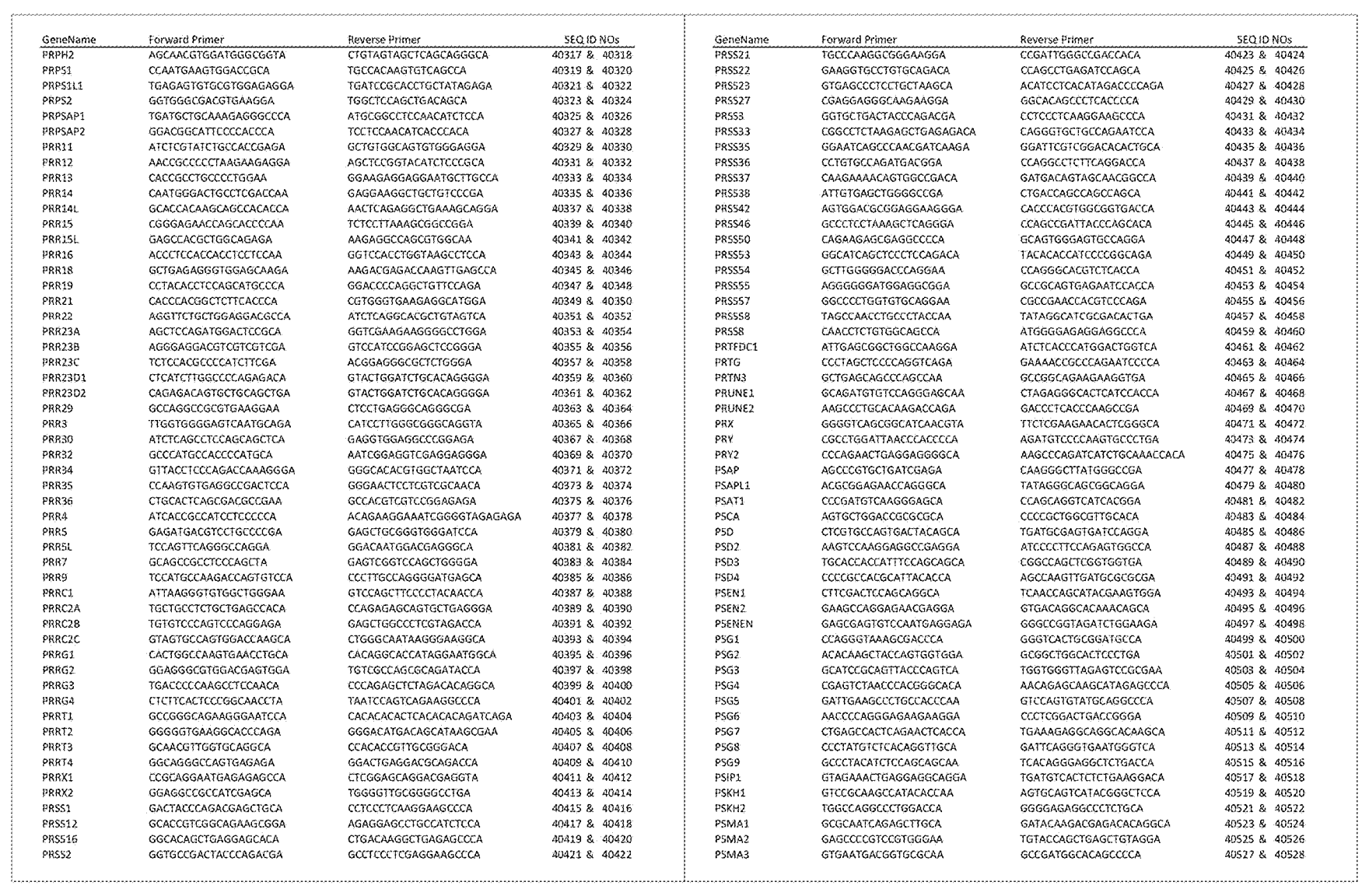
Figure 1:
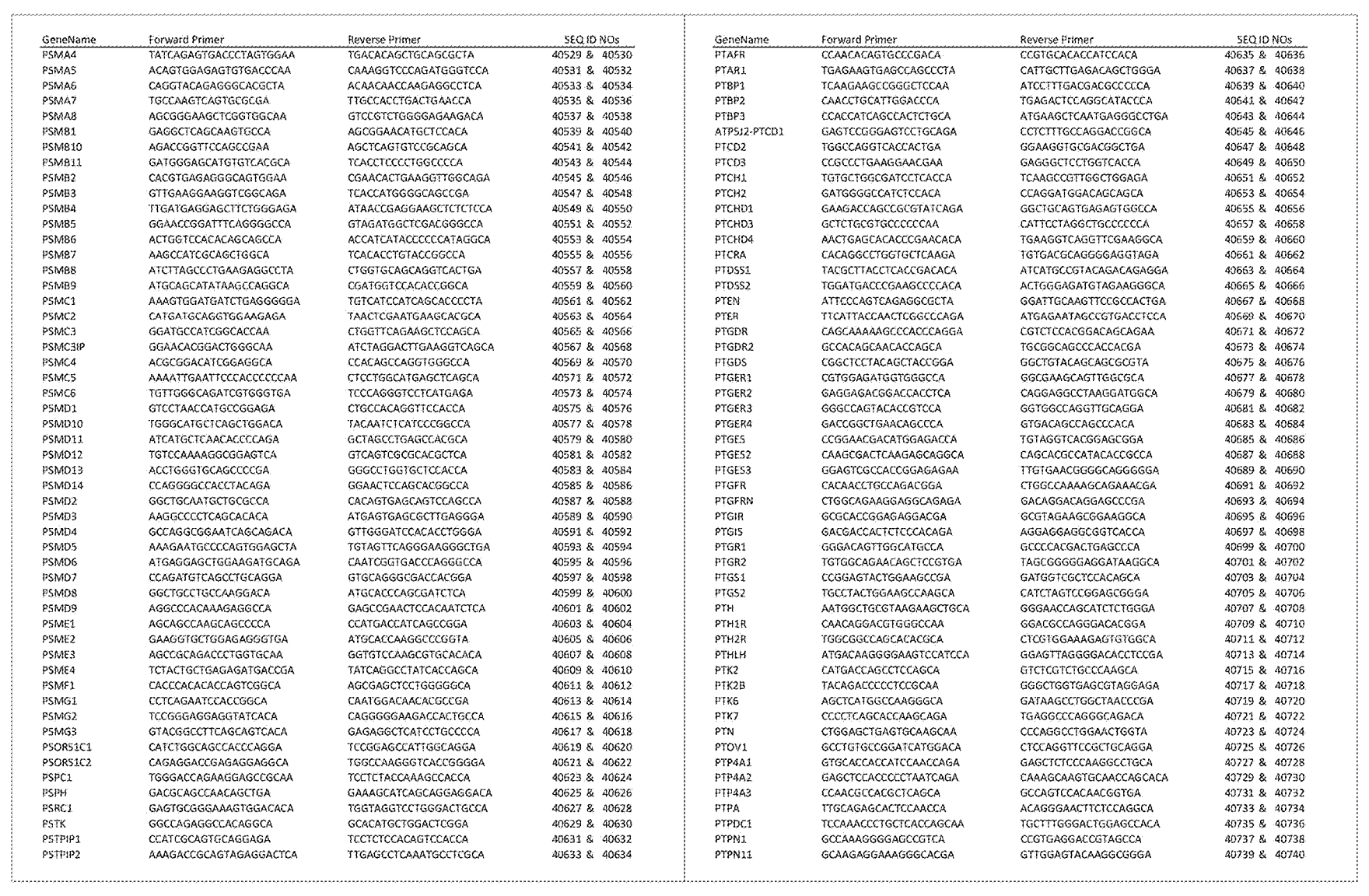
Figure 1:
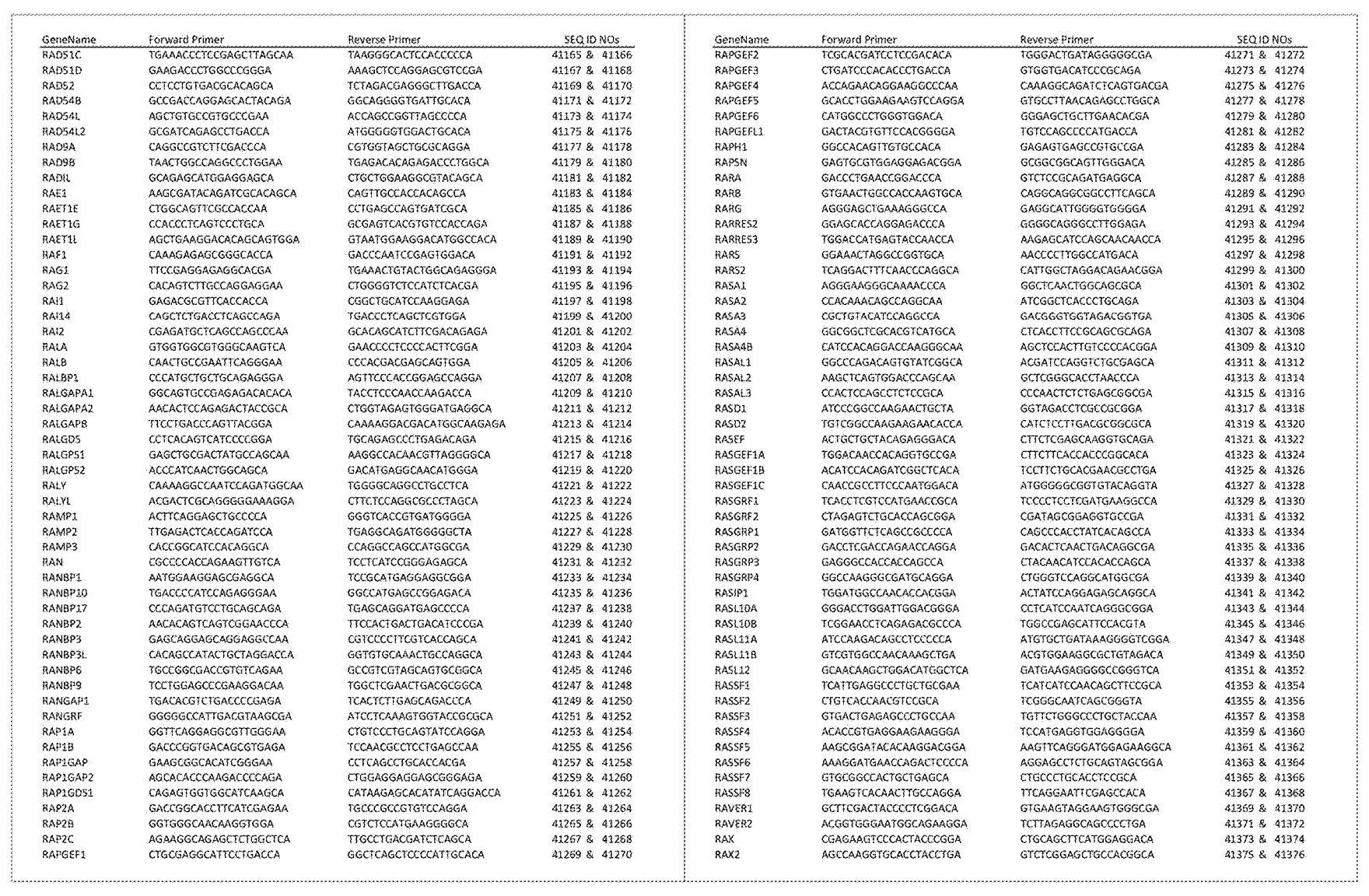
Figure 1:
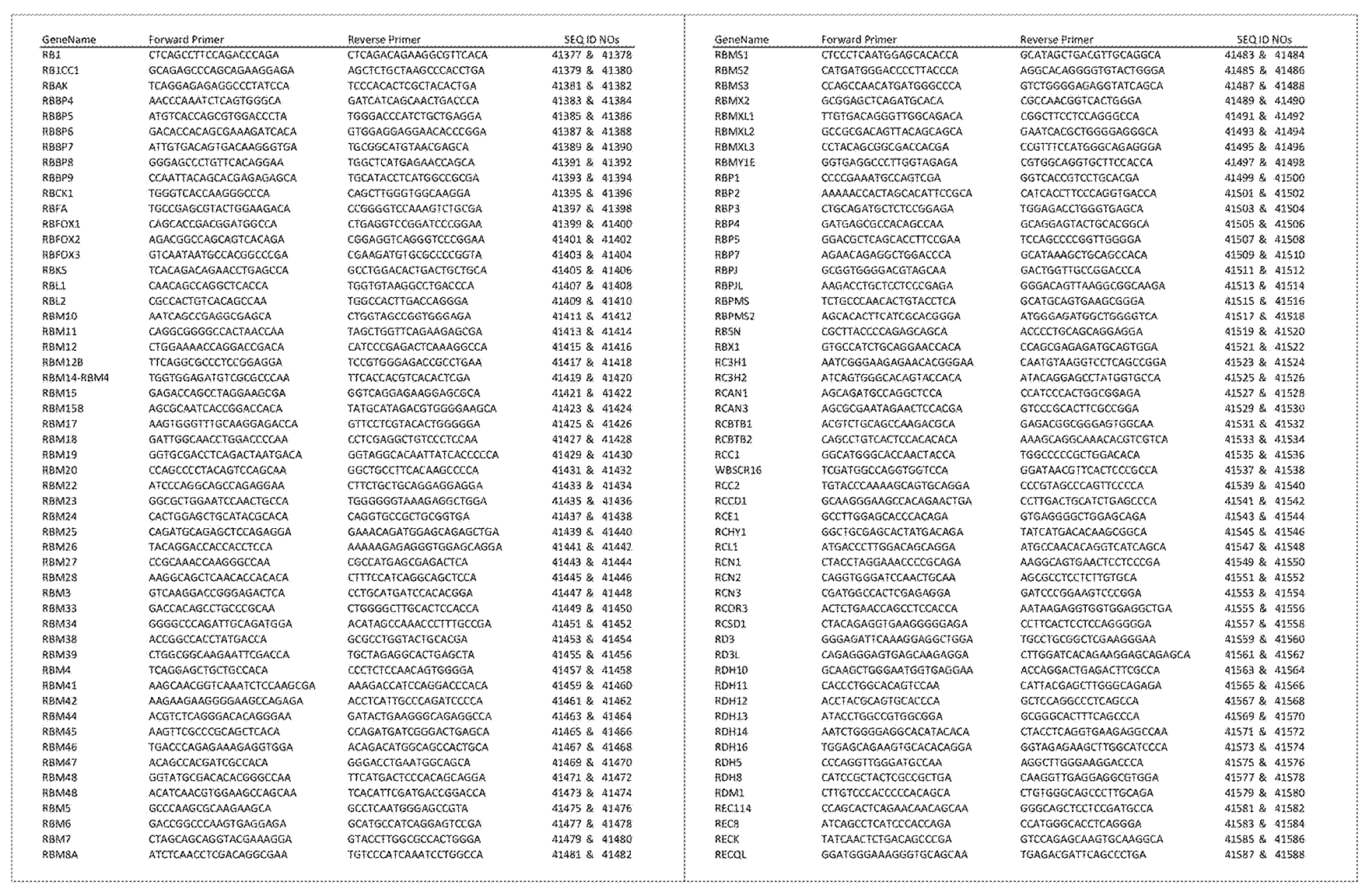
Figure 1:
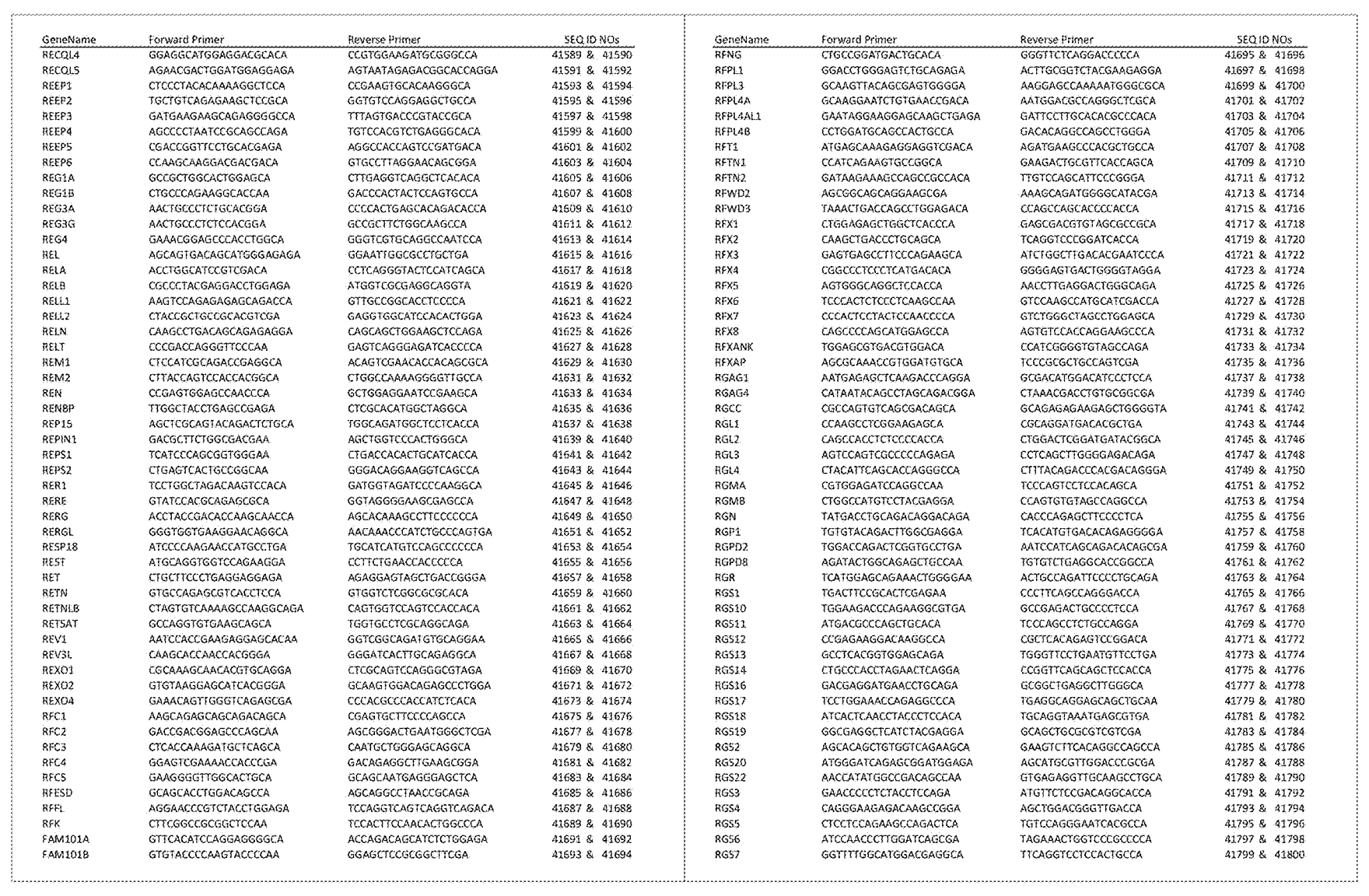
Figure 1:
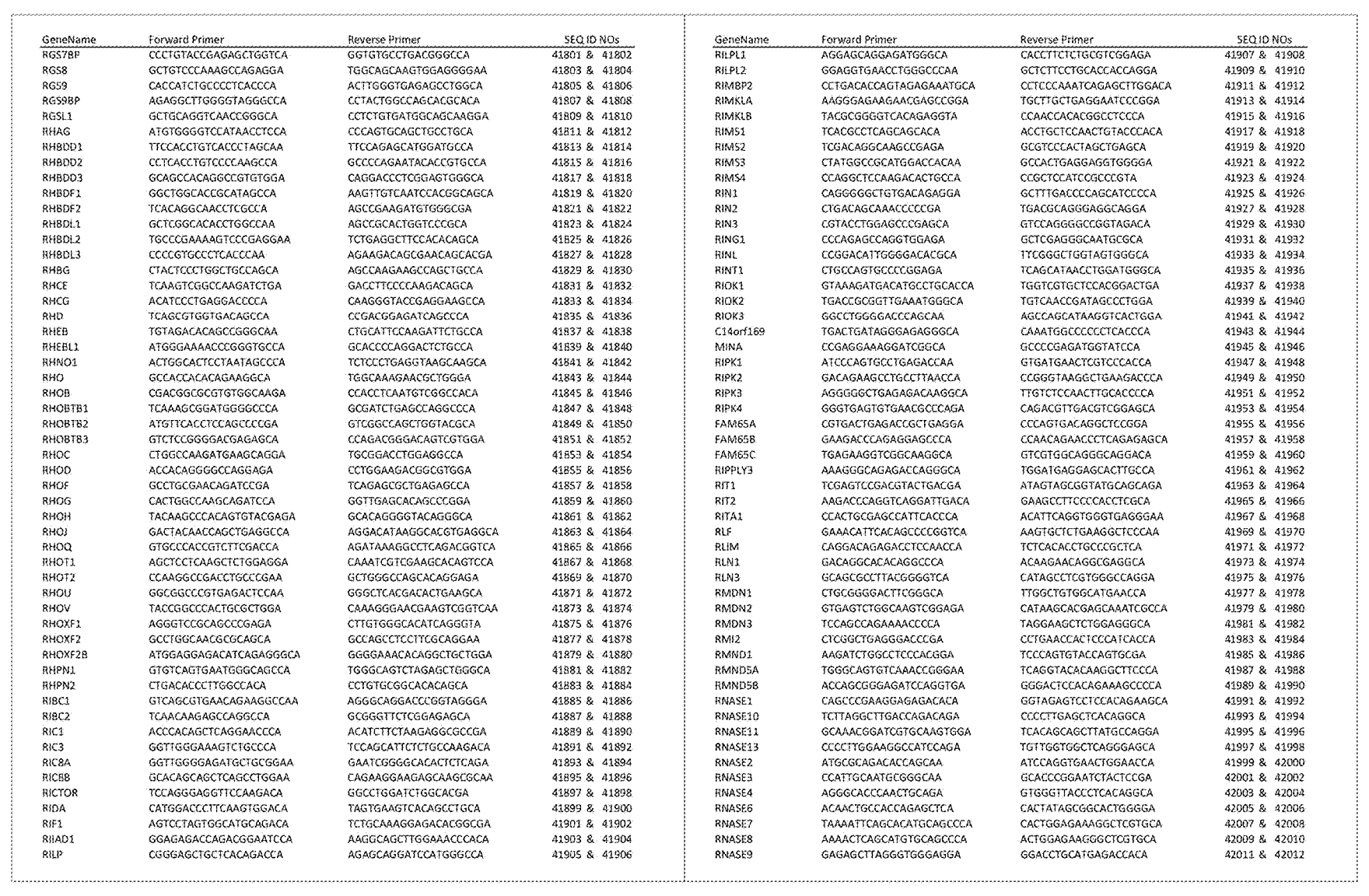
Figure 1:
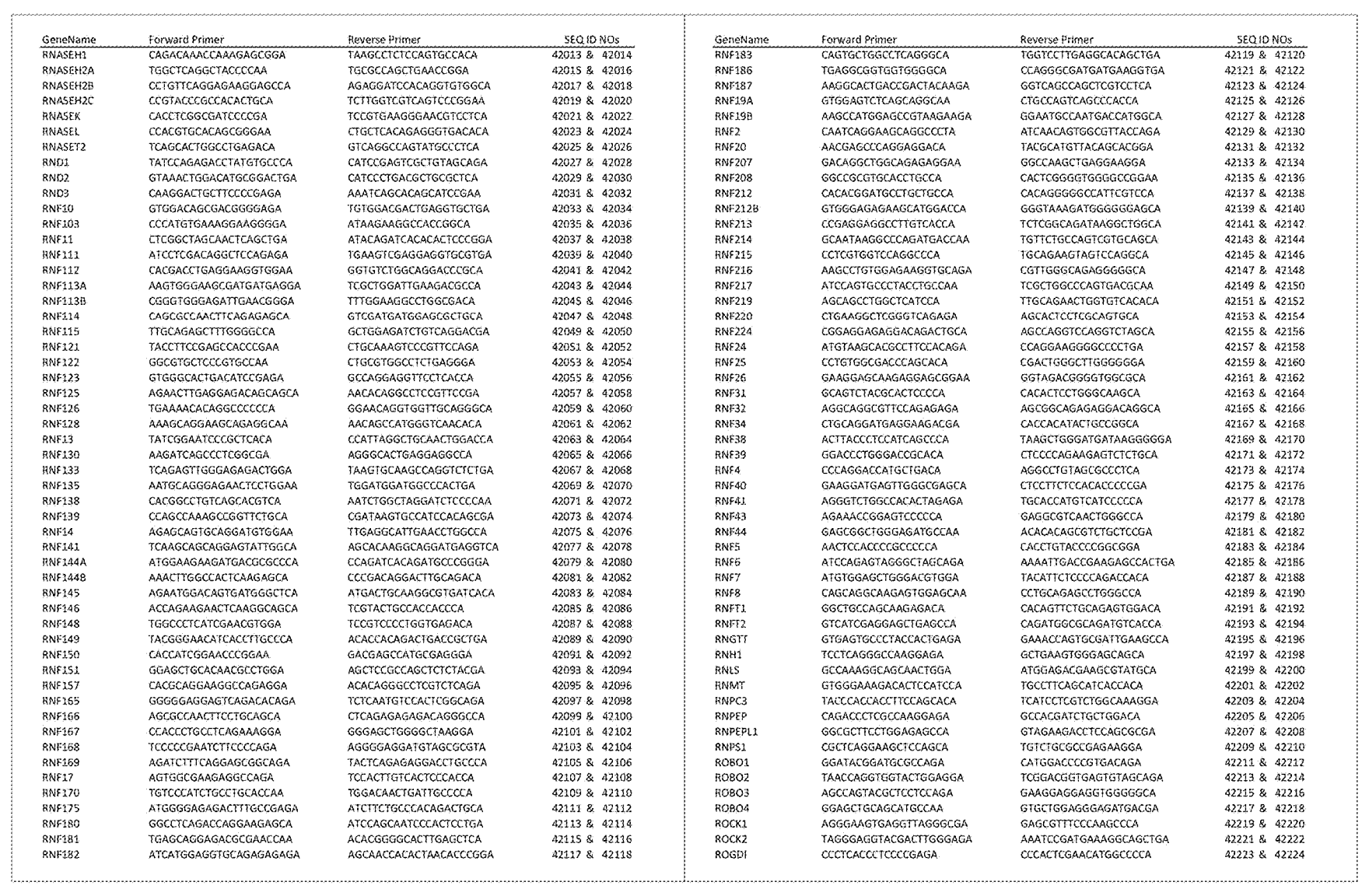
Figure 1:
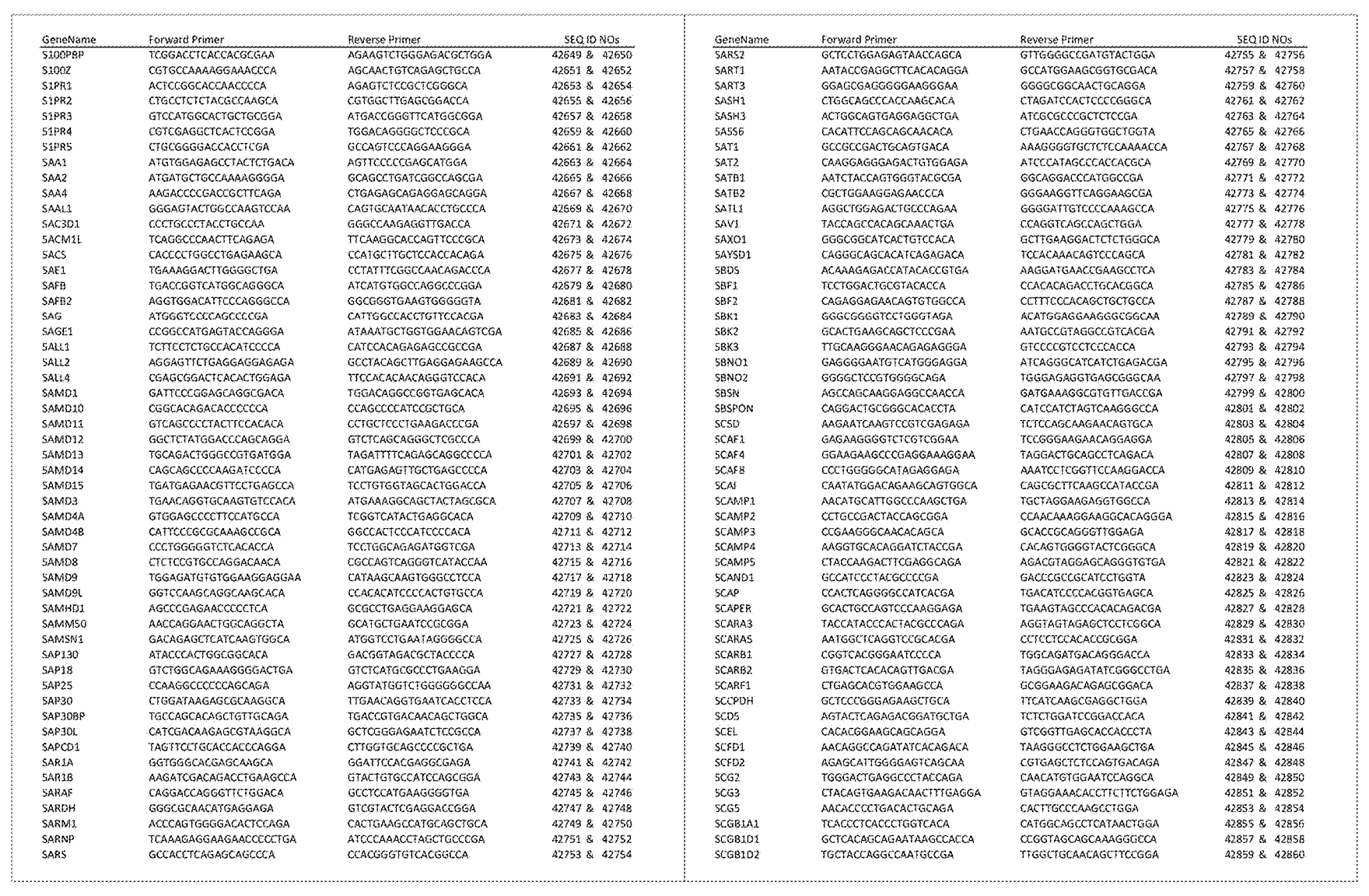
Figure 1:
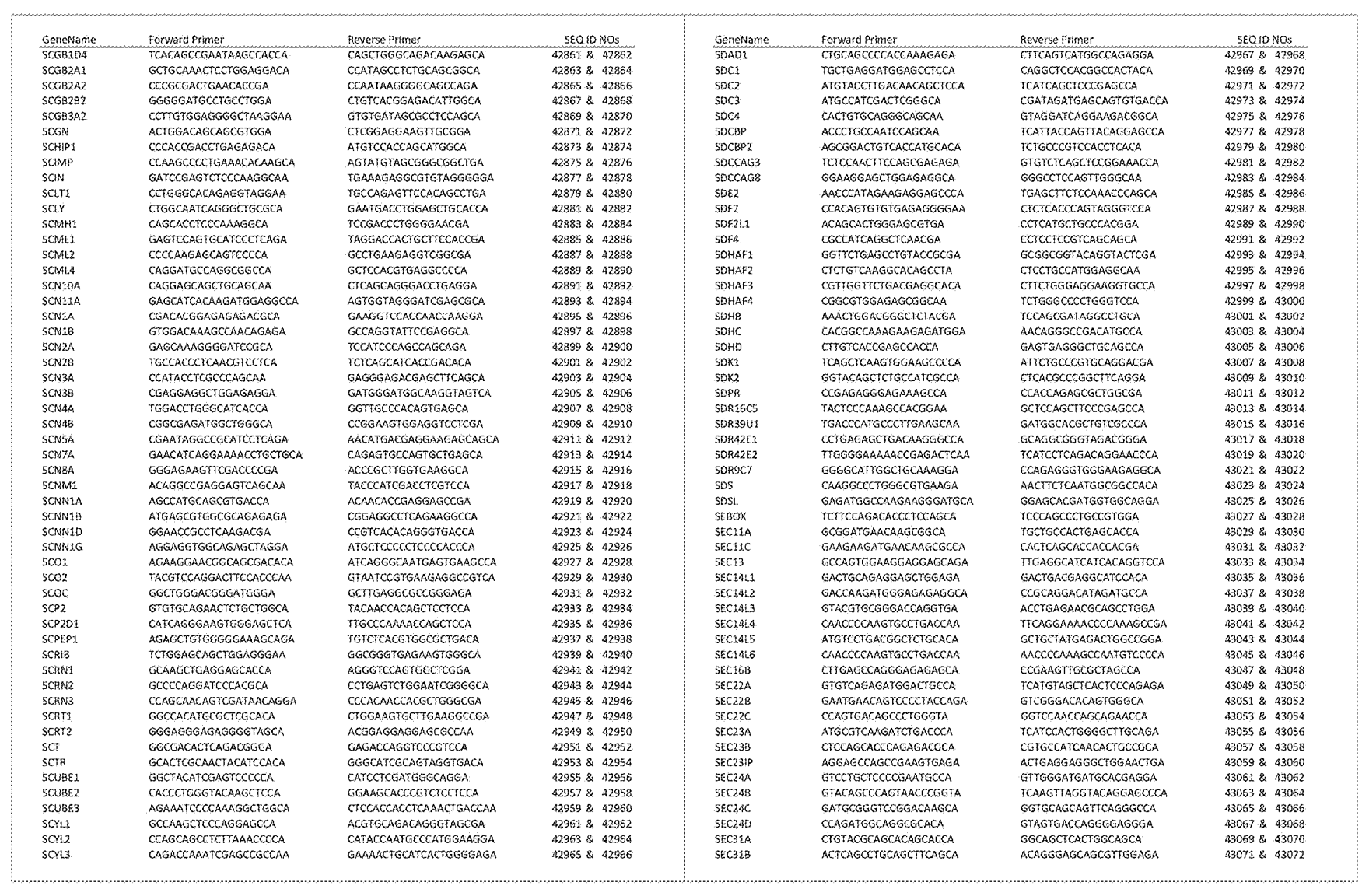
Figure 1:
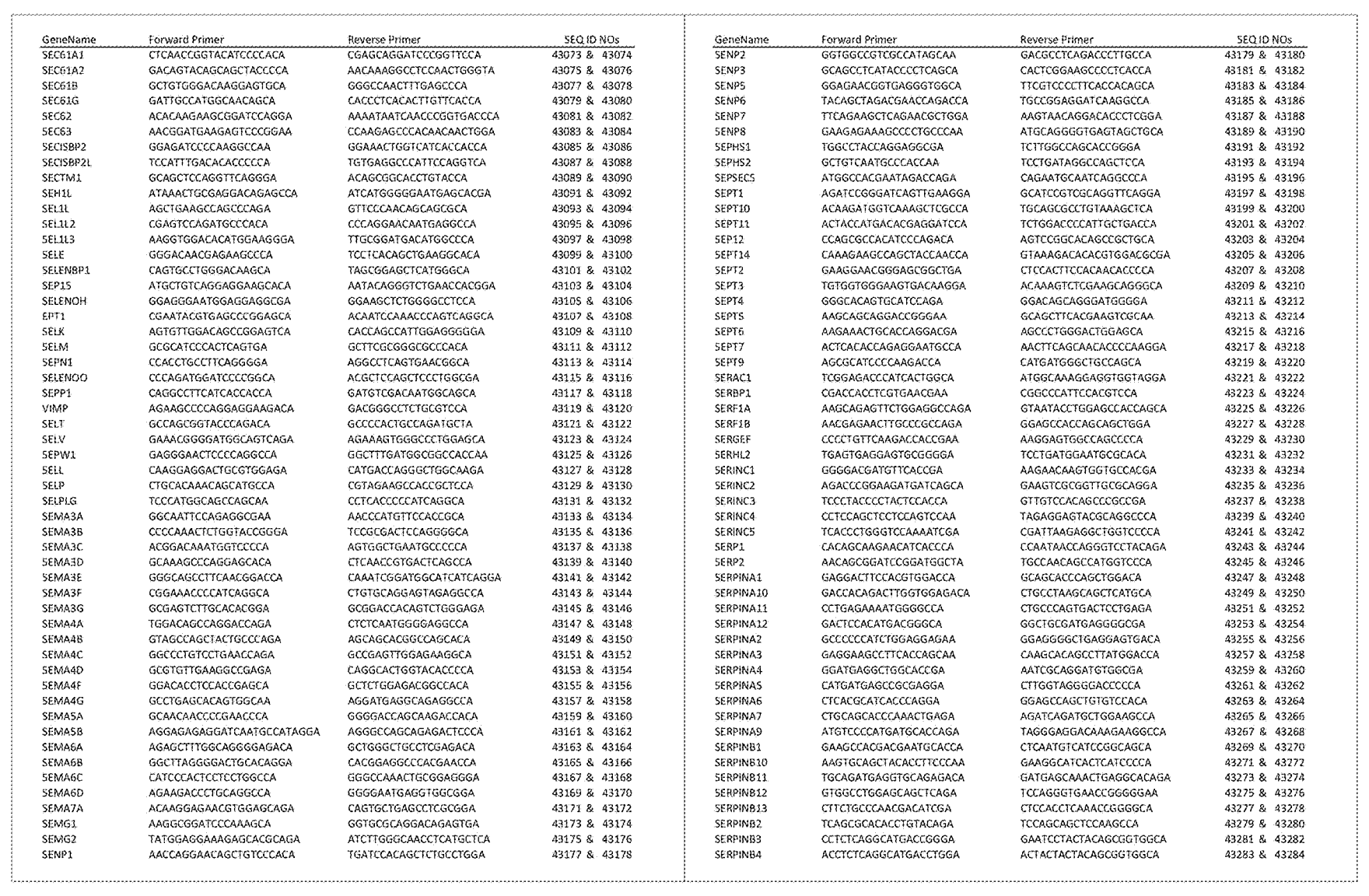
Figure 1:
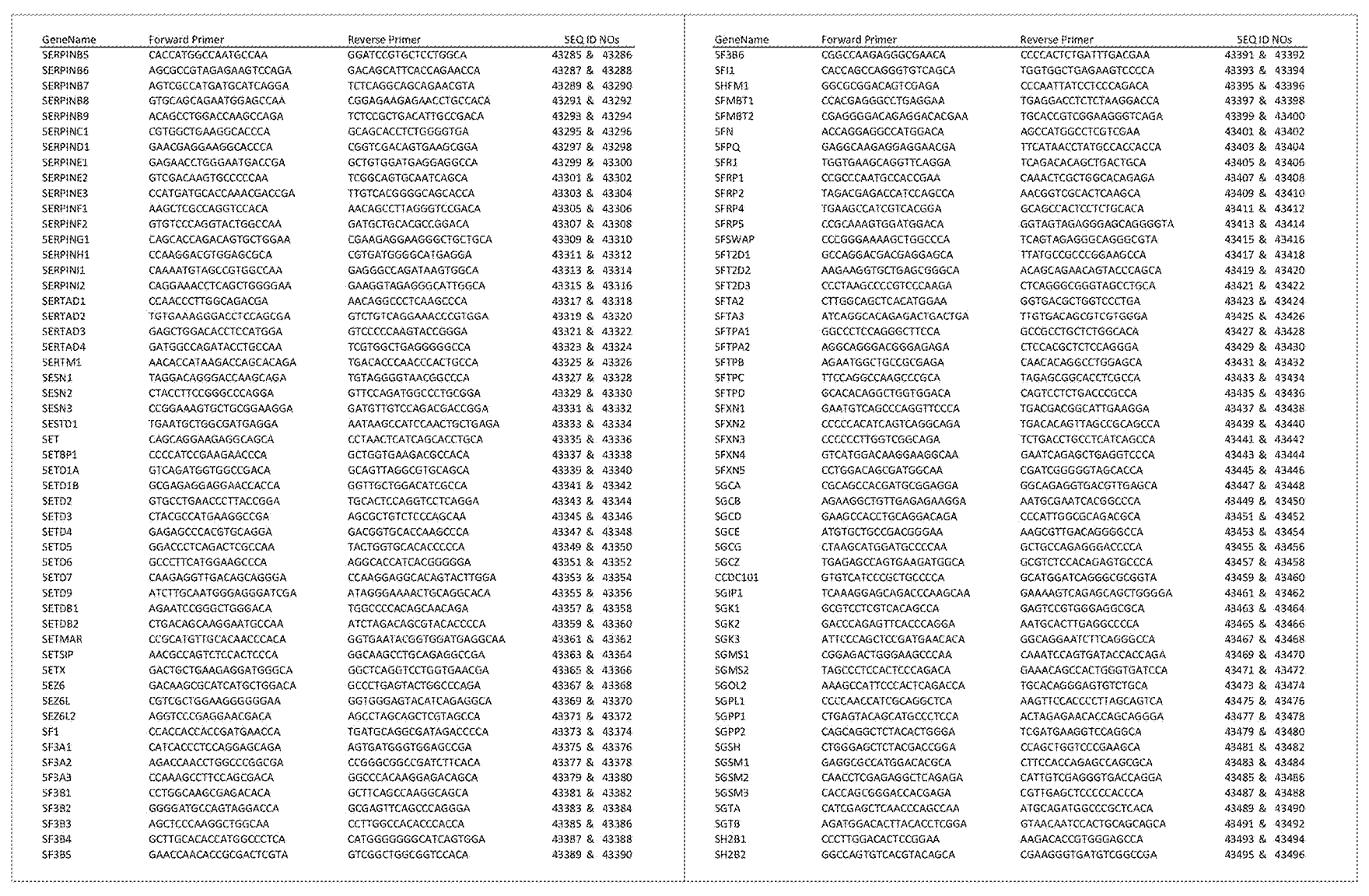
Figure 1:
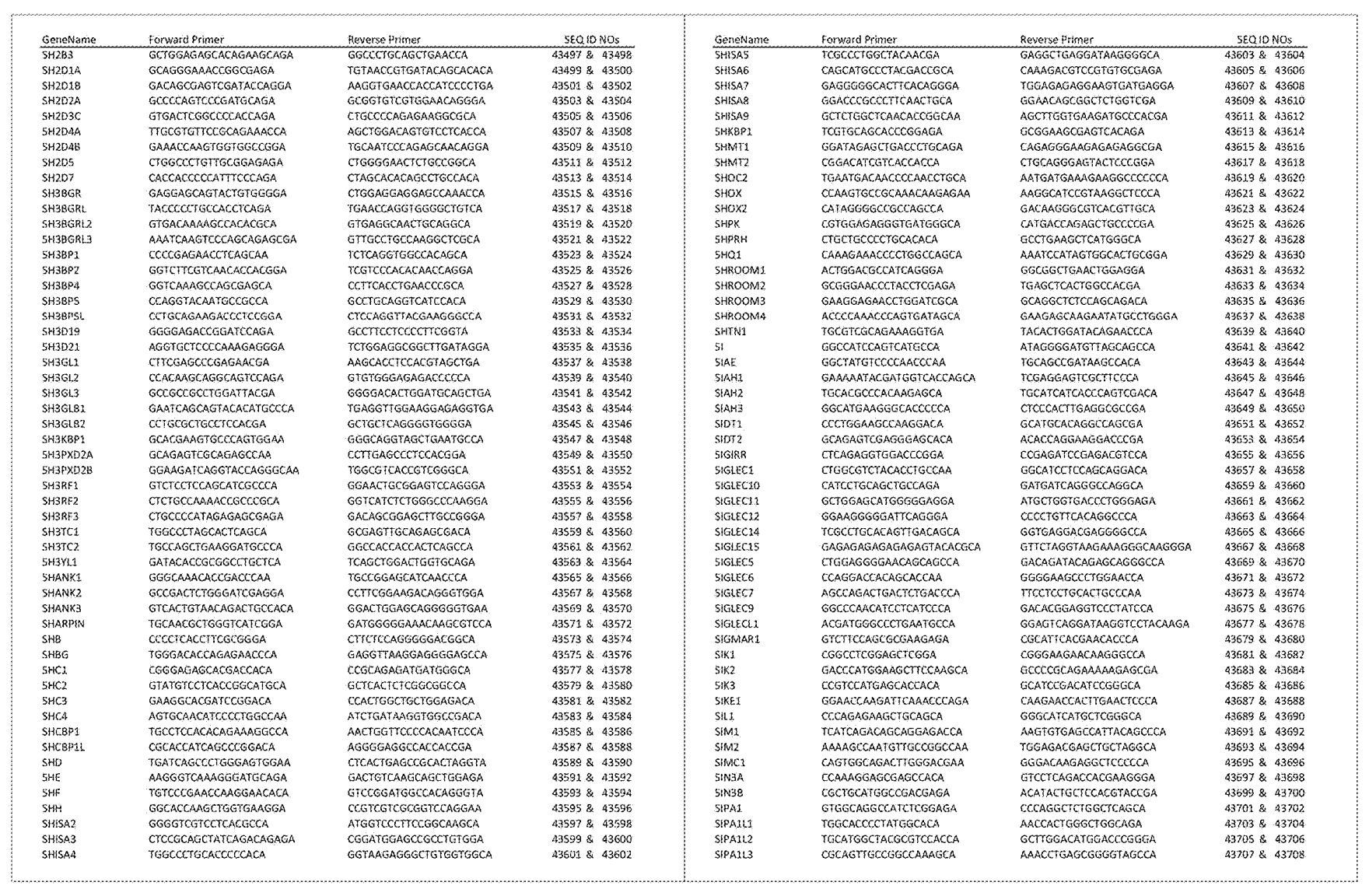
Figure 1:
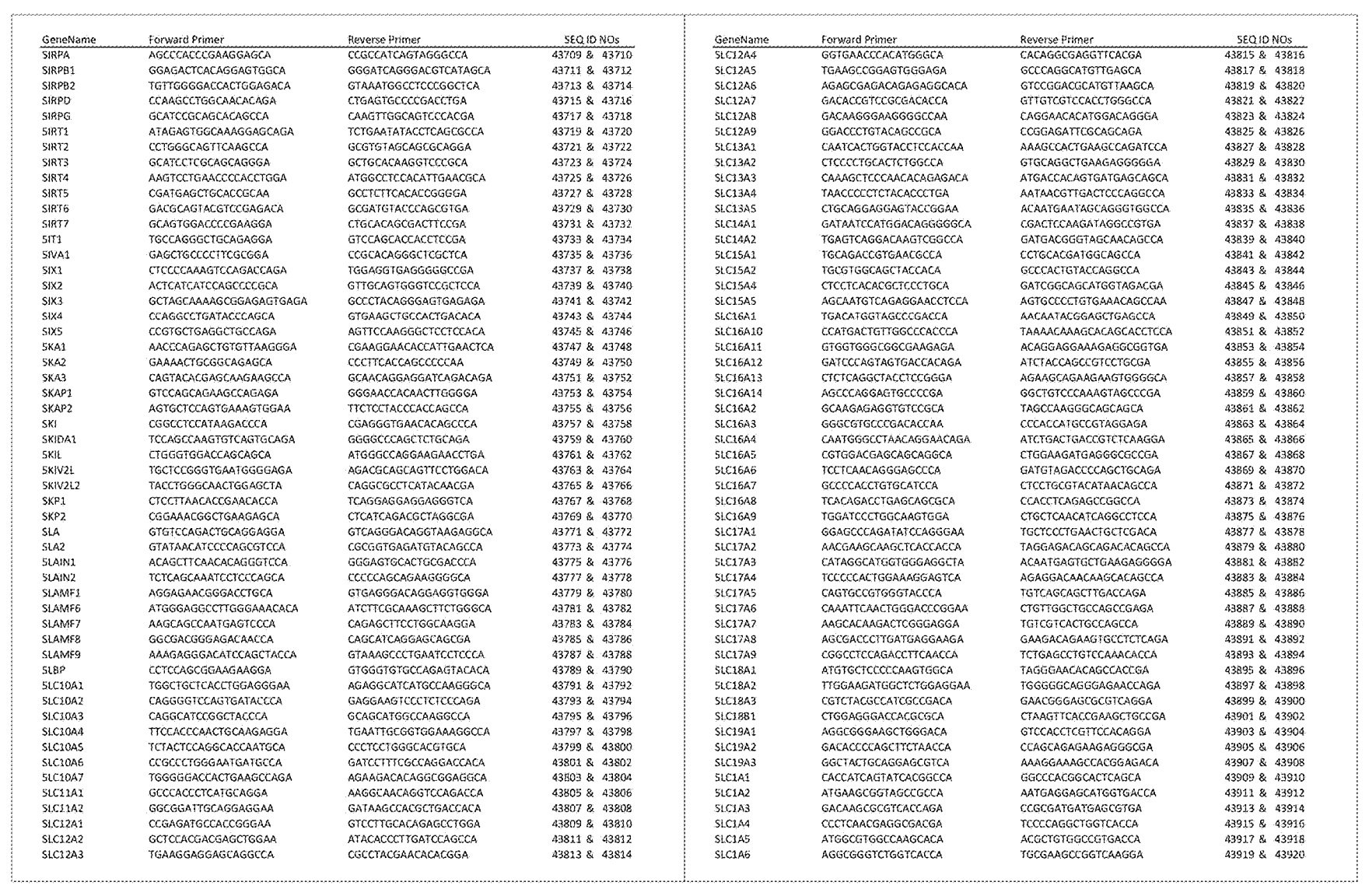
Figure 1:
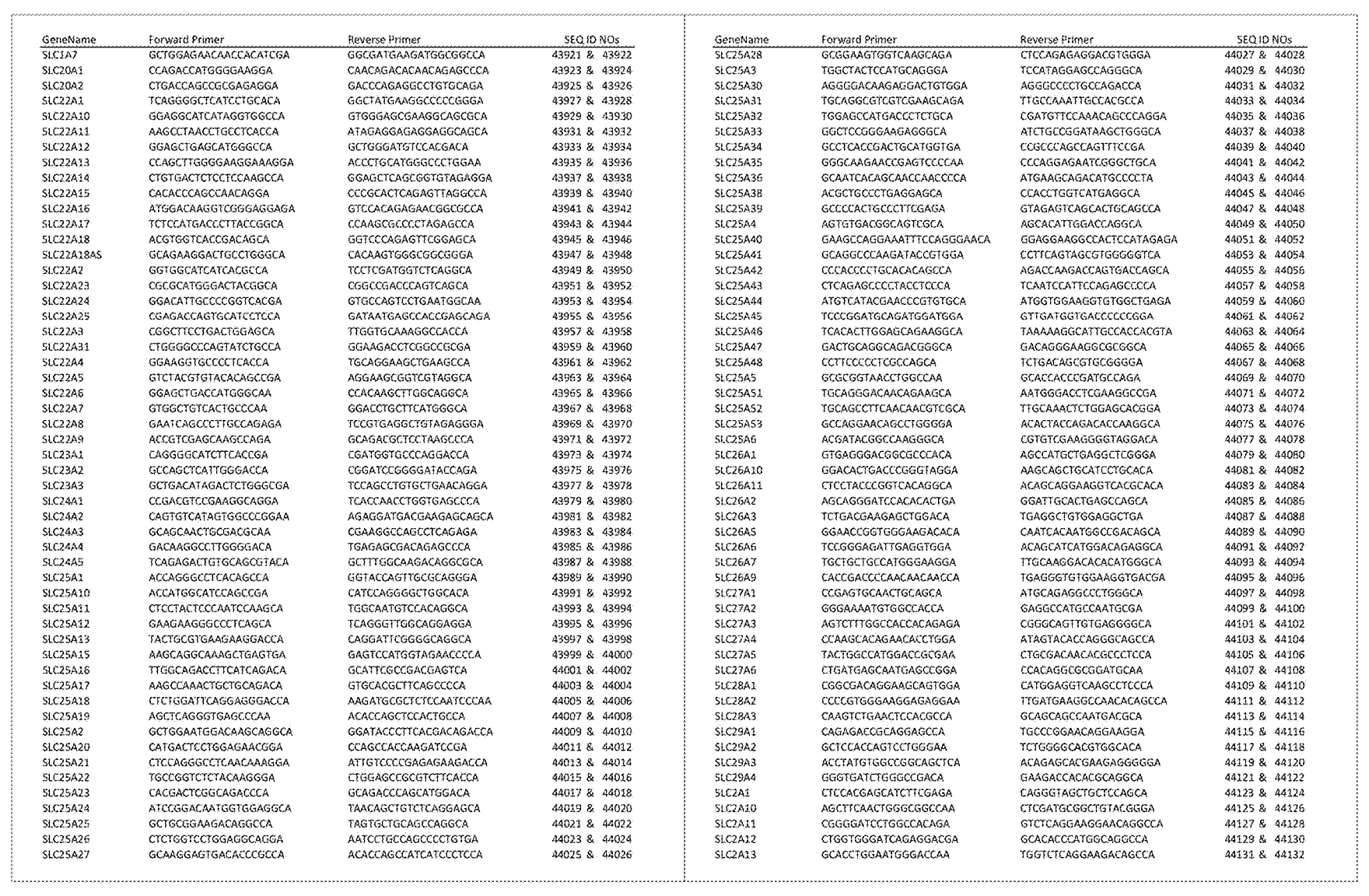
Figure 1:
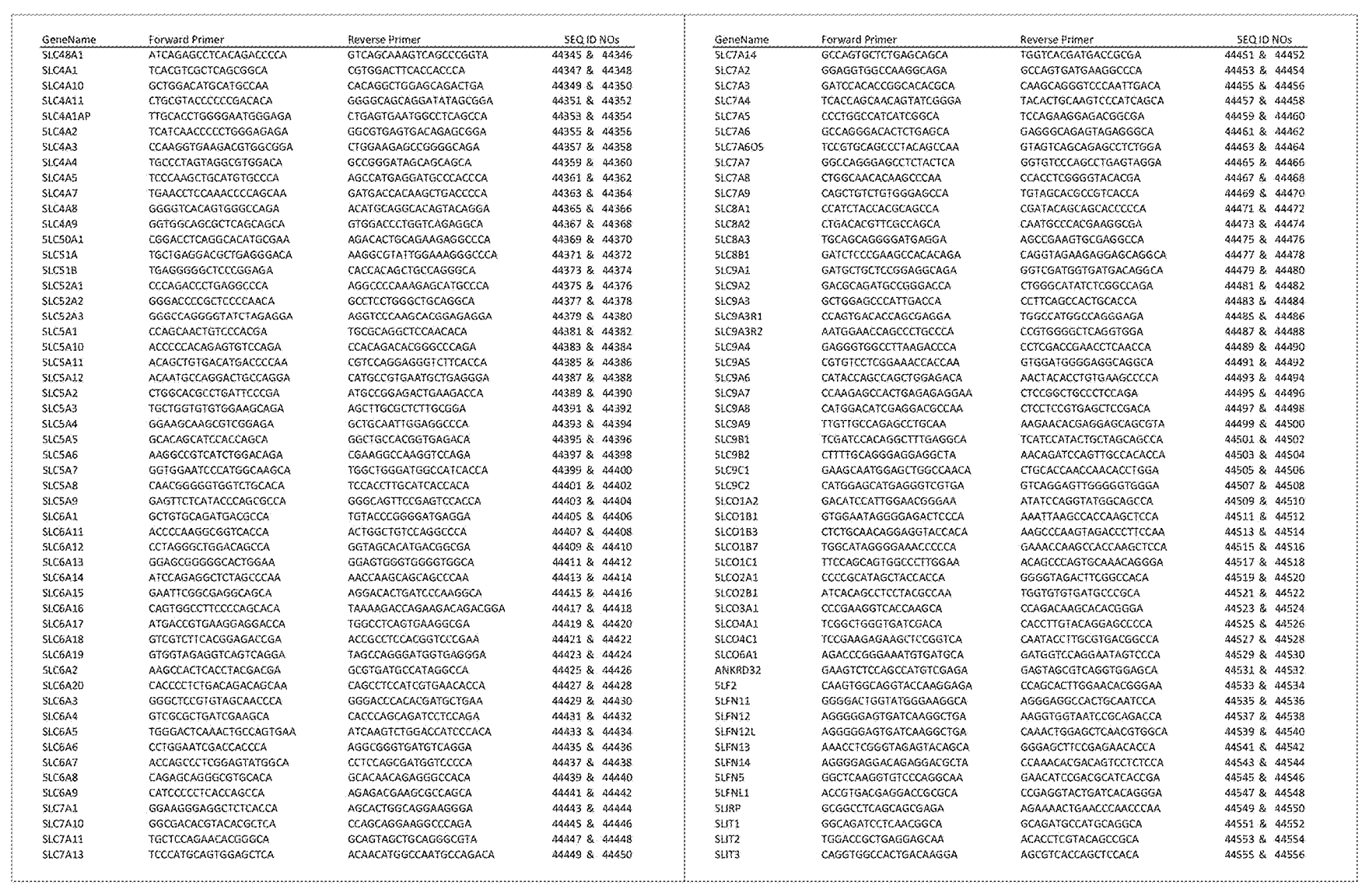
Figure 1:
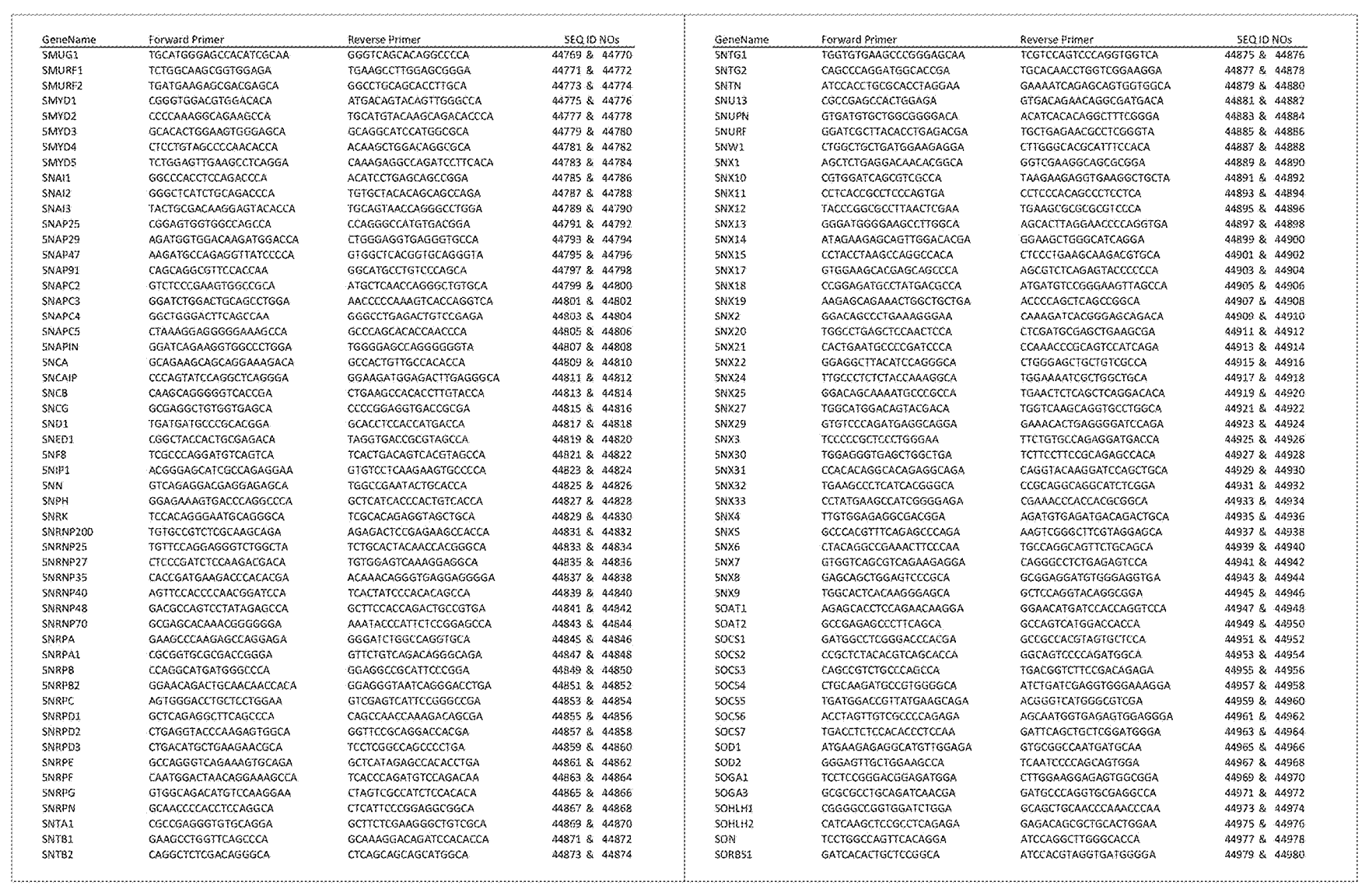
Figure 1:
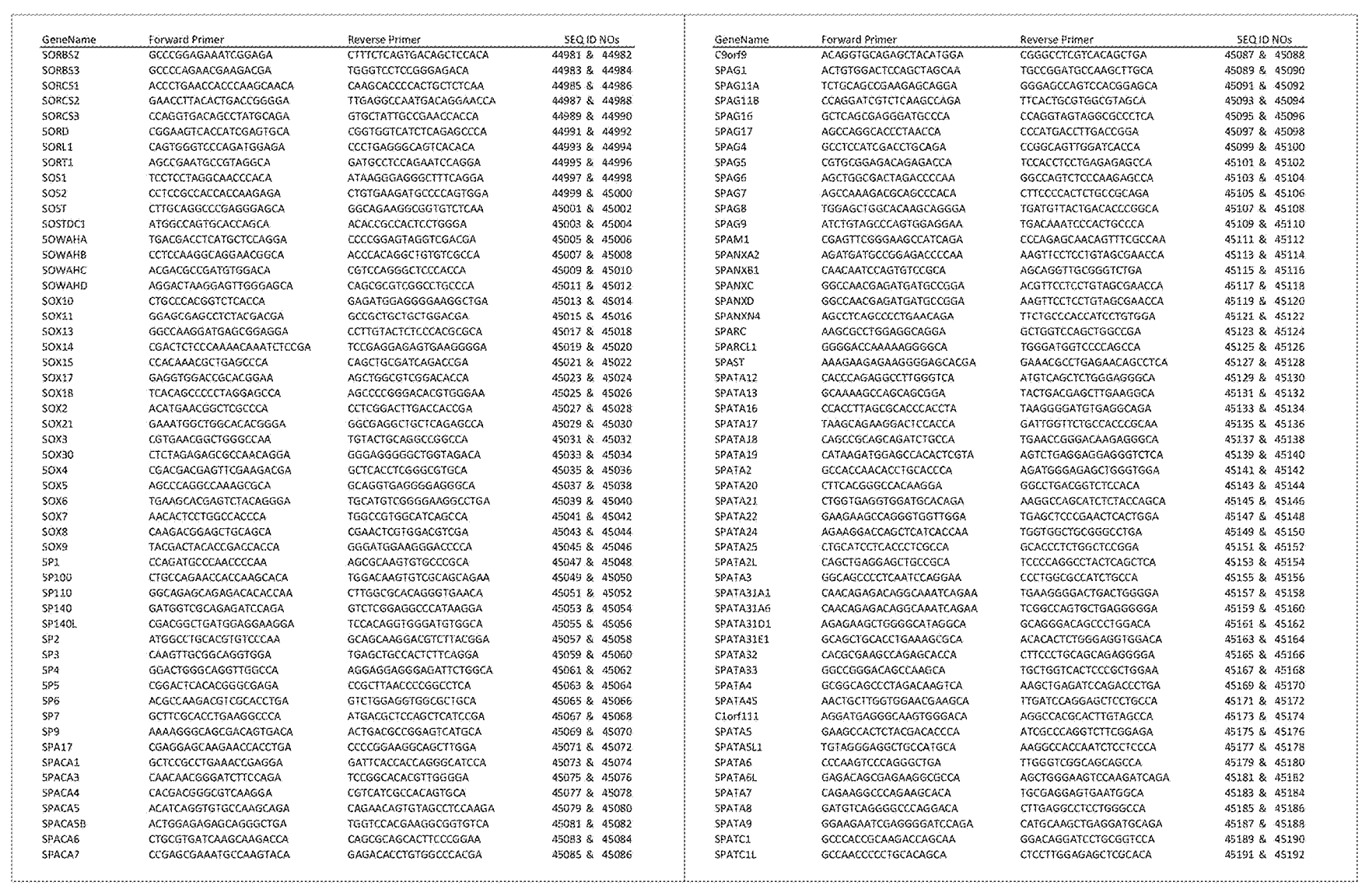
Figure 1:
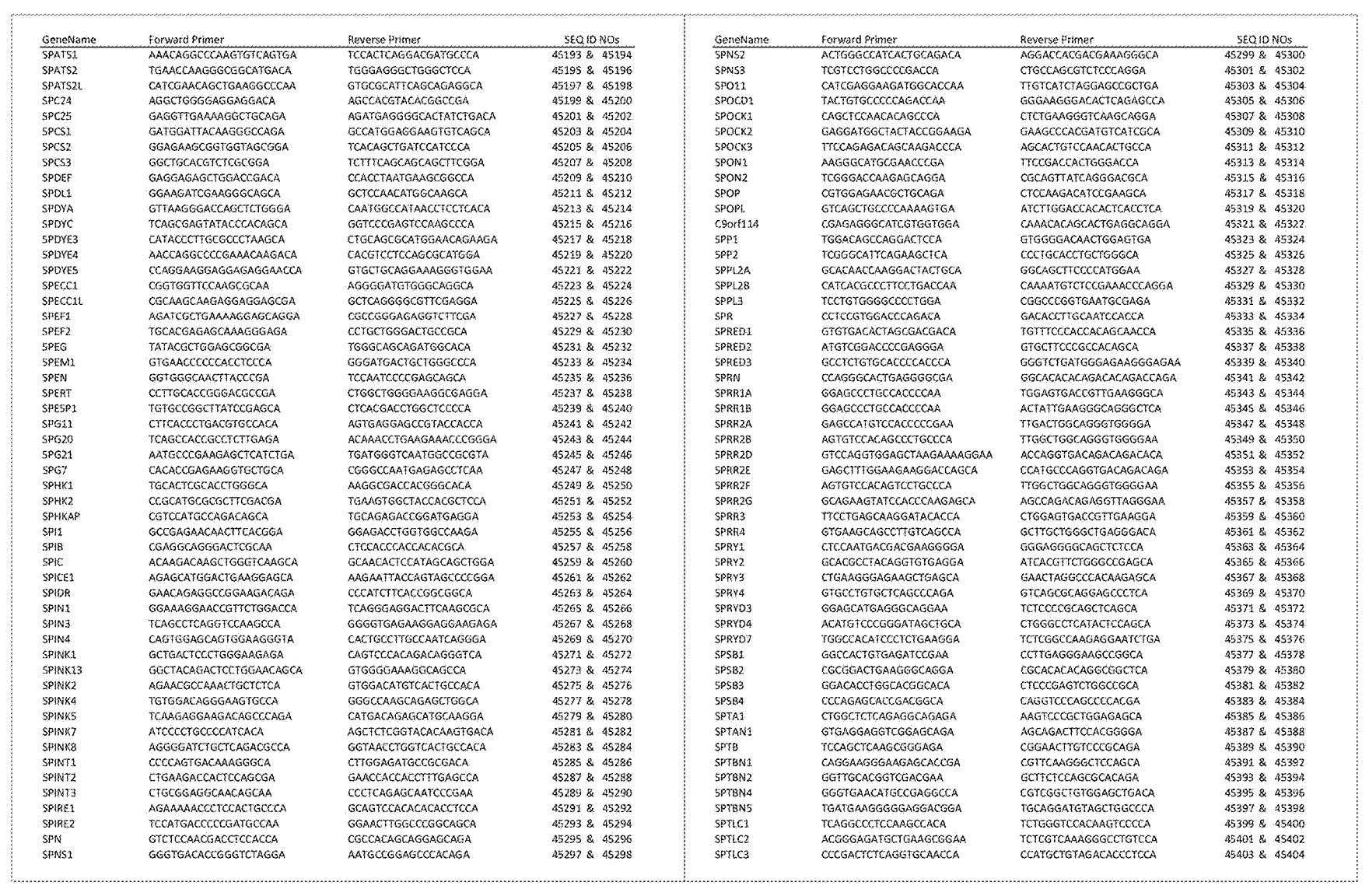
Figure 1:
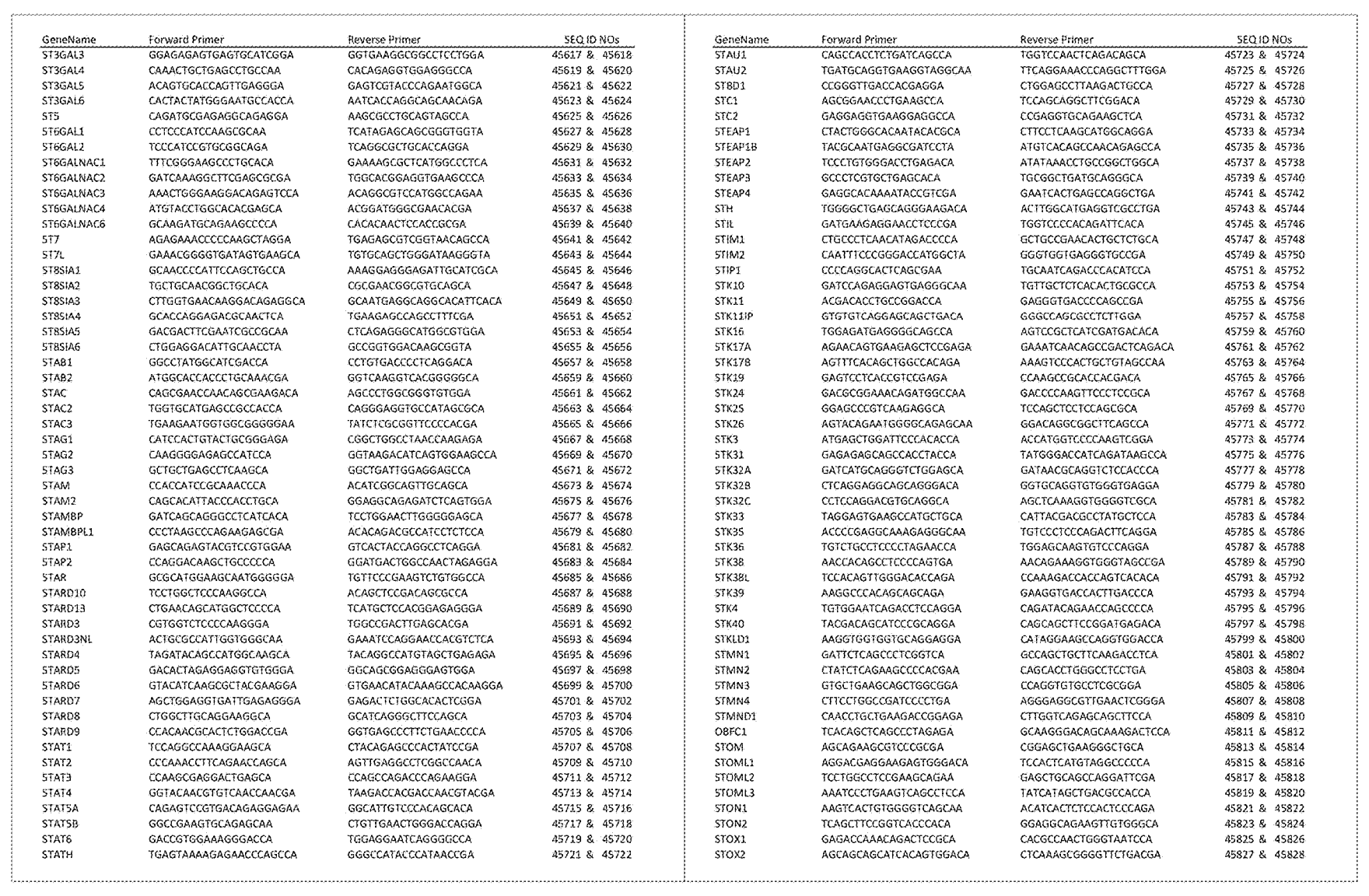
Figure 1:
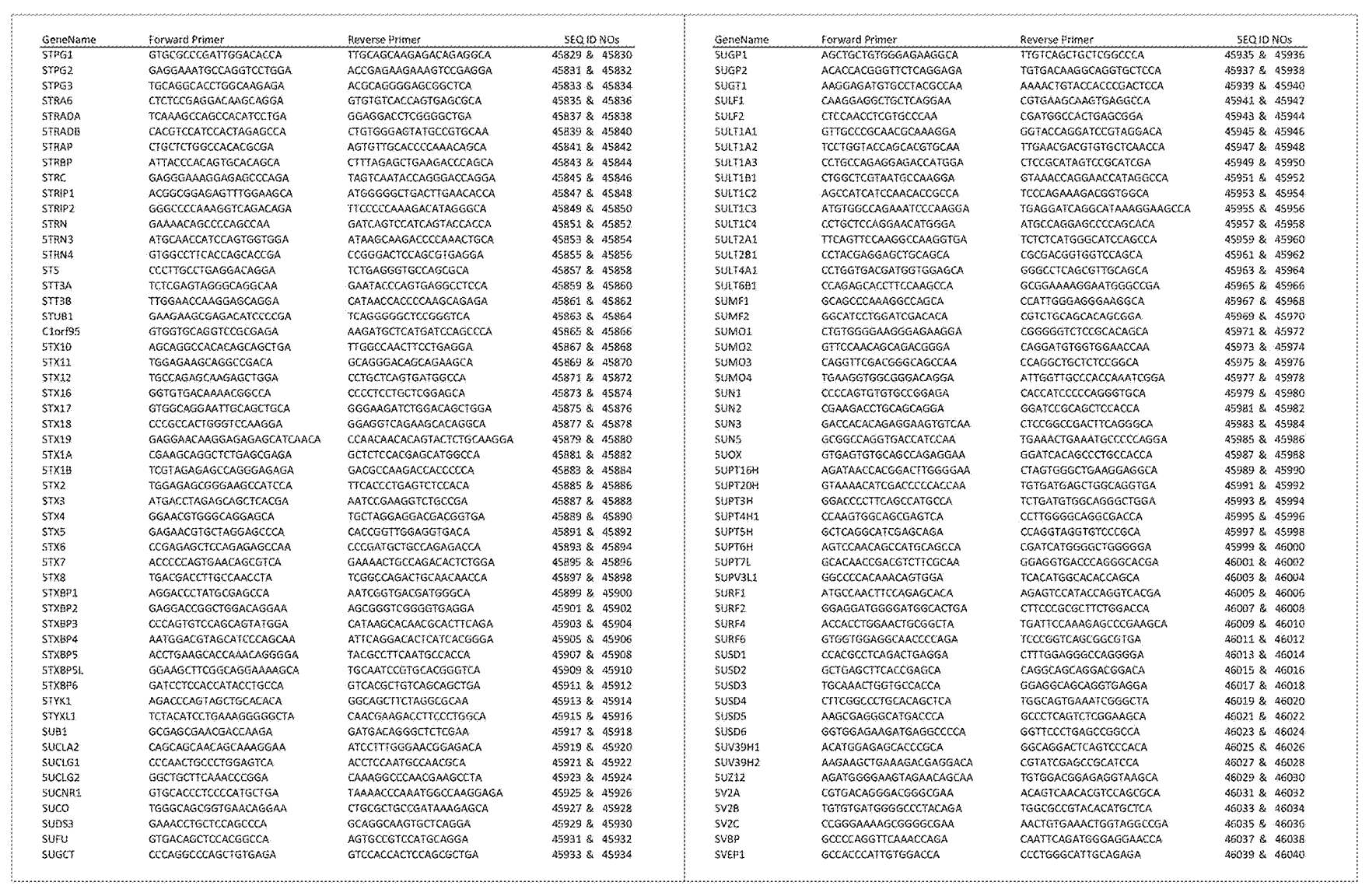
Figure 1:
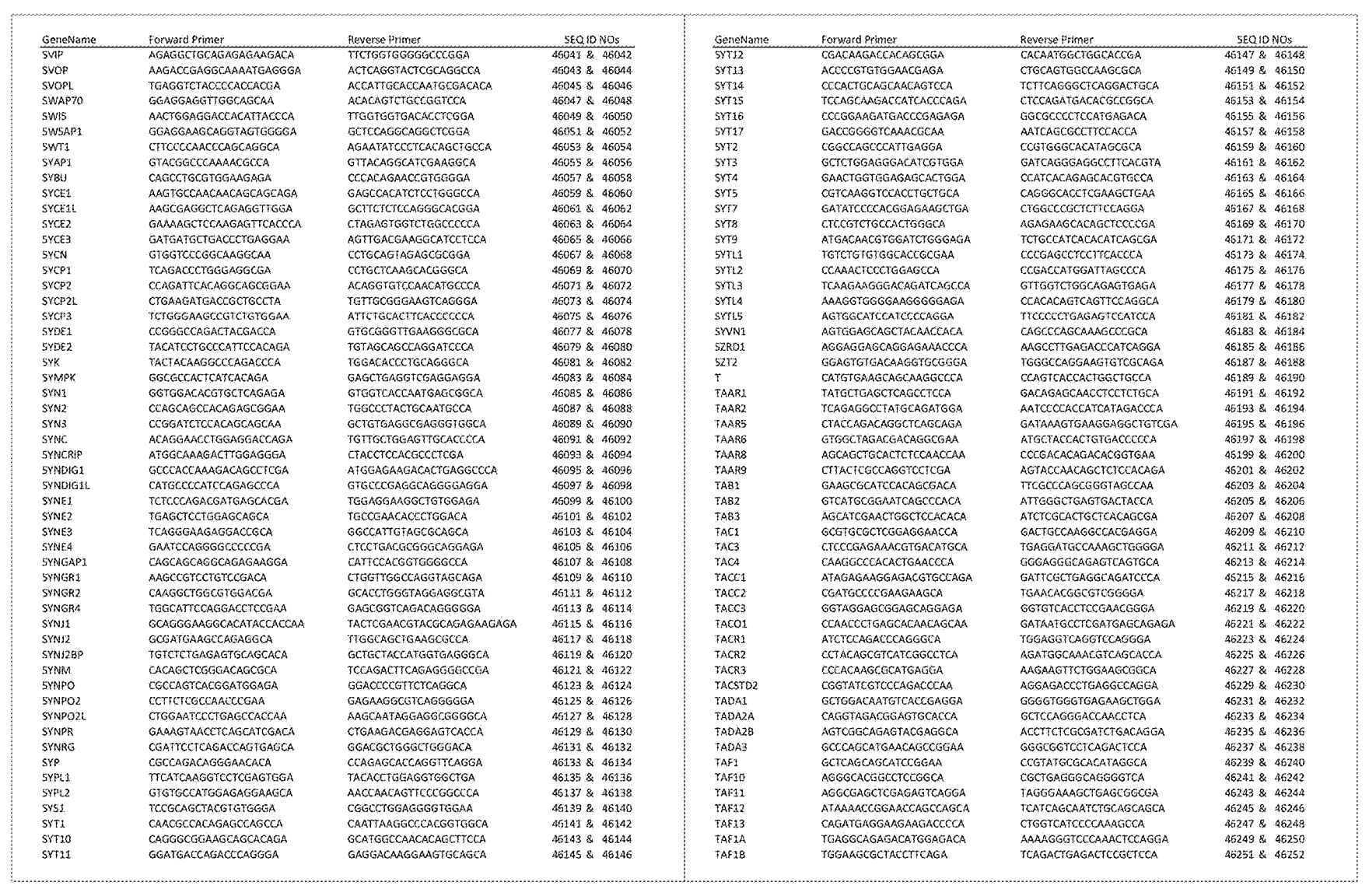
Figure 1:
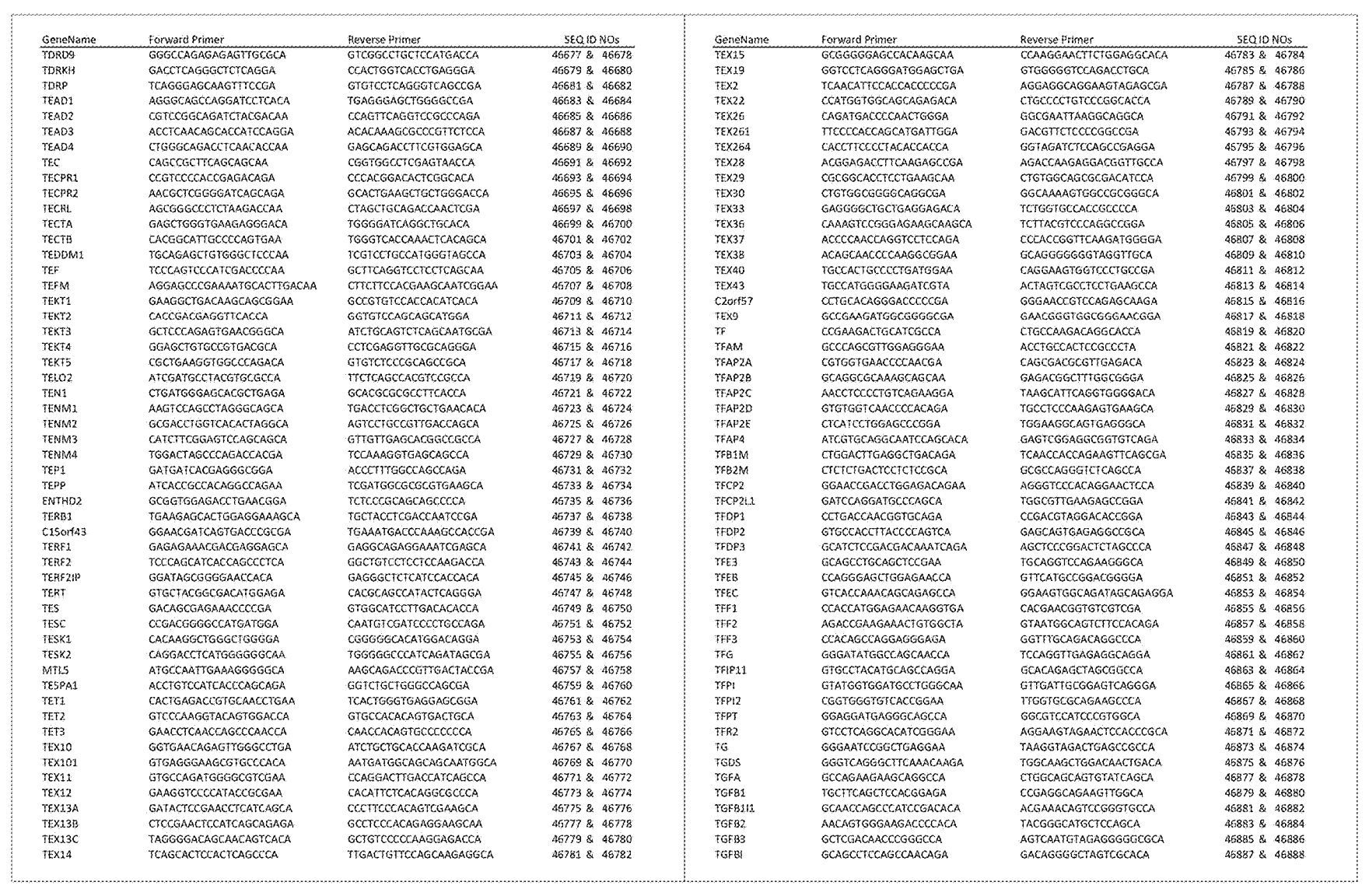
Figure 1:
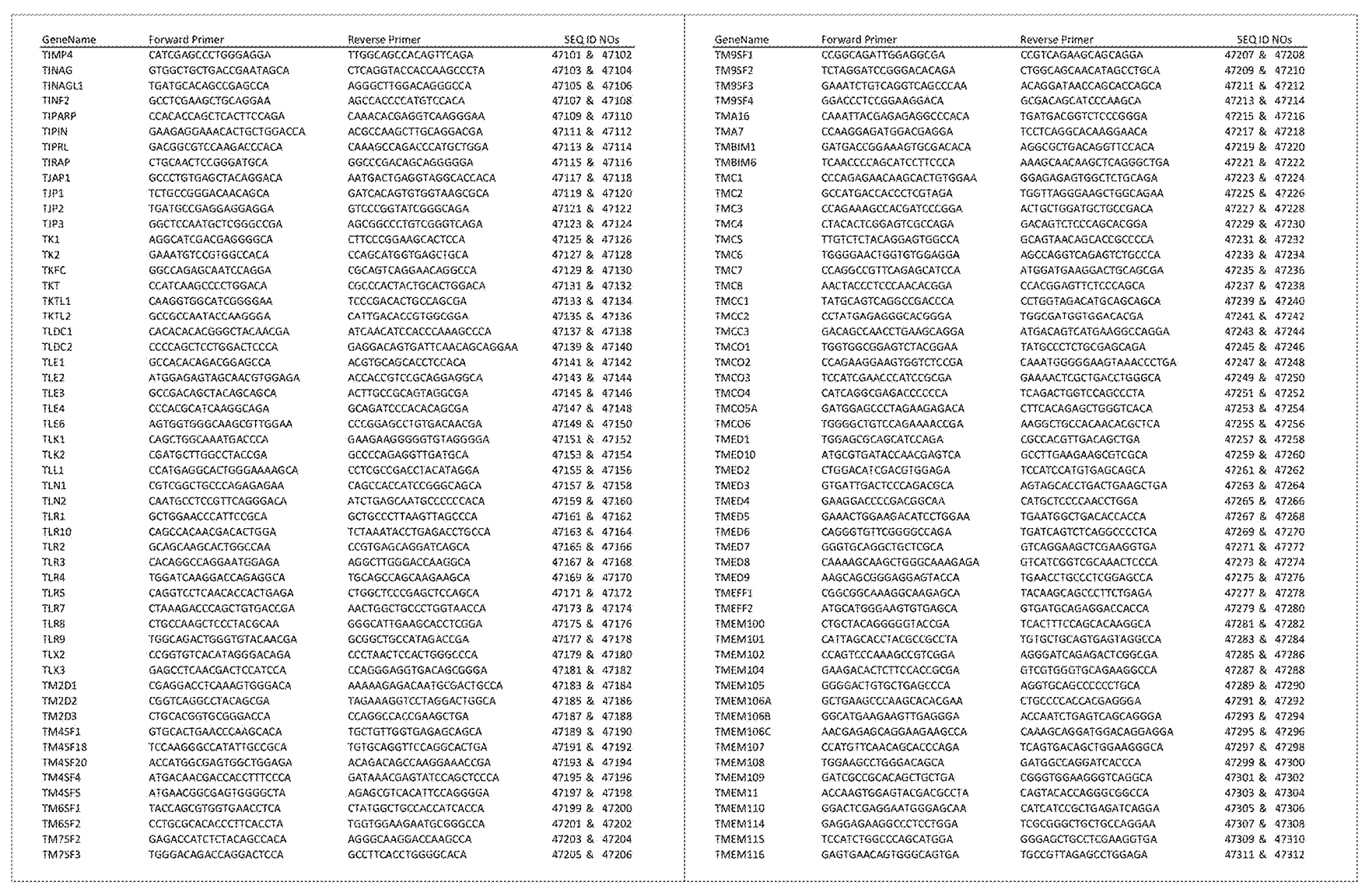
Figure 1:
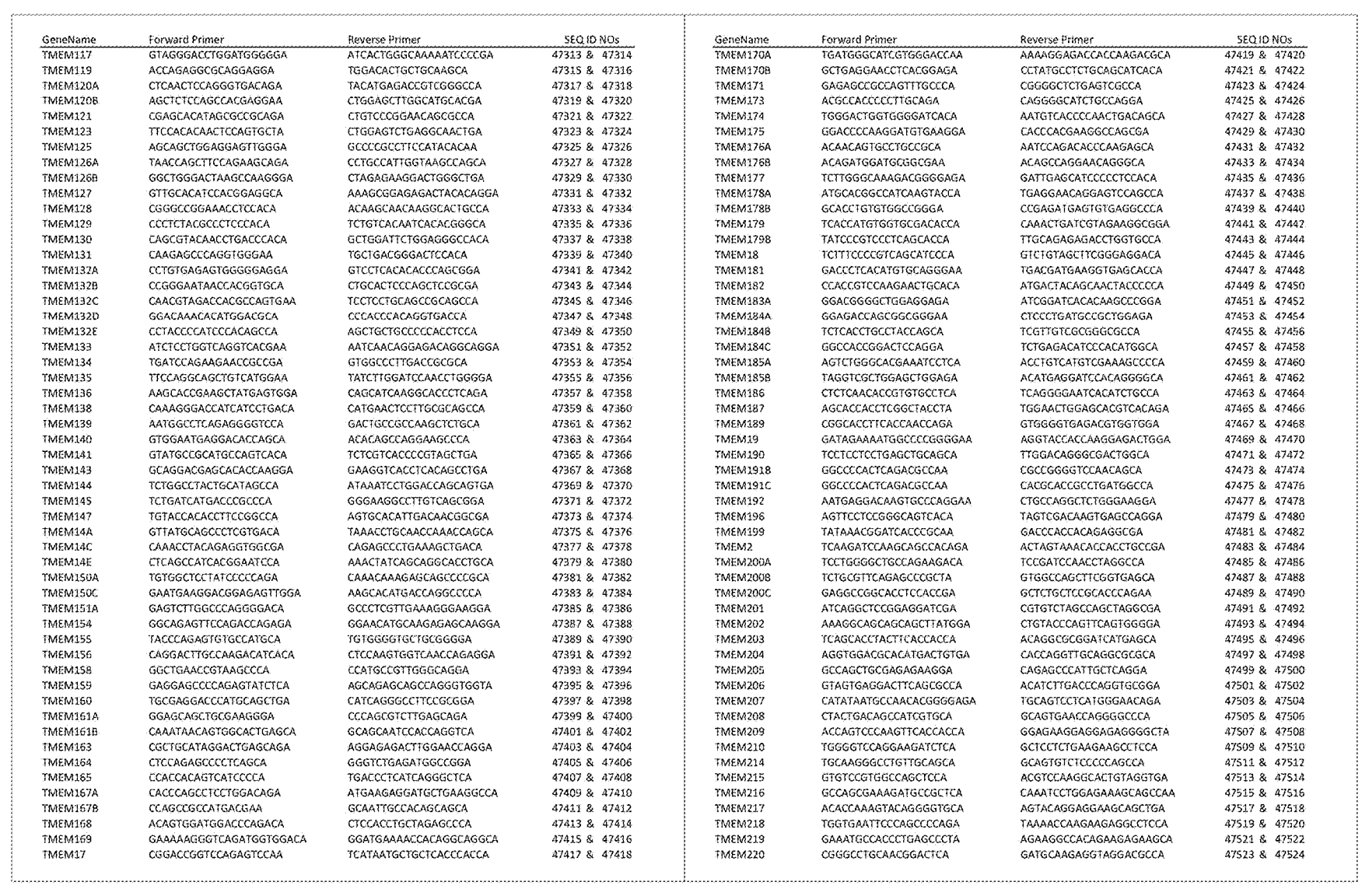
Figure 1:
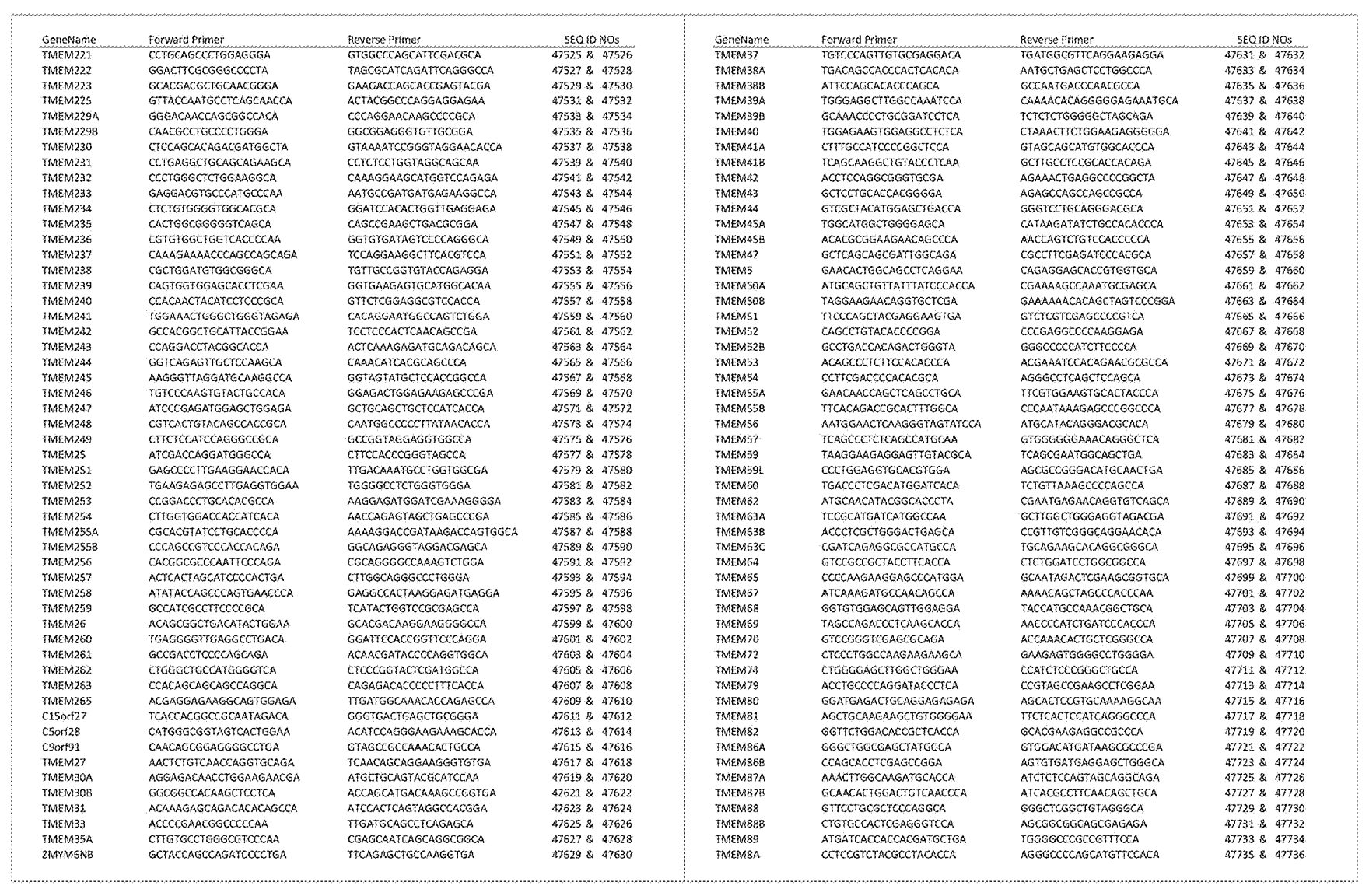
Figure 1:
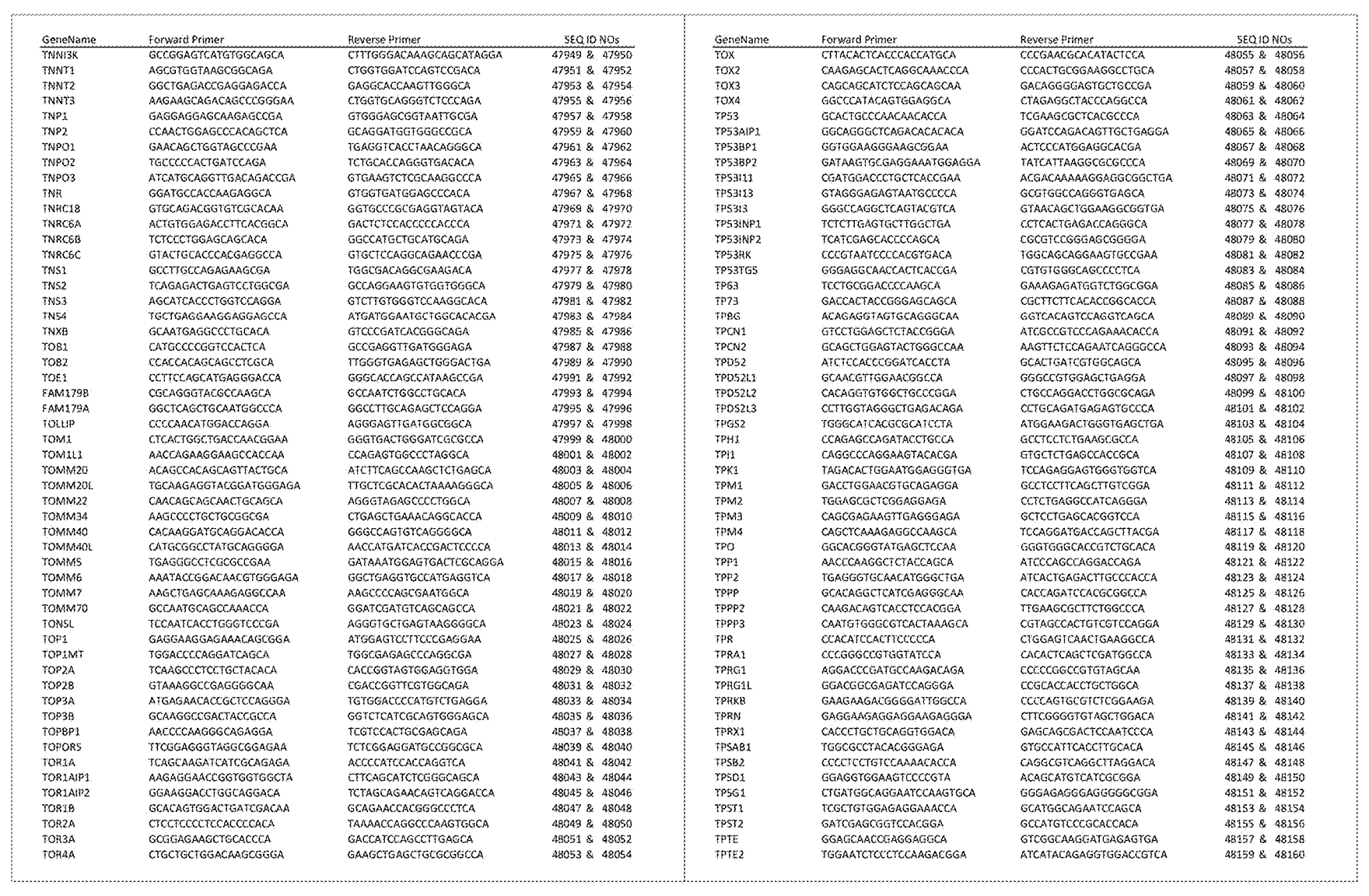
Figure 1:
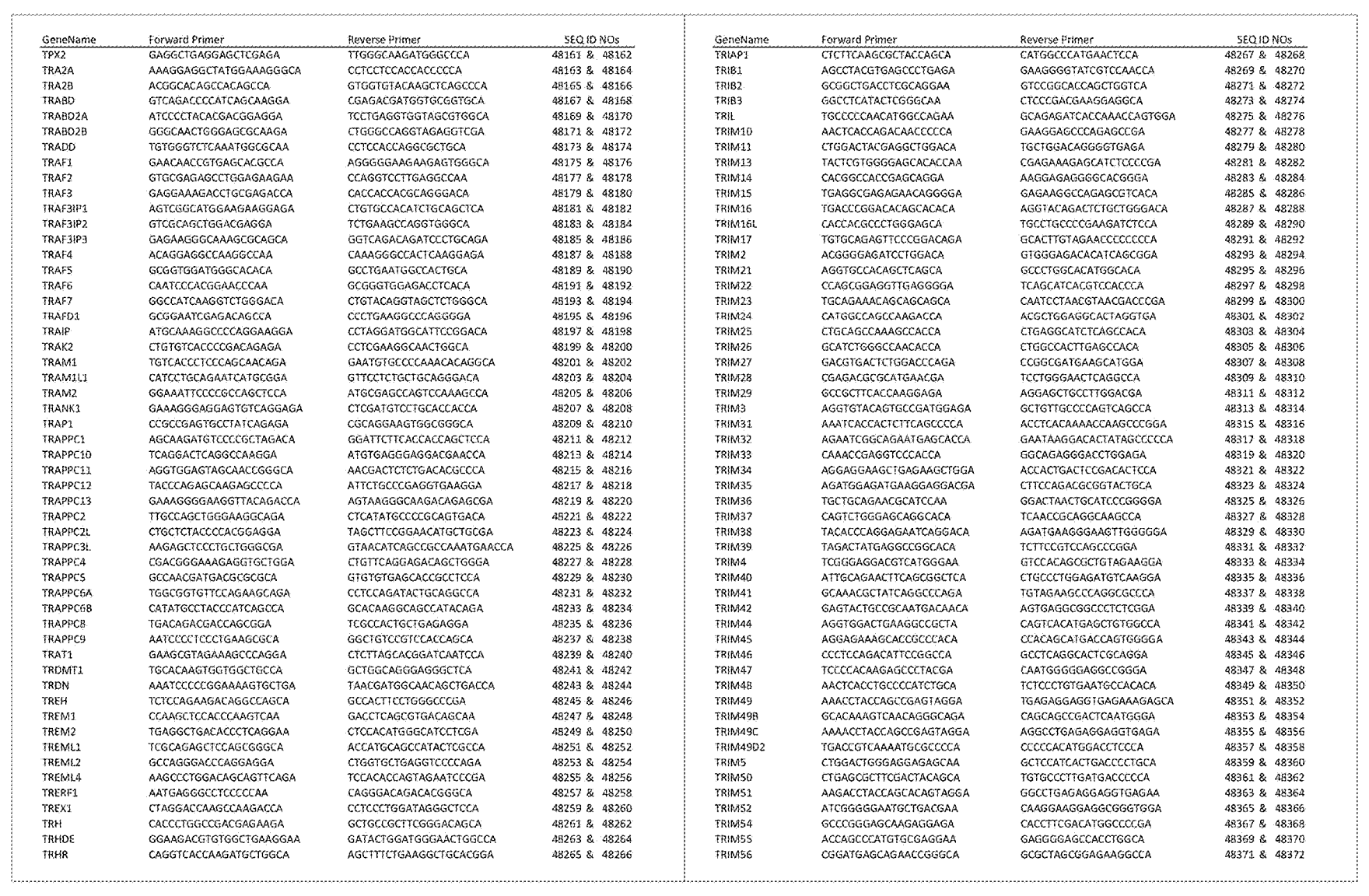
Figure 1:
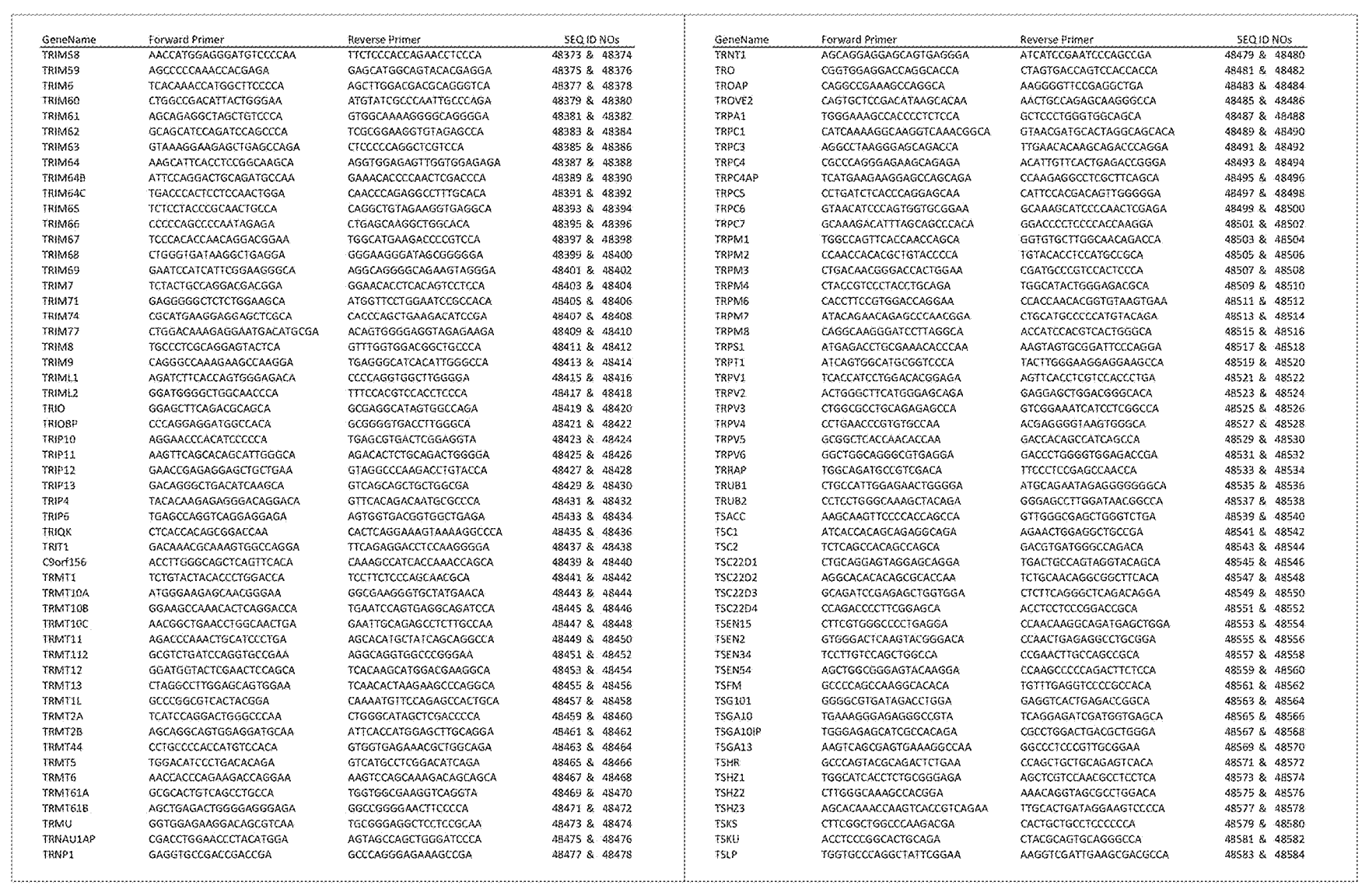
Figure 1:
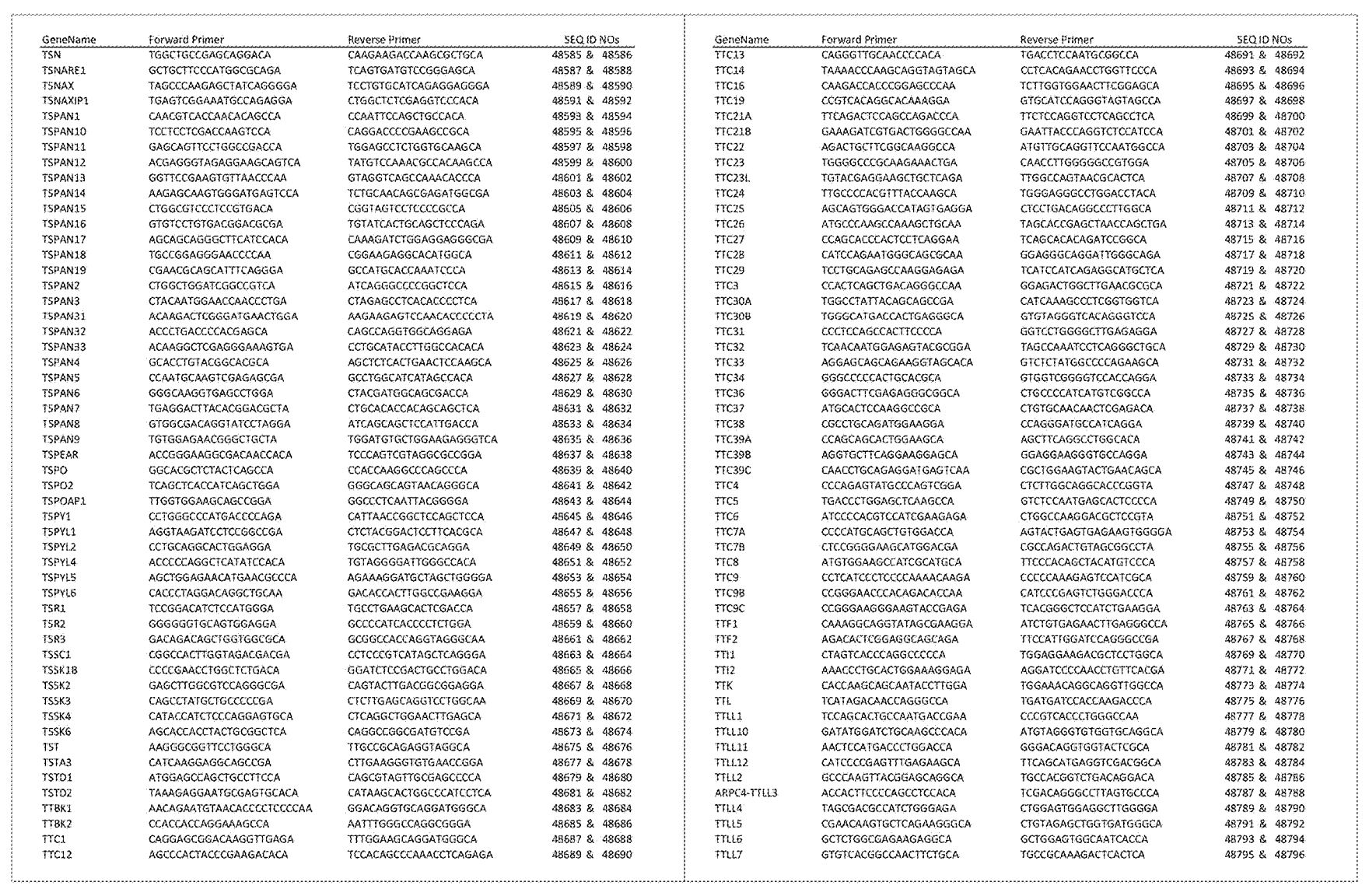
Figure 1:
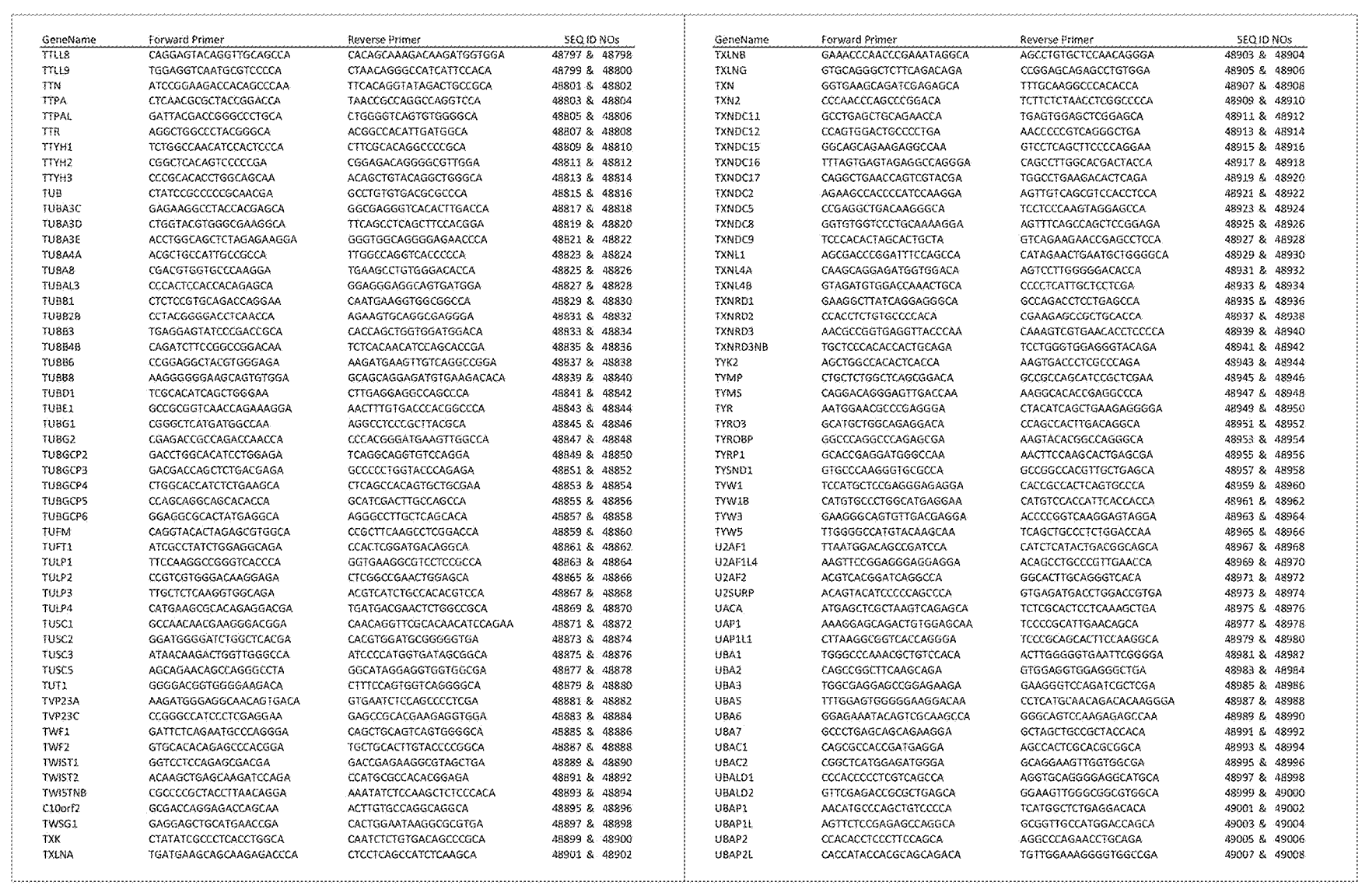
Figure 1:
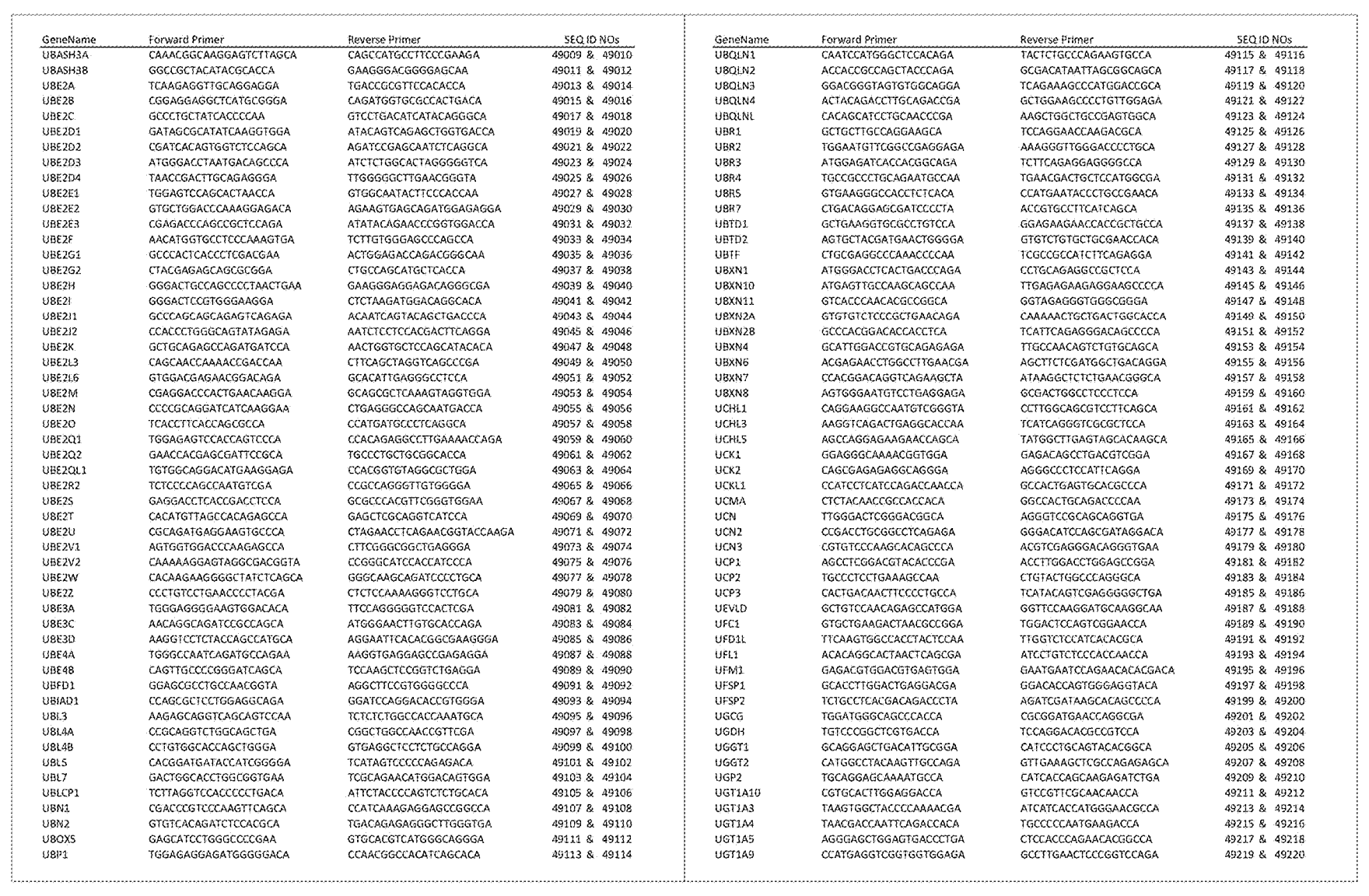
Figure 1:
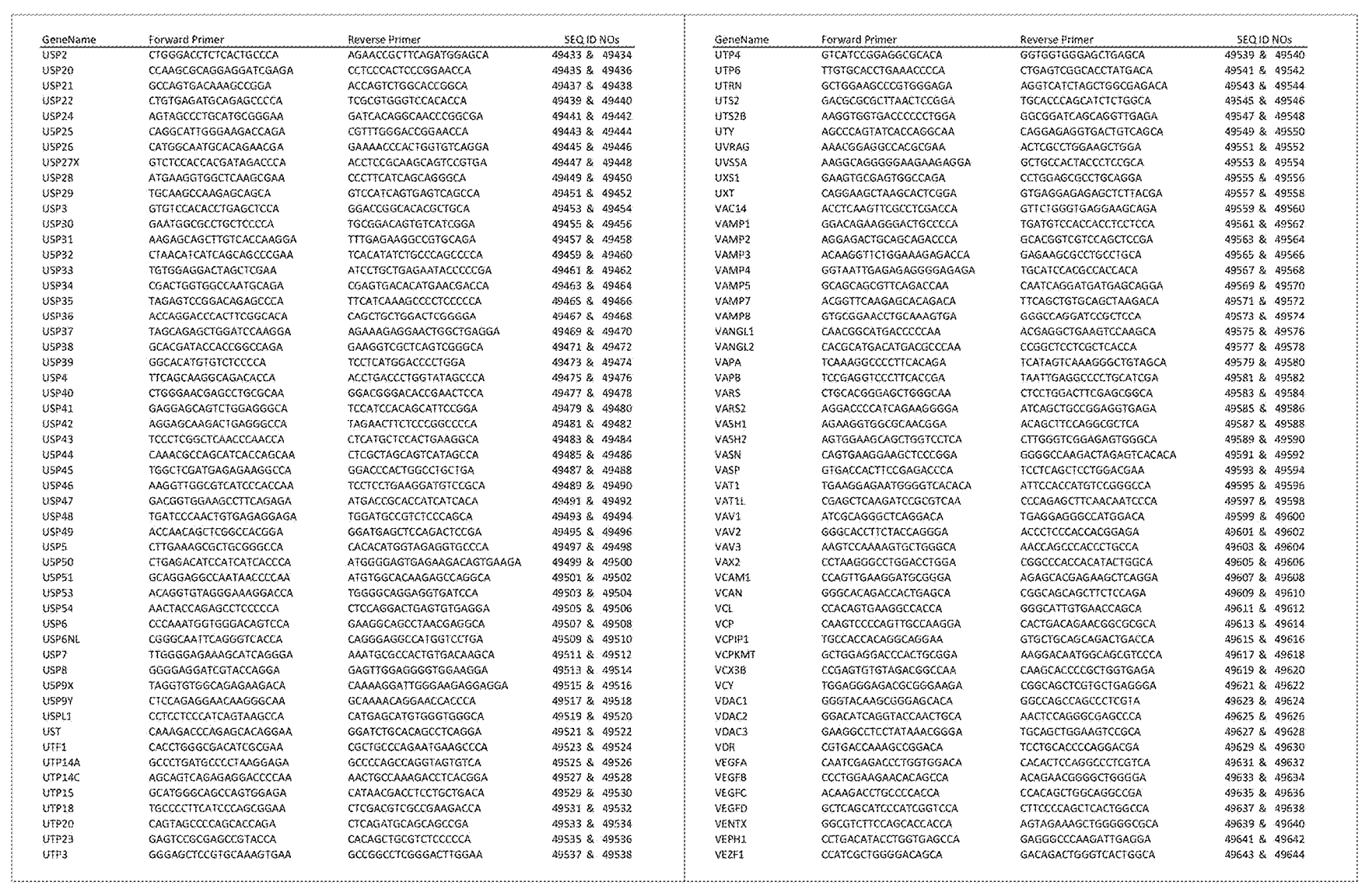
Figure 1:
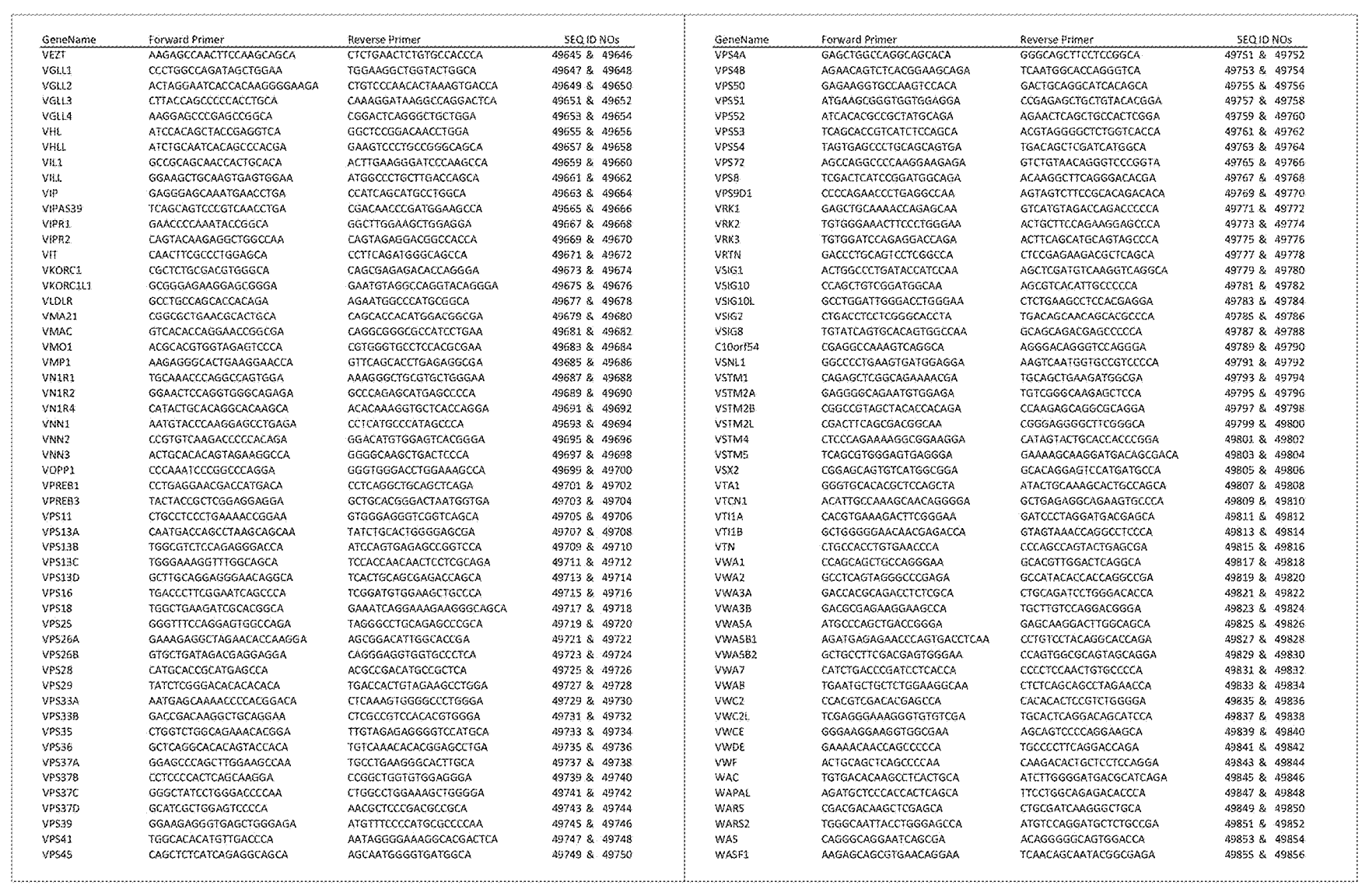
Figure 1:
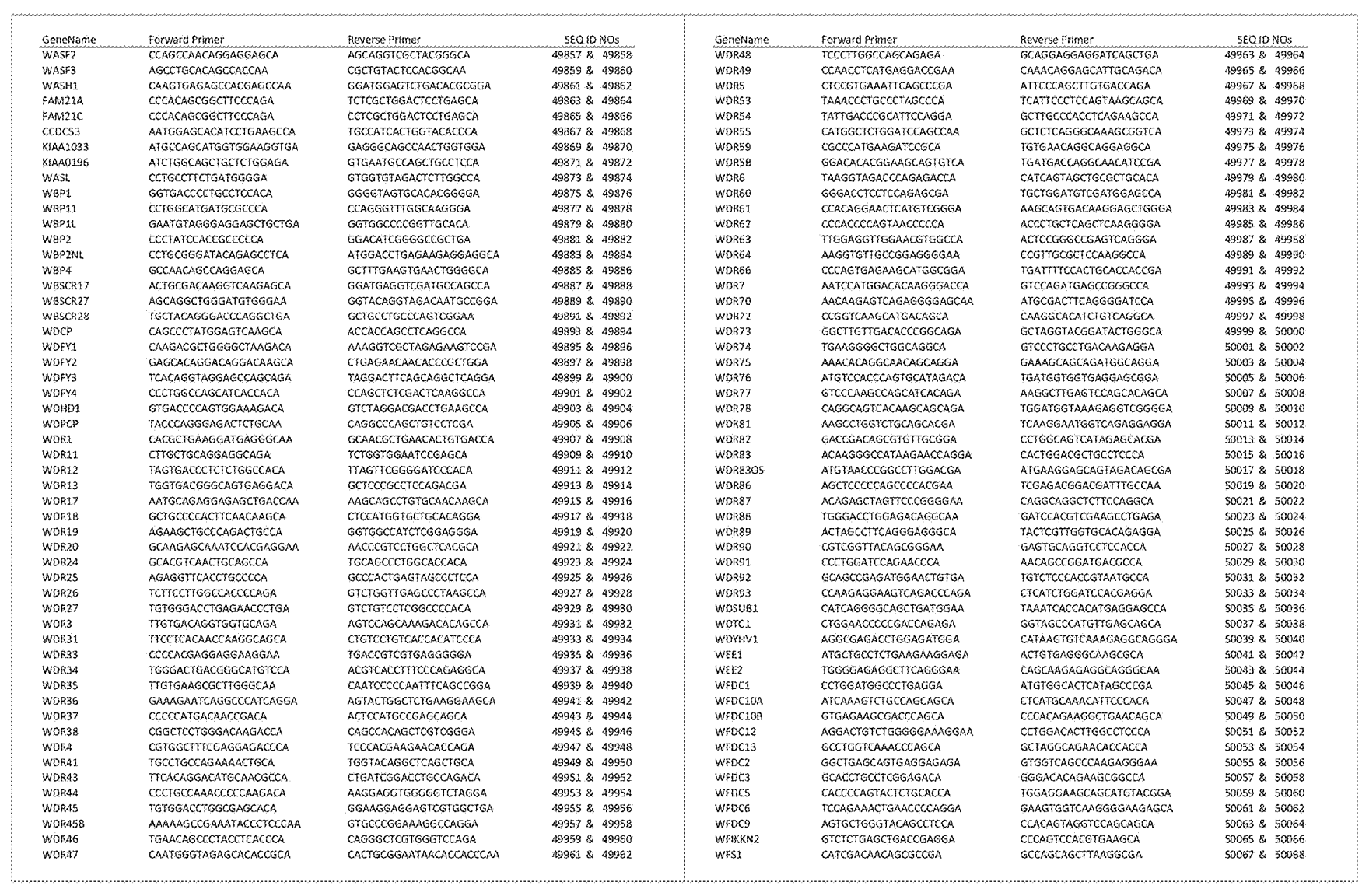
Figure 1:
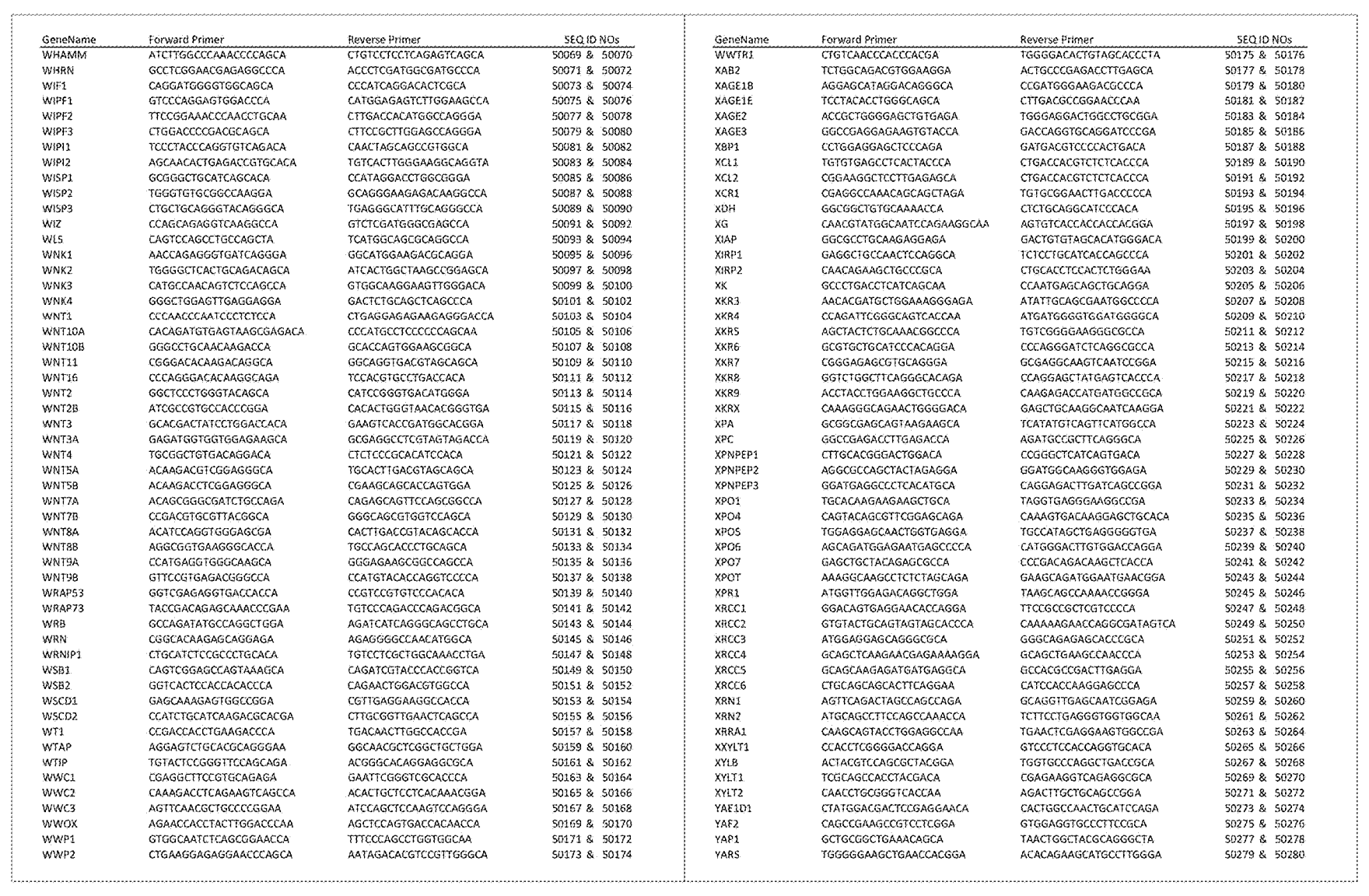
Figure 1:
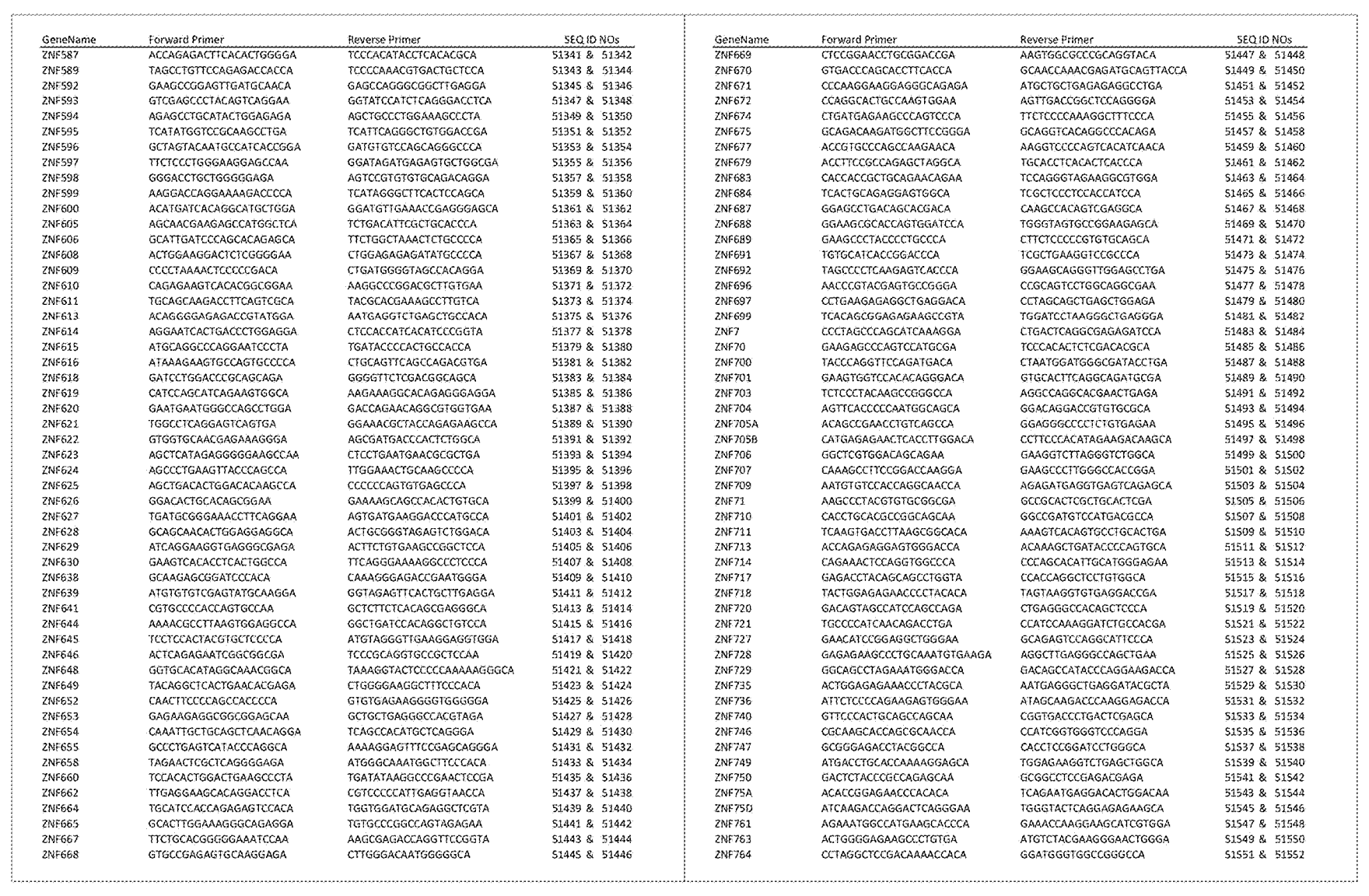
Figure 1:
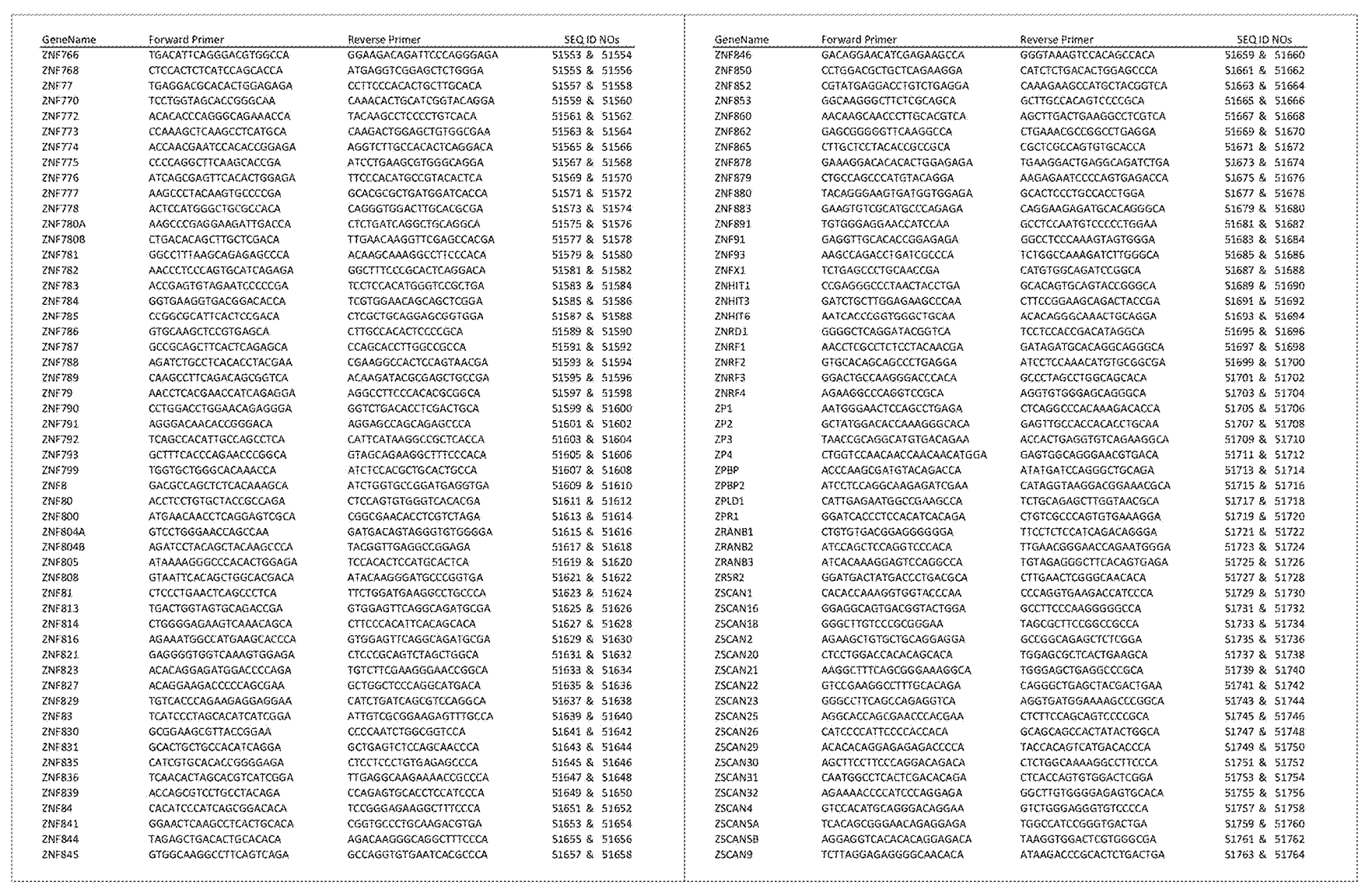
Figure 1:
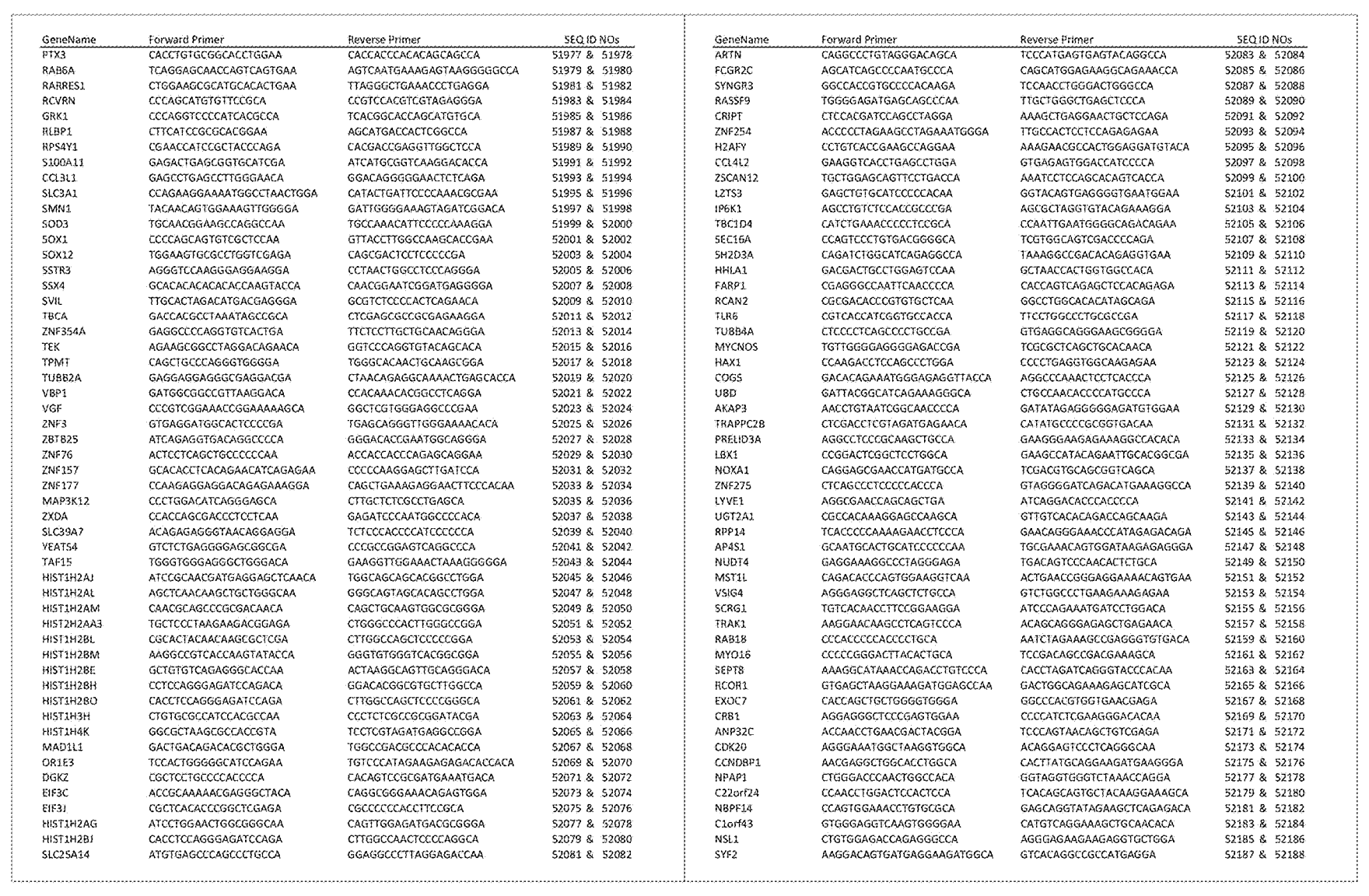
Figure 1:
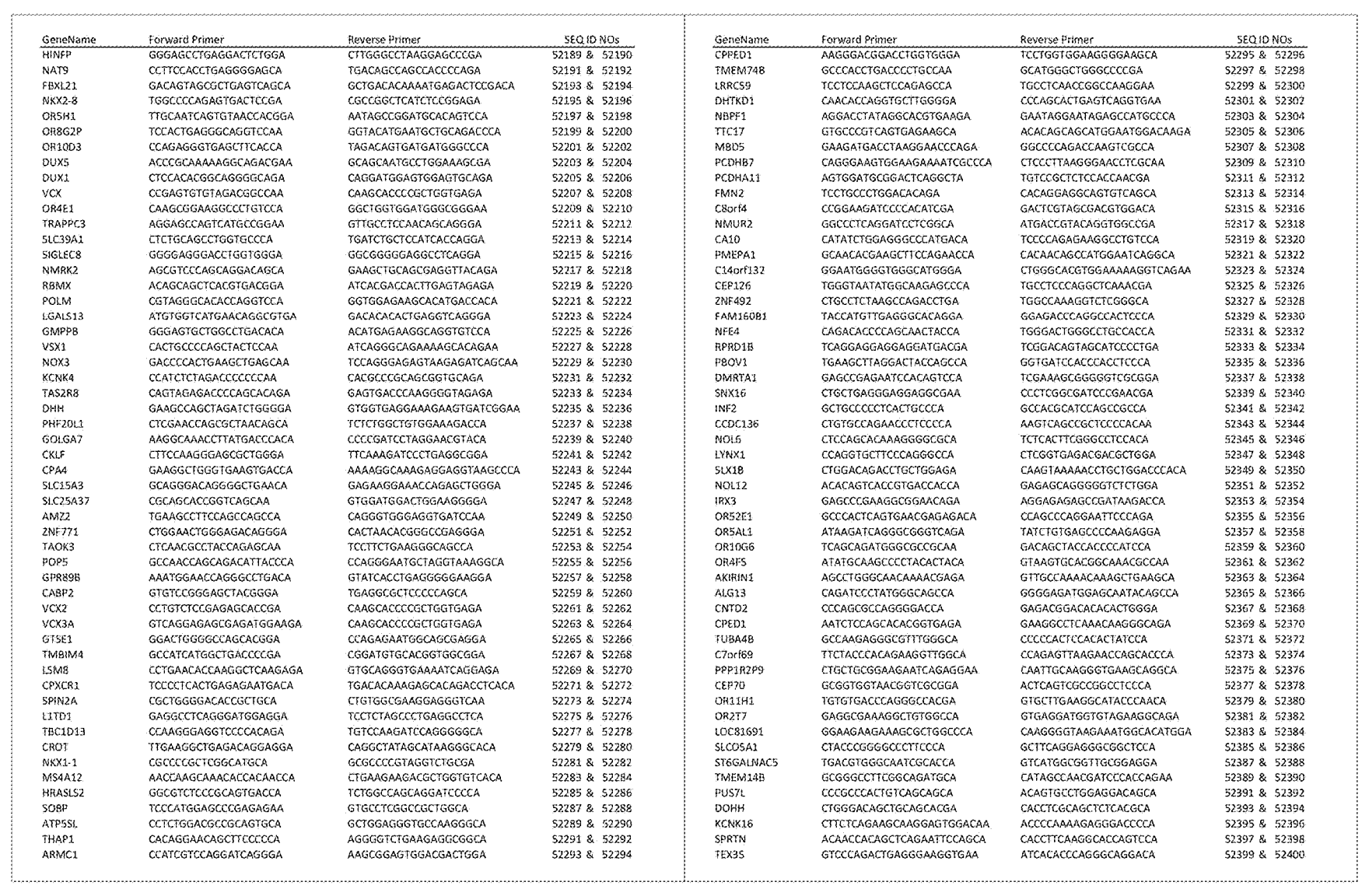
Figure 1:
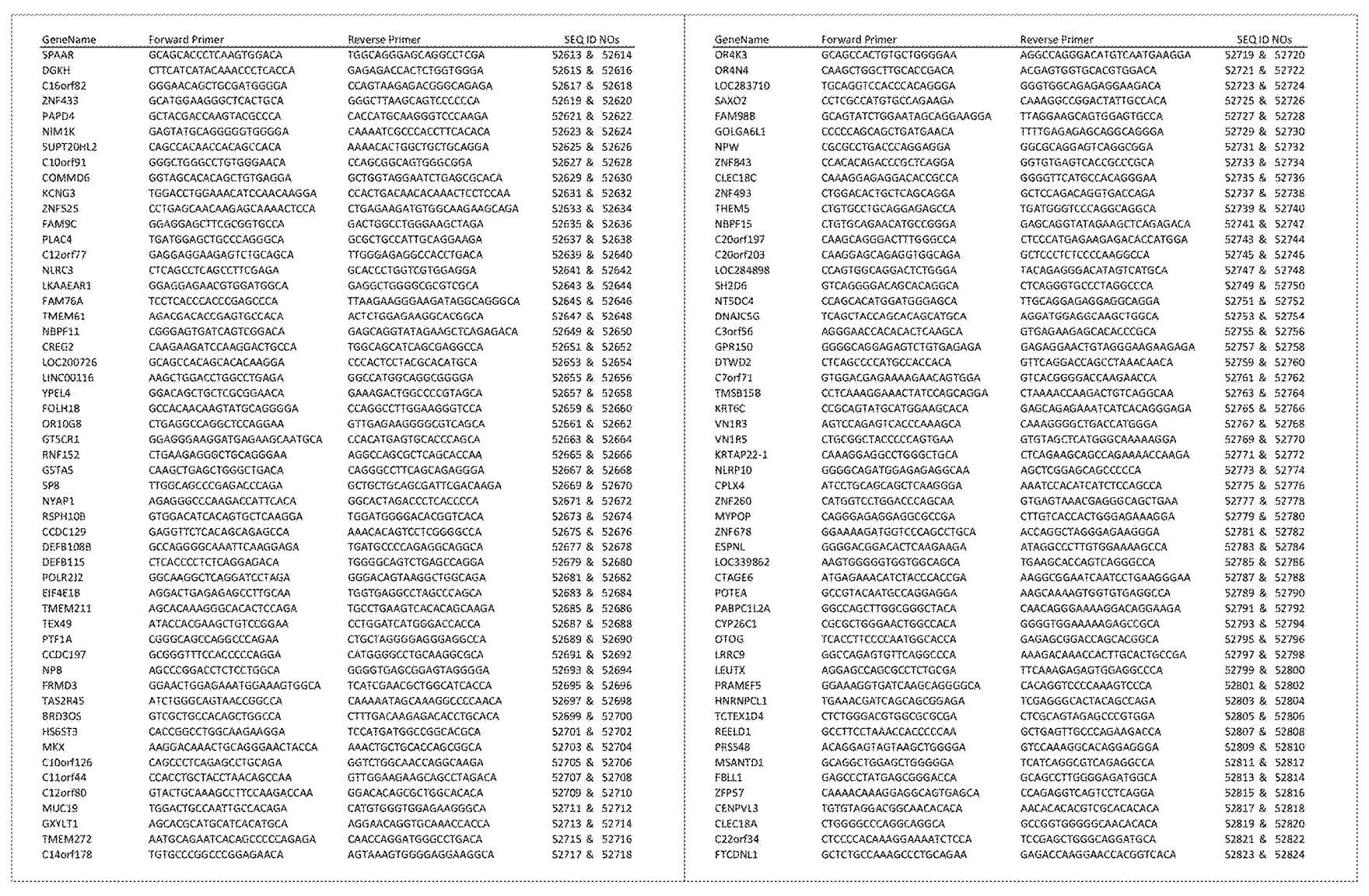
Figure 1:
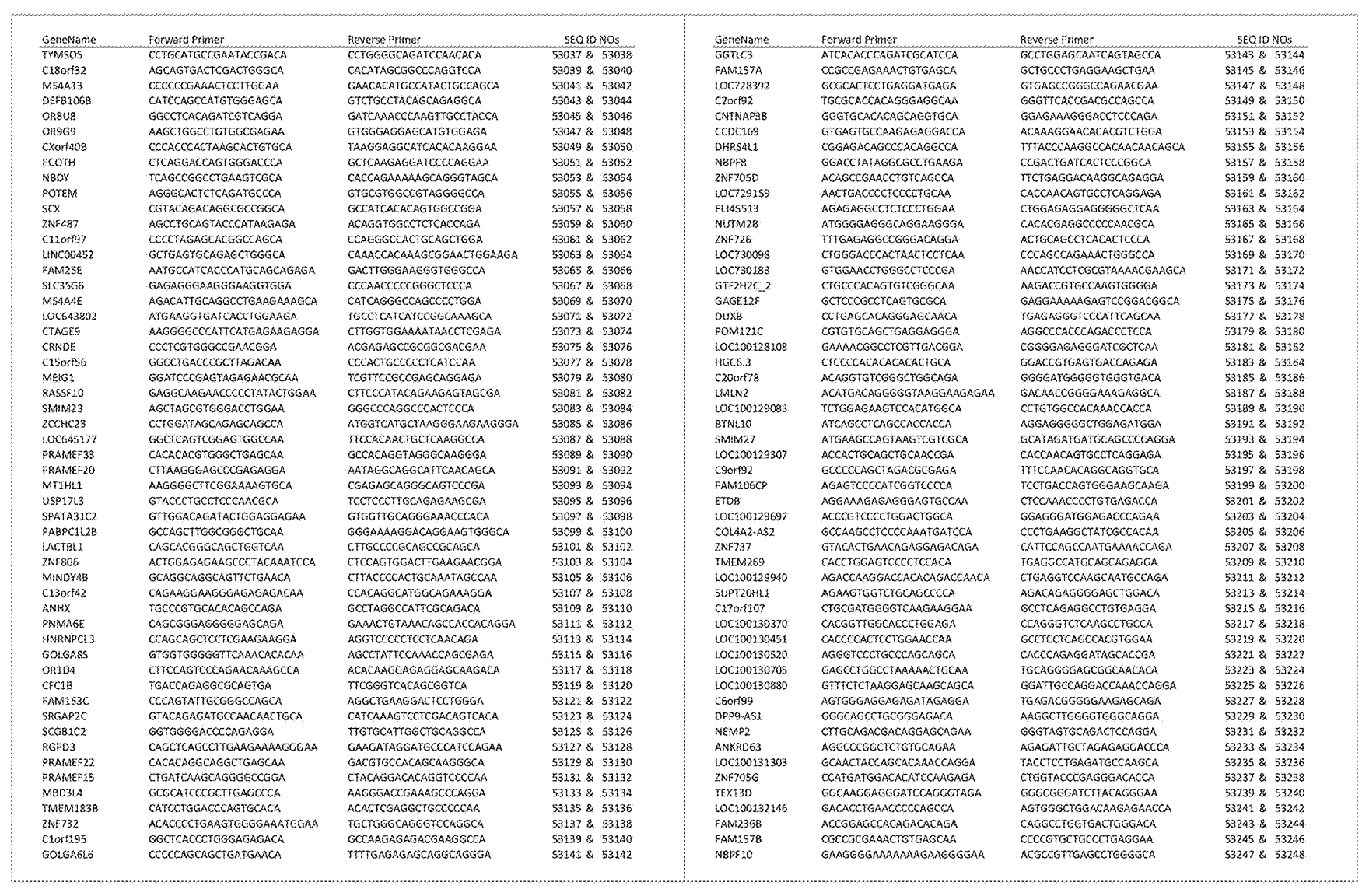
Figure 1:
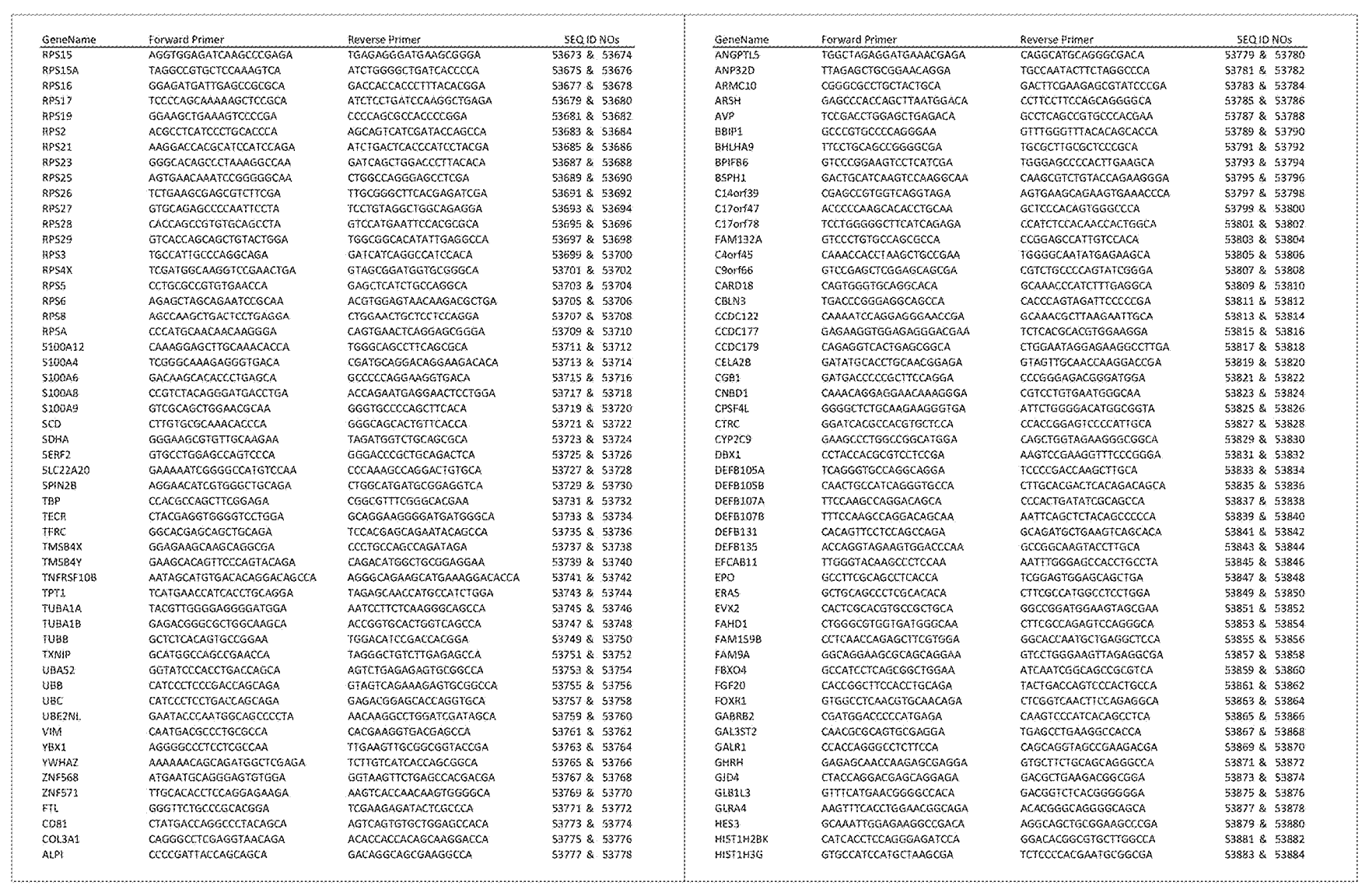
Figure 1:
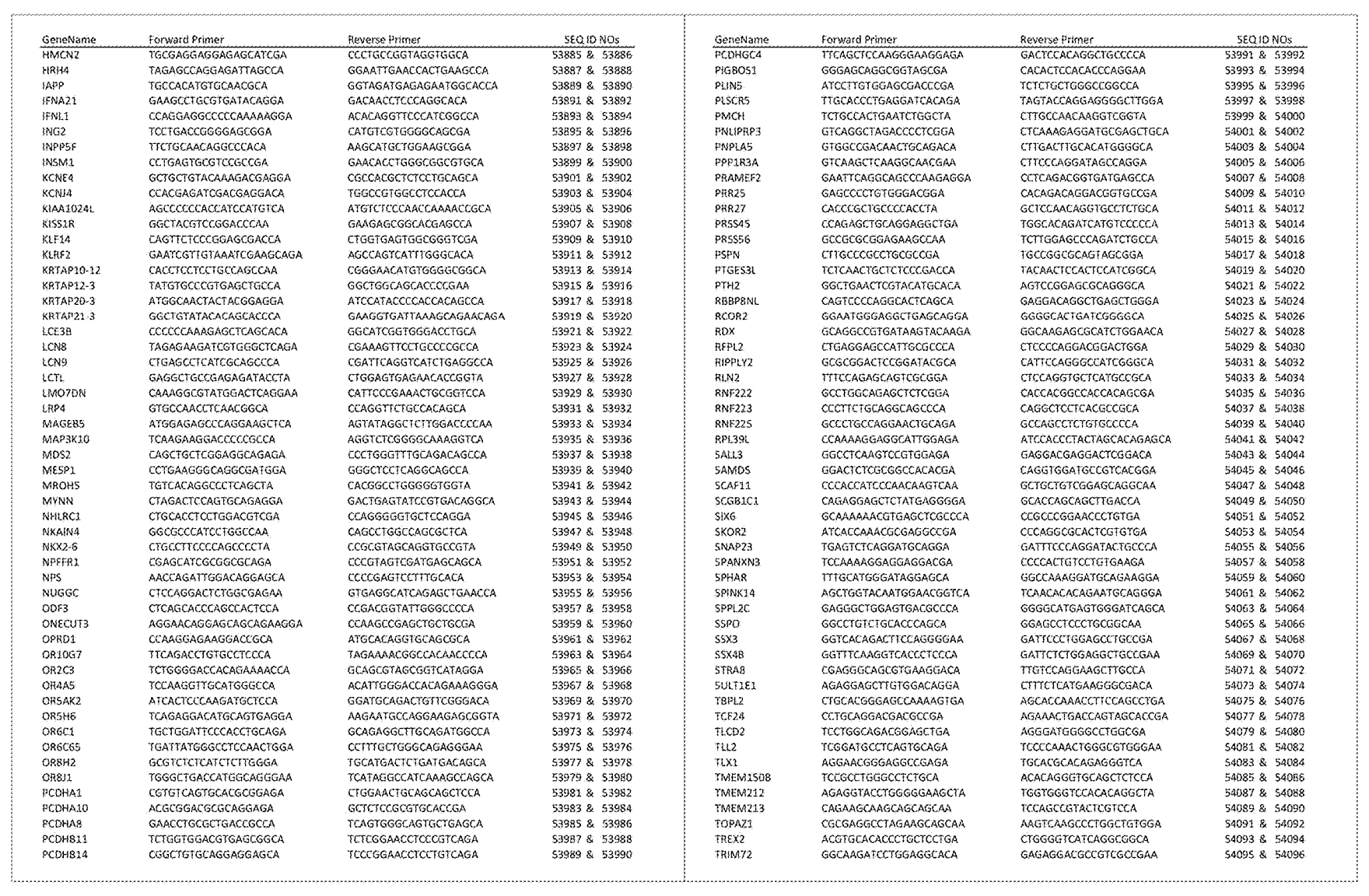

FIG. 1 provides the listing of genes and gene specific primer domains found in a set of gene specific primers, according to any embodiments of the invention. Each of the sequences listed in the column named "Forward Primer" provides a sequence of a gene specific domain of a forward primer that amplifies the gene listed in the corresponding row. Each of the sequences listed in the column named "Reverse Primer" provides a sequence of a gene specific domain of a reverse primer that amplifies the gene listed in the corresponding row.

FIG. 2 provides a representation of an amplicon ready for next generation sequencing that is produced using a set of gene specific primers, in accordance with an embodiment of the invention.

DETAILED DESCRIPTION

Figure 3:
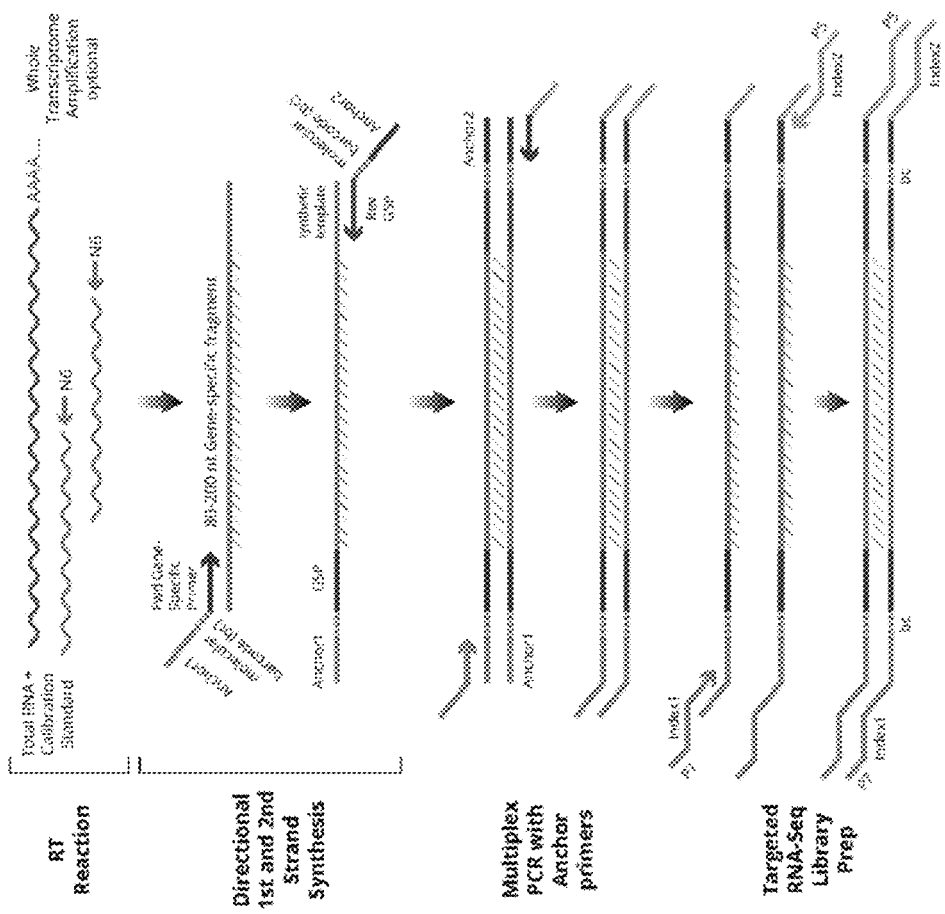
FIG. 3 provides schematic illustration of a protocol for preparing sequencing ready amplicons using a set of gene specific primers, as reported in the Experimental Section, below.

Sets of experimentally validated gene specific primer pairs are provided. Embodiments of the sets include 10 or more gene specific primer pairs of forward and reverse primers. The forward and reverse primers of each primer pair include gene specific primers that are experimentally validated as suitable for use in a multiplex amplification assay. In some instances, each of the forward and reverse primers includes an anchor domain that includes a universal primer binding site. The sets find use in a variety of different applications, including high-throughput sequencing applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges may be presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Additionally, certain embodiments of the disclosed devices and/or associated methods can be represented by drawings which may be included in this application. Embodiments of the devices and their specific spatial characteristics and/or abilities include those shown or substantially shown in the drawings or which are reasonably inferable from the drawings. Such characteristics include, for example, one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal; distal), and/or numbers (e.g., three surfaces; four surfaces), or any combinations thereof. Such spatial characteristics also include, for example, the lack (e.g., specific absence of) one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal), and/or numbers (e.g., three surfaces), or any combinations thereof.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of the invention, embodiments of various methods will be discussed first in greater detail, followed by a review of various applications in which the methods find use as well as kits that find use in various embodiments of the invention.

Methods

As summarized above, methods are provided for producing primer extension product compositions by a multiplex protocol from a target nucleic acid template composition and a set of gene specific primer pairs. By "primer extension product composition" is meant a nucleic acid composition that includes nucleic acids which are primer extension products. Primer extension products are deoxyribonucleic acids that include a primer domain at the 5' end covalently bonded to a synthesized domain at the 3' end, which synthesized domain is a domain of base residues added by a polymerase mediated reaction to the 3' end of the primer domain in a sequence that is dictated by a template nucleic acid to which the primer domain is hybridized during production of the primer extension product. Primer extension product compositions may include double stranded nucleic acids that include a template nucleic acid strand hybridized to a primer extension product strand, e.g., as described above, where in some instances these double stranded nucleic acids double deoxyribonucleic acid (dsDNA) molecules. The length of the primer extension products and/or double stranded nucleic acids that incorporate the same in the primer extension product compositions may vary, wherein in some instances the nucleic acids have a length ranging from 50 to 1000 nt, such as 60 to 400 nt and including 70 to 250 nt. The number of distinct nucleic acids that differ from each other by sequence in the primer extension product compositions produced via methods of the invention may also vary, ranging in some instances from 10 to 25,000, such as 100 to 20,000 and including 1,000 to 10,000, 10,000 to 20,000, 15,000 to 20,000 and 15,000 to 19,000.

As summarized above, aspects of the invention include producing primer extension product compositions by contacting a target nucleic acid template composition with a set of gene specific primers, e.g., as described in greater detail below, under primer extension reaction conditions.

Sets of Gene Specific Primer Sets

As summarized above, in methods of the invention a target nucleic acid template composition is contacted with a set of gene specific primers, i.e., a collection of gene specific primer pairs of known sequence, under primer extension reaction conditions. While the number of primer pairs in a given set may vary, as desired, in some instances the number of primer pairs in a given set is 10 or more, such as 20 or more, 30 or more, 40 or more, 50 or more, 60 or more, 70 or more, 80 or more, 90 or more, 100 or more, 125 or more, 250 or more, 500 or more, including 1000 or more, 200 or more, 5000 or more, 8000 or more, 10,000 or more 15,000 or more, 18,000 or more and 20,000 or more. In some instances, the number of gene specific primer pairs that is present in the set is 25,000 or less, such as 20,000 or less. As such, in some embodiments the number of gene specific primer pairs in the set that is contacted with the target nucleic acid template composition ranges from 10 to 25,000, such as 50 to 20,000, including 1,000 to 10,000, e.g., 2,500 to 8,500, and 10,000 to 20,000, e.g., 15,000 to 19,000.

Gene specific primer pairs present in a given set of the invention are made up of a forward primer and a reverse primer, wherein the forward and reverse primers of each primer pair include gene specific domains that are experimentally validated as suitable for use in a multiplex amplification assay. By "experimentally validated as suitable for use in a multiplex amplification assay" is meant that the set of primers for each target gene in a given set has been experimentally tested in a multiplex amplification assay, such as described in the Experimental section below, and the best performing primer set is selected based on parameters, e.g., one or more functional parameters, e.g., as described in greater detail below. While the multiplex amplification assay employed to experimentally validate a set of primers may vary, in some instances the protocol employed includes a first step of, for each target gene selected from the genome-wide set of human or mouse genes, selecting a region that is conservative for different mRNA isoforms, following which a set of forward and reverse PCR primers which are complementary and specific for the selected gene region are designed. The primers may be designed using any convenient algorithm and/or software tool, e.g., such as the Primer3 algorithm, Primer Design Tool from NCI, etc. The melting temperature of the selected primers may vary, ranging in some instances from 60° C. to 80° C., such as 65° C. to 80° C. Furthermore, the primers may be selected that lack significant secondary structures, or self-complementarity (e.g., primers may be selected with less than 4-bp complementary regions) and cross-complementarity to each other of less than 10 nt complementarity region. The length of the selected PCR primers may vary, and in some instances ranges from 15 to 25 nt, such as 16 to 24 nt, with GC-content of between 45% to 85%, such as 50% to 75%. In order to avoid primer/dimer formation in a multiplex RT-PCR assay, the selected primers in some embodiments are designed with the nucleotide A at the 3'-end and biased GCA-rich composition with reduced percentage of T nucleotides, where in some instances the percentage of T is 20% or less, such as 15% or less, including 10% or less, down to 0%. Following primer design, homology searching for similar PCR primer binding domain(s) in other RNA species (such as available in GeneBank), e.g., via BLAST or Thermo-Blast algorithm, is performed in order to select primers specific only to the target region of interest. Next, the resultant primer set is ranked based on the distance between primers with the preferred size of amplicons, e.g., which ranges in some instances between 60 to 250 bp. Following this ranking, a set of at least 1 primer pair, such as 3 or more, e.g., 5 or more, up to 12 or more, but in some instances not exceeding 12 primer pairs, is synthesized and functionally validated in a multiplex RT-PCR-NGS (next generation sequencing) assay, e.g., using the protocol disclosed in the Experimental section, below. In some embodiments, e.g., those specific for mutation profiling in clinically actionable or driver cancer genes, a complete set of PCR primers is designed and validated which allows one to amplify a set of overlapping amplicons that cover the complete mRNA sequence from the 5'- to the 3'-end. Primers present in sets of gene specific primers of the invention may be experimentally validated using any convenient protocol. In some instances, the experimentally validated gene specific domains are validated in a multiplex amplification assay with a synthetic control template mix which mimics the natural target template sequences and includes binding sites for the whole set of gene-specific primer pairs and/or a universal natural template mix derived from multiple different mammalian tissues or cell types. Specifically, as a template for multiplex RT-PCR assay, a set (usually between 3 to 6) of natural total universal RNAs, e.g., including a mix of several RNAs isolated from human or mouse cell lines or tissue samples (e.g., available from Takara-Clontech, Agilent, QiagenOrigene, etc.) may be employed as a natural nucleic acid control. In addition (or alternatively) to the set of the natural control template nucleic acids, a mix of the synthetic control template nucleic acids, e.g., one that has been synthesized on the surface of custom microarrays (e.g., Custom Array) and designed for the each target amplicon, may be employed. In such synthetic control templates, the templates include the sequence of the both PCR primer-binding site domains and the full-length or truncated in the middle cDNA region between PCR primers which correspond to the primer extension domain. In some functional validation assays, two synthetic template concentrations (e.g., 10-fold difference) may be employed in order to measure expression level (number of specific reads) in a manner that is not dependent on the amount of starting universal RNA template. The length of synthetic control templates may vary, ranging in some instances from 100 to 160, such as 110 to 160, including 120 to 160 nt. The amplification products generated in the multiplex RT-PCR assays may be quantitatively analyzed by sequence analysis using conventional NGS instruments (e.g., available from Illumina and other commercial vendors). The NGS data generated for different templates and experimental conditions may be scaled to the same number of total reads (usually total 10,000,000 reads), aligned with the sequences of PCR primer domain and downstream extended domain sequences for the each target amplicon. The number of specific reads corresponding to the each target amplicon may be measured as the number of correctly aligned sequences for the each PCR primer pair and downstream extended domain sequences. In addition, for each primer pair, the number of non-specific (off-target) reads for the amplicons may be calculated which has correct the PCR primer domain but different, non-target extended domain sequences. The set of PCR primer pairs designed for the each target gene may then be ranked using the set of criteria described below. The highest rank PCR primer pair for the each target gene is first selected based on highest number of specific reads (e.g., 100 or more, such as 500 or more and including 1,000 specific reads) and minimum number of non-specific reads (e.g., 2-fold less than number of specific reads, but not exceeding 5,000, or such as 2,000 reads) measured across all universal RNAs and control synthetic template. Next, the highest activity PCR primer set may be selected from among other primers which demonstrate a common pattern of expression among different natural universal RNAs used in the assay. Common pattern of expression between different primers sets indicates that they target the same conservative cDNA region, rather than a unique target region specific for particular mRNA isoform(s). In some embodiments, the human PCR primers are selected which effectively amplified target regions from human but not from the mouse universal RNAs. In other embodiments, e.g., those specific for detection of clinically actionable mutations, not one but a complete set of PCR primers are selected which amplify amplicons overlapping the whole mRNA/cDNA sequence. In some embodiments, screening for the highest specific activity primers using both 60° C. and 65° C. extension temperature are identified. Using these two different conditions enables the identification of set of primer pairs which demonstrates similar (e.g., less than 2-fold difference) specific activity across several control templates and universal RNAs. In some instances, if a PCR primer set which has high specific activity in both control synthetic template (e.g., less than 500 reads) and in all universal RNAs (e.g., less than 100 reads) for any target gene is not identified, a new candidate set PCR primer sets for the failed gene(s) is designed and validation protocol repeated until a suitable set is found. As a result of functional validation experiments, one can select at least one PCR primer set for the each target gene of interest that has high sensitivity and selectivity, e.g., for at least 90%, such as 95% or more target genes of interest.

The gene specific primers are configured to hybridize to a target nucleic acid sequence for which they are specific at locations that are separated by a known or predetermined distance, i.e., a template distance. The length of the template distance may vary, ranging in some instances from 50 to 750 bp, such as 60 to 500 bp, including 60 to 300 bp, e.g., 70 to 250 bp. As such, the product nucleic acid which is produced from the gene specific primers may have a central domain, i.e., extension domain, corresponding to the template nucleic acid from which it is produced (i.e., will have a sequence complementary to as sequence of the template nucleic acid from which it is produced) that varies in length, ranging in some instances from 50 to 750 nt, such as 60 to 500 nt, including 60 to 400 nt, e.g., 60 to 300 nt, including 80 to 200 nt.

A given gene specific primer at least includes a multiplex experimentally validated gene specific domain, e.g., as described above. The length of the gene specific domain may vary, so long as the domain serves to specifically hybridize to a target nucleic acid under hybridization conditions of interest. An example of such hybridization conditions is hybridization at 50° C. or higher and 0.1×SSC (15 mM sodium chloride/1.5 mM sodium citrate). In some embodiments, these hybridization conditions may be defined by length and nucleotide sequence of the gene-specific domains of the PCR primers, composition of PCR buffer, properties of DNA polymerase and conditions used in the primer extension step. Primer extensions temperatures may vary, ranging in some instances from 50 to 75, such as 60 to 72° C. As disclosed in Experimental section below, in one of the embodiment a primer extension step is employed in which extension occurs between 60 and 65° C. using Phusion II DNA polymerase, HF or GC buffer reagents available from Thermo-Fisher. Both length and specific nucleotide sequence of PCR primer define the hybridization condition at the primer extension step. In some embodiments, the length and specific sequence of the gene specific domains of the PCR primers is selected in order to provide efficient binding and extension at 60 and 65° C. under the PCR conditions used in the primer extension step. Such conditions may provide or high efficiency and specificity of the primer extension in PCR reaction conditions. In some embodiments, the primer length and sequence may be adjusted to perform an extension step at 68° C. or even 72° C.

In order to control efficiency and specificity of primer extension step, the length of the gene specific domain of the forward and reverse primers may vary, in some instances the length ranges from 10 to 50 nt, such as 10 to 30 nt, including 14 to 22 nt or 16 to 24 nt. Each primer of the gene specific primer set may include only a gene specific domain, or may include one or more additional domains as desired, e.g., anchor domains, NGS adaptor domains, labels or label domains, etc., e.g., as described below. In some embodiments where additional domains are present, each primer pair may include primers ranging in length from 10 to 75 nt, such as from 15 to 60 nt, including from 24 to 45 nt.

Where desired, the gene-specific primer domain of the each primer is GCA- and/or GCT-rich. By GCA- and/or GCT-rich is meant that the gene-specific primer domain has a substantial portion of G, C, A- and/or G, C, T nucleotides. While the number of such nucleotides in a gene specific primer domain may vary, in some instance the number of such sequences ranges from 75% to 100%, such as 85% to 100%. As the gene specific primer domains of such embodiments are GCA- and/or GCT-rich, the GC content of the gene specific primer domains is also high. While the GC content may vary, in some instances the GC content ranges from 40 to 90%, such as 45 to 85%, including 50 to 85%, e.g., 50 to 80%.

Depending on the particular application, the set of gene specific primers may be designed to target a wide range of mammalian genes, and pathogenic genes from a wide range of pathogenic organisms, like viruses, bacteria, fungi, etc. which could be present in the human or mammalian bodies. Of interest in certain applications are human and mammalian species (mouse, rat, monkey) which are commonly used as a model organisms to study human diseases and pathogenic organisms which are associated or induce human diseases. In order to be analyzed in accordance with embodiments of the invention, genes may be present in the mammalian cells of fluids. In some embodiments, the genes are selected only from a group of protein coding genes or/and selected from the group of genes which code non-coding RNAs, micro RNAs, mitochondrial RNAs, regulatory RNAs, etc. In some instances, the set of the selected genes is genome-wide, such that it covers all genes present in the genome of an organism. In other embodiments, the genes are selected from a group of the genes which could transcribed or expressed in the organism and present in the biological samples in the form of RNA or expressed DNA. The genome-wide set of genes specific for human, model and pathogenic organisms is a specific interest in some instances, and may be used to develop a set of genome-wide targeted RNA expression Assays based on the disclosed multiplex PCR assay. Genome-wide sets of PCR primers may vary in number, and in some instances are configured to assay 18,000 or more, such as 20,000 or more and 25,000 or more, such as 30,000 or more genes. Additional sets of PCR primers may be configured based on a genome-wide set of genes from a wide range of viral, bacterial and eukaryotic pathogenic organisms. In another embodiment, the set of gene specific primers may be configured to produce primer extension products from a subset of specific genes selected from the genome-wide set of genes. One of these subsets is the subset of cancer associated genes. By "cancer associated genes" is meant genes that have been shown to be associated with initiation, development, diagnostic, treatment of cancer. Such genes could be involved in, i.e., implicated in, or be diagnostic of, or otherwise of interest in, the study and/or treatment of cancer, i.e., any of various malignant neoplasms characterized by the proliferation of anaplastic cells that tend to invade surrounding tissue and metastasize to new body sites. As such, cancer associate genes that may be represented in a given set of gene specific primers include, but are not limited to: cancer hallmark genes, pan cancer driver genes, pathway and signaling network genes, drug metabolism genes, extracellular proteome genes, drug target genes (including those of FDA approved and/or clinical trial targets), cell lineage genes, Immunity Mechanisms & Immunotherapy Markers, immunotherapy drug target genes, known biomarkers, epigenetics genes, etc.

In another embodiment, the subset of the cancer associated genes is employed in developing of Cancer Clinically Actionable 26 assay for profiling all clinically actionable mutations in the set of 26 human genes (ABL1, AKT1, ALK, BRAF, CDK4, CDK6, CDKN2A, EGFR, ERBB2, FGFR1, FGFR2, FLT3, KDR, KIT, KRA, MET, NRAS, PDGFRA, PIK3CA, PIK3R1, PTCH1, PTEN, PTPN11, RET, ROS1, SMO). This assay includes the additional set of multiplex PCR primers designed and validated to amplify the set of overlapping amplicons which cover the whole mRNA sequence of the target genes.

In some instances, the set of gene specific primer pairs includes primers configured to produce primer extension products for 10 or more genes listed in Table 1. As such, the set of gene specific primers employed in a given method may represent at least some of the genes listed in Table 1 (See FIG. 1), i.e., will include primer pairs that correspond to at least some of the genes listed in Table 1. A primer pair is considered to correspond to a given gene if the primers of the pair specifically hybridize to sequences of the gene. It is understood based on the current prior-art knowledge, the selected primer pair sequences could include all or only portion of the primer sequences disclosed in the Table 1, so long as they provide for the desired gene specificity. Modification in the specific sequences of the PCR primers, such as mutations, deletion, extensions, using nucleotide analogs, etc., may be present so long as the functionality of the primers in the primer extension step is maintained. The number of genes from Table 1 represented in the set of gene specific primers may vary, ranging from 10 to 19,000, including 10 to 18,000, 10 to 17,000, 10 to 15,000, 10 to 10,000, 10 to 8,000, such as 25 to 18,500, 25 to 15,000, 15 to 10,000, 25 to 7,500, including 50 to 18,000, 50 to 12,000, 50 to 8,000, and 50 to 5,000, where in some instances the number is 25 or more, including 50 or more, such as 100 or more, 250 or more, 500 or more, 1,000 or more, 1,500 or more, 2,500 or more, 5,000 or more, 7,500 or more, 8,000 or more, 10,000 or more, 15,000 or more, 18,000 or more and 19,000 or more, up to and including all of the genes listed in Table 1. In some instances, the set of gene specific primers includes primer pairs having gene specific sequences listed in Table 1. The number of gene specific primer pairs having gene specific sequences listed in Table 1 that may be present in a given set of gene specific primers may vary, where in some instances the number ranges from 10 to 24,000, 10 to 22,000, 10 to 20,000, 10 to 18,000, 10 to 15,000, 10 to 10,000 and 10 to 8,000, such as 25 to 21,000, 25 to 19,000, 25 to 17,000, 25 to 14,000, 25 to 8,500 and 25 to 7,500, including 50 to 20,000, 50 to 15,000, 50 to 10,000 and 50 to 5,000, where in some instances the number of primer pairs present in the set is 25 or more, including 50 or more, such as 100 or more, 250 or more, 500 or more, 1,000 or more, 1,500 or more, 2,500 or more, 5,000 or more, 7,500 or more, 8,500 or more, 10,000 or more, 12,000 or more, 15,000 or more, 18,000 or more, 20,000 or more, 24,000 or more, up to and including all of the primer pairs listed in Table 1. Subsets of the genes listed in Table 1 that may be employed in a given assay may vary. Specific subsets of interest that may be employed in a given assay include, but are not limited to: Cancer Core 125 subset, PanCancer 540 subset, Cancer Immunotherapy 1,740 subset, Tumor Microenvironment 2,500 subset, or any specific set of genes selected based on specific functions, expression, or association with human diseases, and the like.

In some instances, set and subsets of primer pairs of interest may include all or a subset of the primer pairs defined by the respective sequence identifiers as presented in Table 1, including but not limited to e.g., the primer pairs represented by SEQ ID NOs: 37-54152 or a subset thereof, such as e.g., the primer pairs of SEQ ID NOs: 37-16166, the primer pairs of SEQ ID NOs:16167-54152 or a subset thereof. Essentially any combination of primers, including all the primers, identified by the sequence identifiers provided in Table 1 may be assembled to form a set or subset of primer pairs of the present disclosure.

Sets and subsets of primer pairs may be configured to include or exclude multiple primer pairs for a particular gene. For example, a set or subset of primer pairs may include no or essentially no two or more primer pairs that target the same gene. Correspondingly, a set or subset of primer pairs may include two or more different primer pairs that target the same gene. Where two or more primer pairs for a particular gene are included in a set or subset, the primer pairs may or may not share the same forward primer or the same reverse primer. For example, in some instances, two primer pairs for a single gene may include the same forward primer but have different reverse primers, the same reverse primer but have different forward primers, or have different forward primers and different reverse primers.

As described above, in some instances, a set or subset of primer pairs may be configured such that no two primer pairs target the same gene, i.e., there is only one primer pair for each gene included in the set or subset. In some instances, the number of different primer pairs targeting the same gene may be low, including but not limited to e.g., 10 or less primer pairs targeting the each gene of the set or subset, such as 5 or less, 4 or less, 3 or less or no more than 2 primer pairs targeting each gene of the genes of a set or subset. In some instances, 10% or less of the genes of a set or subset may be targeted by more than one primer pair, including 8% or less, 7% or less, 5% or less, 3% or less, 2% or less and 1% or less.

In some instances the methods include selecting the set of gene specific primers from a provided master library of gene specific primers, e.g., choosing a subset of primer pairs from an initial collection of primer pairs. For example, the methods may include selecting a subset of primer pairs (and thereby identify the primer pairs of a set of gene specific primers to be employed in methods of the invention, such as described above) that correspond to genes from Table 1, where the number of primer pairs in the selected subset may vary, ranging in some instances from 10 to 19,000, 10 to 15,000, to 10 10,000 and 10 to 8,000, such as 25 to 18,500, 25 to 12,000, 25 to 8,500, 25 to 7,500, including 50 to 15,000, 50 to 10,000, 50 to 5,000, where in some instances the number is 25 or more, including 50 or more, such as 100 or more, 250 or more, 500 or more, 1,000 or more, 1,500 or more, 2,500 or more, 5,000 or more, 7,500 or more, 8,500 or more, 10,000 or more, 15,000 or more, and 18,000 or more.

The disparate primer pairs of a given set are present in substantially the same, if not the same amount. As such, in some instances, the copy number of any given primer pair in a set does not vary from the copy number of any other primer pair of the set by a value of 100% or less, such as 50% or less. A given primer pair may be present in a set in any desired amount, where in some instances the amount ranges from 10% to 1000%, such as 20% to 500%. The final concentration of the each primer in the primer extension step may vary, and in some instances ranges from 1 to 50 nM, such as 2 to 40 nM, where examples of specific concentrations of interest include 1 nM, 2 nM, 5 nM, 10 nM, 20 nM and 50 nM.

The sets of gene specific primers, e.g., as described above, are non-naturally occurring compositions. In some instances, the sets of gene specific primers include domains or regions that are not naturally occurring sequences and/or are not naturally joined to the gene specific primer domains in naturally occurring nucleic acids. For example, as described in greater detail below, the gene specific domains may be joined to one or more synthetic domains, e.g., universal primer binding site domains, indexing domains, barcode domains, adaptor domains, etc. In some instance the gene specific primers may include one or more moieties that are not present in naturally occurring nucleic acids, e.g., label moieties (e.g., directly detectable labels, such as fluorescent labels, indirectly detectable labels, e.g., components of a signal producing system, etc.), non-naturally occurring nucleotides, etc. In some instances the sets of gene specific primers are present in a vehicle that does not include one or more constituents found in naturally occurring nucleic acid compositions. For example, the vehicle may lack one or more cellular constituents, e.g., proteins, organelles, cell walls, etc. In some instances, the set of gene specific primers are the only nucleic acids present in the composition. In some instances, the composition is an aqueous composition, where the aqueous composition lacks non-nucleic acid cellular constituents and/or may include one or more components that are not present in biological samples, e.g., synthetic buffering agents, etc.

Target Nucleic Acid Template Compositions

The target nucleic acid template compositions employed in methods of the invention are nucleic acid compositions made of nucleic acids of various length. In some instances, nucleic acids having a length of 10 bases or longer, 20 bases or longer, 50 bases or longer, 100 bases or longer, 500 bases or longer, 1000 bases or longer, 2000 bases or longer, 3000 bases or longer, 4000 bases or longer, 5000 bases or longer may be present in the target nucleic acid compositions. In some instances, the nucleic acids present in the target template nucleic acid compositions have a length that is 2500 bases or less, such as 20,000 bases or less, including 15,000 bases or less.

In the broadest sense, the nucleic acids of the target nucleic acid template compositions may be deoxyribonucleic acids or ribonucleic acids. In certain aspects, the nucleic acids making up the template nucleic acid composition are deoxyribonucleic acids, such that the target nucleic acid template composition is a template deoxyribonucleic acid composition (template DNA composition). Template DNA compositions may include, but are not limited to, genomic DNA or fragments thereof, complementary DNA (or "cDNA", e.g., synthesized from any RNA or DNA of interest), recombinant DNA (e.g., plasmid DNA), or the like. In some instances, the target nucleic acid composition that is contacted with the set of gene specific primers may be made up of ribonucleic acids, such as messenger RNA (mRNA), etc.

The template nucleic acid may be present in any nucleic acid sample of interest, including but not limited to, a nucleic acid sample isolated from a single cell, a plurality of cells (e.g., cultured cells), a tissue, an organ, or an organism (e.g., bacteria, yeast, or the like). In certain aspects, the nucleic acid sample is isolated from a cell(s), tissue, organ, and/or the like of a mammal (e.g., a human, a rodent (e.g., a mouse), or any other mammal of interest). Samples that may be employed in certain embodiments include samples obtained from biopsies, xenografts, blood or components thereof, e.g., PBMCs, FFPE, fine needle aspirates (FNAs), etc. In other aspects, the nucleic acid sample is isolated from a source other than a mammal, such as bacteria, yeast, insects (e.g., *drosophila*), amphibians (e.g., frogs (e.g., *Xenopus*)), viruses, plants, or any other non-mammalian nucleic acid sample source. As mentioned above, in some embodiments, the nucleic acid sample that includes the template nucleic acid is isolated from a single cell. In other aspects, the nucleic acid sample that includes the template nucleic acid is isolated from 2, 3, 4, 5, 6, 7, 8, 9, 10 or more, 20 or more, 50 or more, 100 or more, or 500 or more cells. According to certain embodiments, the nucleic acid sample that includes the template nucleic acid is isolated from 500 or less, 100 or less, 50 or less, 20 or less, 10 or less, 9, 8, 7, 6, 5, 4, 3, or 2 cells.

Approaches, reagents and kits for isolating nucleic acids from such sources are known in the art. For example, kits for isolating nucleic acids from a source of interest—such as the NucleoSpin®, NucleoMag® and NucleoBond® genomic DNA or RNA isolation kits by Clontech Laboratories, Inc. (Mountain View, Calif.)—are commercially available. In certain aspects, the nucleic acid is isolated from a fixed biological sample, e.g., formalin-fixed, paraffin-embedded (FFPE) tissue. Nucleic acids from FFPE tissue may be isolated using commercially available kits—such as the NucleoSpin® FFPE DNA or RNA isolation kits by Clontech Laboratories, Inc. (Mountain View, Calif.).

In certain aspects, the subject methods include producing the target nucleic acid template composition from a precursor nucleic acid. For example, where the target template nucleic acid composition is a cDNA composition, the methods may include producing the cDNA composition from an initial nucleic acid sample, such as an mRNA sample. Such methods may include, but are not limited to, generating double stranded cDNA from random primers, oligo dT primers, oligo dT primers with molecular barcodes, gene-specific primers, etc., via reverse transcriptase mediated protocol, which may or may not include the use of a template switch oligonucleotide, as desired.

When it is desirable to control the size of the template nucleic acid that is combined into the reaction mixture, a nucleic acid sample isolated from a source of interest may be subjected to shearing/fragmentation, e.g., to generate a template nucleic acid that is shorter in length as compared to a precursor non-sheared nucleic acid (e.g., genomic DNA, full-length mRNA, and/or the like) in the original sample. The template nucleic acid may be generated by a shearing/fragmentation strategy including, but not limited to, passing the sample one or more times through a micropipette tip or fine-gauge needle, nebulizing the sample, sonicating the sample (e.g., using a focused-ultrasonicator by Covaris, Inc. (Woburn, Mass.)), bead-mediated shearing, enzymatic shearing (e.g., using one or more DNA- or RNA-shearing enzymes), chemical based fragmentation, e.g., using divalent cations (e.g., $Mg^{2+}$, $Mn^{2+}$, and/or $Zn^{2+}$), fragmentation buffer (e.g., a high pH buffer), and/or heat, or any other suitable approach for shearing/fragmenting a precursor nucleic acid to generate a shorter template nucleic acid. In certain aspects, the template nucleic acid generated by shearing/fragmentation of a starting nucleic acid sample has a length of from 50 to 10,000 nucleotides, from 100 to 5000 nucleotides, from 150 to 2500 nucleotides, from 200 to 1000 nucleotides, e.g., from 250 to 500 nucleotides in length, for example.

In some instances, preparation of the target nucleic acid template composition includes combining an initial nucleic acid composition with a control template mix, e.g., to produce a target nucleic acid template composition that is spiked with a control template mix, which mix may be made up of synthetic nucleic acids, naturally occurring nucleic acids or a combination thereof. In some instances, the control template mix is a synthetic control template mix that includes control template nucleic acids having sequences that mimic but are different from the sequences of target template nucleic acids. Where desired, the control template nucleic acids comprise binding sites for the whole set of gene-specific primer pairs employed in a given assay in amount ranging from 0.1 to 50%. Further details regarding control template mixes of interest are provided above.

Primer Extension Product Production

As reviewed above, aspects of the methods include contacting a set of gene specific primers, e.g., as described above, with a target nucleic acid template composition under primer extension reaction conditions. By "primer extension reaction conditions" is meant reaction conditions that permit polymerase-mediated extension of a 3' end of a nucleic acid strand, i.e., primer, hybridized to a template nucleic acid. Achieving suitable reaction conditions may include selecting reaction mixture components, concentrations thereof, and a reaction temperature to create an environment in which the polymerase is active and the relevant nucleic acids in the reaction interact (e.g., hybridize) with one another in the desired manner.

The concentration of gene specific primers in the primer extension reaction mixture produced upon combination of the template nucleic acid and the set of gene specific primers may vary, as desired. In some instances, each primer of the gene specific primer pairs is employed at a concentration ranging from 1 to 50 nM, such as 2 to 25 nM, including 5 to 10 nM. The amount of target template nucleic acid that is combined with the set of gene specific primers and other reagents, e.g., as described below, to produce a primer extension reaction mixture may also vary. In some instances, the target nucleic acid template composition is combined into the reaction mixture such that the final concentration of nucleic acid in the reaction mixture ranges from 1 fg/µL to 10 µg/µL, such as from 1 pg/µL to 5 µg/µL, such as from 0.1 ng/µL to 50 ng/µL, such as from 0.5 ng/µL to 20 ng/µL, including from 1 ng/µL to 10 ng/µL.

In producing the primer extension reaction mixture, the set of gene specific primers and target template nucleic acid composition are combined with a number of additional reagents, which may vary as desired. A variety of polymerases may be employed when practicing the subject methods. Reference to a particular polymerase, such as those exemplified below, will be understood to include functional variants thereof unless indicated otherwise. Examples of useful polymerases include DNA polymerases, e.g., where the template nucleic acid is DNA. In some instances, DNA polymerases of interest include, but are not limited to: thermostable DNA polymerases, such as may be obtained from a variety of bacterial species, including *Thermus aquaticus* (Taq), *Thermus thermophilus* (Tth), *Thermus filiformis, Thermus flavus, Thermococcus literalis*, and *Pyrococcus furiosus* (Pfu). Alternatively, where the target template nucleic acid composition is made up of RNA, the polymer may be a reverse transcriptase (RT), where examples of reverse transcriptases include Moloney Murine Leukemia Virus reverse transcriptase (MMLV RT), SuprScript II, SuperScript III, MaxiScript reverse transcriptase (Thermo-Fsher), *Bombyx mori* reverse transcriptase (e.g., *Bombyx mori* R2 non-LTR element reverse transcriptase), SMARTScribe™ reverse transcriptase and PrimeScript™ reverse transcriptase.

Primer extension reaction mixtures also include dNTPs. In certain aspects, each of the four naturally-occurring dNTPs (dATP, dGTP, dCTP and dTTP) are added to the reaction mixture. For example, dATP, dGTP, dCTP and dTTP may be added to the reaction mixture such that the final concentration of each dNTP is from 0.01 to 100 mM, such as from 0.1 to 10 mM, including 0.5 to 5 mM (e.g., 1 mM). According to one embodiment, at least one type of nucleotide added to the reaction mixture is a non-naturally occurring nucleotide, e.g., a modified nucleotide having a binding or other moiety (e.g., a fluorescent moiety) attached thereto, a nucleotide analog, or any other type of non-naturally occurring nucleotide that finds use in the subject methods or a downstream application of interest.

In addition to the template nucleic acid, primers, the polymerase, and dNTPs, the reaction mixture may include buffer components that establish an appropriate pH, salt concentration (e.g., KCl concentration), metal cofactor concentration (e.g., $Mg^{2+}$ or $Mn^{2+}$ concentration), and the like, for the extension reaction and template switching to occur. Other components may be included, such as one or more nuclease inhibitors (e.g., an RNase inhibitor and/or a DNase inhibitor), one or more additives for facilitating amplification/replication of GC rich sequences (e.g., GC-Melt™ reagent (Clontech Laboratories, Inc. (Mountain View, Calif.)), betaine, single-stranded binding proteins (e.g., T4 Gene 32, cold shock protein A (CspA), and/or the like) DMSO, ethylene glycol, 1,2-propanediol, or combinations thereof), one or more molecular crowding agents (e.g., polyethylene glycol, or the like), one or more enzyme-stabilizing components (e.g., DTT present at a final concentration ranging from 1 to 10 mM (e.g., 5 mM)), and/or any other reaction mixture components useful for facilitating polymerase-mediated extension reactions and template-switching.

The primer extension reaction mixture can have a pH suitable for the primer extension reaction and template-switching. In certain embodiments, the pH of the reaction mixture ranges from 5 to 9, such as from 7 to 9, including from 8 to 9, e.g., 8 to 8.5. In some instances, the reaction mixture includes a pH adjusting agent. pH adjusting agents of interest include, but are not limited to, sodium hydroxide, hydrochloric acid, phosphoric acid buffer solution, citric acid buffer solution, and the like. For example, the pH of the reaction mixture can be adjusted to the desired range by adding an appropriate amount of the pH adjusting agent.

The temperature range suitable for production of the product nucleic acid may vary according to factors such as the particular polymerase employed, the melting temperatures of any optional primers employed, etc. According to one embodiment, the primer extension reaction conditions include bringing the reaction mixture to a temperature ranging from 4 to 72° C., such as from 16 to 70° C., e.g., 37 to 65° C., such as 60° C. to 65° C. The temperature of the reaction mixture may be maintained for a sufficient period of time for polymerase mediated, template directed primer extension to occur. While the period of time may vary, in some instances the period of time ranges from 5 to 60 minutes, such as 15 to 45 minutes, e.g., 30 minutes.

Where desired, the primer extension reaction conditions may include one or more temperature cycling steps. For example, in some instances, the primer extension product composition is produced by a method that includes first contacting the target nucleic acid template composition with a first primer subset that includes the forward primers of the set of primer pairs under primer extension reaction conditions to produce a forward primer extension product composition; increasing the temperature to denature the resultant product and template strands and inactivate any additional enzymatic activity (e.g., exonuclease I activity added after extension step to degrade PCR primers) present in the forward primer extension product composition (where the elevated temperature may vary, ranging in some instances from 90 to 100° C., such as 95° C.) and then contacting the resultant denatured forward primer extension product composition with a second primer subset that includes the reverse primers of the set of primer pairs under primer extension reaction conditions to produce the desired primer extension product composition. Where desired, the primer extensions products and template nucleic acids may be separated from any free forward primers prior to contact with the set of reverse primers. The extended DNA products after the first and second extension steps may be purified from the excess of the primers using any convenient protocol, including primer digestion with exonucleases (exonucleclease I) or purification, such as Magnetic beads or spin columns, etc.

Contact of the target nucleic acid template composition and the set of gene specific primers, e.g., as described above, results in the production of a primer extension product composition, e.g., as described above. The resultant primer extension product composition may be employed as is, or further processed as desired, depending on the particular application being performed.

Amplicon Production

In some instances, the primer extension product composition is employed as an intermediate composition in methods of producing multiple amplicons from the initial target nucleic acid template composition. The term "amplicon" is employed in its conventional sense to refer to a piece of DNA that is the product of artificial amplification or replication events, e.g., as produced using various methods including polymerase chain reactions (PCR), ligase chain reactions (LCR), etc.

In embodiments of such methods, the gene specific primers of the primer sets, e.g., as described above, may include additional domains that are employed in subsequent amplification steps to produce the desired amplicon composition. For example, each of the forward and reverse primers of a given primer pair in the set of gene specific primers may include an anchor domain comprising a universal priming site. The length of the anchor domain may vary, as desired. In some instances, the anchor domains of each primer pair range in length from 10 to 50 nt, such as 10 to 30 nt, e.g., 10 to 24, including 10 to 23 nt. Where desired, the anchor domains may include PCR suppression sequences. PCR suppression sequences are sequences configured to suppress the formation of non-target DNA during PCR amplification reactions, e.g., via the production of pan-like structures. Such sequences, when present, may vary in length, ranging in some instances from 5 to 25 nt, such as 7 to 21, including 7 to 20 nt. PCR suppression sequences of interest include, but are not limited to, those sequences described in U.S. Pat. No. 5,565,340; the disclosure of which is herein incorporated by references. An example of forward and reverse anchor domains that include PCR suppression sequences are: AGCACCGACCAGCAGACA (SEQ ID NO:01) and AGACACGACCAGCCACGA (SEQ ID NO:02). When present, these anchor domains are 5' of the gene specific domains of the primers.

Where anchor domains, e.g., as described above, are included in the gene specific primers, the anchor domains, i.e., forward and reverse anchor domains, may be common in all of the gene specific primers of the set, such that all of the forward gene specific primers of the set include anchor domains having the same sequence and all of the reverse gene specific primers of the set include anchor domains having the same sequence. In such instances, the primer extension product composition will include universal primer binding sites which may then be exploited during subsequent amplification.

As such, embodiments of the methods include combining the primer extension product composition and universal forward and reverse primers under amplification conditions sufficient to produce the desired product amplicon composition. The forward and reverse universal primers are configured to bind to the common forward and reverse anchor domains and thereby nucleic acids present in the primer extension product compositions. The universal forward and reverse primers may vary in length, ranging in some instances from 10 to 75 nt, such as 15 to 60 nt. In some instances, the universal forward and reverse primers include one or more additional domains, such as but not limited to: an indexing domain, a clustering domain, a Next Generation Sequencing (NGS) adaptor domain (i.e., high-throughput sequencing (HTS) adaptor domain), etc. Alternatively, these domains may be introduced during one or more subsequent steps, such as one or more subsequent amplification reactions, e.g., as described in greater detail below. The amplification reaction mixture will include, in addition to the primer extension product composition and universal forward and reverse primers, other reagents, as desired, such polymerase, dNTPs, buffering agents, etc., e.g., as described above.

Amplification conditions may vary. In some instances the reaction mixture is subjected to polymerase chain reaction (PCR) conditions. PCR conditions include a plurality of reaction cycles, where each reaction cycle includes: (1) a denaturation step, (2) an annealing step, and (3) a polymerization step. The number of reaction cycles will vary depending on the application being performed, an may be 1 or more, including 2 or more, such as 3 or more, e.g., four or more, and in some instances may be 15 or more, such as 20 or more and including 60 or more, where the number of different cycles will typically range from about 20 to 40. The denaturation step includes heating the reaction mixture to an elevated temperature and maintaining the mixture at the elevated temperature for a period of time sufficient for any double stranded or hybridized nucleic acid present in the reaction mixture to dissociate. For denaturation, the temperature of the reaction mixture may be raised to, and maintained at, a temperature ranging from 85 to 100° C., such as from 90 to 98° C. and including 93 to 96° C. for a period of time ranging from 3 to 120 sec, such as 5 to 30 sec. Following denaturation, the reaction mixture will be subjected to conditions sufficient for primer annealing to template DNA present in the mixture. The temperature to which the reaction mixture is lowered to achieve these conditions may be chosen to provide optimal efficiency and specificity, and in some instances ranges from about 50 to 75° C., such as 55 to 70° C. and including 60 to 68° C. Annealing conditions may be maintained for a sufficient period of time, e.g., ranging from 15 sec to 30 min, such as from 30 sec to 5 min. Following annealing of primer to template DNA or during annealing of primer to template DNA, the reaction mixture may be subjected to conditions sufficient to provide for polymerization of nucleotides to the primer ends in manner such that the primer is extended in a 5' to 3' direction using the DNA to which it is hybridized as a template, i.e. conditions sufficient for enzymatic production of primer extension product. To achieve polymerization conditions, the temperature of the reaction mixture may be raised to or maintained at a temperature ranging from 65 to 75, such as from about 67 to 73° C. and maintained for a period of time ranging from 15 sec to 20 min, such as from 30 sec to 5 min. The above cycles of denaturation, annealing and polymerization may be performed using an automated device, typically known as a thermal cycler. Thermal cyclers that may be employed are described in U.S. Pat. Nos. 5,612,473; 5,602,756; 5,538,871; and 5,475,610, the disclosures of which are herein incorporated by reference.

The product amplicon composition of this first amplification reaction will include amplicons corresponding to the gene specific domains that are present in the initial target nucleic acid composition and are bounded by primer pairs present in the employed set of gene specific primers. In some instances, the number of distinct amplicons of differing sequence in this initial amplicon composition ranges from 10 to 19,000, 10 to 15,000, 10 to 10,000, and 10 to 8,000, such as 25 to 18,500, 25 to 12,000, 25 to 8,000, and 25 to 7,500, including 50 to 15,000, 50 to 10,000 and 50 to 5,000, where in some instances the number of distinct amplicons present in this initial amplicon composition is 25 or more, including 50 or more, such as 100 or more, 250 or more, 500 or more, 1,000 or more, 1,500 or more, 2,500 or more, 5,000 or more, 7,500 or more, 8,500 or more, 10,000 or more, 15,000 or more, 18,000 or more. In some instances, this initial amplicon composition includes sequences found in at least a subset of the genes listed in Table 1, e.g., a subset of 10 to 19,000, such as 10 to 15,000, 10 to 10,000, 10 to 8,000, such as 25 to 18,500, 25 to 12,000, 25 to 7,500, including 50 to 15,000, 50 to 10,000 and 50 to 5,000 of the genes listed in Table 1, or in some instances the amplicon composition includes sequences found in all of the genes listed in Table 1. A subject amplicon composition may include or exclude multiple different product amplicons corresponding to same gene as amplified by two or more different primer pairs directed to the gene. The multiple product amplicons making up the amplicon composition may vary in length, ranging in length in some instances from 100 to 1000, such as 125 to 750, including 150 to 700 nt.

The initial product amplicon composition may be employed in a variety of different applications, including evaluation of the expression profile of the sample from which the template target nucleic acid was obtained. In such instances, the expression profile may be obtained from the amplicon composition using any convenient protocol, such as but not limited to differential gene expression analysis, array-based gene expression analysis, NGS sequencing, etc.

For example, the amplicon composition may be employed in hybridization assays in which a nucleic acid array that displays "probe" nucleic acids for each of the genes to be assayed/profiled in the profile to be generated is employed. In these assays, the amplicon composition is first prepared from the initial target nucleic acid sample being assayed as described above, where preparation may include labeling of the target nucleic acids with a label, e.g., a member of signal producing system. Following amplicon production, e.g., as described above, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions, and unbound nucleic acid is then removed. The resultant pattern of hybridized nucleic acid provides information regarding expression for each of the genes that have been probed, where the expression information is in terms of whether or not the gene is expressed and, typically, at what level, where the expression data, i.e., expression profile (e.g., in the form of a transcriptome), may be both qualitative and quantitative.

Alternatively, non-array based methods for quantitating the levels of one or more nucleic acids in a sample may be employed, including quantitative PCR, real-time quantitative PCR, and the like. (For general details concerning real-time PCR see Real-Time PCR: An Essential Guide, K. Edwards et al., eds., Horizon Bioscience, Norwich, U.K. (2004)).

In some instances, the method further includes sequencing the multiple product amplicons, e.g., by using a Next Generation Sequencing (NGS) protocol. In such instances, if not already present, the methods may include modifying the initial amplicon composition to include one or more components employed in a given NGS protocol, e.g., sequencing platform adaptor constructs, indexing domains, clustering domains, etc.

By "sequencing platform adapter construct" is meant a nucleic acid construct that includes at least a portion of a nucleic acid domain (e.g., a sequencing platform adapter nucleic acid sequence) or complement thereof utilized by a sequencing platform of interest, such as a sequencing platform provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest.

In certain aspects, the sequencing platform adapter construct includes a nucleic acid domain selected from: a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); where the construct may include one or more additional domains, such as but not limited to: a sequencing primer binding domain or clustering domain (e.g., a domain to which the Read 1 or Read 2 primers of the Illumina® platform may bind); a barcode or indexing domain (e.g., a domain that uniquely identifies the sample source of the nucleic acid being sequenced to enable sample multiplexing by marking every molecule from a given sample with a specific barcode or "tag"); a barcode sequencing primer binding domain (a domain to which a primer used for sequencing a barcode binds); a molecular identification domain (e.g., a molecular index tag, such as a randomized tag of 4, 6, or other number of nucleotides) for uniquely marking molecules of interest to determine expression levels based on the number of instances a unique tag is sequenced; a complement of any such domains; or any combination thereof. In certain aspects, a barcode domain (e.g., sample index tag) and a molecular identification domain (e.g., a molecular index tag) may be included in the same nucleic acid.

The sequencing platform adapter constructs may include nucleic acid domains (e.g., "sequencing adapters") of any length and sequence suitable for the sequencing platform of interest. In certain aspects, the nucleic acid domains are from 4 to 200 nucleotides in length. For example, the nucleic acid domains may be from 4 to 100 nucleotides in length, such as from 6 to 75, from 8 to 50, or from 10 to 40 nucleotides in length. According to certain embodiments, the sequencing platform adapter construct includes a nucleic acid domain that is from 2 to 8 nucleotides in length, such as from 9 to 15, from 16-22, from 23-29, or from 30-36 nucleotides in length.

The nucleic acid domains may have a length and sequence that enables a polynucleotide (e.g., an oligonucleotide) employed by the sequencing platform of interest to specifically bind to the nucleic acid domain, e.g., for solid phase amplification and/or sequencing by synthesis of the cDNA insert flanked by the nucleic acid domains. Example nucleic acid domains include the P5 (5'-AATGATACGGCGAC-CACCGA-3') (SE ID NO:03), P7 (5'-CAAGCAGAA-GACGGCATACGAGAT-3')(SEQ ID NO:04), Read 1 primer (5'-ACACTCTTTCCCTACACGACGCTCTTCC-GATCT-3') (SEQ ID NO:05) and Read 2 primer (5'-GTGACTGGAGTTCAGACGTGTGCTCTTCCGATCT-3') (SEQ ID NO:06) domains employed on the Illumina®- based sequencing platforms. Other example nucleic acid domains include the A adapter (5'-CCATCT-CATCCCTGCGTGTCTCCGACTCAG-3')(SEQ ID NO:07) and P1 adapter (5'-CCTCTC-TATGGGCAGTCGGTGAT-3')(SEQ ID NO:08) domains employed on the Ion Torrent™-based sequencing platforms.

The nucleotide sequences of nucleic acid domains useful for sequencing on a sequencing platform of interest may vary and/or change over time. Adapter sequences are typically provided by the manufacturer of the sequencing platform (e.g., in technical documents provided with the sequencing system and/or available on the manufacturer's website). Based on such information, the sequence of the sequencing platform adapter construct of the template switch oligonucleotide (and optionally, a first strand synthesis primer, amplification primers, and/or the like) may be designed to include all or a portion of one or more nucleic acid domains in a configuration that enables sequencing the nucleic acid insert (corresponding to the template nucleic acid) on the platform of interest.

The sequencing adaptors may be added to the amplicons of the initial amplicon composition using any convenient protocol, where suitable protocols that may be employed include, but are not limited to: amplification protocols, ligation protocols, etc. In some instances, amplification protocols are employed. In such instances, the initial amplicon composition may be combined with forward and reverse sequencing adaptor primers that include one or more sequencing adaptor domains, e.g., as described above, as well as domains that bind to universal primer sites found in all of the amplicons in the composition, e.g., the forward and reverse anchor domains, such as described above. As reviewed above, amplification conditions may include the addition of forward and reverse sequencing adaptor primers configured to bind to the common forward and reverse anchor domains and thereby amplify all or a desired portion of the product nucleic acid, dNTPs, and a polymerase suitable for effecting the amplification (e.g., a thermostable polymerase for polymerase chain reaction), where examples of such conditions are further described above. The forward and reverse sequencing adaptor primers employed in these embodiments may vary in length, ranging in length in some instances from 20 to 60 nt, such as 25 to 50 nt. Addition of NGS sequencing adaptors results in the production of a composition which is configured for sequencing by a NGS sequencing protocol, i.e., an NGS library.

In certain aspects, the methods of the present disclosure further include subjecting the NGS library to NGS protocol. Next Generation Sequencing (NGS) is a technique capable of sequencing millions of DNA molecules in parallel. The protocol may be carried out on any suitable NGS sequencing platform. NGS platforms of interest include, but are not limited to, a sequencing platform provided by Illumina® (e.g., the HiSeq™, MiSeq™ and/or NextSeq™ sequencing systems); Ion Torrent™ (e.g., the Ion PGM™ and/or Ion Proton™ sequencing systems); Pacific Biosciences (e.g., the PACBIO RS II Sequel sequencing system); Life Technologies™ (e.g., a SOLiD sequencing system); Roche (e.g., the 454 GS FLX+ and/or GS Junior sequencing systems); or any other sequencing platform of interest. The NGS protocol will vary depending on the particular NGS sequencing system employed. Detailed protocols for sequencing an NGS library, e.g., which may include further amplification (e.g., solid-phase amplification), sequencing the amplicons, and analyzing the sequencing data are available from the manufacturer of the NGS system employed. Protocols for performing next generation sequencing, including methods of processing the sequencing data, e.g., to count and tally sequences and assemble transcriptome data therefrom, are further described in published United States Patent Application 20150344938, the disclosure of which is herein incorporated by reference.

Utility

The subject methods find use in a variety of applications, including expression profiling or transcriptome determination applications where a sample is evaluated to obtain an expression profile of the sample. By "expression profile" is meant the expression level of a gene of interest in a sample, which may be a single cell or a combination of multiple cells (e.g., as determined by quantitating the level of an RNA or protein encoded by the gene of interest), or a set of expression levels of a plurality (e.g., 2 or more) of genes of interest. In certain aspects, the expression profile includes expression level data for 1, 2 or more, 5 or more, 10 or more, 20 or more, 50 or more, 100 or more, 200 or more, 300 or more, 400 or more, 500 or more, 1,000 or more, 5,000 or more, 10,000 or more, 15,000 or more, e.g., 18,000 or more genes of interest. According to one embodiment, the expression profile includes expression level data of from 50 to 8000 genes of interest, e.g., from 1000 to 5000 genes of interest. In some embodiments, the expression profile includes expression level data of from 50 to 19,000 genes of interest, e.g., from 1000 to 18,000 genes of interest. In certain aspects, the methods may be employed detecting and/or quantitating the expression of all or substantially all of the cancer associated genes transcribed in a target cell. In certain aspects, the methods may be employed detecting and/or quantitating the expression of all or substantially all of the genes transcribed by an organism, e.g., a mammal, such as a human or mouse, in a target cell. The terms "expression" and "gene expression" include transcription and/or translation of nucleic acid material. For example, gene expression profiling may include detecting and/or quantitating one or more of any RNA species transcribed from the genomic DNA of the target cell, including pre-mRNAs, mRNAs, non-coding RNAs, microRNAs, small RNAs, regulatory RNAs, and any combination thereof.

Expression levels of an expressed sequence are optionally normalized by reference or comparison to the expression level(s) of one or more control expressed genes, including but not limited to, ACTB, GAPDH, HPRT-1, RPL25, RPS30, and combinations thereof. These "normalization genes" have expression levels that are relatively constant among target cells in the cellular sample.

According to certain embodiments, the expression profile includes "binary" or "qualitative" information regarding the expression of each gene of interest in a target cell. That is, in such embodiments, for each gene of interest, the expression profile only includes information that the gene is expressed or not expressed (e.g., above an established threshold level) in the sample being analyzed, e.g., tissue, cell, etc. In other embodiments, the expression profile includes quantitative information regarding the level of expression (e.g., based on rate of transcription, rate of splicing and/or RNA abundance) of one or more genes of interest. A qualitative and/or quantitative expression profile from the sample may be compared to, e.g., a comparable expression profile generated from other samples and/or one or more reference profiles from cells known to have a particular biological phenotype or condition (e.g., a disease condition, such as a tumor cell; or treatment condition, such as a cell treated with an agent, e.g., a drug). When the profiles being compared are quantitative expression profiles, the comparison may include determining a fold-difference between one or more genes in the expression profile of a target cell and the corresponding genes in the expression profile(s) of one or more different target cells in the cellular sample, or the corresponding genes in a reference cell or cellular sample. Alternatively, or additionally, the expression profile may include information regarding the relative expression levels of different genes in a single target cell. In certain aspects, the fold difference in intercellular expression levels or intracellular expression levels can be determined to be 0.1 or more, 0.5 fold or more, 1 fold or more, 1.5 fold or more, 2 fold or more, 2.5 fold or more, 3 fold or more, 4 fold or more, 5 fold or more, 6 fold or more, 7 fold or more, 8 fold or more, 9 fold or more, or more than 10 fold or more, for example.

In some instances, the methods may be employed to determine the transcriptome of a sample. The term "transcriptome" is employed in its conventional sense to refer to the set of all messenger RNA molecules in one cell or a population of cells. In some instances, a transcriptome includes the amount or concentration of each RNA molecule in addition to the molecular identities. The methods described herein may be employed in detecting and/or quantitating the expression of all genes or substantially all genes of the transcriptome of an organism, e.g., a mammalian organism, such as a human or a mouse, for a particular target cell or a population of cells.

Expression profiles obtained using methods of the invention may be employed in a variety of applications. For example, an expression profile may be indicative of the biological condition of the sample or host from which the sample is obtained, including but not limited to a disease condition (e.g., a cancerous condition, metastatic potential, an epithelial mesenchymal transition (EMT) characteristic, and/or any other disease condition of interest), the condition of the cell in response to treatment with any physical action (e.g., heat shock, hypoxia, normoxia, hydrodynamic stress, radiation, and/or the like), the condition of the cell in response to treatment with chemical compounds (e.g., drugs, cytotoxic agents, nutrients, salts, and/or the like) or biological extracts or entities (e.g., viruses, bacteria, other cell types, growth factors, biologics, and/or the like), and/or any other biological condition of interest (e.g. immune response, senescence, inflammation, motility, and/or the like).

Embodiments of the invention find further application in tumor microenvironment analysis applications. Transcriptome data obtained, e.g., as described above, may be employed to determine the cellular constitution of a tumor sample, e.g., to provide an evaluation of the types of cells present in a tumor sample, such as infiltrating hematopoietic cells, tumor cells and bulk tissue cells. For example, transcriptome data may be employed to assess whether a tumor sample does not does not include infiltrating immune cells, including those of the adaptive and/or innate immune system, such as but not limited to: T, B, natural killer, nmonocyte, granulocytes, neutrophils, basophils, platelets, and their myeloid and lymphoid progenitor cells, hematopoietic stem cells, and the like. Such information may be used, e.g., in therapy determination applications, for example where the presence of infiltrating immune cells indicates that a patient will be responsive to immunotherapy while the absence of infiltrating immune cells indicates that a patient will not be responsive to immunotherapy. As such, aspects of the invention include methods of therapy determination, where a patient tumor sample is evaluated to assess the tumor microenvironment and a determination to employ an immunotherapy protocol is made if the tumor microenvironment includes infiltrating tumor cells and a determination is made to employ a non-immunotherapy treatment regimen if the tumor microenvironment lacks infiltrating immune cells. Transcriptome data, e.g., produced as described above, also finds use in other non-clinical applications. For example, such day finds use predictive and prognostic biomarker discovery applications, evaluation of cancer immunoediting mechanism applications, drug target discovery and the like.

Compositions

Aspects of the invention further include various compositions. Compositions of the invention may include, e.g., one or more of any of the reaction mixture components described above with respect to the subject methods. For example, the compositions may include one or more of a target nucleic acid template (e.g., genomic DNA sample, cDNA sample, RNA sample, etc.), a polymerase (e.g., a thermostable polymerase), a set of gene specific primers, dNTPs, a salt, a metal cofactor, one or more nuclease inhibitors (e.g., an RNase inhibitor), one or more enzyme-stabilizing components (e.g., DTT), or any other desired reaction mixture component(s). Also provided are compositions that include a primer extension product composition, e.g., as described above. Also provided are amplicon compositions and NGS libraries, such as described above.

The subject compositions may be present in any suitable environment. According to one embodiment, the composition is present in a reaction tube (e.g., a 0.2 mL tube, a 0.5 mL tube, a 1.5 mL tube, or the like) or a well. In certain aspects, the composition is present in two or more (e.g., a plurality of) reaction tubes or wells (e.g., a plate, such as a 96-well plate). The tubes and/or plates may be made of any suitable material, e.g., polypropylene, or the like. In certain aspects, the tubes and/or plates in which the composition is present provide for efficient heat transfer to the composition (e.g., when placed in a heat block, water bath, thermocycler, and/or the like), so that the temperature of the composition may be altered within a short period of time, e.g., as necessary for a particular enzymatic reaction to occur. According to certain embodiments, the composition is present in a thin-walled polypropylene tube, or a plate having thin-walled polypropylene wells. Other suitable environments for the subject compositions include, e.g., a microfluidic chip (e.g., a "lab-on-a-chip device"). The composition may be present in an instrument configured to bring the composition to a desired temperature, e.g., a temperature-controlled water bath, heat block, or the like. The instrument configured to bring the composition to a desired temperature may be configured to bring the composition to a series of different desired temperatures, each for a suitable period of time (e.g., the instrument may be a thermocycler).

Kits

Aspects of the present disclosure also include kits. The kits may include, e.g., one or more of any of the reaction mixture components described above with respect to the subject methods. For example, the kits may include one or more of: a set of gene specific primers, a polymerase (e.g., a thermostable polymerase, a reverse transcriptase, or the like), dNTPs, a salt, a metal cofactor, one or more nuclease inhibitors (e.g., an RNase inhibitor and/or a DNase inhibitor), one or more molecular crowding agents (e.g., polyethylene glycol, or the like), one or more enzyme-stabilizing components (e.g., DTT), or any other desired kit component(s), such as solid supports, e.g., tubes, beads, microfluidic chips, etc.

Components of the kits may be present in separate containers, or multiple components may be present in a single container. For example, the template switch oligonucleotide and the template switching polymerase may be provided in the same tube, or may be provided in different tubes. In certain embodiments, it may be convenient to provide the components in a lyophilized form, so that they are ready to use and can be stored conveniently at room temperature.

In addition to the above-mentioned components, a subject kit may further include instructions for using the components of the kit, e.g., to practice the subject method. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, Hard Disk Drive (HDD), portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

Experimental

I. Protocol for Producing Sets of Experimentally Validated Gene-Specific Primers.

A. Background

All cancers share common characteristics, such as abnormal cell proliferation, with the potential to invade and spread to other parts of the body—'hallmarks of cancer.' While certain features are consistent across all cancers, each cancer is distinct due to its unique composition, molecular signature, and sensitivity to therapeutics. Recently, our molecular understanding of cancer causation and progression has been greatly enabled by next-generation genome sequencing and other large-scale genomics approaches/methodologies, leading to the discovery and development of molecularly targeted drugs and companion diagnostics for personalized treatment.

Molecular diagnostics is a rapidly growing area of translational research and medicine, with new technologies and applications rapidly emerging. Significantly, quantitative real-time PCR is a valuable technology/platform routinely used for molecular diagnostics of diseases such as cancer. However, in order to successfully introduce highly multiplexed PCR-based diagnostics into the clinical setting, new multiplex PCR technologies must be developed that can cost-effectively and reliably identify cancer-associated mutant genes, or gene expression patterns associated with neoplastic disease and progression. Unfortunately, PCR target specificity is a major concern due to the underlying variability in the physicochemical characteristics of the amplified sequences (e.g. GC content, flanking regions and secondary structures), resulting in the imbalance/skewing of the PCR reaction and the subsequent outcomes. Furthermore, false positives associated with cross-reacting targets and primer-primer interactions; reduce assay robustness, specificity, and sensitivity.

B. Goal: Primer design is a complex and unsolved problem. To this end, we describe the development of a novel in silico multiplex primer design pipeline to unambiguously access primer quality—defined here as the ability to efficiently and specifically amplify the desired template fragments in a complex reaction—on the basis of the primer sequences, target template and the reference/background genome sequence. Subsequently, we used the aforementioned resource and experimentally validated all PCR primers, resulting in multiplex PCR primers with uniform properties. Herein, we describe a novel methodology, which integrates multiplex (suppression PCR) with massively parallel sequencing for high-throughput gene expression/genetic profiling of clinically relevant disease genes.

C. Methods & Design

Our primer design pipeline consists of four major steps: (1) identify all primer binding-site positions among all possible DNA/RNA template sequences; (2) evaluate the binding stability of the entire primer sequence using the NN model to calculate the duplex stability formed by the sub-sequence and the primer sequence (only thermodynamically stable mismatches are allowed); (3) filter amplicons by size and target region position and (4) in silico designed primer pairs are experimentally validated using high-throughput array synthesis for primers/corresponding target regions and used under a common PCR thermal profile, facilitating the evaluation of target transcripts of a large number genes in parallel using NexGen Sequencing.

D. In Silico Multiplex Primer Design.

Standard methods for primer design (ad hoc) compute a variety of quality metrics in order to evaluate various aspects of primer quality and then combine these individual metrics into a final score using a weighted sum; however, the weight for each individual quality metric must be specified in order to obtain the final primer pair score. To circumvent these difficulties/limitations we use machine-learning algorithms and a high quality training set we experimentally generated (directly comparable data points), to develop a classifier algorithm that identifies multiplex PCR primers en masse. Briefly, we identify the shortest sequence at the 5'-end of each primer that could bind stably in the target genome/transcriptome. We employ a machine-learning algorithm to determine the optimum primer specificity that focuses on the 5'-end of the primer and identify the shortest primer that has sufficient stability such that, at equilibrium, a pre-specified fraction of molecules in the target database with exact complementarity to the primer would be bound. Importantly, the core features used for prediction were the individual nucleotides and adjacent nucleotides indexed by position in the PCR target site. In addition, general rules concerning optimal primer length, CG content, annealing and melting temperature, secondary structure issues were included. Since oligonucleotide primers are hypothesized to be specific and provide the optimal annealing and melting temperatures, primers of 15-18 bp were considered to be the best for target sequences in target regions and GC content of >50% <67%. Finally, in selecting apposite primer-probe candidates, the variability of the target genome and existence of common mutations were taken into account. A large number of potential primer-probe combinations were selected from either CODS or RefSeq and analyzed for melting temperature ($T_m$), self-complementarity, and secondary structure. BLAST (Basic Local Alignment Search Tool) searches were performed on all candidate primer and probe oligonucleotides to assess their potential for cross-reactivity with other multiplex target sequences or cross-reactivity with other species.

E. Description of Tree Boost Algorithm.

A decision tree is a flow chart-like tree structure, where each internal node denotes a test of an attribute, each branch represents an outcome of the test and leaf nodes represent classes or class distributions. Tree growing at a specific node is terminated when at least one class has equal or <cases than the minimal cases, preventing a tree from sub-dividing into overly specific nodes that have little supporting data. Importantly, unlike other machine-learning algorithms, decision trees are adaptable, easy to interpret, and produce highly accurate models using both categorical and continuous data variables. Accordingly, we used a modified tree classification algorithm (facilitates the ensemble of weak learners until an acceptable low training error was achieved) to develop a novel in silico multiplex primer design system (~2000 features). Initially, each training pattern (including primer thermodynamic properties, secondary structure prediction of target mRNA species and base positions at biologically relevant positions) received a weight that determined its probability of being selected for a training set for an individual component classifier. We first initialized the weights across the training set to be uniform. On each iteration k, we drew a random training set according to these weights and then trained the component classifier Ck on the patterns selected. Next, we increased weights of training patterns misclassified by Ck and decreased weights of the patterns correctly classified by Ck. Patterns chosen according to this distribution were used to train the next classifier, Ck+1, and the process iterated (Ckmax). Finally, K-fold cross-validation was performed k times (folds), and each of the k-sub samples was used once as the validation data. The k results obtained from the k-folds were then averaged to produce a single estimation of model performance.

F. High-Throughput Oligo Synthesis for Experimental Validation

Oligonucleotide libraries consisting of complex mixtures of oligonucleotides ranging in length from 150-200 base pairs were manufactured by Custom Array Technologies under contract. Oligonucleotides were synthesized in spatially distinct locations using standard phosphoramidite chemistry on a silylated 6.625×6 inch wafer using an automated tool designed by Agilent Technologies. The solid support used in synthesis was a flat, non-porous silane coated glass rather than a locally curved, porous surface traditionally used. The coupling steps used inkjet-printing technologies to deliver the appropriate amount of activator and phosphoramidite monomer to specific spatial locations on the solid support under anhydrous conditions. Oxidation and detrytilation reactions were performed in dedicated flowcells using novel mechanical operations and fluid management steps to eliminate the depurination side reaction limiting synthesis of long oligonucleotides. After deprotection and release, oligonucleotides were recovered and concentrated by lyophilization in 2 mL tubes. Each Oligo Library yields 10 pmol of nucleic acid material equally divided among up to 55,000 user-defined, unique sequences. In another embodiment, the PCR primers were synthesized using conventional phosphoramidate chemistry and mixed together at approximately equal concentration by IDT and MWG-Operon companies.

Multiplex PCR primers with cognate target sequences were screened en masse. Uniformity of amplification, including primer efficiency, primer specificity and dynamic range (minimum 100 fold) were determined from multiplex reaction kinetic data. Finally, functionally validated primers were selected as experimentally validated primers for use in sets of experimental validated gene specific primers.

II. Multiplex PCR Assay

A. Design of Primers for Anchor Addition, First and Second PCR Steps

Design of Forward and Reverse PCR Gene-specific primers with anchor6 (Fwd-anchor6-GSP primers) and anchor7 (Rev-anchor7-GSP primers) with 3'-extended suppression portion and universal PCR primers (F-MP6GAC and R-MP7CAG) to amplify anchored cDNA/genDNA fragments by PCR.

Sequences that are underlined are the common PCR suppression portions, and those in italics and bold are unique sequences for Fwd or Rev primers, respectively, and GSP is the gene-specific primer domain.

(SEQ ID NOS: 09, 10, 11 and 12)

```
F-MP6GAC     AGCAGCACCGACCAGCAGAC
Fwd-Anc6-GSP     AGCACCGACCAGCAGACA-GSP>
                                 cDNA/genDNA
                         <GSP-AGACACGACCAGCCACGA    Rev-Anc7-GSP
                              GACACGACCAGCCACGAGCA  R-MP7CAG
```

Sequencing Primers for NextSeq500:
SeqDNA-RevAnc7

(SEQ ID NO: 013)

ACGACGAGCACCGACCAGCACAGA

SeqIND-FwdAnc7

(SEQ ID NO: 014)

TCTGTGCTGGTCGGTGCTCGTCGT

SeqIND-RevAnc6

(SEQ ID NO: 015)

TGTCTGCTGGTCGGTGCTGCTGCT

SeqDNA-FwdAnc6

(SEQ ID NO: 016)

AGCAGCAGCACCGACCAGCAGACA

The resultant structure of amplified cDNA/genomicDNA products after the anchor addition step using mix of Fwd-anchor6-GSPs and Rev-anchor7-GSPs shown above and a first PCR step using universal F-MP6GAC and R-MP7CAG primers as shown above is provide below:

```
                                 (SEQ ID NO: 017 and 018)
AGCAGCACCGACCAGCAGACA-GSP-DNA(60-400 n)-GSP-

TCTGTGCTGGTCGGTGCTCGT

TCGTCGTGGCTGGTCGTCTGT-GSP-DNA(60-400 n)-GSP-

AGACACGACCAGCCACGAGCA
```

The structure of amplified cDNA/genDNA products were then subjected to a second round of PCR to add Illumina P7, P5 sequencing adaptors.

Protocol for HT sequencing in Next Seq500 machine:

Read 1: SeqDNA-RevAnc7 >35 cycles

Ind 1: SeqIND-RevAnc6 >6 cycles

Ind 2: SeqIND-FwdAnc7 >6 cycles

Read 2: SeqDNA-FwdAnc6 >35 cycles

PCR primers for the second PCR step >amplification of cDNA/DNA with anchor6 and anchor7 tailed cDNA/genDNA products generated by extension of cDNA/genDNA with multiplex primers Fwd-:

```
Set of Forward Indexing Primers for 2nd PCR step:
FP7-A6Ind-A
                                 (SEQ ID NOS: 019-24)
AGCAGAAGACGGCATACGAGATATACGACAGCAGCAGCACCGACCAGCA

GACA

FP7-A6Ind-B
AGCAGAAGACGGCATACGAGATACTGATGAGCAGCAGCACCGACCAGCA

GACA

FP7-A6Ind-C
AGCAGAAGACGGCATACGAGATAGCATCAAGCAGCAGCACCGACCAGCA

GACA

FP7-A6Ind-D
AGCAGAAGACGGCATACGAGATAAGTCGTAGCAGCAGCACCGACCAGCA

GACA

FP7-A6Ind-E
AGCAGAAGACGGCATACGAGATATCGCATAGCAGCAGCACCGACCAGCA

GACA

FP7-A6Ind-F
AGCAGAAGACGGCATACGAGATACATAGCAGCAGCAGCACCGACCAGCA

GACA

Set of Reverse Indexing Primers for 2nd PCR step:
RP5-A7Ind-A
                                 (SEQ ID NOS: 25-30)
ACGGCGACCACCGAGATCTACACATACGACACGACGAGCACCGACCAG

CACAGA

RP5-A7Ind-B
ACGGCGACCACCGAGATCTACACACTGATGACGACGAGCACCGACCAG

CACAGA

RP5-A7Ind-C
ACGGCGACCACCGAGATCTACACAGCATCAACGACGAGCACCGACCAG

CACAGA

RP5-A7Ind-D
ACGGCGACCACCGAGATCTACACAAGTCGTACGACGAGCACCGACCAG

CACAGA

RP5-A7Ind-E
ACGGCGACCACCGAGATCTACACATCGCATACGACGAGCACCGACCAG

CACAGA

RP5-A7Ind-F
ACGGCGACCACCGAGATCTACACACATAGCACGACGAGCACCGACCAG

CACAGA
```

After a second PCR step with Fwd and Rev indexed primers and sequences of primers for sequencing cDNA/genDNA inserts and indexes is provided in FIG. 2. (SEQ ID NOS: 31-36)

B. Protocol for Multiplex RT-PCR amplification of target genes for expression profiling or mutation analysis starting from total RNA (1 ng-1 μg) or genomic DNA (10 ng-1 μg) mixed with normalization standards control RNA/DNA templates.

Step 1. Total RNAs (mixed with synthetic control RNA templates) was converted to cDNA in 20-μl of reaction mix using random primer (N6-5 uM) using Maxima RT (Thermo-Fisher) at 50° C. using reagents and supplier protocol.

Step 2. cDNA or genomic DNA (10 ng-1 μg) was primed (add universal anchors 6 and 7) using mix of Forward-anchor6-GSPs and Reverse-anchor7-GSPs primers (10 nM final concentration for the each primer) in 50-μl reaction mix comprising 1×HF Buffer, dNTP (200 uM) and Phusion II (1/100 dilution)(Thermo-Fisher) for 2 cycles at (98° C., 10 sec, 60° C., 1 min, 72° C. for 30 sec) and treated with exoI (40μ) at 37° C. for 30-min.

Step 3. $1^{st}$ PCR >whole volume (50-μl) of anchored DNA fragments (from Step 2) were amplified in 100-μl reaction mix for 12 cycles comprising 1×HF Buffer, dNTP (200 uM), universal PCR primers F-MP6GAC and R-MP7CAG and Phusion II (1/100 dilution)(Thermo-Fisher) for 12 cycles at (98° C. for 10 sec, 60° C. for 10 sec, 72° C. for 20 sec).

Step 4. $2^{nd}$ PCR >5-μl aliquot of 1st PCR was amplified in 100-μl of PCR mix comprising 1×HF Buffer, dNTP (200 μM), indexed Fwd and Rev PCR primers (specific for the each sample) and Phusion II (1/100 dilution)(Thermo-Fisher) for 12-20 cycles at (98° C. for 10 sec, 60° C. for 10 sec, 72° C. for 20 sec). The amplified PCR products were analyzed in 3.5% agarose-1×TAE gel to optimize the cycle number and finally digested with exoI (20 u) and Shrimp alkaline phosphatase (10 u) (New England Biolabs), incubated and 37° C. for 30 min, inactivated at 65° C. for 15 min and purified in Qia PCR column. Purified PCR products were quantitated and different samples were mixed together (at equal amount) and sequenced directly (after dilution to 10 nM) in NextSeq500 using Illumina protocol and reagents for 75 or 300 cycles.

III. Next Generation Sequencing Applications

Recently developed targeted approaches reduce NGS data complexity and generate qualitative sequencing information by measurement of a subset of targets per technical replicate with minimal sample usage. Nonetheless, targeted approaches reported thus far have limited clinical utility due to several scientific challenges, such as a prior determining which genetic markers have the most clinical significance and identifying key genetic variants that are correlated with a specific drug response. Furthermore, technical limitations due to skewing/inaccurate quantitative representation of clinical targets and inter-library variation confound their utility in the clinical setting.

Cancer is a complex multigenic disease characterized by diverse genetic and epigenetic alterations, A comprehensive catalog of all types of variants in cancer opens novel and inimitable opportunities for understanding the mechanism of cancer onset or progression and facilitates a more personalized approach to clinical care, including improved risk stratification and treatment selection. Next-generation sequencing (NGS) is now a major driver in translational/genetic research, providing a powerful way to study DNA or RNA from clinical specimens. For example, transcriptome profiling can unambiguously define a unique gene expression signature for each tumor that may prove useful for both disease classification and prognosis. Unfortunately, the cost and complexity of whole genome DNA sequencing or transcriptome RNA-sequencing data sets represent barriers to use of these methodologies in routine molecular diagnostic testing.

A. Cancer Core 125 Panel for Quantitative Expression and Mutation Profiling

1. Abstract

We have developed the Cancer Core 125 (CC125) assay to simultaneously quantitatively profile expression, copy number, and mutation level of 125 key cancer genes using multiplex PCR amplification from both total RNA and genomic DNA followed by Next-Gen Sequencing (NGS). The built-in internal calibration standards allow calibration and adjusting of digital NGS data depending on the level of intrinsic noise and quality of samples. The CC125 assay provides quantitative digital expression data for 125 key cancer genes with a 1,000-fold dynamic range and sensitivity down to the 100-cell level as well as the mutation profile of 750 driver mutations with sensitivity down to 1%. The CC125 panel includes the top 50 most mutated genes, 73 targets for FDA-approved anti-cancer drugs, and a comprehensive set of hereditary and prognostic genes used in clinical diagnostics. The CC125 assay provides a cost-effective strategy for the discovery of novel diagnostic and prognostic biomarkers in xenograft, biopsy, blood, and CTC clinical samples.

Cancer Core 125 quantitative multiplex PCR-HT sequencing panel provides first in the class assay that allows one to perform comprehensive molecular profiling at both RNA and DNA level. Moreover, the unique concept of using internal normalization and noise-correction calibration standards allows to generate high quality, reproducible digital profiling data in a wide range of clinical samples even at the single-cell level. The CC125 panel is developed specifically for the set of the biomarkers critical for prediction efficacy of anti-cancer drugs.

2. Summary

The CC125 assay employs computationally-predicted genome-wide set of PCR primers for multiplex PCR which are functionally (i.e., experimentally) validated, e.g., as described above. The unique multiplex primer design minimizes primer dimerization and cross-reactivity while enhancing specificity and efficacy. A single-test tube PCR-Next Gen Sequencing protocols for profiling of up to 2,000 genes is provided. The assay is a fully customizable assay pipeline for simultaneous gene expression, mutation hotspot, and copy-number variation (CNV) analysis in both RNA and DNA obtained from the same sample 3. Conclusion A novel functionally validated assay, Cancer Core 125, includes analysis of 125 key cancer genes that include 50 most mutated genes, 73 targets of FDA-approved anti-cancer drugs and comprehensive set of hereditary and prognostic genes. The assay employs internal calibration allows for absolute quantitation of target product. The assay may be employed with various cell lines and a broad range of clinical specimens (e.g., xenograft, biopsy, FFPE, blood and FNA). This quantitative, multiplexed, high throughput approach leverages the power of NGS and PCR technologies and allows one to obtain simultaneous gene expression, and DNA hotspots in a limited amount of biological sample. The platform is applicable for novel biomarker discovery, for prognostic and diagnostic applications. Currently, a portfolio of such assays are in development to address specific disease areas.

B. Cancer Immunotherapy Diagnostic Panel

1. Introduction

There is ample evidence that development of novel prognostic and predictive biomarkers is a critical step for selecting patients predisposed to respond to existing and novel immunotherapy treatments and their combinations. The Cancer Immunotherapy 2500 (CI2500) assay allows one to dissect cancer immunosurveillance mechanisms and discover novel prognostic and predictive immune response gene signatures.

2. Material and Method

The CI 2,500 assay was developed to quantitatively profile expression of 500 key cancer genes using multiplex PCR amplification from both total RNA and genomic DNA followed by HT sequencing. The built-in internal calibration standards allow calibration and adjusting of digital HT sequencing data depending on the level of intrinsic noise and quality of samples. The C1500 assay also provides quantitative expression data of 2000 key cancer immune-related genes with 1,000-fold dynamic range and sensitivity down to 100 cells in whole lysate and isolated cell fractions from frozen xenograft clinical samples.

3. Results and Discussion

The CI 2500 panel includes 15 experimentally validated core gene signatures which predict efficacy of immunotherapy in several cancer types, including melanoma, colorectal, breast, and lung cancers. Furthermore, the core signatures were expanded by developing an immunotherapy computational functional interaction network model used for predicting key nodes in pathways specific for antigen presentation and recognition, inhibition, activation and motility of immune cells, adhesion, and apoptosis of cancer cells. The CI 2500 panel also includes a set of genes specific primers for detection in the tumor microenvironment of activated immune cells of adaptive and innate immunity and a set of housekeeping genes with constant expression between different cancer types. The CI 2,500 assay may be employed in profiling of key mechanisms of breast cancer tumors used to escape from immunosurveillance.

4. Conclusion

Immunoprofiling of the tumor microenvironment with the CI 2,500 gene panel enables researchers to discover prognostic and predictive immune response biomarker signatures. The predictive signatures have the potential to stratify cancer patients for responses to the growing number of immunotherapeutic treatments.

D. ImmunoCancer Assay for Predictive Diagnostics in Cancer Therapy

Immunoprofiling of tumor microenvironment with the ImmunoCancer assay arms investigators with a contemporary instrument for building therapy predictive gene expression signatures. Predictive signatures allow individual cancer patients and their physicians to optimize therapeutic choices from the growing repertoire of immunotherapeutic options or chemotherapy Cancer immunotherapy is getting broad recognition nowadays due to a substantially higher number of responders than in the past. The immunotherapeutic modality is not just getting competitive, but sometimes even superior over traditional chemo- and radiotherapy modalities. Encouraging results including unprecedented numbers of complete responses are seen in pre-clinical animal experiments and human clinical trials. Nevertheless, numbers of immunotherapy non-responders are still high.

The situation when patients with one and the same tumor type are challenged to choose a therapy from the option of several different modalities is already real for some tumor types and could be foreseen as critical in the future. To provide help to physicians and their patients in making an informed decision, an urgent development of predictive diagnostics is needed to pre-identify individual patients with higher chances of response to the immunotherapeutic modality in general, and to some particular immunotherapeutic approaches in particular. Such approaches include active immunomodulating therapies with cytokines, like IL2, or INFalpha, monoclonal antibodies, specifically those that block cancer counterattack upon host immunity, such as anti-PD-1/PD-L1 antibodies, therapeutic vaccination, adoptive therapy with activated and/or genetically-modified T cells or multiplied tumor infiltrating lymphocytes.

In identifying immune gene signatures to predict responders, ImmunoCancer assay fits most of existing immunotherapeutic approaches that are used to treat various cancer types.

Recent work has suggested the existence among cancer patients of two broad categories, each characterized with a specific type of tumor escape from immunosurveillance (Gajewski et al., "Innate and adaptive immune cells in the tumor microenvironment," Nat. Immunol (2013) 14:1014-22). Within one of them, the tumor microenvironment is almost void of infiltrating immune cells. The absence of cellular substrate to perform immunosurveillance corresponds to poor response of patients of this category to current immunotherapeutic approaches. Tumors within the second category, demonstrate an inflamed phenotype that is characterized by the presence in the microenvironment of activated cells of adaptive and/or innate immunity. Since no tumor destruction has occurred in spite of the presence of immune cells, these tumors appear to resist immune attack by inducing an immunosuppression of infiltrating immune cells. Tumors of this category seem to be responsive to various immunotherapeutic schedules. Major success should be expected from the schedules that are directed to specifically de-repress a dominating immunosuppressive mechanism of a given tumor.

The ImmunoCancer assay is created as a prototype predictive diagnostic assay to ultimately identify potential responders to the immunotherapeutic modality in general and to a specific immunotherapeutic approach in particular for every chosen cancer type, whether it is breast, prostate, lung, colon, or any other solid cancer.

This assay is based on expression immunoprofiling of the two mentioned major gene groups in the tumor tissue. The first one allows one to differentiate tumor microenvironments of inflamed phenotype from microenvironment void of immune cell infiltration. The other one is comprised of genes that are related to the functioning of a whole spectrum of various immune mechanisms, such as antigen presentation, motility of immune cells within tumor interstitium, recognition of targets on the surface of tumor cells, efficient adhesion and killing of cancer cells. The peculiarities of expression of genes from the first group in tumor microenvironment allows to judge on the spectrum of tumor infiltrating leukocytes, if any. The expression profiling for the second group of genes provides gene signatures to conclude on a particular suppressive mechanism or mechanisms that are used by the tumor of a given cancer patient to evade immunosurveillance. Genes from signature sets that have already been proven to have diagnostic value in oncotherapy in several cancer types, including melanoma, colorectal cancer, breast cancer, lung cancer and some others are included in ImmunoCancer assay along with the potentially relevant but yet not proven genes. The major groups, their subgroups and corresponding genes are all present in Table 1.

Within each of the two major gene groups, for those genes that are known as harboring functional polymorphisms, in addition to their expression testing, genotyping of their polymorphic variants will be done. It is important to do, since the "efficient" expression level of a gene is lower than real expression level in carriers of polymorphic gene variant that encode protein variant with lower functional activity than in wild type variant carriers. The genotyping will allows one to perform important expression adjustments for variant carriers in order to define the "efficient" expression level for each of such genes in the microenvironment of their tumors.

Additionally, for genes that encode proteins with two isoforms, membrane and soluble ones, the expression ratio of RNAs encoding each of the isoform will be determined, since the ratio of the two is critical for proper functioning of several major immune mechanisms of the inflammatory immune response.

Together with the above explained principles beyond the gene selection, the profiling of functional genetic polymorphisms and membrane/soluble isoform ratios make the ImmunoCancer assay unique in its potential to reveal predictive diagnostic signatures for cancer immunotherapy responders/non-responders.

Interestingly, unexpected recent data show the potential of the immune profile of a tumor microenvironment to predict an outcome for chemotherapy, as well. These important observations comply with the idea that the successful outcome in chemotherapy occurs in cases when at least some level of internal anti-tumor immunity is preserved. Thus, chemotherapeutic assault seems to be efficient only when working in parallel with elements of host anti-tumor immunity. Conclusions upon the presence and working status of these elements that are made from the data on tumor immunoprofiling with ImmunoCancer assay could be potentially predictive for chemotherapeutic modality, as well.

IV. CancerNet 8K

A. Materials and Methods

1. Step 1-cDNA Synthesis.

10-100 ng of RNA was converted to cDNA using random primer (5 uM) using Maxima RT at 50° C. in 10 µl reaction mix. RT was inactivated at 95° C. for 5 min.

2. Step 2—Stranded Anchor Addition.

cDNA (in 25-µl of 1× Phusion II reaction mix) was primed and extended for 1 cycle at 60° C. extension temperature (30 min) using mix of CancerNet 8K forward primer mix (final concentration of 10 nM of the each primer, gene specific primer domains listed in Table 1 (SEQ ID NOs:37-16166) and anchor domains as reported above), treated with Exol (1-µl, 20 units/up for 20 min at 37° C., inactivated at 95° C. for 5 min, subjected to the second round of extension with CancerNet 8K Reverse primer mix (10 nM each) using the same conditions as for Fwd extension step and treated with exol at 37° C. for 20 min, 50° C. for 10 min and 95° C. for 5 min.

3. Step 3—1st PCR.

1st PCR >anchored DNA fragments (25-µl) were directly amplified in 50-µl of 1× Phusion II reaction mix with universal anchor PCR primers (Fwd and Rev, 0.5 uM each, sequences reported above) for 16 cycles using program (98° C. for 20 sec, 65° C. for 10 sec, 72° C. for 10 sec).

4. Step 4-2nd Nested PCR (P5-index and P7-index addition). 2nd PCR >5-µl aliquot of 1st PCR reaction was amplified in 100-µl using combination of P7-Ind-Fwd and P5-Ind-Rev PCR primers with indexes (0.5 uM each, sequences as reported above) for 5 cycles and analyzed in 3% agarose-EtBr gel for presence of 200-400 bp amplicons. cDNA samples with less yield of PCR products were amplified for extra 1-3 cycles in order to adjust the yield of PCR products. The exol (1.5-4 was added to PCR mix, incubated and 37° C. for 30 min, samples were mix at approximately equal ratio (based on 200-400 bp amplicon band intensity) and purified in Qiagen PCR columns. Purified PCR products were quantitated by measuring OD at 260 nm, and adjusted to 10 nM (2.5 ng/u1).

5. Step 5—HT Sequencing.

cDNA products amplified in CancerNet 8K assay were analyzed in Illumnina NextSeq machine using 75-n paired-end reagent kit using the following program:

Read 1: SeqDNA-Rev>32 cycles; Ind 1:SeqIND-Rev>6 cycles; Ind 2:SeqIND-Fwd>6 cycles;

Read 2: SeqDNA-Fwd>32 cycles.

Representation of gene-specific amplicons in amplified cDNA products were analyzed using custom gene enumeration software developed at Cellecta, Mountain View, Calif.

FIG. 3 provides a schematic represent of the above steps.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

SEQUENCE LISTING

The patent contains a lengthy sequence listing. A copy of the sequence listing is available in electronic form from the USPTO web site (https://seqdata.uspto.gov/?pageRequest=docDetail&DocID=US11655510B2). An electronic copy of the sequence listing will also be available from the USPTO upon request and payment of the fee set forth in 37 CFR 1.19(b)(3).

What is claimed is:

1. A set of 10 or more gene specific primer pairs that produce primer extension products for 10 or more different genes, wherein each primer pair is made up of a forward primer and a reverse primer, wherein the forward and reverse primers comprise gene specific domains selected from SEQ ID NOs: 37 to 54152, wherein for each gene the gene specific domain of the forward primer comprises the sequence of SEQ ID NO: X and the gene specific domain of the reverse primer comprises the sequence of SEQ ID NO: (X+1), wherein X is an odd number from 37 to 54151, wherein the forward and reverse primers further comprise anchor domains comprising universal primer binding sites and common PCR suppression sequences, wherein the anchor domains in all of the forward primers have the same sequence and the anchor domains in all of the reverse primers have the same sequence.

2. The set according to claim 1, wherein the set comprises 100 or more primer pairs.

3. The set according to claim 1, wherein the set comprises 1000 or more primer pairs.

4. The set according to claim 1, wherein the set comprises 27,058 primer pairs.

* * * * *

UNITED STATES PATENT AND TRADEMARK OFFICE
CERTIFICATE OF CORRECTION

PATENT NO. : 11,655,510 B2
APPLICATION NO. : 15/914895
DATED : May 23, 2023
INVENTOR(S) : Alex Chenchik et al.

It is certified that error appears in the above-identified patent and that said Letters Patent is hereby corrected as shown below:

In the Specification

Please replace "GeneBank)," with -- GenBank), -- (Column 5, Line 18).

Please replace "literalis," with -- litoralis, -- (Column 13, Line 27).

Please replace "SuprScript" with -- Superscript -- (Column 13, Line 33).

Please replace "Fsher)," with -- Fisher), -- (Column 13, Line 34).

Please replace "(exonucleclease" with -- (exonuclease -- (Column 14, Lines 55-56).

Please replace "performed, an" with -- performed, and -- (Column 16, Line 7).

Please replace "(SE" with -- (SEQ -- (Column 18, Line 62).

Please replace "3′)(SEQ" with -- 3′) (SEQ -- (Column 18, Line 63).

Please replace "3′)(SEQ" with -- 3′) (SEQ -- (Column 19, Line 3).

Please replace "3′)(SEQ" with -- 3′) (SEQ -- (Column 19, Line 5).

Please replace "does not does not" with -- does not -- (Column 21, Line 54).

Please replace "nmonocyte," with -- monocyte, -- (Column 21, Lines 56-57).

Please replace "genomicDNA" with -- genomic DNA -- (Column 26, Line 66).

Please replace "IIlumina" with -- Illumina -- (Column 27, Line 17).

Signed and Sealed this
Eleventh Day of July, 2023

Katherine Kelly Vidal
*Director of the United States Patent and Trademark Office*

CERTIFICATE OF CORRECTION (continued)
U.S. Pat. No. 11,655,510 B2

Please replace "alterations," with -- alterations. -- (Column 29, Line 19).

Please replace "Gen" with -- Generation -- (Column 29, Line 45).

Please replace "sample" with -- sample. -- (Column 30, Line 17).

Please replace "chemotherapy" with -- chemotherapy. -- (Column 31, Line 32).

Please replace "INFalpha," with -- IFNalpha, -- (Column 31, Line 53).

Please replace "1x Phusion" with -- 1xPhusion -- (Column 33, Line 23).

Please replace "1x Phusion" with -- 1xPhusion -- (Column 33, Line 37).

Please replace "ng/u1)." with -- ng/ul). -- (Column 34, Line 14).

Please replace "Illumnina" with -- Illumina -- (Column 34, Line 17).